(12) United States Patent
Boezio et al.

(10) Patent No.: US 9,012,443 B2
(45) Date of Patent: Apr. 21, 2015

(54) BICYCLIC ARYL AND HETEROARYL SODIUM CHANNEL INHIBITORS

(71) Applicant: Amgen Inc., Thousand Oaks, CA (US)

(72) Inventors: Christiane Boezio, Somerville, MA (US); Howard Bregman, Melrose, MA (US); James R. Coats, Oak Harbor, WA (US); Erin F. Dimauro, Cambridge, MA (US); Thomas Dineen, Somerville, WA (US); Bingfan Du, Cambridge, MA (US); Russell Graceffa, Hampton, NH (US); Charles Kreiman, Belmont, MA (US); Daniel La, Brookline, MA (US); Isaac E. Marx, Cambridge, MA (US); Nagasree Chakka, Lexington, MA (US); Hanh Nho Nguyen, Arlington, MA (US); Emily Anne Peterson, Cambridge, MA (US); Matthew Weiss, Boston, MA (US); Katrina W. Copeland, Sudbury, MA (US); Holly L. Deak, Brookline, MA (US); Alessandro Boezio, Somerville, MA (US)

(73) Assignee: Amgen Inc., Thousand Oaks, CA (US)

( * ) Notice: Subject to any disclaimer, the term of this patent is extended or adjusted under 35 U.S.C. 154(b) by 121 days.

(21) Appl. No.: 13/707,096

(22) Filed: Dec. 6, 2012

(65) Prior Publication Data

US 2013/0150339 A1    Jun. 13, 2013

Related U.S. Application Data

(60) Provisional application No. 61/567,927, filed on Dec. 7, 2011, provisional application No. 61/713,304, filed on Oct. 12, 2012.

(51) Int. Cl.

| | | |
|---|---|---|
| *C07D 498/04* | (2006.01) | |
| *C07D 417/12* | (2006.01) | |
| *C07D 417/14* | (2006.01) | |
| *C07D 401/14* | (2006.01) | |
| *C07D 471/04* | (2006.01) | |
| *A61K 31/433* | (2006.01) | |
| *C07D 403/12* | (2006.01) | |
| *C07D 413/14* | (2006.01) | |
| *C07D 401/12* | (2006.01) | |
| *C07D 403/14* | (2006.01) | |
| *C07D 239/42* | (2006.01) | |
| *C07D 409/14* | (2006.01) | |
| *C07D 413/12* | (2006.01) | |
| *C07D 277/52* | (2006.01) | |
| *C07D 285/08* | (2006.01) | |

(52) U.S. Cl.
CPC ............ *C07D 498/04* (2013.01); *C07D 401/14* (2013.01); *C07D 417/12* (2013.01); *C07D 417/14* (2013.01); *C07D 471/04* (2013.01); *C07D 403/12* (2013.01); *C07D 413/14* (2013.01); *C07D 401/12* (2013.01); *C07D 403/14* (2013.01); *C07D 239/42* (2013.01); *C07D 409/14* (2013.01); *C07D 413/12* (2013.01); *C07D 277/52* (2013.01); *C07D 285/08* (2013.01)

(58) Field of Classification Search
None
See application file for complete search history.

(56) References Cited

FOREIGN PATENT DOCUMENTS

| | | |
|---|---|---|
| WO | 9640641 A1 | 12/1996 |
| WO | 9832732 A1 | 1/1998 |
| WO | 2004103980 A1 | 12/2004 |
| WO | 2006122014 A2 | 11/2006 |
| WO | 2006124744 A1 | 11/2006 |
| WO | WO 2007089018 A1 * | 8/2007 |

OTHER PUBLICATIONS

Woodruff-Pak, "Inactivation of Sodium Channel Scn8A (Nav1.6) in Purkinje Neurons Impairs Learning in Morris Water Maze and Delay but Not Trace Eyeblink Classical Conditioning", Behavioral Neuroscience 2006, vol. 120, No. 2, 229-240.

Johannessen Landmark, "Antiepileptic Drugs in Non-Epilepsy Disorders", CNS Drugs 2008; 22 (1): 27-47.

Do et al., "Subthreshold Sodium Currents and Pacemaking of Subthalamic Neurons: Modulation by Slow Inactivation", Neuron, vol. 39, 109-120, Jul. 3, 2003.

Drenth et al., "SCN9A Mutations Define Primary Erythermalgia as a Neuropathic Disorder of Voltage Gated Sodium Channels", J Invest Dermatol 124:1333-1338, 2005.

(Continued)

*Primary Examiner* — Yong Chu
(74) *Attorney, Agent, or Firm* — Elsa D. Lemoine

(57) ABSTRACT

The present invention provides compounds of Formula I, or pharmaceutically acceptable salts thereof, that are inhibitors of voltage-gated sodium channels, in particular Nav 1.7.

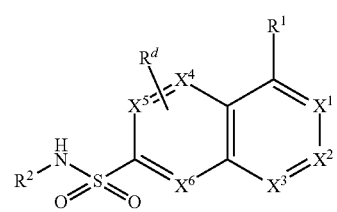

The compounds are useful for the treatment of diseases treatable by inhibition of sodium channels such as pain disorders. Also provided are pharmaceutical compositions containing compounds of the present invention.

32 Claims, No Drawings

(56) References Cited

OTHER PUBLICATIONS

Fertleman et al, "SCN9A Mutations in Paroxysmal Extreme Pain Disorder: Allelic Variants Underlie Distinct Channel Defects and Phenotypes", Neuron 52, 767-774, Dec. 7, 2006.

Gillet et al., "Voltage-gated Sodium Channel Activity Promotes Cysteine Cathepsin-dependent Invasiveness and Colony Growth of Human Cancer Cells", Journal of Biological Chemistry, vol. 384, No. 13•Mar. 27, 2009.

MacFarlane et al., "Loss-of-function mutations in the Nav1.7 gene underlie congenital indifference to pain in multiple human populations", Clin Genet 2007: 71: 311-319.

Goldin, "Resurgence of Sodium Channel Research", Annu. Rev. Physiol. 2001. 63:871-94.

Hamann et al., "Motor disturbances in mice with deficiency of the sodium channel gene Scn8a show features of human dystonia", Experimental Neurology 184 (2003) 830-838.

Haufe et al., "The promiscuous nature of the cardiac sodium current", Journal of Molecular and Cellular Cardiology 42 (2007) 469-477.

Kim et al., "BACE1 regulates voltage-gated sodium channels and neuronal activity", Nature Cell Biology vol. 91 | No. 7 | Jul. 2007.

McKinney et al., "Exaggerated emotional behavior in mice heterozygous null for the sodium channel Scn8a (Nav1.6)", Genes, Brain and Behavior (2008) 7: 629-638.

Morinville et al., "Distribution of the Voltage-Gated Sodium Channel NaV1.7 in the Rat: Expression in the Autonomic and Endocrine Systems", The Journal of Comparative Neurology 504:680-689 (2007).

Cox et al., "An SCN9A channelopathy causes congenital inability to experience pain", Nature, vol. 444| Dec. 15, 2006| doi:10.1038/nature05413.

Ettinger et al, "Use of Antiepileptic Drugs for Nonepileptic Conditions: Psychiatric Disorders and Chronic Pain", Neurotherapeutics, vol. 4, No. 1, 2007.

Puopolo et al, "Roles of Subthreshold Calcium Current and Sodium Current in Spontaneous Firing of Mouse Midbrain Dopamine Neurons", The Journal of Neuroscience, Jan. 17, 2007 • 27(3):645-656.

Waxman, "Axonal conduction and injury in multiple sclerosis: the role of sodium channels", Nature Reviews | Neuroscience, vol. 7 | Dec. 2006 | 933.

Wood et al., "Voltage-Gated Sodium Channel Blockers; Target Validation and Therapeutic Potential", Current Topics in Medicinal Chemistry, 2005, 5, 529-537.

Yang et al., "Mutations in SCN9A, encoding a sodium channel alpha subunit, in patients with primary erythermalgia", J Med Genet 2004;41:171-174. doi: 10.1136/jmg.2003.012153.

\* cited by examiner

BICYCLIC ARYL AND HETEROARYL SODIUM CHANNEL INHIBITORS

FIELD OF THE INVENTION

The present invention provides compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., 3$^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential" *Curr. Top Med. Chem.* 5:529-537, 2005). Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway.

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," *J. Med. Genet.* 41:171-174, 2004; Drenth J. P. H., te Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception. Accordingly, a therapeutic agent that inhibits Nav 1.7 should effectively treat pain in humans. The present invention provides compounds that are inhibitors of Nav 1.7.

SUMMARY OF THE INVENTION

In embodiment 1, the present invention provides compounds of Formula I, or pharmaceutically acceptable salts thereof,

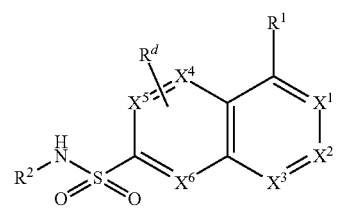

wherein:
$X^1$ is $CR^a$ or N;
$X^2$ is $CR^a$ or N;
$X^3$ is $CR^a$ or N;
$X^4$ is $CR^d$ or N;
$X^5$ is $CR^d$ or N;
$X^6$ is $CR^d$ or N;
each $R^a$ is independently hydrogen, halo, —OH, —NR$^b$R$^b$, —C$_{1-6}$alkyl, —OC$_{1-6}$alkyl. —C$_{1-6}$haloalkyl, —OC$_{1-6}$haloalkyl or —CN;
$R^1$ is —CN, —N(R$^e$)(CR$^e$R$^e$)$_m$A, —(C=O)N(R$^e$)(CR$^e$R$^e$)$_m$CF$_3$, —C(=O)A, —O(CR$^e$R$^e$)$_m$A, —O(CR$^e$R$^e$)$_m$OA, —(C=O)C$_{1-6}$alkyl or a 5 to 10 membered aryl or heteroaryl, or a 3 to 10 membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a C=O group, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, —OC$_{1-6}$alkylCF$_3$, —OC$_{1-6}$alkylCN, —C$_{1-6}$alkylOC$_{1-6}$alkyl, —(SO$_2$)C$_{1-6}$alkyl, —(SO$_2$)NR$^b$R$^b$, hydroxyC$_{1-6}$alkyl, —CF$_3$, —CHF$_2$, —CH$_2$F, —OCF$_3$, —OCHF$_2$, —OCH$_2$F, —(CR$^e$R$^e$)$_m$CN, —C(=O)NR$^b$R$^b$, —C(=O)OR$^b$, —(CR$^e$R$^e$)$_m$A, —N(R$^e$)(CR$^e$R$^e$)$_m$A, —(C=N)OC$_{1-6}$alkyl, —(C=O)N(R$^e$)(CR$^e$R$^e$)$_m$A, —(C=O)N(R$^e$)(CR$^e$R$^e$)$_m$CF$_3$, —O(CR$^e$R$^e$)$_m$A, —O(CR$^e$R$^e$)$_m$OA or —C(=O)A;
A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, —NR$^b$R$^b$, —C$_{1-6}$alkyl, —OC$_{1-6}$alkyl, —(CR$^e$R$^e$)$_m$OH, hydroxyC$_{1-6}$alkyl, —CF$_3$, —CHF$_2$, —CH$_2$F, —OCF$_3$, —OCHF$_2$, —OCH$_2$F, —CN, —C(=O)NR$^b$R$^b$, —O(CR$^e$R$^e$)$_m$B or —(CR$^e$R$^e$)$_m$B;

B is a 5 to 6 membered aryl, heteroaryl or heterocycloalkyl group, where the heteroaryl or heterocycloalkyl group can have from 1 to 3 heteroatoms independently selected from O, N or S, or a 3 to 5 membered cycloalkyl group, and the aryl, heteroaryl cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, —CN or —C(=O)NR$^b$R$^b$;

R$^2$ is —(C=O)C$_{1-6}$alkyl, —(C=O)C$_{1-6}$haloalkyl or a 5 to 10 membered aryl or heteroaryl, or a 3 to 10 membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a C=O group, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F, —CN or —C(=O)NR$^b$R$^b$;

each n is independently 0, 1, 2, 3 or 4;
each m is independently 0, 1, 2, 3 or 4;
each R$^b$ is independently hydrogen or —C$_{1-6}$alkyl;
each R$^c$ is independently hydrogen or —C$_{1-6}$alkyl;
each R$^d$ is independently hydrogen, halo, —CN, —NR$^c$R$^c$, —OH, —C$_{1-6}$alkyl, —C$_{1-6}$haloalkyl, —OC$_{1-6}$haloalkyl or —OC$_{1-6}$alkyl; and
each R$^e$ is independently hydrogen, halo, —CN, —NR$^c$R$^c$, —OH, —C$_{1-6}$alkyl, —OC$_{1-6}$alkyl or a 5 to 6 membered heterocycloalkyl group having from 1 to 3 heteroatoms independently selected from O, N or S,
provided that the compound is not 1-(4-fluoro-2-(pyrimidin-5-yl)phenyl)-N-(thiazol-2-yl)isoquinoline-6-sulfonamide;
1-(4-fluoro-2-(pyrimidin-2-yloxy)phenyl)-N-(thiazol-2-yl)isoquinoline-6-sulfonamide;
5-methoxy-4-(2-methoxy-4-(trifluoromethyl)phenyl)-N-(thiazol-2-yl)quinoline-7-sulfonamide;
5-cyano-N-phenyl-2-naphthalenesulfonamide;
N-(3,4-dimethyl-5-isoxazolyl)-5-(1-piperidinyl)-2-naphthalenesulfonamide; or
N-(3,4-dimethyl-5-isoxazolyl)-5-[(phenylmethyl)amino]-2-naphthalenesulfonamide.

In embodiment 1a, the present invention provides compounds of Formula I, or pharmaceutically acceptable salts thereof,

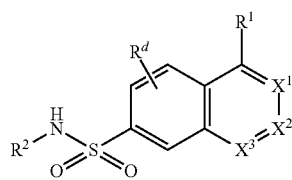

I wherein:
X$^1$ is CR$^a$ or N;
X$^2$ is CR$^a$ or N;
X$^3$ is CR$^a$ or N;
each R$^a$ is independently hydrogen, halo, —OH, —C$_{1-6}$alkyl, —OC$_{1-6}$alkyl or —CN;
R$^1$ is a 5 to 10 membered aryl or heteroaryl, or a 3 to 10 membered cycloalkyl or heterocycloalkyl group, where the heteroaryl or heterocycloalkyl group can have from 1 to 3 heteroatoms independently selected from O, N or S, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, —CN, —C(=O)NR$^b$R$^b$, —C(=O)OR$^b$ or A;

A is a 5 to 6 membered aryl, heteroaryl or heterocycloalkyl group, where the heteroaryl or heterocycloalkyl group can have from 1 to 3 heteroatoms independently selected from O, N or S, and the aryl, heteroaryl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, —CN or —C(=O)NR$^b$R$^b$, R$^2$ is a 5 to 10 membered aryl or heteroaryl, or a 3 to 10 membered cycloalkyl or heterocycloalkyl group, where the heteroaryl or heterocycloalkyl group can have from 1 to 3 heteroatoms independently selected from O, N or S, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F, —CN or —C(=O)NR$^b$R$^b$;

each n is independently 0, 1, 2, 3 or 4;
each R$^b$ is independently hydrogen or —C$_{1-6}$alkyl;
R$^c$ is hydrogen or —C$_{1-6}$alkyl; and
R$^d$ is hydrogen, halo, —C$_{1-6}$alkyl or —OC$_{1-6}$alkyl.

In embodiment 1b, the present invention provides compounds of Formula I, or pharmaceutically acceptable salts thereof, wherein one or two of X$^1$, X$^2$ and X$^3$ is N and the other is CR$^a$, wherein R$^a$ is —OH. Thus, the invention also includes compounds of Formula I, having the following general structure (tautomer of X$^1$, X$^2$ or X$^3$=C—OH):

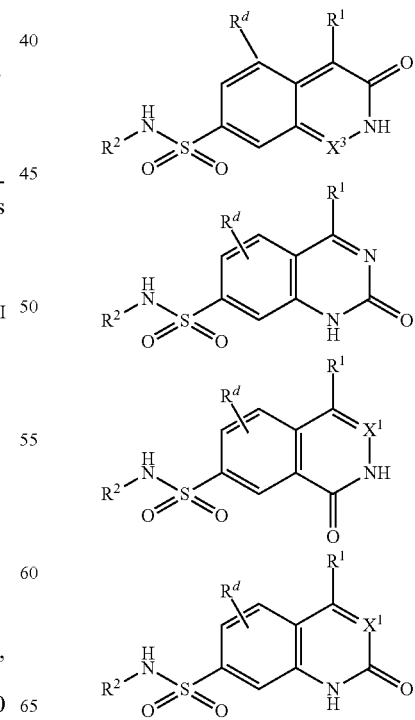

wherein $R^1$, $X^1$, $X^3$, $R^2$ and $R^d$ are as defined herein above or below.

In embodiment 1c, the present invention provides compounds in accordance with any one of embodiments 1 or 1a, or a pharmaceutically acceptable salt thereof, wherein one of $X^1$, $X^2$ and $X^3$ is N and the other two of $X^1$, $X^2$ and $X^3$ is $CR^a$.

In embodiment 1d, the present invention provides compounds in accordance with any one of embodiments 1 or 1a, or a pharmaceutically acceptable salt thereof, wherein two of $X^1$, $X^2$ and $X^3$ is N and the other one of $X^1$, $X^2$ and $X^3$ is $CR^a$.

In embodiment 1e, the present invention provides compounds in accordance with any one of embodiments 1 or 1a, or a pharmaceutically acceptable salt thereof, wherein one of $X^1$, $X^2$ and $X^3$ is N and the other two of $X^1$, $X^2$ and $X^3$ is CH.

In embodiment 1f, the present invention provides compounds in accordance with any one of embodiments 1 or 1a, or a pharmaceutically acceptable salt thereof, wherein two of $X^1$, $X^2$ and $X^3$ is N and the other one of $X^1$, $X^2$ and $X^3$ is CH.

In embodiment 2, the present invention provides compounds in accordance with any one of embodiments 1, 1a or 1b, or pharmaceutically acceptable salts thereof, wherein $X^1$ is CH.

In embodiment 3, the present invention provides compounds in accordance with any one of embodiments 1, 1a or 1b, or pharmaceutically acceptable salts thereof, wherein $X^1$ is N.

In embodiment 4, the present invention provides compounds in accordance with any one of embodiments 1-1f to 3, or pharmaceutically acceptable salts thereof, wherein $X^2$ is CH.

In embodiment 5, the present invention provides compounds in accordance with any one of embodiments 1-1f to 3, or pharmaceutically acceptable salts thereof, wherein $X^2$ is N.

In embodiment 6, the present invention provides compounds in accordance with any one of embodiments 1-1f to 5, or pharmaceutically acceptable salts thereof, wherein $X^3$ is CH.

In embodiment 7, the present invention provides compounds in accordance with any one of embodiments 1-1f to 5, or pharmaceutically acceptable salts thereof, wherein $X^3$ is N.

In embodiment 8, the present invention provides compounds in accordance with any one of embodiments 1-1a, or a pharmaceutically acceptable salt thereof, wherein $X^1$, $X^2$ and $X^3$ are CH.

In embodiment 9, the present invention provides compounds in accordance with any one of embodiments 1 or 1a, or pharmaceutically acceptable salts thereof, wherein $X^1$ is N, and $X^2$ and $X^3$ are CH.

In embodiment 10, the present invention provides compounds in accordance with any one of embodiments 1 or 1a, or pharmaceutically acceptable salts thereof, wherein $X^1$ is N, $X^2$ is CH and $X^3$ is $CR^a$.

In embodiment 11, the present invention provides compounds in accordance with any one of embodiments 1 or 1a, or pharmaceutically acceptable salts thereof, wherein $X^1$ is N, $X^2$ is N and $X^3$ is CH.

In embodiment 12, the present invention provides compounds in accordance with any one of embodiments 1 or 1a, or pharmaceutically acceptable salts thereof, wherein $X^1$ is CH, $X^2$ is N and $X^3$ is N.

In embodiment 13, the present invention provides compounds in accordance with any one of embodiments 1 or 1a, or pharmaceutically acceptable salts thereof, wherein $X^1$ is N, $X^2$ is CH and $X^3$ is N.

In embodiment 14, the present invention provides compounds in accordance with any one of embodiments 1 or 1a, or pharmaceutically acceptable salts thereof, wherein $X^1$ is CH, $X^2$ is CH and $X^3$ is N.

In embodiment 15, the present invention provides compounds in accordance with any one of embodiments 1 or 1a, or a pharmaceutically acceptable salt thereof, wherein $X^1$ is CH, $X^2$ is N and $X^3$ is CH.

In embodiment 16, the present invention provides compounds in accordance with any one of embodiments 1 to 15, or pharmaceutically acceptable salts thereof, wherein $X^4$ is CH.

In embodiment 17, the present invention provides compounds in accordance with any one of embodiments 1 to 15, or pharmaceutically acceptable salts thereof, wherein $X^5$ is CH.

In embodiment 18, the present invention provides compounds in accordance with embodiment 1, or pharmaceutically acceptable salts thereof, wherein $X^1$ is N, $X^2$ is CH, $X^3$ is CH, $X^4$ is N and $X^5$ is CH.

In embodiment 19, the present invention provides compounds in accordance with embodiment 1, or pharmaceutically acceptable salts thereof, wherein $X^1$ is CH, $X^2$ is CH, $X^3$ is N, $X^4$ is CH and $X^5$ is N.

In embodiment 20, the present invention provides compounds in accordance with any one of embodiments 1, 1a or 1b to 19, or pharmaceutically acceptable salts thereof, wherein $R^1$ is a 6 membered aryl, heteroaryl or heterocycloalkyl group, where the heteroaryl or heterocycloalkyl group can have from 1 to 3 heteroatoms independently selected from O, N or S, and the aryl, heteroaryl or heterocycloalkyl group can be unsubstituted or substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, —CN, —C(=O)$NR^bR^b$ —C(=O)$OR^b$ or A; and A is a 5 to 6 membered aryl or heteroaryl group, where the heteroaryl group can have from 1 to 3 heteroatoms independently selected from O, N or S, and the aryl, or heteroaryl group can be unsubstituted or substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, —CN, or —C(=O)$NR^bR^b$.

In embodiment 21, the present invention provides compounds in accordance with any one of embodiments 1, 1a or 1b to 19, or pharmaceutically acceptable salts thereof, wherein $R^1$ is phenyl, substituted phenyl, morpholino, substituted morpholino, pyridyl or substituted pyridyl.

In embodiment 22, the present invention provides compounds in accordance with any one of embodiments 1, 1a or 1b to 19, or pharmaceutically acceptable salts thereof, wherein $R^1$ is phenyl, substituted phenyl, morpholino, substituted morpholino, pyridyl or substituted pyridyl, wherein any substituents are independently selected from —$CF_3$, halo, —$OCH_3$, 5 membered heteroaryl, substituted 5 membered heteroaryl, 6 membered heteroaryl, substituted 6 membered heteroaryl, 6 membered aryl, substituted 6 membered aryl, —$C_{1-6}$alkyl, —$OCF_3$, —$OCHF_2$, —$OCH_2F$, —C(=O)N($CH_3$)$_2$, —C(OH)($CH_3$)$_2$, —C(=O)$OCH_3$, —CN, $NH_2$, —C(=O)$NH_2$ or —$OCHF_2$.

In embodiment 23, the present invention provides compounds in accordance with any one of embodiments 1, 1a or 1b to 19, or pharmaceutically acceptable salts thereof, wherein $R^1$ is —N($R^e$)($CR^eR^e$)$_m$A.

In embodiment 24, the present invention provides compounds in accordance with any one of embodiments 1, 1a or Ib to 19, or pharmaceutically acceptable salts thereof, wherein R¹ is —N(H)(CH$_2$)$_m$A.

In embodiment 25, the present invention provides compounds in accordance with any one of embodiments 1, 1a or Ib to 19, or a pharmaceutically acceptable salt thereof, wherein R¹ is —N(R$^e$)(CR$^e$R$^e$)$_m$A.

In embodiment 26, the present invention provides compounds in accordance with any one of embodiments 1, 1a or Ib to 19, or pharmaceutically acceptable salts thereof, wherein R¹ is —N(H)(CH$_2$)$_m$A.

In embodiment 27, the present invention provides compounds in accordance with any one of embodiments 1, 1a or Ib to 19, or pharmaceutically acceptable salts thereof, wherein R¹ is —O(CR$^e$R$^e$)$_m$A.

In embodiment 28, the present invention provides compounds in accordance with any one of embodiments 1, 1a or Ib to 19, or pharmaceutically acceptable salts thereof, wherein R¹ is —O(CH$_2$)$_m$A.

In embodiment 29, the present invention provides compounds in accordance with any one of embodiments 1, 1a or Ib to 28, or pharmaceutically acceptable salts thereof, wherein R² is thiadiazoylyl, substituted thiadiazoylyl, thiazolyl, substituted thiazolyl, oxazolyl, substituted oxazolyl, pyrimidinyl, substituted pyrimidinyl, isoxazolyl, substituted isoxazolyl, pyrazolyl, substituted pyrazolyl, pyridyl, substituted pyridyl, pyridazinyl, substituted pyridazinyl, pyrazinyl or substituted pyrazinyl.

In embodiment 30, the present invention provides compounds in accordance with any one of embodiments 1 to 28, or pharmaceutically acceptable salts thereof, wherein R² is thiadiazolyl.

In embodiment 31, the present invention provides compounds in accordance with any one of embodiments 1 to 28, or pharmaceutically acceptable salts thereof, wherein R² is pyrimidinyl.

In embodiment 32, the present invention provides compounds in accordance with any one of embodiments 1 to 28, or pharmaceutically acceptable salts thereof, wherein R² is thiazolyl.

In embodiment 33, the present invention provides compounds in accordance with any one of embodiments 1, 1a or Ib to 28, or pharmaceutically acceptable salts thereof, wherein R² is substituted thiazolyl.

In embodiment 34, the present invention provides compounds in accordance with any one of embodiments 1 to 33 or pharmaceutically acceptable salts thereof, wherein R$^d$ is hydrogen.

In embodiment 35, the present invention provides compounds in accordance with any one of embodiments 1 or 1a, or pharmaceutically acceptable salts thereof, wherein X¹, X² and X³ are CH and R² is thiadiazolyl.

In embodiment 36, the present invention provides compounds in accordance with any one of embodiments 1 or 1a, or pharmaceutically acceptable salts thereof, wherein R² is thiadiazolyl and X¹ is N and X² and X³ are CH.

In embodiment 37, the present invention provides compounds in accordance with any of claims 1, to 36, or a pharmaceutically acceptable salt thereof, wherein X⁶ is CH.

In embodiment 38, the present invention provides a compound, or a pharmaceutically acceptable salt thereof, selected from:
5-(2-(1-methyl-1H-pyrazol-5-yl)-4-(trifluoromethyl)phenyl)-N-(1,2,4-thiadiazol-5-yl)naphthalene-2-sulfonamide;
5-(2-(pyridin-4-yl)-4-(trifluoromethyl)phenyl)-N-(1,2,4-thiadiazol-5-yl)naphthalene-2-sulfonamide;
5-(2-bromo-4-fluorophenyl)-N-(1,2,4-thiadiazol-5-yl)naphthalene-2-sulfonamide;
5-(2-chloro-4-(trifluoromethoxy)phenyl)-N-(1,2,4-thiadiazol-5-yl)naphthalene-2-sulfonamide;
5-(2-chloro-4-fluorophenyl)-N-(1,2,4-thiadiazol-5-yl)naphthalene-2-sulfonamide;
5-(2-chloro-4-methylphenyl)-N-(1,2,4-thiadiazol-5-yl)naphthalene-2-sulfonamide;
5-(pyridin-4-yl)-N-(1,2,4-thiadiazol-5-yl)naphthalene-2-sulfonamide;
5-(2-chlorophenyl)-N-(1,2,4-thiadiazol-5-yl)naphthalene-2-sulfonamide;
5-phenyl-N-(1,2,4-thiadiazol-5-yl)naphthalene-2-sulfonamide;
5-(2-ethoxy-4-(trifluoromethyl)phenyl)-N-(1,2,4-thiadiazol-5-yl)naphthalene-2-sulfonamide;
5-(2-methyl-4-(trifluoromethyl)phenyl)-N-(1,2,4-thiadiazol-5-yl)naphthalene-2-sulfonamide;
5-(2-methoxy-4-(trifluoromethyl)phenyl)-N-(1,2,4-thiadiazol-5-yl)naphthalene-2-sulfonamide;
5-morpholino-N-(1,2,4-thiadiazol-5-yl)naphthalene-2-sulfonamide;
5-(2-phenylmorpholino)-N-(1,2,4-thiadiazol-5-yl)naphthalene-2-sulfonamide;
5-(2-methyl-2-phenylmorpholino)-N-(1,2,4-thiadiazol-5-yl)naphthalene-2-sulfonamide;
5-(2-methylmorpholino)-N-(1,2,4-thiadiazol-5-yl)naphthalene-2-sulfonamide;
methyl 4-(6-(N-(1,2,4-thiadiazol-5-yl)sulfamoyl)naphthalen-1-yl)morpholine-2-carboxylate;
5-(2-ethylmorpholino)-N-(1,2,4-thiadiazol-5-yl)naphthalene-2-sulfonamide;
4-(6-(N-(1,2,4-thiadiazol-5-yl)sulfamoyl)naphthalen-1-yl)-n,n-dimethylmorpholine-2-carboxamide;
5-(2-(2-hydroxypropan-2-yl)morpholino)-N-(1,2,4-thiadiazol-5-yl)naphthalene-2-sulfonamide;
5-(2-(1H-pyrazol-4-yl)-4-(trifluoromethyl)phenyl)-N-(1,2,4-thiadiazol-5-yl)naphthalene-2-sulfonamide;
5-(2-cyano-4-(trifluoromethyl)phenyl)-N-(1,2,4-thiadiazol-5-yl)naphthalene-2-sulfonamide;
5-(2-bromo-4-(trifluoromethyl)phenyl)-N-(1,2,4-thiadiazol-5-yl)naphthalene-2-sulfonamide;
5-(4-chloro-2-(difluoromethoxy)phenyl)-N-(1,2,4-thiadiazol-5-yl)naphthalene-2-sulfonamide;
5-(4-chloro-2-(1-methyl-1h-pyrazol-5-yl)phenyl)-N-(1,2,4-thiadiazol-5-yl)naphthalene-2-sulfonamide;
5-(4-chloro-2-(1,2,3,6-tetrahydropyridin-4-yl)phenyl)-N-(1,2,4-thiadiazol-5-yl)naphthalene-2-sulfonamide;
5-(4-chloro-2-(1H-pyrazol-4-yl)phenyl)-N-(1,2,4-thiadiazol-5-yl)naphthalene-2 sulfonamide;
5-(4-chloro-2-(pyridin-4-yl)phenyl)-N-(1,2,4-thiadiazol-5-yl)naphthalene-2-sulfonamide;
5-(2-chloro-4-(trifluoromethyl)phenyl)-N-(1,2,4-thiadiazol-5-yl)naphthalene-2-sulfonamide;
5-(4-chloro-2-methoxyphenyl)-N-(1,2,4-thiadiazol-5-yl)naphthalene-2-sulfonamide;
5-(2-amino-4-chlorophenyl)-N-(1,2,4-thiadiazol-5-yl)naphthalene-2-sulfonamide;
2-(6-(N-(1,2,4-thiadiazol-5-yl)sulfamoyl)naphthalen-1-yl)-5-(trifluoromethyl)benzamide;
5-(4-chloro-2-methylphenyl)-N-(1,2,4-thiadiazol-5-yl)naphthalene-2-sulfonamide;
5-(4-chlorophenyl)-N-(1,2,4-thiadiazol-5-yl)naphthalene-2-sulfonamide;
5-(4-chloro-2-fluorophenyl)-N-(1,2,4-thiadiazol-5-yl)naphthalene-2-sulfonamide;

5-(2-fluoro-4-(trifluoromethyl)phenyl)-N-(1,2,4-thiadiazol-5-yl)naphthalene-2-sulfonamide;
N-(1,2,4-thiadiazol-5-yl)-5-(4-(trifluoromethyl)phenyl)naphthalene-2-sulfonamide;
5-(2-hydroxy-4-(trifluoromethyl)phenyl)-N-(1,2,4-thiadiazol-5-yl)naphthalene-2-sulfonamide;
5-(4-chloro-2-(trifluoromethyl)phenyl)-N-(1,2,4-thiadiazol-5-yl)naphthalene-2-sulfonamide;
5-(2,4-dichlorophenyl)-N-(1,2,4-thiadiazol-5-yl)naphthalene-2-sulfonamide;
5-(2-methoxy-4-(trifluoromethyl)phenyl)-N-(thiazol-2-yl)naphthalene-2-sulfonamide;
5-(2-methoxy-4-(trifluoromethyl)phenyl)-N-(pyrimidin-4-yl)naphthalene-2-sulfonamide;
5-(4-chloro-2-methoxyphenyl)-N-(1-(2-(dimethylamino)ethyl)-1h-pyrazol-3-yl)naphthalene-2-sulfonamide;
5-(4-chloro-2-methoxyphenyl)-N-(5-methylisoxazol-3-yl)naphthalene-2-sulfonamide;
5-(4-chloro-2-methoxyphenyl)-N-(oxazol-2-yl)naphthalene-2-sulfonamide;
5-(4-chloro-2-methoxyphenyl)-N-(thiazol-2-yl)naphthalene-2-sulfonamide;
5-(2-(1-methyl-1H-pyrazol-5-yl)-4-(trifluoromethyl)phenyl)-N-(thiazol-2-yl)naphthalene-2-sulfonamide;
N-(pyrimidin-4-yl)-5-(2-(1,2,3,6-tetrahydropyridin-4-yl)-4-(trifluoromethyl)phenyl)naphthalene-2-sulfonamide;
5-(2-chloro-4-(trifluoromethyl)phenyl)-N-(oxazol-2-yl)naphthalene-2-sulfonamide;
1-(2-bromo-4-(trifluoromethyl)phenyl)-N-(1,2,4-thiadiazol-5-yl)isoquinoline-6-sulfonamide;
1-(2-chloro-4-(trifluoromethyl)phenyl)-N-(thiazol-2-yl)isoquinoline-6-sulfonamide;
1-(2-chloro-4-(trifluoromethyl)phenyl)-N-(3-methoxypyridin-4-yl)isoquinoline-6-sulfonamide;
1-(2-(pyridin-4-yl)-4-(trifluoromethyl)phenyl)-N-(1,2,4-thiadiazol-5-yl)isoquinoline-6-sulfonamide;
1-(2-(1-methyl-1H-pyrazol-5-yl)-4-(trifluoromethyl)phenyl)-N-(1,2,4-thiadiazol-5-yl)isoquinoline-6-sulfonamide;
1-(2-(1H-pyrazol-4-yl)-4-(trifluoromethyl)phenyl)-N-(1,2,4-thiadiazol-5-yl)isoquinoline-6-sulfonamide;
1-(2-chloro-4-(trifluoromethyl)phenyl)-N-(1,2,4-thiadiazol-5-yl)isoquinoline-6-sulfonamide;
1-(3-chloro-4-(trifluoromethyl)phenyl)-N-(1,2,4-thiadiazol-5-yl)isoquinoline-6-sulfonamide;
1-(2-hydroxy-4-(trifluoromethyl)phenyl)-N-(1,2,4-thiadiazol-5-yl)isoquinoline-6-sulfonamide;
1-(2,4-dimethoxyphenyl)-N-(1,2,4-thiadiazol-5-yl)isoquinoline-6-sulfonamide;
N-(1,2,4-thiadiazol-5-yl)-1-(2,4,6-trimethoxyphenyl)isoquinoline-6-sulfonamide;
1-(2,4-dichlorophenyl)-N-(1,2,4-thiadiazol-5-yl)isoquinoline-6-sulfonamide;
1-(4-chloro-2-methylphenyl)-N-(1,2,4-thiadiazol-5-yl)isoquinoline-6-sulfonamide;
1-(4-chloro-2-(trifluoromethyl)phenyl)-N-(1,2,4-thiadiazol-5-yl)isoquinoline-6-sulfonamide;
1-(4-chlorophenyl)-N-(1,2,4-thiadiazol-5-yl)isoquinoline-6-sulfonamide;
1-(2-(pyridin-4-yl)-4-(trifluoromethyl)phenyl)-N-(pyrimidin-4-yl)isoquinoline-6-sulfonamide;
1-(2-bromo-4-(trifluoromethyl)phenyl)-N-(pyrimidin-4-yl)isoquinoline-6-sulfonamide;
1-(2-methoxy-4-(trifluoromethyl)phenyl)-N-(pyrimidin-4-yl)isoquinoline-6-sulfonamide;
1-(2-(1-methyl-1,2,3,6-tetrahydropyridin-4-yl)-4-(trifluoromethyl)phenyl)-N-(pyrimidin-4-yl)isoquinoline-6-sulfonamide;
N-(pyrimidin-4-yl)-1-(2-(1,2,3,6-tetrahydropyridin-4-yl)-4-(trifluoromethyl)phenyl)isoquinoline-6-sulfonamide 2,2,2-trifluoroacetate;
1-(2-(1,2,3,6-tetrahydropyridin-4-yl)-4-(trifluoromethyl)phenyl)-N-(thiazol-2-yl)isoquinoline-6-sulfonamide;
1-(2-(pyridin-4-yl)-4-(trifluoromethyl)phenyl)-N-(thiazol-2-yl)isoquinoline-6-sulfonamide;
1-(2-(1-methyl-1,2,3,6-tetrahydropyridin-4-yl)-4-(trifluoromethyl)phenyl)-N-(thiazol-2-yl)isoquinoline-6-sulfonamide;
1-morpholino-N-(thiazol-2-yl)isoquinoline-6-sulfonamide;
5-(2-(1-methyl-1H-pyrazol-5-yl)-4-(trifluoromethyl)phenyl)-N-(pyrimidin-4-yl)naphthalene-2-sulfonamide;
5-(2-(pyridin-4-yl)-4-(trifluoromethyl)phenyl)-N-(pyrimidin-4-yl)naphthalene-2-sulfonamide;
5-(2-(1-methyl-1,2,3,6-tetrahydropyridin-4-yl)-4-(trifluoromethyl)phenyl)-N-(pyrimidin-4-yl)naphthalene-2-sulfonamide;
5-(2-(1,2,3,6-tetrahydropyridin-4-yl)-4-(trifluoromethyl)phenyl)-N-(thiazol-2-yl)naphthalene-2-sulfonamide;
5-(2-(1-methyl-1,2,3,6-tetrahydropyridin-4-yl)-4-(trifluoromethyl)phenyl)-N-(thiazol-2-yl)naphthalene-2-sulfonamide;
5-(2-chloro-4-(trifluoromethyl)phenyl)-N-(thiazol-2-yl)naphthalene-2-sulfonamide;
5-(2-phenylpyrrolidin-1-yl)-N-(thiazol-2-yl)naphthalene-2-sulfonamide;
5-(2-(1-(azetidin-3-yl)-1H-pyrazol-5-yl)-4-(trifluoromethyl)phenyl)-N-(thiazol-2-yl)naphthalene-2-sulfonamide;
5-(2-(1-(1-methylazetidin-3-yl)-1H-pyrazol-5-yl)-4-(trifluoromethyl)phenyl)-N-(thiazol-2-yl)naphthalene-2-sulfonamide; or
5-(2-phenylpyrrolidin-1-yl)-N-(1,2,4-thiadiazol-5-yl)naphthalene-2-sulfonamide.

In embodiment 39, the present invention provides a compound, or a pharmaceutically acceptable salt thereof, selected from:
5-(2-(4-methylpiperazin-1-yl)-4-(trifluoromethyl)phenyl)-N-(thiazol-2-yl)naphthalene-2-sulfonamide;
5-(2-(pyridin-3-yl)pyrrolidin-1-yl)-N-(1,2,4-thiadiazol-5-yl)naphthalene-2-sulfonamide;
(S)-5-(2-(pyridin-3-yl)pyrrolidin-1-yl)-N-(1,2,4-thiadiazol-5-yl)naphthalene-2-sulfonamide;
(R)-5-(2-(pyridin-3-yl)pyrrolidin-1-yl)-N-(1,2,4-thiadiazol-5-yl)naphthalene-2-sulfonamide;
5-(2-(pyridin-4-yl)pyrrolidin-1-yl)-N-(1,2,4-thiadiazol-5-yl)naphthalene-2-sulfonamide;
((S)-5-(2-(pyridin-4-yl)pyrrolidin-1-yl)-N-(1,2,4-thiadiazol-5-yl)naphthalene-2-sulfonamide;
(R)-5-(2-(pyridin-4-yl)pyrrolidin-1-yl)-N-(1,2,4-thiadiazol-5-yl)naphthalene-2-sulfonamide;
5-(2-methylpyrrolidin-1-yl)-N-(1,2,4-thiadiazol-5-yl)naphthalene-2-sulfonamide;
5-(2-phenylazetidin-1-yl)-N-(1,2,4-thiadiazol-5-yl)naphthalene-2-sulfonamide;
5-(2-oxopyrrolidin-1-yl)-N-(1,2,4-thiadiazol-5-yl)naphthalene-2-sulfonamide;
5-(2-methoxyphenyl)-N-(1,2,4-thiadiazol-5-yl)naphthalene-2-sulfonamide;
5-(pyrrolidin-2-yl)-N-(1,2,4-thiadiazol-5-yl)naphthalene-2-sulfonamide;
5-(1-(pyridin-2-yl)pyrrolidin-2-yl)-N-(1,2,4-thiadiazol-5-yl)naphthalene-2-sulfonamide;

5-(1-benzylpyrrolidin-2-yl)-N-(1,2,4-thiadiazol-5-yl)naphthalene-2-sulfonamide;
5-(1-benzylpyrrolidin-2-yl)-N-(thiazol-2-yl)naphthalene-2-sulfonamide;
5-(benzylamino)-N-(1,2,4-thiadiazol-5-yl)naphthalene-2-sulfonamide;
5-(benzyl(methyl)amino)-N-(1,2,4-thiadiazol-5-yl)naphthalene-2-sulfonamide;
5-(1-benzoylpyrrolidin-2-yl)-N-(thiazol-2-yl)naphthalene-2-sulfonamide;
5-(1-(tetrahydro-2H-pyran-4-yl)pyrrolidin-2-yl)-N-(thiazol-2-yl)naphthalene-2-sulfonamide;
(S)-5-(1-(tetrahydro-2H-pyran-4-yl)pyrrolidin-2-yl)-N-(thiazol-2-yl)naphthalene-2-sulfonamide;
(R)-5-(1-(tetrahydro-2H-pyran-4-yl)pyrrolidin-2-yl)-N-(thiazol-2-yl)naphthalene-2-sulfonamide;
5-(1-(cyanomethyl)-5-fluoro-1H-indol-2-yl)-N-(pyrimidin-4-yl)naphthalene-2-sulfonamide;
5-(5-fluoro-1-methyl-1h-indol-2-yl)-N-(pyrimidin-4-yl)naphthalene-2-sulfonamide;
N-(5-fluorothiazol-2-yl)-5-(2-methoxy-4-(trifluoromethyl)phenyl)naphthalene-2-sulfonamide;
N-(5-fluorothiazol-2-yl)-5-(2-(1,2,3,6-tetrahydropyridin-4-yl)-4-(trifluoromethyl)phenyl)naphthalene-2-sulfonamide;
N-(5-fluorothiazol-2-yl)-5-(2-(1-methylpiperidin-4-yl)-4-(trifluoromethyl)phenyl)naphthalene-2-sulfonamide;
N-(5-fluorothiazol-2-yl)-5-(2-(1-methyl-1h-imidazol-5-yl)-4-(trifluoromethyl)phenyl)naphthalene-2-sulfonamide;
N-(5-fluorothiazol-2-yl)-5-(2-(1-methyl-1h-imidazol-2-yl)-4-(trifluoromethyl)phenyl)naphthalene-2-sulfonamide;
5-(2-(1H-imidazol-1-yl)-4-(trifluoromethyl)phenyl)-N-(5-fluorothiazol-2-yl)naphthalene-2-sulfonamide;
N-(5-fluorothiazol-2-yl)-5-(2-(piperidin-4-yl)-4-(trifluoromethyl)phenyl)naphthalene-2-sulfonamide;
5-(5-fluoro-1H-indol-2-yl)-N-(pyrimidin-4-yl)naphthalene-2-sulfonamide;
5-(3-methoxy-[1,1'-biphenyl]-4-yl)-N-(pyrimidin-4-yl)naphthalene-2-sulfonamide;
5-(2-(1-methylpiperidin-4-yl)-4-(trifluoromethyl)phenyl)-N-(pyrimidin-4-yl)naphthalene-2-sulfonamide;
5-(2-(methylsulfonyl)-4-(trifluoromethyl)phenyl)-N-(pyrimidin-4-yl)naphthalene-2-sulfonamide;
5-(2-(3-fluoroazetidin-3-yl)-4-(trifluoromethyl)phenyl)-N-(pyrimidin-4-yl)naphthalene-2-sulfonamide;
5-(2-(2,5-dihydro-1H-pyrrol-3-yl)-4-(trifluoromethyl)phenyl)-N-(pyrimidin-4-yl)naphthalene-2-sulfonamide;
5-(2-(piperidin-4-yl)-4-(trifluoromethyl)phenyl)-N-(pyrimidin-4-yl)naphthalene-2-sulfonamide;
5-(2-(1H-imidazol-1-yl)-4-(trifluoromethyl)phenyl)-N-(pyrimidin-4-yl)naphthalene-2-sulfonamide;
5-(2-(1-methyl-1,2,5,6-tetrahydropyridin-3-yl)-4-(trifluoromethyl)phenyl)-N-(pyrimidin-4-yl)naphthalene-2-sulfonamide;
5-(2-(1-methyl-1H-imidazol-5-yl)-4-(trifluoromethyl)phenyl)-N-(pyrimidin-4-yl)naphthalene-2-sulfonamide;
5-(2-(1-methyl-1H-imidazol-2-yl)-4-(trifluoromethyl)phenyl)-N-(pyrimidin-4-yl)naphthalene-2-sulfonamide;
5-(4-cyclopropyl-2-methoxyphenyl)-N-(pyrimidin-4-yl)naphthalene-2-sulfonamide;
1-(4-fluoro-2-(pyridin-4-yl)phenyl)-N-(thiazol-2-yl)isoquinoline-6-sulfonamide;
1-(2-(2,5-dihydrofuran-3-yl)-4-fluorophenyl)-N-(thiazol-2-yl)isoquinoline-6-sulfonamide;
1-(pyridin-3-ylmethoxy)-N-(pyrimidin-4-yl)isoquinoline-6-sulfonamide;
1-(4-fluoro-2-(1-methyl-1H-pyrazol-4-yl)phenyl)-N-(thiazol-2-yl)isoquinoline-6-sulfonamide;
1-((5-phenyloxazol-4-yl)methoxy)-N-(pyrimidin-4-yl)isoquinoline-6-sulfonamide;
(S)-1-((1-(4-chlorophenoxy)propan-2-yl)oxy)-N-(pyrimidin-4-yl)isoquinoline-6-sulfonamide;
1-(3-(4-chlorophenyl)propoxy)-N-(pyrimidin-4-yl)isoquinoline-6-sulfonamide;
1-((1-(4-chlorobenzyl)-1H-imidazol-2-yl)methoxy)-N-(pyrimidin-4-yl)isoquinoline-6-sulfonamide;
(R)-1-((4-benzylmorpholin-2-yl)methoxy)-N-(pyrimidin-4-yl)isoquinoline-6-sulfonamide;
1-((1-cyanocyclopropyl)methoxy)-N-(pyrimidin-4-yl)isoquinoline-6-sulfonamide;
1-((1H-indazol-4-yl)methoxy)-N-(pyrimidin-4-yl)isoquinoline-6-sulfonamide;
1-((3-cyanobenzyl)oxy)-N-(pyrimidin-4-yl)isoquinoline-6-sulfonamide;
1-((5-methyl-2-phenyl-2H-1,2,3-triazol-4-yl)methoxy)-N-(pyrimidin-4-yl)isoquinoline-6-sulfonamide;
1-(2-methoxy-5-(trifluoromethyl)phenyl)-N-(pyrimidin-4-yl)isoquinoline-6-sulfonamide;
1-(2-methoxyphenyl)-N-(pyrimidin-4-yl)isoquinoline-6-sulfonamide;
N-(pyrimidin-4-yl)-1-(4-(trifluoromethyl)phenyl) isoquinoline-6-sulfonamide;
1-(4,5-difluoro-2-methoxyphenyl)-N-(pyrimidin-4-yl)isoquinoline-6-sulfonamide;
1-(6-chloro-4-methoxypyridin-3-yl)-N-(pyrimidin-4-yl)isoquinoline-6-sulfonamide;
1-(2-methoxypyridin-3-yl)-N-(pyrimidin-4-yl)isoquinoline-6-sulfonamide;
1-(2,6-dimethoxypyridin-3-yl)-N-(pyrimidin-4-yl)isoquinoline-6-sulfonamide;
1-(5-chloro-2-methoxyphenyl)-N-(pyrimidin-4-yl)isoquinoline-6-sulfonamide;
1-(2,5-dimethoxyphenyl)-N-(pyrimidin-4-yl)isoquinoline-6-sulfonamide;
1-(5-fluoro-2-methoxyphenyl)-N-(pyrimidin-4-yl)isoquinoline-6-sulfonamide;
1-(2-methoxy-5-methylphenyl)-N-(pyrimidin-4-yl)isoquinoline-6-sulfonamide;
1-(5-cyano-2-methoxyphenyl)-N-(pyrimidin-4-yl)isoquinoline-6-sulfonamide;
1-(2-methoxy-5-(trifluoromethoxy)phenyl)-N-(pyrimidin-4-yl)isoquinoline-6-sulfonamide;
1-(2-methoxy-3-(trifluoromethyl)phenyl)-N-(pyrimidin-4-yl)isoquinoline-6-sulfonamide;
1-(2-methoxy-4-(trifluoromethoxy)phenyl)-N-(pyrimidin-4-yl)isoquinoline-6-sulfonamide;
1-(4-fluoro-2-methoxy-5-methylphenyl)-N-(pyrimidin-4-yl)isoquinoline-6-sulfonamide;
1-(3-methoxynaphthalen-2-yl)-N-(pyrimidin-4-yl)isoquinoline-6-sulfonamide;
1-(2-chloro-4-(trifluoromethyl)phenyl)-N-(pyrimidin-4-yl)isoquinoline-6-sulfonamide;
1-(3-fluoro-2-methoxyphenyl)-N-(pyrimidin-4-yl)isoquinoline-6-sulfonamide;
1-(2-fluoro-6-methoxyphenyl)-N-(pyrimidin-4-yl)isoquinoline-6-sulfonamide;
1-(4-cyano-2-methylphenyl)-N-(pyrimidin-4-yl)isoquinoline-6-sulfonamide;
1-(4-chloro-2-methoxyphenyl)-N-(pyrimidin-4-yl)isoquinoline-6-sulfonamide;
1-(4,5-dichloro-2-methoxyphenyl)-N-(pyrimidin-4-yl)isoquinoline-6-sulfonamide;

1-(benzo[b]thiophen-7-yl)-N-(pyrimidin-4-yl)isoquinoline-6-sulfonamide;
1-(2-fluoro-5-(trifluoromethyl)phenyl)-N-(pyrimidin-4-yl)isoquinoline-6-sulfonamide;
1-(1-methyl-1H-indol-7-yl)-N-(pyrimidin-4-yl)isoquinoline-6-sulfonamide;
1-(1,5-dimethyl-1H-indazol-6-yl)-N-(pyrimidin-4-yl)isoquinoline-6-sulfonamide;
1-(5-fluoro-2-methoxypyridin-3-yl)-N-(pyrimidin-4-yl)isoquinoline-6-sulfonamide;
1-(4-fluoro-2-methoxyphenyl)-N-(pyrimidin-4-yl)isoquinoline-6-sulfonamide;
1-(5-chloro-2-methoxypyridin-3-yl)-N-(pyrimidin-4-yl)isoquinoline-6-sulfonamide;
1-(3-methoxypyridin-4-yl)-N-(pyrimidin-4-yl)isoquinoline-6-sulfonamide;
1-(4-methoxypyridin-3-yl)-N-(pyrimidin-4-yl)isoquinoline-6-sulfonamide;
1-(2,6-dimethoxyphenyl)-N-(pyrimidin-4-yl)isoquinoline-6-sulfonamide;
1-(2,4-dimethoxyphenyl)-N-(pyrimidin-4-yl)isoquinoline-6-sulfonamide;
1-(2-ethoxyphenyl)-N-(pyrimidin-4-yl)isoquinoline-6-sulfonamide;
N-(pyrimidin-4-yl)-1-(2-(2,2,2-trifluoroethoxy)phenyl)isoquinoline-6-sulfonamide;
1-(2-methoxy-4-methylphenyl)-N-(thiazol-2-yl)isoquinoline-6-sulfonamide;
1-(5-chloro-2-methoxypyridin-3-yl)-N-(thiazol-2-yl)isoquinoline-6-sulfonamide;
1-(4,5-dichloro-2-methoxyphenyl)-N-(thiazol-2-yl)isoquinoline-6-sulfonamide;
N-(thiazol-2-yl)-1-(o-tolyl)isoquinoline-6-sulfonamide;
1-(2-chlorophenyl)-N-(thiazol-2-yl)isoquinoline-6-sulfonamide;
1-(2-methoxy-5-(trifluoromethyl)phenyl)-N-(thiazol-2-yl)isoquinoline-6-sulfonamide;
1-(2-methoxy-4-(trifluoromethyl)phenyl)-N-(6-methoxypyrimidin-4-yl)isoquinoline-6-sulfonamide;
1-(2-methoxy-4-(trifluoromethyl)phenyl)-N-(2-methylpyrimidin-4-yl)isoquinoline-6-sulfonamide;
N-(5-fluoropyrimidin-4-yl)-1-(2-methoxy-4-(trifluoromethyl)phenyl)isoquinoline-6-sulfonamide;
1-(2-methoxy-4-(trifluoromethyl)phenyl)-N-(1,3,4-thiadiazol-2-yl)isoquinoline-6-sulfonamide;
1-(2-methoxy-4-(trifluoromethyl)phenyl)-N-(pyridazin-3-yl)isoquinoline-6-sulfonamide;
1-(2-methoxy-4-(trifluoromethyl)phenyl)-N-(pyrazin-2-yl)isoquinoline-6-sulfonamide;
1-(2-methoxy-4-(trifluoromethyl)phenyl)-N-(6-methylpyrimidin-4-yl)isoquinoline-6-sulfonamide;
1-(2-methoxy-4-(trifluoromethyl)phenyl)-N-(pyrimidin-2-yl)isoquinoline-6-sulfonamide;
1-(4-fluoro-2-hydroxyphenyl)-N-(thiazol-2-yl)isoquinoline-6-sulfonamide;
1-(4-fluoro-2-(pyridazin-3-yloxy)phenyl)-N-(thiazol-2-yl)isoquinoline-6-sulfonamide;
1-(4-fluoro-2-(pyridin-2-yloxy)phenyl)-N-(thiazol-2-yl)isoquinoline-6-sulfonamide;
1-(2-(cyanomethoxy)-4-fluorophenyl)-N-(thiazol-2-yl)isoquinoline-6-sulfonamide;
1-(3,4-dichlorophenoxy)-N-(pyrimidin-4-yl)isoquinoline-6-sulfonamide;
1-(2-methoxyphenyl)-N-(1,2,4-thiadiazol-5-yl)isoquinoline-6-sulfonamide;
1-(2-methoxy-4-(trifluoromethyl)phenyl)-N-(1,2,4-thiadiazol-5-yl)isoquinoline-6-sulfonamide;
1-(2-methoxy-4-(trifluoromethyl)phenyl)-N-(thiazol-2-yl)isoquinoline-6-sulfonamide;
N-(5-cyanothiazol-2-yl)-1-(2-methoxy-4-(trifluoromethyl)phenyl)isoquinoline-6-sulfonamide;
N-(5-fluorothiazol-2-yl)-1-(2-methoxy-4-(trifluoromethyl)phenyl)isoquinoline-6-sulfonamide;
1-(3'-fluoro-3-methoxy-[1,1'-biphenyl]-4-yl)-N-(pyrimidin-4-yl)isoquinoline-6-sulfonamide;
1-(3'-cyano-3-methoxy-[1,1'-biphenyl]-4-yl)-N-(pyrimidin-4-yl)isoquinoline-6-sulfonamide;
1-(4-chloro-2-methoxyphenyl)-N-(thiazol-2-yl)isoquinoline-6-sulfonamide;
1-(3'-fluoro-3-methoxy-[1,1'-biphenyl]-4-yl)-N-(thiazol-2-yl)isoquinoline-6-sulfonamide;
1-(2-methoxy-4-(1-methyl-1h-pyrazol-4-yl)phenyl)-N-(thiazol-2-yl)isoquinoline-6-sulfonamide;
1-(2-methoxy-4-(pyridin-3-yl)phenyl)-N-(thiazol-2-yl)isoquinoline-6-sulfonamide;
1-(4-cyano-2-methoxyphenyl)-N-(thiazol-2-yl)isoquinoline-6-sulfonamide;
1-(4-cyano-2-methoxyphenyl)-N-(pyrimidin-4-yl)isoquinoline-6-sulfonamide;
1-(1-phenyl-1H-pyrrol-3-yl)-N-(thiazol-2-yl)isoquinoline-6-sulfonamide;
1-(5-methyl-1-phenyl-1H-pyrazol-4-yl)-N-(thiazol-2-yl)isoquinoline-6-sulfonamide;
1-(4-chloro-2-methylphenyl)-N-(thiazol-2-yl)isoquinoline-6-sulfonamide;
1-(4-cyano-2-methylphenyl)-N-(thiazol-2-yl)isoquinoline-6-sulfonamide;
4-fluoro-1-(2-methoxyphenyl)-N-(thiazol-2-yl)isoquinoline-6-sulfonamide;
4-fluoro-1-(2-methoxy-4-(trifluoromethyl)phenyl)-N-(thiazol-2-yl)isoquinoline-6-sulfonamide;
4-fluoro-1-(4-fluoro-2-methoxyphenyl)-N-(thiazol-2-yl)isoquinoline-6-sulfonamide;
1-(4-cyano-2-methoxyphenyl)-4-fluoro-N-(thiazol-2-yl)isoquinoline-6-sulfonamide;
1-(4-chloro-2-methoxyphenyl)-4-fluoro-N-(thiazol-2-yl)isoquinoline-6-sulfonamide;
4-fluoro-1-(2-methoxy-4-(trifluoromethyl)phenyl)-N-(pyrimidin-4-yl)isoquinoline-6-sulfonamide;
1-(4-chloro-2-methoxyphenyl)-4-fluoro-N-(pyrimidin-4-yl)isoquinoline-6-sulfonamide;
1-(4-cyano-2-methoxyphenyl)-4-fluoro-N-(pyrimidin-4-yl)isoquinoline-6-sulfonamide;
3-chloro-1-(2-methoxy-4-(trifluoromethyl)phenyl)-N-(thiazol-2-yl)isoquinoline-6-sulfonamide;
3-cyano-1-(2-methoxy-4-(trifluoromethyl)phenyl)-N-(thiazol-2-yl)isoquinoline-6-sulfonamide;
3-methoxy-1-(2-methoxy-4-(trifluoromethyl)phenyl)-N-(thiazol-2-yl)isoquinoline-6-sulfonamide;
1-(2-methoxy-4-(trifluoromethyl)phenyl)-3-(methylamino)-N-(thiazol-2-yl)isoquinoline-6-sulfonamide;
3-(dimethylamino)-1-(2-methoxy-4-(trifluoromethyl)phenyl)-N-(thiazol-2-yl)isoquinoline-6-sulfonamide;
1-(4-(difluoromethyl)-2-methoxyphenyl)-N-(thiazol-2-yl)isoquinoline-6-sulfonamide;
1-(2-(methoxymethyl)-4-(trifluoromethyl)phenyl)-N-(thiazol-2-yl)isoquinoline-6-sulfonamide;
methyl 2-(6-(N-(thiazol-2-yl)sulfamoyl)isoquinolin-1-yl)-5-(trifluoromethyl)benzimidate;
2-(6-(N-(thiazol-2-yl)sulfamoyl)isoquinolin-1-yl)-5-(trifluoromethyl)benzamide;
1-(2-fluoro-4-(trifluoromethyl)phenyl)-N-(thiazol-2-yl)isoquinoline-6-sulfonamide;

1-(2-(1h-imidazol-1-yl)-4-(trifluoromethyl)phenyl)-N-(thiazol-2-yl)isoquinoline-6-sulfonamide;
1-(2-(2,3-dihydroxypropyl)-4-(trifluoromethyl)phenyl)-N-(thiazol-2-yl)isoquinoline-6-sulfonamide;
4-methoxy-1-(2-methoxy-4-(trifluoromethyl)phenyl)-N-(thiazol-2-yl)isoquinoline-6-sulfonamide;
4-hydroxy-1-(2-methoxy-4-(trifluoromethyl)phenyl)-N-(thiazol-2-yl)isoquinoline-6-sulfonamide;
1-(4-fluoro-2-methoxyphenyl)-4-hydroxy-N-(thiazol-2-yl)isoquinoline-6-sulfonamide;
4-hydroxy-1-(2-methoxyphenyl)-N-(thiazol-2-yl)isoquinoline-6-sulfonamide;
1-(2-bromo-4-(trifluoromethyl)phenyl)-N-(thiazol-2-yl)isoquinoline-6-sulfonamide;
1-(2-phenylpyrrolidin-1-yl)-N-(1,2,4-thiadiazol-5-yl)isoquinoline-6-sulfonamide;
1-(2-phenylpyrrolidin-1-yl)-N-(thiazol-2-yl)isoquinoline-6-sulfonamide;
(R)-1-(2-phenylpyrrolidin-1-yl)-N-(thiazol-2-yl)isoquinoline-6-sulfonamide;
(S)-1-(2-phenylpyrrolidin-1-yl)-N-(thiazol-2-yl)isoquinoline-6-sulfonamide;
4-cyano-1-(2-methoxy-4-(trifluoromethyl)phenyl)-N-(thiazol-2-yl)isoquinoline-6-sulfonamide;
1-(4-chloro-2-methoxyphenyl)-4-cyano-N-(2,4-dimethoxybenzyl)-N-(thiazol-2-yl)isoquinoline-6-sulfonamide;
4-cyano-1-(2-methoxy-4-(trifluoromethyl)phenyl)-N-(pyrimidin-4-yl)isoquinoline-6-sulfonamide;
1-(3-phenylpyrrolidin-1-yl)-N-(thiazol-2-yl)isoquinoline-6-sulfonamide;
1-(1-methyl-1h-pyrrol-2-yl)-N-(thiazol-2-yl)isoquinoline-6-sulfonamide;
1-(1-(tetrahydro-2h-pyran-4-yl)pyrrolidin-2-yl)-N-(thiazol-2-yl)isoquinoline-6-sulfonamide;
1-(1-(2-methoxyethyl)pyrrolidin-2-yl)-N-(thiazol-2-yl)isoquinoline-6-sulfonamide;
1-(4-(3,4-dichlorophenyl)piperazin-1-yl)-N-(thiazol-2-yl)isoquinoline-6-sulfonamide;
1-(2-methoxy-4-(trifluoromethyl)phenyl)-N-(4-oxothiazolidin-2-ylidene)isoquinoline-6-sulfonamide;
1-(4-chloro-2-methoxyphenyl)-N-(thiazol-2-yl)phthalazine-6-sulfonamide;
1-(4-fluoro-2-methoxyphenyl)-N-(thiazol-2-yl)phthalazine-6-sulfonamide;
1-(4-cyano-2-methoxyphenyl)-N-(thiazol-2-yl)phthalazine-6-sulfonamide;
1-(2-methoxyphenyl)-N-(thiazol-2-yl)phthalazine-6-sulfonamide;
1-(2-methoxy-4-(trifluoromethyl)phenyl)-N-(thiazol-2-yl)phthalazine-6-sulfonamide;
1-(2-methoxy-4-(trifluoromethyl)phenyl)-N-(pyrimidin-4-yl)phthalazine-6-sulfonamide;
N-(5-fluorothiazol-2-yl)-1-(2-methoxy-4-(trifluoromethyl)phenyl)phthalazine-6-sulfonamide;
1-(4-fluoro-2-methoxyphenyl)-N-(5-fluorothiazol-2-yl)phthalazine-6-sulfonamide;
1-(4-cyano-2-methoxyphenyl)-N-(thiazol-2-yl)phthalazine-6-sulfonamide;
1-(2-methoxyphenyl)-N-(thiazol-2-yl)phthalazine-6-sulfonamide;
4-(2-methoxy-4-(trifluoromethyl)phenyl)-N-(thiazol-2-yl)cinnoline-7-sulfonamide;
4-(2-methoxy-4-(trifluoromethyl)phenyl)-N-(pyrimidin-4-yl)cinnoline-7-sulfonamide;
4-(2-methoxy-4-(trifluoromethyl)phenyl)-N-(thiazol-2-yl)quinazoline-7-sulfonamide;
4-(2-methoxy-4-(trifluoromethyl)phenyl)-N-(pyrimidin-4-yl)quinazoline-7-sulfonamide;
N-(5-fluorothiazol-2-yl)-4-(2-methoxy-4-(trifluoromethyl)phenyl)quinazoline-7-sulfonamide;
4-(2-methoxy-4-(trifluoromethyl)phenyl)-N-(oxazol-2-yl)quinazoline-7-sulfonamide;
4-(2-methoxy-4-(trifluoromethyl)phenyl)-N-(1,2,4-thiadiazol-5-yl)quinazoline-7-sulfonamide;
4-(4-(difluoromethyl)-2-methoxyphenyl)-N-(thiazol-2-yl)quinazoline-7-sulfonamide;
4-(4-chloro-2-methoxyphenyl)-N-(thiazol-2-yl)quinazoline-7-sulfonamide;
4-(2-methoxy-4-(trifluoromethyl)phenyl)-N-(1,3,4-thiadiazol-2-yl)quinazoline-7-sulfonamide;
4-(4-cyano-2-methoxyphenyl)-N-(thiazol-2-yl)quinazoline-7-sulfonamide;
4-(5-chloro-4-(difluoromethyl)-2-methoxyphenyl)-N-(thiazol-2-yl)quinazoline-7-sulfonamide;
4-(4-fluoro-2-methoxyphenyl)-N-(thiazol-2-yl)quinazoline-7-sulfonamide;
4-(2-methoxyphenyl)-N-(thiazol-2-yl)quinazoline-7-sulfonamide;
4-(4-cyano-2-methoxyphenyl)-N-(thiazol-2-yl)quinoline-7-sulfonamide;
4-(4-fluoro-2-methoxyphenyl)-N-(thiazol-2-yl)quinoline-7-sulfonamide;
4-(4-chloro-2-methoxyphenyl)-N-(thiazol-2-yl)quinoline-7-sulfonamide;
4-(2-methoxy-4-(trifluoromethyl)phenyl)-N-(thiazol-2-yl)quinoline-7-sulfonamide;
4-(2-methoxyphenyl)-N-(thiazol-2-yl)quinoline-7-sulfonamide;
4-(2-chloro-4-(trifluoromethyl)phenyl)-N-(thiazol-2-yl)quinoline-7-sulfonamide;
4-(2-methoxy-4-(trifluoromethyl)phenyl)-N-(pyrimidin-4-yl)quinoline-7-sulfonamide;
4-(4-cyano-2-methoxyphenyl)-N-(pyrimidin-4-yl)quinoline-7-sulfonamide;
4-(2-methoxyphenyl)-N-(pyrimidin-4-yl)quinoline-7-sulfonamide;
4-(2-methoxy-4-(trifluoromethyl)phenyl)-5-methyl-N-(thiazol-2-yl)quinoline-7-sulfonamide;
3-amino-4-(2-methoxy-4-(trifluoromethyl)phenyl)-N-(thiazol-2-yl)quinoline-7-sulfonamide;
3-cyano-4-(2-methoxy-4-(trifluoromethyl)phenyl)-N-(thiazol-2-yl)quinoline-7-sulfonamide;
4-(2-methoxy-4-(trifluoromethyl)phenyl)-N-(pyrimidin-4-yl)isoquinoline-7-sulfonamide;
4-(4-cyano-2-methoxyphenyl)-N-(pyrimidin-4-yl)isoquinoline-7-sulfonamide;
4-(2-methoxyphenyl)-N-(pyrimidin-4-yl)isoquinoline-7-sulfonamide;
4-(2-methoxy-4-(trifluoromethyl)phenyl)-N-(thiazol-2-yl)isoquinoline-7-sulfonamide;
4-(2-methoxyphenyl)-N-(thiazol-2-yl)isoquinoline-7-sulfonamide;
4-(4-fluoro-2-methoxyphenyl)-N-(thiazol-2-yl)isoquinoline-7-sulfonamide;
8-(2-methoxy-4-(trifluoromethyl)phenyl)-N-(thiazol-2-yl)-1,7-naphthyridine-3-sulfonamide;
8-(2-methoxy-4-(trifluoromethyl)phenyl)-N-(pyrimidin-4-yl)-1,7-naphthyridine-3-sulfonamide;
1-(2-methoxy-4-(trifluoromethyl)phenyl)-4-oxo-N-(thiazol-2-yl)-3,4-dihydrophthalazine-6-sulfonamide
4-(2-methoxy-4-(trifluoromethyl)phenyl)-N-(thiazol-2-yl)-1,6-naphthyridine-7-sulfonamide;

1-((1-methyl-1H-1,2,4-triazol-5-yl)methoxy)-N-(pyrimidin-4-yl)isoquinoline-6-sulfonamide;
1-(2-(1H-1,2,3-triazol-1-yl)ethoxy)-N-(pyrimidin-4-yl)isoquinoline-6-sulfonamide;
1-((6,7-dihydro-5H-pyrazolo[5,1-b][1,3]oxazin-2-yl)methoxy)-N-(pyrimidin-4-yl)isoquinoline-6-sulfonamide;
1-((2-morpholinopyridin-3-yl)methoxy)-N-(pyrimidin-4-yl)isoquinoline-6-sulfonamide;
1-(2,2-difluoro-2-(tetrahydro-2H-pyran-4-yl)ethoxy)-N-(pyrimidin-4-yl)isoquinoline-6-sulfonamide;
1-(3-(6-methylpyridin-2-yl)propoxy)-N-(pyrimidin-4-yl)isoquinoline-6-sulfonamide;
1-((4-(1H-imidazol-1-yl)benzyl)oxy)-N-(pyrimidin-4-yl)isoquinoline-6-sulfonamide;
N-(pyrimidin-4-yl)-1-(3-(5-(trifluoromethyl)-1H-pyrazol-4-yl)propoxy)isoquinoline-6-sulfonamide;
1-(2-(1H-pyrrol-1-yl)ethoxy)-N-(pyrimidin-4-yl)isoquinoline-6-sulfonamide;
1-((4-morpholinobenzyl)oxy)-N-(pyrimidin-4-yl)isoquinoline-6-sulfonamide;
1-(2-(1-methyl-1H-pyrazol-4-yl)ethoxy)-N-(pyrimidin-4-yl)isoquinoline-6-sulfonamide;
1-(1-methyl-1H-indazol-7-yl)-N-(pyrimidin-4-yl)isoquinoline-6-sulfonamide;
1-(1,4-dimethyl-1H-indazol-5-yl)-N-(pyrimidin-4-yl)isoquinoline-6-sulfonamide;
1-(1,6-dimethyl-1H-indazol-5-yl)-N-(pyrimidin-4-yl)isoquinoline-6-sulfonamide;
1-(1,5-dimethyl-1H-indazol-4-yl)-N-(pyrimidin-4-yl)isoquinoline-6-sulfonamide;
N-(pyrimidin-4-yl)-1-(quinolin-8-yl)isoquinoline-6-sulfonamide;
1-(3,5-dimethylisoxazol-4-yl)-N-(pyrimidin-4-yl)isoquinoline-6-sulfonamide;
1-(1-methyl-3-(trifluoromethyl)-1H-pyrazol-5-yl)-N-(pyrimidin-4-yl)isoquinoline-6-sulfonamide;
1-(2-methoxy-4-(trifluoromethyl)phenyl)-N-(2-methoxypyrimidin-4-yl)isoquinoline-6-sulfonamide;
N-((1-(2-methoxy-4-(trifluoromethyl)phenyl)isoquinolin-6-yl)sulfonyl)acetamide;
1-(1-methyl-1H-imidazol-2-yl)-N-(thiazol-2-yl)isoquinoline-6-sulfonamide;
N-(pyrimidin-4-yl)-1-(1-(tetrahydro-2H-pyran-4-yl)pyrrolidin-2-yl)isoquinoline-6-sulfonamide;
5-cyano-N-(1,2,4-thiadiazol-5-yl)naphthalene-2-sulfonamide; or
methyl 6-(N-(1,2,4-thiadiazol-5-yl)sulfamoyl)-1-naphthoate.

In embodiment 40, the present invention provides a compound, or a pharmaceutically acceptable salt thereof, selected from each compound exemplified herein, either individually or collectively, in examples 319 through 545.

In embodiment 41, the present invention provides a compound, or a pharmaceutically acceptable salt thereof, individually selected from compound example 319-example 545, disclosed herein.

In various other embodiments, the present invention provides one or more compounds, or pharmaceutically acceptable salts thereof, selected from examples 319-322, 324, 326, 329-351, 355, 358, 361, 364, 365, 366, 368, 369, 370, 371, 373-375, 392-395, 399, 404-406, 409, 411, 413, 419-422, 441-449, 452, 457, 459, 460, 462, 464-472, 481-482, 484-495, 497-498, 501, 505, 507, 509-515, 521-525, 527-532 and 544.

In embodiment 42, the present invention provides multiple compounds, or their pharmaceutically acceptable salts thereof, selected from examples 319-322, 324, 326, 329-351, 355, 358, 361, 364, 365, 366, 368, 369, 370, 371, 373-375, 392-395, 399, 404-406, 409, 411, 413, 419-422, 441-449, 452, 457, 459, 460, 462, 464-472, 481-482, 484-495, 497-498, 501, 505, 507, 509-515, 521-525, 527-532 and 544.

In embodiment 43, the present invention provides a compound, or a pharmaceutically acceptable salt thereof, individually selected from examples 319-322, 324, 326, 329-351, 355, 358, 361, 364, 365, 366, 368, 369, 370, 371, 373-375, 392-395, 399, 404-406, 409, 411, 413, 419-422, 441-449, 452, 457, 459, 460, 462, 464-472, 481-482, 484-495, 497-498, 501, 505, 507, 509-515, 521-525, 527-532 and 544.

In various other embodiments, the present invention provides one or more compounds, or pharmaceutically acceptable salts thereof, selected from examples 320-322, 330-336, 338-351, 355, 364, 365, 366, 368, 369, 373, 392, 441-442, 444-449, 460, 462, 466-467, 469-472, 484-485, 488, 490-495, 505, 507, 509, 511-512, 521-525 and 527-531.

In embodiment 44, the present invention provides methods of treating pain, the methods comprising administering to a patient in need thereof a therapeutically effective amount of a compound in accordance with any one of embodiments 1 or 1a to 43, or a pharmaceutically acceptable salt thereof.

In embodiment 45, the present invention provides methods of embodiment 44 wherein the treatment is for chronic pain, acute pain, neuropathic pain, pain associated with rheumatoid arthritis, pain associated with osteoarthritis or pain associated with cancer.

In embodiment 46, the present invention provides pharmaceutical compositions comprising a compound in accordance with any one of embodiments 1 or 1a to 43, or a pharmaceutically acceptable salt thereof, and a pharmaceutically acceptable excipient.

DETAILED DESCRIPTION OF THE INVENTION

The present invention provides compounds of Formula I, as defined above, or pharmaceutically acceptable salts thereof. The present invention also provides pharmaceutical compositions comprising a compound of Formula I, or pharmaceutically acceptable salts thereof, and methods of treating diseases and/or conditions, such as pain, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "hydroxy$C_{1-6}$alkyl" means a straight or branched alkyl chain having one to six carbons and substituted with one or more hydroxyl groups. Representative examples of hydroxy$C_{1-6}$alkyl groups include hydroxymethyl (—$CH_2OH$), 2-hydroxyethyl, 3-hydroxypropyl, 2,3-dihydroxypropyl (—$CH_2CH(OH)CH_2OH$), 3-hydroxyisopropyl, 4-hydroxybutyl and the like. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$ perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heteroatoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo[b]thienyl, benzo[c]thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent. Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptoms of a particular disease or condition, or prevents or delays the onset of one of more symptoms of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformLy over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics,* 4:75-83 (2007)), epilepsy: ibid., and Gonzalez, Termin, Wilson, *Methods and Principles in Medicinal Chemistry,* 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J. Mol. Cell Cardiol.* 42(3): 469-477, 2007), schizophrenia, neuroprotection after stroke, drug and alcohol abuse (Johannessen L. C., *CNS Drugs* 22(1) 27-47, 2008), Alzheimer's (Kim D. Y., et. al., *Nat. Cell. Biol.* 9(7):755-764, 2007), and cancer (Gillet L., et. al., *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may also be used to treat obesity and facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component. Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$)alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Another example of tautomerism is as follows:

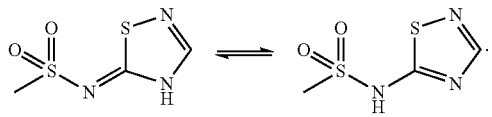

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{31}$P, $^{32}$P, $^{35}$S, $^{18}$F, and $^{36}$Cl. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 μm, 5 to 100% CH$_3$CN in H$_2$O with 0.1% TFA for 15 min at 1.5 mL/min; System B: Zorbax SB-C8, 4.6×75 mm, 10 to 90% CH$_3$CN in H$_2$O with 0.1% formic acid for 12 min at 1.0 mL/min) (Agilent Technologies, Santa Clara, Calif.). Silica gel chromatography was generally performed with prepacked silica gel cartidges (Biotage, Uppsala, Sweden or Teledyne-Isco, Lincoln, Nebr.). $^1$H NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

The following abbreviations may be used herein:
AmPhos 4-(di-tert-butylphosphino)-N,N-dimethylaniline
AcCl acetyl chloride
ACN acetonitrile
AcOH acetic acid
aq or aq. aqueous
BOC or Boc tert-butyloxycarbonyl
DAST diethylaminosulfur trifluoride
DCM dichloromethane
DMAP 4-dimethylaminopyridine
DMB dimethoxybenzyl
DME dimethoxyethane
DMF N,N-dimethylformamide
DMSO dimethyl sulfoxide
Dppf, DPPF or dppf 1,1'-bis(diphenylphosphino)ferrocene
ESI or ES electrospray ionization
Et ethyl
Et$_2$O diethyl ether
Et$_3$N triethylamine
EtOAc ethyl acetate
eq or eq. equivalent
g grams
h hour
HPLC high pressure liquid chromatography
iPr isopropyl
iPr$_2$NEt N-ethyl diisopropylamine (Hunig's base)
KOAc potassium acetate
KHMDS potassium hexamethyldisilazide
LC MS, LCMS, LC-MS or LC/MS liquid chromatography mass spectroscopy
LHMDS or LiHMDS lithium hexamethyldisilazide
m/z mass divided by charge
Me methyl
MeOH methanol
MeCN or ACN acetonitrile
mg milligrams
min minutes
mL milliliters
MPLC medium pressure liquid chromatography
MS mass spectra
NaHMDS sodium hexamethyldisilazide
NBS N-bromosuccinimide
NCS N-chlorosuccinimide
n-BuLi n-butyllithium
NMR nuclear magnetic resonance
Pd$_2$(dba)$_3$ tris(dibenzylideneacetone)dipalladium(0)
Ph phenyl
PMB p-methoxybenzyl
Pr or PR or PG protecting group
RT or rt room temperature
SCX strong cation exchange
SEM 2-(trimethylsilyl)ethoxymethyl
SFC supercritical fluid chromatography
TBAF tetra-n-butylammonium fluoride
t-BuOH tert-butanol
TIPS-Cl triisopropylsilyl chloride
TFA trifluoroacetic acid
THF tetrahydrofuran
UV ultraviolet
xantphos 4,5-bis(diphenylphosphino)-9,9-dimethylxanthene
X-Phos 2-dicyclohexylphosphino-2',4',6'-triisopropyl-1,1'-biphenyl

EXAMPLES

General Synthetic Schemes

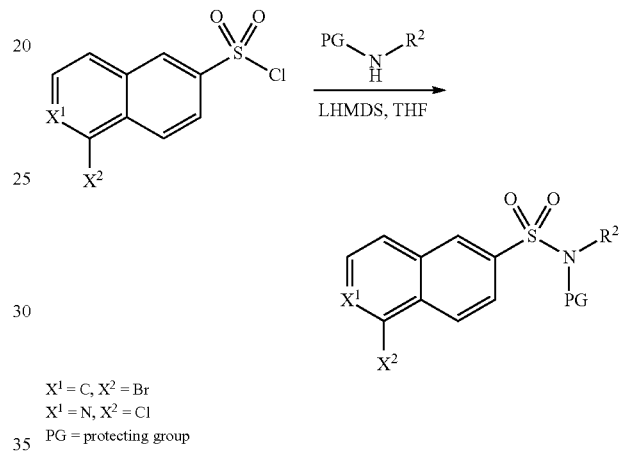

$X^1 = C, X^2 = Br$
$X^1 = N, X^2 = Cl$
PG = protecting group

Amine coupling with a sulfonyl chloride can be performed with a base (such as LHMDS, NaHMDS, KHMDS, Cs$_2$CO$_3$, K$_2$CO$_3$, K$_3$PO$_4$ or Na$_2$CO$_3$) and an amine which may be protected with a benzyl, DMB, PMB, SEM or allyl group (PG is a protecting group). This reaction can be performed in various solvents such as THF, diethyl ether, DME or dioxane. It is also possible to perform this chemistry without protecting groups in appropriate cases.

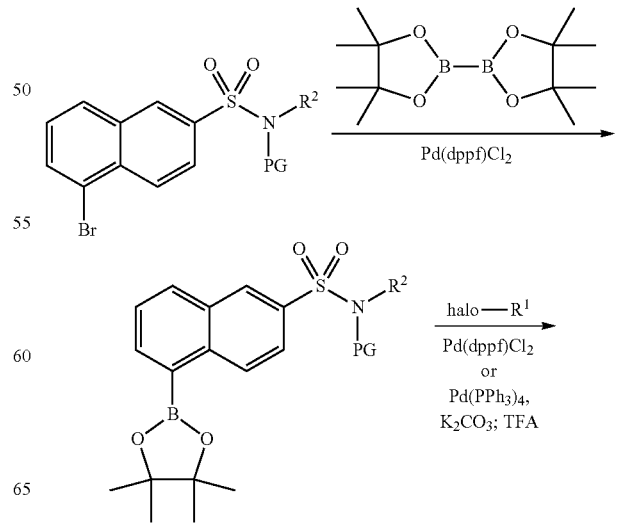

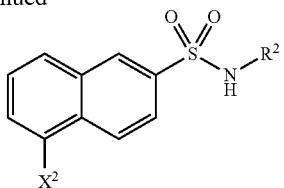

Boronic ester intermediates can be constructed through a Pd-catalyzed coupling with a boron source such as bis(pinacolato)diboron, a catalyst (such as Pd (AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). The resulting boronic ester or acid can subsequently be coupled employing a catalyst (such as Pd (AmPhos)$_2$Cl$_2$, Pd(dppf)Cl$_2$ or Pd(PPh$_3$)$_4$) in the presence of a base (such as Cs$_2$CO$_3$, K$_2$CO$_3$, K$_3$PO$_4$ or Na$_2$CO$_3$), and solvents (such as aqueous 1,4-dioxane, DME, EtOH, DMF or t-BuOH). The removal of the protecting group can be done thermally during the coupling reaction or by using acid or reductive conditions (such as TFA, HCl, Pd/C in hydrogen atmosphere, etc.).

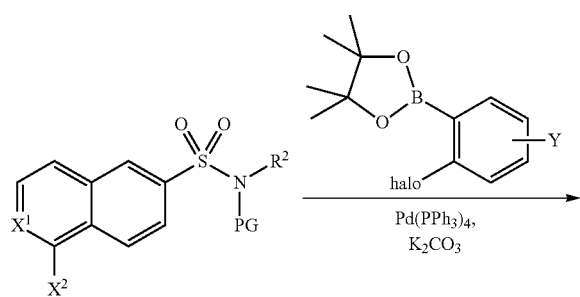

$X^1 = C, X^2 = Br$
$X^1 = N, X^2 = Cl$

The Suzuki reaction can be achieved using a variety of bases (such as Cs$_2$CO$_3$, K$_2$CO$_3$, K$_3$PO$_4$ or Na$_2$CO$_3$), catalysts (such as Pd (AmPhos)$_2$Cl$_2$, Pd(dppf)Cl$_2$ or Pd(PPh$_3$)$_4$), and solvents (such as aqueous 1,4-dioxane, DME, EtOH, DMF or t-BuOH). The subsequent coupling can be performed with various reaction partners (M) to install a R$^e$ group (such as boronic acids, stannanes, Grignard or zinc reagents) and catalysts (such as Pd (AmPhos)$_2$Cl$_2$, Pd(dppf)Cl$_2$ or Pd(PPh$_3$)$_4$).

The removal of the protecting group can be done thermally during the coupling reaction or by using acid or reductive conditions (such as TFA, HCl, Pd/C in hydrogen atmosphere, etc.).

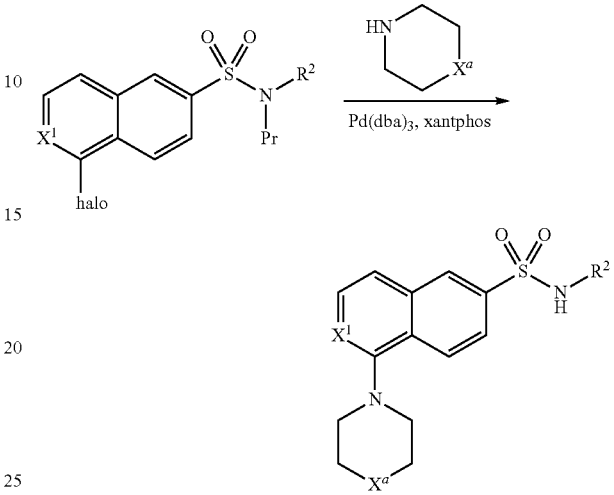

Naphthalenes ($X^1$=CH) or isoquinolines ($X^1$=N) can be substituted through coupling with cyclic amines employing catalysts (such as Pd$_2$(dba)$_3$/xantphos, Pd (AmPhos)$_2$Cl$_2$, Pd(dppf)Cl$_2$ or Pd(PPh$_3$)$_4$) in solvents (such as 1,4-dioxane, DME, DMF or toluene). $X^a$ can be O or NR.

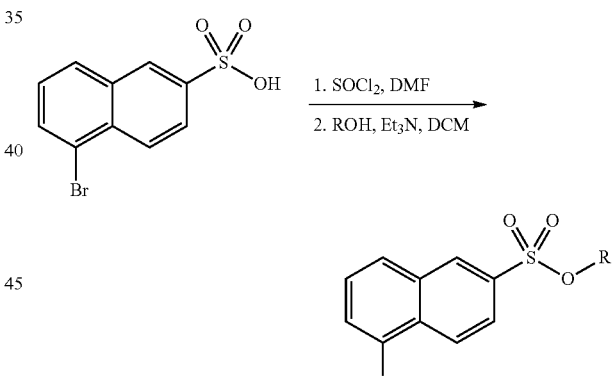

Naphthalene sulfonic acid can be converted to sulfonyl chloride employing a chlorinating agent (such as SO$_2$Cl$_2$, ClSO$_3$H, POCl$_3$, PCl$_5$ or cyanuric trichloride) in various solvents (such as DCM, DCE or DMF). The resulting sulfonyl chloride can be converted into a sulfonic ester with an alcohol (ROH) (such as pentafluorophenol or trifluoroethanol).

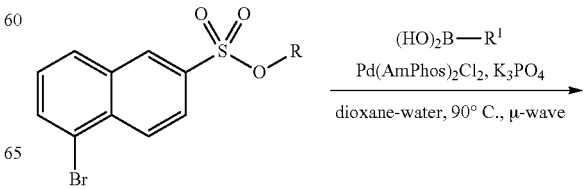

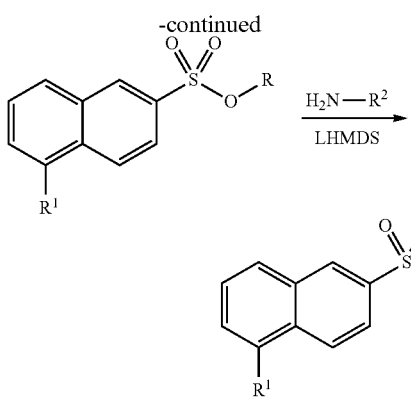

The Suzuki reaction can be achieved using a variety of bases (such as $Cs_2CO_3$, $K_2CO_3$, $K_3PO_4$ or $Na_2CO_3$), catalysts (such as Pd $(AmPhos)_2Cl_2$, $Pd(dppf)Cl_2$ or $Pd(PPh_3)_4$), and solvents (such as aqueous 1,4-dioxane, DME, EtOH, DMF or t-BuOH). Amine coupling with a sulfonic ester can be performed with a base (such as LHMDS, NaHMDS, KHMDS, $Cs_2CO_3$, $K_2CO_3$, $K_3PO_4$ or $Na_2CO_3$). Alternatively, the sulfonic ester can be hydrolized with a base (such as LiOH, KOH or NaOH) which can be converted to the sulfonyl chloride as stated above. Amine coupling with the resulting sulfonyl chloride can be performed with a base (such as LHMDS, NaHMDS, KHMDS, $Cs_2CO_3$, $K_2CO_3$, $K_3PO_4$ or $Na_2CO_3$).

INTERMEDIATE A

INTERMEDIATE A: N-(2,4-DIMETHOXYBENZYL)-1,2,4-THIADIAZOL-5-AMINE

To a solution of 1,2,4-thiadiazol-5-amine (150 g, 1.48 mol, 1.1 eq.) and 2,4-dimethoxybenzaldehyde (224.1 g, 1.35 mol, 1 eq.) in anhydrous DCM (6 L) was added chlorotitanium triisopropoxide (771.3 g, 2.96 mol, 2.2 eq.) slowly over 15 minutes. The resulting yellow solution was stirred for 30 min and then treated with sodium triacetoxyborohydride (715.3 g, 3.38 mol, 2.5 eq.) portionwise (Note: the reaction temperature increased from RT to 34° C.). After 2 hours, LC/MS analysis showed that Intermediate A was formed as the major product. The reaction mixture was cooled using an ice and water bath and neutralized with saturated aqueous $NaHCO_3$ to a pH of about 7. The resulting thick slurry was passed through diatomaceous Earth® (diatomaceous earth) and washed with DCM. The white solid left on the diatomaceous Earth® (diatomaceous earth) was collected, put into a flask, charged with DCM and water and then stirred well. The resulting slurry was again passed through diatomaceous Earth® (diatomaceous earth) and washed with DCM. All the filtrates were combined. The organic layer was separated, dried, filtered and concentrated. The oily residue was purified by column chromatography using silica gel (40 to 63 μm, 23-400 mesh) eluting with 5-10% EtOAc in Hexanes-DCM (1:1), to afford Intermediate A (160 g) as a white solid. MS (ESI, positive ion) m/z: 252.3. $^1$H NMR (400 MHz, DMSO-$d_6$): δ ppm 8.68 (s, 1H), 7.89 (s, 1H), 7.17 (d, J=8.2 Hz, 1H), 6.57 (s, 1H), 6.49 (d, J=8.3 Hz, 1H), 4.37 (d, J=5.2 Hz, 2H), 3.80 (s, 3H), 3.75 (s, 3H).

INTERMEDIATES B, C, D AND E

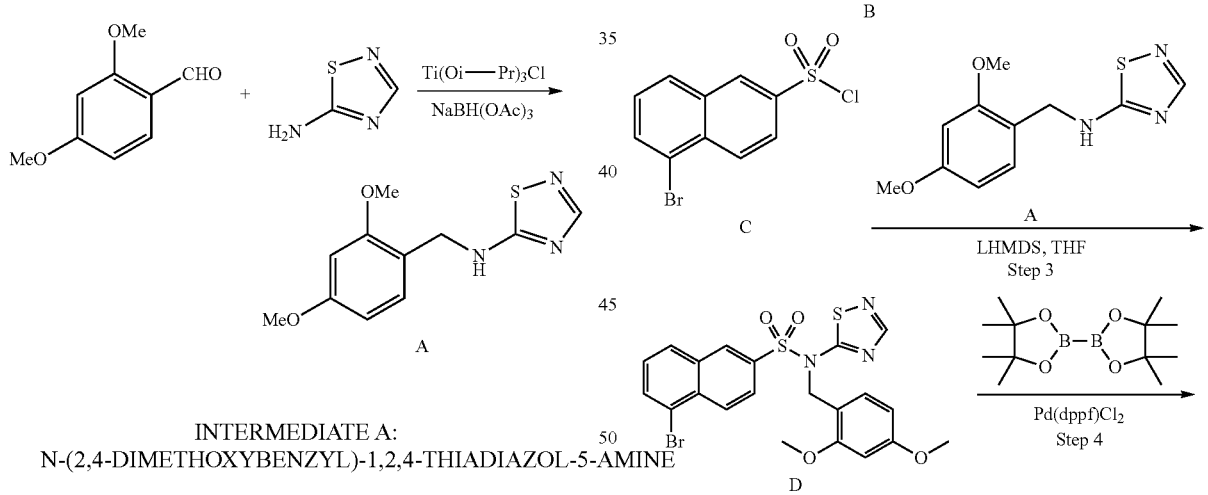

INTERMEDIATE B: 5-BROMONAPHTHALENE-2-SULFONIC ACID

Step 1: To a cold solution of 5-aminonaphthalene-2-sulfonic acid (380 g, 1.70 mol, 1 eq.; Alfa Aesar, Ward Hill, Mass.) in aqueous NaOH (0.85 M, 2.4 L, 2.04 mol, 1.2 eq.) was added aqueous HBr (48%, 519 mL, 4.59 mol, 2.7 eq.) slowly. The resulting suspension was cooled to −5° C. and a solution of NaNO$_2$ (129 g, 1.87 mol, 1.1 eq) in water (280 mL) was added dropwise with stirring, keeping the internal temperature below 0° C. The reaction mixture was stirred at −5 to 0° C. for 30 min (Note: The formation of the diazonium salt could be detected by LC/MS) and urea (12.3 g, 0.20 mol, 0.12 eq.) was added to decompose excess nitrite. The diazonium salt was added dropwise (1 h) with stirring to a heated (70° C.) solution of CuBr (243.9 g, 1.70 mol, 1 eq.) in aqueous HBr (48%, 1038.5 mL, 9.18 mol, 5.4 eq.). The mixture was then stirred at 80° C. for 30 min LC/MS analysis showed that Intermediate B was formed as the major product. The mixture was cooled to room temperature and stirred overnight. The precipitate was filtered, washed with water, and dried under a vacuum, affording Intermediate B (370 g) as a grey solid. MS (ESI): 286.9 [M]$^+$; $^1$H NMR (300 MHz, DMSO-d$_6$) δ ppm 8.23 (brs, 1H), 8.09 (t, J=9.0 Hz, 2H), 7.90 (d, J=9.0 Hz, 2H), 7.47 (t, J=9.0 Hz, 2H).

INTERMEDIATE C: 5-BROMONAPHTHALENE-2-SULFONYL CHLORIDE

Step 2: To a suspension of Intermediate B (287.1 g, 1.0 mol, 1 eq) in anhydrous DMF (1 L) was added SOCl$_2$ (145.9 mL, 2 mol, 2 eq) dropwise keeping the temperature below 30° C. The resulting yellow solution was stirred at RT for 1.5 h (LC/MS analysis showed that Intermediate B was consumed), diluted with DCM (4 L), treated with ice water (4 Kg), and then stirred well. The DCM layer was separated, washed with water (2 L×3), dried, filtered and concentrated to give Intermediate C (220 g) as a yellow solid.

INTERMEDIATE D: 5-BROMO-N-(2,4-DIMETHOXYBENZYL)-N-(1,2,4-THIADIAZOL-5-YL)NAPHTHALENE-2-SULFONAMIDE

Step 3: A solution of Intermediate C (160 g, 0.64 mol, 1.0 eq) in anhydrous THF (3 L) was cooled to −40° C. and charged with LHMDS (1M in THF, 0.96 L, 0.96 mol, 1.5 eq.) dropwise, keeping the temperature below 0° C. The resulting mixture was stirred at 0° C. for 10 min and then cooled to −40° C. To it was added a solution of Intermediate A (214 g, 0.70 mol, 1.1 eq) in anhydrous THF (300 mL) dropwise, keeping the temperature below 0° C. The mixture was allowed to warm to RT gradually. LC/MS analysis showed that Intermediate D was formed as the major product. The reaction mixture was quenched with 1 N HCl to pH 5. Phases were separated. The aqueous layer was extracted with EtOAc (500 mL×2). The organic layers were combined, washed with 1 M NaOH (500 mL×2) and brine to remove sulfonic acid Intermediate B generated from excess Intermediate C, dried, and concentrated. The residue was crystallized from hot acetone affording Intermediate D (182 g) as an off-white solid. MS (ESI): 542.0 [M+Na]$^+$; $^1$H NMR (300 MHz, DMSO-d$_6$) δ ppm 8.65 (d, J=1.8 Hz, 1H), 8.41 (s, 1H), 8.28 (d, J=8.7 Hz, 1H), 8.25 (d, J=8.7 Hz, 1H), 8.13 (d, J=7.5 Hz, 1H), 7.96 (dd, J=9.0, 1.8 Hz, 1H), 7.63 (t, J=8.8 Hz, 1H), 7.00 (d, J=8.4 Hz, 1H), 6.35 (d, J=8.4 Hz, 1H), 6.33 (s, 1H), 5.21 (s, 2H), 3.66 (s, 3H), 3.63 (s, 3H).

INTERMEDIATE E: N-(2,4-DIMETHOXYBENZYL)-5-(4,4,5,5-TETRAMETHYL-1,3,2-DIOXABOROLAN-2-YL)-N-(1,2,4-THIADIAZOL-5-YL)NAPHTHALENE-2-SULFONAMIDE

Step 4: A mixture of Intermediate D (100 g, 0.19 mol, 1 eq.), bis(pinacolato)diboron (73.2 g, 0.29 mol, 1.5 eq.), KOAc (55.9 g, 0.57 mol, 3 eq.) and Pd(dppf)Cl$_2$ DCM (7.76 g, 0.0095 mol, 0.05 eq) in anhydrous 1,4-dioxane (500 mL) was degassed with N$_2$ for 10 min and then heated at 80° C. for 5 hours. LC/MS analysis showed that Intermediate D was consumed. The reaction mixture was cooled to RT, quenched with brine (400 mL), and stirred well. Phases were separated. The aqueous layer was extracted with DCM (500 mL×2). The organic layers were combined, washed with brine, dried and concentrated. The residue was passed through a short silica gel pad to remove Pd and other polar impurities by washing with DCM. The DCM solution was concentrated and the residue was triturated with MeOH, affording Intermediate E (102 g) as a white solid. MS (ESI): 568.2 [M+H]$^+$; $^1$H NMR (300 MHz, DMSO-d$_6$) δ ppm 8.80 (d, J=8.7 Hz, 1H), 8.63 (d, J=1.8 Hz, 1H), 8.38 (s, 1H), 8.34 (d, J=8.1 Hz, 1H), 8.19 (dd, J=6.9, 1.2 Hz, 1H), 7.91 (dd, J=8.7, 1.8 Hz, 1H), 7.43 (dt, J=8.1, 1.8 Hz, 1H), 7.02 (d, J=8.7 Hz, 1H), 6.40 (s, 1H), 6.39 (d, J=8.1 Hz, 1H), 5.18 (s, 2H), 3.70 (s, 3H), 3.66 (s, 3H), 1.38 (s, 12H).

INTERMEDIATES F AND G

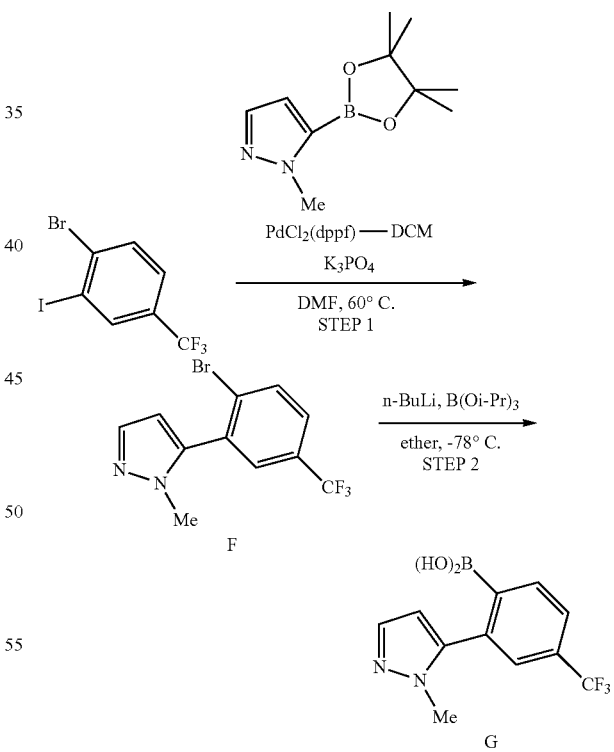

INTERMEDIATE F: 5-(2-BROMO-5-(TRIFLUOROMETHYL)PHENYL)-1-METHYL-1H-PYRAZOLE

Step 1: A round-bottom flask was charged with 1-bromo-2-iodo-4-(trifluoromethyl)benzene (5.00 g, 14.25 mmol;

Combi-blocks, San Diego, Calif.), 1-methyl-1H-pyrazole-5-boronic acid pinacol ester (3.41 g, 16.39 mmol), potassium phosphate (6.05 g, 28.5 mmol) and Pd(dppf)Cl$_2$CH$_2$Cl$_2$ (1.164 g, 1.425 mmol). The flask was flushed with Ar, and DMF (47.5 mL) was then added. The flask was sealed, heated to 60° C. for 12 h, and then stirred at room temperature for 48 h. The mixture was diluted with water and extracted with EtOAc (three times). The combined organics were washed with brine, dried and concentrated under a vacuum. The product was purified by chromatography using silica gel (0 to 100% EtOAc/Heptane) to yield 5-(2-bromo-5-(trifluoromethyl)phenyl)-1-methyl-1H-pyrazole (2.956 g, 9.69 mmol) as a brown solid. $^1$H NMR (400 MHz, DMSO-d$_6$) δ ppm=8.06 (td, J=0.7, 8.1 Hz, 1H), 7.86-7.73 (m, 2H), 7.53 (d, J=2.0 Hz, 1H), 6.41 (d, J=2.0 Hz, 1H), 3.64 (s, 3H); m/z (ESI) 305.0 (M+H)$^+$.

INTERMEDIATE G: (2-(1-METHYL-1H-PYRAZOL-5-YL)-4-(TRIFLUOROMETHYL)PHENYL) BORONIC ACID

Step 2: An 250 mL round-bottom flask was charged with 5-(2-bromo-5-(trifluoromethyl)phenyl)-1-methyl-1H-pyrazole (Intermediate F) (2.956 g, 9.69 mmol), diethyl ether (74.5 mL), and triisopropyl borate (2.70 mL, 11.63 mmol). The flask was cooled to −78° C. for 10 min, after which butyllithium (2.5M in hexanes) (4.65 mL, 11.63 mmol) was added dropwise. The mixture was stirred for 30 min, and then warmed to room temperature. A 2N aq. NaOH solution (100 mL) was added, and the resulting biphasic mixture was stirred vigorously for 1 h. The mixture was diluted with water, and the layers separated. The ethereal layer was extracted with water (twice) and the water layers were combined and washed with diethyl ether. The ether layers were back-extracted once more, and all aqueous layers combined and acidified to a pH of about 2 with 6N aq. HCl to give a clear solution. The aqueous layer was extracted with ethyl acetate (twice), and the combined organics were dried over sodium sulfate, filtered and concentrated. The residue was concentrated from DCM to give (2-(1-methyl-1H-pyrazol-5-yl)-4-(trifluoromethyl)phenyl)boronic acid (2.36 g, 8.74 mmol) as a yellow solid. m/z (ESI) 271.2 (M+H)$^+$.

INTERMEDIATE AA: (2-(PYRIDIN-4-YL)-4-(TRIFLUOROMETHYL)PHENYL)BORONIC ACID

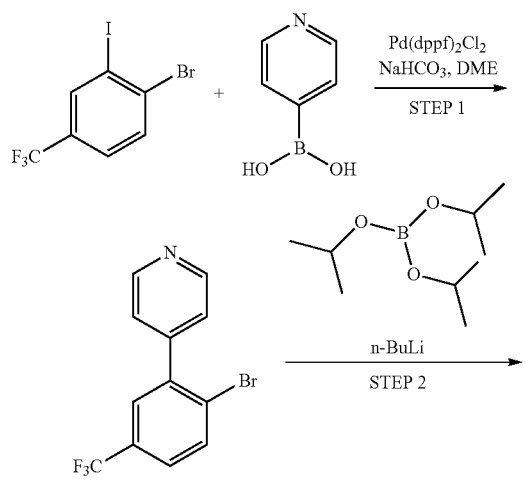

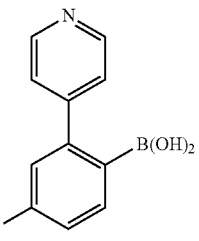

STEP 1:
4-(2-BROMO-5-(TRIFLUOROMETHYL)PHENYL)PYRIDINE

To a solution of compound 1-bromo-2-iodo-4-(trifluoromethyl)benzene (10 g, 28.4 mmol) and pyridin-4-ylboronic acid (7 g, 34.1 mmol) in dimethoxyethane (150 mL) and water (50 mL), sodium bicarbonate (9.54 g, 113.6 mmol) was added. The reaction mixture was purged with nitrogen for 15 minutes and Pd(dppf)$_2$Cl$_2$ (2.3 g, 2.84 mmol) was added. The reaction was stirred at 90° C. for 5 h. Then the reaction mixture was diluted with water (500 mL) extracted with ethyl acetate (2×200 mL). Organic layer was combined, dried over sodium sulfate, filtered and concentrated under a vacuum to give the compound which was further purified by column chromatography using silica gel (100 to 200 mesh) and 0% to 30% ethyl acetate/hexane as eluent to obtain 4-(2-bromo-5-(trifluoromethyl)phenyl)pyridine (6.7 g, 77.6%) as an off white solid. MS (ESI, positive ion) [M+1]$^+$: 301.98; $^1$H NMR (400 MHz, DMSO) δ 8.71 (d, J=5.9 Hz, 2H), 8.05 (d, J=8.2 Hz, 1H), 7.84-7.75 (d, J=11.3 Hz, 2H), 7.50 (d, J=5.9 Hz, 2H).

STEP 2: (2-(PYRIDIN-4-YL)-4-(TRIFLUOROMETHYL)PHENYL)BORONIC ACID

A round bottom flask was charged with 4-(2-bromo-5-(trifluoromethyl)phenyl)pyridine (2.0 g, 6.62 mmol), diethyl ether (50.9 ml), and triisopropyl borate (1.845 ml, 7.94 mmol). The flask was cooled to −78° C. for 10 minutes after which butyllithium (1.7 M in hexanes) (4.67 ml, 7.94 mmol) was added dropwise. The reaction was stirred for 30 minutes. The dry-ice bath was removed and 2N aqueous NaOH solution (50 mL) was added. The resulting biphasic mixture was stirred vigorously for one hour. The mixture was diluted with water, and the layers were separated. The diethyl ether was then extracted with water (×2) and the water layers were combined and washed twice with diethyl ether. The aqueous layer was neutralized to about pH 7 with 1N aqueous HCl solution and extracted with ethyl acetate (three times). The combined organic layers were dried over sodium sulfate, filtered and concentrated to afford (2-(pyridin-4-yl)-4-(trifluoromethyl)phenyl)boronic acid as an off-white solid. m/z (ESI) 268.1 (M+H)+.

EXAMPLE 1

5-(2-(1-METHYL-1H-PYRAZOL-5-YL)-4-(TRIFLUOROMETHYL)PHENYL)-N-(1,2,4-THIADIAZOL-5-YL)NAPHTHALENE-2-SULFONAMIDE

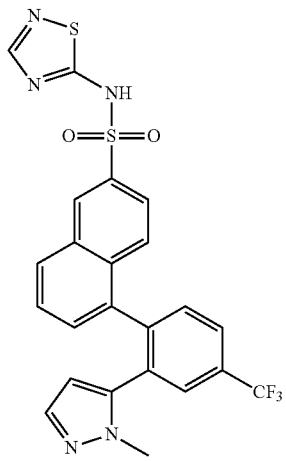 [SMILES: Cn1nccc1-c1cc(C(F)(F)F)ccc1-c1cccc2cc(S(=O)(=O)Nc3ncns3)ccc12]

A microwave vial was charged with Intermediate D (0.100 g, 0.192 mmol), potassium carbonate (0.133 g, 0.961 mmol), (2-(1-methyl-1H-pyrazol-5-yl)-4-(trifluoromethyl)phenyl)boronic acid, Intermediate G (0.078 g, 0.288 mmol) and tetrakis(triphenylphosphine)palladium(0) (0.022 g, 0.019 mmol). The solids were diluted with dioxane (1.281 mL) and water (0.641 mL), and the reaction was heated under microwave irradiation at 100° C. for 30 min. The reaction mixture was diluted with water and washed with DCM. The organic layer was discarded and the water layer was then acidified with 1N HCl, and washed three times with DCM. The combined organics were dried using a phase separator (Radleys Discovery Technologies, Essex, UK), and then concentrated under a vacuum to yield material, which was purified by MPLC (PuriFlash HP column, 15μ, 25 g, Interchim, San Pedro, Calif.), eluting with 0 to 10% methanol in DCM to yield 5-(2-(1-methyl-1H-pyrazol-5-yl)-4-(trifluoromethyl)phenyl)-N-(1,2,4-thiadiazol-5-yl)naphthalene-2-sulfonamide (0.0179 g, 0.035 mmol) as a light yellow solid. $^1$H NMR (400 MHz, DMSO-d$_6$) δ ppm 3.49 (s, 3H) 5.82 (d, J=1.86 Hz, 1H) 7.08 (d, J=1.96 Hz, 1H) 7.49 (dd, J=7.09, 1.12 Hz, 1H) 7.57-7.63 (m, 2H) 7.70-7.75 (m, 2H) 7.95 (s, 1H) 7.98 (m, J=8.50 Hz, 1H) 8.15 (d, J=8.31 Hz, 1H) 8.37 (s, 1H) 8.46 (d, J=1.86 Hz, 1H); m/z (ESI) 516.0 (M+H)+.

EXAMPLE 2

5-(2-(PYRIDIN-4-YL)-4-(TRIFLUOROMETHYL)PHENYL)-N-(1,2,4-THIADIAZOL-5-YL)NAPHTHALENE-2-SULFONAMIDE

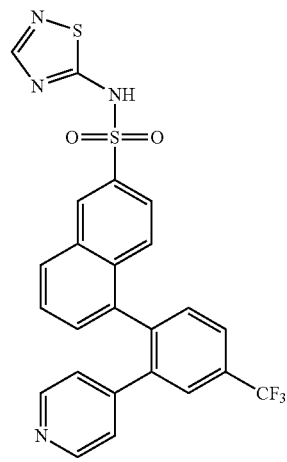 [SMILES: O=S(=O)(Nc1ncns1)c1ccc2c(-c3ccc(C(F)(F)F)cc3-c3ccncc3)cccc2c1]

The title compound was prepared in an analogous manner to that of EXAMPLE 1, except that (2-(pyridin-4-yl)-4-(trifluoromethyl)phenyl)boronic acid (Intermediate AA) was used in place of (2-(1-methyl-1H-pyrazol-5-yl)-4-(trifluoromethyl)phenyl)boronic acid. $^1$H NMR (400 MHz, DMSO-d$_6$) δ ppm 7.08 (d, J=5.97 Hz, 2H) 7.36 (d, J=7.34 Hz, 1H) 7.47-7.57 (m, 2H) 7.64-7.73 (m, 2H) 7.85-7.98 (m, 3H) 8.07 (d, J=8.51 Hz, 1H) 8.28 (d, J=5.97 Hz, 2H) 8.34 (d, J=1.37 Hz, 1H). m/z (ESI) 513.0 (M+H)+.

EXAMPLE 3

5-(2-BROMO-4-FLUOROPHENYL)-N-(1,2,4-THIADIAZOL-5-YL)NAPHTHALENE-2-SULFONAMIDE

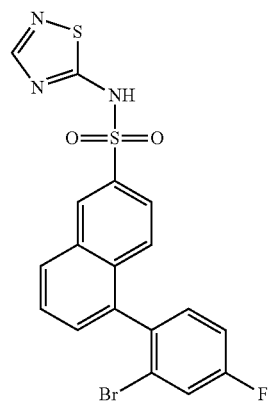 [SMILES: O=S(=O)(Nc1ncns1)c1ccc2c(-c3ccc(F)cc3Br)cccc2c1]

The title compound was prepared in an analogous manner to that of EXAMPLE 1, except that (2-bromo-4-fluorophenyl)boronic acid (Combi-Blocks, San Diego, Calif.) was used in place of (2-(1-methyl-1H-pyrazol-5-yl)-4-(trifluoromethyl)phenyl)boronic acid. Purification was completed using reverse-phase preparative HPLC (Column: Phenomenex 150×30 mm, 5 μm, $C_{18}$ column, Phenomenex, Torrance, Calif.; 0.1% TFA in $CH_3CN/H_2O$, gradient 25% to 90% over 20 min) $^1H$ NMR (400 MHz, DMSO-$d_6$) δ ppm 7.40-7.46 (m, 1H) 7.46-7.51 (m, 2H) 7.55 (dd, J=7.04, 1.17 Hz, 1H) 7.74 (dd, J=8.27, 7.09 Hz, 1H) 7.79 (ddd, J=8.78, 4.57, 2.20 Hz, 2H) 8.28 (d, J=8.41 Hz, 1H) 8.47 (s, 1H) 8.58 (d, J=1.96 Hz, 1H). m/z (ESI) 463.9 (M+H)$^+$.

EXAMPLE 4

5-(2-CHLORO-4-(TRIFLUOROMETHOXY)PHENYL)-N-(1,2,4-THIADIAZOL-5-YL)NAPHTHALENE-2-SULFONAMIDE

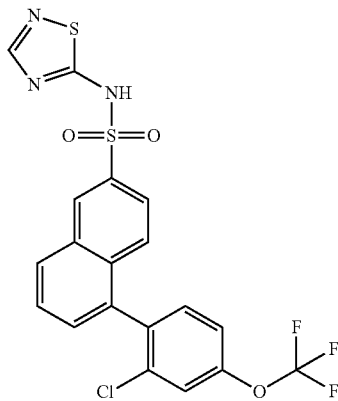 [SMILES: O=S(=O)(Nc1ncns1)c1ccc2c(-c3ccc(OC(F)(F)F)cc3Cl)cccc2c1]

The title compound was prepared in an analogous manner to that of EXAMPLE 1, except that (2-chloro-4-(trifluoromethoxy)phenyl)boronic acid (Combi-Blocks, San Diego, Calif.) was used in place of (2-(1-methyl-1H-pyrazol-5-yl)-4-(trifluoromethyl)phenyl)boronic acid and the reaction mixture was heated in a microwave for 10 minutes at 100° C. Purification was completed using reverse-phase preparative HPLC (Column: Phenomenex 150×30 mm, 5 μm, $C_{18}$ column Phenomenex, Torrance, Calif.; 0.1% TFA in $CH_3CN/H_2O$, gradient 25% to 90% over 20 min) $^1H$ NMR (400 MHz, DMSO-$d_6$) δ ppm 7.50 (d, J=8.90 Hz, 1H) 7.53-7.58 (m, 1H) 7.58-7.64 (m, 2H) 7.76 (m, J=7.70, 7.70 Hz, 1H) 7.79-7.84 (m, 2H) 8.31 (d, J=8.22 Hz, 1H) 8.47 (s, 1H) 8.59 (d, J=1.66 Hz, 1H); m/z (ESI) 486.0 (M+H)$^+$.

EXAMPLE 5

5-(2-CHLORO-4-FLUOROPHENYL)-N-(1,2,4-THIADIAZOL-5-YL)NAPHTHALENE-2-SULFONAMIDE

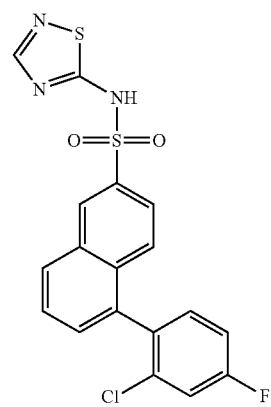 [SMILES: O=S(=O)(Nc1ncns1)c1ccc2c(-c3ccc(F)cc3Cl)cccc2c1]

The title compound was prepared in an analogous manner to that of EXAMPLE 1, except that (2-chloro-4-fluorophenyl)boronic acid (Frontier Scientific, Logan, Utah) was used in place of (2-(1-methyl-1H-pyrazol-5-yl)-4-(trifluoromethyl)phenyl)boronic acid and the reaction mixture was heated in a microwave for 90 minutes at 80° C. Purification was completed using reverse-phase preparative HPLC (Column: Phenomenex 150×30 mm, 5 μm, $C_{18}$ column Phenomenex, Torrance, Calif.; 0.1% TFA in $CH_3CN/H_2O$, gradient 25% to 90% over 20 min) $^1H$ NMR (400 MHz, DMSO-$d_6$) δ ppm 7.40 (td, J=8.46, 2.64 Hz, 1H) 7.51 (dt, J=8.71, 3.03 Hz, 2H) 7.58 (dd, J=7.04, 1.17 Hz, 1H) 7.67 (dd, J=8.90, 2.64 Hz, 1H) 7.71-7.82 (m, 2H) 8.29 (d, J=8.41 Hz, 1H) 8.47 (s, 1H) 8.58 (d, J=1.96 Hz, 1H); m/z (ESI) 420.0 (M+H)$^+$.

EXAMPLE 6

5-(2-CHLORO-4-METHYLPHENYL)-N-(1,2,4-THIADIAZOL-5-YL)NAPHTHALENE-2-SULFONAMIDE

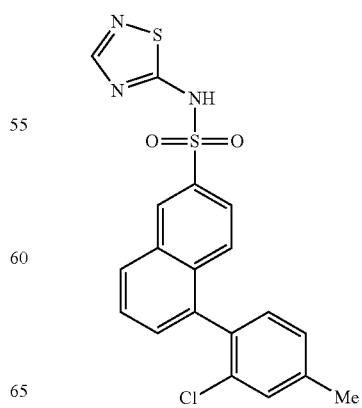

The title compound was prepared in an analogous manner to that of EXAMPLE 1, except that (2-chloro-4-methylphenyl)boronic acid (Alfa Aesar, Ward Hill, Mass.) was used in place of (2-(1-methyl-1H-pyrazol-5-yl)-4-(trifluoromethyl)phenyl)boronic acid and the reaction mixture was heated in a microwave for 10 minutes at 100° C. Purification was completed using reverse-phase preparative HPLC (Column: Phenomenex 150×30 mm, 5 μm, $C_{18}$ column Phenomenex, Torrance, Calif.; 0.1% TFA in $CH_3CN/H_2O$, gradient 25% to 90% over 20 min) $^1$H NMR (400 MHz, DMSO-$d_6$) δ ppm 2.42 (s, 3H) 7.31 (d, J=0.78 Hz, 2H) 7.48-7.53 (m, 2H) 7.54 (dd, J=7.09, 1.12 Hz, 1H) 7.73 (dd, J=8.31, 7.14 Hz, 1H) 7.78 (dd, J=8.90, 1.96 Hz, 1H) 8.26 (d, J=8.41 Hz, 1H) 8.46 (s, 1H) 8.56 (d, J=1.86 Hz, 1H); m/z (ESI) 416.0 (M+H)$^+$.

EXAMPLE 7

5-(PYRIDIN-4-YL)-N-(1,2,4-THIADIAZOL-5-YL)NAPHTHALENE-2-SULFONAMIDE

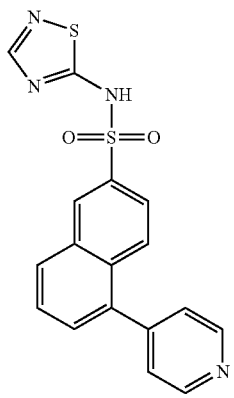 [SMILES: O=S(=O)(Nc1ncns1)c1ccc2c(-c3ccncc3)cccc2c1]

The title compound was prepared in an analogous manner to that of EXAMPLE 1, except that 4-pyridineboronic acid was used in place of (2-(1-methyl-1H-pyrazol-5-yl)-4-(trifluoromethyl)phenyl)boronic acid and the first organic wash was performed with diethyl ether. The compound was purified by reverse-phase preparative HPLC (Column: Phenomenex 150×30 mm, 5 μm, $C_{18}$ column, Phenomenex, Torrance, Calif.; 0.1% TFA in $CH_3CN/H_2O$, gradient 25% to 90% over 22 min) to provide 5-(pyridin-4-yl)-N-(1,2,4-thiadiazol-5-yl)naphthalene-2-sulfonamide as a white solid. $^1$H NMR (400 MHz, DMSO-$d_6$) δ ppm 7.69-7.75 (m, 1H) 7.77-7.88 (m, 4H) 7.96 (d, J=8.90 Hz, 1H) 8.36 (d, J=8.22 Hz, 1H) 8.49 (s, 1H) 8.63 (d, J=2.05 Hz, 1H) 8.86 (m, J=6.30 Hz, 2H); m/z (ESI) 368.8 (M+H)$^+$.

EXAMPLE 8

5-(2-CHLOROPHENYL)-N-(1,2,4-THIADIAZOL-5-YL)NAPHTHALENE-2-SULFONAMIDE

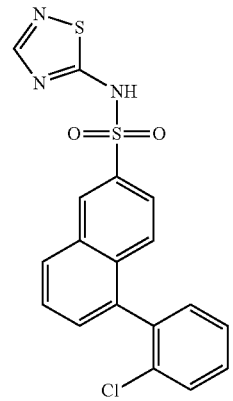 [SMILES: O=S(=O)(Nc1ncns1)c1ccc2c(-c3ccccc3Cl)cccc2c1]

A microwave vial was charged with Intermediate D (0.100 g, 0.192 mmol), 2-chlorobenzeneboronic acid (0.090 g, 0.576 mmol) (Sigma-Aldrich, St. Louis, Mo.), cesium carbonate (0.250 g, 0.769 mmol) and Pd(dppf)$Cl_2CH_2Cl_2$ (0.016 g, 0.019 mmol). The vial was flushed with argon, and then dioxane (0.582 mL) and water (0.058 mL) were added in sequence. The vial was sealed and heated at 100° C. overnight until complete conversion to the desired product. The reaction was diluted with DCM, and washed with water (twice). The aqueous was then acidified with 1N HCl, and extracted with DCM (three times). The organics were dried using a phase separator and concentrated under a vacuum. The material was purified by reverse-phase preparative HPLC (Column: Phenomenex 150×30 mm, 5 μm, $C_{18}$ column, Phenomenex, Torrance, Calif.; 0.1% TFA in $CH_3CN/H_2O$, gradient 25% to 90% over 22 min) to provide 5-(2-chlorophenyl)-N-(1,2,4-thiadiazol-5-yl)naphthalene-2-sulfonamide (0.019 g, 0.047 mmol) as a white solid. $^1$H NMR (400 MHz, DMSO-$d_6$) δ ppm 7.41-7.46 (m, 1H) 7.47-7.60 (m, 4H) 7.66 (dd, J=7.73, 1.57 Hz, 1H) 7.75 (dd, J=8.17, 7.19 Hz, 1H) 7.79 (dd, J=8.90, 1.96 Hz, 1H) 8.28 (d, J=8.41 Hz, 1H) 8.47 (s, 1H) 8.58 (d, J=1.86 Hz, 1H); m/z (ESI) 402.0 (M+H)+.

EXAMPLE 9

5-PHENYL-N-(1,2,4-THIADIAZOL-5-YL)NAPH-THALENE-2-SULFONAMIDE

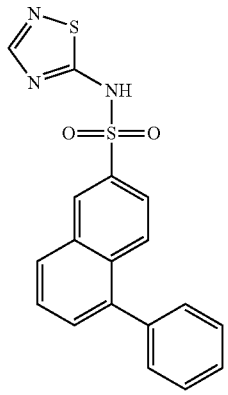 [SMILES: O=S(=O)(Nc1ncns1)c1ccc2c(-c3ccccc3)cccc2c1]

The title compound was prepared in an analogous manner to that of EXAMPLE 8, except that phenylboronic acid (Sigma-Aldrich, St. Louis, Mo.) was used in place of 2-chlorobenzeneboronic acid and the reaction mixture was heated to 100° C. for 6 h. $^1$H NMR (400 MHz, DMSO-$d_6$) δ ppm 7.45-7.52 (m, 3H) 7.52-7.58 (m, 2H) 7.61 (dd, J=7.14, 1.17 Hz, 1H) 7.73 (dd, J=8.07, 7.19 Hz, 1H) 7.80 (dd, J=9.00, 2.05 Hz, 1H) 7.94 (d, J=9.00 Hz, 1H) 8.23 (d, J=8.22 Hz, 1H) 8.47 (s, 1H) 8.56 (d, J=1.96 Hz, 1H); m/z (ESI) 368.0 (M+H)+.

EXAMPLE 10

5-(2-ETHOXY-4-(TRIFLUOROMETHYL)PHE-NYL)-N-(1,2,4-THIADIAZOL-5-YL)NAPHTHA-LENE-2-SULFONAMIDE

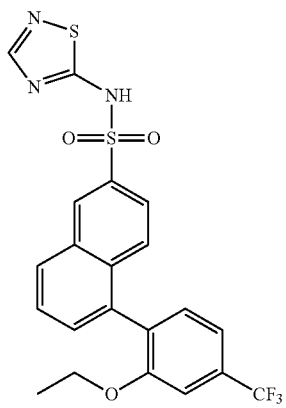 [SMILES: CCOc1cc(C(F)(F)F)ccc1-c1cccc2cc(S(=O)(=O)Nc3ncns3)ccc12]

The title compound was prepared in an analogous manner to that of EXAMPLE 8, except that (2-ethoxy-4-(trifluoromethyl)phenyl)boronic acid (Combi-Blocks, San Diego, Calif.) was used in place of 2-chlorobenzeneboronic acid. In addition, the initial organic wash was performed with diethyl ether, instead of dichloromethane. $^1$H NMR (400 MHz, DMSO-$d_6$) δ ppm 0.97 (t, J=6.94 Hz, 3H) 4.09 (qd, J=6.86, 3.86 Hz, 2H) 7.41-7.51 (m, 3H) 7.54-7.61 (m, 2H) 7.68-7.79 (m, 2H) 8.23 (d, J=8.31 Hz, 1H) 8.44 (s, 1H) 8.54 (d, J=1.86 Hz, 1H); m/z (ESI) 480.0 (M+H)+.

EXAMPLE 11

5-(2-METHYL-4-(TRIFLUOROMETHYL)PHE-NYL)-N-(1,2,4-THIADIAZOL-5-YL)NAPHTHA-LENE-2-SULFONAMIDE

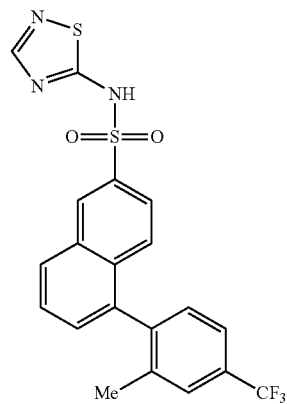 [SMILES: Cc1cc(C(F)(F)F)ccc1-c1cccc2cc(S(=O)(=O)Nc3ncns3)ccc12]

The title compound was prepared in an analogous manner to that of EXAMPLE 8, except that (2-methyl-4-(trifluoromethyl)phenyl)boronic acid (Combi-Blocks, San Diego, Calif.) was used in place of (2-ethoxy-4-(trifluoromethyl)phenyl)boronic acid. $^1$H NMR (400 MHz, DMSO-$d_6$) δ ppm 2.02 (s, 3H) 7.43 (s, 1H) 7.46 (s, 1H) 7.56 (dd, J=6.99, 1.03 Hz, 1H) 7.69 (d, J=7.34 Hz, 1H) 7.72-7.82 (m, 3H) 8.28 (d, J=8.22 Hz, 1H) 8.46 (s, 1H) 8.59 (d, J=1.76 Hz, 1H); m/z (ESI) 450.0 (M+H)+.

EXAMPLE 12

5-(2-METHOXY-4-(TRIFLUOROMETHYL)PHE-NYL)-N-(1,2,4-THIADIAZOL-5-YL)NAPHTHA-LENE-2-SULFONAMIDE

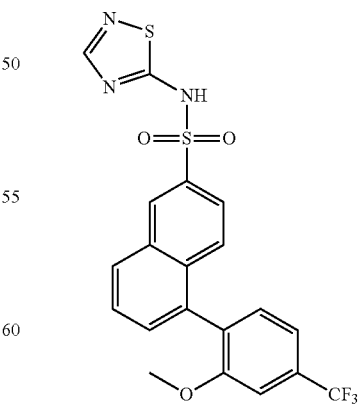

The title compound was prepared in an analogous manner to that of EXAMPLE 10, except that (2-methoxy-4-(trifluoromethyl)phenyl)boronic acid (Combi-Blocks, San Diego, Calif.) was used in place of (2-ethoxy-4-(trifluoromethyl)phenyl)boronic acid. $^1$H NMR (400 MHz, DMSO-$d_6$) δ ppm 3.73 (s, 3H) 7.43-7.51 (m, 3H) 7.52-7.59 (m, 2H) 7.68-7.78 (m, 2H) 8.24 (d, J=8.70 Hz, 1H) 8.44 (s, 1H) 8.54 (d, J=1.86 Hz, 1H); m/z (ESI) 466.0 (M+H)$^+$.

EXAMPLE 13

5-MORPHOLINO-N-(1,2,4-THIADIAZOL-5-YL)NAPHTHALENE-2-SULFONAMIDE

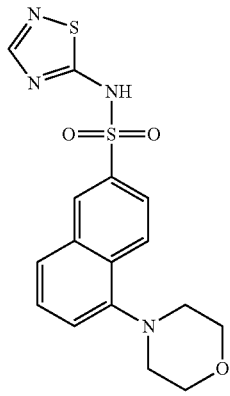 [SMILES: O=S(=O)(Nc1ncns1)c1ccc2c(N3CCOCC3)cccc2c1]

A vial was charged with Intermediate D (0.100 g, 0.192 mmol), xantphos (0.022 g, 0.038 mmol), morpholine (0.020 mL, 0.231 mmol) (Sigma-Aldrich, St. Louis, Mo.), Pd$_2$(dba)$_3$ (0.018 g, 0.019 mmol) and cesium carbonate (0.125 g, 0.384 mmol). The mixture was diluted with toluene (1.922 mL), purged with nitrogen, and stirred at 100° C. for 3.5 h until complete consumption of starting material. The reaction mixture was cooled, water was added, and the aqueous layer was extracted with ethyl acetate. The combined organics were dried over sodium sulfate, filtered and concentrated under a vacuum. DCM (2.0 mL) was added, followed by TFA (2.0 mL) and the reaction was stirred at RT for 5 minutes. The reaction was concentrated under a vacuum and purified by reverse-phase preparative HPLC (Column: Phenomenex 150×30 mm, 5 μm, C$_{18}$ column, Phenomenex, Torrance, Calif.; 0.1% TFA in CH$_3$CN/H$_2$O, gradient 25% to 90% over 22 min) to provide 5-morpholino-N-(1,2,4-thiadiazol-5-yl)naphthalene-2-sulfonamide (0.053 g, 0.141 mmol) as a white solid. $^1$H NMR (400 MHz, DMSO-$d_6$) δ ppm 2.96-3.05 (m, 4H) 3.82-3.90 (m, 4H) 7.31 (dd, J=7.53, 0.78 Hz, 1H) 7.59 (t, J=7.82 Hz, 1H) 7.80 (dd, J=8.95, 1.91 Hz, 1H) 7.87 (d, J=8.31 Hz, 1H) 8.31 (d, J=8.90 Hz, 1H) 8.45 (d, J=1.96 Hz, 1H) 8.48 (s, 1H); m/z (ESI) 377.0 (M+H)$^+$.

EXAMPLE 14

5-(2-PHENYLMORPHOLINO)-N-(1,2,4-THIADIAZOL-5-YL)NAPHTHALENE-2-SULFONAMIDE

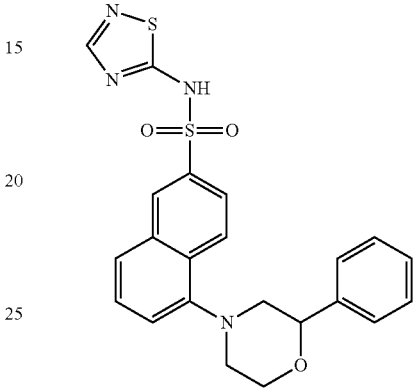

The title compound was prepared in an analogous manner to that of EXAMPLE 13, except that 2-phenylmorpholine hydrochloride (ASDI, Newark, Del.) was used in place of morpholine. $^1$H NMR (400 MHz, DMSO-$d_6$) δ ppm 2.78-2.88 (m, 1H) 2.96 (td, J=11.32, 3.28 Hz, 1H) 3.21-3.36 (m, 2H) 4.02-4.17 (m, 2H) 4.84-4.92 (m, 1H) 7.25-7.39 (m, 4H) 7.46 (d, J=7.14 Hz, 2H) 7.56 (t, J=7.87 Hz, 1H) 7.80-7.91 (m, 2H) 8.42 (d, J=8.90 Hz, 1H) 8.46 (d, J=1.86 Hz, 1H) 8.49 (s, 1H). m/z (ESI) 453.0 (M+H)$^+$. The enantiomers were separated by SFC (Chiralpak® OJ-H column 2×25 cm, 50% CO$_2$/50% methanol, flowrate: 65 mL/min) to yield 5-(2-phenylmorpholino)-N-(1,2,4-thiadiazol-5-yl)naphthalene-2-sulfonamide (isomer 1-first eluting peak): $^1$H NMR (400 MHz, DMSO-$d_6$ δ ppm 2.79-2.87 (m, 1H) 2.97 (td, J=11.44, 3.42 Hz, 1H) 3.21-3.35 (m, 2H) 4.03-4.17 (m, 2H) 4.89 (dd, J=10.12, 2.20 Hz, 1H) 7.26-7.39 (m, 4H) 7.44-7.46 (m, 1H) 7.46-7.48 (m, 1H) 7.56 (t, J=7.87 Hz, 1H) 7.81-7.89 (m, 2H) 8.41 (d, J=8.90 Hz, 1H) 8.45 (d, J=1.96 Hz, 1H) 8.46 (s, 1H); m/z (ESI) 452.8 (M+H)$^+$) and 5-(2-phenylmorpholino)-N-(1,2,4-thiadiazol-5-yl)naphthalene-2-sulfonamide (isomer 2-second eluting peak): $^1$H NMR (400 MHz, DMSO-$d_6$ δ ppm 2.83 (dd, J=11.44, 10.27 Hz, 1H) 2.97 (td, J=11.37, 3.37 Hz, 1H) 3.20-3.35 (m, 2H) 4.03-4.17 (m, 2H) 4.89 (dd, J=10.07, 2.05 Hz, 1H) 7.26-7.39 (m, 4H) 7.45 (s, 1H) 7.46-

7.49 (m, 1H) 7.53-7.59 (m, 1H) 7.82-7.89 (m, 2H) 8.42 (d, J=8.90 Hz, 1H) 8.45 (d, J=1.86 Hz, 1H) 8.47 (s, 1H). m/z (ESI) 452.8 (M+H)⁺).

EXAMPLE 15

5-(2-METHYL-2-PHENYLMORPHOLINO)-N-(1,2,4-THIADIAZOL-5-YL)NAPHTHALENE-2-SULFONAMIDE

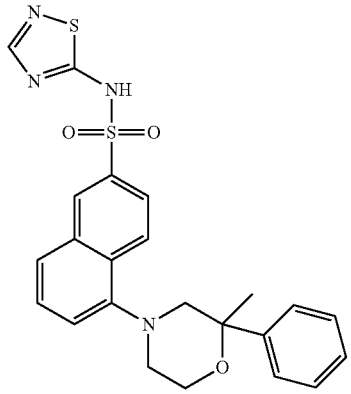 [SMILES: CC1(c2ccccc2)CN(c2cccc3cc(S(=O)(=O)Nc4ncns4)ccc23)CCO1]

The title compound was prepared in an analogous manner to that of EXAMPLE 13, except that 2-methyl-2-phenylmorpholine (ASDI, Newark, Del.) was used in place of morpholine and the reaction mixture was heated overnight. ¹H NMR (400 MHz, DMSO-d₆) δ ppm 1.60 (br. s., 3H) 2.95-3.01 (m, 2H) 3.26 (d, J=11.84 Hz, 1H) 3.33-3.44 (m, 1H) 3.85-3.92 (m, 1H) 3.96-4.07 (m, 1H) 7.23-7.29 (m, 1H) 7.32-7.41 (m, 3H) 7.48 (m, J=7.30 Hz, 2H) 7.60 (t, J=7.87 Hz, 1H) 7.75 (d, J=9.19 Hz, 1H) 7.89 (d, J=8.22 Hz, 1H) 8.13-8.20 (m, 1H) 8.45 (d, J=1.86 Hz, 1H) 8.48 (s, 1H); m/z (ESI) 466.8 (M+H)⁺.

EXAMPLE 16

5-(2-METHYLMORPHOLINO)-N-(1,2,4-THIADIAZOL-5-YL)NAPHTHALENE-2-SULFONAMIDE

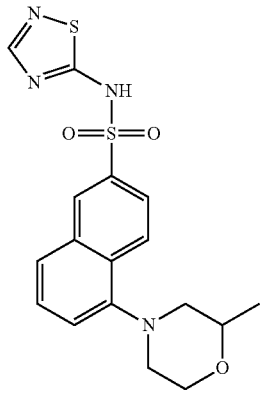 [SMILES: CC1CN(c2cccc3cc(S(=O)(=O)Nc4ncns4)ccc23)CCO1]

The title compound was prepared in an analogous manner to that of EXAMPLE 13, except that 2-methylmorpholine (ASDI, Newark, Del.) was used in place of morpholine and the reaction mixture was heated overnight. ¹H NMR (400 MHz, DMSO-d₆) δ ppm 1.14 (d, J=6.26 Hz, 3H) 2.52-2.57 (m, 1H) 2.84 (td, J=11.32, 3.28 Hz, 1H) 3.06-3.14 (m, 1H) 3.18 (d, J=11.54 Hz, 1H) 3.81-3.96 (m, 3H) 7.29 (d, J=6.85 Hz, 1H) 7.58 (t, J=7.83 Hz, 1H) 7.80 (dd, J=8.95, 1.91 Hz, 1H) 7.86 (d, J=8.31 Hz, 1H) 8.30 (d, J=9.00 Hz, 1H) 8.44 (d, J=1.86 Hz, 1H) 8.47 (s, 1H); m/z (ESI) 390.8 (M+H)⁺.

EXAMPLE 17

METHYL 4-(6-(N-(1,2,4-THIADIAZOL-5-YL)SULFAMOYL)NAPHTHALEN-1-YL)MORPHOLINE-2-CARBOXYLATE

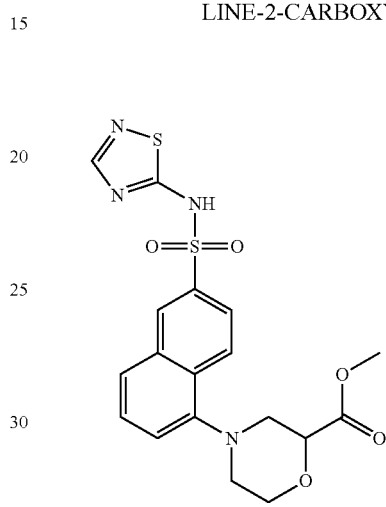

The title compound was prepared in an analogous manner to that of EXAMPLE 13, except that morpholine-2-carboxylate hydrochloride (ASDI, Newark, Del.) was used in place of morpholine and the reaction mixture was heated overnight. ¹H NMR (400 MHz, DMSO-d₆) δ ppm 2.93-3.02 (m, 1H) 3.09 (d, J=12.13 Hz, 1H) 3.13-3.20 (m, 1H) 3.27 (d, J=10.17 Hz, 1H) 3.73 (s, 3H) 3.85-3.93 (m, 1H) 4.07-4.15 (m, 1H) 4.56-4.61 (m, 1H) 7.35 (d, J=6.94 Hz, 1H) 7.59 (t, J=7.87 Hz, 1H) 7.81 (dd, J=8.90, 1.96 Hz, 1H) 7.90 (d, J=8.12 Hz, 1H) 8.30 (d, J=9.00 Hz, 1H) 8.43-8.46 (m, 2H); m/z (ESI) 434.8 (M+H)⁺.

EXAMPLE 18

5-(2-ETHYLMORPHOLINO)-N-(1,2,4-THIADIAZOL-5-YL)NAPHTHALENE-2-SULFONAMIDE

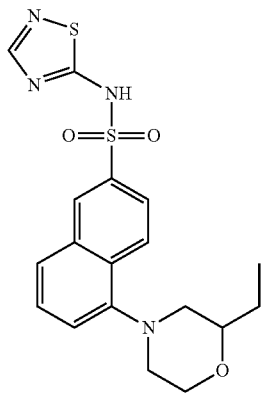 [SMILES: CCC1CN(c2cccc3cc(S(=O)(=O)Nc4ncns4)ccc23)CCO1]

The title compound was prepared in an analogous manner to that of EXAMPLE 13, except that 2-ethylmorpholine (ASDI, Newark, Del.) was used in place of morpholine and the reaction mixture was heated overnight. $^1$H NMR (400 MHz, DMSO-d$_6$) δ ppm 0.93 (t, J=7.48 Hz, 3H) 1.41-1.56 (m, 2H) 2.56 (dd, J=11.54, 9.98 Hz, 1H) 2.85 (td, J=11.40, 2.93 Hz, 1H) 3.06-3.14 (m, 1H) 3.18 (d, J=11.54 Hz, 1H) 3.61-3.72 (m, 1H) 3.85 (td, J=11.13, 2.30 Hz, 1H) 3.91-3.99 (m, 1H) 7.30 (d, J=6.85 Hz, 1H) 7.58 (t, J=7.87 Hz, 1H) 7.80 (dd, J=8.90, 1.96 Hz, 1H) 7.86 (d, J=8.22 Hz, 1H) 8.30 (d, J=9.00 Hz, 1H) 8.44 (d, J=1.86 Hz, 1H) 8.47 (s, 1H); m/z (ESI) 404.8 (M+H)⁺.

EXAMPLE 19

4-(6-(N-(1,2,4-THIADIAZOL-5-YL)SULFAMOYL)NAPHTHALEN-1-YL)-N,N-DIMETHYLMORPHOLINE-2-CARBOXAMIDE

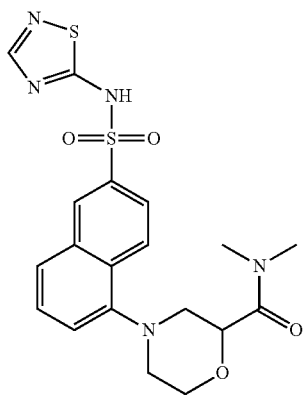 [SMILES: CN(C)C(=O)C1CN(c2cccc3cc(S(=O)(=O)Nc4ncns4)ccc23)CCO1]

The title compound was prepared in an analogous manner to that of EXAMPLE 13, except that N,N-dimethylmorpholine-2-carboxamide hydrochloride (ASDI, Newark, Del.) was used in place of morpholine and the reaction mixture was heated overnight. $^1$H NMR (400 MHz, DMSO-d$_6$) δ ppm 2.83 (s, 3H) 2.87-3.03 (m, 2H) 3.10 (s, 3H) 3.12-3.22 (m, 2H) 3.93-4.05 (m, 2H) 4.64 (dd, J=9.59, 2.45 Hz, 1H) 7.33 (d, J=6.94 Hz, 1H) 7.59 (t, J=7.87 Hz, 1H) 7.79 (dd, J=8.95, 1.91 Hz, 1H) 7.87 (d, J=8.22 Hz, 1H) 8.36 (d, J=9.00 Hz, 1H) 8.45 (d, J=1.86 Hz, 1H) 8.46 (s, 1H); m/z (ESI) 447.8 (M+H)⁺.

EXAMPLE 20

5-(2-(2-HYDROXYPROPAN-2-YL)MORPHOLINO)-N-(1,2,4-THIADIAZOL-5-YL)NAPHTHALENE-2-SULFONAMIDE

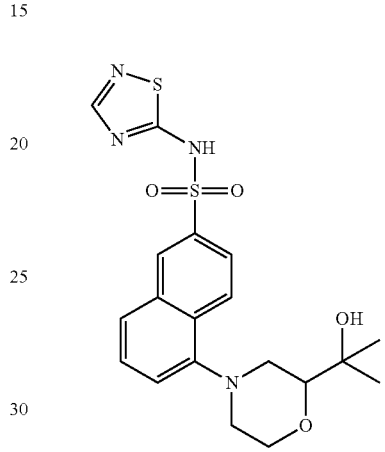

The title compound was prepared in an analogous manner to that of EXAMPLE 13, except that 2-(morpholin-2-yl)propan-2-ol hydrochloride (ASDI, Newark, Del.) was used in place of morpholine and the reaction mixture was heated overnight. $^1$H NMR (400 MHz, DMSO-d$_6$) δ ppm 1.04-1.11 (m, 3H) 1.17 (s, 3H) 2.59-2.67 (m, 1H) 2.85 (td, J=11.66, 3.28 Hz, 1H) 3.10 (d, J=11.74 Hz, 1H) 3.34 (d, J=11.54 Hz, 1H) 3.53 (dd, J=10.07, 1.66 Hz, 1H) 3.81-3.90 (m, 1H) 3.98-4.05 (m, 1H) 7.32 (d, J=6.94 Hz, 1H) 7.58 (t, J=7.87 Hz, 1H) 7.79 (dd, J=9.00, 1.96 Hz, 1H) 7.86 (d, J=8.31 Hz, 1H) 8.29 (d, J=9.00 Hz, 1H) 8.45 (d, J=1.86 Hz, 1H) 8.48 (s, 1H); m/z (ESI) 434.8 (M+H)⁺.

INTERMEDIATE H

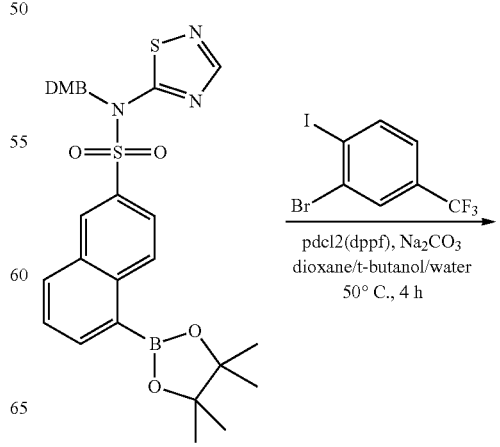

-continued

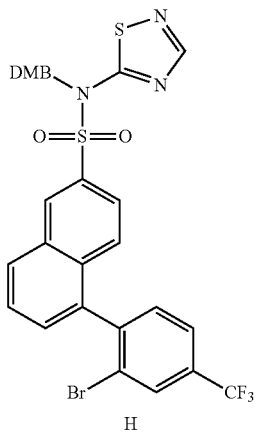

H

INTERMEDIATE H: 5-(2-BROMO-4-(TRIFLUO-
ROMETHYL)PHENYL)-N-(2,4-DIMETHOXY-
BENZYL)-N-(1,2,4-THIADIAZOL-5-YL)NAPH-
THALENE-2-SULFONAMIDE

A reaction vessel was charged with N-(2,4-dimethoxybenzyl)-5-(4,4,5,5-tetramethyl-1,3,2-dioxaborolan-2-yl)-N-(1,2,4-thiadiazol-5-yl)naphthalene-2 sulfonamide (Intermediate E) (4 g, 7.05 mmol), 2-bromo-1-iodo-4-(trifluoromethyl)benzene (4.95 g, 14.10 mmol) and Pd(dppf)Cl$_2$ DCM (1.151 g, 1.410 mmol). Dioxane (35.2 mL) and t-butanol (35.2 mL) were added to the reaction mixture followed by sodium carbonate in water (1.9 M) (11.13 mL, 21.15 mmol). The reaction vial was then swept with nitrogen and sealed with a screw cap. The resulting mixture was then heated to 50° C. and stirred for 4 hours. LC/MS indicated that the product was formed. The resulting mixture was transferred to a separatory funnel containing water and the aqueous layer was washed three times with DCM. The organic layers were combined, dried with MgSO$_4$, filtered and concentrated to a dark oil which was purified by MPLC using 120 g silica gel column eluting with 0 to 70% EtOAc in heptane) to afford 5-(2-bromo-4-(trifluoromethyl)phenyl)-N-(2,4-dimethoxybenzyl)-N-(1,2,4-thiadiazol-5-yl)naphthalene-2-sulfonamide (3.27 g, 4.92 mmol) as a white solid. m/z (ESI) 685.8 [M+Na]$^+$.

EXAMPLE 21

5-(2-(1H-PYRAZOL-4-YL)-4-(TRIFLUOROM-
ETHYL)PHENYL)-N-(1,2,4-THIADIAZOL-5-YL)
NAPHTHALENE-2-SULFONAMIDE

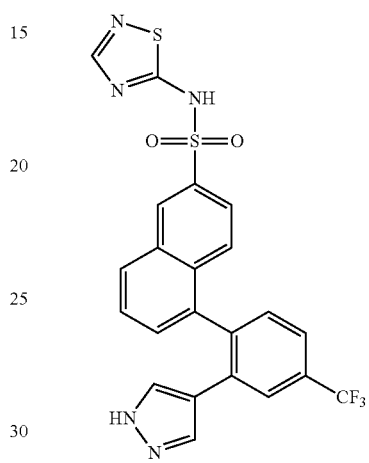

A vial containing tert-butyl 4-(4,4,5,5-tetramethyl-1,3,2-dioxaborolan-2-yl)-1H-pyrazole-1-carboxylate (0.177 g, 0.602 mmol), Intermediate H (0.200 g, 0.301 mmol), Pd(dppf)Cl$_2$ CH$_2$Cl$_2$ (0.025 g, 0.030 mmol) and cesium carbonate (0.392 g, 1.204 mmol) were diluted with dioxane (0.912 mL) and water (0.091 mL). The vial was flushed with argon and heated at 90° C. for 1 h until complete conversion was observed by LC/MS. The reaction was cooled to RT, and diluted with DCM, then washed with water. The aqueous layer was extracted with DCM, and then the combined organics were washed with brine, dried using a phase separator, and concentrated under a vacuum. DCM (2.0 mL) was added, along with TFA (2.0 mL), and the reaction was stirred for 20 minutes at RT until clean conversion to the desired product. The reaction was concentrated under a vacuum, and then purified by reverse-phase preparative HPLC (Column: Phenomenex 150×30 mm, 5 μm, C$_{18}$ column, Phenomenex, Torrance, Calif.; 0.1% TFA in CH$_3$CN/H$_2$O, gradient 25% to 90% over 22 min) to provide 5-(2-(1H-pyrazol-4-yl)-4-(trifluoromethyl)phenyl)-N-(1,2,4-thiadiazol-5-yl)naphthalene-2-sulfonamide (0.083 g, 0.166 mmol) as a light-yellow solid. $^1$H NMR (400 MHz, DMSO-d$_6$) δ ppm 7.01-7.16 (m, 2H) 7.42 (d, J=9.00 Hz, 1H) 7.52 (m, J=7.90 Hz, 2H) 7.59-7.63 (m, 1H) 7.64-7.69 (m, 1H) 7.70-7.80 (m, 2H) 8.04 (s, 1H)

8.30 (d, J=8.02 Hz, 1H) 8.43-8.50 (m, 1H) 8.55 (d, J=1.76 Hz, 1H); m/z (ESI) 501.8 (M+H)$^+$.

EXAMPLE 22

5-(2-CYANO-4-(TRIFLUOROMETHYL)PHENYL)-N-(1,2,4-THIADIAZOL-5-YL)NAPHTHALENE-2-SULFONAMIDE

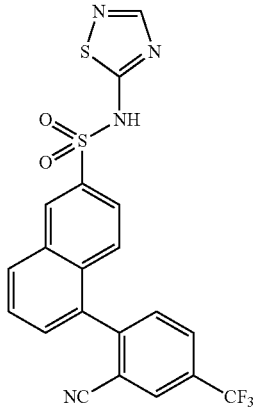 [SMILES: N#Cc1cc(C(F)(F)F)ccc1-c1cccc2cc(S(=O)(=O)Nc3ncns3)ccc12]

A pressure vessel was charged with 5-bromo-N-(2,4-dimethoxybenzyl)-N-(1,2,4-thiadiazol-5-yl)naphthalene-2-sulfonamide (Intermediate D) (150 mg, 0.288 mmol), potassium carbonate (199 mg, 1.441 mmol), (2-cyano-4-(trifluoromethyl)phenyl)boronic acid (124 mg, 0.576 mmol), tetrakis(triphenylphosphine)palladium(0) (33.3 mg, 0.029 mmol), dioxane (1922 µl) and water (961 µl). The reaction was heated in a microwave to 100° C. for 60 min. Additional (2-cyano-4-(trifluoromethyl)phenyl)boronic acid (124 mg, 0.576 mmol) and tetrakis(triphenylphosphine)palladium(0) (33.3 mg, 0.029 mmol) were added and the resulting mixture was heated in a microwave at 100° C. for an additional hour. After heating the mixture was allowed to cool to room temperature, the organic layer was separated and the organic layer was concentrated. The resulting product was purified by MPLC (40 g silica gel column, eluting with 0% to 50% EtOAc in heptane) to afford a white solid that was further purified by reverse phase HPLC (Column: Xbridge 19×100 mm, 5 µm, Waters, Milford, Mass., Flow rate: 40 mL/min, Mobile phase: 0.1% NH$_4$OH in ACN and water). The fractions containing product were dried under a vacuum to afford 5-(2-cyano-4-(trifluoromethyl)phenyl)-N-(1,2,4-thiadiazol-5-yl)naphthalene-2-sulfonamide (2.1 mg, 0.004 mmol) as a white solid. $^1$H NMR (500 MHz, DMSO-d$_6$) δ ppm 7.58 (d, J=8.76 Hz, 1H) 7.69-7.74 (m, 1H) 7.75-7.83 (m, 2H) 7.87 (d, J=8.01 Hz, 1H) 8.16-8.24 (m, 2H) 8.34 (d, J=8.34 Hz, 1H) 8.52-8.57 (m, 2H); m/z (ESI) 461.0 (M+H)$^+$.

EXAMPLE 23

5-(2-BROMO-4-(TRIFLUOROMETHYL)PHENYL)-N-(1,2,4-THIADIAZOL-5-YL)NAPHTHALENE-2-SULFONAMIDE

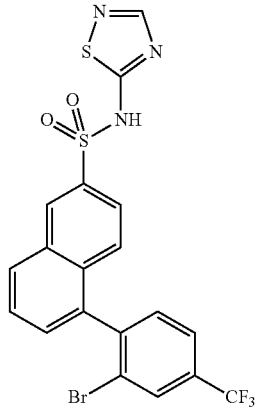 [SMILES: O=S(=O)(Nc1ncns1)c1ccc2c(-c3ccc(C(F)(F)F)cc3Br)cccc2c1]

To a solution of 5-(2-bromo-4-(trifluoromethyl)phenyl)-N-(2,4-dimethoxybenzyl)-N-(1,2,4-thiadiazol-5-yl)naphthalene-2-sulfonamide (3.27 g, 4.92 mmol) in DCM (49.2 mL, 4.92 mmol) was added TFA (1.896 mL, 24.60 mmol). The resulting mixture was stirred at room temperature. After 30 min, LC/MS showed mainly desired product. The mixture was stirred for an additional hour at room temperature until the reaction was complete. The mixture was partially concentrated until a white solid crashed out. The solid was filtered, washed with diethyl ether and dried to afford 5-(2-bromo-4-(trifluoromethyl)phenyl)-N-(1,2,4-thiadiazol-5-yl)naphthalene-2-sulfonamide (2.4 g, 4.67 mmol). $^1$H NMR (500 MHz, DMSO-d$_6$) δ ppm 7.58 (d, J=8.76 Hz, 1H) 7.68-7.74 (m, 1H) 7.74-7.83 (m, 2H) 7.87 (d, J=8.01 Hz, 1H) 8.16-8.24 (m, 2H) 8.34 (d, J=8.34 Hz, 1H) 8.52-8.57 (m, 2H); m/z (ESI) 513.7 (M+H)$^+$.

INTERMEDIATE I

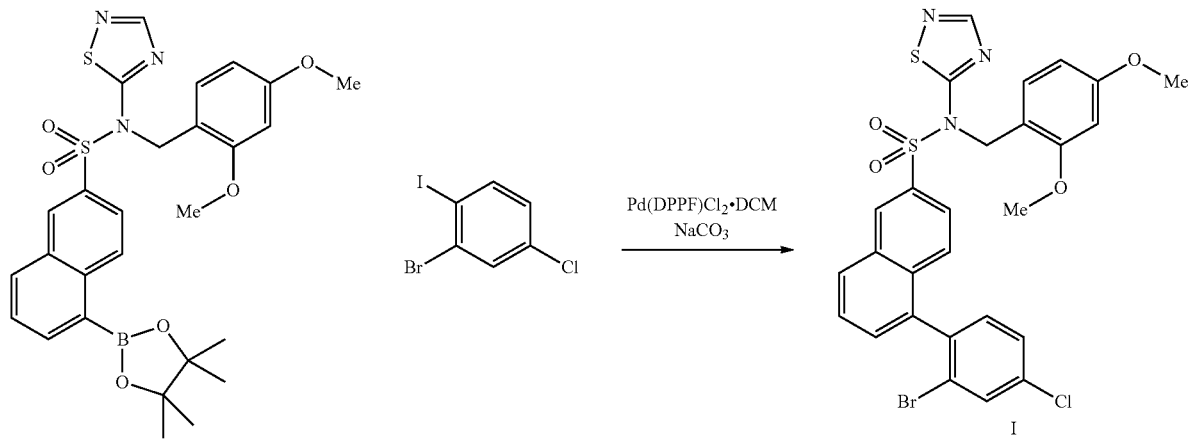

INTERMEDIATE I: 5-(2-BROMO-4-CHLOROPHENYL)-N-(2,4-DIMETHOXYBENZYL)-N-(1,2,4-THIADIAZOL-5-YL)NAPHTHALENE-2-SULFONAMIDE (INT A7)

A pressure vessel was charged with N-(2,4-dimethoxybenzyl)-5-(4,4,5,5-tetramethyl-1,3,2-dioxaborolan-2-yl)-N-(1,2,4-thiadiazol-5-yl)naphthalene-2-sulfonamide (Intermediate E) (5.00 g, 8.81 mmol), 2-bromo-4-chloro-1-iodobenzene (5.59 g, 17.6 mmol) and Pd(dppf) Cl$_2$ DCM (1.44 g, 1.76 mmol). Dioxane (44.1 mL) and t-butanol (44.1 mL) were added to the reaction vial followed by 1.9 M sodium carbonate in water (13.9 mL, 26.4 mmol). The reaction vial was then swept with nitrogen and sealed with a screw cap. The reaction mixture was stirred and sonicated for 5 min. The resulting light red mixture was then heated to 50° C. After 2 h, LC/MS indicated about 90% conversion of boronic ester to the desired product as [M+Na]$^+$=652. The mixture was cooled to room temperature and filtered through a fritted funnel with EtOAc (150 mL). The filtrate was washed with brine. The organic layers were combined, dried with MgSO$_4$, filtered and concentrated to afford a black oil. The mixture was purified by MPLC (300 g silica gel column eluting with 0 to 50% EtOAc:Heptane) to afford a white solid. MS (ESI): 651.8 [M+Na]$^+$; $^1$H NMR (400 MHz, DMSO-d$_6$) δ ppm 3.64 (s, 3H), 3.66 (s, 3H), 5.18 (d, J=16 Hz, 1H), 5.24 (d, J=16 Hz, 1H), 6.31-6.41 (m, 2H), 6.95-7.04 (d, J=9 Hz, 1H), 7.46 (d, J=8.3 Hz, 1H), 7.50 (d, J=8.9 Hz, 1H), 7.64 (d, J=6.1 Hz, 2H), 7.78-7.80 (m, 2H), 7.98 (d, J=2.25 Hz, 1H), 8.30 (d, J=9.4 Hz, 1H), 8.38 (s, 1H), 8.65 (m, 1H).

INTERMEDIATE J

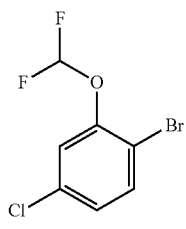

INTERMEDIATE J: 1-BROMO-4-CHLORO-2-(DIFLUOROMETHOXY)BENZENE

The title compound was prepared according to the procedure disclosed in Published PCT Patent Application No. WO2011/003065 A2. To a solution of 2-bromo-5-chlorophenol (4.34 g, 20.92 mmol) (the oil from above) in N,N-dimethylformamide (21.8 mL, 20.9 mmol) was added sodium chlorodifluoroacetate (7.34 g, 48.1 mmol), cesium carbonate (9.54 g, 29.3 mmol), and water (2.18 mL, 20.9 mmol). The reaction was stirred at 100° C. for 16 h. The reaction was cooled to room temperature and partitioned between EtOAc (100 mL) and water (50 mL). The aqueous layer was extracted with EtOAc (2×70 mL). The organic layers were combined and washed with water (2×50 mL), 10% aq. citric acid (1×30 mL), brine, dried over MgSO$_4$, filtered, and concentrated to afford 1-bromo-4-chloro-2-(difluoromethoxy)benzene (4.35 g, 16.9 mmol). $^1$H NMR (400 MHz, DMSO-d$_6$) δ ppm 7.30 (dd, J=2.3, 8.6 Hz, 1H), 7.37 (t, J=73 Hz, 1H), 7.49 (dt, J=2.40, 0.81 Hz, 1H), 7.79 (d, J=8.6 Hz, 1H).

INTERMEDIATE K

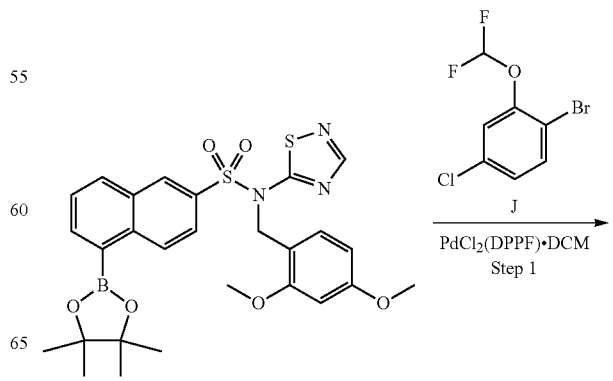

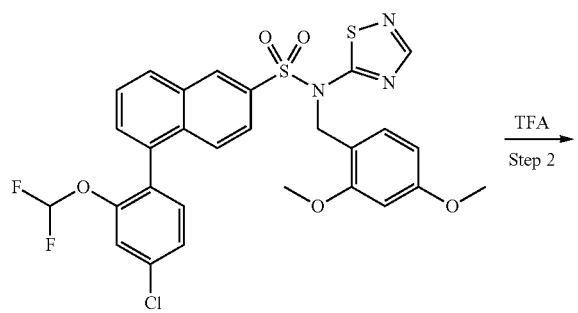

K

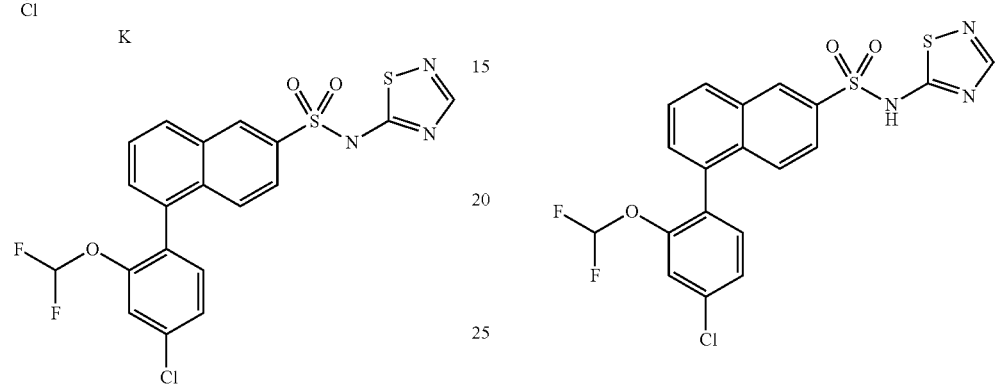

Example 24

INTERMEDIATE K. 5-(4-CHLORO-2-(DIFLUOROMETHOXY)PHENYL)-N-(2,4-DIMETHOXYBENZYL)-N-(1,2,4-THIADIAZOL-5-YL)NAPHTHALENE-2-SULFONAMIDE

Step 1: A microwave vial was charged with N-(2,4-dimethoxybenzyl)-5-(4,4,5,5-tetramethyl-1,3,2-dioxaborolan-2-yl)-N-(1,2,4-thiadiazol-5-yl)naphthalene-2-sulfonamide (Intermediate E) (130 mg, 0.229 mmol), 1-bromo-4-chloro-2-(difluoromethoxy)benzene (Intermediate J) (118 mg, 0.458 mmol) and Pd(dppf)Cl$_2$DCM (37.4 mg, 0.046 mmol). Dioxane (1145 μl) and t-butanol (1145 μl) were added to the reaction vial followed by sodium carbonate in water (362 μl, 0.687 mmol, 1.9 M). The vial was purged with nitrogen and sealed. The mixture was stirred and sonicated for 5 min. The resulting light red mixture was then heated in a microwave at 100° C. for 30 min LC/MS indicated complete conversion of boronic ester to the desired product. The reaction was cooled to rt and filtered through a fritted funnel with an aid of DCM (15 mL). The filtrate was acidified with 2N aqueous HCl to a pH of about 1. After stirring for 5 min at room temperature, the product was extracted with DCM (2×20 mL). The organic layers were combined, washed with brine, dried over MgSO$_4$, filtered, and concentrated to afford a dark oil. MS (ESI): 639.8 [M+Na]$^+$

EXAMPLE 24

5-(4-CHLORO-2-(DIFLUOROMETHOXY)PHENYL)-N-(1,2,4-THIADIAZOL-5-YL)NAPHTHALENE-2-SULFONAMIDE

Step 2: The compound from Step 1 (Intermediate K) was dissolved in 1 mL of DCM. Then TFA (88 μl, 1.145 mmol) was added. After stirring for 1 h at rt, LC/MS showed incomplete conversion of starting material. Then 0.05 mL of TFA was added. After another 30 min, the reaction mixture was concentrated. The product was purified by reverse phase LC using a Phenomenex Gemini 5 μm, C$_{18}$, 110 Å, 150×30 mm column eluting with a mixture of 0.1% TFA in acetonitrile/water. Fractions containing the product were concentrated. The product was purified further by reversed phase LC using 0.1% NH$_4$OH in ACN and water as mobile phase to provide 5-(4-chloro-2-(difluoromethoxy)phenyl)-N-(1,2,4-thiadiazol-5-yl)naphthalene-2-sulfonamide (3 mg, 6.41 mmol). LC/MS (ESI): 468.0 [M+H]$^+$; $^1$H NMR (500 MHz, DMSO-d$_6$) δ ppm 7.15 (t, J=73 Hz, 1H), 7.43-7.52 (m, 5H), 7.69 (t, J=8.2 Hz, 1H), 7.74 (dd, J=1.9, 8.9 Hz, 1H), 8.11 (s, 1H), 8.21 (d, J=8.3 Hz, 1H), 8.46 (d, J=1.8 Hz, 1H).

INTERMEDIATE L

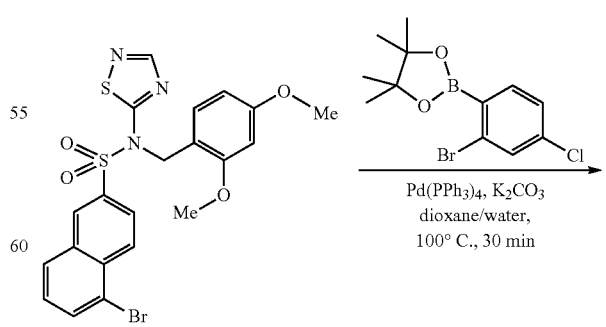

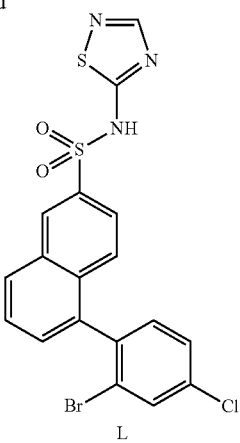

L

INTERMEDIATE L: 5-(2-BROMO-4-CHLOROPHENYL)-N-(1,2,4-THIADIAZOL-5-YL)NAPHTHALENE-2-SULFONAMIDE

A pressure vessel was charged with 2-(2-bromo-4-chlorophenyl)-4,4,5,5-tetramethyl-1,3,2-dioxaborolane (0.732 g, 2.306 mmol), potassium carbonate (1.328 g, 9.61 mmol), 5-bromo-N-(2,4-dimethoxybenzyl)-N-(1,2,4-thiadiazol-5-yl)naphthalene-2-sulfonamide (Intermediate D) (1 g, 1.922 mmol), tetrakis(triphenylphosphine)palladium(0) (0.222 g, 0.191 mmol) in dioxane (12.81 mL) and water (6.41 mL). The reaction was heated in an oil bath at 100° C. for 35 min. LC/MS indicated that the desired product (M+H=479.8) was generated. Water was added to the mixture and washed with EtOAc. The water layer was acidified with 5% HCl (15 mL) and washed with EtOAc again to afford a light yellow solid. The product was used in the next reaction without further purification. m/z (ESI) 480.0 (M+H)$^+$.

EXAMPLE 25

5-(4-CHLORO-2-(1-METHYL-1H-PYRAZOL-5-YL)PHENYL)-N-(1,2,4-THIADIAZOL-5-YL)NAPHTHALENE-2-SULFONAMIDE

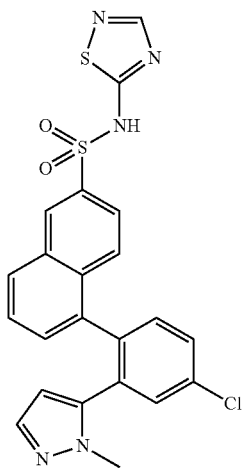 [SMILES: Cn1nccc1-c1cc(Cl)ccc1-c1cccc2cc(S(=O)(=O)Nc3ncns3)ccc12]

A pressure vessel was charged with 5-(2-bromo-4-chlorophenyl)-N-(1,2,4-thiadiazol-5-yl)naphthalene-2-sulfonamide (80 mg, 0.166 mmol), potassium carbonate (115 mg, 0.832 mmol), (1-methyl-1H-pyrazol-5-yl)boronic acid (84 mg, 0.666 mmol), tetrakis(triphenylphosphine)palladium(0) (19.23 mg, 0.017 mmol), dioxane (1109 μl) and water (555 μl). The reaction was heated in a microwave at 100° C. for 30 min. The resulting mixture was concentrated and purified by reverse phase HPLC (Column: Xbridge 19×100 mm, 5 μm, Waters, Milford, Mass., Flow rate: 40 mL/min, Mobile phase: 0.1% TFA in ACN and water). The fractions containing product were dried under a vacuum to provide a white solid 5-(4-chloro-2-(1-methyl-1H-pyrazol-5-yl)phenyl)-N-(1,2,4-thiadiazol-5-yl)naphthalene-2-sulfonamide (5 mg, 0.01 mmol). $^1$H NMR (500 MHz, DMSO-d$_6$) δ ppm 3.48 (s, 3H) 7.01 (s, 1H) 7.05 (d, J=1.82 Hz, 1H) 7.11 (s, 1H) 7.21 (s, 1H) 7.43 (d, J=6.41 Hz, 1H) 7.49 (d, J=8.55 Hz, 1H) 7.53-7.64 (m, 3H) 7.64-7.75 (m, 3H) 8.11 (d, J=8.23 Hz, 1H) 8.34 (s, 1H) 8.43 (d, J=1.60 Hz, 1H); m/z (ESI) 482.0 (M+H)$^+$.

EXAMPLE 26

5-(4-CHLORO-2-(1,2,3,6-TETRAHYDROPYRIDIN-4-YL)PHENYL)-N-(1,2,4-THIADIAZOL-5-YL)NAPHTHALENE-2-SULFONAMIDE

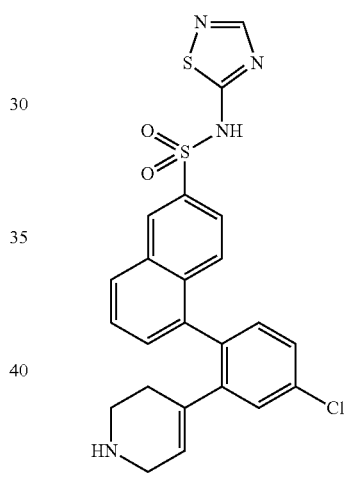

A pressure vessel was charged with 5-(2-bromo-4-chlorophenyl)-N-(1,2,4-thiadiazol-5-yl)naphthalene-2-sulfonamide (80 mg, 0.166 mmol), potassium carbonate (115 mg, 0.832 mmol), 4-(4,4,5,5-tetramethyl-1,3-dioxolan-2-yl)-1,2,3,6-tetrahydropyridine (141 mg, 0.666 mmol) (Frontier Scientific, Inc., Logan, Utah), tetrakis(triphenylphosphine)palladium(0) (19.23 mg, 0.017 mmol), dioxane (1109 μl) and water (555 μl). The reaction mixture was heated in the microwave at 100° C. for 30 min. The mixture was then cooled to room temperature and the organic layer was separated from the aqueous layer by pipet. The resulting organic layer was the injected as is onto a reverse phase HPLC apparatus for purification (Column: Xbridge 19×100 mm, 5 μm, Waters, Milford, Mass., Flow rate: 40 mL/min, Mobile phase: 0.1% TFA in ACN and water). The fractions containing product were dried under a vacuum to provide a white solid. 5-(4-chloro-2-(1,2,3,6-tetrahydropyridin-4-yl)phenyl)-N-(1,2,4-thiadiazol-5-yl)naphthalene-2-sulfonamide (6 mg, 0.012 mmol). $^1$H NMR (500 MHz, DMSO-d$_6$) δ ppm 1.78-1.90 (m, 1H) 1.90-2.06 (m, 1H) 2.62-2.72 (m, 1H) 2.77 (dt, J=12.18, 5.88 Hz, 1H) 5.59 (br. s., 1H) 7.30 (d, J=8.12 Hz, 1H) 7.39-7.44 (m, 2H) 7.50 (td, J=5.53, 2.94 Hz, 2H) 7.58-7.63 (m, 1H)

7.71-7.76 (m, 1H) 7.82 (s, 1H) 8.12 (d, J=8.23 Hz, 1H) 8.39 (d, J=1.71 Hz, 1H); m/z (ESI) 483.0 (M+H)+.

EXAMPLE 27

5-(4-CHLORO-2-(1H-PYRAZOL-4-YL)PHENYL)-N-(1,2,4-THIADIAZOL-5-YL)NAPHTHALENE-2 SULFONAMIDE

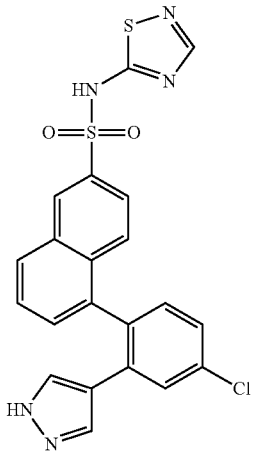 [SMILES: O=S(=O)(Nc1ncns1)c1ccc2c(-c3ccc(Cl)cc3-c3cn[nH]c3)cccc2c1]

A pressure vessel was charged with 5-(2-bromo-4-chlorophenyl)-N-(2,4-dimethoxybenzyl)-N-(1,2,4-thiadiazol-5-yl)naphthalene-2-sulfonamide (0.8 g, 1.268 mmol), potassium carbonate (1.227 g, 8.88 mmol), tert-butyl 4-(4,4,5,5-tetramethyl-1,3,2-dioxaborolan-2-yl)-1H-pyrazole-1-carboxylate (0.748 g, 2.54 mmol), tetrakis(triphenylphosphine)palladium(0) (0.147 g, 0.127 mmol), dioxane (8.45 mL) and water (4.23 mL). The reaction was heated in a microwave at 100° C. for 30 min. The reaction mixture was cooled to room temperature and 2N HCl (10 mL) was then added dropwise to neutralize the base. The aqueous layer was then washed with DCM (three times). The organic layers were combined and dried over sodium sulfate, filtered over a layer of diatomaceous Earth® (diatomaceous earth) and concentrated under a vacuum to provide a yellow oil. To this oil was added DCM (12.68 mL, 1.268 mmol) and TFA (0.488 mL, 6.34 mmol). The resulting mixture was stirred for 1 h at rt. LC/MS indicated that the dimethoxybenzyl (DMB)-protected intermediate remained. The mixture was then heated to 50° C. for 1 h. LC/MS indicated that the desired product (M+H=467.8) was generated. The mixture was concentrated, diluted with DCM (3 mL) and purified by reverse phase HPLC using a Phenomenex Gemini 5 μm, C$_{18}$, 110 Å, 150×30 mm column eluting with a mixture of 0.1% TFA in acetonitrile/water. The fractions containing product were dried to provide a white solid. 5-(4-chloro-2-(1H-pyrazol-4-yl)phenyl)-N-(1,2,4-thiadiazol-5-yl)naphthalene-2-sulfonamide (0.165 g, 0.352 mmol). $^1$H NMR (500 MHz, DMSO-d$_6$) δ ppm 2.08 (s, 2H) 2.54 (s, 1H) 7.02 (br. s., 2H) 7.30 (d, J=8.23 Hz, 1H) 7.40-7.47 (m, 2H) 7.56 (d, J=7.05 Hz, 1H) 7.65 (dd, J=8.87, 1.92 Hz, 1H) 7.69-7.76 (m, 1H) 7.79 (d, J=2.14 Hz, 1H) 8.26 (d, J=8.23 Hz, 1H) 8.44 (s, 1H) 8.53 (d, J=1.71 Hz, 1H); m/z (ESI) 467.8 (M+H)+.

EXAMPLE 28

5-(4-CHLORO-2-(PYRIDIN-4-YL)PHENYL)-N-(1,2,4-THIADIAZOL-5-YL)NAPHTHALENE-2-SULFONAMIDE

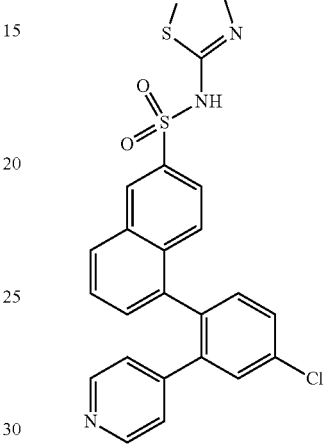

A pressure vessel was charged with 5-(2-bromo-4-chlorophenyl)-N-(1,2,4-thiadiazol-5-yl)naphthalene-2-sulfonamide (80 mg, 0.166 mmol), potassium carbonate (115 mg, 0.832 mmol), pyridin-4-ylboronic acid (30.7 mg, 0.250 mmol), tetrakis(triphenylphosphine)palladium(0) (19.23 mg, 0.017 mmol), dioxane (1109 μl) and water (555 μl). The reaction mixture was heated in a microwave at 100° C. for 30 min. The mixture was then cooled to room temperature and the organic layer was separated from the aqueous layer by pipet. The resulting organic layer was then injected as is onto a reverse phase HPLC for purification (Column: Xbridge 19×100 mm, 5 μm, Waters, Milford, Mass., Flow rate: 40 mL/min, Mobile phase: 0.1% TFA in ACN and water). The fractions containing product were dried under a vacuum to provide 5-(4-chloro-2-(pyridin-4-yl)phenyl)-N-(1,2,4-thiadiazol-5-yl)naphthalene-2-sulfonamide (5 mg, 0.01 mmol) as a white solid. $^1$H NMR (500 MHz, DMSO-d$_6$) δ ppm 2.54 (s, 2H) 7.04 (d, J=5.98 Hz, 2H) 7.36-7.41 (m, 1H) 7.46 (d, J=8.76 Hz, 1H) 7.51-7.60 (m, 2H) 7.63-7.70 (m, 3H) 8.09 (d, J=8.33 Hz, 1H) 8.16 (s, 1H) 8.26 (d, J=5.56 Hz, 2H) 8.39 (d, J=1.71 Hz, 1H); m/z (ESI) 479.0 (M+H)+.

EXAMPLE 29

5-(2-CHLORO-4-(TRIFLUOROMETHYL)PHENYL)-N-(1,2,4-THIADIAZOL-5-YL)NAPHTHALENE-2-SULFONAMIDE

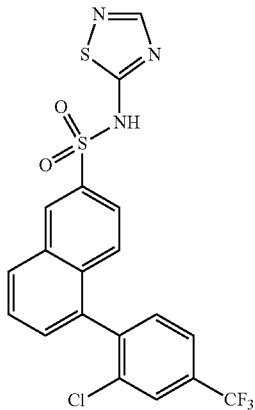

A pressure vessel was charged with 5-bromo-N-(2,4-dimethoxybenzyl)-N-(1,2,4-thiadiazol-5-yl)naphthalene-2-sulfonamide (Intermediate D) (110 mg, 0.211 mmol), potassium carbonate (146 mg, 1.057 mmol), (2-chloro-4-(trifluoromethyl)phenyl)boronic acid (56.9 mg, 0.254 mmol), tetrakis(triphenylphosphine)palladium(0) (24.42 mg, 0.021 mmol), dioxane (1409 μl) and water (705 μl). The reaction was heated in a microwave at 100° C. for 30 min. The mixture was then cooled to room temperature and the organic layer was separated from the aqueous layer by pipet. The resulting organic layer was then injected as is onto a reverse phase HPLC (Column: Gemini 150×30 mm, 5 μm, Phenomenex, Torrance, Calif., Flow rate: 40 mL/min, Mobile phase: 0.1% TFA in ACN and water). The fractions containing product were combined and saturated aq. NaHCO$_3$ (15 mL) was added. The aqueous layer was washed with ethyl acetate (1×100 mL). The combined organic layers were dried over sodium sulfate, filtered and concentrated under a vacuum to provide 5-(2-chloro-4-(trifluoromethyl)phenyl)-N-(1,2,4-thiadiazol-5-yl)naphthalene-2-sulfonamide (10 mg, 0.021 mmol) as a white solid. $^1$H NMR (400 MHz, DMSO-d$_6$) δ ppm 7.22 (d, J=8.90 Hz, 1H) 7.36 (dd, J=7.09, 1.03 Hz, 1H) 7.43-7.58 (m, 4H) 7.65 (d, J=7.92 Hz, 1H) 7.85 (s, 1H) 7.99-8.09 (m, 2H) 8.31 (d, J=1.76 Hz, 1H); m/z (ESI) 470 (M+H)+.

EXAMPLE 30

5-(4-CHLORO-2-METHOXYPHENYL)-N-(1,2,4-THIADIAZOL-5-YL)NAPHTHALENE-2-SULFONAMIDE

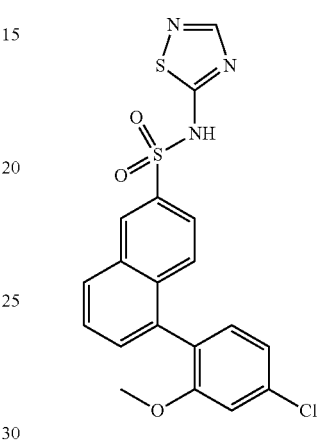

A pressure vial was charged with 5-bromo-N-(2,4-dimethoxybenzyl)-N-(1,2,4-thiadiazol-5-yl)naphthalene-2-sulfonamide (80 mg, 0.154 mmol), tetrakis(triphenylphosphine)palladium(0) (17.76 mg, 0.015 mmol), potassium carbonate (106 mg, 0.769 mmol), (4-chloro-2-methoxyphenyl)boronic acid (57.3 mg, 0.307 mmol), dioxane (1025 μl) and water (512 μl). The vial was swept with nitrogen and sealed with a cap and then heated in a microwave at 100° C. for 30 min. The mixture was purified by reverse phase HPLC (Column: Xbridge 19×100 mm, 5 um, Waters, Milford, Mass., Flow rate: 40 mL/min, Mobile phase: 0.1% TFA in ACN and water). The fractions containing product were dried under a vacuum to afford 5-(4-chloro-2-methoxyphenyl)-N-(1,2,4-thiadiazol-5-yl)naphthalene-2-sulfonamide 2,2,2-trifluoroacetate (10.7 mg, 16 mmol) as a white solid. $^1$H NMR (500 MHz, DMSO-d$_6$) δ ppm −3.67 (s, 3H) 7.16 (dd, J=8.02, 1.95 Hz, 1H) 7.24-7.28 (m, 2H) 7.50-7.58 (m, 2H) 7.67-7.75

(m, 2H) 8.20 (d, J=8.36 Hz, 1H) 8.43 (s, 1H) 8.52 (d, J=1.72 Hz, 1H); m/z (ESI) 432.0 (M+H)⁺.

EXAMPLE 31

5-(2-AMINO-4-CHLOROPHENYL)-N-(1,2,4-THIADIAZOL-5-YL)NAPHTHALENE-2-SULFONAMIDE

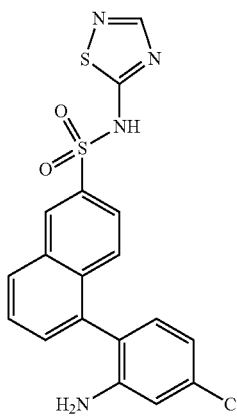

The title compound was prepared in an analogous manner to that of EXAMPLE 30, except that (2-amino-4-chlorophenyl)boronic acid was used in place of (4-chloro-2-methoxyphenyl)boronic acid. ¹H NMR (500 MHz, DMSO-d₆) δ ppm −5.74 (s, 1H) 6.68 (dd, J=8.02, 2.06 Hz, 1H) 6.86 (d, J=2.18 Hz, 1H) 6.95 (d, J=8.02 Hz, 1H) 7.53 (d, J=6.07 Hz, 1H) 7.63 (d, J=8.94 Hz, 1H) 7.69-7.79 (m, 2H) 8.21 (d, J=8.25 Hz, 1H) 8.43 (s, 1H) 8.53 (d, J=1.72 Hz, 1H); m/z (ESI) 416.0 (M+H)⁺.

EXAMPLE 32

2-(6-(N-(1,2,4-THIADIAZOL-5-YL)SULFAMOYL) NAPHTHALEN-1-YL)-5-(TRIFLUOROMETHYL) BENZAMIDE

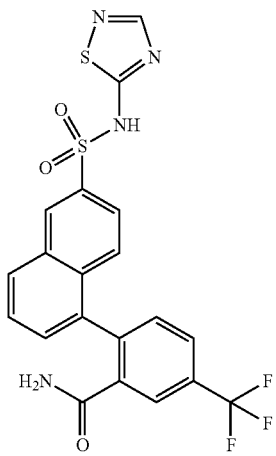 [SMILES: NC(=O)c1cc(C(F)(F)F)ccc1-c1cccc2cc(S(=O)(=O)Nc3ncns3)ccc12]

The title compound was prepared in an analogous manner to that of EXAMPLE 30, except that (2-carbamoyl-4 (trifluoromethyl)phenyl)boronic acid was used in place of (4-chloro-2-methoxyphenyl)boronic acid. ¹H NMR (500 MHz, DMSO-d₆) δ ppm −7.52 (s, 2H) 7.61-7.93 (m, 4H) 7.87 (d, J=8.01 Hz, 1H) 8.04 (d, J=9.28 Hz, 1H) 8.19 (d, J=8.25 Hz, 1H) 8.36 (s, 1H) 8.42 (d, J=1.72 Hz, 1H). 8.57 (d, J=1.98 Hz, 1H); m/z (ESI) 479.0 (M+H)⁺.

EXAMPLE 33

5-(4-CHLORO-2-METHYLPHENYL)-N-(1,2,4-THIADIAZOL-5-YL)NAPHTHALENE-2-SULFONAMIDE

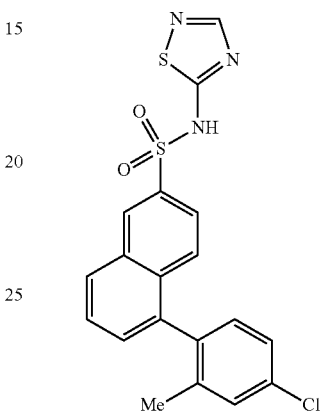

The title compound was prepared in an analogous manner to that of EXAMPLE 30, except that (4-chloro-2-methylphenyl)boronic acid was used in place of (4-chloro-2-methoxyphenyl)boronic acid. ¹H NMR (500 MHz, DMSO-d₆) δ ppm −3.17 (s, 3H) 7.23 (d, J=8.02 Hz, 1H) 7.39 (dd, J=8.08, 2.12 Hz, 1H) 7.46-7.69 (m, 6H) 7.71-7.78 (m, 1H) 8.24 (d, J=8.36 Hz, 1H) 8.44 (s, 1H) 8.56 (d, J=1.83 Hz, 1H); m/z (ESI) 415.0 (M+H)⁺.

EXAMPLE 34

5-(4-CHLOROPHENYL)-N-(1,2,4-THIADIAZOL-5-YL)NAPHTHALENE-2-SULFONAMIDE

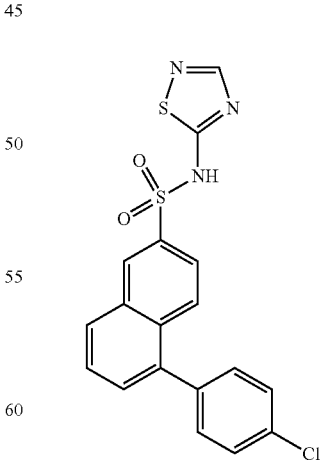

The title compound was prepared in an analogous manner to that of EXAMPLE 30, except that (4-chlorophenyl)boronic acid was used in place of (4-chloro-2-methoxyphenyl) boronic acid. ¹H NMR (500 MHz, DMSO-d₆) δ ppm 7.48-

7.55 (m, 2H) 7.57-7.63 (m, 3H) 7.69-7.77 (m, 1H) 7.81 (dd, J=8.94, 1.95 Hz, 1H) 7.91 (d, J=9.05 Hz, 1H) 8.24 (d, J=8.25 Hz, 1H) 8.45 (s, 1H) 8.56 (d, J=1.83 Hz, 1H); m/z (ESI) 401.0 (M+H)$^+$.

EXAMPLE 35

5-(4-CHLORO-2-FLUOROPHENYL)-N-(1,2,4-THIADIAZOL-5-YL)NAPHTHALENE-2-SULFONAMIDE

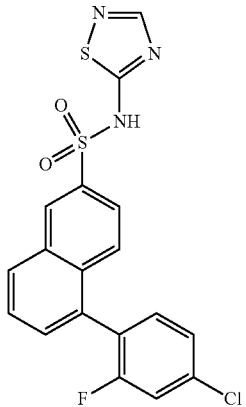 [SMILES: O=S(=O)(Nc1ncns1)c1ccc2c(-c3ccc(Cl)cc3F)cccc2c1]

The title compound was prepared in an analogous manner to that of EXAMPLE 30, except that (4-chloro-2-fluorophenyl)boronic acid was used in place of (4-chloro-2-methoxyphenyl)boronic acid. $^1$H NMR (500 MHz, DMSO-d$_6$) δ ppm −7.46-7.54 (m, 2H) 7.62-7.70 (m, 3H) 7.73-7.83 (m, 2H) 8.30 (d, J=8.25 Hz, 1H) 8.45 (s, 1H) 8.58 (d, J=1.83 Hz, 1H); m/z (ESI) 419.0 (M+H)$^+$.

EXAMPLE 36

5-(2-FLUORO-4-(TRIFLUOROMETHYL)PHENYL)-N-(1,2,4-THIADIAZOL-5-YL)NAPHTHALENE-2-SULFONAMIDE

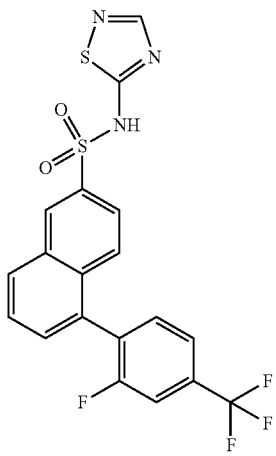 [SMILES: O=S(=O)(Nc1ncns1)c1ccc2c(-c3ccc(C(F)(F)F)cc3F)cccc2c1]

The title compound was prepared in an analogous manner to that of EXAMPLE 30, except that (2-fluoro-4 (trifluoromethyl)phenyl)boronic acid was used in place of (4-chloro-2-methoxyphenyl)boronic acid. $^1$H NMR (500 MHz, DMSO-d$_6$) δ ppm −3.17 (br. s., 1H) 7.67-7.84 (m, 6H) 7.90 (d, J=9.28 Hz, 1H) 8.34 (d, J=8.25 Hz, 1H) 8.45 (s, 1H) 8.60 (d, J=1.72 Hz, 1H); m/z (ESI) 453.0 (M+H)$^+$.

EXAMPLE 37

N-(1,2,4-THIADIAZOL-5-YL)-5-(4-(TRIFLUOROMETHYL)PHENYL)NAPHTHALENE-2-SULFONAMIDE

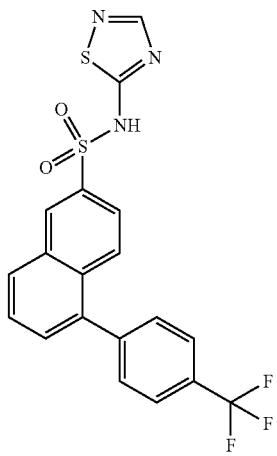 [SMILES: O=S(=O)(Nc1ncns1)c1ccc2c(-c3ccc(C(F)(F)F)cc3)cccc2c1]

The title compound was prepared in an analogous manner to that of EXAMPLE 30, except that (4-(trifluoromethyl)phenyl)boronic acid was used in place of (4-chloro-2-methoxyphenyl)boronic acid. $^1$H NMR (500 MHz, DMSO-d$_6$) δ ppm −7.66 (dd, J=7.05, 0.97 Hz, 1H) 7.71-7.78 (m, 3H) 7.82 (dd, J=8.93, 1.95 Hz, 1H) 7.90 (d, J=8.48 Hz, 3H) 8.29 (d, J=8.25 Hz, 1H) 8.45 (s, 1H) 8.59 (d, J=1.83 Hz, 1H); m/z (ESI) 435.0 (M+H)$^+$.

EXAMPLE 38

5-(2-HYDROXY-4-(TRIFLUOROMETHYL)PHENYL)-N-(1,2,4-THIADIAZOL-5-YL)NAPHTHALENE-2-SULFONAMIDE

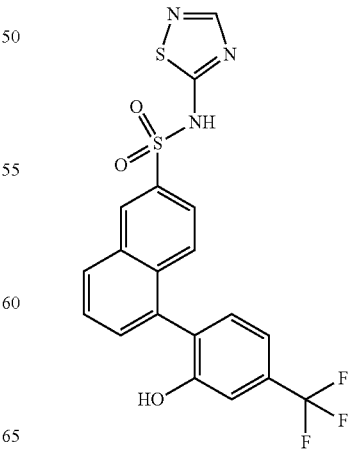

The title compound was prepared in an analogous manner to that of EXAMPLE 30, except that (2-hydroxy-4-(trifluoromethyl)phenyl)boronic acid was used in place of (4-chloro-2-methoxyphenyl)boronic acid. $^1$H NMR (500 MHz, DMSO-d$_6$) δ ppm −7.07 (s, 1H) 7.27-7.33 (m, 2H) 7.41 (d, J=8.25 Hz, 1H) 7.53 (d, J=7.10 Hz, 1H) 7.58 (d, J=8.94 Hz, 1H) 7.63-7.82 (m, 2H) 8.17-8.33 (m, 2H) 8.48 (d, J=1.60 Hz, 1H) 10.17 (s, 1H); m/z (ESI) 452.0 (M+H)$^+$.

EXAMPLE 39

5-(4-CHLORO-2-(TRIFLUOROMETHYL)PHENYL)-N-(1,2,4-THIADIAZOL-5-YL)NAPHTHALENE-2-SULFONAMIDE

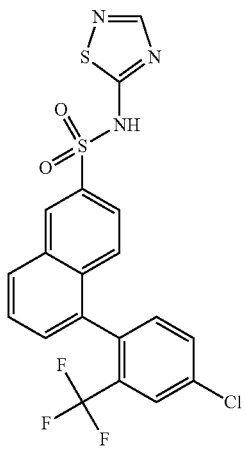 [SMILES: O=S(=O)(Nc1ncns1)c1ccc2c(-c3ccc(Cl)cc3C(F)(F)F)cccc2c1]

The title compound was prepared in an analogous manner to that of EXAMPLE 30, except that (4-chloro-2-(trifluoromethyl)phenyl)boronic acid was used in place of (4-chloro-2-methoxyphenyl)boronic acid. $^1$H NMR (500 MHz, DMSO-d6) δ ppm −6.97 (s, 1H) 7.61 (s, 1H) 7.55 (s, 1H) 7.61-7.65 (m, 1H) 7.51-7.72 (m, 2H) 7.76 (dd, J=8.94, 1.83 Hz, 1H) 7.82 (d, J=2.06 Hz, 1H) 8.04 (s, 1H) 8.36 (d, J=8.48 Hz, 1H) 8.42 (s, 1H); m/z (ESI) 470.0 (M+H)$^+$.

EXAMPLE 40

5-(2,4-DICHLOROPHENYL)-N-(1,2,4-THIADIAZOL-5-YL)NAPHTHALENE-2-SULFONAMIDE

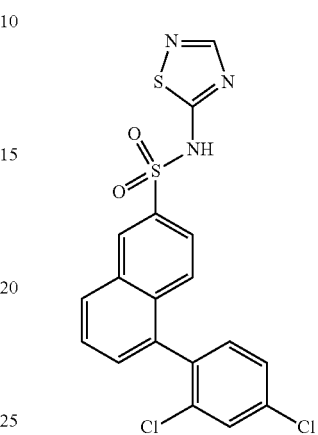

The title compound was prepared in an analogous manner to that of EXAMPLE 30, except that (2,4-dichlorophenyl)boronic acid was used in place of (4-chloro-2-methoxyphenyl)boronic acid. $^1$H NMR (500 MHz, DMSO-d$_6$) δ ppm −6.97 (s, 1H) 7.07 (s, 1H) 7.17 (s, 1H) 7.41-7.49 (m, 1H) 7.51-7.72 (m, 3H) 7.76 (dd, J=8.94, 1.83 Hz, 1H) 7.82 (d, J=2.06 Hz, 1H) 8.10 (s, 1H) 8.22 (d, J=8.48 Hz, 1H) 8.48 (s, 1H). m/z (ESI) 436.0 (M+H)$^+$.

INTERMEDIATE M

INTERMEDIATE M: PERFLUOROPHENYL 5-BROMONAPHTHALENE-2-SULFONATE

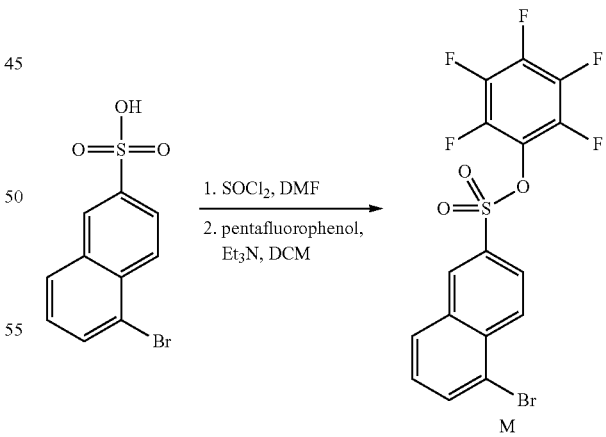

A 15-mL round-bottom flask was charged with 5-bromonaphthalene-2-sulfonic acid (2.346 g, 8.17 mmol) and DMF (8.17 mL) to give a green suspension. Thionyl chloride (1.193 mL, 16.34 mmol) was added dropwise, and the resulting orange mixture was stirred for 2 h. The mixture was poured into ice and extracted with DCM (three times). The combined organic extracts were washed with water, dried over sodium sulfate, filtered and concentrated. The residue was dissolved in DCM (35 mL), and the resulting solution was added to 2,3,4,5,6-pentafluorophenol (2.256 g, 12.26 mmol). Triethylamine (1.708 mL, 12.26 mmol) was added dropwise, and the resulting mixture was stirred for 30 min and then concentrated. The residue was taken up in DCM and filtered. The filtrate was concentrated, and the product was purified by chromatography on silica gel (0 to 20% EtOAc/Heptane) to afford perfluorophenyl 5-bromonaphthalene-2-sulfonate (2.4426 g, 5.39 mmol) as a light-yellow solid. $^1$H NMR (400 MHz, CHLOROFORM-d) δ ppm=8.64-8.46 (m, 2H), 8.13-7.95 (m, 3H), 7.63-7.47 (m, 1H).

INTERMEDIATE N

INTERMEDIATE N: PERFLUOROPHENYL 5-(2-METHOXY-4-(TRIFLUOROMETHYL)PHENYL)NAPHTHALENE-2-SULFONATE

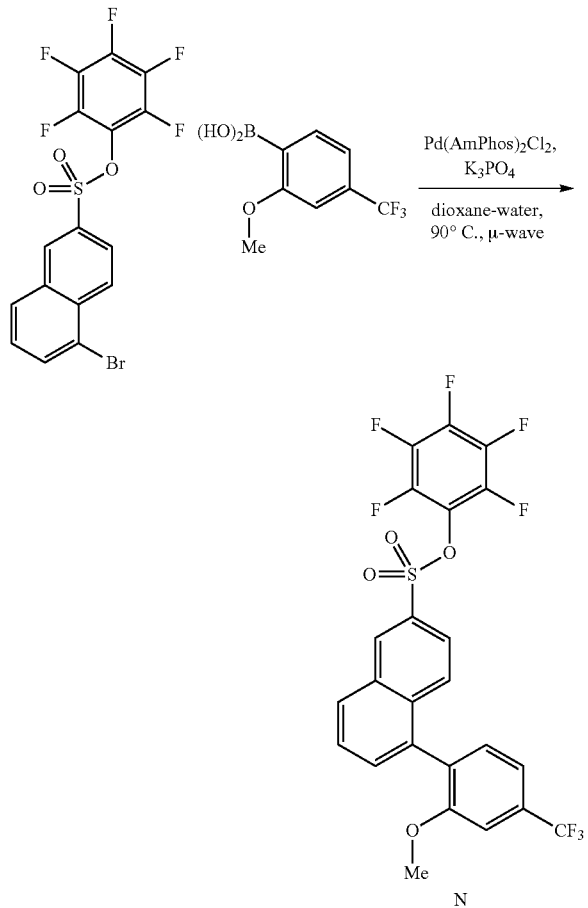

A vial was charged with perfluorophenyl 5-bromonaphthalene-2-sulfonate (285.84 mg, 0.631 mmol), (2-methoxy-4-(trifluoromethyl)phenyl)boronic acid (277 mg, 1.261 mmol), potassium phosphate (402 mg, 1.892 mmol), and Pd(AmPhos)$_2$Cl$_2$ (22.33 mg, 0.032 mmol). The vial was flushed with Ar (g), then dioxane (1577 µl) and water (526 µl) was added. The vial was sealed and heated in a microwave for 20 min at 90° C. The mixture was diluted with water and extracted with EtOAc (three times). The combined organic extracts were dried over sodium sulfate, filtered and concentrated. The product was purified by chromatography on silica gel (0 to 20% EtOAc/Heptane) to give perfluorophenyl 5-(2-methoxy-4-(trifluoromethyl)phenyl)naphthalene-2-sulfonate (228.1 mg, 0.416 mmol) as a white foam. $^1$H NMR (400 MHz, CHLOROFORM-d) δ ppm=8.62 (d, J=1.9 Hz, 1H), 8.07 (d, J=8.2 Hz, 1H), 7.85 (dd, J=2.0, 9.0 Hz, 1H), 7.79-7.71 (m, 2H), 7.64 (dd, J=1.3, 7.1 Hz, 1H), 7.47-7.38 (m, 2H), 7.29 (s, 1H), 3.77 (s, 3H).

EXAMPLE 41

5-(2-METHOXY-4-(TRIFLUOROMETHYL)PHENYL)-N-(THIAZOL-2-YL)NAPHTHALENE-2-SULFONAMIDE

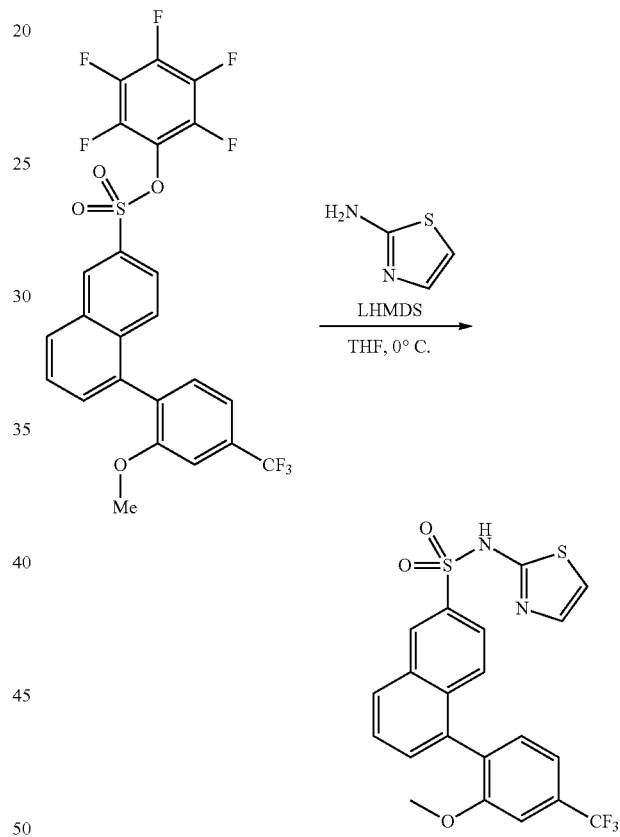

A vial was charged with perfluorophenyl 5-(2-methoxy-4-(trifluoromethyl)phenyl)naphthalene-2-sulfonate (77.62 mg, 0.142 mmol), THF (1415 µl), and thiazol-2-amine (21.26 mg, 0.212 mmol). The vial was cooled in an ice bath for 5 min, then lithium bis(trimethylsilyl)amide (1M in THF) (354 µl, 0.354 mmol) was added dropwise over 1 min. LC/MS after 5 min showed mostly the desired product. After a total of 20 min, the reaction was quenched by the addition of acetic acid (0.1 mL). The resulting mixture was warmed to room temperature and concentrated. The product was purified by chromatography on silica gel (0 to 5% MeOH/DCM) to give 5-(2-methoxy-4-(trifluoromethyl)phenyl)-N-(thiazol-2-yl)naphthalene-2-sulfonamide (59.52 mg, 0.128 mmol) as an off-white foam. $^1$H NMR (400 MHz, DMSO-d$_6$) δ ppm=12.79 (br. s., 1H), 8.51 (d, J=1.9 Hz, 1H), 8.21 (d, J=8.3

Hz, 1H), 7.81-7.65 (m, 2H), 7.57-7.41 (m, 5H), 7.26 (d, J=4.6 Hz, 1H), 6.84 (d, J=4.6 Hz, 1H), 3.73 (s, 3H); m/z (ESI) 465.0 (M+H)⁺.

EXAMPLE 42

5-(2-METHOXY-4-(TRIFLUOROMETHYL)PHENYL)-N-(PYRIMIDIN-4-YL)NAPHTHALENE-2-SULFONAMIDE

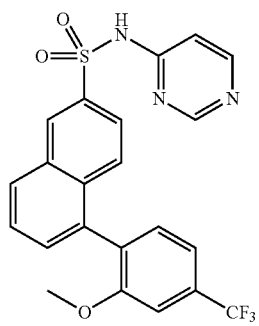 [SMILES: COc1cc(C(F)(F)F)ccc1-c1cccc2cc(S(=O)(=O)Nc3ccncn3)ccc12]

The title compound was prepared in an analogous manner to that of EXAMPLE 41, except that pyrimidin-4-amine was used in place of thiazol-2-amine, and the desired product, 5-(2-methoxy-4-(trifluoromethyl)phenyl)-n-(pyrimidin-4-yl)naphthalene-2-sulfonamide, was isolated as an off-white solid. ¹H NMR (400 MHz, DMSO-d₆) δ ppm=8.66 (s, 1H), 8.58 (s, 1H), 8.34-8.19 (m, 2H), 7.83 (dd, J=1.9, 8.9 Hz, 1H), 7.76-7.67 (m, 1H), 7.54 (t, J=8.3 Hz, 2H), 7.50-7.44 (m, 3H), 7.05 (d, J=6.0 Hz, 1H), 3.72 (s, 3H); m/z (ESI) 459.9 (M+H)⁺.

INTERMEDIATES O, P AND Q

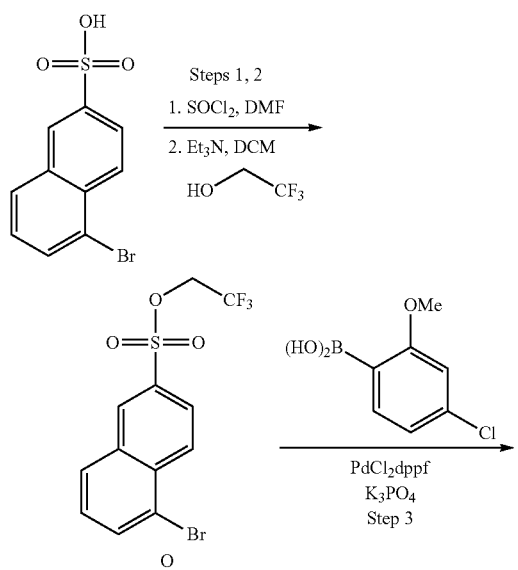

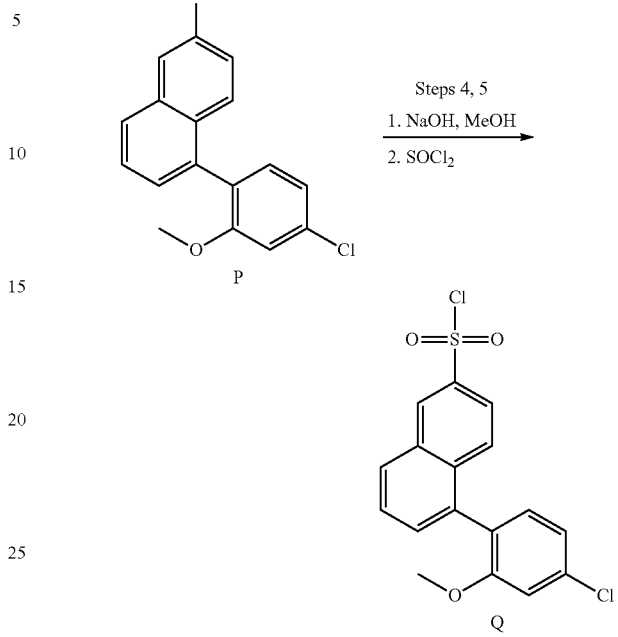

5-BROMONAPHTHALENE-2-SULFONYL CHLORIDE

Step 1: To a round bottom flask was added 5-bromonaphthalene-2-sulfonic acid (5.00 g, 17.41 mmol), followed by DMF (17.41 mL) to generate a deep green heterogeneous solution. Thionyl chloride (2.54 mL, 34.8 mmol) was added dropwise using a syringe at rt, and the solution turned orange and heat was evolved. The solution became homogeneous. The solution was maintained at rt for 18 h. The resulting orange solution was poured into a separatory funnel containing ice and diluted with DCM (200 mL). When the ice melted, the mixture was shaken and then the resulting layers were separated. The aqueous layer was extracted with DCM (1×50 mL). The combined organic layers were washed with water (3×200 mL), then dried over Na₂SO₄ and concentrated to provide 5-bromonaphthalene-2-sulfonyl chloride (5.00 g, 16.36 mmol) as a brown oil, which was used immediately without further purification.

INTERMEDIATE O: 2,2,2-TRIFLUOROETHYL 5-BROMONAPHTHALENE-2-SULFONATE

Step 2: A round bottom flask was charged with 5-bromonaphthalene-2-sulfonyl chloride (5.00 g, 16.36 mmol) and CH₂Cl₂ (16.36 mL) was added. To this solution was added 2,2,2-trifluoroethanol (1.542 mL, 21.27 mmol) followed by triethylamine (3.42 mL, 24.54 mmol). The resulting solution was maintained at rt for 1 h and then concentrated. The residue was purified by MPLC using a silica gel column (80 g) using a 98:2 Heptane:EtOAc to 100% EtOAc gradient to afford 2,2,2-trifluoroethyl 5-bromonaphthalene-2-sulfonate (2.49 g, 6.75 mmol) as a white amorphous solid.

INTERMEDIATE P: 2,2,2-TRIFLUOROETHYL 5-(4-CHLORO-2-METHOXYPHENYL)NAPHTHALENE-2-SULFONATE

Step 3: A vial was charged with 2,2,2-trifluoroethyl 5-bromonaphthalene-2-sulfonate (0.211 g, 0.572 mmol), (4-chloro-2-methoxyphenyl)boronic acid (0.128 g, 0.687 mmol), potassium phosphate (0.486 g, 2.289 mmol), and Pd(dppf)Cl$_2$ CH$_2$Cl$_2$ (0.047 g, 0.057 mmol). The vial was sealed with a septum cap and flushed with N$_2$. Dioxane (2.60 mL) and water (0.260 mL) were added and the mixture was sparged with N$_2$ for 1 minute, then heated at 84° C. for 2 h. The resulting mixture was filtered through diatomaceous Earth® (diatomaceous earth) and concentrated to a residue for purification by MPLC. The residue was taken up in minimal CH$_2$Cl$_2$ and absorbed onto a 5 g loading cartridge and passed through a silica gel column (12 g) using a 98:2 Heptane:EtOAc to 100% EtOAc gradient to afford 2,2,2-trifluoroethyl 5-(4-chloro-2-methoxyphenyl)naphthalene-2-sulfonate (0.176 g, 0.409 mmol) as a colorless amorphous solid.

SODIUM 5-(4-CHLORO-2-METHOXYPHENYL) NAPHTHALENE-2-SULFONATE

Step 4: A round bottomed flask was charged with 2,2,2-trifluoroethyl 5-(4-chloro-2-methoxyphenyl)naphthalene-2-sulfonate (1.729 g, 4.01 mmol) and CH$_2$Cl$_2$ (8.03 mL). Sodium hydroxide (2M in MeOH) (4.01 mL, 8.03 mmol) was added at rt. The solution was capped and maintained at rt for 18 h resulting in a white precipitate. The white solid was collected by vacuum filtration, rinsing with diethyl ether to yield sodium 5-(4-chloro-2-methoxyphenyl)naphthalene-2-sulfonate (1.481 g, 3.99 mmol) as a fluffy white solid. The solid was used directly without further purification.

INTERMEDIATE Q: 5-(4-CHLORO-2-METHOXYPHENYL)NAPHTHALENE-2-SULFONYL CHLORIDE

Step 5: A round bottom flask was charged with sodium 5-(4-chloro-2-methoxyphenyl)naphthalene-2-sulfonate (0.137 g, 0.369 mmol) and a septum was attached and the flask flushed with N$_2$. DMF (1.232 mL) was added followed by thionyl chloride (0.081 mL, 1.108 mmol) by syringe at rt, an exotherm was observed. The solution was maintained at rt for 1 h, and then poured into a separatory funnel containing ice. The resulting mixture was extracted with DCM (2×15 mL). The combined organic layers were washed with water (2×10 mL) and brine (1×10 mL) and dried over Na$_2$SO$_4$ and concentrated to give 5-(4-chloro-2-methoxyphenyl)naphthalene-2-sulfonyl chloride (0.121 g, 0.329 mmol), which was used immediately without further purification.

EXAMPLE 43

5-(4-CHLORO-2-METHOXYPHENYL)-N-(1-(2-(DIMETHYLAMINO)ETHYL)-1H-PYRAZOL-3-YL)NAPHTHALENE-2-SULFONAMIDE

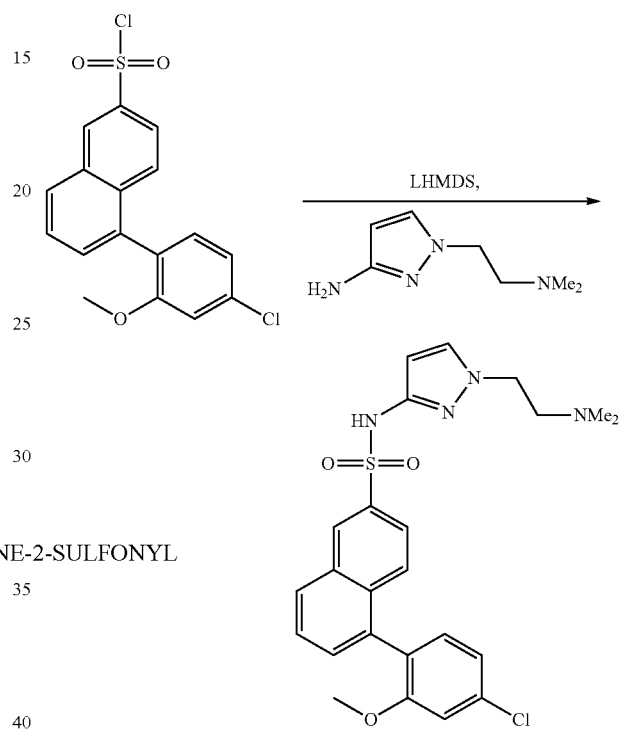

A vial was charged with 1-(2-(dimethylamino)ethyl)-1H-pyrazol-3-amine (76 mg, 0.49 mmol) and then sealed with a septum cap. THF (1 mL) was added under N$_2$ flow and the solution was cooled to −78° C. To the solution was added lithium bis(trimethylsilyl)amide (0.817 μl, 0.817 μmol) using a syringe. The solution as maintained at −78° C. for 25 min, then a THF solution of 5-(4-chloro-2-methoxyphenyl)naphthalene-2-sulfonyl chloride (0.498 μl, 0.408 μmol) was added using a syringe. The solution was then warmed to 0° C., maintained for 20 min and then acetic acid (0.12 mL, 2.0 mmol) was added by syringe. The solution was concentrated and the residue was taken up in minimal MeOH/DMSO and purified by preparative HPLC using a Phenomenex Gemini 5 μm, C$_{18}$, 110 Å column eluting with a mixture of 0.1% TFA in acetonitrile/water: 20 to 90% CH$_3$CN:H$_2$O over 15 min. Clean fractions were combined and concentrated to afford 5-(4-chloro-2-methoxyphenyl)-N-(1-(2-(dimethylamino) ethyl)-1H-pyrazol-3-yl)naphthalene-2-sulfonamide 2,2,2-trifluoroacetate (71.4 mg, 0.12 mmol) as an off white solid. $^1$H NMR (500 MHz, DMSO-d$_6$) δ ppm 2.61 (s, 6H) 3.52 (br. s., 1H) 3.67 (s, 3H) 4.30 (t, J=6.33 Hz, 2H) 6.04 (d, J=2.35 Hz, 1H) 7.17 (dd, J=8.02, 1.95 Hz, 1H) 7.23-7.30 (m, 2H) 7.51-

7.59 (m, 2H) 7.61-7.79 (m, 3H) 8.16 (d, J=8.31 Hz, 1H) 8.50 (d, J=1.72 Hz, 1H) 9.70 (br. s., 1H) 10.71 (s, 1H); m/z (ESI, −ve ion) 483.0 (M−H)⁻.

EXAMPLE 44

5-(4-CHLORO-2-METHOXYPHENYL)-N-(5-METHYLISOXAZOL-3-YL)NAPHTHALENE-2-SULFONAMIDE

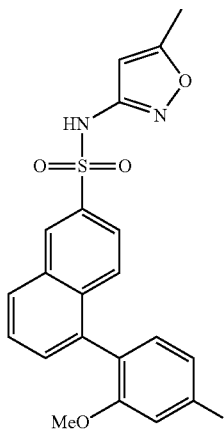

This product was prepared as described in Example 43, employing 5-methylisoxazol-3-amine (48.0 mg, 0.49 mmol) and 5-(4-chloro-2-methoxyphenyl)naphthalene-2-sulfonyl chloride (0.498 μl, 0.408 μmol) to provide 5-(4-chloro-2-methoxyphenyl)-N-(5-methylisoxazol-3-yl)naphthalene-2-sulfonamide (55.8 mg, 0.13 mmol) as an off-white solid. ¹H NMR (500 MHz, DMSO-d₆) δ ppm 2.27 (s, 3H), 3.67 (s, 3H), 6.19 (s, 1H), 7.12-7.21 (m, 1H), 7.23-7.31 (m, 2H), 7.53-7.64 (m, 2H), 7.69-7.81 (m, 2H), 8.21 (d, J=8.30 Hz, 1H), 8.59 (d, J=1.78 Hz, 1H), 11.55 (br. s., 1H); m/z (ESI, +ve ion) 429.9 (M+H)⁺.

EXAMPLE 45

5-(4-CHLORO-2-METHOXYPHENYL)-N-(OXAZOL-2-YL)NAPHTHALENE-2-SULFONAMIDE

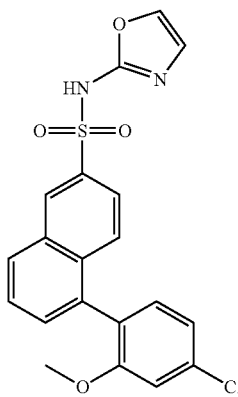

This product was prepared as described in EXAMPLE 43 using 2-aminoxazole instead of 1-(2-(dimethylamino)ethyl)-1H-pyrazol-3-amine. The mixture was purified by MPLC. The residue was taken up in minimal CH₂Cl₂ and absorbed onto a 5 g silica loading column and passed through a silica gel column (40 g), eluting with a gradient of 5% to 100% EtOAc in heptanes, to provide 5-(4-chloro-2-methoxyphenyl)-N-(oxazol-2-yl)naphthalene-2-sulfonamide (0.018 g, 0.043 mmol) as white solid. ¹H NMR (400 MHz, DMSO-d₆) δ ppm 3.69 (s, 3H) 7.17 (dd, J=8.02, 1.96 Hz, 1H) 7.24-7.31 (m, 3H) 7.48-7.57 (m, 2H) 7.60 (d, J=1.66 Hz, 1H) 7.69 (dd, J=8.27, 7.09 Hz, 1H) 7.79 (dd, J=8.90, 1.96 Hz, 1H) 8.16 (d, J=8.41 Hz, 1H) 8.55 (d, J=1.96 Hz, 1H); m/z (ESI, +ve ion) 414.9 (M+H)⁺.

EXAMPLE 46

5-(4-CHLORO-2-METHOXYPHENYL)-N-(THIAZOL-2-YL)NAPHTHALENE-2-SULFONAMIDE

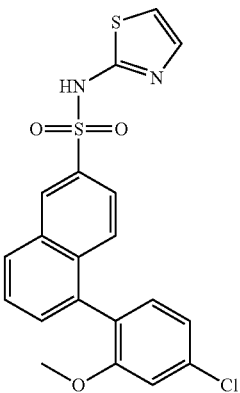 [SMILES: COc1cc(Cl)ccc1-c1cccc2cc(S(=O)(=O)Nc3nccs3)ccc12]

The title compound was prepared as described in EXAMPLE 43, using 2-aminothiazole instead of 1-(2-(dimethylamino)ethyl)-1H-pyrazol-3-amine. The residue was taken up in minimal CH₂Cl₂ and absorbed onto a 5 g silica loading column and passed through a silica gel column (12 g), eluting with a gradient of 0% to 100% EtOAc in heptanes, to provide 5-(4-chloro-2-methoxyphenyl)-N-(thiazol-2-yl)naphthalene-2-sulfonamide (0.015 g, 0.035 mmol) as a tan solid. ¹H NMR (400 MHz, DMSO-d₆) δ ppm 3.68 (s, 3H) 6.84 (d, J=4.60 Hz, 1H) 7.17 (d, J=7.73 Hz, 1H) 7.22-7.31 (m, 3H) 7.52 (dd, J=19.95, 7.92 Hz, 2H) 7.63-7.79 (m, 2H) 8.18 (d, J=8.31 Hz, 1H) 8.50 (s, 1H); m/z (ESI, +ve ion) 430.8 (M+H)$^+$.

INTERMEDIATES R, S AND T

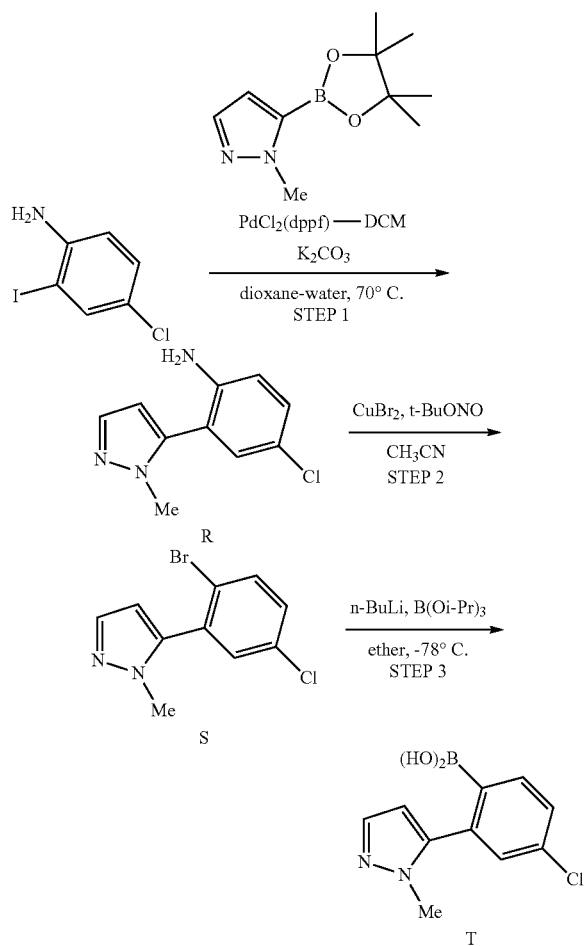

INTERMEDIATE R: 4-CHLORO-2-(1-METHYL-1H-PYRAZOL-5-YL)ANILINE

Step 1: A 250-mL round-bottomed flask was charged with 4-chloro-2-iodoaniline (6.189 g, 24.42 mmol), 1-methyl-5-(4,4,5,5-tetramethyl-1,3,2-dioxaborolan-2-yl)-1H-pyrazole (7.62 g, 36.6 mmol), potassium carbonate (13.50 g, 98 mmol), and Pd(dppf) Cl$_2$CH$_2$Cl$_2$ (0.997 g, 1.221 mmol). The flask was flushed with Ar, then 1,4-dioxane (61.0 mL) and water (20.35 mL) were added in sequence. A reflux condenser was attached, and the flask was heated to 70° C. for 4 h. After being cooled to room temperature, the mixture was diluted with water and EtOAc, which resulted in an emulsion (a small amount of brine was added to clear the emulsion). The layers were separated, and the aq. layer was extracted with EtOAc (twice). The combined organic extracts were dried over sodium sulfate, filtered and concentrated. The residue was partially purified by chromatography on silica gel (30 to 80% EtOAc/Heptane). The partially purified product was taken up in a boiling mixture of heptane (100 mL) and EtOAc (5 mL) to give a murky solution. A 250 mL flask containing the solid was charged with heptane (100 mL). The mixture was cooled to room temperature after 3 h, then the solid was collected by filtration, washed with heptane (3×50 mL), and dried under a stream of N$_2$ for 20 min to give 4-chloro-2-(1-methyl-1H-pyrazol-5-yl)aniline (3.732 g, 17.97 mmol) as a light purple solid. $^1$H NMR (400 MHz, DMSO-d$_6$) δ ppm=7.50 (d, J=1.9 Hz, 1H), 7.16 (dd, J=2.6, 8.7 Hz, 1H), 7.02 (d, J=2.5 Hz, 1H), 6.78 (d, J=8.7 Hz, 1H), 6.29 (d, J=1.8 Hz, 1H), 5.07 (s, 2H), 3.65 (s, 3H). m/z (ESI) 208.2 (M+H)$^+$.

INTERMEDIATE S: 5-(2-BROMO-5-CHLOROPHENYL)-1-METHYL-1H-PYRAZOLE

Step 2: A 100-mL flask was charged with copper(II) bromide (2.472 g, 11.07 mmol) and acetonitrile (45 mL) to give a green suspension. 1,1-Dimethylethyl nitrite (1.462 mL, 11.07 mmol) was added, and the resulting dark green mixture was stirred for 20 min. The flask was cooled in an ice bath for 10 min, then a solution of 4-chloro-2-(1-methyl-1H-pyrazol-5-yl)aniline (1.149 g, 5.53 mmol) in acetonitrile (5 mL with a 2 mL flask/syringe wash) was added dropwise. The resulting mixture was stirred for 72 h at room temperature. The mixture was diluted with water and extracted with EtOAc (three times), and the combined organic extracts were dried over sodium sulfate, filtered and concentrated. The residue was purified twice by chromatography on silica gel (0 to 100% EtOAc/Heptane) to give 5-(2-bromo-5-chlorophenyl)-1-methyl-1H-pyrazole (0.9923, 3.65 mmol) as a brown oil. m/z (ESI) 271.0 (M+H)$^+$.

INTERMEDIATE T: (4-CHLORO-2-(1-METHYL-1H-PYRAZOL-5-YL)PHENYL)BORONIC ACID

Step 3: A 50-mL round-bottom flask was charged with 5-(2-bromo-5-chlorophenyl)-1-methyl-1H-pyrazole (992.0 mg, 3.65 mmol), diethyl ether (18 mL), and triisopropyl borate (1 mL, 4.38 mmol). The flask was cooled in a dry ice-acetone bath for 10 min, then n-BuLi (1.91 mL, 4.38 mmol) was added dropwise over a couple of minutes. Following the addition, the cooling bath was removed, and the mixture was warmed to room temperature. An aq. 2N NaOH solution (20 mL, 40 mmol) was added, and the resulting mixture was stirred vigorously for 2 h. The mixture was diluted with water and diethyl ether. The layers were separated, and the ethereal layer was extracted with water (twice). The aq. layers were combined, and the combined aq. mixture as washed with diethyl ether. The etheral layer was back-extracted once more, and the aq. layers were all combined. The combined aq. solution was acidified to about pH 1 with 3N aq. HCl to give a clear solution. The aq. solution was extracted with EtOAc (three times), and the combined organic extracts were dried over sodium sulfate, filtered and concentrated. The residue was taken up in DCM and concentrated under a vacuum to give (4-chloro-2-(1-methyl-1H- pyrazol-5-yl)phenyl)boronic acid (660 mg, 2.79 mmol) as a light-yellow foam. m/z (ESI) 237.0 (M+H)+.

INTERMEDIATES U AND V

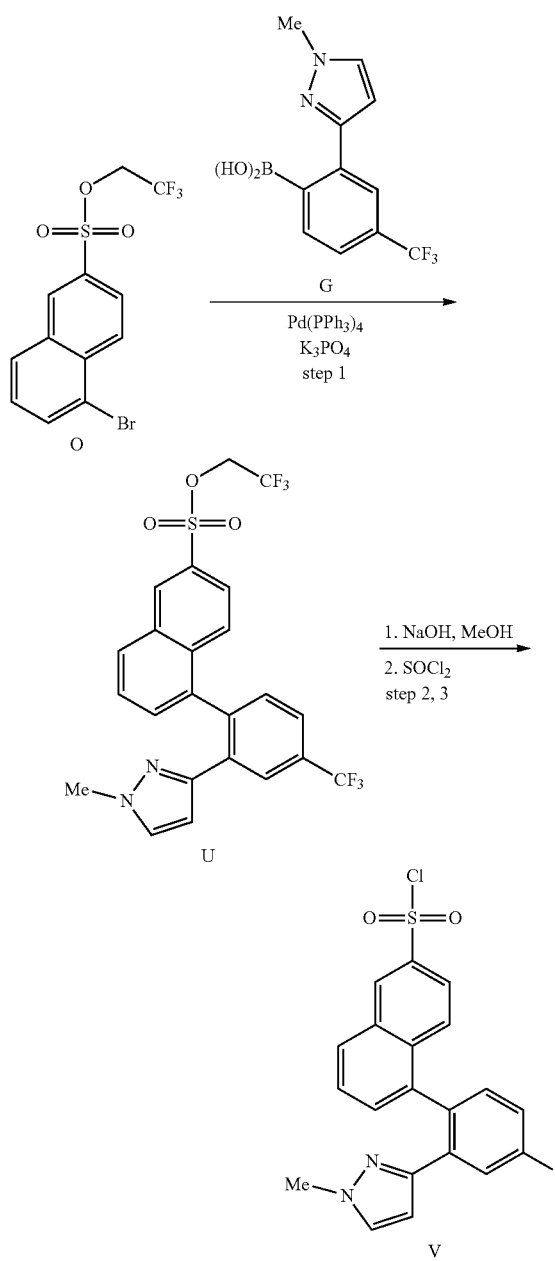

INTERMEDIATE U: 2,2,2-TRIFLUOROETHYL 5-(2-(1-METHYL-1H-PYRAZOL-3-YL)-4-(TRIFLUOROMETHYL)PHENYL)NAPHTHALENE-2-SULFONATE

Step 1: A reaction vial was charged with 2,2,2-trifluoroethyl 5-bromonaphthalene-2-sulfonate (0.082 g, 0.222 mmol), (2-(1-methyl-1H-pyrazol-5-yl)-4-(trifluoromethyl)phenyl)boronic acid (0.072 g, 0.267 mmol), potassium phosphate tribasic (0.074 mL, 0.889 mmol) and Pd(PPh$_3$)$_4$ (0.026 g, 0.022 mmol). To this solid mixture was added dioxane (1.010 mL) followed by water (0.101 mL). The head space of the vial was swept with nitrogen and the vial was heated in an oil bath to 80° C. After stirring for 2 hours, LC/MS indicated that the reaction was complete. This reaction mixture was transferred to a separatory funnel containing water and the aqueous layer was washed three times with EtOAc. The organic layers were combined, dried with MgSO$_4$, filtered and concentrated to an oil. The mixture was concentrated and purified by MPLC using 80 g of silica gel eluting with 0 to 40% EtOAc in hexanes to afford 0.11 g of 2,2,2-trifluoroethyl 5-(2-(1-methyl-1H-pyrazol-3-yl)-4-(trifluoromethyl)phenyl)naphthalene-2-sulfonate.

INTERMEDIATE V: 5-(2-(1-METHYL-1H-PYRAZOL-3-YL)-4-(TRIFLUOROMETHYL)PHENYL) NAPHTHALENE-2-SULFONIC ACID

Step 2: To a solution of 2,2,2-trifluoroethyl 5-(2-(1-methyl-1H-pyrazol-5-yl)-4-(trifluoromethyl)phenyl)naphthalene-2-sulfonate (0.11 g, 0.214 mmol) in DCM (1.425 mL) at room temperature was added sodium hydroxide (2M in MeOH) (0.225 mL, 0.449 mmol). The resulting solution was stirred for overnight. The solution was then diluted with DCM and transferred to a separatory funnel containing water. The water layer was washed twice with DCM, separated and concentrated to a solid. This solid was taken to the next step without further purification. m/z (ESI, +ve ion) 431.1 (M−1).

Step 3: To a solution of 5-(2-(1-methyl-1H-pyrazol-5-yl)-4-(trifluoromethyl)phenyl)naphthalene-2-sulfonic acid (from Step 2) (0.093 g, 0.214 mmol) in DMF (0.428 mL) was added thionyl chloride (0.031 mL, 0.428 mmol) at 0° C. After 20 minutes LC/MS indicated that the sulfonic acid starting material was converted to the desired product. The reaction mixture was then transferred to a separatory funnel containing water and DCM. The layers were separated and the organic layer was washed twice with water. The resulting organic layer was dried with MgSO$_4$, filtered and concentrated to an oil. m/z (ESI, +ve ion) 450.9 (M+1).

EXAMPLE 47

5-(2-(1-METHYL-1H-PYRAZOL-5-YL)-4-(TRIFLUOROMETHYL)PHENYL)-N-(THIAZOL-2-YL)NAPHTHALENE-2-SULFONAMIDE

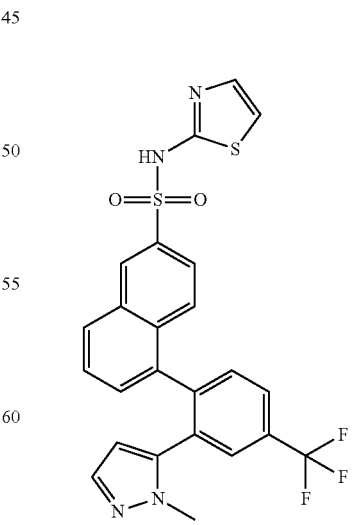

A round bottom flask was charged with 2-aminothiazole (20.26 mg, 0.202 mmol) and sealed with septum. THF (1686

μl) was added and the solution was cooled to 0° C. A THF solution of lithium bis(trimethylsilyl)amide (253 μl, 0.253 mmol, 1 M) was added and the solution was maintained at 0° C. for 5 min To this solution was added 5-(2-(1-methyl-1H-pyrazol-5-yl)-4-(trifluoromethyl)phenyl)naphthalene-2-sulfonyl chloride (76.0 mg, 0.169 mmol) as a solution in THF (3 mL total). After 15 minutes at 0° C., saturated aqueous NH$_4$Cl (1 mL) was added to the reaction mixture. The reaction mixture was partitioned between saturated aqueous NH$_4$Cl (10 mL) and EtOAc (15 mL). The layers were separated and the aqueous layer was extracted with EtOAc (2×10 mL). The combined organic extracts were dried over Na$_2$SO$_4$ and concentrated under a vacuum. The residue was taken up in minimal DMSO and purified by preparative HPLC (column: Phenomenex C$_{18}$ 150×30 mm, 5 μm (Phenomenex, Torrance, Calif.): 20 to 90% CH$_3$CN:H$_2$O (1% TFA modifier) over 15 min). Fractions were combined and concentrated to afford 5-(2-(1-methyl-1H-pyrazol-5-yl)-4-(trifluoromethyl)phenyl)-N-(thiazol-2-yl)naphthalene-2-sulfonamide (50.0 mg, 0.097 mmol) as a white amorphous solid. $^1$H NMR (400 MHz, d$_6$-acetone) δ ppm 3.50 (s, 3H) 5.84 (d, J=1.86 Hz, 1H) 6.74 (d, J=4.69 Hz, 1H) 7.02 (d, J=1.96 Hz, 1H) 7.19 (d, J=4.70 Hz, 1H) 7.46 (d, J=7.04 Hz, 1H) 7.51-7.59 (m, 1H) 7.64 (d, J=8.90 Hz, 1H) 7.72 (d, J=8.02 Hz, 1H) 7.75-7.82 (m, 1H) 7.87 (s, 1H) 7.94 (d, J=8.12 Hz, 1H) 8.05 (d, J=8.31 Hz, 1H) 8.44 (s, 1H); m/z (ESI, +ve ion) 515.2 (M+H)$^+$.

INTERMEDIATES W, X AND Y

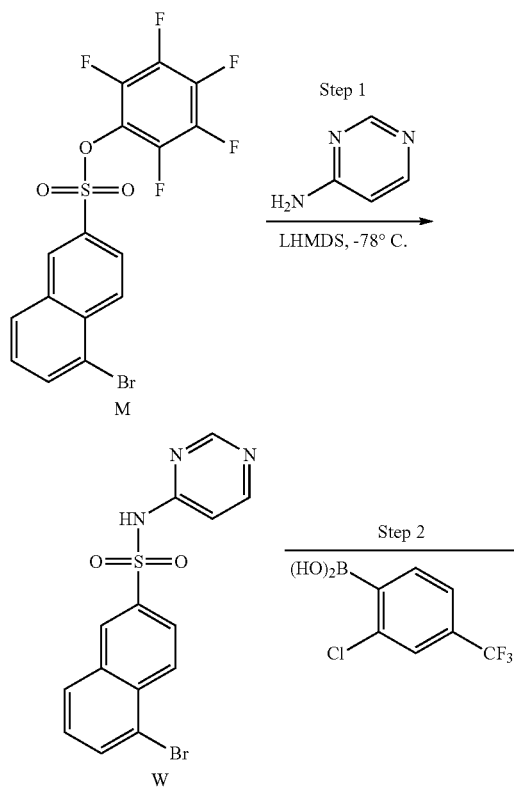

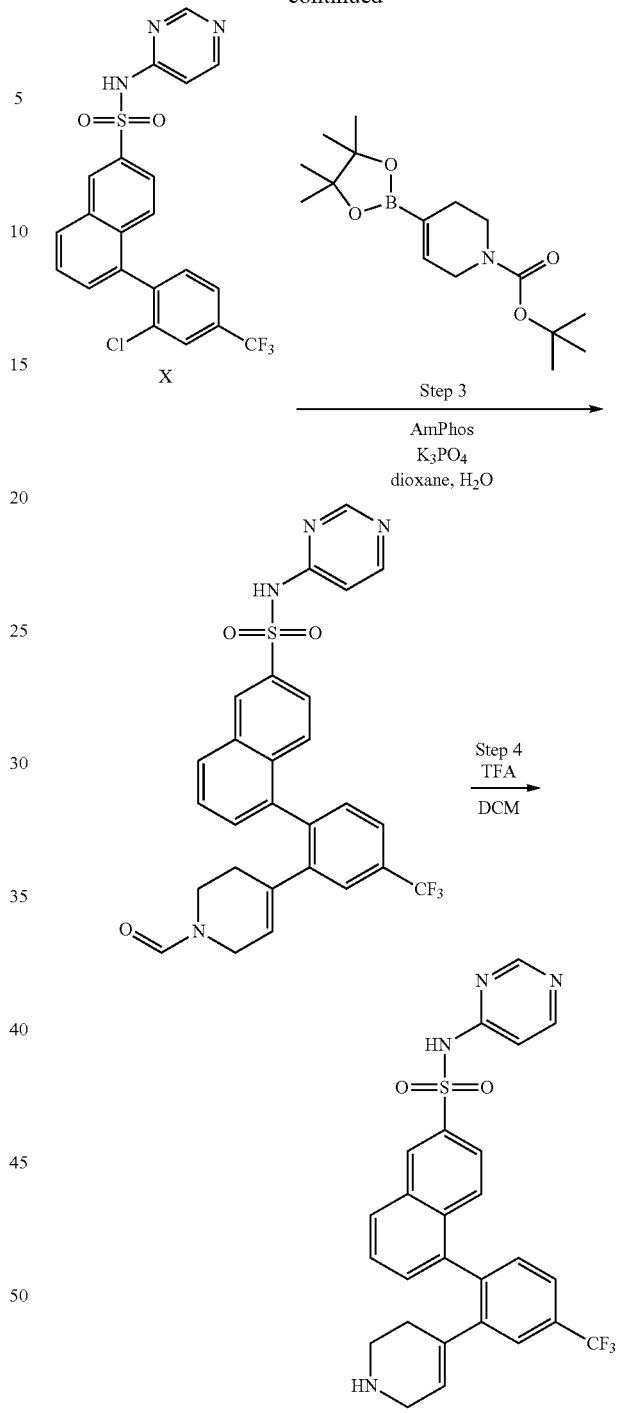

INTERMEDIATE W: 5-BROMO-N-(PYRIMIDIN-4-YL)NAPHTHALENE-2-SULFONAMIDE

Step 1: A round bottom flask was charged with perfluorophenyl 5-bromonaphthalene-2-sulfonate (Intermediate M) (0.677 g, 1.494 mmol) and pyrimidin-4-amine (0.185 g, 1.942 mmol). A septum was attached and the flask flushed with N$_2$. THF (7.47 mL) was added and the solution was cooled to −78° C., lithium bis(trimethylsilyl)amide (1.195 mL, 1.195 mmol) was added and after addition was complete, the cold bath was removed and the solution was allowed to warm to rt. After 30 min at rt, acetic acid (0.257 mL, 4.48 mmol) was added to the solution to produce a precipitate. The mixture was concentrated and the resulting tan solid was suspended in DCM (20 mL) and collected by vacuum filtration to provide 5-bromo-N-(pyrimidin-4-yl)naphthalene-2-sulfonamide (0.54 g) as a tan solid, which was of sufficient purity for further use.

INTERMEDIATE X: 5-(2-CHLORO-4-(TRIFLUO-ROMETHYL)PHENYL)-N-(PYRIMIDIN-4-YL)NAPHTHALENE-2-SULFONAMIDE

Step 2: A microwave vial was charged with 5-bromo-N-(pyrimidin-4-yl)naphthalene-2-sulfonamide (Intermediate W) (0.508 g, 1.395 mmol), (2-chloro-4-(trifluoromethyl)phenyl)boronic acid (0.469 g, 2.092 mmol), potassium phosphate (0.888 g, 4.18 mmol), and 1,1-bis[(di-t-butyl-p-methylaminophenyl]palladium(ii) chloride (0.099 g, 0.139 mmol). The vial was sealed with a septum cap and flushed with $N_2$. Dioxane (3.49 mL) and water (1.162 mL) were added and the mixture was sparged for 5 min with $N_2$. The mixture was heated in a microwave at 90° C. for 30 min. The resulting mixture was diluted with EtOAc (5 mL) and decanted from insoluble solids. The resulting solution was concentrated for purification by MPLC. The residue was taken up in minimal $CH_2Cl_2$ and absorbed onto a 5 g loading cartridge and passed through a silica gel column (12 g) using a 98:2 Heptane:EtOAc (with 5% EtOH additive) to 100% EtOAc (5% EtOH additive) gradient to afford 5-(2-chloro-4-(trifluoromethyl)phenyl)-N-(pyrimidin-4-yl)naphthalene-2-sulfonamide (0.485 g, 1.046 mmol) as a orange amorphous solid.

INTERMEDIATE Y: TERT-BUTYL 4-(2-(6-(N-(PYRIMIDIN-4-YL)SULFAMOYL)NAPHTHA-LEN-1-YL)-5-(TRIFLUOROMETHYL)PHENYL)-5,6-DIHYDROPYRIDINE-1(2H)-CARBOXYLATE

Step 3: A microwave vial was charged with 5-(2-chloro-4-(trifluoromethyl)phenyl)-N-(pyrimidin-4-yl)naphthalene-2-sulfonamide (Intermediate X) (82.5 mg, 0.178 mmol), tert-butyl 4-(4,4,5,5-tetramethyl-1,3,2-dioxaborolan-2-yl)-5,6-dihydropyridine-1(2H)-carboxylate (110 mg, 0.356 mmol), potassium phosphate (113 mg, 0.534 mmol), and 1,1-bis[(di-t-butyl-p-methylaminophenyl]palladium(II) chloride (12.59 mg, 0.018 mmol). The vial was sealed, flushed with $N_2$ and dioxane (1334 µl) and water (445 µl) was added. The mixture was sparged for 5 min with $N_2$. The mixture was heated in a microwave at 110° C. for 4 h. The mixture was concentrated for purification by MPLC. The residue was taken up in minimal $CH_2Cl_2$ and absorbed onto a 5 g loading cartridge and passed through a silica gel column (12 g) using a 98:2 Heptane:EtOAc to 100% EtOAc (with 1% constant EtOH additive) gradient to afford tert-butyl 4-(2-(6-(N-(pyrimidin-4-yl)sulfamoyl)naphthalen-1-yl)-5-(trifluoromethyl)phenyl)-5,6-dihydropyridine-1(2H)-carboxylate (50.0 mg, 0.082 mmol) as a light-yellow amorphous solid.

EXAMPLE 48

N-(PYRIMIDIN-4-YL)-5-(2-(1,2,3,6-TETRAHY-DROPYRIDIN-4-YL)-4-(TRIFLUOROMETHYL) PHENYL)NAPHTHALENE-2-SULFONAMIDE

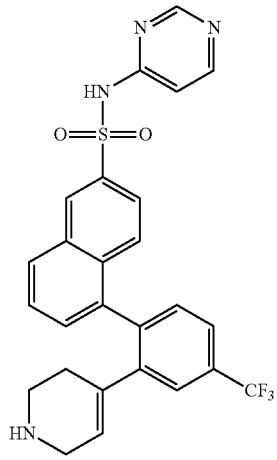 [SMILES: O=S(=O)(Nc1ccncn1)c1ccc2c(-c3ccc(C(F)(F)F)cc3C3=CCNCC3)cccc2c1]

Step 4: A round bottom flask was charged with tert-butyl 4-(2-(6-(N-(pyrimidin-4-yl)sulfamoyl)naphthalen-1-yl)-5-(trifluoromethyl)phenyl)-5,6-dihydropyridine-1(2H)-carboxylate (Intermediate Y) (0.031 g, 0.051 mmol) and DCM (0.508 mL) and trifluoroacetic acid (3.91 µl, 0.051 mmol) was added. The resulting solution was maintained at rt for 18 h and then concentrated. The residue was taken up in minimal MeOH/DMSO and purified by preparative HPLC (Phenomenex $C_{18}$ 150×30 mm, 5 µm: 25 to 85% $CH_3CN:H_2O$ (1% TFA modifier) over 15 min). Fractions were combined and concentrated to afford N-(pyrimidin-4-yl)-5-(2-(1,2,3,6-tetrahydropyridin-4-yl)-4-(trifluoromethyl)phenyl)naphthalene-2-sulfonamide 2,2,2-trifluoroacetate (8.8 mg, 0.014 mmol) as a colorless film. $^1$H NMR (400 MHz, $CD_3OD$) δ ppm 1.98-2.28 (m, 2H) 2.73-2.97 (m, 2H) 3.41-3.62 (m, 2H) 5.70 (dt, J=3.15, 1.60 Hz, 1H) 7.16 (dd, J=6.36, 1.08 Hz, 1H) 7.52 (d, J=8.02 Hz, 1H) 7.60 (dd, J=7.04, 1.17 Hz, 1H) 7.64 (d, J=9.00 Hz, 1H) 7.68-7.82 (m, 3H) 7.94 (dd, J=8.90, 1.96

Hz, 1H) 8.17 (d, J=8.31 Hz, 1H) 8.30 (d, J=6.06 Hz, 1H) 8.59 (s, 1H) 8.71 (d, J=1.86 Hz, 1H); m/z (ESI, +ve ion) 510.9 (M+H)⁺.

INTERMEDIATE Z

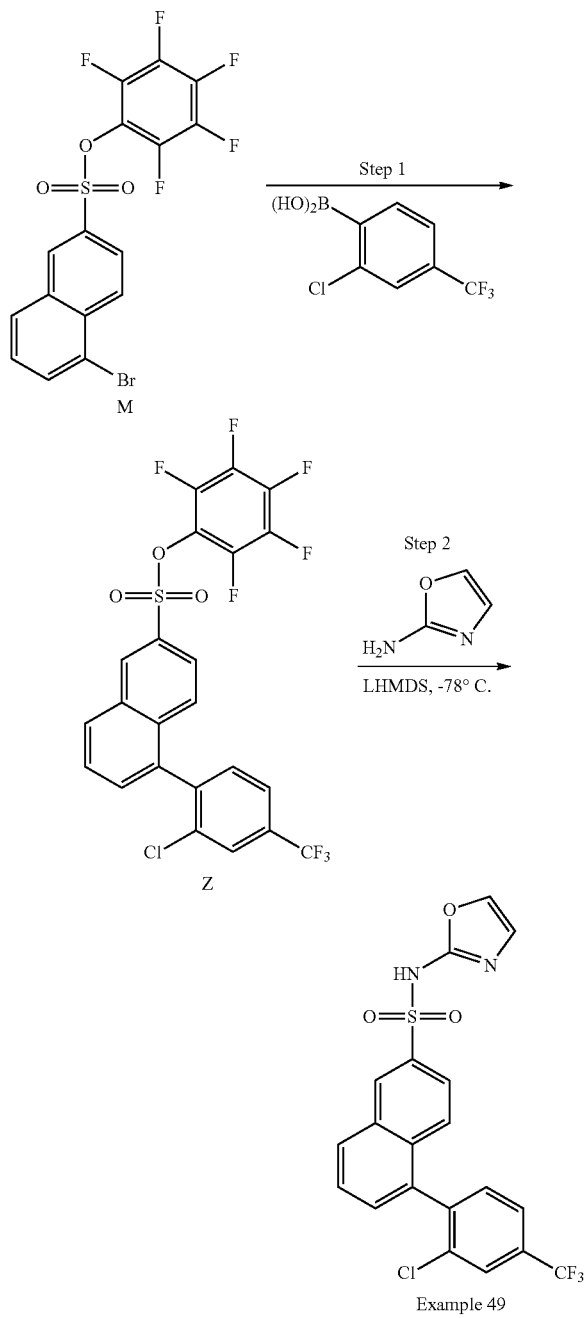

INTERMEDIATE Z: PERFLUOROPHENYL 5-(2-CHLORO-4-(TRIFLUOROMETHYL)PHENYL) NAPHTHALENE-2-SULFONATE

Step 1: This product was prepared as described in EXAMPLE 48, Step 2 using perfluorophenyl 5-bromonaphthalene-2-sulfonate (Intermediate M) instead of 5-bromo-N-(pyrimidin-4-yl)naphthalene-2-sulfonamide. The residue was taken up in minimal CH₂Cl₂ and absorbed onto a 5 g loading cartridge and passed through a silica gel column (40 g) using a gradient from 5% to 100% EtOAc to Heptanes to give desired product perfluorophenyl 5-(2-chloro-4-(trifluoromethyl)phenyl)naphthalene-2-sulfonate (0.530 g, 0.959 mmol) as an orange oil, which was of sufficient purity for further use.

EXAMPLE 49

5-(2-CHLORO-4-(TRIFLUOROMETHYL)PHENYL)-N-(OXAZOL-2-YL)NAPHTHALENE-2-SULFONAMIDE

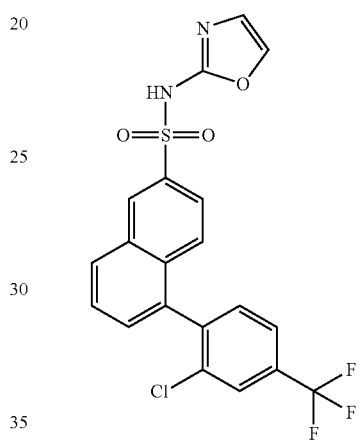

Step 2: This product was prepared as described in EXAMPLE 41, using perfluorophenyl 5-(2-chloro-4-(trifluoromethyl)phenyl)naphthalene-2-sulfonate and oxazole-2-amine instead of perfluorophenyl 5-bromonaphthalene-2-sulfonate and thiazole-2-amine. The residue was taken up in minimal CH₂Cl₂ and absorbed onto a 5 g loading cartridge and passed through a silica gel column (12 g) using a gradient from 5% to 100% EtOAc to Heptanes and then triturated with an IPA/DCM/Heptanes mixture to give desired product 5-(2-chloro-4-(trifluoromethyl)phenyl)-N-(oxazol-2-yl)naphthalene-2-sulfonamide (0.010 g, 0.022 mmol) as an off-white solid. ¹H NMR (400 MHz, CHLOROFORM-d) δ ppm 6.88 (d, J=1.76 Hz, 2H) 7.09 (d, J=1.76 Hz, 1H) 7.45-7.60 (m, 3H) 7.62-7.78 (m, 2H) 7.82-7.96 (m, 2H) 8.08 (d, J=8.61 Hz, 1H) 8.60 (d, J=1.76 Hz, 1H); m/z (ESI, +ve ion) 453.0 (M+H)⁺.

INTERMEDIATE AAA

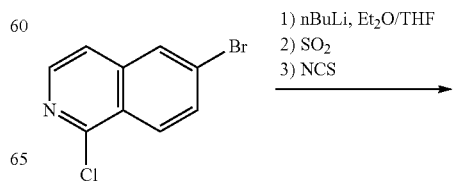

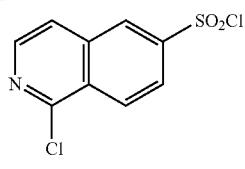

AAA

INTERMEDIATE AAA: 1-CHLOROISOQUINOLINE-6-SULFONYL CHLORIDE

A 1 L round bottom flask was charged with 6-bromo-1-chloro-isoquinoline (10.1 g, 41.6 mmol) and diethyl ether (416 mL) and THF (41.6 mL, 41.6 mmol) to give a light yellow solution. The flask was cooled in a dry ice and acetone bath for 20 min, then 2.5 M n-butyllithium in hexanes (18.3 mL, 43.6 mmol) was added dropwise over 5 min to give a dark solution. After 10 min, LC/MS of an aliquot in MeOH showed conversion of 6-bromo-1-chloro-isoquinoline to mainly 1-chloroisoquinoline. Sulfur dioxide (g) was condensed into the reaction mixture from a lecture bottle (warmed by a warm water bath to make sure there was a positive pressure of $SO_2(g)$ which was monitored by an oil bubbler) using a needle for 15 min to give a yellow suspension. After 20 min, LC/MS of an aliquot in MeOH showed consumption of 6-bromo-1-chloro-isoquinoline to 1-chloroisoquinoline-6-sulfinic acid. The chlorination step should be performed at −78° C. Solid n-chlorosuccinimide (5.55 g, 41.6 mmol) was added in three portions at −78° C. The cold bath was removed and the mixture was warmed to room temperature. After 2 hours, 1.2 g of NCS and 100 mL of THF were added at room temperature. After stirring for another 30 min at room temperature, LC/MS of an aliquot in MeOH showed mainly sulfonyl chloride product. After another 30 min, the solid was filtered with an aid of 100 mL of THF. The yellow filtrate was concentrated and placed under vacuum overnight to afford a yellow solid. The next day, the solid was triturated with i-PrOH (30 mL) at room temperature, filtered quickly (left on the frit for less than 3 min), and dried under a vacuum to give a beige solid. The filtrate was concentrated, absorbed onto a plug of silica gel, and purified by chromatography through a silica gel column (120 g), eluting with a gradient of 0% to 20% EtOAc in heptane, to provide a second batch. MS (ESI): 262 [M+H]$^+$; $^1$H NMR (400 MHz, CDCl$_3$) δ ppm 7.82 (d, J=5.2 Hz, 1H), 8.23 (dd, J=9.00, 1.96 Hz, 1H), 8.53 (d, J=5.67 Hz, 1H), 8.58-8.65 (m, 2H).

INTERMEDIATES BB, CC AND DD

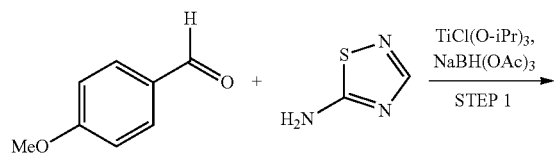

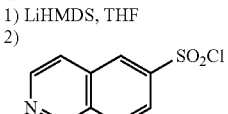

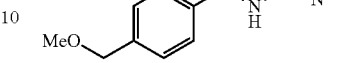

BB

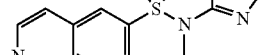

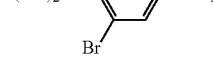

CC

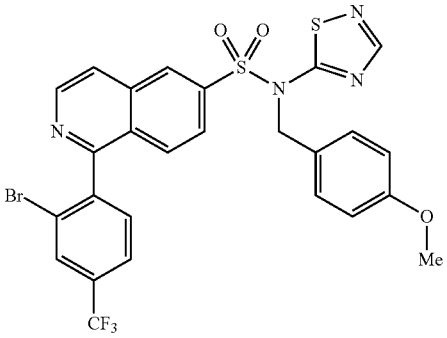

DD

INTERMEDIATE BB. N-(4-METHOXYBENZYL)-1,2,4-THIADIAZOL-5-AMINE

Step 1: To a suspension of 4-methoxybenzaldehyde (10.0 g, 73.4 mmol) and 1,2,4-thiadiazol-5-amine (7.40 g, 73.4 mmol) in dichloromethane (200 mL) was added chlorotitanium triisopropoxide (28.6 g, 110 mmol) portionwise over 5 min. After stirring for 3 hours, sodium triacetoxyborohydride (38.9 g, 184 mmol) was added portionwise at 0° C. and allowed to stir for additional 1 hour. The reaction was cooled in an ice and water mixture, quenched with saturated NaHCO$_3$ solution (300 mL) and extracted with dichloromethane (2×300 mL). The organic layer was separated, dried over Na$_2$SO$_4$, filtered and concentrated to obtain the product, which was purified by column chromatography using silica gel (100 to 200 mesh) and 0 to 30% ethyl acetate in hexane to give 5.5 g of as an off-white solid. MS (ESI, positive) m/z: 222.1; $^1$H NMR (400 MHz, DMSO-d$_6$) δ 8.89 (s, 1H), 7.92 (s, 1H), 7.27 (d, J=8.5 Hz, 2H), 6.91 (d, J=8.5 Hz, 2H), 4.42 (d, J=5.4 Hz, 2H), 3.73 (s, 3H).

INTERMEDIATE CC. 1-CHLORO-N-(4-METHOXYBENZYL)-N-(1,2,4-THIADIAZOL-5-YL)ISOQUINOLINE-6-SULFONAMIDE

Step 2: To a solution of N-(4-methoxybenzyl)-1,2,4-thiadiazol-5-amine (1.40 g, 6.33 mmol) in THF (42.2 mL) at −70° C. under an argon atmosphere was added lithium bis(trimethylsilyl)amide, 1.0 M solution in tetrahydrofuran (6.96 mL, 6.96 mmol) dropwise. The reaction mixture was removed from cooling and stirred for 45 min. The mixture was again cooled to −70° C. (internal temperature) to give a yellow suspension. Then solid 1-chloroisoquinoline-6-sulfonyl chloride (1.82 g, 6.96 mmol) was added in one portion. After 15 min, the mixture was warmed to room temperature and concentrated. The residue was absorbed onto a plug of silica gel and purified by chromatography through a silica gel column (80 g), eluting with a gradient of 0% to 50% EtOAc in hexane, to provide 1-chloro-N-(4-methoxybenzyl)-N-(1,2,4-thiadiazol-5-yl)isoquinoline-6-sulfonamide (0.73 g, 1.633 mmol) as an orange solid. MS (ESI): 447.0 [M+H]+; $^1$H NMR (500 MHz, DMSO-d$_6$) δ ppm 3.65 (s, 3H), 5.24 (s, 2H), 6.77 (m, J=8.66 Hz, 2H), 7.28 (m, J=8.66 Hz, 2H), 8.10 (dd, J=5.9, 10.8 Hz, 1H), 8.15 (d, J=6.4 Hz, 1H), 8.42 (d, J=8.6 Hz, 1H), 8.45 (s, 1H), 8.50 (d, J=5.56 Hz, 1H), 8.77 (d, J=1.71 Hz, 1H).

INTERMEDIATE DD. 1-(2-BROMO-4-(TRIFLUOROMETHYL)PHENYL)-N-(4-METHOXYBENZYL)-N-(1,2,4-THIADIAZOL-5-YL)ISOQUINOLINE-6-SULFONAMIDE

Step 3: A glass pressure tube was charged with 1-chloro-N-(4-methoxybenzyl)-N-(1,2,4-thiadiazol-5-yl)isoquinoline-6-sulfonamide (690 mg, 1.54 mmol), potassium carbonate (107 mg, 7.72 mmol), 2-bromo-4-(trifluoromethyl)phenylboronic acid (498 mg, 1.85 mmol), tetrakis(triphenylphosphine)palladium(0) (178 mg, 0.154 mmol) in dioxane (10.300 mL) and water (5.15 mL). The reaction was purged with argon. The tube was sealed and heated in an oil bath at 100° C. After 35 min, the reaction was cooled down to room temperature. The mixture was extracted with EtOAc (3×30 mL). The organic layers were separated, combined, dried over MgSO$_4$, filtered and concentrated to afford a yellow residue. The residue was absorbed onto a plug of silica gel and purified by chromatography through a silica gel column (40 g), eluting with a gradient of 0% to 20% DCM in heptane to remove PPh$_3$ and then 20 to 90% DCM in heptane to provide 1-(2-bromo-4-(trifluoromethyl)phenyl)-N-(4-methoxybenzyl)-N-(1,2,4-thiadiazol-5-yl)isoquinoline-6-sulfonamide (0.86 g, 1.353 mmol) as a yellow solid. MS (ESI): 634.0 [M+H]+; $^1$H NMR (400 MHz, DMSO-d$_6$) δ ppm 3.64 (s, 3H), 5.24 (s, 2H), 6.78 (d, J=8.90 Hz, 2H), 7.27 (d, J=8.80 Hz, 2H), 7.69 (d, J=10 Hz, 1H), 7.75 (d, J=8 Hz, 1H), 7.91-7.99 (m, 2H), 8.23-8.26 (m, 2H), 8.46 (s, 1H), 8.81-8.84 (m, 2H).

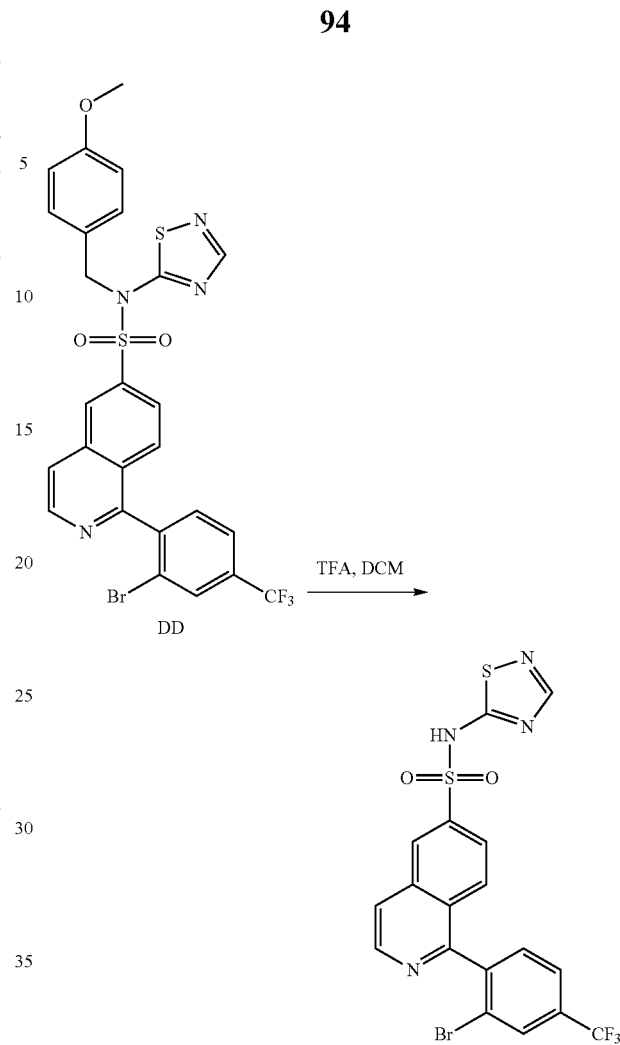

EXAMPLE 50

1-(2-BROMO-4-(TRIFLUOROMETHYL)PHENYL)-N-(1,2,4-THIADIAZOL-5-YL)ISOQUINOLINE-6-SULFONAMIDE

To a solution of 1-(2-bromo-4-(trifluoromethyl)phenyl)-N-(4-methoxybenzyl)-N-(1,2,4-thiadiazol-5-yl)isoquinoline-6-sulfonamide (INTERMEDIATE DD, 100 mg, 0.157 mmol) in DCM (1574 μl) was added TFA (60.6 μl, 0.787 mmol). The mixture was stirred at room temperature. After 2 h, LC/MS showed mainly the desired product. The reaction mixture was concentrated and dissolved in 3 ml of DMSO. This solution was injected onto the reverse phase HPLC (Xbridge 10 μm, C18, 19×100 mm column eluting with 0.1% NH$_4$OH in ACN and water as the mobile phase) ultimately affording 1-(2-bromo-4-(trifluoromethyl)phenyl)-N-(1,2,4-thiadiazol-5-yl)isoquinoline-6-sulfonamide (10.6 mg, 0.021 mmol). MS (ESI): 514.8 [M+H]+; $^1$H NMR (500 MHz, DMSO-d6) δ ppm 7.68 (d, J=8.87 Hz, 1H), 7.76 (d, J=7.80

Hz, 1H), 7.90-7.98 (m, 2H), 8.22-8.26 (m, 2H), 8.48 (s, 1H), 8.65 (m, 1H), 8.76 (d, J=5.66 Hz, 1H).

INTERMEDIATE EE

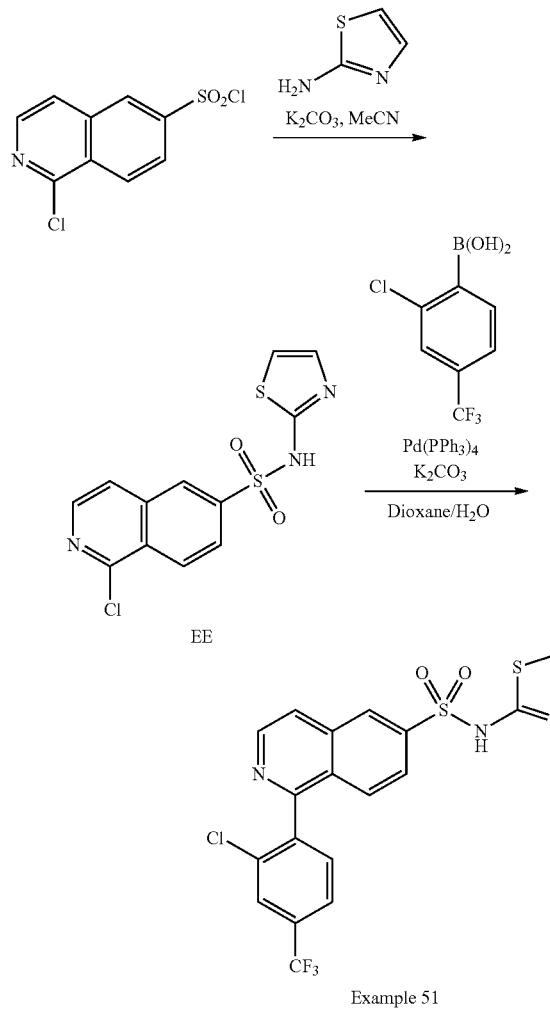

EE

INTERMEDIATE EE: 1-CHLORO-N-(THIAZOL-2-YL)ISOQUINOLINE-6-SULFONAMIDE

Step 1: Potassium carbonate (7.97 g, 57.7 mmol) was added to solution of thiazol-2-amine (0.963 g, 9.61 mmol) in acetonitrile (48.1 mL). After stirring for 5 min at room temperature, 1-chloroisoquinoline-6-sulfonyl chloride (2.52 g, 9.61 mmol) was added. After 2 days, a suspension was formed and an LC/MS of an aliquot in DCM showed consumption of starting material and formation of product. The solid was filtered off with the aid of DCM (50 mL) to provide ((1-chloroisoquinolin-6-yl)sulfonyl)(thiazol-2-yl)amide that was carried on to the next step. MS (ESI): 325.8 [M+Na]$^+$.

EXAMPLE 51

1-(2-CHLORO-4-(TRIFLUOROMETHYL)PHENYL)-N-(THIAZOL-2-YL)ISOQUINOLINE-6-SULFONAMIDE

Step 2: A glass pressure tube was charged with 1-chloro-N-(thiazol-2-yl)isoquinoline-6-sulfonamide (3.13 g, 9.61 mmol), potassium carbonate (6.64 g, 48.0 mmol), (2-chloro-4-(trifluoromethyl)phenyl)boronic acid (3.23 g, 14.41 mmol), tetrakis(triphenylphosphine)palladium(0) (1.11 g, 0.961 mmol), dioxane (64.0 mL) and water (32.0 mL). The reaction vessel was purged with argon, sealed and heated in an oil bath to 90° C. After 45 min, the reaction was cooled down to room temperature. The layers were separated. The aqueous layer was washed with EtOAc (3×10 mL). The organic layers were combined, dried over MgSO$_4$, filtered and concentrated to afford a yellow residue. The residue was loaded onto a column with the aid of 15 mL of DCM and purified by chromatography through a silica gel column (120 g), eluting with a gradient of 0% to 50% 90:10:1 DCM:MeOH:NH$_4$OH in DCM, to provide 1.79 g of a brown foam. The product was purified again by reverse phase HPLC using Xbridge 10 μm, C$_{18}$, 19×100 mm column eluting with 0.1% NH$_4$OH in ACN and water as the mobile phase to afford 1-(2-chloro-4-(trifluoromethyl)phenyl)-N-(thiazol-2-yl)isoquinoline-6-sulfonamide (455 mg, 0.968 mmol). MS (ESI): 469.6 [M+Na]$^+$. $^1$H NMR (400 MHz, DMSO-d$_6$) δ ppm 6.87 (d, J=4.60 Hz, 1H), 7.28 (d, J=4.60 Hz, 1H), 7.68 (d, J=8.90 Hz, 1H), 7.79 (d, J=7.92 Hz, 1H), 7.88-7.96 (m, 2H), 8.12 (s, 1H), 8.23 (d, J=5.77 Hz, 1H), 8.61 (d, J=1.66 Hz, 1H), 8.75 (d, J=5.77 Hz, 1H), 12.92 (br. s., 1H).

EXAMPLE 52

1-(2-CHLORO-4-(TRIFLUOROMETHYL)PHENYL)-N-(3-METHOXYPYRIDIN-4-YL)ISOQUINOLINE-6-SULFONAMIDE

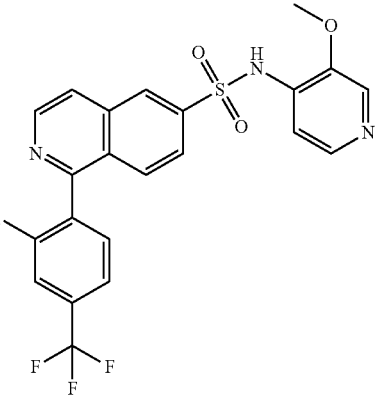

1-CHLORO-N-(3-METHOXYPYRIDIN-4-YL)ISOQUINOLINE-6-SULFONAMIDE

Step 1: The title compound was prepared in an analogous manner to that of Example 51, Step 1, except that 3-methoxypyridin-4-amine was used in place of thiazol-2-amine 349 mg, (0.998 mmol) of desired product were obtained. MS (ESI): 350.0 [M+H]$^+$.

1-(2-CHLORO-4-(TRIFLUOROMETHYL)PHENYL)-N-(3-METHOXYPYRIDIN-4-YL)ISOQUINOLINE-6-SULFONAMIDE

Step 2: The title compound was prepared in an analogous manner to that of Example 51, Step 2, except that 1-chloro-N-(3-methoxypyridin-4-yl)isoquinoline-6-sulfonamide was used in place of 1-chloro-N-(thiazol-2-yl)isoquinoline-6-sulfonamide. 134 mg (0.271 mmol) of desired product were obtained. MS (ESI): 494.0 [M+H]$^+$; $^1$H NMR (500 MHz, DMSO-d$_6$) δ ppm 3.69 (s, 3H), 7.11 (d, J=8.98 Hz, 1H), 7.36 (dd, J=8.98, 3.10 Hz, 1H), 7.68 (d, J=8.98 Hz, 2H), 7.73-7.83 (m, 2H), 7.88-7.95 (m, 2H), 8.05-8.10 (m, 1H), 8.18-8.20 (m, 1H), 8.62-8.66 (m, 1H) 8.73, (d, J=5.66 Hz, 1H).

INTERMEDIATE FF

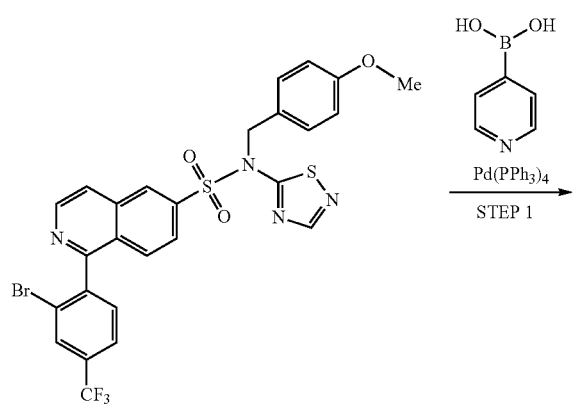

INTERMEDIATE FF. N-(4-METHOXYBENZYL)-1-(2-(PYRIDIN-4-YL)-4-(TRIFLUOROMETHYL)PHENYL)-N-(1,2,4-THIADIAZOL-5-YL)ISOQUINOLINE-6-SULFONAMIDE

Step 1: A microwave vial was charged with 1-(2-bromo-4-(trifluoromethyl)phenyl)-N-(4-methoxybenzyl)-N-(1,2,4-thiadiazol-5-yl)isoquinoline-6-sulfonamide (100 mg, 0.157 mmol), potassium carbonate (109 mg, 0.787 mmol), 4-pyridineboronic acid (77 mg, 0.629 mmol), tetrakis(triphenylphosphine)palladium(0) (18.18 mg, 0.016 mmol), dioxane (1049 μl) and water (525 μl). The vial was purged with argon, sealed and heated in a microwave at 100° C. for 35 min. The reaction was cooled to room temperature, diluted with 60 mL of EtOAc, dried over MgSO$_4$, filtered and concentrated. The material was absorbed onto a plug of silica gel and purified by chromatography through a silica gel column (40 g), eluting with a gradient of 0% to 100% (90:10 MeOH:DCM) in DCM, to provide a yellow glass, N-(4-methoxybenzyl)-1-(2-(pyridin-4-yl)-4-(trifluoromethyl)phenyl)-N-(1,2,4-thiadiazol-5-yl)isoquinoline-6-sulfonamide (100 mg, 0.158 mmol). This material was carried on to the next step. MS (ESI): 634.0 [M+H]$^+$.

EXAMPLE 53

1-(2-(PYRIDIN-4-YL)-4-(TRIFLUOROMETHYL)PHENYL)-N-(1,2,4-THIADIAZOL-5-YL)ISOQUINOLINE-6-SULFONAMIDE

Step 2: To a solution of N-(4-methoxybenzyl)-1-(2-(pyridin-4-yl)-4-(trifluoromethyl)phenyl)-N-(1,2,4-thiadiazol-5-yl)isoquinoline-6-sulfonamide (100 mg, 0.158 mmol) in DCM (1578 μl) was added TFA (60.8 μl, 0.789 mmol). The reaction mixture was stirred at room temperature. After 2 hours, LC/MS showed mainly product. Purification was done using a Phenomenex Gemini 5 μm, C$_{18}$, 110 Å, 150×30 mm column with 0.1% TFA in ACN and water as mobile phase to afford 1-(2-(pyridin-4-yl)-4-(trifluoromethyl)phenyl)-N-(1,2,4-thiadiazol-5-yl)isoquinoline-6-sulfonamide (6.2 mg, 0.012 mmol, 7.65%). MS (ESI): 514.0 [M+H]$^+$; $^1$H NMR (500 MHz, DMSO-d$_6$) δ ppm 7.19-7.22 (m, 2H), 7.80 (s, 2H), 7.85 (d, J=8.01 Hz, 1H), 8.01-8.06 (m, 2H), 8.11 (d, J=5.77 Hz, 1H), 8.37 (br. s., 2H), 8.47 (s, 1H), 8.54 (s, 1H), 8.61 (d, J=5.66 Hz, 1H).

EXAMPLE 54

1-(2-(1-METHYL-1H-PYRAZOL-5-YL)-4-(TRIFLUOROMETHYL)PHENYL)-N-(1,2,4-THIADIAZOL-5-YL)ISOQUINOLINE-6-SULFONAMIDE

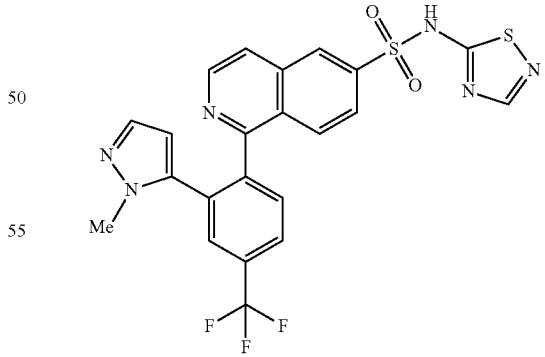

The title compound was prepared in an analogous manner to that of Example 53, Step 1 and, except that (1-methyl-1H-pyrazol-5-yl)boronic acid was used in place of 4-pyridineboronic acid in Step 1. Eight mg of the title compound were obtained. MS (ESI): 517.0 [M+H]$^+$; $^1$H NMR (500 MHz, DMSO-d$_6$) δ ppm 3.61 (s, 3H), 7.02 (d, J=2.5 Hz, 1H), 7.53-

7.64 (m, 2H), 7.71 (d, J=8.5 Hz, 1H), 7.80-7.84 (m, 2H), 8.01-8.10 (m, 3H), 8.49 (s, 1H), 8.52 (d, J=2 Hz, 1H), 8.64 (d, J=4.7 Hz, 1H).

EXAMPLE 55

1-(2-(1H-PYRAZOL-4-YL)-4-(TRIFLUOROM-ETHYL)PHENYL)-N-(1,2,4-THIADIAZOL-5-YL) ISOQUINOLINE-6-SULFONAMIDE

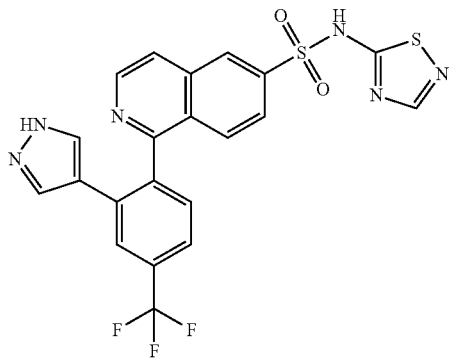 [SMILES: O=S(=O)(Nc1ncns1)c1ccc2c(-c3ccc(C(F)(F)F)cc3-c3cn[nH]c3)nccc2c1]

The title compound was prepared in an analogous manner to that of Example 53, except that (1H-pyrazol-5-yl)boronic acid was used in place of 4-pyridineboronic acid in Step 1. Eight mg of the titled compound were obtained. MS (ESI): 503.0 [M+H]$^+$; $^1$H NMR (500 MHz, DMSO-d$_6$) δ ppm 7.07 (br s, 2H), 7.56 (d, J=8.9 Hz, 1H), 7.62 (d, J=8.0 Hz, 1H), 7.76-7.78 (m, 2H), 8.04 (s, 1H), 8.23 (d, J=5.8 Hz, 1H), 8.49 (s, 1H), 8.59 (s, 1H), 8.77 (d, J=5.7 Hz, 1H).

INTERMEDIATE X

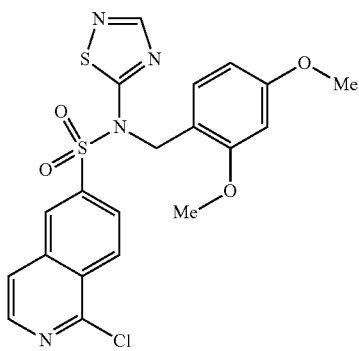 [SMILES: COc1ccc(CN(c2ncns2)S(=O)(=O)c2ccc3c(Cl)nccc3c2)c(OC)c1]

INTERMEDIATE X: (1-CHLORO-N-(2,4-DIMETHOXYBENZYL)-N-(1,2,4-THIADIAZOL-5-YL)ISOQUINOLINE-6-SULFONAMIDE

A 250 mL round bottom flask was charged with N-(2,4-dimethoxybenzyl)-1,2,4-thiadiazol-5-amine (2.291 g, 9.12 mmol) and THF (45.6 mL). The resulting mixture was cooled in a dry ice and acetone bath for 10 min. To this solution was added lithium bis(trimethylsilyl)amide (13.68 mL, 13.68 mmol) dropwise over 30 seconds. The ice bath was removed for 10 minutes and then the flask was returned to the bath for an additional 5 minutes. A solution of 1-chloroisoquinoline-6-sulfonyl chloride (2.39 g, 9.12 mmol) in 7 mL of THF was then added dropwise over 5 minutes. The ice bath was removed and the resulting mixture stirred for 30 minutes. LC/MS indicated that the desired product was generated. The reaction mixture was concentrated, taken up in minimal DCM, loaded onto a cartridge and purified by silica gel chromatography (330 g), using 0 to 30% Heptane: EtOAc. Fractions containing the product were combined and concentrated to afford (1-chloro-N-(2,4-dimethoxybenzyl)-N-(1,2,4-thiadiazol-5-yl)isoquinoline-6-sulfonamide (1.58 g, 3.31 mmol) as a white solid.

EXAMPLE 56

1-(2-CHLORO-4-(TRIFLUOROMETHYL)PHE-NYL)-N-(1,2,4-THIADIAZOL-5-YL)ISOQUINO-LINE-6-SULFONAMIDE

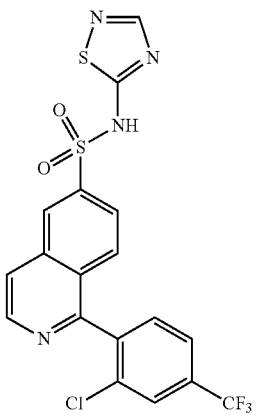 [SMILES: O=S(=O)(Nc1ncns1)c1ccc2c(-c3ccc(C(F)(F)F)cc3Cl)nccc2c1]

A pressure vessel was charged with (2-chloro-4-(trifluoromethyl)phenyl)boronic acid (56.5 mg, 0.252 mmol), potassium carbonate (145 mg, 1.048 mmol), 1-chloro-N-(2,4-dimethoxybenzyl)-N-(1,2,4-thiadiazol-5-yl)isoquinoline-6-sulfonamide (100 mg, 0.210 mmol), tetrakis(triphenylphosphine)palladium(0) (24.23 mg, 0.021 mmol), dioxane (1398 µl) and water (699 µl). The reaction vessel was swept with nitrogen, sealed with a cap and then heated in a microwave at 100° C. for 30 minutes. The mixture was cooled to room temperature. The organic layer was separated by pipet and then purified by reverse phase HPLC (Column: Gemini 150×30 mm, 5 µm, Phenomenex, Torrance, Calif., Flow rate: 40 mL/min, Mobile phase: 0.1% TFA in ACN and water). The fractions containing pure product were dried under a vacuum to provide 1-(2-chloro-4-(trifluoromethyl)phenyl)-N-(1,2,4-thiadiazol-5-yl)isoquinoline-6-sulfonamide (22 mg, 0.047 mmol) as a white solid. $^1$H NMR (500 MHz, DMSO-d$_6$) δ ppm 3.57 (br. s., 1H) 3.63-3.80 (m, 1H) 7.70 (d, J=8.82 Hz, 1H) 7.79 (d, J=7.90 Hz, 1H) 7.86-7.96 (m, 1H) 8.12 (s, 1H) 8.25 (d, J=5.61 Hz, 1H) 8.47 (s, 1H) 8.65 (d, J=1.49 Hz, 1H) 8.77 (d, J=5.73 Hz, 1H); m/z (ESI) 471.0 (M+H)⁺.

EXAMPLE 57

1-(3-CHLORO-4-(TRIFLUOROMETHYL)PHENYL)-N-(1,2,4-THIADIAZOL-5-YL)ISOQUINOLINE-6-SULFONAMIDE

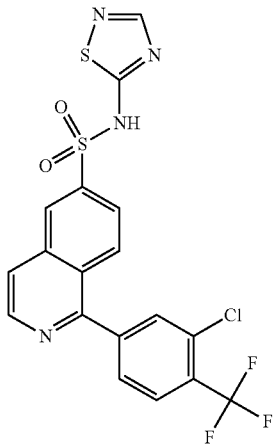 [SMILES: O=S(=O)(Nc1ncns1)c1ccc2c(-c3ccc(C(F)(F)F)c(Cl)c3)nccc2c1]

A pressure vial was charged with 1-chloro-N-(2,4-dimethoxybenzyl)-N-(1,2,4-thiadiazol-5-yl)isoquinoline-6-sulfonamide (80 mg, 0.168 mmol), tetrakis(triphenylphosphine)palladium(0) (19.38 mg, 0.017 mmol), potassium carbonate (116 mg, 0.839 mmol), 3-chloro-4-(trifluoromethyl)phenyl)boronic acid, dioxane (1118 μl) and water (559 μl). The resulting mixture was swept with nitrogen, sealed with a cap and then heated in a microwave at 100° C. for 30 minutes. The mixture was cooled to room temperature. The organic layer was separated by pipet and then purified by reverse phase HPLC (Column: Xbridge 19×100 mm, 5 μm, Waters, Milford, Mass., Flow rate: 40 mL/min, Mobile phase: 0.1% TFA in ACN and water). The fractions containing product were dried under a vacuum to afford 1-(3-chloro-4-(trifluoromethyl)phenyl)-N-(1,2,4-thiadiazol-5-yl)isoquinoline-6-sulfonamide as a white solid. ¹H NMR (500 MHz, DMSO-d₆) δ ppm −3.10 (br. s., 1H) 3.64 (br. s., 1H) 3.74 (s, 1H) 7.92-7.97 (m, 1H) 8.03 (dd, J=8.31, 1.78 Hz, 1H) 8.13-8.21 (m, 2H) 8.48 (s, 1H) 8.64 (d, J=1.60 Hz, 1H) 8.75 (d, J=5.61 Hz, 1H); m/z (ESI) 471.0 (M+H)⁺.

EXAMPLE 58

1-(2-HYDROXY-4-(TRIFLUOROMETHYL)PHENYL)-N-(1,2,4-THIADIAZOL-5-YL)ISOQUINOLINE-6-SULFONAMIDE

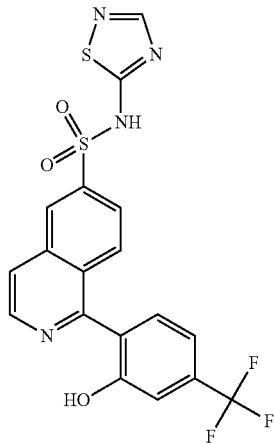 [SMILES: O=S(=O)(Nc1ncns1)c1ccc2c(-c3ccc(C(F)(F)F)cc3O)nccc2c1]

The title compound was prepared in an analogous manner to that of Example 57, except that (2-hydroxy-4-(trifluoromethyl)phenyl)boronic acid was used in place of 3-chloro-4-(trifluoromethyl)phenyl)boronic acid. ¹H NMR (500 MHz, DMSO-d6) δ ppm −3.74 (d, J=17.76 Hz, 1H) 7.30-7.38 (m, 1H) 7.54 (d, J=7.79 Hz, 1H) 7.78-7.85 (m, 1H) 7.89-7.94 (m, 1H) 8.16 (d, J=5.73 Hz, 1H) 8.48 (s, 1H) 8.59 (d, J=1.60 Hz, 1H) 8.72 (d, J=5.73 Hz, 1H) 10.35-10.46 (m, 1H); m/z (ESI) 453.0 (M+H)⁺.

EXAMPLE 59

1-(2,4-DIMETHOXYPHENYL)-N-(1,2,4-THIADIAZOL-5-YL)ISOQUINOLINE-6-SULFONAMIDE

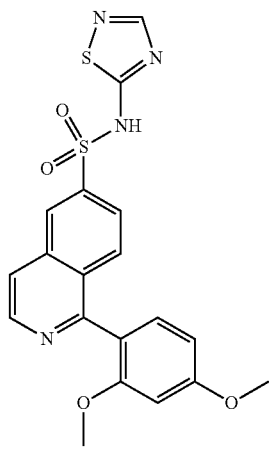 [SMILES: COc1ccc(-c2nccc3cc(S(=O)(=O)Nc4ncns4)ccc23)c(OC)c1]

The title compound was prepared in an analogous manner to that of Example 57, except that (2,4-dimethoxyphenyl)

boronic acid was used in place of 3-chloro-4-(trifluoromethyl)phenyl)boronic acid. $^1$H NMR (500 MHz, DMSO-d$_6$) δ ppm −3.02 (d, J=15.92 Hz, 1H) 3.59 (s, 3H) 3.58-3.74 (m, 1H) 3.65 (s, 3H) 6.70-6.78 (m, 1H) 7.29 (d, J=8.25 Hz, 1H) 7.79 (d, J=8.94 Hz, 1H) 7.88 (dd, J=8.94, 1.83 Hz, 1H) 8.10 (d, J=5.73 Hz, 1H) 8.43 (s, 1H) 8.55 (d, J=1.60 Hz, 1H) 8.66 (d, J=5.73 Hz, 1H); m/z (ESI) 429.0 (M+H)$^+$.

EXAMPLE 60

N-(1,2,4-THIADIAZOL-5-YL)-1-(2,4,6-TRIMETHOXYPHENYL)ISOQUINOLINE-6-SULFONAMIDE

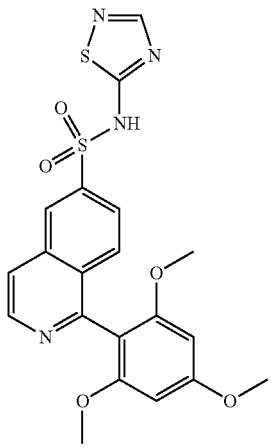 [SMILES: COc1cc(OC)c(-c2nccc3cc(S(=O)(=O)Nc4ncns4)ccc23)c(OC)c1]

The title compound was prepared in an analogous manner to that of Example 57, except that (2,4,6-trimethoxyphenyl)boronic acid was used in place of 3-chloro-4-(trifluoromethyl)phenyl)boronic acid. $^1$H NMR (500 MHz, DMSO-d6) δ ppm 3.53 (br. s., 1H) 3.61 (s, 5H) 3.71-3.85 (m, 4H) 3.90 (s, 3H) 4.12 (br. s., 1H) 6.45 (s, 1H) 7.80 (d, J=8.82 Hz, 1H) 7.95 (dd, J=8.88, 1.66 Hz, 1H) 8.27 (d, J=5.38 Hz, 1H) 8.47 (s, 1H) 8.64 (s, 1H) 8.71 (d, J=6.07 Hz, 1H); m/z (ESI) 459.0 (M+H)$^+$.

EXAMPLE 61

1-(2,4-DICHLOROPHENYL)-N-(1,2,4-THIADIAZOL-5-YL)ISOQUINOLINE-6-SULFONAMIDE

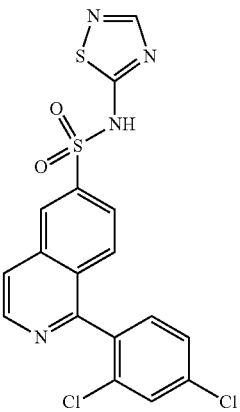 [SMILES: O=S(=O)(Nc1ncns1)c1ccc2c(-c3ccc(Cl)cc3Cl)nccc2c1]

The title compound was prepared in an analogous manner to that of Example 57, except that (2,4-dichlorophenyl)boronic acid was used in place of 3-chloro-4-(trifluoromethyl)phenyl)boronic acid. $^1$H NMR (500 MHz, DMSO-d$_6$) δ ppm −3.78 (br. s., 1H) 7.57 (d, J=8.13 Hz, 1H) 7.64 (dd, J=8.25, 1.95 Hz, 1H) 7.71 (d, J=8.94 Hz, 1H) 7.86 (d, J=1.95 Hz, 1H) 7.92 (dd, J=8.88, 1.89 Hz, 1H) 8.21 (d, J=5.61 Hz, 1H) 8.48 (s, 1H) 8.63 (d, J=1.60 Hz, 1H) 8.74 (d, J=5.61 Hz, 1H); m/z (ESI) 438.0 (M+H)$^+$.

EXAMPLE 62

1-(4-CHLORO-2-METHYLPHENYL)-N-(1,2,4-THIADIAZOL-5-YL)ISOQUINOLINE-6-SULFONAMIDE

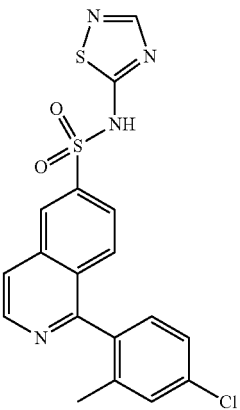 [SMILES: Cc1cc(Cl)ccc1-c1nccc2cc(S(=O)(=O)Nc3ncns3)ccc12]

The title compound was prepared in an analogous manner to that of Example 57, except that (4-chloro-2-methylphenyl)boronic acid was used in place of 3-chloro-4-(trifluoromethyl)phenyl)boronic acid. $^1$H NMR (500 MHz, DMSO-d$_6$) δ ppm 3.67 (d, J=13.98 Hz, 3H) 3.78-3.99 (m, 1H) 7.42 (dd, J=8.19, 2.00 Hz, 1H) 7.51-7.57 (m, 1H) 7.59-7.64 (m, 1H) 7.71 (d, J=8.93 Hz, 1H) 7.90 (dd, J=8.94, 1.83 Hz, 1H) 8.17 (d, J=5.73 Hz, 1H) 8.48 (s, 1H) 8.62 (d, J=1.60 Hz, 1H) 8.73 (d, J=5.73 Hz, 1H); m/z (ESI) 417.0 (M+H)+.

EXAMPLE 63

1-(4-CHLORO-2-(TRIFLUOROMETHYL)PHENYL)-N-(1,2,4-THIADIAZOL-5-YL)ISOQUINOLINE-6-SULFONAMIDE

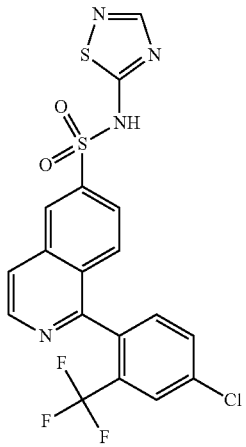 [SMILES: O=S(=O)(Nc1ncns1)c1ccc2c(-c3ccc(Cl)cc3C(F)(F)F)nccc2c1]

The title compound was prepared in an analogous manner to that of Example 57, except that (4-chloro-2-(trifluoromethyl)phenyl)boronic acid was used in place of 3-chloro-4-(trifluoromethyl)phenyl)boronic acid. $^1$H NMR (500 MHz, DMSO-d$_6$) δ ppm 2.54 (s, 1H) 3.06 (br. s., 1H) 3.70-3.93 (m, 1H) 7.63 (dd, J=19.07, 8.53 Hz, 1H) 7.84-7.94 (m, 1H) 8.06 (d, J=1.95 Hz, 1H) 8.21 (d, J=5.61 Hz, 1H) 8.46 (s, 1H) 8.62 (d, J=1.60 Hz, 1H) 8.70 (d, J=5.73 Hz, 1H); m/z (ESI) 471.0 (M+H)+.

EXAMPLE 64

1-(4-CHLOROPHENYL)-N-(1,2,4-THIADIAZOL-5-YL)ISOQUINOLINE-6-SULFONAMIDE

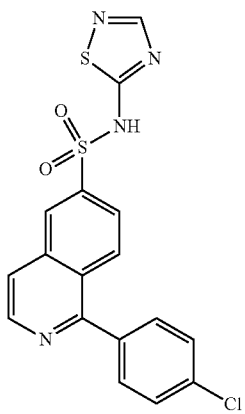 [SMILES: O=S(=O)(Nc1ncns1)c1ccc2c(-c3ccc(Cl)cc3)nccc2c1]

The title compound was prepared in an analogous manner to that of Example 57, except that (4-chlorophenyl)boronic acid was used in place of 3-chloro-4-(trifluoromethyl)phenyl)boronic acid. $^1$H NMR (500 MHz, DMSO-d$_6$) δ ppm −3.17 (s, 2H) 3.75 (br. s., 1H) 7.64 (d, J=8.36 Hz, 1H) 7.72 (d, J=8.48 Hz, 1H) 7.94 (dd, J=8.99, 1.78 Hz, 1H) 8.14-8.17 (m, 1H) 8.47 (s, 1H) 8.61 (d, J=1.72 Hz, 1H) 8.72 (d, J=5.61 Hz, 1H); m/z (ESI) 403.0 (M+H)+.

INTERMEDIATE GG: 1-CHLORO-N-(PYRIMIDIN-4-YL)ISOQUINOLINE-6-SULFONAMIDE

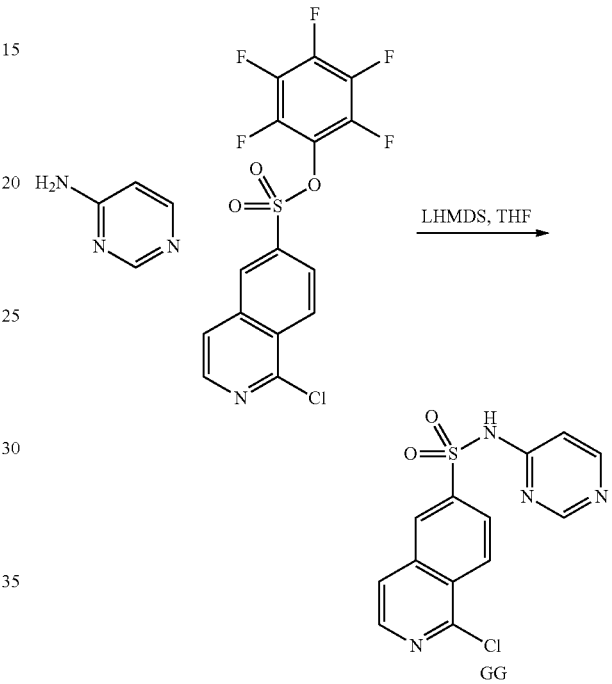

A 50 mL round-bottom flask was charged with perfluorophenyl 1-chloroisoquinoline-6-sulfonate (660 mg, 1.611 mmol), pyrimidin-4-amine (169 mg, 1.772 mmol), and THF (8054 µl) to give an orange solution. The flask was cooled in an ice bath for 5 min, then lithium bis(trimethylsilyl)amide (1M in THF) (3544 µl, 3.54 mmol) was added at a rapid, dropwise rate. After 20 min, the mixture was quenched by the addition of glacial acetic acid (0.5 mL), resulting in a thick slurry. The mixture was diluted with THF and MeOH and concentrated, and the residue was concentrated from EtOAc (three times). The residue was then suspended in EtOAc, sonicated for 1 min, then filtered. The collected solid was washed with EtOAc (once), then dried under a stream of N$_2$ (g), then under a vacuum to give 676.5 mg of a tan solid. The material was taken up in DCM, sonicated for 30 s, then filtered. The collected solid was washed with DCM (twice), dried under a stream of N$_2$ (g), then dried under a high vacuum to give 583 mg of a tan solid. The mixture was taken up in boiling methanol, cooled to room temperature, then filtered. The collected solid was washed with methanol, then dried to give 1-chloro-N-(pyrimidin-4-yl)isoquinoline-6-sulfonamide (154.84 mg, 0.483 mmol) as a tan solid. An additional crop of product was obtained by chromatographic purification of the mother liquor on silica gel (0 to 10% MeOH/DCM) to give an additional 110 mg of product as s tan solid. $^1$H NMR (400 MHz, DMSO-d$_6$) δ=13.58-12.66 (br s., 1H), 8.75-

8.66 (m, 1H), 8.55 (s, 1H), 8.47-8.37 (m, 2H), 8.26-8.11 (m, 3H), 7.07-6.90 (m, 1H). m/z (ESI) 321.2 (M+H)+.

EXAMPLE 65

1-(2-(PYRIDIN-4-YL)-4-(TRIFLUOROMETHYL) PHENYL)-N-(PYRIMIDIN-4-YL)ISOQUINO- LINE-6-SULFONAMIDE

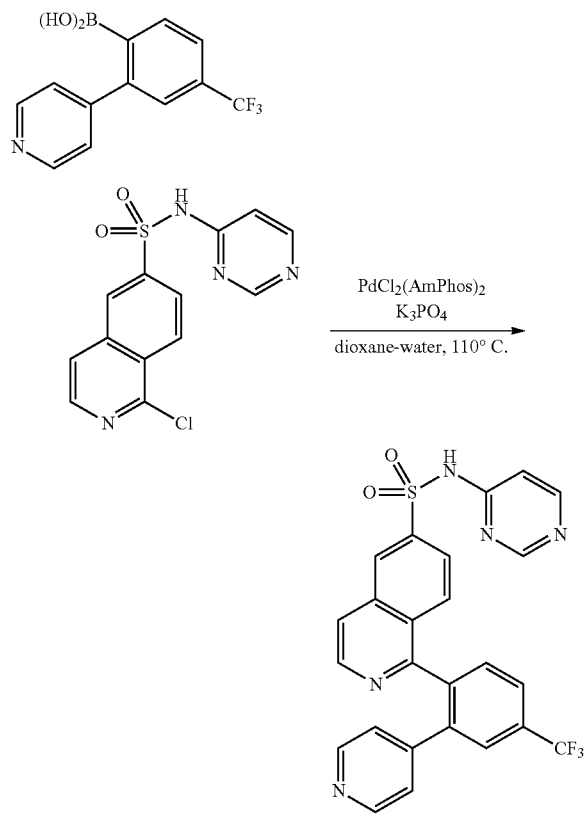

A vial was charged with 1-chloro-N-(pyrimidin-4-yl)iso- quinoline-6-sulfonamide (50 mg, 0.137 mmol), (2-(pyridin- 4-yl)-4-(trifluoromethyl)phenyl)boronic acid (54.9 mg, 0.206 mmol), Pd(AmPhos)$_2$Cl$_2$ (9.71 mg, 0.014 mmol), potassium phosphate (87 mg, 0.412 mmol), dioxane (514 µl), and water (171 µl). The vial was sealed and heated in a microwave reactor for 20 min at 110° C. The mixture was extracted with EtOAc (three times). The combined organic extracts were concentrated. The residue was purified by chromatography on silica gel with 0 to 7% MeOH/DCM, then 7 to 10% MeOH/DCM to give 28 mg of an off-white solid. The material was dissolved in MeOH, then loaded onto 1 g SCX-2 column (Biotage AB, Uppsala, SE). The column was eluted with MeOH, then with 2N ammonia in methanol. The basic fraction was concentrated, and the residue was concentrated from DCM/heptane to give 1-(2-(pyridin-4-yl)-4-(trifluo- romethyl)phenyl)-N-(pyrimidin-4-yl)isoquinoline-6-sul- fonamide (24.82 mg, 0.049 mmol) as an off-white solid. $^1$H NMR (400 MHz, DMSO-d$_6$) δ ppm=8.66-8.59 (m, 1H), 8.54 (br. s., 1H), 8.47 (br. s., 1H), 8.25 (d, J=5.2 Hz, 2H), 8.15 (d, J=6.0 Hz, 1H), 8.07 (d, J=6.0 Hz, 1H), 8.01 (d, J=8.0 Hz, 1H), 7.97 (br. s., 1H), 7.83 (d, J=8.0 Hz, 2H), 7.66 (d, J=9.0 Hz, 1H), 7.01 (d, J=4.9 Hz, 2H), 6.86 (d, J=5.8 Hz, 1H). m/z (ESI) 508.2 (M+H)+.

EXAMPLE 66

1-(2-BROMO-4-(TRIFLUOROMETHYL)PHE- NYL)-N-(PYRIMIDIN-4-YL)ISOQUINOLINE-6- SULFONAMIDE

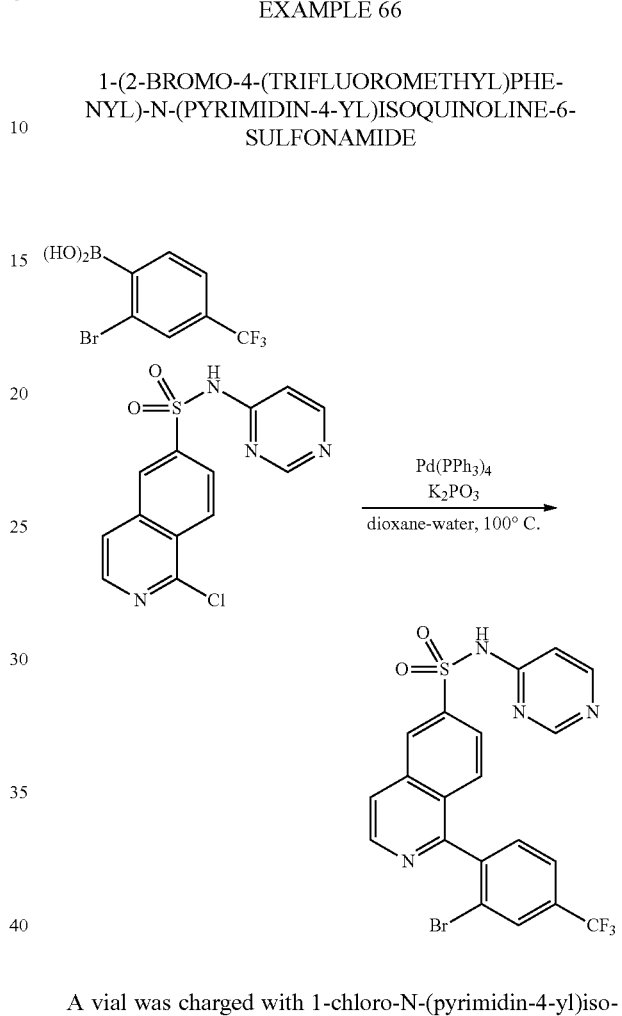

A vial was charged with 1-chloro-N-(pyrimidin-4-yl)iso- quinoline-6-sulfonamide (148 mg, 0.461 mmol), (2-bromo- 4-(trifluoromethyl)phenyl)boronic acid (149 mg, 0.554 mmol), potassium carbonate (319 mg, 2.307 mmol), and Pd(Ph$_3$P)$_4$ (26.7 mg, 0.023 mmol). The vial was flushed with Ar (g), then dioxane (1730 µl) and water (577 µl) was added. The vial was sealed and heated in a microwave reactor for 2 h at 100° C. LC/MS looked the same. An additional portion of (2-bromo-4-(trifluoromethyl)phenyl)boronic acid (149 mg, 0.554 mmol) was added, and the mixture was heated for an additional 40 min at 100° C. in the microwave. An additional portion of boronic acid (about 130 mg) was added, and the mixture heated for another 1 h. The mixture was extracted with EtOAc (three times), and the combined organic extracts were concentrated. The crude product was purified by chromatography on silica gel with 0 to 10% MeOH/DCM to give about 212 mg of a solid. The material was repurified by chromatography on silica gel with 0 to 100% EtOAc/Heptane to give 1-(2-bromo-4-(trifluoromethyl)phenyl)-N-(pyrimi- din-4-yl)isoquinoline-6-sulfonamide (98.21 mg, 0.193 mmol) as a white solid. $^1$H NMR (400 MHz, DMSO-d$_6$) δ ppm=13.68-12.77 (br. s, 1H), 8.78-8.69 (m, 2H), 8.57 (s, 1H), 8.31-8.18 (m, 3H), 8.03-7.93 (m, 2H), 7.76 (d, J=8.0 Hz, 1H), 7.66 (d, J=9.0 Hz, 1H), 7.03 (br. s., 1H). m/z (ESI) 509.0 (M+H)+.

EXAMPLE 67

1-(2-METHOXY-4-(TRIFLUOROMETHYL)PHENYL)-N-(PYRIMIDIN-4-YL)ISOQUINOLINE-6-SULFONAMIDE

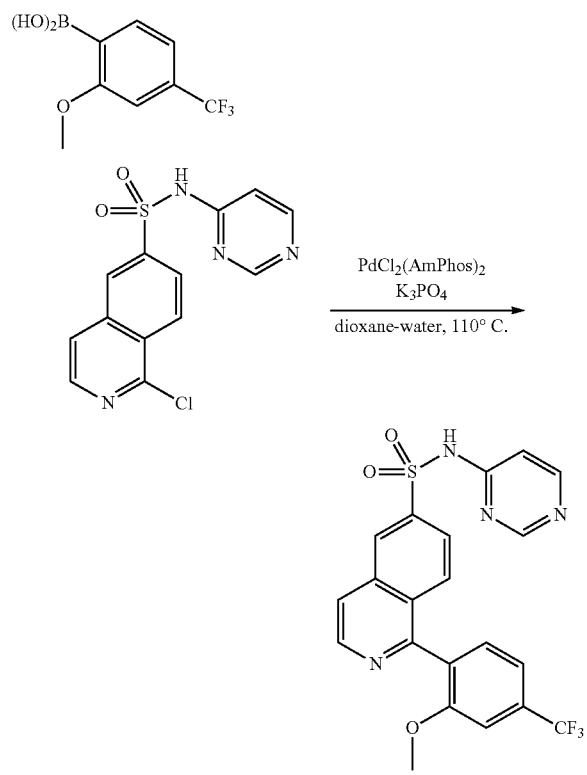

The title compound was prepared in an analogous manner to that described for EXAMPLE 64, except that (2-methoxy-4-(trifluoromethyl)phenyl)boronic acid was used as the boronic acid, and the desired product, 1-(2-methoxy-4-(trifluoromethyl)phenyl)-N-(pyrimidin-4-yl)isoquinoline-6-sulfonamide, was obtained as a cream-colored solid. $^1$H NMR (400 MHz, DMSO-d$_6$) δ ppm=13.54-12.61 (m, 1H), 8.70 (d, J=5.7 Hz, 2H), 8.55 (s, 1H), 8.22 (d, J=6.6 Hz, 1H), 8.14 (d, J=5.7 Hz, 1H), 7.94 (dd, J=1.8, 8.9 Hz, 1H), 7.69 (d, J=8.8 Hz, 1H), 7.60-7.44 (m, 3H), 7.00 (d, J=6.5 Hz, 1H), 3.77-3.69 (m, 3H). m/z (ESI) 461.2 (M+H)+.

EXAMPLE 68

1-(2-(1-METHYL-1,2,3,6-TETRAHYDROPYRIDIN-4-YL)-4-(TRIFLUOROMETHYL)PHENYL)-N-(PYRIMIDIN-4-YL)ISOQUINOLINE-6-SULFONAMIDE

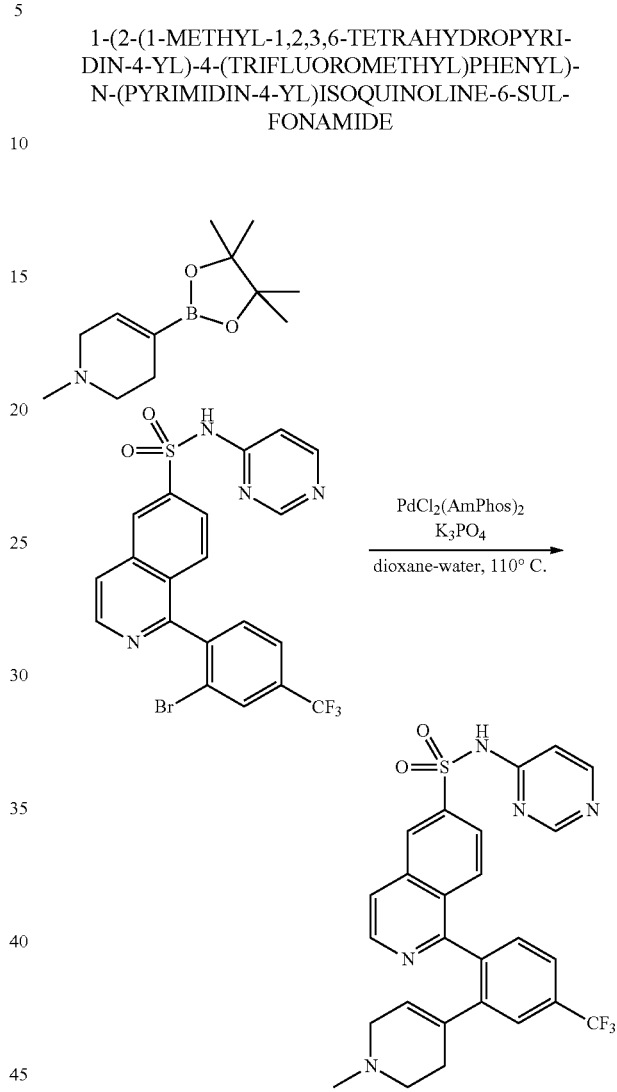

A vial was charged with 1-(2-bromo-4-(trifluoromethyl)phenyl)-N-(pyrimidin-4-yl)isoquinoline-6-sulfonamide (42.16 mg, 0.083 mmol), 1-methyl-4-(4,4,5,5-tetramethyl-1,3,2-dioxaborolan-2-yl)-1,2,3,6-tetrahydropyridine (27.7 mg, 0.124 mmol) Pd(AmPhos)$_2$Cl$_2$ (2.93 mg, 4.14 μmol), potassium phosphate (52.7 mg, 0.248 mmol), dioxane (414 μl), and water (138 μl). The vial was sealed and heated in a microwave reactor for 30 min at 100° C. The mixture was extracted with EtOAc (three times). The combined organic extracts were concentrated. The residue was purified by chromatography on silica gel, eluting with 5 to 10% MeOH/DCM, then with 15% MeOH/EtOAc, and finally with a solution of 20% of 2N ammonia in methanol in DCM. The fractions containing product were collected and concentrated. The residue was dissolved in DCM and filtered through cotton. The filtrate was concentrated to give 1-(2-(1-methyl-1,2,3,6-tetrahydropyridin-4-yl)-4-(trifluoromethyl)phenyl)-N-(pyrimidin-4-yl)isoquinoline-6-sulfonamide (41.4 mg, 0.079 mmol) as an off-white solid. $^1$H NMR (400 MHz, DMSO-d$_6$) δ ppm=8.63 (d, J=5.7 Hz, 1H), 8.55 (d, J=1.5 Hz, 1H), 8.35 (s, 1H), 8.08 (d, J=5.8 Hz, 1H), 8.01 (d, J=6.2 Hz, 1H), 7.91 (dd, J=1.8, 8.9 Hz, 1H), 7.83 (d, J=8.1 Hz, 1H), 7.76 (s, 1H), 7.63 (dd, J=8.4, 19.4 Hz, 2H), 6.72 (d, J=6.2 Hz, 1H), 5.37 (br. s., 1H), 2.98 (br. s., 2H), 2.52 (br. s., 2H), 2.20 (s, 3H), 2.16-1.96 (m, 2H). m/z (ESI) 526.2 (M+H)⁺.

EXAMPLE 69

N-(PYRIMIDIN-4-YL)-1-(2-(1,2,3,6-TETRAHYDROPYRIDIN-4-YL)-4-(TRIFLUOROMETHYL)PHENYL)ISOQUINOLINE-6-SULFONAMIDE 2,2,2-TRIFLUOROACETATE

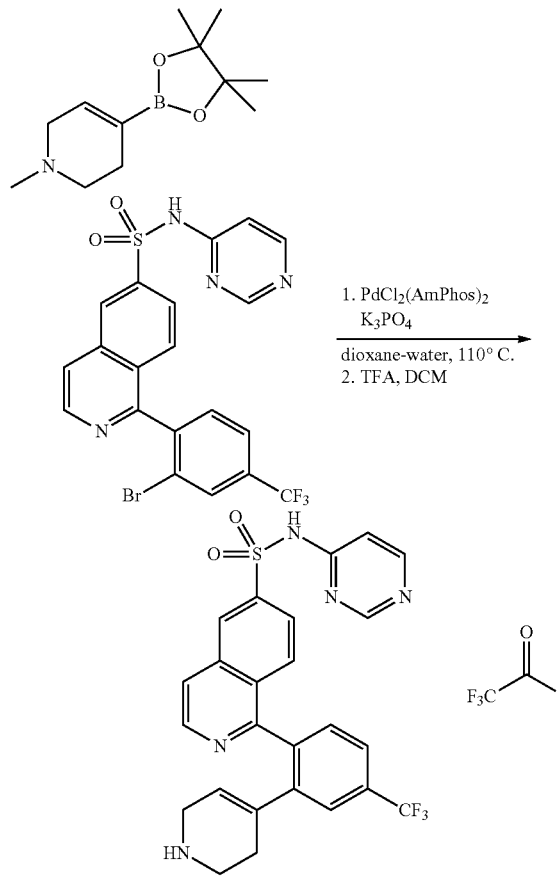

A vial was charged with 1-(2-bromo-4-(trifluoromethyl)phenyl)-N-(pyrimidin-4-yl)isoquinoline-6-sulfonamide (38.65 mg, 0.076 mmol), tert-butyl 4-(4,4,5,5-tetramethyl-1,3,2-dioxaborolan-2-yl)-5,6-dihydropyridine-1(2H)-carboxylate (35.2 mg, 0.114 mmol), Pd(AmPhos)₂Cl₂ (2.69 mg, 3.79 µmol), potassium phosphate (48.3 mg, 0.228 mmol), dioxane (379 µl), and water (126 µl). The vial was sealed and heated in a microwave reactor for 30 min at 100° C. The mixture was extracted with EtOAc (three times). The combined organic extracts were concentrated. The residue was chromatography on silica gel with 5-10% MeOH/DCM to give 53.81 mg of a white solid. The solid was dissolved in DCM (1 mL) and TFA (0.5 mL), and the resulting solution was stirred for 1 h. The mixture was concentrated, and the residue was triturated with diethyl ether and sonicated for 1 min to give an off-white solid. The solid was collected by filtration on a membrane filter, washed with diethyl ether, dried under a stream of N₂ (g) for 5 min, then dried under a high vacuum to give N-(pyrimidin-4-yl)-1-(2-(1,2,3,6-tetrahydropyridin-4-yl)-4-(trifluoromethyl)phenyl)isoquinoline-6-sulfonamide 2,2,2-trifluoroacetate (35.75 mg, 0.057 mmol) as an off-white solid. ¹H NMR (400 MHz, DMSO-d₆) δ ppm=8.70 (d, J=5.6 Hz, 2H), 8.61-8.47 (m, 3H), 8.24 (br. s., 1H), 8.18 (d, J=5.7 Hz, 1H), 7.96 (dd, J=1.6, 8.9 Hz, 1H), 7.86 (d, J=8.5 Hz, 1H), 7.79-7.70 (m, 2H), 7.65 (d, J=7.7 Hz, 1H), 7.07-6.90 (m, 1H), 5.51 (br. s., 1H), 3.33 (br. s., 2H), 2.85 (br. s., 2H), 2.09 (br. s., 2H). m/z (ESI) 512.2 (M+H)⁺.

EXAMPLE 70

1-(2-(1,2,3,6-TETRAHYDROPYRIDIN-4-YL)-4-(TRIFLUOROMETHYL)PHENYL)-N-(THIAZOL-2-YL)ISOQUINOLINE-6-SULFONAMIDE

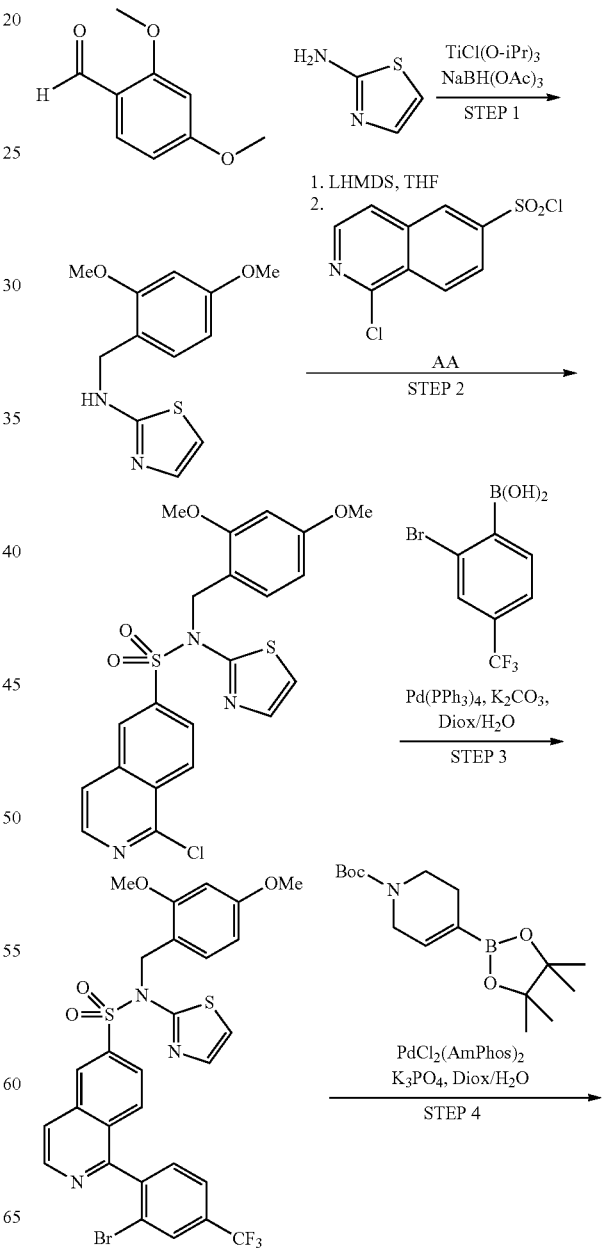

-continued

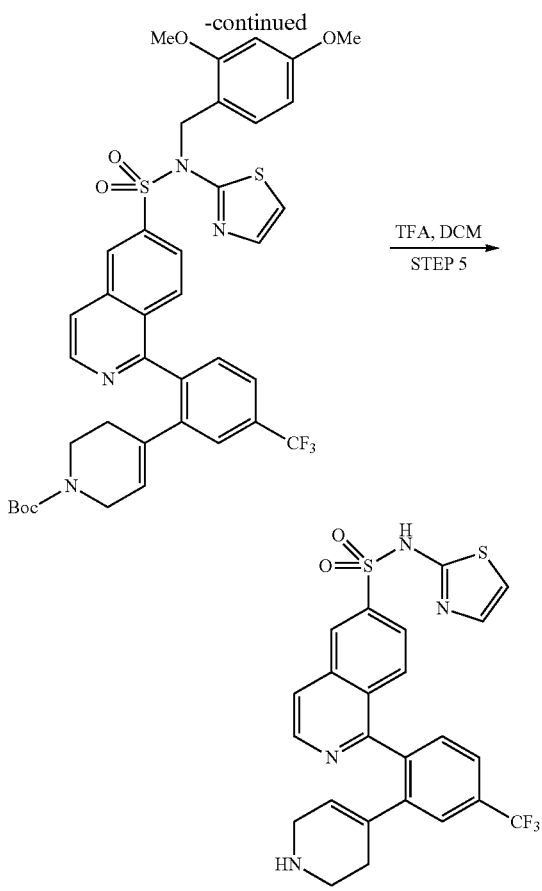

STEP 1: N-(2,4-DIMETHOXYBENZYL)-4-FLUORO-3-NITRO-N-(1,2,4-THIADIAZOL-5-YL)BENZENESULFONAMIDE

The title compound was prepared in an analogous manner to that of INTERMEDIATE BB, Step 1, except that thiazol-2-amine was used in place of 1,2,4-thiadiazol-5-amine and 2,4-dimethoxybenzaldehyde was used in place of 4-methoxybenzaldehyde. m/z (ESI) 251.1 (M+H)$^+$.

STEP 2: 1-CHLORO-N-(2,4-DIMETHOXYBENZYL)-N-(THIAZOL-2-YL)ISOQUINOLINE-6-SULFONAMIDE

A solution of N-(2,4-dimethoxybenzyl)thiazol-2-amine (0.546 g, 2.182 mmol) in THF (7 mL) was cooled in a dry ice-acetone bath for 5 minutes. Lithium bis(trimethylsilyl)amide (1M in THF) (2.381 ml, 2.381 mmol) was added dropwise, then the flask was removed from the cooling bath for 5 min. The flask was again cooled into a dry ice-acetone bath for 20 min, resulting in the formation of a thick slurry. A suspension of 1-chloroisoquinoline-6-sulfonyl chloride (0.520 g, 1.984 mmol) in THF (5 mL) was added dropwise, then the cooling bath was removed. The reaction was stirred for one hour. The reaction was quenched with saturated ammonium chloride solution, diluted with ethyl acetate and washed with water. The aqueous layer was extracted with ethyl acetate, and the combined organic layers were dried with sodium sulfate, filtered, and concentrated. The filtrate was purified by silica gel chromatography on a 40 g silica column with 0 to 30% EtOAc/Heptane. The product containing fractions were combined and concentrated to afford a white solid. The solid was triturated with methanol and stirred for five minutes. The solution was filtered and the solids were washed with methanol. The solids were dried under a vacuum to afford 1-chloro-N-(2,4-dimethoxybenzyl)-N-(thiazol-2-yl)isoquinoline-6-sulfonamide as a white solid. m/z (ESI) 498.1 (M+H)$^+$.

STEP 3: 1-(2-BROMO-4-(TRIFLUOROMETHYL)PHENYL)-N-(2,4-DIMETHOXYBENZYL)-N-(THIAZOL-2-YL)ISOQUINOLINE-6-SULFONAMIDE

A microwave vial was charged with 1-chloro-N-(2,4-dimethoxybenzyl)-N-(thiazol-2-yl)isoquinoline-6-sulfonamide (0.075 g, 0.158 mmol), (2-bromo-4-(trifluoromethyl)phenyl)boronic acid (0.064 g, 0.236 mmol), tetrakis(triphenylphosphine)palladium(0) (0.018 g, 0.016 mmol), and potassium carbonate (0.109 g, 0.788 mmol). Dioxane (1.182 ml) and water (0.394 ml) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified by silica gel chromatography (12 g column, gradient elution 0 to 50% EtOAc:Heptane) to afford 1-(2-bromo-4-(trifluoromethyl)phenyl)-N-(2,4-dimethoxybenzyl)-N-(thiazol-2-yl)isoquinoline-6-sulfonamide as a white solid. m/z (ESI) 664.1 (M+H)$^+$.

STEP 4: TERT-BUTYL 4-(2-(6-(N-(2,4-DIMETHOXYBENZYL)-N-(THIAZOL-2-YL)SULFAMOYL)ISOQUINOLIN-1-YL)-5-(TRIFLUOROMETHYL)PHENYL)-5,6-DIHYDROPYRIDINE-1(2H)-CARBOXYLATE

A microwave vial was charged with 1-(2-bromo-4-(trifluoromethyl)phenyl)-N-(2,4-dimethoxybenzyl)-N-(thiazol-2-yl)isoquinoline-6-sulfonamide (0.063 g, 0.095 mmol), tert-butyl 4-(4,4,5,5-tetramethyl-1,3,2-dioxaborolan-2-yl)-5,6-dihydropyridine-1(2H)-carboxylate (0.044 g, 0.142 mmol), Pd(AmPhos)$_2$Cl$_2$ (6.71 mg, 9.48 µmol), and potassium phosphate (0.070 g, 0.332 mmol). Dioxane (0.474 ml) and water (0.158 ml) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified by silica gel chromatography (12 g column, gradient elution 0 to 50% EtOAc:Heptane) to afford tert-butyl 4-(2-(6-(N-(2,4-dimethoxybenzyl)-N-(thiazol-2-yl)sulfamoyl)isoquinolin-1-yl)-5-(trifluoromethyl)phenyl)-5,6-dihydropyridine-1(2H)-carboxylate as an off-white solid. m/z (ESI) 767.3 (M+H)$^+$.

STEP 5

EXAMPLE 70

1-(2-(1,2,3,6-TETRAHYDROPYRIDIN-4-YL)-4-(TRIFLUOROMETHYL)PHENYL)-N-(THIAZOL-2-YL)ISOQUINOLINE-6-SULFONAMIDE

Tert-butyl 4-(2-(6-(N-(2,4-dimethoxybenzyl)-N-(thiazol-2-yl)sulfamoyl)isoquinolin-1-yl)-5-(trifluoromethyl)phenyl)-5,6-dihydropyridine-1(2H)-carboxylate (0.073 g, 0.095 mmol) was dissolved in 1 mL of DCM and TFA (0.073 ml, 0.948 mmol) was added. The reaction was stirred overnight at room temperature. The solution was concentrated and concentrated from DCM two more times. The resulting yellow solid was triturated with diethyl ether and stirred for 15 minutes. The solution was filtered and the solids were washed with diethyl ether. The material was dissolved in methanol and loaded onto an SCX ion exchange column (pre-wetted with methanol) (Biotage AB, Uppsala, SE). The column was washed several times with methanol, then the product was liberated with 2.0 M ammonia/methanol solution. The filtrate was concentrated to afford 1-(2-(1,2,3,6-tetrahydropyridin-4-yl)-4-(trifluoromethyl)phenyl)-N-(thiazol-2-yl)isoquinoline-6-sulfonamide as a light yellow solid. $^1$H NMR (400 MHz, DMSO-$d_6$) δ=8.60 (d, J=5.7 Hz, 1H), 8.44 (d, J=1.5 Hz, 1H), 8.05 (d, J=5.4 Hz, 1H), 7.93-7.79 (m, 2H), 7.72 (s, 1H), 7.61 (dd, J=8.4, 16.3 Hz, 2H), 6.96 (d, J=3.9 Hz, 1H), 6.52 (d, J=3.9 Hz, 1H), 5.49 (br. s., 1H), 3.24 (br. s., 2H), 2.72 (t, J=5.8 Hz, 2H), 2.04 (br. s., 2H). m/z (ESI) 517.2 (M+H)$^+$.

EXAMPLE 71

1-(2-(PYRIDIN-4-YL)-4-(TRIFLUOROMETHYL)PHENYL)-N-(THIAZOL-2-YL)ISOQUINOLINE-6-SULFONAMIDE

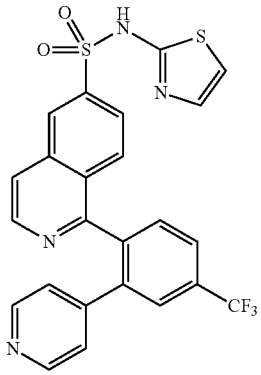 [SMILES: O=S(=O)(Nc1nccs1)c1ccc2c(-c3ccc(C(F)(F)F)cc3-c3ccncc3)nccc2c1]

The title compound was prepared in an analogous manner to that of Example 70, Steps 4 and 5, except that pyridin-4-ylboronic acid was used in place of tert-butyl 4-(4,4,5,5-tetramethyl-1,3,2-dioxaborolan-2-yl)-5,6-dihydropyridine-1(2H)-carboxylate. $^1$H NMR (400 MHz, DMSO-$d_6$) δ=12.88 (br. s., 1H), 8.61 (d, J=5.7 Hz, 1H), 8.49 (d, J=1.6 Hz, 1H), 8.31-8.23 (m, 2H), 8.09 (d, J=5.4 Hz, 1H), 8.01 (d, J=8.0 Hz, 1H), 7.97 (s, 1H), 7.86-7.80 (m, J=8.0 Hz, 1H), 7.79-7.75 (m, 1H), 7.74-7.69 (m, 1H), 7.28 (d, J=4.6 Hz, 1H), 7.07-6.98 (m, 2H), 6.87 (d, J=4.6 Hz, 1H). m/z (ESI) 513.2 (M+H)$^+$.

EXAMPLE 72

1-(2-(1-METHYL-1,2,3,6-TETRAHYDROPYRIDIN-4-YL)-4-(TRIFLUOROMETHYL)PHENYL)-N-(THIAZOL-2-YL)ISOQUINOLINE-6-SULFONAMIDE

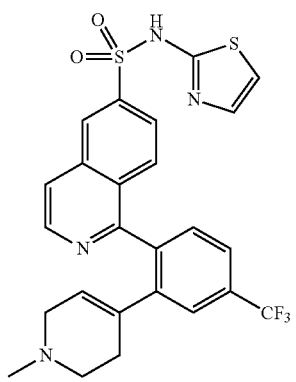 [SMILES: CN1CC=C(c2cc(C(F)(F)F)ccc2-c2nccc3cc(S(=O)(=O)Nc4nccs4)ccc23)CC1]

The title compound was prepared in an analogous manner to that of Example 70, Steps 4 and 5, except that 1-methyl-4-(4,4,5,5-tetramethyl-1,3,2-dioxaborolan-2-yl)-1,2,3,6-tetrahydropyridine was used in place of tert-butyl 4-(4,4,5,5-tetramethyl-1,3,2-dioxaborolan-2-yl)-5,6-dihydropyridine-1(2H)-carboxylate. $^1$H NMR (400 MHz, DMSO-$d_6$) δ=8.66 (d, J=5.7 Hz, 1H), 8.52 (d, J=1.7 Hz, 1H), 8.11 (d, J=5.5 Hz, 1H), 7.91-7.79 (m, 2H), 7.74 (s, 1H), 7.65 (dd, J=5.7, 8.4 Hz, 2H), 7.19 (d, J=4.4 Hz, 1H), 6.77 (d, J=4.4 Hz, 1H), 5.32 (br. s., 1H), 2.77-2.59 (m, 2H), 2.21 (br. s., 2H), 2.04 (s, 3H), 1.99 (d, J=10.8 Hz, 2H). m/z (ESI) 531.2 (M+H)$^+$.

EXAMPLE 73

1-MORPHOLINO-N-(THIAZOL-2-YL)ISOQUINOLINE-6-SULFONAMIDE

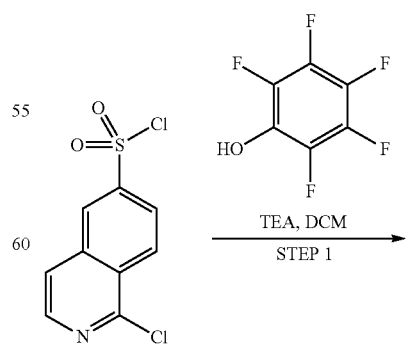

-continued

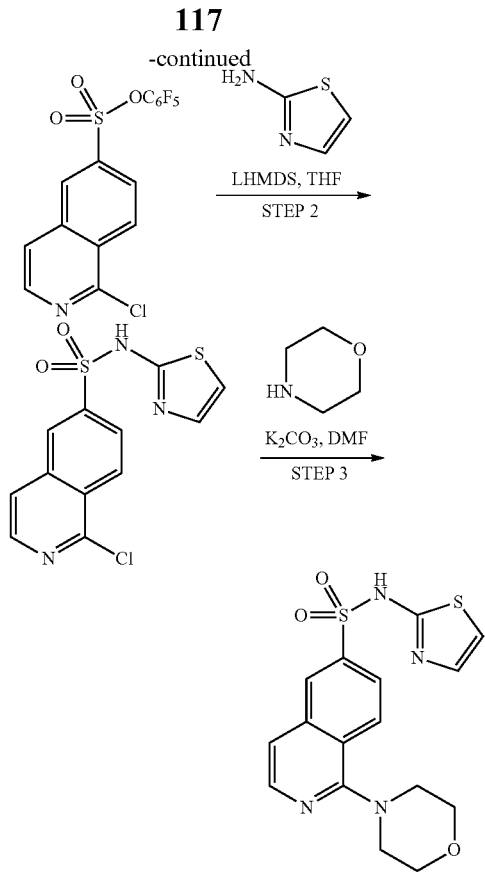

STEP 1: PERFLUOROPHENYL 1-CHLOROISOQUINOLINE-6-SULFONATE 2,3,4,5,6-Pentafluorophenol (2.73 g, 14.82 mmol) was dissolved in DCM (49.4 ml). 1-chloroisoquinoline-6-sulfonyl chloride (2.59 g, 9.88 mmol) was added, followed by the dropwise addition of triethylamine (2.066 ml, 14.82 mmol). The reaction was stirred overnight at room temperature. The reaction was concentrated and purified by silica gel chromatography (40 g column, gradient elution 0 to 50% Et$_2$O: Heptane) to afford perfluorophenyl 1-chloroisoquinoline-6-sulfonate as a white solid. m/z (ESI) 410.0 (M+H)$^+$.

STEP 2: 1-CHLORO-N-(THIAZOL-2-YL)ISOQUINOLINE-6-SULFONAMIDE

A flask containing thiazol-2-amine (0.185 g, 1.843 mmol), perfluorophenyl 1-chloroisoquinoline-6-sulfonate (0.719 g, 1.755 mmol), and THF (0.163 mL) was cooled to 0° C. LHMDS (1.0 M in THF) (3.86 ml, 3.86 mmol) was added dropwise and the reaction was stirred for 5 minutes at 0° C. The reaction was quenched with saturated ammonium chloride solution, diluted with ethyl acetate and washed with water. The aqueous layer was extracted with ethyl acetate, and the combined organic layers were dried with sodium sulfate, filtered, and concentrated. The material was triturated in DCM and loaded onto a silica gel cartridge. The tan solid remaining at the top of the cartridge was scraped into a flask and put aside. The remaining material was purified by silica gel chromatography (40 g column, gradient elution 0 to 100% EtOAc:Heptane with a 10% MeOH:DCM flush). The product fractions were combined with the previously isolated material to afford 1-chloro-N-(thiazol-2-yl)isoquinoline-6-sulfonamide as a tan solid. m/z (ESI) 326.0 (M+H)$^+$.

STEP 3

EXAMPLE 73

1-MORPHOLINO-N-(THIAZOL-2-YL)ISOQUINOLINE-6-SULFONAMIDE 1-chloro-N-(thiazol-2-yl)isoquinoline-6-sulfonamide (0.200 g, 0.614 mmol) and potassium carbonate (0.424 g, 3.07 mmol) were dissolved in DMF (4.09 ml). Morpholine (0.535 ml, 6.14 mmol) was added and the reaction was stirred overnight at 110° C. The reaction was diluted with water and extracted twice with ethyl acetate. The aqueous layer was acidified to a pH of about 1 with concentrated HCl solution and extracted twice with ethyl acetate. The aqueous layer was passed through an SCX ion exchange column (pre-wetted with methanol) (Biotage AB, Uppsala, SE), then the column was washed several times with methanol. The product was liberated with ammonia solution in methanol. The process was repeated with the aqueous filtrate and a new SCX column. The product-containing filtrates were combined and concentrated to afford crude product as an orange solid. The material was purified by silica gel chromatography (40 g column, gradient elution 0-10% MeOH:DCM) to afford 1-morpholino-N-(thiazol-2-yl)isoquinoline-6-sulfonamide as a light yellow solid. $^1$H NMR (400 MHz, DMSO-d$_6$) δ=12.86 (br. s., 1H), 8.38 (d, J=1.9 Hz, 1H), 8.28-8.19 (m, 2H), 7.86 (dd, J=1.9, 8.9 Hz, 1H), 7.62 (d, J=5.5 Hz, 1H), 7.28 (d, J=4.6 Hz, 1H), 6.87 (d, J=4.6 Hz, 1H), 3.88-3.80 (m, 4H), 3.35-3.26 (m, 4H). m/z (ESI) 377.2 (M+H)$^+$.

EXAMPLE 74

5-(2-(1-METHYL-1H-PYRAZOL-5-YL)-4-(TRIFLUOROMETHYL)PHENYL)-N-(PYRIMIDIN-4-YL)NAPHTHALENE-2-SULFONAMIDE

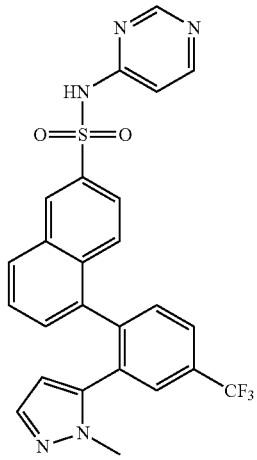 [SMILES: Cn1nccc1-c1cc(C(F)(F)F)ccc1-c1cccc2cc(S(=O)(=O)Nc3ccncn3)ccc12]

The title compound was prepared in a similar manner to INTERMEDIATE X using 5-(2-chloro-4-(trifluoromethyl)phenyl)-N-(pyrimidin-4-yl)naphthalene-2-sulfonamide (57.0 mg, 0.123 mmol), (1-methyl-1H-pyrazol-5-yl)boronic acid (30.9 mg, 0.246 mmol), potassium phosphate (78 mg, 0.369 mmol), and 1,1-bis[(di-t-butyl-p-methylaminophenyl]

palladium(ii) chloride (8.70 mg, 0.012 mmol) to provide 5-(2-(1-methyl-1H-pyrazol-5-yl)-4-(trifluoromethyl)phenyl)-N-(pyrimidin-4-yl)naphthalene-2-sulfonamide 2,2,2-trifluoroacetate (6.3 mg, 0.01 mmol) after purification by trifluoroacetic acid modified preparative HPLC. $^1$H NMR (400 MHz, d$_6$-acetone) δ ppm 3.51 (s, 3H) 6.98 (d, J=1.86 Hz, 1H) 7.25 (d, J=5.87 Hz, 1H) 7.54-7.60 (m, 1H) 7.62-7.68 (m, 1H) 7.74 (dd, J=12.96, 8.46 Hz, 2H) 7.90 (s, 1H) 7.92-8.02 (m, 2H) 8.15 (d, J=8.41 Hz, 1H) 8.43 (d, J=5.48 Hz, 1H) 8.59-8.74 (m, 2H); m/z (ESI, +ve ion) 510.3 (M+H)$^+$.

EXAMPLE 75

5-(2-(PYRIDIN-4-YL)-4-(TRIFLUOROMETHYL)PHENYL)-N-(PYRIMIDIN-4-YL)NAPHTHALENE-2-SULFONAMIDE

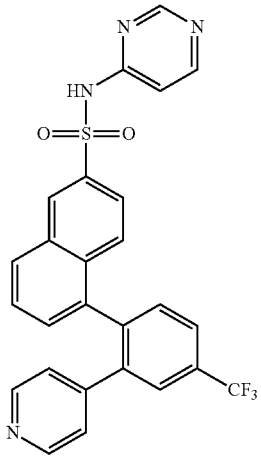 [SMILES: O=S(=O)(Nc1ccncn1)c1ccc2c(-c3ccc(C(F)(F)F)cc3-c3ccncc3)cccc2c1]

The title compound was prepared in a similar manner to INTERMEDIATE X using 5-(2-chloro-4-(trifluoromethyl)phenyl)-N-(pyrimidin-4-yl)naphthalene-2-sulfonamide (112.0 mg, 0.241 mmol), pyridine-4-boronic acid hydrate (59.4 mg, 0.483 mmol), potassium phosphate (154 mg, 0.724 mmol), and 1,1-bis[(di-t-butyl-p-methylaminophenyl]palladium(ii) chloride (17.10 mg, 0.024 mmol) to provide 5-(2-(pyridin-4-yl)-4-(trifluoromethyl)phenyl)-N-(pyrimidin-4-yl)naphthalene-2-sulfonamide bis(2,2,2-trifluoroacetate) (110 mg, 0.150 mmol) after after purification by trifluoroacetic acid modified preparative HPLC. $^1$H NMR (400 MHz, MeOH) δ ppm 7.12 (d, J=6.16 Hz, 1H) 7.56-7.69 (m, 3H) 7.73 (d, J=6.46 Hz, 2H) 7.79 (d, J=7.92 Hz, 1H) 7.89 (dd, J=8.90, 1.66 Hz, 1H) 8.00-8.09 (m, 2H) 8.13 (d, J=7.83 Hz, 1H) 8.29 (d, J=6.36 Hz, 1H) 8.48 (d, J=6.36 Hz, 2H) 8.56-8.72 (m, 2H); m/z (ESI, +ve ion) 507.0 (M+H)$^+$.

EXAMPLE 76

5-(2-(1-METHYL-1,2,3,6-TETRAHYDROPYRIDIN-4-YL)-4-(TRIFLUOROMETHYL)PHENYL)-N-(PYRIMIDIN-4-YL)NAPHTHALENE-2-SULFONAMIDE

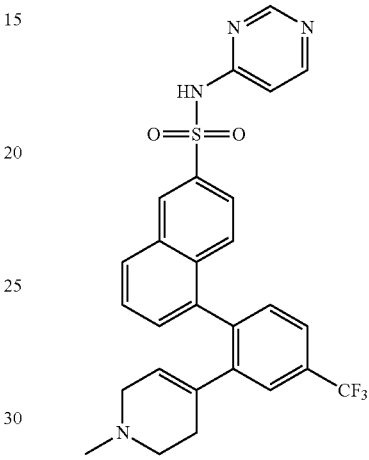

To a round bottom flask charged with N-(pyrimidin-4-yl)-5-(2-(1,2,3,6-tetrahydropyridin-4-yl)-4-(trifluoromethyl)phenyl)naphthalene-2-sulfonamide (EXAMPLE 48, 167.0 mg, 0.327 mmol) was added MeOH (3271 μl), then formaldehyde (265 μl, 3.27 mmol). The solution was maintained at rt for 15 min, then sodium triacetoxyhydroborate (693 mg, 3.27 mmol) was added portionwise. After 10 min, the reaction mixture was partitioned between ice and saturated NaHCO$_3$ and EtOAc. The layers were separated and the aqueous layer was extracted with EtOAc (1×25 mL). The combined organic extracts were washed with brine (1×20 mL) and dried over Na$_2$SO$_4$ and concentrated under a vacuum. The residue was taken up in minimal MeOH and purified by reverse phase preparative HPLC (20 to 80% CH$_3$CN:H2O (1% TFA modifier) over 15 min). Clean fractions were combined and concentrated to afford 5-(2-(1-methyl-1,2,3,6-tetrahydropyridin-4-yl)-4-(trifluoromethyl)phenyl)-N-(pyrimidin-4-yl)naphthalene-2-sulfonamide 2,2,2-trifluoroacetate (190 mg, 0.298 mmol) as a off-white amorphous solid. $^1$H NMR (400 MHz, MeOH) δ ppm 1.98-2.47 (m, 2H) 2.49-2.90 (m, 4H) 3.08-3.28 (m, 1H) 3.37-3.58 (m, 1H) 3.64-3.90 (m, 1H) 5.68 (d, J=8.51 Hz, 1H) 7.16 (dd, J=6.36, 0.98 Hz, 1H) 7.54 (d, J=8.02 Hz, 1H) 7.58-7.69 (m, 2H) 7.70-7.85 (m, 3H) 7.94 (d, J=8.61 Hz, 1H) 8.18 (d, J=8.31 Hz, 1H) 8.30 (d, J=6.36 Hz, 1H) 8.60 (s, 1H) 8.72 (d, J=1.37 Hz, 1H); m/z (ESI, +ve ion) 525.2 (M+H)⁺.
EXAMPLES 77 AND 78
5-(2-(1,2,3,6-TETRAHYDROPYRIDIN-4-YL)-4-(TRIFLUOROMETHYL)PHENYL)-N-(THIAZOL-2-YL)NAPHTHALENE-2-SULFONAMIDE AND 5-(2-(1-METHYL-1,2,3,6-TETRAHYDROPYRIDIN-4-YL)-4-(TRIFLUOROMETHYL)PHENYL)-N-(THIAZOL-2-YL)NAPHTHALENE-2-SULFONAMIDE
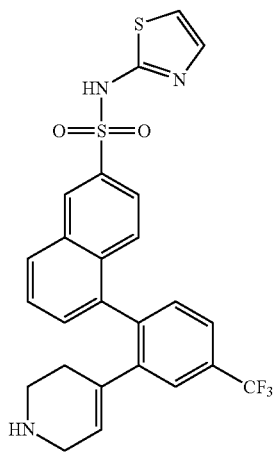
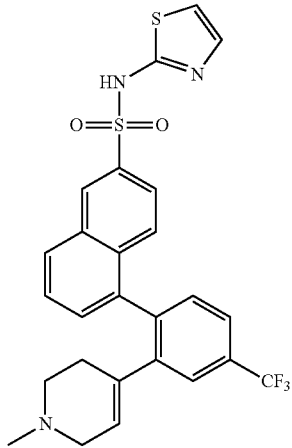
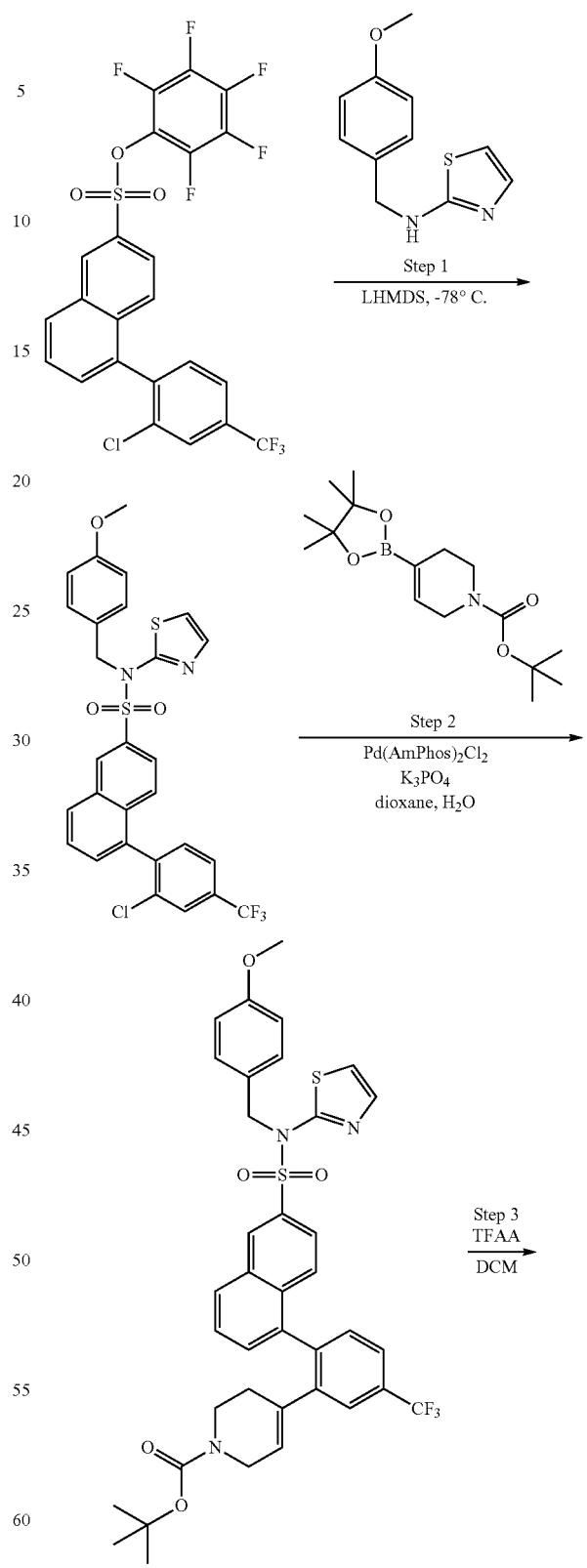

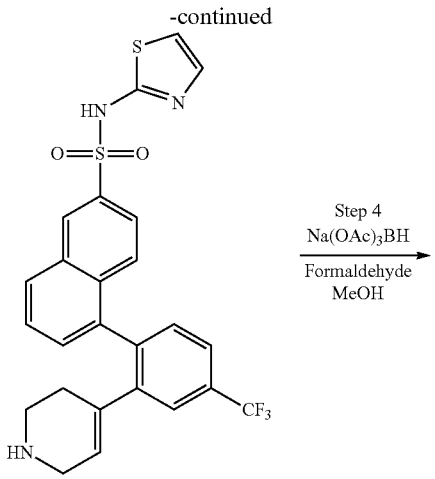

Example 77

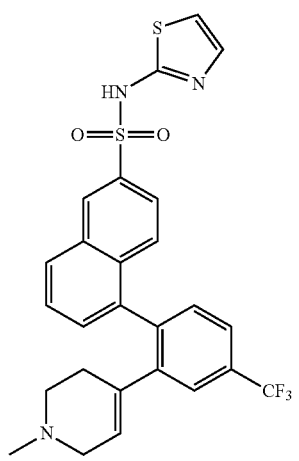

Example 78

STEP 1: 5-(2-CHLORO-4-(TRIFLUOROMETHYL) PHENYL)-N-(4-METHOXYBENZYL)-N-(THIAZOL-2-YL)NAPHTHALENE-2-SULFONAMIDE

The title compound was prepared in an analogous manner to that of intermediate W, except that N-(4-methoxybenzyl)thiazol-2-amine was used in place of 4-aminopyrimidine and perfluorophenyl 5-(2-chloro-4-(trifluoromethyl)phenyl)naphthalene-2-sulfonate (intermediate Z) was used instead of perfluorophenyl 5-bromonaphthalene-2-sulfonate. MS (ESI, positive) m/z: 588.9.

STEP 2: TERT-BUTYL 4-(2-(6-(N-(4-METHOXYBENZYL)-N-(THIAZOL-2-YL)SULFAMOYL)NAPHTHALEN-1-YL)-5-(TRIFLUOROMETHYL)PHENYL)-5,6-DIHYDROPYRIDINE-1(2H)-CARBOXYLATE

The title compound was prepared in an analogous manner to that of intermediate Y, except that 5-(2-chloro-4-(trifluoromethyl)phenyl)-N-(4-methoxybenzyl)-N-(thiazol-2-yl)naphthalene-2-sulfonamide was used instead of 5-(2-chloro-4-(trifluoromethyl)phenyl)-N-(pyrimidin-4-yl)naphthalene-2-sulfonamide.

STEP 3

EXAMPLE 77

The title compound was prepared in an analogous manner to that of EXAMPLE 48, except that tert-butyl-4-(2-(6-(N-(4-methoxybenzyl)-N-(thiazol-2-yl)sulfamoyl)naphthalen-1-yl)-5-(trifluoromethyl)phenyl)-5,6-dihydropyridine-1(2H)-carboxylate was used instead of tert-butyl 4-(2-(6-(N-(pyrimidin-4-yl)sulfamoyl)naphthalen-1-yl)-5-(trifluoromethyl)phenyl)-5,6-dihydropyridine-1(2H)-carboxylate. $^1$H NMR (500 MHz, DMSO-$d_6$) δ ppm 1.81-2.20 (m, 2H) 2.66-2.94 (m, 2H) 6.84 (d, J=4.70 Hz, 1H) 7.26 (d, J=4.59 Hz, 1H) 7.54 (dd, J=7.53, 2.72 Hz, 2H) 7.59 (d, J=8.65 Hz, 1H) 7.65-7.72 (m, 2H) 7.74-7.87 (m, 2H) 8.25 (d, J=8.44 Hz, 1H) 8.54 (d, J=1.71 Hz, 3H). m/z (ESI, +ve ion) 516.0 (M+H)$^+$.

STEP 4

EXAMPLE 78

5-(2-(1-METHYL-1,2,3,6-TETRAHYDROPYRIDIN-4-YL)-4-(TRIFLUOROMETHYL)PHENYL)-N-(THIAZOL-2-YL)NAPHTHALENE-2-SULFONAMIDE

The title compound was prepared in an analogous manner to that of EXAMPLE 76, except that 5-(2-(1,2,3,6-tetrahydropyridin-4-yl)-4-(trifluoromethyl)phenyl)-N-(thiazol-2-yl)naphthalene-2-sulfonamide was used instead of N-(pyrimidin-4-yl)-5-(2-(1,2,3,6-tetrahydropyridin-4-yl)-4-(trifluoromethyl)phenyl)naphthalene-2-sulfonamide. $^1$H NMR (500 MHz, DMSO-$d_6$) δ ppm 1.99 (s, 3H) 2.08 (s, 1H) 2.59-2.71 (m, 2H) 6.68 (d, J=4.27 Hz, 1H) 6.89 (d, J=4.59 Hz, 1H) 7.12 (d, J=4.27 Hz, 1H) 7.37 (d, J=4.81 Hz, 1H) 7.42-7.57 (m, 3H) 7.59-7.69 (m, 2H) 7.69-7.82 (m, 1H) 8.09-8.24 (m, 1H) 8.46 (s, 1H) 8.55 (s, 1H). m/z (ESI, +ve ion)

EXAMPLE 79

5-(2-CHLORO-4-(TRIFLUOROMETHYL)PHENYL)-N-(THIAZOL-2-YL)NAPHTHALENE-2-SULFONAMIDE

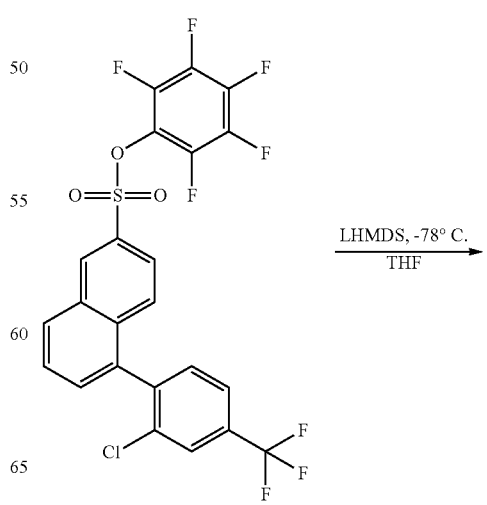

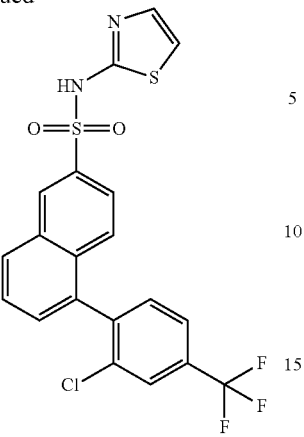

To a vial charged with perfluorophenyl 5-(2-chloro-4-(trifluoromethyl)phenyl)naphthalene-2-sulfonate (0.200 g, 0.362 mmol) and THF (1 mL), was added thiazol-2-amine (0.040 g, 0.398 mmol) as a solution in THF (2 mL). The solution was cooled to −78° C., and a THF solution of lithium bis(trimethylsilyl)amide (0.724 ml, 0.724 mmol, 1M) was added dropwise by syringe. The solution was maintained at −78° C. for 5 min and then allowed to warm to rt. The solution was concentrated and the crude residue was absorbed onto a 5 g plug of silica gel and purified by chromatography through a silica gel column (40 g), eluting with a gradient of 5% to 90% EtOAc in hexane, to provide 5-(2-chloro-4-(trifluoromethyl)phenyl)-N-(thiazol-2-yl)naphthalene-2-sulfonamide (0.112 g, 0.239 mmol) as a white solid. $^1$H NMR (500 MHz, DMSO-$d_6$) δ ppm 6.83 (d, J=4.59 Hz, 1H) 7.24 (d, J=4.59 Hz, 1H) 7.47 (d, J=8.98 Hz, 1H) 7.60 (d, J=7.16 Hz, 1H) 7.66-7.83 (m, 3H) 7.88 (d, J=8.23 Hz, 1H) 8.09 (s, 1H) 8.29 (d, J=8.33 Hz, 1H) 8.56 (d, J=1.71 Hz, 1H) 12.80 (br. s., 1H); m/z (ESI, +ve ion) 468.9 (M+H)$^+$.

EXAMPLE 80

5-(2-PHENYLPYRROLIDIN-1-YL)-N-(THIAZOL-2-YL)NAPHTHALENE-2-SULFONAMIDE

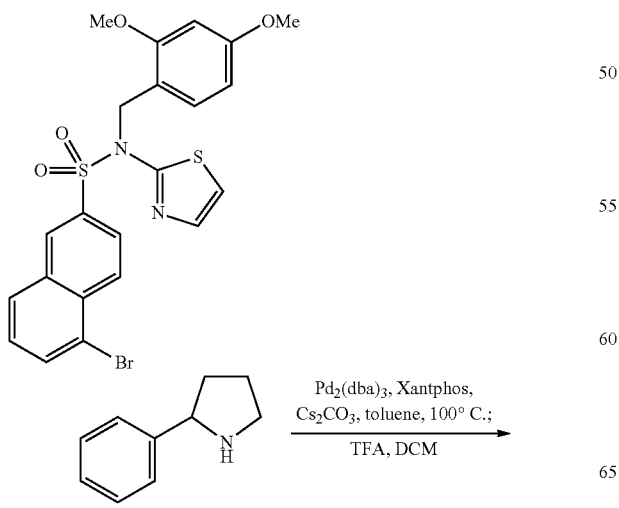

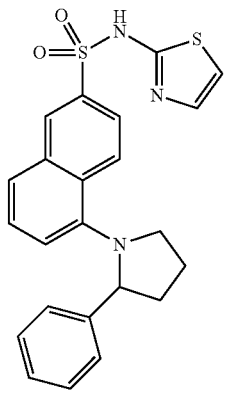

A vial was charged with 5-bromo-N-(2,4-dimethoxybenzyl)-N-(thiazol-2-yl)naphthalene-2-sulfonamide (51.89 mg, 0.100 mmol), Xantphos (11.56 mg, 0.020 mmol), Pd$_2$(dba)$_3$ (9.15 mg, 9.99 µmol), and cesium carbonate (65.1 mg, 0.200 mmol). The vial was flushed with Ar (g), then toluene (999 µl) and 2-phenylpyrrolidine (19.12 µl, 0.130 mmol) were added in sequence. The vial was sealed and heated to 100° C. for 18 h. The mixture was partitioned between EtOAc and water. The layers were separated, and the organic extract was washed with brine. The combined aq. layers were extracted with EtOAc, and the organic layers were combined. The combined solution was dried over sodium sulfate, filtered, and concentrated. The residue was purified by chromatography on silica gel (0 to 50% EtOAc/Heptane) to give a clear oil. This oil was taken up in DCM (1 mL) and TFA (0.5 mL). After 2 h, the mixture was diluted with MeOH, then concentrated. The residue was taken up in diethyl ether, sonicated, then filtered. The collected solid was washed with diethyl ether (twice), dried under a stream of N$_2$ (g) for 10 min, then dried under a high vacuum to give 5-(2-phenylpyrrolidin-1-yl)-N-(thiazol-2-yl)naphthalene-2-sulfonamide (15.25 mg, 0.035 mmol) as a white solid. $^1$H NMR (400 MHz, DMSO-$d_6$) δ ppm=12.76 (br. s., 1H), 8.45 (d, J=9.0 Hz, 1H), 8.31 (d, J=1.7 Hz, 1H), 7.77 (dd, J=2.0, 8.9 Hz, 1H), 7.59 (d, J=8.1 Hz, 1H), 7.40 (d, J=7.1 Hz, 2H), 7.33 (t, J=7.9 Hz, 1H), 7.26 (d, J=4.6 Hz, 1H), 7.18 (t, J=7.5 Hz, 2H), 7.12-7.04 (m, 2H), 6.82 (d, J=4.6 Hz, 1H), 4.86-4.77 (m, 1H), 4.20-4.10 (m, 1H), 3.02

(dt, J=4.7, 8.9 Hz, 1H), 2.47-2.39 (m, 1H), 2.16-2.05 (m, 1H), 2.00-1.78 (m, 2H). m/z (ESI) 436.2 (M+H)+.

INTERMEDIATE HH: 6-(N-(2,4-DIMETHOXY-BENZYL)-N-(THIAZOL-2-YL)SULFAMOYL)-1-NAPHTHOIC ACID

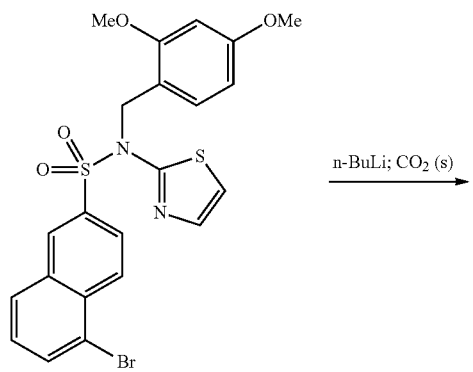

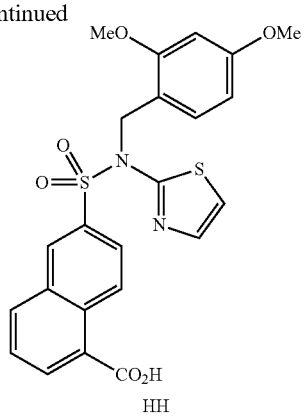

HH

A 15 mL round-bottom flask was charged 5-bromo-N-(2,4-dimethoxybenzyl)-N-(thiazol-2-yl)naphthalene-2-sulfonamide (454.14 mg, 0.874 mmol) and THF (8743 µl) to give an orange opaque mixture. The flask was cooled in a dry ice-acetone bath for 5 min, then n-butyllithium (2.33 M in THF) (450 µl, 1.049 mmol) was added dropwise over 20 s. After 20 min, a couple of pieces of dry ice were washed with DCM to remove any water/ice, and then the pieces were added directly to the flask. The cooling bath was removed. When the mixture had warmed to room temperature, it was diluted with a 0.5 N aq. HCl solution, diluted with water, and extracted with DCM (three times). The combined organic extracts were dried over sodium sulfate, filtered, and concentrated. The crude product was purified by chromatography on a 40 g silica gel column with 10% MeOH/DCM to give 6-(N-(2,4-dimethoxybenzyl)-N-(thiazol-2-yl)sulfamoyl)-1-naphthoic acid (224 mg, 0.462 mmol) as a white solid. m/z (ESI) 483.0 (M−H)+.

EXAMPLE 81

5-(2-(1-(AZETIDIN-3-YL)-1H-PYRAZOL-5-YL)-4-(TRIFLUOROMETHYL)PHENYL)-N-(THIAZOL-2-YL)NAPHTHALENE-2-SULFONAMIDE

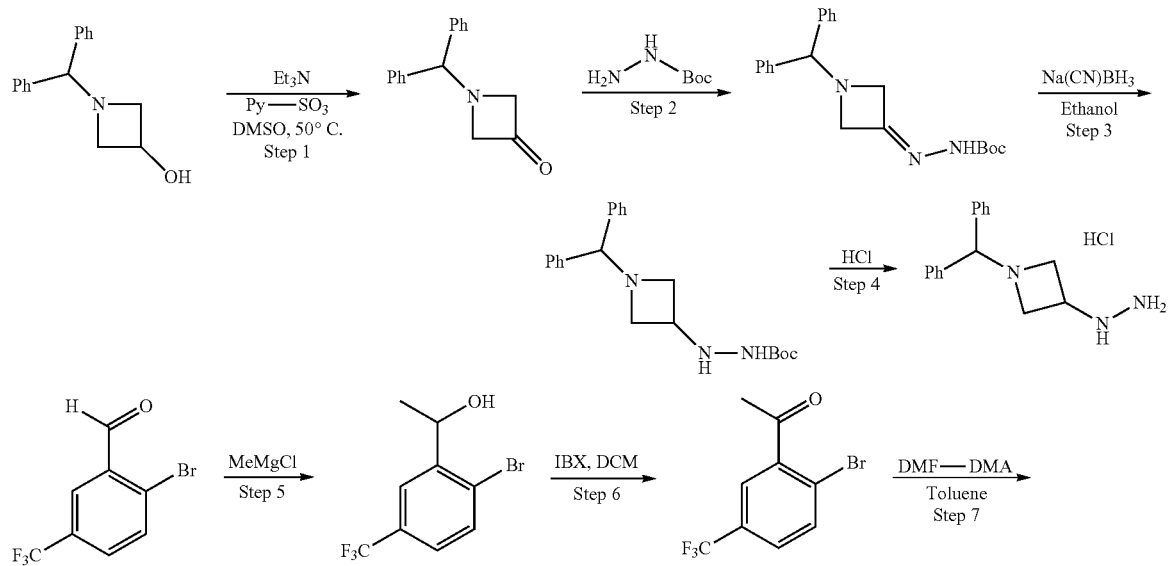

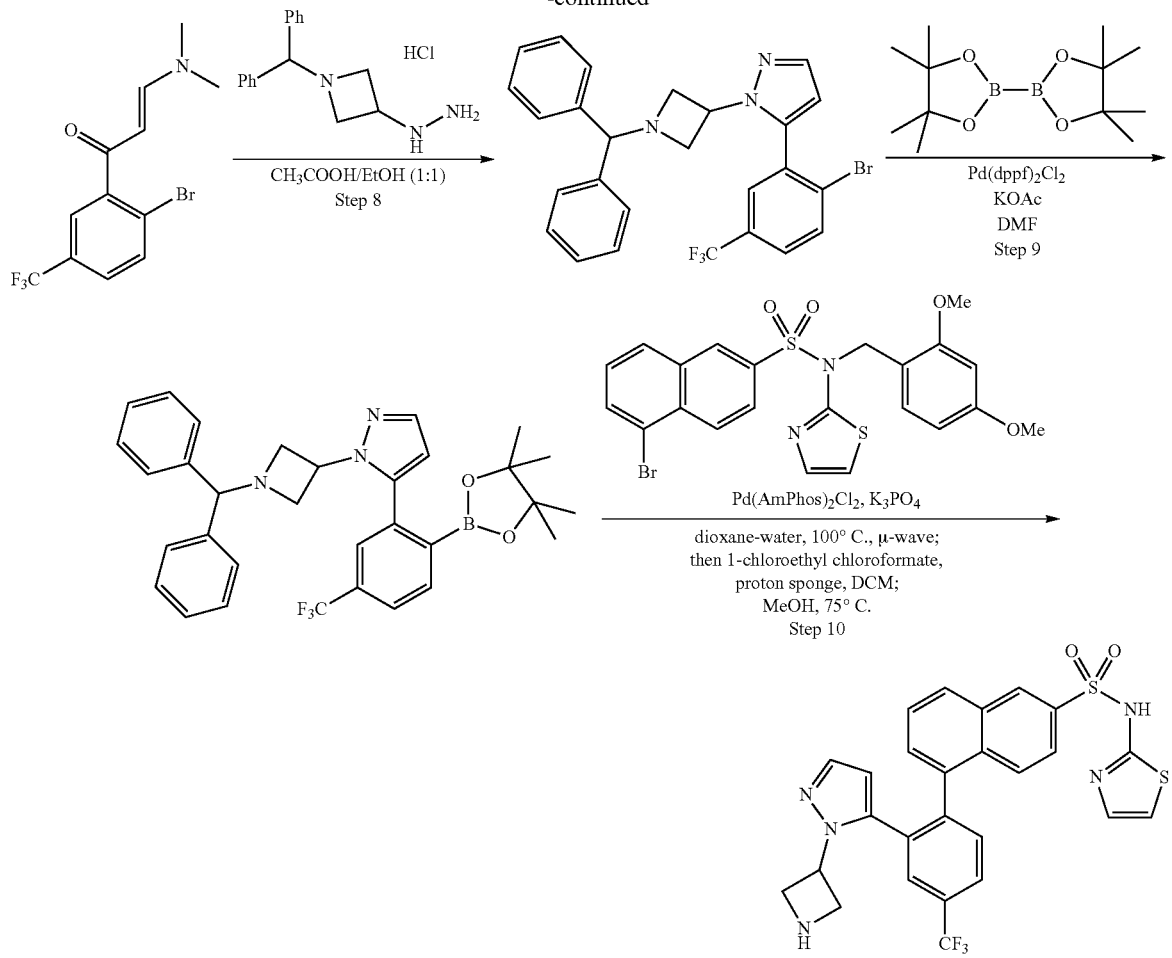

STEP 1: 1-BENZHYDRYLAZETIDIN-3-ONE

The title compound was prepared as described in WO2010079443A1. To a solution of compound 1-benzhydrylazetidin-3-ol (20 g, 28.4 mmol) in the triethyl amine (60 mL) was added a solution of sulfur trioxide pyridine complex (SO$_3$.Py) (40 g, 251.6 mmol) in dimethylsulfoxide (260 mL) under a nitrogen atmosphere at 25° C. The reaction was stirred at 50° C. for 2 h. Then the reaction mixture was cooled back to 25° C., diluted with water (500 mL), and extracted with ethyl acetate (2×500 mL). Organic part was dried over sodium sulfate, filtered, and concentrated under a vacuum to give a crude compound which was further purified by column chromatography using silica gel (100 to 200 mesh) eluting with 0% to 20% ethyl acetate in hexanes to provide 1-benzhydrylazetidin-3-one (11.7 g) as a white solid. MS (ESI, positive ion) m/z (M+1): 238.30. $^1$H NMR (400 MHz, DMSO) δ 7.50 (d, J=7.5 Hz, 4H), 7.30 (t, J=7.5 Hz, 4H), 7.20 (t, J=7.3 Hz, 2H), 4.82 (s, 1H), 4.00 (s, 4H).

STEP 2: TERT-BUTYL 2-(1-BENZHYDRYLAZETIDIN-3-YLIDENE)HYDRAZINECARBOXYLATE

The title compound was prepared as described in WO2010079443A1. To a solution of compound 1-benzhydrylazetidin-3-one (11.7 g, 49.3 mmol) in the methanol (150 mL), tert-butyl hydrazinecarboxylate (6.51 g, 49.3 mmol) was added. Then glacial acetic acid (5.92 mL) was added dropwise at 0° C. The reaction was stirred at 25° C. for 5 h under a nitrogen atmosphere. Then the solvent was evaporated off. The residue was dissolved in dichloromethane (200 mL) and washed with water (2×500 mL). The organic part was dried over sodium sulfate, filtered and concentrated under a vacuum to give the crude tert-butyl 2-(1-benzhydrylazetidin-3-ylidene)hydrazinecarboxylate (16.9 g, 97%) as a white solid. This material was used as is for the next step. MS (ESI, positive ion) m/z (M+1): 352.19.

STEP 3: TERT-BUTYL 2-(1-BENZHYDRYLAZETIDIN-3-YL)HYDRAZINECARBOXYLATE

The title compound was prepared as described in WO2010079443A1. To a solution of tert-butyl 2-(1-benzhydrylazetidin-3-ylidene)hydrazinecarboxylate (16.9 g, 48.1 mmol) in acetic acid (150 mL), sodium cyanoborohydride (3 g, 48.1 mmol) was added portionwise at 25° C. and stirred at the same temperature for 4 h under a nitrogen atmosphere. The solvent was completely evaporated off. The pH was adjusted to 8 to 10 with 1 M aqueous sodium hydroxide solution. The whole was extracted with dichloromethane (2×500 mL). Organic part was dried over sodium sulfate, filtered and concentrated in vacuum to give the crude tert-butyl 2-(1-benzhydrylazetidin-3-yl)hydrazinecarboxylate (16 g, 94%) as a white solid. This material was used as is for the next reaction. MS (ESI, positive ion) m/z (M+1): 354.4. $^1$H NMR (400 MHz, DMSO) δ 8.26 (s, 1H), 7.40 (d, J=7.5 Hz, 4H), 7.26 (t, J=7.5 Hz, 4H), 7.16 (t, J=7.2 Hz, 2H), 4.68 (t, J=4.6 Hz, 1H), 4.33 (s, 1H), 3.50 (dd, J=12.5, 6.2 Hz, 1H), 3.16 (t, J=7.0 Hz, 2H), 2.78 (t, J=6.9 Hz, 2H), 1.36 (s, 9H).

STEP 4: 1-BENZHYDRYL-3-HYDRAZINYLAZETIDINE HYDROCHLORIDE SALT

The title compound was prepared as described in WO2010079443A1. To a mixture of tert-butyl 2-(1-benzhydrylazetidin-3-yl)hydrazinecarboxylate (16 g) and 4 N HCl in dioxane (10 mL/1 g) was stirred at 25° C. for 3 h. The solvent was completely evaporated off to obtain a crude product. The crude product was washed with diethyl ether to obtain a white solid, 1-benzhydryl-3-hydrazinylazetidine hydrochloride (15.5 g). This was used as is for the next step.

STEP 5: 1-(2-BROMO-5-(TRIFLUOROMETHYL)PHENYL) ETHANOL

To a solution of 2-bromo-5-(trifluoromethyl)benzaldehyde (10 g, 39.6 mmol) in THF (40 mL), methyl magnesium chloride (3 M in THF) (26.4 mL, 79.3 mmol) was added at –78° C. dropwise. The reaction was warmed to 25° C. and stirred at this temperature for 1 h under a nitrogen atmosphere. Then the reaction mixture was diluted with water (200 mL) extracted with ethyl acetate (2×200 mL). Organic part was dried over sodium sulfate, filtered and concentrated in vacuum to give the crude compound which was further purified by column chromatography using silica gel (100 to 200 mesh) eluting with 0% to 10% ethyl acetate in hexanes to afford 1-(2-bromo-5-(trifluoromethyl)phenyl)ethanol (10.4 g, 98%) as a clear liquid. MS (ESI, Negative ion) m/z (M–1): 267.0. $^1$H NMR (400 MHz, DMSO) δ 7.87 (s, 1H), 7.80 (d, J=8.2 Hz, 1H), 7.55 (d, J=8.0 Hz, 1H), 5.68 (d, J=4.2 Hz, 1H), 5.03-4.94 (m, 1H), 1.32 (d, J=6.3 Hz, 3H).

STEP 6: 1-(2-BROMO-5-(TRIFLUOROMETHYL)PHENYL) ETHANONE

To a solution of compound 1-(2-bromo-5-(trifluoromethyl)phenyl)ethanol (10.4 g, 44.6 mmol) in the dimethylsulfoxide (50 mL), 2-iodoxybenzoic acid (25 g, 89.2 mmol) at 0° C. The reaction was warmed to 25° C. and stirred at this temperature for 2 hours under a nitrogen atmosphere. Then the reaction mixture was diluted with water (500 mL), extracted with ethyl acetate (2×500 mL). Organic part was dried over sodium sulfate, filtered and concentrated under a vacuum to give the crude compound 1-(2-bromo-5-(trifluoromethyl)phenyl)ethanone (15 g), as a brown liquid. $^1$H NMR (400 MHz, DMSO) δ 8.03 (s, 1H), 7.95 (d, J=8.4 Hz, 1H), 7.76 (d, J=8.4 Hz, 1H), 2.62 (s, 3H).

STEP 7: (E)-1-(2-BROMO-5-(TRIFLUOROMETHYL)PHENYL)-3-(DIMETHYLAMINO)PROP-2-EN-1-ONE

To a solution of 1-(2-bromo-5-(trifluoromethyl)phenyl) ethanone (15 g, 56.1 mmol) in the toluene (130 mL), N,N'-dimethylformamide dimethylacetal (15 mL, 84.2 mmol) was added. The reaction was stirred at 120° C. for 6 hours under a nitrogen atmosphere. After cooling to rt, the reaction mixture was diluted with water (500 mL), and extracted with ethyl acetate (2×500 mL). Organic part was dried over sodium sulfate, filtered and concentrated under a vacuum to give the crude compound (E)-1-(2-bromo-5-(trifluoromethyl)phenyl)-3-(dimethylamino)prop-2-en-1-one, (20 g) as a brown solid. This material was used for the next reaction. MS (ESI, positive ion) m/z (M+1): 322.

STEP 8: 1-(1-BENZHYDRYLAZETIDIN-3-YL)-5-(2-BROMO-5-(TRIFLUOROMETHYL)PHENYL)-1H-PYRAZOLE

To a solution of compound 1-benzhydryl-3-hydrazinylazetidine hydrochloride (15.5 g, 49.6 mmol) in ethanol (150 mL), a mixture of (E)-1-(2-bromo-5-(trifluoromethyl)phenyl)-3-(dimethylamino)prop-2-en-1-one (16 g, 49.6 mmol) in acetic acid (15 mL) was added slowly at 0° C. The reaction was stirred at the same temperature for 8 h. After warming to rt, the solvent was completely evaporated off. The residue was diluted with ethyl acetate (500 mL), washed with water (500 mL), and saturated aqueous sodium bicarbonate (30 mL). Organic part was dried over sodium sulfate, filtered and concentrated under a vacuum to give the crude which was further purified by column chromatography using silica gel (100 to 200 mesh) eluting with 0% to 10% ethyl acetate in hexanes to obtain 1-(1-benzhydrylazetidin-3-yl)-5-(2-bromo-5-(trifluoromethyl)phenyl)-1H-pyrazole (10 g, 39.3%) as a sticky yellow solid. MS (ESI, positive ion) m/z (M+1): 512.01. $^1$H NMR (400 MHz, DMSO) δ 8.03 (d, J=8.3 Hz, 1H), 7.80 (d, J=8.5 Hz, 1H), 7.77 (s, 1H), 7.68 (d, J=1.5 Hz, 1H), 7.43 (d, J=7.4 Hz, 4H), 7.26 (t, J=7.5 Hz, 4H), 7.17 (t, J=7.3 Hz, 2H), 6.41 (d, J=1.5 Hz, 1H), 4.66-4.59 (m, 1H), 4.57 (s, 1H), 3.46 (dt, J=26.3, 7.3 Hz, 4H).

STEP 9: 1-(1-BENZHYDRYLAZETIDIN-3-YL)-5-(5-(TRIFLUOROMETHYL)-2-(4,4,5-TRIMETHYL-1,3,2-DIOXABOROLAN-2-YL)PHENYL)-1H-PYRAZOLE

To a solution of compound 1-(1-benzhydrylazetidin-3-yl)-5-(2-bromo-5-(trifluoromethyl)phenyl)-1H-pyrazole (3 g, 5.8 mmol) in dioxane (90 mL), was added bispinnacolatodiboron (4.46 g, 17.5 mmol), and potassium acetate (1.72 g, 17.5 mmol), the reaction mixture was purged with nitrogen for 15 minutes. Then Pd(dppf)$_2$Cl$_2$.DCM (478 mg, 0.58 mmol) was added. The whole was heated at 110° C. for 5 h under a nitrogen atmosphere. The reaction was cooled to rt. After diluting with ethyl acetate (200 mL), the whole was filtered through a pad of diatomaceous earth with an aid of EtOAc. The filtrate was concentrated under a vacuum to obtain the crude, which was further purified by column chromatography using neutral alumina and hexanes as eluent to obtain an off-white solid. The product was further recrystallized with pentane to afford 1-(1-benzhydrylazetidin-3-yl)-5-(2-(4,4,5,5-tetramethyl-1,3,2-dioxaborolan-2-yl)-5-(trifluoromethyl)phenyl)-1H-pyrazole (2 g) as an off-white solid. MS (ESI, positive ion) m/z (M+1): 560.29. $^1$H NMR (400 MHz, DMSO) δ 7.85 (q, J=8.2 Hz, 2H), 7.63 (s, 1H), 7.57 (s, 1H), 7.41 (d, J=7.4 Hz, 4H), 7.25 (t, J=7.6 Hz, 4H), 7.16 (t, J=7.1 Hz, 2H), 6.25 (s, 1H), 4.57 (t, J=7.2 Hz, 1H), 4.53 (s, 1H), 3.39 (dt, J=15.7, 6.5 Hz, 4H), 1.01 (s, 12H).

STEP 10: 5-(2-(1-(AZETIDIN-3-YL)-1H-PYRAZOL-5-YL)-4-(TRIFLUOROMETHYL)PHENYL)-N-(THIAZOL-2-YL)NAPHTHALENE-2-SULFONAMIDE

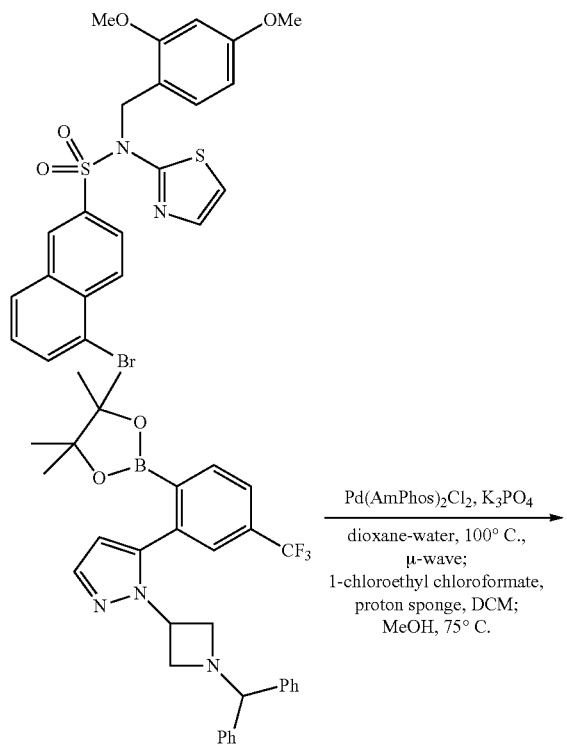

A vial was charged with 5-bromo-N-(2,4-dimethoxybenzyl)-N-(thiazol-2-yl)naphthalene-2-sulfonamide (292.08 mg, 0.562 mmol), 5-bromo-N-(2,4-dimethoxybenzyl)-N-(thiazol-2-yl)naphthalene-2-sulfonamide (292.08 mg, 0.562 mmol), Pd(AmPhos)$_2$Cl$_2$ (19.91 mg, 0.028 mmol), potassium phosphate (358 mg, 1.687 mmol), dioxane (2812 µl), and water (937 µl). The vial was sealed and heated in a microwave reactor for 30 min at 100° C. The mixture was diluted with water and extracted with EtOAc (twice). The combined organic extracts were dried over sodium sulfate, filtered, and concentrated. The residue was purified by chromatography on silica gel with 20 to 70% EtOAc/Heptane to give 5-(2-(1-(1-benzhydrylazetidin-3-yl)-1H-pyrazol-5-yl)-4-(trifluoromethyl)phenyl)-N-(2,4-dimethoxybenzyl)-N-(thiazol-2-yl)naphthalene-2-sulfonamide as an off-white solid. A portion of this material (97.97 mg, 0.112 mmol) was dissolved in DCM (2 mL) and treated successively with proton sponge (1,8-bis(dimethylamino)naphthalene) (55.4 mg, 0.258 mmol) and 1-chloroethyl chloroformate (25.5 µl, 0.236 mmol). The resulting mixture was stirred for 5 h, then concentrated. The residue was taken up in MeOH (3 mL) and transferred to a microwave vial. The vial was heated to 75° C. for 5 h in a microwave reactor. The reaction mixture was concentrated, and the crude product was purified by chromatography on silica gel (5% MeOH/DCM) to give 5-(2-(1-(azetidin-3-yl)-1H-pyrazol-5-yl)-4-(trifluoromethyl)phenyl)-N-(thiazol-2-yl)naphthalene-2-sulfonamide (38.07 mg, 0.069 mmol) as a tan solid. $^1$H NMR (400 MHz, DMSO-$d_6$) δ ppm=8.42 (d, J=1.7 Hz, 1H), 8.13 (d, J=8.4 Hz, 1H), 8.06-8.01 (m, 1H), 7.94 (s, 1H), 7.76 (d, J=8.1 Hz, 1H), 7.70 (dd, J=1.8, 8.9 Hz, 1H), 7.62-7.52 (m, 2H), 7.44 (d, J=6.2 Hz, 1H), 7.39 (d, J=1.9 Hz, 1H), 7.20 (d, J=4.5 Hz, 1H), 6.77 (d, J=4.5 Hz, 1H), 6.02 (d, J=1.8 Hz, 1H), 5.06-4.93 (m, 1H), 4.22-4.12 (m, 1H), 4.23-4.12 (m, 1H), 4.02-3.98 (m, 1H), 4.00 (d, J=8.4 Hz, 1H), 3.97 (br. s., 1H), 3.76-3.57 (m, 3H). m/z (ESI) 556.2 (M+H)$^+$.

EXAMPLE 82

5-(2-(1-(1-METHYLAZETIDIN-3-YL)-1H-PYRAZOL-5-YL)-4-(TRIFLUOROMETHYL)PHENYL)-N-(THIAZOL-2-YL)NAPHTHALENE-2-SULFONAMIDE

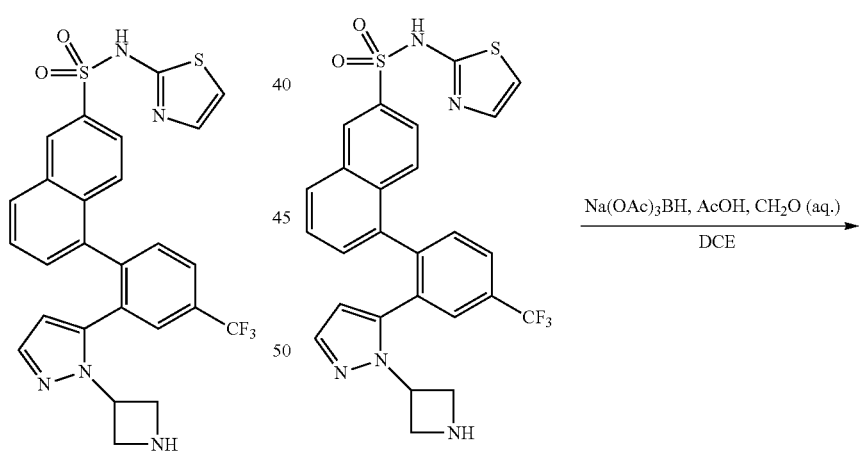

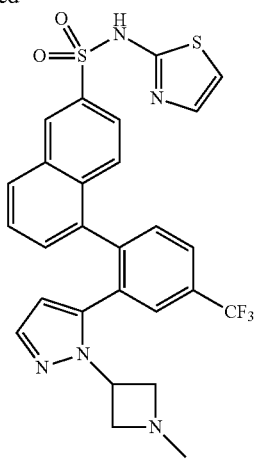

A flask was charged with 5-(2-(1-(azetidin-3-yl)-1H-pyrazol-5-yl)-4-(trifluoromethyl)phenyl)-N-(thiazol-2-yl)naphthalene-2-sulfonamide (26.25 mg, 0.047 mmol), DCE (1 mL), AcOH (0.05 mL), and formaldehyde (37% aq.) (10.55 μl, 0.142 mmol). The mixture was stirred for 2 min, then sodium triacetoxyborohydride (20.03 mg, 0.094 mmol) was added in one portion. The resulting mixture was stirred for 3 h, then concentrated. The residue was dissolve in MeOH, and this solution was loaded onto a 500 mg SCX-2 ion exchange column (Biotage AB, Uppsala, SE). The column was eluted with methanol, then with 2N ammonia in methanol. The basic fraction was concentrated to afford 5-(2-(1-(1-methylazetidin-3-yl)-1H-pyrazol-5-yl)-4-(trifluoromethyl)phenyl)-N-(thiazol-2-yl)naphthalene-2-sulfonamide (23.53 mg, 0.041 mmol) as a beige-solid. $^1$H NMR (400 MHz, DMSO-$d_6$) δ ppm=8.40 (s, 1H), 8.09 (d, J=7.9 Hz, 1H), 8.00 (d, J=6.9 Hz, 1H), 7.82 (s, 1H), 7.74 (d, J=8.4 Hz, 2H), 7.62-7.51 (m, 2H), 7.39 (d, J=6.8 Hz, 1H), 7.29 (s, 1H), 7.15 (d, J=4.1 Hz, 1H), 6.71 (d, J=4.0 Hz, 1H), 5.99 (s, 1H), 4.59 (td, J=7.3, 14.2 Hz, 1H), 3.66-3.59 (m, 1H), 3.33 (t, J=7.0 Hz, 1H), 3.09-2.95 (m, 2H), 2.27 (s, 3H). m/z (ESI) 570.2 (M+H)$^+$.

EXAMPLE 83

5-(2-PHENYLPYRROLIDIN-1-YL)-N-(1,2,4-THIADIAZOL-5-YL)NAPHTHALENE-2-SULFONAMIDE

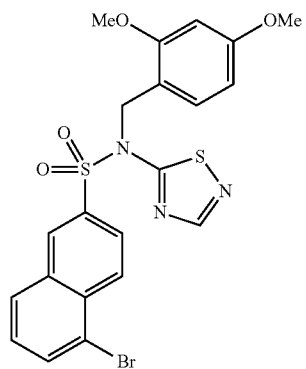

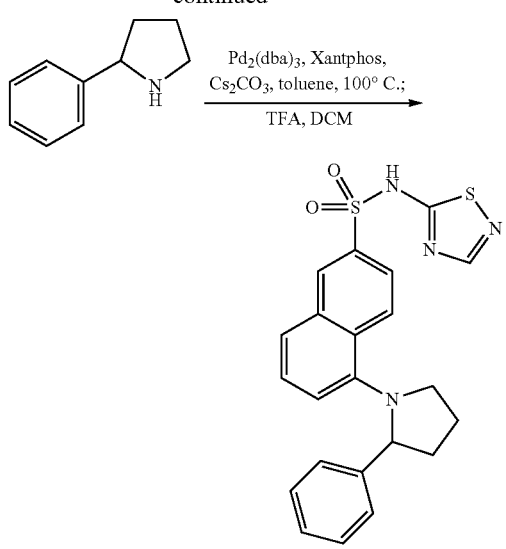

A vial was charged with 5-bromo-N-(2,4-dimethoxybenzyl)-N-(1,2,4-thiadiazol-5-yl)naphthalene-2-sulfonamide (205 mg, 0.394 mmol), Xantphos (45.6 mg, 0.079 mmol), Pd$_2$(dba)$_3$ (36.1 mg, 0.039 mmol), and cesium carbonate (257 mg, 0.788 mmol). The vial was flushed with Ar (g), then toluene (3939 μl) and 2-phenylpyrrolidine (81 μl, 0.551 mmol) were added in sequence. The vial was sealed and heated at 100° C. for 16 h. The reaction mixture was partitioned between EtOAc and water. The layers were separated, and the organic extract was washed with brine. The combined aq. layers were extracted with EtOAc, and the organic layers were combined. The combined solution was washed with brine, dried over sodium sulfate, filtered, and concentrated. The residue was purified by chromatography on silica gel with 0 to 50% EtOAc/Heptane to give a clear oil. This material was dissolved in DCM (2 mL) and TFA (1 mL), and the resulting mixture was stirred for 2 h. The mixture was diluted with MeOH, then concentrated. The crude product was purified by chromatography on silica gel with 0 to 5% MeOH/DCM to give 5-(2-phenylpyrrolidin-1-yl)-N-(1,2,4-thiadiazol-5-yl)naphthalene-2-sulfonamide (76.7 mg, 0.176 mmol) as a light-yellow solid. $^1$H NMR (400 MHz, DMSO-$d_6$) δ ppm=8.55-8.46 (m, 2H), 8.34 (d, J=2.1 Hz, 1H), 7.78 (dd, J=2.1, 9.0 Hz, 1H), 7.63 (d, J=8.2 Hz, 1H), 7.43-7.33 (m, 3H), 7.22-7.16 (m, 2H), 7.12-7.06 (m, 2H), 4.82 (dd, J=6.3, 9.1 Hz, 1H), 4.19-4.12 (m, 1H), 3.03 (dt, J=4.5, 8.9 Hz, 1H), 2.47-2.40 (m, 1H), 2.14-2.10 (m, 1H), 2.00-1.79 (m, 2H). m/z (ESI) 437.2 (M+H)⁺.

INTERMEDIATE II: N-(2,4-DIMETHOXYBEN-ZYL)-5-(4,4,5,5-TETRAMETHYL-1,3,2-DIOX-ABOROLAN-2-YL)-N-(THIAZOL-2-YL)NAPH-THALENE-2-SULFONAMIDE

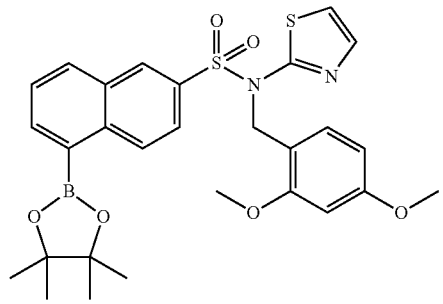

Intermediate II was synthesized in a similar manner to Intermediate E, using N-(2,4-dimethoxybenzyl)thiazol-2-amine instead of N-(2,4-dimethoxybenzyl)-1,2,4-thiadiazol-5-amine (Intermediate A) in Step 3, to yield N-(2,4-dimethoxybenzyl)-5-(4,4,5,5-tetramethyl-1,3,2-dioxaborolan-2-yl)-N-(thiazol-2-yl)naphthalene-2-sulfonamide as a white solid. m/z (ESI) 567.3 (M+H)⁺.

INTERMEDIATE JJ: 1-(2-BROMO-5-(TRIFLUO-ROMETHYL)PHENYL)-4-METHYLPIPERAZINE

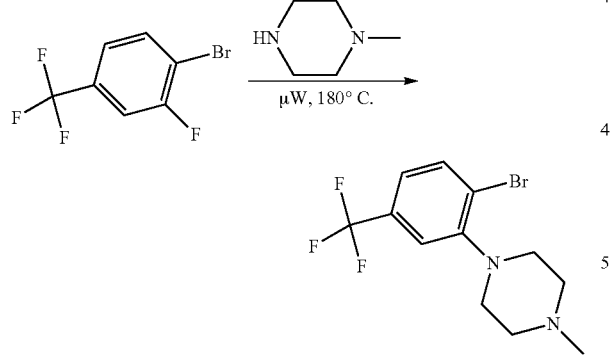

A microwave vial was charged with 1-methylpiperazine (1.371 ml, 12.35 mmol) and 4-bromo-3-fluorobenzotrifluoride (1.000 ml, 4.12 mmol), and was heated under microwave irradiation at 180° C. for 90 minutes. The reaction was concentrated under a vacuum, and the solids were then filtered and washed with DCM (the solids contained minor amounts of product but were disposed of). The filtrate was then concentrated under a vacuum to yield 1-(2-bromo-5-(trifluoromethyl)phenyl)-4-methylpiperazine. The material was carried forward without further purification. m/z (ESI) 323.0 (M+H)⁺.

INTERMEDIATE KK: N-(2,4-DIMETHOXYBEN-ZYL)-5-(PYRROLIDIN-2-YL)-N-(1,2,4-THIADIA-ZOL-5-YL)NAPHTHALENE-2-SULFONAMIDE

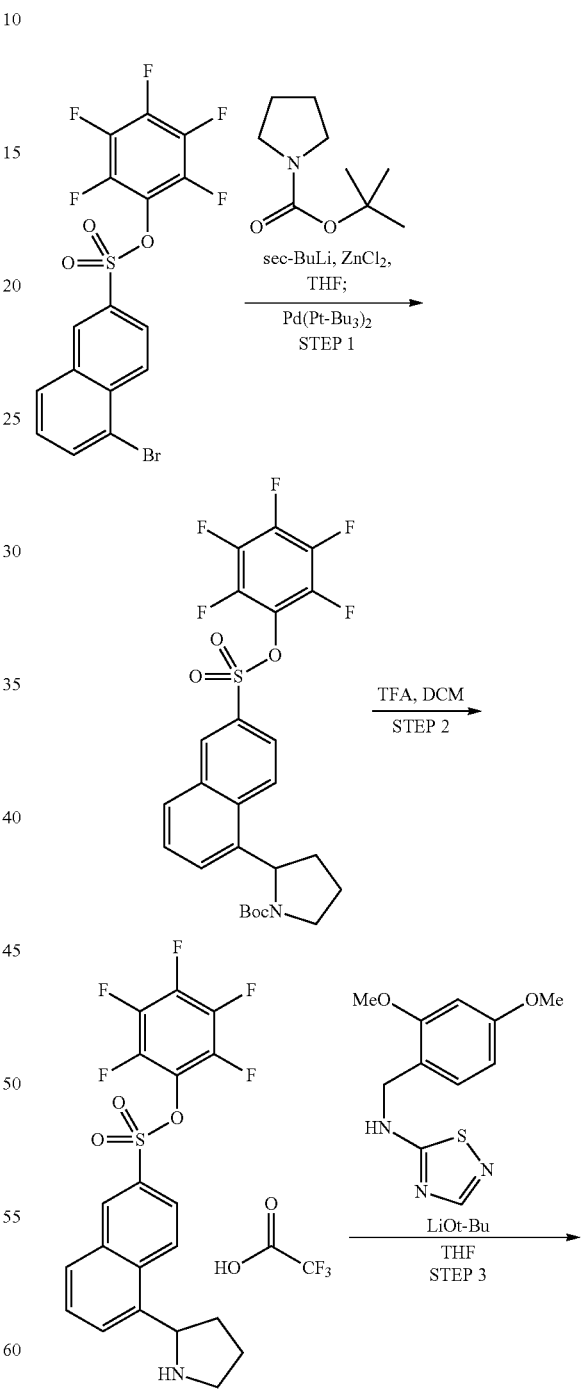

-continued

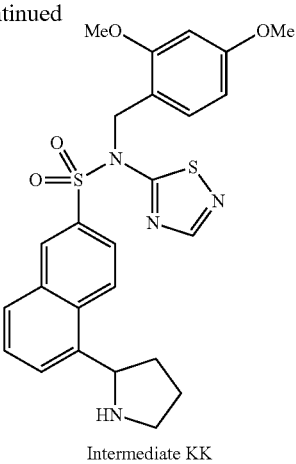

Intermediate KK

STEP 1: TERT-BUTYL 2-(6-((PERFLUOROPHE-NOXY)SULFONYL)NAPHTHALEN-1-YL)PYR-ROLIDINE-1-CARBOXYLATE

A 100-mL round-bottom flask was charged with tert-butyl 1-pyrrolidinecarboxylate (Sigma-Aldrich, St. Louis, Mo., 0.774 ml, 4.41 mmol) and THF (22.07 ml) to give a clear solution. The flask was flushed with Ar (g), then cooled in a −30° C. dry ice-acetone bath for 10 min. sec-butyllithium (1.4 M in cyclohexane) (3.15 ml, 4.41 mmol) was added dropwise over 2 min. The resulting mixture was stirred for 15 min, during which time the bath had warmed to −25° C., then zinc chloride (1M in diethyl ether) (3.31 ml, 3.31 mmol) was added dropwise. The cooling bath was removed. After 25 min, a solid mixture of perfluorophenyl 5-bromonaphthalene-2-sulfonate (Intermediate M, 1.00 g, 2.207 mmol), palladium(ii) acetate (0.050 g, 0.221 mmol), and tri-tert-butylphosphonium tetrafluoroborate (0.064 g, 0.221 mmol) was added in one portion. The resulting mixture was stirred further for 2 h. A 30% aq ammonium hydroxide solution (1 mL) was added, and the mixture was stirred vigorously for 10 min. The mixture was then filtered through diatomaceous earth with the aid of ethyl acetate. The filtrate was washed with 0.5N aq. HCl, and the aq. layer was extracted with EtOAc. The combined organic layers were washed with brine, dried over magnesium sulfate, filtered, and concentrated. The residue was purified by chromatography on silica gel (40-g, 0 to 30% EtOAc/Heptane) to give tert-butyl 2-(6-((perfluorophenoxy)sulfonyl)naphthalen-1-yl)pyrrolidine-1-carboxylate (709.11 mg, 1.305 mmol, 59.1% yield) as a white solid: $^1$H NMR (400 MHz, DMSO-$d_6$) δ ppm=8.85-8.73 (m, 1H), 8.49 (d, J=9.0 Hz, 1H), 8.17 (d, J=8.2 Hz, 1H), 7.99 (d, J=8.3 Hz, 1H), 7.80-7.68 (m, 1H), 7.62-7.42 (m, 1H), 5.81-5.50 (m, 1H), 3.77-3.65 (m, 1H), 3.62-3.49 (m, 1H), 1.98-1.60 (m, 3H), 1.42 (br. s., 4H), 1.29-1.19 (m, 1H), 0.92 (s, 5H); m/z (ESI) 488.2 (M+H-t-Bu)$^+$.

STEP 2: PERFLUOROPHENYL 5-(PYRROLIDIN-2-YL)NAPHTHALENE-2-SULFONATE 2,2,2-TRIFLUOROACETATE

A 25-mL round-bottom flask was charged with tert-butyl 2-(6-((perfluorophenoxy)sulfonyl)naphthalen-1-yl)pyrrolidine-1-carboxylate (674 mg, 1.240 mmol), DCM (4960 μl), and trifluoroacetic acid (2389 μl, 31.0 mmol) to give a clear, very lightly-colored solution After 1 h, the mixture was concentrated, and the residue was taken up in diethyl ether and sonicated, resulting in the formation of a white solid. The mixture was filtered, and the collected solid was washed with diethyl ether, dried over a stream of N2 (g) for 20 min, then dried under vacuum for 30 min to give perfluorophenyl 5-(pyrrolidin-2-yl)naphthalene-2-sulfonate 2,2,2-trifluoroacetate (647 mg, 1.161 mmol, 94% yield) as a white solid: m/z (ESI) 444.2 (M+H)$^+$.

STEP 3: N-(2,4-DIMETHOXYBENZYL)-5-(PYRROLIDIN-2-YL)-N-(1,2,4-THIADIAZOL-5-YL) NAPHTHALENE-2-SULFONAMIDE

A round-bottom flask was charged with perfluorophenyl 5-(pyrrolidin-2-yl)naphthalene-2-sulfonate 2,2,2-trifluoroacetate (104.73 mg, 0.188 mmol), N-(2,4-dimethoxybenzyl)-1,2,4-thiadiazol-5-amine (56.7 mg, 0.225 mmol), and THF (1879 μl) to give a clear solution. The flask was cooled in a dry ice-acetone bath for 10 min, then lithium tert-butoxide (Sigma-Aldrich, St. Louis, Mo., 1M in hexane) (413 μl, 0.413 mmol) was added dropwise. After 35 min, the flask was submerged in an ice-bath for 2 h. The mixture was diluted with saturated aq ammonium chloride, then extracted with EtOAC (3×). The combined organic extracts were dried over sodium sulfate, filtered, and concentrated. The residue was purified by chromatography on silica gel (12-g, 0 to 10% MeOH/DCM) to give N-(2,4-dimethoxybenzyl)-5-(pyrrolidin-2-yl)-N-(1,2,4-thiadiazol-5-yl)naphthalene-2-sulfonamide (61.5 mg, 0.120 mmol, 64.1% yield) as a white foam: $^1$H NMR (400 MHz, DMSO-$d_6$) δ ppm=8.55 (d, J=2.2 Hz, 1H), 8.41-8.33 (m, 2H), 8.01 (dd, J=7.7, 19.2 Hz, 2H), 7.78 (dd, J=2.2, 9.1 Hz, 1H), 7.68-7.61 (m, 1H), 7.03-6.95 (m, 1H), 6.36 (qd, J=2.3, 4.5 Hz, 2H), 5.18 (s, 2H), 4.77 (t, J=7.4 Hz, 1H), 3.67 (s, 3H), 3.63 (s, 3H), 3.12-2.95 (m, 2H), 2.40-2.30 (m, 1H), 1.83-1.72 (m, 2H), 1.51-1.40 (m, 1H); m/z (ESI) 511.4 (M+H)$^+$.

INTERMEDIATE LL: PERFLUOROPHENYL 5-(1-BENZYLPYRROLIDIN-2-YL)NAPHTHALENE-2-SULFONATE

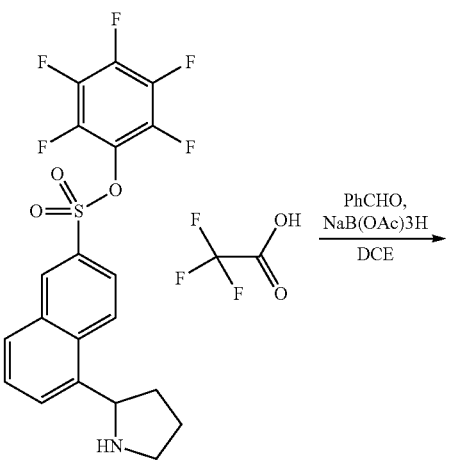

-continued

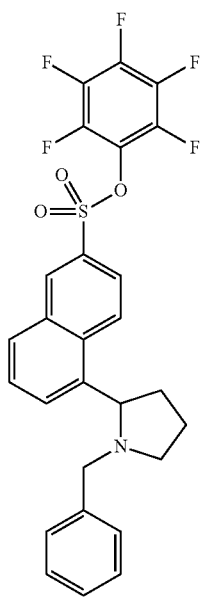

Intermediate LL

A 10-mL round-bottom flask was charged with perfluorophenyl 5-(pyrrolidin-2-yl)naphthalene-2-sulfonate 2,2,2-trifluoroacetate (from STEP 2 of INTERMEDIATE KK) (56.79 mg, 0.102 mmol), DCE (509 μl), and benzaldehyde (31.0 μl, 0.306 mmol) to give a suspension. Sodium triacetoxyborohydride (43.2 mg, 0.204 mmol) was added, followed by an additional portion of DCE (509 μl) to thin the mixture. After 1 h, a saturated aq. Rochelle's salt solution (3 mL) and DCM (2 mL) were added, and the resulting mixture was stirred vigorously for 3 h. The mixture was diluted with water and extracted with DCM (3×). The combined organic extracts were dried over sodium sulfate, filtered, and concentrated. The residue was purified by chromatography on a 12-g with 0 to 40% EtOAc/Heptane to give perfluorophenyl 5-(1-benzylpyrrolidin-2-yl)naphthalene-2-sulfonate (52.93 mg, 0.099 mmol, 97% yield) as a clear oil: $^1$H NMR (400 MHz, DMSO-$d_6$) δ ppm=8.86-8.70 (m, 2H), 8.22-8.10 (m, 2H), 8.00 (dd, J=2.2, 9.1 Hz, 1H), 7.81-7.73 (m, 1H), 7.33-7.26 (m, 4H), 7.25-7.17 (m, 1H), 4.20 (t, J=8.2 Hz, 1H), 3.77 (d, J=13.2 Hz, 1H), 3.20 (d, J=13.2 Hz, 1H), 3.13-3.02 (m, 1H), 2.48-2.40 (m, 1H), 2.33 (q, J=9.2 Hz, 1H), 1.93-1.82 (m, 2H), 1.78-1.60 (m, 1H); m/z (ESI) 534.4 (M+H)$^+$.

INTERMEDIATE MM: 6-(N-(1,2,4-THIADIAZOL-5-YL)SULFAMOYL)-1-NAPHTHOIC ACID

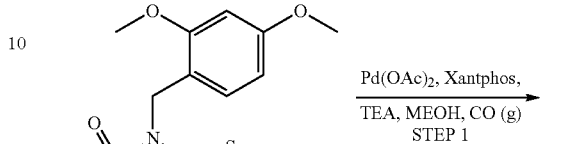

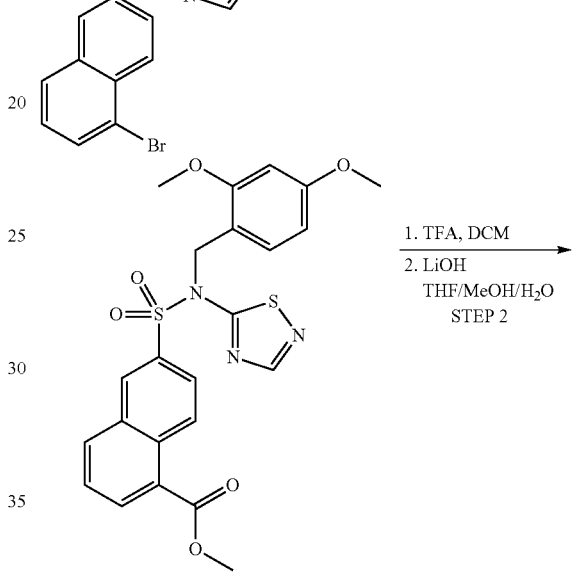

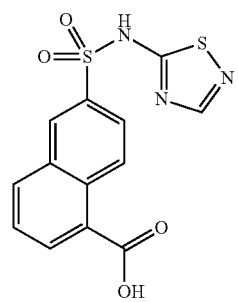

Intermediate MM

STEP 1: METHYL 6-(N-(2,4-DIMETHOXYBENZYL)-N-(1,2,4-THIADIAZOL-5-YL)SULFAMOYL)-1-NAPHTHOATE

A 500-mL two-neck flask was charged with 5-bromo-N-(2,4-dimethoxybenzyl)-N-(1,2,4-thiadiazol-5-yl)naphthalene-2-sulfonamide (Intermediate D, 10 g, 19.22 mmol), palladium (ii) acetate (0.216 g, 0.961 mmol), and Xantphos (1.112 g, 1.922 mmol). Triethylamine (77 ml, 19.22 mmol), toluene (48.0 ml), and methanol (15.55 ml, 384 mmol) were added, and the reaction was fitted with a reflux condenser. The reaction was evacuated and back-filled with carbon monoxide three times, and then the reaction was heated to 70° C. and stirred for four hours under an atmosphere of carbon monoxide. The reaction was filtered through a pad of diatomaceous earth, which was thoroughly washed with ethyl acetate. The filtrate was concentrated, triturated in ethyl acetate and filtered. The solid was collected and the filtrate was concentrated. The trituration procedure was repeated twice, and the solids resulting from each trituration were combined with the previously isolated material. After the third trituration, the mother liquor was purified via column chromatography (RediSep Gold 80 g silica gel column, gradient elution 0-50% EtOAc:Heptane). The clean product fractions were combined with the previously isolated material and the resulting slurry was concentrated to afford methyl 6-(N-(2,4-dimethoxybenzyl)-N-(1,2,4-thiadiazol-5-yl)sulfamoyl)-1-naphthoate as a light yellow solid. m/z (ESI) 500.3 (M+H)+.

STEP 2: 6-(N-(1,2,4-THIADIAZOL-5-YL)SULFAMOYL)-1-NAPHTHOIC ACID

Methyl 6-(N-(2,4-dimethoxybenzyl)-N-(1,2,4-thiadiazol-5-yl)sulfamoyl)-1-naphthoate (7.10 g, 14.21 mmol) was dissolved in 100 mL of DCM and TFA (10.95 ml, 142 mmol) was added. The reaction was stirred for 30 minutes at room temperature. The material was concentrated, dissolved in methanol, and re-concentrated to afford a light yellow solid. The solid was dissolved in THF (47.4 ml), methanol (47.4 ml), and water (47.4 ml). Lithium hydroxide (1.021 g, 42.6 mmol) was added and the reaction was stirred overnight at room temperature. The reaction was concentrated and dissolved in concentrated HCl solution. The solution was stirred for 5 minutes and filtered. The resulting white solid was washed with water, dried under a nitrogen blanket, and collected to afford 6-(N-(1,2,4-thiadiazol-5-yl)sulfamoyl)-1-naphthoic acid (Intermediate MM) as an off-white solid. m/z (ESI) 336.2 (M+H)+.

INTERMEDIATE NN: N-(2,4-DIMETHOXYBENZYL)-5-(PYRROLIDIN-2-YL)-N-(THIAZOL-2-YL)NAPHTHALENE-2-SULFONAMIDE

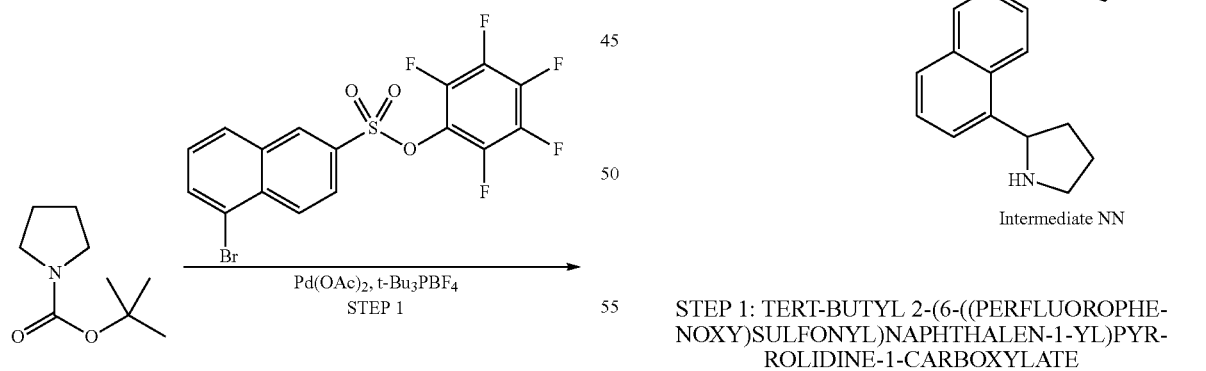

STEP 1: TERT-BUTYL 2-(6-((PERFLUOROPHENOXY)SULFONYL)NAPHTHALEN-1-YL)PYRROLIDINE-1-CARBOXYLATE

A 250-mL round-bottom flask was charged with tert-butyl 1-pyrrolidinecarboxylate (1.679 ml, 9.58 mmol) and THF (47.9 ml) to give a clear solution. The flask was flushed with Ar (g), then cooled in a −30° C. dry ice-acetone bath for 10 min. Sec-butyllithium (1.4 M in cyclohexane) (6.84 ml, 9.58 mmol) was added dropwise over 2 min. The resulting mixture was stirred for 15 min, during which time the bath had warmed to −25° C., then zinc chloride (1M in diethyl ether) (7.18 ml, 7.18 mmol) was added dropwise. The cooling bath was removed. After 25 min, a solid mixture of perfluorophenyl 5-bromonaphthalene-2-sulfonate (Intermediate M, 2.17 g, 4.79 mmol), palladium(ii) acetate (0.108 g, 0.479 mmol), and tri-tert-butylphosphonium tetrafluoroborate (0.139 g, 0.479 mmol) was added in one portion. The resulting mixture was stirred overnight at room temperature. A 30% aq. ammonium hydroxide solution was added, and the mixture was stirred vigorously for 10 min. The mixture was then filtered through diatomaceous earth with the aid of ethyl acetate. The filtrate was washed with 0.5N aq. HCl, and the aq. layer was extracted with EtOAc. The combined organic layers were washed with brine, dried over sodium sulfate, filtered, and concentrated. The residue was purified by chromatography on silica gel (80-g Redi-Sep column, 0-30% EtOAc/Heptane) to give tert-butyl 2-(6-((perfluorophenoxy)sulfonyl)naphthalen-1-yl)pyrrolidine-1-carboxylate as a light yellow solid. LC/MS ionized for 488.2 (desired product—t-Bu). m/z (ESI) 488.3 (M+H)$^+$.

STEP 2: PERFLUOROPHENYL 5-(PYRROLIDIN-2-YL)NAPHTHALENE-2-SULFONATE 2,2,2-TRIFLUOROACETATE

A round-bottom flask was charged with tert-butyl 2-(6-((perfluorophenoxy)sulfonyl)naphthalen-1-yl)pyrrolidine-1-carboxylate (0.315 g, 0.580 mmol) and DCM (3.0 mL) to give a light yellow solution. TFA (1.786 ml, 23.18 mmol) was added in one portion to give a yellow solution. The reaction was stirred for four hours. The reaction was concentrated, dissolved in diethyl ether, and sonicated until a fine white solid triturated out of solution. The solids were filtered, washed with diethyl ether, and vacuum dried overnight to afford perfluorophenyl 5-(pyrrolidin-2-yl)naphthalene-2-sulfonate 2,2,2-trifluoroacetate as an off-white solid. m/z (ESI) 444.0 (M+H)$^+$.

STEP 3: N-(2,4-DIMETHOXYBENZYL)-5-(PYRROLIDIN-2-YL)-N-(THIAZOL-2-YL)NAPHTHALENE-2-SULFONAMIDE

A round-bottom flask was charged with perfluorophenyl 5-(pyrrolidin-2-yl)naphthalene-2-sulfonate 2,2,2-trifluoroacetate (0.234 g, 0.420 mmol), N-(2,4-dimethoxybenzyl) thiazol-2-amine (0.126 g, 0.504 mmol), and THF (4.20 ml) to give a clear solution. The flask was cooled in an dry ice-acetone bath for 10 min, then lithium bis(trimethylsilyl)amide (1M in THF) (0.924 ml, 0.924 mmol) was added dropwise over 30 seconds. The reaction was stirred for 30 minutes, then the cooling bath was removed and the reaction was stirred for 30 minutes. The mixture was diluted with saturated aq. ammonium chloride solution, then extracted with EtOAc (2×). The combined organic extracts were dried over sodium sulfate, filtered, and concentrated. The residue was purified by chromatography on silica gel (12-g, 0 to 10% MeOH/DCM) to give N-(2,4-dimethoxybenzyl)-5-(pyrrolidin-2-yl)-N-(thiazol-2-yl)naphthalene-2-sulfonamide as a white foam. (ESI) 510.2 (M+H)$^+$.

INTERMEDIATE OO: N-(4-METHOXYBENZYL)PYRIMIDIN-4-AMINE

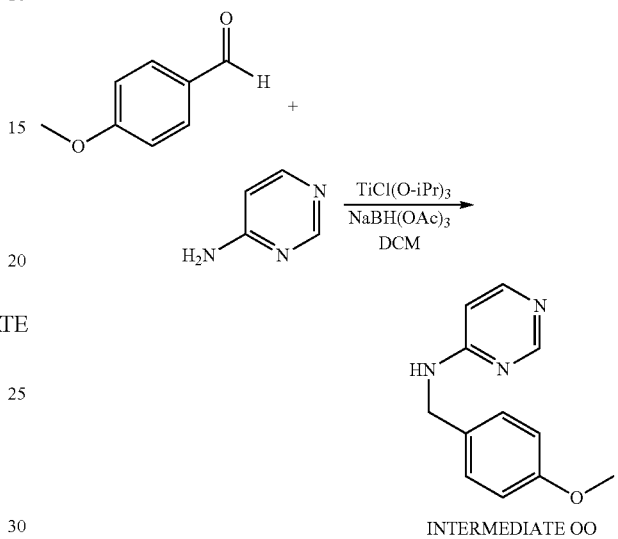

INTERMEDIATE OO p-Anisaldehyde (320 g, 2.35 mol, 1.0 equiv; Aldrich, St. Louis, Mo.) and 4-aminopyrimidine (246 g, 2.58 mol, 1.1 equiv; AK Scientific, Inc., Union City, Calif.) were dissolved in anhydrous DCM (8.0 L). To this solution under N$_2$ atmosphere at room temperature was added a solution of Ti (Oi-Pr)$_3$Cl (1348 g, 5.17 mol, 2.2 equiv; Aldrich) in anhydrous DCM (1 L) in one portion and the reaction mixture was stirred at room temperature for 30 minutes. The reaction mixture was then cooled to 10° C. and NaBH(OAc)$_3$ (1495 g, 7.05 mol, 3.0 equiv; Aldrich) was added in portions over 30 min followed by the addition of acetic acid (10 mL). (Note: A mild exotherm of 10-19° C. was observed). Upon completion of the addition, the reaction mixture was allowed to warm up to room temperature and stirred overnight. The reaction was monitored using LC/MS. Product formation was observed along with many other peaks. Upon completion the reaction mixture was quenched slowly and carefully pouring over a well-stirred saturated aqueous NaHCO$_3$ (30 L). The crude product was then extracted with dichloromethane (3×12 L) and the organic extracts were combined, washed with brine (5 L), dried over Na$_2$SO$_4$, and concentrated under reduced pressure. The crude residue was initially triturated with hexanes to obtain a solid. The crude solid was further triturated with MTBE to remove most of the impurities. The crude product was purified using column chromatography eluting with MeOH/ethyl acetate (2:98 to 5:95) to afford N-(4-methoxybenzyl)pyrimidin-4-amine (INTERMEDIATE OO) as a white solid with >99% purity (129 g, 26% yield). $^1$H NMR (400 MHz, DMSO) δ ppm 8.40 (s, 1H), 8.02 (d, J=6.1 Hz, 1H), 7.82 (t, J=6.0 Hz, 1H), 7.24 (d, J=8.0 Hz, 2H), 6.98-6.77 (m, 2H), 6.48 (s, 1H), 4.43 (s, 2H), 3.72 (s, 3H). m/z (ESI) 216.0 (M+H)⁺

INTERMEDIATE PP AND QQ: 5-BROMO-N-(4-METHOXYBENZYL)-N-(PYRIMIDIN-4-YL) NAPHTHALENE-2-SULFONAMIDE AND N-(4-METHOXYBENZYL)-N-(PYRIMIDIN-4-YL)-5-(4,4,5,5-TETRAMETHYL-1,3,2-DIOXABOROLAN-2-YL)NAPHTHALENE-2-SULFONAMIDE

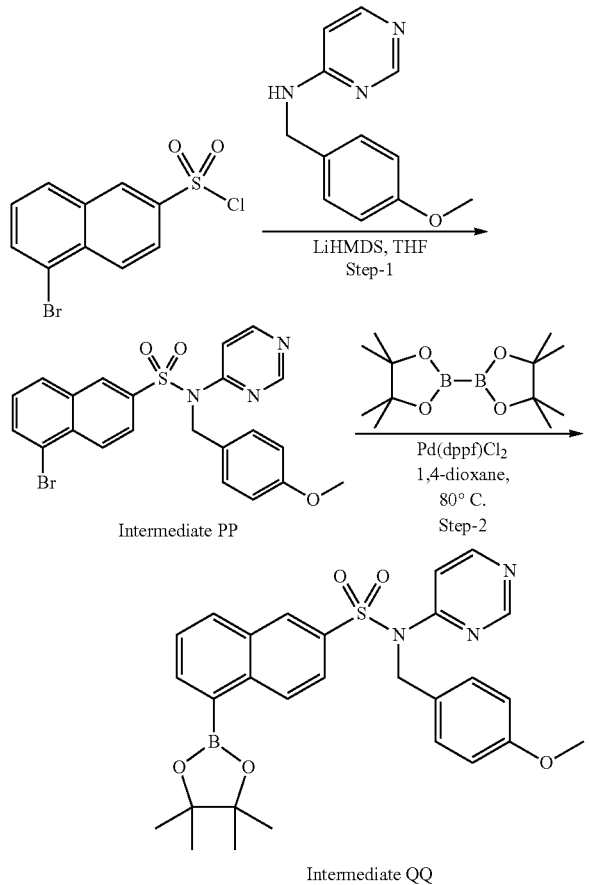

STEP-1: 5-BROMO-N-(4-METHOXYBENZYL)-N-(PYRIMIDIN-4-YL)NAPHTHALENE-2-SULFONAMIDE (INTERMEDIATE PP)

To a solution of INTERMEDIATE OO (20.0 g, 92.9 mmol) in THF (200 mL) was added LiHMDS (1M in THF, 186 mL, Aldrich) at −78° C. The reaction mixture was stirred at 0° C. for 20 min. The reaction mixture was re-cooled to −78° C. and a solution of INTERMEDIATE C (42.5 g, 139 mmol) in THF (100 mL) was added. The reaction mixture was allowed to stir at room temperature for 1 h. The reaction was quenched with ice-cold water (500 mL) and extracted with ethyl acetate (2×500 mL). The combined organic layer was dried over sodium sulfate, filtered, and concentrated under reduced pressure to obtain the crude material which was purified by column chromatography (neutral alumina, elution 0-10% ethyl acetate in hexanes) to obtain INTERMEDIATE PP (4.0 g, 9.0%) as an off-white solid. ¹H NMR (400 MHz, DMSO-d₆) δ ppm 8.83 (s, 1H), 8.75 (d, J=1.8 Hz, 1H), 8.59 (d, J=5.9 Hz, 1H), 8.27 (dd, J=15.1, 8.6 Hz, 2H), 8.12 (d, J=7.4 Hz, 1H), 8.01 (dd, J=9.0, 1.9 Hz, 1H), 7.63 (t, J=7.9 Hz, 1H), 7.50 (d, J=5.9 Hz, 1H), 7.29 (d, J=8.7 Hz, 2H), 6.88 (d, J=8.7 Hz, 2H), 5.31 (s, 2H), 3.71 (s, 3H). m/z (ESI) 484.1 (M+H)⁺.

STEP-2: N-(4-METHOXYBENZYL)-N-(PYRIMIDIN-4-YL)-5-(4,4,5,5-TETRAMETHYL-1,3,2-DIOXABOROLAN-2-YL)NAPHTHALENE-2-SULFONAMIDE (INTERMEDIATE QQ)

A mixture of INTERMEDIATE PP (3.00 g, 6.19 mmol), bis(pinacolato)diboron (2.35 g, 9.28 mmol) and KOAc (1.80 g, 18.6 mmol) in dioxane (20 mL) was degassed with N₂ for 10 min. PdCl₂(dppf).DCM (252 mg, 0.309 mmol) was added and the reaction mixture was heated at 80° C. for 5 h. The reaction mixture was cooled to room temperature, diluted with ethyl acetate (100 mL), and passed through a diatomaceous earth bed. The filtrate was washed with water (50 mL). The organic layer was dried over sodium sulfate, filtered and concentrated under reduced pressure to obtain the crude material which was purified by column chromatography (silica gel: 100 to 200 mesh, elution 0 to 20% ethyl acetate in hexanes) to obtain INTERMEDIATE QQ (1.9 g, 56%) as an off-white solid. H NMR (400 MHz, DMSO) δ ppm 8.82 (s, 1H), 8.80-8.73 (m, 1H), 8.66 (d, J=2.2 Hz, 1H), 8.57 (d, J=5.9 Hz, 1H), 8.30 (d, J=8.4 Hz, 1H), 8.16 (dd, J=7.1, 1.3 Hz, 1H), 7.96-7.86 (m, 1H), 7.70 (t, J=7.6 Hz, 1H), 7.57-7.51 (m, 1H), 7.35-7.27 (m, 2H), 6.93-6.84 (m, 2H), 5.32 (s, 2H), 3.71 (s, 3H), 1.37 (s, 12H). m/z (ESI) 532.1 (M+H)⁺.

INTERMEDIATE RR: TERT-BUTYL 5-FLUORO-2-(4,4,5,5-TETRAMETHYL-1,3,2-DIOXABOROLAN-2-YL)-1H-INDOLE-1-CARBOXYLATE

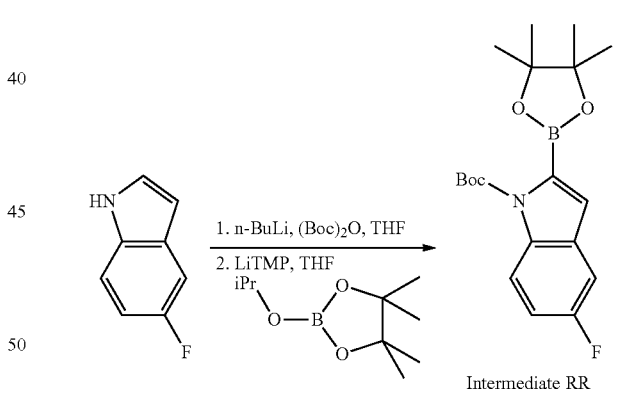

A solution of 5-fluoro-1H-indole (1.300 g, 9.62 mmol) in 10 mL THF was cooled to −10° C. and was treated with n-butyllithium (4.23 ml, 10.58 mmol). After stirring for 10 minutes, the reaction mixture was treated with di-tert-butyl dicarbonate (1N in THF) (9.62 ml, 9.62 mmol) and was allowed to stir at room temperature for one hour. LC/MS showed mostly product. A separate solution of 2,2,6,6-tetramethylpiperidine (2.59 ml, 14.43 mmol) in 15 mL of THF was cooled to 0° C. and was treated with n-butyllithium (5.77 ml, 14.43 mmol) After stirring for 20 minutes, this solution was charged to an addition funnel. The original reaction mixture was treated with 2-isopropoxy-4,4,5,5-tetramethyl-1,3,2-dioxaborolane (2.68 ml, 14.43 mmol) followed by drop wise addition of the LiTMP solution at room temperature.

After stirring for one hour, LC/MS showed exclusively product, so the reaction mixture was poured into a solution of brine and 1N citric acid (~1:1) and was extracted with DCM. The organics were dried over MgSO4 and concentrated. Purification of the crude residue by column chromatography (0-50% EtOAc/heptane) gave tert-butyl 5-fluoro-2-(4,4,5,5-tetramethyl-1,3,2-dioxaborolan-2-yl)-1H-indole-1-carboxylate (INTERMEDIATE RR; 1.636 g, 4.53 mmol, 47.1% yield). m/z (ESI) 384.3 (M+Na)+.

INTERMEDIATE SS: 5-(5-FLUORO-1H-INDOL-2-YL)-N-(4-METHOXYBENZYL)-N-(PYRIMIDIN-4-YL)NAPHTHALENE-2-SULFONAMIDE

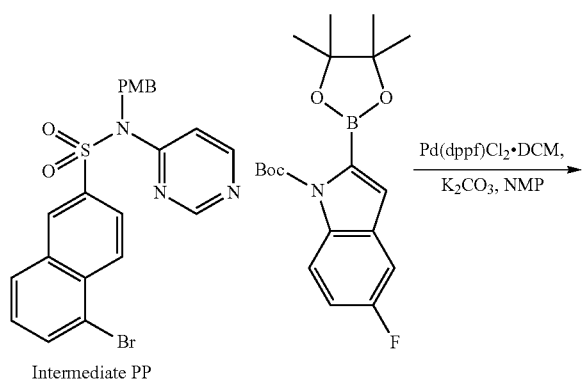

Intermediate PP

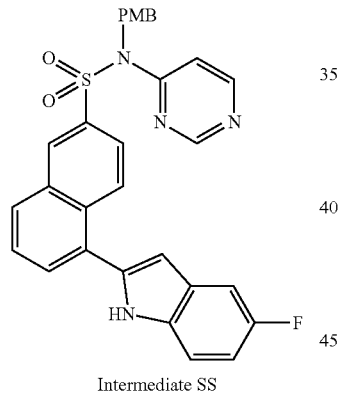

Intermediate SS

A microwave vial charged with PdCl$_2$(dppf)-CH$_2$Cl$_2$ adduct (0.126 g, 0.155 mmol), INTERMEDIATE RR (1.119 g, 3.10 mmol), 5-bromo-N-(4-methoxybenzyl)-N-(pyrimidin-4-yl)naphthalene-2-sulfonamide (INTERMEDIATE PP, 0.750 g, 1.548 mmol), potassium carbonate (0.856 g, 6.19 mmol), and 3 mL of NMP was heated to 130° C. in the microwave for 30 minutes. LC/MS showed deprotected starting material so 1.5 mL water was added (immediately bubbled over and lost some material), and the reaction mixture was transferred to a flask and heated to 100° C. for an additional hour. LC/MS showed mostly product, so the reaction mixture was poured into aq. saturated NH$_4$Cl solution and was extracted with DCM. The organics were dried over MgSO$_4$ and concentrated. Purification of the crude residue by column chromatography (0-100% EtOAc/heptane) gave 5-(5-fluoro-1H-indol-2-yl)-N-(4-methoxybenzyl)-N-(pyrimidin-4-yl)naphthalene-2-sulfonamide (0.413 g, 0.767 mmol, 49.5% yield). m/z (ESI) 539.1 (M+H)+

INTERMEDIATES TT AND UU: 5-BROMO-N-(5-FLUOROTHIAZOL-2-YL)-N-((2-(TRIMETHYLSILYL)ETHOXY)METHYL)NAPHTHALENE-2-SULFONAMIDE AND N-(5-FLUOROTHIAZOL-2-YL)-5-(4,4,5,5-TETRAMETHYL-1,3,2-DIOXABOROLAN-2-YL)-N-((2-(TRIMETHYLSILYL)ETHOXY)METHYL)NAPHTHALENE-2-SULFONAMIDE

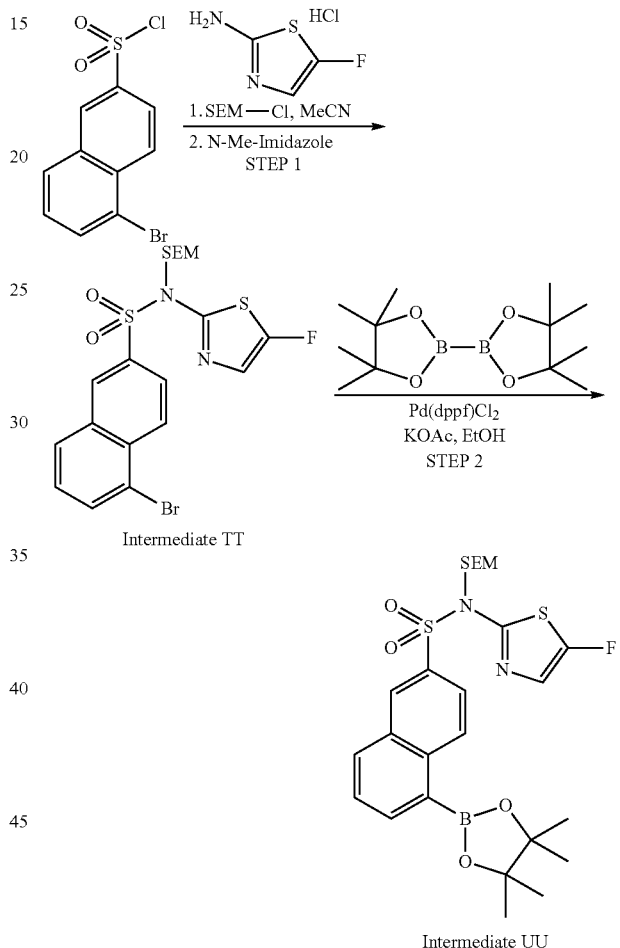

STEP 1: 5-BROMO-N-(5-FLUOROTHIAZOL-2-YL)-N-((2-(TRIMETHYLSILYL)ETHOXY)METHYL)NAPHTHALENE-2-SULFONAMIDE

A solution of 5-fluorothiazol-2-amine hydrochloride (16.14 g, 104 mmol) and triethylamine (14.55 ml, 104 mmol) in 40 mL of DMF was allowed to stir at room temperature for 20 minutes. The reaction mixture was cooled to 0° C. and 2-trimethylsilylethoxymethyl chloride (SEM-Cl) (19.72 ml, 111 mmol) was added. After 10 minutes, the cooling bath was removed and the reaction mixture was allowed to stir at room temperature for one hour. LC/MS showed mostly desired intermediate, so the reaction mixture was treated with INTERMEDIATE C (31.900 g, 104 mmol) and was diluted with 200 mL THF. 1-methylimidazole (24.90 ml, 313 mmol)

was added, and the reaction mixture was allowed to stir for an additional 2 hours. LC/MS showed mostly desired product, so the reaction mixture was concentrated. The crude residue was dissolved in DCM and was washed with 1N citric acid. The resulting suspension was filtered to remove the precipitate and break up the suspension. The organic layer was dried over MgSO₄ and concentrated. Purification of the crude residue by silica gel column chromatography (0 to 50% EtOAc/heptane) gave 5-bromo-N-(5-fluorothiazol-2-yl)-N-((2-(trimethylsilyl)ethoxy)methyl)naphthalene-2-sulfonamide (Intermediate TT; 29.16 g, 56.3 mmol, 54.0% yield). m/z (ESI) 517.9 (M+H)+.

STEP 2: N-(5-FLUOROTHIAZOL-2-YL)-5-(4,4,5,5-TETRAMETHYL-1,3,2-DIOXABOROLAN-2-YL)-N-((2-(TRIMETHYLSILYL)ETHOXY)METHYL)NAPHTHALENE-2-SULFONAMIDE

A solution of PdCl₂(dppf)-CH₂Cl₂ adduct (0.199 g, 0.243 mmol), bis(pinacolato)diboron (1.484 g, 5.84 mmol), 5-bromo-N-(5-fluorothiazol-2-yl)-N-((2-(trimethylsilyl)ethoxy)methyl)naphthalene-2-sulfonamide (2.52 g, 4.87 mmol), and potassium acetate (1.912 g, 19.48 mmol) in 18 mL EtOH was heated to 90° C. overnight. LC/MS showed mostly product and reduced starting material. The reaction mixture was concentrated. The crude residue was dissolved in DCM and washed with water. The organics were dried over MgSO4 and concentrated. Purification of the crude residue by silica gel column chromatography (0-30% EtOAc/heptane) gave N-(5-fluorothiazol-2-yl)-5-(4,4,5,5-tetramethyl-1,3,2-dioxaborolan-2-yl)-N-((2-(trimethylsilyl)ethoxy)methyl)naphthalene-2-sulfonamide (Intermediate UU; 2.30 g, 4.07 mmol, 84% yield) as a ~1:1 mixture with de-brominated starting material.

INTERMEDIATE VV: TERT-BUTYL 4-(2-(4,4,5,5-TETRAMETHYL-1,3,2-DIOXABOROLAN-2-YL)-5-(TRIFLUOROMETHYL)PHENYL)-5,6-DIHYDROPYRIDINE-1(2H)-CARBOXYLATE

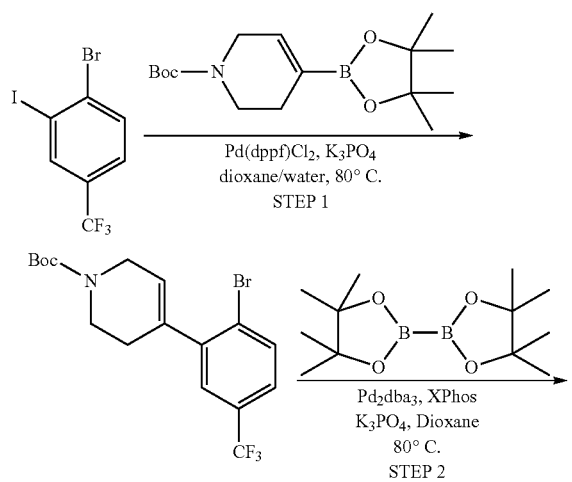

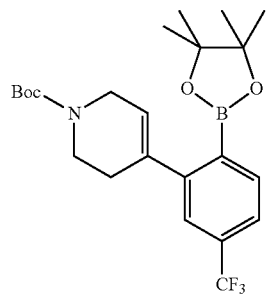

Intermediate VV

STEP 1: TERT-BUTYL 4-(2-BROMO-5-(TRIFLUOROMETHYL)PHENYL)-5,6-DIHYDROPYRIDINE-1(2H)-CARBOXYLATE

A solution of PdCl₂(dppf)-CH₂Cl₂ adduct (0.582 g, 0.712 mmol), tert-butyl 4-(4,4,5,5-tetramethyl-1,3,2-dioxaborolan-2-yl)-5,6-dihydropyridine-1(2H)-carboxylate (4.63 g, 14.96 mmol), 1-bromo-2-iodo-4-(trifluoromethyl)benzene (2.298 ml, 14.25 mmol), and potassium phosphate (9.07 g, 42.7 mmol) in 50 mL dioxane/25 mL water was heated to 80° C. for 2 hours. LC/MS showed mostly product, so the reaction mixture was poured into water and was extracted with DCM. The organics were dried over MgSO₄ and concentrated. Purification of the crude residue by silica gel column chromatography (0-30% EtOAc/heptane) gave tert-butyl 4-(2-bromo-5-(trifluoromethyl)phenyl)-5,6-dihydropyridine-1(2H)-carboxylate (4.05 g, 9.97 mmol, 70.0% yield) as a clear oil. m/z (ESI) 430.2 (M+Na)+.

STEP 2: TERT-BUTYL 4-(2-(4,4,5,5-TETRAMETHYL-1,3,2-DIOXABOROLAN-2-YL)-5-(TRIFLUOROMETHYL)PHENYL)-5,6-DIHYDROPYRIDINE-1(2H)-CARBOXYLATE

A flask charged with XPhos (1.498 g, 3.14 mmol), Pd₂(dba)₃ (0.959 g, 1.048 mmol), bis(pinacolato)diboron (10.64 g, 41.9 mmol), tert-butyl 4-(2-bromo-5-(trifluoromethyl)phenyl)-5,6-dihydropyridine-1(2H)-carboxylate (8.513 g, 20.96 mmol), potassium phosphate (17.79 g, 84 mmol), and 100 mL dioxane was degassed and heated to 80° C. overnight. LC/MS showed mostly product, so the reaction mixture was diluted with heptane, filtered, and concentrated. Purification of the crude residue by silica gel column chromatography (0 to 15% EtOAc/heptane) gave tert-butyl 4-(2-(4,4,5,5-tetramethyl-1,3,2-dioxaborolan-2-yl)-5-(trifluoromethyl)phenyl)-

5,6-dihydropyridine-1(2H)-carboxylate (10.64 g, 23.47 mmol, 112% yield). m/z (ESI) 476.1 (M+Na)+.

INTERMEDIATE WW: 4-(2-BROMO-5-(TRIF-LUOROMETHYL)PHENYL)-1-METHYLPIPERIDINE

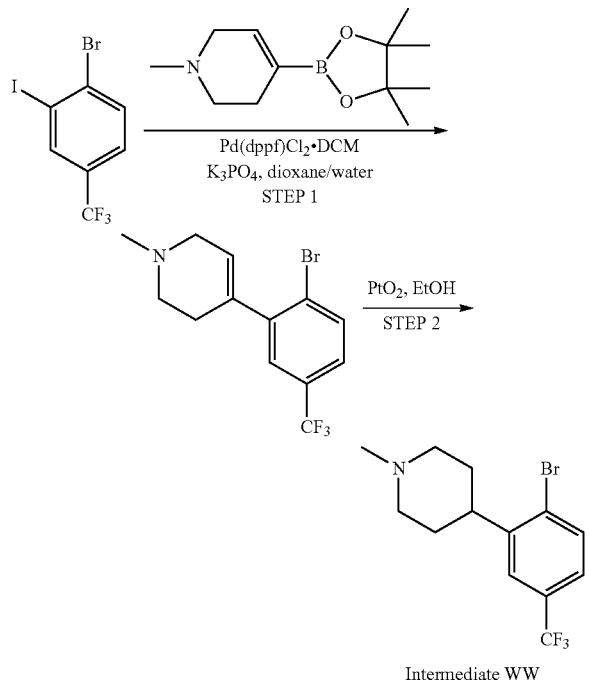

Intermediate WW

STEP 1: 4-(2-BROMO-5-(TRIFLUOROMETHYL)PHENYL)-1-METHYL-1,2,3,6-TETRAHYDROPYRIDINE

A solution of Pd(Ph$_3$P)$_4$ (0.986 g, 0.854 mmol), 1-methyl-4-(4,4,5,5-tetramethyl-1,3,2-dioxaborolan-2-yl)-1,2,3,6-tetrahydropyridine (2.000 g, 8.96 mmol), 1-bromo-2-iodo-4-(trifluoromethyl)benzene (1.377 ml, 8.54 mmol), and potassium phosphate (5.44 g, 25.6 mmol) in 20 mL dioxane 10 mL water was heated to 90° C. for one hour. LC/MS showed mostly product, so the reaction mixture was poured into water and extracted with DCM. The organics were dried over MgSO$_4$ and concentrated. Purification of the crude residue by silica gel column chromatography (0 to 97% EtOAc/heptane, 3% MeOH) gave 4-(2-bromo-5-(trifluoromethyl)phenyl)-1-methyl-1,2,3,6-tetrahydropyridine. m/z (ESI) 320.1 (M+H)+.

STEP 2: 4-(2-BROMO-5-(TRIFLUOROMETHYL)PHENYL)-1-METHYLPIPERIDINE (INTERMEDIATE WW)

4-(2-bromo-5-(trifluoromethyl)phenyl)-1-methyl-1,2,3,6-tetrahydropyridine was dissolved in 20 mL ethanol and the solution was treated with platinum (iv) oxide (0.194 g, 0.854 mmol), and was placed under 45 psi H$_2$ for one hour. LC/MS showed product and debrominated product, so the reaction mixture was diluted with DCM, filtered through a plug of diatomaceous earth and was concentrated. Purification of the crude residue by silica gel column chromatography (0 to 97% EtOAc/heptane, 3% MeOH) gave 4-(2-bromo-5-(trifluoromethyl)phenyl)-1-methylpiperidine (0.065 g, 0.202 mmol, 2.363% yield). m/z (ESI) 322.0 (M+Na)+;

INTERMEDIATE XX: 5-(2-BROMO-5-(TRIFLUOROMETHYL)PHENYL)-1-METHYL-1H-IMIDAZOLE

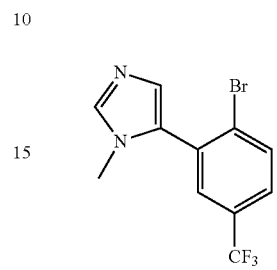

A solution of PdCl$_2$(dppf)-CH$_2$Cl$_2$ adduct (0.233 g, 0.285 mmol), 1-methyl-2-(tributylstannyl)imidazole (2.189 ml, 6.84 mmol), 1-bromo-2-iodo-4-(trifluoromethyl)benzene (0.919 ml, 5.70 mmol), and potassium fluoride (1.656 g, 28.5 mmol) in 6 mL DMF was heated to 80° C. overnight. LC/MS showed product, so the reaction mixture was poured into water and was extracted with DCM. The organics were dried over MgSO$_4$ and concentrated. Purification of the crude residue by silica gel column chromatography (0 to 100% EtOAc/heptane) gave 2-(2-bromo-5-(trifluoromethyl)phenyl)-1-methyl-1H-imidazole (1.122 g, 3.68 mmol, 64.5% yield). m/z (ESI) 307.2 (M+H)+.

INTERMEDIATE YY: 2-(2-BROMO-5-(TRIFLUOROMETHYL)PHENYL)-1-METHYL-1H-IMIDAZOLE

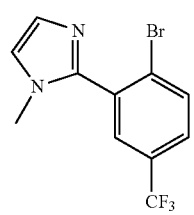

Intermediate YY was synthesized in a similar manner to INTERMEDIATE XX, using 1-methyl-5-(tributylstannyl)-1H-imidazole instead of 1-methyl-2-(tributylstannyl)imidazole to yield 5-(2-bromo-5-(trifluoromethyl)phenyl)-1-methyl-1H-imidazole (1.500 g, 4.92 mmol, 86% yield). m/z (ESI) 307.2 (M+H)+;

INTERMEDIATE ZZ: 1-(2-BROMO-5-(TRIFLUOROMETHYL)PHENYL)-1H-IMIDAZOLE

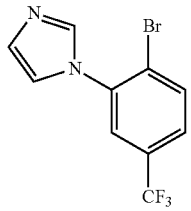 [SMILES: FC(F)(F)c1ccc(Br)c(-n2ccnc2)c1]

A microwave vial charged with potassium tert-butoxide (1.108 g, 9.88 mmol), 1H-imidazole (0.672 g, 9.88 mmol), 1-bromo-2-fluoro-4-(trifluoromethyl)benzene (1.180 ml, 8.23 mmol), and 10 mL dioxane was heated to 180° C. in the microwave for 2 hours. LC/MS showed mostly product, so the reaction mixture was poured into water and was extracted with DCM. The organics were dried over MgSO4 and concentrated. The crude residue was purified by silica gel column chromatography (0 to 100% EtOAc/heptane) yielding 1-(2-bromo-5-(trifluoromethyl)phenyl)-1H-imidazole (1.277 g, 4.39 mmol, 53.3% yield). m/z (ESI) 291.9 (M+H)+.

INTERMEDIATE BBB: TERT-BUTYL 4-(2-BROMO-5-(TRIFLUOROMETHYL)PHENYL)PIPERIDINE-1-CARBOXYLATE

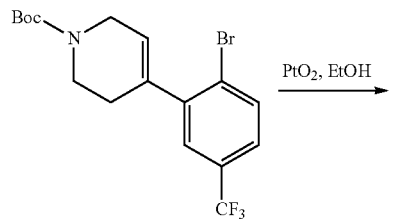

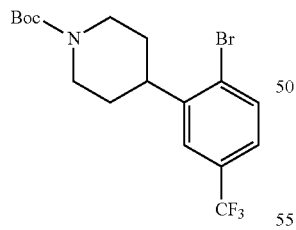

A solution of tert-butyl 4-(2-bromo-5-(trifluoromethyl)phenyl)-5,6-dihydropyridine-1(2H)-carboxylate (from Step 1 of Intermediate VV; 2.435 g, 5.99 mmol) in 20 mL EtOH was treated with platinum(iv) oxide (0.136 g, 0.599 mmol) and was placed under 45 psi H2 for one hour. LC/MS showed mostly product and de-brominated product. The reaction mixture was diluted with DCM and was filtered through diatomaceous earth. The filtrate was concentrated then purified directly by column chromatography (0 to 15% EtOAc/heptane) yielding tert-butyl 4-(2-bromo-5-(trifluoromethyl)phenyl)piperidine-1-carboxylate (0.970 g, 2.376 mmol, 39.6% yield). m/z (ESI) 431.0 (M+Na)+.

INTERMEDIATES CCC AND DDD: 5-BROMO-N-(PYRIMIDIN-4-YL)-N-((2-(TRIMETHYLSILYL)ETHOXY)METHYL)NAPHTHALENE-2-SULFONAMIDE AND N-(PYRIMIDIN-4-YL)-5-(4,4,5,5-TETRAMETHYL-1,3,2-DIOXABOROLAN-2-YL)-N-((2-(TRIMETHYLSILYL)ETHOXY)METHYL)NAPHTHALENE-2-SULFONAMIDE

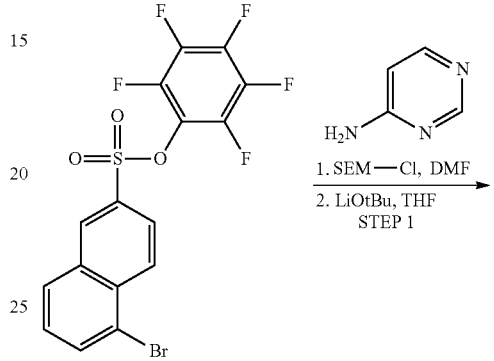

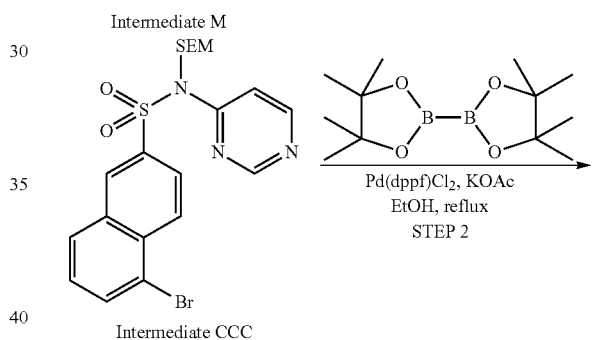

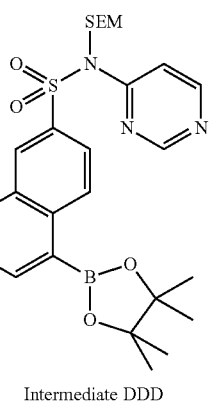

STEP 1: 5-BROMO-N-(PYRIMIDIN-4-YL)-N-((2-(TRIMETHYLSILYL)ETHOXY)METHYL)NAPHTHALENE-2-SULFONAMIDE

A solution of pyrimidin-4-amine (0.944 g, 9.93 mmol) in 10 mL DMF was treated with SEM-Cl (1.761 ml, 9.93 mmol) and was allowed to stir at room temperature 30 minutes. Perfluorophenyl 5-bromonaphthalene-2-sulfonate (INTERMEDIATE M; 4.50 g, 9.93 mmol) was added and the reaction mixture was treated with lithium tert-butoxide 1N in THF (19.86 ml, 19.86 mmol) drop wise. After stirring for one hour, the reaction mixture was concentrated. The crude residue was diluted with DCM, washed with water, the organics dried over MgSO4 and concentrated. The material (INTERMEDIATE CCC) was carried forward crude without further purification.

STEP 2: N-(PYRIMIDIN-4-YL)-5-(4,4,5,5-TETRAMETHYL-1,3,2-DIOXABOROLAN-2-YL)-N-((2-(TRIMETHYLSILYL)ETHOXY)METHYL)NAPHTHALENE-2-SULFONAMIDE 5-bromo-N-(pyrimidin-4-yl)-N-((2-(trimethylsilyl)ethoxy)methyl)naphthalene-2-sulfonamide (INTERMEDIATE CCC) was then dissolved in 30 mL EtOH and was treated with $PdCl_2$(dppf)-$CH_2Cl_2$ adduct (0.811 g, 0.993 mmol), bis(pinacolato)diboron (5.04 g, 19.86 mmol), and potassium acetate (3.90 g, 39.7 mmol) and was heated to reflux over the weekend. The reaction mixture was diluted with DCM and was washed with water. The organics were dried over $MgSO_4$ and concentrated. Purification of the crude residue by silica gel column chromatography (0 to 100% EtOAc/heptane) gave N-(pyrimidin-4-yl)-5-(4,4,5,5-tetramethyl-1,3,2-dioxaborolan-2-yl)-N-((2-(trimethylsilyl)ethoxy)methyl)naphthalene-2-sulfonamide (INTERMEDIATE DDD; 1.122 g, 2.072 mmol, 20.86% yield).

INTERMEDIATE EEE: 1-BROMO-2-(METHYLSULFONYL)-4-(TRIFLUOROMETHYL)BENZENE

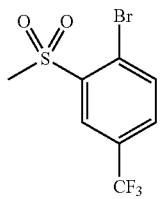

A solution of 1-bromo-2-iodo-4-(trifluoromethyl)benzene (1.608 ml, 9.97 mmol) in 20 mL THF was treated with isopropylmagnesium chloride (2N in diethyl ether) (4.99 ml, 9.97 mmol) and was allowed to stir for 30 minutes. The reaction mixture was cooled to 0° C. and was quenched with mesyl-Cl (0.777 ml, 9.97 mmol). After stirring for one hour, the reaction mixture was concentrated. Purification of the crude residue by reverse phase column chromatography [10 to 100% (0.1% NH4OH in MeOH)/(0.1% NH4OH in water)] gave 1-bromo-2-(methylsulfonyl)-4-(trifluoromethyl)benzene (1.36 g, 4.49 mmol, 45.0% yield). m/z (ESI) 305.1 (M+H)+.

INTERMEDIATE FFF: TERT-BUTYL 3-(2-BROMO-5-(TRIFLUOROMETHYL)PHENYL)-3-FLUOROAZETIDINE-1-CARBOXYLATE

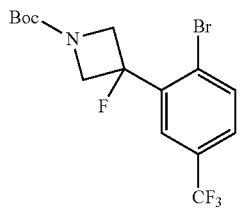

A solution of 1-bromo-2-iodo-4-(trifluoromethyl)benzene (1.608 ml, 9.97 mmol) in 20 mL THF was treated with isopropylmagnesium chloride 2N in diethyl ether (4.99 ml, 9.97 mmol) and was allowed to stir for 30 minutes. The reaction mixture was cooled to 0° C. and was quenched with tert-butyl 3-oxoazetidine-1-carboxylate (2.049 g, 11.97 mmol). After stirring for an additional 30 minutes, the reaction mixture was poured into 1N citric acid solution and was extracted with DCM. The organics were dried over $MgSO_4$ and concentrated. The crude residue was dissolved in 20 mL THF, was cooled to −10° C., and was treated with deoxofluor (2.023 ml, 10.97 mmol). The reaction mixture was allowed to warm to room temperature overnight. LC/MS showed product, so the reaction mixture was poured into saturated $NaHCO_3$ solution and was extracted with DCM. The organics were dried over $MgSO_4$ and concentrated. Purification of the crude residue by silica gel column chromatography (0 to 50% EtOAc/heptane) gave tert-butyl 3-(2-bromo-5-(trifluoromethyl)phenyl)-3-fluoroazetidine-1-carboxylate (0.600 g, 1.507 mmol, 15.11% yield).

INTERMEDIATE GGG: TERT-BUTYL 3-(2-BROMO-5-(TRIFLUOROMETHYL)PHENYL)-2,5-DIHYDRO-1H-PYRROLE-1-CARBOXYLATE

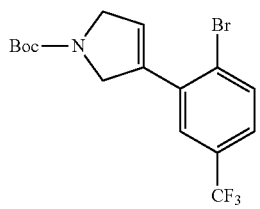 [SMILES: CC(C)(C)OC(=O)N1CC=C(c2cc(C(F)(F)F)ccc2Br)C1]

A solution of $PdCl_2$(dppf)-$CH_2Cl_2$ adduct (0.349 g, 0.427 mmol), 1-bromo-2-iodo-4-(trifluoromethyl)benzene (1.500 g, 4.27 mmol), tert-butyl 3-(4,4,5,5-tetramethyl-1,3,2-dioxaborolan-2-yl)-2,5-dihydro-1H-pyrrole-1-carboxylate (ASW MedChem, Inc., New Brunswick, N.J., 1.893 g, 6.41 mmol), and potassium carbonate (3.54 g, 25.6 mmol) in 15 mL dioxane/7.5 mL water was heated to 100° C. for 1 hour. LC/MS showed product, so the reaction mixture was cooled to room temperature and the aqueous layer was removed. The organics were concentrated then purified directly by reverse phase column chromatography [Redisep Gold C18, 20-100% (0.1% NH4OH in MeOH)/(0.1% NH4OH in water)] yielding tert-butyl 3-(2-bromo-5-(trifluoromethyl)phenyl)-2,5-dihydro-1H-pyrrole-1-carboxylate (1.040 g, 2.65 mmol, 62.0% yield). m/z (ESI) 413.9 (M+Na)+.

INTERMEDIATE HHH: 5-(2-BROMO-5-(TRIFLUOROMETHYL)PHENYL)-1-METHYL-1,2,3,6-TETRAHYDROPYRIDINE

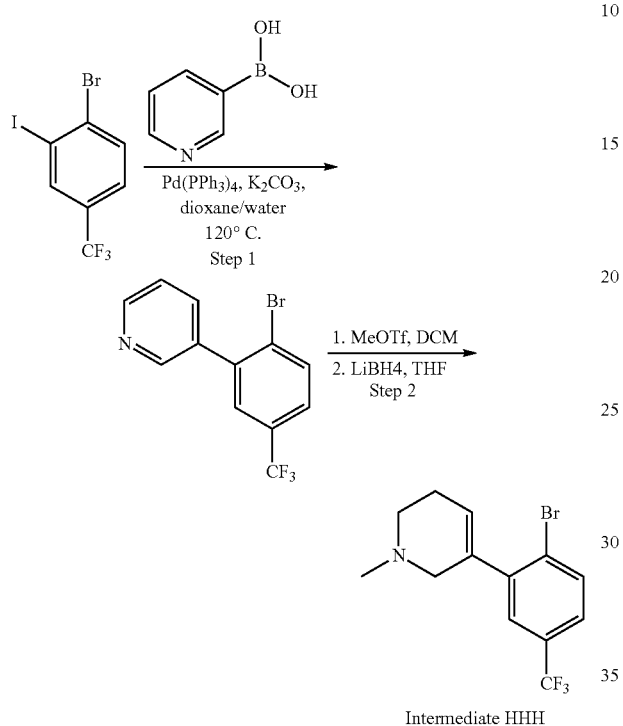

Intermediate HHH

STEP 1: 3-(2-BROMO-5-(TRIFLUOROMETHYL)PHENYL)PYRIDINE

A solution of Pd(Ph$_3$P)$_4$ (1.410 g, 1.220 mmol), 1-bromo-2-iodo-4-(trifluoromethyl)benzene (3.94 ml, 24.41 mmol), pyridin-3-ylboronic acid (3.00 g, 24.41 mmol), and potassium carbonate (13.49 g, 98 mmol) in 32 mL dioxane and 16 mL water was heated to 120° C. overnight. LC/MS showed incomplete conversion, so an additional portion of pyridin-3-ylboronic acid (3.00 g, 24.41 mmol) and potassium carbonate (13.49 g, 98 mmol) were added and the reaction mixture was heated to 120° C. for 3 hours. LC/MS showed no further conversion, so the reaction mixture was poured into water and was extracted with DCM. The organics were then concentrated. Purification of the crude residue by column chromatography (0-100% EtOAc/heptane) gave 3-(2-bromo-5-(trifluoromethyl)phenyl)pyridine (5.150 g, 17.05 mmol, 69.8% yield) as a yellow solid. m/z (ESI) 303.9 (M+H)⁺.

STEP 2: 5-(2-BROMO-5-(TRIFLUOROMETHYL)PHENYL)-1-METHYL-1,2,3,6-TETRAHYDROPYRIDINE

A solution of 3-(2-bromo-5-(trifluoromethyl)phenyl)pyridine (2.000 g, 6.62 mmol) in 13 mL DCM was treated with methyl trifluoromethanesulfonate (0.802 ml, 7.28 mmol) and was allowed to stir at room temperature for one hour. LC/MS showed mostly product so the reaction mixture was treated with sodium triacetoxyborohydride (4.21 g, 19.86 mmol) and was allowed to stir at room temperature overnight. LC/MS showed only a small amount of product, so the reaction mixture was concentrated then taken back up in 12 mL THF and cooled to 0° C. lithium borohydride (3.31 ml, 6.62 mmol) was added, and the reaction mixture was allowed to stir for one hour. LC/MS showed mostly product, so the reaction mixture was quenched with 7N ammonia in MeOH and was allowed to stir over the weekend. The reaction mixture was poured into water and was extracted with DCM. The organics were concentrated the purified directly by reverse phase column chromatography yielding 5-(2-bromo-5-(trifluoromethyl)phenyl)-1-methyl-1,2,3,6-tetrahydropyridine (0.860 g, 2.69 mmol, 40.6% yield) with impurities. m/z (ESI) 321.9 (M+H)+.

INTERMEDIATE III: 2-(4-CYCLOPROPYL-2-METHOXYPHENYL)-4,4,5,5-TETRAMETHYL-1,3,2-DIOXABOROLANE

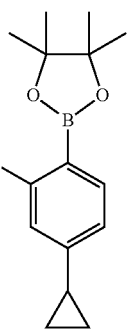

A solution of PdCl$_2$(dppf)-CH$_2$Cl$_2$ adduct (1.391 g, 1.703 mmol), cyclopropylboronic acid (4.39 g, 51.1 mmol), 1-bromo-4-iodo-2-methoxybenzene (10.66 g, 34.1 mmol), and potassium carbonate (18.83 g, 136 mmol) in 100 mL dioxane/50 mL water was heated to 120° C. for 8 hours. LC/MS showed mostly product, so the reaction mixture was diluted with heptane and was washed with saturated NaHCO$_3$ solution. The organics were dried over MgSO$_4$ and concentrated. The crude residue was taken up in 100 mL dioxane, was treated with Pd$_2$(dba)$_3$ (0.399 g, 1.703 mmol), dicyclohexyl(2',4',6'-triisopropyl-[1,1'-biphenyl]-2-yl)phosphine (4.06 g, 8.52 mmol), bis(pinacolato)diboron (12.98 g, 51.1 mmol), and potassium phosphate (28.9 g, 136 mmol) and was heated to 120° C. overnight. LC/MS showed product, so the reaction mixture was diluted with heptane then filtered through a plug of diatomaceous earth. The filtrate was concentrated then purified directly by silica gel column chromatography (0-25% EtOAc/heptane) yielding 2-(4-cyclopropyl- 2-methoxyphenyl)-4,4,5,5-tetramethyl-1,3,2-dioxaborolane (2.68 g, 9.78 mmol, 28.7% yield). m/z (ESI) 297.3 (M+Na)+

INTERMEDIATES JJJ and KKK: 1-chloro-N-(4-methoxybenzyl)-N-(thiazol-2-yl)isoquinoline-6-sulfonamide & 1-(2-bromo-4-fluorophenyl)-N-(4-methoxybenzyl)-N-(thiazol-2-yl)isoquinoline-6-sulfonamide

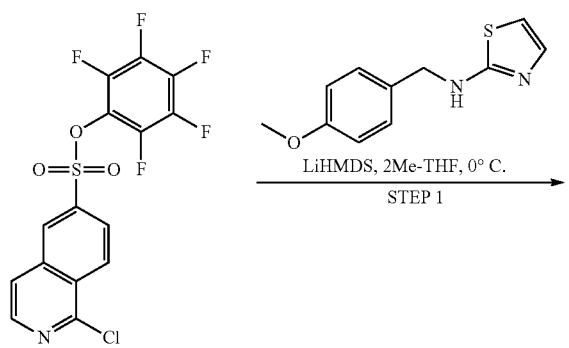

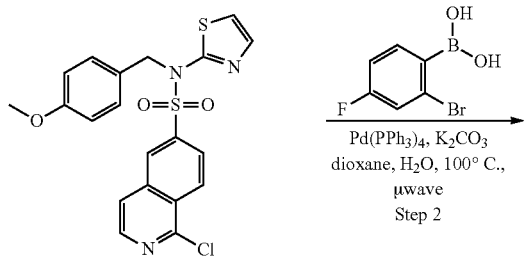

Intermediate JJJ

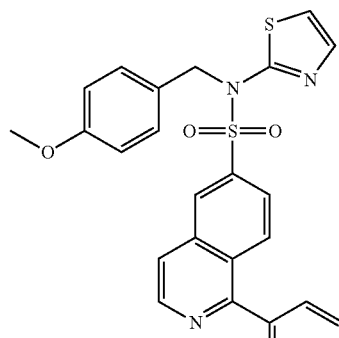

Intermediate KKK

STEP 1: 1-CHLORO-N-(4-METHOXYBENZYL)-N-(THIAZOL-2-YL)ISOQUINOLINE-6-SULFONAMIDE

To a flask containing an ice cold suspension of N-(4-methoxybenzyl)thiazol-2-amine (0.423 g, 1.922 mmol) in 2Me-THF (7.04 ml) was added lithium bis(trimethylsilyl)amide (2.014 ml, 2.014 mmol) dropwise over 10 min. The mixture was stirred for 15 min prior to the addition of a solution of perfluorophenyl 1-chloroisoquinoline-6-sulfonate (see Example 73, Step 1) (0.750 g, 1.831 mmol) in 2Me-THF (3.5 ml). After 1 hr of stirring (ice melt) LC-MS indicated about 65% conversion to product with starting ester and amine present. The mixture was re-cooled to 0° C. and additional LiHMDS (0.5 eq) was added. The mixture was allowed to stir and slowly warm to room temperature overnight. LC-MS indicated about 90% conversion to desired product. The reaction was quenched by the addition of acetic acid (~2 ml) and the resulting mixture (some precipitate formation) was dried under reduced pressure and purified with a 40 g silicycle HP column ramping EtOAc in heptane (0 to 50%) providing product 1-chloro-N-(4-methoxybenzyl)-N-(thiazol-2-yl)isoquinoline-6-sulfonamide (Intermediate JJJ) (0.530 g, 1.188 mmol, 64.9% yield) as a white foam. $^1$H NMR (400 MHz, CHLOROFORM-d) δ ppm 3.71 (s, 3H) 5.11 (s, 2H) 6.69-6.76 (m, 2H) 7.04 (d, J=3.62 Hz, 1H) 7.26-7.33 (m, 2H) 7.42 (d, J=3.62 Hz, 1H) 7.59-7.64 (m, 1H) 7.85 (dd, J=8.95, 1.81 Hz, 1H) 8.21 (d, J=1.76 Hz, 1H) 8.33-8.41 (m, 2H). m/z (ESI) 446.1 (M+H)$^+$.

STEP 2: 1-(2-BROMO-4-FLUOROPHENYL)-N-(4-METHOXYBENZYL)-N-(THIAZOL-2-YL)ISOQUINOLINE-6-SULFONAMIDE

To a microwave vial charged with 1-chloro-N-(4-methoxybenzyl)-N-(thiazol-2-yl)isoquinoline-6-sulfonamide (0.053 g, 0.119 mmol) was added (2-bromo-4-fluorophenyl)boronic acid (Combi-Blocks, San Diego, Calif.) (0.042 g, 0.190 mmol), potassium carbonate (0.082 g, 0.594 mmol), dioxane (0.594 ml) and water (0.198 ml). The mixture was purged with argon prior to the addition of Pd(PPh$_3$)$_4$ (0.014 g, 0.012 mmol). The vessel was sealed and irradiated at 100° C. for 30 mins affording fairly clean conversion to desired product. The organic phase was decanted, the aqueous rinsed with EtOAc and the EtOAc decanted. The combined organics were dried under reduced pressure and purified with a 25 g HP silicycle column ramping EtOAc in heptane (0-45%, then isocratic at 45%) to provide product as an off-white foam 1-(2-bromo-4-fluorophenyl)-N-(4-methoxybenzyl)-N-(thiazol-2-yl)isoquinoline-6-sulfonamide (Intermediate KKK) (54 mg, 0.092 mmol, 78% yield) with minor impurities according to LC/MS and NMR (~20% impurity). m/z (ESI) 582.2/584.2 (M+H)+.

INTERMEDIATE LLL: PERFLUOROPHENYL 1-(2-METHOXY-4-(TRIFLUOROMETHYL)PHENYL)ISOQUINOLINE-6-SULFONATE

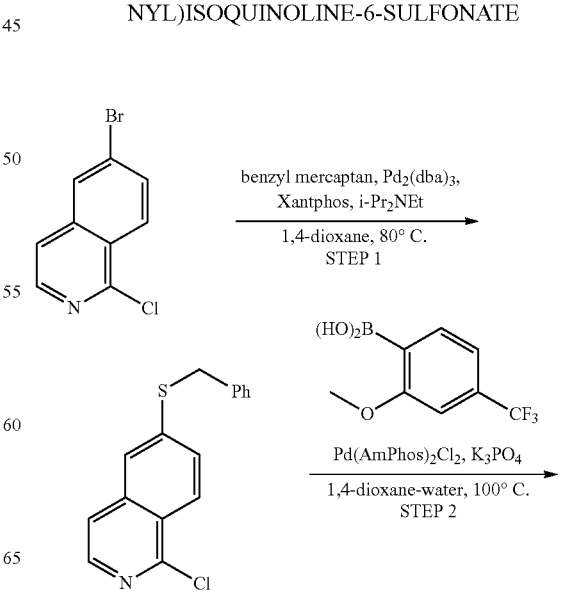

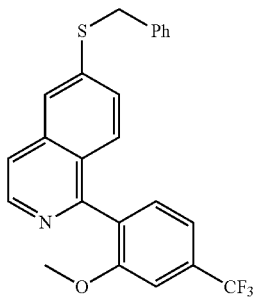

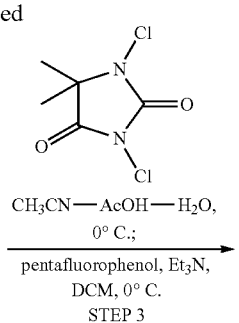

CH₃CN—AcOH—H₂O, 0° C.;
pentafluorophenol, Et₃N, DCM, 0° C.
STEP 3

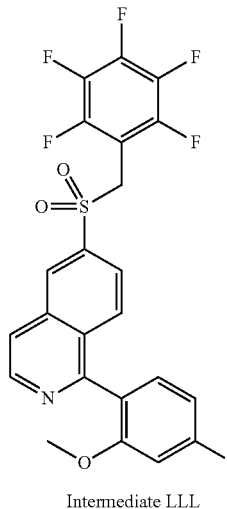

Intermediate LLL

STEP 1: 6-(BENZYLTHIO)-1-CHLOROISOQUINOLINE

A round-bottom flask was charged with 6-bromo-1-chloroisoquinoline (1.574 ml, 10.86 mmol), Xantphos (0.314 g, 0.543 mmol), and Pd₂(dba)₃ (0.249 g, 0.271 mmol). The flask was flushed with Ar (g), then 1,4-dioxane (21.72 ml), n,n-diisopropylethylamine (3.79 ml, 21.72 mmol), and benzyl mercaptan (1.349 ml, 11.40 mmol) were added in sequence. The flask was fitted with a reflux condenser and heated to 80° C. for 1 h. The mixture was cooled and concentrated under a vacuum. The crude product was purified by chromatography on silica gel (80-g Redi-Sep Gold column, 25-g silica gel loading column, 0-40% EtOAc/Heptane) to give a yellow solid. The solid was suspended in heptane, sonicated, and filtered. The collected solid was washed with heptane, dried under a stream of N2 (g), then dried under vacuum for to give 6-(benzylthio)-1-chloroisoquinoline as an off-white powder: $^1$H NMR (400 MHz, CHLOROFORM-d) δ ppm=8.26-8.10 (m, 2H), 7.63-7.51 (m, 2H), 7.46-7.39 (m, 3H), 7.37-7.28 (m, 3H), 4.31 (s, 2H); m/z (ESI) 286.2 (M+H)⁺.

STEP 2: 6-(BENZYLTHIO)-1-(2-METHOXY-4-(TRIFLUOROMETHYL)PHENYL)ISOQUINOLINE

A round-bottom flask was charged with 6-(benzylthio)-1-chloroisoquinoline (3.101 g, 10.85 mmol)-(2-methoxy-4-(trifluoromethyl)phenyl)boronic acid (2.86 g, 13.02 mmol), Pd(AmPhos)2Cl2 (0.384 g, 0.543 mmol), potassium phosphate (6.91 g, 32.6 mmol), 1,3-dioxane (27.1 ml), and water (9.04 ml). The vial was flushed with Ar (g), fitted with a reflux condenser, and placed in a 100° C. heating bath for 45 min. The mixture was cooled to room temperature, then diluted with water and extracted with EtOAc (2×). The combined organic extracts were dried over sodium sulfate, filtered, and concentrated. The crude product was purified by chromatography on silica gel (120-g, 10 to 40% EtOAc/Heptane) to give 6-(benzylthio)-1-(2-methoxy-4-(trifluoromethyl)phenyl) isoquinoline (4.47 g, 10.51 mmol, 97% yield) as a light-yellow solid: $^1$H NMR (400 MHz, CHLOROFORM-d) δ ppm=8.58 (d, J=5.8 Hz, 1H), 7.66 (d, J=1.8 Hz, 1H), 7.56-7.47 (m, 3H), 7.45-7.26 (m, 8H), 4.31 (s, 2H), 3.76 (s, 3H); m/z (ESI) 426.2 (M+H)⁺.

STEP 3: PERFLUOROPHENYL 1-(2-METHOXY-4-(TRIFLUOROMETHYL)PHENYL)ISOQUINOLINE-6-SULFONATE

A round-bottom flask was charged with 6-(benzylthio)-1-(2-methoxy-4-(trifluoromethyl)phenyl)isoquinoline (4.47 g, 10.51 mmol), acetonitrile (99 ml), acetic acid (3.71 ml), and water (2.472 ml) to give a thin suspension. The flask was cooled in an ice-bath for 15 min, then 1,3-dichloro-5,5-dimethylimidazolidine-2,4-dione (4.14 g, 21.01 mmol) was added in one portion, leading to a solution (12:40 am). After 1 h, 2,3,4,5,6-pentafluorophenol (2.321 g, 12.61 mmol) and triethylamine (2.197 ml, 15.76 mmol) were added in sequence (the base was added dropwise), and the cooling bath was removed. After 1 h, additional portions of 2,3,4,5,6-pentafluorophenol (0.967 g, 5.25 mmol) and triethylamine (0.732 ml, 5.25 mmol) were added. After another 1 h, an additional portion of triethylamine (0.732 ml, 5.25 mmol) was added. The mixture was stirred for 10 more min, then concentrated under a vacuum. The residue was dissolved in DCM and loaded onto a 25-g silica gel loading column. The column was briefly dried under vacuum, then eluted onto a pre-equilibrated 120-g Redi-Sep Gold column with 0-30% EtOAc/Heptane to give perfluorophenyl 1-(2-methoxy-4-(trifluoromethyl)phenyl)isoquinoline-6-sulfonate (5.45 g, 9.92 mmol, 94% yield) as a white foam: $^1$H NMR (400 MHz, DMSO-d₆) δ ppm=8.94 (d, J=2.0 Hz, 1H), 8.84 (d, J=5.7 Hz, 1H), 8.23 (dd, J=0.5, 5.7 Hz, 1H), 8.05 (dd, J=2.0, 8.9 Hz, 1H), 7.90 (d, J=9.0 Hz, 1H), 7.66 (d, J=7.5 Hz, 1H), 7.59-7.49 (m, 2H), 3.76 (s, 3H); m/z (ESI) 550.2 (M+H)⁺.

INTERMEDIATE LLL-ALTERNATIVE PROCEDURE: PERFLUOROPHENYL 1-(2-METHOXY-4-(TRIFLUOROMETHYL)PHENYL)ISOQUINOLINE-6-SULFONATE

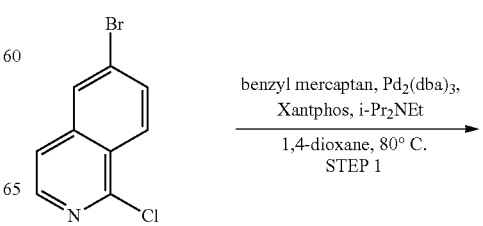

benzyl mercaptan, Pd₂(dba)₃, Xantphos, i-Pr₂NEt
1,4-dioxane, 80° C.
STEP 1

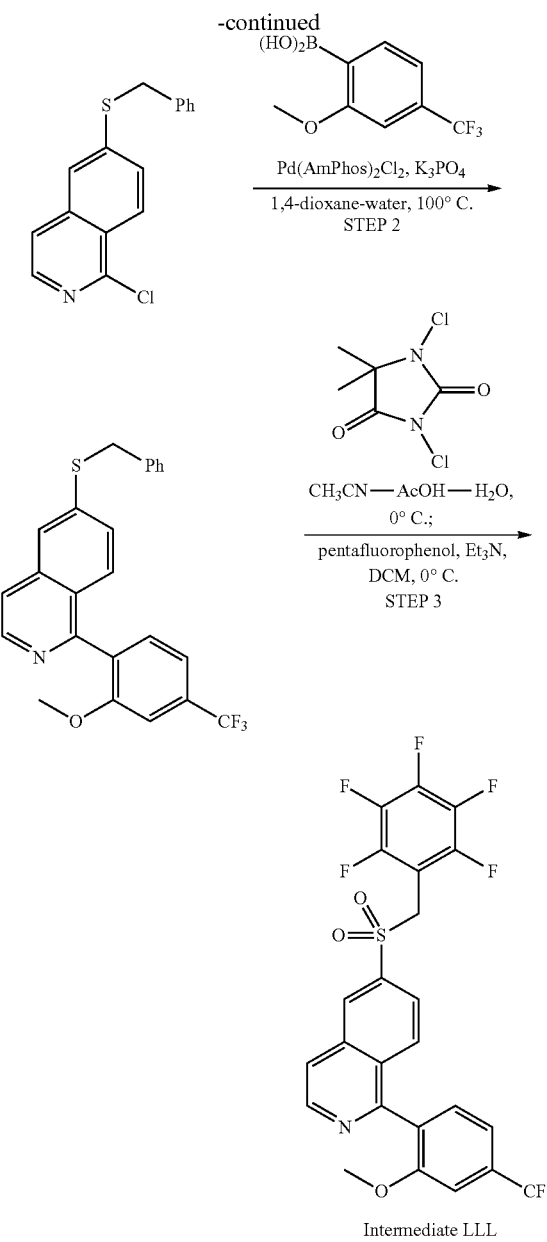

Intermediate LLL

STEP 1: 6-(BENZYLTHIO)-1-CHLOROISOQUINOLINE

A three-neck 2 L flask equipped with an overhead stirrer, a thermocouple and a nitrogen inlet was charged with 6-bromo-1-chloroisoquinoline (60.0 g, 247 mmol), xantphos (7.16 g, 12.4 mmol) and Pd$_2$(dba)$_3$ (5.66 g, 6.19 mmol) in that order. The flask was evacuated. To the reaction flask was charged sparged dioxane (540 mL) and DIPEA (64.8 mL, 371 mmol). The flask was purged with N2 and warmed to 63° C. upon which a solution of phenylmethanethiol (30.5 mL, 260 mmol) in 180 mL of sparged dioxane was charged to the reaction mixture dropwise over 1 hr. The reaction was completed according to LC/MS. The solids were filtered off. The filtrate was concentrated down to a low volume. 500 mL of isopropanol was added into a separate flask. The concentrated product solution was charged slowly to the flask containing isopropanol. The product crystallized out of the solution. The resulting slurry was stirred at RT for 2 hours. The slurry was cooled to 0° C., filtered, washed with 50% IPA/heptanes, and dried under a vacuum with nitrogen sweep. The product was obtained as yellow solids (44.3 g; 63% isolated yield). $^1$H NMR (400 MHz, CHLOROFORM-d) δ ppm=8.26-8.10 (m, 2H), 7.63-7.51 (m, 2H), 7.46-7.39 (m, 3H), 7.37-7.28 (m, 3H), 4.31 (s, 2H); m/z (ESI) 286.2 (M+H)+.

STEP 2: 6-(BENZYLTHIO)-1-(2-METHOXY-4-(TRIFLUOROMETHYL)PHENYL)ISOQUINOLINE

A three-neck 2 L flask equipped with an overhead stirrer, a thermocouple, a condenser and a nitrogen inlet was charged with 6-(benzylthio)-1-chloroisoquinoline (23 g, 80 mmol), (2-methoxy-4-(trifluoromethyl)phenyl)boronic acid (22.1 g, 101 mmol), potassium phosphate (51.2 g, 241 mmol) and Amphos (2.85 g, 4.02 mmol) in that order. The flask was evacuated. In a separate flask was charged with dioxane (230 mL) and water (57.5 mL). The solvent solution was sparged with nitrogen and charged to the reaction flask. The reaction flask was purged with nitrogen and warmed to reflux. After 1 hr, the reaction was complete according to LC/MS. The whole was cooled to 0° C., charged with DCM and water. The organic layer was separated, dried over sodium sulfate, filtered, and concentrated down to afford black oil. Isopropanol was added into the black oil and the whole was concentrated again to fully remove DCM and dioxane. The black residue was charged with 200 mL of isopropanol. The product crystallized out of solution. The slurry was stirred for 2 hrs at RT and cooled to 0° C. for 1 hr. The product was filtered off, washed with 30% isopropanol/heptane solution, and dried under vacuum with a nitrogen sweep. The product was obtained as gray solids (24.1 g, 70.4%; >99% purity via LC/MS at 215 nm). $^1$H NMR (400 MHz, CHLOROFORM-d) δ ppm=8.58 (d, J=5.8 Hz, 1H), 7.66 (d, J=1.8 Hz, 1H), 7.56-7.47 (m, 3H), 7.45-7.26 (m, 8H), 4.31 (s, 2H), 3.76 (s, 3H); m/z (ESI) 426.2 (M+H)+.

STEP 3: PERFLUOROPHENYL 1-(2-METHOXY-4-(TRIFLUOROMETHYL)PHENYL)ISOQUINOLINE-6-SULFONATE

A three-neck 2 L flask equipped with an overhead stirrer, a thermocouple and a nitrogen inlet was charged with 6-(benzylthio)-1-(2-methoxy-4-(trifluoromethyl)phenyl)isoquinoline (24.1 g, 56.6 mmol), acetonitrile (241 mL), AcOH (29.9 mL) and water (19.8 mL). The resulting mixture was cooled to 0 to 5° C. upon which solid 1,3-dichloro-5,5-dimethylimidazolidine-2,4-dione (22.3 g, 113 mmol) was charged portionwise while maintaining temperature <5° C. Addition was exothermic. After stirring for 1 hr at 0° C., LCMS indicated that the reaction was complete. 2,3,4,5,6-Pentafluorophenol (20.9 g, 113 mmol) was added into the reaction as a solution in 20 mL ACN. Then triethylamine (21.7 mL, 156 mmol) was added dropwise via syringe over 2 hrs. When the reaction was completed according to LCMS, the whole was diluted with DCM and water. The organic layer was separated, dried over sodium sulfate, filtered, and concentrated to dryness. The product was purified via silica gel column chromatography eluting with DCM. Fractions containing the product were collected, combined and concentrated to afford the desired product as amorphous foam (23.8 g; 76% yield, 95% purity at 254 nm). $^1$H NMR (400 MHz, DMSO-d$_6$) δ ppm=8.94 (d, J=2.0 Hz, 1H), 8.84 (d, J=5.7 Hz, 1H), 8.23 (dd, J=0.5, 5.7 Hz, 1H), 8.05 (dd, J=2.0, 8.9 Hz, 1H), 7.90 (d, J=9.0 Hz, 1H), 7.66 (d, J=7.5 Hz, 1H), 7.59-7.49 (m, 2H), 3.76 (s, 3H); m/z (ESI) 550.2 (M+H)+.

INTERMEDIATE MMM: 5-FLUORO-N-(4-METHOXYBENZYL)THIAZOL-2-AMINE

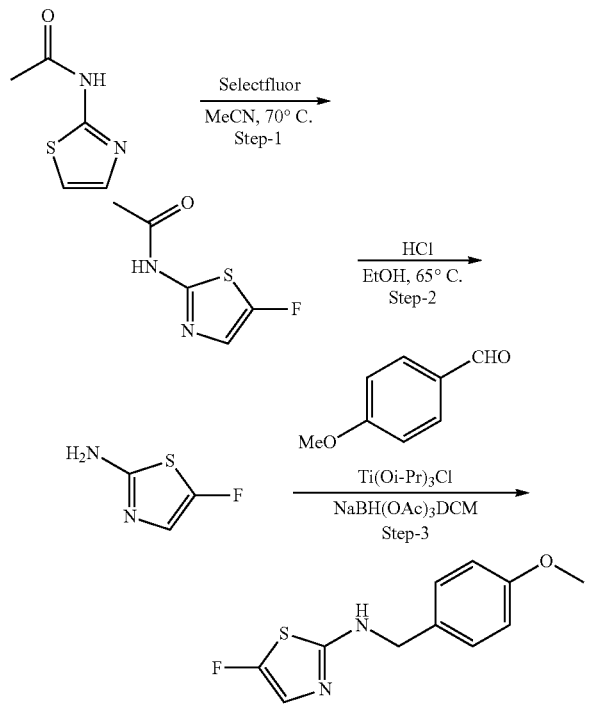

Intermediate MMM

STEP 1: N-(5-FLUOROTHIAZOL-2-YL)ACETAMIDE

To a solution of N-(thiazol-2-yl)acetamide (150 g, 1056 mmol, Combi-Blocks, San Diego, Calif.) in acetonitrile (3 L) was added 1-chloromethyl-4-fluoro-1,4-diazoniabicyclo[2.2.2]octane bis(tetrafluoroborate) (Selectfluor®) (486 g, 1373 mmol, Air Products, Allentown, Pa.) and the mixture was heated at 80° C. for 4 h. The reaction mixture was cooled to room temperature, concentrated under reduced pressure and water (2 L) was added. The mixture was extracted with ethyl acetate (2×1.5 L). The combined organic extract was washed with saturated aqueous NaHCO₃ (1.5 L) and 2N HCl (1 L). The organic layer was dried over sodium sulfate, filtered and concentrated under reduced pressure to obtain the crude N-(5-fluorothiazol-2-yl)acetamide (70.0 g, crude) which was used for next reaction without any purification. m/z (ESI) 161.0 (M+H)+

STEP 2: 5-FLUOROTHIAZOL-2-AMINE

To a solution of N-(5-fluorothiazol-2-yl)acetamide (70.0 g, 437 mmol) in ethanol (500 mL), conc. HCl (300 mL) was added and the reaction mixture was stirred at 80° C. for 16 h. The reaction mixture was concentrated under reduced pressure and the residue was dissolved in water. The mixture was neutralized with aqueous saturated NaHCO₃ solution (500 mL) and extracted with ethyl acetate (2×1000 mL). The combined organic extract was dried over sodium sulfate, filtered and concentrated under reduced pressure to obtain the crude 5-fluorothiazol-2-amine (15.0 g, crude) which was used for next reaction without any purification. m/z (ESI) 119.0 (M+H)⁺.

STEP 3: 5-FLUORO-N-(4-METHOXYBENZYL)THIAZOL-2-AMINE

To a solution of 5-fluorothiazol-2-amine (15.0 g, 127 mmol) and 4-methoxybenzaldehyde (17.3 g, 127 mmol, Spectrochem) in dichloromethane (1.0 L) was added TiCl(O-ⁱPr)₃ (66.1 g, 254 mmol, Aldrich). The mixture was stirred at room temperature for 3 h. The reaction mixture was cooled to 0° C. and NaBH(OAc)₃ (108 g, 508 mmol) was added in portions and stirred at room temperature for 16 h. The reaction mixture (in portions of 200 mL) was quenched with saturated NaHCO₃ solution (100 mL) and extracted with dichloromethane (2×500 mL). The combined organic layer was dried over sodium sulfate, filtered and concentrated under reduced pressure to obtain the crude material which was further purified by column chromatography (silica gel 100 to 200 mesh and 50 to 100% dichloromethane in hexanes) to obtain 5-fluoro-N-(4-methoxybenzyl)thiazol-2-amine (20.0 g, 45%) as brown solid. ¹H NMR (400 MHz, DMSO) δ 7.84 (t, J=5.7 Hz, 1H), 7.37-7.13 (m, 2H), 6.89 (dd, J=6.4, 2.2 Hz, 2H), 6.77 (d, J=2.4 Hz, 1H), 4.28 (d, J=5.6 Hz, 2H), 3.73 (s, 3H). m/z (ESI) 239.0 (M+H)⁺.

INTERMEDIATE NNN: PERFLUOROPHENYL 1-(4-CHLORO-2-METHOXYPHENYL)ISOQUINOLINE-6-SULFONATE

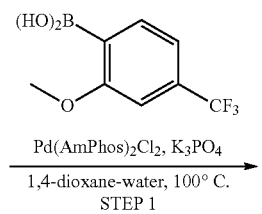

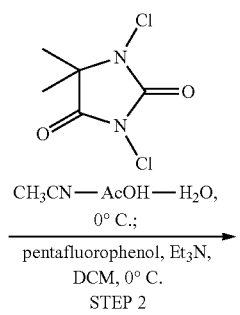

169

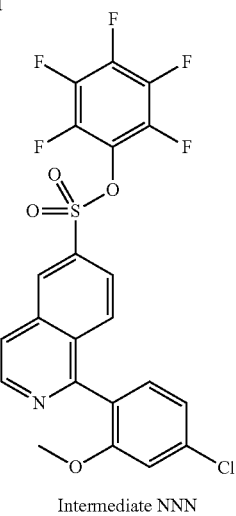

Intermediate NNN

STEP 1: 6-(BENZYLTHIO)-1-(4-CHLORO-2-METHOXYPHENYL)ISOQUINOLINE

A round-bottom flask was charged with 6-(benzylthio)-1-chloroisoquinoline (from STEP 1 of INTERMEDIATE LLL) (688.23 mg, 2.408 mmol), (4-chloro-2-methoxyphenyl)boronic acid (494 mg, 2.65 mmol), Pd(AmPhos)$_2$Cl$_2$ (85 mg, 0.120 mmol), potassium phosphate (1534 mg, 7.22 mmol), dioxane (6020 μl), and water (2007 μl). The vial was flushed with Ar (g), then 1,4-dioxane (6020 μl) and water (2007 μl) were added. The vial was sealed and heated in a Biotage Initiator microwave reactor for 30 min at 100° C. The mixture was cooled to room temperature, then diluted with water and extracted with EtOAc (2×). The combined organic extracts were dried over sodium sulfate, filtered, and concentrated. The crude product was purified by chromatography on silica gel (40-g, 10 to 40%, then 40-70% EtOAc/Heptane, 25-g silica gel loading column) to give 6-(benzylthio)-1-(4-chloro-2-methoxyphenyl)isoquinoline (704.36 mg, 1.797 mmol, 74.6% yield) as a light-yellow foam: $^1$H NMR (400 MHz, CHLOROFORM-d) δ ppm=8.56 (d, J=5.8 Hz, 1H), 7.65 (d, J=1.9 Hz, 1H), 7.55-7.48 (m, 2H), 7.44-7.39 (m, 2H), 7.38-7.27 (m, 5H), 7.11 (dd, J=1.9, 8.1 Hz, 1H), 7.04 (d, J=1.9 Hz, 1H), 4.30 (s, 2H), 3.70 (s, 3H); m/z (ESI) 392.2 (M+H)+.

STEP 2: PERFLUOROPHENYL 1-(4-CHLORO-2-METHOXYPHENYL)ISOQUINOLINE-6-SULFONATE

A round-bottom flask was charged with 6-(benzylthio)-1-(4-chloro-2-methoxyphenyl)isoquinoline (700 mg, 1.786 mmol), acetonitrile (1.68E+04 μl), acetic acid (630 μl), and water (420 μl) to give a thin suspension. The flask was cooling in an ice-bath for 15 min, then 1,3-dichloro-5,5-dimethylimidazolidine-2,4-dione (704 mg, 3.57 mmol) was added in one portion, leading to an solution. After 20 min, 2,3,4,5,6-pentafluorophenol (493 mg, 2.68 mmol) and triethylamine (1245 μl, 8.93 mmol) were added in sequence. The cooling bath was removed after a few minutes, and the mixture was warmed to room temperature. The mixture was treated with silica gel then concentrated. More silica gel was added, and the mixture was concentrated from DCM. The impregnated silica gel was eluted onto a pre-equilibrated 40-g column with 0 to 50% EtOAc/Heptane to give perfluorophenyl 1-(4-chloro-2-meth-

170 oxyphenyl)isoquinoline-6-sulfonate (Intermediate NNN; 432 mg, 0.837 mmol, 46.9% yield) as a white foam. NMR and LC/MS indicated the material was about 82% pure. m/z (ESI) 516.0 (M+H)+.

INTERMEDIATE OOO: 1-CHLORO-N-(2,4-DIMETHOXYBENZYL)-N-(THIAZOL-2-YL)ISOQUINOLINE-6-SULFONAMIDE

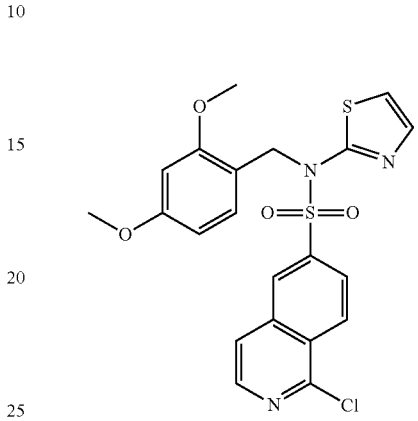

A solution of N-(2,4-dimethoxybenzyl)thiazol-2-amine (0.642 g, 2.56 mmol) in tetrahydrofuran (9.39 ml) was cooled in a dry ice-acetone bath for 5 min. Lithium bis(trimethylsilyl)amide (1M in THF) (2.68 ml, 2.68 mmol) was added drop wise, then the flask was removed from the cooling bath for 5 min. The flask was again cooled into a dry ice-acetone bath for 20 min, resulting in the formation of a thick slurry. A solution of perfluorophenyl 1-chloroisoquinoline-6-sulfonate (see Example 73, Step 1; 1.0 g, 2.441 mmol) in THF (5 mL) was added drop wise, and the reaction was stirred for 30 minutes. The reaction was warmed to room temperature and quenched with saturated ammonium chloride solution, diluted with ethyl acetate and washed with water. The aqueous layer was extracted with ethyl acetate, and the combined organic layers were dried with sodium sulfate, filtered, and concentrated. The filtrate was purified by chromatography on an 80-g with 0 to 50% EtOAc/Heptane to afford 1-chloro-N-(2,4-dimethoxybenzyl)-N-(thiazol-2-yl)isoquinoline-6-sulfonamide (INTERMEDIATE OOO) as a white solid. (ESI) 498.2 (M+Na)+.

INTERMEDIATE PPP: 1-CHLORO-N-(2,4-DIMETHOXYBENZYL)-4-FLUORO-N-(THIAZOL-2-YL)ISOQUINOLINE-6-SULFONAMIDE

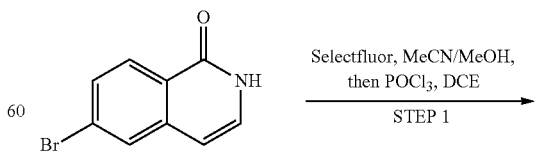

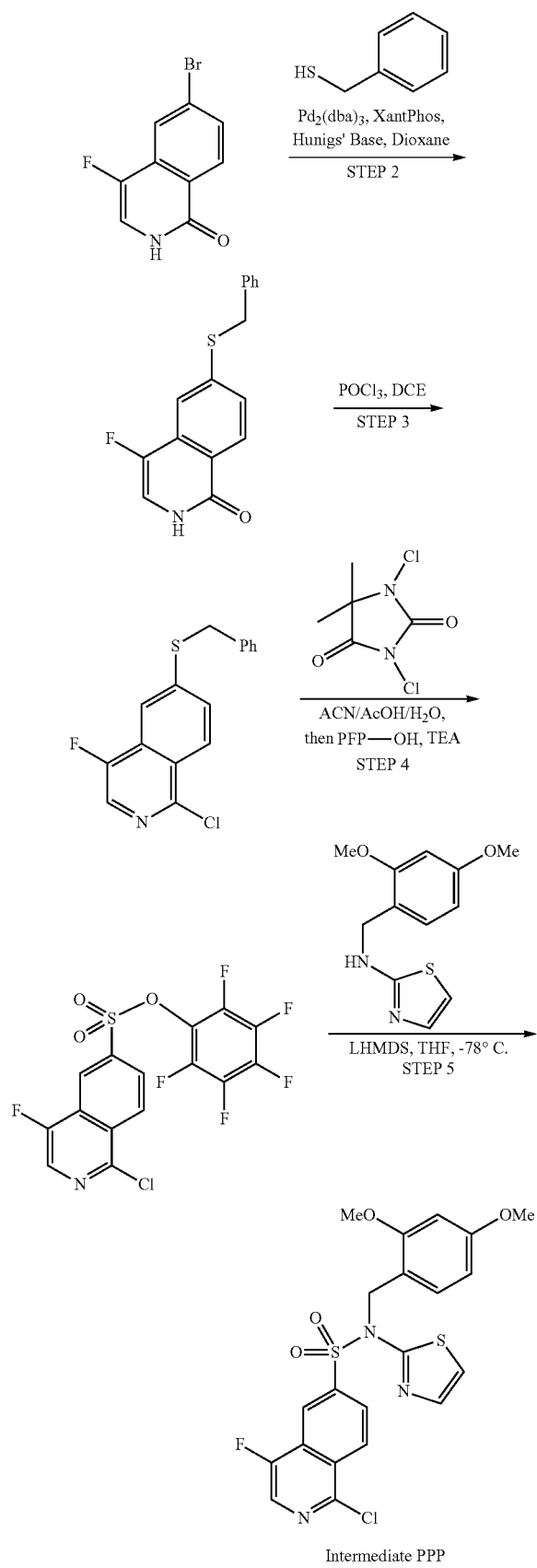

STEP 1:
6-BROMO-4-FLUOROISOQUINOLIN-1(2H)-ONE

A round bottom flask was charged with 6-bromo-2h-isoquinolin-1-one (5.0 g, 22.32 mmol) and 1-chloromethyl-4-fluoro-1,4-diazoniabicyclo[2.2.2]octane bis(tetrafluoroborate) (Selectfluor®) (9.49 g, 26.8 mmol, Air Products, Allentown, Pa.). Methanol (55.8 ml) and acetonitrile (55.8 ml) were added and the reaction was heated to 50° C. and stirred for one hour. The reaction was concentrated, dissolved in DCE (110 mL), and POCl₃ (4.16 ml, 44.6 mmol) was added. The reaction was stirred at 50° C. for one hour. The reaction was quenched into ice water and extracted with ethyl acetate. The combined organic layers were dried with sodium sulfate, filtered, and concentrated to afford crude 6-bromo-4-fluoroisoquinolin-1(2H)-one as a light pink solid. (ESI) 242.1 $(M+H)^+$.

STEP 2:
6-(BENZYLTHIO)-4-FLUOROISOQUINOLIN-1(2H)-ONE

A vial was charged with 6-bromo-4-fluoroisoquinolin-1(2H)-one (3.88 g, 16.03 mmol), Xantphos (0.464 g, 0.802 mmol), and Pd₂(dba)₃ (0.367 g, 0.401 mmol). The flask was flushed with Ar (g), then dioxane (32.1 ml), benzyl mercaptan (2.086 ml, 17.63 mmol), and n,n-diisopropylethylamine (5.60 ml, 32.1 mmol) were added in sequence. The reaction was heated to 110° C. and stirred for one hour. The reaction was diluted with water and stirred for 30 minutes. The solution was filtered and the solids were washed with water and dried under a nitrogen blanket overnight. The solids were triturated in ethyl acetate, stirred for two hours, and filtered. The solids were washed with ethyl acetate and vacuum dried to afford 6-(benzylthio)-4-fluoroisoquinolin-1(2H)-one as a yellow/green solid. (ESI) 286.2 $(M+H)^+$.

STEP 3:
6-(BENZYLTHIO)-1-CHLORO-4-FLUOROISOQUINOLINE

A vial was charged with 6-(benzylthio)-4-fluoroisoquinolin-1(2H)-one (0.083 g, 0.291 mmol) and DCE (1.454 ml). POCl₃ (0.136 ml, 1.454 mmol) was added and the reaction was stirred overnight at 90° C. The reaction was quenched into ice water and extracted with ethyl acetate. The aqueous layer was extracted with ethyl acetate, and the combined organic layers were dried with sodium sulfate, filtered, and concentrated to afford crude 6-(benzylthio)-1-chloro-4-fluoroisoquinoline as a light yellow solid. The material was carried forward without further purification. (ESI) 304.1 $(M+H)^+$.

STEP 4: PERFLUOROPHENYL 1-CHLORO-4-FLUOROISOQUINOLINE-6-SULFONATE

A round-bottom flask was charged with 6-(benzylthio)-1-chloro-4-fluoroisoquinoline (0.088 g, 0.290 mmol), acetonitrile (2.73 ml), acetic acid (0.102 ml), and water (0.068 ml) to give a thin suspension. The flask was cooled in an ice-bath for 10 min, then 1,3-dichloro-5,5-dimethylimidazolidine-2,4-dione (0.114 g, 0.579 mmol) was added in one portion, leading to a solution. The reaction was stirred for 30 minutes. 2,3,4,5,6-pentafluorophenol (0.061 ml, 0.579 mmol) was added followed by drop wise addition of triethylamine (0.101 ml, 0.724 mmol). The reaction was stirred for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (12 g, gradient elution 0 to 25% EtOAc: Heptane) to afford perfluorophenyl 1-chloro-4-fluoroisoquinoline-6-sulfonate as a clear colorless oil. (ESI) 428.1 (M+H)+.

STEP 5: 1-CHLORO-N-(2,4-DIMETHOXYBENZYL)-4-FLUORO-N-(THIAZOL-2-YL)ISOQUINOLINE-6-SULFONAMIDE

A solution of N-(2,4-dimethoxybenzyl)thiazol-2-amine (0.031 g, 0.123 mmol) in tetrahydrofuran (0.450 ml) was cooled in a dry ice-acetone bath for 5 min. Lithium bis(trimethylsilyl)amide (1M in THF) (0.129 ml, 0.129 mmol) was added drop wise, then the flask was removed from the cooling bath for 5 min. The flask was again cooled into a dry ice-acetone bath for 20 min, resulting in the formation of a thick slurry. A solution of perfluorophenyl 1-chloro-4-fluoroisoquinoline-6-sulfonate (0.050 g, 0.117 mmol) in THF (0.25 mL) was added drop wise, and the reaction was stirred for 30 minutes. The reaction was warmed to room temperature and quenched with saturated ammonium chloride solution, diluted with ethyl acetate and washed with water. The aqueous layer was extracted with ethyl acetate, and the combined organic layers were dried with sodium sulfate, filtered, and concentrated. The filtrate was purified by chromatography on a 12-g column with 0 to 100% EtOAc/Heptane to afford 1-chloro-N-(2,4-dimethoxybenzyl)-4-fluoro-N-(thiazol-2-yl)isoquinoline-6-sulfonamide (INTERMEDIATE PPP) as an oily solid. (ESI) 516.2 (M+H)+.

INTERMEDIATE QQQ: 1-CHLORO-4-FLUORO-N-(4-METHOXYBENZYL)-N-(PYRIMIDIN-4-YL)ISOQUINOLINE-6-SULFONAMIDE

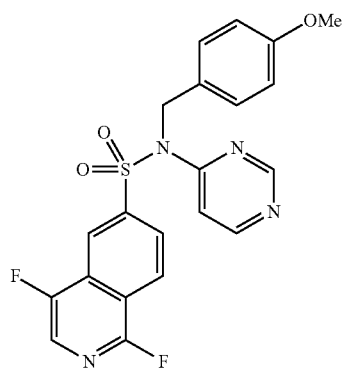 [SMILES: COc1ccc(CN(c2ccncn2)S(=O)(=O)c2ccc3c(F)ncc(F)c3c2)cc1]

Intermediate QQQ was prepared in a similar manner to Intermediate PPP, except that N-(4-methoxybenzyl)pyrimidin-4-amine was used instead of N-(2,4-dimethoxybenzyl)thiazol-2-amine in step 5. The final compound was purified via column chromatography (40 g silica gel column, gradient elution 0 to 75% EtOAc:Heptane) to afford 1-chloro-4-fluoro-N-(4-methoxybenzyl)-N-(pyrimidin-4-yl)isoquinoline-6-sulfonamide as a white oily solid. (ESI) 459.2 (M+H)+.

INTERMEDIATE RRR: 3-CHLORO-1-(2-METHOXY-4-(TRIFLUOROMETHYL)PHENYL)-N-(4-METHOXYBENZYL)-N-(THIAZOL-2-YL)ISOQUINOLINE-6-SULFONAMIDE

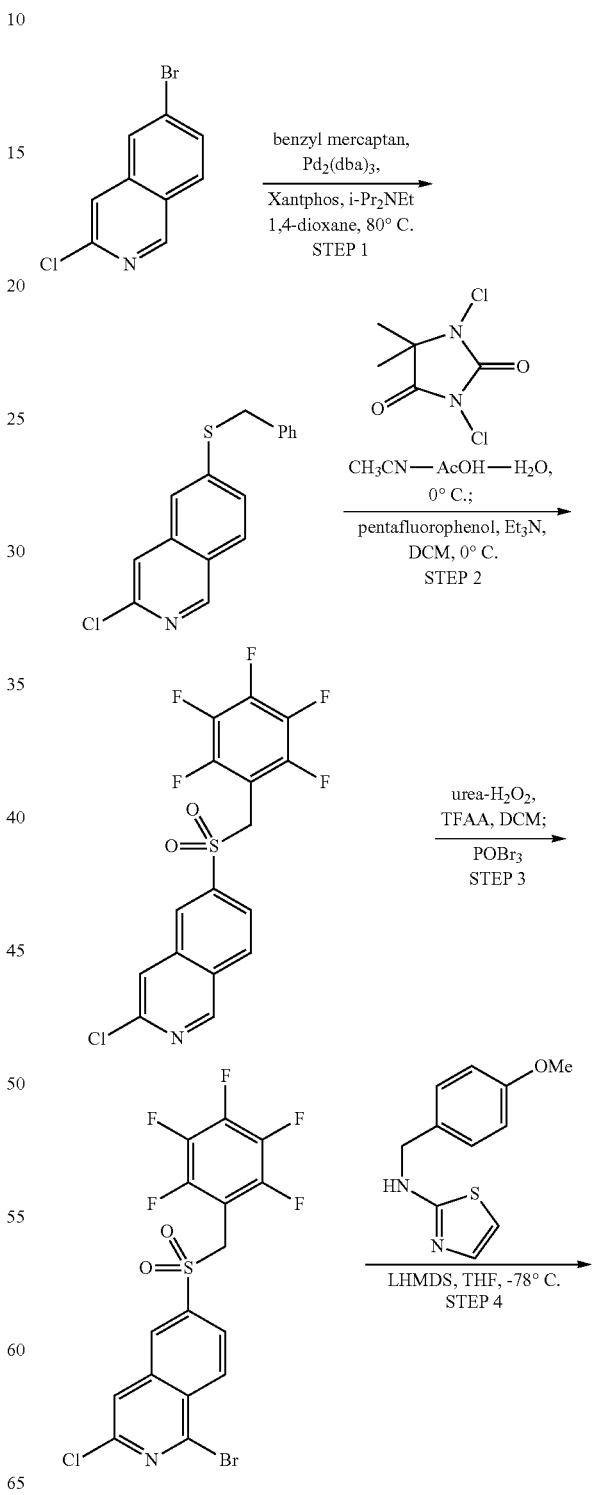

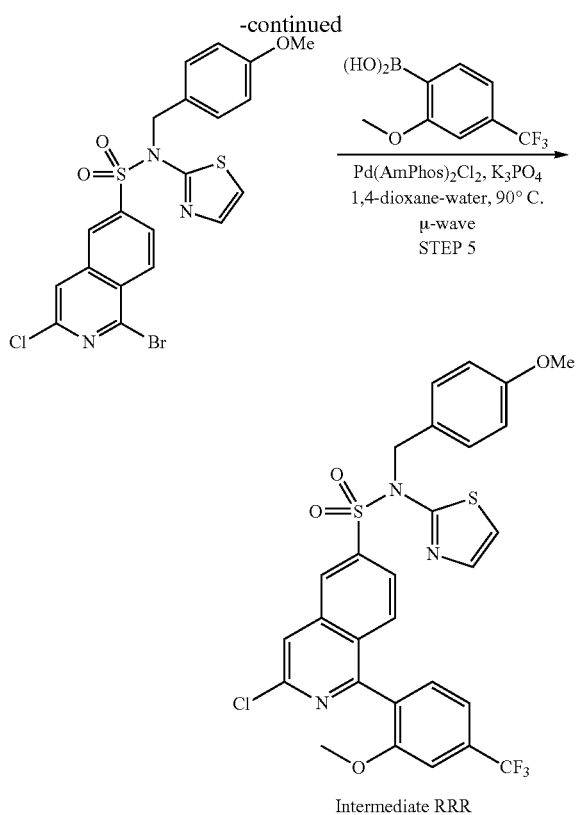

Intermediate RRR

STEP 1: 6-(BENZYLTHIO)-3-CHLOROISOQUINOLINE

A pressure vessel was charged with 6-bromo-3-chloroisoquinoline (1.3307 g, 5.49 mmol), Xantphos (0.159 g, 0.274 mmol), and Pd$_2$(dba)$_3$ (0.126 g, 0.137 mmol). The vessel was flushed with Ar (g), then 1,4-dioxane (10.97 ml), N,N-diisopropylethylamine (1.917 ml, 10.97 mmol), and benzyl mercaptan (0.682 ml, 5.76 mmol) were added in sequence. The vessel was sealed and heated in an 80° C. heating bath for 16 h. The mixture was cooled, diluted with EtOAc, and filtered through diatomaceous earth. The filtrate was concentrated, and the residue was purified by chromatography on silica gel (25-g silica gel loading column, 0 to 30% EtOAC/Heptane) to give 6-(benzylthio)-3-chloroisoquinoline (1.398 g, 4.89 mmol, 89% yield) as a light-yellow solid: $^1$H NMR (400 MHz, CHLOROFORM-d) δ ppm=8.94 (s, 1H), 7.81 (d, J=8.6 Hz, 1H), 7.55 (d, J=0.2 Hz, 1H), 7.50-7.39 (m, 4H), 7.38-7.28 (m, 3H), 4.30 (s, 2H); m/z (ESI) 286.2 (M+H)+.

STEP 2: PERFLUOROPHENYL 3-CHLOROISOQUINOLINE-6-SULFONATE

A round-bottom flask was charged with 6-(benzylthio)-3-chloroisoquinoline (1.363 g, 4.77 mmol), acetonitrile (44.9 ml), and acetic acid (1.683 ml) to give a suspension. The flask was sonicated for 10 min to give an opaque yellow mixture. Water (1.122 ml) was added, and the mixture became a thin suspension. The flask was cooled in an ice-water bath for 20 min, then 1,3-dichloro-5,5-dimethylimidazolidine-2,4-dione (1.879 g, 9.54 mmol) was added in one portion, resulting in the formation of a clear solution within 20 sec. After 15 min, 2,3,4,5,6-pentafluorophenol (1.756 g, 9.54 mmol) and triethylamine (2.66 ml, 19.08 mmol) were added in sequence. After another 25 min of stirring, the mixture was diluted with EtOAc (50 mL) and washed with water (2×50 ml), washed with brine, dried over sodium sulfate, filtered, and concentrated. The residue was dissolved in DCM and purified by chromatography on silica gel (40-g column, 25-g silica gel loading column, 0 to 30% EtOAc/Heptane) to give perfluorophenyl 3-chloroisoquinoline-6-sulfonate (1.69522 g, 4.14 mmol, 87% yield) as a clear oil contaminated with some pentafluorophenol: m/z (ESI) 286.2 (M+H)+.

STEP 3: PERFLUOROPHENYL 1-BROMO-3-CHLOROISOQUINOLINE-6-SULFONATE

A round-bottom flask was charged with perfluorophenyl 3-chloroisoquinoline-6-sulfonate (1.21 g, 2.95 mmol) and DCM (11.81 ml) to give a clear solution. Urea compound with hydrogen peroxide (1:1) (0.556 g, 5.91 mmol) was added, resulting in a suspension. The flask was cooled in an ice-water bath for 10 min, then 2,2,2-trifluoroacetic anhydride (0.834 ml, 5.91 mmol) was added over 20 s. The cooling bath was removed, the flask was sealed, and the mixture was stirred overnight for 15 h. An additional portion of TFAA (0.3 mL) was added, and the mixture was stirred for 5 h. The mixture was carefully quenched with saturated aq. sodium bicarbonate solution (50 mL), then diluted with water and extracted with DCM (3×). The cloudy organic layer was stirred over sodium sulfate for 2 min, which resulted in the formation of an orange solution. The mixture was filtered, and the filtrate was concentrated under a vacuum. The residue was dissolved in DCM (5 mL) to give an orange solution. Phosphoryl tribromide (1.693 g, 5.91 mmol) was added in one portion, and the mixture was stirred further at room temperature. After 1 h, the mixture was poured into ice, then diluted with water and DCM. When it had achieved room temperature, the layers were separated. The aq. layer was extracted with DCM (2×), and the combined organic extracts were dried over sodium sulfate, filtered, and concentrated. The aq. layer was further diluted with water and extracted with DCM (2×). The combined organic extracts were dried over sodium sulfate, filtered, and concentrated with residue from the first organic extraction. The combined residue was purified by chromatography on silica gel (40-g Redi-Sep Gold column, 25-g loading column, 0-40% EtOAc/Heptane) to give perfluorophenyl 1-bromo-3-chloroisoquinoline-6-sulfonate (0.482 g, 0.986 mmol, 33.4% yield) as a white solid: m/z (ESI) 488.0 (M+H)+.

STEP 4: 1-BROMO-3-CHLORO-N-(4-METHOXYBENZYL)-N-(THIAZOL-2-YL)ISOQUINOLINE-6-SULFONAMIDE

A round-bottom flask was charged with N-(4-methoxybenzyl)thiazol-2-amine (238 mg, 1.081 mmol) and THF (4912 μl) to give an opaque solution. The flask was cooled in a dry ice-acetone bath for 5 min to give a milky suspension, then lithium bis(trimethylsilyl)amide (1M in THF) (1081 μl, 1.081 mmol) was added. The flask was removed from the bath for 2 min to give a clear solution, then resubmerged. The mixture appeared to remain a solution. After 5 min, a solution of perfluorophenyl 1-bromo-3-chloroisoquinoline-6-sulfonate (480 mg, 0.982 mmol) in THF (3 mL with a 2 mL wash) was added drop wise. After 25 min, the mixture was diluted with saturated aq. ammonium chloride solution and warmed to room temperature. The mixture was diluted with water and extracted with EtOAc. The organic extract was dried over sodium sulfate, filtered, and concentrated. The residue was purified by chromatography on silica gel (0 to 40% EtOAc/

Heptane) to give 1-bromo-3-chloro-N-(4-methoxybenzyl)-N-(thiazol-2-yl)isoquinoline-6-sulfonamide (481 mg, 0.916 mmol, 93% yield) as a white foam: $^1$H NMR (400 MHz, CHLOROFORM-d) δ ppm=8.32 (d, J=9.0 Hz, 1H), 8.04 (d, J=1.8 Hz, 1H), 7.83 (dd, J=1.9, 9.0 Hz, 1H), 7.67 (s, 1H), 7.44 (d, J=3.6 Hz, 1H), 7.30 (d, J=8.8 Hz, 2H), 7.07 (d, J=3.5 Hz, 1H), 6.75-6.71 (m, 2H), 5.12 (s, 2H), 3.74 (s, 3H). m/z (ESI) 546.0 (M+H)+.

STEP 5: 3-CHLORO-1-(2-METHOXY-4-(TRIFLUOROMETHYL)PHENYL)-N-(4-METHOXYBENZYL)-N-(THIAZOL-2-YL)ISOQUINOLINE-6-SULFONAMIDE

This reaction was conducted in two separate vials. For the first reaction, a vial was charged with 1-bromo-3-chloro-N-(4-methoxybenzyl)-N-(thiazol-2-yl)isoquinoline-6-sulfonamide (57.11 mg, 0.109 mmol), (2-methoxy-4-(trifluoromethyl)phenyl)boronic acid (25.1 mg, 0.114 mmol), Pd(AmPhos)$_2$Cl$_2$ (3.85 mg, 5.44 µmol), potassium phosphate (69.3 mg, 0.326 mmol), 1,4-dioxane (408 µl), and water (136 µl). The vial was flushed with Ar (g), then sealed and heated in a microwave reactor for 15 min at 90° C. A second vial was charged with 1-bromo-3-chloro-N-(4-methoxybenzyl)-N-(thiazol-2-yl)isoquinoline-6-sulfonamide (422 mg, 0.804 mmol), (2-methoxy-4-(trifluoromethyl)phenyl)boronic acid (186 mg, 0.844 mmol), Pd(AmPhos)$_2$Cl$_2$ (28.5 mg, 0.040 mmol), potassium phosphate (512 mg, 2.412 mmol), 1,4-dioxane (3015 µl), and water (1005 µl). The vial was flushed with Ar (g), then sealed and heated in a Biotage Initiator microwave reactor for 15 min at 90° C. The reaction mixtures from each vial were combined, and the combined mixture was extracted with EtOAc (3×). The combined organic extracts were concentrated, and the residue was purified by chromatography on silica gel (40-g column, 20 to 60% EtOAc/Heptane) to give 3-chloro-1-(2-methoxy-4-(trifluoromethyl)phenyl)-N-(4-methoxybenzyl)-N-(thiazol-2-yl)isoquinoline-6-sulfonamide (Intermediate RRR; 500.9 mg, 0.808 mmol, 89% yield) as an off-white foam: $^1$H NMR (400 MHz, CHLOROFORM-d) δ ppm=8.15 (t, J=1.1 Hz, 1H), 7.77 (s, 1H), 7.68-7.65 (m, 2H), 7.50 (s, 1H), 7.44-7.38 (m, 2H), 7.30 (d, J=8.8 Hz, 2H), 7.27 (s, 1H), 7.04 (d, J=3.6 Hz, 1H), 6.73 (d, J=8.8 Hz, 2H), 5.11 (s, 2H), 3.76 (s, 3H), 3.73 (s, 3H); m/z (ESI) 620.2 (M+H)$^+$.

INTERMEDIATE SSS: 1-CHLORO-N-(THIAZOL-2-YL)-N-((2-(TRIMETHYLSILYL)ETHOXY)METHYL)ISOQUINOLINE-6-SULFONAMIDE

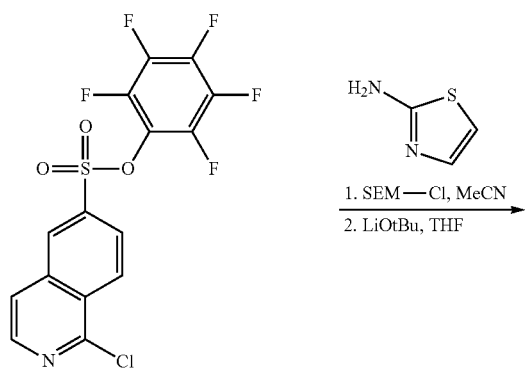

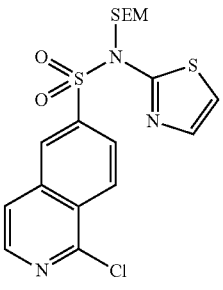

Intermediate SSS

A solution of thiazol-2-amine (0.134 g, 1.342 mmol) in 3 mL MeCN was treated with SEM-Cl (0.238 ml, 1.342 mmol) and was allowed to stir at room temperature for 30 minutes. LC/MS showed mostly product, so the reaction mixture was treated with perfluorophenyl 1-chloroisoquinoline-6-sulfonate (See, Example 73, Step 1; 0.500 g, 1.220 mmol) and was cooled to −10° C. Lithium tert-butoxide (1N in THF) (2.441 ml, 2.441 mmol) was added, and the reaction mixture was allowed to warm to room temperature overnight. The reaction mixture was poured into water and was extracted with DCM. The organics were dried over MgSO$_4$ and concentrated. Purification of the crude residue by silica gel column chromatography (0 to 100% EtOAc/heptane) gave 1-chloro-N-(thiazol-2-yl)-N-((2-(trimethylsilyl)ethoxy)methyl)isoquinoline-6-sulfonamide (0.220 g, 0.482 mmol, 39.5% yield). m/z (ESI) 456.0 (M+H)+;

INTERMEDIATE TTT: 2-(4-(DIFLUOROMETHYL)-2-METHOXYPHENYL)-4,4,5,5-TETRAMETHYL-1,3,2-DIOXABOROLANE

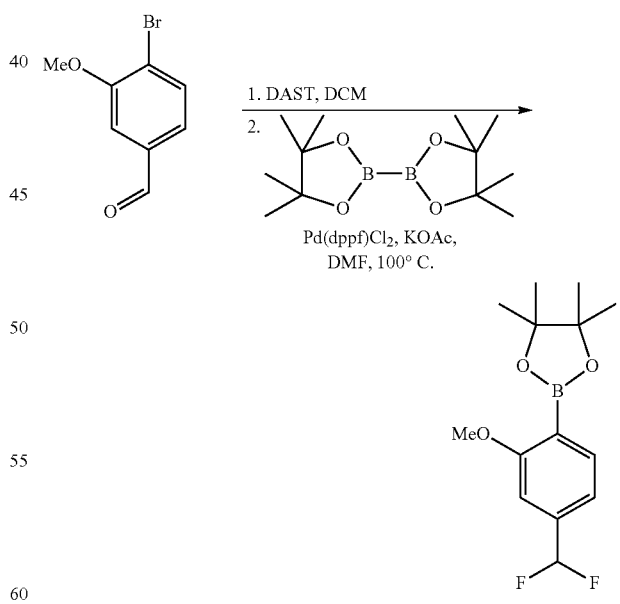

A solution of 4-bromo-3-methoxybenzaldehyde (Combi-Blocks, San Diego, Calif., 1.832 g, 8.52 mmol) in 25 mL of DCM was cooled to 0° C. and was treated with DAST (1.407 ml, 10.65 mmol) drop wise over 10 minutes. After stirring for one hour, little conversion was observed, so the reaction mixture was gently heated to reflux with a heat gun and was then allowed to stir at room temperature overnight. The reaction mixture was poured into saturated NaHCO₃ solution (aq) and was extracted with DCM. The organics were dried over MgSO₄ and concentrated. The crude residue was taken up in 20 mL of DMF, was treated with bis(pinacolato)diboron (3.25 g, 12.78 mmol), PdCl₂(dppf)-CH₂Cl₂ adduct (0.696 g, 0.852 mmol), and potassium acetate (3.34 g, 34.1 mmol) and was heated to 100° C. overnight. The reaction mixture was allowed to cool to room temperature and was diluted with DCM. The reaction mixture was filtered through a plug of diatomaceous earth and the filtrate was concentrated. Purification of the crude residue by silica gel column chromatography (0 to 50% EtOAc/heptane) gave 2-(4-(difluoromethyl)-2-methoxyphenyl)-4,4,5,5-tetramethyl-1,3,2-dioxaborolane (0.948 g, 3.34 mmol, 39.2% yield). m/z (ESI) 285.3 (M+Na)+;

INTERMEDIATE UUU: 2-(2-(METHOXYMETHYL)-4-(TRIFLUOROMETHYL)PHENYL)-4,4,5,5-TETRAMETHYL-1,3,2-DIOXABOROLANE

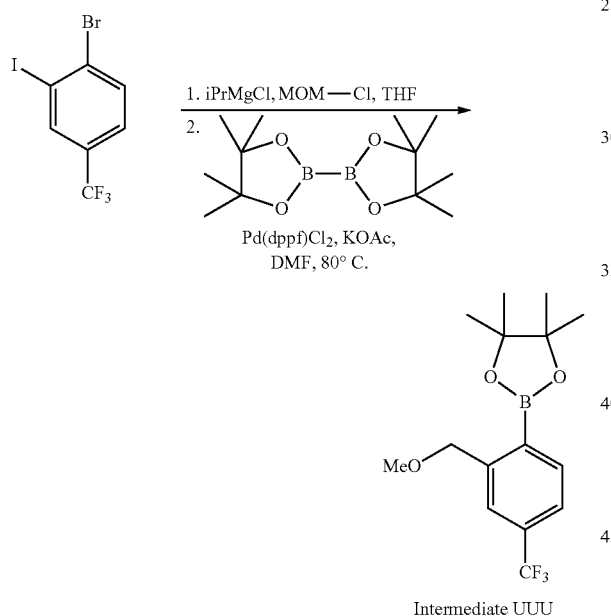

Intermediate UUU

A solution of 1-bromo-2-iodo-4-(trifluoromethyl)benzene (1.000 g, 2.85 mmol) in 3 mL of THF was treated with isopropylmagnesium chloride (1.567 ml, 3.13 mmol) and was allowed to stir for 10 minutes. MOM-Cl (0.260 ml, 3.42 mmol) was added, and the reaction mixture was heated to reflux for one hour. The reaction mixture was poured into 1N aqueous HCl and was extracted with DCM. The organics were dried over MgSO₄ and concentrated. The crude residue was taken up in 3 mL of DMF, treated with PdCl₂(dppf)-CH₂Cl₂ adduct (0.233 g, 0.285 mmol), bis(pinacolato)diboron (1.447 g, 5.70 mmol), and potassium acetate (1.119 g, 11.40 mmol) and was heated to 80° C. for 72 hours. The reaction mixture was diluted with DCM and was filtered through a plug of diatomaceous earth. The filtrate was concentrated then purified directly by silica gel column chromatography (0 to 50% EtOAc/heptane) yielding 2-(2-(methoxymethyl)-4-(trifluoromethyl)phenyl)-4,4,5,5-tetramethyl-1,3,2-dioxaborolane (0.741 g, 2.344 mmol, 82% yield). m/z (ESI) 317.1 (M+H)+

INTERMEDIATE VVV: 6-(benzylthio)-1-chloro-4-methoxyisoquinoline

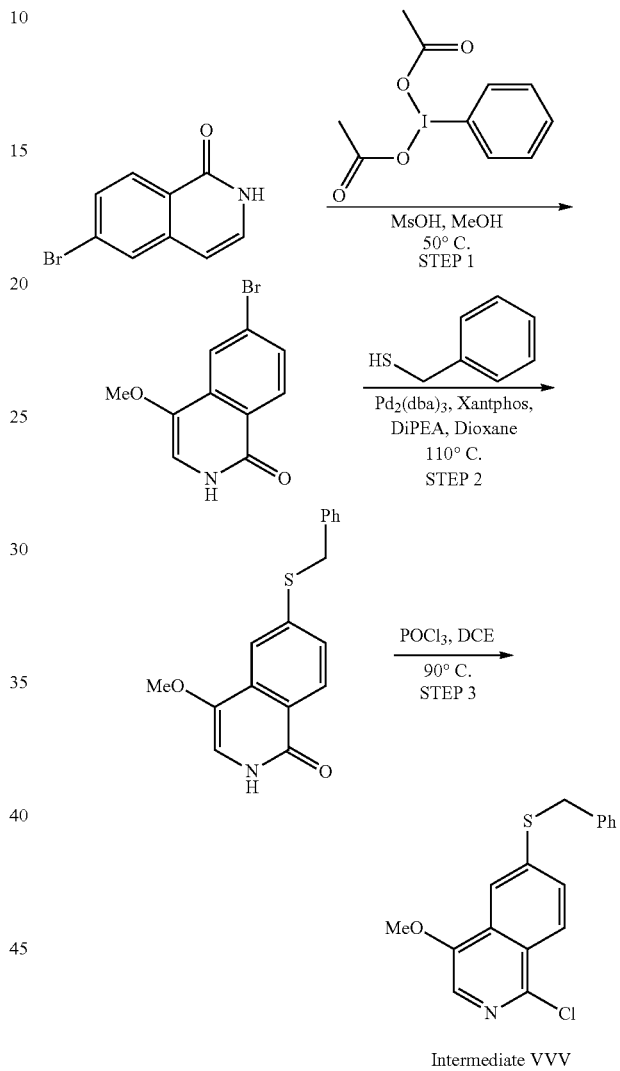

Intermediate VVV

STEP 1: 6-BROMO-4-METHOXYISOQUINOLIN-1(2H)-ONE

A round bottom flask was charged with 6-bromo-2h-isoquinolin-1-one (1.0 g, 4.46 mmol), methanol (8 mL), and methanesulfonic acid (0.290 ml, 4.46 mmol) and the flask was cooled to 0° C. In a separate flask, iodosobenzene diacetate (1.581 g, 4.91 mmol) was dissolved in methanol (8 mL) and added to the reaction. The reaction was warmed to room temperature and stirred for one hour, then heated to 50° C. and stirred overnight. The reaction was concentrated and triturated with isopropanol. The solution was stirred for 10 minutes, then filtered. The solids were washed with isopropanol and vacuum dried to afford 6-bromo-4-methoxyisoquinolin-1(2H)-one as a tan solid. (ESI) 254.1 (M+H

STEP 2: 6-(BENZYLTHIO)-4-METHOXYISOQUINOLIN-1(2H)-ONE

The title compound was prepared in an analogous manner to that of Intermediate PPP, Step 2, except that 6-bromo-4-methoxyisoquinolin-1(2H)-one was used instead of 6-bromo-4-fluoroisoquinolin-1(2H)-one to afford 6-(benzylthio)-4-methoxyisoquinolin-1(2H)-one as a brown solid. (ESI) 298.3 (M+H)+.

STEP 3: 6-(BENZYLTHIO)-1-CHLORO-4-METHOXYISOQUINOLINE

A vial was charged with 6-(benzylthio)-4-methoxyisoquinolin-1(2H)-one (0.933 g, 3.14 mmol) and DCE (15.69 ml). POCl$_3$ (0.585 ml, 6.27 mmol) was added and the reaction was stirred overnight at 90° C. The reaction was diluted with ethyl acetate and washed with water. The aqueous layer was extracted with ethyl acetate, and the combined organic layers were dried with sodium sulfate, filtered, and concentrated to afford crude 6-(benzylthio)-1-chloro-4-methoxyisoquinoline (Intermediate VVV) as a brown solid. (ESI) 316.3 (M+H)+.

INTERMEDIATE WWW: 1-CHLORO-N-(2,4-DIMETHOXYBENZYL)-4-HYDROXY-N-(THIAZOL-2-YL)ISOQUINOLINE-6-SULFONAMIDE

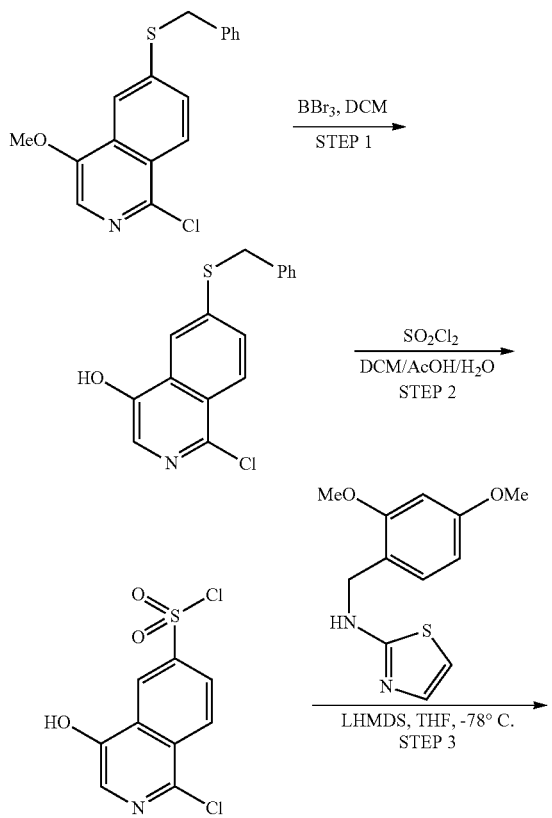

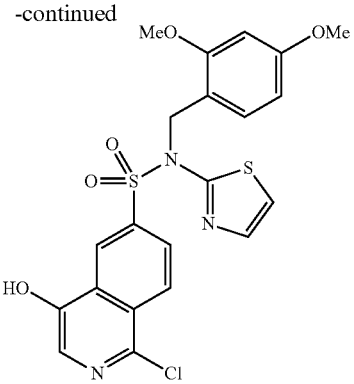

Intermediate WWW

STEP 1: 6-(BENZYLTHIO)-1-CHLOROISOQUINOLIN-4-OL 6-(benzylthio)-1-chloro-4-methoxyisoquinoline (Intermediate VVV; 0.400 g, 1.267 mmol) was dissolved in DCM (12.67 ml) and cooled to 0° C. Boron tribromide (0.487 ml, 5.06 mmol) was added and the reaction was stirred for 30 minutes, then warmed to room temperature and stirred overnight. The reaction was cooled to 0° C. and carefully quenched with saturated sodium bicarbonate solution. The reaction was diluted with ethyl acetate and the layers were separated. The aqueous layer was extracted with ethyl acetate, and the combined organic layers were dried with sodium sulfate, filtered, and concentrated to afford crude 6-(benzylthio)-1-chloroisoquinolin-4-ol as an orange solid. (ESI) 302.1 (M+H)+.

STEP 2: 1-CHLORO-4-HYDROXYISOQUINOLINE-6-SULFONYL CHLORIDE

A round-bottom flask was charged with 6-(benzylthio)-1-chloroisoquinolin-4-ol (0.280 g, 0.928 mmol), DCM (8.84 ml), acetic acid (0.221 ml), and water (0.221 ml) to give a thin suspension. The flask was cooled in an ice-bath for 10 min, then sulfuryl chloride (0.226 ml, 2.78 mmol) was added in one portion, leading to a solution. The reaction was stirred for 30 minutes, then warmed to room temperature and stirred for one hour. The reaction was concentrated and purified via column chromatography (40 g silica gel column, gradient elution 0 to 100% EtOAc:Heptane) to afford 1-chloro-4-hydroxyisoquinoline-6-sulfonyl chloride (as a light pink solid. (ESI) 280.1 (M+H)+.

STEP 3: 1-CHLORO-N-(2,4-DIMETHOXYBENZYL)-4-HYDROXY-N-(THIAZOL-2-YL)ISOQUINOLINE-6-SULFONAMIDE

The title compound was prepared in an analogous manner to that of Intermediate PPP, Step 5, except that 1-chloro-4-hydroxyisoquinoline-6-sulfonyl chloride was used instead of perfluorophenyl 1-chloro-4-fluoroisoquinoline-6-sulfonate. The final compound was purified via column chromatography (40 g silica gel column, gradient elution 0 to 50% EtOAc: Heptane) to afford 1-chloro-N-(2,4-dimethoxybenzyl)-4-hydroxy-N-(thiazol-2-yl)isoquinoline-6-sulfonamide as a yellow solid. (ESI) 492.2 (M+H)+.

INTERMEDIATE XXX: perfluorophenyl 1-chloro-4-cyanoisoquinoline-6-sulfonate

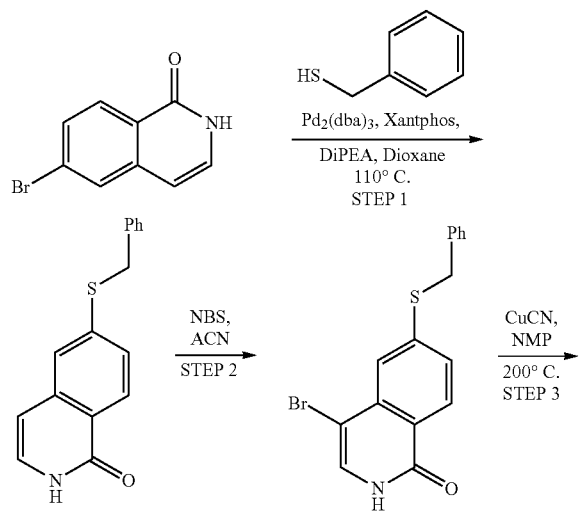

Intermediate XXX

STEP 1: 6-(BENZYLTHIO)ISOQUINOLIN-1(2H)-ONE

The title compound was prepared in an analogous manner to that of Intermediate PPP, Step 2, except that 6-bromoisoquinolin-1(2H)-one was used instead of 6-bromo-4-fluoroisoquinolin-1(2H)-one to afford 6-(benzylthio)isoquinolin-1(2H)-one as a dark yellow solid. (ESI) 268.3 (M+H)+.

STEP 2: 6-(BENZYLTHIO)-4-BROMOISOQUINOLIN-1(2H)-ONE

A round bottom flask was charged with 6-(benzylthio)isoquinolin-1(2H)-one (1.1 g, 4.11 mmol), NBS (0.732 g, 4.11 mmol), and acetonitrile (20.57 ml). The reaction was stirred overnight at room temperature. The reaction was diluted with ethyl acetate and washed with water. The aqueous layer was extracted with ethyl acetate, and the combined organic layers were washed with brine, dried with sodium sulfate, filtered, and concentrated to afford a brown solid. The solid was triturated in DCM and filtered. The solids were isolated to afford 6-(benzylthio)-4-bromoisoquinolin-1(2H)-one as a silver solid. m/z (ESI) 346.1 (M+H)+.

STEP 3: 6-(benzylthio)-1-oxo-1,2-dihydroisoquinoline-4-carbonitrile

A vial was charged with 6-(benzylthio)-4-bromoisoquinolin-1(2H)-one (0.583 g, 1.684 mmol), copper (i) cyanide (0.052 ml, 1.684 mmol), and NMP (8.42 ml). The reaction was heated to 200° C. and stirred for four hours. The reaction was diluted with ethyl acetate and washed with water. The aqueous layer was extracted with ethyl acetate, and the combined organic layers were dried with sodium sulfate, filtered, and concentrated. The material was purified via column chromatography (40 g silica gel column, gradient elution 0 to 10% MeOH:EtOAc) to afford 6-(benzylthio)-1-oxo-1,2-dihydroisoquinoline-4-carbonitrile as a brown solid. m/z (ESI) 293.1 (M+H)+.

STEP 4: 6-(BENZYLTHIO)-1-CHLOROISOQUINOLINE-4-CARBONITRILE

A vial was charged with 6-(benzylthio)-1-oxo-1,2-dihydroisoquinoline-4-carbonitrile (0.492 g, 1.683 mmol) and DCE (8.41 ml). POCl$_3$ (0.314 ml, 3.37 mmol) was added and the reaction was stirred overnight at 90° C. The reaction was diluted with ethyl acetate and washed with water. The aqueous layer was extracted with ethyl acetate, and the combined organic layers were dried with sodium sulfate, filtered, and concentrated. The material was purified via column chromatography (40 g silica gel column, gradient elution 0 to 100% EtOAc:Heptane) to afford 6-(benzylthio)-1-chloroisoquinoline-4-carbonitrile as a brown solid. m/z (ESI) 311.1 (M+H)+.

STEP 5: PERFLUOROPHENYL 1-CHLORO-4-CYANOISOQUINOLINE-6-SULFONATE

The titled compound was prepared in an analogous manner to that of Intermediate PPP, Step 4 except that 6-(benzylthio)-1-chloroisoquinoline-4-carbonitrile was used instead of 6-(benzylthio)-1-chloro-4-fluoroisoquinoline. The product was purified via column chromatography (40 g silica gel column, gradient elution 0 to 50% EtOAc:Heptane) to afford perfluorophenyl 1-chloro-4-cyanoisoquinoline-6-sulfonate as a clear oil. m/z (ESI) 436.1 (M+H)+.

INTERMEDIATE YYY: 1-CHLORO-4-CYANO-N-(2,4-DIMETHOXYBENZYL)-N-(THIAZOL-2-YL)ISOQUINOLINE-6-SULFONAMIDE

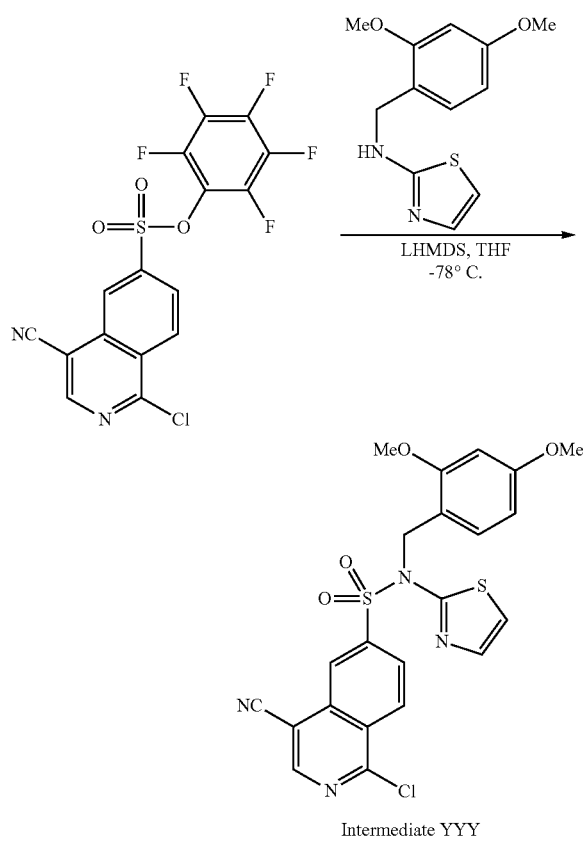

Intermediate YYY

Intermediate YYY was synthesized in a manner similar to Intermediate PPP, Step 5, except that perfluorophenyl 1-chloro-4-cyanoisoquinoline-6-sulfonate (Intermediate XXX) was used instead of perfluorophenyl 1-chloro-4-fluoroisoquinoline-6-sulfonate (from Intermediate PPP, step 4). The final compound was purified via column chromatography (40 g silica gel column, gradient elution 0 to 50% EtOAc: Heptane) to afford 1-chloro-4-cyano-N-(2,4-dimethoxybenzyl)-N-(thiazol-2-yl)isoquinoline-6-sulfonamide as a bright yellow solid. (ESI) 501.2 (M+H)+.

INTERMEDIATE ZZZ: PERFLUOROPHENYL 1-(PYRROLIDIN-2-YL)ISOQUINOLINE-6-SULFONATE 2,2,2-TRIFLUOROACETATE

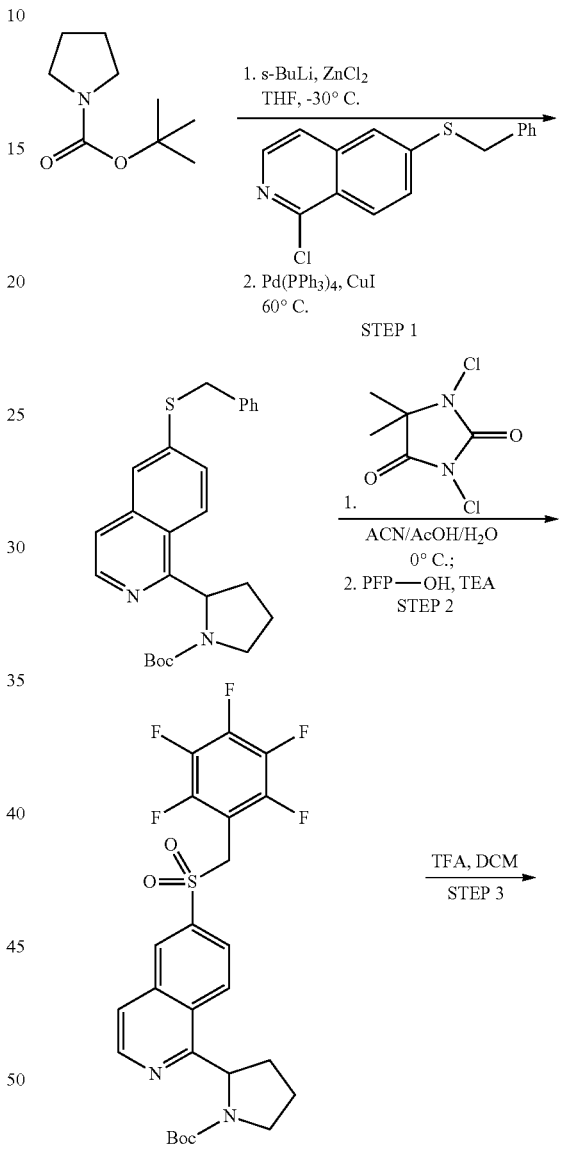

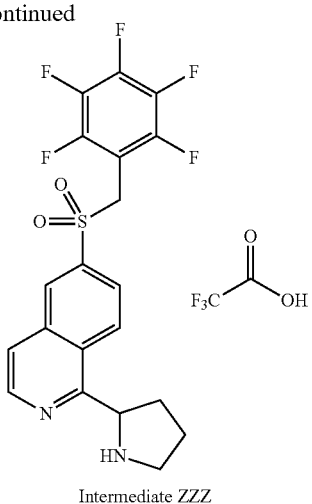

Intermediate ZZZ

STEP 1: TERT-BUTYL 2-(6-(BENZYLTHIO)ISOQUINOLIN-1-YL)PYRROLIDINE-1-CARBOXYLATE

A 100-mL round-bottom flask was charged with tert-butyl 1-pyrrolidinecarboxylate (1.625 ml, 9.27 mmol) and THF (23.33 ml) to give a clear solution. The flask was flushed with Ar (g), then cooled in a −30° C. dry ice-acetone bath for 10 min. Sec-butyllithium (1.4 M in cyclohexane) (8.75 ml, 12.25 mmol) was added drop wise over 5 min. The resulting mixture was stirred for 10 minutes at −30° C., then zinc chloride (1.0 M in diethyl ether) (7.00 ml, 7.00 mmol) was added drop wise. The reaction was stirred for 5 minutes, then the cooling bath was removed. After 25 min, a solid mixture of 6-(benzylthio)-1-chloroisoquinoline (from Intermediate LLL, step 1; 1.0 g, 3.50 mmol), Pd(Ph₃P)₄ (0.809 g, 0.700 mmol), and copper(i) iodide (0.333 g, 1.750 mmol) was added in one portion. The reaction was capped and stirred at 60° C. for one hour. The reaction was filtered through a pad of diatomaceous earth, washing thoroughly with ethyl acetate. The filtrate was concentrated and purified via column chromatography (80 g silica gel column, gradient elution 0 to 100% EtOAc:Heptane followed by a 20% MeOH/EtOAc flush) to afford tert-butyl 2-(6-(benzylthio)isoquinolin-1-yl)pyrrolidine-1-carboxylate as a yellow solid. (ESI) 421.3 (M+H)⁺.

STEP 2: TERT-BUTYL 2-(6-((PERFLUOROPHENOXY)SULFONYL)ISOQUINOLIN-1-YL)PYRROLIDINE-1-CARBOXYLATE

A round-bottom flask was charged with tert-butyl 2-(6-(benzylthio)isoquinolin-1-yl)pyrrolidine-1-carboxylate (1.41 g, 3.35 mmol), acetonitrile (31.6 ml), acetic acid (1.183 ml), and water (0.789 ml). The flask was cooled in an ice-bath for 10 min, then 1,3-dichloro-5,5-dimethylimidazolidine-2,4-dione (1.321 g, 6.71 mmol) was added in one portion and the reaction was stirred for 30 minutes. 2,3,4,5,6-pentafluorophenol (0.527 ml, 5.03 mmol) was added, then triethylamine (1.869 ml, 13.41 mmol) was added drop wise. The mixture was stirred for several minutes, then the cooling bath was removed and the reaction was stirred for 30 minutes. The reaction was concentrated and purified via silica gel column chromatography, 80 g, gradient elution 0 to 50% EtOAc: Heptane) to afford tert-butyl 2-(6-((perfluorophenoxy)sulfonyl)isoquinolin-1-yl)pyrrolidine-1-carboxylate as a white solid. LC-MS showed a small impurity present, but the material was carried forward without further purification. (ESI) 545.1 (M+H)⁺.

STEP 3: PERFLUOROPHENYL 1-(PYRROLIDIN-2-YL)ISOQUINOLINE-6-SULFONATE 2,2,2-TRIFLUOROACETATE

A round-bottom flask was charged with tert-butyl 2-(6-((perfluorophenoxy)sulfonyl)isoquinolin-1-yl)pyrrolidine-1-carboxylate (1.02 g, 1.873 mmol) and DCM (5.0 mL) to give a light yellow solution. TFA (1.443 ml, 18.73 mmol) was added in one portion to give a yellow solution. The reaction was stirred for two hours. The reaction was concentrated, dissolved in diethyl ether, and sonicated until a fine white solid triturated out of solution. The solids were filtered, washed with diethyl ether, and vacuum dried overnight to afford perfluorophenyl 1-(pyrrolidin-2-yl)isoquinoline-6-sulfonate 2,2,2-trifluoroacetate as a white solid. (ESI) 445.3 (M+H)⁺.

INTERMEDIATE AAAA: 1-CHLORO-N-(2,4-DIMETHOXYBENZYL)-N-(THIAZOL-2-YL)PHTHALAZINE-6-SULFONAMIDE

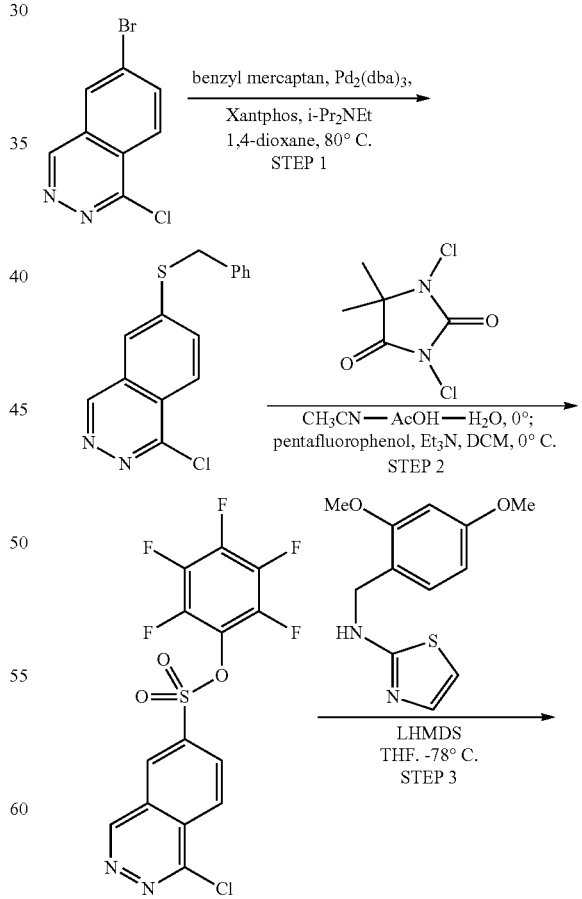

189

-continued

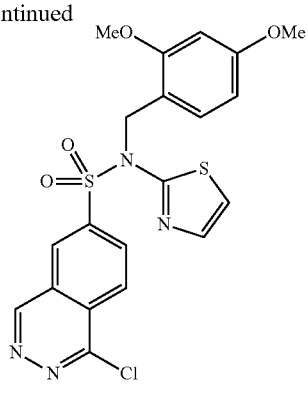

Intermediate AAAA

STEP 1: 6-(BENZYLTHIO)-1-CHLOROPHTHALAZINE

A two-neck round-bottom flask was charged with 6-bromo-1-chlorophthalazine (Pharmablock, Nanjing Hi-Tech Zone, China, 4.44 g, 18.24 mmol), Xantphos (0.528 g, 0.912 mmol), and $Pd_2(dba)_3$ (0.417 g, 0.456 mmol). 1,4-dioxane (36.5 ml) and N,N-diisopropylethylamine (6.37 ml, 36.5 mmol) were added. The flask was fitted with a reflux condenser and placed in an 80° C. heating bath. After 5 min, benzyl mercaptan (2.265 ml, 19.15 mmol) was added drop wise. After 20 min. the mixture was cooled, then concentrated under a vacuum. EtOAc (about 25 mL) was added to the residue, and the flask was rotated on the rotovap in a 40° C. bath for 1.5 h. This removed most of the solid from the sides of the flask. The flask was sonicated for 30 s, then the mixture was concentrated under a vacuum. The residue was taken up in EtOAc to form a thick slurry. The flask was sonicated for 30 s, then the mixture was filtered. The collected solid was washed with several large volumes of EtOAc (until the filtrates were essentially colorless). The filtrate was concentrated, and the residue was purified by chromatography on silica gel (80-g column with a 25-g silica gel loading column, 0 to 50% EtOAc/Heptane, then 50 to 100% EtOAc/Heptane). The resulting solid was taken up in heptane, sonicated for 30 s, then filtered. The collected solid was washed with heptane (3×, which removed some of the yellow color), and dried under a stream of N2 (g) for 20 min to give 6-(benzylthio)-1-chlorophthalazine (3.975 g, 13.86 mmol, 76% yield) as a light-orange powder: $^1$H NMR (400 MHz, CHLOROFORM-d) δ ppm=9.28 (d, J=0.7 Hz, 1H), 8.14 (d, J=8.8 Hz, 1H), 7.82 (dd, J=1.9, 8.8 Hz, 1H), 7.69 (d, J=1.8 Hz, 1H), 7.45-7.28 (m, 5H), 4.35 (s, 2H); m/z (ESI) 287.2 $(M+H)^+$.

STEP 2: PERFLUOROPHENYL 1-CHLOROPHTHALAZINE-6-SULFONATE

A round-bottom flask was charged with 6-(benzylthio)-1-chlorophthalazine (2.20 g, 7.67 mmol), acetonitrile (72.2 ml), acetic acid (2.71 ml), and water (1.805 ml) to give a clear, orange solution. The flask was cooling in an ice-bath for 10 min, then 1,3-dichloro-5,5-dimethylimidazolidine-2,4-dione (3.02 g, 15.34 mmol) was added in one portion. After 30 min, 2,3,4,5,6-pentafluorophenol (2.82 g, 15.34 mmol) and triethylamine (4.28 ml, 30.7 mmol) were added in sequence. After 30 min, the mixture was diluted with EtOAc (100 mL), washed with water (50 ml), washed with 0.5 N aq. HCl (100 mL), washed with brine, and dried over sodium sulfate. The residue was dissolved in DCM and loaded onto a chilled 25-g silica gel loading column. The column was dried with a vacuum hose, then eluted onto a pre-equilibrated 80-g column with 0 to 50% EtOAc/Heptane to give perfluorophenyl 1-chlorophthalazine-6-sulfonate (2.134 g, 5.20 mmol, 67.7% yield) as a yellow solid: $^1$H NMR (400 MHz, CHLOROFORM-d) δ ppm=9.64 (d, J=0.7 Hz, 1H), 8.72 (d, J=1.8 Hz, 1H), 8.65-8.59 (m, 1H), 8.56-8.50 (m, 1H); m/z (ESI) 411.2 $(M+H)^+$.

STEP 3: 1-CHLORO-N-(2,4-DIMETHOXYBENZYL)-N-(THIAZOL-2-YL)PHTHALAZINE-6-SULFONAMIDE

A round-bottom flask was charged with N-(2,4-dimethoxybenzyl)thiazol-2-amine (181 mg, 0.723 mmol) and THF (3287 μl) to give a clear solution. The flask was cooled in a dry ice-acetone bath for 5 min, then lithium bis(trimethylsilyl)amide (1M in THF) (723 μl, 0.723 mmol) was added. The flask was removed from the bath for 2 min, then resubmerged. After 5 min, a solution of perfluorophenyl 1-chlorophthalazine-6-sulfonate (270 mg, 0.657 mmol) in THF (0.7 mL with a 0.3 mL wash) was added drop wise. After 5 min, the dry ice-acetone bath was swapped out for an ice-water bath. After 1 h, the mixture was diluted with saturated aq ammonium chloride solution and EtOAc. The layers were separated, and the aq. layer was washed with brine, dried over sodium sulfate, filtered, and concentrated. The residue was purified by chromatography on silica gel (40-g column, 20 to 70% EtOAc/Heptane) to give 1-chloro-N-(2,4-dimethoxybenzyl)-N-(thiazol-2-yl)phthalazine-6-sulfonamide (112 mg, 0.235 mmol, 35.7% yield) as a cream-colored solid: m/z (ESI) 477.2 $(M+H)^+$.

INTERMEDIATE BBBB: 1-(2-METHOXY-4-(TRIFLUOROMETHYL)PHENYL)PHTHALAZINE-6-SULFONYL CHLORIDE

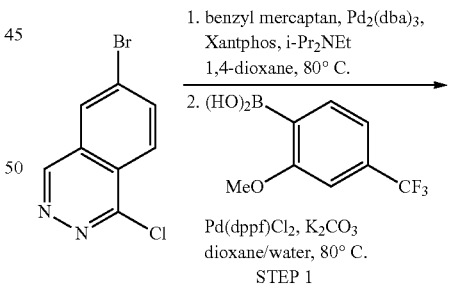

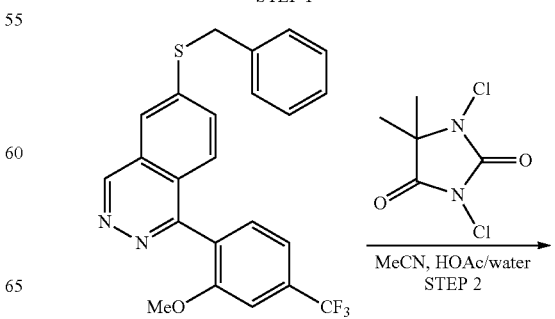

-continued

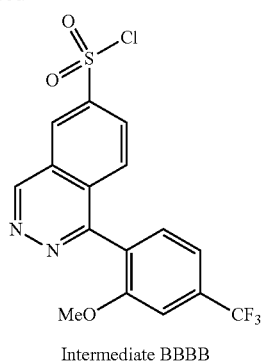

Intermediate BBBB

STEP 1: 6-(BENZYLTHIO)-1-(2-METHOXY-4-(TRIFLUOROMETHYL)PHENYL)PHTHALAZINE

A solution of 6-bromo-1-chlorophthalazine (0.500 g, 2.053 mmol), Pd$_2$(dba)$_3$ (0.047 g, 0.051 mmol), Xantphos (0.059 g, 0.103 mmol), and n,n-diisopropylethylamine (1.076 ml, 6.16 mmol) in 6 mL of dioxane was heated to 60° C. and was treated with benzyl mercaptan (0.243 ml, 2.053 mmol) drop wise. After stirring for one hour, LC/MS showed product and bis coupled product. (2-methoxy-4-(trifluoromethyl)phenyl)boronic acid (0.407 g, 1.848 mmol), potassium carbonate (1.135 g, 8.21 mmol), PdCl$_2$(dppf)-CH$_2$Cl$_2$ adduct (0.168 g, 0.205 mmol), and 2 mL of water were added and the reaction mixture was heated to 80° C. overnight. LC/MS showed mostly product, so the reaction mixture was allowed to cool to room temperature. The aqueous layer was removed, and the organics were concentrated. Purification of the crude residue by silica gel column chromatography (0 to 100% EtOAc/heptane) gave 6-(benzylthio)-1-(2-methoxy-4-(trifluoromethyl)phenyl)phthalazine (0.340 g, 0.797 mmol, 38.8% yield). m/z (ESI) 427.2 (M+H)+

STEP 2: 1-(2-METHOXY-4-(TRIFLUOROMETHYL)PHENYL)PHTHALAZINE-6-SULFONYL CHLORIDE

A solution of 6-(benzylthio)-1-(2-methoxy-4-(trifluoromethyl)phenyl)phthalazine 2 (0.340 g, 0.797 mmol) in 20 mL of MeCN, 0.75 mL of acetic acid, and 0.5 mL of water (20/0.75/0.5 ratio) was cooled to 0° C. and was treated with 1,3-dichloro-5,5-dimethylimidazolidine-2,4-dione (0.314 g, 1.595 mmol). After stirring for one hour, LC/MS showed mostly product, so the reaction mixture was diluted with DCM and was treated with MgSO$_4$. After stirring for 10 minutes, the reaction mixture was filtered and concentrated. Purification of the crude residue by silica gel column chromatography (0 to 40% EtOAc/heptane) gave 1-(2-methoxy-4-(trifluoromethyl)phenyl)phthalazine-6-sulfonyl chloride (0.200 g, 0.497 mmol, 62.3% yield).

INTERMEDIATE CCCC: 1-CHLORO-N-(5-FLUOROTHIAZOL-2-YL)-N-(4-METHOXYBENZYL) PHTHALAZINE-6-SULFONAMIDE

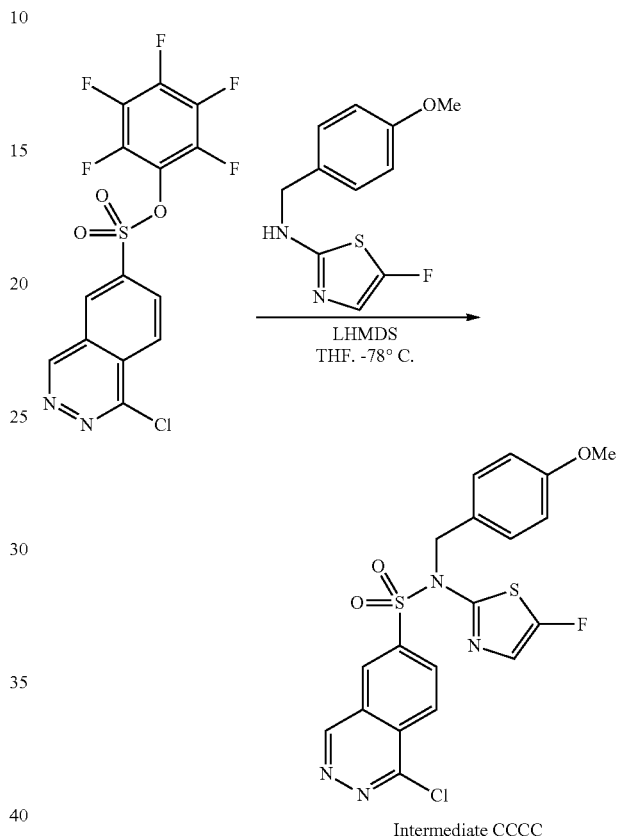

Intermediate CCCC

A round-bottom flask was charged with 5-fluoro-N-(4-methoxybenzyl)thiazol-2-amine (Intermediate MMM) (184 mg, 0.774 mmol) and THF (1 mL) to give a clear, light-orange solution. The flask was cooled in a dry ice-acetone bath for 5 min to give a suspension. Lithium bis(trimethylsilyl)amide (1M in THF) (774 μl, 0.774 mmol) was added drop wise to give a clay-colored suspension. The mixture was stirred for 15 min, after which time it was a solution. A solution of perfluorophenyl 1-chlorophthalazine-6-sulfonate (from Intermediate AAAA, Step 2; 265 mg, 0.645 mmol) in THF (1 mL with a 0.25 mL syringe/vial wash) was added drop wise. After 45 min, the mixture was diluted with saturated aq ammonium chloride and extracted with EtOAc. The organic extract was dried over sodium sulfate, filtered, and concentrated. The residue was purified by chromatography on silica gel (40-g column, 20 to 70% EtOAc/Heptane) to give 1-chloro-N-(5-fluorothiazol-2-yl)-N-(4-methoxybenzyl)phthalazine-6-sulfonamide (129 mg, 0.277 mmol, 43.0% yield) as a cream-colored solid: m/z (ESI) 465.2 (M+H)+.

INTERMEDIATE DDDD: 4-(2-METHOXY-4-(TRI-FLUOROMETHYL)PHENYL)QUINAZOLINE-7-SULFONYL CHLORIDE

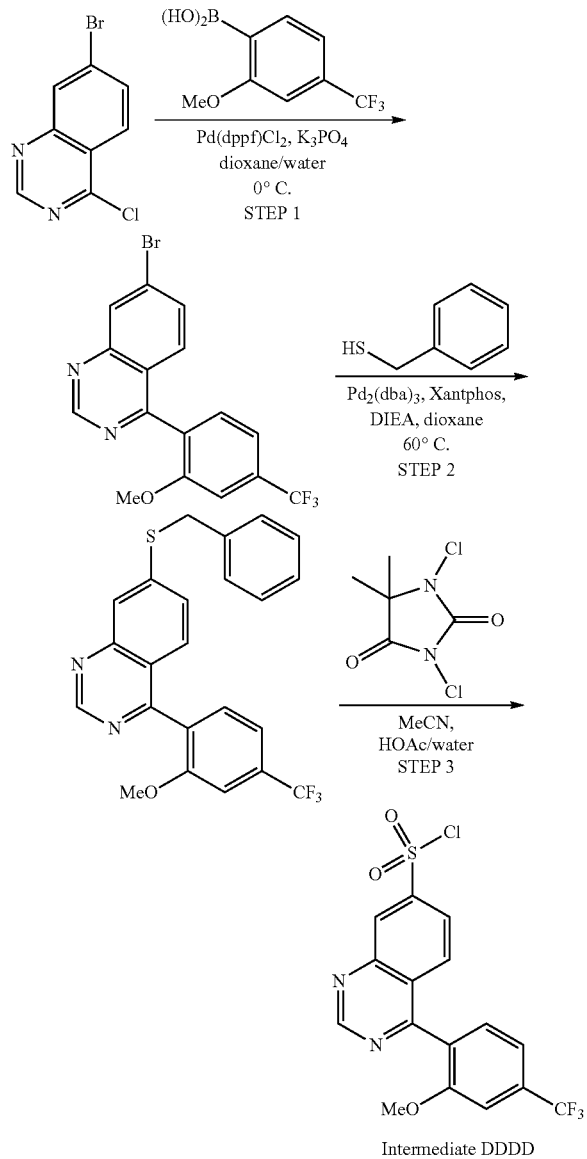

Intermediate DDDD

STEP 1: 7-BROMO-4-(2-METHOXY-4-(TRIFLUO-ROMETHYL)PHENYL)QUINAZOLINE

A solution of PdCl$_2$(dppf)-CH$_2$Cl$_2$ adduct (0.402 g, 0.493 mmol), 2-methoxy-4-(trifluoromethyl)phenyl)boronic acid (Combi-Blocks, San Diego, Calif.; 3.97 g, 18.07 mmol), 7-bromo-4-chloroquinazoline (Synnovator, Inc., Raleigh, N.C., 4.000 g, 16.43 mmol), and potassium phosphate (13.95 g, 65.7 mmol) in 33 mL of dioxane was cooled to 0° C., was treated with 11 mL of water and was allowed to stir for 30 minute then room temperature overnight. The reaction mixture was diluted with DCM and filtered through a plug of diatomaceous earth. The aqueous layer was removed and the organics concentrated to yield crude material which was carried forward without further purification. m/z (ESI) 384.9 (M+H)+

STEP 2: 7-(BENZYLTHIO)-4-(2-METHOXY-4-(TRIFLUOROMETHYL)PHENYL)QUINAZO-LINE

Crude 7-bromo-4-(2-methoxy-4-(trifluoromethyl)phenyl) quinazoline was dissolved in 33 mL of dioxane, was treated with Pd$_2$(dba)$_3$ (0.376 g, 0.411 mmol), Xantphos (0.475 g, 0.821 mmol), and n,n-diisopropylethylamine (8.61 ml, 49.3 mmol), and was heated to 60° C. Benzyl mercaptan (1.943 ml, 16.43 mmol) was added, and the reaction mixture was allowed to stir for one hour at 60° C. The reaction mixture was concentrated and was purified by silica gel column chromatography (0 to 75% EtOAc/heptane) to yield 7-(benzylthio)-4-(2-methoxy-4-(trifluoromethyl)phenyl)quinazoline (4.616 g, 10.82 mmol, 65.9% yield) with minor impurities. m/z (ESI) 427.2 (M+H)+.

STEP 3: 4-(2-METHOXY-4-(TRIFLUOROM-ETHYL)PHENYL)QUINAZOLINE-7-SULFONYL CHLORIDE

A solution of 7-(benzylthio)-4-(2-methoxy-4-(trifluoromethyl)phenyl)quinazoline (4.560 g, 10.69 mmol) in 44 mL of DCM and 0.44 mL of a 3:2 HOAc/water solution was cooled to 0° C. and was treated with 1,3-dichloro-5,5-dimethylimidazolidine-2,4-dione (4.21 g, 21.39 mmol). After stirring for 15 minutes, the reaction mixture was diluted with water. The layers were separated, and the organics were dried over MgSO$_4$ and concentrated. Purification of the crude residue by silica gel column chromatography gave 4-(2-methoxy-4-(trifluoromethyl)phenyl)quinazoline-7-sulfonyl chloride (2.475 g, 6.14 mmol, 57.5% yield) as a yellow solid. m/z (ESI) 402.9 (M+H)+.

INTERMEDIATE EEEE: 4-(4-(DIFLUOROM-ETHYL)-2-METHOXYPHENYL)QUINAZOLINE-7-SULFONYL CHLORIDE

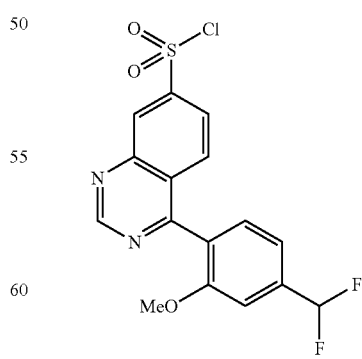

Intermediate EEEE was synthesized in a similar manner to Intermediate DDDD, using 2-(4-(difluoromethyl)-2-methoxyphenyl)-4,4,5,5-tetramethyl-1,3,2-dioxaborolane instead of 2-methoxy-4-(trifluoromethyl)phenyl)boronic acid in the first step. m/z (ESI) 385.2

INTERMEDIATE FFFF:
4-(4-CHLORO-2-METHOXYPHENYL)QUINAZOLINE-7-SULFONYL CHLORIDE

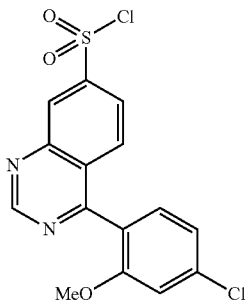 [SMILES: COc1cc(Cl)ccc1-c1ncnc2cc(S(=O)(=O)Cl)ccc12]

Intermediate FFFF was synthesized in a similar manner to Intermediate DDDD, using (4-chloro-2-methoxyphenyl)boronic acid instead of 2-methoxy-4-(trifluoromethyl)phenyl)boronic acid in the first step. m/z (ESI) 371.1

INTERMEDIATE GGGG: 3-METHOXY-4-(4,4,5,5-TETRAMETHYL-1,3,2-DIOXABOROLAN-2-YL)BENZONITRILE

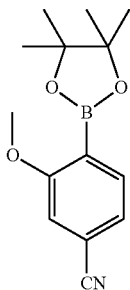 [SMILES: COc1cc(C#N)ccc1B1OC(C)(C)C(C)(C)O1]

A solution of 4-bromo-3-methoxybenzonitrile (Combi-Blocks, San Diego, Calif., 2.500 g, 11.79 mmol) in 100 mL of diethyl ether was cooled to −78° C. and was treated with n-butyllithium (4.95 ml, 12.38 mmol). After stirring for 10 minutes, 2-isopropoxy-4,4,5,5-tetramethyl-1,3,2-dioxaborolane (3.07 ml, 16.51 mmol) was added, and the cooling bath was removed. After stirring for an additional 2 hours, LC/MS showed mostly product, so the reaction mixture was quenched with saturated NH$_4$Cl solution. After stirring for 20 minutes, the reaction mixture was poured into a separatory funnel charged with EtOAc. The organic layer was separated, dried over MgSO4 and concentrated. Purification of the crude residue by silica gel column chromatography (0 to 100% EtOAc/heptane) gave 3-methoxy-4-(4,4,5,5-tetramethyl-1,3, 2-dioxaborolan-2-yl)benzonitrile (1.62 g, 6.25 mmol, 53.0% yield) with minor impurities. m/z (ESI) 260.1 (M+H)+

INTERMEDIATE HHHH:
4-(4-CYANO-2-METHOXYPHENYL)QUINAZOLINE-7-SULFONYL CHLORIDE

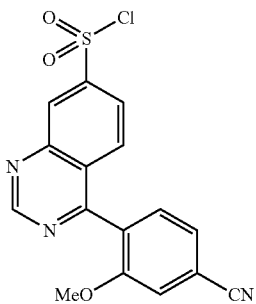 [SMILES: COc1cc(C#N)ccc1-c1ncnc2cc(S(=O)(=O)Cl)ccc12]

Intermediate HHHH was synthesized in a similar manner to Intermediate DDDD, using 3-methoxy-4-(4,4,5,5-tetramethyl-1,3,2-dioxaborolan-2-yl)benzonitrile (Intermediate GGGG) instead of 2-methoxy-4-(trifluoromethyl)phenyl)boronic acid in the first step. m/z (ESI) 360.0

INTERMEDIATE IIII: 2-(5-CHLORO-4-(DIFLUOROMETHYL)-2-METHOXYPHENYL)-4,4,5,5-TETRAMETHYL-1,3,2-DIOXABOROLANE

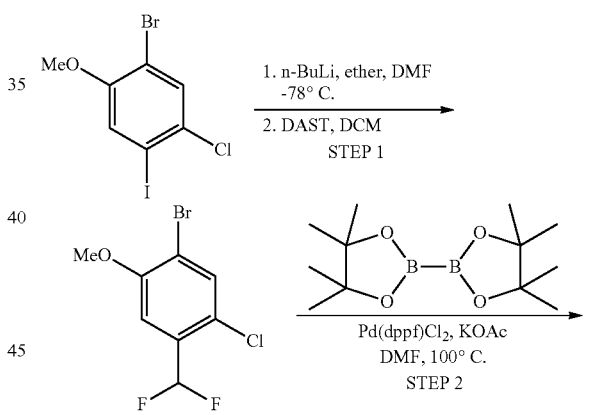

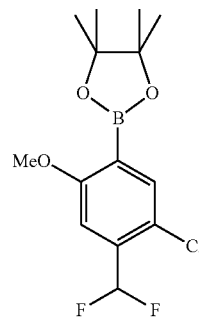

Intermediate IIII

STEP 1: 1-BROMO-5-CHLORO-4-(DIFLUOROMETHYL)-2-METHOXYBENZENE

A solution of 2-bromo-4-chloro-5-iodoanisole (3.50 g, 10.08 mmol) in 40 mL of diethyl ether was cooled to −78° C.

and was treated with n-butyllithium (2.5M in hexanes; 4.23 ml, 10.58 mmol). After stirring for 10 minutes, the reaction mixture was quenched with DMF (1.560 ml, 20.15 mmol) and the cooling bath was removed. The reaction mixture was quenched with MeOH and saturated aqueous NH$_4$Cl solution. The reaction mixture was poured into water and extracted with DCM. The organics were dried over MgSO$_4$ and concentrated. The crude residue was dissolved in 10 mL of DCM and was treated with DAST (1.464 ml, 11.08 mmol). After stirring overnight, the reaction mixture was poured into saturated NaHCO$_3$ solution (aq) and was extracted with DCM. The organics were dried over MgSO$_4$ and concentrated. Purification of the crude residue by silica gel column chromatography (0 to 20% EtOAc/heptane) gave 1-bromo-5-chloro-4-(difluoromethyl)-2-methoxybenzene (1.55 g, 5.71 mmol, 56.7% yield).

STEP 2: 2-(5-CHLORO-4-(DIFLUOROMETHYL)-2-METHOXYPHENYL)-4,4,5,5-TETRAMETHYL-1,3,2-DIOXABOROLANE

A solution of PdCl$_2$(dppf)-CH$_2$Cl$_2$ adduct (0.466 g, 0.571 mmol), bis(pinacolato)diboron (2.175 g, 8.56 mmol), 1-bromo-5-chloro-4-(difluoromethyl)-2-methoxybenzene (1.550 g, 5.71 mmol), and potassium acetate (2.241 g, 22.84 mmol) in 6 ml of DMF was heated to 100° C. overnight. The reaction mixture was diluted with DCM, filtered through a plug of diatomaceous earth and concentrated under a vacuum. Purification of the crude residue by silica gel column chromatography (0 to 20% EtOAc/heptane) gave 2-(5-chloro-4-(difluoromethyl)-2-methoxyphenyl)-4,4,5,5-tetramethyl-1,3,2-dioxaborolane (0.630 g, 1.978 mmol, 34.6% yield). m/z (ESI) 237.0 (M+H)+

INTERMEDIATE JJJJ: 4-(5-CHLORO-4-(DIFLUOROMETHYL)-2-METHOXYPHENYL)QUINAZOLINE-7-SULFONYL CHLORIDE

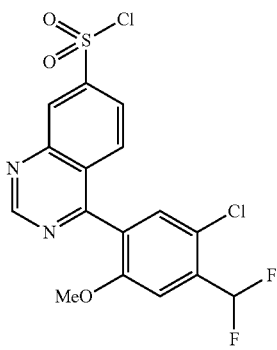 [SMILES: COc1cc(C(F)F)c(Cl)cc1-c1ncnc2cc(S(=O)(=O)Cl)ccc12]

Intermediate JJJJ was synthesized in a similar manner to Intermediate DDDD, using 2-(5-chloro-4-(difluoromethyl)-2-methoxyphenyl)-4,4,5,5-tetramethyl-1,3,2-dioxaborolane (Intermediate IIII) instead of 2-methoxy-4-(trifluoromethyl)phenyl)boronic acid in the first step. m/z (ESI) 459.0 (M+H)+

INTERMEDIATE KKKK: 4-chloro-N-(2,4-dimethoxybenzyl)-N-(thiazol-2-yl)quinazoline-7-sulfonamide

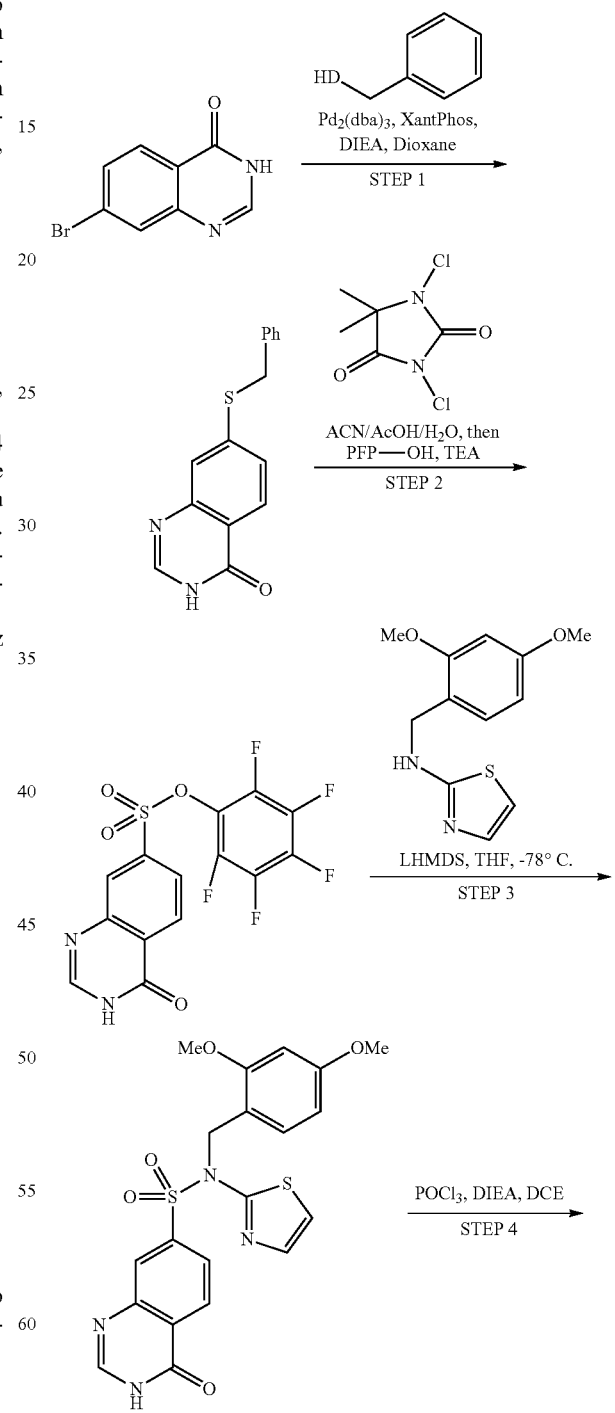

-continued

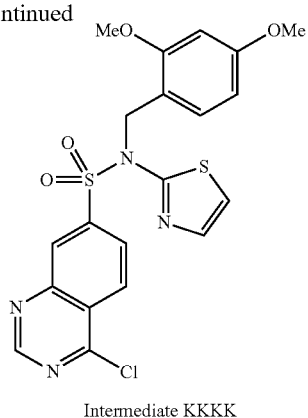

Intermediate KKKK

STEP 1: 7-(BENZYLTHIO)QUINAZOLIN-4(3H)-ONE

A round bottom flask was charged with 7-bromoquinazolin-4(3H)-one (10 g, 44.4 mmol), Xantphos (1.286 g, 2.222 mmol), and $Pd_2(dba)_3$ (1.017 g, 1.111 mmol). The flask was flushed with Ar (g), then dioxane (89 ml), benzyl mercaptan (5.52 ml, 46.7 mmol), and n,n-diisopropylethylamine (15.52 ml, 89 mmol) were added in sequence. The reaction was fitted with a reflux condenser, heated to 90° C., and stirred for one hour. The reaction was diluted with water and filtered. The solids were washed thoroughly with water, then air dried for several hours and triturated with ethyl acetate. After stirring overnight, the solids were filtered, washed with ethyl acetate, and vacuum dried over a nitrogen blanket overnight to afford 7-(benzylthio)quinazolin-4(3H)-one as a light yellow solid. (ESI) 269.1 $(M+H)^+$.

STEP 2: PERFLUOROPHENYL 4-OXO-3,4-DIHYDROQUINAZOLINE-7-SULFONATE

A round-bottom flask was charged with 7-(benzylthio) quinazolin-4(3H)-one (1.0 g, 3.73 mmol), acetonitrile (35.1 ml), acetic acid (1.315 ml), and water (0.877 ml) to give a thin suspension. The flask was cooled in an ice-bath for 10 min, then 1,3-dichloro-5,5-dimethylimidazolidine-2,4-dione (1.468 g, 7.45 mmol) was added in one portion, leading to a solution. The reaction was stirred for one hour. 2,3,4,5,6-pentafluorophenol (0.781 ml, 7.45 mmol) was added followed by drop wise addition of triethylamine (1.299 ml, 9.32 mmol). The reaction was stirred for 90 minutes. The reaction was concentrated, diluted with ethyl acetate and washed with water. The aqueous layer was extracted with ethyl acetate, and the combined organic layers were dried with sodium sulfate, filtered, and concentrated. The material was dissolved in DCM and loaded onto a silica gel cartridge, leaving a white solid on top. The solid was scraped out of the cartridge and set aside. The remaining material was purified via silica gel column chromatography (40 g, gradient elution 0 to 50% EtOAc: Heptane) and combined with the previously isolated material to afford perfluorophenyl 4-oxo-3,4-dihydroquinazoline-7-sulfonate as a white solid. (ESI) 393.0 $(M+H)^+$.

STEP 3: N-(2,4-DIMETHOXYBENZYL)-4-OXO-N-(THIAZOL-2-YL)-3,4-DIHYDROQUINAZOLINE-7-SULFONAMIDE

A solution of N-(2,4-dimethoxybenzyl)thiazol-2-amine (0.791 g, 3.16 mmol) in tetrahydrofuran (11.57 ml) was cooled in a dry ice-acetone bath for 5 min. Lithium bis(trimethylsilyl)amide (1M in THF) (3.31 ml, 3.31 mmol) was added drop wise, then the flask was removed from the cooling bath for 5 min. The flask was again cooled into a dry ice-acetone bath for 20 min, resulting in the formation of a thick slurry. A solution of perfluorophenyl 4-oxo-3,4-dihydroquinazoline-7-sulfonate (1.18, 3.01 mmol) in THF (12 mL) was added drop wise, and the reaction was stirred for 30 minutes. An additional equivalent of lithium bis(trimethylsilyl)amide (1M in THF) (3.31 ml, 3.31 mmol) was added and the reaction was stirred for 30 minutes. The reaction was warmed to room temperature and quenched with saturated ammonium chloride solution, diluted with ethyl acetate and washed with water. The aqueous layer was extracted three times with ethyl acetate, and the combined organic layers were dried with sodium sulfate, filtered, and concentrated. The material was dissolved in ethyl acetate and loaded onto a silica cartridge, leaving a tan solid on top. The solid was scraped out of the cartridge and set aside. The remaining material was purified by chromatography on a 40-g silica gel column with 0 to 100% EtOAc/Heptane followed by a 10% MeOH/DCM flush. The product containing fractions were concentrated and combined with the previously isolated material to afford N-(2,4-dimethoxybenzyl)-4-oxo-N-(thiazol-2-yl)-3,4-dihydroquinazoline-7-sulfonamide as a tan solid. (ESI) 481.1 $(M+Na)^+$.

STEP 4: 4-CHLORO-N-(2,4-DIMETHOXYBENZYL)-N-(THIAZOL-2-YL)QUINAZOLINE-7-SULFONAMIDE

N-(2,4-dimethoxybenzyl)-4-oxo-N-(thiazol-2-yl)-3,4-dihydroquinazoline-7-sulfonamide (0.990 g, 2.159 mmol) was dissolved in toluene (10.80 ml) and $POCl_3$ (0.403 ml, 4.32 mmol) was added. The reaction was stirred for 90 minutes at room temperature, then heated to 90° C. and stirred for four hours. The reaction was diluted with ethyl acetate and washed with saturated sodium bicarbonate solution. The aqueous layer was extracted twice with ethyl acetate, and the combined organic layers were dried with sodium sulfate, filtered, and concentrated to afford a brown oily solid. The solid was triturated in heptane, stirred for 30 minutes, and filtered. The resulting material was vacuum dried to afford crude 4-chloro-N-(2,4-dimethoxybenzyl)-N-(thiazol-2-yl)quinazoline-7-sulfonamide as a free flowing tan solid. (ESI) 499.1 $(M+Na)^+$.

INTERMEDIATE LLLL: 4-CHLORO-N-(4-METHOXYBENZYL)-N-(THIAZOL-2-YL)QUINOLINE-7-SULFONAMIDE

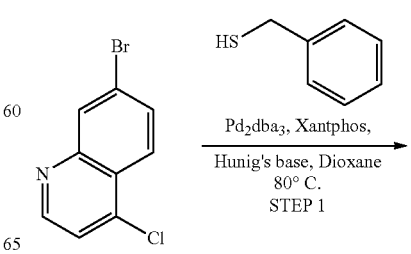

-continued

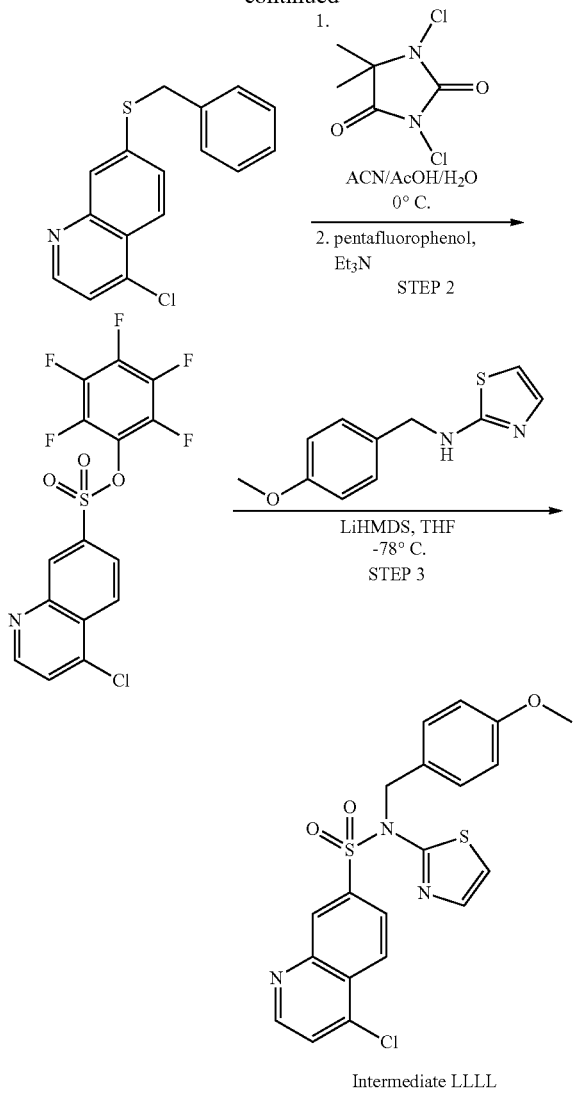

STEP 1: 7-(BENZYLTHIO)-4-CHLOROQUINOLINE

A 250-mL 3-neck round-bottom flask was charged with 7-bromo-4-chloroquinoline (BioBlocks, Inc., San Diego, Calif.; 7.000 g, 28.9 mmol), Xantphos (0.835 g, 1.443 mmol), and $Pd_2(dba)_3$ (0.661 g, 0.722 mmol), and after flushing with argon, dioxane (57.7 ml) and n,n-diisopropylethylamine (10.08 ml, 57.7 mmol) were added in sequence. The flask was fitted with a reflux condenser, and was placed in a heating bath at 80° C. for 10 minutes, after which benzyl mercaptan (3.58 ml, 30.3 mmol) was added drop wise via syringe. The reaction was stirred for 20 minutes until completion. The material was diluted with water, and washed with DCM (x3), and the combined organics were dried via phase separator (Radley's Technology) and concentrated under a vacuum. Upon dissolving the material in DCM, solids remained out of solution, and they were filtered off and washed with DCM. The corresponding filtrate was concentrated under a vacuum and purified via silica gel chromatography (120-g column) eluting with 0 to 100% ethyl acetate in heptanes to yield 7-(benzylthio)-4-chloroquinoline (7.35 g, 25.7 mmol, 89% yield) as a light yellow solid. m/z (ESI) 286.0 $(M+H)^+$.

STEP 2: PERFLUOROPHENYL 4-CHLOROQUINOLINE-7-SULFONATE

A round-bottom flask was charged with 7-(benzylthio)-4-chloroquinoline (7.35 g, 25.7 mmol), acetonitrile (242 ml), acetic acid (9.08 ml), and water (6.05 ml), and after cooling the suspension in an ice bath for 10 minutes, 1,3-dichloro-5,5-dimethylimidazolidine-2,4-dione (10.13 g, 51.4 mmol) was added in one portion to form a heterogeneous solution. After 20 minutes, conversion to 4-chloroquinoline-7-sulfonyl chloride was observed, and 2,3,4,5,6-pentafluorophenol (9.47 g, 51.4 mmol) was added, followed by drop wise addition of triethylamine (8.96 ml, 64.3 mmol). After 40 minutes, the mixture was diluted with EtOAc (200 mL) and washed with water (2×200 mL) and brine, and then dried over sodium sulfate. After filtration and concentration under a vacuum, the material was purified via silica gel chromatography (120-g column) eluting with 0 to 35% ethyl acetate in heptane to yield perfluorophenyl 4-chloroquinoline-7-sulfonate (10.54 g, 25.7 mmol, 100% yield) as a light yellow oily solid. m/z (ESI) 410.1 $(M+H)^+$.

STEP 3: 4-CHLORO-N-(4-METHOXYBENZYL)-N-(THIAZOL-2-YL)QUINOLINE-7-SULFONAMIDE

A solution of N-(4-methoxybenzyl)thiazol-2-amine (0.306 g, 1.389 mmol) in THF (5.29 ml) was cooled to −78° C. for 10 minutes, and lithium bis(trimethylsilyl)amide (1.0M solution in THF) (1.323 ml, 1.323 mmol) was added drop wise. The cold bath was removed for 5 minutes, and then the reaction vessel was re-cooled to −78° C. for 10 minutes. A solution of perfluorophenyl 4-chloroquinoline-7-sulfonate (0.542 g, 1.323 mmol) in THF (2.65 ml, 1.323 mmol) was added drop wise, and the reaction was stirred for 15 minutes until complete conversion to the desired product. After warming to RT, the reaction was quenched with sat. aq ammonium chloride solution, diluted with EtOAc (5 mL) and washed with water (10 mL×2). The combined organics were dried over sodium sulfate, filtered and concentrated. The material was then purified via silica gel chromatography (40-g column) eluting with 0 to 100% ethyl acetate in heptanes, to yield 4-chloro-N-(4-methoxybenzyl)-N-(thiazol-2-yl)quinoline- 7-sulfonamide (0.481 g, 1.079 mmol, 82% yield) as a white solid. m/z (ESI) 446.1 (M+H)+.

INTERMEDIATE MMMM:
4-CHLORO-N-(PYRIMIDIN-4-YL)QUINOLINE-7-SULFONAMIDE 7-sulfonamide (0.053 g, 0.165 mmol, 67.7% yield) as a light brown solid (carried forward crude). m/z (ESI) 321.0 (M+H)+.

INTERMEDIATE NNNN: 3-AMINO-4-(2-METHOXY-4-(TRIFLUOROMETHYL)PHENYL)-N-(4-METHOXYBENZYL)-N-(THIAZOL-2-YL)QUINOLINE-7-SULFONAMIDE

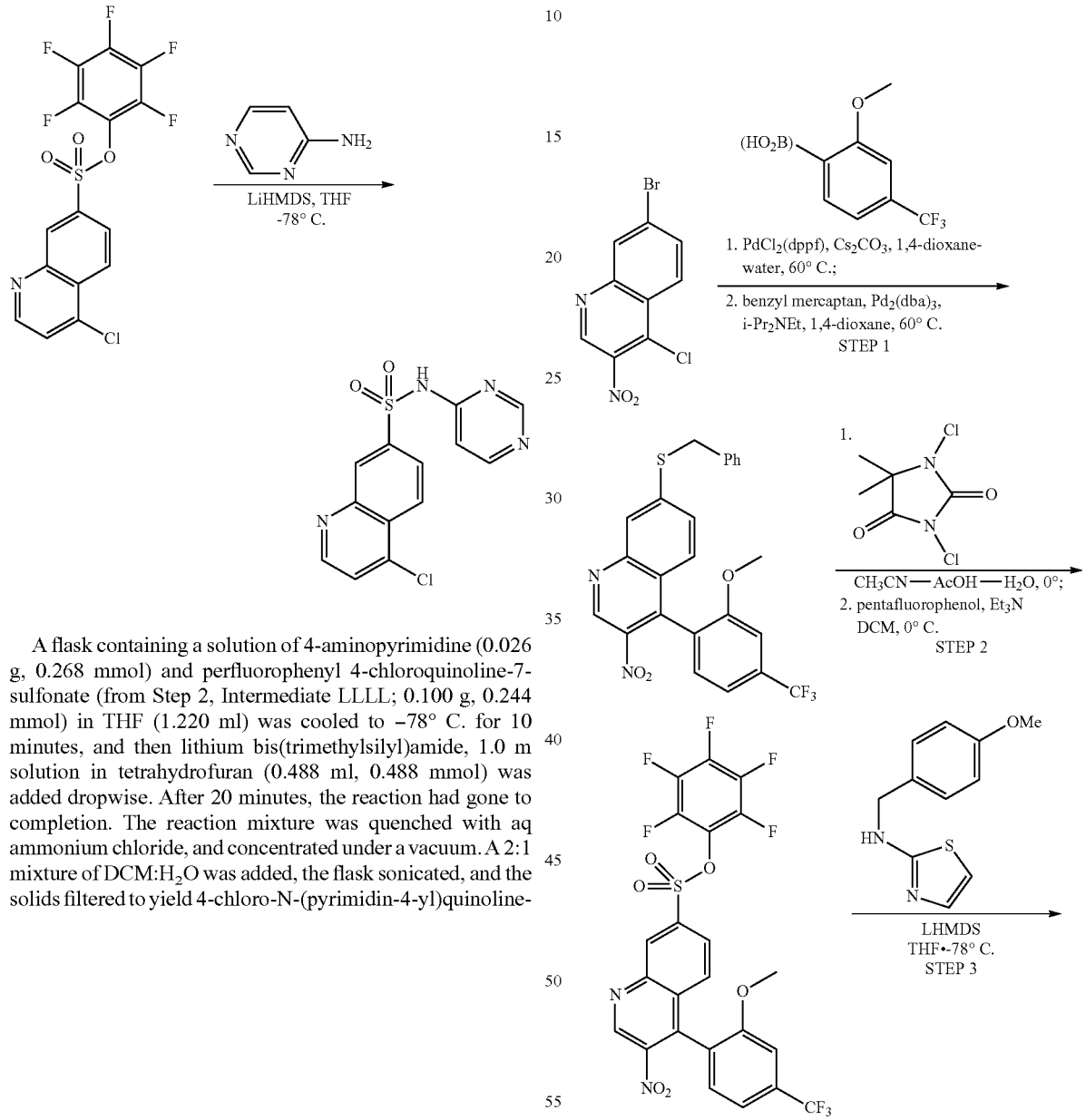

A flask containing a solution of 4-aminopyrimidine (0.026 g, 0.268 mmol) and perfluorophenyl 4-chloroquinoline-7-sulfonate (from Step 2, Intermediate LLLL; 0.100 g, 0.244 mmol) in THF (1.220 ml) was cooled to −78° C. for 10 minutes, and then lithium bis(trimethylsilyl)amide, 1.0 m solution in tetrahydrofuran (0.488 ml, 0.488 mmol) was added dropwise. After 20 minutes, the reaction had gone to completion. The reaction mixture was quenched with aq ammonium chloride, and concentrated under a vacuum. A 2:1 mixture of DCM:H$_2$O was added, the flask sonicated, and the solids filtered to yield 4-chloro-N-(pyrimidin-4-yl)quinoline-

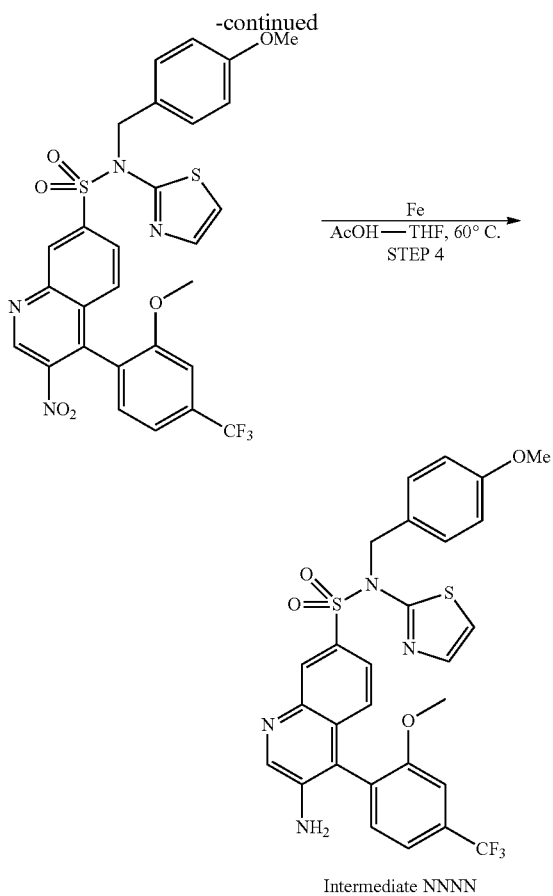

Intermediate NNNN

STEP 1: 7-(BENZYLTHIO)-4-(2-METHOXY-4-(TRIFLUOROMETHYL)PHENYL)-3-NITROQUINOLINE

A round-bottom flask was charged with 7-bromo-4-chloro-3-nitroquinoline (1.083 g, 3.77 mmol, from Capot Chemical, Zhejiang, China), (2-methoxy-4-(trifluoromethyl)phenyl) boronic acid (0.911 g, 4.14 mmol), potassium carbonate (1.562 g, 11.30 mmol), and PdCl$_2$(dppf) (0.138 g, 0.188 mmol). The flask was flushed with Ar (g), then 1,4-dioxane (9.42 ml) and water (3.14 ml) were added. The flask was fitted with a reflux condenser and lowered into a 60° C. oil bath for 45 min. The mixture was diluted with water and extracted with EtOAc (2×). The combined organic extracts were dried over sodium sulfate, filtered, and concentrated. The residue was taken up in 1,4-dioxane (9.42 ml). Xantphos (0.109 g, 0.188 mmol), Pd$_2$(dba)$_3$ (0.086 g, 0.094 mmol), n,n-diisopropylethylamine (1.316 ml, 7.53 mmol), and benzyl mercaptan (0.490 ml, 4.14 mmol) were added in sequence. The reflux condenser was attached, and the flask was heated to 60° C. for 2 h. The mixture was cooled to room temperature, diluted with EtOAc, then filtered through diatomaceous earth. The filtrate was concentrated, and the residue was purified by chromatography on silica gel (40-g column, 25-g silica gel loading column, 0 to 40% EtOAc/Heptane) to give 7-(benzylthio)-4-(2-methoxy-4-(trifluoromethyl)phenyl)-3-nitroquinoline (1.4698 g, 3.12 mmol, 83% yield) as a yellow solid. NMR indicated a 70:30 mixture of desired product to bis-coupling byproduct form the first step. m/z (ESI) 471.2 (M+H)$^+$.

STEP 2: PERFLUOROPHENYL 4-(2-METHOXY-4-(TRIFLUOROMETHYL)PHENYL)-3-NITRO-QUINOLINE-7-SULFONATE

A round-bottom flask was charged with 7-(benzylthio)-4-(2-methoxy-4-(trifluoromethyl)phenyl)-3-nitroquinoline (1.4698 g, 2.343 mmol), acetonitrile (22.05 ml), acetic acid (0.827 ml), and water (0.551 ml) to give a clear, orange solution. The flask was cooled in an ice-water bath for 15 min to give a yellow suspension, then 1,3-dichloro-5,5-dimethylimidazolidine-2,4-dione (0.923 g, 4.69 mmol) was added in one portion, resulting in the formation of a clear solution within 20 s. After 25 min, 2,3,4,5,6-pentafluorophenol (0.647 g, 3.51 mmol) and triethylamine (1.306 ml, 9.37 mmol) were added in sequence. The mixture was stirred for 30 min, then diluted with EtOAc (50 mL) and washed with water (2×50 ml), washed with brine, dried over sodium sulfate, filtered, and concentrated. The residue was dissolved in DCM and purified by chromatography on silica gel (40-g column, 25-g silica gel loading column, 0 to 40% EtOAc/Heptane) to give 1.51 g of a yellow solid. NMR showed a 3:1 mix of desired product to bis-coupling byproduct from STEP 1. This equated to a product purity of 77 wt %. The material was used directly in the next step. m/z (ESI) 595.2 (M+H)$^+$.

STEP 3: 4-(2-METHOXY-4-(TRIFLUOROMETHYL)PHENYL)-N-(4-METHOXYBENZYL)-3-NITRO-N-(THIAZOL-2-YL)QUINOLINE-7-SULFONAMIDE

A round-bottom flask was charged with N-(4-methoxybenzyl)thiazol-2-amine (0.353 g, 1.603 mmol) and THF (7.29 ml) to give an opaque solution. The flask was cooled in a dry ice-acetone bath for 5 min to give a milky suspension, then lithium bis(trimethylsilyl)amide (1M in THF) (1.603 ml, 1.603 mmol) was added. The flask was removed from the bath for 5 min to give a clear solution, then resubmerged. The mixture appeared to remain a solution. After 5 min, a solution of perfluorophenyl 4-(2-methoxy-4-(trifluoromethyl)phenyl)-3-nitroquinoline-7-sulfonate (1.125 g, 1.457 mmol) in THF (3 mL with a 2 mL wash) was added drop wise. The mixture was stirred for 45 min, then diluted with saturated aq ammonium chloride solution and warmed to room temperature. The mixture was diluted with water and extracted with EtOAc (2×). The combined organic extracts were dried over sodium sulfate, filtered, and concentrated. The residue was purified by chromatography on silica gel (40-g column, 0 to 40% EtOAc/Heptane) to give 4-(2-methoxy-4-(trifluoromethyl)phenyl)-N-(4-methoxybenzyl)-3-nitro-N-(thiazol-2-yl)quinoline-7-sulfonamide (0.759 g, 1.204 mmol, 83% yield) as a yellow foam. m/z (ESI) 631.2 (M+H)+.

STEP 4: 3-AMINO-4-(2-METHOXY-4-(TRIFLUOROMETHYL)PHENYL)-N-(4-METHOXYBENZYL)-N-(THIAZOL-2-YL)QUINOLINE-7-SULFONAMIDE

A round-bottom flask was charged with 4-(2-methoxy-4-(trifluoromethyl)phenyl)-N-(4-methoxybenzyl)-3-nitro-N-(thiazol-2-yl)quinoline-7-sulfonamide (0.759 g, 1.204 mmol), THF (2.006 ml), and acetic acid (2.006 ml) to give a yellow solution. Iron (0.672 g, 12.04 mmol) powder was added, and the flask was fitted with a reflux condenser and placed in a 60° C. heating bath. The mixture was stirred for 50 min, then cooled to room temperature, diluted with THF, and filtered through diatomaceous earth with the aid of THF. The filtrate was concentrated. The residue was concentrated from DCM/heptane (2×), then concentrated from DCM to give 3-amino-4-(2-methoxy-4-(trifluoromethyl)phenyl)-N-(4-methoxybenzyl)-N-(thiazol-2-yl)quinoline-7-sulfonamide (0.714 g, 1.189 mmol, 99% yield) as a tan foam. m/z (ESI) 601.2 (M+H)+.
INTERMEDIATES OOOO and PPPP: 4-BROMO-N-(PYRIMIDIN-4-YL)ISOQUINOLINE-7-SULFONAMIDE and 4-BROMO-N-(4-METHOXYBENZYL)-N-(THIAZOL-2-YL)ISOQUINOLINE-7-SULFONAMIDE
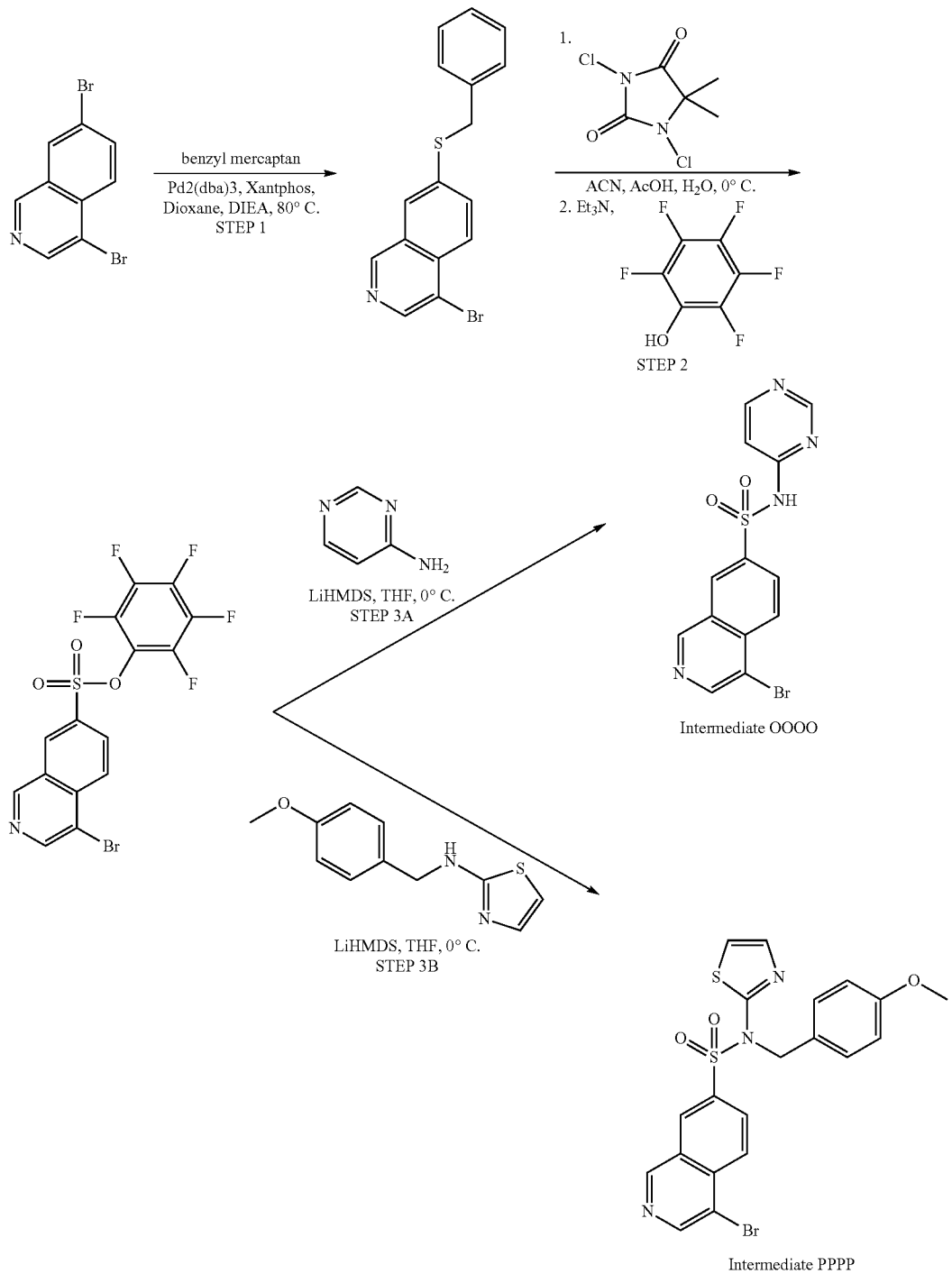

STEP 1: 7-(BENZYLTHIO)-4-BROMOISOQUINOLINE

To a vial charged with 4,7-dibromoisoquinoline (Pharmabridge, Inc., Doylestown, Pa.) (0.783 g, 2.73 mmol) was added dioxane (10.91 ml), DIEA (0.953 ml, 5.46 mmol), Xantphos (0.316 g, 0.546 mmol), Pd$_2$(dba)$_3$ (0.250 g, 0.273 mmol) and benzyl mercaptan (0.323 ml, 2.73 mmol). The vessel was sealed and heated to 60° C. for 4 hrs affording conversion to desired product as the primary species. The mixture was dried under reduced pressure and the crude material purified with a 40 HP silicycle column (SiliCycle, Inc. Quebec City, Canada) ramping EtOAc in heptane (0 to 25%, then isocratic at 25%, with 10% DCM isocratic throughout) providing product 7-(benzylthio)-4-bromoisoquinoline (0.573 g, 1.735 mmol, 63.6% yield), obtained as an orange solid. m/z (ESI) 330.2 (M+H)$^+$.

STEP 2: PERFLUOROPHENYL 4-BROMOISOQUINOLINE-7-SULFONATE

To a vial charged with 7-(benzylthio)-4-bromoisoquinoline (0.570 g, 1.726 mmol) was added acetonitrile (16.24 ml), acetic acid (0.609 ml), water (0.406 ml). The resulting solution was cooled in an ice water bath and 1,3-dichloro-5,5-dimethyl-2-imidazolidinedione (0.453 ml, 3.45 mmol) was added. After 1 hr LC/MS of the resulting solution indicated product, 4-bromoisoquinoline-7-sulfonyl chloride, as the primary species. m/z (ESI) 306.0 (M+H)$^+$. To the mixture was added 2,3,4,5,6-pentafluorophenol (0.361 ml, 3.45 mmol) and triethylamine (0.962 ml, 6.90 mmol) affording a yellow solution. After 45 min LC/MS indicated conversion to desired product (PFP ester). The mixture was diluted with EtOAc and extracted with H$_2$O. The aqueous phase was extracted with EtOAc. The combined organics were dried with Na$_2$SO$_4$, filtered, and dried under reduced pressure. The crude material was purified with a 40 g silicycle HP column (SiliCycle, Inc. Quebec City, Canada) ramping EtOAc in heptane (0-15%) providing product as a pale yellow oil, perfluorophenyl 4-bromoisoquinoline-7-sulfonate (0.618 g, 1.361 mmol, 79% yield). m/z (ESI) 454.1 (M+H)$^+$.

STEP 3A: 4-BROMO-N-(PYRIMIDIN-4-YL)ISOQUINOLINE-7-SULFONAMIDE

To a flask containing ice cold suspension of pyrimidin-4-amine (0.402 g, 4.23 mmol) in THF (5.42 ml) was added lithium bis(trimethylsilyl)amide (1M in THF) (1.550 ml, 1.550 mmol) drop wise over 10 min. The mixture was stirred for 15 min providing a white suspension. A solution of perfluorophenyl 4-bromoisoquinoline-7-sulfonate (0.640 g, 1.409 mmol) in THF (5.0 ml) was added drop wise and the resulting mixture stirred for 1 hr. To the solution was added acetic acid (500 µl) and the solution dried under reduced pressure. The crude material was purified with a 40 g HP Silicycle column (SiliCycle, Inc. Quebec City, Canada) ramping EtOAc in heptane (0 to 25%) to elute starting material, then MeOH in DCM (0 to 20%) providing product which had coeluted with aminopyrimidine. The mixture was purified with a 10 g PE-AX column (Biotage AB, Uppsala, Sweden) washing with MeOH, then about 3% HCl in MeOH to provide 4-bromo-N-(pyrimidin-4-yl)isoquinoline-7-sulfonamide (Intermediate OOOO) (0.125 g, 0.342 mmol, 24.29% yield) as a white solid (possibly HCl salt). m/z (ESI) 365.1 (M+H)$^+$.

STEP 3B: 4-BROMO-N-(4-METHOXYBENZYL)-N-(THIAZOL-2-YL)ISOQUINOLINE-7-SULFONAMIDE

To a flask charged with N-(4-methoxybenzyl)thiazol-2-amine (180 mg, 0.816 mmol) was added THF (3 ml) and the resulting mixture cooled in an ice water bath prior to the addition of lithium bis(trimethylsilyl)amide (1M in THF) (855 µl, 0.855 mmol). The resulting light brown solution was stirred for 15 min at 0° C. prior to the addition of a solution of perfluorophenyl 4-bromoisoquinoline-7-sulfonate (353 mg, 0.777 mmol) in THF (2 ml), followed by 1 ml THF wash. The resulting solution was allowed to stir and warm slowly to room temperature (ice melt). After 2 hr LC/MS indicated about 70% conversion fairly cleanly, with starting amine and PFP ester present (no change from 1 hr). The solution was cooled back to 0° C. and 0.5 eq LiHMDS (1 M) was added. After 1 hr LC/MS indicated complete consumption of starting material. To the mixture was added 400 µl acetic acid and the mixture was dried under reduced pressure and purified with a 40 g HP Silicycle column (SiliCycle, Inc. Quebec City, Canada) ramping EtOAc in heptane (0 to 50%, 10% DCM throughout) affording product as a white solid 4-bromo-N-(4-methoxybenzyl)-N-(thiazol-2-yl)isoquinoline-7-sulfonamide (Intermediate PPPP) (202 mg, 0.412 mmol, 53.0% yield). m/z (ESI) 490.0 (M+H)$^+$.

EXAMPLE 84

5-(2-(4-METHYLPIPERAZIN-1-YL)-4-(TRIFLUOROMETHYL)PHENYL)-N-(THIAZOL-2-YL)NAPHTHALENE-2-SULFONAMIDE 2,2,2-TRIFLUOROACETATE

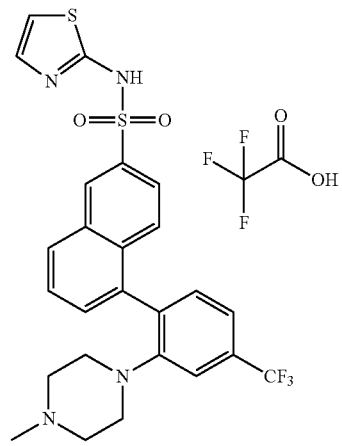

A microwave vial was charged with N-(2,4-dimethoxybenzyl)-5-(4,4,5,5-tetramethyl-1,3,2-dioxaborolan-2-yl)-N-(thiazol-2-yl)naphthalene-2-sulfonamide (Intermediate II, 0.200 g, 0.353 mmol), 1-(2-bromo-5-(trifluoromethyl)phenyl)-4-methylpiperazine (Intermediate JJ, 0.228 g, 0.706 mmol), and PdCl$_2$(dppf)-CH$_2$Cl$_2$ adduct (0.058 g, 0.071 mmol). Dioxane (1.765 ml) and t-BuOH (1.765 ml) were added, followed by sodium carbonate (2.0M in H$_2$O) (0.530 ml, 1.059 mmol). The reaction was purged with nitrogen, and then heated at 50° C. overnight. After cooling to RT, the solids were filtered through a frit and washed with ethyl acetate. The filtrate was then washed with brine, and the organics were dried over magnesium sulfate, filtered and concentrated to yield a dark oil. Before deprotection, the material was dissolved in methanol and purified further with a strong cation exchange-column (SCX) (product eluted with the methanol/ammonia wash). After concentration, the material was diluted with DCM (1.0 mL) and TFA was added (1.0 mL). The reaction was stirred for 30 minutes at which time the reaction was concentrated under a vacuum. The material was purified via reverse-phase preparative HPLC using 0.1% TFA in $CH_3CN/H_2O$, gradient 25% to 90% over 20 min to provide 5-(2-(4-methylpiperazin-1-yl)-4-(trifluoromethyl)phenyl)-N-(thiazol-2-yl)naphthalene-2-sulfonamide 2,2,2-trifluoroacetate (0.064 g, 0.099 mmol, 28.0% yield) as a tan glass. $^1$H NMR (400 MHz, DMSO-$d_6$) δ ppm 1.98-2.17 (m, 1H) 2.23-2.42 (m, 1H) 2.76-2.95 (m, 2H) 3.00-3.15 (m, 4H) 3.17 (s, 3H) 6.85 (d, J=4.60 Hz, 1H) 7.27 (d, J=4.60 Hz, 1H) 7.45-7.57 (m, 3H) 7.65-7.82 (m, 4H) 8.25 (d, J=7.63 Hz, 1H) 8.55 (d, J=1.86 Hz, 1H) 9.61 (br. s., 1H) 12.81 (br. s., 1H). m/z (ESI) 533.0 (M+H)$^+$.

EXAMPLE 85

5-(2-(PYRIDIN-3-YL)PYRROLIDIN-1-YL)-N-(1,2,4-THIADIAZOL-5-YL)NAPHTHALENE-2-SULFONAMIDE

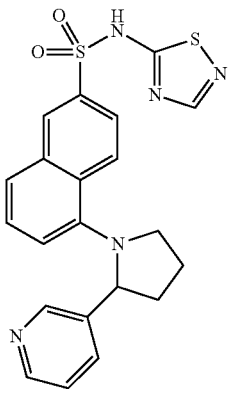 [SMILES: O=S(=O)(Nc1ncns1)c1ccc2c(N3CCCC3c3cccnc3)cccc2c1]

The title compound was prepared in an analagous manner to that described for the preparation of Example 83 except that 3-(pyrrolidin-2-yl)pyridine (ASDI, Newark, Del.) was used in place of 2-phenylpyrrolidine. The desired product, 5-(2-(pyridin-3-yl)pyrrolidin-1-yl)-n-(1,2,4-thiadiazol-5-yl)naphthalene-2-sulfonamide, was isolated as a yellow solid: $^1$H NMR (400 MHz, DMSO-$d_6$) δ ppm=8.78 (d, J=1.8 Hz, 1H), 8.55-8.45 (m, 3H), 8.37 (d, J=1.9 Hz, 1H), 8.16 (d, J=7.9 Hz, 1H), 7.84-7.76 (m, 1H), 7.69 (d, J=8.3 Hz, 1H), 7.53 (dd, J=5.2, 7.9 Hz, 1H), 7.39 (t, J=7.9 Hz, 1H), 7.20 (d, J=7.4 Hz, 1H), 5.09-4.96 (m, 1H), 4.23-4.09 (m, 1H), 3.05 (dt, J=4.6, 8.7 Hz, 1H), 2.56-2.51 (m, 1H), 2.22-2.12 (m, 1H), 2.06-1.85 (m, 2H); m/z (ESI) 438.2 (M+H)$^+$.

EXAMPLE 86 AND EXAMPLE 87

(S)-5-(2-(PYRIDIN-3-YL)PYRROLIDIN-1-YL)-N-(1,2,4-THIADIAZOL-5-YL)NAPHTHALENE-2-SULFONAMIDE COMPOUND WITH DIETHYLAMINE (1:1) AND (R)-5-(2-(PYRIDIN-3-YL)PYRROLIDIN-1-YL)-N-(1,2,4-THIADIAZOL-5-YL)NAPHTHALENE-2-SULFONAMIDE COMPOUND WITH DIETHYLAMINE (1:1)

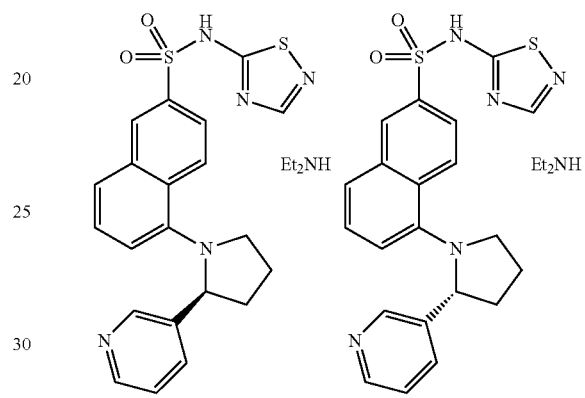

A sample of material from Example 85 was separated by SFC on a Chiralpak AY column (Chiral Technologies, West Chester, Pa., 2×25 cm). The column was eluted with 35% methanol/acetonitrile containing 0.2% diethylamine/65% $CO_2$ at 80 mL/min.

Peak 1 eluted at 0.73 min to give a tan solid. The stereochemistry was arbitrarily assigned as (S) to give (S)-5-(2-(pyridin-3-yl)pyrrolidin-1-yl)-N-(1,2,4-thiadiazol-5-yl) naphthalene-2-sulfonamide compound with diethylamine (1:1) as a tan solid: $^1$H NMR (400 MHz, DMSO-$d_6$) δ ppm=8.61 (d, J=1.8 Hz, 1H), 8.35 (d, J=8.9 Hz, 1H), 8.29 (dd, J=1.5, 4.7 Hz, 1H), 8.19 (m, 3H), 7.82 (s, 1H), 7.79-7.72 (m, 2H), 7.55 (d, J=8.1 Hz, 1H), 7.30 (t, J=7.9 Hz, 1H), 7.18 (dd, J=4.7, 7.8 Hz, 1H), 7.07 (d, J=7.5 Hz, 1H), 4.86 (dd, J=6.6, 9.1 Hz, 1H), 4.17-4.08 (m, 1H), 3.03-2.88 (m, 5H), 2.48-2.42 (m, 1H), 2.17-2.09 (m, 1H), 2.03-1.81 (m, 2H), 1.15 (t, J=7.3 Hz, 6H); m/z (ESI) 438.3 (M+H)$^+$.

Peak 2 eluted at 1.41 min to give a tan solid. The stereochemistry was arbitrarily assigned as (R) to give (R)-5-(2-(pyridin-3-yl)pyrrolidin-1-yl)-N-(1,2,4-thiadiazol-5-yl) naphthalene-2-sulfonamide compound with diethylamine (1:1) as a tan solid: $^1$H NMR (400 MHz, DMSO-$d_6$) δ ppm=8.61 (d, J=1.8 Hz, 1H), 8.35 (d, J=8.9 Hz, 1H), 8.29 (dd, J=1.5, 4.7 Hz, 1H), 8.19 (m, 3H), 7.82 (s, 1H), 7.79-7.72 (m, 2H), 7.55 (d, J=8.1 Hz, 1H), 7.30 (t, J=7.9 Hz, 1H), 7.18 (dd, J=4.7, 7.8 Hz, 1H), 7.07 (d, J=7.5 Hz, 1H), 4.86 (dd, J=6.6, 9.1 Hz, 1H), 4.17-4.08 (m, 1H), 3.03-2.88 (m, 5H), 2.48-2.42

(m, 1H), 2.17-2.09 (m, 1H), 2.03-1.81 (m, 2H), 1.15 (t, J=7.3 Hz, 6H); m/z (ESI) 438.3 (M+H)+.

EXAMPLE 88

5-(2-(PYRIDIN-4-YL)PYRROLIDIN-1-YL)-N-(1,2,4-THIADIAZOL-5-YL)NAPHTHALENE-2-SULFONAMIDE

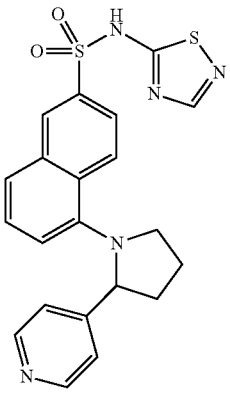

The title compound was prepared in an analagous manner to that described for the preparation of Example 83 except that 4-(pyrrolidin-2-yl)pyridine (ASDI, Newark, Del.) was used in place of 2-phenylpyrrolidine. The desired product, 5-(2-(pyridin-4-yl)pyrrolidin-1-yl)-N-(1,2,4-thiadiazol-5-yl)naphthalene-2-sulfonamide, was isolated as an orange solid: $^1$H NMR (400 MHz, DMSO-$d_6$) δ ppm=8.77-8.73 (m, 1H), 8.58 (d, J=6.5 Hz, 2H), 8.54-8.45 (m, 2H), 8.38 (d, J=2.0 Hz, 1H), 7.86-7.76 (m, 4H), 7.70 (d, J=8.2 Hz, 1H), 7.41-7.35 (m, 1H), 7.15 (d, J=7.4 Hz, 1H), 5.10 (dd, J=7.0, 9.0 Hz, 1H), 4.23-4.15 (m, 1H), 3.12-3.05 (m, 1H), 2.60-2.53 (m, 1H), 2.15 (td, J=3.6, 7.5 Hz, 1H), 2.09-1.97 (m, 1H), 1.92-1.81 (m, 1H); m/z (ESI) 438.3 (M+H)+.

EXAMPLE 89 AND EXAMPLE 90

((S)-5-(2-(PYRIDIN-4-YL)PYRROLIDIN-1-YL)-N-(1,2,4-THIADIAZOL-5-YL)NAPHTHALENE-2-SULFONAMIDE COMPOUND WITH DIETHYLAMINE (1:1) AND (R)-5-(2-(PYRIDIN-4-YL)PYRROLIDIN-1-YL)-N-(1,2,4-THIADIAZOL-5-YL)NAPHTHALENE-2-SULFONAMIDE COMPOUND WITH DIETHYLAMINE (1:1)

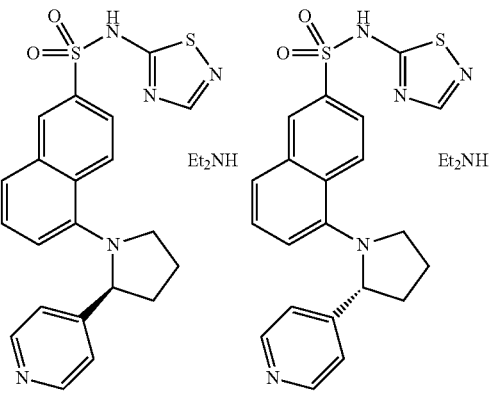 [SMILES: "Et2NH" ; "Et2NH" ; O=S(=O)(Nc1ncns1)c1ccc2c(N3CCC[C@H]3c3ccncc3)cccc2c1 ; O=S(=O)(Nc1ncns1)c1ccc2c(N3CCC[C@@H]3c3ccncc3)cccc2c1]

A sample of material from Example 88 was separated by SFC on a WHELK-O column (Regis Technologies, Morton Grove, Ill., 2×25 cm). The column was eluted with 55% methanol containing 0.2% diethylamine/45% $CO_2$ at 80 mL/min:

Peak 1 eluted at 1.92 min to give a yellow solid. The stereochemistry was arbitrarily assigned as (S) to give (S)-5-(2-(pyridin-4-yl)pyrrolidin-1-yl)-N-(1,2,4-thiadiazol-5-yl)naphthalene-2-sulfonamide compound with diethylamine (1:1) as a tan solid: $^1$H NMR (400 MHz, DMSO-$d_6$) δ ppm=8.41-8.32 (m, 3H), 8.25-8.03 (m, 3H), 7.82 (s, 1H), 7.77 (dd, J=1.9, 8.9 Hz, 1H), 7.55 (d, J=8.2 Hz, 1H), 7.39-7.35 (m, 2H), 7.28 (t, J=7.8 Hz, 1H), 7.01 (d, J=7.5 Hz, 1H), 4.86 (dd, J=6.7, 9.3 Hz, 1H), 4.18-4.10 (m, 1H), 3.00 (dt, J=4.8, 9.0 Hz, 1H), 2.93 (q, J=7.2 Hz, 4H), 2.48-2.43 (m, 1H), 2.16-2.06 (m, 1H), 2.02-1.91 (m, 1H), 1.87-1.76 (m, 1H), 1.16 (t, J=7.2 Hz, 6H); m/z (ESI) 438.4 (M+H)+.

Peak 2 eluted at 1.92 min to give a yellow solid. The stereochemistry was arbitrarily assigned as (R) to give (R)-5-(2-(pyridin-4-yl)pyrrolidin-1-yl)-N-(1,2,4-thiadiazol-5-yl)naphthalene-2-sulfonamide compound with diethylamine (1:1) as a tan solid: $^1$H NMR (400 MHz, DMSO-$d_6$) δ ppm=8.41-8.32 (m, 3H), 8.25-8.03 (m, 3H), 7.82 (s, 1H), 7.77 (dd, J=1.9, 8.9 Hz, 1H), 7.55 (d, J=8.2 Hz, 1H), 7.39-7.35 (m, 2H), 7.28 (t, J=7.8 Hz, 1H), 7.01 (d, J=7.5 Hz, 1H), 4.86 (dd, J=6.7, 9.3 Hz, 1H), 4.18-4.10 (m, 1H), 3.00 (dt, J=4.8, 9.0 Hz, 1H), 2.93 (q, J=7.2 Hz, 4H), 2.48-2.43 (m, 1H), 2.16-2.06 (m, 1H), 2.02-1.91 (m, 1H), 1.87-1.76 (m, 1H), 1.16 (t, J=7.2 Hz, 6H); m/z (ESI) 438.4 (M+H)+.

EXAMPLE 91

5-(2-METHYLPYRROLIDIN-1-YL)-N-(1,2,4-THIADIAZOL-5-YL)NAPHTHALENE-2-SULFONAMIDE

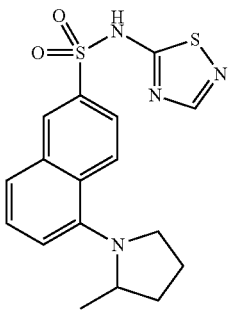 [SMILES: CC1CCCN1c1cccc2cc(S(=O)(=O)Nc3ncns3)ccc12]

The title compound was prepared in an analogous manner to that described for the preparation of Example 83 except that 2-methylpyrrolidine (Sigma-Aldrich, St. Louis, Mo.) was used in place of 2-phenylpyrrolidine. The desired product, 5-(2-methylpyrrolidin-1-yl)-n-(1,2,4-thiadiazol-5-yl)naphthalene-2-sulfonamide, was isolated as a yellow solid: $^1$H NMR (400 MHz, DMSO-$d_6$) δ ppm=8.49 (s, 1H), 8.39 (d, J=1.9 Hz, 1H), 8.29 (d, J=9.1 Hz, 1H), 7.74 (dd, J=2.0, 9.0 Hz, 2H), 7.54 (t, J=7.9 Hz, 1H), 7.22 (d, J=7.7 Hz, 1H), 3.85-3.75 (m, 2H), 2.88 (br. s., 1H), 2.27-2.18 (m, 1H), 1.96 (td, J=4.0, 7.6 Hz, 1H), 1.86-1.76 (m, 1H), 1.70-1.58 (m, 1H), 0.99 (d, J=6.0 Hz, 3H); m/z (ESI) 375.3 (M+H)+.

EXAMPLE 92

5-(2-PHENYLAZETIDIN-1-YL)-N-(1,2,4-THIADIAZOL-5-YL)NAPHTHALENE-2-SULFONAMIDE

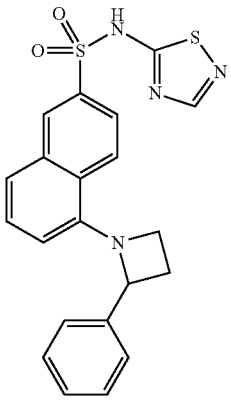 [SMILES: O=S(=O)(Nc1ncns1)c1ccc2c(N3CCC3c3ccccc3)cccc2c1]

The title compound was prepared in an analogous manner to that described for the preparation of Example 83 except that 2-phenylazetidine (Pharmachem Laboratories, Kearny, N.J.) was used in place of 2-phenylpyrrolidine. The desired product, 5-(2-phenylazetidin-1-yl)-n-(1,2,4-thiadiazol-5-yl) naphthalene-2-sulfonamide, was isolated as a yellow solid: $^1$H NMR (400 MHz, DMSO-$d_6$) δ ppm=8.34 (s, 1H), 8.23-8.10 (m, 2H), 7.64 (dd, J=1.9, 9.0 Hz, 1H), 7.34-7.24 (m, 2H), 7.21-7.12 (m, 2H), 7.07 (d, J=1.2 Hz, 2H), 6.92 (d, J=8.3 Hz, 1H), 4.29 (t, J=5.2 Hz, 1H), 3.41-3.32 (m, 1H), 3.22-3.06 (m, 1H), 2.11 (td, J=4.7, 9.2 Hz, 1H), 2.06-1.93 (m, 1H); m/z (ESI) 432.2 (M+H)+.

EXAMPLE 93

5-(2-OXOPYRROLIDIN-1-YL)-N-(1,2,4-THIADIAZOL-5-YL)NAPHTHALENE-2-SULFONAMIDE

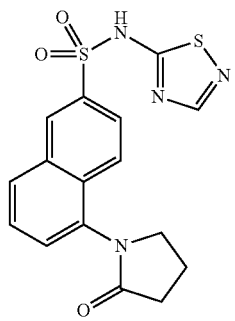 [SMILES: O=C1CCCN1c1cccc2cc(S(=O)(=O)Nc3ncns3)ccc12]

The title compound was prepared in an analagous manner to that described for the preparation of Example 83 except that pyrrolidin-2-one (Sigma-Aldrich, St. Louis, Mo.) was used in place of 2-phenylpyrrolidine. The desired product, 5-(2-oxopyrrolidin-1-yl)-N-(1,2,4-thiadiazol-5-yl)naphthalene-2-sulfonamide, was isolated as an off-white solid: $^1$H NMR (400 MHz, DMSO-$d_6$) δ ppm=8.54 (s, 1H), 8.44 (s, 1H), 8.18 (d, J=8.1 Hz, 1H), 7.94 (d, J=8.9 Hz, 1H), 7.81 (d, J=8.9 Hz, 1H), 7.74-7.67 (m, 1H), 7.66-7.61 (m, 1H), 3.83 (t, J=6.6 Hz, 2H), 2.59-2.52 (m, 2H), 2.30-2.20 (m, 2H); m/z (ESI) 375.2 (M+H)+.

EXAMPLE 94

5-(2-METHOXYPHENYL)-N-(1,2,4-THIADIAZOL-5-YL)NAPHTHALENE-2-SULFONAMIDE

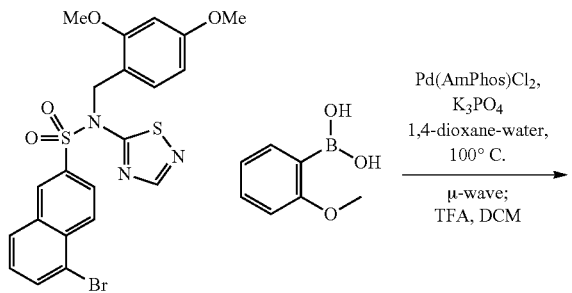

-continued

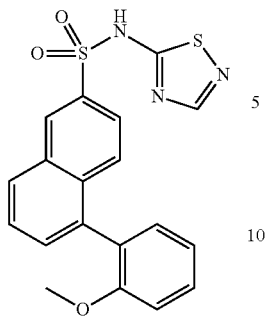

A vial was charged with 5-bromo-N-(2,4-dimethoxybenzyl)-N-(1,2,4-thiadiazol-5-yl)naphthalene-2-sulfonamide (INTERMEDIATE D) (73.69 mg, 0.142 mmol), 2-methoxyphenylboronic acid (43.0 mg, 0.283 mmol), Pd(AmPhos)$_2$Cl$_2$ (5.01 mg, 7.08 μmol), potassium phosphate (90 mg, 0.425 mmol), 1,4-dioxane (708 μl), and water (236 μl). The vial was sealed and heated in a microwave reactor for 30 min at 100° C. The mixture was diluted with water and extracted with EtOAc (3×). The combined organic extracts were concentrated. The residue was dissolved in DCM (1 mL) and TFA (0.5 mL). After 2 h, the mixture was diluted with MeOH and filtered through diatomaceous earth with the aid of DCM. The filtrate was concentrated. The residue was purified twice by chromatography on silica gel (12-g columns, first with 0 to 5% MeOH/DCM, then with 2.5% MeOH/DCM), and the resulting material was dissolved in DCM and loaded onto a 1-g PE-AX ion exchange column (Biotage AB, Uppsala, Sweden). The column was flushed with 1:1 MeOH/DCM, then eluted with 10% HCl/MeOH (made by dissolving 1 mL on conc. HCl in 9 mL of MeOH). The acidic fraction was concentrated to give 5-(2-methoxyphenyl)-N-(1,2,4-thiadiazol-5-yl)naphthalene-2-sulfonamide (41.62 mg, 0.105 mmol, 74.0% yield) as an off-white solid: $^1$H NMR (400 MHz, DMSO-d$_6$) δ ppm=8.59-8.44 (m, 2H), 8.20 (d, J=8.2 Hz, 1H), 7.77-7.66 (m, 2H), 7.58 (d, J=8.9 Hz, 1H), 7.54-7.45 (m, 2H), 7.26-7.16 (m, 2H), 7.13-7.05 (m, 1H), 3.63 (s, 3H); m/z (ESI) 398.2 (M+H)$^+$.

EXAMPLE 95

5-(PYRROLIDIN-2-YL)-N-(1,2,4-THIADIAZOL-5-YL)NAPHTHALENE-2-SULFONAMIDE 2,2,2-TRIFLUOROACETATE

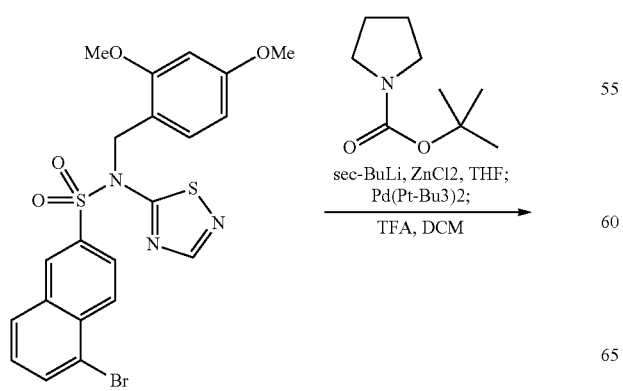

-continued

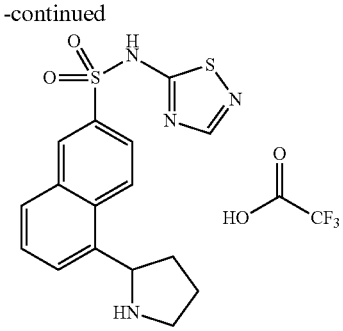

A vial was flushed with Ar (g), then tert-butyl 1-pyrrolidinecarboxylate (84 μl, 0.480 mmol) and THF (2402 μl) were added to give a clear, colorless solution. The vial was cooled in a −35 to −30° C. dry ice-acetone bath for 10 min. sec-butyllithium (1.4 M in cyclohexane) (343 μl, 0.480 mmol) was then added dropwise over 1 min. The resulting cloudy, yellow solution was stirred for 10 min in the cooling bath, then zinc chloride (1M in diethyl ether) (360 μl, 0.360 mmol) was added dropwise. The cooling bath was then removed. The mixture was stirred for 30 min to give a clear, colorless solution. 5-Bromo-N-(2,4-dimethoxybenzyl)-N-(1,2,4-thiadiazol-5-yl)naphthalene-2-sulfonamide (Intermediate D, 125 mg, 0.240 mmol) and bis(tri-t-butylphosphine)palladium(0) (12.28 mg, 0.024 mmol) were then added to give a cloudy mixture. The vial was sealed and placed in a 60° C. heating bath for 3 h. After cooling to room temperature, a 30% aq. ammonium hydroxide solution (0.5 mL) was added, and the mixture was stirred vigorously for 30 min. The mixture was then filtered through diatomaceous earth with the aid of diethyl ether. The filtrate was washed with 0.5 N aq. HCl (10 mL), washed with brine, dried over magnesium sulfate, filtered, and concentrated. The residue was purified by chromatography on silica gel (12-g column, 10 to 50% EtOAc/Heptane) to give 105.5 mg of a white solid. This material was dissolved in DCM (1 mL) to give a clear, colorless solution. TFA (0.5 mL) was added, and the resulting mixture was stirred for 2 h. The mixture was diluted with MeOH and filtered through diatomaceous earth with MeOH. The filtrate was concentrated to give about 74 mg of an oil. The residue was taken up in DCM/MeOH, and this solution was purified by reverse-phase HPLC (5 to 50% CH$_3$CN/H$_2$O with 0.1% TFA). The fractions containing the desired product were combined and concentrated under a vacuum. The residue was concentrated from DCM to give 5-(pyrrolidin-2-yl)-N-(1,2,4-thiadiazol-5-yl)naphthalene-2-sulfonamide 2,2,2-trifluoroacetate (36.41 mg, 0.077 mmol, 46.9% yield) as a white solid: $^1$H NMR (400 MHz, DMSO-d$_6$) δ ppm=9.48 (br. s., 1H), 8.82 (br. s., 1H), 8.56 (s, 1H), 8.39 (t, J=4.5 Hz, 2H), 8.28 (d, J=8.4 Hz, 1H), 7.97-7.88 (m, 2H), 7.78-7.70 (m, 1H), 5.51-5.37 (m, J=7.8, 7.8 Hz, 1H), 3.42 (br. s., 2H), 2.49-2.41 (m, 1H), 2.29-2.06 (m, 3H); m/z (ESI) 361.2 (M+H)+.

EXAMPLE 96

5-(1-(PYRIDIN-2-YL)PYRROLIDIN-2-YL)-N-(1,2,4-THIADIAZOL-5-YL)NAPHTHALENE-2-SULFONAMIDE

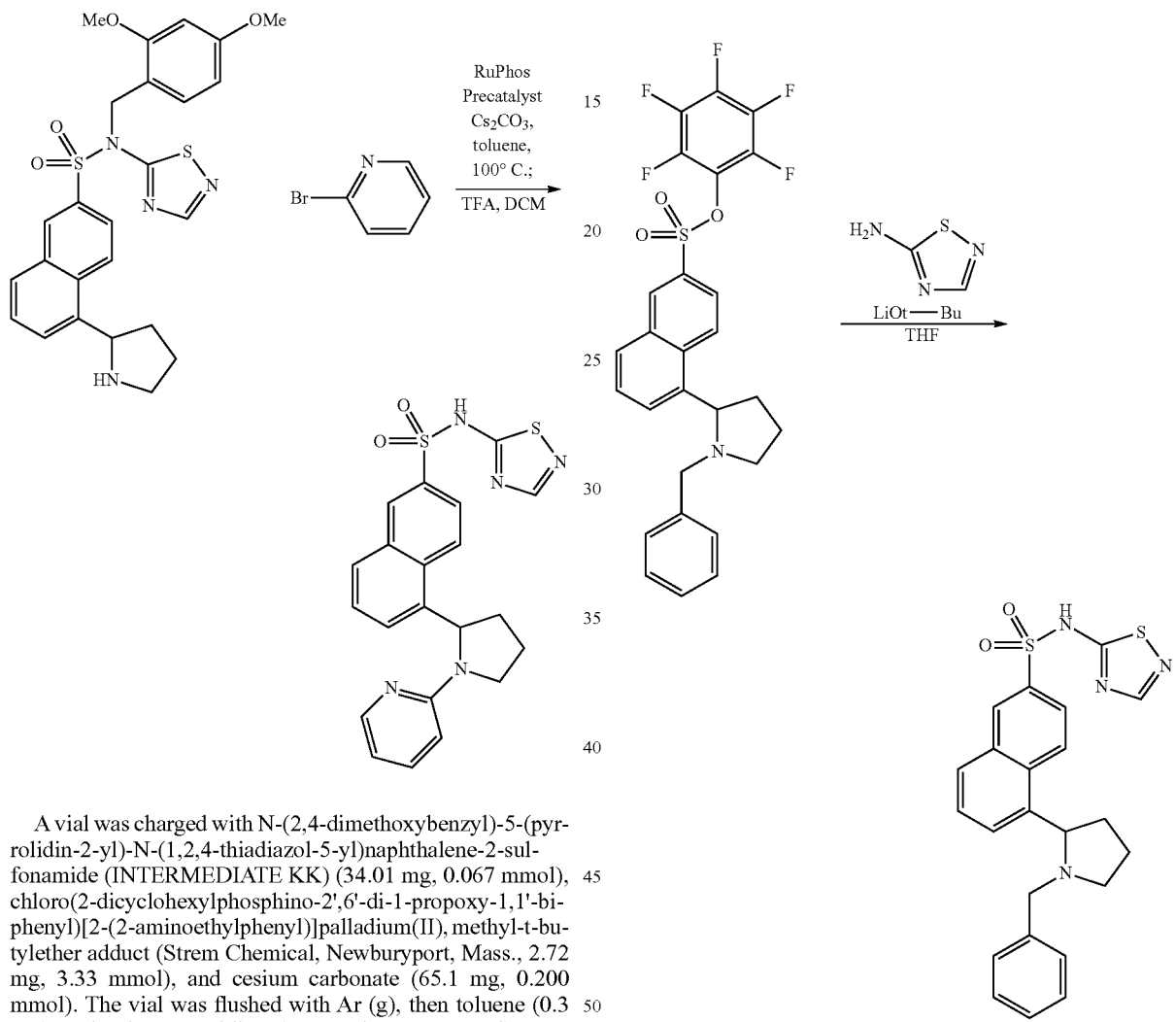

A vial was charged with N-(2,4-dimethoxybenzyl)-5-(pyrrolidin-2-yl)-N-(1,2,4-thiadiazol-5-yl)naphthalene-2-sulfonamide (INTERMEDIATE KK) (34.01 mg, 0.067 mmol), chloro(2-dicyclohexylphosphino-2',6'-di-1-propoxy-1,1'-biphenyl)[2-(2-aminoethylphenyl)]palladium(II), methyl-t-butylether adduct (Strem Chemical, Newburyport, Mass., 2.72 mg, 3.33 mmol), and cesium carbonate (65.1 mg, 0.200 mmol). The vial was flushed with Ar (g), then toluene (0.3 mL) and 2-bromopyridine (19.05 µl, 0.200 mmol) were added. The vial was sealed and placed in a 100° C. heating bath. After 4 h, an additional portion of catalyst (about 3 mg) was added, and the vial was heated for an additional 16 h. Additional portions of catalyst (6 mg) and cesium carbonate (about 55 mg) were added, and the vial was returned to the heat for 5 h. The mixture was cooled to room temperature, diluted with EtOAc, and filtered through diatomaceous earth. The filtrate was concentrated. The residue was purified by chromatography on silica gel (12-g column, 0 to 10% MeOH/DCM) to give 5-(1-(pyridin-2-yl)pyrrolidin-2-yl)-N-(1,2,4-thiadiazol-5-yl)naphthalene-2-sulfonamide (9.7 mg, 0.022 mmol, 33.3% yield) as a yellow solid: $^1$H NMR (400 MHz, DMSO-$d_6$) δ ppm=8.54 (d, J=2.0 Hz, 1H), 8.45 (s, 1H), 8.38 (d, J=9.2 Hz, 1H), 8.12 (d, J=8.2 Hz, 1H), 8.02-7.88 (m, 2H), 7.72 (br. s., 1H), 7.56-7.48 (m, 1H), 7.33 (d, J=6.9 Hz, 1H), 6.79 (t, J=6.4 Hz, 1H), 6.61 (br. s., 1H), 5.91 (d, J=7.8 Hz, 1H), 4.04 (t, J=8.6 Hz, 1H), 3.77-3.62 (m, 1H), 2.71-2.59 (m, 1H), 2.17-2.05 (m, 1H), 2.01-1.84 (m, 2H); m/z (ESI) 438.4 (M+H)+.

EXAMPLE 97

5-(1-BENZYLPYRROLIDIN-2-YL)-N-(1,2,4-THIADIAZOL-5-YL)NAPHTHALENE-2-SULFONAMIDE

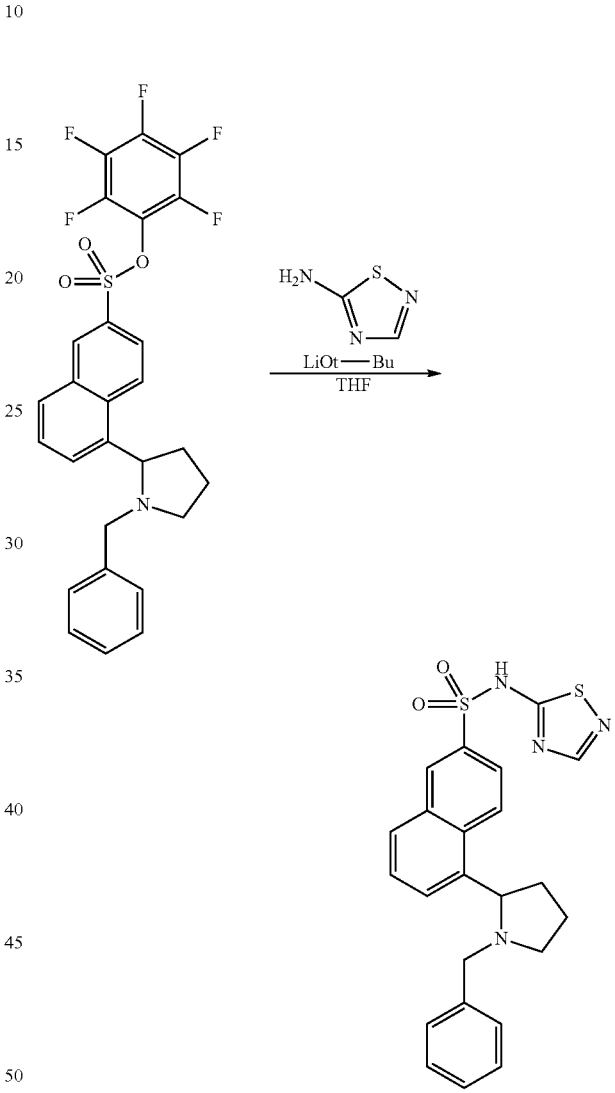

A flask was charged with perfluorophenyl 5-(1-benzylpyrrolidin-2-yl)naphthalene-2-sulfonate (INTERMEDIATE LL) (24.8 mg, 0.046 mmol), 1,2,4-thiadiazol-5-amine (5.64 mg, 0.056 mmol), and THF (465 µl) to give a clear, colorless solution. The flask was cooled in an ice-bath for 5 min, then lithium 2-methylpropan-2-olate (1M in hexane) (102 µl, 0.102 mmol) was added dropwise. After 1 h, the mixture was loaded directly onto a 5-g silica gel loading column with the aid of DCM. The column was dried under vacuum, then eluted onto a prequilibrated 12-g silica gel column with 0 to 10% MeOH/DCM to give 5-(1-benzylpyrrolidin-2-yl)-N-(1,2,4-thiadiazol-5-yl)naphthalene-2-sulfonamide (12.69 mg, 0.028 mmol, 60.6% yield) as a white solid: $^1$H NMR (400 MHz, DMSO-$d_6$) δ ppm=8.46-8.33 (m, 2H), 8.07 (d, J=8.0 Hz, 1H), 8.02 (s, 1H), 7.97 (d, J=7.1 Hz, 1H), 7.83 (dd, J=1.9, 8.9 Hz, 1H), 7.65 (t, J=7.7 Hz, 1H), 7.34-7.21 (m, 5H), 4.62 (br. s., 1H), 3.91 (d, J=13.0 Hz, 1H), 3.24 (br. s., 4H), 1.97 (d, J=14.1 Hz, 2H), 1.86-1.72 (m, 1H); m/z (ESI) 451.4 (M+H)+.

EXAMPLE 98

5-(1-BENZYLPYRROLIDIN-2-YL)-N-(THIAZOL-2-YL)NAPHTHALENE-2-SULFONAMIDE

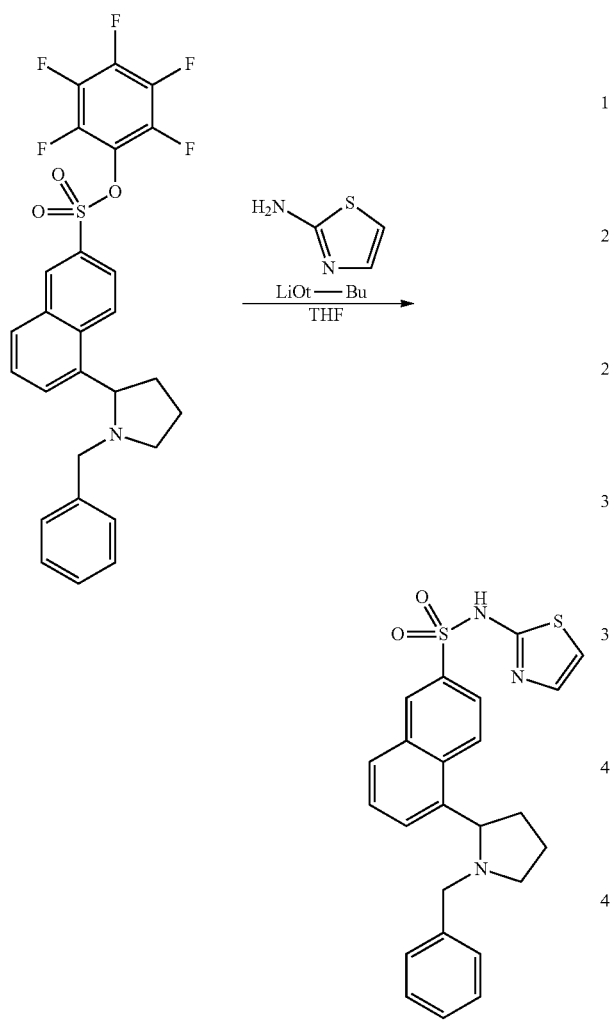

A flask was charged with perfluorophenyl 5-(1-benzylpyrrolidin-2-yl)naphthalene-2-sulfonate (Intermediate LL, 21.5 mg, 0.040 mmol), thiazol-2-amine (4.84 mg, 0.048 mmol), and THF (403 μl) to give a clear, colorless solution. The flask was cooled in an dry ice-acetone bath for 5 min, then lithium 2-methylpropan-2-olate (1M in hexane) (89 μl, 0.089 mmol) was added dropwise. The resulting mixture was stirred for 1 min, then the flask was lowered into an ice-bath. After 1 h, the mixture was warmed to room temperature then was loaded directly onto a 5-g silica gel loading column with the aid of DCM. The column was dried under vacuum, then eluted onto a prequilibrated 12-g column with 0 to 10% MeOH/DCM to give 5-(1-benzylpyrrolidin-2-yl)-N-(thiazol-2-yl)naphthalene-2-sulfonamide (15.85 mg, 0.035 mmol, 87% yield) as an off-white solid: $^1$H NMR (400 MHz, DMSO-$d_6$) δ ppm=12.97-12.23 (m, 1H), 8.51 (d, J=9.1 Hz, 1H), 8.46 (d, J=1.9 Hz, 1H), 8.09-7.96 (m, 2H), 7.83 (dd, J=2.1, 9.0 Hz, 1H), 7.69-7.61 (m, 1H), 7.29 (d, J=4.4 Hz, 4H), 7.27-7.24 (m, 1H), 7.24-7.20 (m, 1H), 6.83 (d, J=4.6 Hz, 1H), 4.16 (t, J=8.2 Hz, 1H), 3.78 (d, J=13.2 Hz, 1H), 3.15 (d, J=13.2 Hz, 1H), 3.07 (td, J=4.6, 9.1 Hz, 1H), 2.47-2.38 (m, 1H), 2.30 (q, J=8.6 Hz, 1H), 1.89-1.79 (m, 2H), 1.68-1.57 (m, 1H); m/z (ESI) 450.4 (M+H)+.

EXAMPLE 99

5-(benzylamino)-N-(1,2,4-thiadiazol-5-yl)naphthalene-2-sulfonamide

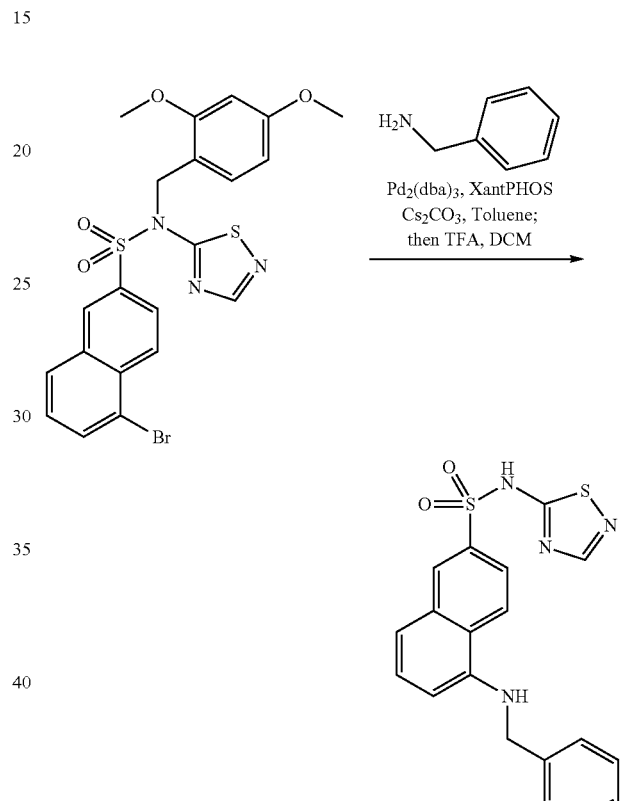

A vial was charged with 5-bromo-N-(2,4-dimethoxybenzyl)-N-(1,2,4-thiadiazol-5-yl)naphthalene-2-sulfonamide (Intermediate D, 0.100 g, 0.192 mmol), Pd$_2$(dba)$_3$ (0.018 g, 0.019 mmol), Xantphos (0.022 g, 0.038 mmol), and toluene (1.922 ml). Benzylamine (0.042 ml, 0.384 mmol) was added and the reaction was stirred for one hour at 100° C. The reaction was filtered through a plug of diatomaceous earth, which was then washed with ethyl acetate. The filtrate was concentrated, dissolved in 1 mL of DCM, and TFA (0.1 ml, 1.298 mmol) was added. The reaction was concentrated and purified via HPLC (50-95% MeCN:H$_2$O with 0.1% TFA modifier) to afford 5-(benzylamino)-N-(1,2,4-thiadiazol-5-yl)naphthalene-2-sulfonamide as a white solid. $^1$H NMR (400 MHz, DMSO-$d_6$) δ ppm=8.48 (s, 1H), 8.42 (d, J=9.1 Hz, 1H), 8.28 (d, J=2.0 Hz, 1H), 7.70 (dd, J=2.0, 9.0 Hz, 1H), 7.39

(d, J=7.6 Hz, 2H), 7.34-7.27 (m, 4H), 7.24-7.17 (m, 1H), 6.51 (dd, J=2.2, 6.6 Hz, 1H), 4.50 (s, 2H). m/z (ESI) 397.3 (M+H)⁺.

EXAMPLE 100

5-(benzyl(methyl)amino)-N-(1,2,4-thiadiazol-5-yl)naphthalene-2-sulfonamide

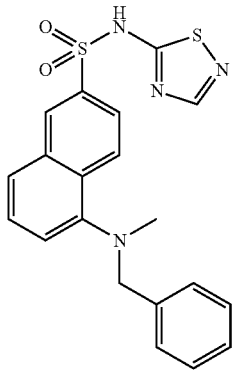 [SMILES: CN(Cc1ccccc1)c1cccc2cc(S(=O)(=O)Nc3ncns3)ccc12]

Example 100 was synthesized in a similar manner as Example 99, using N-methylbenzylamine instead of benzylamine to yield title compound as a white solid. ¹H NMR (400 MHz, DMSO-d₆) δ ppm=8.49-8.39 (m, 3H), 7.82 (td, J=2.1, 8.8 Hz, 2H), 7.54 (t, J=7.8 Hz, 1H), 7.39-7.29 (m, 5H), 7.27-7.21 (m, 1H), 4.27 (s, 2H), 2.73 (s, 3H). m/z (ESI) 411.2 (M+H)⁺.

EXAMPLE 101

5-(1-BENZOYLPYRROLIDIN-2-YL)-N-(THIAZOL-2-YL)NAPHTHALENE-2-SULFONAMIDE

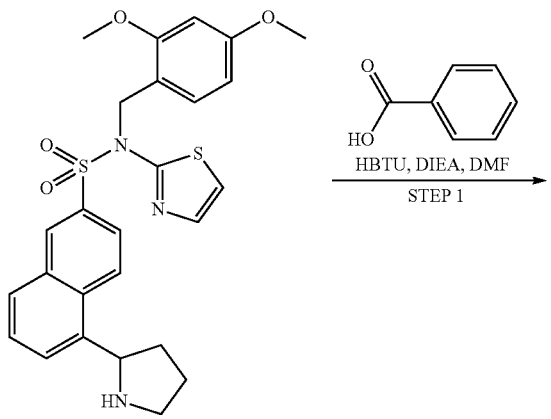

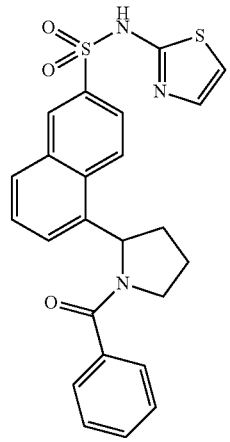

STEP 1: 5-(1-BENZOYLPYRROLIDIN-2-YL)-N-(2,4-DIMETHOXYBENZYL)-N-(THIAZOL-2-YL)NAPHTHALENE-2-SULFONAMIDE

N-(2,4-dimethoxybenzyl)-5-(pyrrolidin-2-yl)-N-(thiazol-2-yl)naphthalene-2-sulfonamide (Intermediate NN, 0.033 g, 0.065 mmol) and HBTU (0.037 g, 0.097 mmol) were dissolved in DMF (0.324 mL). Hunig's base (0.034 mL, 0.194 mmol) and benzoic acid (0.016 g, 0.130 mmol) were added and the reaction was stirred for four hours at room temperature. The reaction was diluted with ethyl acetate and washed with water. The aqueous layer was extracted with ethyl acetate, and the combined organic layers were dried with sodium sulfate, filtered, and concentrated. The material was purified via column chromatography (12 g silica gel column, gradient elution 0 to 100% EtOAc:Heptane) to afford 5-(1-benzoylpyrrolidin-2-yl)-N-(2,4-dimethoxybenzyl)-N-(thiazol-2-yl)naphthalene-2-sulfonamide as an off-white solid. m/z (ESI) 614.3 (M+H)⁺.

STEP 2: 5-(1-BENZOYLPYRROLIDIN-2-YL)-N-(THIAZOL-2-YL)NAPHTHALENE-2-SULFONAMIDE 5-(1-benzoylpyrrolidin-2-yl)-N-(2,4-dimethoxybenzyl)-N-(thiazol-2-yl)naphthalene-2-sulfonamide (0.040 g, 0.065 mmol) was dissolved in DCM and TFA (0.1 mL, 1.298 mmol) was added. The reaction was stirred for 15 minutes at room temperature. The reaction was diluted with methanol and concentrated. The material was triturated in diethyl ether, filtered, and the solids were washed with diethyl ether. The solids were collected and vacuum dried overnight to afford 5-(1-benzoylpyrrolidin-2-yl)-N-(thiazol-2-yl)naphthalene-2-sulfonamide as a white solid. ¹H NMR (400 MHz, DMSO-d₆) δ=12.79 (br. s., 1H), 8.48 (s, 1H), 8.38 (d, J=8.8 Hz, 1H), 8.11-7.95 (m, 1H), 7.87 (d, J=9.3 Hz, 1H), 7.75-7.57 (m, 4H), 7.49 (br. s., 3H), 7.26 (br. s., 1H), 7.17-6.96 (m, 1H), 6.84 (d, J=4.2 Hz, 1H), 5.94 (br. s., 1H), 3.90 (br. s., 1H), 3.58 (br. s., 1H), 2.70-2.58 (m, 1H), 1.89 (br. s., 2H), 1.74 (br. s., 1H). m/z (ESI) 464.2 (M+H)⁺.

EXAMPLE 102

5-(1-(TETRAHYDRO-2H-PYRAN-4-YL)PYRROLIDIN-2-YL)-N-(THIAZOL-2-YL)NAPHTHALENE-2-SULFONAMIDE 2,2,2-TRIFLUOROACETATE

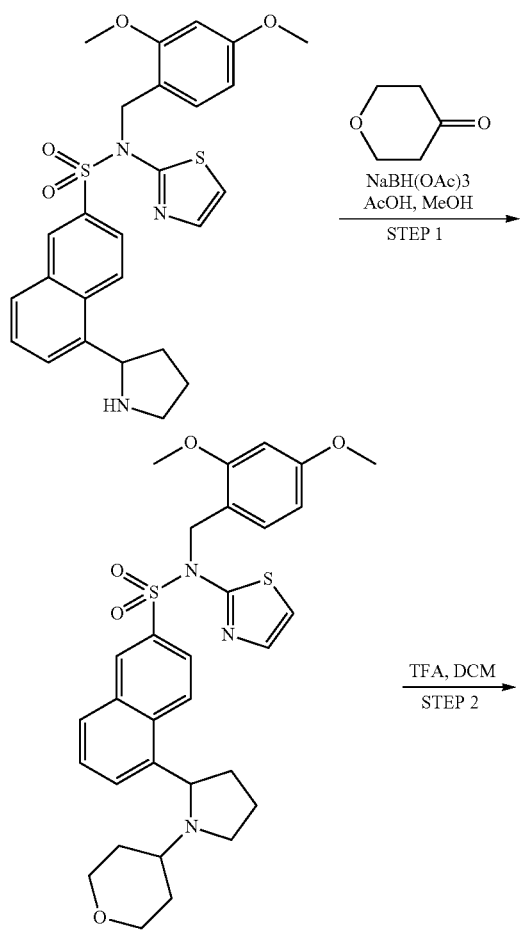

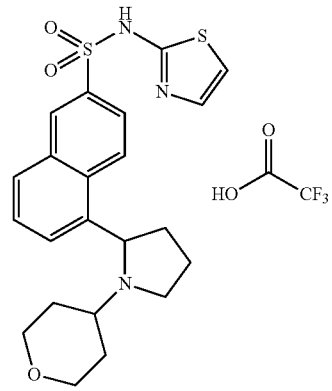

STEP 1: N-(2,4-DIMETHOXYBENZYL)-5-(1-(TETRAHYDRO-2H-PYRAN-4-YL)PYRROLIDIN-2-YL)-N-(THIAZOL-2-YL)NAPHTHALENE-2-SULFONAMIDE

N-(2,4-dimethoxybenzyl)-5-(pyrrolidin-2-yl)-N-(thiazol-2-yl)naphthalene-2-sulfonamide (Intermediate NN, 0.033 g, 0.065 mmol) and tetrahydro-4h-pyran-4-one (8.97 μl, 0.097 mmol) were dissolved in DCM (0.648 ml). Sodium triacetoxyborohydride (0.041 g, 0.194 mmol) and acetic acid (5.56 μl, 0.097 mmol) were added and the reaction was stirred for three hours at room temperature. 1M sodium hydroxide solution was added followed by ethyl acetate, and the reaction was stirred for one hour. The aqueous layer was extracted with ethyl acetate, and the combined organic layers were dried with sodium sulfate, filtered, and concentrated to afford crude N-(2,4-dimethoxybenzyl)-5-(1-(tetrahydro-2H-pyran-4-yl)pyrrolidin-2-yl)-N-(thiazol-2-yl)naphthalene-2-sulfonamide as an off-white solid. m/z (ESI) 594.3 (M+H)⁺.

STEP 2: 5-(1-(TETRAHYDRO-2H-PYRAN-4-YL)PYRROLIDIN-2-YL)-N-(THIAZOL-2-YL)NAPHTHALENE-2-SULFONAMIDE 2,2,2-TRIFLUOROACETATE

N-(2,4-dimethoxybenzyl)-5-(1-(tetrahydro-2H-pyran-4-yl)pyrrolidin-2-yl)-N-(thiazol-2-yl)naphthalene-2-sulfonamide (0.038 g, 0.065 mmol) was dissolved in DCM (1 mL) and TFA (0.1 ml, 1.298 mmol) was added. The reaction was stirred for 30 minutes at room temperature. The reaction was concentrated, triturated with diethyl ether, and filtered. The solids were washed with diethyl ether and vacuum dried overnight to afford 5-(1-(tetrahydro-2H-pyran-4-yl)pyrrolidin-2-yl)-N-(thiazol-2-yl)naphthalene-2-sulfonamide 2,2,2-trifluoroacetate as a white solid. ¹H NMR (400 MHz, DMSO-d₆) δ ppm=12.79 (br. s., 1H), 9.65 (br. s., 1H), 8.55 (br. s., 1H), 8.43 (d, J=9.1 Hz, 1H), 8.27 (d, J=7.2 Hz, 1H), 8.04 (d, J=7.3 Hz, 1H), 7.91 (d, J=8.9 Hz, 1H), 7.82-7.72 (m, 1H), 7.27 (d, J=4.6 Hz, 1H), 6.85 (d, J=4.5 Hz, 1H), 5.61 (d, J=6.1 Hz, 1H), 3.91-3.68 (m, 5H), 3.63-3.45 (m, 3H), 3.13 (t, J=11.3 Hz, 3H), 2.71-2.57 (m, 2H), 2.20 (br. s., 2H), 1.98 (br. s., 1H), 1.84 (d, J=10.5 Hz, 1H), 1.65 (br. s., 2H), 1.51 (br. s., 1H). m/z (ESI) 444.2 (M+H)+.

EXAMPLE 103

(S)-5-(1-(TETRAHYDRO-2H-PYRAN-4-YL)PYRROLIDIN-2-YL)-N-(THIAZOL-2-YL)NAPHTHALENE-2-SULFONAMIDE COMPOUND WITH DIETHYLAMINE (1:1)

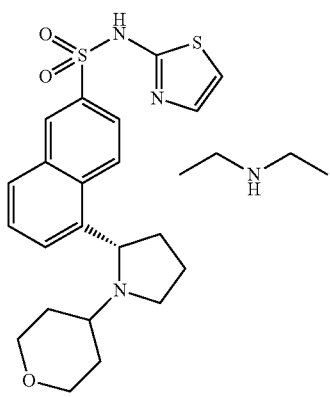

5-(1-(tetrahydro-2H-pyran-4-yl)pyrrolidin-2-yl)-N-(thiazol-2-yl)naphthalene-2-sulfonamide (Example 131) was purified via SFC chiral chromatography (Chiralpak AS-H, 2×15 cm column, 53% methanol with 0.2% diethylamine/$CO_2$, 100 bar (10,000 kPA), 60 ml/min) to afford (S)-5-(1-(tetrahydro-2H-pyran-4-yl)pyrrolidin-2-yl)-N-(thiazol-2-yl)naphthalene-2-sulfonamide compound with diethylamine (1:1) as a light brown solid (stereochemistry randomly assigned). $^1$H NMR (400 MHz, DMSO-$d_6$) δ ppm=8.33 (s, 1H), 8.26 (d, J=8.8 Hz, 1H), 7.94-7.83 (m, 2H), 7.78 (d, J=8.6 Hz, 1H), 7.53 (t, J=7.5 Hz, 1H), 7.00 (br. s., 1H), 6.54 (br. s., 1H), 4.53 (dd, J=4.8, 9.1 Hz, 1H), 3.80 (d, J=11.3 Hz, 1H), 3.65 (d, J=11.4 Hz, 1H), 3.31 (br. s., 2H), 3.23 (d, J=5.8 Hz, 1H), 3.19-3.04 (m, 3H), 2.92 (q, J=7.2 Hz, 3H), 2.71-2.54 (m, 3H), 2.42-2.29 (m, 1H), 1.74 (d, J=8.6 Hz, 4H), 1.55-1.42 (m, 3H), 1.15 (t, J=7.2 Hz, 8H). m/z (ESI) 444.2 (M+H)+.

EXAMPLE 104

(R)-5-(1-(TETRAHYDRO-2H-PYRAN-4-YL)PYRROLIDIN-2-YL)-N-(THIAZOL-2-YL)NAPHTHALENE-2-SULFONAMIDE COMPOUND WITH DIETHYLAMINE (1:1)

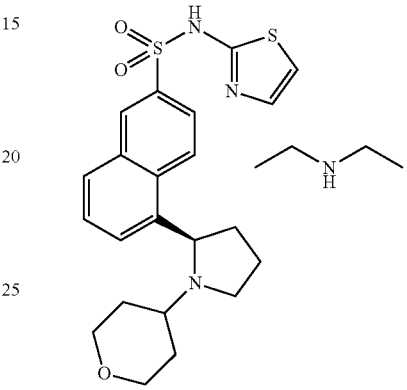

5-(1-(tetrahydro-2H-pyran-4-yl)pyrrolidin-2-yl)-N-(thiazol-2-yl)naphthalene-2-sulfonamide (Example 102) was purified via SFC chiral chromatography (Chiralpak AS-H, 2×15 cm column, 53% methanol with 0.2% diethylamine/CO2, 100 bar (10,000 kPA), 60 ml/min) to afford (R)-5-(1-(tetrahydro-2H-pyran-4-yl)pyrrolidin-2-yl)-N-(thiazol-2-yl)naphthalene-2-sulfonamide compound with diethylamine (1:1) as a light brown solid (stereochemistry randomly assigned). $^1$H NMR (400 MHz, DMSO-$d_6$) δ ppm=8.31 (s, 1H), 8.24 (d, J=9.1 Hz, 1H), 7.86 (d, J=7.6 Hz, 2H), 7.78 (d, J=8.9 Hz, 1H), 7.51 (t, J=7.7 Hz, 1H), 6.95 (br. s., 1H), 6.48 (br. s., 1H), 4.53 (dd, J=4.9, 8.9 Hz, 1H), 3.80 (d, J=10.3 Hz, 1H), 3.65 (d, J=10.0 Hz, 1H), 3.32 (br. s., 2H), 3.25-3.19 (m, 1H), 3.18-3.04 (m, 2H), 2.91 (q, J=7.2 Hz, 4H), 2.69-2.53 (m, 3H), 2.35 (td, J=9.6, 19.4 Hz, 1H), 1.74 (d, J=8.7 Hz, 4H), 1.54-1.43 (m, 3H), 1.15 (t, J=7.2 Hz, 8H). m/z (ESI) 444.4 (M+H)+.

EXAMPLE 105

5-(1-(CYANOMETHYL)-5-FLUORO-1H-INDOL-2-YL)-N-(PYRIMIDIN-4-YL)NAPHTHALENE-2-SULFONAMIDE

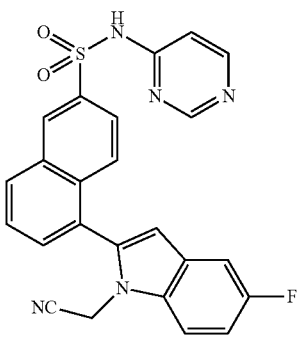 [SMILES: N#CCn1c(-c2cccc3cc(S(=O)(=O)Nc4ccncn4)ccc23)cc2cc(F)ccc21]

A solution of INTERMEDIATE SS (0.137 g, 0.254 mmol) in 1 mL of THF was treated with bromoacetonitrile (0.053 ml, 0.763 mmol) followed by dropwise addition of lithium tert-butoxide (1.0 M solution in THF) (0.763 ml, 0.763 mmol). After stirring for one hour, LC/MS showed incomplete addition, so an additional portion of bromoacetonitrile (0.053 ml, 0.763 mmol) and lithium tert-butoxide (1.0 M solution in THF) (0.763 ml, 0.763 mmol) were added. After stirring for one hour, LC/MS showed mostly product, so TFA (0.392 ml, 5.09 mmol) was added, and the reaction mixture was heated to 100° C. for 4 hours. LC/MS showed some deprotected product, so the reaction mixture was concentrated. Purification of the crude residue by reverse phase column chromatography [$C_{18}$ 20 g, 10 to 100% (0.1% NH$_4$OH in MeOH)/(0.1% NH$_4$OH in water)] gave 5-(1-(cyanomethyl)-5-fluoro-1H-indol-2-yl)-N-(pyrimidin-4-yl)naphthalene-2-sulfonamide (0.019 g, 0.042 mmol, 16.33% yield). $^1$H NMR (MeCN-d$_3$) δ ppm: 8.73 (s, 1H), 8.52 (s, 1H), 8.23-8.31 (m, 2H), 7.92 (dd, J=8.9, 2.0 Hz, 1H), 7.76-7.84 (m, 3H), 7.56 (dd, J=9.0, 4.4 Hz, 1H), 7.42 (dd, J=9.5, 2.5 Hz, 1H), 7.17 (td, J=9.2, 2.5 Hz, 1H), 7.10 (d, J=6.2, 1H), 6.74 (s, 1H), 4.68-4.97 (m, 2H). m/z (ESI) 458.0 (M+H)+.

EXAMPLE 106

5-(5-FLUORO-1-METHYL-1H-INDOL-2-YL)-N-(PYRIMIDIN-4-YL)NAPHTHALENE-2-SULFONAMIDE

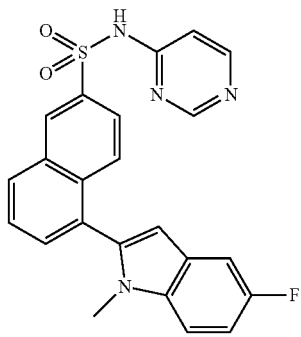 [SMILES: Cn1c(-c2cccc3cc(S(=O)(=O)Nc4ccncn4)ccc23)cc2cc(F)ccc21]

A solution of INTERMEDIATE SS (0.112 g, 0.208 mmol) in 1 mL of THF was treated with lithium tert-butoxide (1.0 M solution in THF) (0.229 ml, 0.229 mmol) and was allowed to stir for 10 minutes. Iodomethane (0.016 ml, 0.260 mmol) was added, and the reaction mixture was allowed to stir for an additional 2 hours. LC/MS showed mostly product, so TFA (0.320 ml, 4.16 mmol) was added, and the reaction mixture was heated to 100° C. for 4 hours. LC/MS showed some deprotected product, so the reaction mixture was concentrated. Purification of the crude residue by reverse phase column chromatography [10 to 100% (0.1% NH$_4$OH in MeOH)/(0.1% NH$_4$OH in water)] gave 5-(5-fluoro-1-methyl-1H-indol-2-yl)-N-(pyrimidin-4-yl)naphthalene-2-sulfonamide (0.008 g, 0.018 mmol, 8.90% yield). $^1$H NMR (MeCN-d$_3$) δ ppm: 8.71 (s, 1H), 8.53 (s, 1H), 8.29 (d, J=6.1 Hz, 1H), 8.23 (dd, J=6.7, 2.7 Hz, 1H), 7.90 (dd, J=9.0, 2.0 Hz, 1H), 7.70-7.82 (m, 3H), 7.45 (dd, J=8.9, 4.5 Hz, 1H), 7.34 (dd, J=9.8, 2.5 Hz, 1H), 7.00-7.14 (m, 2H), 6.59 (s, 1H), 3.45 (s, 3H). m/z (ESI) 433.0 (M+H)+.

EXAMPLE 107

N-(5-FLUOROTHIAZOL-2-YL)-5-(2-METHOXY-4-(TRIFLUOROMETHYL)PHENYL)NAPHTHALENE-2-SULFONAMIDE

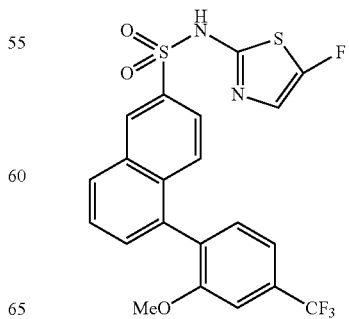

A microwave vial charged with PdCl₂(dppf)-CH₂Cl₂ adduct (0.039 g, 0.048 mmol), (2-methoxy-4-(trifluoromethyl)phenyl)boronic acid (0.319 g, 1.449 mmol), INTERMEDIATE TT (0.500 g, 0.966 mmol), potassium carbonate (0.401 g, 2.90 mmol), and 3 mL of EtOH was heated to 150° C. in the microwave for 30 minutes. LC/MS showed deprotected product, so the reaction mixture was concentrated. Purification of the crude residue by reverse phase column chromatography [25 to 100% (0.1% NH₄OH in MeOH)/(0.1% NH₄OH in water)] gave N-(5-fluorothiazol-2-yl)-5-(2-methoxy-4-(trifluoromethyl)phenyl)naphthalene-2-sulfonamide (0.048 g, 0.099 mmol, 10.30% yield). ¹H NMR (DMSO-d₆) δ ppm: 8.50 (s, 1H), 8.21 (d, J=8.4 Hz, 1H), 7.66-7.76 (m, 2H), 7.50-7.56 (m, 2H), 7.47 (s, 3H), 7.26 (s, 1H), 3.74 (s, 3H). m/z (ESI) 483.0 (M+H)+.

EXAMPLE 108

N-(5-FLUOROTHIAZOL-2-YL)-5-(2-(1,2,3,6-TETRAHYDROPYRIDIN-4-YL)-4-(TRIFLUOROMETHYL)PHENYL)NAPHTHALENE-2-SULFONAMIDE

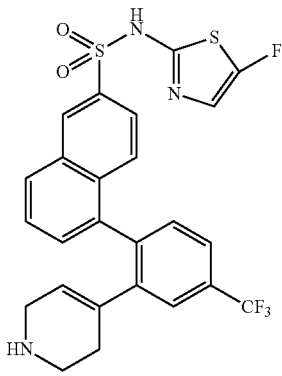 [SMILES: O=S(=O)(Nc1ncc(F)s1)c1ccc2c(-c3ccc(C(F)(F)F)cc3C3=CCNCC3)cccc2c1]

A solution of PdCl₂(dppf)-CH₂Cl₂ adduct (0.270 g, 0.331 mmol), INTERMEDIATE VV (1.500 g, 3.31 mmol), INTERMEDIATE TT (1.712 g, 3.31 mmol), and potassium carbonate (1.829 g, 13.24 mmol) in 10 mL DMF was heated to 120° C. overnight. LC/MS showed some product (without the —SEM group), so the reaction mixture was diluted with DCM and filtered through a plug of diatomaceous earth. The filtrate was concentrated and the crude residue was treated with 4N HCl in dioxane (8.27 ml, 33.1 mmol) and was allowed to stir at room temperature overnight. LC/MS showed product, so the reaction mixture was concentrated. Purification of the crude residue by reverse phase column chromatography [10 to 100% (0.1% NH₄OH in MeOH)/(0.1% NH₄OH in water)] gave N-(5-fluorothiazol-2-yl)-5-(2-(1,2,3,6-tetrahydropyridin-4-yl)-4-(trifluoromethyl)phenyl)naphthalene-2-sulfonamide (0.035 g, 0.066 mmol, 1.982% yield). ¹H NMR (DMSO-d₆) δ ppm: 8.39 (s, 1H), 8.15 (d, J=8.3 Hz, 1H), 7.67-7.84 (m, 4H), 7.58-7.66 (m, 1H), 7.41-7.56 (m, 3H), 6.65 (s, 1H), 5.68 (br. s., 1H), 3.40-3.47 (m, 2H), 2.72-2.89 (m, 2H), 2.55-2.68 (m, 2H). m/z (ESI) 534.0 (M+H)+.

EXAMPLE 109

N-(5-FLUOROTHIAZOL-2-YL)-5-(2-(1-METHYLPIPERIDIN-4-YL)-4-(TRIFLUOROMETHYL)PHENYL)NAPHTHALENE-2-SULFONAMIDE

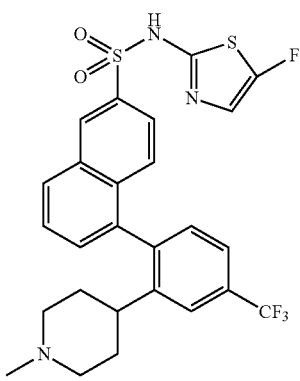 [SMILES: CN1CCC(c2cc(C(F)(F)F)ccc2-c2cccc3cc(S(=O)(=O)Nc4ncc(F)s4)ccc23)CC1]

A solution of INTERMEDIATE UU (0.230 g, 0.407 μmol), PdCl₂(dppf)-CH₂Cl₂ adduct (0.033 g, 0.041 μmol), INTERMEDIATE WW (0.164 g, 0.41 mmol), and potassium phosphate (0.259 g, 1.220 mmol) in 3 mL dioxane/1.5 mL water was heated to 100° C. for 1 hour and then at 80° C. overnight. LC/MS showed mostly product, so the reaction mixture was cooled to room temperature and the aqueous layer was discarded. The reaction mixture was treated with 4N HCl in dioxane (1.017 ml, 4.07 mmol) and was heated to 90° C. for one hour. LC/MS showed mostly product, so the reaction mixture was concentrated. Purification of the crude residue by reverse phase column chromatography [Redisep Gold C-18, 10 to 100% (0.1% NH₄OH in MeOH)/(0.1% NH₄OH in water)] gave 5-(2-(1-methylpiperidin-4-yl)-4-(trifluoromethyl)phenyl)-N-(thiazol-2-yl)naphthalene-2-sulfonamide (2.7 mg, 1.1%). ¹H NMR (d₆-acetone) δ ppm: 8.53 (s, 1H), 8.14 (d, J=8.3 Hz, 1H), 7.88 (s, 1H), 7.81 (d, J=8.9 Hz, 1H), 7.62-7.71 (m, 2H), 7.49 (d, J=7.0 Hz, 1H), 7.41 (d, J=7.9 Hz, 1H), 7.34 (d, J=8.9 Hz, 1H), 6.67 (s, 1H), 3.04-3.22 (m, 2H), 2.39-2.51 (m, 4H), 2.08-2.29 (m, 4H), 1.57-1.83 (m, 2H). m/z (ESI) 598.2 (M+H)+.

EXAMPLE 110

N-(5-FLUOROTHIAZOL-2-YL)-5-(2-(1-METHYL-1H-IMIDAZOL-5-YL)-4-(TRIFLUOROMETHYL)PHENYL)NAPHTHALENE-2-SULFONAMIDE

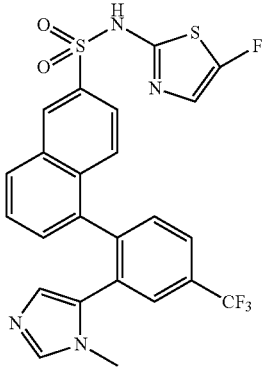 [SMILES: Cn1cncc1-c1cc(C(F)(F)F)ccc1-c1cccc2cc(S(=O)(=O)Nc3ncc(F)s3)ccc12]

Example 110 was synthesized in a similar manner to Example 109, using INTERMEDIATE XX instead of INTERMEDIATE WW. ¹H NMR (acetone) δ ppm: 8.46 (d, J=1.8 Hz, 1H), 8.09 (d, J=8.3 Hz, 1H), 7.90-7.96 (m, 1H), 7.84-7.89 (m, 1H), 7.80 (dd, J=8.9, 1.9 Hz, 1H), 7.73 (d, J=8.0 Hz, 1H), 7.56-7.69 (m, 2H), 7.52 (dd, J=7.1, 1.2 Hz, 1H), 7.26 (s, 1H), 7.03 (s, 1H), 6.49 (d, J=0.9 Hz, 1H), 3.40 (s, 3H). m/z (ESI) 533.0 (M+H)⁺.

EXAMPLE 111

N-(5-FLUOROTHIAZOL-2-YL)-5-(2-(1-METHYL-1H-IMIDAZOL-2-YL)-4-(TRIFLUOROMETHYL)PHENYL)NAPHTHALENE-2-SULFONAMIDE

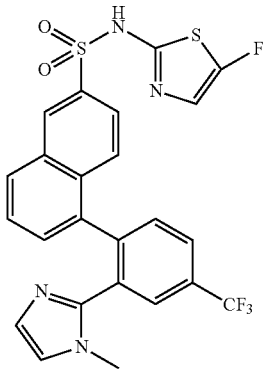 [SMILES: Cn1ccnc1-c1cc(C(F)(F)F)ccc1-c1cccc2cc(S(=O)(=O)Nc3ncc(F)s3)ccc12]

Example 111 was synthesized in a similar manner to Example 109, using Intermediate YY instead of Intermediate WW. ¹H NMR (acetone) δ ppm: 8.46 (s, 1H), 8.09 (d, J=8.3 Hz, 1H), 7.89-7.95 (m, 1H), 7.85-7.89 (m, 1H), 7.80 (d, J=8.9 Hz, 1H), 7.73 (d, J=7.9 Hz, 1H), 7.58-7.69 (m, 2H), 7.52 (d, J=7.1 Hz, 1H), 7.26 (s, 1H), 7.04 (s, 1H), 6.49 (s, 1H), 3.40 (s, 3H). m/z (ESI) 533.0 (M+H)⁺.

EXAMPLE 112

5-(2-(1H-IMIDAZOL-1-YL)-4-(TRIFLUOROMETHYL)PHENYL)-N-(5-FLUOROTHIAZOL-2-YL)NAPHTHALENE-2-SULFONAMIDE

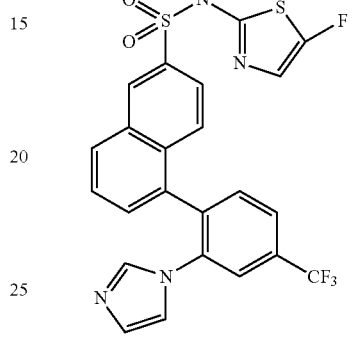

Example 112 was synthesized in a similar manner to Example 109, using Intermediate ZZ instead of Intermediate WW. ¹H NMR (acetone) δ ppm: 8.48 (s, 1H), 8.16 (d, J=8 Hz, 1H), 7.97 (s, 1H), 7.74-7.83 (m, 2H), 7.57-7.68 (m, 4H), 7.43 (s, 1H), 7.05 (s, 1H), 6.93 (s, 1H), 6.64 (s, 1H). m/z (ESI) 519.0 (M+H)+

EXAMPLE 113

N-(5-FLUOROTHIAZOL-2-YL)-5-(2-(PIPERIDIN-4-YL)-4-(TRIFLUOROMETHYL)PHENYL)NAPHTHALENE-2-SULFONAMIDE

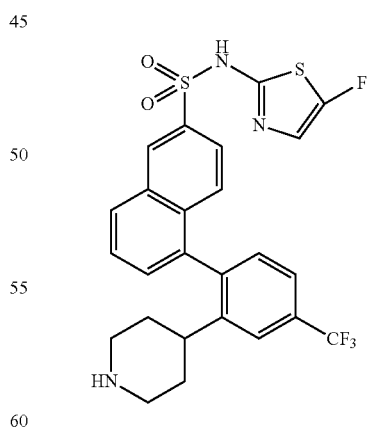

Example 113 was synthesized in a similar manner to Example 109, using Intermediate BBB instead of Intermediate WW. ¹H NMR (DMSO-d₆) δ ppm: 8.40 (s, 1H), 8.17 (d, J=8.2 Hz, 1H), 7.69-7.76 (m, 3H), 7.66 (dd, J=8.1, 7.1 Hz, 1H), 7.39-7.47 (m, 2H), 7.30 (d, J=9.0 Hz, 1H), 6.57 (s, 1H), 3.06-3.24 (m, 2H), 2.55-2.73 (m, 2H), 1.59-2.02 (m, 5H). m/z (ESI) 536.0 (M+H)+.

EXAMPLE 114

5-(5-FLUORO-1H-INDOL-2-YL)-N-(PYRIMIDIN-4-YL)NAPHTHALENE-2-SULFONAMIDE

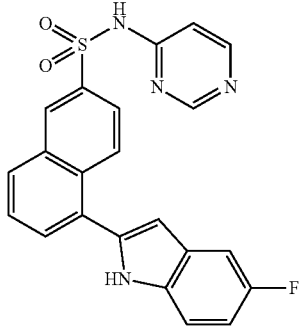 [SMILES: O=S(=O)(Nc1ccncn1)c1ccc2c(-c3cc4cc(F)ccc4[nH]3)cccc2c1]

A microwave vial charged with $PdCl_2$(dppf)-$CH_2Cl_2$ adduct (0.104 g, 0.127 mmol), INTERMEDIATE RR (0.550 g, 1.523 mmol), INTERMEDIATE CCC (0.627 g, 1.269 mmol), potassium carbonate (0.701 g, 5.08 mmol), and 3 mL NMP was heated to 150° C. in the microwave for one hour. LC/MS showed mostly deprotected product, so the reaction mixture was poured into 1N citric acid and was extracted with DCM. The organics were dried over $MgSO_4$ and concentrated. Purification of the crude residue by column chromatography (0 to 100% EtOAc/heptane) gave 5-(5-fluoro-1H-indol-2-yl)-N-(pyrimidin-4-yl)naphthalene-2-sulfonamide (0.220 g, 0.526 mmol, 41.4% yield). $^1$H NMR (MeCN-$d_3$) δ ppm: 8.68 (s, 1H), 8.53 (s, 1H), 8.43 (d, J=9.1 Hz, 1H), 8.28 (d, J=6.0 Hz, 1H), 8.15 (d, J=8.2 Hz, 1H), 7.96 (d, J=9.0 Hz, 1H), 7.85 (d, J=7.1 Hz, 1H), 7.69-7.77 (m, 1H), 7.46 (dd, J=8.9, 4.6 Hz, 1H), 7.34 (dd, J=9.9, 2.5 Hz, 1H), 7.11 (d, J=6.2 Hz, 1H), 7.00 (t, J=9.2 Hz, 1H), 6.76 (s, 1H). m/z (ESI) 419.0 (M+H)+.

EXAMPLE 115

5-(3-METHOXY-[1,1'-BIPHENYL]-4-YL)-N-(PYRIMIDIN-4-YL)NAPHTHALENE-2-SULFONAMIDE

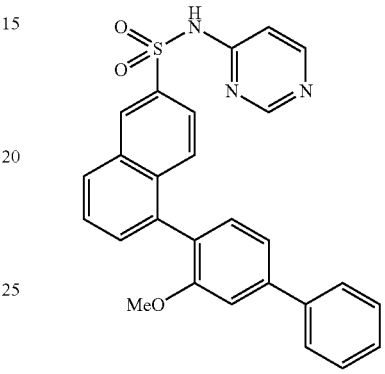

A solution of $PdCl_2$(dppf)-$CH_2Cl_2$ adduct (0.060 g, 0.074 mmol), 1-bromo-4-iodo-2-methoxybenzene (0.347 g, 1.108 mmol), phenylboronic acid (0.135 g, 1.108 mmol), and potassium phosphate (0.941 g, 4.43 mmol) in 3 mL dioxane 1.5 mL water was heated to 90° C. for 1 hour. LC/MS showed mostly product so INTERMEDIATE DDD (0.400 g, 0.739 mmol) was added followed by an additional portion of $PdCl_2$(dppf)-$CH_2Cl_2$ adduct (0.060 g, 0.074 mmol), and the reaction mixture was heated to 90° C. for 1 hour. LC/MS showed product so the reaction mixture was poured into water and extracted with DCM. The organics were dried over $MgSO_4$ and concentrated. Purification of the crude residue by silica gel column chromatography (0 to 100% EtOAc/heptane) gave 5-(3-methoxy-[1,1'-biphenyl]-4-yl)-N-(pyrimidin-4-yl)-N-(2-(trimethylsilyl)ethoxy)methyl)naphthalene-2-sulfonamide (0.060 g, 0.100 mmol, 13.59% yield). m/z (ESI) 598.2 (M+H)$^+$. The material was dissolved in 2 mL THF and was treated with 4N HCl in dioxane (1.004 ml, 4.01 mmol), heated to reflux with a heat gun, then was allowed to stir at room temperature for 2 hours. LC/MS showed mostly product, so the reaction mixture was concentrated. Purification of the crude residue by reverse phase column chromatography [$C_{18}$, 10 to 100% (0.1% $NH_4OH$ in MeOH)/(0.1% $NH_4OH$ in water)] gave 5-(3-methoxy-[1,1'-biphenyl]-4-yl)-N-(pyrimidin-4-yl)naphthalene-2-sulfonamide (0.023 g, 0.049 mmol, 49.0% yield). $^1$H NMR (acetone) δ ppm: 8.75 (s, 1H), 8.66 (s, 1H), 8.45 (d, J=6.0 Hz, 1H), 8.18 (d, J=8.2 Hz, 1H), 7.95 (d, J=9.0 Hz, 1H), 7.71-7.83 (m, 4H), 7.63 (d, J=7.0 Hz, 1H), 7.47-7.55 (m, 2H), 7.38-7.46 (m, 3H), 7.28-7.37 (m, 2H), 3.78 (s, 3H). m/z (ESI) 468.2 (M+H)+.

EXAMPLE 116

5-(2-(1-METHYLPIPERIDIN-4-YL)-4-(TRIFLUO-ROMETHYL)PHENYL)-N-(PYRIMIDIN-4-YL) NAPHTHALENE-2-SULFONAMIDE

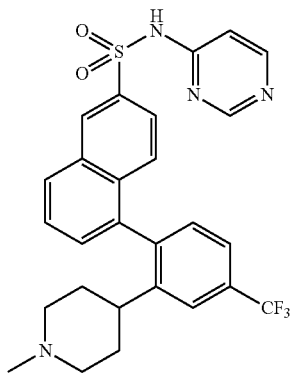 [SMILES: CN1CCC(c2cc(C(F)(F)F)ccc2-c2cccc3cc(S(=O)(=O)Nc4ccncn4)ccc23)CC1]

Example 116 was synthesized in a similar manner to Example 109, using INTERMEDIATE DDD instead of INTERMEDIATE UU. $^1$H NMR (acetone) δ ppm: 8.61 (s, 1H), 8.39 (s, 1H), 8.12 (d, J=8.3 Hz, 1H), 8.02 (d, J=6.0 Hz, 1H), 7.91 (d, J=8.9 Hz, 1H), 7.81 (s, 1H), 7.62-7.70 (m, 2H), 7.49 (d, J=7.0 Hz, 1H), 7.39 (dd, J=16.5, 8.4 Hz, 2H), 6.90 (d, J=6.0 Hz, 1H), 2.79-2.96 (m, 2H), 2.29 (td, J=11.6, 3.1 Hz, 1H), 2.18 (s, 3H), 1.64-2.03 (m, 4H), 1.49-1.62 (m, 2H). m/z (ESI) 527.1 (M+H)+.

EXAMPLE 117

5-(2-(METHYLSULFONYL)-4-(TRIFLUOROM-ETHYL)PHENYL)-N-(PYRIMIDIN-4-YL)NAPH-THALENE-2-SULFONAMIDE

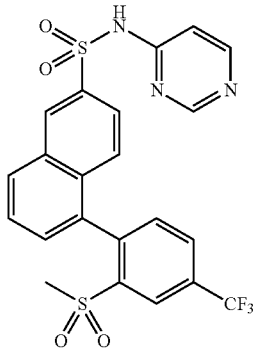 [SMILES: CS(=O)(=O)c1cc(C(F)(F)F)ccc1-c1cccc2cc(S(=O)(=O)Nc3ccncn3)ccc12]

A solution of PdCl$_2$(dppf)-CH$_2$Cl$_2$ adduct (0.030 g, 0.037 mmol), INTERMEDIATE EEE (0.123 g, 0.406 mmol), INTERMEDIATE DDD (0.200 g, 0.369 mmol), and potassium phosphate (0.235 g, 1.108 mmol) in 3 mL dioxane/1.5 mL water was heated to 80° C. for 2 hours. LC/MS showed product, so the reaction mixture was allowed to cool to room temperature. The reaction mixture was diluted with water and extracted with DCM. The organics were dried over MgSO$_4$ and concentrated. Purification of the crude residue by silica gel column chromatography (0 to 100% EtOAc/heptane) gave 5-(2-(methylsulfonyl)-4-(trifluoromethyl)phenyl)-N-(pyrimidin-4-yl)-N-((2-(trimethylsilyl)ethoxy)methyl)naph-thalene-2-sulfonamide (0.050 g, 0.078 mmol, 21.23% yield). m/z (ESI) 638.0 (M+H)+. The material was dissovled in 1 mL THF and treated with 4N HCl in dioxane (0.196 ml, 0.784 mmol) and was heated to 100° C. for 30 minutes. LC/MS showed mostly product, so the reaction mixture was concentrated. Purification of the crude residue by reverse phase column chromatography [C$_{18}$, 10 to 100% (0.1% NH$_4$OH in MeOH)/(0.1% NH$_4$OH in water)] gave 5-(2-(methylsulfo-nyl)-4-(trifluoromethyl)phenyl)-N-(pyrimidin-4-yl)naphtha-lene-2-sulfonamide (0.018 g, 0.035 mmol, 45.2% yield). $^1$H NMR (MeCN-d$_3$) δ ppm: 8.64 (s, 1H), 8.49 (s, 1H), 8.44 (s, 1H), 8.23 (d, J=6.2 Hz, 1H), 8.18 (d, J=8.2 Hz, 1H), 8.02-8.07 (m, 1H), 7.80 (dd, J=8.9, 2.0 Hz, 1H), 7.70 (dd, J=8.2, 7.1 Hz, 1H), 7.60-7.64 (m, 1H), 7.57 (d, J=8.0 Hz, 1H), 7.38 (d, J=9.0 Hz, 1H), 7.06 (d, J=6.1 Hz, 1H), 2.71 (s, 3H). m/z (ESI) 508.0 (M+H)+.

EXAMPLE 118

5-(2-(3-FLUOROAZETIDIN-3-YL)-4-(TRIFLUO-ROMETHYL)PHENYL)-N-(PYRIMIDIN-4-YL) NAPHTHALENE-2-SULFONAMIDE

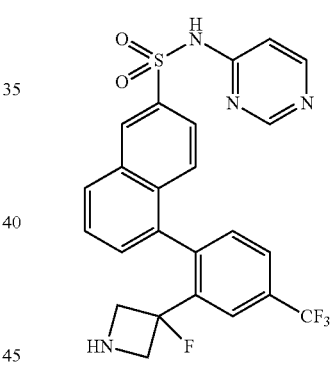

EXAMPLE 118 was synthesized in a similar manner to Example 117, using Intermediate FFF instead of Intermediate EEE, to yield 5-(2-(3-fluoroazetidin-3-yl)-4-(trifluorom-ethyl)phenyl)-N-(pyrimidin-4-yl)naphthalene-2-sulfona-mide (0.048 g, 0.096 mmol, 42.4% yield). $^1$H NMR (DMSO-d$_6$) δ ppm: 8.56 (s, 2H), 8.36 (s, 1H), 8.27 (d, J=8.2 Hz, 1H), 7.95-8.07 (m, 3H), 7.87 (d, J=8.8 Hz, 1H), 7.66-7.73 (m, 1H), 7.63 (d, J=8.1 Hz, 1H), 7.37-7.49 (m, 2H), 6.75 (d, J=6.0 Hz, 1H), 3.65-3.95 (m, 4H). m/z (ESI) 503.0 (M+H)+.

EXAMPLE 119

5-(2-(2,5-DIHYDRO-1H-PYRROL-3-YL)-4-(TRIF-LUOROMETHYL)PHENYL)-N-(PYRIMIDIN-4-YL)NAPHTHALENE-2-SULFONAMIDE

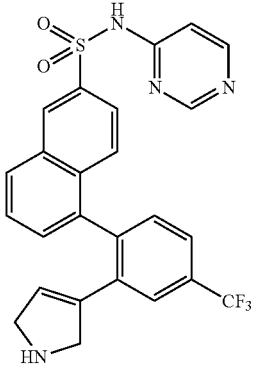 [SMILES: O=S(=O)(Nc1ccncn1)c1ccc2c(-c3ccc(C(F)(F)F)cc3C3=CCNC3)cccc2c1]

A solution of PdCl$_2$(dppf)-CH$_2$Cl$_2$ adduct (0.038 g, 0.046 mmol), Intermediate GGG (0.181 g, 0.462 mmol), Intermediate DDD (0.250 g, 0.462 mmol), and potassium phosphate (0.294 g, 1.385 mmol) in 3 mL dioxane/1.5 mL water was heated to 80° C. for 2 hours. LC/MS showed mostly product, so the reaction mixture was allowed to cool to room temperature. The aqueous layer was removed, and the organics were treated with 4N HCl in dioxane (1.154 ml, 4.62 mmol). After stirring 2 hours at 80° C., LC/MS showed mostly product, so the reaction mixture was concentrated. Purification of the crude residue by reverse phase column chromatography [C$_{18}$, 10 to 100% (0.1% NH$_4$OH in MeOH)/(0.1% NH$_4$OH in water)] gave 5-(2-(2,5-dihydro-1H-pyrrol-3-yl)-4-(trifluoromethyl)phenyl)-N-(pyrimidin-4-yl)naphthalene-2-sulfonamide (0.026 g, 0.052 mmol, 11.34% yield). $^1$H NMR (DMSO-d$_6$) δ ppm: 8.47 (s, 1H), 8.24 (s, 1H), 8.19 (d, J=8.2 Hz, 1H), 7.75-7.89 (m, 4H), 7.64 (dd, J=8.2, 7.1 Hz, 1H), 7.53 (d, J=7.8 Hz, 1H), 7.46 (d, J=7.0 Hz, 1H), 7.32 (d, J=8.8 Hz, 1H), 6.60 (d, J=6.0 Hz, 1H), 5.68 (t, J=2.0 Hz, 1H), 3.66 (d, J=2.6 Hz, 2H), 3.39-3.62 (m, 2H). m/z (ESI) 497.0 (M+H)+

EXAMPLE 120

5-(2-(PIPERIDIN-4-YL)-4-(TRIFLUOROMETHYL)PHENYL)-N-(PYRIMIDIN-4-YL)NAPHTHALENE-2-SULFONAMIDE

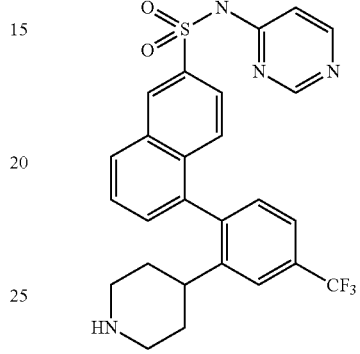

Example 120 was synthesized in a similar manner to Example 119, using Intermediate BBB instead of Intermediate GGG. $^1$H NMR (DMSO-d$_6$) δ ppm: 8.47 (s, 1H), 8.23 (s, 1H), 8.17 (d, J=8.0 Hz, 1H), 7.86 (d, J=6.0 Hz, 1H), 7.79 (d, J=8.8 Hz, 1H), 7.69-7.74 (m, 2H), 7.65 (dd, J=8.3, 7.0 Hz, 1H), 7.38-7.47 (m, 2H), 7.27 (d, J=8.8 Hz, 1H), 6.58 (d, J=6.0 Hz, 1H), 3.06-3.37 (m, 5H), 1.55-1.99 (m, 4H). m/z (ESI) 513.2 (M+H)+

EXAMPLE 121

5-(2-(1H-IMIDAZOL-1-YL)-4-(TRIFLUOROMETHYL)PHENYL)-N-(PYRIMIDIN-4-YL)NAPHTHALENE-2-SULFONAMIDE

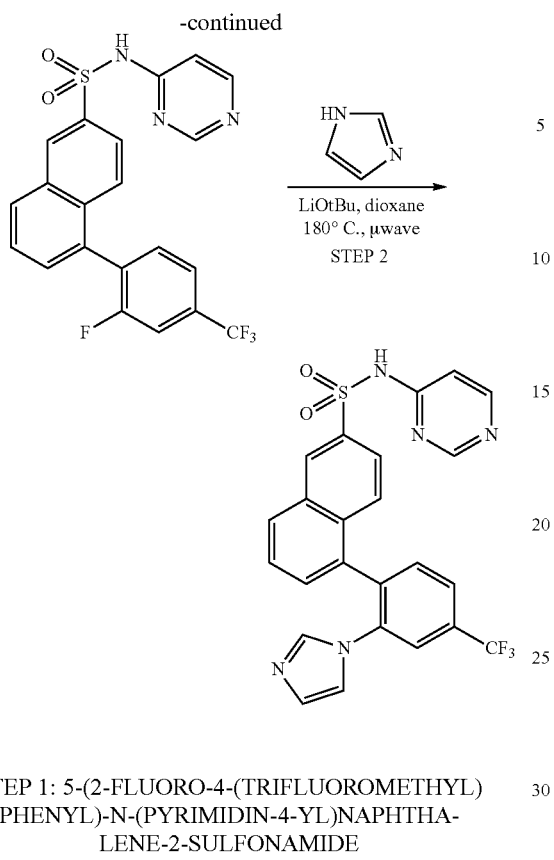

STEP 1: 5-(2-FLUORO-4-(TRIFLUOROMETHYL) PHENYL)-N-(PYRIMIDIN-4-YL)NAPHTHA-LENE-2-SULFONAMIDE

A solution of PdCl$_2$(dppf)-CH$_2$Cl$_2$ adduct (0.075 g, 0.092 mmol), 1-bromo-2-fluoro-4-(trifluoromethyl)benzene (0.247 g, 1.016 mmol), Intermediate DDD (0.500 g, 0.923 mmol), and potassium carbonate (0.510 g, 3.69 mmol) in 4 mL dioxane/2 mL water was heated to 80° C. for 2 hours. LC/MS showed mostly product, so the reaction mixture was allowed to cool to room temperature. The aqueous layer was removed, and the reaction mixture was treated with 4N HCl in dioxane (2.308 ml, 9.23 mmol) and was heated to 80° C. for one hour. LC/MS showed mostly product, so the reaction mixture was concentrated. Purification of the crude residue by reverse phase column chromatography [C$_H$, 10 to 100% (0.1% NH$_4$OH in MeOH)/(0.1% NH$_4$OH in water)] gave 5-(2-fluoro-4-(trifluoromethyl)phenyl)-N-(pyrimidin-4-yl)naphthalene-2-sulfonamide (0.111 g, 0.248 mmol, 26.9% yield). m/z (ESI) 447.9 (M+H)+

STEP 2: 5-(2-(1H-IMIDAZOL-1-YL)-4-(TRIFLUO-ROMETHYL)PHENYL)-N-(PYRIMIDIN-4-YL) NAPHTHALENE-2-SULFONAMIDE

A microwave vial charged with 5-(2-fluoro-4-(trifluoromethyl)phenyl)-N-(pyrimidin-4-yl)naphthalene-2-sulfonamide (0.111 g, 0.248 mmol), 1H-imidazole (0.051 g, 0.744 mmol), 1 mL dioxane, and lithium tert-butoxide (1N in THF) (0.992 ml, 0.992 mmol) was heated to 180° C. in the microwave for 90 minutes. LC/MS showed incomplete reaction, so the reaction mixture was heated to 180° C. for an additional 90 minutes. LC/MS showed mostly product, so the reaction mixture was poured into 1N citric acid solution and was extracted with EtOAc. The organics were concentrated. Purification of the crude residue by reverse phase column chromatography [10 to 100% (0.1% NH4OH in MeOH)/(0.1% NH4OH in water)] gave 5-(2-(1H-imidazol-1-yl)-4-(trifluoromethyl)phenyl)-N-(pyrimidin-4-yl)naphthalene-2-sulfonamide (0.060 g, 0.121 mmol, 48.8% yield). $^1$H NMR (DMSO-d$_6$) δ ppm: 8.57 (s, 1H), 8.54 (s, 1H), 8.20 (d, J=8.3 Hz, 1H), 7.95-8.04 (m, 2H), 7.70-7.80 (m, 2H), 7.62-7.68 (m, 1H), 7.56-7.62 (m, 1H), 7.53 (d, J=9.0 Hz, 1H), 7.48 (s, 1H), 6.98 (d, J=6.3 Hz, 1H), 6.94 (s, 1H), 6.60 (s, 1H). m/z (ESI) 496.0 (M+H)+

EXAMPLE 122

5-(2-(1-METHYL-1,2,5,6-TETRAHYDROPYRI-DIN-3-YL)-4-(TRIFLUOROMETHYL)PHENYL)-N-(PYRIMIDIN-4-YL)NAPHTHALENE-2-SUL-FONAMIDE

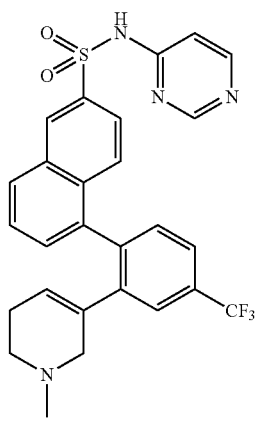 [SMILES: CN1CCC=C(c2cc(C(F)(F)F)ccc2-c2cccc3cc(S(=O)(=O)Nc4ccncn4)ccc23)C1]

Example 122 was synthesized in a similar manner to Example 119, using Intermediate HHH instead of Intermediate GGG. $^1$H NMR (acetone) δ ppm: 8.53 (s, 1H), 8.38 (s, 1H), 8.12 (d, J=6.0 Hz, 1H), 8.04 (d, J=8.2 Hz, 1H), 7.72-7.79 (m, 1H), 7.53-7.68 (m, 3H), 7.39-7.50 (m, 3H), 7.03 (d, J=6.0 Hz, 1H), 5.46 (d, J=3.9 Hz, 1H), 3.19 (s, 2H), 2.69 (d, J=2.0 Hz, 2H), 2.00-2.16 (m, 2H), 1.85 (s, 3H). m/z (ESI) 525.0 (M+H)+

EXAMPLE 123

5-(2-(1-METHYL-1H-IMIDAZOL-5-YL)-4-(TRIF-LUOROMETHYL)PHENYL)-N-(PYRIMIDIN-4-YL)NAPHTHALENE-2-SULFONAMIDE

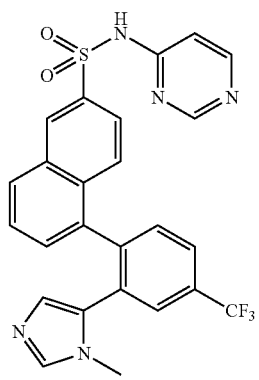 [SMILES: Cn1cncc1-c1cc(C(F)(F)F)ccc1-c1cccc2cc(S(=O)(=O)Nc3ccncn3)ccc12]

Example 123 was synthesized in a similar manner to Example 119, using Intermediate XX instead of Intermediate GGG. $^1$H NMR (acetone) δ ppm: 8.68 (s, 1H), 8.64 (s, 1H), 8.42 (d, J=8.0 Hz, 1H), 8.15 (d, J=8.0 Hz, 1H), 7.90-7.97 (m, 2H), 7.80 (s, 1H), 7.63-7.76 (m, 3H), 7.59 (d, J=8.0 Hz, 1H), 7.22-7.25 (m, 2H), 6.43 (s, 1H), 3.41 (s, 3H). m/z (ESI) 510.0 (M+H)+

EXAMPLE 124

5-(2-(1-METHYL-1H-IMIDAZOL-2-YL)-4-(TRIFLUOROMETHYL)PHENYL)-N-(PYRIMIDIN-4-YL)NAPHTHALENE-2-SULFONAMIDE

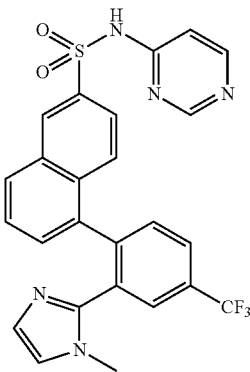 [SMILES: Cn1ccnc1-c1cc(C(F)(F)F)ccc1-c1cccc2cc(S(=O)(=O)Nc3ccncn3)ccc12]

Example 124 was synthesized in a similar manner to Example 119, using Intermediate YY instead of Intermediate GGG. $^1$H NMR (acetone) δ ppm: 8.66 (s, 1H), 8.62 (s, 1H), 8.39 (d, J=6.0 Hz, 1H), 8.14 (d, J=8.0 Hz, 1H), 7.89-7.97 (m, 2H), 7.88 (s, 1H), 7.62-7.75 (m, 3H), 7.57 (d, J=8.0 Hz, 1H), 7.14-7.24 (m, 2H), 6.43 (s, 1H), 3.40 (s, 3H). m/z (ESI) 510.0 (M+H)+

EXAMPLE 125

5-(4-CYCLOPROPYL-2-METHOXYPHENYL)-N-(PYRIMIDIN-4-YL)NAPHTHALENE-2-SULFONAMIDE

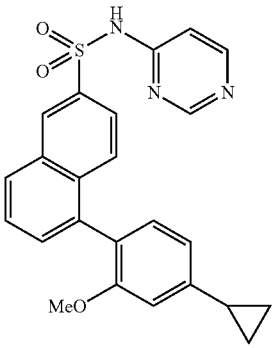 [SMILES: COc1cc(C2CC2)ccc1-c1cccc2cc(S(=O)(=O)Nc3ccncn3)ccc12]

A solution of Pd(Amphos)$_2$Cl$_2$ (0.032 g, 0.045 mmol), Intermediate W (0.163 g, 0.448 mmol), Intermediate III (0.153 g, 0.559 mmol), and potassium phosphate (0.380 g, 1.790 mmol) in 10 mL dioxane/5 mL water was heated to 80° C. for overnight. LC/MS showed mostly product, so the reaction mixture was diluted with EtOAc then washed with 1N citric acid solution. The organic were dried over MgSO$_4$ and concentrated. Purification of the crude residue by reverse phase column chromatography [C$_{18}$, 10-100% (0.1% NH$_4$OH in MeOH)/(0.1% NH$_4$OH in water)] gave 5-(4-cyclopropyl-2-methoxyphenyl)-N-(pyrimidin-4-yl)naphthalene-2-sulfonamide (0.028 g, 0.065 mmol, 14.50% yield). $^1$H NMR (acetone) δ ppm: 8.72 (s, 1H), 8.65 (s, 1H), 8.44 (d, J=6.0 Hz, 1H), 8.14 (d, J=8.3 Hz, 1H), 7.91 (d, J=9.0 Hz, 1H), 7.65-7.73 (m, 2H), 7.53 (d, J=7.1 Hz, 1H), 7.30 (d, J=5.9 Hz, 1H), 7.11 (d, J=7.6 Hz, 1H), 6.91 (s, 1H), 6.81 (d, J=7.8 Hz, 1H), 3.70-3.85 (m, 1H), 3.65 (s, 3H), 0.97-1.07 (m, 2H), 0.75-0.85 (m, 2H). m/z (ESI) 432.0 (M+H)+

EXAMPLE 126

1-(4-FLUORO-2-(PYRIDIN-4-YL)PHENYL)-N-(THIAZOL-2-YL)ISOQUINOLINE-6-SULFONAMIDE

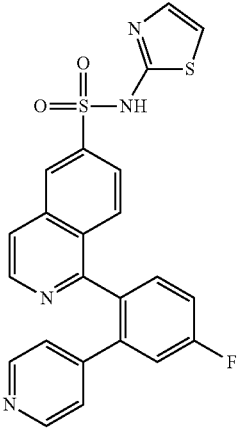 [SMILES: O=S(=O)(Nc1nccs1)c1ccc2c(-c3ccc(F)cc3-c3ccncc3)nccc2c1]

To a microwave vial charged with 1-(2-bromo-4-fluorophenyl)-N-(4-methoxybenzyl)-N-(thiazol-2-yl)isoquinoline-6-sulfonamide (Intermediate KKK) (55 mg, 0.094 mmol) was added 4-pyridineboronic acid (Sigma Aldrich, St. Louis, Mo.) (17.35 mg, 0.141 mmol), potassium carbonate (65.0 mg, 0.471 mmol), dioxane (471 μl), water (157 μl) and the mixture was purged with argon prior to the addition of Pd(PPh$_3$)$_4$ (10.87 mg, 9.41 μmol). The vessel was irradiated for 30 min at 100° C. affording conversion to product as a major species. Further irradiation for 30 min did not improve conversion. The organic layer was decanted, and the aqueous wash with EtOAc and the EtOAc was decanted and the combined organics dried under reduced pressure. To the crude material was added DCM (0.9 ml) followed by TFA (0.4 ml). The resulting orange solution was stirred at room temperature overnight affording complete cleavage of the PMB group. The solution was dried under reduced pressure and purified by a 25 g spherical silica column (15 μm spherical) providing product as a film (17 mg) with boronic acid contamination. The material was repurified with a 1 g PE-AX column (Biotage AB, Uppsala, Sweden) washing with MeOH, then 3% conc. HCl in MeOH. The acidic wash was dried under reduced pressure and lyophilized from MeOH/H$_2$O to provide an off-white solid, 1-(4-fluoro-2-(pyridin-4-yl)phenyl)-N-(thiazol-2-yl)isoquinoline-6-sulfonamide (6 mg, 0.013 mmol, 13.79% yield). $^1$H NMR (500 MHz, DMSO-d$_6$) δ ppm 6.44 (d, J=3.74 Hz, 1H) 6.89 (d, J=3.74 Hz, 1H) 6.98 (d, J=5.77 Hz, 2H) 7.43-7.48 (m, 1H) 7.50 (dd, J=9.67, 2.30 Hz, 1H) 7.54-7.61 (m, 2H) 7.78 (d, J=8.76 Hz, 1H) 7.90 (d, J=5.56 Hz, 1H) 8.26 (d, J=5.88 Hz, 2H) 8.30 (s, 1H) 8.45 (d, J=5.66 Hz, 1H). m/z (ESI) 463.2 (M+H)+.

EXAMPLE 127

1-(2-(2,5-DIHYDROFURAN-3-YL)-4-FLUO-ROPHENYL)-N-(THIAZOL-2-YL)ISOQUINO-LINE-6-SULFONAMIDE TRIFLUOROACETATE

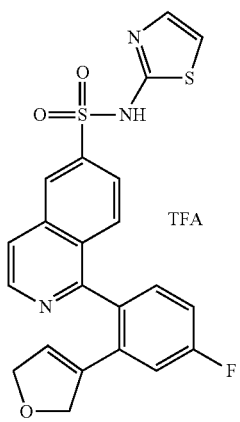 [SMILES: O=S(=O)(Nc1nccs1)c1ccc2c(-c3ccc(F)cc3C3=CCOC3)nccc2c1]

Example 127 was synthesized in a similar manner to Example 126, using thermal heating at 100° C. overnight with 2-(2,5-dihydrofuran-3-yl)-4,4,5,5-tetramethyl-1,3,2-dioxaborolane (Frontier Scientific, Logan, Utah) (29 mg, 0.25 mmol). The crude material was purified sequentially with reverse phase HPLC with NH4OH and TFA modifiers respectively, affording 1-(2-(2,5-dihydrofuran-3-yl)-4-fluorophenyl)-N-(thiazol-2-yl)isoquinoline-6-sulfonamide trifluoroacetate (6 mg, 6%). 1H NMR (400 MHz, DMSO-d6) δ ppm 4.13-4.34 (m, 4H) 5.28 (s, 1H) 6.87 (d, J=4.60 Hz, 1H) 7.28 (d, J=4.50 Hz, 1H) 7.32-7.37 (m, 1H) 7.39-7.46 (m, 2H) 7.63 (d, J=8.90 Hz, 1H) 7.86 (dd, J=8.90, 1.86 Hz, 1H) 8.16 (d, J=5.67 Hz, 1H) 8.56 (d, J=1.76 Hz, 1H) 8.68 (d, J=5.67 Hz, 1H) 12.89 (br. s., 1H). m/z (ESI) 454.2 (M+H)+.

EXAMPLE 128

1-(PYRIDIN-3-YLMETHOXY)-N-(PYRIMIDIN-4-YL)ISOQUINOLINE-6-SULFONAMIDE

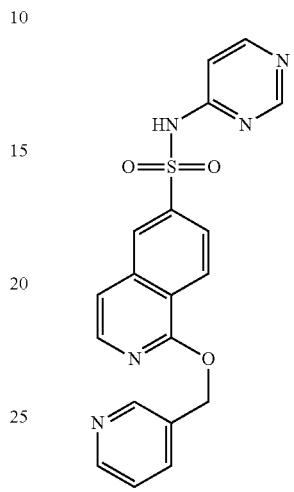

Example 128 was synthesized in a similar manner to Example 130, using pyridin-3-ylmethanol (Sigma Aldrich) (27 mg, 0.248 mmol) instead of (5-phenyloxazol-4-yl)methanol, affording 1-(pyridin-3-ylmethoxy)-N-(pyrimidin-4-yl)isoquinoline-6-sulfonamide (36.5 mg, 58%). 1H NMR (500 MHz, DMSO-d6) δ ppm 5.61 (s, 2H) 6.84 (d, J=6.07 Hz, 1H) 7.43 (dd, J=7.45, 5.04 Hz, 1H) 7.63 (d, J=5.79 Hz, 1H) 7.97 (t, J=6.90 Hz, 2H) 8.11 (t, J=5.30 Hz, 2H) 8.30 (d, J=8.65 Hz, 1H) 8.45 (s, 1H) 8.43 (s, 1H) 8.55 (d, J=3.61 Hz, 1H) 8.77 (s, 1H). m/z (ESI) 394.3 (M+H)+.

EXAMPLE 129

1-(4-FLUORO-2-(1-METHYL-1H-PYRAZOL-4-YL)PHENYL)-N-(THIAZOL-2-YL)ISOQUINO-LINE-6-SULFONAMIDE TRIFLUOROACETATE

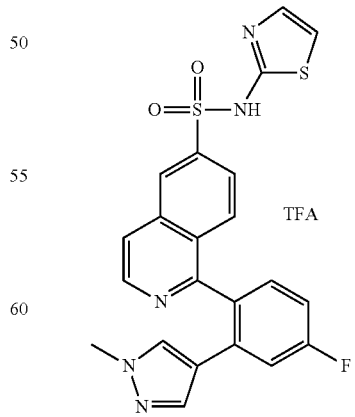

Example 129 was synthesized in a similar manner to Example 126, using thermal heating at 100° C. overnight with 1-methyl-4-(4,4,5,5-tetramethyl-1,3,2-dioxaborolan-2-yl)-1H-pyrazole (Alfa Aesar) (32 mg, 0.25 mmol). The crude material was purified sequentially with reverse phase HPLC with NH$_4$OH and TFA modifiers respectively, affording 1-(4-fluoro-2-(1-methyl-1H-pyrazol-4-yl)phenyl)-N-(thiazol-2-yl)isoquinoline-6-sulfonamide trifluoroacetate (15 mg, 14%). $^1$H NMR (400 MHz, DMSO-d$_6$) δ ppm 6.61 (s, 1H) 6.87 (d, J=4.60 Hz, 1H) 7.19-7.31 (m, 3H) 7.41 (dd, J=8.46, 6.11 Hz, 1H) 7.50-7.58 (m, 2H) 7.77 (dd, J=8.90, 1.86 Hz, 1H) 8.19 (d, J=5.67 Hz, 1H) 8.55 (d, J=1.66 Hz, 1H) 8.71 (d, J=5.67 Hz, 1H) 12.88 (br. s., 1H). m/z (ESI) 466.2 (M+H)$^+$.

EXAMPLE 130

1-((5-PHENYLOXAZOL-4-YL)METHOXY)-N-(PYRIMIDIN-4-YL)ISOQUINOLINE-6-SULFONAMIDE

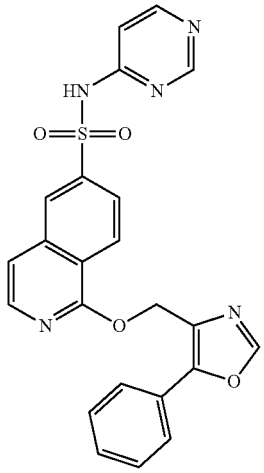 [SMILES: O=S(=O)(Nc1ccncn1)c1ccc2c(OCc3ncoc3-c3ccccc3)nccc2c1]

To a vial charged with (5-phenyloxazol-4-yl)methanol (Sigma Aldrich) (43 mg, 0.248 mmol) was added DMF (500 µl) followed by NaH (60% in mineral oil) (0.013 g, 0.336 mmol). The vial was shaken for 1.5 hr. To the reaction was added a solution of INTERMEDIATE GG (51 mg, 0.16 mmol, in 500 µl DMF). The vial was shaken at room temperature for 2 hr. To the mixture was added IPA (about 1.5 ml) followed by acetic acid (100 µl). The reaction was dried under reduced pressure and purified by preparative reverse-phase HPLC modified by NH$_4$OH affording 1-((5-phenyloxazol-4-yl)methoxy)-N-(pyrimidin-4-yl)isoquinoline-6-sulfonamide (33.2 mg, 45%). $^1$H NMR (500 MHz, DMSO-d$_6$) δ ppm 5.65 (s, 2H) 6.96 (d, J=6.36 Hz, 1H) 7.40-7.46 (m, 1H), 7.50 (t, J=7.53 Hz, 2H) 7.66 (d, J=5.84 Hz, 1H) 7.74 (d, J=7.39 Hz, 2H) 7.96 (d, J=8.71 Hz, 1H), 8.12 (d, J=5.79 Hz, 1H) 8.15-8.26 (m, 2H) 8.45-8.58 (m, 3H). m/z (ESI) 460.2 (M+H)$^+$.

EXAMPLE 131

(S)-1-((1-(4-CHLOROPHENOXY)PROPAN-2-YL)OXY)-N-(PYRIMIDIN-4-YL)ISOQUINOLINE-6-SULFONAMIDE

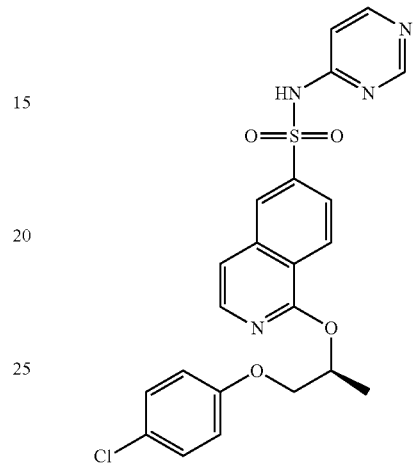

Example 131 was synthesized in a similar manner to Example 130, using (S)-1-(4-chlorophenoxy)propan-2-ol (FSSI) (46 mg, 0.248 mmol) instead of (5-phenyloxazol-4-yl)methanol, affording (S)-1-((1-(4-chlorophenoxy)propan-2-yl)oxy)-N-(pyrimidin-4-yl)isoquinoline-6-sulfonamide (11.2 mg, 15%). $^1$H NMR (500 MHz, DMSO-d$_6$) δ ppm 1.47 (d, J=6.30 Hz, 3H) 4.23-4.38 (m, 2H) 6.79 (s, 1H) 6.94 (d, J=5.73 Hz, 1H) 7.00 (m, J=8.94 Hz, 2H) 7.11 (d, J=9.05 Hz, 1H) 7.29 (m, J=8.82 Hz, 2H) 7.39 (d, J=5.73 Hz, 1H) 7.60 (d, J=5.61 Hz, 1H) 7.87-7.95 (m, 2H) 7.97 (d, J=8.13 Hz, 1H) 8.10 (d, J=5.84 Hz, 1H). m/z (ESI) 471.1 (M)$^+$.

EXAMPLE 132

1-(3-(4-CHLOROPHENYL)PROPOXY)-N-(PYRIMIDIN-4-YL)ISOQUINOLINE-6-SULFONAMIDE

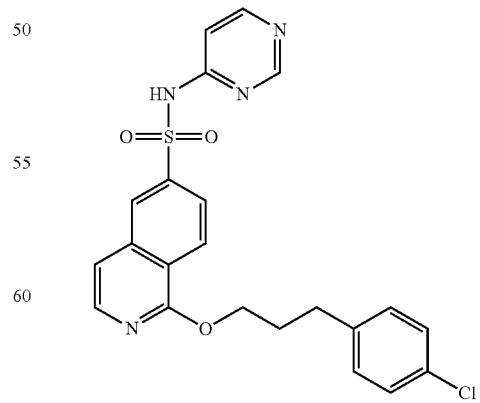

Example 132 was synthesized in a similar manner to Example 130, using 3-(4-chlorophenyl)propan-1-ol (Sigma Aldrich) (42 mg, 0.248 mmol) instead of (5-phenyloxazol-4-yl)methanol, affording 1-(3-(4-chlorophenyl)propoxy)-N-(pyrimidin-4-yl)isoquinoline-6-sulfonamide (35.3 mg, 48%). $^1$H NMR (500 MHz, DMSO-$d_6$) δ ppm 2.10-2.19 (m, 2H) 2.78-2.90 (m, 2H) 4.45 (t, J=6.19 Hz, 2H) 6.99 (d, J=6.13 Hz, 1H) 7.19-7.34 (m, 4H) 7.58 (d, J=5.73 Hz, 1H) 7.98 (d, J=8.65 Hz, 1H) 8.08 (d, J=5.79 Hz, 1H) 8.24 (d, J=8.76 Hz, 2H) 8.48 (s, 1H) 8.55 (s, 1H). m/z (ESI) 454.9 (M)$^+$.

EXAMPLE 133

1-((1-(4-CHLOROBENZYL)-1H-IMIDAZOL-2-YL)METHOXY)-N-(PYRIMIDIN-4-YL)ISO-QUINOLINE-6-SULFONAMIDE

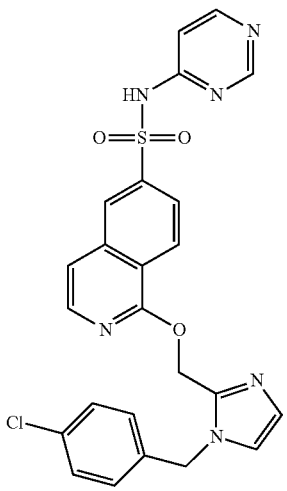 [SMILES: O=S(=O)(Nc1ccncn1)c1ccc2c(OCc3nccn3Cc3ccc(Cl)cc3)nccc2c1]

Example 133 was synthesized in a similar manner to Example 130, using (1-(4-chlorobenzyl)-1H-imidazol-2-yl)methanol (Frontier Scientific, Logan, Utah) (55 mg, 0.248 mmol) instead of (5-phenyloxazol-4-yl)methanol, affording 1-((1-(4-chlorobenzyl)-1H-imidazol-2-yl)methoxy)-N-(pyrimidin-4-yl)isoquinoline-6-sulfonamide (53.9 mg, 67%). $^1$H NMR (500 MHz, DMSO-$d_6$) δ ppm 5.37 (s, 2H) 5.53 (s, 2H) 6.97 (d, J=5.79 Hz, 1H) 7.02 (s, 1H) 7.07 (m, J=8.25 Hz, 2H) 7.24 (m, J=8.25 Hz, 2H) 7.38 (s, 1H) 7.56-7.64 (m, 2H) 7.83 (d, J=7.79 Hz, 1H) 8.10 (d, J=5.90 Hz, 1H) 8.22 (d, J=6.13 Hz, 1H) 8.46 (s, 1H) 8.54 (s, 1H). m/z (ESI) 507.1

EXAMPLE 134

(R)-1-((4-BENZYLMORPHOLIN-2-YL)METH-OXY)-N-(PYRIMIDIN-4-YL)ISOQUINOLINE-6-SULFONAMIDE

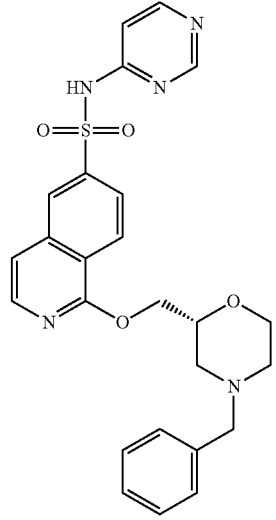 [SMILES: O=S(=O)(Nc1ccncn1)c1ccc2c(OC[C@H]3CN(Cc4ccccc4)CCO3)nccc2c1]

Example 134 was synthesized in a similar manner to Example 130, using (R)-(4-benzylmorpholin-2-yl)methanol (Ark Pharm, Inc., Libertyville, Ill.) (51 mg, 0.248 mmol) instead of (5-phenyloxazol-4-yl)methanol, affording (R)-1-((4-benzylmorpholin-2-yl)methoxy)-N-(pyrimidin-4-yl)isoquinoline-6-sulfonamide (58.3 mg, 74%). $^1$H NMR (500 MHz, DMSO-$d_6$) δ ppm 2.03-2.21 (m, 2H) 2.63 (d, J=11.23 Hz, 1H) 2.89 (d, J=11.00 Hz, 1H) 3.52-3.64 (m, 3H) 3.83 (d, J=11.80 Hz, 1H) 3.94 (br. s., 1H) 4.47 (qd, J=11.25, 5.10 Hz, 2H) 6.92 (d, J=5.96 Hz, 1H) 7.25 (dd, J=8.19, 4.07 Hz, 1H) 7.31 (d, J=4.12 Hz, 4H) 7.59 (d, J=5.73 Hz, 1H) 7.99 (d, J=8.59 Hz, 1H) 8.07 (d, J=5.84 Hz, 1H) 8.14-8.28 (m, 2H) 8.50 (s, 1H) 8.47 (s, 1H). m/z (ESI) 492.4 (M+H)⁺.

EXAMPLE 135

1-((1-CYANOCYCLOPROPYL)METHOXY)-N-(PYRIMIDIN-4-YL)ISOQUINOLINE-6-SULFONAMIDE

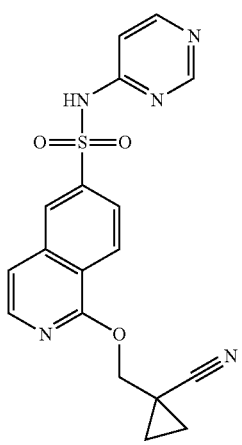 [SMILES: N#CC1(COc2nccc3cc(S(=O)(=O)Nc4ccncn4)ccc23)CC1]

Example 135 was synthesized in a similar manner to Example 130, using 1-(hydroxymethyl)cyclopropanecarbonitrile (Matrix Scientific, Columbia, S.C.) (24 mg, 0.248 mmol) instead of (5-phenyloxazol-4-yl)methanol, affording 1-((1-cyanocyclopropyl)methoxy)-N-(pyrimidin-4-yl)isoquinoline-6-sulfonamide (32.6 mg, 53%). $^1$H NMR (500 MHz, DMSO-d$_6$) δ ppm 1.22-1.44 (m, 4H) 4.53 (s, 2H) 6.90 (d, J=6.30 Hz, 1H) 7.65 (d, J=5.84 Hz, 1H) 8.00-8.12 (m, 2H) 8.15 (d, J=6.41 Hz, 1H) 8.32 (d, J=8.65 Hz, 1H) 8.49 (br. s., 2H). m/z (ESI) 382.2 (M+H)⁺.

EXAMPLE 136

1-((1H-INDAZOL-4-YL)METHOXY)-N-(PYRIMIDIN-4-YL)ISOQUINOLINE-6-SULFONAMIDE

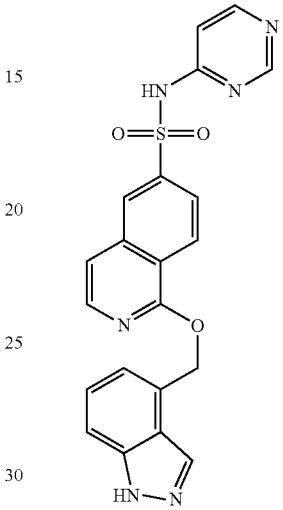

Example 136 was synthesized in a similar manner to Example 130, using (1H-indazol-4-yl)methanol (Ark Pharm, Inc., Libertyville, Ill.) (37 mg, 0.248 mmol) instead of (5-phenyloxazol-4-yl)methanol, affording 1-((1H-indazol-4-yl)methoxy)-N-(pyrimidin-4-yl)isoquinoline-6-sulfonamide (25 mg, 36%). $^1$H NMR (500 MHz, DMSO-d$_6$) δ ppm 5.89 (s, 2H) 6.92 (d, J=6.13 Hz, 1H) 7.27 (d, J=6.70 Hz, 1H) 7.35 (t, J=7.65 Hz, 1H) 7.53 (d, J=8.30 Hz, 1H) 7.61-7.67 (m, 1H) 7.99 (d, J=8.31 Hz, 1H) 8.16 (d, J=6.19 Hz, 1H) 8.14 (d, J=5.84 Hz, 1H) 8.23 (s, 1H) 8.31 (d, J=8.71 Hz, 1H) 8.49 (s, 2H) 13.16 (br. s., 1H). m/z (ESI) 433.3 (M+H)+.

EXAMPLE 137

1-((3-CYANOBENZYL)OXY)-N-(PYRIMIDIN-4-YL)ISOQUINOLINE-6-SULFONAMIDE

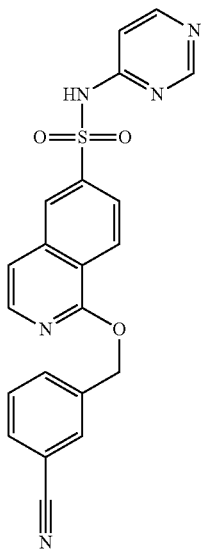 [SMILES: N#Cc1cccc(COc2nccc3cc(S(=O)(=O)Nc4ccncn4)ccc23)c1]

Example 137 was synthesized in a similar manner to Example 130, using 3-(hydroxymethyl)benzonitrile (Alfa Aesar, Ward Hill, Mass.) (33 mg, 0.248 mmol) instead of (5-phenyloxazol-4-yl)methanol, affording 1-((3-cyanobenzyl)oxy)-N-(pyrimidin-4-yl)isoquinoline-6-sulfonamide (30.4 mg, 45%). $^1$H NMR (500 MHz, DMSO-d$_6$) δ ppm 5.63 (s, 2H) 6.98 (d, J=6.47 Hz, 1H) 7.60-7.70 (m, 2H) 7.82 (d, J=7.73 Hz, 1H) 7.90 (d, J=7.85 Hz, 1H) 7.96-8.06 (m, 2H) 8.13 (d, J=5.79 Hz, 1H) 8.21 (d, J=6.07 Hz, 1H) 8.39 (d, J=8.71 Hz, 1H) 8.53 (d, J=6.47 Hz, 2H). m/z (ESI) 418.3 (M+H)+.

EXAMPLE 138

1-((5-METHYL-2-PHENYL-2H-1,2,3-TRIAZOL-4-YL)METHOXY)-N-(PYRIMIDIN-4-YL)ISO-QUINOLINE-6-SULFONAMIDE

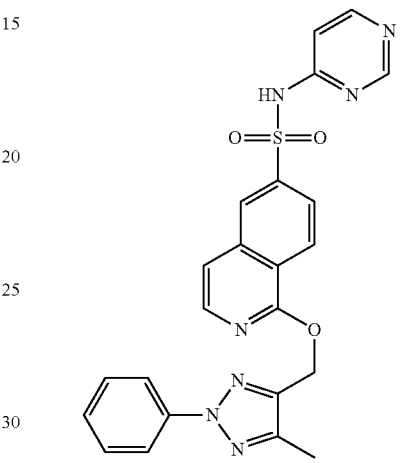

Example 138 was synthesized in a similar manner to Example 130, using (5-methyl-2-phenyl-2H-1,2,3-triazol-4-yl)methanol (Sigma Aldrich) (47 mg, 0.248 mmol) instead of (5-phenyloxazol-4-yl)methanol, affording 1-((5-methyl-2-phenyl-2H-1,2,3-triazol-4-yl)methoxy)-N-(pyrimidin-4-yl)isoquinoline-6-sulfonamide (29.4 mg, 39%). $^1$H NMR (500 MHz, DMSO-d$_6$) δ ppm 2.46 (s, 3H) 5.70 (s, 2H) 6.98 (br. s., 1H) 7.39 (t, J=7.39 Hz, 1H) 7.54 (t, J=7.93 Hz, 2H) 7.68 (d, J=5.78 Hz, 1H) 7.90-8.01 (m, 3H) 8.13-8.25 (m, 2H) 8.30 (d, J=8.76 Hz, 1H) 8.53 (br. s., 2H). m/z (ESI) 474.1 (M+H)⁺.

EXAMPLE 139

1-(2-METHOXY-5-(TRIFLUOROMETHYL)PHENYL)-N-(PYRIMIDIN-4-YL)ISOQUINOLINE-6-SULFONAMIDE

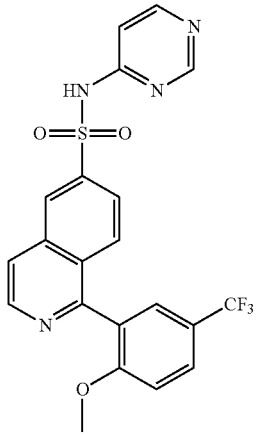 [SMILES: COc1ccc(C(F)(F)F)cc1-c1nccc2cc(S(=O)(=O)Nc3ccncn3)ccc12]

Example 139 was synthesized in a similar manner to Example 65, except that (2-methoxy-5-(trifluoromethyl)phenyl)boronic acid as the boronic acid. ¹H NMR (500 MHz, DMSO-d₆) δ ppm 8.67 (d, J=5.67 Hz, 1H) 8.61 (s, 1H) 8.49 (s, 1H) 8.09-8.18 (m, 2H) 7.88-7.96 (m, 2H) 7.64-7.69 (m, 2H) 7.42 (d, J=8.76 Hz, 1H) 6.92 (d, J=6.42 Hz, 1H) 3.73 (s, 3H); m/z (ESI) 461.1 (M+H)⁺.

EXAMPLE 140

1-(2-METHOXYPHENYL)-N-(PYRIMIDIN-4-YL)ISOQUINOLINE-6-SULFONAMIDE

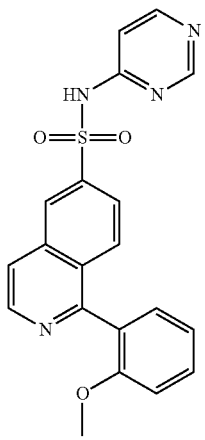 [SMILES: COc1ccccc1-c1nccc2cc(S(=O)(=O)Nc3ccncn3)ccc12]

Example 140 was synthesized in a similar manner to Example 65, except that (2-methoxy boronic was used as boronic acid. ¹H NMR (500 MHz, DMSO-d₆) δ ppm 8.68-8.74 (m, 2H) 8.58 (s, 1H) 8.24 (t, J=5.58 Hz, 2H) 8.01 (d, J=8.88 Hz, 1H) 7.78 (d, J=8.94 Hz, 1H) 7.55-7.62 (m, 1H) 7.36-7.42 (m, 1H) 7.22-7.30 (m, 2H) 7.12-7.19 (m, 2H) 6.98-7.06 (m, 2H); m/z (ESI) 393.1 (M+H)⁺.

EXAMPLE 141

N-(PYRIMIDIN-4-YL)-1-(4-(TRIFLUOROMETHYL)PHENYL)ISOQUINOLINE-6-SULFONAMIDE

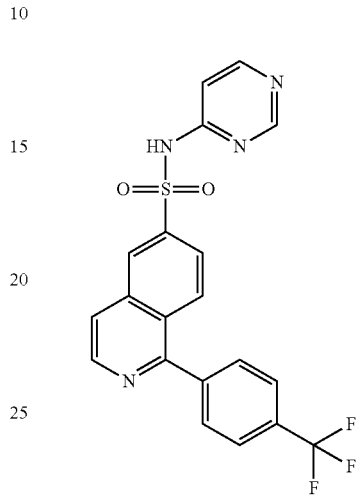

Example 141 was synthesized in a similar manner to Example 65, except that (4-(trifluoromethyl)phenyl)boronic was used as boronic acid. ¹H NMR (400 MHz, DMSO-d₆) δ ppm 8.73 (d, J=5.58 Hz, 1H) 8.68 (s, 1H) 8.51 (s, 1H) 8.14-8.22 (m, 2H) 8.10 (d, J=8.90 Hz, 1H) 8.01 (dd, J=9.05, 1.81 Hz, 1H) 7.88-7.97 (m, 4H) 6.96 (d, J=6.26 Hz, 1H) m/z (ESI) 431.1 (M+H)⁺.

EXAMPLE 142

1-(4,5-DIFLUORO-2-METHOXYPHENYL)-N-(PYRIMIDIN-4-YL)ISOQUINOLINE-6-SULFONAMIDE

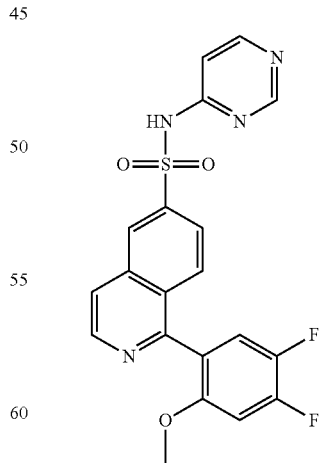

Example 142 was synthesized in a similar manner to Example 65, except that (4,5-difluoro-2-methoxyphenyl)boronic acid was used as boronic acid. ¹H NMR (500 MHz, DMSO-d₆) δ ppm 8.63 (d, J=5.67 Hz, 1H) 8.56 (s, 1H) 8.08

(dd, J=14.35, 5.99 Hz, 1H) 7.38 (dd, J=12.83, 6.76 Hz, 1H) 3.64 (s, 3H); m/z (ESI) 429.2 (M+H)⁺.

EXAMPLE 143

1-(6-CHLORO-4-METHOXYPYRIDIN-3-YL)-N-(PYRIMIDIN-4-YL)ISOQUINOLINE-6-SULFONAMIDE

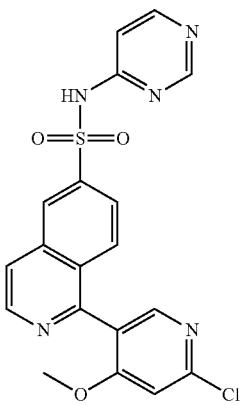 [SMILES: COc1cc(Cl)ncc1-c1nccc2cc(S(=O)(=O)Nc3ccncn3)ccc12]

Example 143 was synthesized in a similar manner to Example 65, except that (6-chloro-4-methoxypyridin-3-yl)boronic acid was used asboronic acid. ¹H NMR (500 MHz, DMSO-d₆) δ ppm 8.61 (d, J=5.61 Hz, 1H) 8.48 (s, 1H) 8.36 (dd, J=4.93, 1.83 Hz, 1H) 8.28 (s, 1H) 8.03 (d, J=5.84 Hz, 1H) 7.89-7.96 (m, 3H) 7.79 (dd, J=7.16, 1.78 Hz, 1H) 7.59 (d, J=8.82 Hz, 1H) 7.19 (dd, J=7.10, 5.04 Hz, 1H) 6.62 (d, J=5.96 Hz, 1H), 3.76 (s, 3H); m/z (ESI) 429.2 (M+H)⁺.

EXAMPLE 144

1-(2-METHOXYPYRIDIN-3-YL)-N-(PYRIMIDIN-4-YL)ISOQUINOLINE-6-SULFONAMIDE

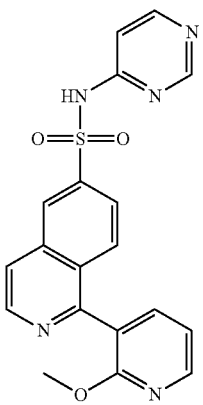 [SMILES: COc1ncccc1-c1nccc2cc(S(=O)(=O)Nc3ccncn3)ccc12]

Example 144 was synthesized in a similar manner to Example 65, except that (2-methoxypyridin-3-yl)boronic acid was used as boronic acid. ¹H NMR (500 MHz, DMSO-d₆) δ ppm 8.61 (d, J=5.61 Hz, 1H) 8.45-8.50 (m, 1H) 8.36 (dd, J=4.98, 1.78 Hz, 1H) 8.28 (s, 1H) 8.03 (d, J=5.61 Hz, 1H) 7.89-7.95 (m, 3H) 7.79 (dd, J=7.16, 1.78 Hz, 1H) 7.59 (d, J=8.82 Hz, 1H) 7.19 (dd, J=7.10, 5.04 Hz, 1H) 6.62 (d, J=5.96 Hz, 1H) 3.76 (s, 3H); m/z (ESI) 394.3 (M+H)⁺.

EXAMPLE 145

1-(2,6-DIMETHOXYPYRIDIN-3-YL)-N-(PYRIMIDIN-4-YL)ISOQUINOLINE-6-SULFONAMIDE

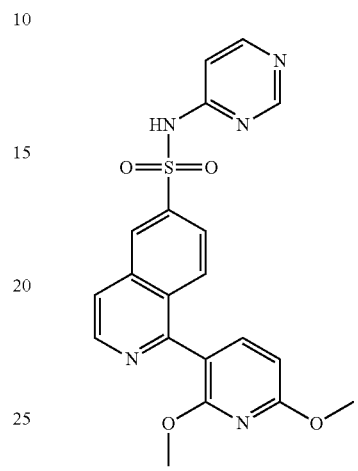

Example 145 was synthesized in a similar manner to Example 65, except that (2,6-dimethoxypyridin-3-yl)boronic acid was used as boronic acid. ¹H NMR (500 MHz, DMSO-d₆) δ ppm 8.61 (d, J=5.61 Hz, 1H) 8.52 (s, 1H) 8.38 (s, 1H) 8.01 (d, J=5.73 Hz, 2H) 8.04 (d, J=6.30 Hz, 1H) 7.92 (dd, J=8.88, 1.66 Hz, 1H) 7.73 (t, J=8.71 Hz, 3H) 6.77 (d, J=6.07 Hz, 1H) 6.57 (d, J=8.02 Hz, 1H) 3.79 (s, 4H) 3.76 (s, 3H); m/z (ESI) 424.3 (M+H)⁺.

EXAMPLE 146

1-(5-CHLORO-2-METHOXYPHENYL)-N-(PYRIMIDIN-4-YL)ISOQUINOLINE-6-SULFONAMIDE

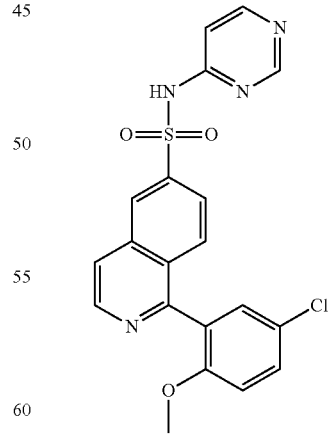

Example 146 was synthesized in a similar manner to Example 65, except that (5-chloro-2-methoxyphenyl)boronic acid was used as boronic acid. ¹H NMR (500 MHz, DMSO-d₆) δ ppm 8.60 (d, J=5.73 Hz, 1H) 8.48 (s, 1H) 8.31 (s, 1H) 8.02 (d, J=5.61 Hz, 1H) 7.96 (d, J=6.19 Hz, 1H) 7.90 (d, J=8.94 Hz, 1H) 7.54-7.62 (m, 2H) 7.36 (d, J=2.63 Hz, 1H) 7.24 (d, J=8.94 Hz, 1H) 6.67 (d, J=5.84 Hz, 1H) 3.64 (s, 3H); m/z (ESI) 427.3 (M+H)⁺.

EXAMPLE 147

1-(2,5-DIMETHOXYPHENYL)-N-(PYRIMIDIN-4-YL)ISOQUINOLINE-6-SULFONAMIDE

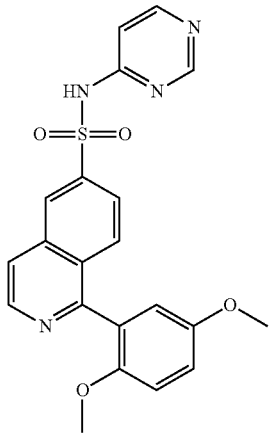 [SMILES: COc1ccc(OC)c(-c2nccc3cc(S(=O)(=O)Nc4ccncn4)ccc23)c1]

Example 177 was synthesized in a similar manner to Example 65, except that (2,5-dimethoxyphenyl)boronic acid was used as boronic acid. ¹H NMR (500 MHz, DMSO-d₆) δ ppm 8.58 (d, J=5.73 Hz, 1H) 8.44 (s, 1H) 8.28 (s, 1H) 7.98 (d, J=5.61 Hz, 1H) 7.93 (d, J=6.07 Hz, 1H) 7.86-7.91 (m, 1H) 7.59 (d, J=8.82 Hz, 1H) 7.13 (d, J=9.05 Hz, 1H) 7.07 (dd, J=8.99, 3.04 Hz, 1H) 6.88 (d, J=2.98 Hz, 1H) 6.62 (d, J=5.96 Hz, 1H) 3.74 (s, 3H) 3.58 (s, 3H); m/z (ESI) 423.2 (M+H)⁺.

EXAMPLE 148

1-(5-FLUORO-2-METHOXYPHENYL)-N-(PYRIMIDIN-4-YL)ISOQUINOLINE-6-SULFONAMIDE

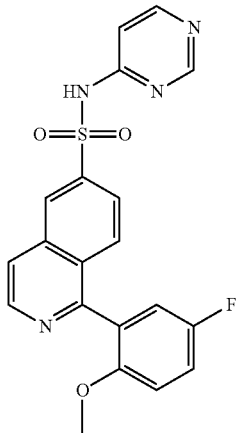 [SMILES: COc1ccc(F)cc1-c1nccc2cc(S(=O)(=O)Nc3ccncn3)ccc12]

Example 148 was synthesized in a similar manner to Example 65, except that (5-fluoro-2-methoxyphenyl)boronic acid was used as boronic acid. ¹H NMR (500 MHz, DMSO-d₆) δ ppm 8.59 (d, J=5.61 Hz, 1H) 8.47 (s, 1H) 8.29 (s, 1H) 8.01 (d, J=5.61 Hz, 1H) 7.94 (d, J=6.07 Hz, 1H) 7.90 (dd, J=8.82, 1.49 Hz, 1H) 7.59 (d, J=8.82 Hz, 1H) 7.35 (td, J=8.62, 3.15 Hz, 1H) 7.16-7.24 (m, 3H) 6.64 (d, J=5.73 Hz, 1H) 3.62 (s, 3H); m/z (ESI) 411.2 (M+H)⁺.

EXAMPLE 149

1-(2-METHOXY-5-METHYLPHENYL)-N-(PYRIMIDIN-4-YL)ISOQUINOLINE-6-SULFONAMIDE

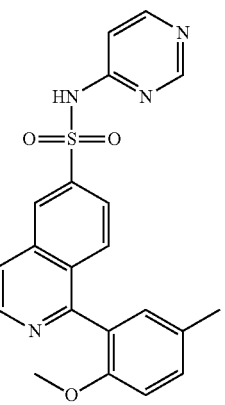

Example 149 was synthesized in a similar manner to Example 65, except that (2-methoxy-5-methyl phenyl)boronic acid was used as boronic acid. ¹H NMR (500 MHz, DMSO-d₆) δ ppm 8.58 (d, J=5.61 Hz, 1H) 8.45 (s, 1H) 8.30 (s, 1H) 7.96 (dd, J=9.22, 5.90 Hz, 3H) 7.88 (dd, J=8.82, 1.60 Hz, 1H) 7.58 (d, J=8.82 Hz, 1H) 7.30 (d, J=8.36 Hz, 1H) 7.06-7.13 (m, 3H) 6.66 (d, J=6.07 Hz, 1H) 3.60 (s, 3H) 2.30 (s, 3H); m/z (ESI) 407.3 (M+H)⁺.

EXAMPLE 150

1-(5-CYANO-2-METHOXYPHENYL)-N-(PYRIMIDIN-4-YL)ISOQUINOLINE-6-SULFONAMIDE

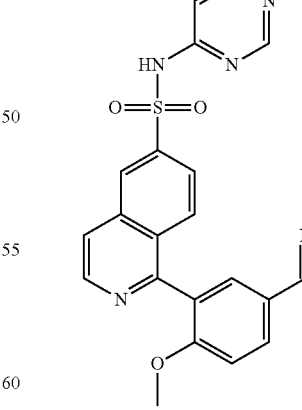

Example 150 was synthesized in a similar manner to Example 65, except that (2-methoxy-5-cyanophenyl)boronic acid was used as boronic acid. ¹H NMR (500 MHz, DMSO-d₆) δ ppm 8.63 (d, J=5.73 Hz, 1H) 8.54 (s, 1H) 8.37 (s, 1H) 8.08 (d, J=5.61 Hz, 2H) 7.99-8.05 (m, 3H) 7.91 (dd, J=8.94, 1.49 Hz, 1H) 7.81 (d, J=2.06 Hz, 1H) 7.60 (d, J=8.82 Hz, 1H) 7.41 (d, J=8.82 Hz, 1H) 6.76 (d, J=6.19 Hz, 1H) 3.74 (s, 3H); m/z (ESI) 418.3 (M+H)⁺.

EXAMPLE 151

1-(2-METHOXY-5-(TRIFLUOROMETHOXY)PHENYL)-N-(PYRIMIDIN-4-YL)ISOQUINOLINE-6-SULFONAMIDE

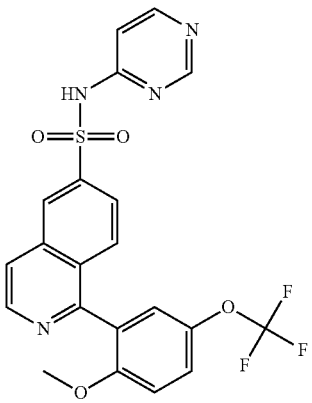 [SMILES: COc1ccc(OC(F)(F)F)cc1-c1nccc2cc(S(=O)(=O)Nc3ccncn3)ccc12]

Example 151 was synthesized in a similar manner to Example 65, except that (2-methoxy-5-(trifluoromethoxy)phenyl)boronic acid was used as boronic acid. ¹H NMR (500 MHz, DMSO-d₆) δ ppm 8.62 (d, J=5.73 Hz, 1H) 8.50 (s, 1H) 8.33 (s, 1H) 8.04 (d, J=5.61 Hz, 1H) 7.99 (d, J=6.07 Hz, 1H) 7.88-7.94 (m, 1H) 7.61 (d, J=8.82 Hz, 1H) 7.50-7.57 (m, 1H) 7.27-7.36 (m, 2H) 6.70 (d, J=6.07 Hz, 1H) 3.68 (s, 3H); m/z (ESI) 477.2 (M+H)⁺.

EXAMPLE 152

1-(2-METHOXY-3-(TRIFLUOROMETHYL)PHENYL)-N-(PYRIMIDIN-4-YL)ISOQUINOLINE-6-SULFONAMIDE

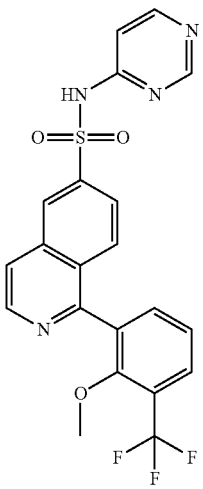 [SMILES: COc1c(-c2nccc3cc(S(=O)(=O)Nc4ccncn4)ccc23)cccc1C(F)(F)F]

Example 152 was synthesized in a similar manner to Example 65, except that (2-methoxy-3-(trifluoromethyl)phenyl)boronic acid was used as boronic acid. ¹H NMR (500 MHz, DMSO-d₆) δ ppm 8.74 (d, J=5.67 Hz, 1H) 8.64 (s, 1H) 8.46 (s, 1H) 8.18 (d, J=5.67 Hz, 1H) 8.13 (d, J=6.41 Hz, 1H) 7.97 (dd, J=8.85, 1.63 Hz, 1H) 7.87 (d, J=6.76 Hz, 1H) 7.60-7.80 (m, 2H) 7.48 (t, J=7.62 Hz, 1H) 6.89 (d, J=6.18 Hz, 1H) 3.04-3.21 (m, 3H); m/z (ESI) 461.1 (M+H)⁺.

EXAMPLE 153

1-(2-METHOXY-4-(TRIFLUOROMETHOXY)PHENYL)-N-(PYRIMIDIN-4-YL)ISOQUINOLINE-6-SULFONAMIDE

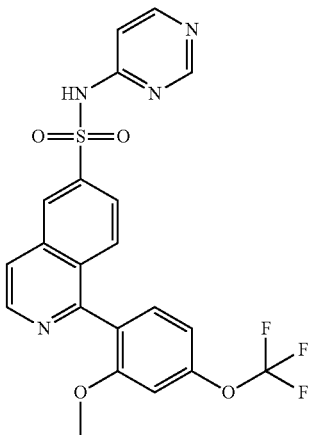 [SMILES: COc1cc(OC(F)(F)F)ccc1-c1nccc2cc(S(=O)(=O)Nc3ccncn3)ccc12]

Example 153 was synthesized in a similar manner to Example 65, except that (2-methoxy-4-(trifluoromethoxy)phenyl)boronic acid was used as boronic acid. ¹H NMR (500 MHz, DMSO-d₆) δ ppm 8.65 (d, J=5.67 Hz, 1H) 8.51-8.59 (m, 1H) 8.45 (s, 1H) 8.02-8.13 (m, 2H) 7.76-7.95 (m, 1H) 7.66 (d, J=8.88 Hz, 1H) 7.46 (d, J=8.25 Hz, 1H) 7.22 (s, 1H)

7.11 (d, J=9.28 Hz, 1H) 6.87 (d, J=6.18 Hz, 1H) 3.62-3.73 (m, 3H); m/z (ESI) 477.2 (M+H)+.

EXAMPLE 154

1-(4-FLUORO-2-METHOXY-5-METHYLPHENYL)-N-(PYRIMIDIN-4-YL)ISOQUINOLINE-6-SULFONAMIDE

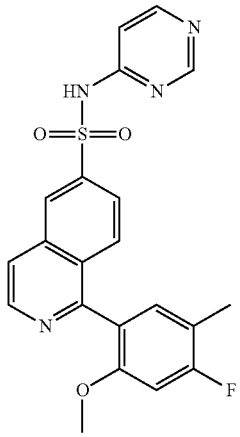 [SMILES: COc1cc(F)c(C)cc1-c1nccc2cc(S(=O)(=O)Nc3ccncn3)ccc12]

Example 154 was synthesized in a similar manner to Example 65, except that (4-fluoro-2-methoxy-5-methylphenyl)boronic acid was used as boronic acid. $^1$H NMR (500 MHz, DMSO-$d_6$) δ ppm 8.57-8.65 (m, 2H) 8.52 (s, 1H) 8.19 (d, J=6.53 Hz, 1H) 8.06 (d, J=5.73 Hz, 1H) 7.92 (d, J=8.94 Hz, 1H) 7.70 (d, J=9.00 Hz, 1H) 7.24 (d, J=8.94 Hz, 1H) 7.08 (d, J=11.97 Hz, 1H) 6.96 (d, J=5.84 Hz, 1H) 3.62 (s, 3H) 2.22 (s, 3H) 1.23 (s, 1H) 1.12-1.19 (m, 1H); m/z (ESI) 425.3 (M+H)+.

EXAMPLE 155

1-(3-METHOXYNAPHTHALEN-2-YL)-N-(PYRIMIDIN-4-YL)ISOQUINOLINE-6-SULFONAMIDE

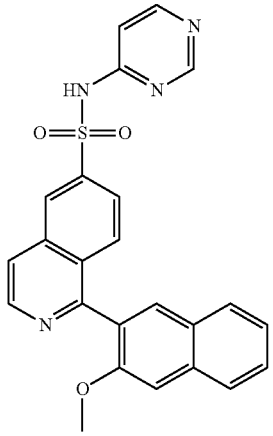 [SMILES: COc1cc2ccccc2cc1-c1nccc2cc(S(=O)(=O)Nc3ccncn3)ccc12]

Example 155 was synthesized in a similar manner to Example 65, except that (3-methoxynaphthalen-2-yl)boronic acid was used as boronic acid. $^1$H NMR (400 MHz, CHLOROFORM-d, DMSO-d6) δ ppm 8.62-8.69 (m, 1H) 8.56 (br. s., 1H) 8.47 (s, 1H) 8.23 (s, 1H) 7.70-7.91 (m, 7H) 7.41-7.51 (m, 1H) 7.26-7.38 (m, 2H) 7.07 (s, 1H) 6.00 (d, J=16.33 Hz, 1H) 3.72 (t, J=2.25 Hz, 3H); m/z (ESI) 443.3 (M+H)+.

EXAMPLE 156

1-(2-CHLORO-4-(TRIFLUOROMETHYL)PHENYL)-N-(PYRIMIDIN-4-YL)ISOQUINOLINE-6-SULFONAMIDE

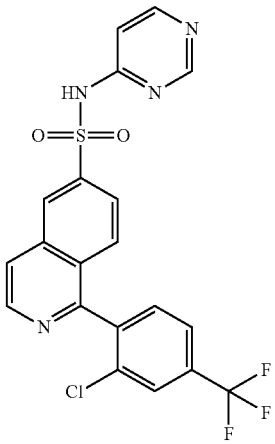 [SMILES: O=S(=O)(Nc1ccncn1)c1ccc2c(-c3ccc(C(F)(F)F)cc3Cl)nccc2c1]

Example 156 was synthesized in a similar manner to Example 65, except that (2-chloro-4-(trifluoromethyl)phenyl)boronic acid was used as boronic acid. $^1$H NMR (500 MHz, DMSO-$d_6$) δ ppm 8.71-8.80 (m, 2H) 8.58 (br. s., 1H) 8.24 (br. s., 2H) 8.12 (s, 1H) 7.99 (d, J=8.59 Hz, 1H) 7.93 (d, J=7.67 Hz, 1H) 7.79 (d, J=8.02 Hz, 1H) 7.68 (d, J=8.82 Hz, 1H) 7.04 (br. s., 1H); m/z (ESI) 465.2 (M+H)+.

EXAMPLE 157

1-(3-FLUORO-2-METHOXYPHENYL)-N-(PYRIMIDIN-4-YL)ISOQUINOLINE-6-SULFONAMIDE

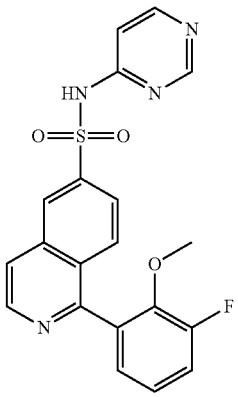 [SMILES: COc1c(F)cccc1-c1nccc2cc(S(=O)(=O)Nc3ccncn3)ccc12]

Example 157 was synthesized in a similar manner to Example 65, except that (3-fluoro-2-methoxyphenyl)boronic acid was used as boronic acid. $^1$H NMR (500 MHz, DMSO-$d_6$) δ ppm 8.65-8.74 (m, 2H) 8.57 (s, 1H) 8.25 (br. s., 1H) 8.16 (d, J=5.73 Hz, 1H) 7.98 (dd, J=8.88, 1.66 Hz, 1H) 7.77 (d, J=8.94 Hz, 1H) 7.47 (ddd, J=11.74, 8.25, 1.32 Hz, 1H) 7.27 (td, J=7.93, 4.87 Hz, 1H) 7.20 (d, J=7.33 Hz, 1H) 7.04 (br. s., 1H) 3.57 (d, J=1.37 Hz, 3H); m/z (ESI) 411.2 (M+H)⁺.

EXAMPLE 158

1-(2-FLUORO-6-METHOXYPHENYL)-N-(PYRIMIDIN-4-YL)ISOQUINOLINE-6-SULFONAMIDE

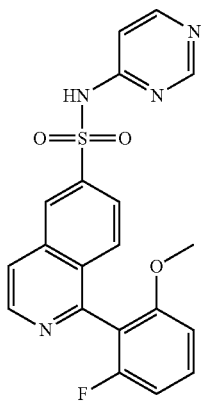 [SMILES: COc1cccc(F)c1-c1nccc2cc(S(=O)(=O)Nc3ccncn3)ccc12]

Example 158 was synthesized in a similar manner to Example 65, except that (2-fluoro-6-methoxyphenyl)boronic acid was used as boronic acid. ¹H NMR (400 MHz, DMSO-$d_6$) δ ppm 8.64 (d, J=5.58 Hz, 1H) 8.51 (s, 1H) 8.32 (s, 1H) 8.05 (d, J=5.38 Hz, 1H) 7.97 (br. s., 1H) 7.91 (d, J=8.80 Hz, 1H) 7.55 (d, J=6.85 Hz, 2H) 7.07 (d, J=7.92 Hz, 1H) 6.99 (t, J=8.56 Hz, 1H) 6.69 (br. s., 1H) 3.60-3.69 (m, 3H); m/z (ESI) 411.2 (M+H)⁺.

EXAMPLE 159

1-(4-CYANO-2-METHYLPHENYL)-N-(PYRIMIDIN-4-YL)ISOQUINOLINE-6-SULFONAMIDE

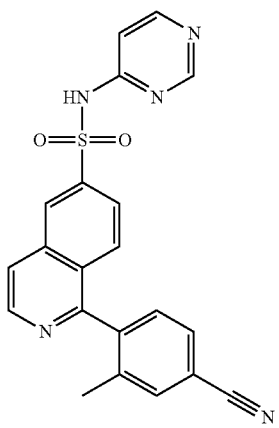 [SMILES: Cc1cc(C#N)ccc1-c1nccc2cc(S(=O)(=O)Nc3ccncn3)ccc12]

Example 159 was synthesized in a similar manner to Example 65, except that (4-cyano-2-methylphenyl)boronic was used as boronic acid. ¹H NMR (500 MHz, DMSO-$d_6$) δ ppm 8.69-8.76 (m, 2H) 8.57 (s, 1H) 8.24 (br. s., 1H) 8.19 (d, J=5.61 Hz, 1H) 7.97 (dd, J=8.82, 1.60 Hz, 1H) 7.93 (s, 1H) 7.83 (d, J=7.90 Hz, 1H) 7.63 (d, J=8.82 Hz, 1H) 7.52 (d, J=7.90 Hz, 1H) 2.01 (s, 3H); m/z (ESI) 402.2 (M+H)⁺.

EXAMPLE 160

1-(4-CHLORO-2-METHOXYPHENYL)-N-(PYRIMIDIN-4-YL)ISOQUINOLINE-6-SULFONAMIDE

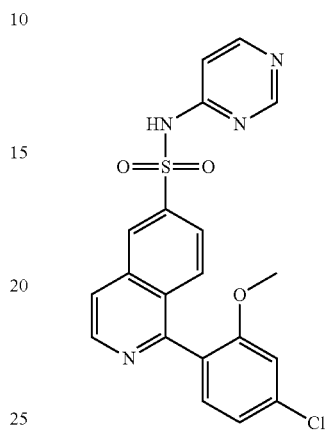

Example 160 was synthesized in a similar manner to Example 65, except that (4-chloro-2-methoxyphenyl)boronic acid was used boronic acid. ¹H NMR (500 MHz, DMSO-$d_6$) δ ppm 8.65-8.72 (m, 2H) 8.58 (s, 1H) 8.25 (br. s., 1H) 8.14 (d, J=5.73 Hz, 1H) 7.96 (dd, J=8.88, 1.66 Hz, 1H) 7.74 (d, J=8.93 Hz, 1H) 7.37 (d, J=8.13 Hz, 1H) 7.33 (d, J=1.72 Hz, 1H) 7.20 (dd, J=8.02, 1.83 Hz, 1H) 7.04 (br. s., 1H) 3.17 (s, 3H); m/z (ESI) 427.3 (M+H)⁺.

EXAMPLE 161

1-(4,5-DICHLORO-2-METHOXYPHENYL)-N-(PYRIMIDIN-4-YL)ISOQUINOLINE-6-SULFONAMIDE

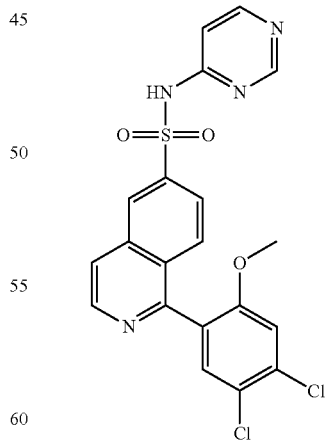

Example 161 was synthesized in a similar manner to Example 65, except that (4,5-dichloro-2-methoxyphenyl)boronic acid was used as boronic acid. ¹H NMR (500 MHz, DMSO-$d_6$) δ ppm 8.63-8.72 (m, 2H) 8.57 (br. s., 1H) 8.25 (br. s., 1H) 8.14 (d, J=5.50 Hz, 1H) 7.95 (d, J=8.71 Hz, 1H) 7.76

(d, J=8.82 Hz, 1H) 7.61 (s, 1H) 7.53 (s, 1H) 7.04 (br. s., 1H), 3.68 (s, 3H); m/z (ESI) 461.0 (M+H)$^+$.

EXAMPLE 162

1-(BENZO[B]THIOPHEN-7-YL)-N-(PYRIMIDIN-4-YL)ISOQUINOLINE-6-SULFONAMIDE

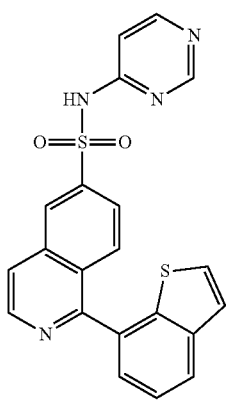 [SMILES: O=S(=O)(Nc1ccncn1)c1ccc2c(-c3cccc4ccsc34)nccc2c1]

Example 162 was synthesized in a similar manner to Example 65, except that benzo[b]thiophen-7-ylboronic acid was used as boronic acid. $^1$H NMR (500 MHz, DMSO-d$_6$) δ ppm 8.79 (d, J=5.61 Hz, 1H) 8.74 (br. s., 1H) 8.57 (s, 1H) 8.17-8.30 (m, 2H) 7.94-8.10 (m, 3H) 7.78 (d, J=5.38 Hz, 1H) 7.54-7.65 (m, 3H) 7.04 (br. s., 1H); m/z (ESI) 419.1 (M+H)$^+$.

EXAMPLE 163

1-(2-FLUORO-5-(TRIFLUOROMETHYL)PHENYL)-N-(PYRIMIDIN-4-YL)ISOQUINOLINE-6-SULFONAMIDE

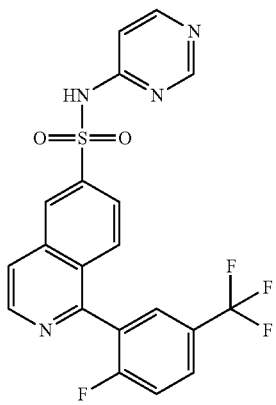 [SMILES: O=S(=O)(Nc1ccncn1)c1ccc2c(-c3cc(C(F)(F)F)ccc3F)nccc2c1]

Example 163 was synthesized in a similar manner to Example 65, except that (2-fluoro-5-(trifluoromethyl)phenyl)boronic acid was used as boronic acid. $^1$H NMR (500 MHz, DMSO-d$_6$) δ ppm 8.70-8.81 (m, 2H) 8.57 (s, 1H) 8.24 (d, J=5.61 Hz, 2H) 8.02 (d, J=7.22 Hz, 3H) 7.86 (d, J=7.10 Hz, 1H) 7.70 (t, J=8.99 Hz, 1H) 7.03 (br. s., 1H); m/z (ESI) 448.1 (M+H)$^+$.

EXAMPLE 164

1-(1-METHYL-1H-INDOL-7-YL)-N-(PYRIMIDIN-4-YL)ISOQUINOLINE-6-SULFONAMIDE

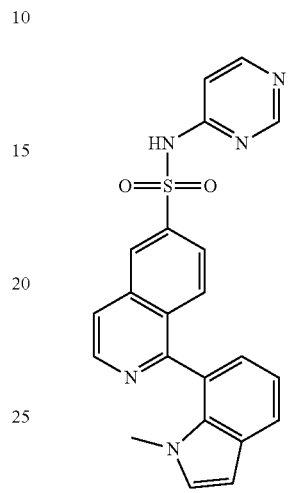

Example 164 was synthesized in a similar manner to Example 65, except that (1-methyl-1H-indol-7-yl)boronic acid was used as boronic acid. $^1$H NMR (500 MHz, DMSO-d$_6$) δ ppm 8.72-8.79 (m, 2H) 8.58 (s, 1H) 8.24 (d, J=5.27 Hz, 2H) 7.98 (d, J=8.71 Hz, 1H) 7.75 (d, J=8.36 Hz, 2H) 7.27 (d, J=2.86 Hz, 1H) 7.17 (t, J=7.50 Hz, 1H) 7.10 (d, J=6.99 Hz, 1H) 7.03 (br. s., 1H) 6.57 (d, J=2.98 Hz, 1H) 2.90 (s, 3H); m/z (ESI) 416.0 (M+H)$^+$.

EXAMPLE 165

1-(1,5-DIMETHYL-1H-INDAZOL-6-YL)-N-(PYRIMIDIN-4-YL)ISOQUINOLINE-6-SULFONAMIDE

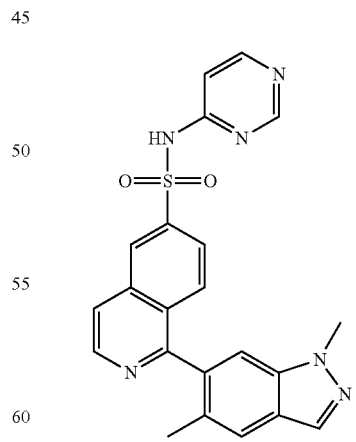

Example 165 was synthesized in a similar manner to Example 65, except that (1,5-dimethyl-1H-indazol-6-yl)boronic acid was used as boronic acid. $^1$H NMR (400 MHz, DMSO-d$_6$) δ ppm 8.71-8.77 (m, 2H) 8.58 (s, 1H) 8.25 (d, J=6.46 Hz, 1H) 8.21 (d, J=5.67 Hz, 1H) 8.08 (d, J=0.88 Hz, 1H) 7.95 (dd, J=8.90, 1.86 Hz, 1H) 7.75 (s, 1H) 7.70 (d, J=8.90 Hz, 1H) 7.64 (s, 1H) 7.04 (br. s., 1H) 4.01 (s, 3H) 3.96 (s, 3H); m/z (ESI) 431.1 (M+H)⁺.

EXAMPLE 166

1-(5-FLUORO-2-METHOXYPYRIDIN-3-YL)-N-(PYRIMIDIN-4-YL)ISOQUINOLINE-6-SULFONAMIDE

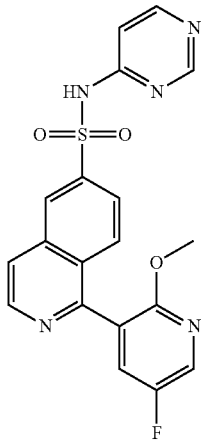 [SMILES: COc1ncc(F)cc1-c1nccc2cc(S(=O)(=O)Nc3ccncn3)ccc12]

Example 166 was synthesized in a similar manner to Example 65, except that (5-fluoro-2-methoxypyridin-3-yl)boronic acid was used as boronic acid. ¹H NMR (500 MHz, DMSO-d₆) δ ppm 8.62 (d, J=5.73 Hz, 1H) 8.50 (s, 1H) 8.36 (d, J=2.98 Hz, 1H) 8.29 (s, 1H) 8.07 (d, J=5.73 Hz, 1H) 7.90-7.97 (m, 2H) 7.86 (dd, J=8.19, 2.92 Hz, 1H) 7.65 (d, J=8.82 Hz, 1H) 6.64 (d, J=5.96 Hz, 1H) 3.75 (s, 3H); m/z (ESI) 412.0 (M+H)⁺.

EXAMPLE 167

1-(4-FLUORO-2-METHOXYPHENYL)-N-(PYRIMIDIN-4-YL)ISOQUINOLINE-6-SULFONAMIDE

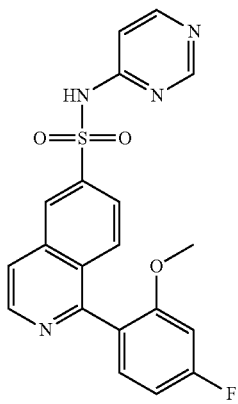 [SMILES: COc1cc(F)ccc1-c1nccc2cc(S(=O)(=O)Nc3ccncn3)ccc12]

Example 167 was synthesized in a similar manner to Example 65, except that (4-fluoro-2-methoxyphenyl)boronic acid was used as boronic acid. ¹H NMR (500 MHz, DMSO-d₆) δ ppm 8.58 (d, J=5.61 Hz, 1H) 8.44 (s, 1H) 8.27 (s, 1H) 7.98 (d, J=5.73 Hz, 1H) 7.86-7.94 (m, 2H) 7.57 (d, J=8.94 Hz, 1H) 7.34 (t, J=7.62 Hz, 1H) 7.11 (dd, J=11.51, 2.23 Hz, 1H) 6.93 (td, J=8.39, 2.35 Hz, 1H) 6.61 (d, J=5.96 Hz, 1H) 3.66 (s, 3H); m/z (ESI) 411.0 (M+H)⁺.

EXAMPLE 168

1-(5-CHLORO-2-METHOXYPYRIDIN-3-YL)-N-(PYRIMIDIN-4-YL)ISOQUINOLINE-6-SULFONAMIDE

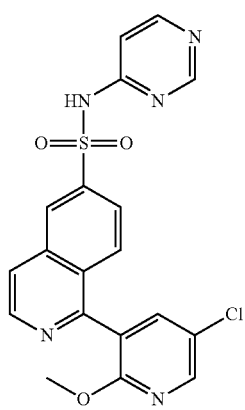 [SMILES: COc1ncc(Cl)cc1-c1nccc2cc(S(=O)(=O)Nc3ccncn3)ccc12]

Example 168 was synthesized in a similar manner to Example 65, except that (5-chloro-2-methoxypyridin-3-yl)boronic acid was used as boronic acid. ¹H NMR (500 MHz, DMSO-d₆) δ ppm 8.68 (d, J=5.61 Hz, 1H) 8.64 (s, 1H) 8.50 (s, 1H) 8.43 (d, J=2.52 Hz, 1H) 8.14 (d, J=5.73 Hz, 1H) 8.17 (d, J=6.41 Hz, 1H) 7.94-8.00 (m, 2H) 7.75 (d, J=8.94 Hz, 1H) 6.93 (d, J=6.41 Hz, 1H) 3.76 (s, 3H); m/z (ESI) 428.0 (M+H)⁺.

EXAMPLE 169

1-(3-METHOXYPYRIDIN-4-YL)-N-(PYRIMIDIN-4-YL)ISOQUINOLINE-6-SULFONAMIDE

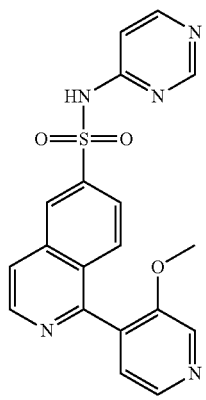 [SMILES: COc1cnccc1-c1nccc2cc(S(=O)(=O)Nc3ccncn3)ccc12]

Example 169 was synthesized in a similar manner to Example 65, except that (3-methoxypyridin-4-yl)boronic acid was used as boronic acid. ¹H NMR (500 MHz, DMSO-d₆) δ ppm 8.64 (d, J=5.73 Hz, 1H) 8.59 (s, 1H) 8.54 (s, 1H) 8.33-8.43 (m, 2H) 8.09 (d, J=5.73 Hz, 1H) 8.02 (d, J=6.07 Hz, 1H) 7.89-7.95 (m, 1H) 7.61 (d, J=8.82 Hz, 1H) 7.38 (d, J=4.58 Hz, 1H) 6.73 (d, J=6.19 Hz, 1H) 3.78 (s, 3H); m/z (ESI) 394.0 (M+H)⁺.

EXAMPLE 170

1-(4-METHOXYPYRIDIN-3-YL)-N-(PYRIMIDIN-4-YL)ISOQUINOLINE-6-SULFONAMIDE

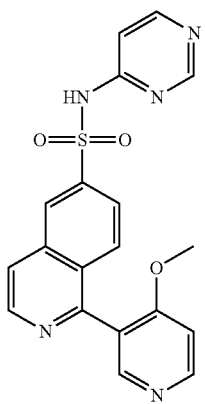 [SMILES: COc1ccncc1-c1nccc2cc(S(=O)(=O)Nc3ccncn3)ccc12]

Example 170 was synthesized in a similar manner to Example 65, except that (4-methoxypyridin-3-yl)boronic acid was used as boronic acid. ¹H NMR (500 MHz, DMSO-d₆) δ ppm 8.62 (d, J=5.84 Hz, 1H) 8.65 (d, J=5.73 Hz, 1H) 8.54 (s, 1H) 8.38 (d, J=8.94 Hz, 2H) 8.02-8.10 (m, 2H) 7.92 (d, J=8.94 Hz, 1H) 7.64 (d, J=8.82 Hz, 1H) 7.28 (d, J=5.84 Hz, 1H) 6.76 (d, J=6.07 Hz, 1H) 3.75 (s, 3H); m/z (ESI) 394.0 (M+H)⁺.

EXAMPLE 171

1-(2,6-DIMETHOXYPHENYL)-N-(PYRIMIDIN-4-YL)ISOQUINOLINE-6-SULFONAMIDE

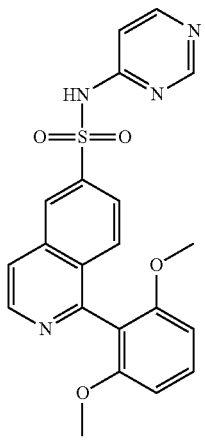 [SMILES: COc1cccc(OC)c1-c1nccc2cc(S(=O)(=O)Nc3ccncn3)ccc12]

Example 171 was synthesized in a similar manner to Example 65, except that (2,6-dimethoxyphenyl)boronic acid was used as boronic acid. ¹H NMR (500 MHz, DMSO-d₆) δ ppm 8.61-8.68 (m, 2H) 8.57 (s, 1H) 8.24 (d, J=6.53 Hz, 1H) 8.03 (d, J=5.73 Hz, 1H) 7.88-7.93 (m, 1H) 7.59 (d, J=8.94 Hz, 1H) 7.47 (t, J=8.36 Hz, 1H) 7.03 (d, J=5.27 Hz, 1H) 6.84 (d, J=8.48 Hz, 2H) 3.56 (s, 6H); m/z (ESI) 423.0 (M+H)⁺.

EXAMPLE 172

1-(2,4-DIMETHOXYPHENYL)-N-(PYRIMIDIN-4-YL)ISOQUINOLINE-6-SULFONAMIDE

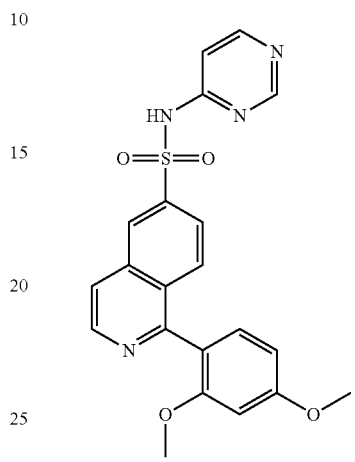

Example 172 was synthesized in a similar manner to Example 65, except that (2,4-dimethoxyphenyl)boronic acid was used as boronic acid. ¹H NMR (500 MHz, DMSO-d₆) δ ppm 8.75 (s, 1H) 8.70 (d, J=5.96 Hz, 1H) 8.58 (s, 1H) 8.31 (d, J=6.19 Hz, 1H) 8.24 (d, J=6.41 Hz, 1H) 8.06 (d, J=8.82 Hz, 1H) 7.90 (d, J=8.82 Hz, 1H) 7.38 (d, J=8.36 Hz, 1H) 7.02 (br. s., 1H) 6.82 (d, J=2.18 Hz, 1H) 6.77 (dd, J=8.42, 2.12 Hz, 2H) 3.89 (s, 3H); m/z (ESI) 423.0 (M+H)⁺.

EXAMPLE 173

1-(2-ETHOXYPHENYL)-N-(PYRIMIDIN-4-YL)ISOQUINOLINE-6-SULFONAMIDE

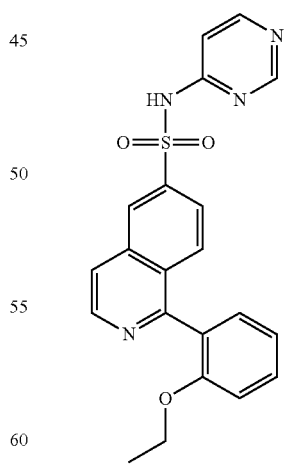

Example 173 was synthesized in a similar manner to Example 65, except that (2-ethoxyphenyl)boronic acid was used as boronic acid. ¹H NMR (500 MHz, DMSO-d₆) δ ppm 8.70-8.78 (m, 2H) 8.56 (s, 1H) 8.29 (d, J=5.96 Hz, 1H) 8.24 (d, J=6.53 Hz, 1H) 8.04 (d, J=8.71 Hz, 1H) 7.85 (d, J=8.82

Hz, 1H) 7.58 (t, J=7.10 Hz, 1H) 7.45 (d, J=7.45 Hz, 1H) 7.25 (d, J=8.36 Hz, 1H) 7.16 (t, J=7.39 Hz, 1H) 7.00 (d, J=6.64 Hz, 1H) 4.01 (q, J=6.87 Hz, 2H) 0.89 (t, J=6.93 Hz, 3H); m/z (ESI) 407.0 (M+H)+.

EXAMPLE 174

N-(PYRIMIDIN-4-YL)-1-(2-(2,2,2-TRIFLUORO-ETHOXY)PHENYL)ISOQUINOLINE-6-SUL-FONAMIDE

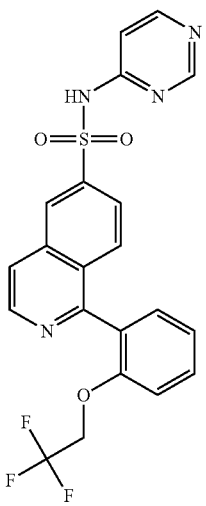 [SMILES: O=S(=O)(Nc1ccncn1)c1ccc2c(-c3ccccc3OCC(F)(F)F)nccc2c1]

Example 174 was synthesized in a similar manner to Example 65, except that (2-(2,2,2-trifluoroethoxy)phenyl) boronic acid was used as boronic acid. $^1$H NMR (500 MHz, DMSO-d$_6$) δ ppm 8.62-8.72 (m, 2H) 8.55 (s, 1H) 8.25 (br. s., 1H) 8.11 (d, J=5.61 Hz, 1H) 7.92 (dd, J=8.82, 1.60 Hz, 1H) 7.73 (d, J=8.93 Hz, 1H) 7.53-7.62 (m, 1H) 7.43 (dd, J=7.45, 1.49 Hz, 1H) 7.33 (d, J=8.36 Hz, 1H) 7.24 (t, J=7.39 Hz, 1H) 4.67 (q, J=8.74 Hz, 2H); m/z (ESI) 461.0 (M+H)+.

EXAMPLE 175

1-(2-METHOXY-4-METHYLPHENYL)-N-(THIA-ZOL-2-YL)ISOQUINOLINE-6-SULFONAMIDE

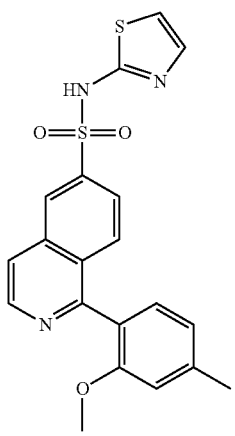 [SMILES: COc1cc(C)ccc1-c1nccc2cc(S(=O)(=O)Nc3nccs3)ccc12]

A microwave vial containing Cs$_2$CO$_3$ (0.175 g, 0.538 mmol), (2-methoxy 4-methyl phenyl)boronic acid (27 mg, 0.175 mmol) and 1-chloro-N-(4-methoxybenzyl)-N-(thiazol-2-yl)isoquinoline-6-sulfonamide (Intermediate JJJ; 0.06 g, 0.135 mmol) in DME (1.500 ml) and water (0.225 ml) was purged with nitrogen and Pd(PPh$_3$)$_4$ (0.016 g, 0.013 mmol) was added and the reaction was irradiated under microwave irradiation at 125° C. for 1.5 h. The aqueous layer was discarded and the organic layer was concentrated. To this was then added DCM (1 mL) and TFA (0.5 mL) and the reaction was shaken for 2 h. The reaction mixture was purified by reverse-phase chromatography with 0.1% NH$_4$OH in ACN and water as mobile phase to obtain 1-(2-methoxy-4-methylphenyl)-N-(thiazol-2-yl)isoquinoline-6-sulfonamide (28 mg, 51%) as a light yellow solid. $^1$H NMR (500 MHz, DMSO-d$_6$) δ ppm 12.87 (br. s., 1H) 8.65 (d, J=5.61 Hz, 1H) 8.51 (s, 1H) 8.05 (d, J=5.73 Hz, 1H) 7.85 (dd, J=8.88, 1.66 Hz, 1H) 7.71 (d, J=8.94 Hz, 1H) 7.27 (d, J=4.58 Hz, 1H) 7.20 (d, J=7.56 Hz, 1H) 7.04 (s, 1H) 6.93 (d, J=7.45 Hz, 1H) 6.87 (d, J=4.58 Hz, 1H) 3.63 (s, 3H) 2.43 (s, 3H); m/z (ESI) 416.0 (M+H)+.

EXAMPLE 176

1-(5-CHLORO-2-METHOXYPYRIDIN-3-YL)-N-(THIAZOL-2-YL)ISOQUINOLINE-6-SULFONA-MIDE

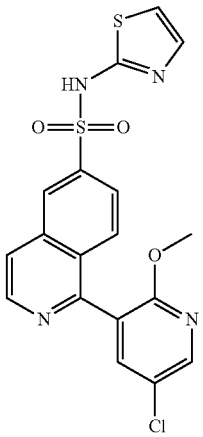 [SMILES: COc1ncc(Cl)cc1-c1nccc2cc(S(=O)(=O)Nc3nccs3)ccc12]

Example 176 was synthesized in a similar manner to Example 175, using (5-chloro-2-methoxypyridin-3-yl)boronic acid in place of (2-methoxy 4-methyl phenyl)boronic acid. $^1$H NMR (500 MHz, DMSO-d$_6$) δ ppm 12.92 (s, 1H) 8.69 (d, J=5.56 Hz, 1H) 8.57 (s, 1H) 8.44 (d, J=2.67 Hz, 1H) 8.16 (d, J=5.56 Hz, 1H) 7.98 (d, J=2.14 Hz, 1H) 7.89 (d, J=8.12 Hz, 1H) 7.79 (d, J=8.65 Hz, 1H) 7.28 (d, J=4.49 Hz, 1H) 6.87 (d, J=4.59 Hz, 1H) 3.77 (s, 3H); m/z (ESI) 433.1 (M+H)$^+$.

EXAMPLE 177

1-(4,5-DICHLORO-2-METHOXYPHENYL)-N-(THIAZOL-2-YL)ISOQUINOLINE-6-SULFONAMIDE

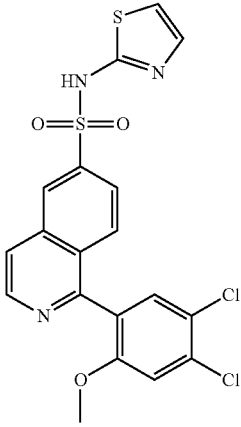 [SMILES: COc1cc(Cl)c(Cl)cc1-c1nccc2cc(S(=O)(=O)Nc3nccs3)ccc12]

Example 177 was synthesized in a similar manner to Example 175, using (4,5-dichloro-2-methoxyphenyl)boronic acid in place of (2-methoxy 4-methyl phenyl)boronic acid. $^1$H NMR (500 MHz, DMSO-d$_6$) δ ppm 12.89 (br. s., 1H) 8.67 (d, J=5.61 Hz, 1H) 8.54 (s, 1H) 8.12 (d, J=5.73 Hz, 1H) 7.87 (dd, J=8.82, 1.60 Hz, 1H) 7.75 (d, J=8.94 Hz, 1H) 7.60 (s, 1H) 7.52 (s, 1H) 7.28 (d, J=4.47 Hz, 1H) 6.87 (d, J=4.58 Hz, 1H) 3.69 (s, 3H); m/z (ESI) 465.8 (M+H)$^+$.

EXAMPLE 178

N-(THIAZOL-2-YL)-1-(O-TOLYL)ISOQUINOLINE-6-SULFONAMIDE

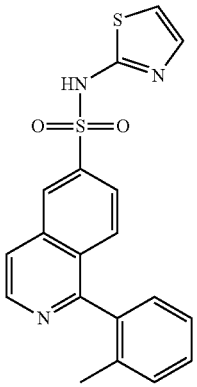 [SMILES: Cc1ccccc1-c1nccc2cc(S(=O)(=O)Nc3nccs3)ccc12]

Example 178 was synthesized in a similar manner to Example 175, using o-tolylboronic acid in place of (2-methoxy 4-methyl phenyl)boronic acid. $^1$H NMR (500 MHz, DMSO-d$_6$) δ ppm 8.70 (d, J=5.67 Hz, 1H) 8.57 (s, 1H) 8.11 (d, J=5.67 Hz, 1H) 7.88 (dd, J=8.85, 1.63 Hz, 1H) 7.66 (d, J=8.82 Hz, 1H) 7.37-7.47 (m, 2H) 7.35 (s, 1H) 7.25-7.31 (m, 2H) 6.87 (d, J=4.52 Hz, 1H) 1.97 (s, 3H); m/z (ESI) 382.0 (M+H)$^+$.

EXAMPLE 179

1-(2-CHLOROPHENYL)-N-(THIAZOL-2-YL)ISOQUINOLINE-6-SULFONAMIDE

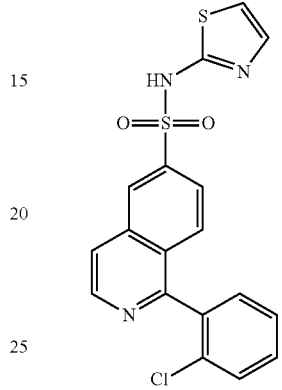

Example 179 was synthesized in a similar manner to Example 175, using (2-chlorophenyl)boronic acid in place of (2-methoxy 4-methyl phenyl)boronic acid. $^1$H NMR (500 MHz, DMSO-d$_6$) δ ppm 12.89 (br. s., 1H) 8.71 (d, J=5.67 Hz, 1H) 8.59 (s, 1H) 8.17 (d, J=5.67 Hz, 1H) 7.91 (dd, J=8.88, 1.60 Hz, 1H) 7.49-7.68 (m, 5H) 7.28 (d, J=4.53 Hz, 1H) 6.74-6.90 (m, 1H); m/z (ESI) 402.0 (M+H)$^+$.

EXAMPLE 180

1-(2-METHOXY-5-(TRIFLUOROMETHYL)PHENYL)-N-(THIAZOL-2-YL)ISOQUINOLINE-6-SULFONAMIDE

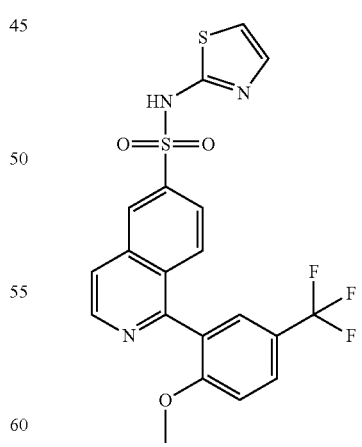

Example 180 was synthesized in a similar manner to Example 175, using (5-chloro-2-methoxypyridin-3-yl)boronic acid in place of (2-methoxy-5-(trifluoromethyl)phenyl) boronic acid. $^1$H NMR (400 MHz, DMSO-d$_6$) δ ppm 8.65 (d, J=5.58 Hz, 1H) 8.49 (s, 1H) 8.09 (d, J=5.77 Hz, 1H) 7.84-7.94

(m, 2H) 7.62-7.68 (m, 2H) 7.43 (d, J=8.71 Hz, 1H) 7.13 (d, J=4.60 Hz, 1H) 6.70 (d, J=2.93 Hz, 1H) 3.75 (s, 3H); m/z (ESI) 466.0 (M+H)+.

EXAMPLE 181

1-(2-METHOXY-4-(TRIFLUOROMETHYL)PHENYL)-N-(6-METHOXYPYRIMIDIN-4-YL)ISOQUINOLINE-6-SULFONAMIDE

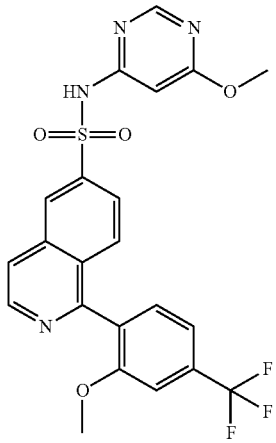 [SMILES: COc1cc(NS(=O)(=O)c2ccc3c(-c4ccc(C(F)(F)F)cc4OC)nccc3c2)ncn1]

To a vial containing 6-methoxypyrimidin-4-amine (0.063, 0.503 mmol) in 2Me-THF (1 ml) was added lithium bis(trimethylsilyl)amide (237 µl, 0.237 mmol) at −78° C. and stirred for 1 h. To this was then added a solution of perfluorophenyl 1-(2-methoxy-4-(trifluoromethyl)phenyl)isoquinoline-6-sulfonate (Intermediate LLL; 100 mg, 0.182 mmol) in 2Me-THF (1 ml) at −78° C. dropwise and stirred for 1 h. Reaction mixture was quenched with 3 drops of methanol and purified via reverse-phase chromatography with 0.1% NH4OH in ACN and water as mobile phase to obtain 1-(2-methoxy-4-(trifluoromethyl)phenyl)-N-(6-methoxypyrimidin-4-yl)isoquinoline-6-sulfonamide (0.005 g, 6%) as white solid. 1H NMR (400 MHz, CHLOROFORM-d) δ ppm 8.77 (d, J=5.77 Hz, 1H) 8.63 (s, 1H) 8.52-8.56 (m, 1H) 7.82-7.89 (m, 2H) 7.77 (d, J=8.80 Hz, 1H) 7.50 (d, J=7.83 Hz, 1H) 7.41 (d, J=8.12 Hz, 1H) 7.28 (br. s., 2H) 3.96 (s, 3H) 3.75 (s, 3H); m/z (ESI) 491.1 (M+H)+.

EXAMPLE 182

1-(2-METHOXY-4-(TRIFLUOROMETHYL)PHENYL)-N-(2-METHYLPYRIMIDIN-4-YL)ISOQUINOLINE-6-SULFONAMIDE

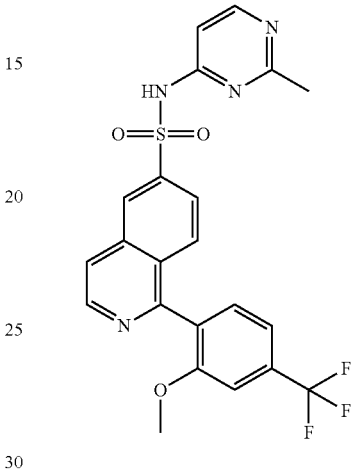

Example 182 was synthesized in a similar manner to Example 181, using 2-methylpyrimidin-4-amine in place of 6-methoxypyrimidin-4-amine 1H NMR (400 MHz, DMSO-d6) δ ppm 8.68 (d, J=5.67 Hz, 1H) 8.63 (s, 1H) 8.12 (d, J=5.77 Hz, 1H) 7.94 (d, J=10.56 Hz, 1H) 7.68 (d, J=9.29 Hz, 1H) 7.55-7.59 (m, 1H) 7.47-7.53 (m, 2H) 3.74 (s, 3H) 1.91 (s, 4H); m/z (ESI) 475.2 (M+H)+.

EXAMPLE 183

N-(5-FLUOROPYRIMIDIN-4-YL)-1-(2-METHOXY-4-(TRIFLUOROMETHYL)PHENYL)ISOQUINOLINE-6-SULFONAMIDE

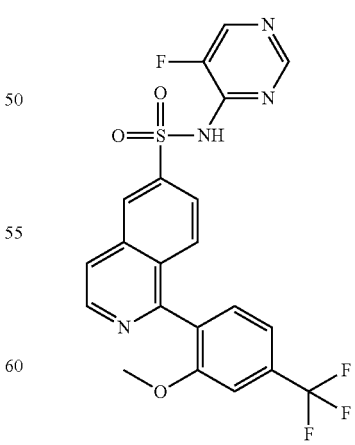

Example 183 was synthesized in a similar manner to Example 181, using 5-fluoropyrimidin-4-amine in place of 6-methoxypyrimidin-4-amine. 1H NMR (400 MHz, DMSO-d$_6$) δ ppm 8.62 (d, J=5.67 Hz, 1H) 8.54 (d, J=1.37 Hz, 1H) 8.02-8.08 (m, 3H) 7.96 (dd, J=8.80, 1.76 Hz, 1H) 7.53-7.59 (m, 2H) 7.46-7.51 (m, 2H) 3.74 (s, 3H); m/z (ESI) 479.0 (M+H)$^+$.

EXAMPLE 184

1-(2-METHOXY-4-(TRIFLUOROMETHYL)PHENYL)-N-(1,3,4-THIADIAZOL-2-YL)ISOQUINOLINE-6-SULFONAMIDE

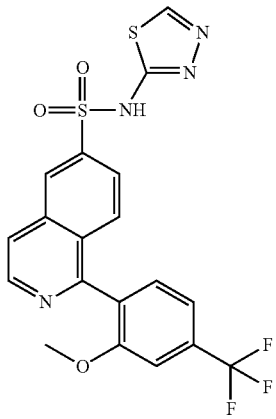 [SMILES: COc1cc(C(F)(F)F)ccc1-c1nccc2cc(S(=O)(=O)Nc3nncs3)ccc12]

Example 184 was synthesized in a similar manner to Example 181, using 1,3,4-thiadiazol-2-amine in place of 6-methoxypyrimidin-4-amine $^1$H NMR (400 MHz, CHLOROFORM-d) δ ppm 8.75 (d, J=5.67 Hz, 1H) 8.51 (d, J=1.66 Hz, 1H) 8.24 (s, 1H) 7.91 (dd, J=8.85, 1.81 Hz, 1H) 7.81 (d, J=5.67 Hz, 1H) 7.75 (d, J=8.90 Hz, 1H) 7.50 (d, J=7.73 Hz, 1H) 7.38-7.42 (m, 1H) 7.28 (br. s., 1H) 3.75 (s, 3H); m/z (ESI) 467.0 (M+H)$^+$.

EXAMPLE 185

1-(2-METHOXY-4-(TRIFLUOROMETHYL)PHENYL)-N-(PYRIDAZIN-3-YL)ISOQUINOLINE-6-SULFONAMIDE

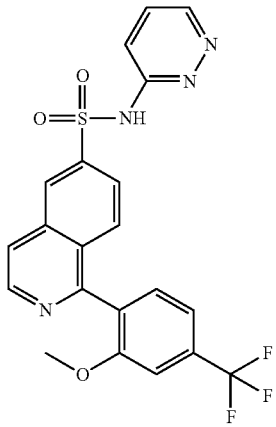 [SMILES: COc1cc(C(F)(F)F)ccc1-c1nccc2cc(S(=O)(=O)Nc3cccnn3)ccc12]

Example 185 was synthesized in a similar manner to Example 181, using pyridazin-3-amine in place of 6-methoxypyrimidin-4-amine $^1$H NMR (400 MHz, DMSO-d$_6$) δ ppm 8.68 (d, J=5.67 Hz, 1H) 8.59 (d, J=1.56 Hz, 1H) 8.33 (dd, J=4.11, 1.17 Hz, 1H) 8.09 (d, J=5.67 Hz, 1H) 7.91 (dd, J=8.85, 1.81 Hz, 1H) 7.79 (d, J=9.68 Hz, 1H) 7.66 (d, J=8.80 Hz, 1H) 7.54-7.63 (m, 2H) 7.47-7.52 (m, 2H) 3.74 (s, 3H); m/z (ESI) 461.0 (M+H)$^+$.

EXAMPLE 186

1-(2-METHOXY-4-(TRIFLUOROMETHYL)PHENYL)-N-(PYRAZIN-2-YL)ISOQUINOLINE-6-SULFONAMIDE

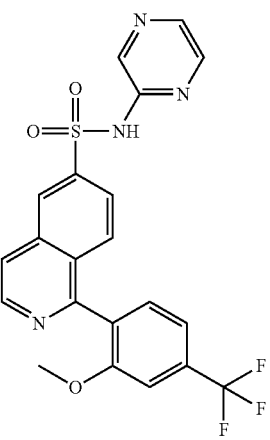 [SMILES: COc1cc(C(F)(F)F)ccc1-c1nccc2cc(S(=O)(=O)Nc3cnccn3)ccc12]

Example 186 was synthesized in a similar manner to Example 181, using pyrazin-2-amine in place of 6-methoxypyrimidin-4-amine $^1$H NMR (400 MHz, DMSO-d$_6$) δ ppm 8.76 (d, J=1.66 Hz, 1H) 8.73 (d, J=5.67 Hz, 1H) 8.40 (s, 1H) 8.22 (d, J=2.74 Hz, 1H) 8.16-8.20 (m, 2H) 7.99 (dd, J=8.90, 1.96 Hz, 1H) 7.76 (d, J=9.00 Hz, 1H) 7.55-7.59 (m, 1H) 7.47-7.52 (m, 2H) 3.73 (s, 3H); m/z (ESI) 461.3 (M+H)+.

EXAMPLE 187

1-(2-METHOXY-4-(TRIFLUOROMETHYL)PHENYL)-N-(6-METHYLPYRIMIDIN-4-YL)ISOQUINOLINE-6-SULFONAMIDE

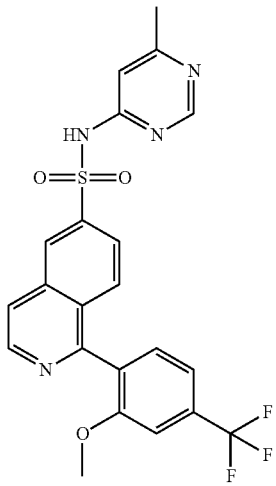 [SMILES: COc1cc(C(F)(F)F)ccc1-c1nccc2cc(S(=O)(=O)Nc3cc(C)ncn3)ccc12]

Example 187 was synthesized in a similar manner to Example 181, using 6-methylpyrimidin-4-amine in place of 6-methoxypyrimidin-4-amine ¹H NMR (400 MHz, DMSO-d₆) δ ppm 8.65-8.74 (m, 3H) 8.47 (s, 1H) 8.15 (d, J=5.67 Hz, 1H) 7.95 (dd, J=8.90, 1.76 Hz, 1H) 7.70 (d, J=8.90 Hz, 1H) 7.55-7.60 (m, 1H) 7.47-7.54 (m, 2H) 2.31 (s, 3H); m/z (ESI) 475.0 (M+H)+.

EXAMPLE 188

1-(2-METHOXY-4-(TRIFLUOROMETHYL)PHENYL)-N-(PYRIMIDIN-2-YL)ISOQUINOLINE-6-SULFONAMIDE

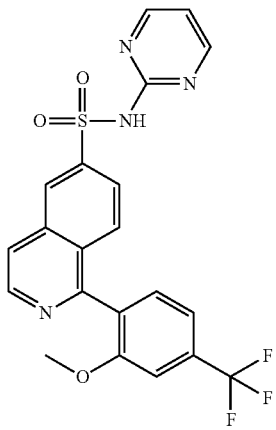 [SMILES: COc1cc(C(F)(F)F)ccc1-c1nccc2cc(S(=O)(=O)Nc3ncccn3)ccc12]

Example 188 was synthesized in a similar manner to Example 181, using pyrimidin-2-amine in place of 6-methoxypyrimidin-4-amine ¹H NMR (400 MHz, CHLORO-FORM-d) δ ppm 8.64 (d, J=1.66 Hz, 1H) 8.57 (d, J=5.77 Hz, 1H) 8.48 (d, J=4.99 Hz, 2H) 7.95 (dd, J=8.95, 1.81 Hz, 1H) 7.76 (d, J=5.67 Hz, 1H) 7.61 (d, J=8.90 Hz, 1H) 7.28 (d, J=7.73 Hz, 1H) 7.17 (d, J=7.82 Hz, 1H) 7.06 (s, 1H) 6.86 (t, J=4.99 Hz, 1H) 3.56 (s, 3H); m/z (ESI) 461.0 (M+H)+.

EXAMPLE 189

1-(4-FLUORO-2-HYDROXYPHENYL)-N-(THIAZOL-2-YL)ISOQUINOLINE-6-SULFONAMIDE

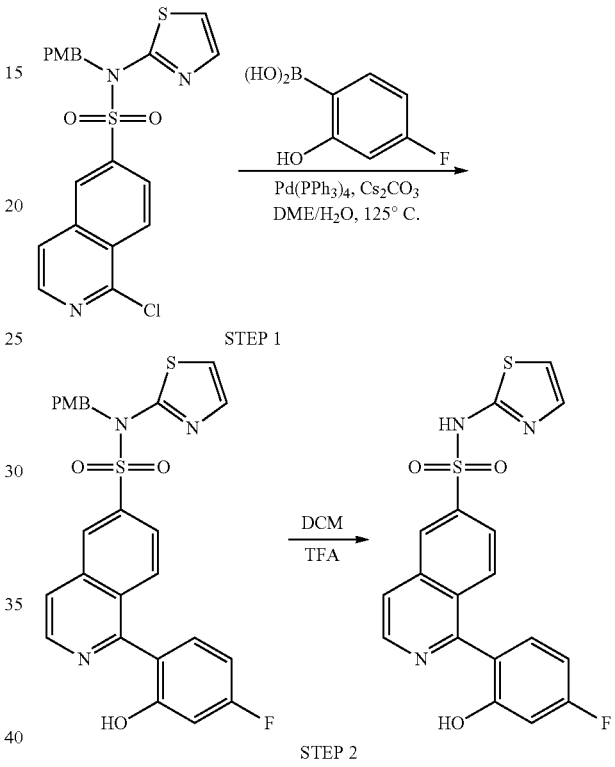

STEP 1: 1-(4-FLUORO-2-HYDROXYPHENYL)-N-(4-METHOXYBENZYL)-N-(THIAZOL-2-YL)ISOQUINOLINE-6-SULFONAMIDE

A vial containing a suspension of Cs₂CO₃ (0.292 g, 0.897 mmol), (4-fluoro-2-hydroxyphenyl)boronic acid (0.045 g, 0.292 mmol) and 1-chloro-N-(4-methoxybenzyl)-N-(thiazol-2-yl)isoquinoline-6-sulfonamide (Intermediate JJJ; 0.1 g, 0.224 mmol) in DME (2.5 ml) and water (0.375 ml) was degassed with nitrogen and tetrakis(triphenylphosphine)palladium (0.026 g, 0.022 mmol) was added. The vial was sealed and heated under microwave irradiation at 125° C. for 30 min. The aqueous layer was discarded using a pipette and the organic layer was concentrated and purified by silica gel chromatography (25 g column, eluting with Hex:EtOAc (0 to 50%)). Pure fractions were combined and concentrated to obtain 1-(4-fluoro-2-hydroxyphenyl)-N-(4-methoxybenzyl)-N-(thiazol-2-yl)isoquinoline-6-sulfonamide (0.108 g, 0.207 mmol, 92% yield) as light yellow solid.

STEP 2: 1-(4-FLUORO-2-HYDROXYPHENYL)-N-(THIAZOL-2-YL)ISOQUINOLINE-6-SULFONAMIDE 1-(4-fluoro-2-hydroxyphenyl)-N-(4-methoxybenzyl)-N-(thiazol-2-yl)isoquinoline-6-sulfonamide was dissolved in DCM (1 ml) and TFA (1 ml) and stirred at ambient temperature for 2 h. The mixture was purified by reverse phase chromatography, eluting with 0.1% NH$_4$OH in ACN and water as mobile phase to obtain 1-(4-fluoro-2-hydroxyphenyl)-N-(thiazol-2-yl)isoquinoline-6-sulfonamide (20 mg, 22%). $^1$H NMR (400 MHz, DMSO-d$_6$) δ ppm 12.88 (br. s., 1H) 10.19 (s, 1H) 8.65 (d, J=5.67 Hz, 1H) 8.51 (d, J=1.56 Hz, 1H) 8.06 (d, J=5.87 Hz, 1H) 7.78-7.91 (m, 2H) 7.34 (t, J=7.78 Hz, 1H) 7.26 (d, J=4.50 Hz, 1H) 6.76-6.88 (m, 3H). m/z (ESI) 402.0 (M+H)$^+$.

EXAMPLE 190

1-(4-FLUORO-2-(PYRIDAZIN-3-YLOXY)PHENYL)-N-(THIAZOL-2-YL)ISOQUINOLINE-6-SULFONAMIDE

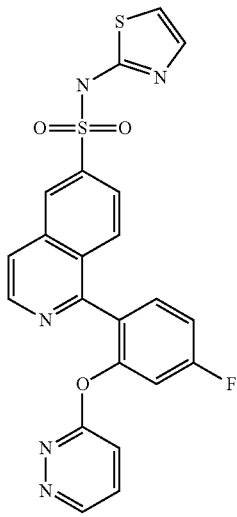 [SMILES: O=S(=O)(Nc1nccs1)c1ccc2c(-c3ccc(F)cc3Oc3cccnn3)nccc2c1]

A vial containing a suspension of Cs$_2$CO$_3$ (0.035 ml, 0.431 mmol), 3-chloropyridazine (0.016 g, 0.144 mmol) and 1-(4-fluoro-2-hydroxyphenyl)-N-(4-methoxybenzyl)-n-(thiazol-2-yl)isoquinoline-6-sulfonamide (from Example 219, Step 1; 75 mg, 0.144 mmol) in DMF (1438 ml) was heated to 100° C. for 3 days. The crude mixture was filtered through SPE (Solid Phase Extraction Frit) and to the filtrate was then added TFA (1 mL) and the solution was stirred at ambient temperature for 2 h. Reaction mixture was purified by reverse phase chromatography, eluting with 0.1% NH$_4$OH in ACN and water as mobile phase to obtain 1-(4-fluoro-2-(pyridazin-3-yloxy)phenyl)-N-(thiazol-2-yl)isoquinoline-6-sulfonamide (23 mg, 37%) as off white solid. $^1$H NMR (400 MHz, DMSO-d$_6$) δ ppm 8.79 (dd, J=4.50, 1.27 Hz, 1H) 8.56 (d, J=5.67 Hz, 1H) 8.46 (d, J=1.76 Hz, 1H) 8.01 (d, J=5.67 Hz, 1H) 7.87 (d, J=8.90 Hz, 1H) 7.77 (dd, J=8.90, 1.86 Hz, 1H) 7.64 (dd, J=8.71, 6.55 Hz, 1H) 7.41-7.48 (m, 2H) 7.35 (td, J=8.49, 2.49 Hz, 1H) 7.27 (d, J=4.60 Hz, 1H) 6.98 (dd, J=8.90, 1.27 Hz, 1H) 6.84-6.90 (m, 2H); m/z (ESI) 478.0 (M+H)$^+$.

EXAMPLE 191

1-(4-FLUORO-2-(PYRIDIN-2-YLOXY)PHENYL)-N-(THIAZOL-2-YL)ISOQUINOLINE-6-SULFONAMIDE

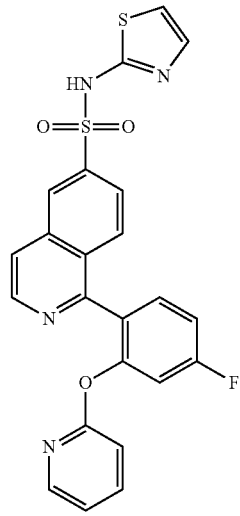 [SMILES: O=S(=O)(Nc1nccs1)c1ccc2c(-c3ccc(F)cc3Oc3ccccn3)nccc2c1]

Example 191 was synthesized in a similar manner to Example 190, using 2-fluoropyridine in place of 3-chloropyridazine. $^1$H NMR (400 MHz, DMSO-d$_6$) δ ppm 8.52 (d, J=5.67 Hz, 1H) 8.37 (s, 1H) 7.91-7.96 (m, 2H) 7.74-7.84 (m, 2H) 7.57 (dd, J=8.41, 6.85 Hz, 1H) 7.51 (td, J=7.73, 2.05 Hz, 1H) 7.20-7.29 (m, 2H) 7.11 (d, J=4.11 Hz, 1H) 6.89 (dd, J=6.46, 5.09 Hz, 1H) 6.67 (d, J=4.30 Hz, 1H) 6.50 (d, J=8.22 Hz, 1H); m/z (ESI) 479.0 (M+H)+.

EXAMPLE 192

1-(2-(CYANOMETHOXY)-4-FLUOROPHENYL)-N-(THIAZOL-2-YL)ISOQUINOLINE-6-SULFONAMIDE

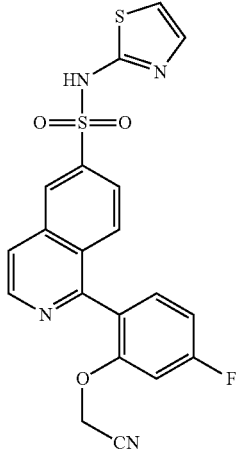 [SMILES: N#CCOc1cc(F)ccc1-c1nccc2cc(S(=O)(=O)Nc3nccs3)ccc12]

To an ice cold solution of 1-(4-fluoro-2-hydroxyphenyl)-N-(4-methoxybenzyl)-n-(thiazol-2-yl)isoquinoline-6-sulfonamide (from Example 219, Step 1; 0.1 g, 0.192 mmol) and bromoacetonitrile (0.383 mmol) in THF (1.917 mL) under nitrogen was added NaH, 60% dispersion in mineral oil (0.018 g, 0.767 mmol) and the temperature was slowly raised to ambient temperature and stirred for 16 h. Mixture was quenched with methanol (5 drops) and diluted with DCM and filtered through SPE. The filtrate was concentrated and the material was diluted with DCM (1 mL) and TFA (1 mL), and stirred for 2 h at ambient temperature. The mixture was purified by reverse phase chromatography, eluting with 0.1% NH4OH in ACN and water as mobile phase to obtain 1-(2-(cyanomethoxy)-4-fluorophenyl)-N-(thiazol-2-yl)isoquinoline-6-sulfonamide. $^1$H NMR (400 MHz, DMSO-d$_6$) δ ppm 8.66 (d, J=5.67 Hz, 1H) 8.50 (d, J=1.66 Hz, 1H) 8.08 (d, J=5.67 Hz, 1H) 7.86 (dd, J=8.85, 1.81 Hz, 1H) 7.66 (d, J=8.80 Hz, 1H) 7.46 (dd, J=8.41, 6.75 Hz, 1H) 7.37 (dd, J=11.05, 2.35 Hz, 1H) 7.08-7.17 (m, 2H) 6.73 (d, J=4.30 Hz, 1H) 5.14 (s, 2H); m/z (ESI) 441.2 (M+H)+.

EXAMPLE 193

1-(3,4-DICHLOROPHENOXY)-N-(PYRIMIDIN-4-YL)ISOQUINOLINE-6-SULFONAMIDE

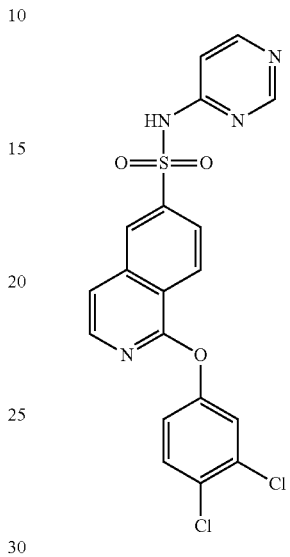

A vial containing a mixture of Cs$_2$CO$_3$ (305 mg, 0.935 mmol), 3,4-dichlorophenol (0.076 g, 0.468 mmol) and Intermediate GG (0.1 g, 0.312 mmol) was shaken on a reaction shaker at 110° C. for 16 h. The crude mixture was filtered through an SPE and purified by reverse phase chromatography, eluting with 0.1% NH$_4$OH in ACN and water as mobile phase to obtain 1-(3,4-dichlorophenoxy)-N-(pyrimidin-4-yl)isoquinoline-6-sulfonamide (10 mg, 7%) as an off white solid. $^1$H NMR (400 MHz, DMSO-d$_6$) δ ppm 8.59 (s, 1H) 8.53 (s, 1H) 8.47 (d, J=8.80 Hz, 1H) 8.21 (d, J=5.97 Hz, 1H) 8.09 (dd, J=8.75, 1.81 Hz, 1H) 8.06 (d, J=5.77 Hz, 1H) 7.80 (d, J=5.87 Hz, 1H) 7.71-7.75 (m, 2H) 7.36 (dd, J=8.75, 2.69 Hz, 1H) 6.96 (d, J=5.77 Hz, 1H); m/z (ESI) 447.2 (M+H)+.

EXAMPLE 194

1-(2-METHOXYPHENYL)-N-(1,2,4-THIADIAZOL-5-YL)ISOQUINOLINE-6-SULFONAMIDE

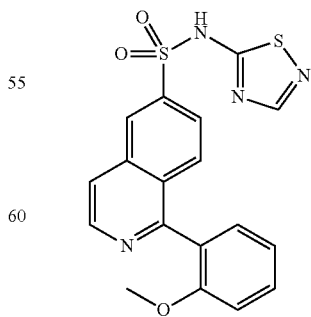

A vial was charged with 1-chloro-N-(2,4-dimethoxybenzyl)-N-(1,2,4-thiadiazol-5-yl)isoquinoline-6-sulfonamide (INTERMEDIATE X) (79.4 mg, 0.166 mmol), 2-methoxyphenylboronic acid (50.6 mg, 0.333 mmol), Pd(AmPhos)$_2$Cl$_2$ (5.89 mg, 8.32 μmol), potassium phosphate (106 mg, 0.499 mmol), 1,4-dioxane (832 μl), and water (277 μl). The vial was sealed and heated in a microwave reactor for 30 min at 100° C. The mixture was extracted with EtOAc (3×). The combined organic extracts were concentrated. The residue was dissolved in DCM (1 mL) and TFA (0.5 mL). After 2 h, the mixture was diluted with methanol and concentrated. The residue was purified by chromatography on silica gel (12-g column with 0 to 10% MeOH/DCM) to give 1-(2-methoxyphenyl)-N-(1,2,4-thiadiazol-5-yl)isoquinoline-6-sulfonamide (34.26 mg, 0.086 mmol, 51.6% yield) as a light-yellow solid: $^1$H NMR (400 MHz, DMSO-d$_6$) δ ppm=8.71 (d, J=5.8 Hz, 1H), 8.61 (d, J=1.7 Hz, 1H), 8.51 (s, 1H), 8.18 (d, J=5.8 Hz, 1H), 7.91 (dd, J=1.8, 8.9 Hz, 1H), 7.77 (d, J=8.9 Hz, 1H), 7.63-7.50 (m, 1H), 7.37 (dd, J=1.6, 7.4 Hz, 1H), 7.25 (d, J=8.2 Hz, 1H), 7.15 (t, J=7.4 Hz, 1H), 3.66 (s, 3H); m/z (ESI) 399.2 (M+H)+.

EXAMPLE 195

1-(2-METHOXY-4-(TRIFLUOROMETHYL)PHENYL)-N-(1,2,4-THIADIAZOL-5-YL)ISOQUINOLINE-6-SULFONAMIDE

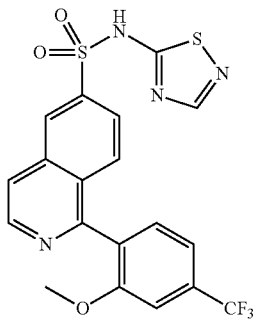 [SMILES: COc1cc(C(F)(F)F)ccc1-c1nccc2cc(S(=O)(=O)Nc3ncns3)ccc12]

A round-bottom flask was charged with N-(2,4-dimethoxybenzyl)-1,2,4-thiadiazol-5-amine (50.3 mg, 0.200 mmol) and THF (1 mL) to give a clear, light-orange solution. The flask was cooled in a dry ice-acetone bath for 5 min to give a suspension. Lithium bis(trimethylsilyl)amide (1M in THF) (200 μl, 0.200 mmol) was added dropwise. After about 5 min, a solution of perfluorophenyl 1-(2-methoxy-4-(trifluoromethyl)phenyl)isoquinoline-6-sulfonate (INTERMEDIATE LLL; 100 mg, 0.182 mmol) in THF (0.5 mL with a 0.25 mL syringe/vial wash) was added drop wise. After another 2 min, the flask was placed in an ice-water bath. The mixture was stirred for another 20 min, then diluted with saturated aq ammonium chloride and extracted with EtOAc (2×). The combined organic extracts were dried over sodium sulfate, filtered, and concentrated. The residue was purified by chromatography on silica gel (12-g column, 10 to 50% EtOAc/Heptane). The desired product was collected with some of the excess amine to give a white foam. The solid was taken up in DCM (1 mL) and TFA (0.5 mL). After 2 h, the mixture was diluted with methanol and concentrated. The crude product was purified by chromatography on silica gel (12-g column, 0 to 10% MeOH/DCM) to give 1-(2-methoxy-4-(trifluoromethyl)phenyl)-N-(1,2,4-thiadiazol-5-yl)isoquinoline-6-sulfonamide (56.9 mg, 0.122 mmol, 67.0% yield) as a white powder: $^1$H NMR (400 MHz, DMSO-d$_6$) δ ppm=8.73 (d, J=5.7 Hz, 1H), 8.61 (d, J=1.9 Hz, 1H), 8.51 (s, 1H), 8.18 (d, J=5.3 Hz, 1H), 7.89 (dd, J=1.9, 8.9 Hz, 1H), 7.74 (d, J=8.9 Hz, 1H), 7.61-7.43 (m, 3H), 3.75 (s, 3H). m/z (ESI) 467.2 (M+H)+.

EXAMPLE 196

1-(2-METHOXY-4-(TRIFLUOROMETHYL)PHENYL)-N-(THIAZOL-2-YL)ISOQUINOLINE-6-SULFONAMIDE

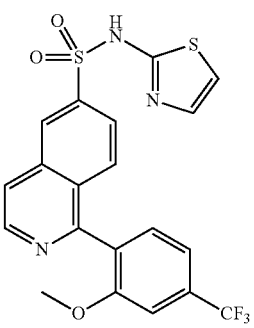 [SMILES: COc1cc(C(F)(F)F)ccc1-c1nccc2cc(S(=O)(=O)Nc3nccs3)ccc12]

A solution of perfluorophenyl 1-(2-methoxy-4-(trifluoromethyl)phenyl)isoquinoline-6-sulfonate (INTERMEDIATE LLL) (425.75 mg, 0.775 mmol), thiazol-2-amine (78 mg, 0.775 mmol), and THF (3875 μl) was cooled in an ice-water bath for 15 min, then lithium bis(trimethylsilyl)amide (1M in THF) (1627 μl, 1.627 mmol) was added drop wise. After 30 min, the mixture was warmed to room temperature and loaded onto a 25-g silica gel loading column with DCM. The column was dried under vacuum for 5 min then eluted onto a pre-equilibrated 40-g silica gel column with 0 to 10% MeOH/DCM to give a yellow solid. The mixture was concentrated from DCM (2×). The residue was then taken up in DCM, sonicated, filtered, washed with DCM (3×), and dried under a stream of N$_2$ (g) to give a white solid. The white solid was crushed with a spatula then dried under high vacuum to give 1-(2-methoxy-4-(trifluoromethyl)phenyl)-N-(thiazol-2-yl)isoquinoline-6-sulfonamide (271 mg, 0.582 mmol, 75% yield) as a white solid: $^1$H NMR (400 MHz, DMSO-d$_6$) δ ppm=12.89 (br. s., 1H), 8.69 (d, J=5.7 Hz, 1H), 8.55 (d, J=1.8 Hz, 1H), 8.13 (d, J=5.7 Hz, 1H), 7.87 (dd, J=1.9, 8.9 Hz, 1H), 7.70 (d, J=8.9 Hz, 1H), 7.60-7.45 (m, 3H), 7.28 (d, J=4.6 Hz, 1H), 6.87 (d, J=4.6 Hz, 1H), 3.74 (s, 3H); m/z (ESI) 466.2 (M+H)+.

EXAMPLE 197

N-(5-CYANOTHIAZOL-2-YL)-1-(2-METHOXY-4-(TRIFLUOROMETHYL)PHENYL)ISOQUINO-LINE-6-SULFONAMIDE

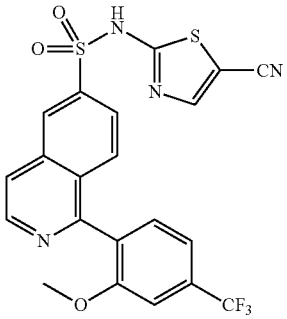 [SMILES: COc1cc(C(F)(F)F)ccc1-c1nccc2cc(S(=O)(=O)Nc3ncc(C#N)s3)ccc12]

Example 197 was synthesized in a similar manner to Example 196, except that 2-aminothiazole-5-carbonitrile (2 equiv, Sigma-Aldrich Co, St. Louis, Mo.) was used in place of 2-aminothiazole. The desired product, N-(5-cyanothiazol-2-yl)-1-(2-methoxy-4-(trifluoromethyl)phenyl)isoquinoline-6-sulfonamide, was isolated as a yellow solid: $^1$H NMR (400 MHz, DMSO-$d_6$) δ ppm=8.67 (d, J=5.7 Hz, 1H), 8.51 (d, J=1.6 Hz, 1H), 8.12 (d, J=5.5 Hz, 1H), 8.01 (s, 1H), 7.86 (dd, J=1.9, 8.9 Hz, 1H), 7.66 (d, J=8.8 Hz, 1H), 7.58-7.54 (m, 1H), 7.52-7.46 (m, 2H), 3.74 (s, 3H); m/z (ESI) 491.2 (M+H)+.

EXAMPLE 198

N-(5-FLUOROTHIAZOL-2-YL)-1-(2-METHOXY-4-(TRIFLUOROMETHYL)PHENYL)ISOQUINO-LINE-6-SULFONAMIDE 2,2,2-TRIFLUOROAC-ETATE

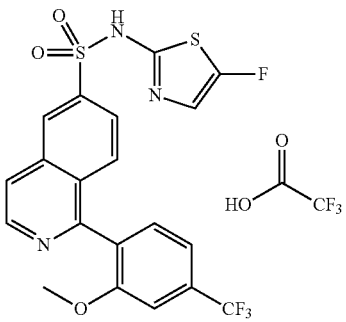 [SMILES: COc1cc(C(F)(F)F)ccc1-c1nccc2cc(S(=O)(=O)Nc3ncc(F)s3)ccc12 ; O=C(O)C(F)(F)F]

Example 198 was synthesized in a similar manner to Example 195, except that 5-fluoro-N-(4-methoxybenzyl)thiazol-2-amine (INTERMEDIATE MMM) was used in place of N-(4-methoxybenzyl)thiazol-2-amine. The desired product, n-(5-fluorothiazol-2-yl)-1-(2-methoxy-4-(trifluoromethyl)phenyl)isoquinoline-6-sulfonamide 2,2,2-trifluoroacetate, was isolated as a light-yellow solid: $^1$H NMR (400 MHz, DMSO-$d_6$) δ ppm=12.76 (br. s., 1H), 8.72 (d, J=5.7 Hz, 1H), 8.58 (d, J=1.8 Hz, 1H), 8.18 (d, J=5.5 Hz, 1H), 7.88 (dd, J=1.9, 8.9 Hz, 1H), 7.74 (d, J=8.9 Hz, 1H), 7.63-7.47 (m, 3H), 7.39 (s, 1H), 3.75 (s, 3H); m/z (ESI) 484.2 (M+H)+.

EXAMPLE 199

1-(3'-FLUORO-3-METHOXY-[1,1'-BIPHENYL]-4-YL)-N-(PYRIMIDIN-4-YL)ISOQUINOLINE-6-SULFONAMIDE 2,2,2-TRIFLUOROACETATE

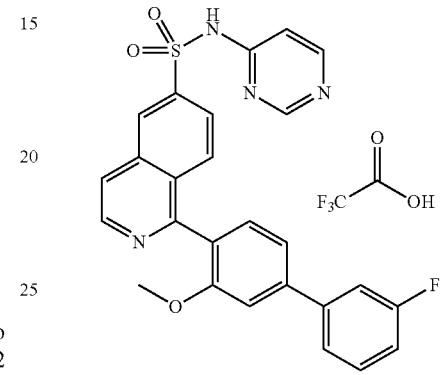

A vial was charged with 1-(4-chloro-2-methoxyphenyl)-N-(pyrimidin-4-yl)isoquinoline-6-sulfonamide (53.86 mg, 0.126 mmol), (3-fluorophenyl)boronic acid (35.3 mg, 0.252 mmol), dicyclohexyl(2',6'-dimethoxy-[1,1'-biphenyl]-2-yl)phosphine (5.18 mg, 0.013 mmol), palladium(ii) acetate (1.416 mg, 6.31 μmol), and potassium phosphate (80 mg, 0.379 mmol). The vial was flushed with Ar (g), then THF (0.5 mL) and water (0.05 mL) were added in sequence. The vial was sealed and placed in a 90° C. heating bath for 8 h. The mixture was cooled to room temperature, diluted with brine, and extracted with EtOAc (3×). The combined organic extracts were concentrated. The crude product was purified by chromatography on silica gel (12-g column with 5 to 10% MeOH/DCM). The material thus obtained was dissolved in methanol and filtered. The filtrate was subjected to reverse-phase HPLC (25 to 70% CH$_3$CN/H$_2$O with 0.1% TFA). Fractions containing product were combined and concentrated. The resulting residue was concentrated from DCM, then DCM/heptane to give 1-(3'-fluoro-3-methoxy-[1,1'-biphenyl]-4-yl)-N-(pyrimidin-4-yl)isoquinoline-6-sulfonamide 2,2,2-trifluoroacetate as a yellow solid: $^1$H NMR (400 MHz, DMSO-$d_6$) δ ppm=8.75-8.67 (m, 2H), 8.59 (s, 1H), 8.26 (br. s., 1H), 8.15 (d, J=5.7 Hz, 1H), 7.98 (dd, J=1.9, 8.9 Hz, 1H), 7.81 (d, J=8.9 Hz, 1H), 7.74-7.67 (m, 2H), 7.57 (dt, J=6.3, 8.0

Hz, 1H), 7.53-7.43 (m, 3H), 7.27 (dt, J=2.1, 8.7 Hz, 1H), 7.05 (br. s., 1H), 3.77 (s, 3H); m/z (ESI) 487.2 (M+H)+.

EXAMPLE 200

1-(3'-CYANO-3-METHOXY-[1,1'-BIPHENYL]-4-YL)-N-(PYRIMIDIN-4-YL)ISOQUINOLINE-6-SULFONAMIDE

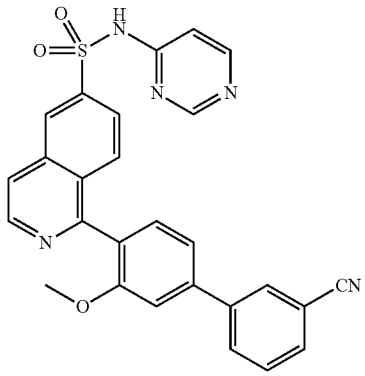 [SMILES: COc1cc(-c2cccc(C#N)c2)ccc1-c1nccc2cc(S(=O)(=O)Nc3ccncn3)ccc12]

A microwave vial was charged with 1-(4-chloro-2-methoxyphenyl)-N-(pyrimidin-4-yl)isoquinoline-6-sulfonamide (53.42 mg, 0.125 mmol), (3-cyanophenyl)boronic acid (55.2 mg, 0.375 mmol), potassium phosphate (106 mg, 0.501 mmol), and chloro(2-dicyclohexylphosphino-2',6'-dimethoxy-1,1'-biphenyl)[2-(2-aminoethylphenyl)]palladium(II) methyl-t-butylether adduct (Strem Chemical, Newburyport, Mass.) (9.52 mg, 0.013 mmol). The vial was flushed with Ar (g), then 1,4-dioxane (501 µl) and water (125 µl) were added. The vial was sealed and heated to 120° C. for 30 min in a microwave reactor. The mixture was extracted with EtOAc (3×). The combined organic extracts were concentrated. The crude product was purified by chromatography on silica gel (0 to 10% MeOH/DCM) to give 1-(3'-cyano-3-methoxy-[1,1'-biphenyl]-4-yl)-N-(pyrimidin-4-yl)isoquinoline-6-sulfonamide (37.15 mg, 0.075 mmol, 60.2% yield) as a yellow solid: $^1$H NMR (400 MHz, DMSO-$d_6$) δ ppm=13.00 (br. s., 1H), 8.70 (d, J=5.7 Hz, 1H), 8.66 (d, J=1.4 Hz, 1H), 8.58 (s, 1H), 8.37 (d, J=1.6 Hz, 1H), 8.30-8.17 (m, 2H), 8.15-8.05 (m, 1H), 8.01-7.94 (m, 1H), 7.92-7.86 (m, 1H), 7.81-7.70 (m, 2H), 7.60-7.43 (m, 3H), 7.03 (d, J=6.5 Hz, 1H), 3.78 (s, 3H); m/z (ESI) 494.2 (M+H)+.

EXAMPLE 201

1-(4-CHLORO-2-METHOXYPHENYL)-N-(THIAZOL-2-YL)ISOQUINOLINE-6-SULFONAMIDE

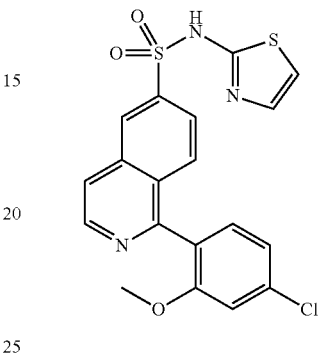

A vial was charged with perfluorophenyl 1-(4-chloro-2-methoxyphenyl)isoquinoline-6-sulfonate (INTERMEDIATE NNN) (82.4 mg, 0.160 mmol), thiazol-2-amine (17.60 mg, 0.176 mmol), and THF (799 µl) to give a clear, colorless solution. The vial was cooled in an ice-water bath for 10 min, then lithium bis(trimethylsilyl)amide (1M in THF) (335 µl, 0.335 mmol) was added drop wise. After 30 min, the mixture was warmed to room temperature and loaded onto a 5-g silica gel loading column with the aid of DCM. The column was dried under vacuum for 5 min then eluted onto a pre-equilibrated 12-g column with 0 to 10% MeOH/DCM to give 1-(4-chloro-2-methoxyphenyl)-N-(thiazol-2-yl)isoquinoline-6-sulfonamide (54 mg, 0.125 mmol, 78% yield) as an off-white solid: $^1$H NMR (400 MHz, DMSO-$d_6$) δ ppm=13.21-11.96 (m, 1H), 8.73-8.62 (m, 1H), 8.52 (d, J=1.8 Hz, 1H), 8.17-8.02 (m, 1H), 7.85 (dd, J=1.9, 8.9 Hz, 1H), 7.75-7.66 (m, 1H), 7.36-7.25 (m, 3H), 7.18 (dd, J=2.0, 8.0 Hz, 1H), 6.85 (d, J=4.6 Hz, 1H), 3.67 (s, 3H); m/z (ESI) 432.2 (M+H)+.

EXAMPLE 202

1-(3'-FLUORO-3-METHOXY-[1,1'-BIPHENYL]-4-YL)-N-(THIAZOL-2-YL)ISOQUINOLINE-6-SULFONAMIDE 2,2,2-TRIFLUOROACETATE

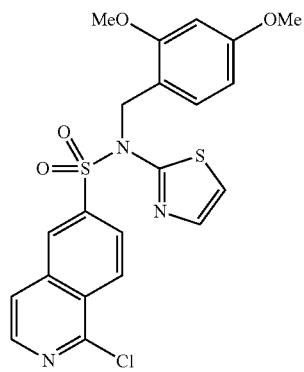
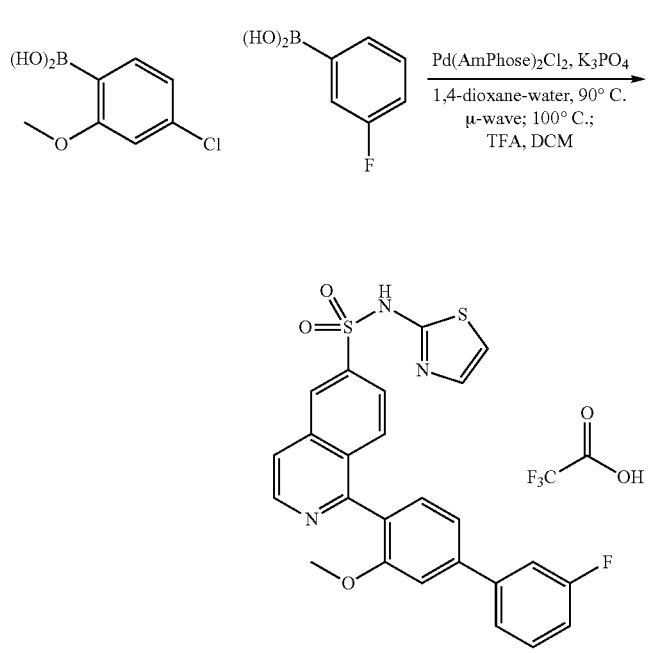

A vial was charged with 1-chloro-N-(2,4-dimethoxybenzyl)-N-(thiazol-2-yl)isoquinoline-6-sulfonamide (INTERMEDIATE OOO) (68.51 mg, 0.144 mmol), (4-chloro-2-methoxyphenyl)boronic acid (29.5 mg, 0.158 mmol), Pd(AmPhos)$_2$Cl$_2$ (5.10 mg, 7.20 mmol), potassium phosphate (92 mg, 0.432 mmol), 1,4-dioxane (540 μl), and water (180 μl). The vial was flushed with Ar (g), then sealed and heated in a microwave reactor for 30 min h at 90° C. (3-fluorophenyl)boronic acid (40.3 mg, 0.288 mmol) was added, and the vial was heated in the microwave reactor for 2 h at 100° C. The layers were separated, and the aq. layer was extracted with EtOAc (2×). The combined organic extracts were concentrated under a vacuum. The residue was taken up in DCM (1 mL) and TFA (0.5 mL). After 30 min, the mixture was diluted with MeOH and filtered through diatomaceous earth with the aid of DCM. The filtrate was concentrated, and the crude product was purified by chromatography on silica gel (12-g, 0 to 10% MeOH/DCM). The product (68 mg of a yellow solid) was isolated with the intermediate phenyl chloride. The material was re-chromatographed with 50-100% EtOAc/Heptane to give an off-white solid. The material was further purified by reverse-phase HPLC (25-70% CH$_3$CN/H$_2$O with 0.1% TFA). Fractions containing product were combined and concentrated. The resulting yellow glass was dried overnight under vacuum, then heated briefly with a heat gun to give 1-(3'-fluoro-3-methoxy-[1,1'-biphenyl]-4-yl)-N-(thiazol-2-yl)isoquinoline-6-sulfonamide 2,2,2-trifluoroacetate (30.28 mg, 0.050 mmol, 34.7% yield) as a yellow solid: $^1$H NMR (400 MHz, DMSO-d$_6$) δ ppm=12.92 (br. s., 1H), 8.72 (d, J=5.8 Hz, 1H), 8.60 (d, J=1.6 Hz, 1H), 8.21 (d, J=5.8 Hz, 1H), 7.96-7.90 (m, 1H), 7.86-7.81 (m, 1H), 7.75-7.66 (m, 2H), 7.62-7.45 (m, 4H), 7.31-7.22 (m, 2H), 6.89 (d, J=4.6 Hz, 1H), 3.78 (s, 3H); m/z (ESI) 492.2 (M+H)+.

EXAMPLE 203

1-(2-METHOXY-4-(1-METHYL-1H-PYRAZOL-4-YL)PHENYL)-N-(THIAZOL-2-YL)ISOQUINOLINE-6-SULFONAMIDE

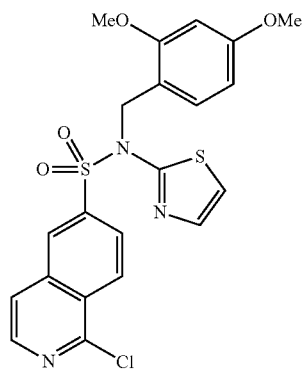
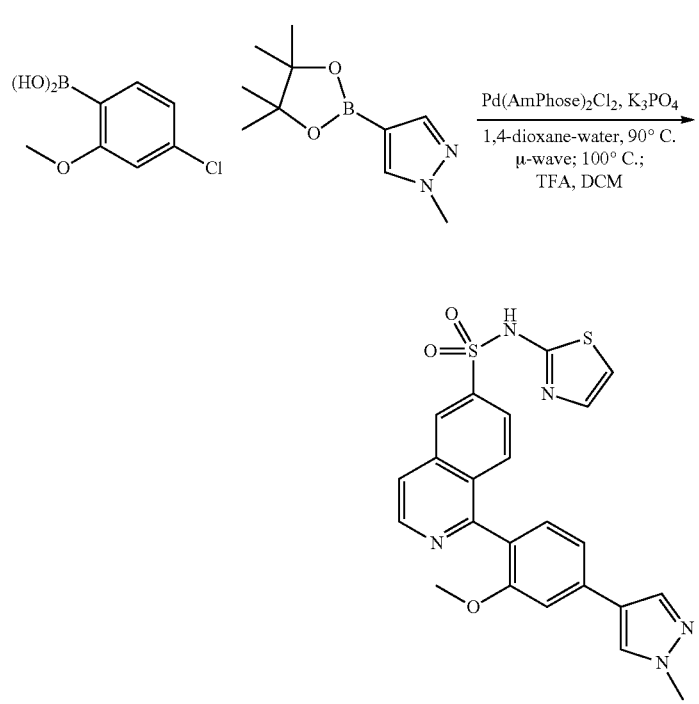

A vial was charged with 1-chloro-N-(2,4-dimethoxybenzyl)-N-(thiazol-2-yl)isoquinoline-6-sulfonamide (INTERMEDIATE OOO) (71.96 mg, 0.151 mmol), (4-chloro-2-methoxyphenyl)boronic acid (31.0 mg, 0.166 mmol), Pd(AmPhos)$_2$Cl$_2$ (5.35 mg, 7.56 μmol), potassium phosphate (128 mg, 0.605 mmol), 1,4-dioxane (567 μl), and water (189 μl). The vial was flushed with Ar (g), then sealed and heated in a microwave reactor for 30 min h at 90° C. At this point, 1-methyl-4-(4,4,5,5-tetramethyl-1,3,2-dioxaborolan-2-yl)-1H-pyrazole (62.9 mg, 0.302 mmol) and additional catalyst (about 3 mg) were added. The vial was resealed and heated in the microwave reactor for 1 h at 100° C. Additional portions of 1-methyl-4-(4,4,5,5-tetramethyl-1,3,2-dioxaborolan-2-yl)-1H-pyrazole (62.9 mg, 0.302 mmol), potassium phosphate (128 mg, 0.605 mmol), and catalyst (about 3 mg) were added, and the vial was heated for 1 h at 100° C. in the microwave. The vial was heated for an additional 2 h at 110° C. The mixture was extracted with EtOAc (3×). The combined organic extracts were concentrated. The residue was dissolved in DCM (1 mL) and TFA (0.5 mL). After 35 min, the mixture was diluted with MeOH and filtered through diatomaceous earth. The filtrate was concentrated. The residue was purified by reverse-phase HPLC (25 to 70% CH$_3$CN/H$_2$O with 0.1% TFA). Fractions containing the desired product were combined in saturated aq. sodium bicarbonate solution with the aid of methanol. The mixture was extracted with DCM (3×). The combined organic extracts were dried over sodium sulfate, filtered, and concentrated to give 1-(2-methoxy-4-(1-methyl-1H-pyrazol-4-yl)phenyl)-N-(thiazol-2-yl)isoquinoline-6-sulfonamide (8.5 mg, 0.018 mmol, 11.77% yield) as a yellow solid: $^1$H NMR (400 MHz, DMSO-d$_6$) δ ppm=12.88 (br. s., 1H), 8.67 (d, J=5.7 Hz, 1H), 8.52 (d, J=1.8 Hz, 1H), 8.29 (s, 1H), 8.06 (d, J=5.6 Hz, 1H), 8.01 (s, 1H), 7.89-7.74 (m, 2H), 7.38 (s, 1H), 7.34-7.24 (m, 3H), 6.87 (d, J=4.6 Hz, 1H), 3.91 (s, 3H), 3.71 (s, 3H); m/z (ESI) 478.2 (M+H)+.

EXAMPLE 204

1-(2-METHOXY-4-(PYRIDIN-3-YL)PHENYL)-N-(THIAZOL-2-YL)ISOQUINOLINE-6-SULFONAMIDE

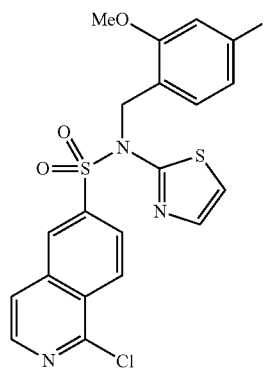
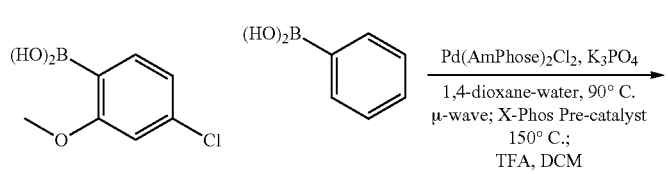
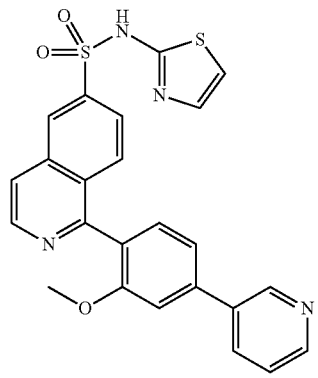

A vial was charged with 1-chloro-N-(2,4-dimethoxybenzyl)-N-(thiazol-2-yl)isoquinoline-6-sulfonamide (INTERMEDIATE OOO) (72.35 mg, 0.152 mmol), (4-chloro-2-methoxyphenyl)boronic acid (31.2 mg, 0.167 mmol), Pd(AmPhos)$_2$Cl$_2$ (5.38 mg, 7.60 μmol), potassium phosphate (129 mg, 0.608 mmol), 1,4-dioxane (570 μl), and water (190 μl). The vial was flushed with Ar (g), then sealed and heated in a microwave reactor for 30 min h at 90° C. At this point, pyridin-3-ylboronic acid (37.4 mg, 0.304 mmol) and additional catalyst (about 3 mg) were added. The vial was resealed and heated in the microwave reactor for 1.5 h at 100° C. The mixture was heated for an additional 30 min at 120° C. LC/MS did not indicate any change. Additional portions of pyridin-3-ylboronic acid (70 mg), potassium phosphate (129 mg) were added, followed by the addition of another catalyst, chloro(2-dicyclohexylphosphino-2',4',6'-tri-1-propyl-1,1'-biphenyl)[2-(2-aminoethyl)phenyl]palladium(II) methyl-t-butylether adduct (16 mg, Strem Chemical, Newburyport, Mass.) The vial was then heated at 90° C. for 30 min, then at 150° C. for 30 min. The mixture was extracted with EtOAc (3×). The combined organic extracts were concentrated. The residue was dissolved in DCM (1 mL) and TFA (0.5 mL). After 1 h, the mixture was diluted with MeOH and filtered through diatomaceous earth. The filtrate was concentrated. The residue was dissolved in MeOH, and the resulting solution was loaded onto a 1-g SCX-2 ion exchange column. The column was eluted with MeOH, then with 2N ammonia in methanol. The basic fraction was concentrated to give about 150 mg of a yellow glass. The material was purified by chromatography on silica gel (12-g column, 0 to 6% MeOH/DCM, then 10% MeOH/DCM) to give 1-(2-methoxy-4-(pyridin-3-yl)phenyl)-N-(thiazol-2-yl)isoquinoline-6-sulfonamide (41.3 mg, 0.087 mmol, 57.3% yield) as an off-white solid: $^1$H NMR (400 MHz, DMSO-d$_6$) δ ppm=12.88 (br. s., 1H), 9.06 (dd, J=0.8, 2.4 Hz, 1H), 8.70 (d, J=5.7 Hz, 1H), 8.64 (dd, J=1.6, 4.8 Hz, 1H), 8.54 (d, J=1.9 Hz, 1H), 8.28-8.20 (m, 1H), 8.10 (d, J=5.3 Hz, 1H), 7.91-7.86 (m, 1H), 7.79 (d, J=8.9 Hz, 1H), 7.59-7.42 (m, 4H), 7.28 (d, J=4.6 Hz, 1H), 6.87 (d, J=4.6 Hz, 1H), 3.77 (s, 3H); m/z (ESI) 475.2 (M+H)+.

EXAMPLE 205

1-(4-CYANO-2-METHOXYPHENYL)-N-(THIAZOL-2-YL)ISOQUINOLINE-6-SULFONAMIDE

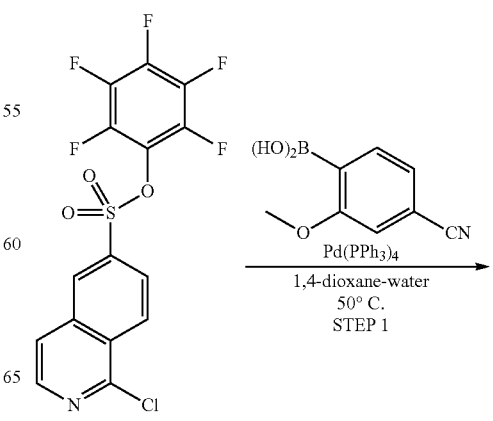

-continued

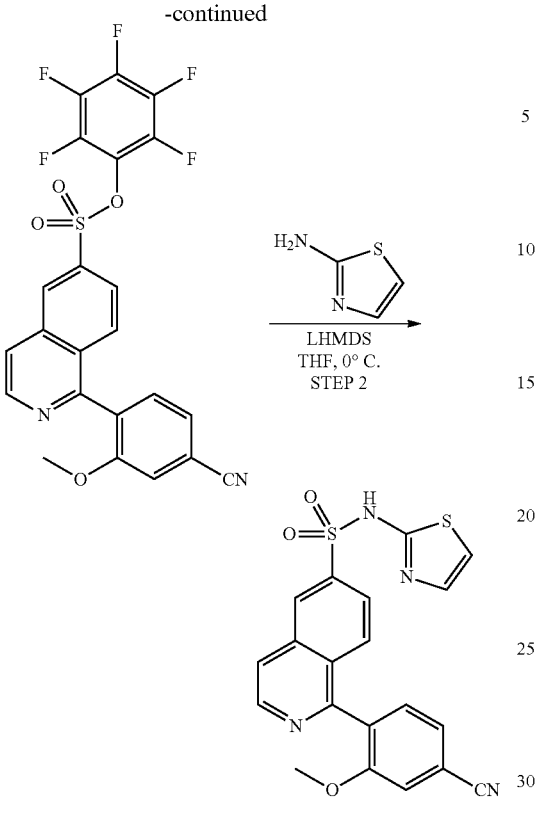

STEP 1: PERFLUOROPHENYL 1-(4-CYANO-2-METHOXYPHENYL)ISOQUINOLINE-6-SULFONATE

A vial was charged with perfluorophenyl 1-chloroisoquinoline-6-sulfonate (see Example 73, Step 1) (210 mg, 0.513 mmol), (4-cyano-2-methoxyphenyl)boronic acid (181 mg, 1.025 mmol), potassium carbonate (213 mg, 1.538 mmol), and Pd(Ph$_3$P)$_4$ (59.2 mg, 0.051 mmol). The vial was flushed with Ar (g), then 1,4-dioxane (1922 µl) and water (641 µl) were added. The vial was sealed and placed in a 50° C. heating bath for 1.5 h. The mixture was diluted with water and extracted with EtOAc (3×). The combined organic extracts were concentrated. The crude product was purified by chromatography on silica gel (40-g column with 0 to 40% EtOAc/Heptane) to give perfluorophenyl 1-(4-cyano-2-methoxyphenyl)isoquinoline-6-sulfonate (172.6 mg, 0.341 mmol, 66.5% yield) as a white foam: $^1$H NMR (400 MHz, CHLOROFORM-d) δ ppm=8.86 (d, J=5.7 Hz, 1H), 8.61 (d, J=2.0 Hz, 1H), 7.99 (dd, J=2.0, 8.9 Hz, 1H), 7.91-7.82 (m, 2H), 7.61-7.57 (m, 1H), 7.54-7.47 (m, 1H), 7.34 (d, J=1.4 Hz, 1H), 3.77 (s, 3H); m/z (ESI) 507.2 (M+H)+.

STEP 2: 1-(4-CYANO-2-METHOXYPHENYL)-N-(THIAZOL-2-YL)ISOQUINOLINE-6-SULFONAMIDE

A vial was charged with perfluorophenyl 1-(4-cyano-2-methoxyphenyl)isoquinoline-6-sulfonate (67.07 mg, 0.132 mmol), thiazol-2-amine (13.26 mg, 0.132 mmol), and THF (662 µl) to give a clear, colorless solution. The vial was cooled in an ice-water bath for 15 min, then lithium bis(trimethylsilyl)amide (1M in THF) (265 µl, 0.265 mmol) was added drop wise. After 20 min, the mixture was loaded onto a 5-g silica gel loading column with DCM. The column was dried under vacuum for 5 min then eluted onto a pre-equilibrated 12-g column with 0 to 10% MeOH/DCM to give 1-(4-cyano-2-methoxyphenyl)-N-(thiazol-2-yl)isoquinoline-6-sulfonamide (56.25 mg, 0.133 mmol, 101% yield) as an off-white foam: $^1$H NMR (400 MHz, DMSO-d$_6$) δ ppm=12.89 (br. s., 1H), 8.70 (d, J=5.7 Hz, 1H), 8.56 (d, J=1.8 Hz, 1H), 8.14 (d, J=5.3 Hz, 1H), 7.87 (dd, J=1.9, 8.8 Hz, 1H), 7.74 (d, J=1.3 Hz, 1H), 7.68 (d, J=8.8 Hz, 1H), 7.64-7.59 (m, 1H), 7.56-7.52 (m, 1H), 7.28 (d, J=4.6 Hz, 1H), 6.88 (d, J=4.6 Hz, 1H), 3.72 (s, 3H); m/z (ESI) 423.2 (M+H)+.

EXAMPLE 206

1-(4-CYANO-2-METHOXYPHENYL)-N-(PYRIMIDIN-4-YL)ISOQUINOLINE-6-SULFONAMIDE

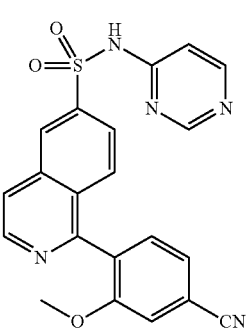 [SMILES: COc1cc(C#N)ccc1-c1nccc2cc(S(=O)(=O)Nc3ccncn3)ccc12]

Example 206 was synthesized in a similar manner to EXAMPLE 205, except that 4-aminopyrimidine was used in place of 2-aminothiazole in STEP 2. The desired product, 1-(4-cyano-2-methoxyphenyl)-N-(pyrimidin-4-yl)isoquinoline-6-sulfonamide, was isolated as an off-white solid: $^1$H NMR (400 MHz, DMSO-d$_6$) δ ppm=13.07 (br. s., 1H), 8.74-8.62 (m, 2H), 8.54 (s, 1H), 8.21 (d, J=6.6 Hz, 1H), 8.17-8.10 (m, 1H), 7.93 (dd, J=1.9, 8.9 Hz, 1H), 7.72 (d, J=1.3 Hz, 1H), 7.66 (d, J=8.9 Hz, 1H), 7.62-7.58 (m, 1H), 7.54-7.51 (m, 1H), 6.99 (d, J=6.6 Hz, 1H), 3.70 (s, 3H); m/z (ESI) 418.2 (M+H)+.

EXAMPLE 207

1-(1-PHENYL-1H-PYRROL-3-YL)-N-(THIAZOL-2-YL)ISOQUINOLINE-6-SULFONAMIDE 2,2,2-TRIFLUOROACETATE

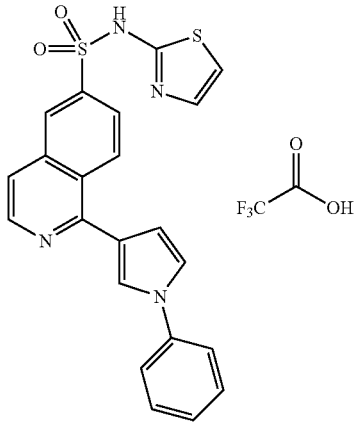 [SMILES: O=S(=O)(Nc1nccs1)c1ccc2c(-c3ccn(-c4ccccc4)c3)nccc2c1 ; O=C(O)C(F)(F)F]

A vial was charged with 1-chloro-N-(2,4-dimethoxybenzyl)-N-(thiazol-2-yl)isoquinoline-6-sulfonamide (Intermediate OOO; 50 mg, 0.105 mmol), 1-phenyl-3-(4,4,5,5-tetramethyl-1,3,2-dioxaborolan-2-yl)-1H-pyrrole (56.5 mg, 0.210 mmol), Pd(AmPhos)$_2$Cl$_2$ (3.72 mg, 5.25 µmol), potassium phosphate (66.9 mg, 0.315 mmol), 1,4-dioxane (394 µl), and water (131 µl). The vial was flushed with Ar (g), then sealed and heated in a microwave reactor for 30 min h at 100° C. The layers were separated, and the aq. layer was extracted with EtOAc (2×). The combined organic extracts were concentrated under a vacuum. The residue was taken up in DCM (1 mL) and TFA (0.5 mL). After 30 min, the mixture was diluted with MeOH and concentrated. The crude product was purified by chromatography on silica gel (12-g column, 0 to 10% MeOH/DCM). The resulting solid was taken up in DCM, sonicated for 1 min, and concentrated. The residue was taken up in DCM, sonicated briefly, then filtered. The collected solid was washed with DCM (2×), dried under a stream of N$_2$ (g) for 30 min, and dried under vacuum to give 1-(1-phenyl-1H-pyrrol-3-yl)-N-(thiazol-2-yl)isoquinoline-6-sulfonamide 2,2,2-trifluoroacetate (47 mg, 0.086 mmol, 82% yield) as a yellow solid: $^1$H NMR (400 MHz, DMSO-d$_6$) δ ppm=12.96 (br. s., 1H), 8.82 (d, J=9.1 Hz, 1H), 8.62 (d, J=5.9 Hz, 2H), 8.15 (br. s., 2H), 8.05 (dd, J=1.8, 8.9 Hz, 1H), 7.78 (dd, J=1.0, 8.6 Hz, 2H), 7.68 (t, J=2.5 Hz, 1H), 7.55 (t, J=8.0 Hz, 2H), 7.42-7.35 (m, 1H), 7.32 (d, J=4.6 Hz, 1H), 6.99-6.95 (m, 1H), 6.91 (d, J=4.5 Hz, 1H); m/z (ESI) 433.2 (M+H)+.

EXAMPLE 208

1-(5-METHYL-1-PHENYL-1H-PYRAZOL-4-YL)-N-(THIAZOL-2-YL)ISOQUINOLINE-6-SULFONAMIDE 2,2,2-TRIFLUOROACETATE

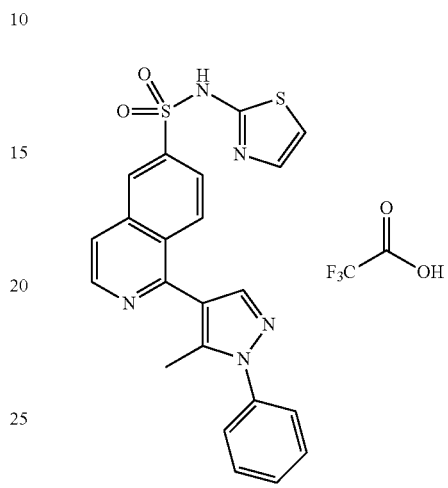

Example 208 was synthesized in a similar manner to EXAMPLE 207, except that 5-methyl-1-phenyl-4-(4,4,5,5-tetramethyl-1,3,2-dioxaborolan-2-yl)-1H-pyrazole was used in place of 1-phenyl-3-(4,4,5,5-tetramethyl-1,3,2-dioxaborolan-2-yl)-1H-pyrrole. The desired product, 1-(5-methyl-1-phenyl-1H-pyrazol-4-yl)-N-(thiazol-2-yl)isoquinoline-6-sulfonamide 2,2,2-trifluoroacetate, was isolated as a yellow solid: $^1$H NMR (400 MHz, DMSO-d$_6$) δ ppm=12.92 (br. s., 1H), 8.71 (d, J=5.7 Hz, 1H), 8.58 (d, J=1.7 Hz, 1H), 8.37 (d, J=8.8 Hz, 1H), 8.12-8.05 (m, 2H), 7.98 (dd, J=1.9, 8.9 Hz, 1H), 7.70-7.57 (m, 4H), 7.55-7.48 (m, 1H), 7.30 (d, J=4.6 Hz, 1H), 6.90 (d, J=4.6 Hz, 1H), 2.39 (s, 3H); m/z (ESI) 448.2 (M+H)+.

EXAMPLE 209

1-(4-CHLORO-2-METHYLPHENYL)-N-(THIAZOL-2-YL)ISOQUINOLINE-6-SULFONAMIDE 2,2,2-TRIFLUOROACETATE

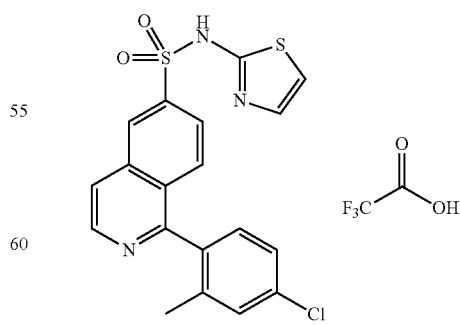

Example 209 was synthesized in a similar manner to Example 207, except that (4-chloro-2-methylphenyl)boronic acid was used in place of 1-phenyl-3-(4,4,5,5-tetramethyl-1, 3,2-dioxaborolan-2-yl)-1H-pyrrole. The desired product, 1-(4-chloro-2-methylphenyl)-N-(thiazol-2-yl)isoquinoline-6-sulfonamide 2,2,2-trifluoroacetate, was isolated as a yellow solid: $^1$H NMR (400 MHz, DMSO-d$_6$) δ ppm=12.90 (br. s., 1H), 8.72 (d, J=5.7 Hz, 1H), 8.60 (d, J=1.8 Hz, 1H), 8.19 (d, J=5.7 Hz, 1H), 7.90 (dd, J=1.9, 8.9 Hz, 1H), 7.70 (d, J=8.8 Hz, 1H), 7.53 (d, J=2.0 Hz, 1H), 7.46-7.32 (m, 2H), 7.28 (d, J=4.6 Hz, 1H), 6.88 (d, J=4.6 Hz, 1H), 1.98 (s, 3H); m/z (ESI) 416.2 (M+H)+.

EXAMPLE 210

1-(4-CYANO-2-METHYLPHENYL)-N-(THIAZOL-2-YL)ISOQUINOLINE-6-SULFONAMIDE 2,2,2-TRIFLUOROACETATE

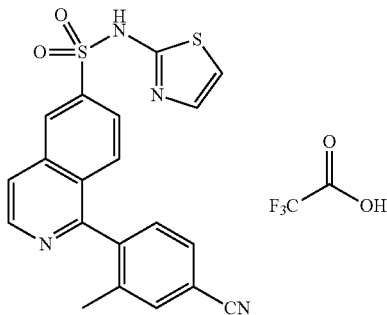 [SMILES: Cc1cc(C#N)ccc1-c1nccc2cc(S(=O)(=O)Nc3nccs3)ccc12 ; O=C(O)C(F)(F)F]

Example 210 was synthesized in a similar manner to Example 207, except that 2-methyl-4-cyanophenylboronic acid was used in place of 1-phenyl-3-(4,4,5,5-tetramethyl-1,3,2-dioxaborolan-2-yl)-1H-pyrrole. The desired product, 1-(4-cyano-2-methylphenyl)-N-(thiazol-2-yl)isoquinoline-6-sulfonamide 2,2,2-trifluoroacetate, was isolated as a yellow solid: $^1$H NMR (400 MHz, DMSO-d$_6$) δ ppm=12.91 (br. s., 1H), 8.74 (d, J=5.7 Hz, 1H), 8.62 (d, J=1.8 Hz, 1H), 8.20 (d, J=5.7 Hz, 1H), 7.95 (d, J=0.7 Hz, 1H), 7.90 (dd, J=1.8, 8.9 Hz, 1H), 7.84 (dd, J=1.1, 7.9 Hz, 1H), 7.65 (d, J=8.8 Hz, 1H), 7.54 (d, J=7.8 Hz, 1H), 7.30 (d, J=4.8 Hz, 1H), 6.89 (d, J=4.5 Hz, 1H), 2.03 (s, 3H). m/z (ESI) 407.2 (M+H)+.

EXAMPLE 211

4-FLUORO-1-(2-METHOXYPHENYL)-N-(THIAZOL-2-YL)ISOQUINOLINE-6-SULFONAMIDE

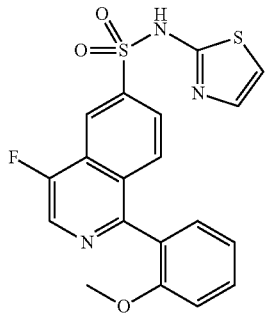 [SMILES: COc1ccccc1-c1ncc(F)c2cc(S(=O)(=O)Nc3nccs3)ccc12]

A vial was charged with 1-chloro-N-(2,4-dimethoxybenzyl)-4-fluoro-N-(thiazol-2-yl)isoquinoline-6-sulfonamide (Intermediate PPP) (58.34 mg, 0.118 mmol), (2-methoxyphenyl)boronic acid (35.9 mg, 0.236 mmol), Pd(AmPhos)$_2$Cl$_2$ (8.36 mg, 0.012 mmol), potassium phosphate (75 mg, 0.354 mmol), 1,4-dioxane (443 µl), and water (148 µl). The vial was flushed with Ar (g), then sealed and heated in a microwave reactor for 30 min h at 90° C. LC/MS showed conversion to the protected product. The mixture was extracted with EtOAc (3×), and the combined organic extracts were concentrated. The residue was dissolved in DCM (1 mL) and TFA (0.5 mL). After 2 h, the mixture was diluted with MeOH and concentrated, and the crude product was purified by chromatography on silica gel (12-g column, 3% MeOH/DCM) to give 4-fluoro-1-(2-methoxyphenyl)-N-(thiazol-2-yl)isoquinoline-6-sulfonamide (49 mg, 0.118 mmol, 100% yield) as a yellow solid: $^1$H NMR (400 MHz, DMSO-d$_6$) δ ppm=12.99 (br. s., 1H), 8.70 (d, J=1.7 Hz, 1H), 8.49 (d, J=1.8 Hz, 1H), 7.99 (dd, J=1.8, 8.9 Hz, 1H), 7.78 (dd, J=1.8, 8.8 Hz, 1H), 7.58-7.50 (m, 1H), 7.38-7.27 (m, 2H), 7.23 (d, J=8.3 Hz, 1H), 7.16-7.10 (m, 1H), 6.89 (d, J=4.6 Hz, 1H), 3.65 (s, 3H); m/z (ESI) 416.2 (M+H)+.

EXAMPLE 212

4-FLUORO-1-(2-METHOXY-4-(TRIFLUOROMETHYL)PHENYL)-N-(THIAZOL-2-YL)ISOQUINOLINE-6-SULFONAMIDE

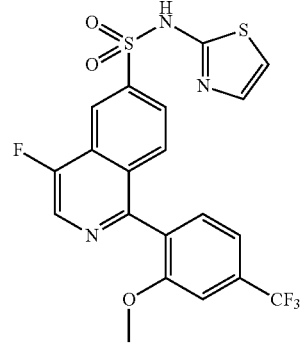

A microwave vial was charged with 1-chloro-N-(2,4-dimethoxybenzyl)-4-fluoro-N-(thiazol-2-yl)isoquinoline-6-sulfonamide (Intermediate PPP; 0.041 g, 0.083 mmol), (2-methoxy-4-(trifluoromethyl)phenyl)boronic acid (0.027 g, 0.125 mmol), Pd(PPh$_3$)$_4$ (9.59 mg, 8.30 µmol), and potassium carbonate (0.057 g, 0.415 mmol). Dioxane (0.415 mL) and water (0.138 mL) were added, the vial was flushed with argon and sealed, and heated in a microwave reactor at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via silica gel chromatography (12 g, gradient elution 0 to 100% EtOAc:Heptane) to afford N-(2,4-dimethoxybenzyl)-4-fluoro-1-(2-methoxy-4-(trifluoromethyl)phenyl)-N-(thiazol-2-yl)isoquinoline-6-sulfonamide. The material was dissolved in DCM and TFA (0.1 mL, 1.298 mmol) was added. The reaction was stirred for 30 minutes at room temperature after which time the reaction was concentrated and triturated with diethyl ether. The solids were filtered, washed with diethyl ether, and vacuum dried to afford 4-fluoro-1-(2-methoxy-4-(trifluoromethyl)phenyl)-N-(thiazol-2-yl)isoquinoline-6-sulfonamide (0.008 g, 0.017 mmol, 19.94% yield) as a white solid. $^1$H NMR (400 MHz, DMSO-$d_6$) δ ppm=13.00 (s, 1H), 8.74 (d, J=1.6 Hz, 1H), 8.51 (d, J=1.4 Hz, 1H), 7.99 (dd, J=1.7, 8.9 Hz, 1H), 7.79 (dd, J=1.8, 9.0 Hz, 1H), 7.61-7.55 (m, 1H), 7.55-7.46 (m, 2H), 7.31 (d, J=4.6 Hz, 1H), 6.90 (d, J=4.6 Hz, 1H), 3.75 (s, 3H). m/z (ESI) 484.2 (M+H)$^+$.

EXAMPLE 213

4-FLUORO-1-(4-FLUORO-2-METHOXYPHENYL)-N-(THIAZOL-2-YL)ISOQUINOLINE-6-SULFONAMIDE

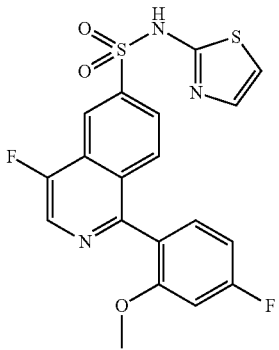 [SMILES: COc1cc(F)ccc1-c1ncc(F)c2cc(S(=O)(=O)Nc3nccs3)ccc12]

Example 213 was synthesized in a similar manner to Example 212, except that (4-fluoro-2-methoxyphenyl)boronic acid was used in place of (2-methoxy-4-(trifluoromethyl)phenyl)boronic acid. The final compound was purified via column chromatography (12 g silica gel column, gradient elution 25 to 100% EtOAc:Heptane) to afford 4-fluoro-1-(4-fluoro-2-methoxyphenyl)-N-(thiazol-2-yl)isoquinoline-6-sulfonamide as a light yellow solid. $^1$H NMR (400 MHz, DMSO-$d_6$) δ ppm=12.99 (br. s., 1H), 8.70 (s, 1H), 8.49 (s, 1H), 7.99 (d, J=8.9 Hz, 1H), 7.79 (d, J=8.4 Hz, 1H), 7.37 (t, J=7.6 Hz, 1H), 7.30 (d, J=4.4 Hz, 1H), 7.21-7.09 (m, 1H), 7.01-6.93 (m, 1H), 6.89 (d, J=4.5 Hz, 1H), 3.67 (s, 3H). m/z (ESI) 434.2 (M+H)$^+$.

EXAMPLE 214

1-(4-CYANO-2-METHOXYPHENYL)-4-FLUORO-N-(THIAZOL-2-YL)ISOQUINOLINE-6-SULFONAMIDE

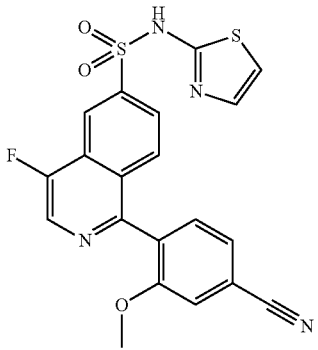 [SMILES: COc1cc(C#N)ccc1-c1ncc(F)c2cc(S(=O)(=O)Nc3nccs3)ccc12]

Example 214 was synthesized in a similar manner to Example 212, except that (4-cyano-2-methoxyphenyl)boronic acid was used in place of (2-methoxy-4-(trifluoromethyl)phenyl)boronic acid. The final compound was purified via column chromatography (12 g silica gel column, gradient elution 25 to 100% EtOAc:Heptane) to afford 1-(4-cyano-2-methoxyphenyl)-4-fluoro-N-(thiazol-2-yl)isoquinoline-6-sulfonamide as a light yellow solid. $^1$H NMR (400 MHz, DMSO-$d_6$) δ ppm=13.00 (s, 1H), 8.75 (d, J=1.5 Hz, 1H), 8.51 (d, J=1.4 Hz, 1H), 7.99 (dd, J=1.8, 8.9 Hz, 1H), 7.79-7.74 (m, 2H), 7.66-7.60 (m, 1H), 7.58-7.51 (m, 1H), 7.31 (d, J=4.6 Hz, 1H), 6.90 (d, J=4.6 Hz, 1H), 3.73 (s, 3H). m/z (ESI) 441.2 (M+H)$^+$.

EXAMPLE 215

1-(4-CHLORO-2-METHOXYPHENYL)-4-FLUORO-N-(THIAZOL-2-YL)ISOQUINOLINE-6-SULFONAMIDE

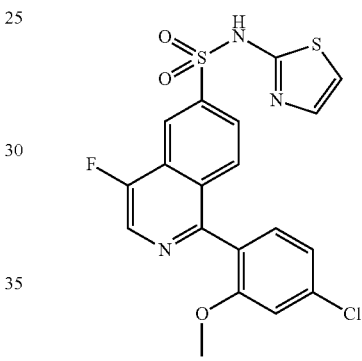

Example 215 was synthesized in a similar manner to Example 212, except that (4-chloro-2-methoxyphenyl)boronic acid was used in place of (2-methoxy-4-(trifluoromethyl)phenyl)boronic acid. The final compound was purified via column chromatography (12 g silica gel column, gradient elution 25 to 100% EtOAc:Heptane) to afford 1-(4-chloro-2-methoxyphenyl)-4-fluoro-N-(thiazol-2-yl)isoquinoline-6-sulfonamide as a white solid. $^1$H NMR (400 MHz, DMSO-$d_6$) δ ppm=12.99 (s, 1H), 8.71 (d, J=1.6 Hz, 1H), 8.49 (d, J=1.8 Hz, 1H), 7.98 (dd, J=1.8, 8.9 Hz, 1H), 7.80 (dd, J=1.8, 8.9 Hz, 1H), 7.36 (d, J=8.0 Hz, 1H), 7.32 (d, J=1.9 Hz, 1H), 7.30 (d, J=4.6 Hz, 1H), 7.20 (dd, J=2.0, 8.0 Hz, 1H), 6.89 (d, J=4.6 Hz, 1H), 3.68 (s, 3H). m/z (ESI) 450.2 (M+H)+.

EXAMPLE 216

4-FLUORO-1-(2-METHOXY-4-(TRIFLUOROM-ETHYL)PHENYL)-N-(PYRIMIDIN-4-YL)ISO-QUINOLINE-6-SULFONAMIDE

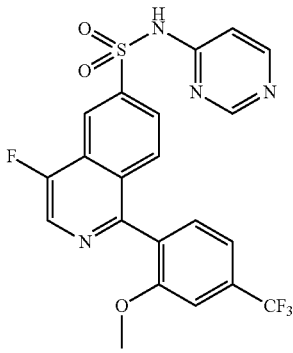 [SMILES: COc1cc(C(F)(F)F)ccc1-c1ncc(F)c2cc(S(=O)(=O)Nc3ccncn3)ccc12]

Example 216 was synthesized in a similar manner to Example 212, except that 1-chloro-4-fluoro-N-(4-methoxybenzyl)-N-(pyrimidin-4-yl)isoquinoline-6-sulfonamide (Intermediate QQQ) and (2-methoxy-4-(trifluoromethyl)phenyl)boronic acid were used as the coupling partners. The final compound was purified via column chromatography (12 g silica gel column, gradient elution 25 to 100% EtOAc:Heptane) to afford 4-fluoro-1-(2-methoxy-4-(trifluoromethyl)phenyl)-N-(pyrimidin-4-yl)isoquinoline-6-sulfonamide as a white solid. $^1$H NMR (400 MHz, DMSO-$d_6$) δ ppm=8.74 (s, 1H), 8.59 (d, J=17.3 Hz, 2H), 8.35-8.13 (m, 1H), 8.06 (d, J=8.9 Hz, 1H), 7.77 (d, J=9.1 Hz, 1H), 7.62-7.56 (m, 1H), 7.54-7.46 (m, 2H), 3.75 (s, 3H). m/z (ESI) 479.2 (M+H)+.

EXAMPLE 217

1-(4-CHLORO-2-METHOXYPHENYL)-4-FLUORO-N-(PYRIMIDIN-4-YL)ISOQUINOLINE-6-SULFONAMIDE

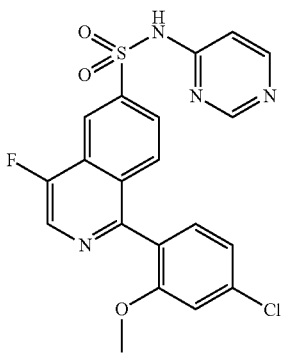 [SMILES: COc1cc(Cl)ccc1-c1ncc(F)c2cc(S(=O)(=O)Nc3ccncn3)ccc12]

Example 217 was synthesized in a similar manner to Example 212, except that 1-chloro-4-fluoro-N-(4-methoxybenzyl)-N-(pyrimidin-4-yl)isoquinoline-6-sulfonamide (Intermediate QQQ) and (4-chloro-2-methoxyphenyl)boronic acid were used as the coupling partners. The final compound was purified via column chromatography (12 g silica gel column, gradient elution 25 to 100% EtOAc:Heptane) to afford 1-(4-chloro-2-methoxyphenyl)-4-fluoro-N-(pyrimidin-4-yl)isoquinoline-6-sulfonamide as a white solid. $^1$H NMR (400 MHz, DMSO-$d_6$) δ ppm=8.70 (s, 1H), 8.58 (d, J=10.4 Hz, 2H), 8.21 (s, 1H), 8.05 (d, J=9.1 Hz, 1H), 7.78 (d, J=8.6 Hz, 1H), 7.40-7.30 (m, 2H), 7.19 (dd, J=2.0, 8.0 Hz, 1H), 7.10-6.80 (m, 1H), 3.67 (s, 3H). m/z (ESI) 445.2 (M+H)+.

EXAMPLE 218

1-(4-cyano-2-methoxyphenyl)-4-fluoro-N-(pyrimidin-4-yl)isoquinoline-6-sulfonamide

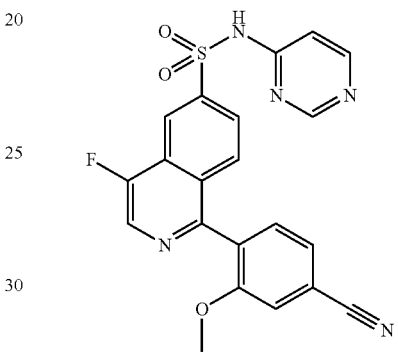

Example 218 was synthesized in a similar manner to Example 212, except that 1-chloro-4-fluoro-N-(4-methoxybenzyl)-N-(pyrimidin-4-yl)isoquinoline-6-sulfonamide (Intermediate QQQ) and (4-cyano-2-methoxyphenyl)boronic acid were used as the coupling partners. The final compound was purified via column chromatography (12 g silica gel column, gradient elution 25 to 100% EtOAc:Heptane) to afford 1-(4-cyano-2-methoxyphenyl)-4-fluoro-N-(pyrimidin-4-yl)isoquinoline-6-sulfonamide as a white solid. $^1$H NMR (400 MHz, DMSO-$d_6$) δ ppm=8.74 (s, 1H), 8.59 (d, J=15.7 Hz, 2H), 8.37-8.14 (m, 1H), 8.05 (d, J=7.4 Hz, 1H), 7.75 (d, J=1.3 Hz, 2H), 7.66-7.60 (m, 1H), 7.57-7.50 (m, 1H), 3.72 (s, 3H). m/z (ESI) 436.2 (M+H)+.

EXAMPLE 219

3-CHLORO-1-(2-METHOXY-4-(TRIFLUOROMETHYL)PHENYL)-N-(THIAZOL-2-YL)ISOQUINOLINE-6-SULFONAMIDE

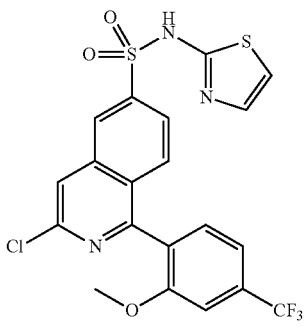 [SMILES: COc1cc(C(F)(F)F)ccc1-c1nc(Cl)cc2cc(S(=O)(=O)Nc3nccs3)ccc12]

A flask was charged with 3-chloro-1-(2-methoxy-4-(trifluoromethyl)phenyl)-N-(4-methoxybenzyl)-N-(thiazol-2-yl)isoquinoline-6-sulfonamide (Intermediate RRR) (58.43 mg, 0.094 mmol), DCM (1 mL), and TFA (0.5 mL) to give a yellow solution (8:45 am). After 30 min of stirring at RT, the mixture was diluted with MeOH and concentrated. The residue was purified by chromatography on silica gel (0-10% MeOH/DCM) to give 47 mg of a light yellow solid. The solid was concentrated from DCM (2×), then taken up in DCM and filtered. The collected solid was washed with DCM (2×), then dried under vacuum for 10 min to give 3-chloro-1-(2-methoxy-4-(trifluoromethyl)phenyl)-n-(thiazol-2-yl)isoquinoline-6-sulfonamide as a white solid: $^1$H NMR (400 MHz, DMSO-$d_6$) δ ppm=12.95 (s, 1H), 8.57 (d, J=1.8 Hz, 1H), 8.39 (s, 1H), 7.87 (dd, J=1.8, 8.9 Hz, 1H), 7.72 (d, J=8.9 Hz, 1H), 7.61 (d, J=7.7 Hz, 1H), 7.56-7.48 (m, 2H), 7.30 (d, J=4.7 Hz, 1H), 6.90 (d, J=4.6 Hz, 1H), 3.76 (s, 3H). m/z (ESI) 500.2 (M+H)+.

EXAMPLE 220

3-CYANO-1-(2-METHOXY-4-(TRIFLUOROMETHYL)PHENYL)-N-(THIAZOL-2-YL)ISOQUINOLINE-6-SULFONAMIDE

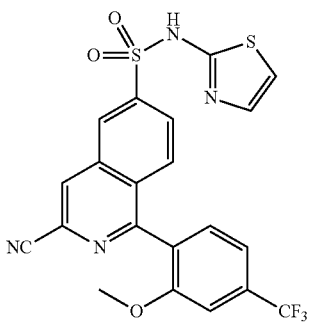 [SMILES: COc1cc(C(F)(F)F)ccc1-c1nc(C#N)cc2cc(S(=O)(=O)Nc3nccs3)ccc12]

A vial was charged with 3-chloro-1-(2-methoxy-4-(trifluoromethyl)phenyl)-N-(4-methoxybenzyl)-N-(thiazol-2-yl)isoquinoline-6-sulfonamide (Intermediate RRR) (59.39 mg, 0.096 mmol), dicyanozinc (22.49 mg, 0.192 mmol), racemic-2-di-t-butylphosphino-1,1'-binaphthyl (Strem Chemical, Newburyport, Mass.) (7.63 mg, 0.019 mmol), palladium(ii) trifluoroacetate (3.18 mg, 9.58 μmol), and zinc (3.13 mg, 0.048 mmol). The vial was flushed with Ar (g), then DMAC (479 μl) was added. The vial was sealed and heated in a 95° C. heating bath for 15 h. The mixture was diluted with water and extracted with EtOAc (4× via pipette). The combined organic extracts were combined and concentrated. The residue was taken up in DCM (1 mL) and TFA (0.5 mL). After 30 min, the mixture was diluted with MeOH, then concentrated. The residue was purified by chromatography on silica gel (12-g column, 0 to 6% MeOH/DCM). The resulting material was concentrated from DCM (3×), then taken up in DCM and filtered through a membrane filter. The collected solid was washed with DCM (2×), dried under a flow of $N_2$ (g), then dried under vacuum to give 3-cyano-1-(2-methoxy-4-(trifluoromethyl)phenyl)-N-(thiazol-2-yl)isoquinoline-6-sulfonamide as an off-white solid: $^1$H NMR (400 MHz, DMSO-$d_6$) δ ppm=12.99 (br. s., 1H), 8.95 (s, 1H), 8.70 (d, J=1.8 Hz, 1H), 8.07 (dd, J=1.9, 8.9 Hz, 1H), 7.83 (d, J=8.9 Hz, 1H), 7.63 (d, J=7.6 Hz, 1H), 7.57-7.50 (m, 2H), 7.31 (d, J=4.5 Hz, 1H), 6.91 (d, J=4.6 Hz, 1H), 3.76 (s, 3H); m/z (ESI) 491.2 (M+H)+.

EXAMPLE 221

3-METHOXY-1-(2-METHOXY-4-(TRIFLUOROMETHYL)PHENYL)-N-(THIAZOL-2-YL)ISOQUINOLINE-6-SULFONAMIDE

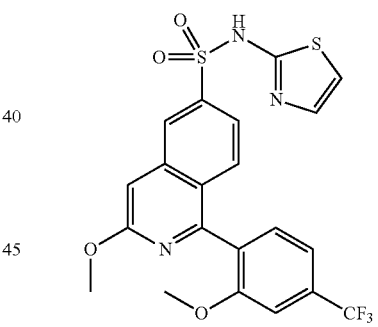

A vial was charged with 3-chloro-1-(2-methoxy-4-(trifluoromethyl)phenyl)-N-(thiazol-2-yl)isoquinoline-6-sulfonamide (Example 249) (35.79 mg, 0.072 mmol), sodium methoxide (25.1 mg, 0.465 mmol), and MeOH (477 μl). The vial was sealed and heated in a 100° C. heating bath for 1 h. The mixture was diluted with DMSO (0.5 mL) to solubilize the solids, and an additional portion of sodium methoxide (25.1 mg, 0.465 mmol) was added. The vial was sealed and heated to 120° C. for 1.5 h. The mixture was cooled to room temperature and diluted with EtOAc, then washed with 1N aq. HCl, washed with water, washed with brine, dried over sodium sulfate, filtered, and concentrated. The residue was purified by chromatography on silica gel (0 to 5% MeOH/DCM) to give 3-methoxy-1-(2-methoxy-4-(trifluoromethyl)phenyl)-N-(thiazol-2-yl)isoquinoline-6-sulfonamide (23.2 mg, 0.047 mmol, 65.4% yield) as an off-white solid: $^1$H NMR (400 MHz, DMSO-$d_6$) δ ppm=12.88 (s, 1H), 8.40 (s, 1H), 7.61-7.56 (m, 3H), 7.55-7.48 (m, 3H), 7.28 (d, J=4.6 Hz, 1H), 6.87 (d, J=4.6 Hz, 1H), 3.95 (s, 3H), 3.76 (s, 3H). m/z (ESI) 496.2 (M+H)+.

EXAMPLE 222

1-(2-METHOXY-4-(TRIFLUOROMETHYL)PHENYL)-3-(METHYLAMINO)-N-(THIAZOL-2-YL)ISOQUINOLINE-6-SULFONAMIDE

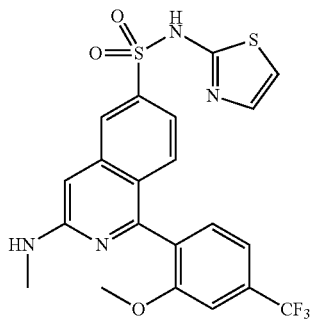 [SMILES: CNc1cc2cc(S(=O)(=O)Nc3nccs3)ccc2c(-c2ccc(C(F)(F)F)cc2OC)n1]

A vial was charged with 3-chloro-1-(2-methoxy-4-(trifluoromethyl)phenyl)-N-(thiazol-2-yl)isoquinoline-6-sulfonamide (Example 249) (34.13 mg, 0.068 mmol) and chloro[2-(dicyclohexylphosphino)-3,6-dimethoxy-2',4',6'-triisopropyl-1,1'-biphenyl][2-(2-aminoethyl)phenyl]palladium(ii) (Strem Chemical, Newburyport, Mass.) (5.45 mg, 6.83 μmol), then flushed with Ar (g). Methanamine (2M in THF) (341 μl, 0.683 mmol) was added to give a solution. Lithium bis(trimethylsilyl)amide (1M in THF) (341 μl, 0.341 mmol) was added, resulting in the formation of a maroon solution. After 15 min, the mixture was diluted with MeOH and concentrated. The residue was purified by chromatography on silica gel (12-g column, 0 to 10% MeOH/DCM) to give 1-(2-methoxy-4-(trifluoromethyl)phenyl)-3-(methylamino)-N-(thiazol-2-yl)isoquinoline-6-sulfonamide (28.58 mg, 0.058 mmol, 85% yield) as a yellow solid: $^1$H NMR (400 MHz, DMSO-d$_6$) δ ppm=12.81 (br. s., 1H), 8.11 (d, J=1.6 Hz, 1H), 7.53-7.42 (m, 3H), 7.36-7.24 (m, 3H), 6.88-6.82 (m, 1H), 6.79-6.71 (m, 2H), 3.75 (s, 3H), 2.82 (d, J=5.0 Hz, 3H); m/z (ESI) 495.2 (M+H)+.

EXAMPLE 223

3-(DIMETHYLAMINO)-1-(2-METHOXY-4-(TRIFLUOROMETHYL)PHENYL)-N-(THIAZOL-2-YL)ISOQUINOLINE-6-SULFONAMIDE

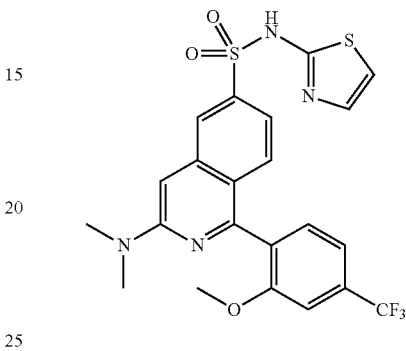

Example 223 was synthesized in a similar manner to Example 222, except that a solution of dimethylamine in THF was used in place of the solution of methylamine in THF. The desired product, 3-(dimethylamino)-1-(2-methoxy-4-(trifluoromethyl)phenyl)-N-(thiazol-2-yl)isoquinoline-6-sulfonamide, was isolated as a yellow solid: $^1$H NMR (400 MHz, DMSO-d$_6$) δ ppm=12.82 (br. s., 1H), 8.17 (d, J=1.5 Hz, 1H), 7.56-7.43 (m, 3H), 7.39-7.21 (m, 3H), 7.05 (s, 1H), 6.90-6.79 (m, 1H), 3.77 (br. s., 3H), 3.10 (s, 6H); m/z (ESI) 509.2 (M+H)+.

EXAMPLE 224

1-(4-(DIFLUOROMETHYL)-2-METHOXYPHENYL)-N-(THIAZOL-2-YL)ISOQUINOLINE-6-SULFONAMIDE

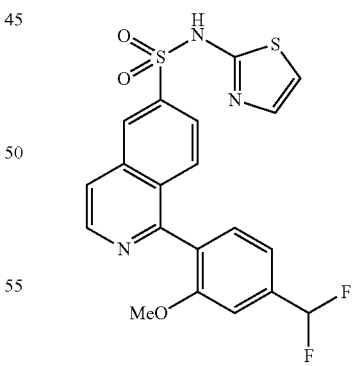

A solution of Intermediate SSS (0.110 g, 0.241 mmol), Intermediate TTT (0.086 g, 0.301 mmol), PdCl$_2$(dppf)-CH$_2$Cl$_2$ adduct (0.020 g, 0.024 mmol), and potassium carbonate (0.133 g, 0.965 mmol) in 1.5 mL of dioxane and 0.5 mL of water was heated to 110° C. for one hour. The reaction mixture was allowed to cool to room temperature, and the aqueous layer was removed. 4N HCl in dioxane (1.809 ml, 7.24 mmol) was added, and the reaction mixture was heated to 110° C. for an additional hour. The reaction mixture was concentrated and purification of the crude residue by reverse phase column chromatography [Redisep Gold C18 50 g, 10-100% (0.1% NH4OH in MeOH)/(0.1% NH4OH in water)] gave 1-(4-(difluoromethyl)-2-methoxyphenyl)-N-(thiazol-2-yl)isoquinoline-6-sulfonamide (0.020 g, 0.045 mmol, 18.53% yield). $^1$H NMR (MeCN-$d_3$) δ ppm: 8.68 (d, J=5.7 Hz, 1H), 8.51 (s, 1H), 7.92 (d, J=5.7 Hz, 1H), 7.86 (d, J=8.9 Hz, 1H), 7.70 (d, J=8.8 Hz, 1H), 7.47 (d, J=7.5 Hz, 1H), 7.29-7.36 (m, 2H), 6.72-7.06 (m, 2H), 6.62 (d, J=4.8 Hz, 1H), 3.71 (s, 3H). m/z (ESI) 448.0 (M+H)+

EXAMPLE 225

1-(2-(METHOXYMETHYL)-4-(TRIFLUOROMETHYL)PHENYL)-N-(THIAZOL-2-YL)ISOQUINOLINE-6-SULFONAMIDE

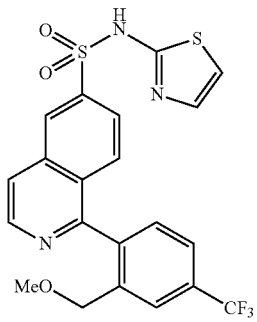 [SMILES: COCc1cc(C(F)(F)F)ccc1-c1nccc2cc(S(=O)(=O)Nc3nccs3)ccc12]

Example 225 was synthesized in a similar manner to Example 224, using Intermediate UUU instead of Intermediate TTT. $^1$H NMR (MeCN-$d_3$) δ ppm: 8.68 (d, J=5.7 Hz, 1H), 8.55 (s, 1H), 7.97 (d, J=6.0 Hz, 1H), 7.93 (s, 1H), 7.87 (d, J=8.9 Hz, 1H), 7.76 (d, J=8.3 Hz, 1H), 7.68 (d, J=8.9 Hz, 1H), 7.53 (d, J=8.0 Hz, 1H), 6.99 (d, J=4.7 Hz, 1H), 6.62 (d, J=4.7 Hz, 1H), 4.25 (bd, J=17.6 Hz, 2H), 3.04 (s, 3H). m/z (ESI) 480.0 (M+H)+

EXAMPLE 226

METHYL 2-(6-(N-(THIAZOL-2-YL)SULFAMOYL)ISOQUINOLIN-1-YL)-5-(TRIFLUOROMETHYL)BENZIMIDATE

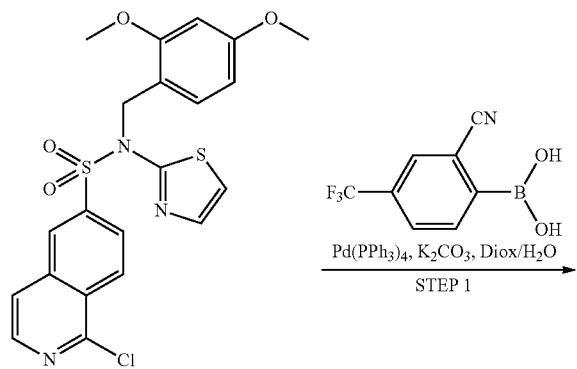

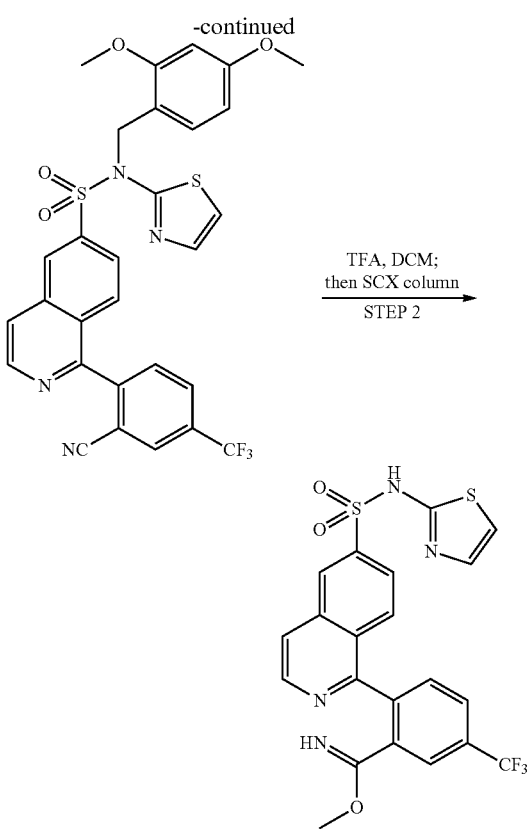

STEP 1: 1-(2-CYANO-4-(TRIFLUOROMETHYL)PHENYL)-N-(2,4-DIMETHOXYBENZYL)-N-(THIAZOL-2-YL)ISOQUINOLINE-6-SULFONAMIDE

The titled compound was prepared in an analogous manner to that of INTERMEDIATE DD, except that 1-chloro-N-(2,4-dimethoxybenzyl)-N-(thiazol-2-yl)isoquinoline-6-sulfonamide (Intermediate OOO) and (2-cyano-4-(trifluoromethyl)phenyl)boronic acid were used as the coupling partners. The material was purified via silica gel column chromatography (12 g, gradient elution 0 to 50% EtOAc:Heptane) to afford 1-(2-cyano-4-(trifluoromethyl)phenyl)-N-(2,4-dimethoxybenzyl)-N-(thiazol-2-yl)isoquinoline-6-sulfonamide as a light yellow solid. m/z (ESI) 629.3 (M+H)$^+$.

STEP 2: METHYL 2-(6-(N-(THIAZOL-2-YL)SULFAMOYL)ISOQUINOLIN-1-YL)-5-(TRIFLUOROMETHYL)BENZIMIDATE 1-(2-cyano-4-(trifluoromethyl)phenyl)-N-(2,4-dimethoxybenzyl)-N-(thiazol-2-yl)isoquinoline-6-sulfonamide (0.011 g, 0.018 mmol) was dissolved in 1 mL of DCM and TFA (0.1 ml, 1.298 mmol) was added. The reaction was stirred for 30 minutes at room temperature. The reaction was concentrated, dissolved in methanol, and passed through an SCX ion exchange column (pre-wetted with methanol). The column was flushed several times with methanol, then the product was liberated by flushing the column several times with 2.0 M ammonia in methanol. The product-containing filtrate was concentrated to afford an orange solid. The material was purified via silica gel column chromatography (12 g silica gel column, gradient elution 0 to 10% MeOH:DCM) to afford methyl 2-(6-(N-(thiazol-2-yl)sulfamoyl)isoquinolin-1-yl)-5-(trifluoromethyl)benzimidate (0.008 g, 0.016 mmol, 9.10% yield) as a white solid. $^1$H NMR (400 MHz, DMSO-d$_6$) δ ppm=12.90 (br. s., 1H), 8.78 (br. s., 1H), 8.66 (d, J=5.6 Hz, 1H), 8.58 (s, 1H), 8.14 (d, J=5.0 Hz, 1H), 8.06 (br. s., 1H), 7.99 (d, J=7.5 Hz, 1H), 7.89-7.83 (m, 1H), 7.77 (d, J=8.5 Hz, 2H), 7.28 (d, J=4.6 Hz, 1H), 6.87 (d, J=4.6 Hz, 1H), 3.02 (s, 3H). m/z (ESI) 493.2 (M+H)$^+$.

EXAMPLE 227

2-(6-(N-(THIAZOL-2-YL)SULFAMOYL)ISO-QUINOLIN-1-YL)-5-(TRIFLUOROMETHYL)BENZAMIDE

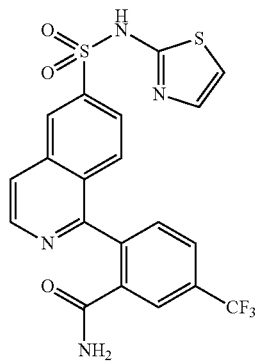 [SMILES: NC(=O)c1cc(C(F)(F)F)ccc1-c1nccc2cc(S(=O)(=O)Nc3nccs3)ccc12]

A microwave vial was charged with 1-chloro-N-(2,4-dimethoxybenzyl)-N-(thiazol-2-yl)isoquinoline-6-sulfonamide (Intermediate OOO; 0.085 g, 0.179 mmol), (2-cyano-4-(trifluoromethyl)phenyl)boronic acid (0.058 g, 0.268 mmol), Pd(PPh$_3$)$_4$ (0.021 g, 0.018 mmol), and potassium carbonate (0.123 g, 0.893 mmol). Dioxane (0.893 ml) and water (0.298 ml) were added, the vial was flushed with argon and sealed, and microwaved at 90° C. for 30 minutes. A small amount of 1-(2-cyano-4-(trifluoromethyl)phenyl)-N-(2,4-dimethoxybenzyl)-N-(thiazol-2-yl)isoquinoline-6-sulfonamide was observed; however the predominant product was observed as the coupling product with hydrolysis of the nitrile. The reaction was diluted with ethyl acetate and washed with water. The aqueous layer was extracted with ethyl acetate, and the combined organic layers were dried with sodium sulfate, filtered, and concentrated. The material was purified via silica gel column chromatography (12 g, gradient elution 0 to 50% EtOAc:Heptane) to afford 1-(2-cyano-4-(trifluoromethyl)phenyl)-N-(2,4-dimethoxybenzyl)-N-(thiazol-2-yl)isoquinoline-6-sulfonamide and 2-(6-(N-(2,4-dimethoxybenzyl)-N-(thiazol-2-yl)sulfamoyl)isoquinolin-1-yl)-5-(trifluoromethyl)benzamide. The protected nitrile was dissolved in 1 mL of DCM and TFA (0.1 ml, 1.298 mmol) was added. The reaction was stirred for 30 minutes at room temperature. The reaction was concentrated, dissolved in methanol, and passed through an SCX ion exchange column (pre-wetted with methanol). The column was flushed several times with methanol, then the product was liberated by flushing the column several times with 2.0 M ammonia in methanol. The product-containing filtrate was concentrated to afford 2-(6-(N-(thiazol-2-yl)sulfamoyl)isoquinolin-1-yl)-5-(trifluoromethyl)benzamide (0.049 g, 0.102 mmol, 57.3% yield) as a white solid. $^1$H NMR (400 MHz, DMSO-d$_6$) δ ppm=12.89 (br. s., 1H), 8.61 (d, J=5.7 Hz, 1H), 8.54 (s, 1H), 8.10-8.03 (m, 3H), 7.98 (d, J=8.4 Hz, 1H), 7.87-7.81 (m, 1H), 7.79-7.68 (m, 2H), 7.34 (br. s., 1H), 7.27 (d, J=4.5 Hz, 1H), 6.86 (d, J=4.5 Hz, 1H). m/z (ESI) 479.2 (M+H)$^+$.

EXAMPLE 228

1-(2-FLUORO-4-(TRIFLUOROMETHYL)PHENYL)-N-(THIAZOL-2-YL)ISOQUINOLINE-6-SULFONAMIDE

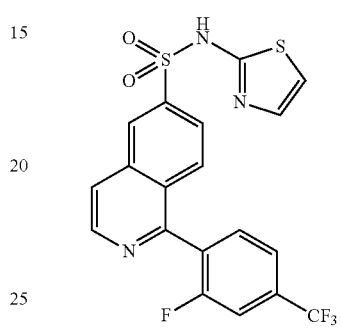

A microwave vial was charged with 1-chloro-N-(2,4-dimethoxybenzyl)-N-(thiazol-2-yl)isoquinoline-6-sulfonamide (Intermediate OOO; 0.250 g, 0.525 mmol), (2-fluoro-4-(trifluoromethyl)phenyl)boronic acid (0.164 g, 0.788 mmol), Pd(PPh$_3$)$_4$ (0.061 g, 0.053 mmol), and potassium carbonate (0.363 g, 2.63 mmol). Dioxane (2.63 mL) and Water (0.875 mL) were added, the vial was flushed with argon and sealed, and heated in a microwave reactor at 90° C. for 30 minutes. The reaction was diluted with ethyl acetate and washed with water. The aqueous layer was extracted with ethyl acetate, and the combined organic layers were dried with sodium sulfate, filtered, and concentrated. The material was purified via silica gel column chromatography (12 g, gradient elution 0 to 50% EtOAc:Heptane) to afford N-(2,4-dimethoxybenzyl)-1-(2-fluoro-4-(trifluoromethyl)phenyl)-N-(thiazol-2-yl)isoquinoline-6-sulfonamide (0.271 g, 0.449 mmol, 85% yield) as a white solid. N-(2,4-dimethoxybenzyl)-1-(2-fluoro-4-(trifluoromethyl)phenyl)-N-(thiazol-2-yl)isoquinoline-6-sulfonamide (35 mg, 0.058 mmol) was dissolved in 1 mL of DCM and TFA (0.1 ml, 1.298 mmol) was added. The reaction was stirred for 30 minutes at room temperature. The reaction was concentrated, dissolved in methanol, and passed through an SCX ion exchange column (pre-wetted with methanol). The column was flushed several times with methanol, then the product was liberated by flushing the column several times with 2.0 M ammonia in methanol. The product-containing filtrate was concentrated to afford 1-(2-fluoro-4-(trifluoromethyl)phenyl)-N-(thiazol-2-yl)isoquinoline-6-sulfonamide as a white solid. $^1$H NMR (400 MHz, DMSO-d$_6$) δ ppm=12.92 (br. s., 1H), 8.77 (d, J=5.7 Hz, 1H), 8.62 (d, J=1.6 Hz, 1H), 8.24 (d, J=5.6 Hz, 1H), 7.99-7.91 (m, 2H), 7.89-7.77 (m, 3H), 7.27 (d, J=4.6 Hz, 1H), 6.87 (d, J=4.6 Hz, 1H). m/z (ESI) 454.1 (M+H)+.

EXAMPLE 229

1-(2-(1H-IMIDAZOL-1-YL)-4-(TRIFLUOROMETHYL)PHENYL)-N-(THIAZOL-2-YL)ISOQUINOLINE-6-SULFONAMIDE

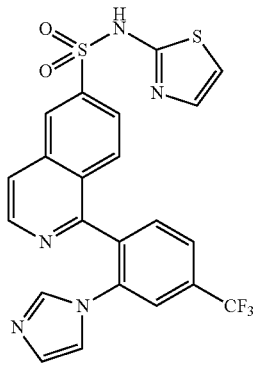 [SMILES: O=S(=O)(Nc1nccs1)c1ccc2c(-c3ccc(C(F)(F)F)cc3-n3ccnc3)nccc2c1]

A microwave vial was charged with 1-(2-fluoro-4-(trifluoromethyl)phenyl)-N-(thiazol-2-yl)isoquinoline-6-sulfonamide (0.090 g, 0.198 mmol), imidazole (0.054 g, 0.794 mmol), and potassium tert-butoxide (0.111 g, 0.992 mmol). DMF (0.992 ml) was added and the reaction was heated in a microwave reactor at 150° C. for one hour. The reaction was diluted with ethyl acetate and washed with water. The aqueous layer was extracted with ethyl acetate, then acidified with concentrated HCl solution and extracted twice with ethyl acetate. The aqueous layer was passed through an SCX ion exchange column (pre-wetted with methanol). The column was flushed several times with methanol, then the product was liberated by flushing the column several times with 2.0 M ammonia in methanol. The ammonia/methanol filtrate was combined with the previously isolated organic layers. The combined organic layers were dried with sodium sulfate, filtered, and concentrated. The material was purified via silica gel column chromatography (12 g, gradient elution 0 to 10% MeOH:DCM) to afford 1-(2-(1H-imidazol-1-yl)-4-(trifluoromethyl)phenyl)-N-(thiazol-2-yl)isoquinoline-6-sulfonamide as a light yellow solid. $^1$H NMR (400 MHz, DMSO-$d_6$) δ ppm=12.90 (br. s., 1H), 8.66 (d, J=5.7 Hz, 1H), 8.50 (d, J=1.6 Hz, 1H), 8.13 (d, J=5.4 Hz, 1H), 8.08 (s, 1H), 8.03 (dd, J=1.2, 8.1 Hz, 1H), 7.88 (d, J=7.9 Hz, 1H), 7.79-7.73 (m, 1H), 7.70-7.63 (m, 1H), 7.48 (t, J=1.0 Hz, 1H), 7.26 (d, J=4.6 Hz, 1H), 6.89-6.81 (m, 2H), 6.62 (t, J=1.1 Hz, 1H). m/z (ESI) 502.2 (M+H)+.

EXAMPLE 230

1-(2-(2,3-DIHYDROXYPROPYL)-4-(TRIFLUOROMETHYL)PHENYL)-N-(THIAZOL-2-YL)ISOQUINOLINE-6-SULFONAMIDE 2,2,2-TRIFLUOROACETATE

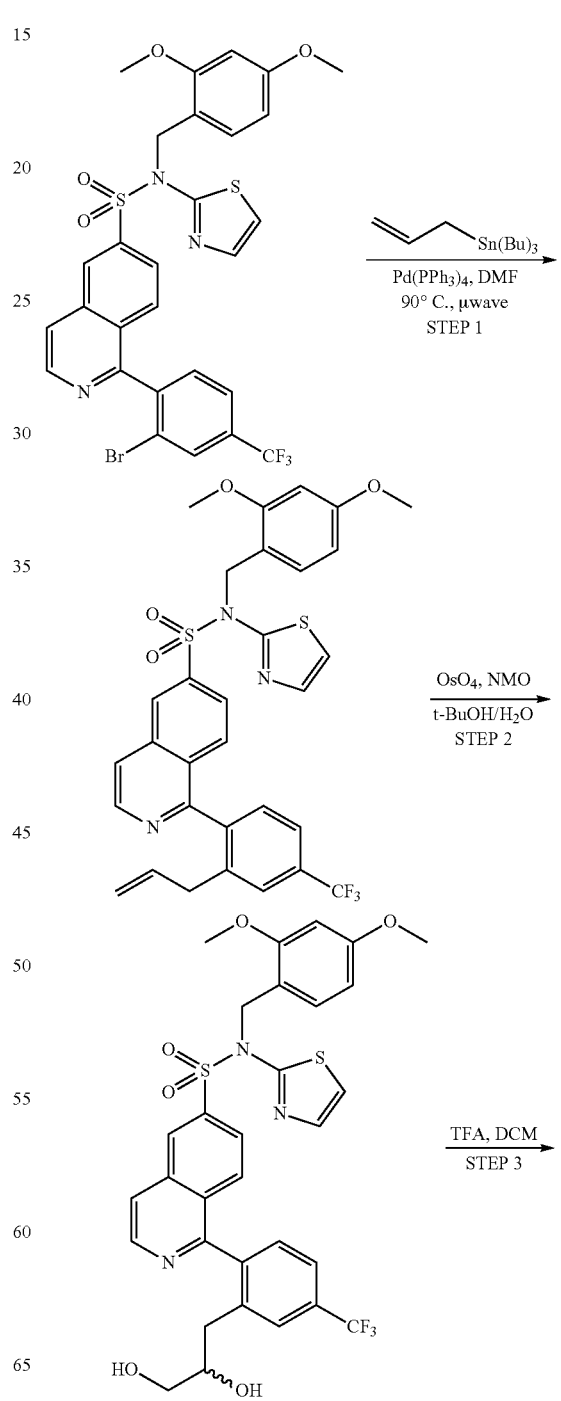

-continued

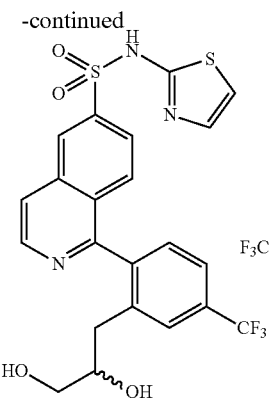

STEP 1: 1-(2-ALLYL-4-(TRIFLUOROMETHYL) PHENYL)-N-(2,4-DIMETHOXYBENZYL)-N-(THIAZOL-2-YL)ISOQUINOLINE-6-SULFONAMIDE

A microwave vial was charged with 1-(2-bromo-4-(trifluoromethyl)phenyl)-N-(2,4-dimethoxybenzyl)-N-(thiazol-2-yl)isoquinoline-6-sulfonamide (see Example 70, step 3; 0.185 g, 0.278 mmol), Pd(PPh$_3$)$_4$ (0.016 g, 0.014 mmol), and DMF (0.557 ml). Allyltributyltin (0.104 ml, 0.334 mmol) was added and the reaction was heated in a microwave reactor at 90° C. for 30 minutes. The reaction was concentrated and purified via column chromatography (40 g silica gel column, gradient elution 0 to 50% EtOAc:Heptane) to afford 1-(2-allyl-4-(trifluoromethyl)phenyl)-N-(2,4-dimethoxybenzyl)-N-(thiazol-2-yl)isoquinoline-6-sulfonamide as a light pink solid. m/z (ESI) 626.3 (M+H)$^+$.

STEP 2: 1-(2-(2,3-DIHYDROXYPROPYL)-4-(TRIFLUOROMETHYL)PHENYL)-N-(2,4-DIMETHOXYBENZYL)-N-(THIAZOL-2-YL)ISOQUINOLINE-6-SULFONAMIDE

A vial was charged with 1-(2-allyl-4-(trifluoromethyl)phenyl)-N-(2,4-dimethoxybenzyl)-N-(thiazol-2-yl)isoquinoline-6-sulfonamide (0.114 g, 0.182 mmol), NMO (0.043 g, 0.364 mmol), t-BuOH (0.607 ml), and water (0.304 ml). Osmium tetroxide (4% aq. soln.) (0.111 ml, 0.018 mmol) was added drop wise and the reaction was stirred for two hours. The reaction was quenched with saturated sodium thiosulfate solution and diluted with ethyl acetate. The aqueous layer was extracted with ethyl acetate, and the combined organic layers were dried with sodium sulfate, filtered, and concentrated. The material was purified via silica gel chromatography (12 g silica gel column, gradient elution 0 to 10% MeOH:DCM) to afford 1-(2-(2,3-dihydroxypropyl)-4-(trifluoromethyl)phenyl)-N-(2,4-dimethoxybenzyl)-N-(thiazol-2-yl)isoquinoline-6-sulfonamide as a clear oil. m/z (ESI) 660.3 (M+H)$^+$.

STEP 3: 1-(2-(2,3-DIHYDROXYPROPYL)-4-(TRIFLUOROMETHYL)PHENYL)-N-(THIAZOL-2-YL)ISOQUINOLINE-6-SULFONAMIDE 2,2,2-TRIFLUOROACETATE 1-(2-(2,3-dihydroxypropyl)-4-(trifluoromethyl)phenyl)-N-(2,4-dimethoxybenzyl)-N-(thiazol-2-yl)isoquinoline-6-sulfonamide (0.120 g, 0.182 mmol) was dissolved in DCM and TFA (0.1 ml, 1.298 mmol) was added. The reaction was stirred for 30 minutes at room temperature. The reaction was concentrated and the material was triturated in diethyl ether. The solids were filtered and washed with diethyl ether, then vacuum dried overnight to afford 1-(2-(2,3-dihydroxypropyl)-4-(trifluoromethyl)phenyl)-N-(thiazol-2-yl)isoquinoline-6-sulfonamide 2,2,2-trifluoroacetate as a yellow solid. $^1$H NMR (400 MHz, DMSO-d$_6$) δ ppm=12.89 (br. s., 1H), 8.71 (dd, J=2.0, 5.7 Hz, 1H), 8.59 (d, J=4.1 Hz, 1H), 8.25-8.12 (m, 1H), 7.94-7.83 (m, 2H), 7.76-7.64 (m, 2H), 7.51 (t, J=7.8 Hz, 1H), 7.28 (d, J=4.4 Hz, 1H), 6.88 (d, J=4.6 Hz, 1H), 4.04 (d, J=4.9 Hz, 1H), 3.53-3.44 (m, 1H), 3.29 (d, J=3.8 Hz, 1H), 3.10-3.02 (m, 1H), 3.02-2.94 (m, 1H), 2.87 (dd, J=4.0, 14.3 Hz, 1H), 2.37-2.29 (m, 1H). m/z (ESI) 510.2 (M+H)$^+$.

EXAMPLE 231

4-METHOXY-1-(2-METHOXY-4-(TRIFLUOROMETHYL)PHENYL)-N-(THIAZOL-2-YL)ISOQUINOLINE-6-SULFONAMIDE 2,2,2-TRIFLUOROACETATE

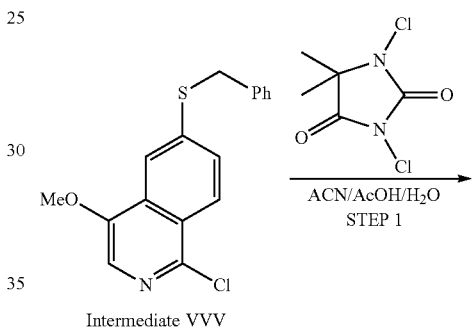

Intermediate VVV

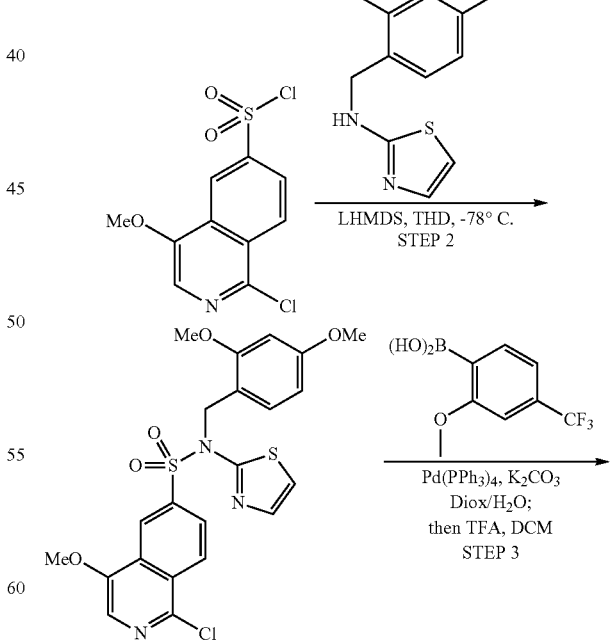

-continued

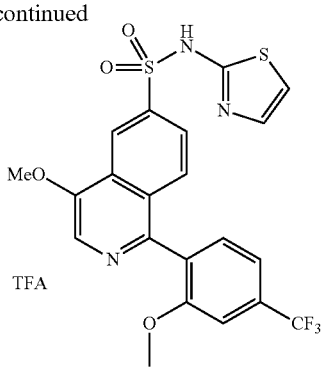

TFA

STEP 1: 1-CHLORO-4-METHOXYISOQUINOLINE-6-SULFONYL CHLORIDE

A round-bottom flask was charged with 6-(benzylthio)-1-chloro-4-methoxyisoquinoline (Intermediate VVV; 0.050 g, 0.158 mmol), acetonitrile (1.490 ml), acetic acid (0.056 ml), and water (0.037 ml) to give a thin suspension. The flask was cooled in a brine-ice bath for 10 min, then 1,3-dichloro-5,5-dimethylimidazolidine-2,4-dione (0.062 g, 0.317 mmol) was added in one portion, leading to a solution. The reaction was stirred for 5 minutes. The reaction was purified via column chromatography (12 g silica gel column, gradient elution 0 to 50% EtOAc:Heptane) to afford 1-chloro-4-methoxyisoquinoline-6-sulfonyl chloride as an off-white solid. m/z (ESI) 294.0 (M+H)+.

STEP 2: 1-CHLORO-N-(2,4-DIMETHOXYBENZYL)-4-METHOXY-N-(THIAZOL-2-YL)ISOQUINOLINE-6-SULFONAMIDE

The title compound was prepared in an analogous manner to that of Intermediate PPP, Step 5, except that 1-chloro-4-methoxyisoquinoline-6-sulfonyl chloride was used instead of perfluorophenyl 1-chloro-4-fluoroisoquinoline-6-sulfonate. The final compound was purified via column chromatography (40 g silica gel column, gradient elution 0 to 100% EtOAc:Heptane) to afford 1-chloro-N-(2,4-dimethoxybenzyl)-4-methoxy-N-(thiazol-2-yl)isoquinoline-6-sulfonamide as a light yellow solid. m/z (ESI) 507.3 (M+H)+.

STEP 3: 4-METHOXY-1-(2-METHOXY-4-(TRIFLUOROMETHYL)PHENYL)-N-(THIAZOL-2-YL)ISOQUINOLINE-6-SULFONAMIDE 2,2,2-TRIFLUOROACETATE

The title compound was prepared in an analogous manner to that of Example 228, except that 1-chloro-N-(2,4-dimethoxybenzyl)-4-methoxy-N-(thiazol-2-yl)isoquinoline-6-sulfonamide and (2-methoxy-4-(trifluoromethyl)phenyl)boronic acid were used as the coupling partners. The final compound was purified via column chromatography (12 g silica gel column, gradient elution 0 to 10% MeOH:EtOAc) to afford 4-methoxy-1-(2-methoxy-4-(trifluoromethyl)phenyl)-N-(thiazol-2-yl)isoquinoline-6-sulfonamide 2,2,2-trifluoroacetate as a yellow solid. $^1$H NMR (400 MHz, DMSO-d6) δ ppm=12.91 (br. s., 1H), 8.63 (d, J=1.4 Hz, 1H), 8.48-8.32 (m, 1H), 7.99-7.84 (m, 1H), 7.73-7.63 (m, 1H), 7.57-7.51 (m, 1H), 7.51-7.45 (m, 2H), 7.28 (d, J=4.6 Hz, 1H), 6.86 (d, J=4.6 Hz, 1H), 4.16 (s, 3H), 3.76-3.71 (m, 3H). m/z (ESI) 496.2 (M+H)+.

EXAMPLE 232

4-HYDROXY-1-(2-METHOXY-4-(TRIFLUOROMETHYL)PHENYL)-N-(THIAZOL-2-YL)ISOQUINOLINE-6-SULFONAMIDE

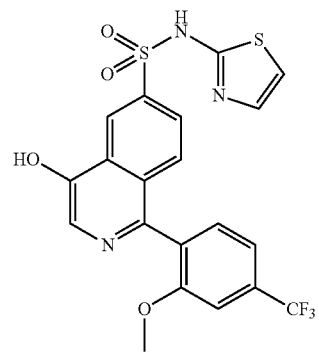

Example 232 was synthesized in a similar manner to Example 228, except that 1-chloro-N-(2,4-dimethoxybenzyl)-4-hydroxy-N-(thiazol-2-yl)isoquinoline-6-sulfonamide and (2-methoxy-4-(trifluoromethyl)phenyl)boronic acid were used as the coupling partners. The final compound was purified via column chromatography (12 g silica gel column, gradient elution 0 to 5% MeOH:DCM) to afford 4-hydroxy-1-(2-methoxy-4-(trifluoromethyl)phenyl)-N-(thiazol-2-yl)isoquinoline-6-sulfonamide as a light yellow solid. $^1$H NMR (400 MHz, DMSO-d$_6$) δ ppm=12.89 (s, 1H), 11.03 (s, 1H), 8.64 (d, J=1.4 Hz, 1H), 8.24 (s, 1H), 7.84 (dd, J=1.8, 8.9 Hz, 1H), 7.60 (d, J=8.9 Hz, 1H), 7.55-7.49 (m, 1H), 7.48-7.42 (m, 2H), 7.28 (d, J=4.6 Hz, 1H), 6.86 (d, J=4.5 Hz, 1H), 3.73 (s, 3H). m/z (ESI) 482.2 (M+H)+.

EXAMPLE 233

1-(4-FLUORO-2-METHOXYPHENYL)-4-HYDROXY-N-(THIAZOL-2-YL)ISOQUINOLINE-6-SULFONAMIDE 2,2,2-TRIFLUOROACETATE

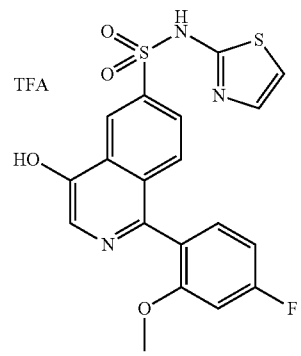 [SMILES: COc1cc(F)ccc1-c1ncc(O)c2cc(S(=O)(=O)Nc3nccs3)ccc12]

TFA

Example 233 was synthesized in a similar manner to Example 228, except that 1-chloro-N-(2,4-dimethoxybenzyl)-4-hydroxy-N-(thiazol-2-yl)isoquinoline-6-sulfonamide and (4-fluoro-2-methoxyphenyl)boronic acid were used as the coupling partners. The final compound was purified via column chromatography (12 g silica gel column, gradient elution 0 to 10% MeOH:DCM) to afford 1-(4-fluoro-2-methoxyphenyl)-4-hydroxy-N-(thiazol-2-yl)isoquinoline-6-sulfonamide 2,2,2-trifluoroacetate as a yellow solid. $^1$H NMR (400 MHz, DMSO-d$_6$) δ ppm=12.89 (br. s., 1H), 10.99 (br. s., 1H), 8.63 (d, J=1.7 Hz, 1H), 8.21 (s, 1H), 7.84 (dd, J=1.8, 8.9 Hz, 1H), 7.62 (d, J=8.9 Hz, 1H), 7.35-7.25 (m, 2H), 7.10 (dd, J=2.3, 11.5 Hz, 1H), 6.92 (dt, J=2.3, 8.4 Hz, 1H), 6.86 (d, J=4.6 Hz, 1H), 3.65 (s, 3H). m/z (ESI) 432.2 (M+H)$^+$.

EXAMPLE 234

4-HYDROXY-1-(2-METHOXYPHENYL)-N-(THIAZOL-2-YL)ISOQUINOLINE-6-SULFONAMIDE 2,2,2-TRIFLUOROACETATE

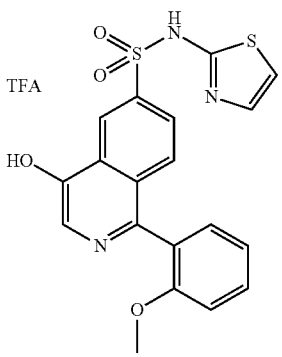 [SMILES: COc1ccccc1-c1ncc(O)c2cc(S(=O)(=O)Nc3nccs3)ccc12]

Example 234 was synthesized in a similar manner to Example 228, except that 1-chloro-N-(2,4-dimethoxybenzyl)-4-hydroxy-N-(thiazol-2-yl)isoquinoline-6-sulfonamide and 2-methoxyphenylboronic acid were used as the coupling partners. The final compound was purified via column chromatography (12 g silica gel column, gradient elution 0 to 10% MeOH:DCM) to afford 4-hydroxy-1-(2-methoxyphenyl)-N-(thiazol-2-yl)isoquinoline-6-sulfonamide 2,2,2-trifluoroacetate as a light yellow solid. $^1$H NMR (400 MHz, DMSO-d$_6$) δ ppm=12.89 (br. s., 1H), 11.03 (br. s., 1H), 8.64 (d, J=1.7 Hz, 1H), 8.21 (s, 1H), 7.85 (dd, J=1.8, 8.9 Hz, 1H), 7.63 (d, J=8.8 Hz, 1H), 7.55-7.46 (m, 1H), 7.35-7.24 (m, 2H), 7.19 (d, J=8.0 Hz, 1H), 7.14-7.06 (m, 1H), 6.86 (d, J=4.5 Hz, 1H), 3.64 (s, 3H). m/z (ESI) 414.2 (M+H)$^+$.

EXAMPLE 235

1-(2-BROMO-4-(TRIFLUOROMETHYL)PHENYL)-N-(THIAZOL-2-YL)ISOQUINOLINE-6-SULFONAMIDE

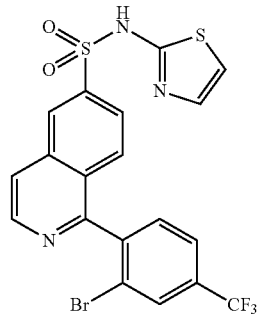 [SMILES: O=S(=O)(Nc1nccs1)c1ccc2c(-c3ccc(C(F)(F)F)cc3Br)nccc2c1]

1-(2-bromo-4-(trifluoromethyl)phenyl)-N-(2,4-dimethoxybenzyl)-N-(thiazol-2-yl)isoquinoline-6-sulfonamide (see Example 70, step 3; 0.100 g, 0.150 mmol) was dissolved in DCM (1 mL). TFA (0.1 mL, 1.298 mmol) was added and the reaction was stirred for 30 minutes. The reaction was concentrated and the material was purified via silica gel column chromatography (12 g, gradient elution 0 to 10% MeOH:DCM) to afford 1-(2-bromo-4-(trifluoromethyl)phenyl)-N-(thiazol-2-yl)isoquinoline-6-sulfonamide as a yellow solid. $^1$H NMR (400 MHz, DMSO-d$_6$) δ ppm=12.92 (br. s., 1H), 8.74 (d, J=5.8 Hz, 1H), 8.62 (d, J=1.4 Hz, 1H), 8.31-8.18 (m, 2H), 7.97 (d, J=7.9 Hz, 1H), 7.91 (dd, J=1.7, 8.9 Hz, 1H), 7.76 (d, J=7.9 Hz, 1H), 7.65 (d, J=8.8 Hz, 1H), 7.29 (d, J=4.3 Hz, 1H), 6.88 (d, J=4.5 Hz, 1H). m/z (ESI) 514.0 (M+H)$^+$.

EXAMPLE 236

1-(2-PHENYLPYRROLIDIN-1-YL)-N-(1,2,4-THIADIAZOL-5-YL)ISOQUINOLINE-6-SULFONAMIDE

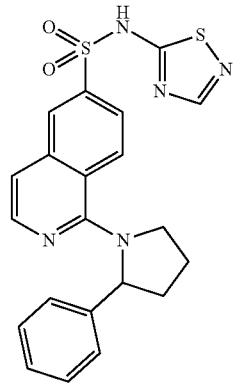 [SMILES: O=S(=O)(Nc1ncns1)c1ccc2c(N3CCCC3c3ccccc3)nccc2c1]

A vial was charged with 1-chloro-N-(2,4-dimethoxybenzyl)-N-(1,2,4-thiadiazol-5-yl)isoquinoline-6-sulfonamide (Intermediate X; 0.080 g, 0.168 mmol), bis(tri-t-butylphosphine)palladium(0) (8.57 mg, 0.017 mmol), and potassium phosphate (0.142 g, 0.671 mmol). Dioxane (1.677 ml) and 2-phenylpyrrolidine (0.074 ml, 0.503 mmol) were added and the reaction was stirred at 90° C. for three hours. The reaction was diluted with ethyl acetate and washed with water. The aqueous layer was extracted with ethyl acetate, and the combined organic layers were dried with sodium sulfate, filtered, and concentrated. The material was purified via column chromatography (12 g silica gel column, gradient elution 0 to 50% EtOAc:Heptane) to afford N-(2,4-dimethoxybenzyl)-1-(2-phenylpyrrolidin-1-yl)-N-(1,2,4-thiadiazol-5-yl)isoquinoline-6-sulfonamide as a clear oil. The material was dissolved in DCM (1 mL) and TFA (0.1 ml, 1.298 mmol) was added. The reaction was stirred for 30 minutes at room temperature. The reaction was concentrated, triturated in diethyl ether, and sonicated until a uniform, off-white solid crashed out of solution. The solid was filtered, washed with diethyl ether, collected, and vacuum dried overnight to afford 1-(2-phenylpyrrolidin-1-yl)-N-(1,2,4-thiadiazol-5-yl)isoquinoline-6-sulfonamide as an off-white solid. $^1$H NMR (400 MHz, DMSO-$d_6$) δ ppm=8.53 (d, J=9.0 Hz, 1H), 8.46 (s, 1H), 8.33 (s, 1H), 7.85 (d, J=6.1 Hz, 1H), 7.80 (d, J=7.4 Hz, 1H), 7.37 (d, J=7.4 Hz, 3H), 7.27 (t, J=7.4 Hz, 2H), 7.22-7.14 (m, 1H), 5.65-5.55 (m, 1H), 4.44-4.31 (m, 1H), 3.92 (br. s., 1H), 2.02 (br. s., 2H), 1.99-1.83 (m, 2H). m/z (ESI) 438.2 (M+H)$^+$.

EXAMPLE 237

1-(2-PHENYLPYRROLIDIN-1-YL)-N-(THIAZOL-2-YL)ISOQUINOLINE-6-SULFONAMIDE

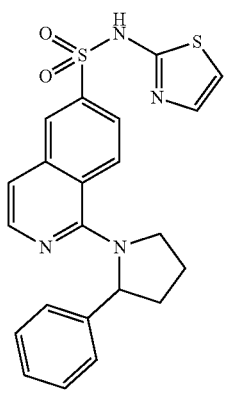 [SMILES: O=S(=O)(Nc1nccs1)c1ccc2c(N3CCCC3c3ccccc3)nccc2c1]

Example 237 was synthesized in a similar manner to Example 236, except that 1-chloro-N-(2,4-dimethoxybenzyl)-N-(thiazol-2-yl)isoquinoline-6-sulfonamide (Intermediate OOO) was used instead of 1-chloro-N-(2,4-dimethoxybenzyl)-N-(1,2,4-thiadiazol-5-yl)isoquinoline-6-sulfonamide (Intermediate X). Isolated 1-(2-cyano-4-(trifluoromethyl)phenyl)-N-(2,4-dimethoxybenzyl)-N-(thiazol-2-yl)isoquinoline-6-sulfonamide as an off-white solid. $^1$H NMR (400 MHz, DMSO-$d_6$) δ ppm=12.87 (br. s., 1H), 8.51 (br. s., 1H), 8.29 (br. s., 1H), 7.84 (br. s., 1H), 7.78 (d, J=9.1 Hz, 1H), 7.36 (d, J=7.4 Hz, 3H), 7.32-7.22 (m, 2H), 7.18 (d, J=5.9 Hz, 1H), 6.87 (d, J=4.4 Hz, 1H), 5.59 (br. s., 1H), 4.36 (br. s., 1H), 3.92 (br. s., 1H), 2.02 (br. s., 2H), 1.90 (br. s., 2H). m/z (ESI) 437.2 (M+H)$^+$.

EXAMPLE 238

(R)-1-(2-phenylpyrrolidin-1-yl)-N-(thiazol-2-yl)isoquinoline-6-sulfonamide

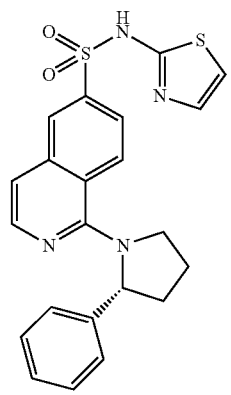 [SMILES: O=S(=O)(Nc1nccs1)c1ccc2c(N3CCC[C@@H]3c3ccccc3)nccc2c1]

1-(2-cyano-4-(trifluoromethyl)phenyl)-N-(2,4-dimethoxybenzyl)-N-(thiazol-2-yl)isoquinoline-6-sulfonamide (Example 267) was purified via SFC chiral chromatography (ChiralPak® AS-H, 2×15 cm column (Daicel Corporation, Osaka, Japan), 40% methanol with 0.2% diethylamine, 70 ml/min, 100 bar (10,000 kPA)) to afford (R)-1-(2-phenylpyrrolidin-1-yl)-N-(thiazol-2-yl)isoquinoline-6-sulfonamide as an off-white solid (stereochemistry randomly assigned). $^1$H NMR (400 MHz, DMSO-$d_6$) δ ppm=12.87 (br. s., 1H), 8.51 (br. s., 1H), 8.29 (br. s., 1H), 7.84 (br. s., 1H), 7.78 (d, J=9.1 Hz, 1H), 7.36 (d, J=7.4 Hz, 3H), 7.32-7.22 (m, 2H), 7.18 (d, J=5.9 Hz, 1H), 6.87 (d, J=4.4 Hz, 1H), 5.59 (br. s., 1H), 4.36 (br. s., 1H), 3.92 (br. s., 1H), 2.02 (br. s., 2H), 1.90 (br. s., 2H). m/z (ESI) 437.2 (M+H)$^+$.

EXAMPLE 239

(S)-1-(2-PHENYLPYRROLIDIN-1-YL)-N-(THIAZOL-2-YL)ISOQUINOLINE-6-SULFONAMIDE

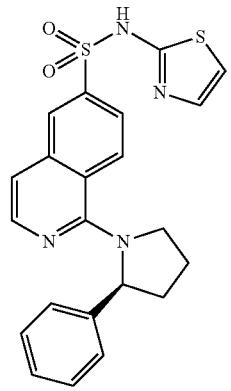 [SMILES: O=S(=O)(Nc1nccs1)c1ccc2c(N3CCC[C@H]3c3ccccc3)nccc2c1]

1-(2-Cyano-4-(trifluoromethyl)phenyl)-N-(2,4-dimethoxybenzyl)-N-(thiazol-2-yl)isoquinoline-6-sulfonamide (Example 267) was purified via SFC chiral chromatography (Chiralpak AS-H, 2×15 cm column, 40% methanol with 0.2% diethylamine, 70 ml/min, 100 bar (10,000 kPA)) to afford (S)-1-(2-phenylpyrrolidin-1-yl)-N-(thiazol-2-yl)isoquinoline-6-sulfonamide as an off-white solid (stereochemistry randomly assigned). $^1$H NMR (400 MHz, DMSO-d$_6$) δ ppm=12.87 (br. s., 1H), 8.51 (br. s., 1H), 8.29 (br. s., 1H), 7.84 (br. s., 1H), 7.78 (d, J=9.1 Hz, 1H), 7.36 (d, J=7.4 Hz, 3H), 7.32-7.22 (m, 2H), 7.18 (d, J=5.9 Hz, 1H), 6.87 (d, J=4.4 Hz, 1H), 5.59 (br. s., 1H), 4.36 (br. s., 1H), 3.92 (br. s., 1H), 2.02 (br. s., 2H), 1.90 (br. s., 2H). m/z (ESI) 437.2 (M+H)$^+$.

EXAMPLE 240

4-CYANO-1-(2-METHOXY-4-(TRIFLUOROMETHYL)PHENYL)-N-(THIAZOL-2-YL)ISOQUINOLINE-6-SULFONAMIDE

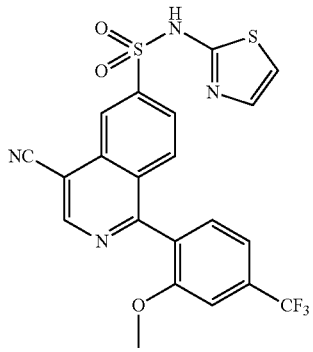

Example 240 was synthesized in a similar manner to Example 228, except that 1-chloro-4-cyano-N-(2,4-dimethoxybenzyl)-N-(thiazol-2-yl)isoquinoline-6-sulfonamide and (2-methoxy-4-(trifluoromethyl)phenyl)boronic acid were used as the coupling partners. The final compound was purified via column chromatography (12 g silica gel column, gradient elution 0 to 10% MeOH:EtOAc) to afford 4-cyano-1-(2-methoxy-4-(trifluoromethyl)phenyl)-N-(thiazol-2-yl)isoquinoline-6-sulfonamide as a yellow solid. $^1$H NMR (400 MHz, DMSO-d$_6$) δ ppm=13.07 (s, 1H), 9.29 (s, 1H), 8.52 (d, J=1.3 Hz, 1H), 8.06 (dd, J=1.8, 8.8 Hz, 1H), 7.92 (d, J=8.9 Hz, 1H), 7.65-7.60 (m, 1H), 7.56 (s, 1H), 7.55-7.52 (m, 1H), 7.32 (d, J=4.5 Hz, 1H), 6.93 (d, J=4.5 Hz, 1H), 3.76 (s, 3H). m/z (ESI) 491.1 (M+H)$^+$.

EXAMPLE 241

1-(4-CHLORO-2-METHOXYPHENYL)-4-CYANO-N-(2,4-DIMETHOXYBENZYL)-N-(THIAZOL-2-YL)ISOQUINOLINE-6-SULFONAMIDE

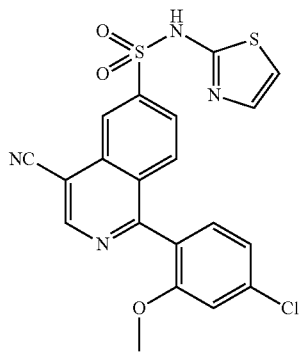 [SMILES: COc1cc(Cl)ccc1-c1ncc(C#N)c2cc(S(=O)(=O)Nc3nccs3)ccc12]

Example 241 was synthesized in a similar manner to Example 228, except that 1-chloro-4-cyano-N-(2,4-dimethoxybenzyl)-N-(thiazol-2-yl)isoquinoline-6-sulfonamide and (4-chloro-2-methoxyphenyl)boronic acid were used as the coupling partners. The final compound was purified via column chromatography (12 g silica gel column, gradient elution 25 to 100% EtOAc:Heptane) to afford 1-(4-chloro-2-methoxyphenyl)-4-cyano-N-(thiazol-2-yl)isoquinoline-6-sulfonamide as a light yellow solid. $^1$H NMR (400 MHz, DMSO-d$_6$) δ ppm=13.06 (s, 1H), 9.26 (s, 1H), 8.58-8.43 (m, 1H), 8.06 (dd, J=1.8, 8.9 Hz, 1H), 7.94 (dd, J=0.6, 8.9 Hz, 1H), 7.42 (d, J=8.1 Hz, 1H), 7.37 (d, J=1.9 Hz, 1H), 7.32 (d, J=4.6 Hz, 1H), 7.24 (dd, J=1.9, 8.1 Hz, 1H), 6.92 (d, J=4.6 Hz, 1H), 3.69 (s, 3H). m/z (ESI) 457.2 (M+H)$^+$.

EXAMPLE 242

4-CYANO-1-(2-METHOXY-4-(TRIFLUOROMETHYL)PHENYL)-N-(PYRIMIDIN-4-YL)ISOQUINOLINE-6-SULFONAMIDE

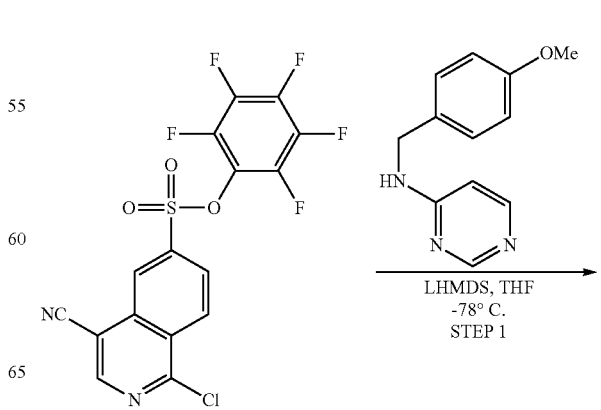

329
-continued

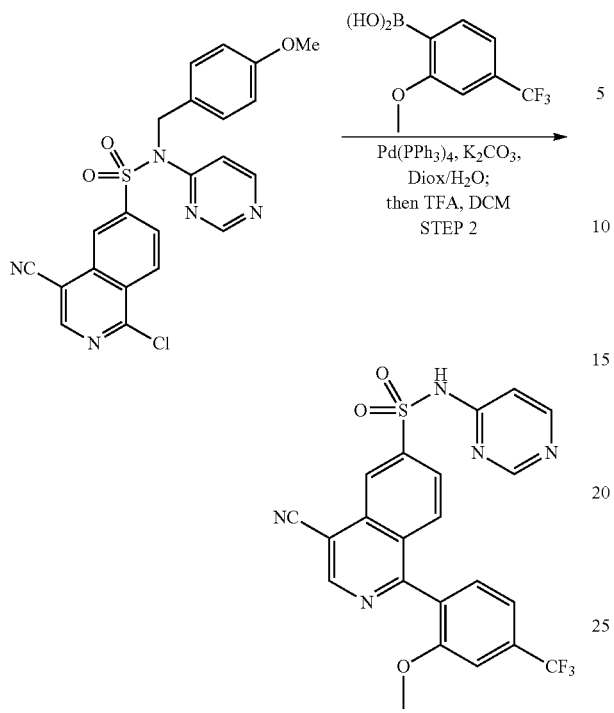

STEP 1: 1-CHLORO-4-CYANO-N-(4-METHOXY-BENZYL)-N-(PYRIMIDIN-4-YL)ISOQUINO-LINE-6-SULFONAMIDE

The title compound was prepared in an analogous manner to that of Intermediate YYY, except that N-(4-methoxybenzyl)pyrimidin-4-amine was used instead of N-(2,4-dimethoxybenzyl)thiazol-2-amine. The final compound was purified via column chromatography (40 g silica gel column, gradient elution 0 to 75% EtOAc:Heptane) to afford 1-chloro-4-fluoro-N-(4-methoxybenzyl)-N-(pyrimidin-4-yl)isoquinoline-6-sulfonamide as a white solid. m/z (ESI) 466.3 (M+H)$^+$.

STEP 2: 4-CYANO-1-(2-METHOXY-4-(TRIFLUO-ROMETHYL)PHENYL)-N-(PYRIMIDIN-4-YL)ISOQUINOLINE-6-SULFONAMIDE

The title compound was prepared in an analogous manner to that of Example 228, except that 1-chloro-4-cyano-N-(4-methoxybenzyl)-N-(pyrimidin-4-yl)isoquinoline-6-sulfonamide and (2-methoxy-4-(trifluoromethyl)phenyl)boronic acid were used as the coupling partners. The final compound was purified via column chromatography (12 g silica gel column, gradient elution 50 to 100% EtOAc:Heptane) to afford 4-cyano-1-(2-methoxy-4-(trifluoromethyl)phenyl)-N-(pyrimidin-4-yl)isoquinoline-6-sulfonamide as a white solid. $^1$H NMR (400 MHz, DMSO-d$_6$) δ ppm=9.30 (s, 1H), 8.68-

330

8.51 (m, 2H), 8.14 (d, J=9.6 Hz, 1H), 7.91 (d, J=8.7 Hz, 1H), 7.67-7.60 (m, 1H), 7.59-7.49 (m, 2H), 3.76 (s, 3H). m/z (ESI) 486.2 (M+H)$^+$.

EXAMPLE 243

1-(3-PHENYLPYRROLIDIN-1-YL)-N-(THIAZOL-2-YL)ISOQUINOLINE-6-SULFONAMIDE

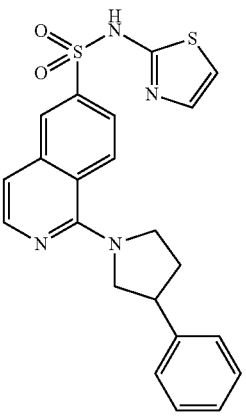 [SMILES: O=S(=O)(Nc1nccs1)c1ccc2c(N3CCC(c4ccccc4)C3)nccc2c1]

1-Chloro-N-(thiazol-2-yl)isoquinoline-6-sulfonamide (from Example 73, step 2; 0.050 g, 0.153 mmol) and potassium carbonate (0.106 g, 0.767 mmol) were dissolved in DMF (1.023 ml). 3-Phenyl-pyrrolidine (0.032 ml, 0.230 mmol) was added and the reaction was stirred overnight at 110° C. The reaction was filtered through a syringe filter and purified via HPLC (25 to 70% MeCN:H$_2$O with 0.1% TFA modifier). The product fractions were combined and concentrated. The material was dissolved in methanol and passed through an SCX ion exchange column (pre-wetted with methanol). The column was flushed with methanol, then the product was liberated by flushing the column with 2 M ammonia in methanol. The filtrate was combined to afford 1-(3-phenylpyrrolidin-1-yl)-N-(thiazol-2-yl)isoquinoline-6-sulfonamide as a light yellow solid. $^1$H NMR (400 MHz, DMSO-d$_6$) δ ppm=8.34 (d, J=8.9 Hz, 1H), 8.16 (d, J=1.9 Hz, 1H), 8.00 (d, J=5.6 Hz, 1H), 7.71 (dd, J=1.9, 8.9 Hz, 1H), 7.40-7.31 (m, 4H), 7.28-7.22 (m, 1H), 7.19 (d, J=5.6 Hz, 1H), 7.11 (d, J=4.2 Hz, 1H), 6.67 (d, J=4.3 Hz, 1H), 4.12-3.97 (m, 2H), 3.94-3.77 (m, 2H), 3.55-3.42 (m, 1H), 2.42-2.27 (m, 1H), 2.19-2.04 (m, 1H). m/z (ESI) 437.2 (M+H)⁺.

EXAMPLE 244

1-(1-METHYL-1H-PYRROL-2-YL)-N-(THIAZOL-2-YL)ISOQUINOLINE-6-SULFONAMIDE

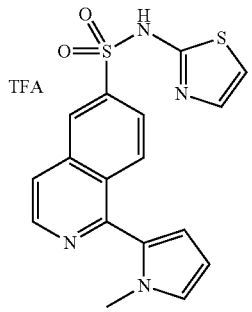 [SMILES: Cn1cccc1-c1nccc2cc(S(=O)(=O)Nc3nccs3)ccc12]

A microwave vial was charged with 1-chloro-N-(2,4-dimethoxybenzyl)-N-(thiazol-2-yl)isoquinoline-6-sulfonamide (Intermediate OOO; 0.050 g, 0.105 mmol), Pd(Ph₃P)₄ (0.012 g, 10.50 µmol), and DMF (0.525 ml). 1-Methyl-2-(tributylstannyl)-1H-pyrrole (0.078 ml, 0.210 mmol) was added and the reaction was heated in a microwave reactor at 90° C. for 30 minutes. The reaction was diluted with ethyl acetate and washed with water. The aqueous layer was extracted with ethyl acetate, and the combined organic layers were dried with sodium sulfate, filtered, and concentrated. The material was purified via silica gel column chromatography (12 g, gradient elution 0 to 100% EtOAc:Heptane with a 10% MeOH/DCM flush) to afford N-(2,4-dimethoxybenzyl)-1-(1-methyl-1H-imidazol-2-yl)-N-(thiazol-2-yl)iso-quinoline-6-sulfonamide as an off-white solid. m/z (ESI) 522.2 (M+H)⁺. The material was dissolved in DCM and TFA (8.09 µl, 0.105 mmol) was added. The reaction was stirred for 30 minutes at room temperature. The reaction was concentrated, triturated with diethyl ether, and filtered. The solids were washed with diethyl ether and the filtrate was concentrated and purified via column chromatography (12 g silica gel column, gradient elution 0 to 10% MeOH:EtOAc) to afford 1-(1-methyl-1H-pyrrol-2-yl)-N-(thiazol-2-yl)isoquinoline-6-sulfonamide as a yellow solid. ¹H NMR (400 MHz, DMSO-d₆) δ ppm=12.93 (br. s., 1H), 9.12 (s, 1H), 8.81 (d, J=5.7 Hz, 1H), 8.64 (s, 1H), 8.34 (d, J=9.0 Hz, 1H), 8.26 (d, J=5.6 Hz, 1H), 8.10 (s, 1H), 8.00 (dd, J=1.9, 8.9 Hz, 1H), 7.30 (d, J=4.5 Hz, 1H), 6.89 (d, J=4.5 Hz, 1H), 3.88 (s, 3H). m/z (ESI) 371.1 (M+H)⁺.

EXAMPLE 245

1-(1-(TETRAHYDRO-2H-PYRAN-4-YL)PYRROLIDIN-2-YL)-N-(THIAZOL-2-YL)ISOQUINOLINE-6-SULFONAMIDE 2,2,2-TRIFLUOROACETATE

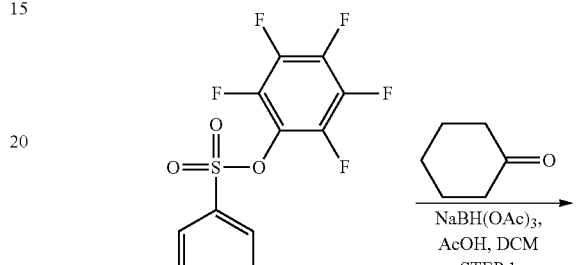

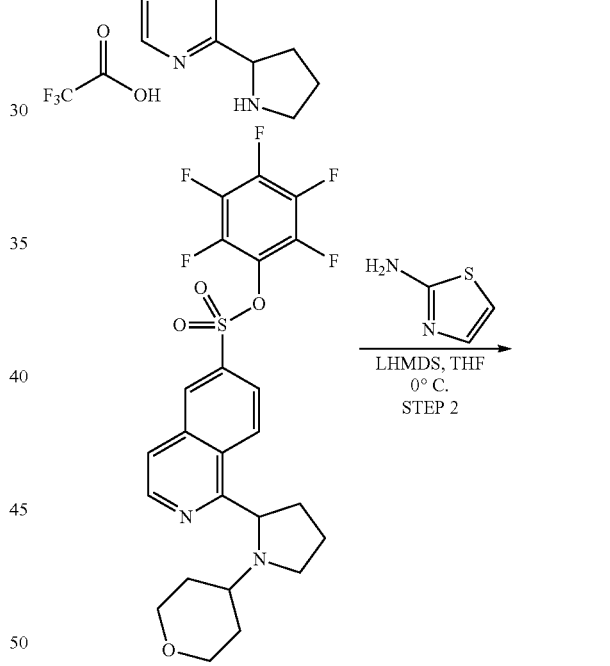

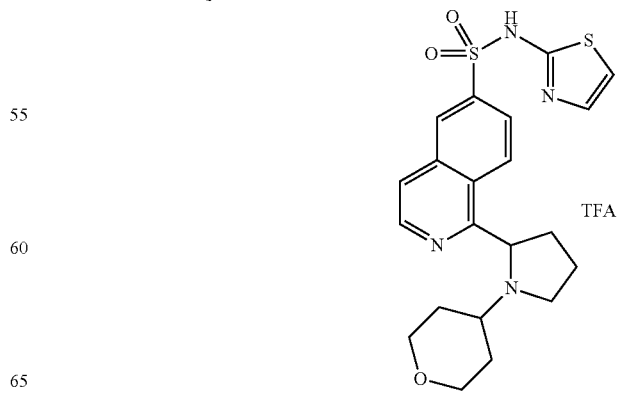

STEP 1: PERFLUOROPHENYL 1-(1-(TETRAHYDRO-2H-PYRAN-4-YL)PYRROLIDIN-2-YL)ISOQUINOLINE-6-SULFONATE

Perfluorophenyl 1-(pyrrolidin-2-yl)isoquinoline-6-sulfonate 2,2,2-trifluoroacetate (Intermediate ZZZ; 0.100 g, 0.179 mmol) and tetrahydro-4h-pyran-4-one (0.025 ml, 0.269 mmol) were dissolved in DCM (1.791 ml). Sodium triacetoxyborohydride (0.114 g, 0.537 mmol) and acetic acid (0.015 ml, 0.269 mmol) were added and the reaction was stirred for one hour at room temperature. Water was added followed by ethyl acetate. The aqueous layer was extracted with ethyl acetate, and the combined organic layers were washed with brine, dried with sodium sulfate, filtered, and concentrated to afford perfluorophenyl 1-(1-(tetrahydro-2H-pyran-4-yl)pyrrolidin-2-yl)isoquinoline-6-sulfonate as an oily blue solid. m/z (ESI) 529.3 (M+H)$^+$.

STEP 2: 1-(1-(TETRAHYDRO-2H-PYRAN-4-YL)PYRROLIDIN-2-YL)-N-(THIAZOL-2-YL)ISOQUINOLINE-6-SULFONAMIDE 2,2,2-TRIFLUOROACETATE

A vial was charged with perfluorophenyl 1-(1-(tetrahydro-2H-pyran-4-yl)pyrrolidin-2-yl)isoquinoline-6-sulfonate (0.063 g, 0.119 mmol), thiazol-2-amine (0.012 g, 0.119 mmol), and THF (0.596 ml) to give a clear, colorless solution. The vial was cooled in an ice-water bath for 15 min, then lithium bis(trimethylsilyl)amide (1M in THF) (0.358 ml, 0.358 mmol) was added drop wise. The reaction was stirred for 30 minutes. The reaction was quenched with saturated ammonium chloride solution and concentrated. The resulting solid was diluted in DMSO and filtered through a syringe filter. The material was purified via HPLC (5 to 50% MeCN:H$_2$O with 1% TFA modifier). The product fractions were combined, concentrated to a minimal volume of water, and frozen in a dry ice/acetone bath. The solid was lyophilized overnight to afford 1-(1-(tetrahydro-2H-pyran-4-yl)pyrrolidin-2-yl)-N-(thiazol-2-yl)isoquinoline-6-sulfonamide 2,2,2-trifluoroacetate as a white solid. NMR confirmed TFA salt. $^1$H NMR (400 MHz, DMSO-d$_6$) δ ppm=12.92 (br. s., 1H), 10.02 (br. s., 1H), 8.65 (d, J=5.8 Hz, 1H), 8.63 (d, J=1.8 Hz, 1H), 8.46 (d, J=8.8 Hz, 1H), 8.23 (d, J=5.7 Hz, 1H), 8.06 (dd, J=1.9, 8.9 Hz, 1H), 7.30 (d, J=4.6 Hz, 1H), 6.90 (d, J=4.6 Hz, 1H), 5.86 (d, J=6.2 Hz, 1H), 3.95-3.74 (m, 4H), 3.60 (br. s., 2H), 3.53-3.40 (m, J=8.0 Hz, 1H), 3.30-3.10 (m, 2H), 2.85-2.70 (m, 1H), 2.20-2.06 (m, 1H), 2.00-1.84 (m, 3H), 1.77 (dq, J=4.7, 12.1 Hz, 1H), 1.66 (d, J=11.2 Hz, 1H), 1.50 (dq, J=4.2, 12.0 Hz, 1H). m/z (ESI) 445.2 (M+H)$^+$.

EXAMPLE 246

1-(1-(2-METHOXYETHYL)PYRROLIDIN-2-YL)-N-(THIAZOL-2-YL)ISOQUINOLINE-6-SULFONAMIDE

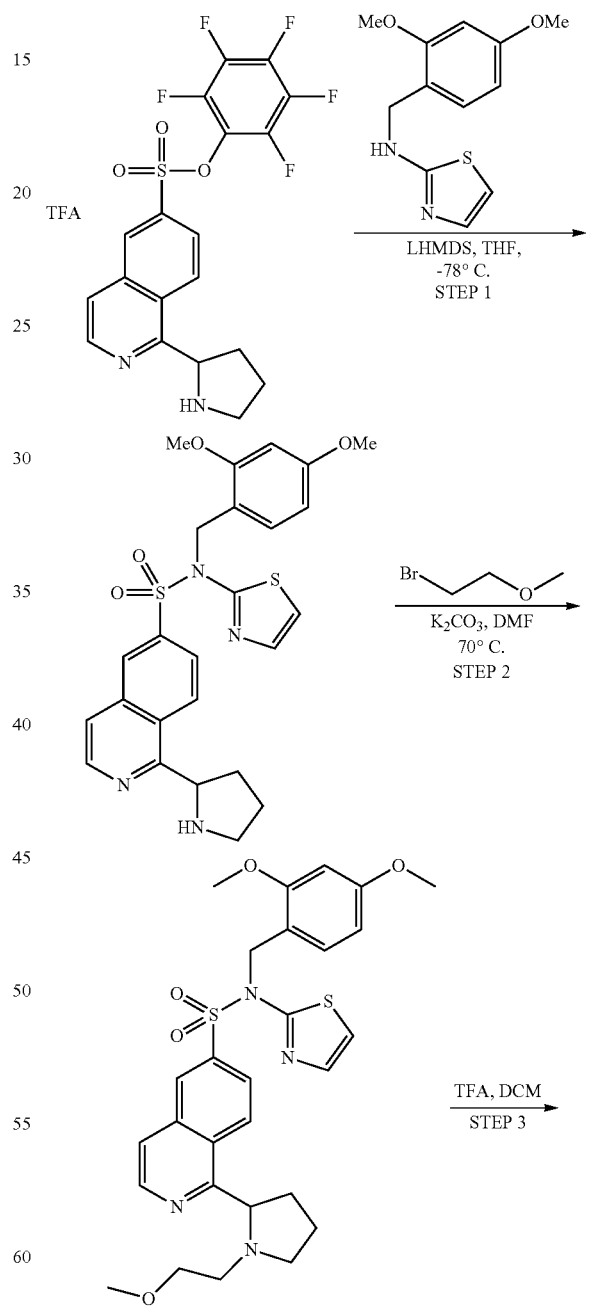

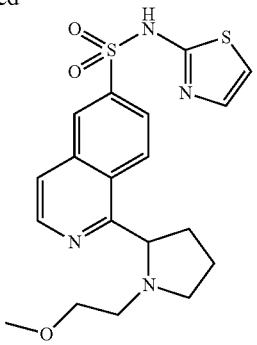

STEP 1: N-(2,4-DIMETHOXYBENZYL)-1-(PYR-ROLIDIN-2-YL)-N-(THIAZOL-2-YL)ISOQUINO-LINE-6-SULFONAMIDE

A solution of perfluorophenyl 1-(pyrrolidin-2-yl)isoquinoline-6-sulfonate 2,2,2-trifluoroacetate (Intermediate ZZZ; 0.350 g, 0.627 mmol) and N-(2,4-dimethoxybenzyl)thiazol-2-amine (0.173 g, 0.689 mmol) in tetrahydrofuran (6.27 ml) was cooled in a dry ice-acetone bath for 10 min. Lithium bis(trimethylsilyl)amide (1M in THF) (1.316 ml, 1.316 mmol) was added drop wise, then the reaction was stirred for 5 minutes. The cooling bath was removed and the reaction was stirred for 30 minutes. The reaction was warmed to room temperature and quenched with saturated ammonium chloride solution (aq), diluted with ethyl acetate and washed with water. The aqueous layer was extracted with ethyl acetate, and the combined organic layers were dried with sodium sulfate, filtered, and concentrated. The filtrate was purified by chromatography on an 80-g silica gel column with 0-100% EtOAc/Heptane followed by a 20% 2.0M ammonia in MeOH/DCM flush to afford N-(2,4-dimethoxybenzyl)-1-(pyrrolidin-2-yl)-N-(thiazol-2-yl)isoquinoline-6-sulfonamide as a light yellow solid. m/z (ESI) 511.3 (M+H)$^+$.

STEP 2: N-(2,4-DIMETHOXYBENZYL)-1-(1-(2-METHOXYETHYL)PYRROLIDIN-2-YL)-N-(THIAZOL-2-YL)ISOQUINOLINE-6-SULFONAMIDE

N-(2,4-dimethoxybenzyl)-1-(pyrrolidin-2-yl)-N-(thiazol-2-yl)isoquinoline-6-sulfonamide (0.050 g, 0.080 mmol) and potassium carbonate (0.055 g, 0.400 mmol) were dissolved in DMF (0.800 ml). 2-Bromoethyl methyl ether (9.03 μl, 0.096 mmol) was added and the reaction was stirred for three hours at 70° C. Water was added followed by ethyl acetate. The aqueous layer was extracted with ethyl acetate, and the combined organic layers dried with sodium sulfate, filtered, and concentrated. The material was purified via silica gel column chromatography (12 g, gradient elution 0 to 20% MeOH: EtOAc with 5% triethylamine modifier) to afford N-(2,4-dimethoxybenzyl)-1-(1-(2-methoxyethyl)pyrrolidin-2-yl)-N-(thiazol-2-yl)isoquinoline-6-sulfonamide as an off white solid. m/z (ESI) 569.3 (M+H)$^+$.

STEP 3: 1-(1-(2-METHOXYETHYL)PYRROLIDIN-2-YL)-N-(THIAZOL-2-YL)ISOQUINOLINE-6-SULFONAMIDE

N-(2,4-dimethoxybenzyl)-1-(1-(2-methoxyethyl)pyrrolidin-2-yl)-N-(thiazol-2-yl)isoquinoline-6-sulfonamide (0.046 g, 0.080 mmol) was dissolved in DCM and TFA (0.1 ml, 1.298 mmol) was added. The reaction was stirred for 30 minutes at room temperature. The reaction was concentrated, dissolved in methanol, and passed through an SCX ion exchange column (pre-wetted with methanol). The column was washed twice with methanol, then the product was liberated by flushing the column several times with a 2.0M ammonia/methanol solution. The product-containing solution was concentrated to afford 1-(1-(2-methoxyethyl)pyrrolidin-2-yl)-N-(thiazol-2-yl)isoquinoline-6-sulfonamide as a light yellow solid. $^1$H NMR (500 MHz, DMSO-d$_6$) δ ppm=8.79 (br. s., 1H), 8.53 (d, J=5.7 Hz, 1H), 8.46 (s, 1H), 8.00 (d, J=5.9 Hz, 1H), 7.93 (d, J=9.0 Hz, 1H), 7.17 (d, J=4.2 Hz, 1H), 6.74 (d, J=4.3 Hz, 1H), 4.60 (br. s., 1H), 3.55 (br. s., 2H), 2.96 (s, 3H), 2.82 (br. s., 1H), 2.71 (br. s., 2H), 2.42 (br. s., 1H), 2.00 (d, J=11.6 Hz, 2H), 1.95 (d, J=12.8 Hz, 1H). m/z (ESI) 419.1 (M+H)$^+$.

EXAMPLE 247

1-(4-(3,4-DICHLOROPHENYL)PIPERAZIN-1-YL)-N-(THIAZOL-2-YL)ISOQUINOLINE-6-SULFONAMIDE

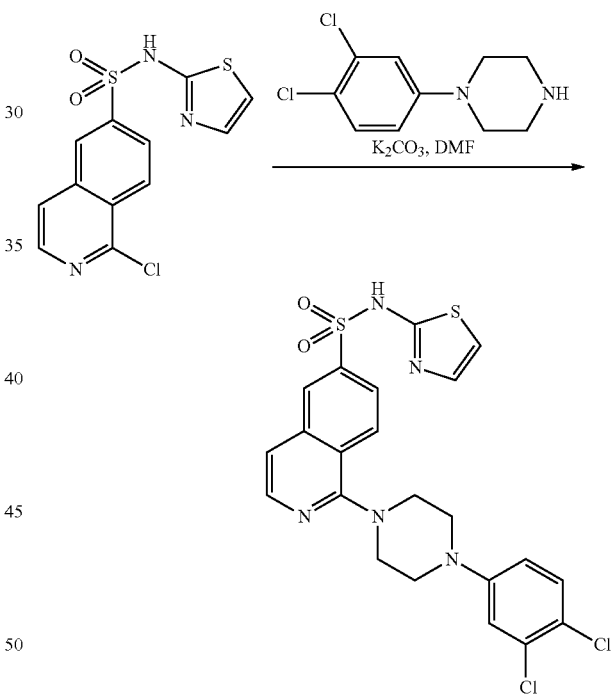

1-Chloro-N-(thiazol-2-yl)isoquinoline-6-sulfonamide (from Example 73, step 2; 0.050 g, 0.153 mmol) and potassium carbonate (0.106 g, 0.767 mmol) were dissolved in DMF (1.023 ml). 1-(3,4-dichlorophenyl)piperazine (0.071 g, 0.307 mmol) was added and the reaction was stirred overnight at 120° C. The reaction was filtered through a syringe filter and purified via HPLC (Phenominex C$_{18}$ column, 150×30 mm, 5 micron; gradient elution 25 to 70% MeCN:H$_2$O with 0.1% TFA modifier). The product fractions were concentrated and passed through a SCX ion exchange column (pre-wetted with methanol). The column was flushed several times with methanol, then the product was liberated by flushing the column several times with 2.0 M ammonia in methanol. The product-containing filtrate was concentrated to afford 1-(4-

(3,4-dichlorophenyl)piperazin-1-yl)-N-(thiazol-2-yl)isoquinoline-6-sulfonamide as a light yellow solid. $^1$H NMR (400 MHz, DMSO-d$_6$) δ ppm=8.40 (d, J=1.8 Hz, 1H), 8.28 (d, J=8.9 Hz, 1H), 8.23 (d, J=5.7 Hz, 1H), 7.88 (dd, J=1.9, 8.8 Hz, 1H), 7.63 (d, J=5.8 Hz, 1H), 7.44 (d, J=9.0 Hz, 1H), 7.28 (d, J=4.6 Hz, 1H), 7.22 (d, J=2.9 Hz, 1H), 7.02 (dd, J=2.8, 9.1 Hz, 1H), 6.87 (d, J=4.6 Hz, 1H), 3.46 (s, 8H). m/z (ESI) 521.1 (M+H)$^+$.

EXAMPLE 248

(E/Z)-1-(2-METHOXY-4-(TRIFLUOROMETHYL)PHENYL)-N-(4-OXOTHIAZOLIDIN-2-YLIDENE)ISOQUINOLINE-6-SULFONAMIDE

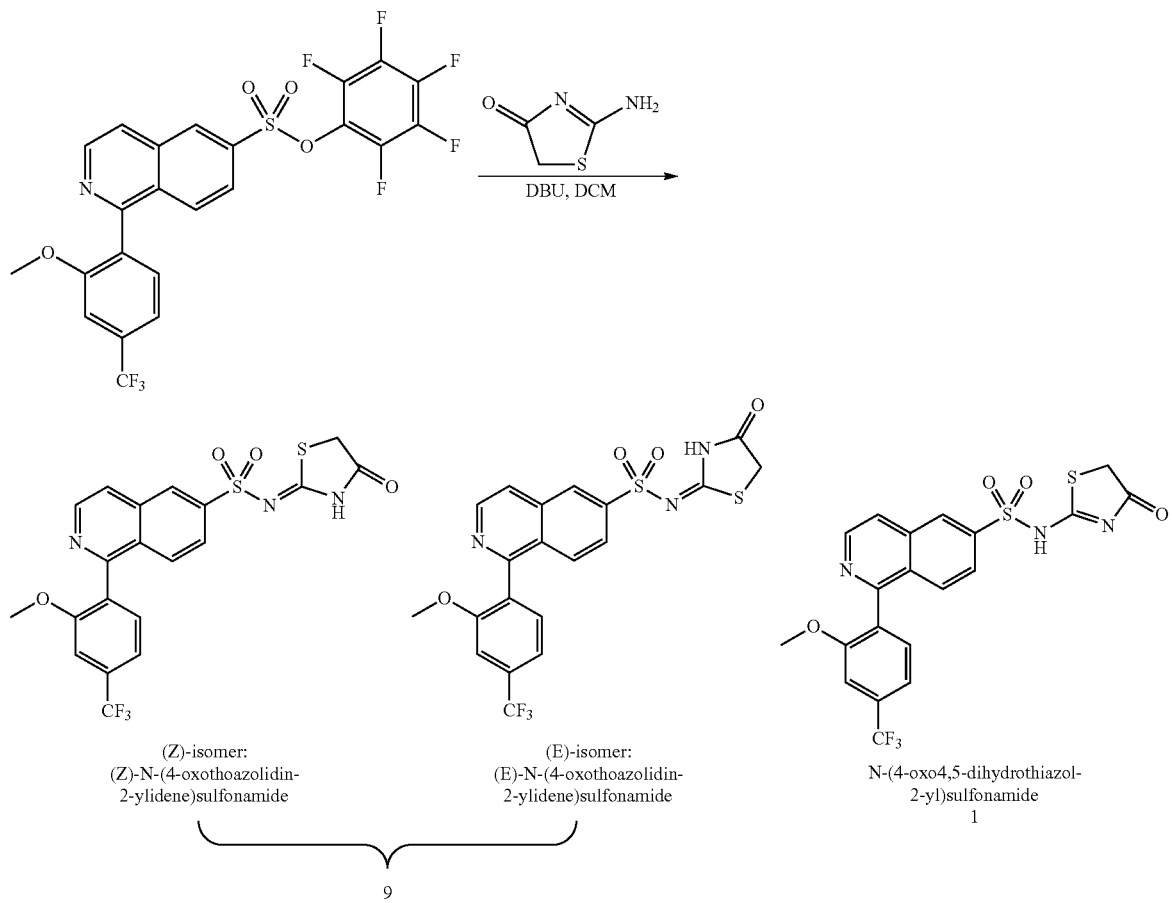

Under an argon atmosphere, a round-bottom flask was charged with pseudothiohydantoin (0.262 g, 2.26 mmol), perfluorophenyl 1-(2-methoxy-4-(trifluoromethyl)phenyl) isoquinoline-6-sulfonate (INTERMEDIATE LLL, 0.62 g, 1.13 mmol), and DCM (11.3 mL) to give a white suspension. Then DBU (0.51 mL, 3.39 mmol) was added drop wise. After 40 min, the reaction was concentrated. The crude material was absorbed onto a plug of silica gel and purified by chromatography through a silica gel column (80 g), eluting with a gradient of 0% to 100% 1M NH$_3$.MeOH in CH$_2$CL$_2$, to provide (E/Z)-1-(2-methoxy-4-(trifluoromethyl)phenyl)-N-(4-oxothiazolidin-2-ylidene)isoquinoline-6-sulfonamide (0.49 g, 90% yield) as a light-yellow solid. $^1$H NMR (400 MHz, DMSO-d$_6$) δ ppm 3.75 (s, 3H), 3.96 (br s, 2H), 7.51-7.61 (m, 3H), 7.74 (d, J=9.0 Hz, 1H), 7.91 (dd, J=9.1, 1.9, 1H), 8.17 (d, J=5.77 Hz, 1H), 8.63 (s, 1H), 8.73 (d, J=5.67 Hz, 1H), 12.6 (br s, 1H). m/z (ESI) 482.0 (M+H)$^+$. NMR analyses via $^{15}$N—H cross-peak confirmed 9:1 of the (E/Z)-1-(2-methoxy-4-(trifluoromethyl)phenyl)-N-(4-oxothiazolidin-2-ylidene)isoquinoline-6-sulfonamide: 1-(2-methoxy-4-(trifluoromethyl)phenyl)-N-(4-oxo-4,5-dihydrothiazol-2-yl)

isoquinoline-6-sulfonamide. The (E/Z) ratio mixture of isomer could not be determined.

EXAMPLE 249

1-(4-CHLORO-2-METHOXYPHENYL)-N-(THIAZOL-2-YL)PHTHALAZINE-6-SULFONAMIDE

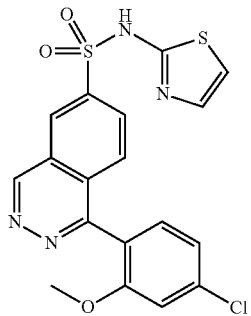 [SMILES: COc1cc(Cl)ccc1-c1nncc2cc(S(=O)(=O)Nc3nccs3)ccc12]

A vial was charged with 1-chloro-N-(2,4-dimethoxybenzyl)-N-(thiazol-2-yl)phthalazine-6-sulfonamide (Intermediate AAAA) (56.22 mg, 0.118 mmol), (4-chloro-2-methoxyphenyl)boronic acid (Combi-Blocks, San Diego, Calif., 26.4 mg, 0.141 mmol), Pd(AmPhos)$_2$Cl$_2$ (4.17 mg, 5.89 μmol), potassium phosphate (75 mg, 0.354 mmol), 1,4-dioxane (442 μl), and water (147 μl). The vial was flushed with Ar (g), then sealed and heated in a microwave reactor for 30 min h at 90° C. LC/MS showed fairly clean protected product. The mixture was extracted with EtOAc (3×), and the combined organic extracts were concentrated. The residue was dissolved in DCM (1 mL) and TFA (0.5 mL). After 2 h, the mixture was diluted with MeOH and filtered through diatomaceous earth with the aid of MeOH. The filtrate was concentrated, and the crude product was purified by chromatography on silica gel (12-g column, 0 to 6% MeOH/DCM) to give 1-(4-chloro-2-methoxyphenyl)-N-(thiazol-2-yl)phthalazine-6-sulfonamide (26.3 mg, 0.061 mmol, 51.5% yield) as a yellow solid: $^1$H NMR (400 MHz, DMSO-d$_6$) δ ppm=12.97 (br. s., 1H), 9.92 (s, 1H), 8.73 (d, J=1.8 Hz, 1H), 8.22 (dd, J=1.9, 8.7 Hz, 1H), 7.77 (d, J=8.7 Hz, 1H), 7.46 (d, J=8.1 Hz, 1H), 7.37 (d, J=1.9 Hz, 1H), 7.32-7.22 (m, 2H), 6.91 (d, J=4.6 Hz, 1H), 3.70 (s, 3H); m/z (ESI) 433.2 (M+H)$^+$.

EXAMPLE 250

1-(4-FLUORO-2-METHOXYPHENYL)-N-(THIAZOL-2-YL)PHTHALAZINE-6-SULFONAMIDE

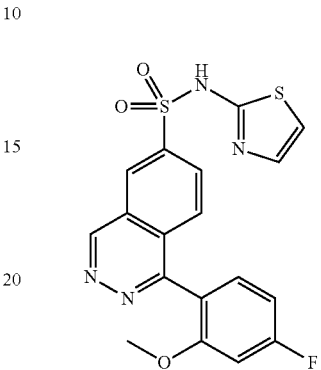

Example 250 was synthesized in a similar manner to Example 249, except that (4-fluoro-2-methoxyphenyl)boronic acid (Sigma-Aldrich, St. Louis, Mo.) was used in place of (4-chloro-2-methoxyphenyl)boronic acid. The desired product, 1-(4-fluoro-2-methoxyphenyl)-N-(thiazol-2-yl)phthalazine-6-sulfonamide, was isolated as light-orange solid: $^1$H NMR (400 MHz, DMSO-d$_6$) δ ppm=12.98 (br. s., 1H), 9.91 (s, 1H), 8.73 (d, J=1.7 Hz, 1H), 8.26-8.19 (m, 1H), 7.76 (d, J=8.7 Hz, 1H), 7.47 (dd, J=6.8, 8.4 Hz, 1H), 7.31 (s, 1H), 7.20 (dd, J=2.3, 11.4 Hz, 1H), 7.01 (dt, J=2.3, 8.4 Hz, 1H), 6.91 (d, J=4.5 Hz, 1H), 3.69 (s, 3H); m/z (ESI) 417.2 (M+H)$^+$.

EXAMPLE 251

1-(4-CYANO-2-METHOXYPHENYL)-N-(THIAZOL-2-YL)PHTHALAZINE-6-SULFONAMIDE

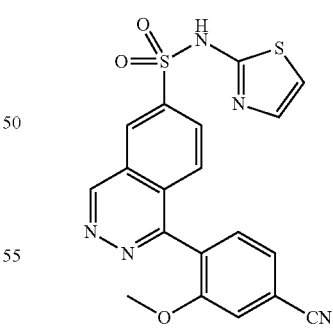

Example 251 was synthesized in a similar manner to Example 249, except that (4-cyano-2-methoxyphenyl)boronic acid (Combi-Blocks, San Diego, Calif.) was used in place of (4-chloro-2-methoxyphenyl)boronic acid. The desired product, 1-(4-cyano-2-methoxyphenyl)-N-(thiazol-2-yl)phthalazine-6-sulfonamide, was isolated as yellow solid: $^1$H NMR (400 MHz, DMSO-d$_6$) δ ppm=12.97 (br. s., 1H), 9.96 (s, 1H), 8.75 (s, 1H), 8.25-8.18 (m, 1H), 7.79 (s, 1H), 7.73 (d, J=8.7 Hz, 1H), 7.68-7.60 (m, 2H), 7.30 (dd, J=4.6, 5.9 Hz, 1H), 3.74 (s, 3H); m/z (ESI) 424.2 (M+H)+.

EXAMPLE 252

1-(2-METHOXYPHENYL)-N-(THIAZOL-2-YL)PHTHALAZINE-6-SULFONAMIDE

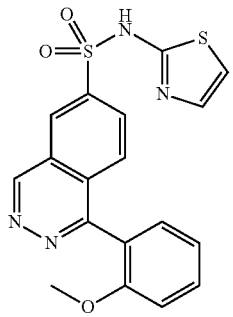 [SMILES: COc1ccccc1-c1nncc2cc(S(=O)(=O)Nc3nccs3)ccc12]

Example 252 was synthesized in a similar manner to Example 249, except that (2-methoxyphenyl)boronic acid (Sigma-Aldrich, St. Louis, Mo.) was used in place of (4-chloro-2-methoxyphenyl)boronic acid. The desired product, 1-(2-methoxyphenyl)-N-(thiazol-2-yl)phthalazine-6-sulfonamide, was isolated as yellow solid: $^1$H NMR (400 MHz, DMSO-$d_6$) δ ppm=12.98 (br. s., 1H), 9.92 (s, 1H), 8.73 (d, J=1.6 Hz, 1H), 8.22 (dd, J=1.8, 8.7 Hz, 1H), 7.74 (d, J=8.7 Hz, 1H), 7.66-7.54 (m, 1H), 7.47-7.39 (m, 1H), 7.36-7.24 (m, 2H), 7.17 (t, J=7.3 Hz, 1H), 6.91 (d, J=4.6 Hz, 1H), 3.67 (s, 3H); m/z (ESI) 399.2 (M+H)+.

EXAMPLE 253

1-(2-METHOXY-4-(TRIFLUOROMETHYL)PHENYL)-N-(THIAZOL-2-YL)PHTHALAZINE-6-SULFONAMIDE

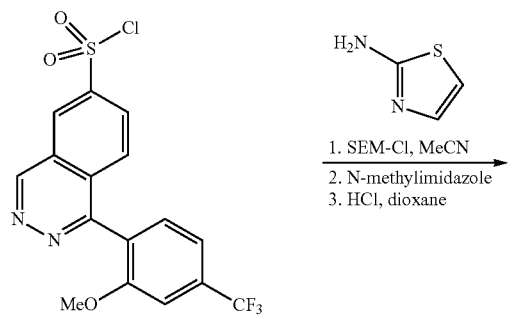

1. SEM-Cl, MeCN
2. N-methylimidazole
3. HCl, dioxane

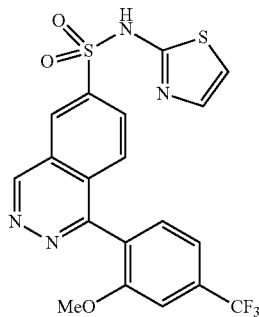

A solution of thiazol-2-amine (0.027 g, 0.273 mmol) in 3 mL of MeCN was treated with SEM-Cl (0.048 ml, 0.273 mmol), and the reaction mixture was allowed to stir for one hour. LC/MS showed mostly product, so 1-(2-methoxy-4-(trifluoromethyl)phenyl)phthalazine-6-sulfonyl chloride (Intermediate BBBB; 0.100 g, 0.248 mmol) was added as a solution in 3 mL of MeCN, followed by 1-methylimidazole (0.049 ml, 0.497 mmol). After stirring at room temperature for an additional hour, LC/MS showed mostly desired product. The reaction mixture was concentrated then dissolved in 4N HCl in dioxanes (1.862 ml, 7.45 mmol), and the reaction mixture was heated to 110° C. for 3 hours. The reaction mixture was concentrated and was purified by reverse phase column chromatography [$C_{18}$ 50 g, 10 to 100% (0.1% NH$_4$OH in MeOH)/(0.1% NH$_4$OH in water)] to yield 1-(2-methoxy-4-(trifluoromethyl)phenyl)-n-(thiazol-2-yl)phthalazine-6-sulfonamide. $^1$H NMR (acetonitrile-$d_3$) δ ppm: 9.70 (s, 1H), 8.63 (s, 1H), 8.20 (d, J=8.7 Hz, 1H), 7.71 (d, J=8.7 Hz, 1H), 7.62 (d, J=7.7 Hz, 1H), 7.45-7.53 (m, 2H), 7.02 (d, J=4.7 Hz, 1H), 6.65 (d, J=4.7 Hz, 1H), 3.75 (s, 3H). m/z (ESI) 467.0 (M+H)+

EXAMPLE 254

1-(2-METHOXY-4-(TRIFLUOROMETHYL)PHENYL)-N-(PYRIMIDIN-4-YL)PHTHALAZINE-6-SULFONAMIDE

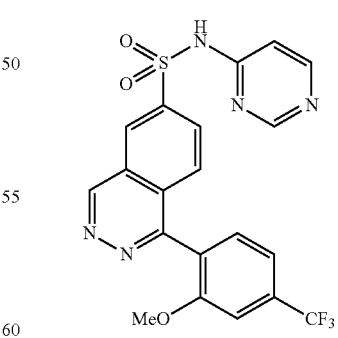

Example 254 was synthesized in a similar manner to Example 253, using 4-aminopyrimidine instead of 2-aminothiazole. $^1$H NMR (acetonitrile-$d_3$) $^1$H NMR δ ppm: 9.70 (s, 1H), 8.74 (s, 1H), 8.43 (s, 1H), 8.28 (d, J=8.7 Hz, 1H), 8.11

(d, J=6.6 Hz, 1H), 7.70 (d, J=8.8 Hz, 1H), 7.61 (d, J=7.6 Hz, 1H), 7.44-7.52 (m, 2H), 6.97 (d, J=6.5 Hz, 1H), 3.73 (s, 3H). m/z (ESI) 462.0 (M+H)+

EXAMPLE 255

N-(5-FLUOROTHIAZOL-2-YL)-1-(2-METHOXY-4-(TRIFLUOROMETHYL)PHENYL)PHTHALAZINE-6-SULFONAMIDE

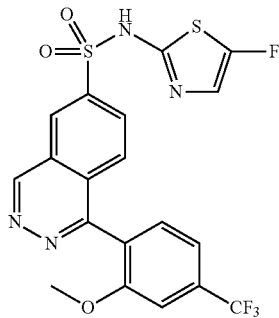 [SMILES: COc1cc(C(F)(F)F)ccc1-c1nncc2cc(S(=O)(=O)Nc3ncc(F)s3)ccc12]

A vial was charged with 1-chloro-N-(5-fluorothiazol-2-yl)-N-(4-methoxybenzyl)phthalazine-6-sulfonamide (Intermediate CCCC) (55.94 mg, 0.120 mmol), (2-methoxy-4-(trifluoromethyl)phenyl)boronic acid (Combi-Blocks, San Diego, Calif., 31.8 mg, 0.144 mmol), Pd(AmPhos)$_2$Cl$_2$ (4.26 mg, 6.02 μmol), potassium phosphate (77 mg, 0.361 mmol), 1,4-dioxane (451 μl), and water (150 μl). The vial was flushed with Ar (g), then sealed and heated in a microwave reactor for 30 min at 90° C. The mixture was extracted with EtOAc (3×), and the combined organic extracts were concentrated. The residue was dissolved in DCM (1 mL) and TFA (0.5 mL). After 30 min, the mixture was diluted with MeOH and concentrated, and the crude product was purified by chromatography on silica gel (12-g column, 0 to 7% MeOH/DCM) to give N-(5-fluorothiazol-2-yl)-1-(2-methoxy-4-(trifluoromethyl)phenyl)phthalazine-6-sulfonamide (35.18 mg, 0.073 mmol, 60.4% yield) as a cream-colored solid: $^1$H NMR (400 MHz, DMSO-d$_6$) δ ppm=12.88 (s, 1H), 9.96 (s, 1H), 8.76 (d, J=1.9 Hz, 1H), 8.22 (dd, J=1.9, 8.7 Hz, 1H), 7.77 (d, J=8.7 Hz, 1H), 7.68 (d, J=7.7 Hz, 1H), 7.60-7.52 (m, 2H), 7.41 (s, 1H), 3.77 (s, 3H); m/z (ESI) 485.2 (M+H)$^+$.

EXAMPLE 256

1-(4-FLUORO-2-METHOXYPHENYL)-N-(5-FLUOROTHIAZOL-2-YL)PHTHALAZINE-6-SULFONAMIDE

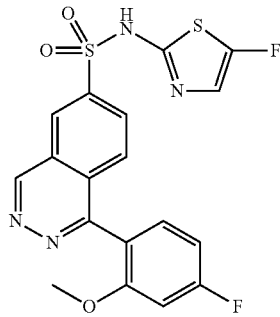 [SMILES: COc1cc(F)ccc1-c1nncc2cc(S(=O)(=O)Nc3ncc(F)s3)ccc12]

Example 256 was synthesized in a similar manner to Example 255, except (4-fluoro-2-methoxyphenyl)boronic acid (Sigma-Aldrich, St. Louis, Mo.) was used in place of (2-methoxy-4-(trifluoromethyl)phenyl)boronic acid. The desired product, 1-(4-fluoro-2-methoxyphenyl)-N-(thiazol-2-yl)phthalazine-6-sulfonamide, was isolated as an off-white solid: $^1$H NMR (400 MHz, DMSO-d$_6$) δ ppm=12.84 (br. s., 1H), 9.91 (s, 1H), 8.73 (d, J=1.7 Hz, 1H), 8.22 (dd, J=1.8, 8.8 Hz, 1H), 7.77 (d, J=8.8 Hz, 1H), 7.48 (dd, J=6.8, 8.3 Hz, 1H), 7.40 (s, 1H), 7.21 (dd, J=2.3, 11.4 Hz, 1H), 7.01 (dt, J=2.3, 8.4 Hz, 1H), 3.69 (s, 3H); m/z (ESI) 435.2 (M+H)$^+$.

EXAMPLE 257

1-(4-CYANO-2-METHOXYPHENYL)-N-(THIAZOL-2-YL)PHTHALAZINE-6-SULFONAMIDE

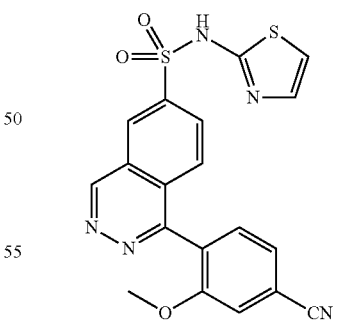

Example 257 was synthesized in a similar manner to Example 255, except (4-cyano-2-methoxyphenyl)boronic acid (Combi-Blocks, San Diego, Calif.) was used in place of (2-methoxy-4-(trifluoromethyl)phenyl)boronic acid. The desired product, 1-(4-cyano-2-methoxyphenyl)-N-(thiazol-2-yl)phthalazine-6-sulfonamide, was isolated as an off-white solid: $^1$H NMR (400 MHz, DMSO-d$_6$) δ ppm=12.85 (br. s., 1H), 9.96 (d, J=0.7 Hz, 1H), 8.76 (d, J=1.9 Hz, 1H), 8.22 (dd, J=1.9, 8.7 Hz, 1H), 7.80 (s, 1H), 7.75 (d, J=8.7 Hz, 1H), 7.71-7.59 (m, 2H), 7.40 (s, 1H), 3.75 (s, 3H); m/z (ESI) 442.2 (M+H)⁺.

EXAMPLE 258

1-(2-METHOXYPHENYL)-N-(THIAZOL-2-YL)PHTHALAZINE-6-SULFONAMIDE

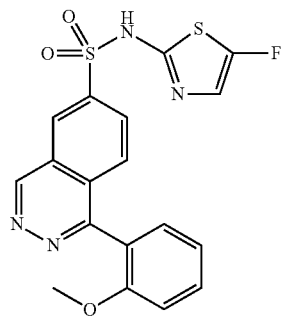 [SMILES: COc1ccccc1-c1nncc2cc(S(=O)(=O)Nc3ncc(F)s3)ccc12]

Example 258 was synthesized in a similar manner to Example 255, except (2-methoxyphenyl)boronic acid (Sigma-Aldrich, St. Louis, Mo.) was used in place of (2-methoxy-4-(trifluoromethyl)phenyl)boronic acid. The desired product, 1-(2-methoxyphenyl)-N-(thiazol-2-yl)phthalazine-6-sulfonamide, was isolated as an off-white solid: ¹H NMR (400 MHz, DMSO-d₆) δ ppm=12.85 (br. s., 1H), 9.91 (s, 1H), 8.73 (d, J=1.6 Hz, 1H), 8.28-8.18 (m, 1H), 7.74 (d, J=8.7 Hz, 1H), 7.67-7.57 (m, 1H), 7.46-7.36 (m, 2H), 7.28 (d, J=8.3 Hz, 1H), 7.18 (t, J=7.4 Hz, 1H), 3.68 (d, J=1.9 Hz, 3H); m/z (ESI) 417.2 (M+H)⁺.

EXAMPLE 259

4-(2-METHOXY-4-(TRIFLUOROMETHYL)PHENYL)-N-(THIAZOL-2-YL)CINNOLINE-7-SULFONAMIDE

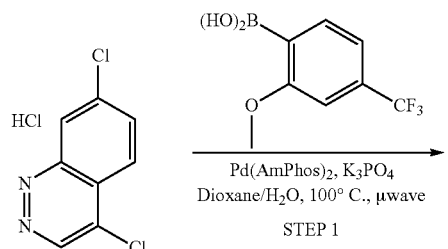

Pd(AmPhos)₂, K₃PO₄
Dioxane/H₂O, 100° C., μwave
STEP 1

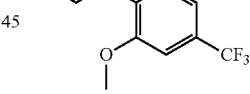

benzyl mercaptan
Pd₂(dba)₃, Xantphos,
Dioxane, DIEA, 60° C.
STEP 2

-continued

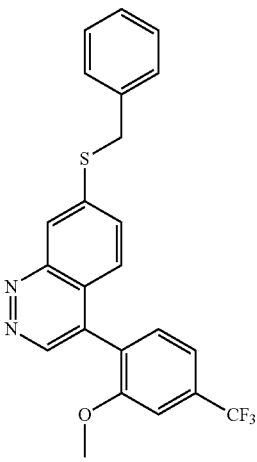

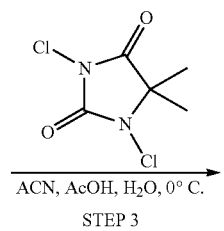

ACN, AcOH, H₂O, 0° C.
STEP 3

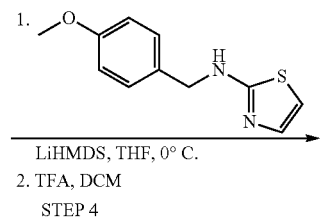

1. 
LiHMDS, THF, 0° C.
2. TFA, DCM
STEP 4

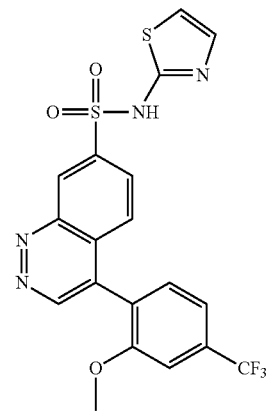 [SMILES: COc1cc(C(F)(F)F)ccc1-c1cnnc2cc(S(=O)(=O)Nc3nccs3)ccc12]

STEP 1: 7-CHLORO-4-(2-METHOXY-4-(TRIF-LUOROMETHYL)PHENYL)CINNOLINE

A microwave vial charged with 4,7-dichlorocinnoline hydrochloride (HDH Pharma, Morrisville, N.C.) (0.400 g, 1.7 mmol), 2-methoxy-4-(trifluoromethyl)phenylboronic acid (Combi-Blocks, San Diego, Calif.) (0.513 g, 1.7 mmol), potassium carbonate (1.172 g, 8.49 mmol), dioxane (6.36 ml) and water (2.1 ml); the system was purged with argon prior to the addition of Pd(PPh$_3$)$_4$ (0.196 g, 0.168 mmol). The mixture was irradiated for 30 min at 100° C. The organic layer was decanted and the aqueous phase was rinsed once with EtOAc. The combined organics were dried under reduced pressure and purified with a 40 g silicycle HP column (SiliCycle, Inc. Quebec City, Canada) ramping EtOAc in heptane (0 to 35%, 10% DCM throughout) providing 7-chloro-4-(2-methoxy-4-(trifluoromethyl)phenyl)cinnoline (0.212 g, 0.626 mmol, 36.8% yield) as a light yellow solid. m/z (ESI) 339.2 (M+H)$^+$.

STEP 2: 7-(BENZYLTHIO)-4-(2-METHOXY-4-TRIFLUOROMETHYL)PHENYL)CINNOLINE

To a 2-5 ml microwave vial charged with 7-chloro-4-(2-methoxy-4-(trifluoromethyl)phenyl)cinnoline (0.140 g, 0.413 mmol) was added Xantphos (0.048 g, 0.083 mmol), Pd$_2$(dba)$_3$ (0.038 g, 0.041 mmol), dioxane (1.653 ml) DIEA (0.144 ml, 0.827 mmol) and benzyl mercaptan (0.051 ml, 0.434 mmol). The mixture was purged with argon and microwave irradiated at 140° C. for 10 hrs. The mixture was filtered through diatomaceous earth, dried under reduced pressure and the crude residue purified with a 40 g HP silicycle column (SiliCycle, Inc. Quebec City, Canada) ramping EtOAc in heptane (0 to 50%, 5% DCM throughout) providing 7-(benzylthio)-4-(2-methoxy-4-(trifluoromethyl)phenyl)cinnoline (0.138 g, 0.324 mmol, 78% yield) as an off-white solid. m/z (ESI) 427.3 (M+H)$^+$.

STEP 3: 4-(2-METHOXY-4-(TRIFLUOROM-ETHYL)PHENYL)CINNOLINE-7-SULFONYL CHLORIDE

To a vial charged with 7-(benzylthio)-4-(2-methoxy-4-(trifluoromethyl)phenyl)cinnoline (138 mg, 0.322 mmol) was added acetonitrile (2.65 ml), acetic acid (100 μl), and water (65 μl). The resulting solution was cooled in an ice water bath and 1,3-dichloro-5,5-dimethyl-2-imidazolidinedione (56 μl, 0.600 mmol) was added and the mixture stirred for 30 min. The mixture was diluted with EtOAc and extracted with H$_2$O. The aqueous phase was extracted with EtOAc. The combined organics were dried with Na$_2$SO$_4$, filtered, and dried under reduced pressure. The crude material was purified with a 25 g silicycle HP column (SiliCycle, Inc. Quebec City, Canada) ramping EtOAc in heptane (0 to 35%, 5% DCM throughout) providing 4-(2-methoxy-4-(trifluoromethyl)phenyl)cinnoline-7-sulfonyl chloride (109 mg, 0.271 mmol, 84% yield) as a yellow oil. m/z (ESI) 403.1 (M+H)$^+$.

STEP 4: 4-(2-METHOXY-4-(TRIFLUOROM-ETHYL)PHENYL)-N-(THIAZOL-2-YL)CINNO-LINE-7-SULFONAMIDE

To a flask containing an ice cold suspension of N-(4-methoxybenzyl)thiazol-2-amine (40.2 mg, 0.182 mmol) in THF (668 μl) was added lithium bis(trimethylsilyl)amide (1M in THF) (191 μl, 0.191 mmol) drop wise over 10 min. The mixture was stirred for 15 min prior to the drop wise addition of a solution of 4-(2-methoxy-4-(trifluoromethyl)phenyl)cinnoline-7-sulfonyl chloride (70 mg, 0.174 mmol) in THF (0.7 ml). The solution was allowed to stir for 1 hr (ice melt) providing a brown solution. To the mixture was added acetic acid (about 100 μl) and the mixture dried under reduced pressure. To the crude material was added DCM (1 ml) followed by TFA (0.3 ml) and the mixture stirred at room temperature for 2 hrs. The mixture was dried under reduced pressure and the crude material purified with a 25 g spherical silica column (15 μm spherical, Interchim) ramping EtOAc in heptane (0 to 70%, 10% DCM isocratic throughout) providing product which was lyophilized from MeOH/H$_2$O to afford 4-(2-methoxy-4-(trifluoromethyl)phenyl)-N-(thiazol-2-yl)cinnoline-7-sulfonamide (34 mg, 0.073 mmol, 41.9% yield) as a light yellow solid. $^1$H NMR (400 MHz, DMSO-d$_6$) μ ppm 3.79 (s, 3H) 6.91 (d, J=4.50 Hz, 1H) 7.32 (d, J=4.60 Hz, 1H) 7.51-7.60 (m, 2H) 7.66 (d, J=7.53 Hz, 1H) 7.77-7.84 (m, 1H) 8.08 (dd, J=8.90, 1.86 Hz, 1H) 8.87 (dd, J=1.81, 0.54 Hz, 1H) 9.45 (s, 1H) 13.03 (br. s., 1H). m/z (ESI) 467.2 (M+H)$^+$.

EXAMPLE 260

4-(2-METHOXY-4-(TRIFLUOROMETHYL)PHE-NYL)-N-(PYRIMIDIN-4-YL)CINNOLINE-7-SUL-FONAMIDE

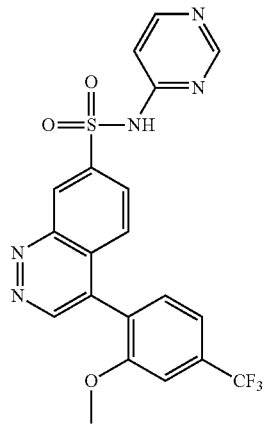 [SMILES: COc1cc(C(F)(F)F)ccc1-c1cnnc2cc(S(=O)(=O)Nc3ccncn3)ccc12]

Example 260 was synthesized in a similar manner to example 259, using pyrimidine-4-amine instead of N-(4-methoxybenzyl)thiazol-2-amine in Step 4 (TFA deprotection not needed). After the reaction was complete, the mixture was dried under reduced pressure, dissolved in DMSO (1.4 ml) and purified by RP-HPLC ramping ACN in H$_2$O (25 to 75%, 0.1% TFA throughout). The product was dried under reduced pressure and free-based with a 2 g SCX-2 column washing with MeOH, then 2M NH$_3$ in MeOH. The basic wash was dried under reduced pressure and lyophilized from MeOH/H$_2$O to afford 4-(2-methoxy-4-(trifluoromethyl)phenyl)-N-(pyrimidin-4-yl)cinnoline-7-sulfonamide (4.4 mg, 9.54 μmol, 9.60% yield) as a light yellow solid. $^1$H NMR (500 MHz, DMSO-d$_6$) δ ppm 3.79 (s, 4H) 6.94 (d, J=6.30 Hz, 1H)

7.51-7.59 (m, 2H) 7.66 (d, J=7.69 Hz, 1H) 7.76 (d, J=8.87 Hz, 1H) 8.12-8.20 (m, 2H) 8.52 (s, 1H) 8.95 (s, 1H) 9.42 (s, 1H). m/z (ESI) 462.2 (M+H)+.

EXAMPLE 261

4-(2-METHOXY-4-(TRIFLUOROMETHYL)PHENYL)-N-(THIAZOL-2-YL)QUINAZOLINE-7-SULFONAMIDE

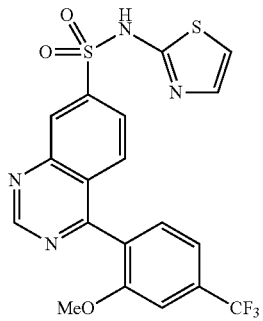 [SMILES: COc1cc(C(F)(F)F)ccc1-c1ncnc2cc(S(=O)(=O)Nc3nccs3)ccc12]

A solution of 4-(2-methoxy-4-(trifluoromethyl)phenyl)quinazoline-7-sulfonyl chloride (Intermediate DDDD; 2.040 g, 5.06 mmol) and thiazol-2-amine (2.54 g, 25.3 mmol) in 40 mL of MeCN was treated with 1-methylimidazole (0.496 ml, 5.06 mmol) and was heated to reflux with a heat gun, and then allowed to stir at room one hour. The reaction mixture was concentrated and the material was purified by silica gel column chromatography (0 to 100% EtOAc/heptane) to yield 4-(2-methoxy-4-(trifluoromethyl)phenyl)-N-(thiazol-2-yl)quinazoline-7-sulfonamide (1.230 g, 2.64 mmol, 52.1% yield). $^1$H NMR (acetonitrile-$d_3$) δ ppm: 9.42 (s, 1H), 8.52 (s, 1H), 7.95 (d, J=8.8 Hz, 1H), 7.77 (d, J=8.7 Hz, 1H), 7.58 (d, J=7.4 Hz, 1H), 7.45-7.51 (m, 2H), 7.01 (d, J=4.8 Hz, 1H), 6.64 (d, J=4.7 Hz, 1H), 3.76 (s, 3H). m/z (ESI) 467.0 (M+H)+

EXAMPLE 262

4-(2-METHOXY-4-(TRIFLUOROMETHYL)PHENYL)-N-(PYRIMIDIN-4-YL)QUINAZOLINE-7-SULFONAMIDE

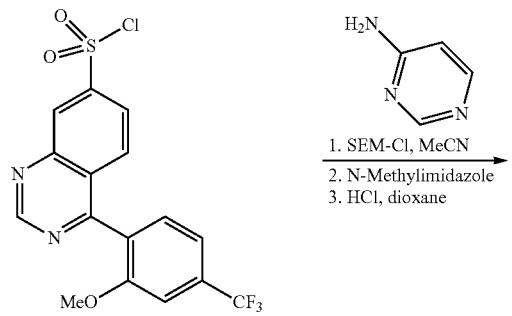

1. SEM-Cl, MeCN
2. N-Methylimidazole
3. HCl, dioxane

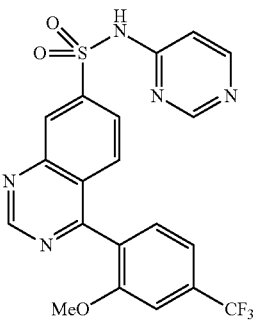

A solution of pyrimidin-4-amine (0.029 g, 0.300 mmol) in 3 mL of MeCN was treated with SEM-Cl (0.053 ml, 0.300 mmol), and the reaction mixture was allowed to stir for one hour. 4-(2-methoxy-4-(trifluoromethyl)phenyl)quinazoline-7-sulfonyl chloride (Intermediate DDDD; 0.110 g, 0.273 mmol) was added as a solution in 3 mL of MeCN, followed by 1-methylimidazole (0.054 ml, 0.546 mmol). After stirring at room temperature for an additional hour, the reaction mixture was concentrated and then dissolved in 1 mL of THF. 4N HCl dioxanes (1.024 ml, 4.10 mmol) was added, and the reaction mixture was heated to 110° C. for one hour. The reaction mixture was concentrated and purification of the crude residue by reverse phase column chromatography [$C_{18}$ 50 g, 10 to 100% (0.1% NH$_4$OH in MeOH)/(0.1% NH$_4$OH in water)] yielded 4-(2-methoxy-4-(trifluoromethyl)phenyl)-N-(pyrimidin-4-yl)quinazoline-7-sulfonamide. $^1$H NMR (acetonitrile-$d_3$) δ ppm: 9.44 (s, 1H), 8.63 (s, 1H), 8.44 (s, 1H), 8.18 (br. s., 1H), 8.03 (d, J=8.8 Hz, 1H), 7.79 (d, J=8.8 Hz, 1H), 7.58 (d, J=7.4 Hz, 1H), 7.43-7.51 (m, 2H), 7.07 (br. s., 1H), 3.75 (s, 3H). m/z (ESI) 462.0 (M+H)+

EXAMPLE 263

N-(5-FLUOROTHIAZOL-2-YL)-4-(2-METHOXY-4-(TRIFLUOROMETHYL)PHENYL)QUINAZOLINE-7-SULFONAMIDE

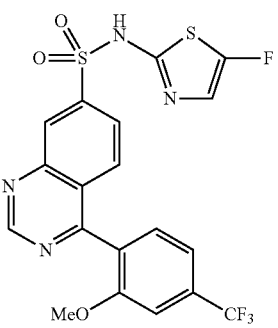 [SMILES: COc1cc(C(F)(F)F)ccc1-c1ncnc2cc(S(=O)(=O)Nc3ncc(F)s3)ccc12]

Example 263 was synthesized in a similar manner to Example 262, using 5-fluorothiazol-2-amine hydrochloride (Milestone Pharmaceuticals, Quebec, Canada) and 1.1 equivalents of triethylamine instead of pyrimidin-4-amine. $^1$H NMR (acetonitrile-$d_3$) δ ppm: 9.43 (s, 1H), 8.50 (s, 1H), 7.94 (d, J=8.8 Hz, 1H), 7.78 (d, J=8.8 Hz, 1H), 7.59 (d, J=7.5 Hz, 1H), 7.44-7.52 (m, 2H), 6.81 (s, 1H), 3.76 (s, 3H). m/z (ESI) 485.0 (M+H)+

EXAMPLE 264

4-(2-METHOXY-4-(TRIFLUOROMETHYL)PHENYL)-N-(OXAZOL-2-YL)QUINAZOLINE-7-SULFONAMIDE

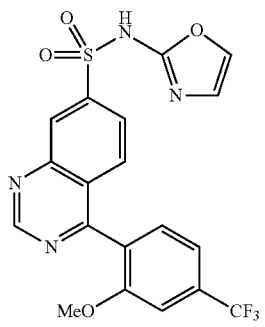 [SMILES: COc1cc(C(F)(F)F)ccc1-c1ncnc2cc(S(=O)(=O)Nc3ncco3)ccc12]

Example 264 was synthesized in a similar manner to Example 262, using oxazol-2-amine instead of pyrimidin-4-amine ¹H NMR (acetonitrile-d₃) δ ppm: 9.55 (s, 1H), 8.79 (s, 1H), 8. (d, J=8.8 Hz, 1H), 8.02 (d, J=7.5 Hz, 1H), 7.56-7.69 (m, 2H), 7.45-7.54 (m, 3H), 3.77-3.79 (m, 3H). m/z (ESI) 451.0 (M+H)+

EXAMPLE 265

4-(2-METHOXY-4-(TRIFLUOROMETHYL)PHENYL)-N-(1,2,4-THIADIAZOL-5-YL)QUINAZOLINE-7-SULFONAMIDE

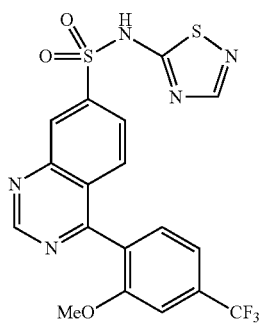 [SMILES: COc1cc(C(F)(F)F)ccc1-c1ncnc2cc(S(=O)(=O)Nc3ncns3)ccc12]

Example 265 was synthesized in a similar manner to Example 262, using 1,2,4-thiadiazol-5-amine (Oakwood Chemical, West Columbia, S.C.) instead of pyrimidin-4-amine. ¹H NMR (acetonitrile-d₃) δ ppm: 9.39 (s, 1H), 8.48 (s, 1H), 7.91-7.98 (m, 2H), 7.71 (d, J=8.8 Hz, 1H), 7.57 (d, J=7.5 Hz, 1H), 7.45-7.50 (m, 2H), 3.74 (s, 3H). m/z (ESI) 468.0 (M+H)+

EXAMPLE 266

4-(4-(DIFLUOROMETHYL)-2-METHOXYPHENYL)-N-(THIAZOL-2-YL)QUINAZOLINE-7-SULFONAMIDE

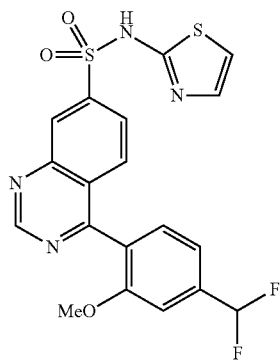 [SMILES: COc1cc(C(F)F)ccc1-c1ncnc2cc(S(=O)(=O)Nc3nccs3)ccc12]

Example 266 was synthesized in a similar manner to Example 261, using Intermediate EEEE instead of Intermediate DDDD. ¹H NMR (acetonitrile-d₃) δ ppm: 9.41 (s, 1H), 8.51 (s, 1H), 7.94 (d, J=8.8 Hz, 1H), 7.78 (d, J=8.8 Hz, 1H), 7.52 (d, J=7.6 Hz, 1H), 7.32-7.40 (m, 2H), 6.74-7.06 (m, 2H), 6.64 (d, J=4.8 Hz, 1H), 3.74 (s, 3H). m/z (ESI) 449.0 (M+H)+

EXAMPLE 267

4-(4-CHLORO-2-METHOXYPHENYL)-N-(THIAZOL-2-YL)QUINAZOLINE-7-SULFONAMIDE

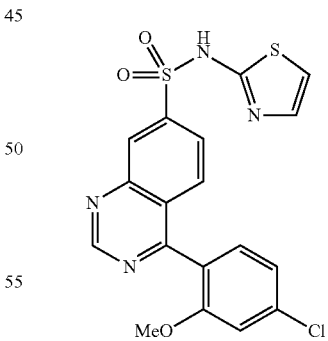

Example 267 was synthesized in a similar manner to Example 261, using Intermediate FFFF instead of Intermediate DDDD. ¹H NMR (acetonitrile-d₃) δ ppm: 9.39 (s, 1H), 8.49 (s, 1H), 7.94 (d, J=8.8 Hz, 1H), 7.80 (d, J=8.8 Hz, 1H), 7.40 (d, J=8.1 Hz, 1H), 7.25 (d, J=1.9 Hz, 1H), 7.19 (dd, J=8.1, 1.9 Hz, 1H), 7.01 (d, J=4.7 Hz, 1H), 6.63 (d, J=4.7 Hz, 1H), 3.70 (s, 3H). m/z (ESI) 433.0 (M+H)+

EXAMPLE 268

4-(2-METHOXY-4-(TRIFLUOROMETHYL)PHENYL)-N-(1,3,4-THIADIAZOL-2-YL)QUINAZOLINE-7-SULFONAMIDE

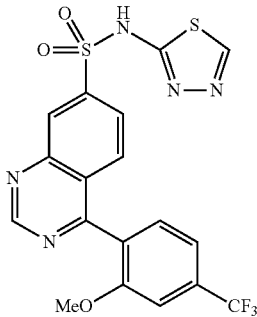 [SMILES: COc1cc(C(F)(F)F)ccc1-c1ncnc2cc(S(=O)(=O)Nc3nncs3)ccc12]

Example 268 was synthesized in a similar manner to Example 261, using 1,3,4-thiadiazol-2-amine (Aldrich) instead of thiazol-2-amine. $^1$H NMR (acetonitrile-d$_3$) δ ppm: 9.44 (s, 1H), 8.52 (s, 1H), 8.41 (s, 1H), 7.90-7.97 (m, 1H), 7.76-7.82 (m, 1H), 7.54-7.61 (m, 1H), 7.45-7.52 (m, 2H), 3.76 (s, 3H). m/z (ESI) 468.0 (M+H)+

EXAMPLE 269

4-(4-CYANO-2-METHOXYPHENYL)-N-(THIAZOL-2-YL)QUINAZOLINE-7-SULFONAMIDE

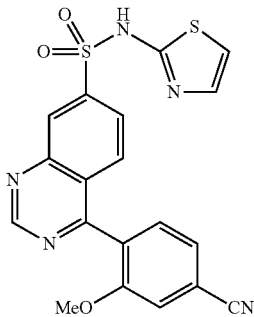 [SMILES: COc1cc(C#N)ccc1-c1ncnc2cc(S(=O)(=O)Nc3nccs3)ccc12]

Example 269 was synthesized in a similar manner to Example 261, using Intermediate HHHH instead of Intermediate DDDD. $^1$H NMR (acetonitrile-d$_3$) δ ppm: 9.42 (s, 1H), 8.52 (s, 1H), 7.95 (d, J=8.8 Hz, 1H), 7.75 (d, J=8.8 Hz, 1H), 7.53-7.58 (m, 3H), 7.01 (d, J=4.7 Hz, 1H), 6.64 (d, J=4.7 Hz, 1H), 3.73 (s, 3H). m/z (ESI) 424.0 (M+H)+

EXAMPLE 270

4-(5-CHLORO-4-(DIFLUOROMETHYL)-2-METHOXYPHENYL)-N-(THIAZOL-2-YL)QUINAZOLINE-7-SULFONAMIDE

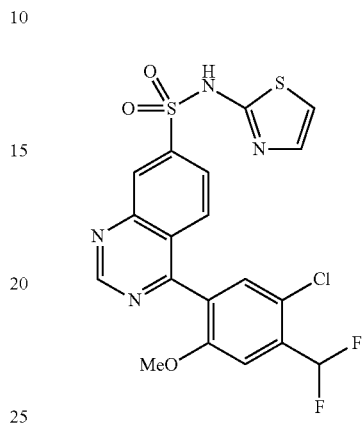

Example 270 was synthesized in a similar manner to Example 261, using Intermediate JJJJ instead of Intermediate DDDD. $^1$H NMR (acetonitrile-d$_3$) δ ppm: 9.42 (s, 1H), 8.52 (s, 1H), 7.96 (d, J=8.8 Hz, 1H), 7.80 (d, J=8.7 Hz, 1H), 7.54 (s, 1H), 7.47 (s, 1H), 6.99-7.29 (m, 2H), 6.64 (d, J=4.7 Hz, 1H), 3.75 (s, 3H). m/z (ESI) 483.0 (M+H)+

EXAMPLE 271

4-(4-FLUORO-2-METHOXYPHENYL)-N-(THIAZOL-2-YL)QUINAZOLINE-7-SULFONAMIDE

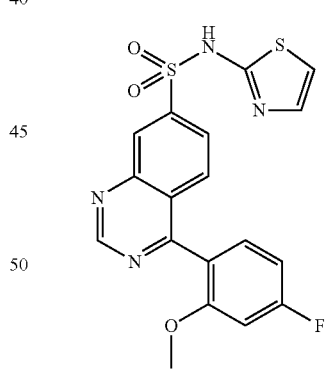

A microwave vial was charged with 4-chloro-N-(2,4-dimethoxybenzyl)-N-(thiazol-2-yl)quinazoline-7-sulfonamide (Intermediate KKKK; 0.040 g, 0.084 mmol), (4-fluoro-2-methoxyphenyl)boronic acid (0.021 g, 0.126 mmol), tetrakis(triphenylphosphine)palladium(0) (9.69 mg, 8.39 μmol), and potassium carbonate (0.058 g, 0.419 mmol). Dioxane (0.419 mL) and water (0.140 mL) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated.

The material was purified via column chromatography (12 g silica gel column, gradient elution 0 to 100% EtOAc:Heptane) to afford N-(2,4-dimethoxybenzyl)-4-(4-fluoro-2-methoxyphenyl)-N-(thiazol-2-yl)quinazoline-7-sulfonamide. The material was dissolved in DCM and TFA (0.1 mL, 1.298 mmol) was added. The reaction was stirred overnight at room temperature. The reaction was concentrated and purified via column chromatography (12 g silica gel column, gradient elution 0 to 10% MeOH:DCM) to afford 4-(4-fluoro-2-methoxyphenyl)-N-(thiazol-2-yl)quinazoline-7-sulfonamide as a white solid. $^1$H NMR (400 MHz, DMSO-$d_6$) δ ppm=13.01 (br. s., 1H), 9.45 (s, 1H), 8.38 (br. s., 1H), 8.06-7.76 (m, 2H), 7.49 (t, J=7.2 Hz, 1H), 7.31 (d, J=4.1 Hz, 1H), 7.21 (d, J=11.2 Hz, 1H), 7.01 (t, J=7.1 Hz, 1H), 6.90 (d, J=4.3 Hz, 1H), 3.70 (br. s., 3H). m/z (ESI) 417.2 (M+H)$^+$.

EXAMPLE 272

4-(2-METHOXYPHENYL)-N-(THIAZOL-2-YL)QUINAZOLINE-7-SULFONAMIDE

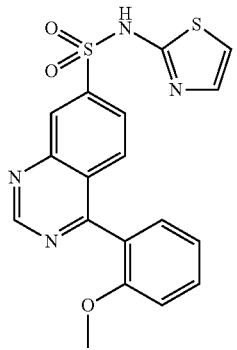 [SMILES: COc1ccccc1-c1ncnc2cc(S(=O)(=O)Nc3nccs3)ccc12]

Example 272 was synthesized in a similar manner to Example 271, except that (2-methoxyphenyl)boronic acid was used instead of (4-fluoro-2-methoxyphenyl)boronic acid to afford 4-(2-methoxyphenyl)-N-(thiazol-2-yl)quinazoline-7-sulfonamide as a white solid. $^1$H NMR (400 MHz, DMSO-$d_6$) δ ppm=13.01 (s, 1H), 9.45 (s, 1H), 8.39 (d, J=1.7 Hz, 1H), 7.96 (dd, J=1.8, 8.8 Hz, 1H), 7.82 (d, J=8.8 Hz, 1H), 7.66-7.57 (m, 1H), 7.43 (dd, J=1.7, 7.4 Hz, 1H), 7.34-7.25 (m, 2H), 7.17 (t, J=7.5 Hz, 1H), 6.90 (d, J=4.6 Hz, 1H), 3.69 (s, 3H). m/z (ESI) 399.2 (M+H)$^+$.

EXAMPLE 273

4-(4-CYANO-2-METHOXYPHENYL)-N-(THIAZOL-2-YL)QUINOLINE-7-SULFONAMIDE

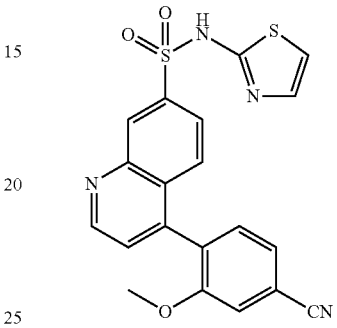

3-Methoxy-4-(4,4,5,5-tetramethyl-1,3,2-dioxaborolan-2-yl)benzonitrile (Intermediate GGGG; 0.093 g, 0.359 mmol), Intermediate LLLL (0.080 g, 0.179 mmol), Pd(PPh$_3$)$_4$ (0.021 g, 0.018 mmol), and K$_2$CO$_3$ (0.074 g, 0.538 mmol) were combined in dioxane (0.673 ml) and water (0.224 ml). The reaction was stirred at 50° C. overnight at which time it was diluted with water (2 mL) and extracted with ethyl acetate (2×2 mL), after which the organics were combined, dried over sodium sulfate, filtered and concentrated under a vacuum. DCM (2.0 mL) was added, followed by TFA (1.0 mL) and the reaction was stirred at RT for 50 minutes until complete deprotection. The material was concentrated under a vacuum, and purified via silica gel chromatography, eluting with 0 to 100% ethyl acetate in heptanes, to yield desired product with a 10% triphenylphosphine oxide impurity. The material was taken up in a mixture of DCM and MeOH and was purified via 500 mg SCX column (product eluted with methanol/ammonia wash). After concentration, 4-(4-cyano-2-methoxyphenyl)-N-(thiazol-2-yl)quinoline-7-sulfonamide (0.048 g, 63%) was obtained as a yellow solid. $^1$H NMR (400 MHz, DMSO-$d_6$) δ ppm 3.74 (s, 3H) 6.85 (d, J=4.60 Hz, 1H) 7.27 (d, J=4.50 Hz, 1H) 7.52 (d, J=7.73 Hz, 1H) 7.56 (d, J=4.40 Hz, 1H) 7.59-7.65 (m, 2H) 7.75 (d, J=1.17 Hz, 1H) 7.85 (dd, J=8.80, 1.86 Hz, 1H) 8.46 (d, J=1.76 Hz, 1H) 9.07 (d, J=4.40 Hz, 1H) 12.89 (br. s., 1H). m/z (ESI) 423.0 (M+H)$^+$.

EXAMPLE 274

4-(4-FLUORO-2-METHOXYPHENYL)-N-(THIAZOL-2-YL)QUINOLINE-7-SULFONAMIDE

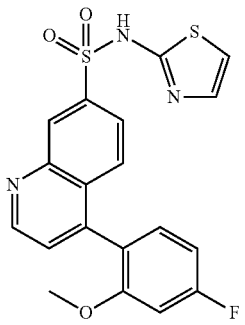 [SMILES: COc1cc(F)ccc1-c1ccnc2cc(S(=O)(=O)Nc3nccs3)ccc12]

Example 274 was synthesized in a similar manner to Example 273, using 4-fluoro-2-methoxyphenylboronic acid in place of 3-methoxy-4-(4,4,5,5-tetramethyl-1,3,2-dioxaborolan-2-yl)benzonitrile. $^1$H NMR (400 MHz, DMSO-d$_6$) δ ppm 3.69 (s, 3H) 6.86 (d, J=4.60 Hz, 1H) 6.97 (td, J=8.41, 2.45 Hz, 1H) 7.17 (dd, J=11.40, 2.40 Hz, 1H) 7.28 (d, J=4.60 Hz, 1H) 7.34 (dd, J=8.41, 6.85 Hz, 1H) 7.52 (d, J=4.40 Hz, 1H) 7.66 (d, J=8.80 Hz, 1H) 7.84 (dd, J=8.80, 1.96 Hz, 1H) 8.45 (d, J=1.86 Hz, 1H) 9.04 (d, J=4.40 Hz, 1H) 12.89 (br. s., 1H). m/z (ESI) 416.0 (M+H)$^+$.

EXAMPLE 275

4-(4-CHLORO-2-METHOXYPHENYL)-N-(THIAZOL-2-YL)QUINOLINE-7-SULFONAMIDE

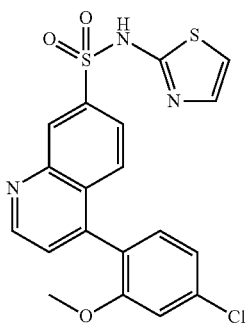 [SMILES: COc1cc(Cl)ccc1-c1ccnc2cc(S(=O)(=O)Nc3nccs3)ccc12]

Example 275 was synthesized in a similar manner to Example 273, using (4-chloro-2-methoxyphenyl)boronic acid in place of 3-methoxy-4-(4,4,5,5-tetramethyl-1,3,2-dioxaborolan-2-yl)benzonitrile. $^1$H NMR (400 MHz, DMSO-d$_6$) δ ppm 3.70 (s, 3H) 6.86 (d, J=4.60 Hz, 1H) 7.21 (dd, J=8.07, 1.91 Hz, 1H) 7.28 (d, J=4.69 Hz, 1H) 7.31-7.35 (m, 2H) 7.53 (d, J=4.40 Hz, 1H) 7.66 (d, J=8.80 Hz, 1H) 7.84 (dd, J=8.80, 1.86 Hz, 1H) 8.45 (d, J=1.86 Hz, 1H) 9.05 (d, J=4.30 Hz, 1H) 12.89 (br. s., 1H). m/z (ESI) 432.0 (M+H)$^+$.

EXAMPLE 276

4-(2-METHOXY-4-(TRIFLUOROMETHYL)PHENYL)-N-(THIAZOL-2-YL)QUINOLINE-7-SULFONAMIDE

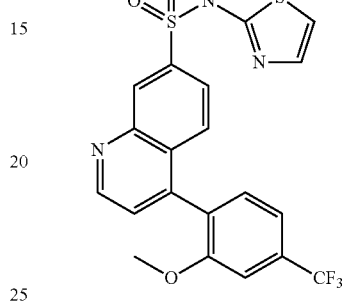

Example 276 was synthesized in a similar manner to Example 273, using 2-methoxy-4-(trifluoromethyl)phenylboronic acid (Combi-Blocks, San Diego, Calif.) in place of 3-methoxy-4-(4,4,5,5-tetramethyl-1,3,2-dioxaborolan-2-yl)benzonitrile. SCX purification was not needed. $^1$H NMR (400 MHz, DMSO-d$_6$) δ ppm 3.76 (s, 3H) 6.86 (d, J=4.60 Hz, 1H) 7.28 (d, J=4.60 Hz, 1H) 7.47-7.56 (m, 3H) 7.58 (d, J=4.40 Hz, 1H) 7.64 (d, J=8.80 Hz, 1H) 7.85 (dd, J=8.85, 1.91 Hz, 1H) 8.47 (d, J=1.76 Hz, 1H) 9.08 (d, J=4.40 Hz, 1H) 12.89 (br. s., 1H). m/z (ESI) 466.0 (M+H)$^+$.

EXAMPLE 277

4-(2-METHOXYPHENYL)-N-(THIAZOL-2-YL)QUINOLINE-7-SULFONAMIDE

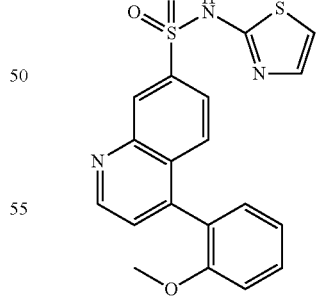

Example 277 was synthesized in a similar manner to Example 273, using 2-methoxyphenylboronic acid in place of 3-methoxy-4-(4,4,5,5-tetramethyl-1,3,2-dioxaborolan-2-yl)benzonitrile. SCX purification was not needed. $^1$H NMR (400 MHz, DMSO-d$_6$) δ ppm 3.67 (s, 3H) 6.86 (d, J=4.60 Hz, 1H) 7.14 (td, J=7.43, 0.88 Hz, 1H) 7.24 (d, J=8.41 Hz, 1H) 7.27-7.31 (m, 2H) 7.51-7.55 (m, 2H) 7.66 (d, J=8.90 Hz, 1H) 7.84

(dd, J=8.80, 1.96 Hz, 1H) 8.45 (d, J=1.76 Hz, 1H) 9.04 (d, J=4.40 Hz, 1H) 12.89 (br. s., 1H). m/z (ESI) 398.0 (M+H)+.

EXAMPLE 278

4-(2-CHLORO-4-(TRIFLUOROMETHYL)PHENYL)-N-(THIAZOL-2-YL)QUINOLINE-7-SULFONAMIDE

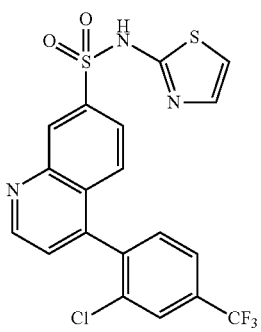 [SMILES: O=S(=O)(Nc1nccs1)c1ccc2c(-c3ccc(C(F)(F)F)cc3Cl)ccnc2c1]

Example 278 was synthesized in a similar manner to Example 273, using 2-chloro-4-(trifluoromethyl)benzeneboronic acid (Synthonix) in place of 3-methoxy-4-(4,4,5,5-tetramethyl-1,3,2-dioxaborolan-2-yl)benzonitrile. SCX purification was not needed. $^1$H NMR (400 MHz, DMSO-$d_6$) δ ppm 6.87 (d, J=4.60 Hz, 1H) 7.29 (d, J=4.60 Hz, 1H) 7.59 (d, J=8.80 Hz, 1H) 7.66 (d, J=4.30 Hz, 1H) 7.76 (d, J=7.92 Hz, 1H) 7.89 (dd, J=8.75, 1.91 Hz, 1H) 7.92-7.98 (m, 1H) 8.16 (s, 1H) 8.51 (d, J=1.66 Hz, 1H) 9.15 (d, J=4.40 Hz, 1H) 12.92 (s, 1H). m/z (ESI) 470.0 (M+H)+.

EXAMPLE 279

4-(2-METHOXY-4-(TRIFLUOROMETHYL)PHENYL)-N-(PYRIMIDIN-4-YL)QUINOLINE-7-SULFONAMIDE

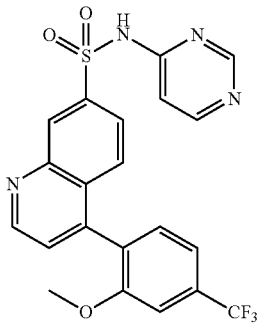 [SMILES: COc1cc(C(F)(F)F)ccc1-c1ccnc2cc(S(=O)(=O)Nc3ccncn3)ccc12]

(2-Methoxy-4-(trifluoromethyl)phenyl)boronic acid (0.069 g, 0.312 mmol), Intermediate MMMM (0.050 g, 0.156 mmol), Pd(PPh$_3$)$_4$ (0.018 g, 0.016 mmol), and K$_2$CO$_3$ (0.065 g, 0.468 mmol) were combined in dioxane (0.585 ml) and water (0.195 ml) and the reaction stirred at 80° C. for 5 h. 1N HCl was added (to pH acidic) and extracted with ethyl acetate (2×5 mL), after which the organics were combined, dried over sodium sulfate, filtered and concentrated under a vacuum. The material was purified via silica gel chromatography, eluting with 0 to 100% ethyl acetate in heptanes, to yield product with a triphenylphosphine oxide impurity. The material was taken up in a mixture of methanol and DCM, and was purified via 2-g SCX column (product eluted cleanly in methanol/ammonia wash). The material was concentrated under a vacuum to yield 4-(2-methoxy-4-(trifluoromethyl)phenyl)-N-(pyrimidin-4-yl)quinoline-7-sulfonamide (0.022 g, 0.048 mmol, 30.7% yield). $^1$H NMR (400 MHz, DMSO-$d_6$) δ ppm 3.76 (s, 3H) 6.82 (d, J=6.55 Hz, 1H) 7.47-7.60 (m, 5H) 7.89 (dd, J=8.80, 1.86 Hz, 1H) 8.09 (d, J=6.16 Hz, 1H) 8.42 (s, 1H) 8.50 (d, J=1.76 Hz, 1H) 9.04 (d, J=4.40 Hz, 1H) (sulfonamide —NH not observed). m/z (ESI) 461.0 (M+H)+.

EXAMPLE 280

4-(4-CYANO-2-METHOXYPHENYL)-N-(PYRIMIDIN-4-YL)QUINOLINE-7-SULFONAMIDE

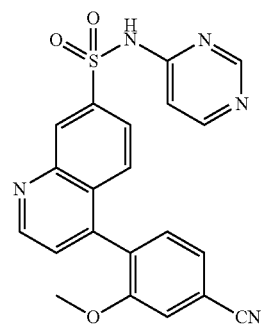 [SMILES: COc1cc(C#N)ccc1-c1ccnc2cc(S(=O)(=O)Nc3ccncn3)ccc12]

Example 280 was synthesized in a similar manner to Example 279, using 3-methoxy-4-(4,4,5,5-tetramethyl-1,3,2-dioxaborolan-2-yl)benzonitrile (Intermediate GGGG) in place of (2-methoxy-4-(trifluoromethyl)phenyl)boronic acid. After adding 1N HCl (to pH acidic), ethyl acetate was added and the layers separated, leaving the product in the aqueous layer. The aqueous layer was loaded directly onto a 2-g SCX column and product eluted cleanly with the methanol/ammonia wash to yield 4-(4-cyano-2-methoxyphenyl)-N-(pyrimidin-4-yl)quinoline-7-sulfonamide (0.050 g, 0.120 mmol, 77% yield). $^1$H NMR (400 MHz, DMSO-$d_6$) δ ppm 3.73 (s, 3H) 6.77 (d, J=6.26 Hz, 1H) 7.49-7.54 (m, 3H) 7.61 (dd, J=7.73, 1.37 Hz, 1H) 7.74 (d, J=1.27 Hz, 1H) 7.88 (dd, J=8.85, 1.81 Hz, 1H) 8.05 (d, J=6.26 Hz, 1H) 8.38 (s, 1H)

8.48 (d, J=1.66 Hz, 1H) 9.03 (d, J=4.40 Hz, 1H) (sulfonamide —NH not observed). m/z (ESI) 418.2 (M+H)⁺.

EXAMPLE 281

4-(2-METHOXYPHENYL)-N-(PYRIMIDIN-4-YL)QUINOLINE-7-SULFONAMIDE

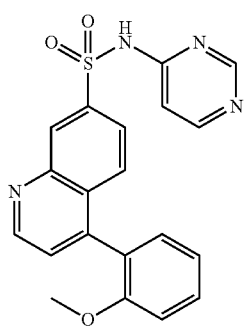 [SMILES: COc1ccccc1-c1ccnc2cc(S(=O)(=O)Nc3ccncn3)ccc12]

Example 281 was synthesized in a similar manner to Example 280, using 2-methoxyphenylboronic acid in place of 3-methoxy-4-(4,4,5,5-tetramethyl-1,3,2-dioxaborolan-2-yl)benzonitrile. ¹H NMR (400 MHz, DMSO-$d_6$) δ ppm 3.66 (s, 3H) 6.84 (d, J=6.75 Hz, 1H) 7.10-7.16 (m, 1H) 7.23 (d, J=8.80 Hz, 1H) 7.28 (dd, J=7.43, 1.66 Hz, 1H) 7.48 (d, J=4.40 Hz, 1H) 7.50-7.56 (m, 1H) 7.59 (d, J=8.80 Hz, 1H) 7.89 (dd, J=8.80, 1.86 Hz, 1H) 8.10 (d, J=6.36 Hz, 1H) 8.43 (s, 1H) 8.49 (d, J=1.76 Hz, 1H) 9.01 (d, J=4.30 Hz, 1H) (sulfonamide —NH not observed). m/z (ESI) 393.0 (M+H)⁺.

EXAMPLE 282

4-(2-METHOXY-4-(TRIFLUOROMETHYL)PHENYL)-5-METHYL-N-(THIAZOL-2-YL)QUINOLINE-7-SULFONAMIDE

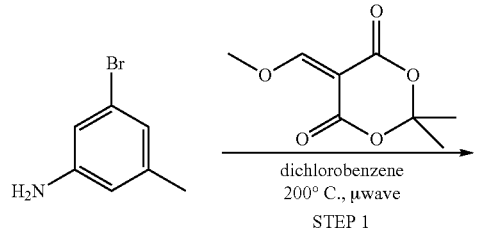

dichlorobenzene
200° C., μwave
STEP 1

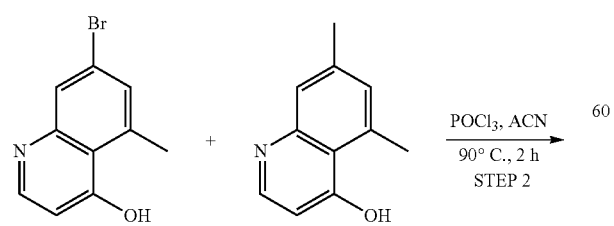

POCl₃, ACN
90° C., 2 h
STEP 2

-continued

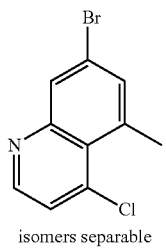

isomers separable benzyl mercaptan
Pd2(dba)3, Xantphos,
Dioxane, DIEA, 60° C.
STEP 3

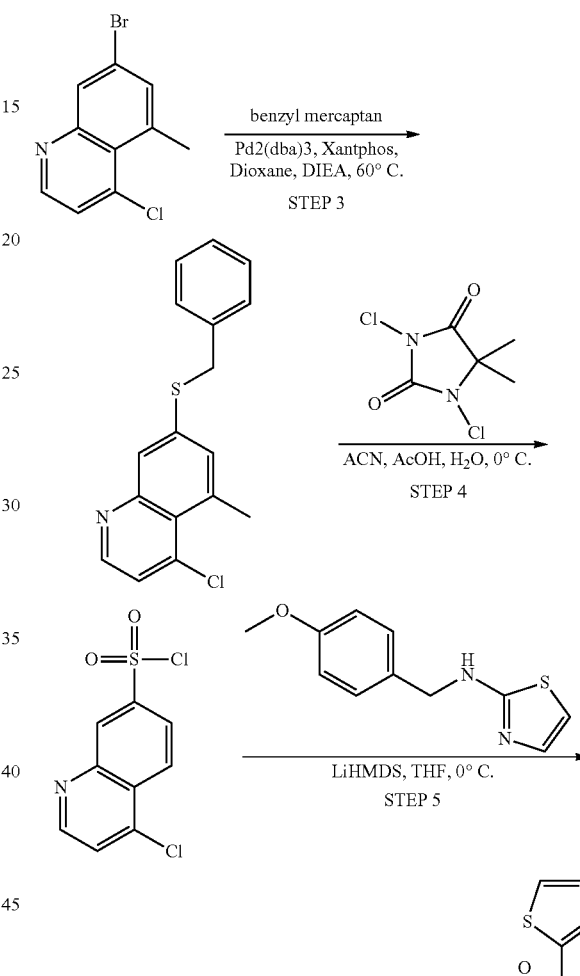

ACN, AcOH, H₂O, 0° C.
STEP 4

LiHMDS, THF, 0° C.
STEP 5

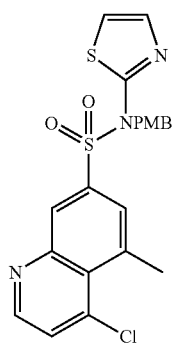

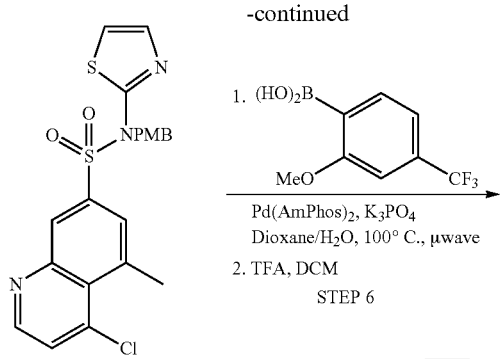

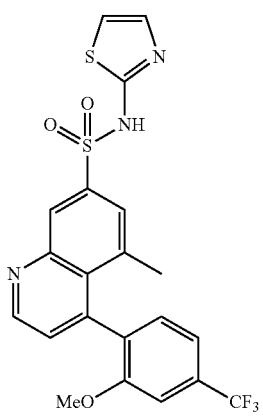

STEP 1: 7-BROMO-5-METHYLQUINOLIN-4-OL & 5-BROMO-7-METHYLQUINOLIN-4-OL

To a microwave vial charged with 3-bromo-5-methylaniline (Combi-Blocks, San Diego, Calif.) (0.110 g, 0.591 mmol) and 5-(methoxymethylene)-2,2-dimethyl-1,3-dioxane-4,6-dione (Matrix Scientific, Columbia, S.C.) (0.116 g, 0.621 mmol) was added 1,2-dichlorobenzene (1.182 ml). The vessel was irradiated in a microwave at 200° C. for 10 min. To the mixture was added diethyl ether and the solid obtained filtered and rinsed with excess diethyl ether to afford a brown solid as a 3:1 mixture of isomeric products (30 mg, 21%) (7-bromo-5-methylquinolin-4-ol=major). m/z (ESI) 238.0/240.0 (M+H)$^+$.

STEP 2: 7-BROMO-4-CHLORO-5-METHYLQUINOLINE

To a vial charged with a mixture of 7-bromo-5-methylquinolin-4-ol and 5-bromo-7-methylquinolin-4-ol (0.09 g, 0.378 mmol) was added acetonitrile (1.890 ml) followed by the addition of POCl$_3$ (0.035 ml, 0.378 mmol). The mixture was heated to 90° C. for 1.5 hr. The mixture was dried under reduced pressure and the crude residue purified with a 25 g Interchim HP spherical silica column (15 µm spherical) (0 to 50%, 10% DCM throughout) providing adequate separation of regioisomers. The major, first eluting isomer was isolated cleanly to yield 7-bromo-4-chloro-5-methylquinoline (48 mg, 0.187 mmol, 49.5% yield) as a white solid. $^1$H NMR (400 MHz, CHLOROFORM-d) δ ppm 3.02 (s, 4H) 7.46 (d, J=4.69 Hz, 1H) 7.50 (dd, J=2.01, 0.93 Hz, 1H) 8.15-8.19 (m, 1H) 8.67 (d, J=4.70 Hz, 1H). m/z (ESI) 256.1 (M+H)$^+$.

STEP 3: 7-(BENZYLTHIO)-4-CHLORO-5-METHYLQUINOLINE

To a vial charged with 7-bromo-4-chloro-5-methylquinoline (0.048 g, 0.187 mmol) was added Xantphos (0.022 g, 0.037 mmol), Pd$_2$(dba)$_3$ (0.017 g, 0.019 mmol), dioxane (0.748 ml), DIEA (0.065 ml, 0.374 mmol) and benzyl mercaptan. The mixture was purged with argon and heated to 60° C. overnight. The mixture was directly loaded onto a 25 HP silicycle column and purified by ramping EtOAc in heptane (0 to 50%, 10% DCM throughout) to provide product as a light yellow solid (35 mg, 62%). $^1$H NMR (400 MHz, CHLOROFORM-d) δ ppm 2.97 (s, 3H) 4.31 (s, 2H) 7.22-7.26 (m, 1H) 7.27-7.31 (m, 1H) 7.31-7.39 (m, 3H) 7.44 (d, J=6.94 Hz, 2H) 7.82 (d, J=1.96 Hz, 1H) 8.61 (d, J=4.70 Hz, 1H). m/z (ESI) 300.2 (M+H)$^+$.

STEP 4: 4-CHLORO-5-METHYLQUINOLINE-7-SULFONYL CHLORIDE

To a vial charged with 7-(benzylthio)-4-chloro-5-methylquinoline (35 mg, 0.117 mmol) was added acetonitrile (1099 µl), acetic acid (41.2 µl), and water (27.5 µl). The resulting solution was cooled in an ice water bath and 1,3-dichloro-5,5-dimethyl-2-imidazolidinedione (30.7 µl, 0.234 mmol) was added. After 10 min LC/MS indicated about a 1:1 mixture of product to sulfoxide intermediate. Another 10 min of stirring did not afford further conversion. Additional 1,3-dichloro-5,5-dimethyl-2-imidazolidinedione (30.7 µl, 0.234 mmol) was added while the mixture was still stirring at 0° C. After 10 min LC/MS indicated complete conversion to desired product. The mixture was diluted with EtOAc and extracted with H$_2$O. The aqueous phase was extracted again with EtOAc. The combined organics were dried under reduced pressure and purified with a 25 g HP silicycle column (SiliCycle, Inc. Quebec City, Canada) ramping EtOAc in heptane (0 to 35%, 5% DCM throughout) providing 4-chloro-5-methylquinoline-7-sulfonyl chloride (30 mg, 0.109 mmol, 93% yield) as a white solid. m/z (ESI) 276.0 (M+H)$^+$.

STEP 5: 4-CHLORO-N-(4-METHOXYBENZYL)-5-METHYL-N-(THIAZOL-2-YL)QUINOLINE-7-SULFONAMIDE

To a flask containing ice cold suspension of N-(4-methoxybenzyl)thiazol-2-amine (25.1 mg, 0.114 mmol) in THF (418 µl) was added lithium bis(trimethylsilyl)amide (1M in THF) (120 µl, 0.120 mmol) dropwise over 10 min. The mixture was stirred for 15 min prior to the drop wise addition of a solution of 4-chloro-5-methylquinoline-7-sulfonyl chloride (30 mg, 0.109 mmol) in THF (0.6 ml). After 30 min LC/MS indicated desired product and methanolysis of the sulfonyl chloride (about 1:1). Additional solid N-(4-methoxybenzyl) thiazol-2-amine (25.1 mg, 0.114 mmol) was added with stirring at room temperature. After 15 min, no further conversion had occurred. Additional LHMDS (0.5 eq) was added after cooling back to 0° C. and stirring continued. After 20 min, LC/MS indicated consumption of sulfonyl chloride (methanolysis) with product visible as a minor species. To the orange/brown solution was added acetic acid (300 µl) and the mixture dried under reduced pressure. The crude material was purified with a 25 g (25 µm spherical) silica column ramping EtOAc in heptane (0-50%, 5% DCM throughout) to provide 4-chloro-N-(4-methoxybenzyl)-5-methyl-N-(thiazol-2-yl)quinoline-7-sulfonamide (6 mg, 0.013 mmol, 12.01% yield) as a white solid. m/z (ESI) 460.3 (M+H)$^+$.

STEP 6

EXAMPLE 282

4-(2-METHOXY-4-(TRIFLUOROMETHYL)PHENYL)-5-METHYL-N-(THIAZOL-2-YL)QUINOLINE-7-SULFONAMIDE

To a microwave vial charged with (2-methoxy-4-(trifluoromethyl)phenyl)boronic acid (3.16 mg, 0.014 mmol), 4-chloro-N-(4-methoxybenzyl)-5-methyl-N-(thiazol-2-yl)quinoline-7-sulfonamide (6 mg, 0.013 mmol), potassium phosphate tribasic (3.24 µl, 0.039 mmol) and 1,1-bis[(di-t-butyl-p-methylaminophenyl]palladium(ii) chloride (0.924 mg, 1.304 µmol) was added dioxane (52.3 µl) and water (17.44 µl). The mixture was irradiated at 100° C. for 30 min affording conversion to desired product according to LC-MS, 4-(2-methoxy-4-(trifluoromethyl)phenyl)-N-(4-methoxybenzyl)-5-methyl-N-(thiazol-2-yl)quinoline-7-sulfonamide. m/z (ESI) 600.2 (M+H)+. The mixture was dried under reduced pressure. To the crude oil was added DCM (0.9 ml) and TFA (0.3 ml) was added at room temperature. After 1 hr of stirring, LC/MS indicated complete PMB cleavage. The mixture was dried under reduced pressure and purified with a 25 g (15 µm spherical silica) column ramping EtOAc in heptane (0 to 100%, 10% DCM throughout) providing product, obtained as a film. The material was lyophilized from MeOH/H$_2$O providing 4-(2-methoxy-4-(trifluoromethyl)phenyl)-5-methyl-N-(thiazol-2-yl)quinoline-7-sulfonamide (2 mg, 4.17 µmol, 32.0% yield) as a yellow film. $^1$H NMR (500 MHz, DMSO-d$_6$) δ ppm 3.75 (s, 3H) 6.86 (d, J=4.59 Hz, 1H) 7.28 (d, J=4.59 Hz, 1H) 7.38 (d, J=4.27 Hz, 1H) 7.41-7.48 (m, 2H) 7.49 (s, 1H) 7.63 (s, 1H) 8.32-8.39 (m, 1H) 8.99 (d, J=4.27 Hz, 1H). m/z (ESI) 480.2 (M+H)+.

EXAMPLE 283

3-AMINO-4-(2-METHOXY-4-(TRIFLUOROMETHYL)PHENYL)-N-(THIAZOL-2-YL)QUINOLINE-7-SULFONAMIDE

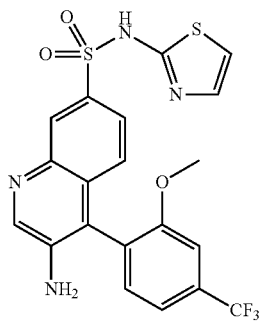 [SMILES: COc1cc(C(F)(F)F)ccc1-c1c(N)cnc2cc(S(=O)(=O)Nc3nccs3)ccc12]

A round-bottom flask was charged with 3-amino-4-(2-methoxy-4-(trifluoromethyl)phenyl)-N-(4-methoxybenzyl)-N-(thiazol-2-yl)quinoline-7-sulfonamide (Intermediate NNNN; 42.59 mg, 0.071 mmol), DCM (1 mL) and TFA (0.5 mL). The mixture was stirred for 1 h, then diluted with MeOH and concentrated. The residue was taken up in DCM and loaded onto a 500-mg SCX-2 ion exchange column (Biotage, LLC). The column was eluted with MeOH, then with 2N ammonia in methanol. The basic fractions were combined and concentrated. The residue was concentrated from DCM to give 3-amino-4-(2-methoxy-4-(trifluoromethyl)phenyl)-N-(thiazol-2-yl)quinoline-7-sulfonamide (30 mg, 0.062 mmol, 88% yield) as a light-yellow solid: $^1$H NMR (400 MHz, DMSO-d$_6$) δ ppm=12.72 (br. s., 1H), 8.65 (s, 1H), 8.22 (d, J=2.0 Hz, 1H), 7.59 (dd, J=2.0, 8.9 Hz, 1H), 7.52-7.44 (m, 2H), 7.42-7.35 (m, 1H), 7.24 (d, J=4.7 Hz, 1H), 7.08 (d, J=8.9 Hz, 1H), 6.81 (d, J=4.6 Hz, 1H), 5.62 (s, 2H), 3.75 (s, 3H); m/z (ESI) 481.2 (M+H)+.

EXAMPLE 284

3-CYANO-4-(2-METHOXY-4-(TRIFLUOROMETHYL)PHENYL)-N-(THIAZOL-2-YL)QUINOLINE-7-SULFONAMIDE

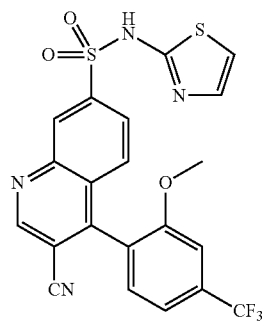 [SMILES: COc1cc(C(F)(F)F)ccc1-c1c(C#N)cnc2cc(S(=O)(=O)Nc3nccs3)ccc12]

A vial was charged with 3-amino-4-(2-methoxy-4-(trifluoromethyl)phenyl)-N-(4-methoxybenzyl)-N-(thiazol-2-yl)quinoline-7-sulfonamide (Intermediate NNNN; 70.9 mg, 0.118 mmol), copper(i) cyanide (21.14 mg, 0.236 mmol), and DMSO (0.5 mL) to give a dark brown solution. The vial was flushed with Ar (g), then sealed and lowered into a 60° C. heating bath. After 5 min, tert-butyl nitrite, 90% (46.8 µl, 0.354 mmol) was added drop wise, and the vial was resealed. After 50 min of heating, the mixture was cooled, then diluted with water and EtOAc. The aq. layer was extracted with water (3×, an emulsion stayed with the organic layer). The organic layer was then washed with brine (cleared the emulsion), dried over sodium sulfate, filtered, and concentrated to give 75 mg of a brown solid. The mixture was taken up in DCM (1 mL) and TFA (0.5 mL). After 25 min, the mixture was diluted with MeOH, then concentrated. The residue was purified by chromatography on silica gel (12-g column, 50 to 100% EtOAc/Heptane) to give about 15 mg of a brown solid containing about 60% desired product. The material was repurified by chromatography on silica gel (12-g column, 25 to 75% EtOAc/Heptane) to give 4.41 mg of the title compound as a light-yellow solid: $^1$H NMR (400 MHz, chloroform-d) δ ppm=9.17 (s, 1H), 8.80 (d, J=1.7 Hz, 1H), 8.00 (dd, J=1.9, 8.8 Hz, 1H), 7.69 (d, J=8.8 Hz, 1H), 7.46 (dd, J=0.7, 7.9 Hz, 1H), 7.40-7.34 (m, 2H), 7.21 (d, J=4.6 Hz, 1H), 6.60 (d, J=4.6 Hz, 1H), 3.83 (s, 3H); m/z (ESI) 491.2 (M+H)+.

EXAMPLE 285

4-(2-METHOXY-4-(TRIFLUOROMETHYL)PHENYL)-N-(PYRIMIDIN-4-YL)ISOQUINOLINE-7-SULFONAMIDE HYDROCHLORIDE

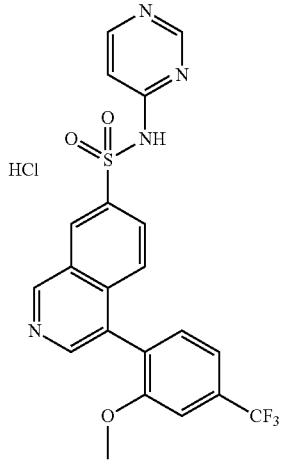 [SMILES: Cl ; COc1cc(C(F)(F)F)ccc1-c1cncc2cc(S(=O)(=O)Nc3ccncn3)ccc12]

To a microwave vial charged with 2-methoxy-4-(trifluoromethyl)phenyl boronic acid (Combi-Blocks, San Diego, Calif.) (0.014 g, 0.063 mmol), 4-bromo-N-(pyrimidin-4-yl)isoquinoline-7-sulfonamide (Intermediate OOOO) (0.023 g, 0.063 mmol), and potassium phosphate tribasic (0.016 ml, 0.189 mmol) was added dioxane (0.253 ml) and water (0.084 ml). The mixture was purged with argon prior to the addition of 1,1-bis[(di-t-butyl-p-methylaminophenyl]palladium(II) chloride (4.46 mg, 6.30 µmol). The mixture was irradiated at 100° C. in a microwave for 30 min. The mixture was loaded directly onto a load column and purified with a 25 g HP spherical silica column (15 µm) ramping DCM:MeOH (90:10) in DCM affording product which had coeluted with a minor impurity. The fractions were filtered through a 2 g PE-AX column (Biotage AB, Uppsala, Sweden) washing with MeOH, then 3% conc. HCl in MeOH providing 4-(2-methoxy-4-(trifluoromethyl)phenyl)-N-(pyrimidin-4-yl)isoquinoline-7-sulfonamide hydrochloride (21 mg, 0.042 mmol, 67.1% yield) as a white solid. $^1$H NMR (400 MHz, DMSO-d$_6$) δ ppm 7.01 (d, J=6.75 Hz, 1H) 7.50-7.56 (m, 2H) 7.57-7.63 (m, 1H) 7.71 (d, J=8.90 Hz, 1H) 8.21-8.28 (m, 2H) 8.60 (s, 1H) 8.65 (s, 1H) 9.02 (d, J=1.76 Hz, 1H) 9.84 (s, 1H). m/z (ESI) 461.2 (M+H)$^+$.

EXAMPLE 286

4-(4-CYANO-2-METHOXYPHENYL)-N-(PYRIMIDIN-4-YL)ISOQUINOLINE-7-SULFONAMIDE HYDROCHLORIDE

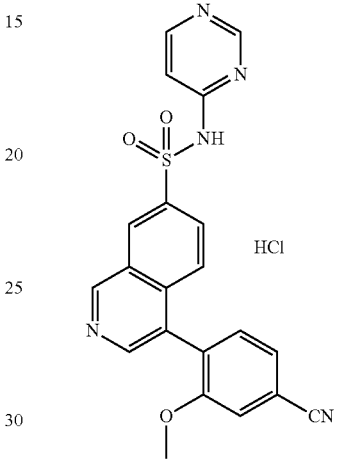

To a microwave vial charged with 3-methoxy-4-(4,4,5,5-tetramethyl-1,3,2-dioxaborolan-2-yl)benzonitrile (Intermediate GGGG) (0.035 g, 0.136 mmol), 4-bromo-N-(pyrimidin-4-yl)isoquinoline-7-sulfonamide (Intermediate OOOO) (0.045 g, 0.123 mmol), and potassium phosphate tribasic (0.031 ml, 0.370 mmol) was added dioxane (0.494 ml) and water (0.165 ml). The mixture was purged with argon prior to the addition of 1,1-bis[(di-t-butyl-p-methylaminophenyl]palladium(II) chloride (8.72 mg, 0.012 mmol). The mixture was irradiated at 100° C. in a microwave for 30 min. The mixture was directly loaded onto a load column and purified with a 25 g (15 µm spherical silica) column ramping DCM:MeOH (90:10) in DCM (0 to 100%) providing product which had coeluted with minor impurities. The mixture was repurified with a 2 g PE-AX column (Biotage AB, Uppsala, Sweden) washing with MeOH then 3% HCl in MeOH. The acidic wash was dried under reduced pressure providing product as a white solid which was lyophilized from MeOH/H$_2$O to afford 4-(4-cyano-2-methoxyphenyl)-N-(pyrimidin-4-yl)isoquinoline-7-sulfonamide hydrochloride (23 mg, 41%) as a fluffy white solid. $^1$H NMR (400 MHz, DMSO-d$_6$) δ ppm 3.76 (br. s., 3H) 7.01 (d, J=6.46 Hz, 1H) 7.54-7.59 (m, 1H) 7.61-7.69 (m, 2H) 7.76 (d, J=1.37 Hz, 1H) 8.21 (dd, J=8.90, 1.86 Hz, 1H) 8.25 (d, J=6.85 Hz, 1H) 8.59-8.62 (m, 2H) 8.98 (d, J=1.76 Hz, 1H) 9.78 (s, 1H). m/z (ESI) 418.2 (M+H)+.

EXAMPLE 287

4-(2-METHOXYPHENYL)-N-(PYRIMIDIN-4-YL)ISOQUINOLINE-7-SULFONAMIDE HYDROCHLORIDE

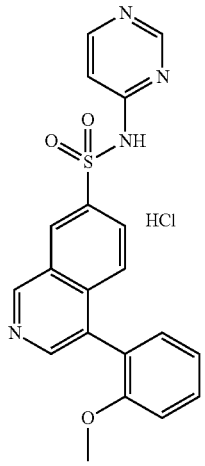 [SMILES: COc1ccccc1-c1cncc2cc(S(=O)(=O)Nc3ccncn3)ccc12 ; Cl]

To a microwave vial charged with (2-methoxyphenyl)boronic acid (Sigma Aldrich, St. Louis, Mo.) (0.021 g, 0.136 mmol), 4-bromo-N-(pyrimidin-4-yl)isoquinoline-7-sulfonamide (Intermediate OOOO; 0.045 g, 0.123 mmol), and potassium phosphate tribasic (0.031 ml, 0.370 mmol) was added dioxane (0.494 ml) and water (0.165 ml). The mixture was purged with argon prior to the addition of 1,1-bis[(di-t-butyl-p-methylaminophenyl]palladium(II) chloride (8.72 mg, 0.012 mmol). The mixture was irradiated at 100° C. for 30 min. The organics were decanted, the aqueous rinsed with EtOAc and the organics combined and dried under reduced pressure. The crude material was dissolved in DMSO (2 ml) and purified with preparative RP-HPLC ramping ACN in H2O (25 to 70%, 0.1% TFA throughout) affording product separation. The product containing eluents was dried under reduced pressure and free-based by loading onto a 2 g SCX-2 column, washing with MeOH, then 2M NH3 in MeOH to afford product, along with minor impurities. The basic wash was dried under reduced pressure and the material was subjected to PE-AX column (Biotage AB, Uppsala, Sweden) purification, washing with MeOH, then 3% HCl in MeOH. The acidic wash was dried under reduced pressure and lyophilized from MeOH/H2O to provide 4-(2-methoxyphenyl)-N-(pyrimidin-4-yl)isoquinoline-7-sulfonamide hydrochloride (23 mg, 0.054 mmol, 43.5% yield) as an off-white solid. 1H NMR (400 MHz, DMSO-d6) δ ppm 7.00 (d, J=6.46 Hz, 1H) 7.13-7.19 (m, 1H) 7.27 (d, J=8.41 Hz, 1H) 7.35 (dd, J=5.33, 2.01 Hz, 1H) 7.51-7.61 (m, 1H) 7.72 (d, J=8.90 Hz, 1H) 8.19-8.30 (m, 2H) 8.55-8.63 (m, 2H) 9.01 (d, J=1.76 Hz, 1H) 9.81 (s, 1H). m/z (ESI) 393.2 (M+H)+.

EXAMPLE 288

4-(2-METHOXY-4-(TRIFLUOROMETHYL)PHENYL)-N-(THIAZOL-2-YL)ISOQUINOLINE-7-SULFONAMIDE

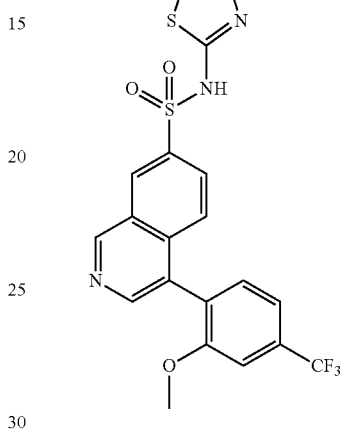

A microwave vial charged with 4-bromo-N-(4-methoxybenzyl)-N-(thiazol-2-yl)isoquinoline-7-sulfonamide (Intermediate PPPP) (0.066 g, 0.135 mmol), 2-methoxy-4-(trifluoromethyl)phenylboronic acid (Combi-Blocks, San Diego, Calif.) (0.044 g, 0.202 mmol), potassium carbonate (0.093 g, 0.673 mmol), dioxane (0.673 ml) and water (0.224 ml) was purged with argon prior to the addition of Pd(PPh3)4 (0.016 g, 0.013 mmol). The vessel was sealed and irradiated at 100° C. for 30 min. The resulting mixture was diluted with EtOAc and extracted with water, the aqueous phase was extracted with EtOAc and the combined organics were dried under reduced pressure. To the crude brown oil was added DCM (3 ml) and TFA (1 ml) and the resulting solution stirred overnight at RT affording conversion to desired product. The mixture was dried under reduced pressure and purified with a 25 g HP spherical silica gel (Interchim, Mouintlucon, France, 15 μm) ramping EtOAc in heptane (0 to 50%, 10% DCM isocratic throughout) providing product as a film which was lyophilized from MeOH/H2O to provide 4-(2-methoxy-4-(trifluoromethyl)phenyl)-N-(thiazol-2-yl)isoquinoline-7-sulfonamide (38 mg, 0.082 mmol, 60.7% yield) as a white solid. 1H NMR (400 MHz, DMSO-d6) δ ppm 6.87 (d, J=4.60 Hz, 1H) 7.28 (d, J=4.60 Hz, 1H) 7.46-7.53 (m, 2H) 7.54-7.59 (m, 1H) 7.61 (d, J=8.90 Hz, 1H) 8.02 (dd, J=8.85, 1.91 Hz, 1H)

8.53 (s, 1H) 8.75 (d, J=1.56 Hz, 1H) 9.55-9.66 (m, 1H) 12.88 (br. s., 1H). m/z (ESI) 466.2 (M+H)$^+$.

EXAMPLE 289

4-(2-methoxyphenyl)-N-(thiazol-2-yl)isoquinoline-7-sulfonamide

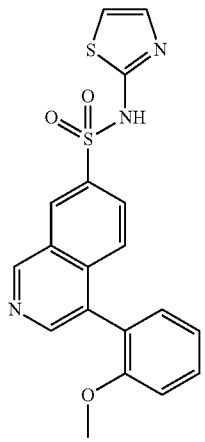 [SMILES: COc1ccccc1-c1cncc2cc(S(=O)(=O)Nc3nccs3)ccc12]

To a microwave vial charged with (2-methoxyphenyl)boronic acid (25.6 mg, 0.168 mmol), 4-bromo-N-(4-methoxybenzyl)-N-(thiazol-2-yl)isoquinoline-7-sulfonamide (Intermediate PPPP) (75 mg, 0.153 mmol), and potassium phosphate tribasic (38.0 µl, 0.459 mmol) was added dioxane (613 µl) and water (204 µl). The mixture was purged with argon prior to the addition of 1,1-bis[(di-t-butyl-p-methylaminophenyl]palladium(II) chloride (10.83 mg, 0.015 mmol). The mixture was irradiated at 100° C. in a microwave for 30 min. The organics were decanted, the aqueous rinsed with EtOAc and the organics combined and dried under reduced pressure. The crude material was dissolved in DCM (1.5 ml) and TFA (0.5 ml) was added and the mixture shaken at room temperature for 2 hrs. The resulting mixture was dried under reduced pressure and purified with a 25 g Interchim HP spherical silica column (Interchim, Mouintlucon, France) (15 µm) ramping EtOAc in heptane (0 to 100%, 10% DCM throughout) with product eluting at 100% polar eluent to afford 4-(2-methoxyphenyl)-N-(thiazol-2-yl)isoquinoline-7-sulfonamide (40 mg, 0.101 mmol, 65.8% yield) as an off-white solid. $^1$H NMR (400 MHz, DMSO-d$_6$) δ ppm 6.87 (d, J=4.60 Hz, 1H) 7.08-7.16 (m, 1H) 7.22 (d, J=8.22 Hz, 1H) 7.25-7.35 (m, 2H) 7.48-7.55 (m, 1H) 7.61 (d, J=8.90 Hz, 1H) 8.00 (dd, J=8.85, 1.91 Hz, 1H) 8.48 (s, 1H) 8.71 (d, J=1.76 Hz, 1H) 9.55 (s, 1H) 12.87 (br. s., 1H). m/z (ESI) 398.2 (M+H)$^+$.

EXAMPLE 290

4-(4-FLUORO-2-METHOXYPHENYL)-N-(THIAZOL-2-YL)ISOQUINOLINE-7-SULFONAMIDE

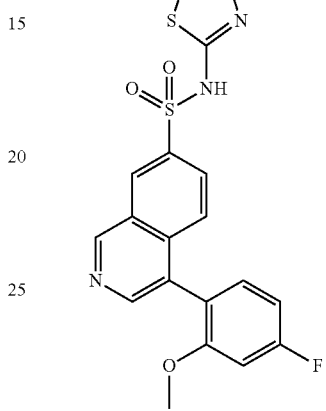

Example 290 was synthesized in a similar manner to Example 289, using (4-fluoro-2-methoxyphenyl)boronic acid instead of (2-methoxyphenyl)boronic acid to afford 4-(4-fluoro-2-methoxyphenyl)-N-(thiazol-2-yl)isoquinoline-7-sulfonamide (56 mg, 0.135 mmol, 88% yield) as a white solid. $^1$H NMR (400 MHz, DMSO-d$_6$) δ ppm 3.68 (s, 3H) 6.87 (d, J=4.60 Hz, 1H) 6.96 (td, J=8.41, 2.45 Hz, 1H) 7.15 (dd, J=11.40, 2.40 Hz, 1H) 7.28 (d, J=4.60 Hz, 1H) 7.35 (dd, J=8.31, 6.94 Hz, 1H) 7.61 (d, J=8.90 Hz, 1H) 8.00 (dd, J=8.90, 1.96 Hz, 1H) 8.46 (s, 1H) 8.71 (d, J=1.66 Hz, 1H) 9.55 (s, 1H) 12.87 (s, 1H). m/z (ESI) 416.2 (M+H)$^+$.

EXAMPLE 291

8-(2-METHOXY-4-(TRIFLUOROMETHYL)PHENYL)-N-(THIAZOL-2-YL)-1,7-NAPHTHYRIDINE-3-SULFONAMIDE

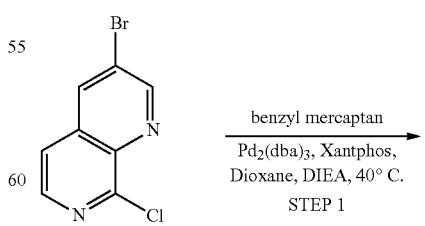

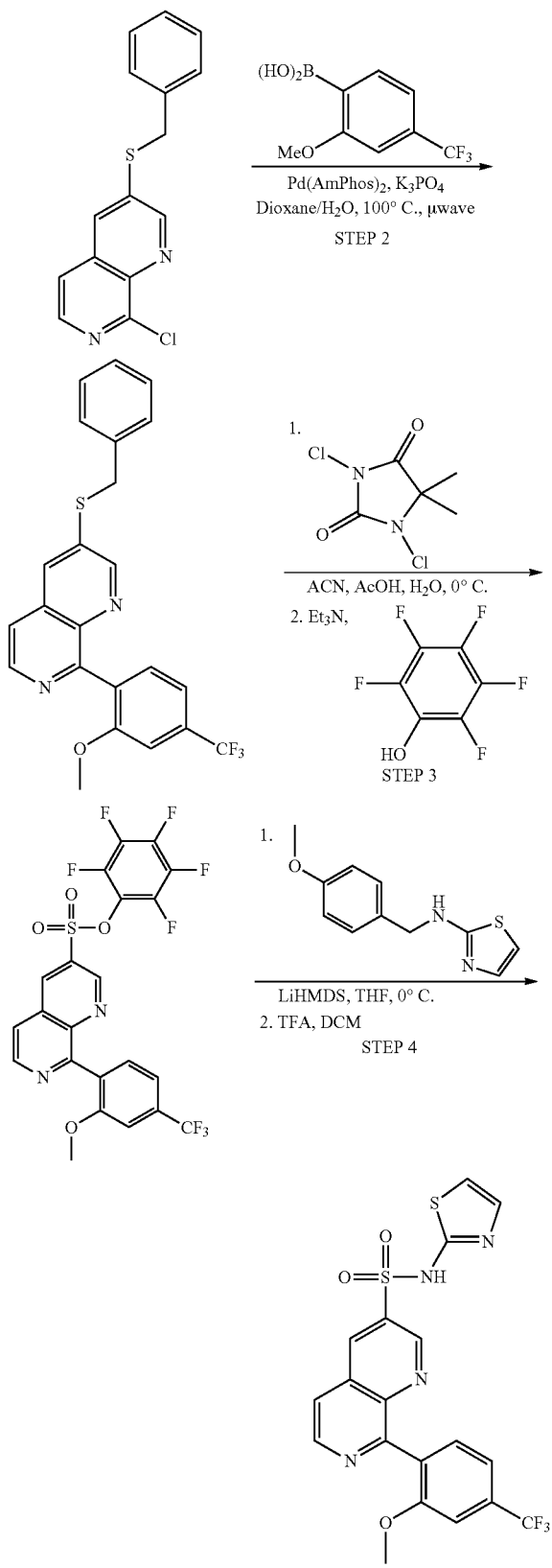

STEP 1:
3-(BENZYLTHIO)-8-CHLORO-1,7-NAPHTHYRIDINE

To a vial charged with 3-bromo-8-chloro-1,7-naphthyridine (Anichem, North Brunswick, N.J.) (360 mg, 1.479 mmol) was added dioxane (5914 µl), DIEA (516 µl, 2.96 mmol), Xantphos (171 mg, 0.296 mmol), Pd$_2$(dba)$_3$ (135 mg, 0.148 mmol) and benzyl mercaptan (184 µl, 1.552 mmol). The vessel was sealed and heated to 40° C. overnight. The mixture was cooled to RT, filtered through diatomaceous earth and dried under reduced pressure. The crude residue was purified with a 25 g silicycle HP column (25 µm spherical silica) ramping EtOAc in heptane (0 to 100%, 10% DCM throughout) to provide 3-(benzylthio)-8-chloro-1,7-naphthyridine (0.218 g, 0.760 mmol, 51.4% yield) as a light yellow solid. m/z (ESI) 287.1 (M+H)$^+$.

STEP 2: 3-(BENZYLTHIO)-8-(2-METHOXY-4-(TRIFLUOROMETHYL)PHENYL)-1,7-NAPHTHYRIDINE

To a vial charged with 2-methoxy-4-(trifluoromethyl)phenyl boronic acid (Combi-Blocks, San Diego, Calif.) (0.268 g, 1.216 mmol), 3-(benzylthio)-8-chloro-1,7-naphthyridine (0.218 g, 0.760 mmol), and potassium phosphate tribasic (0.189 ml, 2.280 mmol) was added dioxane (3.05 ml) and water (1.016 ml). The mixture was purged with argon prior to the addition of 1,1-bis[(di-t-butyl-p-methylaminophenyl]palladium(II) chloride (0.054 g, 0.076 mmol). The vessel was sealed and heated to 60° C. overnight. After cooling to ambient temperature, the mixture was loaded directly onto a silica gel loading column and purified with a 40 g HP spherical column (silicycle) (SiliCycle, Inc. Quebec City, Canada) ramping EtOAc in heptane (0 to 35%, then isocratic at 35%) to provide 3-(benzylthio)-8-(2-methoxy-4-(trifluoromethyl)phenyl)-1,7-naphthyridine (0.295 g, 0.692 mmol, 91% yield) as an off-white foam. m/z (ESI) 427.3 (M+H)$^+$.

STEP 3: PERFLUOROPHENYL 8-(2-METHOXY-4-(TRIFLUOROMETHYL)PHENYL)-1,7-NAPHTHYRIDINE-3-SULFONATE

To a vial charged with 3-(benzylthio)-8-(2-methoxy-4-(trifluoromethyl)phenyl)-1,7-naphthyridine (0.295 g, 0.692 mmol) was added acetonitrile (3.26 ml), acetic acid (0.122 ml) and water (0.081 ml). The resulting solution was cooled in an ice water bath prior to the addition of 1,3-dichloro-5,5-dimethylhydantoin (0.068 ml, 0.519 mmol). After 90 min of stirring (ice melt) LC/MS indicated fairly clean conversion to sulfonyl chloride. To the mixture was added 2,3,4,5,6-pentafluorophenol (0.036 ml, 0.346 mmol) followed by the drop wise addition of triethylamine (0.193 ml, 1.384 mmol). After 15 min LC/MS indicated complete conversion to product. The yellow solution was diluted with EtOAc and extracted with water. The aqueous phase was extracted with EtOAc and the combined organics were dried with Na$_2$SO$_4$, filtered, dried under reduced pressure and the crude oil purified with a 40 g silicycle HP column (SiliCycle, Inc. Quebec City, Canada) ramping EtOAc in heptane (0 to 65%, 5% DCM throughout) to afford perfluorophenyl 8-(2-methoxy-4-(trifluoromethyl)phenyl)-1,7-naphthyridine-3-sulfonate (0.145 g, 0.263 mmol, 76% yield) as a white foam. $^1$H NMR (400 MHz, CHLOROFORM-d) δ ppm 7.30 (s, 1H) 7.45 (dt, J=7.78, 0.81 Hz, 1H) 7.60-7.65 (m, 1H) 7.89 (d, J=5.77 Hz, 1H) 8.90 (d, J=2.35 Hz, 1H) 8.95 (d, J=5.58 Hz, 1H) 9.36 (d, J=2.35 Hz, 1H). m/z (ESI) 551.2 (M+H)$^+$.

STEP 4: 8-(2-METHOXY-4-(TRIFLUOROMETHYL)PHENYL)-N-(THIAZOL-2-YL)-1,7-NAPHTHYRIDINE-3-SULFONAMIDE

To a vial charged with N-(4-methoxybenzyl)thiazol-2-amine (29.4 mg, 0.134 mmol) was added THF (509 µl) and the resulting suspension cooled in an ice water bath prior to the drop wise addition of lithium bis(trimethylsilyl)amide, 1.0 m solution in tetrahydrofuran (134 µl, 0.134 mmol) affording a light red suspension. The mixture was stirred for 20 min at 0° C. prior to the addition, faster than drop wise, of a solution of perfluorophenyl 8-(2-methoxy-4-(trifluoromethyl)phenyl)-1,7-naphthyridine-3-sulfonate (70 mg, 0.127 mmol) in THF (0.5 ml, 0.1 ml rinse). The resulting mixture was allowed to stir and warm slowly to room temp (ice melt) for 1 hr. To the solution was added acetic acid (about 10 drops) and the resulting solution was dried under reduced pressure. To the residue was added DCM (2 ml) and TFA (0.5 ml) and the solution stirred at room temperature for 1 hr. The mixture was dried under reduced pressure and purified with a HP spherical silica column (15 µm spherical, Interchim, Mouintlucon, France) ramping DCM:MeOH (90:10) in DCM (0 to 50%, then isocratic at 50%) to provide product which had eluted with minor impurities. The material was repurified with catch and release using a 1 g PE-AX column (Biotage AB, Uppsala, Sweden) washing with MeOH then 10% v/v conc. HCl in MeOH. The acidic wash was dried under reduced pressure then filtered through a 2 g Si-carbonate column to free-base. The film obtained was lyophilized from MeOH/H$_2$O affording product 8-(2-methoxy-4-(trifluoromethyl)phenyl)-N-(thiazol-2-yl)-1,7-naphthyridine-3-sulfonamide (7 mg, 0.015 mmol, 11.80% yield) as a yellow solid. $^1$H NMR (500 MHz, DMSO-d$_6$) δ ppm 3.69 (s, 3H) 6.60 (d, J=3.85 Hz, 1H) 7.01 (d, J=3.85 Hz, 1H) 7.38-7.46 (m, 2H) 7.52 (d, J=7.91 Hz, 1H) 8.13 (d, J=5.45 Hz, 1H) 8.71 (d, J=5.45 Hz, 1H) 8.81 (d, J=1.82 Hz, 1H) 9.13 (d, J=1.92 Hz, 1H). m/z (ESI) 467.2 (M+H)$^+$.

EXAMPLE 292

8-(2-METHOXY-4-(TRIFLUOROMETHYL)PHENYL)-N-(PYRIMIDIN-4-YL)-1,7-NAPHTHYRIDINE-3-SULFONAMIDE

To a vial charged with N-(4-methoxybenzyl)pyrimidin-4-amine (Intermediate OO; 28.7 mg, 0.134 mmol) was added THF (509 µl) and the resulting clear solution cooled in an ice water bath prior to the drop wise addition of lithium bis (trimethylsilyl)amide, 1.0M solution in tetrahydrofuran (26.0 µl, 0.134 mmol). The mixture was stirred for 20 min at 0° C. prior to the addition, faster than drop wise, of a solution of perfluorophenyl 8-(2-methoxy-4-(trifluoromethyl)phenyl)-1,7-naphthyridine-3-sulfonate (see EXAMPLE 322, STEP 3) (70 mg, 0.127 mmol) in THF (0.5 ml, 0.1 ml rinse). The resulting mixture was allowed to stir and warm slowly to room temp (ice melt) for 1 hr. To the mixture was added acetic acid (about 10 drops) and the resulting solution dried under reduced pressure. The crude residue was purified with a 25 g HP Silicycle column (SiliCycle, Inc. Quebec City, Canada) (0-100% EtOAc in heptane). The crude oil obtained (52 mg) was dissolved in DCM (3 ml) and TFA (0.5 ml) was added and the mixture stirred overnight at room temperature. The material was purified with a 25 g HP spherical silica column (15 µm spherical, Interchim, Mouintlucon, France) ramping DCM:MeOH (90:10) in DCM (0 to 50%) providing product, obtained as a film which was lyophilized from MeOH/H$_2$O to afford 8-(2-methoxy-4-(trifluoromethyl)phenyl)-N-(pyrimidin-4-yl)-1,7-naphthyridine-3-sulfonamide (3 mg, 6.50 mmol, 5.11% yield) as a white powder. $^1$H NMR (500 MHz, DMSO-d$_6$) δ ppm 3.69 (s, 3H) 6.77 (d, J=6.41 Hz, 1H) 7.39-7.47 (m, 2H) 7.54 (d, J=7.91 Hz, 1H) 8.08 (d, J=6.30 Hz, 1H) 8.16 (d, J=5.56 Hz, 1H) 8.44 (s, 1H) 8.75 (d, J=5.56 Hz, 1H) 8.97 (s, 1H) 9.23 (d, J=1.82 Hz, 1H). m/z (ESI) 462.2 (M+H)$^+$.

EXAMPLE 293

1-(2-METHOXY-4-(TRIFLUOROMETHYL)PHENYL)-4-OXO-N-(THIAZOL-2-YL)-3,4-DIHYDROPHTHALAZINE-6-SULFONAMIDE

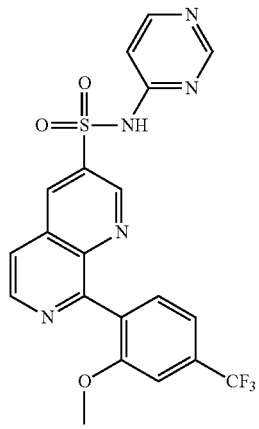 [SMILES: COc1cc(C(F)(F)F)ccc1-c1nccc2cc(S(=O)(=O)Nc3ccncn3)cnc12]

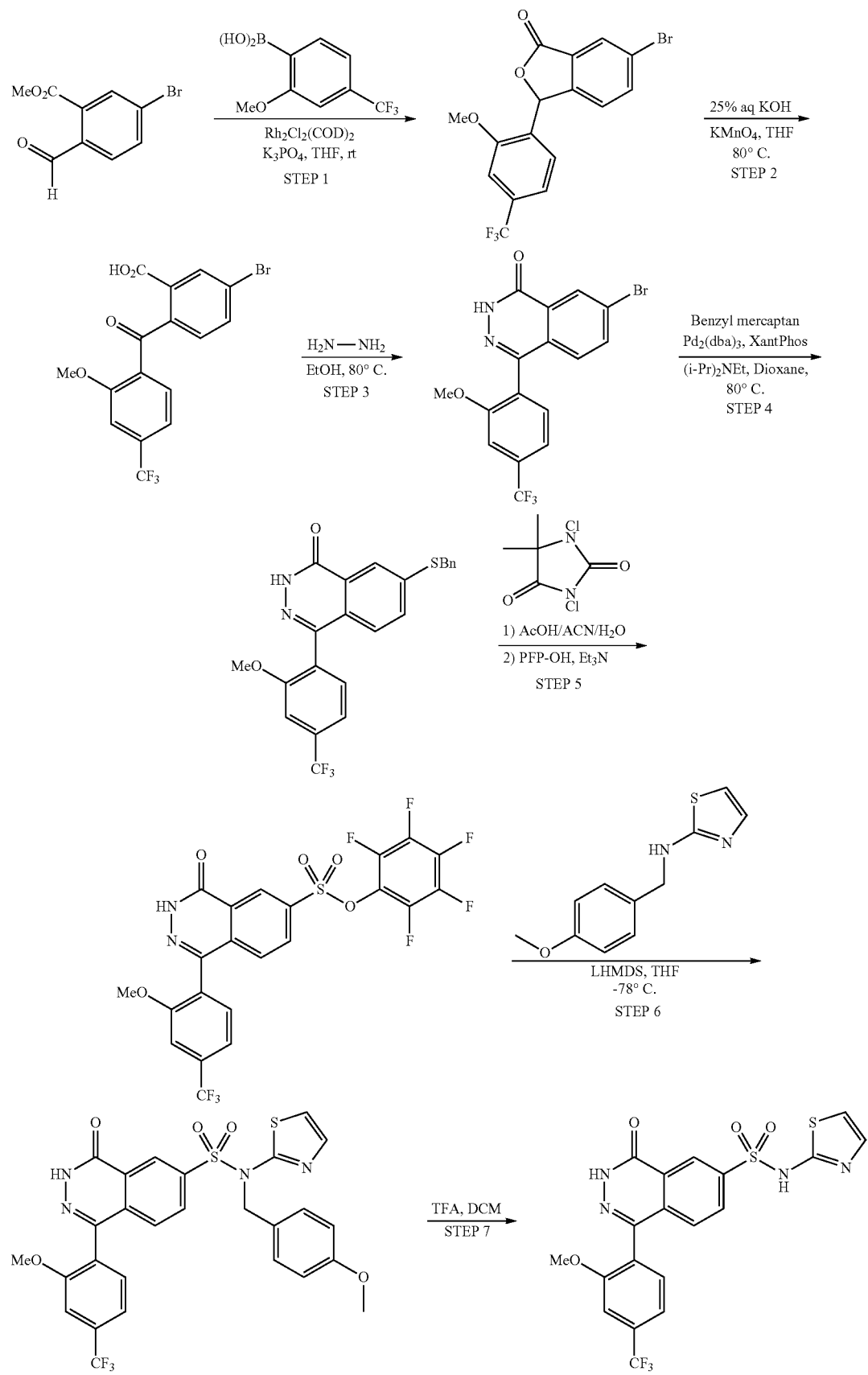

STEP 1: 6-BROMO-3-(2-METHOXY-4-(TRIFLUO-ROMETHYL)PHENYL)ISOBENZOFURAN-1(3H)-ONE

2-Methoxy-4-(trifluoromethyl)phenyl boronic acid (2.05 g, 9.32 mmol; Combi-Blocks, San Diego, Calif.), methyl 5-bromo-2-formylbenzoate (1.51 g, 6.21 mmol; GLSyntech, LLC, Hatfield, Pa.), tripotassium phosphate (5.27 g, 24.9 mmol; freshly ground) and THF (31.1 mL) was added to a vial. The vial was purged with argon. Then chloro(1,5-cyclooctadiene)rhodium(i) dimer (0.153 g, 0.311 mmol; Strem Chemicals, Inc., Newburyport, Mass.) was added. The vial was sealed and stirred at RT. After 1 h, the reaction was filtered and the filtrate was concentrated under a vacuum. The crude material was absorbed onto a plug of silica gel and purified by chromatography through a silica gel column (80 g), eluting with a gradient of 0% to 10% EtOAc in heptane, to provide 6-bromo-3-(2-methoxy-4-(trifluoromethyl)phenyl)isobenzofuran-1(3H)-one (2.06 g, 86% yield) as a brown solid. $^1$H NMR (400 MHz, CDCl$_3$) δ ppm 3.92 (s, 3H), 6.72 (s, 1H), 7.11-7.17 (m, 3H), 7.25 (dt, J=8.2, 0.7 Hz, 1H), 7.65 (dd, J=8.3, 1.7 Hz, 1H), 8.00 (d, J=1.8 Hz, 1H). m/z (ESI) 405.0 (M+H)$^+$. This lactone was not stable on MS.

STEP 2: 5-BROMO-2-(2-METHOXY-4-(TRIFLUO-ROMETHYL)BENZOYL)BENZOIC ACID

To a stirred mixture of 6-bromo-3-(2-methoxy-4-(trifluoromethyl)phenyl)isobenzofuran-1(3H)-one (2.06 g, 5.32 mmol) in KOH (21.3 mL, 5.32 mmol, 25% aqueous solution) and pyridine (10.6 mL) in a pressure tube was added powder potassium permanganate (1.26 g, 7.98 mmol). The reaction was heated at 100° C. After 4 h, the reaction was cooled to RT and the mixture was filtered, and the residue was washed with water. The filtrate was acidified with concentrated HCl until a pH of about 2. The white solid that precipitated out of the solution was filtered off with the aid of water and dried to afford 5-bromo-2-(2-methoxy-4-(trifluoromethyl)benzoyl)benzoic acid (2.16 g, 100% yield). This material was carried on to the next step. m/z (ESI) 405.0 (M+H)$^+$.

STEP 3: 7-BROMO-4-(2-METHOXY-4-(TRIFLUO-ROMETHYL)PHENYL)PHTHALAZIN-1(2H)-ONE

In a screw-cap vial, a mixture 5-bromo-2-(2-methoxy-4-(trifluoromethyl)benzoyl)benzoic acid (2.16 g, 5.36 mmol), hydrazine (0.504 mL, 16.1 mmol), and ethanol (10.7 mL) was heated at 80° C. After 1 h, a light yellow solid precipitated out of the reaction and the reaction was cooled to RT. The solids were filtered with the aid of Et$_2$O and dried to afford a first batch of product as a white solid (1.14 g). The filtrate was concentrated and was absorbed onto a plug of silica gel and purified by chromatography through a silica gel column (40 g), eluting with a gradient of 0% to 20% EtOAc in heptane, to provide a second batch as a white solid (0.41 g). Overall, 7-bromo-4-(2-methoxy-4-(trifluoromethyl)phenyl)phthalazin-1(2H)-one (1.55 g, 73% yield) was obtained. $^1$H NMR (500 MHz, DMSO-d$_6$) δ ppm 3.79 (s, 3H), 7.23 (d, J=8.65 Hz, 1H), 7.45-7.52 (m, 1H), 7.60 (d, J=7.69 Hz, 1H), 7.99 (dd, J=8.66, 2.14 Hz, 1H), 8.39 (d, J=2.03 Hz, 1H). m/z (ESI) 399.0 (M+H)$^+$.

STEP 4: 7-(BENZYLTHIO)-4-(2-METHOXY-4-(TRIFLUOROMETHYL)PHENYL)PH-THALAZIN-1(2H)-ONE

To a pressure tube containing a solution of 7-bromo-4-(2-methoxy-4-(trifluoromethyl)phenyl)phthalazin-1(2H)-one (1.14 g, 2.86 mmol) and N,N-diisopropylethylamine (0.99 mL, 5.71 mmol) in 1,4-dioxane (20 mL) was added XantPhos (0.083 g, 0.143 mmol) and tris(dibenzylideneacetone) dipalladium (0) (0.065 g, 0.071 mmol) followed by (mercaptomethyl)benzene (0.352 mL, 3.00 mmol). The reaction tube was purged with nitrogen. The tube was sealed and heated at 80° C. for 30 min. After cooling to RT, the reaction was filtered over a pad of diatomaceous earth, rinsing well with EtOAc. The filtrate was concentrated. The crude material was absorbed onto a plug of silica gel and purified by chromatography through a silica gel column (120 g), eluting with a gradient of 0% to 50% EtOAc in heptane, to provide 7-(benzylthio)-4-(2-methoxy-4-(trifluoromethyl)phenyl)phthalazin-1(2H)-one (0.76 g, 60% yield) as a yellow solid. $^1$H NMR (500 MHz, CDCl$_3$) δ ppm 3.77 (s, 3H), 4.44 (s, 2H), 7.15 (d, J=8.55 Hz, 1H), 7.21-7.28 (m, 1H), 7.32 (t, J=7.43 Hz, 2H), 7.40-7.50 (m, 4H), 7.57 (d, J=7.69 Hz, 1H), 7.72 (dd, J=8.60, 2.08 Hz, 1H), 8.11 (d, J=1.92 Hz, 1H), 12.85 (s, 1H). m/z (ESI) 443.0 (M+H)$^+$.

STEP 5: PERFLUOROPHENYL 1-(2-METHOXY-4-(TRIFLUOROMETHYL)PHENYL)-4-OXO-3,4-DIHYDROPHTHALAZINE-6-SULFONATE

A round-bottom flask was charged with 7-(benzylthio)-4-(2-methoxy-4-(trifluoromethyl)phenyl)phthalazin-1(2H)-one (0.73 g, 1.650 mmol), acetonitrile (15.5 mL), acetic acid (0.58 mL), and water (0.39 mL) to give a yellow suspension. More MeCN (82 mL) was added. The flask was sonicated to give a yellow suspension. The flask was cooled in an ice-bath for 30 min, then 1,3-dichloro-5,5-dimethylimidazolidine-2,4-dione (0.650 g, 3.30 mmol; Aldrich, St. Louis, Mo.) was added in one portion. The reaction became a light brown suspension within 20 min. After 20 min, 2,3,4,5,6-pentafluorophenol (0.607 g, 3.30 mmol) was added at 0° C. followed by drop wise addition of triethylamine (0.920 mL, 6.60 mmol). After 15 min, the reaction mixture was diluted with EtOAc (50 mL) and washed with water (2×10 mL), washed with brine, dried over sodium sulfate, filtered, and concentrated. The crude material was absorbed onto a plug of silica gel and purified by chromatography through a silica gel column (120 g), eluting with a gradient of 0% to 30% EtOAc in heptane, to provide perfluorophenyl 1-(2-methoxy-4-(trifluoromethyl)phenyl)-4-oxo-3,4-dihydrophthalazine-6-sulfonate (0.81 g, 87% yield) as a white solid. $^1$H NMR (400 MHz, CDCl$_3$) δ ppm 3.15 ppm (s, 1H), 7.31 (s, 1H), 7.45 (d, J=7.8 Hz, 1H), 7.57 (d, J=8.5 Hz, 2H), 8.27 (dd, J=8.6, 2.1 Hz, 1H), 9.10 (d, J=2.1 Hz, 1H), 10.46 (br s, 1H). $^{19}$F NMR (Bruker 376 MHz, CDCl$_3$) δ ppm −150.48 (d, J=15 Hz, 2F), −154.14 (t, J=22.6 Hz, 1F), −160.28 (dd, J=22.6, 15 Hz, 2F). m/z (ESI) 567.0 (M+H)$^+$.

STEP 6: 1-(2-METHOXY-4-(TRIFLUOROM-ETHYL)PHENYL)-N-(4-METHOXYBENZYL)-4-OXO-N-(THIAZOL-2-YL)-3,4-DIHYDRO-PHTHALAZINE-6-SULFONAMIDE

A round-bottom flask was charged with N-(4-methoxybenzyl)thiazol-2-amine (46.7 mg, 0.212 mmol) and THF (1.2 mL) to give a clear solution. The flask was cooled in a dry ice-acetone bath for 5 min to give a suspension. Lithium bis(trimethylsilyl)amide (212 µl, 0.212 mmol, 1M in THF) was added drop wise to give a light yellow solution. The mixture was stirred for 15 min. Then, a solution of perfluorophenyl 1-(2-methoxy-4-(trifluoromethyl)phenyl)-4-oxo-3,4-dihydrophthalazine-6-sulfonate (100 mg, 0.177 mmol) in THF (1.2 mL) was added drop wise. After 1.5 h, more LHMDS (450 μL, 1M in THF) was added at −78° C. After 1 h, the reaction was quenched with saturated aqueous ammonium chloride at −78° C. The reaction was warmed to RT. The product was extracted with EtOAc and the organic extract was dried over sodium sulfate, filtered, and concentrated. The residue was purified by chromatography on silica gel (40-g column, 20 to 50% EtOAc/Heptane) to give 1-(2-methoxy-4-(trifluoromethyl)phenyl)-N-(4-methoxybenzyl)-4-oxo-N-(thiazol-2-yl)-3,4-dihydrophthalazine-6-sulfonamide (40 mg, 38% yield) as an off-white solid. $^1$H NMR (500 MHz, DMSO-d$_6$) δ ppm 3.68 (s, 3H), 3.80 (s, 3H), 5.06 (s, 2H), 6.81 (m, J=8.66 Hz, 2H), 7.21 (m, J=8.66 Hz, 2H), 7.45-7.54 (m, 4H), 7.62 (d, J=7.69 Hz, 1H), 8.13 (dd, J=8.60, 2.08 Hz, 1H), 8.53 (d, J=1.82 Hz, 1H), 13.24 (s, 1H). m/z (ESI) 603.0 (M+H)$^+$.

STEP 7: 1-(2-METHOXY-4-(TRIFLUOROMETHYL)PHENYL)-N-(4-METHOXYBENZYL)-4-OXO-N-(THIAZOL-2-YL)-3,4-DIHYDROPHTHALAZINE-6-SULFONAMIDE 1-(2-Methoxy-4-(trifluoromethyl)phenyl)-N-(4-methoxybenzyl)-4-oxo-N-(thiazol-2-yl)-3,4-dihydrophthalazine-6-sulfonamide (40 mg, 0.066 mmol) was dissolved in DCM (664 μl) and then TFA (25.6 μl, 0.332 mmol) was added at RT. After stirring for 30 min, the reaction was quenched with saturated aqueous NaHCO$_3$ (1 mL). A white solid precipitated out of the solution and was filtered off with the aid of water. The solid was washed with 3 mL of water and dried to afford the product 1-(2-methoxy-4-(trifluoromethyl)phenyl)-4-oxo-N-(thiazol-2-yl)-3,4-dihydrophthalazine-6-sulfonamide (16 mg, 50% yield). $^1$H NMR (500 MHz, DMSO-d$_6$) δ ppm 3.78 (s, 3H), 6.83 (d, J=4.38 Hz, 1H), 7.24 (d, J=4.49 Hz, 1H), 7.41-7.53 (m, 3H), 7.60 (d, J=7.80 Hz, 1H), 8.15 (dd, J=8.49, 1.87 Hz, 1H), 8.63 (d, J=1.82 Hz, 1H), 13.10 (s, 1H). m/z (ESI) 483.0 (M+H)$^+$.

EXAMPLE 294

4-(2-METHOXY-4-(TRIFLUOROMETHYL)PHENYL)-N-(THIAZOL-2-YL)-1,6-NAPHTHYRIDINE-7-SULFONAMIDE

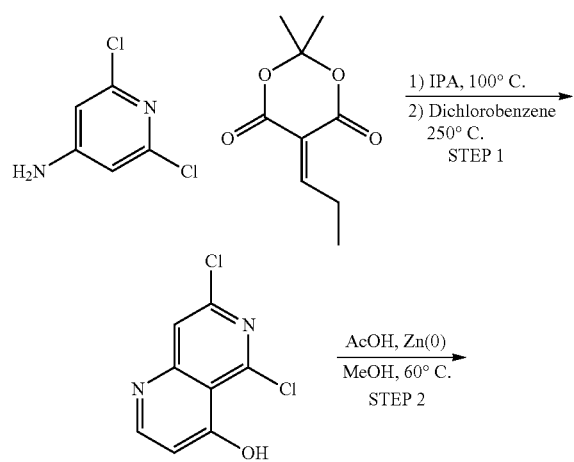

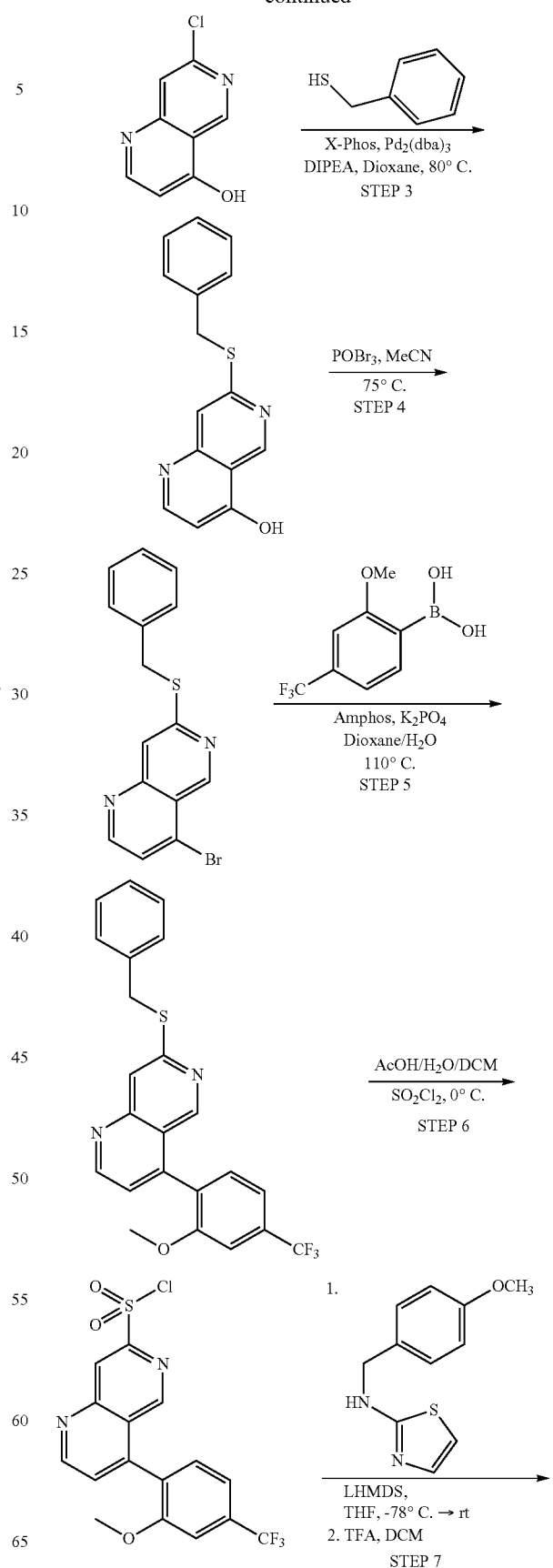

-continued

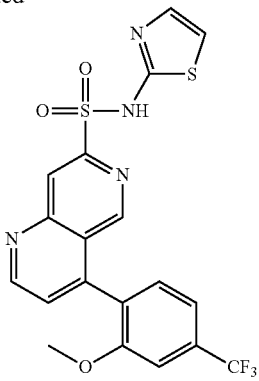

STEP 1
5,7-DICHLORO-1,6-NAPHTHYRIDIN-4-OL

To a flask equipped with a reflux condenser, 2,6-dichloropyridin-4-amine (2.00 g, 12.27 mmol) and 5-(methoxymethylene)-2,2-dimethyl-1,3-dioxane-4,6-dione (2.398 g, 12.88 mmol) were dissolved in IPA (12.00 mL) and heated to 100° C. for 1 hour. The reaction was cooled to room temperature and the solids were filtered. The solids were added to a microwave vial followed by dichlorobenzene (12.00 mL). The vial was capped and heated to 250° C. for 15 minutes. The reaction was purified via silica gel MPLC chromatography (40 g), eluting with 0 to 100% ethyl acetate in heptanes. The fractions were collected and the solvent was removed under reduced pressure to provide 1.63 g of 5,7-dichloro-1,6-naphthyridin-4-ol as an off white solid. m/z (ESI) 215.1 (M+H)+.

STEP 2: 7-CHLORO-1,6-NAPHTHYRIDIN-4-OL 5,7-dichloro-1,6-naphthyridin-4-ol (1.6 g, 7.44 mmol) was added to a round bottom flask, followed by zinc (2.432 g, 37.2 mmol) and MeOH (44.6 mL). Acetic acid (glacial) (4.26 mL, 74.4 mmol) was added and the reaction was heated to 60° C. for 16 hours. The solids were filtered and washed with MeOH (20 mL). The filtrate was concentrated under reduced pressure to provide 1.03 g of 7-chloro-1,6-naphthyridin-4-ol as a white solid which was used without further purification. m/z (ESI) 181.2 (M+H)+.

STEP 3:
7-(BENZYLTHIO)-1,6-NAPHTHYRIDIN-4-OL

A screw cap vial was charged with 7-chloro-1,6-naphthyridin-4-ol (0.500 g, 2.77 mmol), Xantphos (0.080 g, 0.138 mmol), tris(dibenzylideneacetone)dipalladium (0.063 g, 0.069 mmol), 1,4-dioxane (5.54 mL) and DIPEA (0.963 mL, 5.54 mmol). The vial was purged with argon, sealed and heated to 80° C. for 10 minutes. The reaction was cooled to room temperature and benzyl mercaptan (0.385 mL, 3.25 mmol) was added and the reaction was continued heating at 80° C. for an additional 30 minutes. The reaction was cooled to room temperature, diluted with water and extracted with DCM (3×). The combined organics were washed with water and brine, dried over magnesium sulfate, filtered and concentrated. The resulting material was concentrated, dissolved in minimal DCM and purified via column chromatography (silica gel 40 g, gradient elution 0 to 50% EtOAc:Heptane) to afford 0.168 g of 7-(benzylthio)-1,6-naphthyridin-4-ol. m/z (ESI) 269.1 (M+H)+.

STEP 4:
7-(BENZYLTHIO)-4-BROMO-1,6-NAPHTHYRIDINE

To a flask fitted with a reflux condenser was added 7-(benzylthio)-1,6-naphthyridin-4-ol (0.160 g, 0.596 mmol) followed by acetonitrile (2 mL) and phosphorous oxybromide (0.121 mL, 1.193 mmol). The reaction was heated to 65° C. for 1 hour. The reaction was cooled to room temperature and quenched with aqueous sodium bicarbonate (20 mL) and was washed with DCM (20 mL×3). The organic layers were combined, dried over magnesium sulfate, filtered and concentrated. The resulting material was purified via silica gel MPLC (40 g), eluting with 0% to 100% ethyl acetate in heptanes. The fractions were collected and the solvent was removed under reduced pressure to provide 0.145 g of 7-(benzylthio)-4-bromo-1,6-naphthyridine as a yellow solid. m/z (ESI) 333.0 (M+H)+.

STEP 5: 7-(BENZYLTHIO)-4-(2-METHOXY-4-(TRIFLUOROMETHYL)PHENYL)-1,6-NAPHTHYRIDINE

A screw capped vial was charged with 2-methoxy-4-(trifluoromethyl)phenyl boronic acid (0.096 g, 0.438 mmol), 7-(benzylthio)-4-bromo-1,6-naphthyridine (0.145 g, 0.438 mmol), and potassium phosphate tribasic (0.279 ml, 1.313 mmol). Dioxane (1.756 ml) and water (0.585 ml) were added and the vial was purged with argon, followed by addition of Pd(AmPhos)$_2$Cl$_2$ (0.019 g, 0.026 mmol). The vial was capped and heated to 110° C. After 3 hours, the reaction was cooled to room temperature, diluted with water (30 mL), and washed with ethyl acetate (20 mL×3). The organic layers were combined, dried over magnesium sulfate, filtered and concentrated. The resulting material was purified via silica gel MPLC chromatography (40 g), eluting with 0 to 100% ethyl acetate in heptanes. The fractions were collected and the solvent was removed under reduced pressure to provide 0.129 g of 7-(benzylthio)-4-(2-methoxy-4-(trifluoromethyl)phenyl)-1,6-naphthyridine as an off white solid. m/z (ESI) 427.2 (M+H)+.

STEP 6: 4-(2-METHOXY-4-(TRIFLUOROMETHYL)PHENYL)-1,6-NAPHTHYRIDINE-7-SULFONYL CHLORIDE

A round bottomed flask cooled to 0° C., was charged with 7-(benzylthio)-4-(2-methoxy-4-(trifluoromethyl)phenyl)-1,6-naphthyridine (0.129 g, 0.302 mmol), DCM (2.88 ml), acetic acid (0.072 ml), and water (0.072 ml). After stirring for 5 minutes at 0° C., sulfuryl chloride (0.025 ml, 0.302 mmol) was added and stirring was continued for an additional 1 hour at 0° C. The reaction was concentrated, dissolved in minimal DCM and purified via column chromatography (silica gel 40 g, gradient elution 0 to 50% EtOAc:Heptane) to afford 0.093 g of 4-(2-methoxy-4-(trifluoromethyl)phenyl)-1,6-naphthyridine-7-sulfonyl chloride as an off white solid. m/z (ESI) 402.9 (M+H)+.

STEP 7: 4-(2-METHOXY-4-(TRIFLUOROMETHYL)PHENYL)-N-(THIAZOL-2-YL)-1,6-NAPHTHYRIDINE-7-SULFONAMIDE

A round-bottom flask was charged with N-(4-methoxybenzyl)thiazol-2-amine (0.048 g, 0.218 mmol) and THF (1.00 mL), and the vessel was cooled to −78° C. for 15 minutes. LHMDS (1.0 M in THF) (0.238 ml, 0.238 mmol) was then added drop wise over 1 minute. The reaction was stirred for 10 minutes, and then a solution of 4-(2-methoxy-4-(trifluoromethyl)phenyl)-1,6-naphthyridine-7-sulfonyl chloride (0.080 g, 0.199 mmol) in THF (1.00 mL) was added drop wise. The bath was removed, and the resulting mixture was stirred for 45 minutes. The reaction was diluted with saturated ammonium chloride (aq.) solution (30 mL), and was washed with ethyl acetate (20 mL×3). The organic layers were combined, dried over magnesium sulfate, filtered and concentrated. The resulting material was purified via silica gel MPLC chromatography (40 g), eluting with 0 to 100% ethyl acetate in heptanes. The fractions were concentrated under reduced pressure and the resulting material was taken up in DCM (10 mL) and TFA (1 mL) was added. The reaction was stirred for 2 hours and then the solvent was removed under reduced pressure. The resulting material was taken up in DCM (30 mL) and washed with aqueous sodium bicarbonate (sat. solution). The organic layer was dried over magnesium sulfate, filtered and concentrated. The resulting solid was triturated with diethyl ether (20 mL) and filtered. The solid was dried under reduced pressure to provide 0.018 g of 4-(2-methoxy-4-(trifluoromethyl)phenyl)-N-(thiazol-2-yl)-1,6-naphthyridine-7-sulfonamide as an off white solid. $^1$H NMR (400 MHz, DMSO-$d_6$) δ ppm 3.86 (s, 3H) 6.94 (d, J=4.60 Hz, 1H) 7.34 (d, J=4.60 Hz, 1H) 7.56-7.62 (m, 2H) 7.69 (d, J=7.73 Hz, 1H) 7.81 (d, J=4.50 Hz, 1H) 8.47-8.51 (m, 1H) 8.98-9.02 (m, 1H) 9.36 (d, J=4.50 Hz, 1H) 12.99 (br. s., 1H). m/z (ESI) 467.1 (M+H)$^+$.

EXAMPLE 295

1-((1-METHYL-1H-1,2,4-TRIAZOL-5-YL)METHOXY)-N-(PYRIMIDIN-4-YL)ISOQUINOLINE-6-SULFONAMIDE

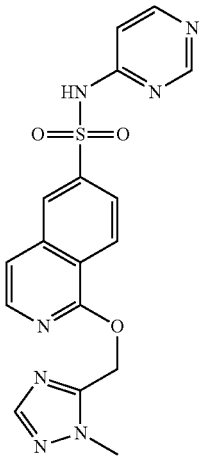 [SMILES: Cn1ncnc1COc1nccc2cc(S(=O)(=O)Nc3ccncn3)ccc12]

Example 327 was synthesized in a similar manner to Example 160, using (1-methyl-1H-1,2,4-triazol-5-yl)methanol (Aldrich, St. Louis, Mo.) (28 mg, 0.248 mmol) instead of (5-phenyloxazol-4-yl)methanol, affording 1-((1-methyl-1H-1,2,4-triazol-5-yl)methoxy)-N-(pyrimidin-4-yl)isoquinoline-6-sulfonamide (45.6 mg, 71%). $^1$H NMR (500 MHz, DMSO-$d_6$) δ ppm 3.99 (s, 3H) 5.70 (s, 2H) 6.90-7.01 (m, 1H) 7.68 (d, J=5.84 Hz, 1H) 7.92 (s, 1H) 8.00 (d, J=8.59 Hz, 1H) 8.14 (d, J=5.84 Hz, 1H) 8.20 (d, J=5.90 Hz, 1H) 8.30 (d, J=8.65 Hz, 1H) 8.48-8.59 (m, 2H). m/z (ESI) 397.9 (M+H)$^+$.

EXAMPLE 296

1-(2-(1H-1,2,3-TRIAZOL-1-YL)ETHOXY)-N-(PYRIMIDIN-4-YL)ISOQUINOLINE-6-SULFONAMIDE

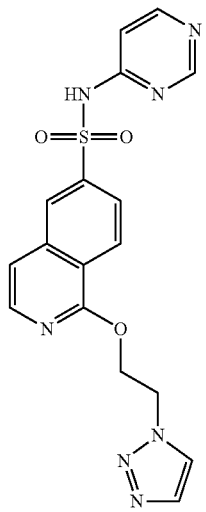 [SMILES: O=S(=O)(Nc1ccncn1)c1ccc2c(OCCn3ccnn3)nccc2c1]

Example 296 was synthesized in a similar manner to Example 130, using 2-(1H-1,2,3-triazol-1-yl)ethanol (Sigma Aldrich, St. Louis, Mo.) (28 mg, 0.248 mmol) instead of (5-phenyloxazol-4-yl)methanol, affording 1-(2-(1H-1,2,3-triazol-1-yl)ethoxy)-N-(pyrimidin-4-yl)isoquinoline-6-sulfonamide (29.7 mg, 46%). $^1$H NMR (500 MHz, DMSO-$d_6$) δ ppm 4.86 (d, J=4.41 Hz, 2H) 4.92 (d, J=4.64 Hz, 2H) 6.89 (d, J=6.19 Hz, 1H) 7.61 (d, J=5.73 Hz, 1H) 7.72 (s, 1H) 7.96 (d, J=8.88 Hz, 1H) 8.08 (d, J=5.79 Hz, 1H) 8.11-8.18 (m, 2H) 8.27 (s, 1H) 8.46 (d, J=9.45 Hz, 2H). m/z (ESI) 397.9 (M+H)⁺.

EXAMPLE 297

1-((6,7-DIHYDRO-5H-PYRAZOLO[5,1-B][1,3]OXAZIN-2-YL)METHOXY)-N-(PYRIMIDIN-4-YL)ISOQUINOLINE-6-SULFONAMIDE

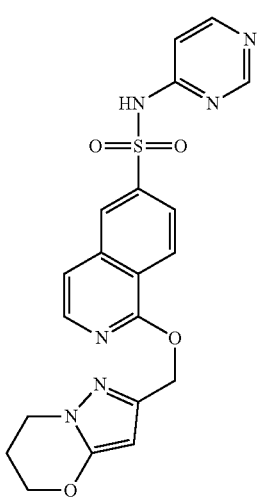 [SMILES: O=S(=O)(Nc1ccncn1)c1ccc2c(OCc3cc4n(n3)CCCO4)nccc2c1]

Example 297 was synthesized in a similar manner to Example 130, using (6,7-dihydro-5H-pyrazolo[5,1-b][1,3]oxazin-2-yl)methanol (Princeton BioMolecular Research, Inc., Monmouth Junction, N.J.) (38 mg, 0.248 mmol) instead of (5-phenyloxazol-4-yl)methanol, affording 1-((6,7-dihydro-5H-pyrazolo[5,1-b][1,3]oxazin-2-yl)methoxy)-N-(pyrimidin-4-yl)isoquinoline-6-sulfonamide (32.7 mg, 47%). ¹H NMR (500 MHz, DMSO-d₆) δ ppm 2.13-2.21 (m, 2H) 4.07 (t, J=6.07 Hz, 2H) 4.17-4.34 (m, 2H) 5.34 (s, 2H) 5.62 (s, 1H) 6.95 (d, J=6.24 Hz, 1H) 7.62 (d, J=5.84 Hz, 1H) 7.98 (d, J=8.65 Hz, 1H) 8.13 (d, J=5.84 Hz, 1H) 8.16-8.29 (m, 2H) 8.51 (s, 1H) 8.48 (s, 1H). m/z (ESI) 439.0 (M+H)⁺.

EXAMPLE 298

1-((2-MORPHOLINOPYRIDIN-3-YL)METHOXY)-N-(PYRIMIDIN-4-YL)ISOQUINOLINE-6-SULFONAMIDE

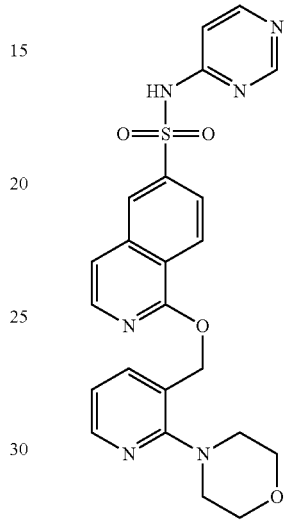

Example 298 was synthesized in a similar manner to Example 130, using (2-morpholinopyridin-3-yl)methanol (Sigma Aldrich) (48 mg, 0.248 mmol) instead of (5-phenyloxazol-4-yl)methanol, affording 1-((2-morpholinopyridin-3-yl)methoxy)-N-(pyrimidin-4-yl)isoquinoline-6-sulfonamide (7.6 mg, 10%). ¹H NMR (500 MHz, DMSO-d₆) δ ppm 3.07 (br. s., 4H) 3.75 (br. s., 4H) 5.34 (s, 2H) 6.75 (d, J=6.70 Hz, 1H) 7.02-7.05 (m, 1H) 7.33 (d, J=5.79 Hz, 2H) 7.53 (d, J=7.85 Hz, 1H) 7.94 (d, J=7.45 Hz, 1H) 8.21 (br. s., 1H) 8.33

(d, J=8.59 Hz, 1H) 8.38 (s, 1H) 8.61 (d, J=5.67 Hz, 1H) 8.77 (s, 1H) 11.59 (br. s., 1H). m/z (ESI) 479.2 (M+H)+.

EXAMPLE 299

1-(2,2-DIFLUORO-2-(TETRAHYDRO-2H-PYRAN-4-YL)ETHOXY)-N-(PYRIMIDIN-4-YL)ISOQUINOLINE-6-SULFONAMIDE

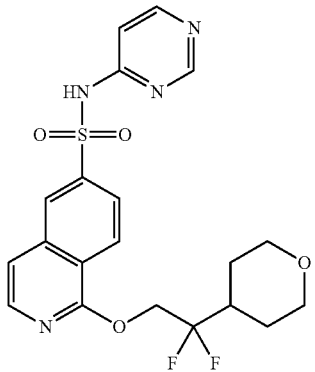 [SMILES: O=S(=O)(Nc1ccncn1)c1ccc2c(OCC(F)(F)C3CCOCC3)nccc2c1]

Example 299 was synthesized in a similar manner to Example 130, using 2,2-difluoro-2-(tetrahydro-2H-pyran-4-yl)ethanol (FSSI) (41 mg, 0.248 mmol) instead of (5-phenyloxazol-4-yl)methanol, affording 1-(2,2-difluoro-2-(tetrahydro-2H-pyran-4-yl)ethoxy)-N-(pyrimidin-4-yl)isoquinoline-6-sulfonamide (40 mg, 56%). $^1$H NMR (500 MHz, DMSO-d$_6$) δ ppm 1.47-1.59 (m, 2H) 1.72 (d, J=12.60 Hz, 2H) 3.87-3.96 (m, 2H) 4.83 (t, J=13.57 Hz, 2H) 6.88 (d, J=6.41 Hz, 1H) 7.68 (d, J=5.84 Hz, 1H) 8.03 (d, J=8.59 Hz, 1H) 8.14 (d, J=6.41 Hz, 1H) 8.11 (d, J=5.73 Hz, 1H) 8.29 (d, J=8.59 Hz, 1H) 8.49 (s, 1H) 8.46 (s, 1H). m/z (ESI) 451.3 (M+H)+.

EXAMPLE 300

1-(3-(6-METHYLPYRIDIN-2-YL)PROPOXY)-N-(PYRIMIDIN-4-YL)ISOQUINOLINE-6-SULFONAMIDE

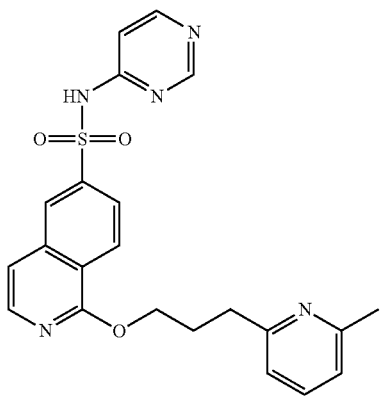 [SMILES: Cc1cccc(CCCOc2nccc3cc(S(=O)(=O)Nc4ccncn4)ccc23)n1]

Example 300 was synthesized in a similar manner to Example 130, using 3-(6-methylpyridin-2-yl)propan-1-ol (Matrix Scientific, Columbia, S.C.) (37 mg, 0.248 mmol) instead of (5-phenyloxazol-4-yl)methanol, affording 1-(3-(6-methylpyridin-2-yl)propoxy)-N-(pyrimidin-4-yl)isoquinoline-6-sulfonamide (9.8 mg, 14%). $^1$H NMR (500 MHz, DMSO-d$_6$) δ ppm 2.17-2.30 (m, 2H) 2.36-2.42 (s, 3H) 2.87-3.10 (m, 2H) 4.50 (t, J=6.21 Hz, 2H) 6.92-7.05 (m, 2H) 7.08 (d, J=7.39 Hz, 1H) 7.49-7.60 (m, 2H) 7.97 (d, J=8.42 Hz, 1H) 8.08 (d, J=5.84 Hz, 1H) 8.21 (d, J=8.65 Hz, 2H) 8.48 (s, 1H) 8.54 (s, 1H). m/z (ESI) 436.3 (M+H)+.

EXAMPLE 301

1-((4-(1H-IMIDAZOL-1-YL)BENZYL)OXY)-N-(PYRIMIDIN-4-YL)ISOQUINOLINE-6-SULFONAMIDE

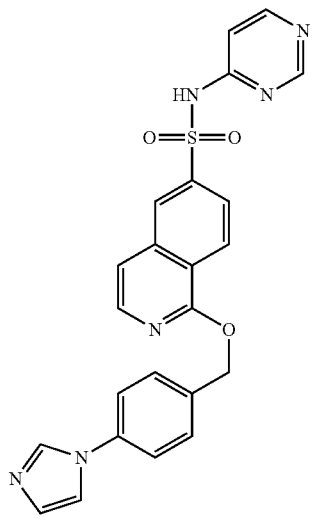 [SMILES: O=S(=O)(Nc1ccncn1)c1ccc2c(OCc3ccc(-n4ccnc4)cc3)nccc2c1]

Example 301 was synthesized in a similar manner to Example 130, using (4-(1H-imidazol-1-yl)phenyl)methanol (Sigma Aldrich, St. Louis, Mo.) (43 mg, 0.248 mmol) instead of (5-phenyloxazol-4-yl)methanol, affording 1-((4-(1H-imidazol-1-yl)benzyl)oxy)-N-(pyrimidin-4-yl)isoquinoline-6-sulfonamide (37.2 mg, 51%). $^1$H NMR (500 MHz, DMSO-d$_6$) δ ppm 5.62 (s, 2H) 6.86 (d, J=6.24 Hz, 1H) 7.11 (s, 1H) 7.62 (d, J=5.73 Hz, 1H) 7.68 (s, 4H) 7.75 (s, 1H) 8.00 (d, J=8.65 Hz, 1H) 8.12 (d, J=5.90 Hz, 2H) 8.26 (s, 1H) 8.31 (d, J=8.76 Hz, 1H) 8.45 (d, J=7.22 Hz, 2H). m/z (ESI) 459.4 (M+H)+.

EXAMPLE 302

N-(PYRIMIDIN-4-YL)-1-(3-(5-(TRIFLUOROMETHYL)-1H-PYRAZOL-4-YL)PROPOXY)ISOQUINOLINE-6-SULFONAMIDE

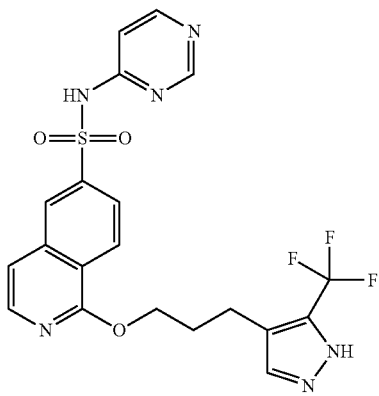 [SMILES: O=S(=O)(Nc1ccncn1)c1ccc2c(OCCCc3cn[nH]c3C(F)(F)F)nccc2c1]

Example 302 was synthesized in a similar manner to Example 130, using 3-(5-(trifluoromethyl)-1H-pyrazol-4-yl)propan-1-ol (Frontier Scientific, Logan, Utah) (48 mg, 0.248 mmol) instead of (5-phenyloxazol-4-yl)methanol, affording N-(pyrimidin-4-yl)-1-(3-(5-(trifluoromethyl)-1H-pyrazol-4-yl)propoxy)isoquinoline-6-sulfonamide (23.5 mg, 31%). $^1$H NMR (500 MHz, DMSO-$d_6$) δ ppm 1.76-1.84 (m, 2H) 2.69 (t, J=7.56 Hz, 2H) 3.49 (t, J=5.99 Hz, 2H) 4.56 (br. s., 1H) 6.94 (d, J=6.24 Hz, 1H) 8.09-8.21 (m, 2H) 8.26 (d, J=5.50 Hz, 1H) 8.51 (s, 1H) 8.53-8.62 (m, 2H) 8.64-8.74 (m, 2H). m/z (ESI) 478.9 (M+H)+.

EXAMPLE 303

1-(2-(1H-PYRROL-1-YL)ETHOXY)-N-(PYRIMIDIN-4-YL)ISOQUINOLINE-6-SULFONAMIDE

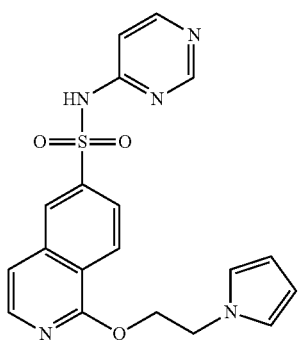 [SMILES: O=S(=O)(Nc1ccncn1)c1ccc2c(OCCn3cccc3)nccc2c1]

Example 303 was synthesized in a similar manner to Example 130, using 2-(1H-pyrrol-1-yl)ethanol (Sigma Aldrich, St. Louis, Mo.) (28 mg, 0.248 mmol) instead of (5-phenyloxazol-4-yl)methanol, affording 1-(2-(1H-pyrrol-1-yl)ethoxy)-N-(pyrimidin-4-yl)isoquinoline-6-sulfonamide (43.9 mg, 70%). $^1$H NMR (500 MHz, DMSO-$d_6$) δ ppm 4.39 (t, J=4.87 Hz, 2H) 4.67 (t, J=5.01 Hz, 2H) 5.98 (s, 2H) 6.87 (s, 2H) 6.97 (d, J=6.13 Hz, 1H) 7.61 (d, J=5.84 Hz, 1H) 8.00 (d, J=8.65 Hz, 1H) 8.09 (d, J=5.79 Hz, 1H) 8.21 (d, J=6.19 Hz, 1H) 8.28 (d, J=8.71 Hz, 1H) 8.49 (s, 1H) 8.53 (s, 1H). m/z (ESI) 396.4 (M+H)+.

EXAMPLE 304

1-((4-MORPHOLINOBENZYL)OXY)-N-(PYRIMIDIN-4-YL)ISOQUINOLINE-6-SULFONAMIDE

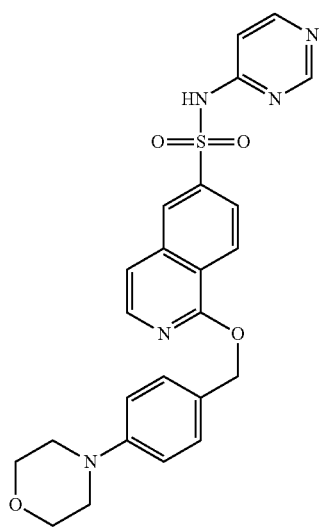 [SMILES: O=S(=O)(Nc1ccncn1)c1ccc2c(OCc3ccc(N4CCOCC4)cc3)nccc2c1]

Example 304 was synthesized in a similar manner to Example 130, using (4-morpholinophenyl)methanol (Sigma Aldrich, St. Louis, Mo.) (48 mg, 0.248 mmol) instead of (5-phenyloxazol-4-yl)methanol, affording 1-((4-morpholinobenzyl)oxy)-N-(pyrimidin-4-yl)isoquinoline-6-sulfonamide (13.4 mg, 18%). $^1$H NMR (500 MHz, DMSO-$d_6$) δ ppm 2.99-3.09 (m, 4H) 3.62-3.76 (m, 4H) 5.17 (s, 2H) 6.66 (d, J=6.93 Hz, 1H) 6.78 (d, J=8.53 Hz, 2H) 7.18 (d, J=8.36 Hz, 2H) 7.27 (t, J=6.44 Hz, 1H) 7.41 (d, J=6.47 Hz, 1H) 7.67 (d, J=8.36 Hz, 1H) 8.03 (s, 1H) 8.13-8.33 (m, 2H) 9.06 (s, 1H) 11.47 (br. s., 1H). m/z (ESI) 478.4 (M+H)⁺.

EXAMPLE 305

1-(2-(1-METHYL-1H-PYRAZOL-4-YL)ETHOXY)-N-(PYRIMIDIN-4-YL)ISOQUINOLINE-6-SULFONAMIDE

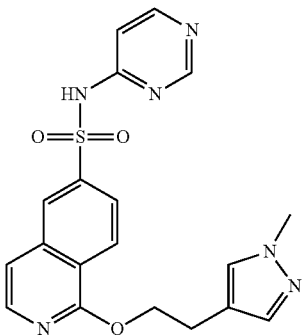 [SMILES: Cn1cc(CCOc2nccc3cc(S(=O)(=O)Nc4ccncn4)ccc23)cn1]

Example 305 was synthesized in a similar manner to Example 130, using 2-(1-methyl-1H-pyrazol-4-yl)ethanol (ChemBridge Corporation, San Diego, Calif.) (31 mg, 0.248 mmol) instead of (5-phenyloxazol-4-yl)methanol, affording 1-(2-(1-methyl-1H-pyrazol-4-yl)ethoxy)-N-(pyrimidin-4-yl)isoquinoline-6-sulfonamide (17.7 mg, 28%). $^1$H NMR (500 MHz, DMSO-$d_6$) δ ppm 2.88-3.10 (m, 2H) 3.77 (s, 3H) 4.57 (t, J=6.59 Hz, 2H) 6.96 (d, J=6.01 Hz, 1H) 7.36 (s, 1H) 7.52-7.64 (m, 2H) 8.00 (d, J=8.76 Hz, 1H) 8.09 (d, J=5.84 Hz, 1H) 8.20 (d, J=6.30 Hz, 1H) 8.30 (d, J=8.65 Hz, 1H) 8.48 (s, 1H) 8.52 (s, 1H). m/z (ESI) 411.1 (M+H)⁺.

EXAMPLE 306

1-(1-METHYL-1H-INDAZOL-7-YL)-N-(PYRIMIDIN-4-YL)ISOQUINOLINE-6-SULFONAMIDE

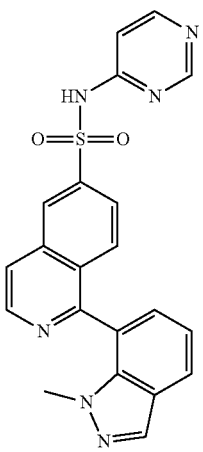 [SMILES: Cn1ncc2cccc(-c3nccc4cc(S(=O)(=O)Nc5ccncn5)ccc34)c21]

Example 306 was synthesized in in a similar manner to Example 65, except that (1-methyl-1H-indazol-7-yl)boronic acid used as boronic acid. $^1$H NMR (500 MHz, DMSO-$d_6$) δ ppm 8.74-8.83 (m, 3H) 8.58 (s, 1H) 8.19-8.30 (m, 4H) 7.96- 8.02 (m, 3H) 7.79 (d, J=8.82 Hz, 1H) 7.42 (d, J=6.87 Hz, 1H) 7.30 (t, J=7.50 Hz, 1H) 7.04 (d, J=5.61 Hz, 1H), 3.22 (s, 3H); m/z (ESI) 417.2 (M+H)⁺.

EXAMPLE 307

1-(1,4-DIMETHYL-1H-INDAZOL-5-YL)-N-(PYRIMIDIN-4-YL)ISOQUINOLINE-6-SULFONAMIDE

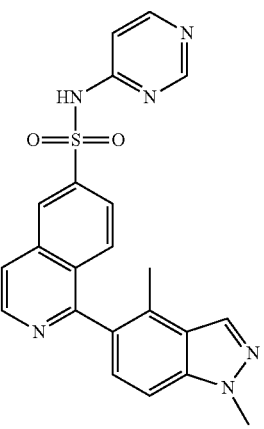 [SMILES: Cc1c(-c2nccc3cc(S(=O)(=O)Nc4ccncn4)ccc23)ccc2c1cnn2C]

Example 307 was synthesized in a similar manner to Example 65, except that (1,4-dimethyl-1H-indazol-5-yl)boronic acid was used as boronic acid. $^1$H NMR (500 MHz, DMSO-$d_6$) δ ppm 8.75-8.83 (m, 2H) 8.58 (s, 1H) 8.33 (d, J=5.84 Hz, 1H) 8.21-8.30 (m, 2H) 8.02 (d, J=8.82 Hz, 1H) 7.77 (d, J=8.94 Hz, 1H) 7.65 (d, J=8.71 Hz, 1H) 7.39 (d, J=8.59 Hz, 1H) 7.03 (br. s., 1H) 4.13 (s, 3H) 2.26 (s, 3H); m/z (ESI) 431.1 (M+H)⁺.

EXAMPLE 308

1-(1,6-DIMETHYL-1H-INDAZOL-5-YL)-N-(PYRIMIDIN-4-YL)ISOQUINOLINE-6-SULFONAMIDE

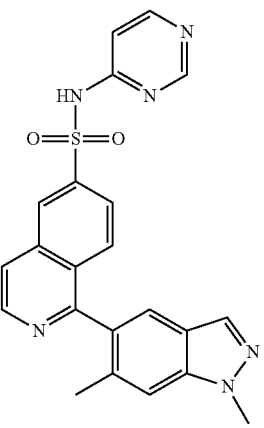 [SMILES: Cc1cc2c(cnn2C)cc1-c1nccc2cc(S(=O)(=O)Nc3ccncn3)ccc12]

Example 308 was synthesized in a similar manner to Example 65, except that (1,6-dimethyl-1H-indazol-5-yl)boronic acid was used as boronic acid. $^1$H NMR (500 MHz, DMSO-d$_6$) δ ppm 8.79 (d, J=5.61 Hz, 1H) 8.73 (s, 1H) 8.57 (s, 1H) 8.19-8.28 (m, 2H) 7.91 (d, J=8.82 Hz, 1H) 7.73 (d, J=8.71 Hz, 1H) 7.52 (d, J=9.05 Hz, 1H) 7.46 (d, J=8.59 Hz, 1H) 7.25 (s, 1H) 7.12 (s, 1H) 6.98-7.08 (m, 1H) 4.05-4.12 (m, 6H) 2.54 (s, 3H) 2.03 (s, 3H); m/z (ESI) 431.1 (M+H)$^+$.

EXAMPLE 309

1-(1,5-DIMETHYL-1H-INDAZOL-4-YL)-N-(PYRIMIDIN-4-YL)ISOQUINOLINE-6-SULFONAMIDE

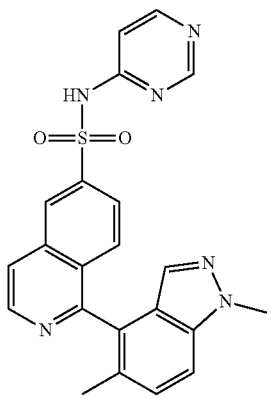 [SMILES: Cc1ccc2c(cnn2C)c1-c1nccc2cc(S(=O)(=O)Nc3ccncn3)ccc12]

Example 309 was synthesized in a similar manner to Example 65, except that (1,5-dimethyl-1H-indazol-4-yl)boronic acid was used as boronic acid. $^1$H NMR (500 MHz, DMSO-d$_6$) δ ppm 8.64 (d, J=5.61 Hz, 1H) 8.52 (s, 1H) 8.32 (s, 1H) 8.00-8.07 (m, 2H) 7.97 (d, J=5.96 Hz, 1H) 7.88 (d, J=8.71 Hz, 1H) 7.64 (d, J=3.09 Hz, 2H) 7.56 (d, J=8.82 Hz, 1H) 6.68 (d, J=5.96 Hz, 1H) 4.09 (s, 3H) 2.54 (s, 4H) 2.08 (s, 3H); m/z (ESI) 431.1 (M+H)$^+$.

EXAMPLE 310

N-(PYRIMIDIN-4-YL)-1-(QUINOLIN-8-YL)ISOQUINOLINE-6-SULFONAMIDE

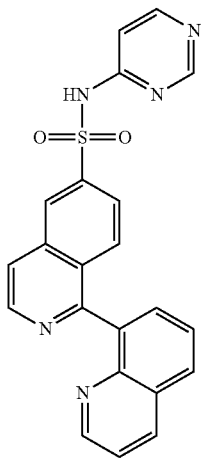 [SMILES: O=S(=O)(Nc1ccncn1)c1ccc2c(-c3cccc4cccnc34)nccc2c1]

Example 310 was synthesized in a similar manner to Example 65, except that quinolin-8-ylboronic acid was used as boronic acid. $^1$H NMR (400 MHz, DMSO-d$_6$) δ ppm 8.65-8.70 (m, 2H) 8.57 (s, 1H) 8.50 (dd, J=8.36, 1.71 Hz, 1H) 8.39 (s, 1H) 8.19 (dd, J=8.12, 1.66 Hz, 1H) 8.10 (d, J=5.67 Hz, 1H) 8.06 (d, J=6.06 Hz, 1H) 7.73-7.85 (m, 3H) 7.55 (dd, J=8.31, 4.21 Hz, 1H) 7.34 (d, J=8.71 Hz, 1H) 6.79 (d, J=5.48 Hz, 1H); m/z (ESI) 414.2 (M+H)$^+$.

EXAMPLE 311

1-(3,5-DIMETHYLISOXAZOL-4-YL)-N-(PYRIMIDIN-4-YL)ISOQUINOLINE-6-SULFONAMIDE

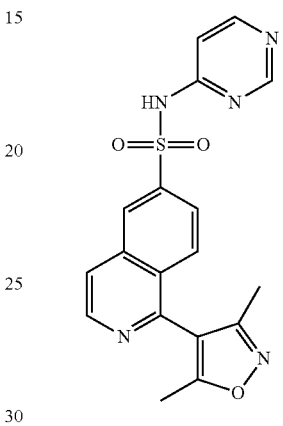

Example 311 was synthesized in a similar manner to Example 65, except that (3,5-dimethylisoxazol-4-yl)boronic acid was used as boronic acid. $^1$H NMR (500 MHz, DMSO-d$_6$) δ ppm 8.71-8.79 (m, 2H) 8.59 (s, 1H) 8.26 (d, J=5.50 Hz, 1H) 8.19 (d, J=5.61 Hz, 1H) 8.05 (d, J=8.71 Hz, 1H) 7.99 (d, J=8.82 Hz, 1H) 7.05 (d, J=6.19 Hz, 1H) 2.29 (s, 3H) 2.13 (s, 3H); m/z (ESI) 381.1 (M+H)$^+$.

EXAMPLE 312

1-(1-METHYL-3-(TRIFLUOROMETHYL)-1H-PYRAZOL-5-YL)-N-(PYRIMIDIN-4-YL)ISOQUINOLINE-6-SULFONAMIDE

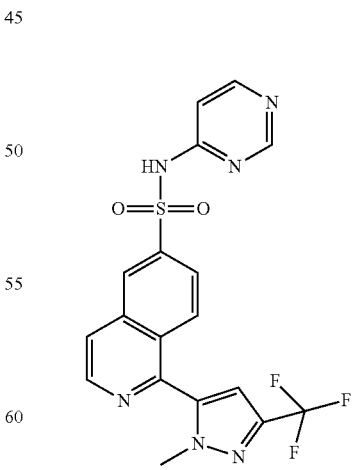

Example 312 was synthesized in a similar manner to Example 65, except that (1-methyl-3-(trifluoromethyl)-1H-pyrazol-5-yl)boronic acid was used as boronic acid. $^1$H NMR (500 MHz, DMSO-d$_6$) δ ppm 8.81 (d, J=5.61 Hz, 1H) 8.75

(br. s., 1H) 8.58 (s, 1H) 8.27 (d, J=5.50 Hz, 2H) 8.19 (d, J=8.82 Hz, 1H) 8.08 (d, J=8.82 Hz, 1H) 7.25 (s, 1H) 3.94 (s, 3H); m/z (ESI) 435.1 (M+H)+.

EXAMPLE 313

1-(2-METHOXY-4-(TRIFLUOROMETHYL)PHENYL)-N-(2-METHOXYPYRIMIDIN-4-YL)ISOQUINOLINE-6-SULFONAMIDE

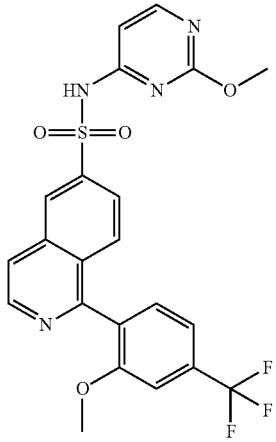 [SMILES: COc1nccc(NS(=O)(=O)c2ccc3c(-c4ccc(C(F)(F)F)cc4OC)nccc3c2)n1]

Example 313 was synthesized in a similar manner to Example 181, using 2-methoxypyrimidin-4-amine in place of 6-methoxypyrimidin-4-amine $^1$H NMR (400 MHz, DMSO-d$_6$) δ ppm 8.71-8.80 (m, 2H) 8.12-8.27 (m, 2H) 7.98 (d, J=8.80 Hz, 1H) 7.77 (d, J=8.22 Hz, 1H) 7.60 (d, J=7.34 Hz, 1H) 7.48-7.56 (m, 2H) 6.62 (d, J=6.06 Hz, 1H) 3.72 (s, 3H) 3.74 (s, 3H); m/z (ESI) 491.1 (M+H)+.

EXAMPLE 314

N-((1-(2-METHOXY-4-(TRIFLUOROMETHYL)PHENYL)ISOQUINOLIN-6-YL)SULFONYL)ACETAMIDE

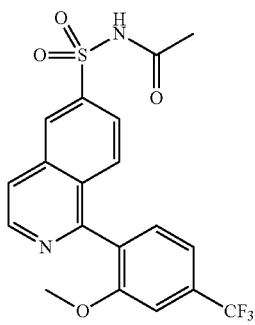 [SMILES: COc1cc(C(F)(F)F)ccc1-c1nccc2cc(S(=O)(=O)NC(C)=O)ccc12]

Example 314 was synthesized in a similar manner to Example 196, except that acetamide was used in place of 2-aminothiazole. The desired product, N-((1-(2-methoxy-4-(trifluoromethyl)phenyl)isoquinolin-6-yl)sulfonyl)acetamide, was isolated as a white solid: $^1$H NMR (400 MHz, DMSO-d$_6$) δ ppm=12.19 (br. s., 1H), 8.90-8.61 (m, 2H), 8.21 (d, J=5.3 Hz, 1H), 7.94 (dd, J=2.0, 8.9 Hz, 1H), 7.79 (d, J=8.9 Hz, 1H), 7.62-7.46 (m, 3H), 3.76 (s, 3H), 1.94 (s, 3H); m/z (ESI) 425.2 (M+H)+.

EXAMPLE 315

1-(1-METHYL-1H-IMIDAZOL-2-YL)-N-(THIAZOL-2-YL)ISOQUINOLINE-6-SULFONAMIDE 2,2,2-TRIFLUOROACETATE

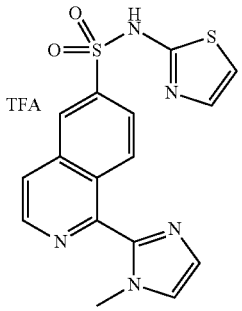 [SMILES: Cn1ccnc1-c1nccc2cc(S(=O)(=O)Nc3nccs3)ccc12]

Example 315 was synthesized in a similar manner to that of Example 244, using 1-methyl-2-(tributylstannyl)imidazole instead of 1-methyl-2-(tributylstannyl)pyrrole. $^1$H NMR (400 MHz, DMSO-d$_6$) δ ppm=12.93 (br. s., 1H), 9.12 (s, 1H), 8.81 (d, J=5.7 Hz, 1H), 8.64 (s, 1H), 8.34 (d, J=9.0 Hz, 1H), 8.26 (d, J=5.6 Hz, 1H), 8.10 (s, 1H), 8.00 (dd, J=1.9, 8.9 Hz, 1H), 7.30 (d, J=4.5 Hz, 1H), 6.89 (d, J=4.5 Hz, 1H), 3.88 (s, 3H). m/z (ESI) 372.2 (M+H)+.

EXAMPLE 316

N-(PYRIMIDIN-4-YL)-1-(1-(TETRAHYDRO-2H-PYRAN-4-YL)PYRROLIDIN-2-YL)ISOQUINOLINE-6-SULFONAMIDE 2,2,2-TRIFLUOROACETATE

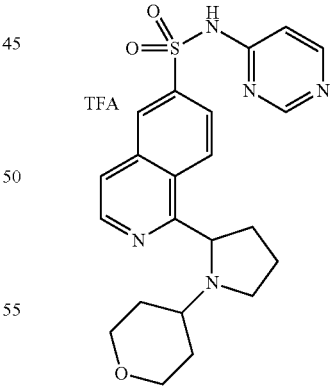

Example 316 was synthesized in a similar manner to that of Example 245, using pyrimidin-4-amine instead of thiazol-2-amine $^1$H NMR (400 MHz, DMSO-d$_6$) δ ppm=10.03 (br. s., 1H), 8.73 (s, 1H), 8.66 (d, J=5.7 Hz, 1H), 8.58 (s, 1H), 8.46 (d, J=8.9 Hz, 1H), 8.23 (d, J=5.8 Hz, 2H), 8.15 (dd, J=1.8, 8.9 Hz, 1H), 7.12-6.92 (m, 1H), 5.94-5.81 (m, 1H), 3.94-3.75 (m, 3H), 3.61 (br. s., 1H), 3.54-3.42 (m, 1H), 3.29-3.11 (m, 2H), 2.84-2.70 (m, 1H), 2.21-2.05 (m, 1H), 2.00-1.84 (m, 3H), 1.77 (dq, J=4.5, 12.1 Hz, 1H), 1.67 (d, J=11.5 Hz, 1H), 1.52 (dq, J=4.3, 12.0 Hz, 1H). m/z (ESI) 440.3 (M+H)$^+$.

EXAMPLE 317

5-CYANO-N-(1,2,4-THIADIAZOL-5-YL)NAPH-THALENE-2-SULFONAMIDE

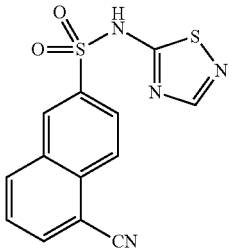 [SMILES: N#Cc1cccc2cc(S(=O)(=O)Nc3ncns3)ccc12]

A microwave vial was charged with Xantphos (44.5 mg, 0.077 mmol) and Pd$_2$(dba)$_3$ (35.2 mg, 0.038 mmol). The vessel was flushed with Ar (g), then DMF (3843 µl) was added. The vessel was sealed and heated in a microwave reactor at 120° C. for 10 min. The mixture was cooled, then a solid mixture of 5-bromo-N-(2,4-dimethoxybenzyl)-N-(1,2,4-thiadiazol-5-yl)naphthalene-2-sulfonamide (Intermediate D; 200 mg, 0.384 mmol) and dicyanozinc (226 mg, 1.922 mmol) was added. The vial was re-sealed and heated in the microwave for 3 h at 120° C. The mixture was then diluted with water and extracted with EtOAc (3×). The combined organic extract was dried over sodium sulfate, filtered, and concentrated. The residue was purified by silica gel chromatography on a 40-g column with 50 to 100% EtOAc/Heptane to give 5-cyano-N-(2,4-dimethoxybenzyl)-N-(1,2,4-thiadiazol-5-yl)naphthalene-2-sulfonamide as an off-white solid. This material was dissolved in DCM (1 mL) and TFA (0.5 mL). The mixture was stirred for 4 h, then diluted with 2-propanol and concentrated. The residue was purified by silica gel chromatography (12-g, with 0 to 10% MeOH/DCM) to give 5-cyano-N-(1,2,4-thiadiazol-5-yl)naphthalene-2-sulfonamide (12.98 mg, 0.041 mmol, 67.5% yield) as an off-white solid. $^1$H NMR (400 MHz, DMSO-d$_6$) δ ppm=8.70 (br. s., 1H), 8.60 (d, J=9.0 Hz, 1H), 8.48 (br. s., 1H), 8.34 (d, J=7.1 Hz, 1H), 8.28 (d, J=8.2 Hz, 1H), 8.10 (d, J=8.5 Hz, 1H), 7.88-7.77 (m, 1H); m/z (ESI) 317.2 (M+H)$^+$.

EXAMPLE 318

METHYL 6-(N-(1,2,4-THIADIAZOL-5-YL)SULFAMOYL)-1-NAPHTHOATE

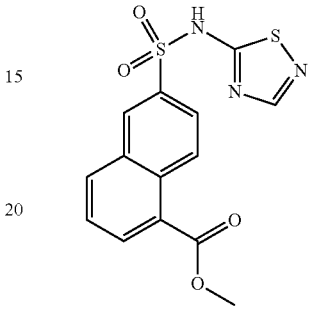

A 500-mL two-neck flask was charged with 5-bromo-N-(2,4-dimethoxybenzyl)-N-(1,2,4-thiadiazol-5-yl)naphthalene-2-sulfonamide (Intermediate D; 10 g, 19.22 mmol), palladium (ii) acetate (0.216 g, 0.961 mmol), and Xantphos (1.112 g, 1.922 mmol). Triethylamine (77 ml, 19.22 mmol), toluene (48.0 ml), and methanol (15.55 ml, 384 mmol) were added, and the reaction was fitted with a reflux condensor. The reaction was evacuated and back-filled with carbon monoxide three times, then the reaction was heated to 70° C. and stirred for four hours under an atmosphere of carbon monoxide. The reaction was filtered through a pad of diatomaceous earth, which was thoroughly washed with ethyl acetate. The filtrate was concentrated, triturated in ethyl acetate and filtered. The solids were collected and the filtrate was concentrated. The trituration procedure was repeated twice, and the solids resulting from each trituration were combined with the previously isolated material. After the third trituration, the mother liquor was purified via column chromatography (80 g silica gel column, gradient elution 0 to 50% EtOAc:Heptane). The clean product fractions were combined with the previously isolated material and the resulting slurry was concentrated to afford methyl 6-(N-(2,4-dimethoxybenzyl)-N-(1,2,4-thiadiazol-5-yl)sulfamoyl)-1-naphthoate as a light yellow solid. m/z (ESI) 500.3 (M+H)$^+$. 60 mg of methyl 6-(N-(2,4-dimethoxybenzyl)-N-(1,2,4-thiadiazol-5-yl)sulfamoyl)-1-naphthoate was dissolved in 1 mL of DCM and TFA (0.1 ml, 1.298 mmol) was added. The reaction was stirred for 30 minutes at room temperature. The material was concentrated, dissolved in acetonitrile and loaded onto a Biotage Isolute® PEAX ion exchange column (Biotage AB, Uppsala, Sweden) (pre-wetted with acetonitrile). The column was flushed several times with acetonitrile, then the product was liberated by flushing the column several times with about 1M HCl solution in MeOH/EtOAc. The second filtrate was concentrated to afford methyl 6-(N-(1,2,4-thiadiazol-5-yl)sulfamoyl)-1-naphthoate. $^1$H NMR (400 MHz, DMSO-d$_6$) δ ppm=8.90 (d, J=9.2 Hz, 1H), 8.60 (d, J=2.0 Hz, 1H), 8.53-8.44 (m, 2H), 8.29 (dd, J=1.3, 7.3 Hz, 1H), 7.96 (dd, J=2.1, 9.2 Hz, 1H), 7.76 (dd, J=7.3, 8.2 Hz, 1H), 3.95 (s, 3H). m/z (ESI) 350.1 (M+H)+.

EXAMPLE 319

6-FLUORO-4-(2-METHOXY-4-(TRIFLUOROM-ETHYL)PHENYL)-N-(THIAZOL-2-YL)QUINO-LINE-7-SULFONAMIDE 2,2,2-TRIFLUOROAC-ETATE

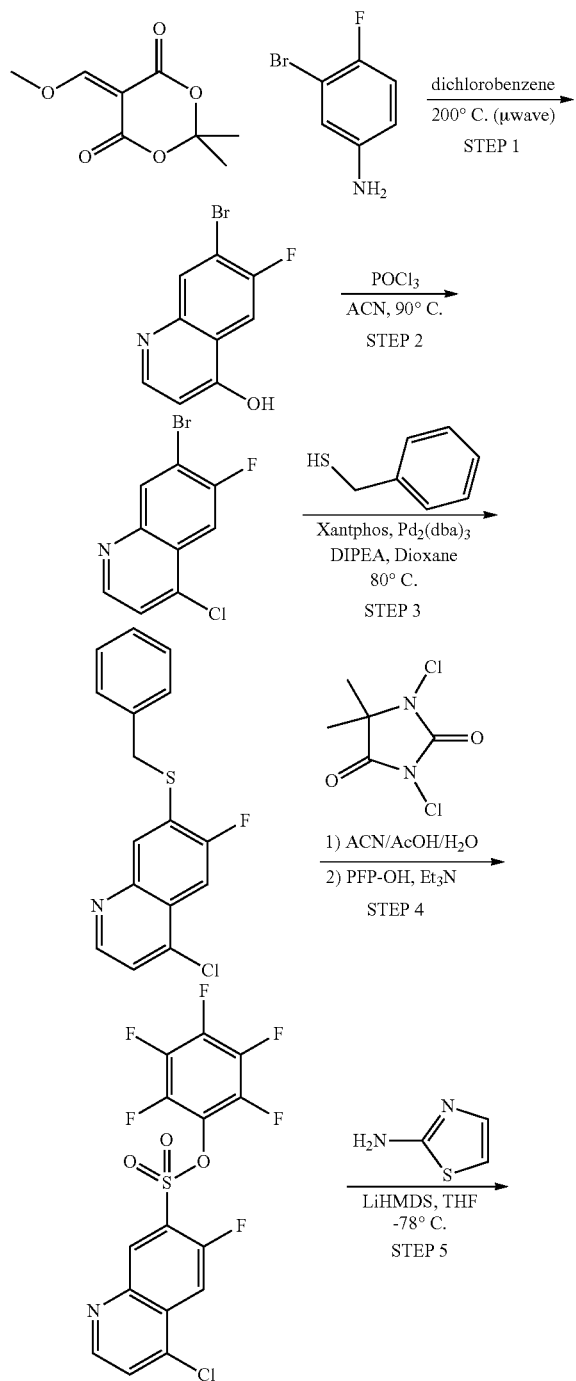

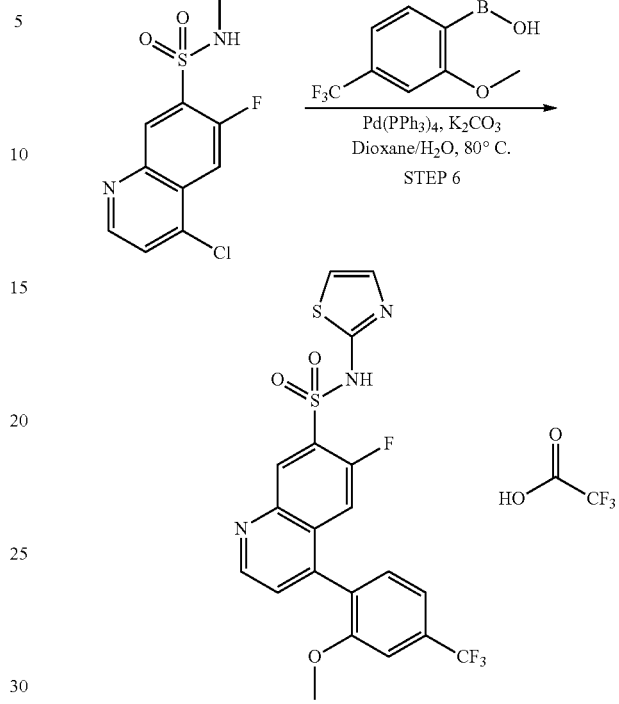

STEP 1: 7-BROMO-6-FLUOROQUINOLIN-4-OL

A glass microwave vial was charged with 5-(methoxymethylene)-2,2-dimethyl-1,3-dioxane-4,6-dione (Bionet; 0.102 g, 0.552 mmol) and 3-bromo-4-fluoroaniline (Matrix Scientific; 0.100 g, 0.526 mmol) in dichlorobenzene (1.00 ml). The reaction mixture was stirred and heated under microwave irradiation (Biotage AB, Inc., Uppsala, Sweden) at 200° C. for 10 min. Diethyl ether was added to the reaction and the solids were filtered, washing well with ether (some product passed through with the filtrate) to yield 61 mg of crude 7-bromo-6-fluoroquinolin-4-ol. Material carried forward without further purification. m/z (ESI) 243.9 (M+H)+.

STEP 2: 7-BROMO-4-CHLORO-6-FLUOROQUINOLINE

A vial was charged with 7-bromo-6-fluoroquinolin-4-ol (0.460 g, 1.900 mmol) and acetonitrile (9.50 ml). Phosphoryl trichloride (0.354 ml, 3.80 mmol) was then added, and the reaction was stirred for 2 h at 90° C. The reaction was diluted with ethyl acetate and washed with water. The aqueous was extracted once more with ethyl acetate, and the combined organics were dried over sodium sulfate, filtered and concentrated in vacuo. The material was then purified via silica gel chromatography eluting with 0-75% ethyl acetate in heptanes to yield 7-bromo-4-chloro-6-fluoroquinoline (0.141 g, 0.541 mmol, 28.5% yield) as a white solid. m/z (ESI) 260.1 (M+H)+.

STEP 3: 7-(BENZYLTHIO)-4-CHLORO-6-FLUOROQUINOLINE

A vial was charged with 7-bromo-4-chloro-6-fluoroquinoline (0.141 g, 0.541 mmol), Xantphos (0.016 g, 0.027 mmol), and Pd$_2$(dba)$_3$ (0.012 g, 0.014 mmol) and after flushing with argon, dioxane (1.083 ml) and n,n-diisopropylethylamine (0.189 ml, 1.083 mmol) were added in sequence. The vial was sealed, and was placed in a heating bath at 80° C. for 10 minutes, after which benzylmercaptan (0.067 ml, 0.568 mmol) was added drop wise via syringe. The reaction was stirred for 30 minutes. The material was diluted with water, and washed with DCM (×3), and the combined organics were dried via phase separator and concentrated in vacuo. The material was purified via silica gel chromatography eluting with 0-50% ethyl acetate in heptane to yield 7-(benzylthio)-4-chloro-6-fluoroquinoline (0.148 g, 0.487 mmol, 90% yield) as a light yellow solid. m/z (ESI) 304.2 (M+H)$^+$.

STEP 4: PERFLUOROPHENYL 4-CHLORO-6-FLUOROQUINOLINE-7-SULFONATE

A round-bottom flask was charged with 7-(benzylthio)-4-chloro-6-fluoroquinoline (0.148 g, 0.487 mmol), acetonitrile (4.59 ml), acetic acid (0.172 ml), and water (0.115 ml), and after cooling the suspension in an ice bath for 10 minutes (material fell out of solution), 1,3-dichloro-5,5-dimethylimidazolidine-2,4-dione (0.192 g, 0.974 mmol) was added in one portion (mixture became homogeneous). After 1 h, conversion to 4-chloro-6-fluoroquinoline-7-sulfonyl chloride was observed (light yellow solution), and 2,3,4,5,6-pentafluorophenol (0.179 g, 0.974 mmol) was added, followed by drop wise addition of triethylamine (0.170 ml, 1.218 mmol). After 25 minutes, the mixture was diluted with EtOAc and washed with water and brine, and then dried over sodium sulfate. After filtration and concentration in vacuo, the material was purified via silica gel chromatography (12-g RediSep Gold column, eluting with 0-50% ethyl acetate in heptane) to yield perfluorophenyl 4-chloro-6-fluoroquinoline-7-sulfonate as a white solid. m/z (ESI) 428.1 (M+H)$^+$.

STEP 5: 4-CHLORO-6-FLUORO-N-(THIAZOL-2-YL)QUINOLINE-7-SULFONAMIDE

A flask containing a solution of 2-aminothiazole (0.039 g, 0.386 mmol) and perfluorophenyl 4-chloro-6-fluoroquinoline-7-sulfonate (0.150 g, 0.351 mmol) in THF (1.754 ml) was cooled to −78° C. for 10 minutes, and then lithium bis(trimethylsilyl)amide, 1.0 m solution in tetrahydrofuran (0.701 ml, 0.701 mmol) was added drop wise (conversion from colorless solution to yellow-orange). After 20 minutes, the reaction was diluted with sat. aq ammonium chloride solution, and was extracted with DCM:MeOH (90:10) (×3). The organics were dried over sodium sulfate, filtered and concentrated in vacuo. The material was taken forward crude. m/z (ESI) 344.0 (M+H)$^+$.

STEP 6: 6-FLUORO-4-(2-METHOXY-4-(TRIFLUOROMETHYL)PHENYL)-N-(THIAZOL-2-YL)QUINOLINE-7-SULFONAMIDE 2,2,2-TRIFLUOROACETATE (2-methoxy-4-(trifluoromethyl)phenyl)boronic acid (0.155 g, 0.704 mmol), 4-chloro-6-fluoro-N-(thiazol-2-yl)quinoline-7-sulfonamide (0.121 g, 0.352 mmol), Pd(PPh$_3$)$_4$ (0.041 g, 0.035 mmol), and K$_2$CO$_3$ (0.146 g, 1.056 mmol) were combined in dioxane (1.320 ml) and water (0.440 ml), and stirred at 80° C. for 1 h, at which time no reaction occurred. Cesium carbonate (0.344 g, 1.056 mmol) was added, along with more Pd(PPh$_3$)$_4$ (0.041 g, 0.035 mmol) and (2-methoxy-4-(trifluoromethyl)phenyl)boronic acid (0.155 g, 0.704 mmol) and the reaction was stirred at 80° C. for 4 h until completion. The reaction was cooled to RT, and water and 0.500 mL of acetic acid (to slightly acidic pH) were added. The material was extracted (×3) with DCM:MeOH (90:10), the organics were combined and dried over sodium sulfate, filtered and concentrated in vacuo. The crude material was absorbed onto a plug of silica gel and purified by silica gel chromatography, eluting with a gradient of 0% to 100% DCM:MeOH:NH$_4$OH to provide material contaminated with triphenylphosphine oxide. The crude was purified once more by reverse-phase preparative HPLC using a Phenomenex Luna column, 5 micron, C18(2), 100 Å, 150×30 mm, 0.1% TFA in CH$_3$CN/H$_2$O, gradient 10% to 90% over 12 min to provide 6-fluoro-4-(2-methoxy-4-(trifluoromethyl)phenyl)-N-(thiazol-2-yl)quinoline-7-sulfonamide 2,2,2-trifluoroacetate (0.030 g, 0.050 mmol, 14.27% yield) as a yellow solid. $^1$H NMR (400 MHz, DMSO-d$_6$) δ ppm 13.09 (br. s., 1H), 9.06 (d, J=4.30 Hz, 1H), 8.53 (d, J=7.04 Hz, 1H), 7.61 (d, J=4.11 Hz, 1H), 7.48-7.57 (m, 3H), 7.27-7.35 (m, 2H), 6.90 (d, J=4.40 Hz, 1H), 3.78 (s, 3H). m/z (ESI) 483.9 (M+H)$^+$.

INTERMEDIATE QQQQ: 4-CHLORO-N-(2,4-DIMETHOXYBENZYL)-N-(1,2,4-THIADIAZOL-5-YL)QUINOLINE-7-SULFONAMIDE

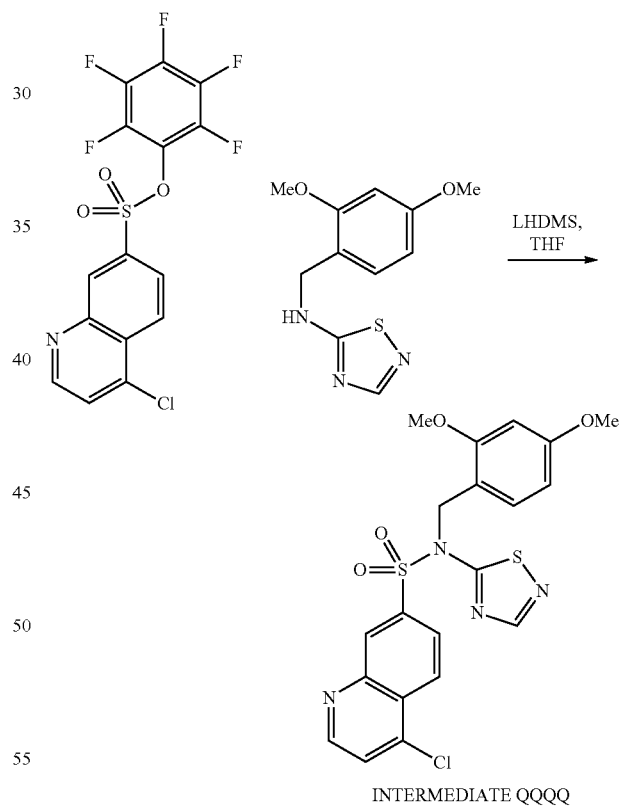

INTERMEDIATE QQQQ

A flask was charged with N-(2,4-dimethoxybenzyl)-1,2,4-thiadiazol-5-amine (302 mg, 1.204 mmol) and THF (5471 µl) to give a clear solution. The flask was cooled in a dry ice-acetone bath for 5 min, and then a solution of perfluorophenyl 4-chloroquinoline-7-sulfonate (448.3 mg, 1.094 mmol) in THF (1 mL with a 0.5 mL syringe wash) was added drop wise. After 1 h, the mixture was diluted with saturated aq. ammonium chloride, water, and EtOAc, and the layers were separated. The organic layer was dried over sodium sulfate, filtered, and concentrated. The residue was purified by chromatography on silica gel (40-g Redi-Sep Gold column, 20-70% EtOAc/Heptane) to give an off-white solid. The solid was taken up in heptane and filtered. The collected solid was washed with heptane (2×), then dried under a stream of $N_2$ (g) for 2 h to give 4-chloro-N-(2,4-dimethoxybenzyl)-N-(1,2,4-thiadiazol-5-yl)quinoline-7-sulfonamide (426 mg, 0.893 mmol, 82% yield) as a white solid. m/z (ESI) 477.0 $(M+H)^+$.

EXAMPLE 320

4-(2-METHOXYPHENYL)-N-(1,2,4-THIADIA-ZOL-5-YL)QUINOLINE-7-SULFONAMIDE 2,2,2-TRIFLUOROACETATE

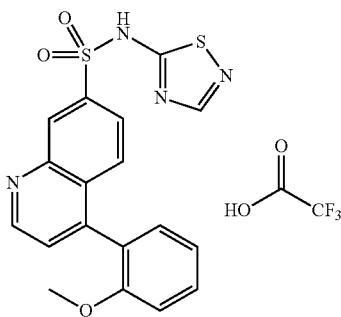

A vial was charged with 4-chloro-N-(2,4-dimethoxybenzyl)-N-(1,2,4-thiadiazol-5-yl)quinoline-7-sulfonamide (INTERMEDIATE QQQQ, 58.7 mg, 0.123 mmol), (2-methoxyphenyl)boronic acid (Combi-Blocks, Inc., San Diego, Calif., 28.1 mg, 0.185 mmol), $Pd(AmPhos)_2Cl_2$ (4.36 mg, 6.15 μmol), potassium phosphate (78 mg, 0.369 mmol), 1,4-dioxane (462 μl), and water (154 μl). The vial was flushed with Ar (g), then sealed and heated in a Biotage Initiator microwave reactor for 30 min at 90° C. The mixture was extracted with EtOAc (3×), and the combined organic extracts were concentrated. The residue was dissolved in DCM (1 mL) and TFA (0.5 mL). After 30 min, the mixture was diluted with MeOH and concentrated, and the crude product was purified by chromatography on silica gel (12-g Redi-Sep Gold column, 0-6% MeOH/DCM) to give 4-(2-methoxyphenyl)-n-(1,2,4-thiadiazol-5-yl)quinoline-7-sulfonamide 2,2,2-trifluoroacetate as a yellow solid. $^1$H NMR (400 MHz, DMSO-$d_6$) δ=9.07 (d, J=4.4 Hz, 1H), 8.50 (s, 1H), 8.46 (d, J=1.9 Hz, 1H), 7.87 (dd, J=2.0, 8.8 Hz, 1H), 7.69 (d, J=8.8 Hz, 1H), 7.58-7.52 (m, 2H), 7.30 (dd, J=1.8, 7.4 Hz, 1H), 7.25 (d, J=8.3 Hz, 1H), 7.14 (dt, J=0.9, 7.4 Hz, 1H), 3.67 (s, 3H). m/z (ESI) 399.7 $(M+H)^+$.

EXAMPLE 321

4-(3'-FLUORO-4-METHOXY-[1,1'-BIPHENYL]-3-YL)-N-(PYRIMIDIN-4-YL)QUINOLINE-7-SULFONAMIDE

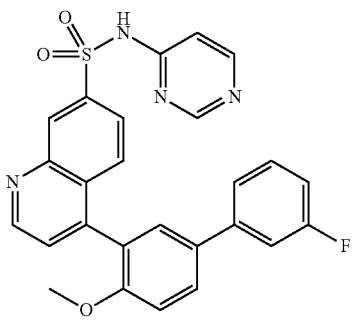 [SMILES: COc1ccc(-c2cccc(F)c2)cc1-c1ccnc2cc(S(=O)(=O)Nc3ccncn3)ccc12]

A vial was charged with 4-chloro-N-(pyrimidin-4-yl)quinoline-7-sulfonamide (INTERMEDIATE OOOO, 103.75 mg, 0.323 mmol), (2-chlorophenyl)boronic acid (53.1 mg, 0.340 mmol), potassium carbonate (134 mg, 0.970 mmol), and $Pd(Ph_3P)_4$ (18.69 mg, 0.016 mmol). The vial was flushed with Ar (g), then 1,4-dioxane (1213 μl) and water (404 μl) were added. The vial was sealed and heated in a Biotage Initiator microwave reactor for 1 h at 100° C. LCMS showed about 5% starting material remaining. (3-fluorophenyl)boronic acid (100 mg, 0.712 mmol), S-Phos Precatalyst (Strem Chemical, Newburyport, Mass., 24.50 mg, 0.032 mmol), dicyclohexyl(2',6'-dimethoxy-[1,1'-biphenyl]-2-yl)phosphine (6.64 mg, 0.016 mmol), and potassium phosphate (206 mg, 0.970 mmol) were added. The vial was heated in the microwave at 100° C. for 1 h. The mixture was extracted with EtOAc (3×). The combined organic extracts were concentrated. The residue was purified by chromatography on silica gel (25-g Interchim 15-micron column, 3.5% MeOH/DCM). Several mixed fractions were discarded. Those fractions containing clean product were combined and concentrated to give 4-(3'-fluoro-4-methoxy-[1,1'-biphenyl]-3-yl)-N-(pyrimidin-4-yl)quinoline-7-sulfonamide (22 mg, 0.045 mmol, 13.98% yield) as an off-white solid. $^1$H NMR (400 MHz, DMSO-$d_6$) δ=13.30-12.39 (m, 1H), 9.13-9.07 (m, 1H), 8.63-8.53 (m, 2H), 8.28 (d, J=5.4 Hz, 1H), 7.93 (ddd, J=2.2, 8.8, 17.8 Hz, 2H), 7.74 (d, J=8.8 Hz, 1H), 7.69-7.62 (m, 2H), 7.59-7.52 (m, 2H), 7.50-7.41 (m, 1H), 7.34 (d, J=8.7 Hz, 1H), 7.17-7.11 (m, 1H), 7.06 (d, J=5.5 Hz, 1H), 3.72 (s, 3H). m/z (ESI) 487.2 (M+H)+.

EXAMPLE 322

4-(4-CHLORO-2-METHYLPHENYL)-N-(1,2,4-THIADIAZOL-5-YL)QUINOLINE-7-SULFONAMIDE

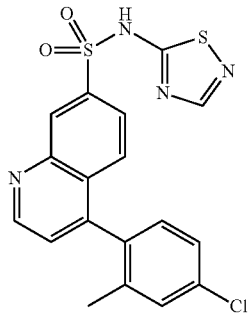 [SMILES: Cc1cc(Cl)ccc1-c1ccnc2cc(S(=O)(=O)Nc3ncns3)ccc12]

A vial was charged with 4-chloro-N-(2,4-dimethoxybenzyl)-N-(1,2,4-thiadiazol-5-yl)quinoline-7-sulfonamide (INTERMEDIATE QQQQ, 55.8 mg, 0.117 mmol), (4-chloro-2-methylphenyl)boronic acid (Indofine Chemical, Hillsborough, N.J., 21.93 mg, 0.129 mmol), Pd(AmPhos)$_2$Cl$_2$ (4.14 mg, 5.85 mmol), potassium phosphate (74.5 mg, 0.351 mmol), 1,4-dioxane (439 µl), and water (146 µl). The vial was flushed with Ar (g), then sealed and heated in a Biotage Initiator microwave reactor for 30 min h at 90° C. LCMS showed two peaks with mass of protected desired product. The mixture was extracted with EtOAc (3×), and the combined organic extracts were concentrated. The residue was dissolved in DCM (1 mL) and TFA (0.5 mL). After 1 h, triflic acid (0.05 mL) was added drop wise. Following an additional 1 h of stirring, the mixture was diluted with 2-PrOH, then concentrated. The residue was purified by chromatography on silica gel (25-g Interchim column, 0-60% EtOAc/Heptane, then with 100% EtOAc). The resulting material was further purified by chromatography on silica gel (12-g Redi-Sep Gold column, 0-6% MeOH/DCM) to give 4-(4-chloro-2-methylphenyl)-N-(1,2,4-thiadiazol-5-yl)quinoline-7-sulfonamide (24.08 mg, 0.058 mmol, 49.4% yield) as a light-yellow solid. $^1$H NMR (400 MHz, DMSO-d$_6$) δ=9.10 (d, J=4.4 Hz, 1H), 8.48 (d, J=1.8 Hz, 1H), 8.42 (s, 1H), 7.88 (dd, J=2.0, 8.8 Hz, 1H), 7.61-7.53 (m, 3H), 7.43 (dd, J=1.9, 8.1 Hz, 1H), 7.29 (d, J=8.1 Hz, 1H), 1.97 (s, 3H). m/z (ESI) 417.2 (M+H)+.

EXAMPLE 323

4-(4-CYANO-2-METHYLPHENYL)-N-(1,2,4-THIADIAZOL-5-YL)QUINOLINE-7-SULFONAMIDE

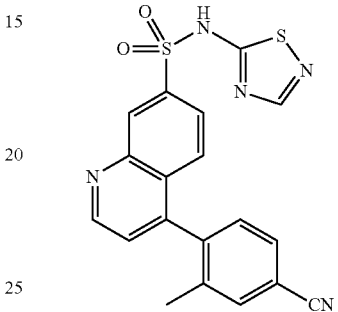

The title compound was prepared in an analogous manner to that described for the preparation of Example 322, except that (4-cyano-2-methylphenyl)boronic acid (35.9 mg, 0.223 mmol) was used in place of (4-chloro-2-methylphenyl)boronic acid. The desired product was isolated as a light-yellow solid: $^1$H NMR (400 MHz, DMSO-d$_6$) δ=9.13 (d, J=4.4 Hz, 1H), 8.51-8.42 (m, 2H), 7.96 (s, 1H), 7.92-7.80 (m, 2H), 7.62-7.46 (m, 3H), 2.01 (s, 3H). m/z (ESI) 408.2 (M+H)+.

EXAMPLE 324

3-CYANO-4-(2-METHOXYPHENYL)-N-(THIAZOL-2-YL)QUINOLINE-7-SULFONAMIDE

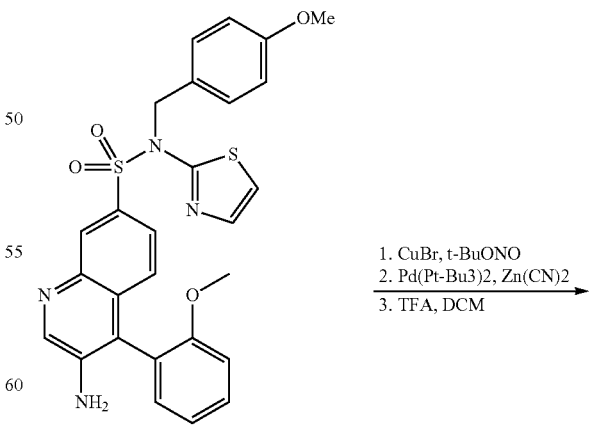

-continued

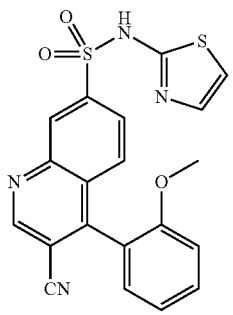 [SMILES: COc1ccccc1-c1c(Br)cnc2cc(S(=O)(=O)Nc3nccs3)ccc12]

STEP 1: 3-BROMO-N-(4-METHOXYBENZYL)-4-(2-METHOXYPHENYL)-N-(THIAZOL-2-YL)QUINOLINE-7-SULFONAMIDE

A round-bottom flask was charged with 3-amino-N-(4-methoxybenzyl)-4-(2-methoxyphenyl)-N-(thiazol-2-yl)quinoline-7-sulfonamide (INTERMEDIATE NNNN, 441 mg, 0.828 mmol), CH$_3$CN (8280 μl), and copper(ii) bromide (92 mg, 0.414 mmol). The vial was flushed with Ar (g), then tert-butyl nitrite, 90% (438 μl, 3.31 mmol) was added. The mixture was stirred for 1 min, and then the flask fitted with a reflux condenser and transferred to a 60° C. heating bath for 20 min. After cooling to room temperature, the mixture was diluted with saturated aq. sodium bicarbonate solution and extracted with EtOAc. The aq. layer was diluted with brine and extracted with EtOAc. This was repeated one additional time, and the combined organic extracts were dried over sodium sulfate, filtered, and concentrated. The residue was purified by chromatography on silica gel (40-g Redi-Sep Gold column, 0-50% EtOAc/Heptane) to give 3-bromo-N-(4-methoxybenzyl)-4-(2-methoxyphenyl)-N-(thiazol-2-yl)quinoline-7-sulfonamide (264 mg, 0.443 mmol, 53.5% yield) as a white foam. m/z (ESI) 596.2 (M+H)$^+$.

STEP 2: 3-CYANO-N-(4-METHOXYBENZYL)-4-(2-METHOXYPHENYL)-N-(THIAZOL-2-YL)QUINOLINE-7-SULFONAMIDE

A vial was charged with 3-bromo-N-(4-methoxybenzyl)-4-(2-methoxyphenyl)-N-(thiazol-2-yl)quinoline-7-sulfonamide (64.6 mg, 0.108 mmol), dicyanozinc (63.6 mg, 0.541 mmol), a spatula tip of zinc dust, and palladium compound with tributylplatinum (1:2) (18.18 mg, 0.022 mmol). The vial was flushed with Ar (g), then DMAC (1 mL) was added. The vial was sealed and placed in a 100° C. heating bath for 4 h. The mixture was cooled to room temperature, and then diluted with water and EtOAc. The layers were separated, and the aq. layer was extracted with EtOAc (2×). The combined organic extracts were dried over sodium sulfate, filtered, and concentrated. The residue was purified by chromatography on silica gel (12-g Redi-Sep Gold column, 20-70% EtOAc/Heptane) to give 3-cyano-N-(4-methoxybenzyl)-4-(2-methoxyphenyl)-N-(thiazol-2-yl)quinoline-7-sulfonamide an off-white solid. m/z (ESI) 543.0 (M+H)$^+$.

STEP 3: 3-CYANO-4-(2-METHOXYPHENYL)-N-(THIAZOL-2-YL)QUINOLINE-7-SULFONAMIDE

A vial was charged with 3-cyano-N-(4-methoxybenzyl)-4-(2-methoxyphenyl)-N-(thiazol-2-yl)quinoline-7-sulfonamide (23.3 mg, 0.043 mmol), DCM (0.5 mL), and TFA (0.25 mL). After 30 min, the mixture was diluted with MeOH and concentrated, and the crude product was purified by chromatography on silica gel (12-g Redi-Sep Gold column, 0-5% MeOH/DCM) to give 3-cyano-4-(2-methoxyphenyl)-N-(thiazol-2-yl)quinoline-7-sulfonamide (13.6 mg, 0.032 mmol, 75.0% yield) as a light-yellow solid. $^1$H NMR (400 MHz, DMSO-d$_6$) δ=12.99 (br. s., 1H), 9.35 (s, 1H), 8.50 (d, J=1.8 Hz, 1H), 7.98 (dd, J=1.9, 8.8 Hz, 1H), 7.72 (d, J=8.9 Hz, 1H), 7.67-7.58 (m, 1H), 7.40 (dd, J=1.7, 7.5 Hz, 1H), 7.35-7.28 (m, 2H), 7.21 (dt, J=0.8, 7.5 Hz, 1H), 6.89 (d, J=4.6 Hz, 1H), 3.71 (s, 3H). m/z (ESI) 423.2 (M+H)$^+$.

EXAMPLE 325

3-BROMO-4-(2-METHOXYPHENYL)-N-(THIAZOL-2-YL)QUINOLINE-7-SULFONAMIDE

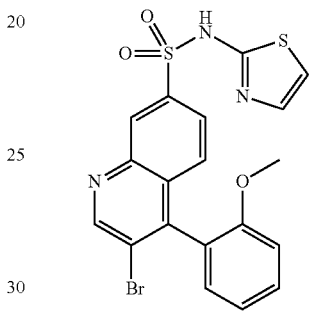

A solution of 3-bromo-N-(4-methoxybenzyl)-4-(2-methoxyphenyl)-N-(thiazol-2-yl)quinoline-7-sulfonamide (from STEP 1 of EXAMPLE 324, 15 mg, 0.025 mmol) in DCM (1 mL) was treated with TFA (0.5 mL). After 30 min, the mixture was diluted with MeOH, and then concentrated in vacuo. The residue was purified by chromatography on silica gel (12-g Redi-Sep Gold column, 0-5% MeOH/DCM) to give 3-bromo-4-(2-methoxyphenyl)-N-(thiazol-2-yl)quinoline-7-sulfonamide (11.8 mg, 0.025 mmol, 99% yield) as a light-yellow solid. $^1$H NMR (400 MHz, DMSO-d$_6$) δ=13.12 (br. s., 1H), 9.06 (d, J=4.4 Hz, 1H), 8.44 (d, J=1.8 Hz, 1H), 7.85 (dd, J=1.9, 8.9 Hz, 1H), 7.69 (s, 1H), 7.62-7.48 (m, 3H), 7.34-7.22 (m, 2H), 7.14 (dt, J=0.7, 7.4 Hz, 1H), 3.67 (s, 3H). m/z (ESI) 476.2 (M+H)$^+$.

EXAMPLE 326

4-(2-METHOXY-4-(TRIFLUOROMETHYL)PHENYL)-6-METHYL-N-(THIAZOL-2-YL)QUINOLINE-7-SULFONAMIDE

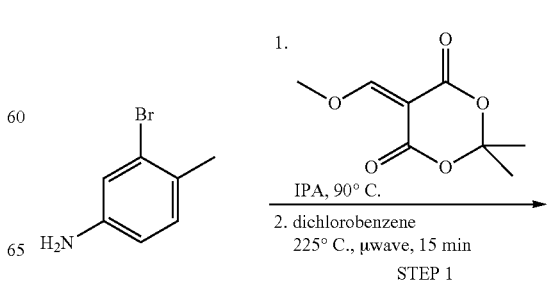

STEP 1

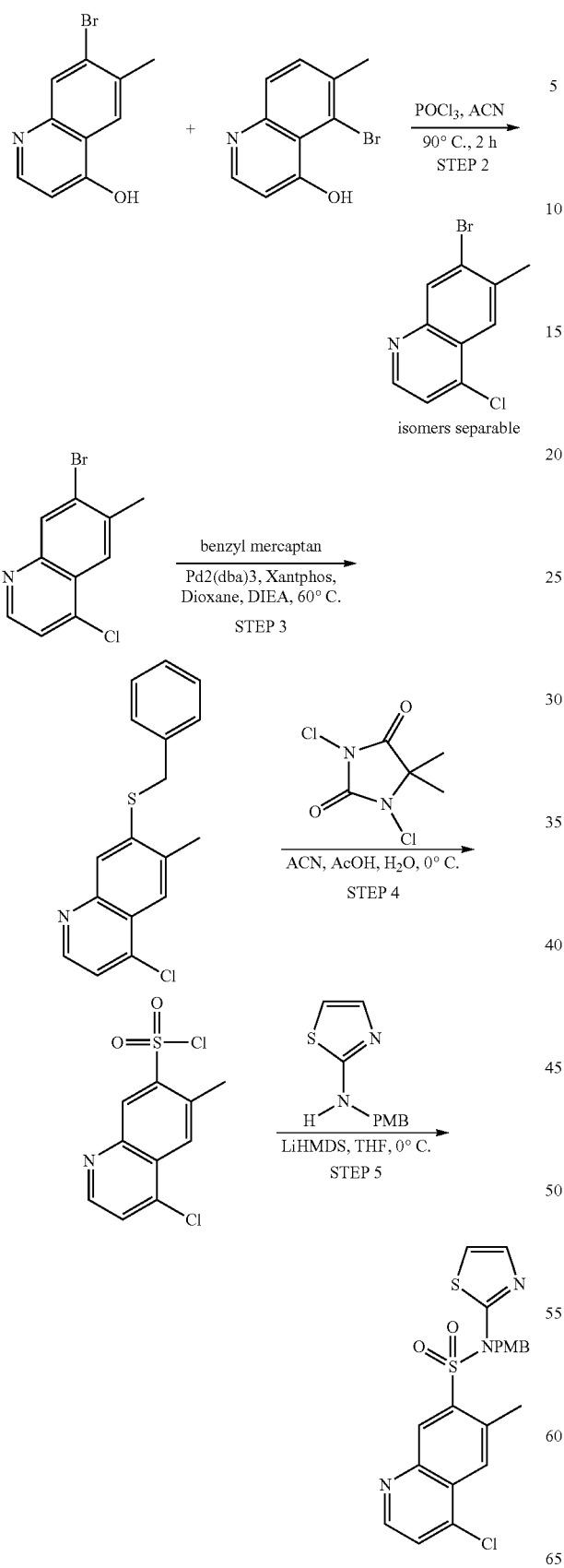

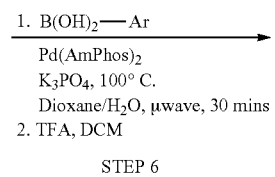

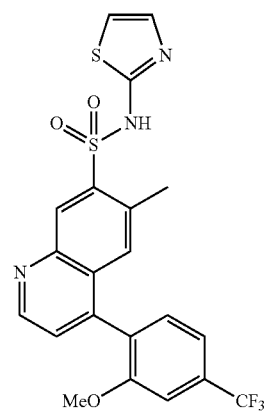

STEP 1: 7-BROMO-6-METHYLQUINOLIN-4-OL

To a vial charged with 3-bromo-4-methylaniline (1.00 g, 5.37 mmol) was added IPA (10.75 ml) and 5-(methoxymethylene)-2,2-dimethyl-1,3-dioxane-4,6-dione (1.001 g, 5.37 mmol) respectively. The mixture was heated to 90° C. for 2 hrs, providing a brown solution which was cooled to room temperature, yielding an orange precipitate which was collected by vacuum filtration affording 5-(((3-bromo-4-methylphenyl)amino)methylene)-2,2-dimethyl-1,3-dioxane-4,6-dione (1.535 g, 4.51 mmol, 84% yield). This solid was transferred to a 5-20 ml microwave vial and 9 ml (0.5M 1,2-dichlorobenzene) was added and the mixture irradiated at 225° C. for 15 min, affording conversion to desired product according to LC-MS. To the suspension was added diethyl ether (~5 ml) to aid in product precipitation. The precipitate was collected via vacuum filtration and washed with ether, affording a brown solid as an isomeric mixture (560 mg). To the filtrate which had some precipitate forming was added heptane affording additional precipitate. This second crop was collected affording another 115 mg of product (53% yield total). m/z (ESI) 238.1/240.1 (M+H)$^+$.

STEP 2: 7-BROMO-4-CHLORO-6-METHYLQUINOLINE

To a flask charged with 7-bromo-6-methylquinolin-4-ol (0.675 g, 2.84 mmol) was added acetonitrile (14.18 ml) and POCl$_3$ (0.277 ml, 2.98 mmol) and the resulting suspension was heated to 90° C. for 2.5 h affording a brown solution and near complete conversion to desired product. The material was added to cold sat. aq. NaHCO$_3$ and extracted with EtOAc (2×). The combined organics were dried with Na$_2$SO$_4$, filtered, and dried under reduced pressure and purified with an 40 g Silicycle HP column ramping EtOAc in heptane (0-50%, 10% DCM throughout) affording isomer separation, both obtained as off-white solids. The first eluting isomer corresponds to product based on the proton NMR, obtained as a light yellow solid, 7-bromo-4-chloro-6-methylquinoline (240 mg, 0.936 mmol, 33.0% yield). $^1$H NMR (400 MHz, CHLOROFORM-d) δ 8.68 (d, J=4.70 Hz, 1H), 8.31 (s, 1H), 7.99 (s, 1H), 7.43 (d, J=4.69 Hz, 1H), 2.59 (s, 3H). m/z (ESI) 256.1/258.1 (M+H)$^+$.

STEP 3: 7-(BENZYLTHIO)-4-CHLORO-6-METHYLQUINOLINE

To a flask charged with 7-bromo-4-chloro-6-methylquinoline (0.240 g, 0.936 mmol) was added Xantphos (0.108 g, 0.187 mmol), Pd$_2$(dba)$_3$ (0.086 g, 0.094 mmol), dioxane (3.74 ml), DIEA (0.327 ml, 1.871 mmol) and benzyl mercaptan (0.111 ml, 0.936 mmol). The vessel was heated at 110° C. for 2 hr affording conversion to desired product. The mixture was cooled to room temperature, filtered through Celite and dried under reduced pressure and purified with a 25 g Interchim column ramping EtOAc in heptane (0-50%, 10% DCM throughout) affording product as a yellow solid with minor impurities, 7-(benzylthio)-4-chloro-6-methylquinoline (0.287 g, 0.957 mmol, 102% yield). m/z (ESI) 300.0 (M+H)$^+$.

STEP 4: 4-CHLORO-6-METHYLQUINOLINE-7-SULFONYL CHLORIDE

To a vial charged with 7-(benzylthio)-4-chloro-6-methylquinoline (287 mg, 0.957 mmol) was added acetonitrile (9 ml), acetic acid (338 μl), and water (225 μl). The resulting solution was cooled in an ice water bath and 1,3-dichloro-5,5-dimethyl-2-imidazolidinedione (251 μl, 1.914 mmol) was added. After 30 min, the mixture was diluted with EtOAc and extracted with H$_2$O. The aqueous phase was extracted again with EtOAc. The combined organics were dried under reduced pressure and purified with a 25 g HP silicycle column ramping EtOAc in heptane (0-35%, 5% DCM throughout) providing 4-chloro-6-methylquinoline-7-sulfonyl chloride (175 mg, 0.634 mmol, 66.2% yield) as a white solid. m/z (ESI) 276.0 (M+H)$^+$.

STEP 5: 4-CHLORO-N-(4-METHOXYBENZYL)-6-METHYL-N-(THIAZOL-2-YL)QUINOLINE-7-SULFONAMIDE

To a flask containing ice cold suspension of N-(4-methoxybenzyl)thiazol-2-amine (147 mg, 0.665 mmol) in THF (2437 μl) was added lithium bis(trimethylsilyl)amide (1M in THF) (1267 μl, 1.267 mmol) faster than drop wise. The mixture was stirred for 15 min prior to the drop wise addition of a solution of 4-chloro-6-methylquinoline-7-sulfonyl chloride (175 mg, 0.634 mmol) in THF (2.0 ml, 0.5 ml wash). The solution was allowed to stir for 20 min (ice melt) providing a brown solution containing primarily product. The mixture was added to a flask containing sat. aq. NH$_4$Cl and ice. The aqueous mixture was extracted 2× with EtOAc and the combined organics were dried with Na$_2$SO$_4$, filtered, and dried under reduced pressure. The crude material was purified with a 25 g HP Silicycle column ramping EtOAc in heptane (0-50%, 10% DCM throughout) to afford product, 4-chloro-N-(4-methoxybenzyl)-6-methyl-N-(thiazol-2-yl)quinoline-7-sulfonamide (162 mg, 0.352 mmol, 55.6% yield) as a yellow solid with about 15% impurity by LC-MS. m/z (ESI) 460.3 (M+H)$^+$.

STEP 6: 4-(2-METHOXY-4-(TRIFLUOROMETHYL)PHENYL)-6-METHYL-N-(THIAZOL-2-YL)QUINOLINE-7-SULFONAMIDE

To a microwave vial charged with (2-methoxy-4-(trifluoromethyl)phenyl)boronic acid (42.1 mg, 0.191 mmol), potassium phosphate tribasic (43.2 μl, 0.522 mmol) and 1,1-bis[(di-t-butyl-p-methylaminophenyl]palladium(II) chloride (12.32 mg, 0.017 mmol) was added dioxane (698 μl) and water (233 μl). The mixture was irradiated at 100° C. for 30 min affording conversion to desired product. The organic layer was decanted and the aqueous extracted with EtOAc. The organics were dried under reduced pressure. The material was dissolved in DCM (1.5 ml) and TFA (0.5 ml) was added. The brown solution was stirred at room temperature for 2 hr affording complete PMB cleavage. The light brown solution was dried under reduced pressure and the crude material purified with a 25 g Interchim column ramping EtOAc in heptane (0-100%) affording product (elution at 100% polar eluent) as a film which was lyophilized from MeOH/H$_2$O to yield 4-(2-methoxy-4-(trifluoromethyl)phenyl)-6-methyl-N-(thiazol-2-yl)quinoline-7-sulfonamide (60 mg, 0.125 mmol, 71.9% yield) as a white powder. $^1$H NMR (400 MHz, DMSO-d$_6$) δ=12.88 (br. s., 1H), 9.00 (d, J=4.3 Hz, 1H), 8.59 (s, 1H), 7.60-7.46 (m, 4H), 7.37 (s, 1H), 7.28 (d, J=4.6 Hz, 1H), 6.83 (d, J=4.6 Hz, 1H), 3.77 (s, 3H), 2.66 (s, 3H). m/z (ESI) 480.2 (M+H)$^+$.

EXAMPLE 327

6-METHOXY-4-(2-METHOXY-4-(TRIFLUOROMETHYL)PHENYL)-N-(THIAZOL-2-YL)QUINOLINE-7-SULFONAMIDE

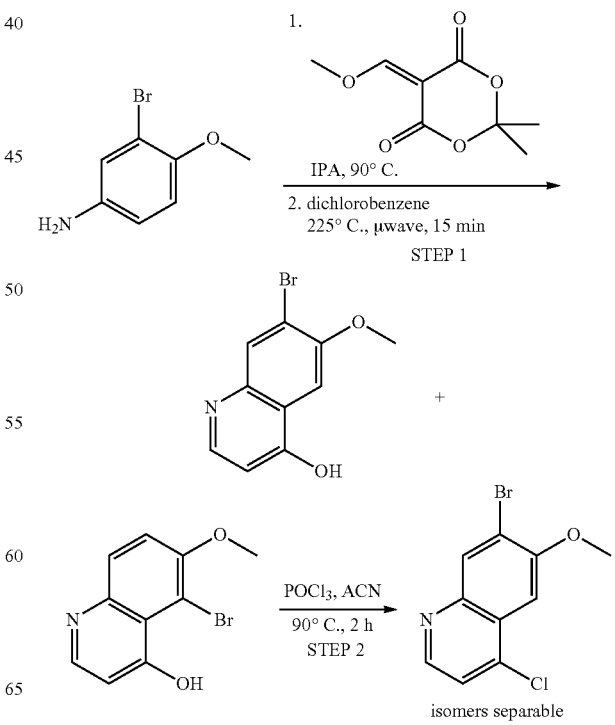

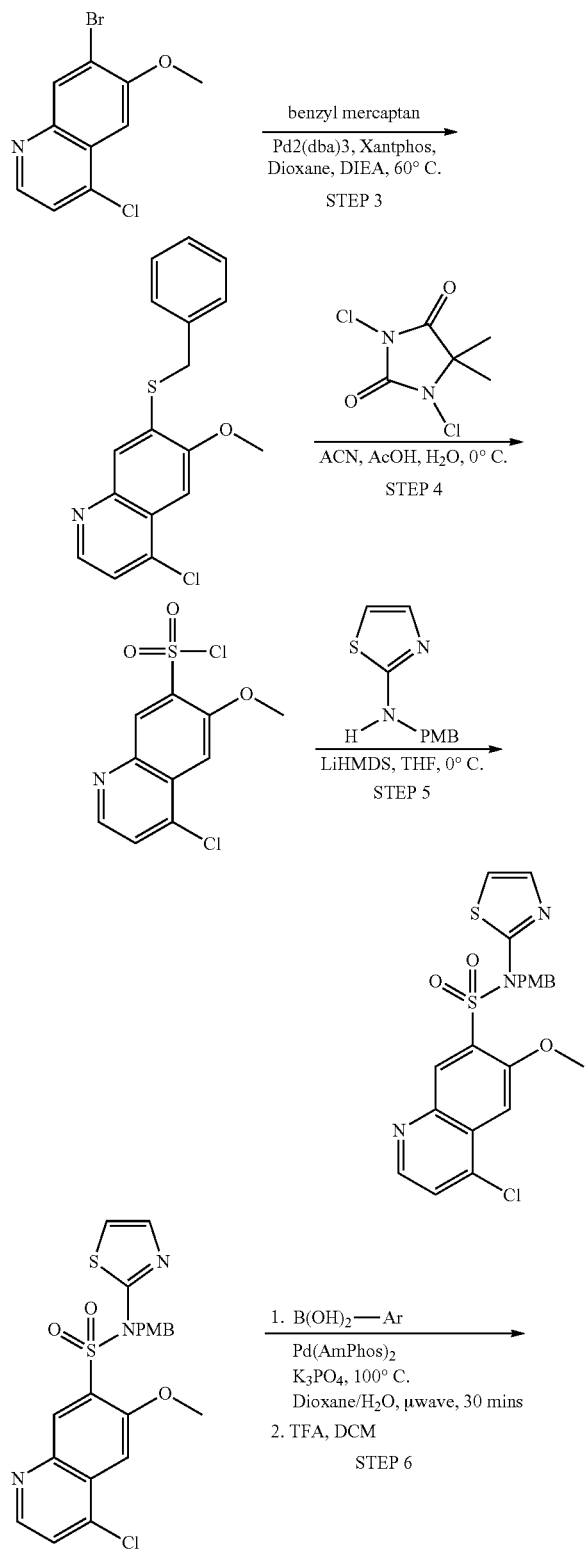

STEP 1: 7-BROMO-6-METHOXYQUINOLIN-4-OL

To a vial charged with 3-bromo-4-methoxyaniline (1.207 g, 5.97 mmol) was added IPA (11.95 ml) and 5-(methoxymethylene)-2,2-dimethyl-1,3-dioxane-4,6-dione (1.112 g, 5.97 mmol) respectively. The mixture was heated to 90° C. for 2 hrs providing a brown solution which was cooled to room temp affording an orange precipitate which was collected by vacuum filtration affording 5-(((3-bromo-4-methoxyphenyl)amino)methylene)-2,2-dimethyl-1,3-dioxane-4,6-dione (1.8 g, 5.05 mmol, 85% yield). This solid was transferred to a 5-20 ml microwave vial and 10 ml (0.5M 1,2-dichlorobenzene) was added and the mixture irradiated at 225° C. for 15 mins affording conversion to desired product according to LC-MS. To the suspension was added diethyl ether (~5 ml) to aid in product precipitation. To precipitate was collected via vacuum filtration and washed with ether, affording a brown solid as an isomeric mixture (~10:1) (595 mg, 39%). m/z (ESI) 256.1 (M+H)+.

STEP 2: 7-BROMO-4-CHLORO-6-METHOXYQUINOLINE

To a flask charged with 7-bromo-6-methoxyquinolin-4-ol (0.595 g, 2.342 mmol) was added Acetonitrile (11.71 ml) and $POCl_3$ (0.229 ml, 2.459 mmol) and the resulting suspension heated to 90° C. for 2.5 hr affording a brown solution and near complete conversion to desired product. The mixture was added to a cooled solution of sat. aq. $NaHCO_3$ and extracted with EtOAc (2×). The combined organics were dried with $Na_2SO_4$, filtered, and dried under reduced pressure. The organic phase was dried under reduced pressure and purified with an 40 g HP silicycle column ramping EtOAc in heptane (0-50%, 10% DCM throughout) affording isomer separation, both obtained as white solids. NMR indicated that the first eluting peak was the desired isomer, obtained as an off-white solid 7-bromo-4-chloro-6-methoxyquinoline (0.240 g, 0.881 mmol, 37.6% yield). The second peak (looked like about 60:40 ratio of product 1 to 2 by MPLC trace) was not isolated. $^1$H NMR (400 MHz, CHLOROFORM-d) δ=8.66 (d, J=4.7 Hz, 1H), 8.38 (s, 1H), 7.49 (d, J=4.7 Hz, 1H), 7.47 (s, 1H), 4.08 (s, 3H). m/z (ESI) 272.1 (M+H)+.

STEP 3: 7-(BENZYLTHIO)-4-CHLORO-6-METHOXYQUINOLINE

To a vial charged with 7-bromo-4-chloro-6-methoxyquinoline (0.240 g, 0.881 mmol) was added Dioxane (3.52 ml), DIEA (0.308 ml, 1.761 mmol), Xantphos (0.102 g, 0.176 mmol), Pd$_2$(dba)$_3$ (0.081 g, 0.088 mmol) and benzyl mercaptan (0.104 ml, 0.881 mmol). The vessel was sealed and heated to 110° C. for 90 mins affording complete conversion according to LC-MS. The mixture was filtered through Celite and dried under reduced pressure and purified with a 25 g Interchim column ramping EtOAc in heptane (0-50%, 10% DCM throughout) affording 7-(benzylthio)-4-chloro-6-methoxyquinoline (322 mg, 1.020 mmol, quant. yield) as a yellow solid with minor impurity. m/z (ESI) 316.3 (M+H)$^+$.

STEP 4: 4-CHLORO-6-METHOXYQUINOLINE-7-SULFONYL CHLORIDE

To a vial charged with 7-(benzylthio)-4-chloro-6-methoxyquinoline (322 mg, 1.020 mmol) was added Acetonitrile (9596 μl), Acetic Acid (360 μl), Water (240 μl). The resulting solution was cooled in an ice water bath and 1,3-dichloro-5,5-dimethyl-2-imidazolidinedione (268 μl, 2.04 mmol) was added. After 1.5 hr (ice melt) LC-MS of the orange solution indicated complete conversion to desired product. The mixture was diluted with EtOAc and extracted with H$_2$O. The aqueous phase was extracted again with EtOAc. The combined organics were dried under reduced pressure and purified with a 40 g HP silicycle column ramping EtOAc in heptane (0-35%, 5% DCM throughout) providing 4-chloro-6-methoxyquinoline-7-sulfonyl chloride (216 mg, 0.739 mmol, 72.5% yield) as a white solid. m/z (ESI) 294.0 (M+H)$^+$.

STEP 5: 4-CHLORO-6-METHOXY-N-(4-METHOXYBENZYL)-N-(THIAZOL-2-YL)QUINOLINE-7-SULFONAMIDE

To a flask containing ice cold suspension of N-(4-methoxybenzyl)thiazol-2-amine (171 mg, 0.776 mmol) in THF (2844 μl) was added lithium bis(trimethylsilyl)amide (1M in THF) (1479 μl, 1.479 mmol) faster than drop wise. The mixture was stirred for 15 mins prior to the drop wise addition of a solution of 4-chloro-6-methoxyquinoline-7-sulfonyl chloride (216 mg, 0.739 mmol) in THF (2.0 ml, 0.4 ml wash). The solution was allowed to stir for 4 hr (ice melt) providing a brown solution containing primarily product according to LC-MS. The mixture was added to a flask containing sat. aq. NH$_4$Cl. The aqueous mixture was extracted 2× with EtOAc and the combined organics were dried with Na$_2$SO$_4$, filtered, and dried under reduced pressure. The crude material was purified with a 40 g HP silicycle column ramping EtOAc in heptane (0-50%, 10% DCM throughout) affording product, 4-chloro-6-methoxy-N-(4-methoxybenzyl)-N-(thiazol-2-yl)quinoline-7-sulfonamide (128 mg, 0.269 mmol, 36.4% yield) as a yellow solid. m/z (ESI) 476.1 (M+H)$^+$.

STEP 6: 6-METHOXY-4-(2-METHOXY-4-(TRIFLUOROMETHYL)PHENYL)-N-(THIAZOL-2-YL)QUINOLINE-7-SULFONAMIDE

To a microwave vial charged with (2-methoxy-4-(trifluoromethyl)phenyl)boronic acid (35.6 mg, 0.162 mmol), 4-chloro-6-methoxy-N-(4-methoxybenzyl)-N-(thiazol-2-yl)quinoline-7-sulfonamide (70 mg, 0.147 mmol), potassium phosphate tribasic (36.5 μl, 0.441 mmol) and 1,1-bis[(di-t-butyl-p-methylaminophenyl]palladium(ii) chloride (10.41 mg, 0.015 mmol) was added Dioxane (590 μl) and Water (197 μl). The mixture was irradiated at 100° C. for 30 mins affording conversion to desired product according to LC-MS. The mixture was dried under reduced pressure. To the crude oil was added DCM (0.9 ml) and TFA (0.3 ml) was added at room temperature. After 1 hr of stirring LC-MS indicated complete PMB cleavage. The mixture was dried under reduced pressure and purified with a 25 g (15 μm spherical silica) column ramping EtOAc in heptane (0-100%, 10% DCM throughout) providing product, obtained as a film. The material was lyophilized from MeOH/H$_2$O providing 6-methoxy-4-(2-methoxy-4-(trifluoromethyl)phenyl)-N-(thiazol-2-yl)quinoline-7-sulfonamide (53 mg, 0.107 mmol, 72.7% yield) as an off-white solid. $^1$H NMR (400 MHz, DMSO-d$_6$) δ ppm 3.62 (s, 3H) 3.80 (s, 3H) 6.83 (s, 1H) 6.88 (d, J=4.60 Hz, 1H) 7.28 (d, J=4.60 Hz, 1H) 7.47-7.54 (m, 3H) 7.57 (d, J=7.63 Hz, 1H) 8.52 (s, 1H) 8.91 (d, J=4.40 Hz, 1H) 12.80 (br. s., 1H). m/z (ESI) 496.2 (M+H)$^+$.

EXAMPLE 328

4-(2-METHOXY-4-(TRIFLUOROMETHYL)PHENYL)-8-METHYL-N-(THIAZOL-2-YL)QUINOLINE-7-SULFONAMIDE

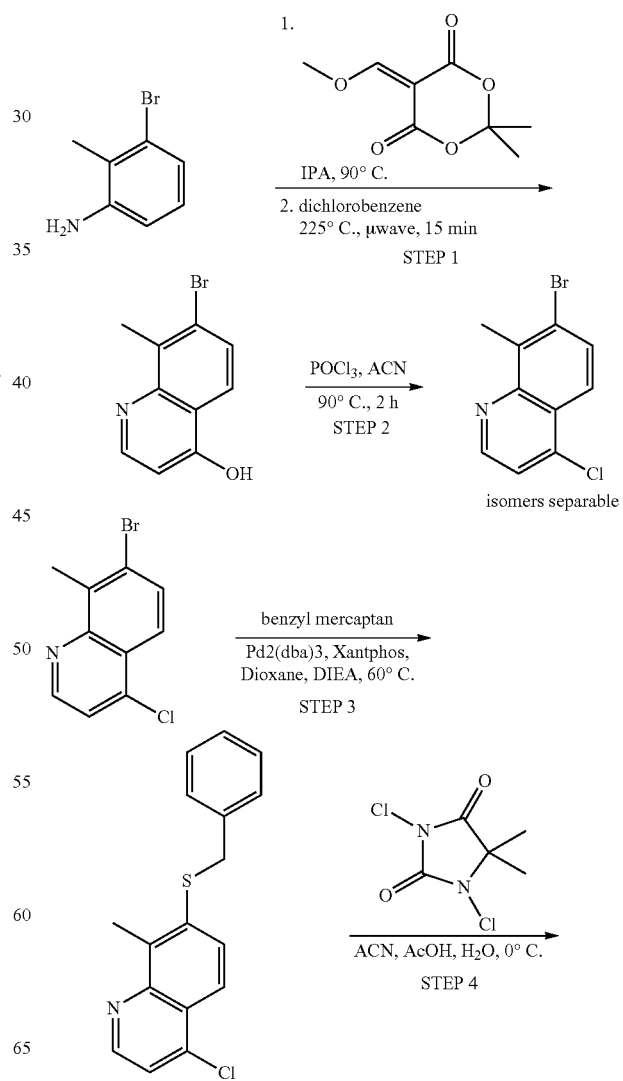

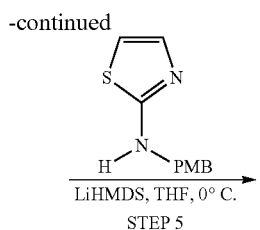

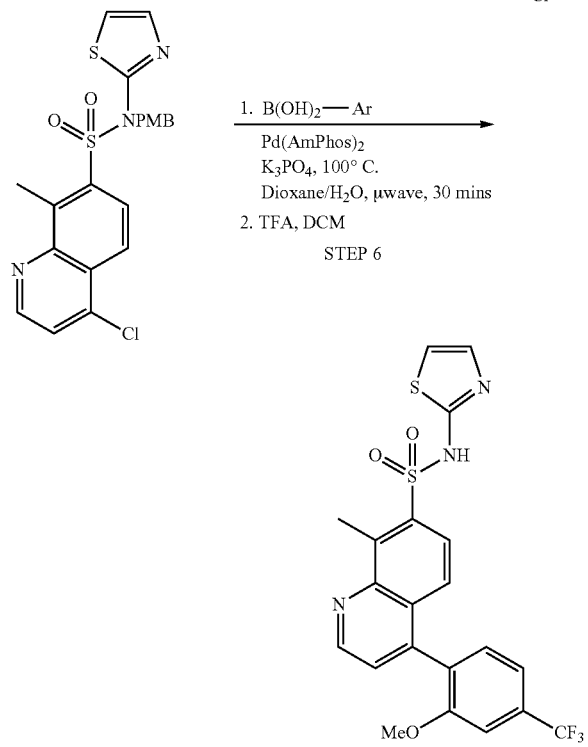

STEP 1: 7-BROMO-8-METHYLQUINOLIN-4-OL

To a vial charged with 3-bromo-2-methylaniline (1.207 g, 6.49 mmol) was added IPA (12.98 ml) and 5-(methoxymethylene)-2,2-dimethyl-1,3-dioxane-4,6-dione (1.208 g, 6.49 mmol) respectively. The mixture was heated to 90° C. for 2 hr providing a brown solution which was cooled to room temp affording an orange precipitate which was collected by vacuum filtration affording 5-(((3-bromo-2-methylphenyl)amino)methylene)-2,2-dimethyl-1,3-dioxane-4,6-dione (1.71 g, 5.03 mmol, 77% yield). This solid was transferred to a 5-20 ml microwave vial and 10 ml (0.5M 1,2-dichlorobenzene) was added and the mixture irradiated at 225° C. for 15 mins affording conversion to desired product according to LC-MS. Much precipitate was present directly following irradiation and cooling. The solid was collected via vacuum filtration and washed with heptane and dried under reduced pressure affording product as a brown solid 7-bromo-8-methylquinolin-4-ol (1.008 g, 4.23 mmol, 65.3% yield). m/z (ESI) 238.1 (M+H)+.

STEP 2: 7-BROMO-4-CHLORO-8-METHYLQUINOLINE

To a flask charged with 7-bromo-8-methylquinolin-4-ol (1.00 g, 4.20 mmol) was added Acetonitrile (21.00 ml) and POCl₃ (0.411 ml, 4.41 mmol) and the resulting suspension heated to 90° C. for 1.5 hrs affording a brown solution and near complete conversion to desired product. The mixture was added to a cooled solution of sat. aq. NaHCO₃ affording a tan precipitate which was collected via vacuum filtration and washed with water and dried under high vacuum affording product as a tan solid. m/z (ESI) 258.0 (M+H)+.

STEP 3: 7-(BENZYLTHIO)-4-CHLORO-8-METHYLQUINOLINE

To a vial charged with 7-bromo-4-chloro-8-methylquinoline (0.950 g, 3.70 mmol) was added Dioxane (14.81 ml), DIEA (1.294 ml, 7.41 mmol), xantphos (0.429 g, 0.741 mmol), Pd₂(dba)₃ (0.339 g, 0.370 mmol) and benzyl mercaptan (0.438 ml, 3.70 mmol). The vessel was sealed and heated to 110° C. for 3 hr affording complete conversion according to LC-MS. The mixture was filtered through Celite and dried under reduced pressure and purified with a 25 g Interchim column ramping EtOAc in heptane (0-50%, 10% DCM throughout) affording product as a yellow oil as a mixture of mono and bis substituted product according to MS as one LC peak, 7-(benzylthio)-4-chloro-8-methylquinoline (1.100 g, 3.67 mmol, 99% yield). m/z (ESI) 300.2 (M+H)+.

STEP 4: 4-CHLORO-8-METHYLQUINOLINE-7-SULFONYL CHLORIDE

To a vial charged with 7-(benzylthio)-4-chloro-8-methylquinoline (1.1 g, 3.67 mmol) was added Acetonitrile (34.5 ml), Acetic Acid (1.295 ml), Water (0.863 ml). The resulting solution was cooled in an ice water bath and 1,3-dichloro-5,5-dimethyl-2-imidazolidinedione (0.964 ml, 7.34 mmol) was added. After 30 min LC-MS of the resulting orange suspension indicated complete conversion to desired product. The mixture was diluted with EtOAc and extracted with H₂O. The aqueous phase was extracted again with EtOAc. The combined organics were dried under reduced pressure and purified with a 25 g HP silicycle column ramping EtOAc in heptane (0-35%, 5% DCM throughout) providing 4-chloro-8-methylquinoline-7-sulfonyl chloride (0.728 g, 2.64 mmol, 71.9% yield) as a white solid. m/z (ESI) 276.0 (M+H)+.

STEP 5: 4-CHLORO-N-(4-METHOXYBENZYL)-8-METHYL-N-(THIAZOL-2-YL)QUINOLINE-7-SULFONAMIDE

To a flask containing ice cold suspension of N-(4-methoxybenzyl)thiazol-2-amine (557 mg, 2.53 mmol) in THF (9.0 ml) was added lithium bis(trimethylsilyl)amide (1M in THF) (4816 μl, 4.82 mmol) faster than drop wise. The mixture was stirred for 15 mins prior to the drop wise addition of a solution of 4-chloro-8-methylquinoline-7-sulfonyl chloride (665 mg, 2.408 mmol) in THF (6.0 ml, 1.0 ml wash). The solution was allowed to stir for 20 mins (ice melt) providing a brown solution containing primarily product according to LC-MS. The mixture was added to a flask containing sat. aq. NH₄Cl and ice. The aqueous mixture was extracted 2× with EtOAc and the combined organics were dried with Na₂SO₄, filtered, and dried under reduced pressure. The crude material was purified with a 25 g HP silicycle column ramping EtOAc in heptane (0-50%, 10% DCM throughout) affording product, 4-chloro-N-(4-methoxybenzyl)-8-methyl-N-(thiazol-2-yl)quinoline-7-sulfonamide (326 mg, 0.709 mmol, 29.4% yield) as a yellow solid. m/z (ESI) 460.3 (M+H)⁺.

STEP 6: 4-(2-METHOXY-4-(TRIFLUOROMETHYL)PHENYL)-8-METHYL-N-(THIAZOL-2-YL)QUINOLINE-7-SULFONAMIDE

To a microwave vial charged with (2-methoxy-4-(trifluoromethyl)phenyl)boronic acid (52.6 mg, 0.239 mmol), 4-chloro-N-(4-methoxybenzyl)-8-methyl-N-(thiazol-2-yl)quinoline-7-sulfonamide (100 mg, 0.217 mmol), potassium phosphate tribasic (54.0 µl, 0.652 mmol) and 1,1-bis[(di-t-butyl-p-methylaminophenyl]palladium(II) chloride (15.39 mg, 0.022 mmol) was added dioxane (872 µl) and water (291 µl). The mixture was irradiated at 100° C. for 30 min affording conversion to desired product according to LC-MS. The organic layer was decanted and the aqueous extracted with EtOAc. The combined organics were dried under reduced pressure. The crude material was dissolved in DCM (3.0 ml) and TFA (1.0 ml) was added. The brown solution was stirred at room temperature for 1 hr affording complete PMB cleavage according to LC-MS. The light brown solution was dried under reduced pressure and the crude material purified with a 25 g Interchim column ramping EtOAc in heptane (0-100%) affording product (elution at 100% polar eluent) 4-(2-methoxy-4-(trifluoromethyl)phenyl)-8-methyl-N-(thiazol-2-yl)quinoline-7-sulfonamide (84 mg, 0.175 mmol, 81% yield) as a tan solid. ¹H NMR (400 MHz, DMSO-d₆) δ=12.81 (s, 1H), 9.08 (d, J=4.3 Hz, 1H), 8.03 (d, J=8.9 Hz, 1H), 7.62-7.45 (m, 4H), 7.43 (d, J=8.9 Hz, 1H), 7.26 (d, J=4.6 Hz, 1H), 6.81 (d, J=4.6 Hz, 1H), 3.13 (s, 3H). m/z (ESI) 480.0 (M+H)⁺.

INTERMEDIATE RRRR: 1-(4-CHLORO-2-METHOXYPHENYL)-N-(4-METHOXYBENZYL)-N-(PYRIMIDIN-4-YL)PHTHALAZINE-6-SULFONAMIDE

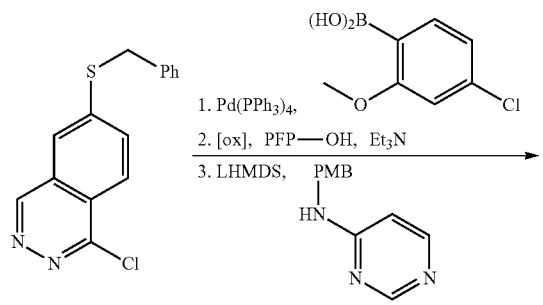

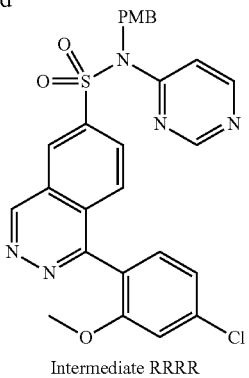

Intermediate RRRR

STEP 1: 6-(BENZYLTHIO)-1-(4-CHLORO-2-METHOXYPHENYL)PHTHALAZINE

A round-bottom flask was charged with 6-(benzylthio)-1-chlorophthalazine (from Step 1 in INTERMEDIATE AAAA, 416.7 mg, 1.453 mmol), 4-chloro-2-methoxyphenyl)boronic acid (Combi-Blocks, Inc., San Diego, Calif., 406 mg, 2.180 mmol), potassium carbonate (602 mg, 4.36 mmol), and Pd(Ph₃P)₄ (168 mg, 0.145 mmol). The flask was flushed with Ar (g), then 1,4-dioxane (5812 µl) and water (1453 µl) were added. A reflux condenser was attached, and the flask was lowered into a 50° C. heating bath for 4 h, then at 70° C. for 30 min. The mixture was heated to 70° C. for 30 min. The mixture was diluted with water and extracted with EtOAc (2×). The combined organic extracts were dried over sodium sulfate, filtered, and concentrated. The residue was purified by chromatography on silica gel (40-g Redi-Sep Gold column, 10-60% EtOAc/Heptane, then with 60-80% EtOAc/Heptane) to give 6-(benzylthio)-1-(4-chloro-2-methoxyphenyl)phthalazine (369 mg, 0.939 mmol, 64.6% yield) as an orange solid. m/z (ESI) 393.0 (M+H)⁺.

STEP 2: PERFLUOROPHENYL 1-(4-CHLORO-2-METHOXYPHENYL)PHTHALAZINE-6-SULFONATE

A round-bottom flask was charged with 6-(benzylthio)-1-(4-chloro-2-methoxyphenyl)phthalazine (369 mg, 0.939 mmol), DCM (8839 µl), acetic acid (331 µl), and water (221 µl) to give a clear, orange solution. The flask was submerged in an ice-water bath. After 5 min, 1,3-dichloro-5,5-dimethylimidazolidine-2,4-dione (379 mg, 1.925 mmol) was added in one portion. After 40 min, an additional portion of 1,3-dichloro-5,5-dimethylimidazolidine-2,4-dione (ca. 180 mg) was added. After 5 min, 2,3,4,5,6-pentafluorophenol (259 mg, 1.409 mmol) was added, then triethylamine (524 µl, 3.76 mmol) was added drop wise. The mixture was stirred for 10 min, then diluted with saturated aq. sodium bicarbonate solution, and the mixture was stirred vigorously for 5 min. The mixture was then extracted with DCM (2×). The combined organic extracts were dried over sodium sulfate, filtered, and concentrated. The residue was purified by chromatography on silica gel (40-g Redi-Sep Gold column, 0-40% EtOAc/Heptane) to give perfluorophenyl 1-(4-chloro-2-methoxyphenyl)phthalazine-6-sulfonate (234 mg, 0.453 mmol, 48.2% yield) as a cream-colored foam. m/z (ESI) 517.0 (M+H)⁺.

STEP 3: 1-(4-CHLORO-2-METHOXYPHENYL)-N-(4-METHOXYBENZYL)-N-(PYRIMIDIN-4-YL)PHTHALAZINE-6-SULFONAMIDE

A round-bottom flask was charged with N-(4-methoxybenzyl)pyrimidin-4-amine (80 mg, 0.371 mmol) and THF (1238 µl) to give a clear solution. The flask was cooled in a dry ice-acetone bath for 5 min, then lithium bis(trimethylsilyl)amide (1M in THF) (371 µl, 0.371 mmol) was added drop wise. The flask was removed from the cooling bath for 3 min, and then re-cooled in the bath. A solution of perfluorophenyl 1-(4-chloro-2-methoxyphenyl)phthalazine-6-sulfonate (128 mg, 0.248 mmol) in THF (1 mL with a 0.5 mL-flask wash) was added drop wise. After another minute, the flask was transferred to an ice-water bath. After 5 min, the mixture was diluted with saturated aq. ammonium chloride and water, then extracted with EtOAc (2×). The combined organic extracts were dried over sodium sulfate, filtered, and concentrated. The residue was purified by chromatography on silica gel (12-g Redi-Sep Gold column, 50-100% EtOAc/Heptane) to give 1-(4-chloro-2-methoxyphenyl)-N-(4-methoxybenzyl)-N-(pyrimidin-4-yl)phthalazine-6-sulfonamide (50 mg, 0.091 mmol, 36.8% yield) as an off-white solid. m/z (ESI) 548.2 (M+H)$^+$.

EXAMPLE 329

1-(3'-FLUORO-3-METHOXY-[1,1'-BIPHENYL]-4-YL)-N-(PYRIMIDIN-4-YL)PHTHALAZINE-6-SULFONAMIDE

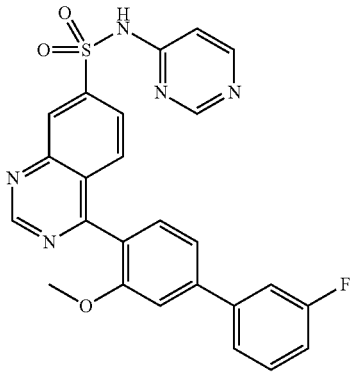 [SMILES: COc1cc(-c2cccc(F)c2)ccc1-c1ncnc2cc(S(=O)(=O)Nc3ccncn3)ccc12]

A vial was charged with 1-(4-chloro-2-methoxyphenyl)-N-(4-methoxybenzyl)-N-(pyrimidin-4-yl)phthalazine-6-sulfonamide (INTERMEDIATE RRRR, 50 mg, 0.091 mmol), (3-fluorophenyl)boronic acid (25.5 mg, 0.182 mmol), dicyclohexyl(2',6'-dimethoxy-[1,1'-biphenyl]-2-yl)phosphine (1.873 mg, 4.56 µmol), chloro(2-dicyclohexylphosphino-2',6'-dimethoxy-1,1'-biphenyl)[2-(2-aminoethylphenyl)]palladium(ii) dichloromethane (6.91 mg, 9.12 µmol) and potassium phosphate (58.1 mg, 0.274 mmol). The vial was flushed with Ar (g), then 1,4-dioxane (0.45 mL) and water (0.04 mL) were added in sequence. The vial was sealed and heated in a Biotage Initiator microwave reactor for 45 min at 90° C. The mixture was extracted with EtOAc (3×), and the combined organic extracts were concentrated. The residue was taken up in DCM (0.5 mL) and TFA (0.25 mL) to give an amber solution. After 15 min, triflic acid (0.02 mL) and TFA (0.5 mL) were added, and the mixture was stirred overnight. The mixture was diluted with MeOH, then concentrated. The residue was dissolved in DCM and saturated aq. sodium bicarbonate solution was added. The layers were separated, and the aq. layer was extracted with DCM (2×). The combined organic extracts were dried over sodium sulfate, filtered, and concentrated. The residue was purified by chromatography on silica gel (12-g Redi-Sep Gold column, 8% MeOH/DCM) to give 1-(3'-fluoro-3-methoxy-[1,1'-biphenyl]-4-yl)-N-(pyrimidin-4-yl)phthalazine-6-sulfonamide (17.41 mg, 0.036 mmol, 39.1% yield) as a yellow solid. $^1$H NMR (400 MHz, DMSO-d$_6$) δ=13.62-12.87 (m, 1H), 9.91 (s, 1H), 8.82 (s, 1H), 8.54 (s, 1H), 8.31 (dd, J=1.8, 8.8 Hz, 1H), 8.24-8.16 (m, 1H), 7.78 (d, J=8.8 Hz, 1H), 7.75-7.67 (m, 2H), 7.63-7.47 (m, 4H), 7.32-7.23 (m, 1H), 6.95 (d, J=6.0 Hz, 1H), 3.78 (s, 3H). m/z (ESI) 488.2 (M+H)$^+$.

EXAMPLE 330

5-(4-CYANO-2-METHOXYPHENYL)-N-(1,2,4-THIADIAZOL-5-YL)NAPHTHALENE-2-SULFONAMIDE

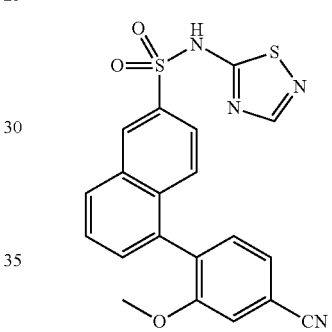

A vial was charged with 5-bromo-N-(4-methoxybenzyl)-N-(1,2,4-thiadiazol-5-yl)naphthalene-2-sulfonamide (INTERMEDIATE D, 82.49 mg, 0.168 mmol), (4-cyano-2-methoxyphenyl)boronic acid (59.5 mg, 0.336 mmol), Pd(AmPhos)$_2$Cl$_2$ (5.96 mg, 8.41 µmol), potassium phosphate (107 mg, 0.505 mmol), 1,4-dioxane (631 µl), and water (210 µl). The vial was flushed with Ar (g), then sealed and heated in a Biotage Initiator microwave reactor for 30 min h at 90° C. The mixture was extracted with EtOAc (3×), and the combined organic extracts were concentrated. The residue was dissolved in DCM (1 mL) and TFA (0.5 mL). After 40 min, the mixture was diluted with MeOH and concentrated. The residue was purified by chromatography on silica gel (12-g Redi-Sep Gold column, 0-50% EtOAc/Heptane) to give a light-yellow solid. The material was concentrated from DCM, and then taken up in DCM. The solvent was mostly removed via pipette, then the solid was again concentrated from DCM to give 5-(4-cyano-2-methoxyphenyl)-N-(1,2,4-thiadiazol-5-yl)naphthalene-2-sulfonamide (35.5 mg, 0.084 mmol, 50.0% yield) as an off-white solid. $^1$H NMR (400 MHz, DMSO-d$_6$) δ=8.54 (d, J=1.9 Hz, 1H), 8.46 (s, 1H), 8.25

(d, J=8.3 Hz, 1H), 7.78-7.67 (m, 3H), 7.61-7.50 (m, 3H), 7.46 (d, J=7.6 Hz, 1H), 3.71 (s, 3H). m/z (ESI) 423.2 (M+H)+.

INTERMEDIATE SSSS: (2-CHLORO-3'-FLUORO-5-METHOXY-[1,1'-BIPHENYL]-4-YL)BORONIC ACID

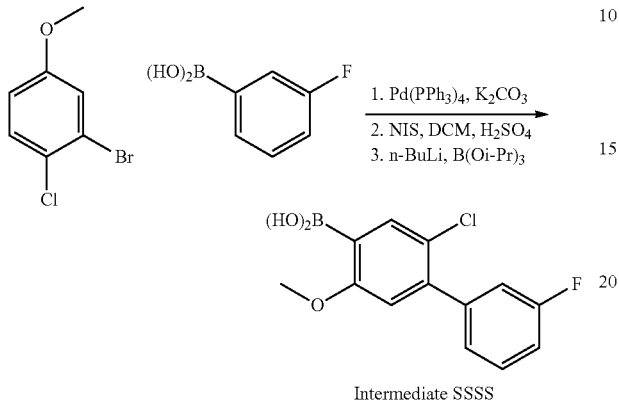

Intermediate SSSS

STEP 1: 2-CHLORO-3'-FLUORO-5-METHOXY-1,1'-BIPHENYL

A round-bottom flask was charged with 3-bromo-4-chloroanisole (1.625 ml, 7.34 mmol), (3-fluorophenyl)boronic acid (1.129 g, 8.07 mmol), potassium carbonate (3.04 g, 22.01 mmol), and tetrakistriphenylphosphine palladium (0) (0.424 g, 0.367 mmol). The flask was flushed with Ar (g), then 1,4-dioxane (19.57 ml) and water (4.89 ml) were added. A reflux condenser was attached, and the flask was lowered into a 90° C. heating bath. After 2 h, the mixture was cooled, diluted with ethyl acetate, and washed with brine. The organic layer was dried over sodium sulfate, filtered, and concentrated. The residue was purified by chromatography on silica gel (80-g Redi-Sep Gold column, 0-10% EtOAc/Heptane) to give an oily solid as product that was used directly in the next step. m/z (ESI) 281.1 (M+H)+.

STEP 2: 2-CHLORO-3'-FLUORO-4-IODO-5-METHOXY-1,1'-BIPHENYL

A round-bottom flask was charged with 2-chloro-3'-fluoro-5-methoxy-1,1'-biphenyl (1.288 g, 5.44 mmol), DCM (8.00 ml), AcOH (8.00 ml), and sulfuric acid (0.160 ml, 2.99 mmol) to give a clear solution. n-Iodosuccinimide (1.224 g, 5.44 mmol) was added in one portion to give a maroon-colored solution. After 7 h, the mixture was diluted with DCM, washed with water, washed with saturated aq. sodium thiosulfate, dried over sodium sulfate, filtered, and concentrated. The residue was purified by chromatography on silica gel (40-g Redi-Sep Gold column, 25-g silica gel column, 0-5% EtOAc/Heptane) give 2-chloro-3'-fluoro-4-iodo-5-methoxy-1,1'-biphenyl (1.68 g, 4.63 mmol, 85% yield) as a clear oil. m/z (ESI) 362.0 (M+H)+.

STEP 3: (2-CHLORO-3'-FLUORO-5-METHOXY-[1,1'-BIPHENYL]-4-YL)BORONIC ACID

A round-bottom flask was charged with 2-chloro-3'-fluoro-4-iodo-5-methoxy-1,1'-biphenyl (1.68 g, 4.63 mmol), triisopropyl borate (1.399 ml, 6.02 mmol), and THF (23.17 ml). The flask was cooled in a dry ice-acetone bath for 10 min, then n-butyllithium (2.5 M in hexane) (2.409 ml, 6.02 mmol) was added drop wise over 1 min. After 40 min, a solution of 2 N aq. NaOH (25 mL) was added. The resulting biphasic mixture was stirred for 10 min, and then partitioned between water and ether. The layers were separated, and the ethereal layer was extracted with water (2×). The combined aq. extracts were washed with ether, and the ethereal layer was back-extracted with water. The combined aq. layers were acidified with 3N aq. HCl (50 mL), and the aq. mixture was extracted with DCM (3×). The combined DCM-layers were dried over sodium sulfate, filtered, and concentrated to give (2-chloro-3'-fluoro-5-methoxy-[1,1'-biphenyl]-4-yl)boronic acid (0.859 g, 3.06 mmol, 66.1% yield) as an oily solid. m/z (ESI) 281.1 (M+H)+.

INTERMEDIATE TTTT: PERFLUOROPHENYL 1-(2-CHLORO-3'-FLUORO-5-METHOXY-[1,1'-BIPHENYL]-4-YL)ISOQUINOLINE-6-SULFONATE

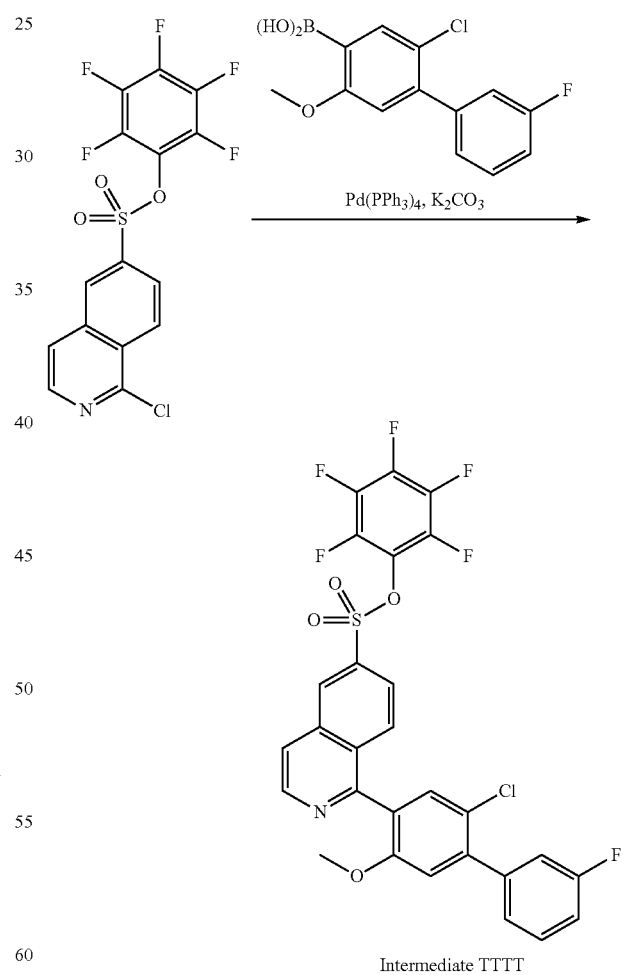

Intermediate TTTT

A round-bottom flask was charged with perfluorophenyl 1-chloroisoquinoline-6-sulfonate (from Step 1 of Example 73, 500 mg, 1.220 mmol), (2-chloro-3'-fluoro-5-methoxy-[1,1'-biphenyl]-4-yl)boronic acid (Intermediate SSSS; 479 mg, 1.709 mmol) potassium carbonate (506 mg, 3.66 mmol), and Pd(Ph₃P)₄ (141 mg, 0.122 mmol). The vial was flushed with Ar (g), then 1,4-dioxane (4576 µl) and water (1525 µl) were added. The flask was fitted with a reflux condenser and heated in a 50° C. heating bath for 40 min. The mixture was partitioned between water and EtOAc. The layers were separated, and the organic layer was washed with brine, dried over sodium sulfate, filtered, and concentrated. The residue was purified by chromatography on silica gel (40-g Redi-Sep Gold column, 25-g silica gel loading column, 0-50% EtOAc/Heptane) to give perfluorophenyl 1-(2-chloro-3'-fluoro-5-methoxy-[1,1'-biphenyl]-4-yl)isoquinoline-6-sulfonate (593.7 mg, 0.973 mmol, 80% yield) as a white foam. m/z (ESI) 609.9 (M+H)⁺.

EXAMPLE 331

1-(2-CHLORO-3'-FLUORO-5-METHOXY-[1,1'-BIPHENYL]-4-YL)-N-(1,2,4-THIADIAZOL-5-YL)ISOQUINOLINE-6-SULFONAMIDE

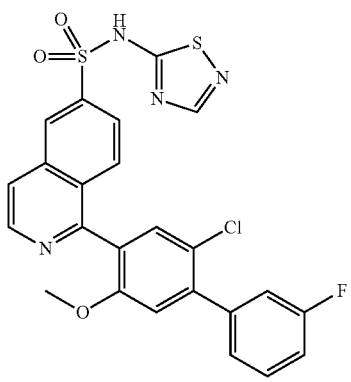 [SMILES: COc1cc(-c2cccc(F)c2)c(Cl)cc1-c1nccc2cc(S(=O)(=O)Nc3ncns3)ccc12]

A vial was charged with perfluorophenyl 1-(2-chloro-3'-fluoro-5-methoxy-[1,1'-biphenyl]-4-yl)isoquinoline-6-sulfonate (INTERMEDIATE TTTT; 71.85 mg, 0.118 mmol), 1,2,4-thiadiazol-5-amine (13.10 mg, 0.130 mmol), and cesium carbonate (115 mg, 0.353 mmol). The vial was flushed with Ar (g), and then acetonitrile (589 µl) was added. After 2 h, the mixture was diluted with EtOAc and 0.5 N aq. HCl. The layers were separated, and the aq. layer was extracted with EtOAc (2×). The combined organic extracts were dried over sodium sulfate, filtered, and concentrated. The residue was concentrated from DCM/MeOH. The residue was then taken up in MeOH and filtered. The collected solid was washed with MeOH (1×), dried under a stream of N₂ (g), then dried under vacuum to give 1-(2-chloro-3'-fluoro-5-methoxy-[1,1'-biphenyl]-4-yl)-N-(1,2,4-thiadiazol-5-yl)isoquinoline-6-sulfonamide (40 mg, 0.076 mmol, 64.4% yield) as an off-white solid. ¹H NMR (400 MHz, DMSO-d₆) δ=8.72 (d, J=5.7 Hz, 1H), 8.60 (d, J=1.7 Hz, 1H), 8.48 (s, 1H), 8.16 (d, J=5.7 Hz, 1H), 7.95-7.90 (m, 1H), 7.88-7.81 (m, 1H), 7.63-7.54 (m, 2H), 7.50-7.41 (m, 2H), 7.36-7.29 (m, 1H), 7.27 (s, 1H), 3.71 (s, 3H). m/z (ESI) 527.2 (M+H)⁺.

EXAMPLE 332

1-(2-CHLORO-3'-FLUORO-5-METHOXY-[1,1'-BIPHENYL]-4-YL)-N-(1,3,4-THIADIAZOL-2-YL)ISOQUINOLINE-6-SULFONAMIDE

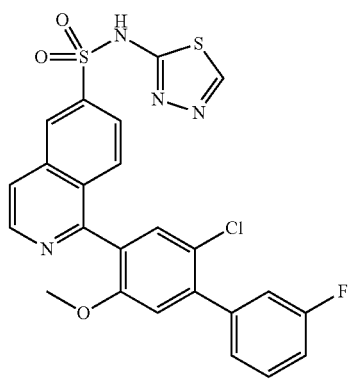 [SMILES: COc1cc(-c2cccc(F)c2)c(Cl)cc1-c1nccc2cc(S(=O)(=O)Nc3nncs3)ccc12]

A vial was charged with perfluorophenyl 1-(2-chloro-3'-fluoro-5-methoxy-[1,1'-biphenyl]-4-yl)isoquinoline-6-sulfonate (INTERMEDIATE TTTT; 68.6 mg, 0.112 mmol), 1,3,4-thiadiazol-2-amine (12.51 mg, 0.124 mmol), and cesium carbonate (110 mg, 0.337 mmol). The vial was flushed with Ar (g), then acetonitrile (562 µl) was added. After stirring overnight, the mixture was diluted with EtOAc and 0.5 N aq. HCl. The layers were separated, and the aq. layer was extracted with EtOAc (2×). The combined organic extracts were dried over sodium sulfate, filtered, and concentrated. The residue was purified by chromatography on silica gel (12-g Redi-Sep Gold column, 0-4% MeOH/DCM). Some fractions were discarded, and the remainder containing product were combined and concentrated to 1-(2-chloro-3'-fluoro-5-methoxy-[1,1'-biphenyl]-4-yl)-N-(1,3,4-thiadiazol-2-yl)isoquinoline-6-sulfonamide (35.19 mg, 0.067 mmol, 59.4% yield) as a white solid. ¹H NMR (400 MHz, DMSO-d₆) δ=14.50 (br. s., 1H), 8.80 (s, 1H), 8.71 (d, J=5.7 Hz, 1H), 8.58 (d, J=1.8 Hz, 1H), 8.14 (d, J=5.6 Hz, 1H), 7.95-7.89 (m, 1H), 7.87-7.79 (m, 1H), 7.62-7.53 (m, 2H), 7.49-7.41 (m, 2H), 7.32 (dt, J=3.0, 8.5 Hz, 1H), 7.27 (s, 1H), 3.71 (s, 3H). m/z (ESI) 527.2 (M+H)+.

EXAMPLE 333

1-(2-CHLORO-3'-FLUORO-5-METHOXY-[1,1'-BIPHENYL]-4-YL)-N-(PYRIMIDIN-4-YL)ISO-QUINOLINE-6-SULFONAMIDE

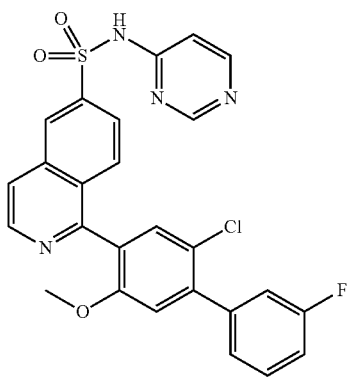 [SMILES: COc1cc(-c2cccc(F)c2)c(Cl)cc1-c1nccc2cc(S(=O)(=O)Nc3ccncn3)ccc12]

A round-bottom flask was charged with perfluorophenyl 1-(2-chloro-3'-fluoro-5-methoxy-[1,1'-biphenyl]-4-yl)isoquinoline-6-sulfonate (INTERMEDIATE TTTT; 72.97 mg, 0.120 mmol) pyrimidin-4-amine (Alfa Aesar, Ward Hill, Mass., 12.52 mg, 0.132 mmol), and THF (598 µl) to give a clear, lightly-colored solution. The flask was cooled in an ice-bath for 5 min, then lithium bis(trimethylsilyl)amide (1M in THF) (251 µl, 0.251 mmol) was added drop wise over 30 s to give a yellow suspension. After 30 min, the mixture was purified directly by chromatography on silica gel (12-g Redi-Sep Gold column, 3.5 MeOH/DCM, then 3.5-10% MeOH/DCM). A few mixed fractions were discarded, and the remainder of fractions containing product were combined and concentrated to give 1-(2-chloro-3'-fluoro-5-methoxy-[1,1'-biphenyl]-4-yl)-N-(pyrimidin-4-yl)isoquinoline-6-sulfonamide (40.83 mg, 0.078 mmol, 65.5% yield) as an off-white solid. $^1$H NMR (400 MHz, DMSO-$d_6$) δ=13.12 (br. s., 1H), 8.71 (s, 1H), 8.67 (s, 1H), 8.57 (s, 1H), 8.24 (d, J=6.6 Hz, 1H), 8.14 (d, J=5.8 Hz, 1H), 7.99 (dd, J=1.8, 8.9 Hz, 1H), 7.81 (d, J=8.9 Hz, 1H), 7.58 (dt, J=6.3, 8.0 Hz, 1H), 7.54 (s, 1H), 7.49-7.40 (m, 2H), 7.35-7.29 (m, 1H), 7.27 (s, 1H), 7.02 (d, J=6.6 Hz, 1H), 3.70 (s, 3H). m/z (ESI) 521.2 (M+H)+.

EXAMPLE 334

1-(2-CHLORO-3'-FLUORO-5-METHOXY-[1,1'-BIPHENYL]-4-YL)-N-(1,2,5-THIADIAZOL-3-YL)ISOQUINOLINE-6-SULFONAMIDE

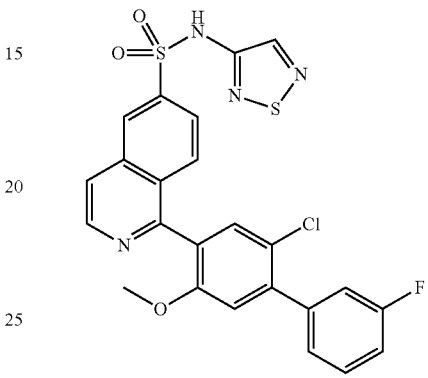

A vial was charged with perfluorophenyl 1-(2-chloro-3'-fluoro-5-methoxy-[1,1'-biphenyl]-4-yl)isoquinoline-6-sulfonate (INTERMEDIATE TTTT; 45 mg, 0.074 mmol), 1,2,5-thiadiazol-3-amine (8.21 mg, 0.081 mmol), and THF (0.5 mL) to give a clear solution. The vial was cooled in an ice-water bath for 5 min, then lithium bis(trimethylsilyl)amide (1M in THF) (162 µl, 0.162 mmol) was added drop wise. After 10 min, the mixture was diluted with a small amount of methanol to give a solution which was purified directly by chromatography on silica gel (12-g Redi-Sep Gold column, 0-5% MeOH/DCM) to give 1-(2-chloro-3'-fluoro-5-methoxy-[1,1'-biphenyl]-4-yl)-N-(1,2,5-thiadiazol-3-yl)isoquinoline-6-sulfonamide (22.2 mg, 0.042 mmol, 57.1% yield) as a light-yellow solid. $^1$H NMR (400 MHz, DMSO-$d_6$) δ=12.50 (br. s., 1H), 8.81-8.69 (m, 2H), 8.50 (s, 1H), 8.18 (d, J=5.4 Hz, 1H), 8.00 (dd, J=1.9, 8.9 Hz, 1H), 7.88 (d, J=8.9 Hz,

EXAMPLE 335

1-(2-CHLORO-3'-FLUORO-5-METHOXY-[1,1'-BIPHENYL]-4-YL)-N-(ISOXAZOL-3-YL)ISO-QUINOLINE-6-SULFONAMIDE

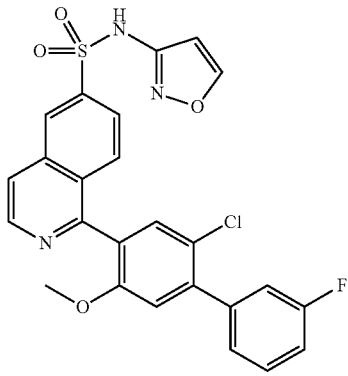 [SMILES: COc1cc(-c2cccc(F)c2)c(Cl)cc1-c1nccc2cc(S(=O)(=O)Nc3ccon3)ccc12]

A vial was charged with isoxazol-3-amine (6.09 microliters, 6.93 mg, 0.082 mmol) (from Aldrich Co.), perfluorophenyl 1-(2-chloro-3'-fluoro-5-methoxy-[1,1'-biphenyl]-4-yl)isoquinoline-6-sulfonate (INTERMEDIATE TTTT, 45.67 mg, 0.075 mmol) and THF (0.5 mL) to give a clear solution. The vial was cooled in an ice-water bath for 10 min, then lithium bis(trimethylsilyl)amide (1M in THF) (65.9 µl, 0.065 mmol) was added. After 40 min, additional portions of amine (10 microliters) and LHMDS solution (0.05 mL) were added. LCMS after 10 min showed mainly the desired product. The mixture was purified directly on silica gel (12-g Redi-Sep Gold column, 0-5% MeOH/DCM) to give 1-(2-chloro-3'-fluoro-5-methoxy-[1,1'-biphenyl]-4-yl)-N-(isoxazol-3-yl)isoquinoline-6-sulfonamide (23.72 mg, 0.047 mmol, 62.1% yield) as an off-white solid. $^1$H NMR (400 MHz, DMSO-$d_6$) δ=11.92 (br. s., 1H), 8.78-8.72 (m, 2H), 8.69 (d, J=1.7 Hz, 1H), 8.16 (d, J=5.5 Hz, 1H), 8.01-7.84 (m, 2H), 7.64-7.53 (m, 2H), 7.49-7.40 (m, 2H), 7.37-7.29 (m, 1H), 7.27 (s, 1H), 6.50 (d, J=1.9 Hz, 1H), 3.70 (s, 3H). m/z (ESI) 510.2 (M+H)$^+$.

INTERMEDIATE UUUU: 2-CHLORO-4-METHOXY-5-(4,4,5,5-TETRAMETHYL-1,3,2-DIOXABOROLAN-2-YL)BENZONITRILE

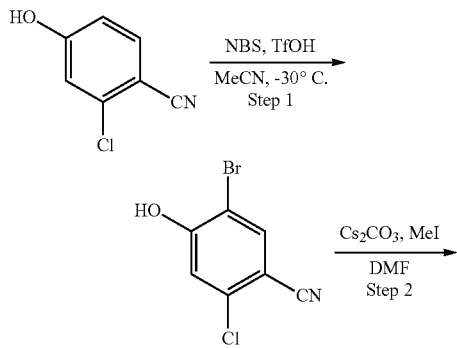

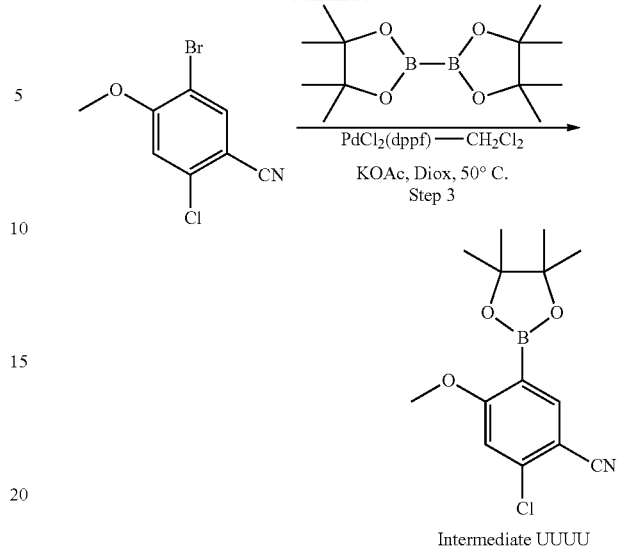

STEP 1: 5-BROMO-2-CHLORO-4-HYDROXYBENZONITRILE

To a solution of 2-chloro-4-hydroxybenzonitrile (10.0 g, 65.11 mmol, Apollo Scientific) in MeCN (200 mL) was added triflic acid (6.32 mL, 71.62 mmol, Spectrochem) and NBS (13.90 g, 78.13 mmol, Spectrochem) at −30° C. The reaction mixture was allowed to warm to RT and stirred for 15 h. The reaction mixture was quenched with saturated aqueous NaHSO$_3$ solution (500 mL) and extracted with ethyl acetate (2×1000 mL). The combined organic layers were washed with water (500 mL), dried over sodium sulfate, filtered and concentrated under reduced pressure to obtain the crude compound which was purified by column chromatography (silica gel 100-200 mesh and 0-6% EtOAc in hexane) to obtain 5-bromo-2-chloro-4-hydroxybenzonitrile (7.0 g, 46.2%) as white solid. m/z (ESI) 230.0 (M−H)$^+$.

STEP 2: 5-BROMO-2-CHLORO-4-METHOXYBENZONITRILE

To a solution of 5-bromo-2-chloro-4-hydroxybenzonitrile (7.0 g, 30.11 mmol) in DMF (70 mL) was added cesium carbonate (19.62 g, 60.22 mmol, GLR Scientific) and MeI (3.74 mL, 60.22 mmol, Spectrochem). The reaction mixture was stirred at room temperature for 16 h. The reaction mixture was quenched with ice cold water (500 mL) and extracted with ethyl acetate (2×500 mL). The combined organic layer was washed with water, dried over sodium sulfate, filtered and concentrated under reduced pressure to obtain the crude compound which was purified by column chromatography (silica gel 100-200 mesh and 0-4% EtOAc in hexane) to obtain 5-bromo-2-chloro-4-methoxybenzonitrile (5.5 g, 74.1%) as white solid. m/z (ESI) N/A (no ionization observed).

STEP 3: 2-CHLORO-4-METHOXY-5-(4,4,5,5-TETRAMETHYL-1,3,2-DIOXABOROLAN-2-YL)BENZONITRILE

To a solution 5-bromo-2-chloro-4-methoxybenzonitrile (5.5 g, 22.31 mmol) and 4,4,4',4',5,5,5',5'-octamethyl-2,2'-bi(1,3,2-dioxaborolane) (8.49 g, 33.46 mmol, RCP) in 1,4- dioxan (100 mL) was added KOAc (5.46 g, 55.77 mmol, Spectrochem) and the reaction mixture was degassed with nitrogen for 20 minutes. PdCl$_2$(dppf)CH$_2$Cl$_2$ (911 mg, 1.11 mmol, GLR) was added and the reaction mixture allowed to stir at 50° C. for 12 h. The reaction mixture was diluted with ethyl acetate (100 mL) and filtered through Celite bed. The filtrate was concentrated under reduced pressure to obtain the crude which was further purified by column chromatography (neutral alumina, 0-70% ethyl acetate in hexane) to obtain the title compound (1.6 g, 24.4%) as off white solid. m/z (ESI) 294 (M+H)$^+$. $^1$H NMR (400 MHz, CDCl$_3$) δ 7.96 (s, 1H), 6.94 (s, 1H), 3.89 (s, 3H), 1.34 (s, 12H).

INTERMEDIATE VVVV: PERFLUOROPHENYL 1-(4-CHLORO-5-CYANO-2-METHOXYPHENYL) ISOQUINOLINE-6-SULFONATE

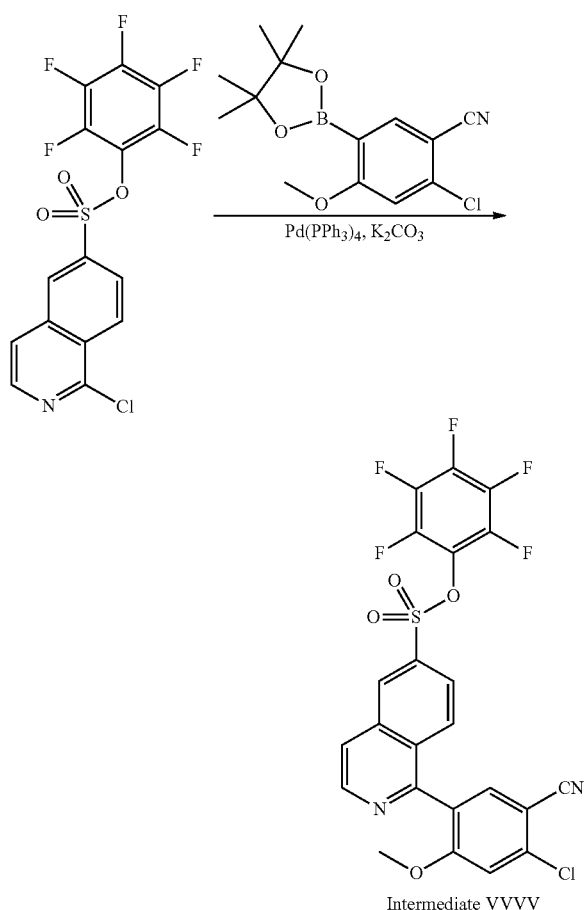

Intermediate VVVV

A round-bottom flask was charged with perfluorophenyl 1-chloroisoquinoline-6-sulfonate (see EXAMPLE 73, Step 1; 555 mg, 1.355 mmol), 2-chloro-4-methoxy-5-(4,4,5,5-tetramethyl-1,3,2-dioxaborolan-2-yl)benzonitrile (INTERMEDIATE UUUU, 477 mg, 1.626 mmol), potassium carbonate (562 mg, 4.06 mmol), and Pd(Ph$_3$P)$_4$ (157 mg, 0.135 mmol). The vial was flushed with Ar (g), then 1,4-dioxane (5080 µl) and water (1693 µl) were added. The flask was lowered into a 50° C. heating bath for 1 h. The reaction mixture was diluted with water and EtOAc. The organic extract was dried over sodium sulfate, filtered, and concentrated. The residue was purified by chromatography on silica gel (40-g Redi-Sep Gold column, 0-50% EtOAc/Heptane) to give perfluorophenyl 1-(4-chloro-5-cyano-2-methoxyphenyl)isoquinoline-6-sulfonate (583.89 mg, 1.080 mmol, 80% yield) as an off-white foam. m/z (ESI) 540.9 (M+H)$^+$.

EXAMPLE 336

1-(4-CHLORO-5-CYANO-2-METHOXYPHENYL)-N-(1,2,4-THIADIAZOL-5-YL)ISOQUINOLINE-6-SULFONAMIDE

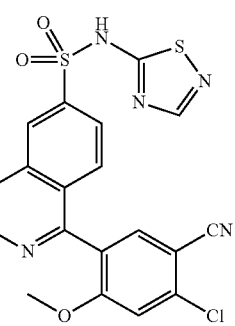

A vial was charged with perfluorophenyl 1-(4-chloro-5-cyano-2-methoxyphenyl)isoquinoline-6-sulfonate (INTERMEDIATE VVVV, 154.38 mg, 0.285 mmol), 1,2,4-thiadiazol-5-amine (34.6 mg, 0.343 mmol), and cesium carbonate (279 mg, 0.856 mmol). Acetonitrile (1427 µl) was added, and the mixture was stirred for 1 h. The mixture was diluted with EtOAc and 0.5 N aq. HCl. The layers were separated, and the organic extract was washed with brine, dried over sodium sulfate, filtered, and concentrated. The residue was purified by chromatography on silica gel (12-g Redi-Sep Gold column, 0-10% MeOH/DCM, product eluted over a long period of time). The resulting white solid was taken up in MeOH and filtered. The collected solid was washed with MeOH (2×), dried under a stream of N$_2$ (g), then dried under vacuum to give 1-(4-chloro-5-cyano-2-methoxyphenyl)-N-(1,2,4-thiadiazol-5-yl)isoquinoline-6-sulfonamide (76.6 mg, 0.167 mmol, 58.6% yield) as a white solid. $^1$H NMR (400 MHz, DMSO-d$_6$) δ=7.43 (d, J=5.7 Hz, 1H), 7.32 (d, J=1.7 Hz, 1H), 7.21 (s, 1H), 6.90 (d, J=5.6 Hz, 1H), 6.70 (s, 1H), 6.62-6.55 (m, 1H), 6.52-6.46 (m, 1H), 6.37 (s, 1H), 2.50 (s, 3H). m/z (ESI) 458.1 (M+H)+.

EXAMPLE 337

1-(4-CHLORO-5-CYANO-2-METHOXYPHENYL)-N-(1,3,4-THIADIAZOL-2-YL)ISOQUINOLINE-6-SULFONAMIDE

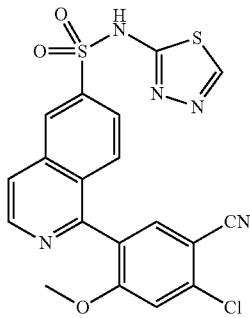 [SMILES: COc1cc(Cl)c(C#N)cc1-c1nccc2cc(S(=O)(=O)Nc3nncs3)ccc12]

A vial was charged with perfluorophenyl 1-(4-chloro-5-cyano-2-methoxyphenyl)isoquinoline-6-sulfonate (INTERMEDIATE VVVV, 145.2 mg, 0.268 mmol), 1,3,4-thiadiazol-2-amine (32.6 mg, 0.322 mmol), and cesium carbonate (262 mg, 0.805 mmol). Acetonitrile (1342 µl) was added, and the mixture was stirred for 2 h. The mixture was diluted with EtOAc and 0.5 N aq. HCl. The layers were separated, and the aq. layer was extracted with 10% MeOH/EtOAc (2×). The combined organic extracts were dried over sodium sulfate, filtered, and concentrated. The residue was concentrated from MeOH, then the mixture was filtered through a membrane filter. The collected solid was washed with MeOH (3×), dried under a stream of $N_2$ (g), then dried under vacuum to give 1-(4-chloro-5-cyano-2-methoxyphenyl)-N-(1,3,4-thiadiazol-2-yl)isoquinoline-6-sulfonamide (65.89 mg, 0.144 mmol, 53.6% yield) as an off-white solid. $^1$H NMR (400 MHz, DMSO-$d_6$) δ=14.51 (br. s., 1H), 8.80 (s, 1H), 8.70 (d, J=5.7 Hz, 1H), 8.58 (d, J=1.6 Hz, 1H), 8.16 (d, J=5.7 Hz, 1H), 7.98 (s, 1H), 7.89-7.82 (m, 1H), 7.80-7.72 (m, 1H), 7.65 (s, 1H), 3.78 (s, 3H). m/z (ESI) 458.2 (M+H)+.

EXAMPLE 338

1-(2-CYANO-3',5'-DIFLUORO-5-METHOXY-[1,1'-BIPHENYL]-4-YL)-N-(1,3,4-THIADIAZOL-2-YL) ISOQUINOLINE-6-SULFONAMIDE

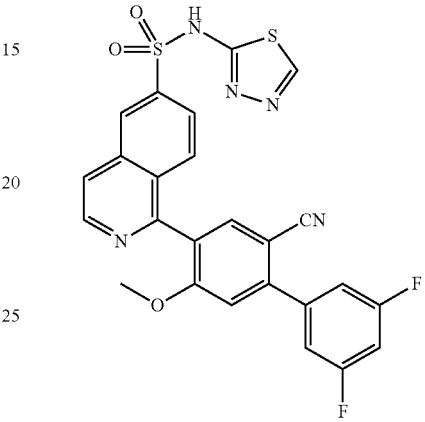

A vial was charged with 1-(4-chloro-5-cyano-2-methoxyphenyl)-N-(1,3,4-thiadiazol-2-yl)isoquinoline-6-sulfonamide (EXAMPLE 337, 59 mg, 0.129 mmol), (3,5-difluorophenyl)boronic acid (40.7 mg, 0.258 mmol), dicyclohexyl (2',6'-dimethoxy-[1,1'-biphenyl]-2-yl)phosphine (1.322 mg, 3.22 µmol), chloro(2-dicyclohexylphosphino-2',6'-dimethoxy-1,1'-biphenyl)[2-(2-aminoethylphenyl)]palladium(ii) dichloromethane (4.88 mg, 6.44 µmol) and potassium phosphate (82 mg, 0.387 mmol). The vial was flushed with Ar (g), then 1,4-dioxane (586 µl) and water (58.6 µl) were added. The vial was sealed and heated in a Biotage Initiator microwave reactor for 1 h at 120° C. The mixture was extracted with EtOAc (3×) and with MeOH-EtOAc. The combined organic extracts were concentrated. The residue was purified by chromatography on silica gel (12-g Redi-Sep Gold column, 0-7.5% MeOH/DCM) to give 57 mg of a cream-colored solid. The solid was taken up in DCM, sonicated, and filtered. The collected solid was washed with DCM (3×), dried under a stream of $N_2$ (g), and dried under vacuum to give 1-(2-cyano-3',5'-difluoro-5-methoxy-[1,1'-biphenyl]-4-yl)-N-(1,3,4-thiadiazol-2-yl)isoquinoline-6-sulfonamide (25 mg, 0.047 mmol, 36.2% yield) as an off-white solid. $^1$H NMR (400 MHz, DMSO-$d_6$) δ=14.52 (br. s., 1H), 8.83-8.77 (m, 1H), 8.73 (d, J=5.7 Hz, 1H), 8.59 (d, J=1.9 Hz, 1H), 8.17 (d, J=5.3 Hz, 1H), 7.98 (s, 1H), 7.90 (dd, J=1.9, 8.9 Hz, 1H), 7.78 (d, J=8.9 Hz, 1H), 7.59-7.52 (m, 2H), 7.51-7.39 (m, 2H), 3.83 (s, 3H). m/z (ESI) 536.2 (M+H)$^+$.

EXAMPLE 339

1-(2-CYANO-5-METHOXY-3'-(TRIFLUOROMETHYL)-[1,1'-BIPHENYL]-4-YL)-N-(1,3,4-THIADIAZOL-2-YL)ISOQUINOLINE-6-SULFONAMIDE

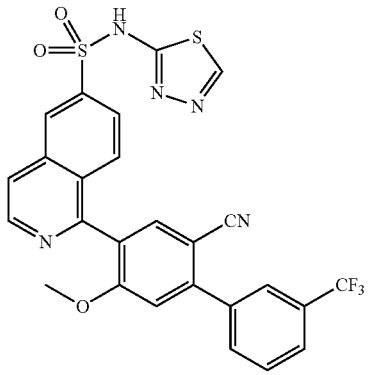 [SMILES: COc1cc(-c2cccc(C(F)(F)F)c2)c(C#N)cc1-c1nccc2cc(S(=O)(=O)Nc3nncs3)ccc12]

A vial was charged with 1-(4-chloro-5-cyano-2-methoxyphenyl)-N-(1,3,4-thiadiazol-2-yl)isoquinoline-6-sulfonamide (EXAMPLE 337, 69.8 mg, 0.152 mmol) (3-(trifluoromethyl)phenyl)boronic acid (57.9 mg, 0.305 mmol), dicyclohexyl(2',6'-dimethoxy-[1,1'-biphenyl]-2-yl)phosphine (3.13 mg, 7.62 μmol), chloro(2-dicyclohexylphosphino-2',6'-dimethoxy-1,1'-biphenyl)[2-(2-aminoethylphenyl)]palladium(ii) dichloromethane (11.55 mg, 0.015 mmol) and potassium phosphate (162 mg, 0.762 mmol). The vial was flushed with Ar (g), then 1,4-dioxane (693 μl) and water (69.3 μl) were added. The vial was sealed and heated in a Biotage Initiator microwave reactor for 1 h at 120° C. The mixture was extracted with EtOAc, MeOH-EtOAc, and MeOH-DCM. The combined organic extracts were concentrated. The residue was purified by chromatography on silica gel (12-g Redi-Sep Gold column, 0-7.5% MeOH/DCM) to give an off-white solid. The solid was taken up in DCM and filtered. The collected solid was washed with DCM (2×), dried under a stream of N$_2$ (g), and dried under vacuum to give 1-(2-cyano-5-methoxy-3'-(trifluoromethyl)-[1,1'-biphenyl]-4-yl)-N-(1,3,4-thiadiazol-2-yl)isoquinoline-6-sulfonamide as a white solid. $^1$H NMR (400 MHz, DMSO-d$_6$) δ=8.80 (s, 1H), 8.73 (d, J=5.7 Hz, 1H), 8.62-8.55 (m, 1H), 8.17 (d, J=5.6 Hz, 1H), 8.11-8.04 (m, 2H), 7.98 (s, 1H), 7.96-7.78 (m, 3H), 7.51 (s, 1H), 7.19 (br. s., 1H), 3.83 (s, 3H). m/z (ESI) 567.9 (M+H)$^+$.

EXAMPLE 340

1-(2-CYANO-3'-FLUORO-5-METHOXY-[1,1'-BIPHENYL]-4-YL)-N-(1,2,4-THIADIAZOL-5-YL)ISOQUINOLINE-6-SULFONAMIDE

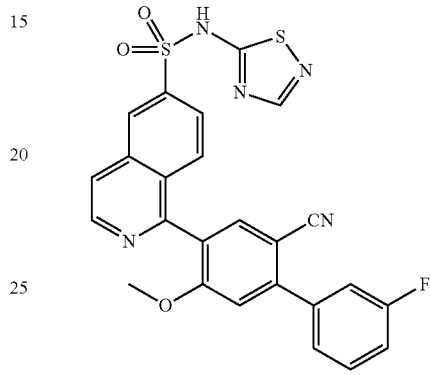

A vial was charged with 1-(4-chloro-5-cyano-2-methoxyphenyl)-N-(1,2,4-thiadiazol-5-yl)isoquinoline-6-sulfonamide (Example 337, 68.14 mg, 0.149 mmol) (3-fluorophenyl)boronic acid (62.5 mg, 0.446 mmol), dicyclohexyl(2',6'-dimethoxy-[1,1'-biphenyl]-2-yl)phosphine (3.05 mg, 7.44 μmol), chloro(2-dicyclohexylphosphino-2',6'-dimethoxy-1,1'-biphenyl)[2-(2-aminoethylphenyl)]palladium(ii) dichloromethane (11.27 mg, 0.015 mmol), and potassium phosphate (158 mg, 0.744 mmol). The vial was flushed with Ar (g), then 1,4-dioxane (676 μl) and water (67.6 μl) were added. The vial was sealed and heated in a Biotage Initiator microwave reactor for 1 h at 120° C. LCMS showed >95% conversion to the desired product. The mixture was extracted with EtOAc (3×), and the combined organic extracts were dried over sodium sulfate, filtered, and concentrated. The residue was purified by chromatography on silica gel (12-g Redi-Sep Gold column, 7.5% MeOH/DCM). The resulting material was taken up in DCM, sonicated, filtered, washed with DCM (2×), dried under a stream of N$_2$ (g), then dried under vacuum to give 1-(2-cyano-3'-fluoro-5-methoxy-[1,1'-biphenyl]-4-yl)-N-(1,2,4-thiadiazol-5-yl)isoquinoline-6-sulfonamide (58.22 mg, 0.112 mmol, 76% yield) as an off-white solid. $^1$H NMR (400 MHz, DMSO-d$_6$) δ=8.72 (d, J=5.7 Hz, 1H), 8.58 (d, J=1.6 Hz, 1H), 8.39 (s, 1H), 8.17 (d, J=5.8 Hz, 1H), 7.96 (s, 1H), 7.91 (dd, J=1.9, 8.9 Hz, 1H), 7.79 (d, J=9.0 Hz, 1H), 7.69-7.58 (m, 3H), 7.45 (s, 1H), 7.41 (dt, J=1.6, 8.5 Hz, 1H), 3.82 (s, 3H). m/z (ESI) 518.2 (M+H)+.

EXAMPLE 341

1-(2-CYANO-3'-FLUORO-5-METHOXY-[1,1'-BIPHENYL]-4-YL)-N-(1,3,4-THIADIAZOL-2-YL)ISOQUINOLINE-6-SULFONAMIDE

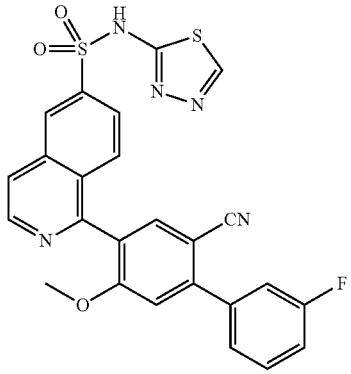 [SMILES: COc1cc(-c2cccc(F)c2)c(C#N)cc1-c1nccc2cc(S(=O)(=O)Nc3nncs3)ccc12]

A vial was charged with 1-(4-chloro-5-cyano-2-methoxyphenyl)-N-(1,3,4-thiadiazol-2-yl)isoquinoline-6-sulfonamide (Example 337, 55.6 mg, 0.121 mmol) (3-fluorophenyl)boronic acid (34.0 mg, 0.243 mmol), dicyclohexyl(2',6'-dimethoxy-[1,1'-biphenyl]-2-yl)phosphine (2.492 mg, 6.07 µmol), chloro(2-dicyclohexylphosphino-2',6'-dimethoxy-1,1'-biphenyl)[2-(2-aminoethylphenyl)]palladium(ii) dichloromethane (9.20 mg, 0.012 mmol), and potassium phosphate (129 mg, 0.607 mmol). The vial was flushed with Ar (g), then 1,4-dioxane (552 µl) and water (55.2 µl) were added. The vial was sealed and heated in a Biotage Initiator microwave reactor for 1 h at 120° C. The mixture was extracted with EtOAc (2×) and 10% MeOH/EtOAc (2×) and the combined organic extracts were dried over sodium sulfate, filtered, and concentrated. The residue was purified by chromatography on silica gel (12-g Redi-Sep Gold column, 0-7.5% MeOH/DCM, a few colored fractions were discarded). The resulting tan solid was taken up in DCM and filtered. The collected solid was washed with DCM (2×), dried under a stream of N₂ (g), then dried under vacuum to give 1-(2-cyano-3'-fluoro-5-methoxy-[1,1'-biphenyl]-4-yl)-N-(1,3,4-thiadiazol-2-yl)isoquinoline-6-sulfonamide (30.69 mg, 0.059 mmol, 48.8% yield) as a white solid. ¹H NMR (400 MHz, DMSO-d₆) δ=14.49 (br. s., 1H), 8.79 (s, 1H), 8.73 (d, J=5.7 Hz, 1H), 8.59 (d, J=1.7 Hz, 1H), 8.17 (d, J=5.8 Hz, 1H), 7.96 (s, 1H), 7.90 (dd, J=1.9, 8.9 Hz, 1H), 7.80 (d, J=8.8 Hz, 1H), 7.68-7.57 (m, 3H), 7.45 (s, 1H), 7.41 (dt, J=1.7, 8.5 Hz, 1H), 3.82 (s, 3H). m/z (ESI) 518.2 (M+H)+.

INTERMEDIATE WWWW: 1-(4-CHLORO-5-CYANO-2-METHOXYPHENYL)-N-(ISOXAZOL-3-YL)ISOQUINOLINE-6-SULFONAMIDE

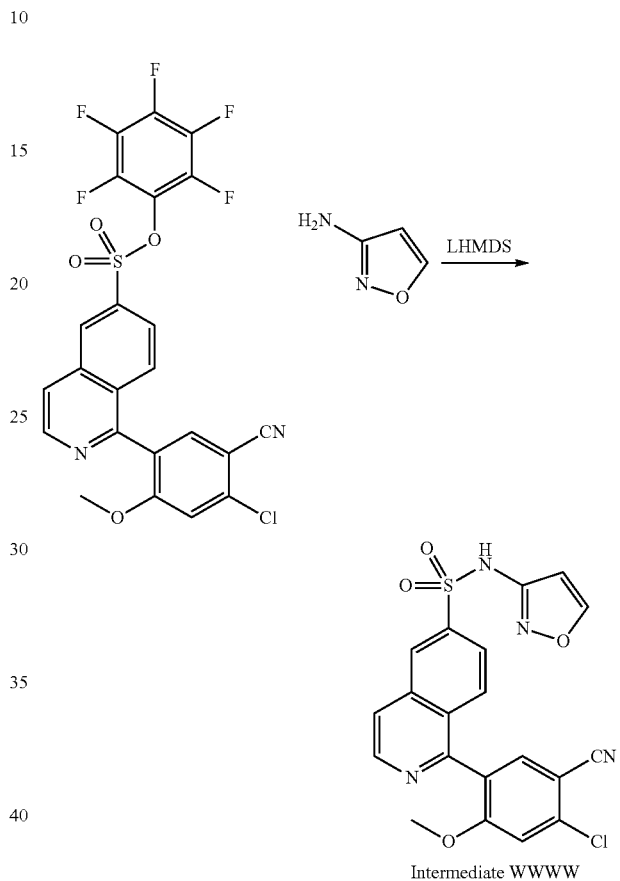

Intermediate WWWW

A round-bottom flask was charged with perfluorophenyl 1-(4-chloro-5-cyano-2-methoxyphenyl)isoquinoline-6-sulfonate (INTERMEDIATE VVVV, 257 mg, 0.475 mmol), isoxazol-3-amine (77 µl, 1.045 mmol), and THF (3 mL) to give a clear solution. The flask was cooled in an ice-water bath for 10 min, then lithium bis(trimethylsilyl)amide (1M in THF) (608 µl, 0.608 mmol) was added. After 40 min, additional portions of isoxazol-3-amine (77 µl, 1.045 mmol) and lithium bis(trimethylsilyl)amide (1M in THF) (608 µl, 0.608 mmol) were added. Following an additional 10 min of stirring, the reaction mixture was loaded directly onto a 25-g silica gel loading column with the aid of DCM. The column was dried under vacuum for 5 min, then eluted onto a pre-equilibrated 25-g SNAP Ultra column with 0-10% MeOH/DCM to give an orange oil. The oil was further by chromatography on silica gel (40-g Redi-Sep Gold column, 4% MeOH/DCM) to give ca. 320 mg of an amber oil. The oil was dissolved in EtOAc, and the organic solution was washed with 0.5 N aq. HCl, dried over sodium sulfate, filtered, and concentrated to give 1-(4-chloro-5-cyano-2-methoxyphenyl)-N-(isoxazol-3-yl)isoquinoline-6-sulfonamide (182 mg, 0.413 mmol, 87% yield) as a clear oil. m/z (ESI) 441.3 (M+H)+.

EXAMPLE 342

1-(2-CYANO-3'-FLUORO-5-METHOXY-[1,1'-BI-PHENYL]-4-YL)-N-(ISOXAZOL-3-YL)ISO-QUINOLINE-6-SULFONAMIDE

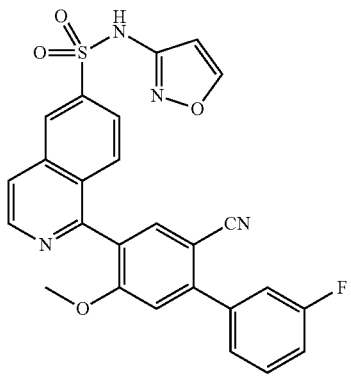

A vial was charged with 1-(4-chloro-5-cyano-2-methoxyphenyl)-N-(isoxazol-3-yl)isoquinoline-6-sulfonamide (INTERMEDIATE WWWW, 95.3 mg, 0.216 mmol), (3-fluorophenyl)boronic acid (60.5 mg, 0.432 mmol), dicyclohexyl(2',6'-dimethoxy-[1,1'-biphenyl]-2-yl)phosphine (2.219 mg, 5.40 μmol), chloro(2-dicyclohexylphosphino-2',6'-dimethoxy-1,1'-biphenyl)[2-(2-aminoethylphenyl)]palladium(ii) dichloromethane (8.19 mg, 10.81 μmol), and potassium phosphate (138 mg, 0.649 mmol). The vial was flushed with Ar (g), then 1,4-dioxane (983 μl) and water (98 μl) were added. The vial was sealed and heated in a Biotage Initiator microwave reactor for 2.5 h at 120° C. Additional portions of (3-fluorophenyl)boronic acid (60.5 mg, 0.432 mmol), chloro(2-dicyclohexylphosphino-2',6'-dimethoxy-1,1'-biphenyl)[2-(2-aminoethylphenyl)]palladium(ii) dichloromethane (8.19 mg, 10.81 μmol), and potassium phosphate (138 mg, 0.649 mmol) were added. The vial was heated for an additional 30 min at 150° C. The mixture organic layer was separated, and the aq. layer was diluted with 0.5 N aq. HCl and extracted with EtOAc (3×). The combined organic extracts were concentrated. The residue was purified by chromatography on silica gel (25-g Interchim 15-micron column, 0-4% MeOH/DCM) to give a light-yellow solid. The material was taken up in DCM, sonicated, and filtered. The collected solid was washed with DCM (2×), dried under a stream of $N_2$ (g), then dried under vacuum to give 1-(2-cyano-3'-fluoro-5-methoxy-[1,1'-biphenyl]-4-yl)-N-(isoxazol-3-yl)isoquinoline-6-sulfonamide (22.04 mg, 0.044 mmol, 20.37% yield) as a white solid. $^1$H NMR (400 MHz, DMSO-$d_6$) δ=11.93 (br. s., 1H), 8.82-8.64 (m, 3H), 8.19 (d, J=5.7 Hz, 1H), 8.01-7.83 (m, 3H), 7.71-7.55 (m, 3H), 7.49-7.33 (m, 2H), 6.50 (d, J=1.7 Hz, 1H), 3.81 (s, 3H). m/z (M+H) 501.0 (M+H)+.

EXAMPLE 343

1-(2-CYANO-3',5'-DIFLUORO-5-METHOXY-[1,1'-BIPHENYL]-4-YL)-N-(ISOXAZOL-3-YL)ISO-QUINOLINE-6-SULFONAMIDE

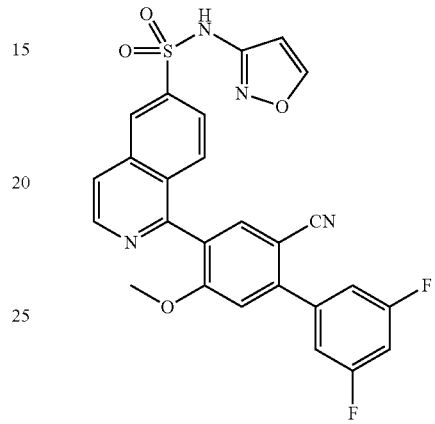

A vial was charged with 1-(4-chloro-5-cyano-2-methoxyphenyl)-N-(isoxazol-3-yl)isoquinoline-6-sulfonamide (INTERMEDIATE WWWW, 76.94 mg, 0.175 mmol), (3,5-difluorophenyl)boronic acid (55.1 mg, 0.349 mmol), dicyclohexyl(2',6'-dimethoxy-[1,1'-biphenyl]-2-yl)phosphine (1.791 mg, 4.36 μmol), chloro(2-dicyclohexylphosphino-2',6'-dimethoxy-1,1'-biphenyl)[2-(2-aminoethylphenyl)]palladium(ii) dichloromethane (6.61 mg, 8.73 μmol), and potassium phosphate (111 mg, 0.524 mmol). The vial was flushed with Ar (g), then 1,4-dioxane (793 μl) and water (79 μl) were added. The vial was sealed and heated in a Biotage Initiator microwave reactor for 1 h at 120° C. and 1 h at 150° C. The organic layer was separated, and the aq. layer was diluted with 0.5 N aq. HCl and extracted with EtOAc (3×). The combined organic extracts were concentrated. The residue was purified by chromatography on silica gel (25-g Interchim 15-micron column, 0-3.5% MeOH/DCM) to give 25.2 mg of a light-yellow solid. The material was taken up in 2-PrOH, sonicated, and filtered. The collected solid was washed with 2-PrOH (2×), dried under a stream of $N_2$ (g), then dried under vacuum to give 1-(2-cyano-3',5'-difluoro-5-methoxy-[1,1'-biphenyl]-4-yl)-N-(isoxazol-3-yl)isoquinoline-6-sulfonamide (12.07 mg, 0.023 mmol, 13.34% yield) as an off-white solid. $^1$H NMR (400 MHz, DMSO-$d_6$) δ=11.94 (br. s., 1H), 8.81-8.60 (m, 3H), 8.20 (d, J=5.7 Hz, 1H), 7.99 (s, 1H), 7.95 (dd, J=1.8, 8.9 Hz, 1H), 7.85 (d, J=9.0 Hz, 1H), 7.58-7.44 (m, 4H), 6.50 (d, J=1.8 Hz, 1H), 3.82 (s, 3H). m/z (M+H) 519.0 (M+H)$^+$.

INTERMEDIATE XXXX: PERFLUOROPHENYL 1-(5-CHLORO-2-METHOXYPHENYL)ISO-QUINOLINE-6-SULFONATE

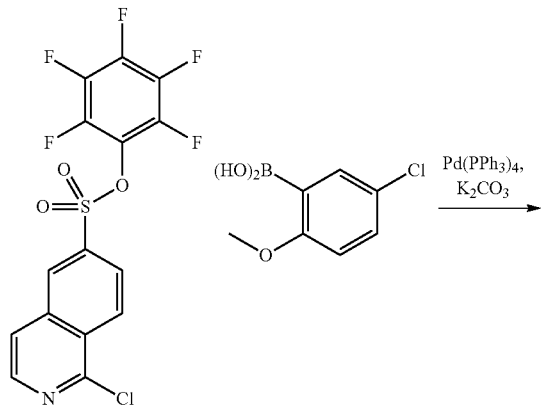

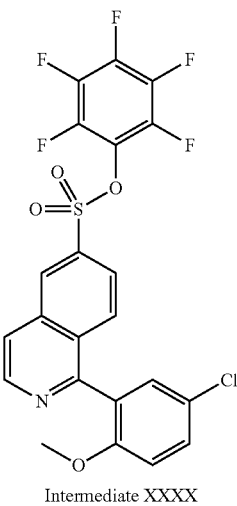

Intermediate XXXX

A round-bottom flask was charged with perfluorophenyl 1-chloroisoquinoline-6-sulfonate (see Example 73, Step 1, 1.12 g, 2.73 mmol), 5-chloro-2-methoxyphenyl)boronic acid (0.764 g, 4.10 mmol), potassium carbonate (1.133 g, 8.20 mmol), and Pd(Ph$_3$P)$_4$ (0.316 g, 0.273 mmol). The vial was flushed with Ar (g), then 1,4-dioxane (10.25 ml) and water (3.42 ml) were added. The flask was fitted with a reflux condenser and heated in a 50° C. heating bath for 2 h. The mixture was diluted with water and extracted with EtOAc (1×). The combined organic extracts were dried over sodium sulfate, filtered, and concentrated. The residue was purified by chromatography on silica gel (40-g Redi-Sep Gold column, 0-50% EtOAc/Heptane) to give perfluorophenyl 1-(5-chloro-2-methoxyphenyl)isoquinoline-6-sulfonate (1.073 g, 2.080 mmol, 76% yield) as a white foam. m/z (ESI) 516.0 (M+H)$^+$.

INTERMEDIATE YYYY: 1-(5-CHLORO-2-METHOXYPHENYL)-N-(1,3,4-THIADIAZOL-2-YL)ISOQUINOLINE-6-SULFONAMIDE

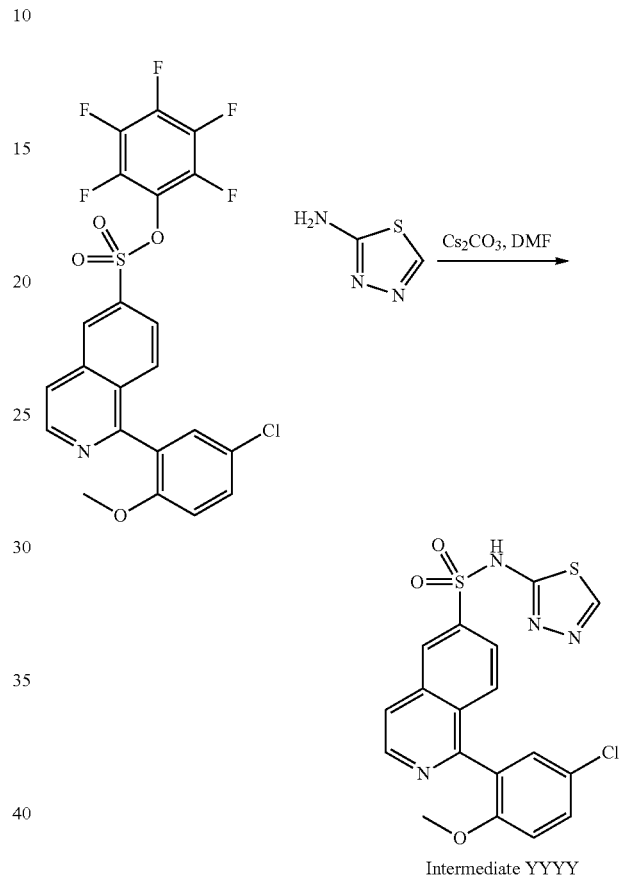

Intermediate YYYY

A round-bottom flask was charged with perfluorophenyl 1-(5-chloro-2-methoxyphenyl)isoquinoline-6-sulfonate (INTERMEDIATE XXXX, 464.57 mg, 0.901 mmol), 1,3,4-thiadiazol-2-amine (182 mg, 1.801 mmol), and cesium carbonate (880 mg, 2.70 mmol). DMF (4503 µl) was added, and the mixture was stirred overnight. The mixture was diluted with EtOAc and 0.5 N aq. HCl. The layers were separated, and the organic extract was washed with brine, dried over sodium sulfate, filtered, and concentrated. The residue was purified by chromatography on silica gel (25-g SNAP Ultra column, 0-7% MeOH/DCM) to give 1-(5-chloro-2-methoxyphenyl)-

N-(1,3,4-thiadiazol-2-yl)isoquinoline-6-sulfonamide (378 mg, 0.873 mmol, 97% yield) as a light-yellow foam. m/z (ESI) 433.2 (M+H)+.

EXAMPLE 344

1-(4-METHOXY-3'-(TRIFLUOROMETHYL)-[1,1'-BIPHENYL]-3-YL)-N-(1,3,4-THIADIAZOL-2-YL)ISOQUINOLINE-6-SULFONAMIDE

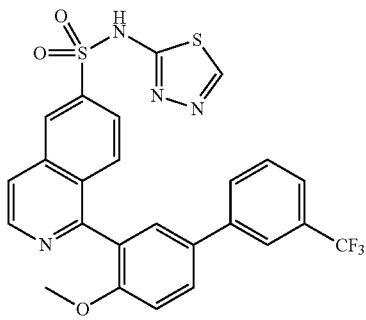 [SMILES: COc1ccc(-c2cccc(C(F)(F)F)c2)cc1-c1nccc2cc(S(=O)(=O)Nc3nncs3)ccc12]

A vial was charged with 1-(5-chloro-2-methoxyphenyl)-N-(1,3,4-thiadiazol-2-yl)isoquinoline-6-sulfonamide (INTERMEDIATE YYYY, 83.06 mg, 0.192 mmol) (3-(trifluoromethyl)phenyl)boronic acid (72.9 mg, 0.384 mmol), dicyclohexyl(2',6'-dimethoxy-[1,1'-biphenyl]-2-yl)phosphine (3.94 mg, 9.59 µmol), chloro(2-dicyclohexylphosphino-2',6'-dimethoxy-1,1'-biphenyl)[2-(2-aminoethylphenyl)]palladium(ii) dichloromethane (14.53 mg, 0.019 mmol) and potassium phosphate (122 mg, 0.576 mmol). The vial was flushed with Ar (g), then 1,4-dioxane (872 µl) and water (87 µl) were added in sequence. The vial was sealed and heated in a Biotage Initiator microwave reactor for 30 min at 120° C. The mixture was extracted with EtOAc (4×), and the combined organic extracts were concentrated. The residue was purified by chromatography on silica gel (12-g Redi-Sep Gold column, 3.5% MeOH/DCM) to give ca. 60 mg of an impure solid. The material was repurified by chromatography on silica gel (12-g Redi-Sep Gold column, 0-5% MeOH/DCM) to give 1-(4-methoxy-3'-(trifluoromethyl)-[1,1'-biphenyl]-3-yl)-N-(1,3,4-thiadiazol-2-yl)isoquinoline-6-sulfonamide (24.38 mg, 0.045 mmol, 23.42% yield) as a light-yellow solid. $^1$H NMR (400 MHz, DMSO-$d_6$) δ=8.79 (s, 1H), 8.71 (d, J=5.7 Hz, 1H), 8.56 (d, J=1.8 Hz, 1H), 8.12 (d, J=5.5 Hz, 1H), 8.04-7.93 (m, 3H), 7.90-7.84 (m, 1H), 7.82-7.78 (m, 1H), 7.75 (d, J=2.4 Hz, 1H), 7.69-7.64 (m, 2H), 7.35 (d, J=8.7 Hz, 1H), 3.72 (s, 3H). m/z (ESI) 543.2 (M+H)+.

EXAMPLE 345

1-(3'-FLUORO-4-METHOXY-[1,1'-BIPHENYL]-3-YL)-N-(1,3,4-THIADIAZOL-2-YL)ISOQUINOLINE-6-SULFONAMIDE

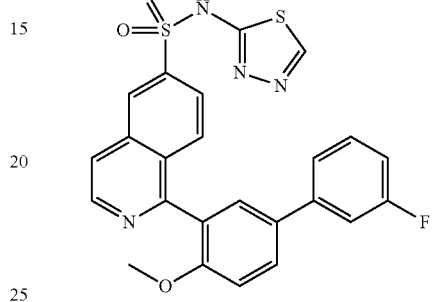

A vial was charged with 1-(5-chloro-2-methoxyphenyl)-N-(1,3,4-thiadiazol-2-yl)isoquinoline-6-sulfonamide (INTERMEDIATE YYYY, 80.18 mg, 0.185 mmol), (3-fluorophenyl)boronic acid (51.8 mg, 0.370 mmol), dicyclohexyl (2',6'-dimethoxy-[1,1'-biphenyl]-2-yl)phosphine (1.901 mg, 4.63 µmol), chloro(2-dicyclohexylphosphino-2',6'-dimethoxy-1,1'-biphenyl)[2-(2-aminoethylphenyl)]palladium(ii) dichloromethane (7.02 mg, 9.26 µmol) and potassium phosphate (118 mg, 0.556 mmol). The vial was flushed with Ar (g), then 1,4-dioxane (842 µl) and water (84 µl) were added. The vial was sealed and heated in a Biotage Initiator microwave reactor for 1.5 h at 100° C. The mixture was extracted with EtOAc (3×). The combined organic extracts were concentrated. The residue was purified by chromatography on silica gel (12-g Redi-Sep Gold column, 3% MeOH/DCM) to give ca. 20.7 mg of a yellow solid. The material was further purified by chromatography on silica gel (12-g Redi-Sep Gold column, 0-100% EtOAc/Heptane) to give 1-(3'-fluoro-4-methoxy-[1,1'-biphenyl]-3-yl)-N-(1,3,4-thiadiazol-2-yl)isoquinoline-6-sulfonamide (14.02 mg, 0.028 mmol, 15.37% yield) as a light-yellow solid. $^1$H NMR (400 MHz, DMSO-$d_6$) δ=8.75 (s, 1H), 8.69 (d, J=5.8 Hz, 1H), 8.53 (d, J=1.8 Hz, 1H), 8.10 (d, J=5.3 Hz, 1H), 7.94-7.83 (m, 2H), 7.77 (d, J=8.8 Hz, 1H), 7.68 (d, J=2.4 Hz, 1H), 7.56-7.50 (m, 2H), 7.45 (dt, J=6.2, 8.0 Hz, 1H), 7.32 (d, J=8.8 Hz, 1H), 7.17-7.10 (m, 1H), 3.70 (s, 3H). m/z (ESI) 493.2 (M+H)+.

EXAMPLE 346

1-(5-CHLORO-2-METHOXYPHENYL)-N-(1,2,4-THIADIAZOL-5-YL)ISOQUINOLINE-6-SULFONAMIDE

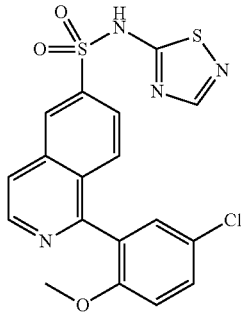 [SMILES: COc1ccc(Cl)cc1-c1nccc2cc(S(=O)(=O)Nc3ncns3)ccc12]

A round-bottom flask was charged with perfluorophenyl 1-(5-chloro-2-methoxyphenyl)isoquinoline-6-sulfonate (INTERMEDIATE XXXX, 150.33 mg, 0.291 mmol), 1,2,4-thiadiazol-5-amine (35.4 mg, 0.350 mmol), and cesium carbonate (285 mg, 0.874 mmol). acetonitrile (1457 μl) was added, and the mixture was stirred for 1.5 h. The mixture was diluted with EtOAc and 0.5 N aq. HCl. The layers were separated, and the organic extract was washed with brine, dried over sodium sulfate, filtered, and concentrated. The residue was concentrated from MeOH. The residue was taken up in MeOH, sonicated, and filtered on a membrane filter. The collected solid was washed with MeOH (3×), dried under a stream of $N_2$ (g), then dried under vacuum to give 1-(5-chloro-2-methoxyphenyl)-N-(1,2,4-thiadiazol-5-yl)isoquinoline-6-sulfonamide (100.0 mg, 0.231 mmol, 79% yield) as a cream-colored solid. $^1$H NMR (400 MHz, DMSO-$d_6$) δ=8.69 (d, J=5.7 Hz, 1H), 8.58 (d, J=1.7 Hz, 1H), 8.49 (s, 1H), 8.15 (d, J=5.5 Hz, 1H), 7.89 (dd, J=1.9, 8.9 Hz, 1H), 7.75 (d, J=8.9 Hz, 1H), 7.59 (dd, J=2.7, 8.9 Hz, 1H), 7.40 (d, J=2.7 Hz, 1H), 7.26 (d, J=9.0 Hz, 1H), 3.65 (s, 3H). m/z (ESI) 432.9 (M+H)+.

EXAMPLE 347

1-(3'-FLUORO-4-METHOXY-[1,1'-BIPHENYL]-3-YL)-N-(1,2,4-THIADIAZOL-5-YL)ISOQUINOLINE-6-SULFONAMIDE

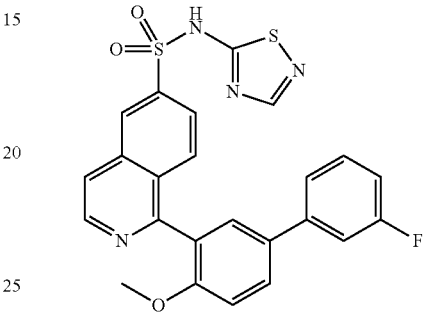

A vial was charged with 1-(5-chloro-2-methoxyphenyl)-N-(1,2,4-thiadiazol-5-yl)isoquinoline-6-sulfonamide (EXAMPLE 346; 88.16 mg, 0.204 mmol) (3-fluorophenyl)boronic acid (57.0 mg, 0.407 mmol), dicyclohexyl(2',6'-dimethoxy-[1,1'-biphenyl]-2-yl)phosphine (2.090 mg, 5.09 mmol), chloro(2-dicyclohexylphosphino-2',6'-dimethoxy-1,1'-biphenyl)[2-(2-aminoethylphenyl)]palladium(ii) dichloromethane (7.71 mg, 10.18 μmol), and potassium phosphate (130 mg, 0.611 mmol). The vial was flushed with Ar (g), then 1,4-dioxane (926 μl) and water (93 μl) were added. The vial was sealed and heated in a Biotage Initiator microwave reactor for 1.5 h at 100° C. then for 1.5 h at 120° C. Additional portions of boronic acid (ca. 50 mg), potassium phosphate (ca. 80 mg), and catalyst (ca. 7 mg) were added. The vial was heated again for 1 h at 120° C. The mixture was extracted with 10% MeOH-EtOAc (3×). The combined organic extracts were concentrated. The residue was purified by chromatography on silica gel (12-g Redi-Sep Gold column, 0-10% MeOH/DCM) to give a yellow solid. The material was further purified by chromatography on silica gel (12-g Redi-Sep Gold column, 7.5% MeOH/DCM) to give 35 mg of a yellow solid. The material was dissolved in DCM and aged for 30 min to give a suspension. The suspension was filtered, and the collected solid was washed with DCM (2×), dried under a stream of $N_2$ (g), then dried under vacuum to give 1-(3'-fluoro-4-methoxy-[1,1'-biphenyl]-3-yl)-N-(1,2,4-thiadiazol-5-yl)isoquinoline-6-sulfonamide (17 mg, 0.035 mmol, 16.95% yield) as a light-yellow solid. $^1$H NMR (400 MHz, DMSO-$d_6$) δ=8.71 (d, J=5.7 Hz, 1H), 8.57 (d, J=1.8 Hz, 1H), 8.43 (s, 1H), 8.14 (d, J=5.6 Hz, 1H), 7.95-7.86 (m, 2H), 7.83-7.77 (m, 1H), 7.69 (d, J=2.4 Hz, 1H), 7.57-7.50 (m, 2H), 7.49-7.42 (m, 1H), 7.33 (d, J=8.8 Hz, 1H), 7.18-7.07 (m, 1H), 3.71 (s, 3H). m/z (ESI) 493.2 (M+H)$^+$.

INTERMEDIATE ZZZZ: 1-CHLORO-N-(4-METHOXYBENZYL)-N-(PYRIMIDIN-4-YL)ISOQUINOLINE-6-SULFONAMIDE

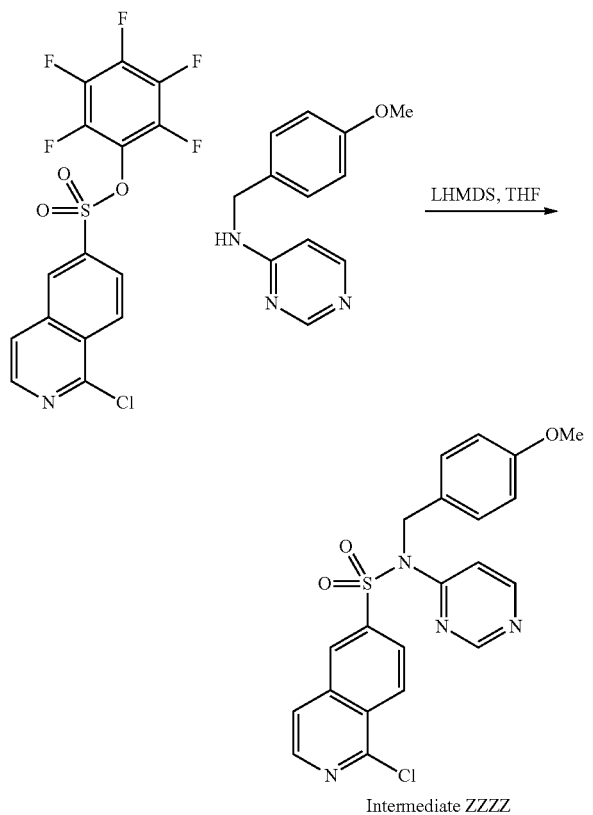

Intermediate ZZZZ

A 100-mL round-bottom flask was charged with N-(4-methoxybenzyl)pyrimidin-4-amine (Intermediate OO; 0.796 g, 3.70 mmol) and THF (16.08 ml). The flask was cooled in a dry ice-acetone bath for 10 min, then lithium bis(trimethylsilyl)amide (1M in THF) (3.70 ml, 3.70 mmol) was added drop wise. The flask was removed from the cooling bath for 5 min, then recooled for 5 min. A solution of perfluorophenyl 1-chloroisoquinoline-6-sulfonate (see EXAMPLE 73, STEP 1, 1.515 g, 3.70 mmol) in THF (4 mL with a 1-mL flask wash) was added drop wise. After 20 min, the flask was switched to an ice-water bath. The mixture was stirred for 20 min, then an additional portion of LHMDS solution (1 mL) was added drop wise. The mixture was warmed to room temperature and quenched by the addition of saturated aq. ammonium chloride. The mixture was extracted with EtOAc (2×), and the combined organic extracts were dried over sodium sulfate, filtered, and concentrated. The residue was purified by chromatography on silica gel (40-g Redi-Sep Gold column, 25-g silica gel loading column, 0-50% EtOAc/Heptante) to give 1-chloro-N-(4-methoxybenzyl)-N-(pyrimidin-4-yl)isoquinoline-6-sulfonamide (648 mg, 1.470 mmol, 39.7% yield) as a tan foam. m/z (ESI) 441.2 (M+H)$^+$.

INTERMEDIATE AAAAA: 1-(5-CHLORO-2-METHOXYPHENYL)-N-(4-METHOXYBENZYL)-N-(PYRIMIDIN-4-YL)ISOQUINOLINE-6-SULFONAMIDE

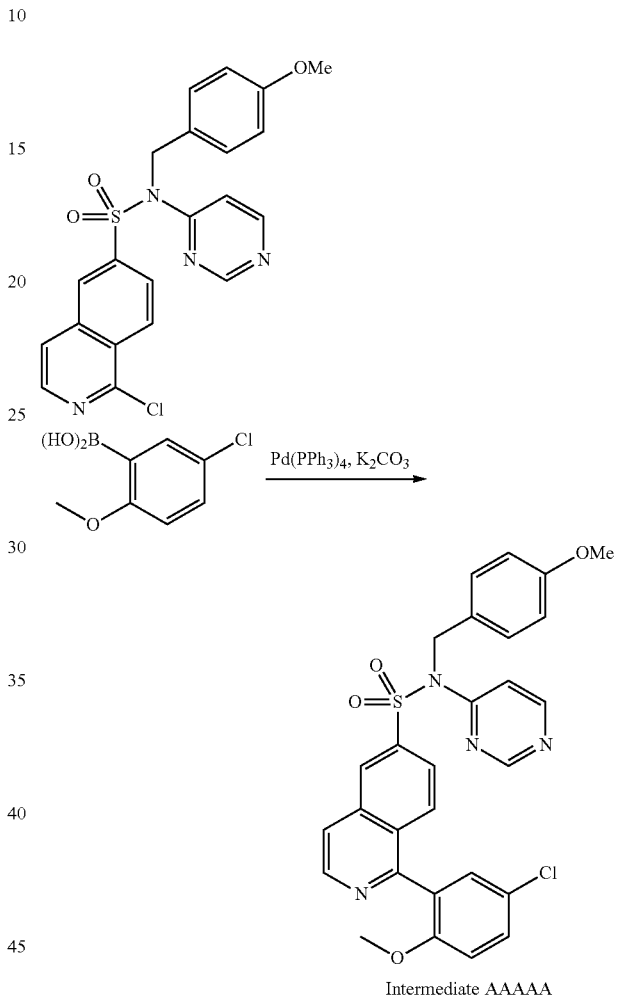

Intermediate AAAAA

A vial was charged with 1-chloro-N-(4-methoxybenzyl)-N-(pyrimidin-4-yl)isoquinoline-6-sulfonamide (INTERMEDIATE ZZZZ; 100 mg, 0.227 mmol), (5-chloro-2-methoxyphenyl)boronic acid (63.4 mg, 0.340 mmol), potassium carbonate (94 mg, 0.680 mmol), and pd(ph3p)4 (26.2 mg, 0.023 mmol). The vial was flushed with Ar (g), then 1,4-dioxane (851 μl) and water (284 μl) were added. The vial was sealed and heated to 100° C. for 30 min in a Biotage Initiator microwave reactor. The mixture was extracted with EtOAc (3×), and the combined organic extracts were concentrated. The residue was purified by chromatography on silica gel (40-g Redi-Sep Gold column, 0-40% EtOAc/Heptane, then 70% EtOAc/Heptane) to give 1-(5-chloro-2-methoxyphenyl)-N-(4-methoxybenzyl)-N-(pyrimidin-4-yl)isoquinoline- 6-sulfonamide (91.2 mg, 0.167 mmol, 73.5% yield) as an off-white foam. m/z (ESI) 547.2 (M+H)+.

EXAMPLE 348

1-(3'-FLUORO-4-METHOXY-[1,1'-BIPHENYL]-3-YL)-N-(PYRIMIDIN-4-YL)ISOQUINOLINE-6-SULFONAMIDE

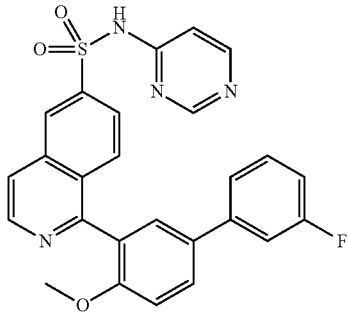 [SMILES: COc1ccc(-c2cccc(F)c2)cc1-c1nccc2cc(S(=O)(=O)Nc3ccncn3)ccc12]

A vial was charged with 1-(5-chloro-2-methoxyphenyl)-N-(4-methoxybenzyl)-N-(pyrimidin-4-yl)isoquinoline-6-sulfonamide (91 mg, 0.166 mmol), (3-fluorophenyl)boronic acid (46.6 mg, 0.333 mmol), dicyclohexyl(2',6'-dimethoxy-[1,1'-biphenyl]-2-yl)phosphine (3.41 mg, 8.32 µmol), chloro(2-dicyclohexylphosphino-2',6'-dimethoxy-1,1'-biphenyl)[2-(2-aminoethylphenyl)]palladium(ii) dichloromethane (12.60 mg, 0.017 mmol), and potassium phosphate (106 mg, 0.499 mmol). The vial was flushed with Ar (g), then 1,4-dioxane (0.45 mL) and water (0.04 mL) were added in sequence. The vial was sealed and heated in a Biotage Initiator microwave reactor for 45 min at 90° C. The mixture was extracted with EtOAc (4×), and the combined organic extracts were concentrated. The residue was taken up in DCM (0.5 mL) and TFA (0.5 mL) to give an amber solution that was stirred overnight. The mixture was diluted with MeOH, then concentrated. The residue was dissolved in DCM and saturated aq. sodium bicarbonate solution was added. The layers were separated, and the aq. layer was extracted with DCM (1×). The combined organic extracts were dried over sodium sulfate, filtered, and concentrated. The residue was purified by chromatography on silica gel (12-g Redi-Sep Gold column, 5% MeOH/DCM) to give 1-(3'-fluoro-4-methoxy-[1,1'-biphenyl]-3-yl)-N-(pyrimidin-4-yl)isoquinoline-6-sulfonamide (51.82 mg, 0.107 mmol, 64.0% yield) as a light-yellow solid. $^1$H NMR (400 MHz, DMSO-d$_6$) δ=13.04 (br. s., 1H), 8.70 (d, J=5.7 Hz, 1H), 8.66 (s, 1H), 8.57 (s, 1H), 8.24 (d, J=5.5 Hz, 1H), 8.11 (d, J=5.7 Hz, 1H), 7.95 (dd, J=1.8, 8.9 Hz, 1H), 7.90 (dd, J=2.4, 8.6 Hz, 1H), 7.77 (d, J=8.9 Hz, 1H), 7.68 (d, J=2.4 Hz, 1H), 7.56-7.49 (m, 3H), 7.45 (dt, J=6.5, 8.0 Hz, 1H), 7.32 (d, J=8.8 Hz, 1H), 7.13 (dt, J=2.1, 8.3 Hz, 1H), 7.03 (d, J=5.4 Hz, 1H), 3.70 (s, 3H). m/z (ESI) 487.2 (M+H)+.

EXAMPLE 349

1-(4-METHOXY-3'-(TRIFLUOROMETHYL)-[1,1'-BIPHENYL]-3-YL)-N-(PYRIMIDIN-4-YL)ISOQUINOLINE-6-SULFONAMIDE

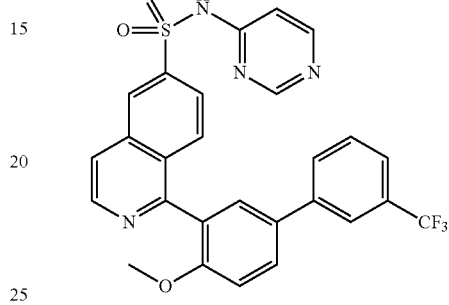

A vial was charged with 1-(5-CHLORO-2-METHOXYPHENYL)-N-(PYRIMIDIN-4-YL)ISOQUINOLINE-6-SULFONAMIDE (Example 146; 64.66 mg, 0.151 mmol) (3-(trifluoromethyl)phenyl)boronic acid (57.5 mg, 0.303 mmol), dicyclohexyl(2',6'-dimethoxy-[1,1'-biphenyl]-2-yl)phosphine (3.11 mg, 7.57 mmol), chloro(2-dicyclohexylphosphino-2',6'-dimethoxy-1,1'-biphenyl)[2-(2-aminoethylphenyl)]palladium(ii) dichloromethane (11.47 mg, 0.015 mmol), and potassium phosphate (96 mg, 0.454 mmol). The vial was flushed with Ar (g), then 1,4-dioxane (689 µl) and water (68.9 µl) were added in sequence. The vial was sealed and heated in a Biotage Initiator microwave reactor for 30 min at 120° C. The mixture was extracted with EtOAc (4×), and the combined organic extracts were concentrated. The residue was purified by chromatography on silica gel (12-g Redi-Sep Gold column, 3.5% MeOH/DCM) to give 1-(4-methoxy-3'-(trifluoromethyl)-[1,1'-biphenyl]-3-yl)-N-(pyrimidin-4-yl)isoquinoline-6-sulfonamide (35.6 mg, 0.066 mmol, 43.8% yield) as a light-yellow solid. $^1$H NMR (400 MHz, DMSO-d$_6$) δ=13.02 (br. s., 1H), 8.76-8.64 (m, 2H), 8.57 (s, 1H), 8.25 (d, J=5.8 Hz, 1H), 8.12 (d, J=5.7 Hz, 1H), 8.04-7.90 (m, 4H), 7.83-7.72 (m, 2H), 7.70-7.62 (m, 2H), 7.35 (d, J=8.7 Hz, 1H), 7.03 (d, J=6.0 Hz, 1H), 3.71 (s, 3H). m/z (ESI) 537.2 (M+H)⁺.

INTERMEDIATE BBBBB: 1-(4-CHLORO-2-METHOXYPHENYL)-N-(4-METHOXYBENZYL)-N-(PYRIMIDIN-4-YL)ISOQUINOLINE-6-SULFONAMIDE

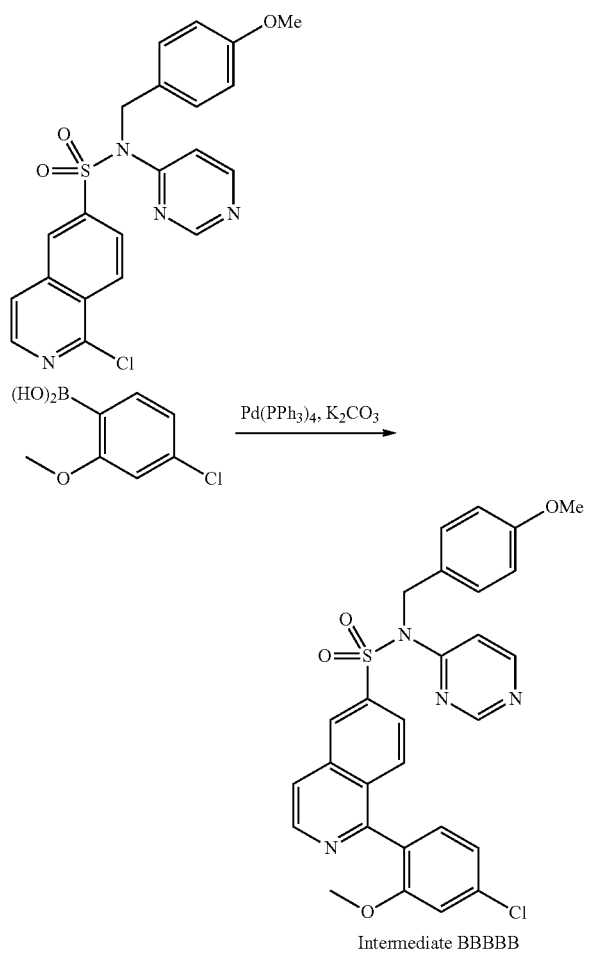

Intermediate BBBBB

A vial was charged with 1-chloro-N-(4-methoxybenzyl)-N-(pyrimidin-4-yl)isoquinoline-6-sulfonamide (INTERMEDIATE ZZZZ, 310.8 mg, 0.705 mmol), (4-chloro-2-methoxyphenyl)boronic acid (197 mg, 1.057 mmol), potassium carbonate (292 mg, 2.115 mmol), and Pd(PPh₃)₄ (81 mg, 0.070 mmol). The vial was flushed with Ar (g), then 1,4-dioxane (2643 µl) and water (881 µl) were added. The vial was sealed and heated to 100° C. for 30 min in a Biotage Initiator microwave reactor. The mixture was extracted with EtOAc (3×), and the combined organic extracts were concentrated. The residue was purified by chromatography on silica gel (40-g Redi-Sep Gold column, 0-40% EtOAc/Heptane) to give 1-(4-chloro-2-methoxyphenyl)-N-(4-methoxybenzyl)-N-(pyrimidin-4-yl)isoquinoline-6-sulfonamide (352 mg, 0.643 mmol, 91% yield) as a cream-colored foam. m/z (ESI) 547.2 (M+H)⁺.

EXAMPLE 350

1-(4'-FLUORO-3-METHOXY-[1,1'-BIPHENYL]-4-YL)-N-(PYRIMIDIN-4-YL)ISOQUINOLINE-6-SULFONAMIDE

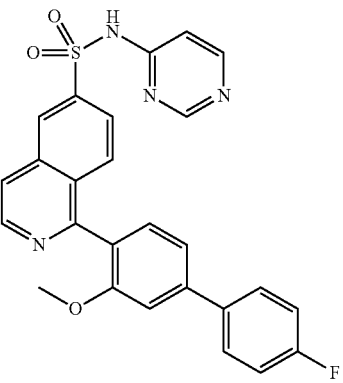 [SMILES: COc1cc(-c2ccc(F)cc2)ccc1-c1nccc2cc(S(=O)(=O)Nc3ccncn3)ccc12]

A vial was charged with 1-(4-chloro-2-methoxyphenyl)-N-(4-methoxybenzyl)-N-(pyrimidin-4-yl)isoquinoline-6-sulfonamide (INTERMEDIATE BBBBB, 42.9 mg, 0.078 mmol), (4-fluorophenyl)boronic acid (21.95 mg, 0.157 mmol), dicyclohexyl(2',6'-dimethoxy-[1,1'-biphenyl]-2-yl)phosphine (1.610 mg, 3.92 µmol), chloro(2-dicyclohexylphosphino-2',6'-dimethoxy-1,1'-biphenyl)[2-(2-aminoethylphenyl)]palladium(ii) dichloromethane (2.97 mg, 3.92 µmol), and potassium phosphate (49.9 mg, 0.235 mmol). The vial was flushed with Ar (g), then THF (0.4 mL) and water (0.04 mL) were added in sequence. The vial was sealed and placed in a 110° C. heating bath overnight, then the mixture was cooled and extracted with EtOAc (3×). The combined organic extracts were concentrated. The residue was taken up in DCM (1 mL), TFA (0.5 mL), and triflic acid (0.05 mL) (8:40 am). After 45 min, the mixture was concentrated. The residue was taken up in EtOAc. The organic solution was washed with saturated aq. sodium bicarbonate solution (2×), dried over sodium sulfate, filtered, and concentrated. The residue was purified by chromatography on silica gel (25-g Interchim 15 micron column, 10% MeOH/DCM) to give 1-(4'-fluoro-3-methoxy-[1,1'-biphenyl]-4-yl)-N-(pyrimidin-4-yl)isoquinoline-6-sulfonamide (28.7 mg, 0.059 mmol, 75% yield) as an off-white solid. ¹H NMR (400 MHz, DMSO-d₆) δ=13.04 (s, 1H), 8.69 (d, J=5.8 Hz, 1H), 8.64 (d, J=1.5 Hz, 1H), 8.56 (s, 1H), 8.23 (d, J=6.2 Hz, 1H), 8.09 (d, J=5.4 Hz, 1H), 7.95 (dd, J=1.9, 8.9 Hz, 1H), 7.91-7.83 (m, 2H), 7.78 (d, J=8.9 Hz, 1H), 7.46-7.39 (m, 3H), 7.38-7.31 (m, 2H), 7.02 (d, J=6.4 Hz, 1H), 3.75 (s, 3H). m/z (ESI) 487.2 (M+H)$^+$.

EXAMPLE 351

1-(3-METHOXY-3'-(TRIFLUOROMETHYL)-[1,1'-BIPHENYL]-4-YL)-N-(PYRIMIDIN-4-YL)ISOQUINOLINE-6-SULFONAMIDE

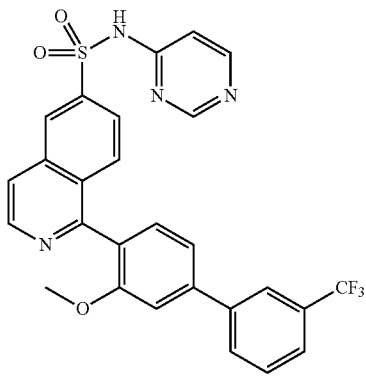 [SMILES: COc1cc(-c2cccc(C(F)(F)F)c2)ccc1-c1nccc2cc(S(=O)(=O)Nc3ccncn3)ccc12]

A vial was charged with 1-(4-chloro-2-methoxyphenyl)-N-(4-methoxybenzyl)-N-(pyrimidin-4-yl)isoquinoline-6-sulfonamide (INTERMEDIATE BBBBB, 75.8 mg, 0.139 mmol). (3-(trifluoromethyl)phenyl)boronic acid (52.6 mg, 0.277 mmol), dicyclohexyl(2',6'-dimethoxy-[1,1'-biphenyl]-2-yl)phosphine (2.84 mg, 6.93 µmol), chloro(2-dicyclohexylphosphino-2',6'-dimethoxy-1,1'-biphenyl)[2-(2-aminoethylphenyl)]palladium(ii) dichloromethane (10.50 mg, 0.014 mmol), and potassium phosphate (88 mg, 0.416 mmol). The vial was flushed with Ar (g), then 1,4-dioxane (630 µl) and water (63.0 µl) were added in sequence. The vial was sealed and heated in a Biotage Initiator microwave reactor for 45 min at 80° C. The mixture was extracted with EtOAc (4×), and the combined organic extracts were concentrated. The residue was taken up in DCM (0.5 mL) and TFA (0.5 mL) to give an amber solution that was stirred overnight. The mixture was diluted with MeOH and concentrated. The mixture was diluted with MeOH and concentrated. The residue was dissolved in DCM and saturated aq. sodium bicarbonate solution was added. The layers were separated, and the aq. layer was extracted with DCM (3×). The combined organic extracts were dried over sodium sulfate, filtered, and concentrated. The residue was purified by chromatography on silica gel (25-g Interchim 15-micron column, 3% MeOH/DCM) to give 1-(3-methoxy-3'-(trifluoromethyl)-[1,1'-biphenyl]-4-yl)-N-(pyrimidin-4-yl)isoquinoline-6-sulfonamide (48 mg, 0.089 mmol, 64.6% yield) as an off-white solid. $^1$H NMR (400 MHz, DMSO-d$_6$) δ=13.07 (br. s., 1H), 8.70 (d, J=5.7 Hz, 1H), 8.66 (d, J=1.2 Hz, 1H), 8.57 (s, 1H), 8.25 (d, J=6.3 Hz, 1H), 8.17-8.09 (m, 3H), 7.96 (dd, J=1.9, 8.9 Hz, 1H), 7.83-7.71 (m, 3H), 7.57-7.43 (m, 3H), 7.03 (d, J=6.1 Hz, 1H), 3.77 (s, 3H). m/z (ESI) 537.0 (M+H)$^+$.

EXAMPLE 352

1-(4-(6-FLUOROPYRIDIN-3-YL)-2-METHOXYPHENYL)-N-(PYRIMIDIN-4-YL)ISOQUINOLINE-6-SULFONAMIDE

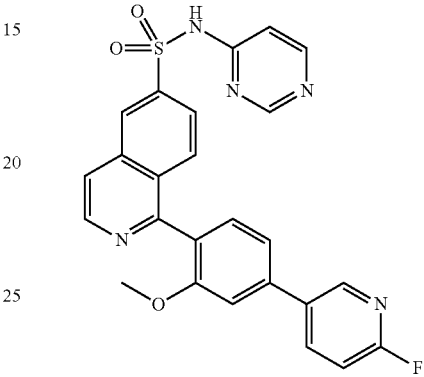

A vial was charged with 1-(4-chloro-2-methoxyphenyl)-N-(4-methoxybenzyl)-N-(pyrimidin-4-yl)isoquinoline-6-sulfonamide (INTERMEDIATE BBBBB, 70.33 mg, 0.129 mmol) (6-fluoropyridin-3-yl)boronic acid (36.2 mg, 0.257 mmol), dicyclohexyl(2',6'-dimethoxy-[1,1'-biphenyl]-2-yl) phosphine (2.64 mg, 6.43 µmol), chloro(2-dicyclohexylphosphino-2',6'-dimethoxy-1,1'-biphenyl)[2-(2-aminoethylphenyl)]palladium(ii) dichloromethane (9.74 mg, 0.013 mmol), and potassium phosphate (82 mg, 0.386 mmol). The vial was flushed with Ar (g), then 1,4-dioxane (584 µl) and water (58.4 µl) were added in sequence. The vial was sealed and heated in a Biotage Initiator microwave reactor for 45 min at 80° C. The mixture was extracted with EtOAc (4×), and the combined organic extracts were concentrated. The residue was taken up in DCM (0.5 mL) and TFA (0.5 mL) to give a solution that was stirred overnight. The mixture was diluted with MeOH and concentrated. The residue was dissolved in DCM and saturated aq. sodium bicarbonate solution was added. The layers were separated, and the aq. layer was extracted with DCM (2×). The combined organic extracts were dried over sodium sulfate, filtered, and concentrated. The residue was purified by chromatography on silica gel (25-g Interchim 15-micron column, 3% MeOH/DCM, then 5% MeOH/DCM) to give 46 mg of a light-yellow solid that was only 80-85% pure by LCMS. The mixture was taken up in MeOH and filtered. The filtrate was purified by reverse-phase HPLC (25-70% CH$_3$CN/H$_2$O with 0.1% TFA). Fractions containing clean desired product were combined in saturated aq. sodium bicarbonate solution and extracted with DCM (3×). The combined organic extracts were dried over sodium sulfate, filtered, and concentrated to give 1-(4-(6-fluoropyridin-3-yl)-2-methoxyphenyl)-N-(pyrimidin-4-yl)isoquinoline-6-sulfonamide (12 mg, 0.025 mmol, 19.15% yield) as an off-white solid. $^1$H NMR (400 MHz, DMSO-d$_6$) δ=13.15 (s, 1H), 8.73 (d, J=2.5 Hz, 1H), 8.70 (d, J=5.7 Hz, 1H), 8.66 (br. s., 1H), 8.58 (s, 1H), 8.46 (dt, J=2.7, 8.2 Hz, 1H), 8.26 (br. s., 1H), 8.11 (d, J=5.8 Hz, 1H), 7.96 (dd, J=1.7, 8.9 Hz, 1H), 7.77

(d, J=9.1 Hz, 1H), 7.54 (d, J=1.2 Hz, 1H), 7.51-7.42 (m, 2H), 7.35 (dd, J=2.8, 8.6 Hz, 1H), 7.05 (br. s., 1H), 3.76 (s, 3H). m/z (ESI) 488.2 (M+H)+.

EXAMPLE 353

1-(5-(3,6-DIHYDRO-2H-PYRAN-4-YL)-2-METHOXYPHENYL)-N-(PYRIMIDIN-4-YL)ISOQUINOLINE-6-SULFONAMIDE

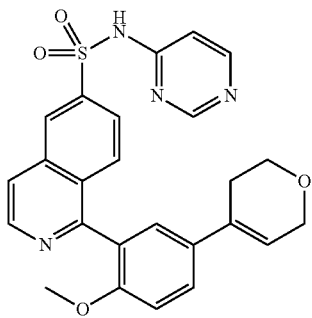 [SMILES: COc1ccc(C2=CCOCC2)cc1-c1nccc2cc(S(=O)(=O)Nc3ccncn3)ccc12]

A vial was charged with 1-(5-chloro-2-methoxyphenyl)-N-(pyrimidin-4-yl)isoquinoline-6-sulfonamide (EXAMPLE 146; 64.07 mg, 0.150 mmol), dihydro-2H-pyran-4-yl)-4,4,5,5-tetramethyl-1,3,2-dioxaborolane (Pharmacore, High Point, N.C.; 47.3 mg, 0.225 mmol), dicyclohexyl(2',6'-dimethoxy-[1,1'-biphenyl]-2-yl)phosphine (3.08 mg, 7.50 µmol), chloro(2-dicyclohexylphosphino-2',6'-dimethoxy-1,1'-biphenyl)[2-(2-aminoethylphenyl)]palladium(ii) dichloromethane (11.37 mg, 0.015 mmol) and potassium phosphate (127 mg, 0.600 mmol). The vial was flushed with Ar (g), then 1,4-dioxane (682 µl) and water (68.2 µl) were added in sequence. The vial was sealed and heated in a Biotage Initiator microwave reactor for 3 h at 100° C. Additional portions of boronic ester (ca. 30 mg) and potassium phosphate (30 mg) were added, and the vial was heated for 20 min at 100° C. in the microwave. The mixture was extracted with EtOAc (2×) and with MeOH-EtOAc (1×), and the combined organic extracts were concentrated. The residue was purified by chromatography on silica gel (12-g Redi-Sep Gold column, 0-10% MeOH/DCM). A few fractions containing product were discarded, and the remainder were combined and concentrated to give 1-(5-(3,6-dihydro-2H-pyran-4-yl)-2-methoxyphenyl)-N-(pyrimidin-4-yl)isoquinoline-6-sulfonamide (39 mg, 0.082 mmol, 54.8% yield) as a light-yellow solid. $^1$H NMR (400 MHz, DMSO-$d_6$) δ=13.04 (s, 1H), 8.71-8.62 (m, 2H), 8.56 (s, 1H), 8.24 (br. s., 1H), 8.09 (d, J=5.6 Hz, 1H), 7.94 (dd, J=1.8, 8.9 Hz, 1H), 7.71 (d, J=9.1 Hz, 1H), 7.61 (dd, J=2.4, 8.7 Hz, 1H), 7.39 (d, J=2.3 Hz, 1H), 7.20 (d, J=8.7 Hz, 1H), 7.02 (br. s., 1H), 6.20 (br. s., 1H), 4.19 (d, J=2.5 Hz, 2H), 3.80 (t, J=5.5 Hz, 2H), 3.65 (s, 3H), 2.44 (br. s., 2H). m/z (ESI) 475.2 (M+H)+.

INTERMEDIATE CCCCC: 1-(4-CHLORO-2-METHOXYPHENYL)-N-(1,3,4-THIADIAZOL-2-YL)ISOQUINOLINE-6-SULFONAMIDE

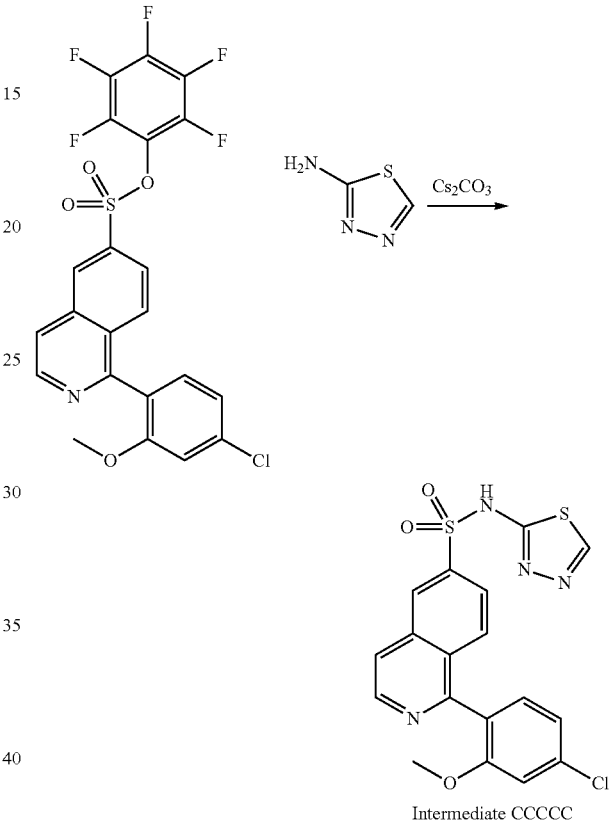

Intermediate CCCCC

A round-bottom flask was charged with perfluorophenyl 1-(4-chloro-2-methoxyphenyl)isoquinoline-6-sulfonate (INTERMEDIATE NNN; 102.15 mg, 0.198 mmol), 1,3,4-thiadiazol-2-amine (40.1 mg, 0.396 mmol), cesium carbonate (194 mg, 0.594 mmol), and DMF (1 mL) (1:30 pm). The mixture was diluted with EtOAc and 0.5 N aq. HCl. The layers were separated, and the organic extract was washed with brine, dried over sodium sulfate, filtered, and concentrated. The residue was purified by chromatography on silica gel (12-g Redi-Sep Gold column, 0-7% MeOH/DCM) to give 1-(4-chloro-2-methoxyphenyl)-N-(1,3,4-thiadiazol-2-yl)

isoquinoline-6-sulfonamide (64.78 mg, 0.150 mmol, 76% yield) as a white solid. m/z (ESI) 433.0 (M+H)+.

EXAMPLE 354

1-(3'-FLUORO-3-METHOXY-[1,1'-BIPHENYL]-4-YL)-N-(1,3,4-THIADIAZOL-2-YL)ISOQUINOLINE-6-SULFONAMIDE 2,2,2-TRIFLUOROACETATE

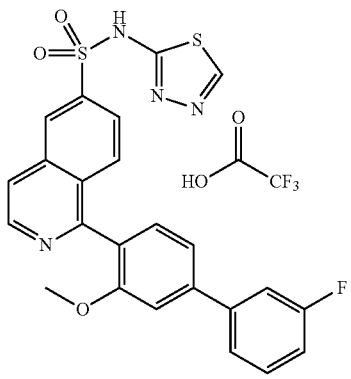

A vial was charged with 1-(4-chloro-2-methoxyphenyl)-N-(1,3,4-thiadiazol-2-yl)isoquinoline-6-sulfonamide (INTERMEDIATE CCCCC, 103.03 mg, 0.238 mmol) (3-fluorophenyl)boronic acid (43.3 mg, 0.309 mmol), dicyclohexyl (2',6'-dimethoxy-[1,1'-biphenyl]-2-yl)phosphine (2.443 mg, 5.95 mmol), chloro(2-dicyclohexylphosphino-2',6'-dimethoxy-1,1'-biphenyl)[2-(2-aminoethylphenyl)]palladium(ii) dichloromethane (9.01 mg, 0.012 mmol), and potassium phosphate (152 mg, 0.714 mmol). The vial was flushed with Ar (g), then 1,4-dioxane (1082 µl) and water (108 µl) were added. The vial was sealed and heated in a Biotage Initiator microwave reactor for 1 h at 120° C. The mixture was extracted with EtOAc (3×). The aq. layer was acidified with 0.5N aq. HCl, then extracted with EtOAc (2×). The combined organic extracts were concentrated. The residue was purified by chromatography on silica gel (12-g Redi-Sep Gold column, 0-4% MeOH/DCM) to give an orange solid. The solid was extracted with boiling 2-PrOH (2×). The decanted solution was cooled to room temperature, then filtered with the aid of 2-PrOH. The collected orange solid was discarded, and the filtrate was concentrated to give a yellow solid. The material was purified further by chromatography on silica gel (25-g Interchim 15-micron column, 4% MeOH/DCM) to give another yellow solid. The solid was dissolved in MeOH-DCM and loaded onto a 1-g PEAX ion-exchange column (Biotage, LLC). The column was eluted with MeOH-DCM, then with 10% HCl (aq.)/MeOH. The acidic fraction was concentrated to give a yellow solid. The solid was taken up in MeOH, and this solution was purified by reverse-phase HPLC (25-75% CH$_3$CN/H$_2$O with 0.1% TFA). Fractions containing clean product were combined and concentrated to give 1-(3'-fluoro-3-methoxy-[1,1'-biphenyl]-4-yl)-N-(1,3,4-thiadiazol-2-yl)isoquinoline-6-sulfonamide 2,2,2-trifluoroacetate (28.6 mg, 0.047 mmol, 19.81% yield). $^1$H NMR (400 MHz, DMSO-d$_6$) δ=14.55 (br. s., 1H), 8.84-8.79 (m, 1H), 8.74 (d, J=5.9 Hz, 1H), 8.65 (d, J=1.3 Hz, 1H), 8.28 (d, J=5.8 Hz, 1H), 7.98-7.87 (m, 2H), 7.75-7.68 (m, 2H), 7.61-7.53 (m, 2H), 7.51 (s, 2H), 7.31-7.24 (m, 1H), 3.79 (s, 3H). m/z (ESI) 493.2 (M+H)+.

EXAMPLE 355

1-(3',5'-DIFLUORO-3-METHOXY-[1,1'-BIPHENYL]-4-YL)-N-(1,3,4-THIADIAZOL-2-YL)ISOQUINOLINE-6-SULFONAMIDE 2,2,2-TRIFLUOROACETATE

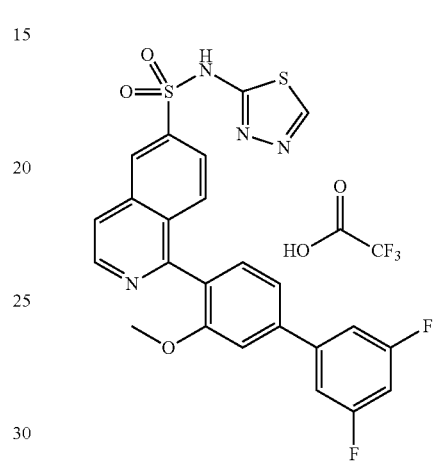

A vial was charged with 1-(4-chloro-2-methoxyphenyl)-N-(1,3,4-thiadiazol-2-yl)isoquinoline-6-sulfonamide (INTERMEDIATE CCCCC, 117 mg, 0.270 mmol). (3,5-difluorophenyl)boronic acid (55.5 mg, 0.351 mmol), dicyclohexyl (2',6'-dimethoxy-[1,1'-biphenyl]-2-yl)phosphine (2.77 mg, 6.76 µmol), chloro(2-dicyclohexylphosphino-2',6'-dimethoxy-1,1'-biphenyl)[2-(2-aminoethylphenyl)]palladium(ii) dichloromethane (10.24 mg, 0.014 mmol) and potassium phosphate (172 mg, 0.811 mmol). The vial was flushed with Ar (g), then 1,4-dioxane (1228 µl) and water (123 µl) were added. The vial was sealed and heated in a Biotage Initiator microwave reactor for 1 h at 120° C. The mixture was extracted with EtOAc (4×). The combined organic extracts were concentrated. The residue was purified by chromatography on silica gel (25-g Interchim 15-micron column, 3% MeOH/DCM) to give a solid. The solid was taken up in MeOH and filtered though a 0.2 micron filter, and the filtrate was purified by reverse-phase HPLC (25-75% CH$_3$CN/H$_2$O with 0.1% TFA). Fractions containing clean product were combined and concentrated. The residue was concentrated from DCM to give 1-(3',5'-difluoro-3-methoxy-[1,1'-biphenyl]-4-yl)-N-(1,3,4-thiadiazol-2-yl)isoquinoline-6-sulfonamide 2,2,2-trifluoroacetate as a light-yellow solid. $^1$H NMR (400 MHz, DMSO-d$_6$) δ=14.53 (br. s., 1H), 8.82 (s, 1H), 8.73 (d, J=5.8 Hz, 1H), 8.61 (d, J=1.7 Hz, 1H), 8.19 (d, J=5.7 Hz, 1H), 7.94-7.89 (m, 1H), 7.85-7.80 (m, 1H), 7.69-7.62 (m, 2H), 7.58-7.52 (m, 2H), 7.50-7.46 (m, 1H), 7.31 (tt, J=2.2, 9.2 Hz, 1H), 3.79 (s, 3H). m/z (ESI) 511.2 (M+H)+.

INTERMEDIATE DDDDD: PERFLUOROPHENYL 1-(4-CHLORO-2-METHYLPHENYL)ISOQUINOLINE-6-SULFONATE

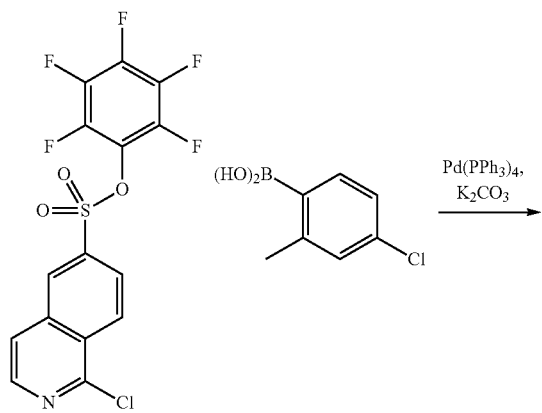

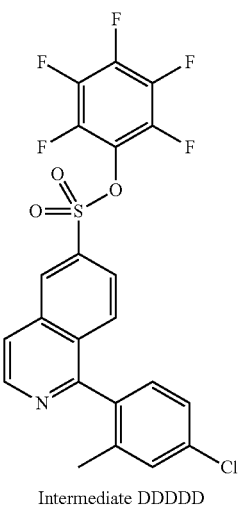

Intermediate DDDDD

A round-bottom flask was charged with perfluorophenyl 1-chloroisoquinoline-6-sulfonate (see EXAMPLE 73, Step 1, 518.97 mg, 1.267 mmol), (4-chloro-2-methylphenyl)boronic acid (324 mg, 1.900 mmol), potassium carbonate (525 mg, 3.80 mmol), and Pd(PPh$_3$)$_4$ (146 mg, 0.127 mmol). The flask was flushed with Ar (g), then 1,4-dioxane (4750 µl) and water (1583 µl) were added. The flask was sealed and heated in a 50° C. heating bath overnight. The mixture was diluted with water and extracted with EtOAc (2×). The combined organic extracts were dried over sodium sulfate, filtered, and concentrated. The residue was purified by chromatography on silica gel (40-g Redi-Sep Gold column, 0-30% EtOAc/Heptane) to give perfluorophenyl 1-(4-chloro-2-methylphenyl)isoquinoline-6-sulfonate (249 mg, 0.498 mmol, 39.3% yield) as a clear oil. m/z (ESI) 500.0 (M+H)+.

EXAMPLE 356

1-(4-CHLORO-2-METHYLPHENYL)-N-(3-METHYL-1,2,4-THIADIAZOL-5-YL)ISOQUINOLINE-6-SULFONAMIDE

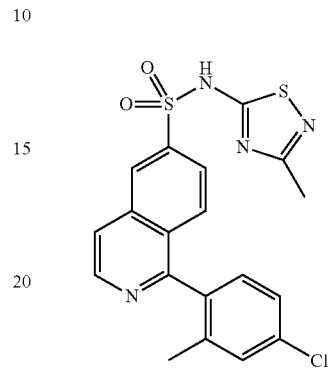

A round-bottom flask was charged with perfluorophenyl 1-(4-chloro-2-methylphenyl)isoquinoline-6-sulfonate (Intermediate DDDDD; 59.9 mg, 0.120 mmol), 3-methyl-1,2,4-thiadiazol-5-amine (27.6 mg, 0.240 mmol), cesium carbonate (117 mg, 0.360 mmol), and DMF (0.6 mL). The vial was sonicated for 20 s, and the mixture was stirred further for 2 h. The mixture was diluted with EtOAc and 0.5 N aq. HCl. The layers were separated, and the organic extract was washed with brine, dried over sodium sulfate, filtered, and concentrated. The residue was purified by chromatography on silica gel (25-g Interchim 15-micron column, 0-5% MeOH/DCM) to give 1-(4-chloro-2-methylphenyl)-N-(3-methyl-1,2,4-thiadiazol-5-yl)isoquinoline-6-sulfonamide (38.94 mg, 0.090 mmol, 75% yield) as a white solid. $^1$H NMR (400 MHz, DMSO-d$_6$) δ=8.72 (d, J=5.7 Hz, 1H), 8.60 (d, J=1.8 Hz, 1H), 8.16 (d, J=5.8 Hz, 1H), 7.89 (dd, J=1.9, 8.9 Hz, 1H), 7.69 (d, J=8.9 Hz, 1H), 7.52 (d, J=1.9 Hz, 1H), 7.44-7.39 (m, 1H), 7.33 (d, J=8.1 Hz, 1H), 2.27 (s, 3H), 1.97 (s, 3H). m/z (ESI) 431.0 (M+H)+.

EXAMPLE 357

1-(4-CHLORO-2-METHYLPHENYL)-N-(PYRIMIDIN-4-YL)ISOQUINOLINE-6-SULFONAMIDE

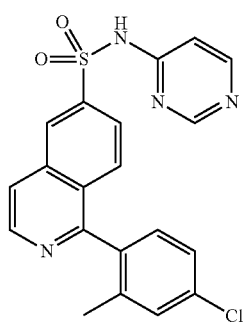 [SMILES: Cc1cc(Cl)ccc1-c1nccc2cc(S(=O)(=O)Nc3ccncn3)ccc12]

A round-bottom flask was charged with perfluorophenyl 1-(4-chloro-2-methylphenyl)isoquinoline-6-sulfonate (IN- TERMEDIATE DDDDD, 189 mg, 0.378 mmol), pyrimidin-4-amine (39.6 mg, 0.416 mmol), and THF (1891 µl) to give a clear, lightly-colored solution. The flask was cooled in an ice-bath for 5 min, then lithium bis(trimethylsilyl)amide (1M in THF) (794 µl, 0.794 mmol) was added drop wise over 30 s to give a yellow suspension. After 15 min, the mixture was quenched by the addition of TFA (0.3 mL), and then concentrated. The residue was concentrated from DCM then from MeOH. The residue was then purified by chromatography on silica gel (12-g Redi-Sep Gold column, 5-10% MeOH/DCM). Fractions containing product were combined and concentrated. The residue was taken up in DCM and filtered. The collected solid was washed with DCM (3×), then dried under a stream of $N_2$ (g) for 20 min to give 1-(4-chloro-2-methylphenyl)-N-(pyrimidin-4-yl)isoquinoline-6-sulfonamide (70.2 mg, 0.171 mmol, 45.2% yield) as a white solid. $^1$H NMR (400 MHz, DMSO-$d_6$) δ=8.72 (d, J=5.7 Hz, 2H), 8.58 (br. s., 1H), 8.26 (br. s., 1H), 8.16 (d, J=5.4 Hz, 1H), 8.00-7.94 (m, 1H), 7.69 (d, J=8.3 Hz, 1H), 7.53 (d, J=2.0 Hz, 1H), 7.46-7.40 (m, 1H), 7.36-7.30 (m, 1H), 7.05 (s, 1H), 1.98 (s, 3H). m/z (ESI) 411.2 (M+H)$^+$.

EXAMPLE 358

1-(3'-FLUORO-3-METHYL-[1,1'-BIPHENYL]-4-YL)-N-(PYRIMIDIN-4-YL)ISOQUINOLINE-6-SULFONAMIDE

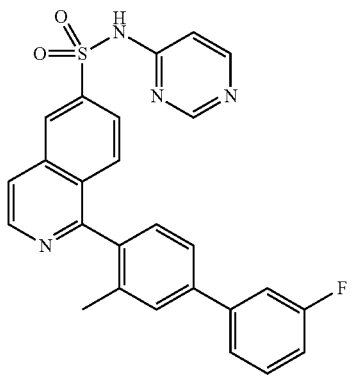 [SMILES: Cc1cc(-c2cccc(F)c2)ccc1-c1nccc2cc(S(=O)(=O)Nc3ccncn3)ccc12]

A vial was charged with 1-(4-chloro-2-methylphenyl)-N-(pyrimidin-4-yl)isoquinoline-6-sulfonamide (EXAMPLE 357; 61.66 mg, 0.150 mmol) (3-fluorophenyl)boronic acid (42.0 mg, 0.300 mmol), dicyclohexyl(2',6'-dimethoxy-[1,1'-biphenyl]-2-yl)phosphine (3.08 mg, 7.50 mmol), chloro(2-dicyclohexylphosphino-2',6'-dimethoxy-1,1'-biphenyl)[2-(2-aminoethylphenyl)]palladium(ii) dichloromethane (11.37 mg, 0.015 mmol) and potassium phosphate (96 mg, 0.450 mmol). The vial was flushed with Ar (g), then 1,4-dioxane (682 µl) and water (68.2 µl) were added in sequence. The vial was sealed and heated in a Biotage Initiator microwave reactor for 1 h 45 min at 100° C. The mixture was extracted with EtOAc (3×). The combined organic extracts were concentrated. The residue was purified by chromatography on silica gel (12-g Redi-Sep Gold column, 3% MeOH/DCM) to give 1-(3'-fluoro-3-methyl-[1,1'-biphenyl]-4-yl)-N-(pyrimidin-4-yl)isoquinoline-6-sulfonamide (29.49 mg, 0.063 mmol, 41.8% yield) as a white solid. $^1$H NMR (400 MHz, DMSO-$d_6$) δ=13.08 (br. s., 1H), 8.77-8.67 (m, 2H), 8.58 (s, 1H), 8.24 (br. s., 1H), 8.15 (d, J=5.6 Hz, 1H), 7.98 (dd, J=1.8, 8.9 Hz, 1H), 7.80-7.72 (m, 2H), 7.71-7.61 (m, 3H), 7.55 (dt, J=6.2, 8.0 Hz, 1H), 7.39 (d, J=7.9 Hz, 1H), 7.28-7.19 (m, 1H), 7.03 (br. s., 1H), 2.06 (s, 3H). m/z (ESI) 471.2 (M+H)$^+$.

EXAMPLE 359

1-(4-CYANO-2-METHYLPHENYL)-N-(1,2,4-THIADIAZOL-5-YL)ISOQUINOLINE-6-SULFONAMIDE

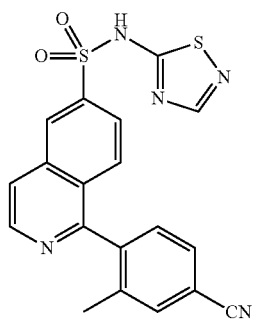 [SMILES: Cc1cc(C#N)ccc1-c1nccc2cc(S(=O)(=O)Nc3ncns3)ccc12]

A vial was charged with 1-chloro-N-(2,4-dimethoxybenzyl)-N-(1,2,4-thiadiazol-5-yl)isoquinoline-6-sulfonamide (INTERMEDIATE X, 75.96 mg, 0.159 mmol), (4-cyano-2-methylphenyl)boronic acid (51.3 mg, 0.319 mmol), Pd(AmPhos)$_2$Cl$_2$ (5.64 mg, 7.96 µmol), potassium phosphate (101 mg, 0.478 mmol), 1,4-dioxane (597 µl), and water (199 µl). The vial was flushed with Ar (g), then sealed and heated in a Biotage Initiator microwave reactor for 30 min h at 90° C. The mixture was extracted with EtOAc (3×), and the combined organic extracts were concentrated. The residue was dissolved in DCM (0.5 mL), TFA (0.25 mL), and triflic acid (0.025 mL) (3:55 pm), and the mixture was stirred for 40 min. The mixture was diluted with 2-PrOH, then concentrated. The residue was purified twice by chromatography on silica gel (12-g Redi-Sep Gold columns), first with 50-100% EtOAc/Heptane, then with 0-6% MeOH/DCM to give 1-(4-cyano-2-methylphenyl)-N-(1,2,4-thiadiazol-5-yl)isoquinoline-6-sulfonamide (27.27 mg, 0.067 mmol, 42.0% yield) as a light-yellow solid. $^1$H NMR (400 MHz, DMSO-$d_6$) δ=8.73 (d, J=5.7 Hz, 1H), 8.62 (d, J=1.6 Hz, 1H), 8.41 (s, 1H), 8.19 (d, J=5.9 Hz, 1H), 7.95-7.92 (m, 1H), 7.89 (dd, J=1.8, 8.9 Hz, 1H), 7.83 (d, J=7.6 Hz, 1H), 7.64 (d, J=8.9 Hz, 1H), 7.52 (d, J=7.9 Hz, 1H), 2.01 (s, 3H). m/z (ESI) 408.2 (M+H)$^+$.

EXAMPLE 360

1-(2-METHOXY-4-NEOPENTYLPHENYL)-N-(PYRIMIDIN-4-YL)ISOQUINOLINE-6-SULFONAMIDE

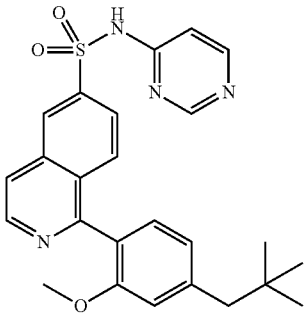 [SMILES: COc1cc(CC(C)(C)C)ccc1-c1nccc2cc(S(=O)(=O)Nc3ccncn3)ccc12]

A vial was charged with 1-(4-chloro-2-methoxyphenyl)-N-(pyrimidin-4-yl)isoquinoline-6-sulfonamide (EXAMPLE 160; 67 mg, 0.157 mmol), dicyclohexyl(2',6'-dimethoxy-[1,1'-biphenyl]-2-yl)phosphine (6.44 mg, 0.016 mmol), and Pd$_2$(dba)$_3$ (7.19 mg, 7.85 mmol). The vial was flushed with Ar (g), then neopentylzinc(II) iodide (0.5 M in THF) (1570 µl, 0.785 mmol) was added. The mixture was sonicated for 30 s to give a suspension. The sealed vial was heated to 70° C. for 2 h then 90° C. overnight. The mixture was diluted with MeOH, filtered through Celite, and concentrated. The residue was purified by chromatography on silica gel (12-g Redi-Sep Gold column, 0-7.5% MeOH/DCM) to give a yellow foam. The material was dissolved in MeOH/DCM and loaded onto a 2-g SCX-2 ion exchange column. The filtrate was concentrated, and the residue was purified by chromatography on silica gel (25-g Interchim 15 micron column, 3.5% MeOH/DCM) to give 1-(2-methoxy-4-neopentylphenyl)-N-(pyrimidin-4-yl)isoquinoline-6-sulfonamide (23.65 mg, 0.051 mmol, 32.6% yield) as a light-yellow solid. $^1$H NMR (400 MHz, DMSO-d$_6$) δ=13.07 (br. s, 1H), 8.70-8.61 (m, 2H), 8.57 (s, 1H), 8.24 (br. s., 1H), 8.06 (d, J=5.8 Hz, 1H), 7.94 (dd, J=1.7, 8.9 Hz, 1H), 7.71 (d, J=8.8 Hz, 1H), 7.22 (d, J=7.6 Hz, 1H), 7.03 (br. s., 1H), 6.96 (s, 1H), 6.89 (d, J=7.6 Hz, 1H), 3.62 (s, 3H), 2.60 (s, 2H), 0.97 (s, 9H). m/z (ESI) 463.2 (M+H)$^+$.

EXAMPLE 361

1-(4-ISOBUTOXY-2-METHOXYPHENYL)-N-(PYRIMIDIN-4-YL)ISOQUINOLINE-6-SULFONAMIDE

STEP 1: 1-(4-HYDROXY-2-METHOXYPHENYL)-N-(4-METHOXYBENZYL)-N-(PYRIMIDIN-4-YL)ISOQUINOLINE-6-SULFONAMIDE

A vial was charged with 1-chloro-N-(4-methoxybenzyl)-N-(pyrimidin-4-yl)isoquinoline-6-sulfonamide (INTERMEDIATE ZZZZ, 122 mg, 0.277 mmol), 3-methoxy-4-(4,4,5,5-tetramethyl-1,3,2-dioxaborolan-2-yl)phenol (138 mg, 0.553 mmol), potassium carbonate (191 mg, 1.384 mmol), and Pd(PPh$_3$)$_4$ (32.0 mg, 0.028 mmol). The vial was flushed with Ar (g), then 1,4-dioxane (1038 µl) and water (346 µl) were added. The vial was sealed and heated to 80° C. for 2 h in a Biotage Initiator microwave reactor. The mixture was extracted with EtOAc (3×), and the combined organic extracts were concentrated. The residue was purified by chromatography on silica gel (25-g Interchim column, 35-85% EtOAc/Heptane, then with 85-100% EtOAc/Heptane) to give 1-(4-hydroxy-2-methoxyphenyl)-N-(4-methoxybenzyl)-N-(pyrimidin-4-yl)isoquinoline-6-sulfonamide (93.6 mg, 0.177 mmol, 64.0% yield) as an off-white solid. m/z (ESI) 529.2 (M+H)$^+$.

STEP 2: 1-(4-ISOBUTOXY-2-METHOXYPHENYL)-N-(PYRIMIDIN-4-YL)ISOQUINOLINE-6-SULFONAMIDE

A vial was charged with 1-(4-hydroxy-2-methoxyphenyl)-N-(4-methoxybenzyl)-N-(pyrimidin-4-yl)isoquinoline-6- sulfonamide (38.07 mg, 0.072 mmol), cesium carbonate (70.4 mg, 0.216 mmol), and DMF (360 µl). Within a few minutes, a deep red solution formed. 1-iodo-2-methylpropane (16.58 µl, 0.144 mmol) was added. The vial was sealed and lowered into a 50° C. heating bath. After 2 h, additional portions of cesium carbonate (70.4 mg, 0.216 mmol) and 1-iodo-2-methylpropane (16.58 µl, 0.144 mmol) were added. The mixture was heated for another 1 h, then it was cooled, diluted with water, and extracted with EtOAc (3×). The combined organic extracts were concentrated. The residue was taken up in DCM (1 mL). The mixture was cooled in an ice-bath for 5 min, then TFA (0.4 mL) was added drop wise. The ice-bath was then removed and an additional portion of TFA (0.4 mL) was added. The mixture was stirred overnight, then was diluted with MeOH and concentrated. The residue was dissolved in DCM and saturated aq. sodium bicarbonate solution was added. The layers were separated, and the aq. layer was extracted with DCM (2×). The combined organic extracts were dried over sodium sulfate, filtered, and concentrated. The residue was purified by chromatography on silica gel (12-g Redi-Sep Gold column, 50-100% EtOAc, then 10% MeOH/DCM) to give 1-(4-isobutoxy-2-methoxyphenyl)-N-(pyrimidin-4-yl)isoquinoline-6-sulfonamide (29.3 mg, 0.063 mmol, 88% yield) as a light-yellow solid. $^1$H NMR (400 MHz, DMSO-d$_6$) δ=13.02 (br. s., 1H), 8.69-8.51 (m, 3H), 8.25 (br. s., 1H), 8.04 (s, 1H), 7.95-7.87 (m, 1H), 7.75 (d, J=8.9 Hz, 1H), 7.23 (d, J=8.3 Hz, 1H), 7.04 (br. s., 1H), 6.74 (d, J=2.2 Hz, 1H), 6.69 (dd, J=2.2, 8.3 Hz, 1H), 3.86 (d, J=6.7 Hz, 2H), 3.63 (s, 3H), 2.08 (quind, J=6.6, 13.2 Hz, 1H), 1.03 (d, J=6.7 Hz, 6H). m/z (ESI) 465.2 (M+H)$^+$.

EXAMPLE 362

1-(2-METHOXY-4-(2,2,2-TRIFLUOROETHOXY) PHENYL)-N-(PYRIMIDIN-4-YL)ISOQUINO-LINE-6-SULFONAMIDE

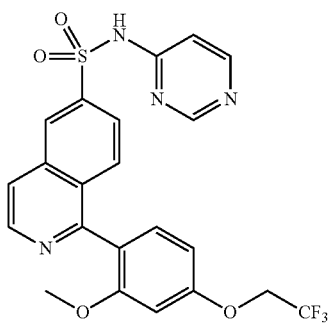 [SMILES: COc1cc(OCC(F)(F)F)ccc1-c1nccc2cc(S(=O)(=O)Nc3ccncn3)ccc12]

A vial was charged with 1-(4-hydroxy-2-methoxyphenyl)-N-(4-methoxybenzyl)-N-(pyrimidin-4-yl)isoquinoline-6-sulfonamide (from EXAMPLE 361, STEP 1; 54 mg, 0.102 mmol), cesium carbonate (100 mg, 0.306 mmol), and DMF (511 µl). 2,2,2-Trifluoroethyl trifluoromethanesulfonate (28.0 µl, 0.204 mmol) was added and the vial was heated to 50° C. for 1 h. The mixture was diluted with water and extracted with EtOAc (3×). The combined organic extracts were concentrated. The residue was dissolved in DCM (1 mL) and TFA (1 mL), and the resulting solution was stirred overnight. The mixture was diluted with MeOH and concentrated. The residue was dissolved in EtOAc and washed with saturated aq. sodium bicarbonate solution. The aq. wash was extracted with EtOAc (2×). The combined organic extracts were dried over sodium sulfate, filtered, and concentrated. The residue was purified by chromatography on silica gel (3.5% MeOH/DCM) to give 1-(2-methoxy-4-(2,2,2-trifluoroethoxy)phenyl)-N-(pyrimidin-4-yl)isoquinoline-6-sulfonamide (32.7 mg, 0.067 mmol, 65.3% yield) as a white solid. $^1$H NMR (400 MHz, DMSO-d$_6$) δ=13.06 (br. s., 1H), 8.70-8.61 (m, 2H), 8.57 (s, 1H), 8.25 (d, J=5.6 Hz, 1H), 8.06 (d, J=5.8 Hz, 1H), 7.94 (dd, J=1.9, 8.9 Hz, 1H), 7.72 (d, J=8.9 Hz, 1H), 7.30 (d, J=8.3 Hz, 1H), 7.03 (d, J=5.1 Hz, 1H), 6.90 (d, J=2.3 Hz, 1H), 6.82 (dd, J=2.3, 8.4 Hz, 1H), 4.89 (q, J=8.9 Hz, 2H), 3.65 (s, 3H). m/z (ESI) 491.2 (M+H)$^+$.

INTERMEDIATE EEEEE: 1-(6-CHLORO-2-METHOXYPYRIDIN-3-YL)-N-(4-METHOXY-BENZYL)-N-(PYRIMIDIN-4-YL)ISOQUINO-LINE-6-SULFONAMIDE

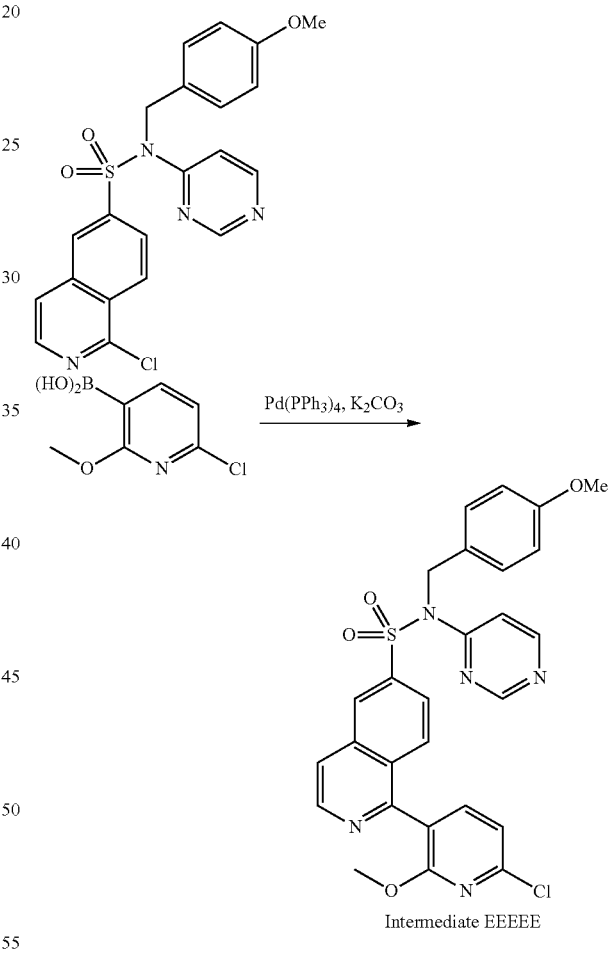

Intermediate EEEEE

A vial was charged with 1-chloro-N-(4-methoxybenzyl)-N-(pyrimidin-4-yl)isoquinoline-6-sulfonamide (INTERMEDIATE ZZZZ, 97 mg, 0.220 mmol), (6-chloro-2-methoxypyridin-3-yl)boronic acid (45.3 mg, 0.242 mmol), potassium carbonate (91 mg, 0.660 mmol), and pd(ph3p)$_4$ (12.71 mg, 0.011 mmol). The vial was flushed with Ar (g), then 1,4-dioxane (825 µl) and water (275 µl) were added. The vial was sealed and heated to 80° C. for 45 min in a Biotage Initiator microwave reactor. LCMS showed primarily the desired product. The mixture was extracted with EtOAc (3×), and the combined organic extracts were concentrated. The residue was purified by chromatography on silica gel (12-g Redi-Sep Gold column, 0-50% EtOAc/Heptane, then 50-100% EtOAc/Heptane) to give 1-(6-chloro-2-methoxypyridin-3-yl)-N-(4-methoxybenzyl)-N-(pyrimidin-4-yl)isoquinoline-6-sulfonamide (117 mg, 0.213 mmol, 97% yield) as a cream-colored foam. m/z (ESI) 548.2 (M+H)+.

EXAMPLE 363

1-(6-(3-FLUOROPHENYL)-2-METHOXYPYRIDIN-3-YL)-N-(PYRIMIDIN-4-YL)ISOQUINOLINE-6-SULFONAMIDE

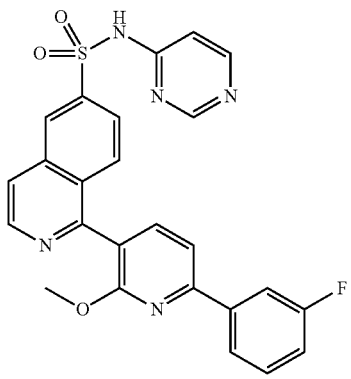 [SMILES: COc1nc(-c2cccc(F)c2)ccc1-c1nccc2cc(S(=O)(=O)Nc3ccncn3)ccc12]

A vial was charged with 1-(6-chloro-2-methoxypyridin-3-yl)-N-(4-methoxybenzyl)-N-(pyrimidin-4-yl)isoquinoline-6-sulfonamide (INTERMEDIATE EEEEE, 64.35 mg, 0.117 mmol). (3-fluorophenyl)boronic acid (32.9 mg, 0.235 mmol), dicyclohexyl(2',6'-dimethoxy-[1,1'-biphenyl]-2-yl)phosphine (2.410 mg, 5.87 µmol), chloro(2-dicyclohexylphosphino-2',6'-dimethoxy-1,1'-biphenyl)[2-(2-aminoethylphenyl)]palladium(ii) dichloromethane (8.89 mg, 0.012 mmol). and potassium phosphate (74.8 mg, 0.352 mmol). The vial was flushed with Ar (g), then 1,4-dioxane (534 µl) and water (53.4 µl) were added in sequence. The vial was sealed and heated in a Biotage Initiator microwave reactor for 45 min at 90° C. The mixture was extracted with EtOAc (4×), and the combined organic extracts were concentrated. The residue was taken up in DCM (0.5 mL) and TFA (0.5 mL) to give a solution that was stirred overnight. The mixture was concentrated. The residue was dissolved in DCM and saturated aq. sodium bicarbonate solution was added. The layers were separated, and the aq. layer was extracted with DCM (2×). The combined organic extracts were dried over sodium sulfate, filtered, and concentrated. The residue was purified by chromatography on silica gel (12-g Redi-Sep Gold column, 4% MeOH/DCM). A few mixed fractions were discarded, and the remainder were combined to give 1-(6-(3-fluorophenyl)-2-methoxypyridin-3-yl)-N-(pyrimidin-4-yl)isoquinoline-6-sulfonamide (29 mg, 0.059 mmol, 50.7% yield) as a light-yellow solid. $^1$H NMR (400 MHz, DMSO-d$_6$) δ=13.11 (br. s., 1H), 8.72 (d, J=5.7 Hz, 1H), 8.68 (s, 1H), 8.57 (s, 1H), 8.24 (d, J=6.7 Hz, 1H), 8.15 (d, J=5.7 Hz, 1H), 8.09 (d, J=7.9 Hz, 1H), 8.07-8.02 (m, 1H), 7.99-7.92 (m, 2H), 7.88-7.82 (m, 2H), 7.59 (dt, J=6.2, 7.9 Hz, 1H), 7.32 (dt, J=2.2, 8.4 Hz, 1H), 7.03 (d, J=6.0 Hz, 1H), 3.90 (s, 3H). m/z (ESI) 488.2 (M+H)+.

INTERMEDIATE FFFFF:
(4-CHLORO-5-FLUORO-2-METHOXYPHENYL)BORONIC ACID

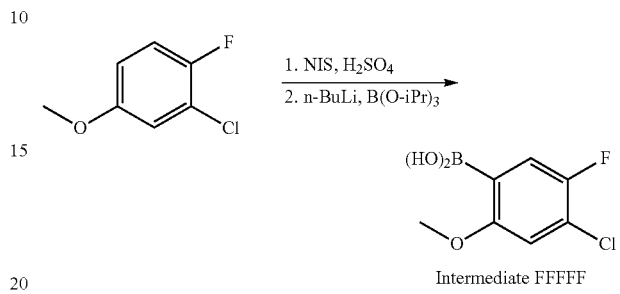

STEP 1:
1-CHLORO-2-FLUORO-4-IODO-5-METHOXYBENZENE

A round-bottom flask was charged with 2-chloro-1-fluoro-4-methoxybenzene (Alfa Aesar, Ward Hill, Mass., 2.714 g, 16.90 mmol), DCM (24.86 ml), AcOH (24.86 ml), and sulfuric acid (0.496 ml, 9.30 mmol) to give a solution. n-iodosuccinimide (3.80 g, 16.90 mmol) was added in a single portion. TLC showed what appeared to be conversion of the starting material to a slightly higher, move UV-active spot. The mixture was diluted with DCM, washed with water (2×), washed with saturated aq. sodium thiosulfate, dried over sodium sulfate, filtered, and concentrated. The residue was purified by chromatography on silica gel (50-g SNAP Ultra column, 0-10% EtOAc/Heptane) to give 3.409 g of a clear oil. This oil was used directly in the next reaction without further purification.

STEP 2:
(4-CHLORO-5-FLUORO-2-METHOXYPHENYL)BORONIC ACID

A round-bottom flask was charged with 1-chloro-2-fluoro-4-iodo-5-methoxybenzene (3.40 g, 11.87 mmol), triisopropyl borate (3.58 ml, 15.43 mmol), and THF (29.7 ml). The flask was cooled in a dry ice-acetone bath for 10 min, then n-butyllithium (2.5 M in hexane) (6.17 ml, 15.43 mmol) was added drop wise over 1 min. After 1 h, a 2N aq. NaOH solution (25 mL) was added, and the mixture was warmed to room temperature. After another 20 min, the mixture was diluted with water then acidified with 6N aq. HCl (40 mL). The mixture was extracted with ether (2×), and the combined organic extracts were dried over magnesium sulfate, filtered, and concentrated. The residue was taken up in DCM and filtered to give 708 mg of a white solid. The filtrate was purified by chromatography on silica gel (50-g SNAP Ultra column, 0-40% EtOAc/Heptane) to give an additional portion of white solid. The two solids were combined to give (4-chloro-5-fluoro-2-methoxyphenyl)boronic acid (1.273 g, 6.23 mmol, 52.5% yield) as a white solid. m/z (ESI) 205.2 (M+H)+.

INTERMEDIATE GGGGG: PERFLUOROPHENYL 1-(4-CHLORO-5-FLUORO-2-METHOXYPHENYL)ISOQUINOLINE-6-SULFONATE

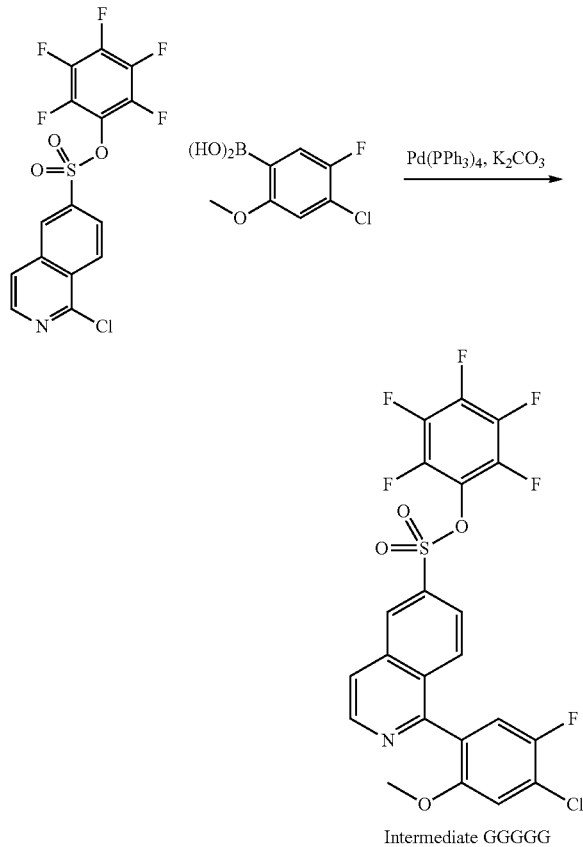

Intermediate GGGGG

A round-bottom flask was charged with perfluorophenyl 1-chloroisoquinoline-6-sulfonate (see EXAMPLE 73, STEP 1, 1.7 g, 4.15 mmol), (4-chloro-5-fluoro-2-methoxyphenyl) boronic acid (INTERMEDIATE FFFFF; 1.272 g, 6.22 mmol), potassium carbonate (1.720 g, 12.45 mmol), and Pd(PPh$_3$)$_4$ (0.479 g, 0.415 mmol). The vial was flushed with Ar (g), then 1,4-dioxane (15.56 ml) and water (5.19 ml) were added. The flask was fitted with a reflux condenser and heated in a 50° C. heating bath for 1 h. The mixture was diluted with water and extracted with EtOAc (2×). The combined organic extracts were dried over sodium sulfate, filtered, and concentrated. The residue was purified by chromatography on silica gel (40-g Redi-Sep Gold column, 0-50% EtOAc/Heptane) to give perfluorophenyl 1-(4-chloro-5-fluoro-2-methoxyphenyl)isoquinoline-6-sulfonate (1.89 g, 3.54 mmol, 85% yield) as a white foam. m/z (ESI) 534.0 (M+H)+.

INTERMEDIATE HHHHH: 1-(4-CHLORO-5-FLUORO-2-METHOXYPHENYL)-N-(1,3,4-THIADIAZOL-2-YL)ISOQUINOLINE-6-SULFONAMIDE

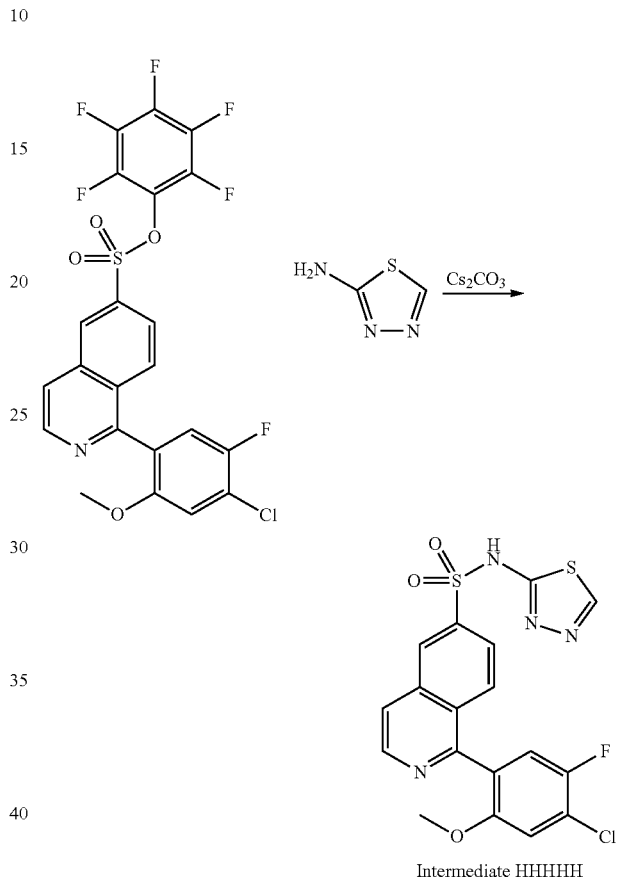

Intermediate HHHHH

A vial was charged with perfluorophenyl 1-(4-chloro-5-fluoro-2-methoxyphenyl)isoquinoline-6-sulfonate (INTERMEDIATE GGGGG, 1.233 g, 2.310 mmol) 1,3,4-thiadiazol-2-amine (0.280 g, 2.77 mmol), and cesium carbonate (2.258 g, 6.93 mmol). Acetonitrile (11.55 ml) was added, and the mixture was stirred overnight. The mixture was diluted with EtOAc and 0.5 N aq. HCl. The layers were separated, and the aq. layer was extracted with EtOAc (2×). The combined organic extracts were dried over sodium sulfate, filtered, and concentrated. The residue was purified by chromatography on silica gel (25-g SNAP Ultra column, 0-5% MeOH/DCM) to give 1-(4-chloro-5-fluoro-2-methoxyphenyl)-N-(1,3,4- thiadiazol-2-yl)isoquinoline-6-sulfonamide (632 mg, 1.402 mmol, 60.7% yield) as an off-white solid. m/z (ESI) 451.0 (M+H)+.

EXAMPLE 364

N-(1,3,4-THIADIAZOL-2-YL)-1-(2,3',5'-TRIFLUORO-5-METHOXY-[1,1'-BIPHENYL]-4-YL)ISOQUINOLINE-6-SULFONAMIDE

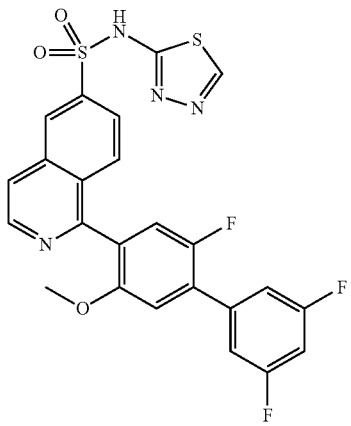 [SMILES: COc1cc(-c2cc(F)cc(F)c2)c(F)cc1-c1nccc2cc(S(=O)(=O)Nc3nncs3)ccc12]

A vial was charged with 1-(4-chloro-5-fluoro-2-methoxyphenyl)-N-(1,3,4-thiadiazol-2-yl)isoquinoline-6-sulfonamide (INTERMEDIATE HHHHH; 88.75 mg, 0.197 mmol). (3,5-difluorophenyl)boronic acid (62.2 mg, 0.394 mmol), dicyclohexyl(2',6'-dimethoxy-[1,1'-biphenyl]-2-yl)phosphine (2.020 mg, 4.92 μmol), chloro(2-dicyclohexylphosphino-2',6'-dimethoxy-1,1'-biphenyl)[2-(2-aminoethylphenyl)]palladium(ii) dichloromethane (7.46 mg, 9.84 μmol), and potassium phosphate (125 mg, 0.590 mmol). The vial was flushed with Ar (g), then 1,4-dioxane (895 μl) and water (89 μl) were added. The vial was sealed and heated in a Biotage Initiator microwave reactor for 1 h at 120° C. The mixture was extracted with EtOAc (4×). The combined organic extracts were concentrated. The residue was purified by chromatography on silica gel (12-g Redi-Sep Gold column, 0-4% MeOH/DCM, then with 4-10% MeOH/DCM) to give N-(1,3,4-thiadiazol-2-yl)-1-(2,3',5'-trifluoro-5-methoxy-[1,1'-biphenyl]-4-yl)isoquinoline-6-sulfonamide (31.54 mg, 0.060 mmol, 30.3% yield) as a yellow solid. $^1$H NMR (400 MHz, DMSO-$d_6$) δ=14.50 (br. s., 1H), 8.78 (s, 1H), 8.71 (d, J=5.7 Hz, 1H), 8.57 (d, J=1.6 Hz, 1H), 8.14 (d, J=5.5 Hz, 1H), 7.90 (dd, J=1.8, 8.9 Hz, 1H), 7.80 (d, J=8.8 Hz, 1H), 7.49 (d, J=7.6 Hz, 2H), 7.43-7.34 (m, 3H), 3.73 (s, 3H). m/z (ESI) 528.9 (M+H)+.

EXAMPLE 365

N-(1,3,4-THIADIAZOL-2-YL)-1-(2,3',4'-TRIFLUORO-5-METHOXY-[1,1'-BIPHENYL]-4-YL)ISOQUINOLINE-6-SULFONAMIDE

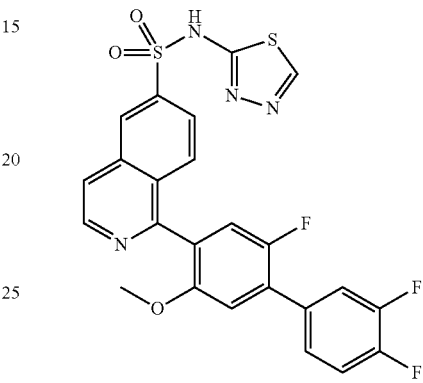

A vial was charged with 1-(4-chloro-5-fluoro-2-methoxyphenyl)-N-(1,3,4-thiadiazol-2-yl)isoquinoline-6-sulfonamide (INTERMEDIATE HHHHH; 103.3 mg, 0.229 mmol). (3,4-difluorophenyl)boronic acid (54.3 mg, 0.344 mmol), dicyclohexyl(2',6'-dimethoxy-[1,1'-biphenyl]-2-yl)phosphine (2.351 mg, 5.73 mmol), chloro(2-dicyclohexylphosphino-2',6'-dimethoxy-1,1'-biphenyl)[2-(2-aminoethylphenyl)]palladium(ii) dichloromethane (8.68 mg, 0.011 mmol). and potassium phosphate (146 mg, 0.687 mmol). The vial was flushed with Ar (g), then 1,4-dioxane (1041 μl) and water (104 μl) were added. The vial was sealed and heated in a Biotage Initiator microwave reactor for 1 h at 120° C. The mixture was extracted with EtOAc (4×). The combined organic extracts were concentrated. The residue was purified by chromatography on silica gel (25-g Interchim 15-micron column, 3.5% MeOH/DCM) to give ca. 80 mg of a yellow solid. The solid was taken up in MeOH, sonicated, and filtered. The collected solid was washed with MeOH (2×), dried under a stream of $N_2$ (g), then dried under vacuum to give N-(1,3,4-thiadiazol-2-yl)-1-(2,3',4'-trifluoro-5-methoxy-[1,1'-biphenyl]-4-yl)isoquinoline-6-sulfonamide (49.13 mg, 0.093 mmol, 40.6% yield) as a cream-colored solid. $^1$H NMR (400 MHz, DMSO-$d_6$) δ=8.80 (s, 1H), 8.71 (d, J=5.8 Hz, 1H), 8.57 (d, J=1.5 Hz, 1H), 8.14 (d, J=5.8 Hz, 1H), 7.94-7.77 (m, 3H), 7.70-7.54 (m, 2H), 7.44-7.27 (m, 2H), 3.72 (s, 3H). m/z (ESI) 529.2 (M+H)+.

EXAMPLE 366

1-(2,3'-DIFLUORO-5-METHOXY-[1,1'-BIPHENYL]-4-YL)-N-(1,3,4-THIADIAZOL-2-YL)ISOQUINOLINE-6-SULFONAMIDE

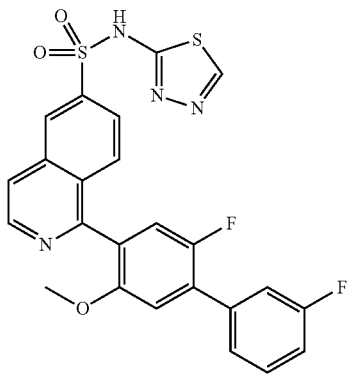 [SMILES: COc1cc(-c2cccc(F)c2)c(F)cc1-c1nccc2cc(S(=O)(=O)Nc3nncs3)ccc12]

A vial was charged with 1-(4-chloro-5-fluoro-2-methoxyphenyl)-N-(1,3,4-thiadiazol-2-yl)isoquinoline-6-sulfonamide (INTERMEDIATE HHHHH; 80.29 mg, 0.178 mmol), (3-fluorophenyl)boronic acid (49.8 mg, 0.356 mmol), dicyclohexyl(2',6'-dimethoxy-[1,1'-biphenyl]-2-yl)phosphine (1.828 mg, 4.45 µmol), chloro(2-dicyclohexylphosphino-2',6'-dimethoxy-1,1'-biphenyl)[2-(2-aminoethylphenyl)]palladium(ii) dichloromethane (6.74 mg, 8.90 µmol), and potassium phosphate (113 mg, 0.534 mmol). The vial was flushed with Ar (g), then 1,4-dioxane (809 µl) and water (81 µl) were added. The vial was sealed and heated in a Biotage Initiator microwave reactor for 1 h at 120° C. The mixture was extracted with EtOAc (3×). The aq. layer was acidified with 0.5N aq. HCl, then extracted with EtOAc (2×). The combined organic extracts were concentrated. The residue was purified by chromatography on silica gel (12-g Redi-Sep Gold column, 0-7.5% MeOH/DCM) to give 1-(2,3'-difluoro-5-methoxy-[1,1'-biphenyl]-4-yl)-N-(1,3,4-thiadiazol-2-yl)isoquinoline-6-sulfonamide (58.84 mg, 0.115 mmol, 64.7% yield) as a light-yellow solid. $^1$H NMR (400 MHz, DMSO-d$_6$) δ=14.50 (br. s., 1H), 8.79 (s, 1H), 8.71 (d, J=5.8 Hz, 1H), 8.57 (d, J=1.8 Hz, 1H), 8.14 (d, J=5.4 Hz, 1H), 7.94-7.88 (m, 1H), 7.85-7.78 (m, 1H), 7.64-7.53 (m, 3H), 7.42-7.27 (m, 3H), 3.72 (s, 3H). m/z (ESI) 511.2 (M+H)+.

EXAMPLE 367

1-(5-FLUORO-2-METHOXY-4-(PYRIDIN-3-YL)PHENYL)-N-(1,3,4-THIADIAZOL-2-YL)ISOQUINOLINE-6-SULFONAMIDE

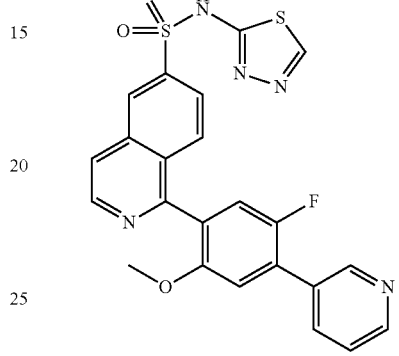

A vial was charged with 1-(4-chloro-5-fluoro-2-methoxyphenyl)-N-(1,3,4-thiadiazol-2-yl)isoquinoline-6-sulfonamide (INTERMEDIATE HHHHH; 74.29 mg, 0.165 mmol) pyridin-3-ylboronic acid (24.30 mg, 0.198 mmol), dicyclohexyl(2',6'-dimethoxy-[1,1'-biphenyl]-2-yl)phosphine (1.691 mg, 4.12 µmol), chloro(2-dicyclohexylphosphino-2',6'-dimethoxy-1,1'-biphenyl)[2-(2-aminoethylphenyl)]palladium(ii) dichloromethane (6.24 mg, 8.24 µmol) and potassium phosphate (105 mg, 0.494 mmol). The vial was flushed with Ar (g), then 1,4-dioxane (749 µl) and water (74.9 µl) were added. The vial was sealed and heated in a Biotage Initiator microwave reactor for 1 h at 120° C. The mixture was extracted with EtOAc (4×). The combined organic extracts were concentrated. The residue was purified by chromatography on silica gel (12-g Redi-Sep Gold column, 0-10% MeOH/DCM) to give 1-(5-fluoro-2-methoxy-4-(pyridin-3-yl)phenyl)-N-(1,3,4-thiadiazol-2-yl)isoquinoline-6-sulfonamide (49.13 mg, 0.100 mmol, 60.4% yield) as a light-yellow solid. $^1$H NMR (400 MHz, DMSO-d$_6$) δ=14.53 (br. s., 1H), 8.93 (s, 1H), 8.78 (s, 1H), 8.71 (d, J=5.7 Hz, 1H), 8.67 (dd, J=1.3, 4.7 Hz, 1H), 8.57 (d, J=1.7 Hz, 1H), 8.14 (d, J=5.8 Hz, 2H), 7.96-7.87 (m, 1H), 7.86-7.78 (m, 1H), 7.63-7.54 (m, 1H), 7.45-7.36 (m, 2H), 3.73 (s, 3H). m/z (ESI) 494.1 (M+H)+.

EXAMPLE 368

1-(4-CHLORO-2-METHOXYPHENYL)-N-(1,2,4-THIADIAZOL-5-YL)ISOQUINOLINE-6-SULFONAMIDE

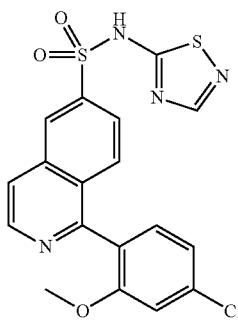

A round-bottom flask was charged with N-(2,4-dimethoxybenzyl)-1,2,4-thiadiazol-5-amine (33.3 mg, 0.172 mmol) and THF (718 µl) to give a clear solution. The flask was cooled in a dry ice-acetone bath for 5 min, then lithium bis(trimethylsilyl)amide (1M in THF) (172 µl, 0.172 mmol) was added drop wise. The flask was removed from the cooling bath for 3 min, then recooled in the bath. A solution of perfluorophenyl 1-(4-chloro-2-methoxyphenyl)isoquinoline-6-sulfonate (INTERMEDIATE NNN, 74.12 mg, 0.144 mmol) in THF (0.6 mL with a 0.4 mL-flask wash) was added drop wise. After another minute, the flask was transferred to an ice-water bath. After 10 min of stirring, the mixture was concentrated, and the residue was taken up in DCM (1 mL) and TFA (0.5 mL). The mixture was stirred for 30 min, then diluted with MeOH and concentrated. The residue was purified by chromatography on silica gel (25-g Interchim column, 25-75% EtOAc/Heptane) to give white solid. The solid was taken up in EtOAc, filtered, washed with EtOAc (3×), dried under a stream of N$_2$ (g), then dried under vacuum to give 1-(4-chloro-2-methoxyphenyl)-N-(1,2,4-thiadiazol-5-yl)isoquinoline-6-sulfonamide (25.5 mg, 0.059 mmol, 41.0% yield) as a white solid. $^1$H NMR (400 MHz, DMSO-d$_6$) δ=8.69 (d, J=5.7 Hz, 1H), 8.57 (d, J=1.9 Hz, 1H), 8.48 (s, 1H), 8.13 (d, J=5.6 Hz, 1H), 7.89-7.89 (m, 0H), 7.91-7.81 (m, 1H), 7.75 (d, J=8.9 Hz, 1H), 7.37 (d, J=8.1 Hz, 1H), 7.32 (d, J=1.9 Hz, 1H), 7.20 (dd, J=1.9, 8.1 Hz, 1H), 3.68 (s, 3H). m/z (ESI) 433.0 (M+H)+.

INTERMEDIATE IIIII: 1-(4-CHLORO-2-METHOXYPHENYL)-N-(2,4-DIMETHOXYBENZYL)-N-(1,2,4-THIADIAZOL-5-YL)ISOQUINOLINE-6-SULFONAMIDE

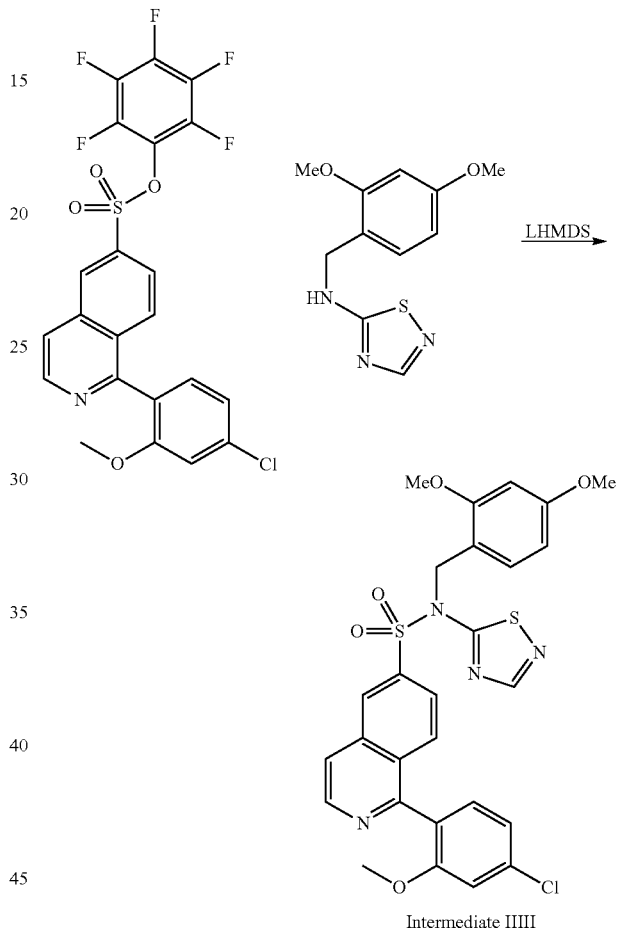

Intermediate IIIII

A round-bottom flask was charged with N-(2,4-dimethoxybenzyl)-1,2,4-thiadiazol-5-amine (117 mg, 0.466 mmol) and THF (1944 µl) to give a clear solution. The flask was cooled in a dry ice-acetone bath for 5 min, then lithium bis(trimethylsilyl)amide (1M in THF) (466 µl, 0.466 mmol) was added drop wise. The flask was removed from the cooling bath for 3 min, then recooled in the bath. A solution of perfluorophenyl 1-(4-chloro-2-methoxyphenyl)isoquinoline-6-sulfonate (INTERMEDIATE NNN, 200.53 mg, 0.389 mmol) in THF (1 mL with a 0.5 mL-flask wash) was added drop wise. After another minute, the flask was transferred to an ice-water bath. After 10 min, the mixture was diluted with saturated aq ammonium chloride and water, then extracted with EtOAc (2×). The combined organic extracts were dried over sodium sulfate, filtered, and concentrated. The residue was purified by chromatography on silica gel (25-g Interchim 25-micron column, 25-75% EtOAc/Heptane) to give 1-(4-chloro-2-methoxyphenyl)-N-(2,4-dimethoxybenzyl)-N-(1,2,4-thiadiazol-5-yl)isoquinoline-6-sulfonamide (217 mg, 0.372 mmol, 96% yield) as a white foam. m/z (ESI) 583.0 (M+H)+.

EXAMPLE 369

1-(3'-FLUORO-3-METHOXY-[1,1'-BIPHENYL]-4-YL)-N-(1,2,4-THIADIAZOL-5-YL)ISOQUINO-LINE-6-SULFONAMIDE

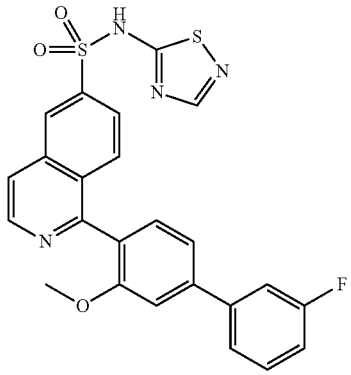 [SMILES: COc1cc(-c2cccc(F)c2)ccc1-c1nccc2cc(S(=O)(=O)Nc3ncns3)ccc12]

A flask was charged with 1-(4-chloro-2-methoxyphenyl)-N-(2,4-dimethoxybenzyl)-N-(1,2,4-thiadiazol-5-yl)isoquinoline-6-sulfonamide (INTERMEDIATE IIIII; 84.8 mg, 0.145 mmol), DCM (1 mL), and TFA (0.5 mL). The resulting solution was stirred for 30 min, then was diluted with MeOH and concentrated. The residue was concentrated from MeOH/DCM, then dried under vacuum in a microwave vial. (3-fluorophenyl)boronic acid (40.7 mg, 0.291 mmol), chloro(2-dicyclohexylphosphino-2',6'-dimethoxy-1,1'-biphenyl)[2-(2-aminoethylphenyl)]palladium(ii) dichloromethane (11.02 mg, 0.015 mmol), dicyclohexyl(2',6'-dimethoxy-[1,1'-biphenyl]-2-yl)phosphine (2.99 mg, 7.27 µmol), and potassium phosphate (154 mg, 0.727 mmol) were added. The vial was flushed with Ar (g), then 1,4-dioxane (661 µl) and water (66.1 µl) were added. The vial was sealed and heated in a Biotage Initiator microwave reactor for 3 h at 100° C. The mixture was extracted with EtOAc (3×). The combined organic extracts were concentrated. The residue was purified by chromatography on silica gel (25-g Interchim 15-micron column, 0-10% MeOH/DCM, then 12-g Redi-Sep Gold column, 6% MeOH/DCM, then 25-g Interchim 15-micron column, 3.5% MeOH/DCM) to give 1-(3'-fluoro-3-methoxy-[1,1'-biphenyl]-4-yl)-N-(1,2,4-thiadiazol-5-yl)isoquinoline-6-sulfonamide (23.3 mg, 0.047 mmol, 32.5% yield) as a light-orange solid. $^1$H NMR (400 MHz, DMSO-$d_6$) δ=8.70 (d, J=5.7 Hz, 1H), 8.56 (d, J=1.6 Hz, 1H), 8.42 (s, 1H), 8.12 (d, J=5.7 Hz, 1H), 7.94-7.87 (m, 1H), 7.80 (d, J=8.8 Hz, 1H), 7.74-7.65 (m, 2H), 7.56 (dt, J=6.4, 8.1 Hz, 1H), 7.52-7.41 (m, 3H), 7.26 (dt, J=2.5, 8.5 Hz, 1H), 3.77 (s, 3H). m/z (ESI) 493.2 (M+H)+.

INTERMEDIATE JJJJJ: (3',5'-DIFLUORO-3-METHOXY-[1,1'-BIPHENYL]-4-YL)BORONIC ACID

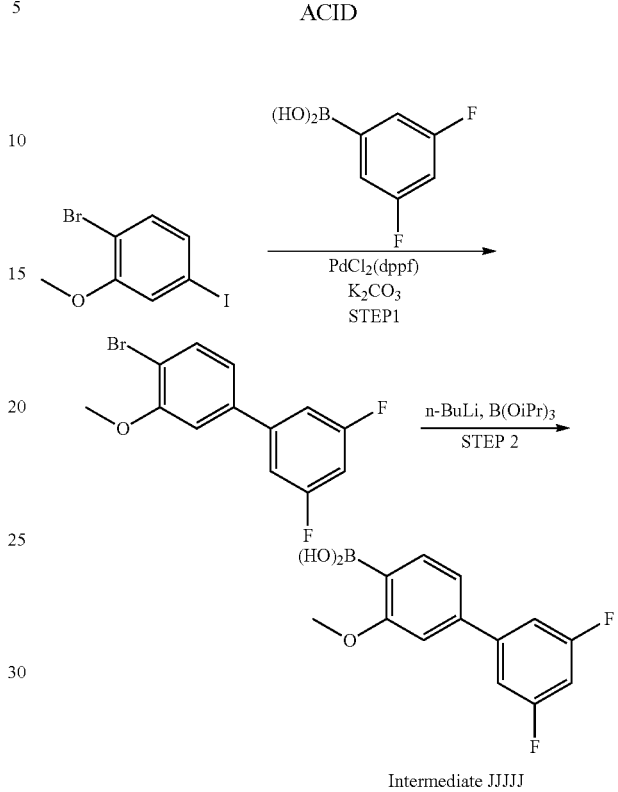

Intermediate JJJJJ

STEP 1: 4-BROMO-3',5'-DIFLUORO-3-METH-OXY-1,1'-BIPHENYL

A round-bottom flask was charged with 1-bromo-4-iodo-2-methoxybenzene (Combi-Blocks, Inc., San Diego, Calif., 6.25 g, 19.97 mmol), (3,5-difluorophenyl)boronic acid (3.47 g, 21.97 mmol), potassium carbonate (8.28 g, 59.9 mmol), and PdCl$_2$(dppf)-CH$_2$Cl$_2$ (0.816 g, 0.999 mmol). The flask was flushed with Ar (g), then 1,4-dioxane (30.0 ml) and water (9.99 ml) were added in sequence. The mixture was stirred at room temperature for 4 h. The reaction mixture was diluted with water and extracted with EtOAc (3×). The combined organic extracts were dried over sodium sulfate, filtered, and concentrated. The residue was taken up in DCM and loaded onto a pre-equilibrated 340-g SNAP Ultra column. The column was eluted with 0-10% EtOAc/Heptane containing 5% DCM. Fractions containing the desired product were combined and concentrated. The residue was taken up in heptane and filtered. The collected solid was washed with heptane (3×), then dried under a stream of N$_2$ (g). The process was repeated with the filtrate to give a second crop of material. The two crops were dried under vacuum to give 4-bromo-3',5'-difluoro-3-methoxy-1,1'-biphenyl as a white solid. $^1$H NMR (400 MHz, DMSO-$d_6$) δ=7.66 (d, J=8.2 Hz, 1H), 7.58-7.49 (m, 2H), 7.40 (d, J=1.9 Hz, 1H), 7.33-7.20 (m, 2H), 3.96 (s, 3H). m/z (ESI) 301.1.

STEP 2: (3',5'-DIFLUORO-3-METHOXY-[1,1'-BIPHENYL]-4-YL)BORONIC ACID

A round-bottom flask was charged with 4-bromo-3',5'-difluoro-3-methoxy-1,1'-biphenyl (5.147 g, 17.21 mmol), triisopropyl borate (4.79 ml, 20.65 mmol), and THF (57.4 ml). The flask was cooled in a dry ice-acetone bath for 10 min, then n-butyllithium (2.5 M in hexane) (8.26 ml, 20.65 mmol) was added drop wise over 1 min. The mixture was stirred for 20 min, then the flask was lowered into an ice-water bath. After 10 min, a 2N aq. NaOH solution was added, the cooling bath was removed, and the mixture was stirred vigorously for 20 min. The mixture was diluted with water and ether. The layers were separated, and the ethereal layer was extracted with water. The combined aq. layers were then acidified with 6N aq. HCl (50 mL). The mixture was filtered, and the collected solid was dried under a stream of $N_2$ (g), for 2 h to give ca. 3.14 g of a white solid. The filtrate was extracted with DCM (3×), and the combined organic extracts were dried over sodium sulfate, filtered, and concentrated to give an additional 260 mg of a white solid. The solids were combined to give (3',5'-difluoro-3-methoxy-[1,1'-biphenyl]-4-yl)boronic acid (3.40 g, 12.88 mmol, 74.8% yield) as a white solid. m/z (ESI) 265.1 $(M+H)^+$.

INTERMEDIATE KKKKK: PERFLUOROPHE-NYL 1-(3',5'-DIFLUORO-3-METHOXY-[1,1'-BI-PHENYL]-4-YL)ISOQUINOLINE-6-SULFONATE

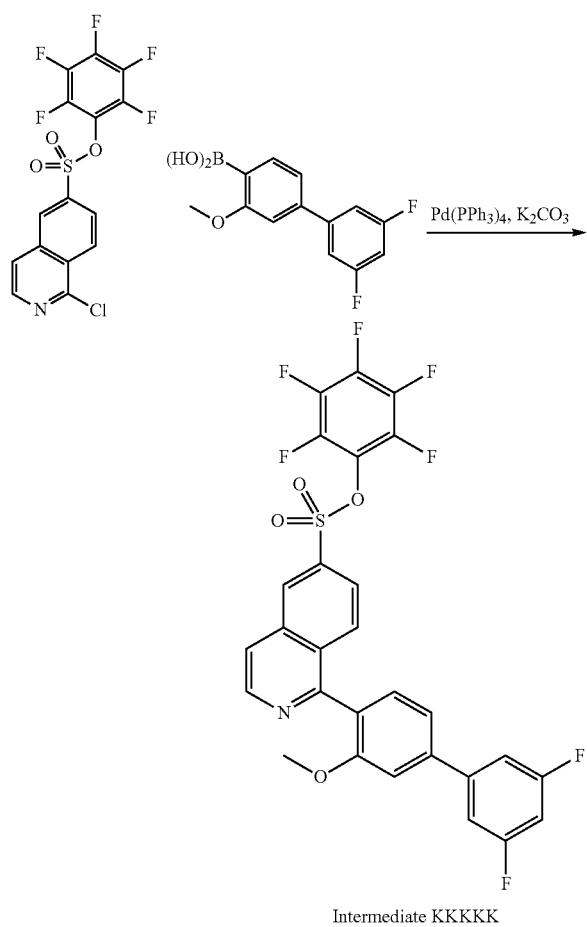

Intermediate KKKKK

A round-bottom flask was charged with perfluorophenyl 1-chloroisoquinoline-6-sulfonate (see EXAMPLE 73, STEP 1, 4.40 g, 10.74 mmol), (3',5'-difluoro-3-methoxy-[1,1'-biphenyl]-4-yl)boronic acid (INTERMEDIATE JJJJJ; 3.40 g, 12.89 mmol), potassium carbonate (4.45 g, 32.2 mmol), and $Pd(Ph_3P)_4$ (1.241 g, 1.074 mmol). The flask was flushed with Ar (g), then 1,4-dioxane (40.3 ml) and water (13.42 ml) were added in sequence. The flask was fitted with a reflux condenser and lowered into a 50° C. heating bath for 1 h. The mixture was diluted with water and extracted with EtOAc (2×). The combined organic extracts were dried over sodium sulfate, filtered, and concentrated. TLC showed two major spots. The residue was purified by chromatography on silica gel (100-g SNAP Ultra column, 0-50% EtOAc/Heptane). Fractions containing the desired product were combined and concentrated to give perfluorophenyl 1-(3',5'-difluoro-3-methoxy-[1,1'-biphenyl]-4-yl)isoquinoline-6-sulfonate (4.179 g, 7.04 mmol, 65.6% yield) as an off-white solid. $^1$H NMR (400 MHz, DMSO-$d_6$) δ=8.93 (d, J=1.6 Hz, 1H), 8.84 (d, J=5.6 Hz, 1H), 8.20 (d, J=5.7 Hz, 1H), 8.07 (dd, J=1.9, 9.0 Hz, 1H), 7.95 (d, J=8.9 Hz, 1H), 7.70-7.62 (m, 2H), 7.59-7.50 (m, 3H), 7.36-7.27 (m, 1H), 3.79 (s, 3H). m/z (ESI) 594.0 $(M+H)^+$.

EXAMPLE 370

1-(3',5'-DIFLUORO-3-METHOXY-[1,1'-BIPHE-NYL]-4-YL)-N-(2-METHYLPYRIMIDIN-4-YL)ISOQUINOLINE-6-SULFONAMIDE

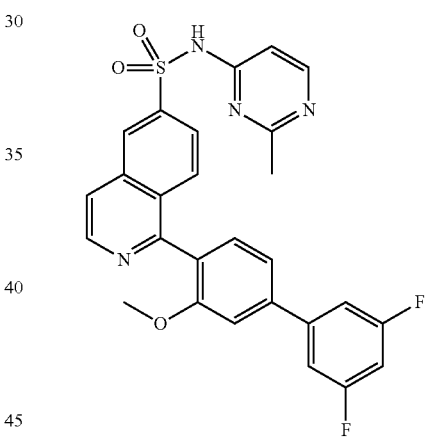

A vial was charged with perfluorophenyl 1-(3',5'-difluoro-3-methoxy-[1,1'-biphenyl]-4-yl)isoquinoline-6-sulfonate (INTERMEDIATE KKKKK; 64.75 mg, 0.109 mmol), 2-methylpyrimidin-4-amine (12.50 mg, 0.115 mmol), and THF (546 µl) (not all the amine dissolved). The vial was cooled in an ice-water bath for 10 min, then lithium bis(trimethylsilyl)amide (1M in THF) (229 µl, 0.229 mmol) was added. After 40 min, the mixture was loaded directly onto a silica gel loading column. The column was eluted onto a pre-equilibrated 12-g Redi-Sep Gold column with 0-5% MeOH/DCM to give 1-(3',5'-difluoro-3-methoxy-[1,1'-biphenyl]-4-yl)-N-(2-methylpyrimidin-4-yl)isoquinoline-6-sulfonamide (28.4 mg, 0.055 mmol, 50.2% yield) as a light-yellow solid. $^1$H NMR (400 MHz, DMSO-$d_6$) δ=13.32 (br. s., 1H), 8.68 (d, J=5.7 Hz, 1H), 8.62 (s, 1H), 8.17-8.03 (m, 2H), 7.95 (dd, J=1.7, 8.9 Hz, 1H), 7.74 (d, J=8.8 Hz, 1H), 7.68-7.59 (m, 2H), 7.56-7.48 (m, 2H), 7.46-7.39 (m, 1H), 7.29 (tt, J=2.2, 9.3 Hz, 1H), 6.90 (br. s., 1H), 3.77 (s, 3H), 2.35 (s, 3H). m/z (ESI) 519.0 (M+H)+.

EXAMPLE 371

1-(3',5'-DIFLUORO-3-METHOXY-[1,1'-BIPHE-NYL]-4-YL)-N-(6-METHYLPYRIMIDIN-4-YL)ISOQUINOLINE-6-SULFONAMIDE

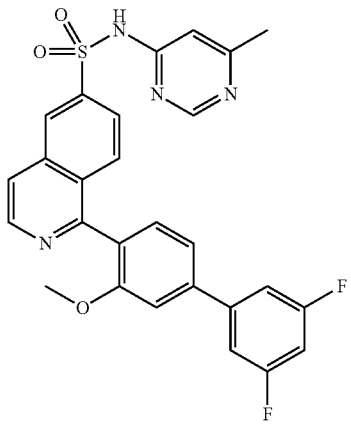 [SMILES: COc1cc(-c2cc(F)cc(F)c2)ccc1-c1nccc2cc(S(=O)(=O)Nc3cc(C)ncn3)ccc12]

A vial was charged with perfluorophenyl 1-(3',5'-difluoro-3-methoxy-[1,1'-biphenyl]-4-yl)isoquinoline-6-sulfonate (INTERMEDIATE KKKKK; 63.5 mg, 0.107 mmol), 6-methylpyrimidin-4-amine (12.26 mg, 0.112 mmol), and THF (535 μl). The vial was cooled in an ice-water bath for 10 min, then lithium bis(trimethylsilyl)amide (1M in THF) (225 μl, 0.225 mmol) was added. After 20 min of stirring, the mixture was loaded directly onto a silica gel loading column. The column was eluted onto a pre-equilibrated 12-g Redi-Sep Gold column with 0-10% MeOH/DCM to give an orange solid. This solid was resubjected to chromatography on silica gel (12-g Redi-Sep Gold column, 4.5% MeOH/DCM) to give 1-(3',5'-difluoro-3-methoxy-[1,1'-biphenyl]-4-yl)-N-(6-methylpyrimidin-4-yl)isoquinoline-6-sulfonamide (26.22 mg, 0.051 mmol, 47.3% yield) as a light-pink solid. $^1$H NMR (400 MHz, DMSO-d$_6$) δ=13.48-12.42 (m, 1H), 8.75-8.62 (m, 2H), 8.47 (s, 1H), 8.11 (d, J=5.6 Hz, 1H), 7.95 (d, J=9.1 Hz, 1H), 7.75 (d, J=8.7 Hz, 1H), 7.63 (d, J=6.9 Hz, 2H), 7.57-7.48 (m, 2H), 7.46-7.40 (m, 1H), 7.34-7.23 (m, 1H), 7.06-6.86 (m, J=17.2 Hz, 1H), 3.77 (s, 3H), 2.31 (s, 3H). m/z (ESI) 519.0 (M+H)+.

EXAMPLE 372

1-(3',5'-DIFLUORO-3-METHOXY-[1,1'-BIPHE-NYL]-4-YL)-N-(1,3,4-OXADIAZOL-2-YL)ISOQUINOLINE-6-SULFONAMIDE

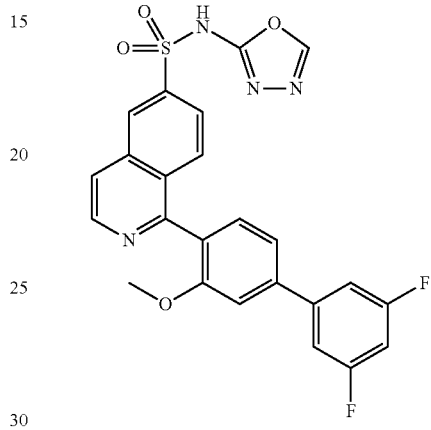

A vial was charged with perfluorophenyl 1-(3',5'-difluoro-3-methoxy-[1,1'-biphenyl]-4-yl)isoquinoline-6-sulfonate (INTERMEDIATE KKKKK; 50.05 mg, 0.084 mmol), 1,3,4-oxadiazol-2-amine (7.89 mg, 0.093 mmol), cesium carbonate (82 mg, 0.253 mmol), and acetonitrile (0.42 mL). After 3 h or stirring, the mixture was diluted with 0.5 N aq. HCl, then extracted with EtOAc (3×), 20% MeOH/EtOAc (2×), and DCM (1×). The combined organic extracts were concentrated. The residue was purified by chromatography on silica gel (12-g Redi-Sep Gold column, 0-7% MeOH/DCM) to give 1-(3',5'-difluoro-3-methoxy-[1,1'-biphenyl]-4-yl)-N-(1,3,4-oxadiazol-2-yl)isoquinoline-6-sulfonamide (19.1 mg, 0.039 mmol, 45.8% yield) as a white foam. $^1$H NMR (400 MHz, DMSO-d$_6$) δ=12.24 (br. s., 1H), 8.82 (d, J=2.0 Hz, 1H), 8.78 (d, J=5.7 Hz, 1H), 8.23 (d, J=5.3 Hz, 1H), 8.17 (s, 1H), 8.00-7.94 (m, 1H), 7.92-7.84 (m, 1H), 7.68-7.60 (m, 2H), 7.58-7.49 (m, 2H), 7.47-7.41 (m, 1H), 7.30 (tt, J=2.3, 9.3 Hz, 1H), 3.78 (s, 3H). m/z (ESI) 495.1 (M+H)+.

EXAMPLE 373

1-(4-CHLORO-2-(CYANOMETHOXY)PHENYL)-N-(THIAZOL-2-YL)ISOQUINOLINE-6-SULFONAMIDE 2,2,2-TRIFLUOROACETATE

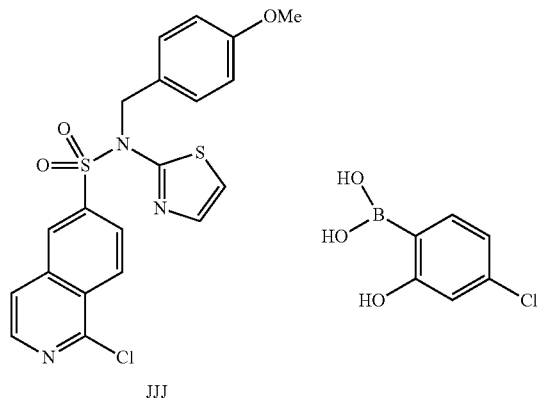

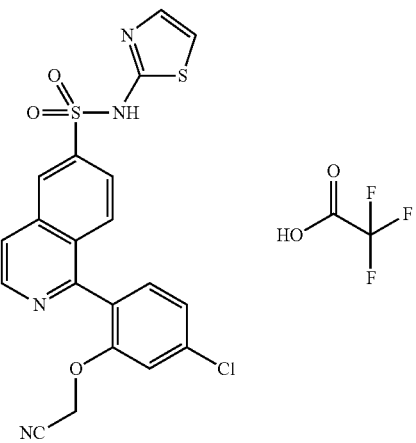

STEP 1: 1-(4-CHLORO-2-HYDROXYPHENYL)-N-(4-METHOXYBENZYL)-N-(THIAZOL-2-YL) ISOQUINOLINE-6-SULFONAMIDE

To a microwave vial charged with 1-chloro-N-(4-methoxybenzyl)-N-(thiazol-2-yl)isoquinoline-6-sulfonamide (Intermediate JJJ) (80 mg, 0.179 mmol), (4-chloro-2-hydroxyphenyl)boronic acid (30.9 mg, 0.179 mmol), potassium carbonate (124 mg, 0.897 mmol) and Pd(Ph$_3$P)$_4$ (20.73 mg, 0.018 mmol) was added dioxane (897 μl) and Water (299 μl) and irradiated at 100° C. for 30 min affording conversion to desired product as the primary species. The organic layer was decanted, the aqueous rinsed with EtOAc and the combined organics dried under reduced pressure. m/z (ESI) 537.9 (M+H)$^+$.

STEP 2: 1-(4-CHLORO-2-(CYANOMETHOXY) PHENYL)-N-(4-METHOXYBENZYL)-N-(THIAZOL-2-YL)ISOQUINOLINE-6-SULFONAMIDE

To the crude material from Step 1 was added DMF (1.5 ml) followed by cesium carbonate (175 mg, 0.538 mmol) and bromoacetonitrile (24.99 μl, 0.359 mmol). The resulting mixture was stirred at 60° C. overnight affording clean conversion to desired product according to LC-MS. The mixture was filtered through Celite with the aid of DCM and the filtrate dried under reduced pressure. m/z (ESI) 577.1 (M+H)$^+$.

STEP 3: 1-(4-CHLORO-2-(CYANOMETHOXY) PHENYL)-N-(THIAZOL-2-YL)ISOQUINOLINE-6-SULFONAMIDE 2,2,2-TRIFLUOROACETATE

To the light brown crude oil from Step 2 was added DCM (3 ml) and TFA (1 ml) and the mixture stirred at room temperature for 30 min affording PMB deprotection. The mixture was dried under reduced pressure and purified using basic, then acidic conditions, respectively affording product (16 mg, 16%). $^1$H NMR (400 MHz, DMSO-d$_6$) δ=12.91 (br. s., 1H), 8.69 (d, J=5.8 Hz, 1H), 8.56 (d, J=1.9 Hz, 1H), 8.14 (d, J=5.2 Hz, 1H), 7.86 (dd, J=1.9, 8.9 Hz, 1H), 7.71 (d, J=8.9 Hz, 1H), 7.54 (d, J=1.9 Hz, 1H), 7.45 (d, J=8.1 Hz, 1H), 7.34 (dd, J=1.9, 8.1 Hz, 1H), 7.28 (d, J=4.6 Hz, 1H), 6.87 (d, J=4.6 Hz, 1H), 5.16 (d, J=1.0 Hz, 2H). m/z (ESI) 457.0 (M+H)$^+$

EXAMPLE 374

1-(2-(CYANOMETHOXY)-4-(TRIFLUOROMETHYL)PHENYL)-N-(THIAZOL-2-YL)ISOQUINOLINE-6-SULFONAMIDE

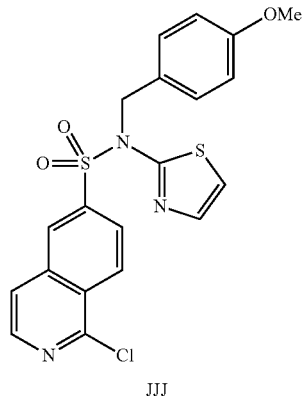 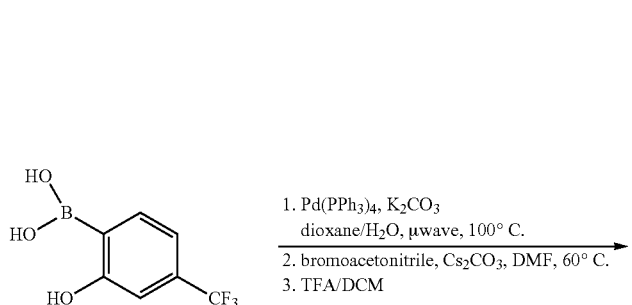 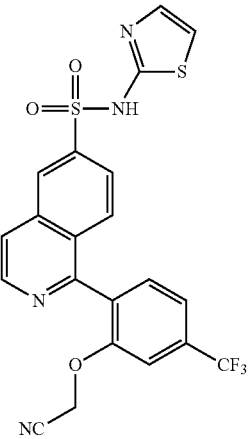

STEP 1: 1-(2-HYDROXY-4-(TRIFLUOROMETHYL)PHENYL)-N-(4-METHOXYBENZYL)-N-(THIAZOL-2-YL)ISOQUINOLINE-6-SULFONAMIDE

To a microwave vial charged with 1-chloro-N-(4-methoxybenzyl)-N-(thiazol-2-yl)isoquinoline-6-sulfonamide (Intermediate JJJ) (87 mg, 0.194 mmol), (2-hydroxy-4-(trifluoromethyl)phenyl)boronic acid (40 mg, 0.194 mmol), potassium carbonate (134 mg, 0.971 mmol) and Pd(Ph$_3$P)$_4$ (22.45 mg, 0.019 mmol) was added Dioxane (971 µl) and Water (324 µl) and irradiated at 100° C. for 30 min affording conversion to desired product as the primary species. The organic layer was decanted, the aqueous rinsed with EtOAc and the combined organics dried under reduced pressure. The crude material was used without further purification. m/z (ESI) 572.3 (M+H)$^+$

STEP 2: 1-(2-(CYANOMETHOXY)-4-(TRIFLUOROMETHYL)PHENYL)-N-(4-METHOXYBENZYL)-N-(THIAZOL-2-YL)ISOQUINOLINE-6-SULFONAMIDE

To a vial charged with 1-(2-hydroxy-4-(trifluoromethyl)phenyl)-N-(4-methoxybenzyl)-N-(thiazol-2-yl)isoquinoline-6-sulfonamide (111 mg, 0.194 mmol) was added DMF (777 µl) and Cs$_2$CO$_3$ (190 mg, 0.583 mmol) and bromoacetonitrile (46.6 mg, 0.39 mmol) respectively. The mixture was heated to 60° C. overnight affording conversion to desired product fairly cleanly. The mixture was dried under reduced pressure and purified with a 25 g Interchim column (25 um silica) ramping EtOAc in heptane (0-100%, 10% DCM throughout) affording product as a light brown solid. m/z (ESI) 611.3 (M+H)$^+$

STEP 3: 1-(2-(CYANOMETHOXY)-4-(TRIFLUOROMETHYL)PHENYL)-N-(THIAZOL-2-YL)ISOQUINOLINE-6-SULFONAMIDE

To a flask containing the solid was added DCM (6 ml) and TFA (2 ml) and the resulting solution stirred for an hour affording complete PMB cleavage. The solution was dried under reduced pressure and purified with a HP Silicycle column ramping DCM:MeOH (90:10) in DCM (0-50%) affording product as a film which was lyophilized from MeOH/H$_2$O providing product 1-(2-(cyanomethoxy)-4-(trifluoromethyl)phenyl)-N-(thiazol-2-yl)isoquinoline-6-sulfonamide (78 mg, 0.159 mmol, 82% yield) as an off-white powder. $^1$H NMR (400 MHz, DMSO-d$_6$) δ=12.91 (br. s., 1H), 8.72 (d, J=5.7 Hz, 1H), 8.58 (d, J=1.8 Hz, 1H), 8.22-8.14 (m, 1H), 7.87 (dd, J=1.8, 8.9 Hz, 1H), 7.75 (s, 1H), 7.72-7.67 (m, 1H), 7.67-7.62 (m, 2H), 7.28 (d, J=4.6 Hz, 1H), 6.87 (d, J=4.6 Hz, 1H), 5.35-5.14 (m, 2H). m/z (ESI) 491.1 (M+H)$^+$.

EXAMPLE 375

1-(2-(CYANOMETHOXY)PHENYL)-N-(THIAZOL-2-YL)ISOQUINOLINE-6-SULFONAMIDE 2,2,2-TRIFLUOROACETATE

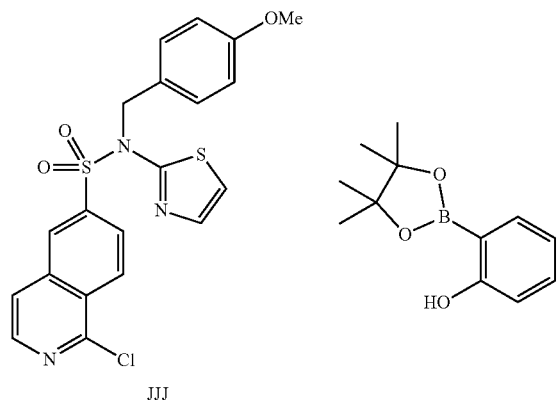

JJJ

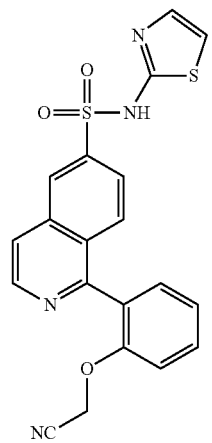

1. Pd(PPh₃)₄, K₂CO₃
   dioxane/H₂O, μwave, 100° C.
2. bromoacetonitrile, Cs₂CO₃, DMF, 60° C.
3. TFA/DCM

STEP 1: 1-(2-HYDROXYPHENYL)-N-(4-METHOXYBENZYL)-N-(THIAZOL-2-YL)ISOQUINOLINE-6-SULFONAMIDE

To a microwave vial charged with 1-chloro-N-(4-methoxybenzyl)-N-(thiazol-2-yl)isoquinoline-6-sulfonamide (Intermediate JJJ) (100 mg, 0.224 mmol), 2-(4,4,5,5-tetramethyl-1,3,2-dioxaborolan-2-yl)phenol (49 mg, 0.224 mmol), potassium carbonate (155 mg, 1.121 mmol) and Pd(Ph₃P)₄ (26 mg, 0.022 mmol) was added Dioxane (1120 μl) and Water (374 μl) and irradiated at 100° C. for 30 min affording conversion to desired product as the primary species. The organic layer was decanted, the aqueous rinsed with EtOAc and the combined organics dried under reduced pressure. The crude material will be used as is for subsequent reactions. m/z (ESI) 504.0 (M+H)⁺

STEP 2: 1-(2-(CYANOMETHOXY)PHENYL)-N-(4-METHOXYBENZYL)-N-(THIAZOL-2-YL)ISOQUINOLINE-6-SULFONAMIDE

To a vial charged with 1-(2-hydroxyphenyl)-N-(4-methoxybenzyl)-N-(thiazol-2-yl)isoquinoline-6-sulfonamide (113 mg, 0.224 mmol) was added DMF (898 μl) and Cs₂CO₃ (219 mg, 0.673 mmol) and bromoacetonitrile (53.8 mg, 0.45 mmol) respectively. The mixture was heated to 60° C. overnight affording conversion to desired product fairly cleanly. m/z (ESI) 543.2 (M+H)⁺. The mixture was dried under reduced pressure and purified with a 25 g Interchim column (25 μm silica) ramping EtOAc in heptane (0-100%, 10% DCM throughout) affording product as a light brown solid. m/z (ESI) 543.2 (M+H)⁺

STEP 3: 1-(2-(CYANOMETHOXY)PHENYL)-N-(THIAZOL-2-YL)ISOQUINOLINE-6-SULFONAMIDE 2,2,2-TRIFLUOROACETATE

To 1-(2-(cyanomethoxy)phenyl)-n-(4-methoxybenzyl)-n-(thiazol-2-yl)isoquinoline-6-sulfonamide, TFA (2 ml) was added and the resulting solution stirred for an hour, affording complete PMB cleavage. The solution was dried under reduced pressure and purified with a 25 g Interchim column (15 μm spherical) ramping DCM:MeOH (90:10) in DCM (0-50%) affording product as a film which was lyophilized from MeOH/H₂O providing a yellow powder (72 mg, 60%). ¹H NMR (400 MHz, DMSO-d₆) δ ppm 5.00-5.16 (m, 2H) 6.88 (d, J=4.60 Hz, 1H) 7.21-7.34 (m, 2H) 7.35-7.49 (m, 2H) 7.59-7.68 (m, 1H) 7.73 (d, J=8.90 Hz, 1H) 7.89 (dd, J=8.85, 1.81 Hz, 1H) 8.18 (d, J=5.87 Hz, 1H) 8.58 (d, J=1.47 Hz, 1H) 8.71 (d, J=5.77 Hz, 1H) 12.92 (br. s., 1H). m/z (ESI) 423.0 (M+H)⁺.

EXAMPLE 376

1-(4-CHLORO-2-(CYANOMETHOXY)PHENYL)-N-(PYRIMIDIN-4-YL)ISOQUINOLINE-6-SULFONAMIDE 2,2,2-TRIFLUOROACETATE

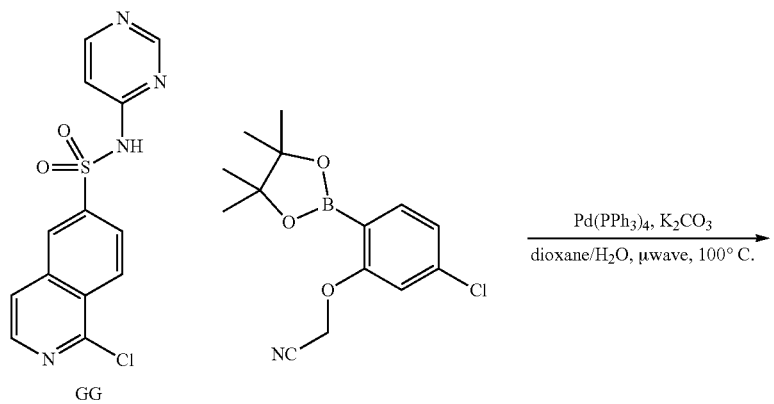

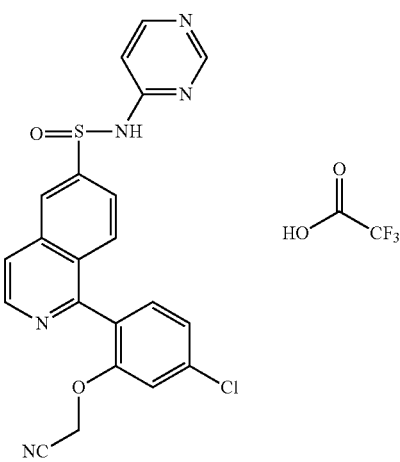

To a microwave vial charged with 2-(5-chloro-2-(4,4,5,5-tetramethyl-1,3,2-dioxaborolan-2-yl)phenoxy)acetonitrile (137 mg, 0.468 mmol) was added Dioxane (935 µl), potassium carbonate (215 mg, 1.559 mmol), 1-chloro-N-(pyrimidin-4-yl)isoquinoline-6-sulfonamide (Intermediate GG) (100 mg, 0.312 mmol), Pd(Ph₃P)₄ (36.0 mg, 0.031 mmol) and Water (312 µl). The mixture was irradiated at 100° C. for 30 mins affording a mixture with product as one of the main species with complete consumption of starting material. The organic layer was decanted and dried under reduced pressure. The crude residue was dissolved in DMSO (1.5 ml) and purified with RP-HPLC (Gilson), 5-50% ACN in H2O with 0.1% TFA throughout affording product as a film upon drying of the product containing eluents. The film was lyophilized from MeOH/H₂O providing product 1-(4-chloro-2-(cyanomethoxy)phenyl)-N-(pyrimidin-4-yl)isoquinoline-6-sulfonamide 2,2,2-trifluoroacetate (26 mg, 15%) as a white solid. ¹H NMR (400 MHz, DMSO-d₆) δ=8.77-8.65 (m, 2H), 8.57 (s, 1H), 8.24 (d, J=6.4 Hz, 1H), 8.18 (d, J=5.7 Hz, 1H), 7.96 (dd, J=1.9, 8.9 Hz, 1H), 7.74 (d, J=9.0 Hz, 1H), 7.54 (d, J=1.9 Hz, 1H), 7.47 (d, J=8.1 Hz, 1H), 7.35 (dd, J=1.8, 8.1 Hz, 1H), 7.02 (d, J=6.7 Hz, 1H), 5.16 (d, J=1.4 Hz, 2H). m/z (ESI) 452.2 (M+H)⁺

EXAMPLE 377

1-(2-FLUORO-5-METHYLPYRIDIN-3-YL)-N-(THIAZOL-2-YL)ISOQUINOLINE-6-SULFONAMIDE

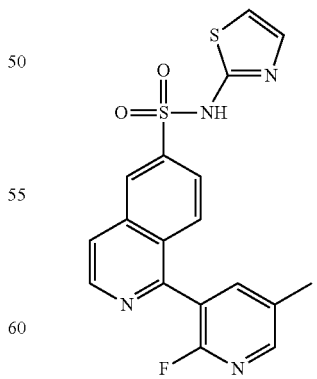

To a microwave vial charged with 1-chloro-N-(4-methoxybenzyl)-N-(thiazol-2-yl)isoquinoline-6-sulfonamide (Intermediate JJJ; 500 mg, 1.121 mmol), 2-fluoro-5-picoline-3-boronic acid (136 µl, 1.121 mmol), potassium carbonate (775 mg, 5.61 mmol) and Pd(Ph₃P)₄ (130 mg, 0.112 mmol) was added Dioxane (5606 μl) and Water (1869 μl) and irradiated at 100° C. for 30 mins affording ~75% conversion to desired product as the primary species. Additional boronic acid (80 mg) and Pd(PPh₃)₄ (65 mg) was added and the mixture irradiated an additional 30 mins at 110° C. affording complete conversion to desired product. The organics were decanted, rinsed with EtOAc and the combined organics were dried under reduced pressure. The crude material was dissolved in DCM (3 ml) and TFA (1 ml) was added and the mixture stirred at room temperature for 2 hrs affording complete PMB cleavage. The crude material was purified with a 25 g Interchim column (25 μm spherical) ramping EtOAc in heptane (0-100%, then isocratic at 100% EtOAc, where product elutes, 10% DCM throughout) affording 1-(2-fluoro-5-methylpyridin-3-yl)-N-(thiazol-2-yl)isoquinoline-6-sulfonamide as a light yellow solid (377 mg, 0.941 mmol, 84% yield). ¹H NMR (400 MHz, DMSO-d₆) δ=12.89 (br. s., 1H), 8.74 (d, J=5.7 Hz, 1H), 8.60 (d, J=1.7 Hz, 1H), 8.26 (s, 1H), 8.21 (d, J=5.6 Hz, 1H), 8.02 (dd, J=2.3, 9.3 Hz, 1H), 7.97-7.91 (m, 1H), 7.91-7.85 (m, 1H), 7.28 (d, J=4.6 Hz, 1H), 6.87 (d, J=4.6 Hz, 1H), 2.40 (s, 3H). m/z (ESI) 401.2 (M+H)⁺

Intermediate LLLLL: 1-(2-FLUORO-5-METH-YLPYRIDIN-3-YL)-N-(PYRIMIDIN-4-YL)ISO-QUINOLINE-6-SULFONAMIDE

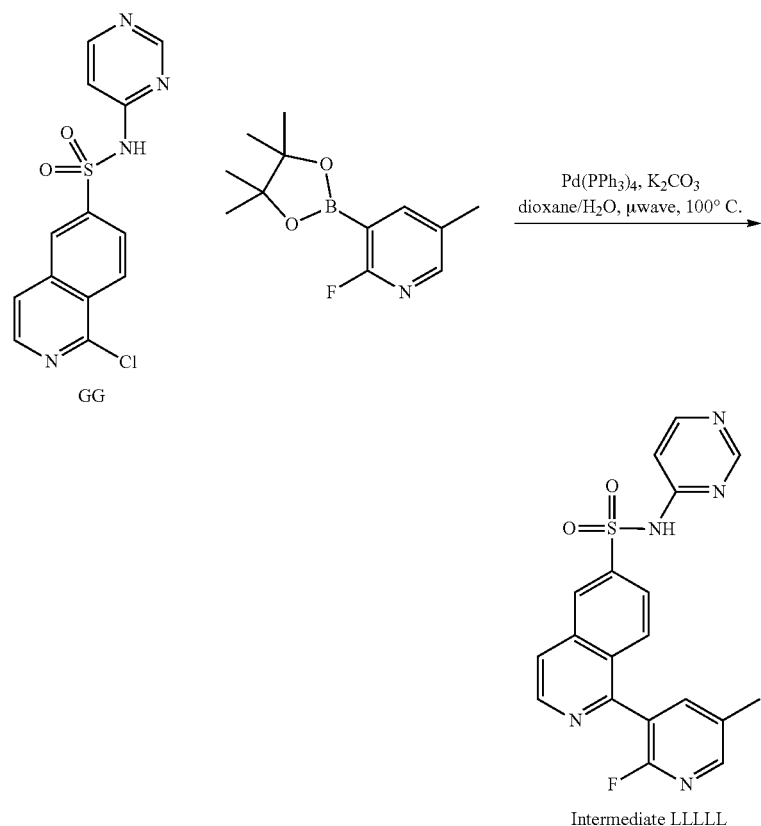

ml) and Water (15.59 ml) and heated thermally to 120° C. After 3 hrs LC-MS indicated about 40% conversion with starting material present. Additional boronic acid was added (1 g) and heating continued at 120° C. for 4 hrs affording ~75% conversion. The mixture was allowed to stir at room temperature over the 3 days under nitrogen afford little to no further conversion. Additional boronic acid (500 mg) and Pd(PPh₃)₄ (500 mg) was added and the mixture heated back to 120° C. for 3 hr affording near complete conversion according to LC-MS. The mixture was cooled to room temperature, transferred to a seperatory funnel, diluted with water and extracted with EtOAc but the material stayed in the aqueous phase, although this wash did remove many impurities (including PPh₃O). The aqueous was washed with DCM, but again the material stuck in the aqueous phase. The aqueous was acidified to ~pH 2 affording a precipitate which was collected as a brown solid, fairly clean product by LC-MS (300 mg). The aqueous was dried to near dryness affording a precipitate which was collected but was mostly salts with some product. The solid and filtrate were combined and silica gel added and the mixture dried under reduced pressure. The material was purified with a 100 g ultra snap column ramping MeOH in DCM (0-50%) affording product (only 400 mg) as a light yellow solid. Much of the material had remained on the dry pack. The dry packed slurry was purified 2× (split into two parts) by loading directly onto a KP-C18-HS 60 g Biotage column using the reverse phase MPLC ramping IPA in H₂O To a microwave vial charged with 1-chloro-N-(pyrimidin-4-yl)isoquinoline-6-sulfonamide (Intermediate GG; 3.00 g, 9.35 mmol), 2-fluoro-5-picoline-3-boronic acid (1.469 ml, 12.16 mmol), potassium carbonate (6.46 g, 46.8 mmol) and Pd(Ph₃P)₄ (1.081 g, 0.935 mmol) was added Dioxane (46.8

(with 1% NH₄OH) (0-100%) affording 1 g of product as a brown solid, in total (1.4 g, 38%). m/z (ESI) 396.2 (M+H)⁺

EXAMPLE 378

1-(5-METHYL-2-(PIPERIDIN-4-YLOXY)PYRI-DIN-3-YL)-N-(THIAZOL-2-YL)ISOQUINOLINE-6-SULFONAMIDE

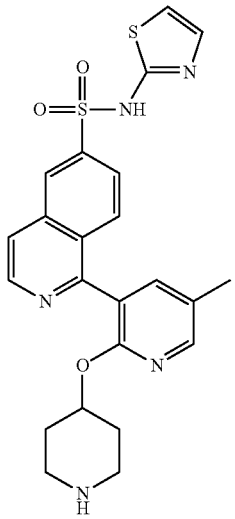 [SMILES: Cc1cnc(OC2CCNCC2)c(-c2nccc3cc(S(=O)(=O)Nc4nccs4)ccc23)c1]

To a vial charged with 1-(2-fluoro-5-methylpyridin-3-yl)-N-(thiazol-2-yl)isoquinoline-6-sulfonamide (Example 377) (50 mg, 0.125 mmol) was added 1-boc-4-hydroxypiperidine (27.6 mg, 0.137 mmol) and DMF (499 μl) and the resulting solution cooled in an ice water bath prior to the addition of NaH (60% in mineral oil) (12.48 mg, 0.312 mmol). The mixture was stirred overnight at room temperature (ice melt) affording conversion to desired product as the primary species. To the light brown solution was added IPA (0.5 ml) and AcOH (50 μl). The resulting mixture was dried under reduced pressure affording a yellow oil to which DCM (1 ml) and TFA (0.3 ml) was added. The resulting mixture was stirred at room temperature for 2 hrs affording no Boc cleavage according to LC-MS. Another 0.7 ml of TFA was added and stirring was continued at room temperature for 2 hr affording complete Boc cleavage. The mixture dried under reduced pressure, dissolved in DMSO (1 ml) and purified with RP-HPLC (Gilson) ramping ACN in H₂O (5-95%, 0.1% TFA modifier) affording separation of impurities. The product containing eluents were dried under reduced pressure and free-based with a 5 g SCX-2 column washing with MeOH, then 2M NH₃ in MeOH. The basic wash was dried under reduced pressure affording a light yellow film which was lyophilized from MeOH/H₂O to provide 1-(5-methyl-2-(piperidin-4-yloxy)pyridin-3-yl)-N-(thiazol-2-yl)isoquinoline-6-sulfonamide as an off-white powder (25 mg, 0.052 mmol, 41.6% yield). ¹H NMR (400 MHz, DMSO-d₆) δ 8.62 (d, J=5.67 Hz, 1H), 8.43 (d, J=1.66 Hz, 1H), 8.16 (dd, J=0.78, 2.45 Hz, 1H), 8.04 (d, J=5.38 Hz, 1H), 7.88 (dd, J=1.71, 8.85 Hz, 1H), 7.66-7.74 (m, 2H), 7.02 (d, J=4.01 Hz, 1H), 6.59 (d, J=4.11 Hz, 1H), 5.27 (td, J=3.47, 6.94 Hz, 1H), 2.91 (br. s., 2H), 2.61-2.79 (m, 2H), 2.30 (s, 3H), 1.86-2.01 (m, 2H), 1.56 (br. s., 2H). m/z (ESI) 482.1 (M+H)⁺

EXAMPLE 379

1-(5-METHYL-2-(2-PHENOXYETHOXY)PYRI-DIN-3-YL)-N-(THIAZOL-2-YL)ISOQUINOLINE-6-SULFONAMIDE

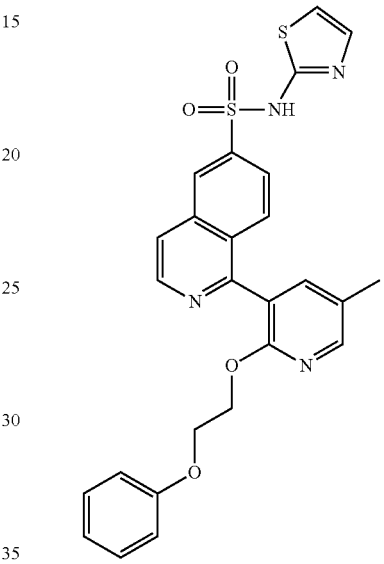

To a vial charged with 2-phenoxyethanol (0.25 mmol) was added 1-(2-fluoro-5-methylpyridin-3-yl)-N-(thiazol-2-yl)isoquinoline-6-sulfonamide (Example 377) (50 mg, 0.125 mmol) and DMSO (499 μl). To the solution was added cesium carbonate (122 mg, 0.375 mmol) and the vessel sealed and shaken overnight at 130° C. The resulting mixture was cooled to room temperature, filtered through a frit rinsing with IPA. The volatiles were dried under reduced pressure and the crude mixture was purified with RP-HPLC (ramping ACN in H₂O, TFA modifier) affording product, 1-(5-methyl-2-(2-phenoxyethoxy)pyridin-3-yl)-n-(thiazol-2-yl)isoquinoline-6-sulfonamide (37 mg, 47%). m/z (ESI) 518.1 (M+H)+

EXAMPLE 380

1-(2-(BENZYLOXY)-5-METHYLPYRIDIN-3-YL)-N-(THIAZOL-2-YL)ISOQUINOLINE-6-SULFONAMIDE

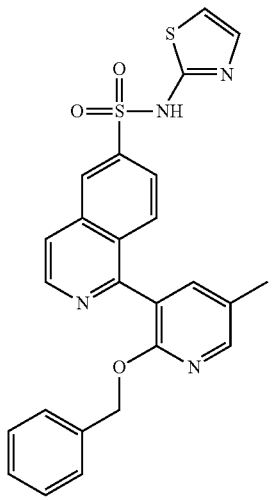 [SMILES: Cc1cnc(OCc2ccccc2)c(-c2nccc3cc(S(=O)(=O)Nc4nccs4)ccc23)c1]

Prepared as described for Example 379 using phenylmethanol (0.25 mmol) instead of 2-phenoxyethanol to afford 1-(2-(benzyloxy)-5-methylpyridin-3-yl)-n-(thiazol-2-yl)isoquinoline-6-sulfonamide (18 mg, 18%). m/z (ESI) 489.0 (M+H)+

EXAMPLE 381

1-(2-(CYCLOBUTYLMETHOXY)-5-METHYLPYRIDIN-3-YL)-N-(THIAZOL-2-YL)ISOQUINOLINE-6-SULFONAMIDE

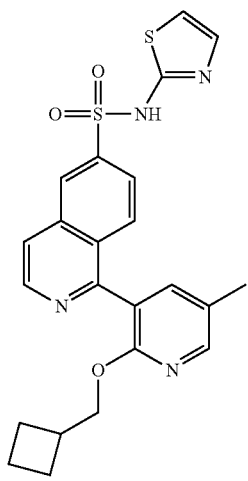 [SMILES: Cc1cnc(OCC2CCC2)c(-c2nccc3cc(S(=O)(=O)Nc4nccs4)ccc23)c1]

Prepared as described for Example 379 using cyclobutylmethanol (0.25 mmol) instead of 2-phenoxyethanol to afford 1-(2-(cyclobutylmethoxy)-5-methylpyridin-3-yl)-n-(thiazol-2-yl)isoquinoline-6-sulfonamide. m/z (ESI) 467.0 (M+H)+

EXAMPLE 382

1-(2-(2-(DIMETHYLAMINO)ETHOXY)-5-METHYLPYRIDIN-3-YL)-N-(PYRIMIDIN-4-YL)ISOQUINOLINE-6-SULFONAMIDE

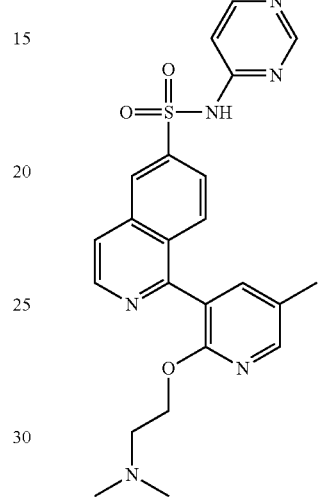

To a solution of 1-(2-fluoro-5-methylpyridin-3-yl)-N-(pyrimidin-4-yl)isoquinoline-6-sulfonamide (Intermediate LLLLL; 42 mg, 0.11 mmol) in DCM (0.425 ml) was added 2-(dimethylamino)ethanol (0.25 mmol) and NaH (60% in mineral oil) (8.92 mg, 0.223 mmol) and the vessel sealed and shaken at room temperature overnight. To the mixture was added IPA carefully (~2 ml) followed by acetic acid (~0.2 ml) and the resulting mixture dried under reduced pressure and purified with RP-HPLC (ramping ACN in H₂O, NH₄OH modified) affording 1-(2-(2-(dimethylamino)ethoxy)-5-methylpyridin-3-yl)-n-(pyrimidin-4-yl)isoquinoline-6-sulfonamide (17.7 mg, 36%). m/z (ESI) 465.1 (M+H)$^+$

EXAMPLE 383

1-(5-METHYL-2-((1-METHYLPIPERIDIN-3-YL)OXY)PYRIDIN-3-YL)-N-(PYRIMIDIN-4-YL)ISOQUINOLINE-6-SULFONAMIDE

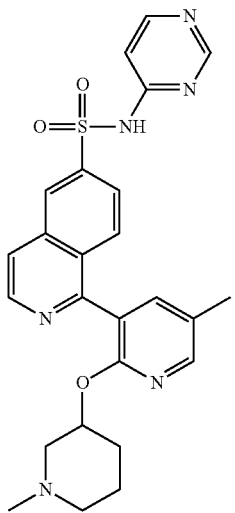 [SMILES: Cc1cnc(OC2CCCN(C)C2)c(-c2nccc3cc(S(=O)(=O)Nc4ccncn4)ccc23)c1]

Prepared as described for Example 382, using 1-methylpiperidin-3-ol (0.25 mmol) instead of 2-(dimethylamino)ethanol to afford 1-(5-methyl-2-((1-methylpiperidin-3-yl)oxy)pyridin-3-yl)-n-(pyrimidin-4-yl)isoquinoline-6-sulfonamide (25.7 mg, 49%). m/z (ESI) 491.2 (M+H)$^+$

EXAMPLE 384

1-(2-(2-HYDROXYPROPAN-2-YL)PHENYL)-N-(THIAZOL-2-YL)ISOQUINOLINE-6-SULFONAMIDE

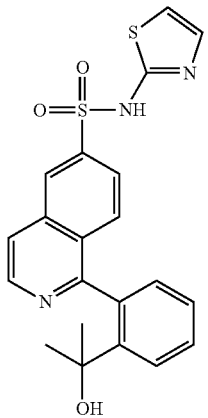 [SMILES: CC(C)(C#N)c1ccccc1-c1nccc2cc(S(=O)(=O)Nc3nccs3)ccc12]

To a microwave vial charged with 1-chloro-N-(4-methoxybenzyl)-N-(thiazol-2-yl)isoquinoline-6-sulfonamide (Intermediate JJJ; 50 mg, 0.112 mmol), potassium carbonate (77 mg, 0.561 mmol) and Pd(Ph$_3$P)$_4$ (12.96 mg, 0.011 mmol) was added dioxane (561 µl), (2-(2-hydroxypropan-2-yl)phenyl)boronic acid (20.18 mg, 0.112 mmol) and Water (187 µl) and irradiated at 100° C. for 30 min affording conversion to desired product (~40%) with starting material remaining. To the mixture was added additional boronate (50 ul) and Pd(Ph$_3$P)$_4$ (12.96 mg, 0.011 mmol) and irradiated another 30 min at 100° C. affording consumption of starting material and product as the primary species. The organic layer was decanted and the aqueous rinsed once with EtOAc and the organics combined and dried under reduced pressure. To the resulting oil was added DCM (2 ml) and TFA (0.6 ml) and the resulting solution stirred at room temperature. The mixture was dried under reduced pressure and purified with a 25 g HP spherical silica gel (15 µm spherical, Interchim) ramping DCM:MeOH (90:10) in DCM (0-100%) affording product as a yellow film which was lyophilized from MeOH/H$_2$O affording a fluffy yellow solid 1-(2-(2-hydroxypropan-2-yl)phenyl)-N-(thiazol-2-yl)isoquinoline-6-sulfonamide 2,2,2-trifluoroacetate (39 mg, 0.072 mmol, 64.5% yield). $^1$H NMR (400 MHz, DMSO-d$_6$) δ=12.92 (br. s., 1H), 8.67-8.55 (m, 2H), 8.27 (br. s., 1H), 7.94 (d, J=8.3 Hz, 1H), 7.77-7.65 (m, 2H), 7.56 (t, J=7.1 Hz, 1H), 7.38 (t, J=7.4 Hz, 1H), 7.29 (d, J=4.6 Hz, 1H), 7.21 (d, J=7.3 Hz, 1H), 6.89 (d, J=4.6 Hz, 1H), 1.37 (s, 3H), 1.24 (s, 4H). m/z (ESI) 426.0 (M+H)$^+$

EXAMPLE 385

1-(2-(2-CYANOPROPAN-2-YL)PHENYL)-N-(THIAZOL-2-YL)ISOQUINOLINE-6-SULFONAMIDE

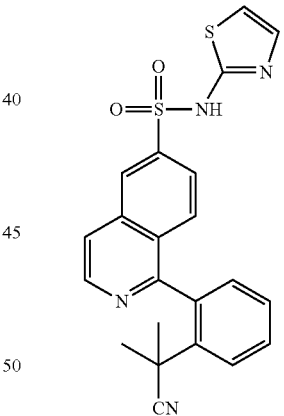

Prepared as described for Example 384 using 2-methyl-2-(2-(4,4,5,5-tetramethyl-1,3,2-dioxaborolan-2-yl)phenyl)propanenitrile instead of (2-(2-hydroxypropan-2-yl)phenyl)

boronic acid to afford product as an off white solid as the TFA salt (52 mg, 46%). Step 1: m/z (ESI) 555.0 (M+H)+, Step 2: m/z (ESI) 435.0 (M+H)+

EXAMPLE 386

1-(2-CYANO-4-(TRIFLUOROMETHYL)PHENYL)-N-(THIAZOL-2-YL)ISOQUINOLINE-6-SULFONAMIDE

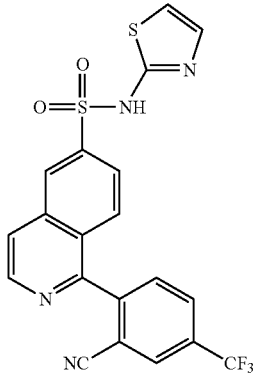 [SMILES: N#Cc1cc(C(F)(F)F)ccc1-c1nccc2cc(S(=O)(=O)Nc3nccs3)ccc12]

Prepared as described for Example 384 using 2-(4,4,5,5-tetramethyl-1,3,2-dioxaborolan-2-yl)-5-(trifluoromethyl)benzonitrile instead of (2-(2-hydroxypropan-2-yl)phenyl)boronic acid to afford product as an off white solid (17 mg, 16%). Step 1: m/z (ESI) 581.2 (M+H)+, Step 2: m/z (ESI) 461.1 (M+H)+

EXAMPLE 387

(R)-1-(5-METHYL-2-((TETRAHYDROFURAN-3-YL)METHOXY)PYRIDIN-3-YL)-N-(THIAZOL-2-YL)ISOQUINOLINE-6-SULFONAMIDE

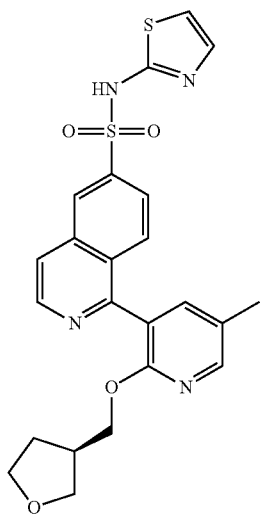 [SMILES: Cc1cnc(OC[C@@H]2CCOC2)c(-c2nccc3cc(S(=O)(=O)Nc4nccs4)ccc23)c1]

Prepared as described for Example 379 using (S)-(tetrahydrofuran-3-yl)methanol (0.25 mmol) instead of 2-phenoxyethanol to afford (R)-1-(5-methyl-2-((tetrahydrofuran-3-yl)methoxy)pyridin-3-yl)-n-(thiazol-2-yl)isoquinoline-6-sulfonamide (21 mg, 28%). m/z (ESI) 483.0 (M+H)+

EXAMPLE 388

1-(2-METHOXY-4-(TRIFLUOROMETHYL)PHENYL)-N-(1,2,5-THIADIAZOL-3-YL)ISOQUINOLINE-6-SULFONAMIDE

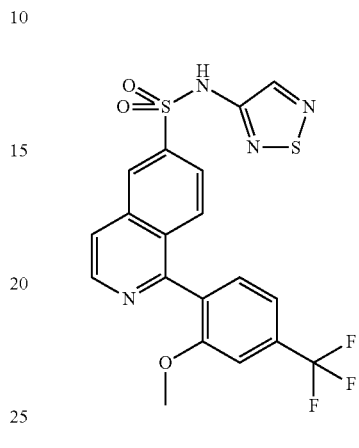

1,2,5-thiadiazol-3-amine (28 mg, 0.273 mmol) (Aquila Pharmtech) and perfluorophenyl 1-(2-methoxy-4-(trifluoromethyl)phenyl)isoquinoline-6-sulfonate (Intermediate LLL; 100 mg, 0.182 mmol) were dissolved in THF (1 mL) in a round bottom flask and cooled to 0° C., then lithium bis(trimethylsilyl)amide (1 M in THF, 364 µl, 0.364 mmol) was added and the reaction was stirred for 30 min. The reaction was quenched with saturated ammonium chloride and extracted with EtOAc (3×). The combined organic extracts were dried over sodium sulfate, filtered, and concentrated via rotary evaporation. The residue was purified using reverse-phase HPLC with a Waters-Xbridge C18, 19×100 mm, 10 µm column with a gradient 5-95% acetonitrile and water with 0.1% ammonium hydroxide modifier to yield 1-(2-methoxy-4-(trifluoromethyl)phenyl)-N-(1,2,5-thiadiazol-3-yl)isoquinoline-6-sulfonamide. m/z (ESI) 467.0 (M+H)+.

EXAMPLE 389

1-(2-METHOXY-4-(TRIFLUOROMETHYL)PHENYL)-N-(OXAZOL-2-YL)ISOQUINOLINE-6-SULFONAMIDE

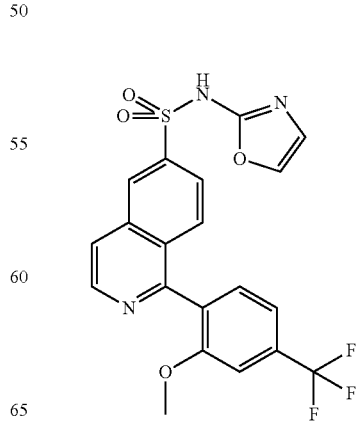

Example 389 was made in analogous fashion to Example 388, utilizing oxazol-2-amine (Bionet) instead of 1,2,5-thiadiazol-3-amine, and utilizing 0.1% TFA as a modifier for the HPLC purification instead of ammonium hydroxide. m/z (ESI) 448.0 (M−H)−.

EXAMPLE 390

1-((1-(2-METHOXY-4-(TRIFLUOROMETHYL) PHENYL)ISOQUINOLIN-6-YL) SULFONYL)-1H-PYRAZOL-3-AMINE

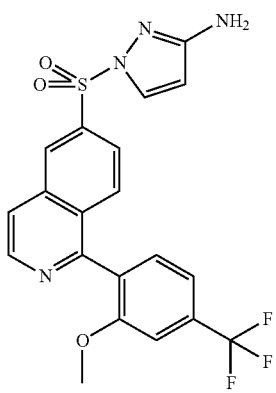 [SMILES: COc1cc(C(F)(F)F)ccc1-c1nccc2cc(S(=O)(=O)n3ccc(N)n3)ccc12]

Example 390 was made in analogous fashion to Example 388, utilizing 3-aminopyrazole (Alfa Aesar) instead of 1,2,5-thiadiazol-3-amine. m/z (ESI) 449.0 (M+H)+.

EXAMPLE 391

1-(2-METHOXY-4-(TRIFLUOROMETHYL)PHENYL)-N-(1,2,4-TRIAZIN-5-YL)ISOQUINOLINE-6-SULFONAMIDE

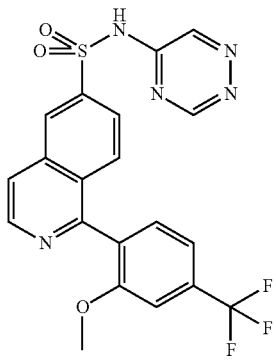 [SMILES: COc1cc(C(F)(F)F)ccc1-c1nccc2cc(S(=O)(=O)Nc3cnncn3)ccc12]

Example 391 was made in analogous fashion to Example 388, utilizing 1,2,4-triazin-5-amine (Aldlab Chemicals) instead of 1,2,5-thiadiazol-3-amine m/z (ESI) 462.0 (M+H)+.

INTERMEDIATE MMMMM: 1-CHLORO-N-(2,4-DIMETHOXYBENZYL)-4-FLUORO-N-(1,2,4-THIADIAZOL-5-YL)ISOQUINOLINE-6-SULFONAMIDE

Intermediate MMMMM

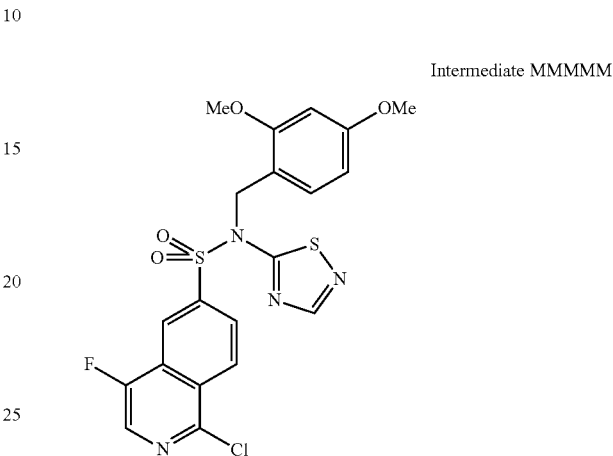

The title compound was prepared in an analogous manner to that of INTERMEDIATE PPP, except that N-(2,4-dimethoxybenzyl)-1,2,4-thiadiazol-5-amine was used instead of N-(2,4-dimethoxybenzyl)thiazol-2-amine in Step 5. The final compound was purified via column chromatography (RediSep Gold 12 g silica gel column, gradient elution 25-100% EtOAc:Heptane) to afford 1-chloro-N-(2,4-dimethoxybenzyl)-4-fluoro-N-(1,2,4-thiadiazol-5-yl)isoquinoline-6-sulfonamide as an off-white solid. (ESI) 517.1 (M+Na)+.

EXAMPLE 392

4-FLUORO-1-(2-METHOXY-4-(TRIFLUOROMETHYL)PHENYL)-N-(1,2,4-THIADIAZOL-5-YL) ISOQUINOLINE-6-SULFONAMIDE

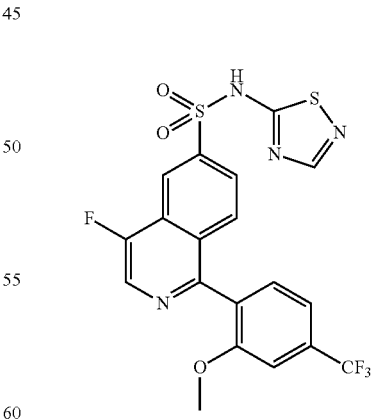

The title compound was prepared in an analogous manner to that of EXAMPLE 228, except that 1-chloro-N-(2,4-dimethoxybenzyl)-4-fluoro-N-(1,2,4-thiadiazol-5-yl)isoquinoline-6-sulfonamide and (2-methoxy-4-(trifluoromethyl)phenyl)boronic acid were used as the coupling partners. The final compound was purified via column chromatography (RediSep Gold 12 g silica gel column, gradient elution 0-10% MeOH:DCM) to afford 4-fluoro-1-(2-methoxy-4-(trifluoromethyl)phenyl)-N-(1,2,4-thiadiazol-5-yl)isoquinoline-6-sulfonamide as an off-white solid. $^1$H NMR (400 MHz, DMSO-$d_6$) δ=8.76 (s, 1H), 8.49 (d, J=9.3 Hz, 2H), 8.00 (d, J=8.4 Hz, 1H), 7.81 (d, J=8.4 Hz, 1H), 7.64-7.42 (m, 3H), 3.75 (s, 3H). m/z (ESI) 485.0 (M+H)$^+$.

EXAMPLE 393

4-FLUORO-1-(2-METHOXYPHENYL)-N-(1,2,4-THIADIAZOL-5-YL)ISOQUINOLINE-6-SULFONAMIDE

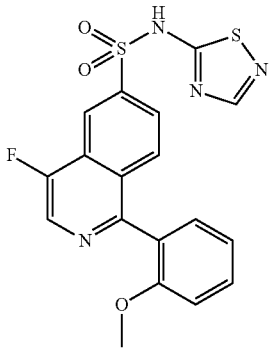 [SMILES: COc1ccccc1-c1ncc(F)c2cc(S(=O)(=O)Nc3ncns3)ccc12]

The title compound was prepared in an analogous manner to that of EXAMPLE 228, except that 1-chloro-N-(2,4-dimethoxybenzyl)-4-fluoro-N-(1,2,4-thiadiazol-5-yl)isoquinoline-6-sulfonamide and (2-methoxyphenyl)boronic acid were used as the coupling partners. The final compound was purified via column chromatography (RediSep Gold 12 g silica gel column, gradient elution 0-10% MeOH:DCM) to afford 4-fluoro-1-(2-methoxyphenyl)-N-(1,2,4-thiadiazol-5-yl)isoquinoline-6-sulfonamide as a grey solid. $^1$H NMR (400 MHz, DMSO-$d_6$) δ=8.72 (s, 1H), 8.49 (s, 2H), 8.01 (dd, J=1.5, 8.9 Hz, 1H), 7.80 (d, J=9.2 Hz, 1H), 7.61-7.51 (m, 1H), 7.33 (dd, J=1.4, 7.4 Hz, 1H), 7.23 (d, J=8.2 Hz, 1H), 7.18-7.08 (m, 1H), 3.65 (s, 3H). m/z (ESI) 417.2 (M+H)$^+$.

EXAMPLE 394

4-FLUORO-1-(4-FLUORO-2-METHOXYPHENYL)-N-(1,2,4-THIADIAZOL-5-YL)ISOQUINOLINE-6-SULFONAMIDE

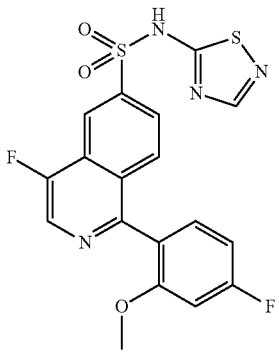

The title compound was prepared in an analogous manner to that of EXAMPLE 228, except that 1-chloro-N-(2,4-dimethoxybenzyl)-4-fluoro-N-(1,2,4-thiadiazol-5-yl)isoquinoline-6-sulfonamide and (4-fluoro-2-methoxyphenyl)boronic acid were used as the coupling partners. The final compound was purified via column chromatography (RediSep Gold 12 g silica gel column, gradient elution 0-10% MeOH:DCM) to afford 4-fluoro-1-(4-fluoro-2-methoxyphenyl)-N-(1,2,4-thiadiazol-5-yl)isoquinoline-6-sulfonamide as an off-white solid. $^1$H NMR (400 MHz, DMSO-$d_6$) δ=8.72 (d, J=1.5 Hz, 1H), 8.49 (s, 2H), 8.00 (dd, J=1.7, 8.9 Hz, 1H), 7.86-7.78 (m, 1H), 7.38 (dd, J=6.9, 8.3 Hz, 1H), 7.16 (dd, J=2.3, 11.4 Hz, 1H), 6.97 (dt, J=2.3, 8.4 Hz, 1H), 3.67 (s, 3H). m/z (ESI) 435.2 (M+H)$^+$.

EXAMPLE 395

1-(4-CYANO-2-METHOXYPHENYL)-4-FLUORO-N-(1,2,4-THIADIAZOL-5-YL)ISOQUINOLINE-6-SULFONAMIDE

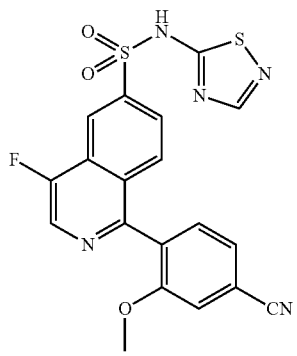

The title compound was prepared in an analogous manner to that of EXAMPLE 228, except that 1-chloro-N-(2,4-dimethoxybenzyl)-4-fluoro-N-(1,2,4-thiadiazol-5-yl)isoquinoline-6-sulfonamide and (4-cyano-2-methoxyphenyl)boronic acid were used as the coupling partners. The final compound was purified via column chromatography (RediSep Gold 12 g silica gel column, gradient elution 0-10% MeOH:DCM) to afford 1-(4-cyano-2-methoxyphenyl)-4-fluoro-N-(1,2,4-thiadiazol-5-yl)isoquinoline-6-sulfonamide as an off-white solid. $^1$H NMR (400 MHz, DMSO-$d_6$) δ=8.76 (d, J=1.4 Hz, 1H), 8.50 (d, J=1.4 Hz, 1H), 8.48 (s, 1H), 8.00

(dd, J=1.7, 8.9 Hz, 1H), 7.79 (d, J=9.0 Hz, 1H), 7.76 (s, 1H), 7.62 (dd, J=1.1, 7.7 Hz, 1H), 7.57-7.52 (m, 1H), 3.72 (s, 3H). m/z (ESI) 442.2 (M+H)+.

EXAMPLE 396

4-FLUORO-1-(2-METHOXYPYRIDIN-3-YL)-N-(THIAZOL-2-YL)ISOQUINOLINE-6-SULFONAMIDE

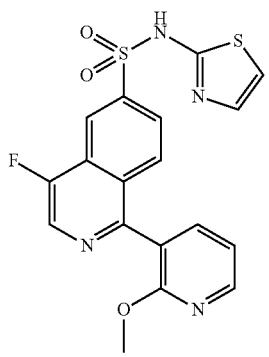 [SMILES: COc1ncccc1-c1ncc(F)c2cc(S(=O)(=O)Nc3nccs3)ccc12]

The title compound was prepared in an analogous manner to that of EXAMPLE 228, except that 1-chloro-N-(2,4-dimethoxybenzyl)-4-fluoro-N-(thiazol-2-yl)isoquinoline-6-sulfonamide and 2-methoxy-3-pyridineboronic acid were used as the coupling partners. The final compound was purified via column chromatography (RediSep Gold 12 g silica gel column, gradient elution 0-10% MeOH:DCM) to afford 4-fluoro-1-(2-methoxypyridin-3-yl)-N-(thiazol-2-yl)isoquinoline-6-sulfonamide as a white solid. $^1$H NMR (400 MHz, DMSO-$d_6$) δ=13.00 (br. s., 1H), 8.73 (d, J=1.3 Hz, 1H), 8.51 (d, J=1.3 Hz, 1H), 8.39 (dd, J=1.9, 4.9 Hz, 1H), 8.01 (dd, J=1.7, 8.9 Hz, 1H), 7.87-7.76 (m, 2H), 7.31 (d, J=4.6 Hz, 1H), 7.22 (dd, J=5.0, 7.2 Hz, 1H), 6.90 (d, J=4.5 Hz, 1H), 3.77 (s, 3H). m/z (ESI) 417.2 (M+H)+.

EXAMPLE 397

1-(2-CYANOPHENYL)-4-FLUORO-N-(THIAZOL-2-YL)ISOQUINOLINE-6-SULFONAMIDE

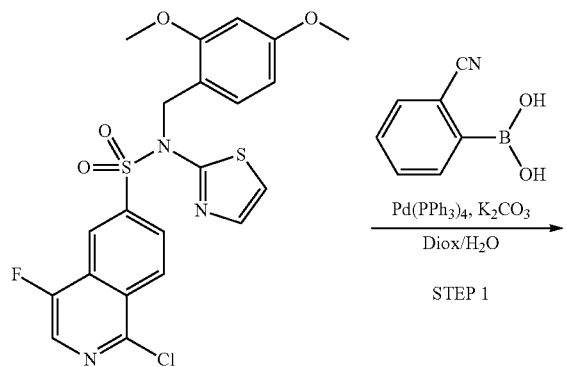

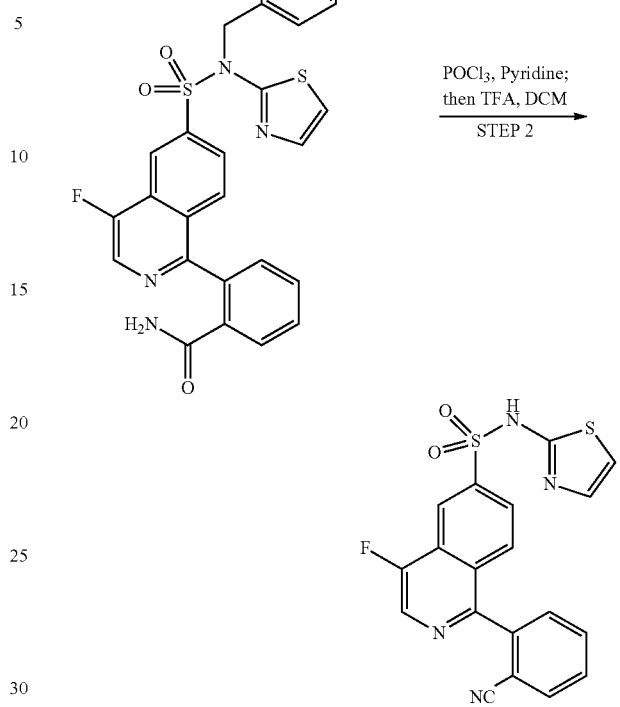

STEP 1: 2-(6-(N-(2,4-DIMETHOXYBENZYL)-N-(THIAZOL-2-YL)SULFAMOYL)-4-FLUOROISOQUINOLIN-1-YL)BENZAMIDE

A microwave vial was charged with 1-chloro-N-(2,4-dimethoxybenzyl)-4-fluoro-N-(thiazol-2-yl)isoquinoline-6-sulfonamide (Intermediate PPP; 0.060 g, 0.121 mmol), (2-cyanophenyl)boronic acid (0.027 g, 0.182 mmol), tetrakis(triphenylphosphine)palladium(0) (0.014 g, 0.012 mmol), and potassium carbonate (0.084 g, 0.607 mmol). Dioxane (0.607 mL) and Water (0.202 mL) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 2-(6-(N-(2,4-dimethoxybenzyl)-N-(thiazol-2-yl)sulfamoyl)-4-fluoroisoquinolin-1-yl)benzamide. (ESI) 579.2 (M+H)+.

STEP 2: 1-(2-CYANOPHENYL)-4-FLUORO-N-(THIAZOL-2-YL)ISOQUINOLINE-6-SULFONAMIDE 2-(6-(N-(2,4-dimethoxybenzyl)-N-(thiazol-2-yl)sulfamoyl)-4-fluoroisoquinolin-1-yl)benzamide was dissolved in pyridine (0.6 mL) and cooled to 0° C. POCl$_3$ (0.023 mL, 0.243 mmol) was added. The reaction was stirred for 5 minutes at room temperature. The reaction was diluted with ethyl acetate and washed with water. The aqueous layer was extracted with ethyl acetate, and the combined organic layers were dried with sodium sulfate, filtered, and concentrated. The material was dissolved in DCM and TFA (0.1 mL, 1.298 mmol) was added. The reaction was stirred for 30 minutes at room temperature. The reaction was concentrated and purified via column chromatography (RediSep Gold 12 g, gradient elution 0-10% MeOH:DCM) to afford 1-(2-cyanophenyl)-4-fluoro-N-(thiazol-2-yl)isoquinoline-6-sulfonamide as a white solid. $^1$H NMR (400 MHz, DMSO-$d_6$) δ=13.02 (br. s., 1H), 8.84 (d, J=1.6 Hz, 1H), 8.57 (d, J=1.3 Hz, 1H), 8.13-8.03 (m, 2H), 7.99-7.86 (m, 2H), 7.83-7.73 (m, 2H), 7.68-7.51 (m, 2H), 7.31 (d, J=4.5 Hz, 1H), 6.90 (d, J=4.6 Hz, 1H). m/z (ESI) 410.9 (M+H)$^+$.

EXAMPLE 398

1-(2-(CYANOMETHOXY)PHENYL)-4-FLUORO-N-(THIAZOL-2-YL)ISOQUINOLINE-6-SULFONAMIDE

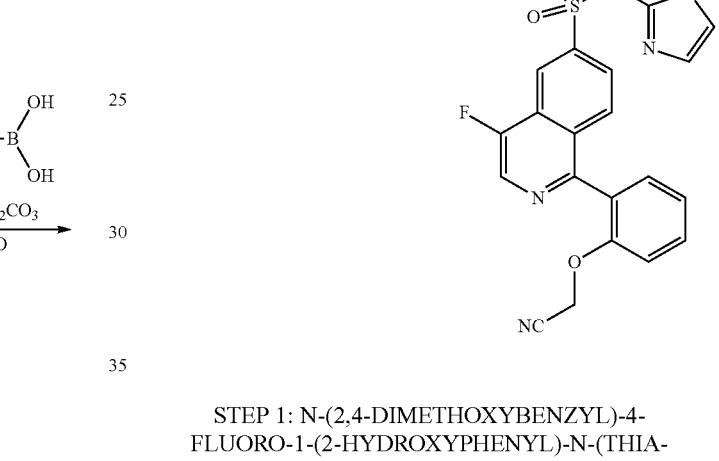

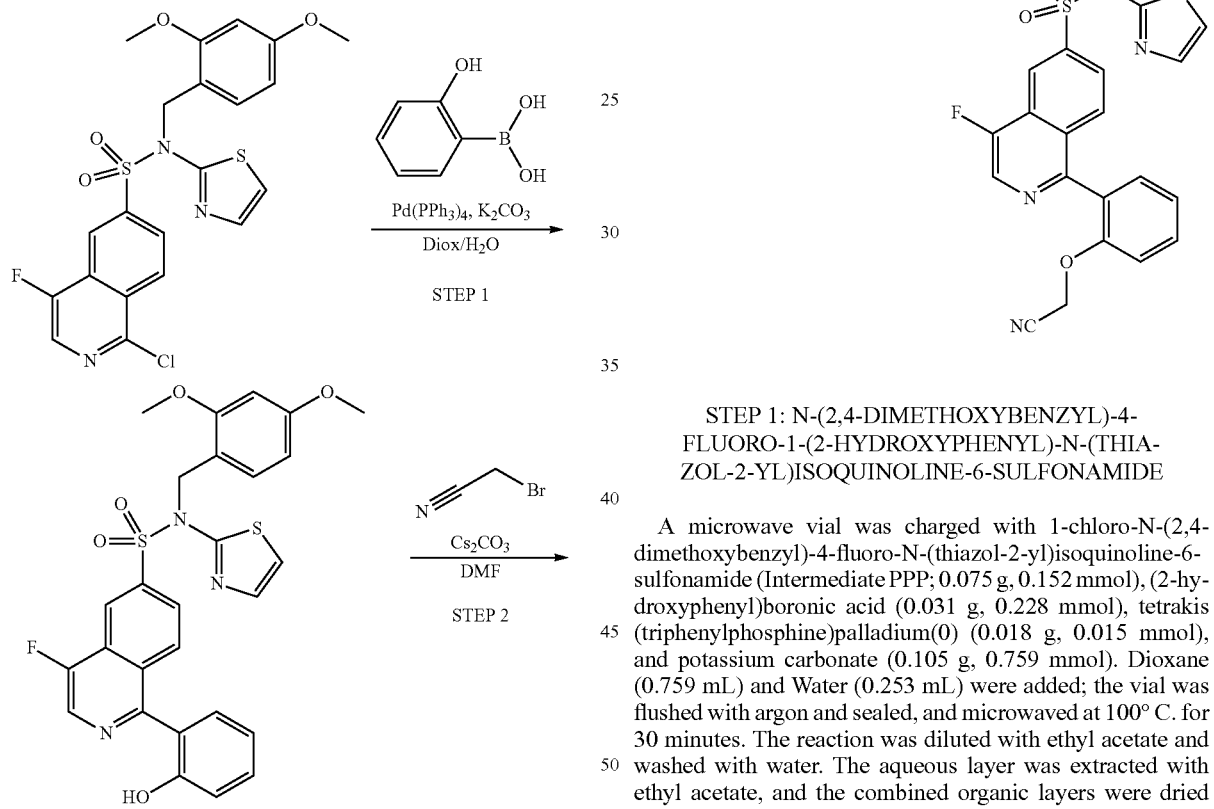

STEP 1: N-(2,4-DIMETHOXYBENZYL)-4-FLUORO-1-(2-HYDROXYPHENYL)-N-(THIAZOL-2-YL)ISOQUINOLINE-6-SULFONAMIDE

A microwave vial was charged with 1-chloro-N-(2,4-dimethoxybenzyl)-4-fluoro-N-(thiazol-2-yl)isoquinoline-6-sulfonamide (Intermediate PPP; 0.075 g, 0.152 mmol), (2-hydroxyphenyl)boronic acid (0.031 g, 0.228 mmol), tetrakis (triphenylphosphine)palladium(0) (0.018 g, 0.015 mmol), and potassium carbonate (0.105 g, 0.759 mmol). Dioxane (0.759 mL) and Water (0.253 mL) were added; the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford N-(2, 4-dimethoxybenzyl)-4-fluoro-1-(2-hydroxyphenyl)-N-(thiazol-2-yl)isoquinoline-6-sulfonamide. (ESI) 522.2 (M+H)$^+$.

STEP 2: 1-(2-(CYANOMETHOXY)PHENYL)-N-(2,4-DIMETHOXYBENZYL)-4-FLUORO-N-(THIAZOL-2-YL)ISOQUINOLINE-6-SULFONAMIDE

N-(2,4-dimethoxybenzyl)-4-fluoro-1-(2-hydroxyphenyl)-N-(thiazol-2-yl)isoquinoline-6-sulfonamide (0.078 g, 0.141 mmol) was dissolved in DMF (0.7 mL) and cesium carbonate (0.148 g, 0.456 mmol) was added, followed by bromoacetonitrile (10.58 μl, 0.152 mmol). The reaction was heated to 60°

C. and stirred overnight. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford 1-(2-(cyanomethoxy)phenyl)-N-(2,4-dimethoxybenzyl)-4-fluoro-N-(thiazol-2-yl)isoquinoline-6-sulfonamide. (ESI) 591.2 (M+H)⁺.

STEP 3: 1-(2-(CYANOMETHOXY)PHENYL)-4-FLUORO-N-(THIAZOL-2-YL)ISOQUINOLINE-6-SULFONAMIDE 1-(2-(cyanomethoxy)phenyl)-N-(2,4-dimethoxybenzyl)-4-fluoro-N-(thiazol-2-yl)isoquinoline-6-sulfonamide (0.084 g, 0.141 mmol) was dissolved in DCM and TFA (0.1 mL, 1.298 mmol) was added. The reaction was stirred for 30 minutes at room temperature. The reaction was concentrated and purified via column chromatography (RediSep Gold 12 g, gradient elution 0-10% MeOH:DCM) to afford 1-(2-(cyanomethoxy)phenyl)-4-fluoro-N-(thiazol-2-yl)isoquinoline-6-sulfonamide as a tan solid. $^1$H NMR (400 MHz, DMSO-$d_6$) δ=13.00 (br. s., 1H), 8.74 (d, J=1.6 Hz, 1H), 8.51 (d, J=1.6 Hz, 1H), 7.98 (dd, J=1.7, 8.9 Hz, 1H), 7.77 (d, J=8.8 Hz, 1H), 7.69-7.59 (m, 1H), 7.48-7.36 (m, 2H), 7.34-7.22 (m, 2H), 6.89 (d, J=4.4 Hz, 1H), 5.09 (s, 2H). m/z (ESI) 441.0 (M+H)⁺.

EXAMPLE 399

4-CYANO-1-(4-FLUORO-2-METHOXYPHENYL)-N-(THIAZOL-2-YL)ISOQUINOLINE-6-SULFONAMIDE

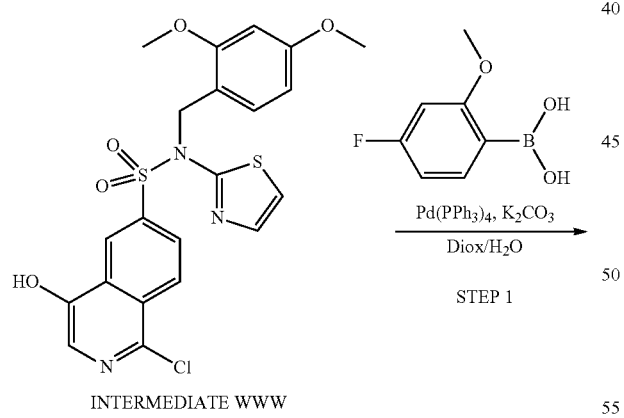

INTERMEDIATE WWW

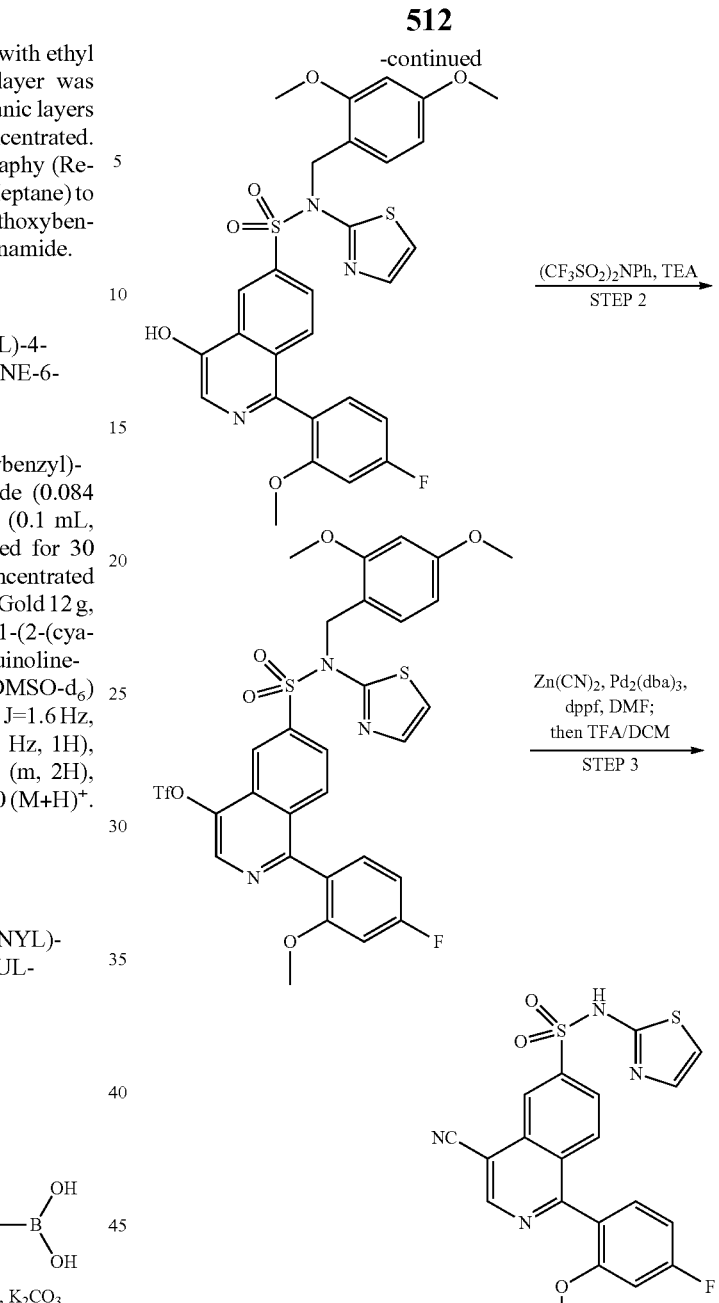

STEP 1: N-(2,4-DIMETHOXYBENZYL)-1-(4-FLUORO-2-METHOXYPHENYL)-4-HYDROXY-N-(THIAZOL-2-YL)ISOQUINOLINE-6-SULFONAMIDE

A microwave vial was charged with 1-chloro-N-(2,4-dimethoxybenzyl)-4-hydroxy-N-(thiazol-2-yl)isoquinoline-6-sulfonamide (INTERMEDIATE WWW) (0.263 g, 0.535 mmol), (4-fluoro-2-methoxyphenyl)boronic acid (0.136 g, 0.802 mmol), tetrakis(triphenylphosphine)palladium(0) (0.062 g, 0.053 mmol), and potassium carbonate (0.369 g, 2.67 mmol). Dioxane (2.67 ml) and Water (0.891 ml) were added, the vial was flushed with argon and sealed, and microwaved at 100° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-100% EtOAc:Heptane) to afford N-(2,4-dimethoxybenzyl)-1-(4-fluoro-2-methoxyphenyl)-4-hydroxy-N-(thiazol-2-yl)isoquinoline-6-sulfonamide. (ESI) 582.2 (M+H)$^+$.

STEP 2: 6-(N-(2,4-DIMETHOXYBENZYL)-N-(THIAZOL-2-YL)SULFAMOYL)-1-(4-FLUORO-2-METHOXYPHENYL)ISOQUINOLIN-4-YL TRIFLUOROMETHANESULFONATE

N-(2,4-dimethoxybenzyl)-1-(4-fluoro-2-methoxyphenyl)-4-hydroxy-N-(thiazol-2-yl)isoquinoline-6-sulfonamide (0.222 g, 0.382 mmol) and 1,1,1-trifluoro-N-phenyl-N-((trifluoromethyl)sulfonyl)methanesulfonamide (0.164 g, 0.458 mmol) were combined in DCM (7.63 ml). Triethylamine (0.160 ml, 1.145 mmol) was added, and the solution was stirred at room temperature overnight. The solution was loaded on a silica cartridge and purified via column chromatography (RediSep 40 g, gradient elution 0-50% EtOAc:Heptane) to afford 6-(N-(2,4-dimethoxybenzyl)-N-(thiazol-2-yl)sulfamoyl)-1-(4-fluoro-2-methoxyphenyl)isoquinolin-4-yl trifluoromethanesulfonate as a white solid. (ESI) 714.2 (M+H)$^+$.

STEP 3: 4-CYANO-1-(4-FLUORO-2-METHOXYPHENYL)-N-(THIAZOL-2-YL)ISOQUINOLINE-6-SULFONAMIDE

A vial was charged with 6-(N-(2,4-dimethoxybenzyl)-N-(thiazol-2-yl)sulfamoyl)-1-(4-fluoro-2-methoxyphenyl)isoquinolin-4-yl trifluoromethanesulfonate (0.140 g, 0.196 mmol), Pd$_2$(dba)$_3$ (0.018 g, 0.020 mmol), 1,1'-bis(diphenylphosphino)ferrocene (0.022 g, 0.039 mmol), and zinc cyanide (0.025 ml, 0.392 mmol). DMF (1.962 ml) was added, and the reaction was stirred at 80° C. for one hour. The reaction was diluted with ethyl acetate and washed with water. The aqueous layer was extracted with ethyl acetate, and the combined organic layers were washed with brine, dried with sodium sulfate, filtered, and concentrated. The material was purified via column chromatography (RediSep Gold 12 g, gradient elution 0-50% EtOAc:Heptane). The material was dissolved in DCM and TFA (0.1 ml, 1.298 mmol) was added. The reaction was stirred at room temperature for 30 minutes. The reaction was concentrated and purified via column chromatography (RediSep Gold 12 g, gradient elution 25-100% EtOAc:Heptane) to afford 4-cyano-1-(4-fluoro-2-methoxyphenyl)-N-(thiazol-2-yl)isoquinoline-6-sulfonamide as an off-white solid. $^1$H NMR (400 MHz, DMSO-d$_6$) δ=13.06 (br. s., 1H), 9.26 (s, 1H), 8.50 (d, J=1.5 Hz, 1H), 8.06 (dd, J=1.7, 8.9 Hz, 1H), 7.94 (d, J=8.9 Hz, 1H), 7.44 (dd, J=6.8, 8.4 Hz, 1H), 7.32 (d, J=4.6 Hz, 1H), 7.20 (dd, J=2.3, 11.4 Hz, 1H), 7.00 (dt, J=2.4, 8.4 Hz, 1H), 6.92 (d, J=4.6 Hz, 1H), 3.68 (s, 3H). m/z (ESI) 441.2 (M+H)$^+$.

EXAMPLE 400

4-CYANO-1-(2-METHOXYPHENYL)-N-(THIAZOL-2-YL)ISOQUINOLINE-6-SULFONAMIDE

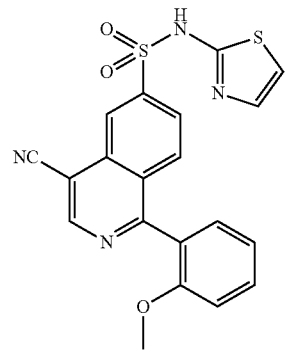 [SMILES: COc1ccccc1-c1ncc(C#N)c2cc(S(=O)(=O)Nc3nccs3)ccc12]

The title compound was prepared in an analogous manner to that of EXAMPLE 399, except that (2-methoxyphenyl)boronic acid was used instead of (4-fluoro-2-methoxyphenyl)boronic acid in STEP 1 to afford 4-fluoro-1-(2-methoxypyridin-3-yl)-N-(thiazol-2-yl)isoquinoline-6-sulfonamide as a yellow solid. $^1$H NMR (400 MHz, DMSO-d$_6$) δ=13.04 (br. s., 1H), 9.25 (s, 1H), 8.50 (d, J=1.5 Hz, 1H), 8.07 (dd, J=1.7, 8.8 Hz, 1H), 7.92 (d, J=8.8 Hz, 1H), 7.63-7.55 (m, 1H), 7.38 (dd, J=1.5, 7.5 Hz, 1H), 7.31 (d, J=4.6 Hz, 1H), 7.27 (d, J=8.3 Hz, 1H), 7.17 (t, J=7.5 Hz, 1H), 6.92 (d, J=4.6 Hz, 1H), 3.66 (s, 3H). m/z (ESI) 423.2 (M+H)$^+$.

EXAMPLE 401

1-(3'-FLUORO-[1,1'-BIPHENYL]-4-YL)-N-(PYRIMIDIN-4-YL)ISOQUINOLINE-6-SULFONAMIDE

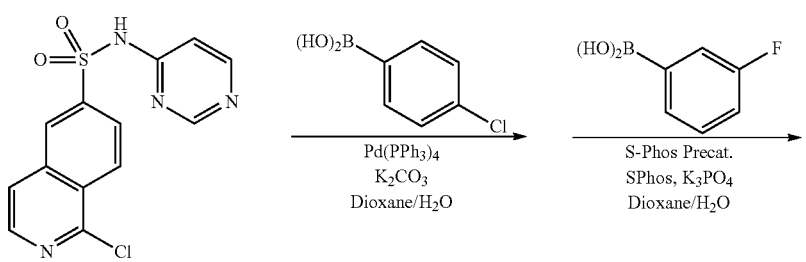

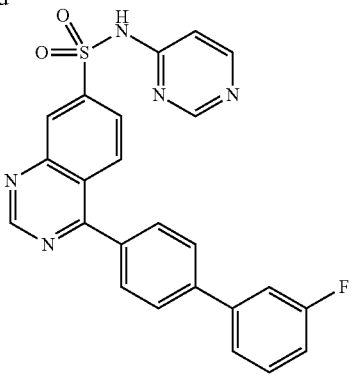

A vial was charged with 1-chloro-N-(pyrimidin-4-yl)isoquinoline-6-sulfonamide (0.075 g, 0.234 mmol), (4-chlorophenyl)boronic acid (0.040 g, 0.257 mmol), Pd(Ph₃P)₄ (0.027 g, 0.023 mmol), and potassium carbonate (0.097 g, 0.701 mmol). The vial was flushed with Ar (g), then 1,4-dioxane (0.877 ml) and Water (0.292 ml) were added in sequence. The vial was sealed and microwaved at 100° C. for 30 minutes. (3-fluorophenyl)boronic acid (0.065 g, 0.468 mmol), dicyclohexyl(2',6'-dimethoxy-[1,1'-biphenyl]-2-yl)phosphine (4.80 mg, 0.012 mmol), and chloro(2-dicyclohexylphosphino-2',6'-dimethoxy-1,1'-biphenyl)[2-(2-aminoethylphenyl)]palladium(ii) dichloromethane (8.86 mg, 0.012 mmol) were added and the reaction was microwaved at 100° C. for 45 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-10% MeOH:DCM) to afford 1-(3'-fluoro-[1,1'-biphenyl]-4-yl)-N-(pyrimidin-4-yl)isoquinoline-6-sulfonamide as a light yellow solid. $^1$H NMR (400 MHz, DMSO-d₆) δ=8.74 (d, J=5.8 Hz, 1H), 8.70 (br. s., 1H), 8.58 (br. s., 1H), 8.23 (d, J=9.1 Hz, 2H), 8.13 (d, J=5.5 Hz, 1H), 8.03 (d, J=9.3 Hz, 1H), 7.92 (d, J=8.3 Hz, 2H), 7.80 (d, J=8.2 Hz, 2H), 7.66 (d, J=8.0 Hz, 2H), 7.60-7.51 (m, 2H), 7.30-7.20 (m, 2H), 7.15-6.97 (m, 1H). m/z (ESI) 457.2 (M+H)⁺.

EXAMPLE 402

1-(3-(3-FLUOROPHENYL)PIPERIDIN-1-YL)-N-(PYRIMIDIN-4-YL)ISOQUINOLINE-6-SULFONAMIDE

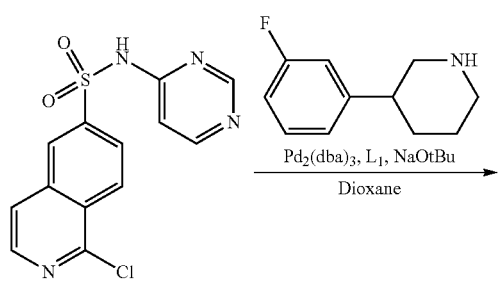

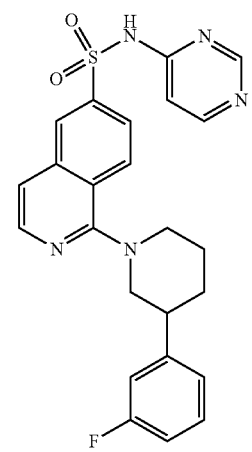

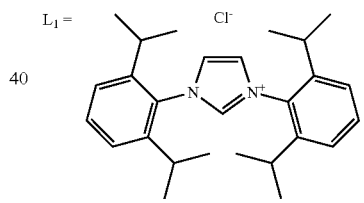

L₁ =

A vial was charged with 1-chloro-N-(pyrimidin-4-yl)isoquinoline-6-sulfonamide (Intermediate GG; 0.200 g, 0.624 mmol), Pd₂(dba)₃ (0.029 g, 0.031 mmol), 1,3-bis(2,6-di-1-propylphenyl)imidazolium chloride (0.027 g, 0.062 mmol), 3-(3-fluorophenyl)piperidine hydrochloride (0.202 g, 0.935 mmol) and sodium tert-butoxide (0.240 g, 2.494 mmol). Dioxane (6.24 ml) was added and the reaction was flushed with argon and stirred at 130° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 40 g, gradient elution 0-10% MeOH:DCM) to afford 1-(3-(3-fluorophenyl)piperidin-1-yl)-N-(pyrimidin-4-yl)isoquinoline-6-sulfonamide as a light yellow solid. $^1$H NMR (400 MHz, DMSO-d₆) δ=8.57 (s, 1H), 8.48 (s, 1H), 8.29-8.25 (m, 1H), 8.23 (d, J=9.0 Hz, 1H), 8.19 (d, J=5.7 Hz, 1H), 7.95 (dd, J=1.8, 8.9 Hz, 1H), 7.57 (d, J=5.8 Hz, 1H), 7.35 (dt, J=6.5, 8.0 Hz, 1H), 7.25-7.16 (m, 2H), 7.08-6.97 (m, 2H), 3.79 (t, J=13.0 Hz, 2H), 3.21-3.10 (m, 1H), 3.08-2.91 (m, 2H), 2.09-1.99 (m, 1H), 1.97-1.83 (m, 2H), 1.79-1.65 (m, 1H). m/z (ESI) 464.2 (M+H)+.

EXAMPLE 403

1-(4-(3-FLUOROPHENYL)-2-METHYLPIPER-AZIN-1-YL)-N-(PYRIMIDIN-4-YL)ISOQUINO-LINE-6-SULFONAMIDE

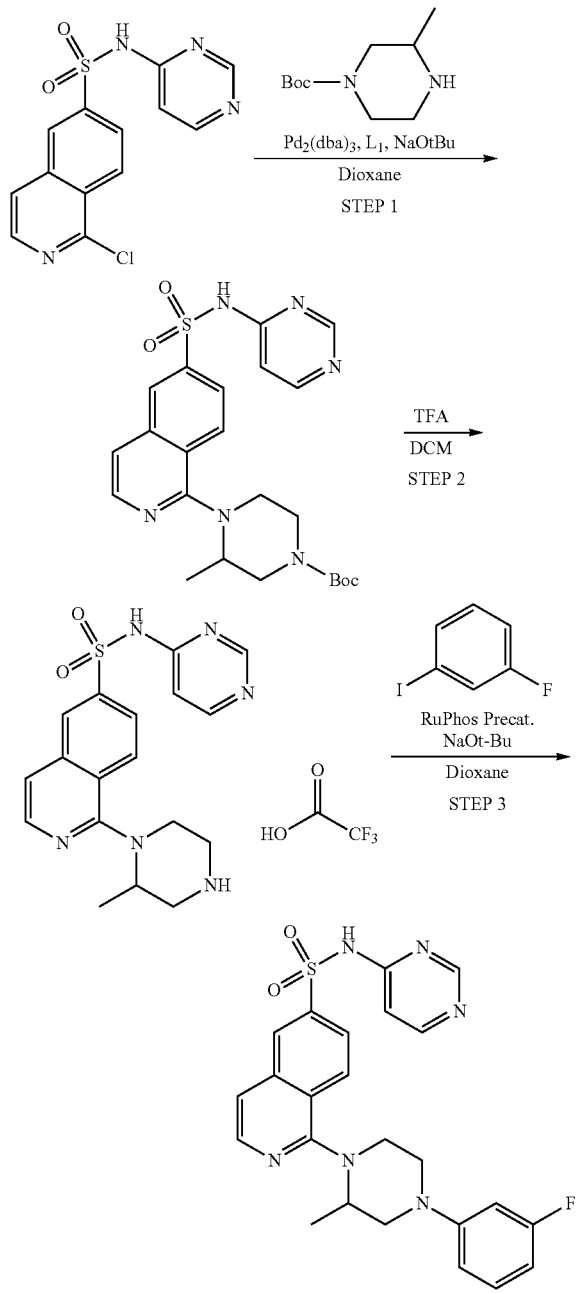

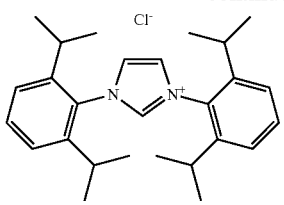

STEP 1: TERT-BUTYL 3-METHYL-4-(6-(N-(PY-RIMIDIN-4-YL)SULFAMOYL)ISOQUINOLIN-1-YL)PIPERAZINE-1-CARBOXYLATE

The title compound was prepared in an analogous manner to that of EXAMPLE 402, except that 4-N-Boc-2-methyl-piperazine was used instead of 3-(3-fluorophenyl)piperidine hydrochloride to afford tert-butyl 3-methyl-4-(6-(N-(pyrimidin-4-yl)sulfamoyl)isoquinolin-1-yl)piperazine-1-carboxylate as a light yellow solid. (ESI) 485.3 (M+H)+.

STEP 2: 1-(2-METHYLPIPERAZIN-1-YL)-N-(PY-RIMIDIN-4-YL)ISOQUINOLINE-6-SULFONA-MIDE 2,2,2-TRIFLUOROACETATE

Tert-butyl 3-methyl-4-(6-(N-(pyrimidin-4-yl)sulfamoyl) isoquinolin-1-yl)piperazine-1-carboxylate (0.043 g, 0.089 mmol) was dissolved in DCM (0.887 ml) and TFA (0.1 ml, 1.298 mmol) was added. The reaction was stirred for one hour at room temperature. The reaction was concentrated, triturated with ether, and filtered. The solids were washed with ether and vacuum dried to afford 1-(2-methylpiperazin-1-yl)-N-(pyrimidin-4-yl)isoquinoline-6-sulfonamide 2,2,2-trifluoroacetate as a yellow solid. (ESI) 385.3 (M+H)+.

STEP 3: 1-(4-(3-FLUOROPHENYL)-2-METH-YLPIPERAZIN-1-YL)-N-(PYRIMIDIN-4-YL)ISO-QUINOLINE-6-SULFONAMIDE

A vial was charged with 1-(2-methylpiperazin-1-yl)-N-(pyrimidin-4-yl)isoquinoline-6-sulfonamide 2,2,2-trifluoro-acetate (0.037 g, 0.074 mmol), ruphos palladium(ii) phen-ethylamine chloride (6.06 mg, 7.42 μmol), and sodium tert-butoxide (0.029 g, 0.297 mmol). Dioxane (0.742 ml) and 1-fluoro-3-iodobenzene (0.013 ml, 0.111 mmol) were added and the reaction was flushed with argon and stirred at 100° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 40 g, gradient elution 0-10% MeOH:DCM) to afford 1-(4-(3-fluorophenyl)-2-methylpiperazin-1-yl)-N-(pyrimidin-4-yl) isoquinoline-6-sulfonamide as a tan solid. $^1$H NMR (400 MHz, DMSO-$d_6$) δ=8.64-8.49 (m, 2H), 8.38-8.21 (m, 3H), 7.97 (d, J=10.1 Hz, 1H), 7.68 (d, J=5.8 Hz, 1H), 7.24 (q, J=8.2 Hz, 1H), 7.05 (br. s., 1H), 6.87-6.76 (m, 2H), 6.56 (dt, J=1.9, 8.2 Hz, 1H), 4.02 (d, J=3.1 Hz, 1H), 3.61-3.44 (m, 3H), 3.29-3.22 (m, 1H), 1.08 (d, J=6.3 Hz, 5H). m/z (ESI) 479.2 (M+H)$^+$.

EXAMPLE 404

1-(4-CHLORO-2-(CYANOMETHOXY)PHENYL)-N-(1,2,4-THIADIAZOL-5-YL)ISOQUINOLINE-6-SULFONAMIDE 2,2,2-TRIFLUOROACETATE

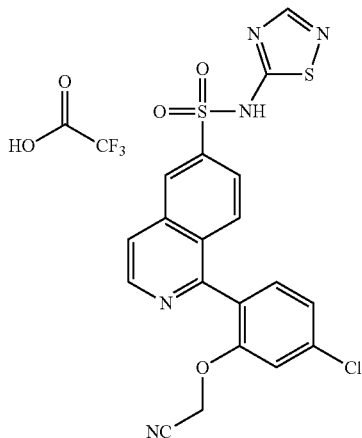 [SMILES: O=C(O)C(F)(F)F ; N#CCOc1cc(Cl)ccc1-c1nccc2cc(S(=O)(=O)Nc3ncns3)ccc12]

The title compound was prepared in an analogous manner to that described for Example 373, using 1-chloro-N-(2,4-dimethoxybenzyl)-N-(1,2,4-thiadiazol-5-yl)isoquinoline-6-sulfonamide (Intermediate X) instead of 1-chloro-N-(4-methoxybenzyl)-N-(thiazol-2-yl)isoquinoline-6-sulfonamide (Intermediate JJJ) in the first step. m/z (ESI) 458.0 (M+H)$^+$.

EXAMPLE 405

1-(4-FLUORO-2-METHOXYPHENYL)-N-(THIAZOL-2-YL)ISOQUINOLINE-6-SULFONAMIDE

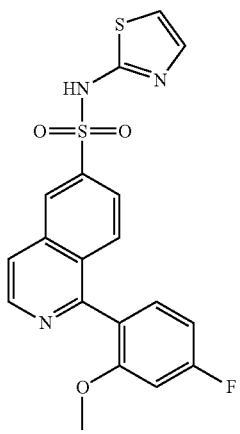 [SMILES: COc1cc(F)ccc1-c1nccc2cc(S(=O)(=O)Nc3nccs3)ccc12]

The title compound was prepared in an analogous manner to that described for Example 189, using (4-fluoro-2-methoxyphenyl)boronic acid in place of (4-fluoro-2-hydroxyphenyl)boronic acid. m/z (ESI) 416.0 (M+H)$^+$.

EXAMPLE 406

1-(2-METHOXYPHENYL)-N-(THIAZOL-2-YL)ISOQUINOLINE-6-SULFONAMIDE

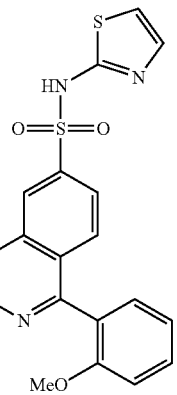

The title compound was prepared in an analogous manner to that described for Example 189, using (2-methoxyphenyl)boronic acid in place of (4-fluoro-2-hydroxyphenyl)boronic acid. m/z (ESI) 398.1 (M+H)$^+$.

EXAMPLE 407

1-(2-METHOXYPYRIDIN-3-YL)-N-(THIAZOL-2-YL)ISOQUINOLINE-6-SULFONAMIDE

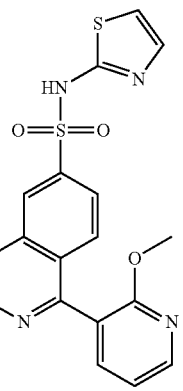

The title compound was prepared in an analogous manner to that described for Example 189, using (2-methoxypyridin- 3-yl)boronic acid in place of (4-fluoro-2-hydroxyphenyl)boronic acid. m/z (ESI) 399.0 (M+H)+.

EXAMPLE 408

1-(6-CHLORO-2-METHOXYPYRIDIN-3-YL)-N-(THIAZOL-2-YL)ISOQUINOLINE-6-SULFONAMIDE

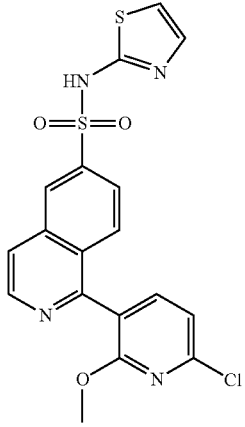 [SMILES: COc1nc(Cl)ccc1-c1nccc2cc(S(=O)(=O)Nc3nccs3)ccc12]

The title compound was prepared in an analogous manner to that described for Example 189, using (6-chloro-2-methoxypyridin-3-yl)boronic acid in place of (4-fluoro-2-hydroxyphenyl)boronic acid. m/z (ESI) 433.1 (M+H)+.

EXAMPLE 409

1-(2-METHOXY-5-(TRIFLUOROMETHYL)PYRIDIN-3-YL)-N-(THIAZOL-2-YL)ISOQUINOLINE-6-SULFONAMIDE

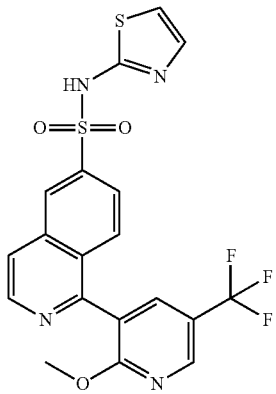 [SMILES: COc1ncc(C(F)(F)F)cc1-c1nccc2cc(S(=O)(=O)Nc3nccs3)ccc12]

The title compound was prepared in an analogous manner to that described for Example 189, using (2-methoxy-5-(trifluoromethyl)pyridin-3-yl)boronic acid in place of (4-fluoro-2-hydroxyphenyl)boronic acid. m/z (ESI) 467.0 (M+H)+.

EXAMPLE 410

1-(5-FLUORO-2-METHOXYPYRIDIN-3-YL)-N-(THIAZOL-2-YL)ISOQUINOLINE-6-SULFONAMIDE

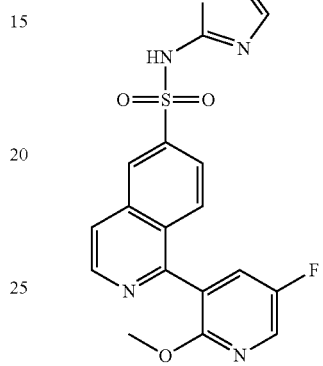

The title compound was prepared in an analogous manner to that described for Example 189, using (2-methoxy-5-(trifluoromethyl)pyridin-3-yl)boronic acid in place of (4-fluoro-2-hydroxyphenyl)boronic acid. m/z (ESI) 417.0 (M+H)+.

EXAMPLE 411

1-(2-METHOXY-5-METHYLPYRIDIN-3-YL)-N-(THIAZOL-2-YL)ISOQUINOLINE-6-SULFONAMIDE

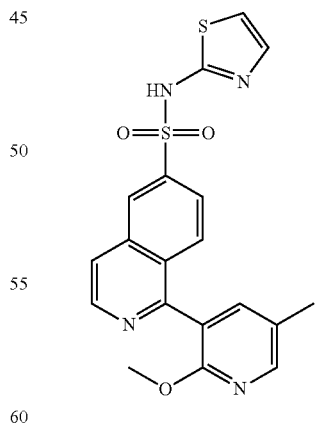

The title compound was prepared in an analogous manner to that described for Example 189, using (2-methoxy-5-methylpyridin-3-yl)boronic acid in place of (4-fluoro-2-hydroxyphenyl)boronic acid. m/z (ESI) 413.0 (M+H)+.

EXAMPLE 412

1-(2-METHOXY-6-METHYLPYRIDIN-3-YL)-N-(THIAZOL-2-YL)ISOQUINOLINE-6-SULFONAMIDE

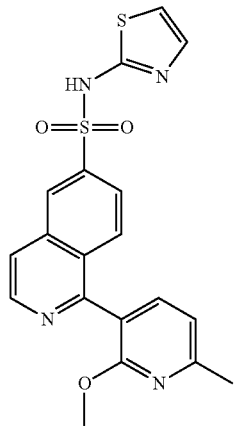 [SMILES: COc1nc(C)ccc1-c1nccc2cc(S(=O)(=O)Nc3nccs3)ccc12]

The title compound was prepared in an analogous manner to that described for Example 189, using (2-methoxy-6-methylpyridin-3-yl)boronic acid in place of (4-fluoro-2-hydroxyphenyl)boronic acid. m/z (ESI) 413.0 (M+H)+.

EXAMPLE 413

1-(2-(DIFLUOROMETHOXY)-5-FLUOROPHENYL)-N-(THIAZOL-2-YL)ISOQUINOLINE-6-SULFONAMIDE

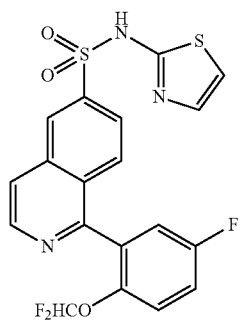 [SMILES: O=S(=O)(Nc1nccs1)c1ccc2c(-c3cc(F)ccc3OC(F)F)nccc2c1]

The title compound was prepared in an analogous manner to that described for Example 189, using (2-(difluoromethoxy)-5-fluorophenyl)boronic acid in place of (4-fluoro-2-hydroxyphenyl)boronic acid. m/z (ESI) 452.1 (M+H)+.

EXAMPLE 414

1-(4-FLUORO-2-((TETRAHYDRO-2H-PYRAN-4-YL)OXY)PHENYL)-N-(THIAZOL-2-YL)ISOQUINOLINE-6-SULFONAMIDE

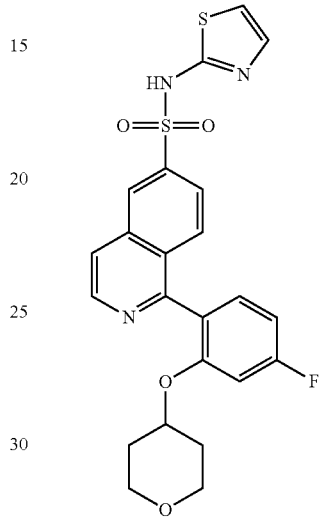

The title compound was prepared in an analogous manner to that described for Example 190, using (4-bromotetrahydro-2H-pyran in place of 3-chloropyridazine. m/z (ESI) 486.0 (M+H)+.

EXAMPLE 415

1-(2-(1-CYANOETHOXY)-4-FLUOROPHENYL)-N-(THIAZOL-2-YL)ISOQUINOLINE-6-SULFONAMIDE

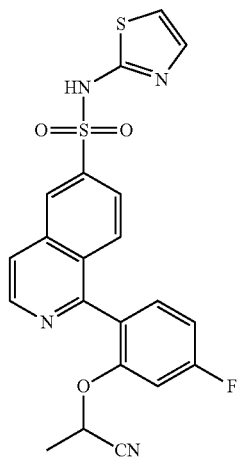 [SMILES: CC(C#N)Oc1cc(F)ccc1-c1nccc2cc(S(=O)(=O)Nc3nccs3)ccc12]

The title compound was prepared in an analogous manner to that described for Example 190, using 2-bromopropanenitrile in place of 3-chloropyridazine. m/z (ESI) 455.1 (M+H)+.

EXAMPLE 416

1-(2-(CYANOFLUOROMETHOXY)-4-FLUOROPHENYL)-N-(THIAZOL-2-YL)ISOQUINOLINE-6-SULFONAMIDE

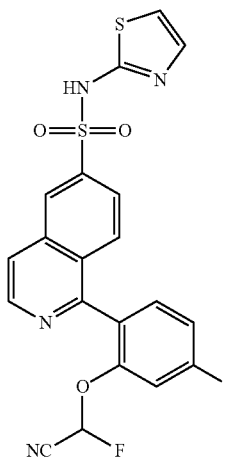

The title compound was prepared in an analogous manner to that described for Example 190, using fluorolodoacetonitrile in place of 3-chloropyridazine. m/z (ESI) 459.0 (M+H)+.

EXAMPLE 417

2-(5-FLUORO-2-(6-(N-(THIAZOL-2-YL)SULFAMOYL)ISOQUINOLIN-1-YL)PHENOXY)ACETAMIDE

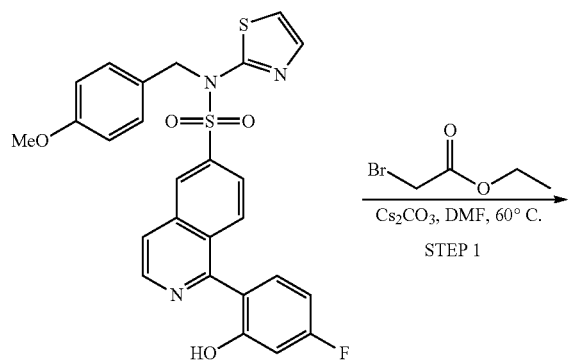

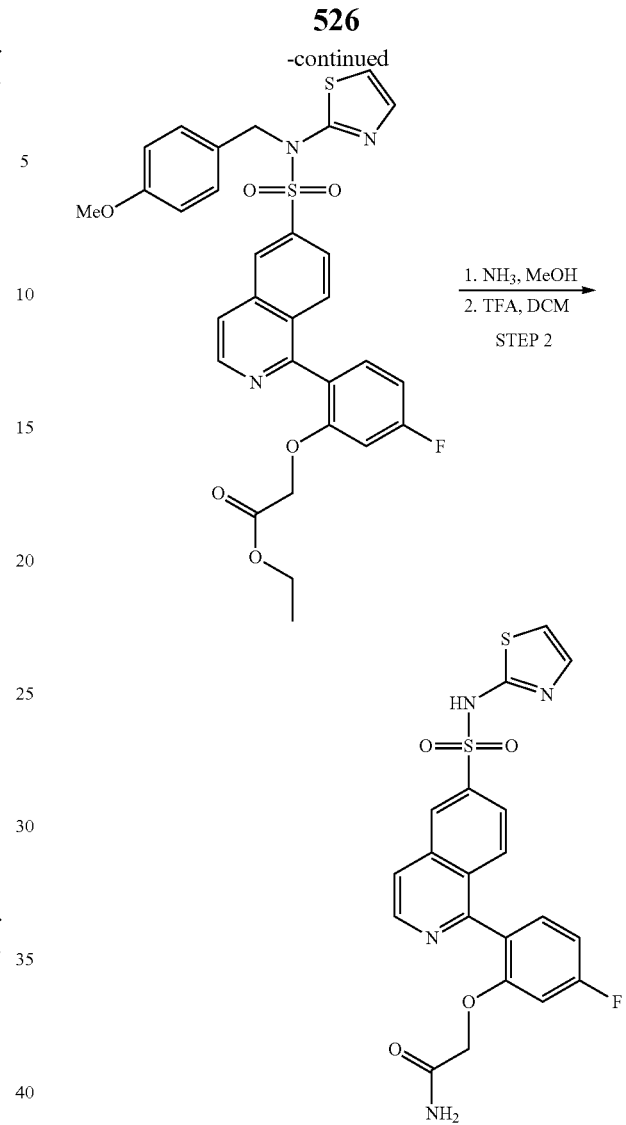

STEP 1: ETHYL 2-(5-FLUORO-2-(6-(N-(4-METHOXYBENZYL)-N-(THIAZOL-2-YL)SULFAMOYL)ISOQUINOLIN-1-YL)PHENOXY)ACETATE

A mixture of Cs$_2$CO$_3$ (0.281 g, 0.863 mmol), ethyl bromoacetate (0.048 ml, 0.431 mmol) and 1-(4-fluoro-2-hydroxyphenyl)-N-(4-methoxybenzyl)-N-(thiazol-2-yl)isoquinoline-6-sulfonamide (From Step 1 in Example 189; 0.15 g, 0.288 mmol) in DMF (2.88 ml) was stirred at 60° C. for 16 h. The reaction mixture was diluted with EtOAc (75 mL) and washed with water (2×50 mL). The organic layer was dried over anhydrous sodium sulfate, concentrated and purified by silica gel chromatography (25 g column), eluting with EtOAc:Hex: 0-50% to obtain ethyl 2-(5-fluoro-2-(6-(N-(4-methoxybenzyl)-N-(thiazol-2-yl)sulfamoyl)isoquinolin-1-yl)phenoxy)acetate as light yellow solid. m/z (ESI) 608.3 (M+H)+.

STEP 2: 2-(5-FLUORO-2-(6-(N-(THIAZOL-2-YL)SULFAMOYL)ISOQUINOLIN-1-YL)PHENOXY)ACETAMIDE

Ethyl 2-(5-fluoro-2-(6-(N-(4-methoxybenzyl)-N-(thiazol-2-yl)sulfamoyl)isoquinolin-1-yl)phenoxy)acetate was dissolved in methanolic ammonia and heated at 60° C. for 16 h in a sealed tube. The reaction mixture was concentrated to obtain 2-(5-fluoro-2-(6-(N-(4-methoxybenzyl)-N-(thiazol-2-yl)sulfamoyl)isoquinolin-1-yl)phenoxy)acetamide as light yellow solid. m/z (ESI) 579.2 (M+H)⁺. This was then dissolved in DCM (1 mL) and 4 drops of TFA were added and the reaction was stirred for 15 min. The reaction mixture was loaded on 10 g silica gel column and eluted with DCM:MeOH (90:10) up to 100% to obtain 2-(5-fluoro-2-(6-(N-(thiazol-2-yl)sulfamoyl)isoquinolin-1-yl)phenoxy)acetamide (3.9 mg, 8.51 μmol, 2.96% yield) as light yellow solid. m/z (ESI) 459.0 (M+H)⁺.

EXAMPLE 418

2937163 (119041-9-2): 1-(6-ISOBUTOXY-2-METHOXYPYRIDIN-3-YL)-N-(PYRIMIDIN-4-YL)ISOQUINOLINE-6-SULFONAMIDE

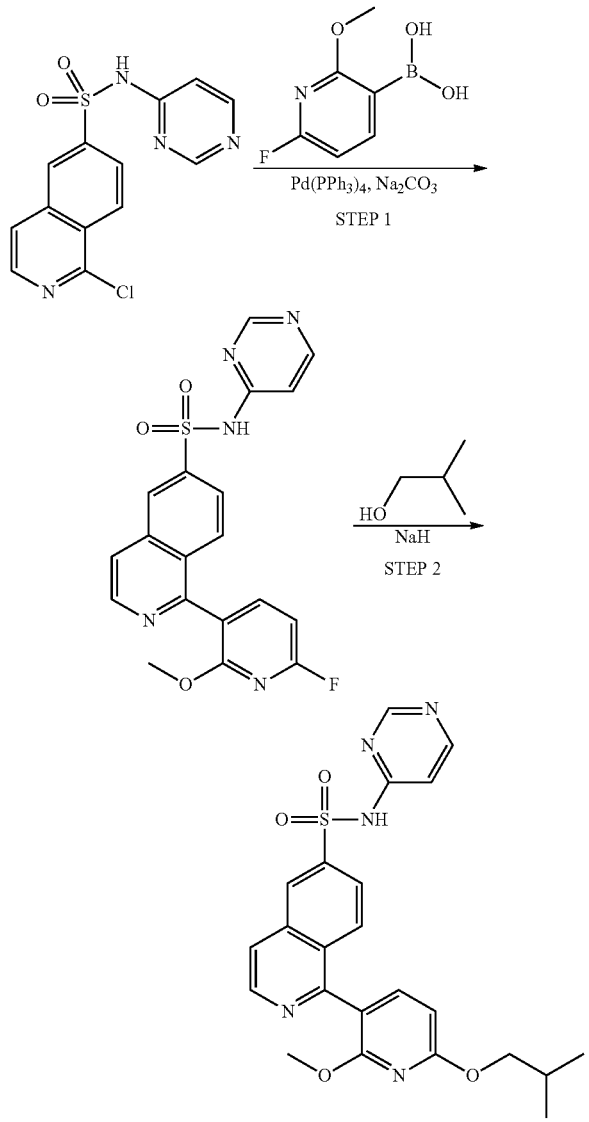

STEP 1: 1-(6-FLUORO-2-METHOXYPYRIDIN-3-YL)-N-(PYRIMIDIN-4-YL)ISOQUINOLINE-6-SULFONAMIDE

To a microwave vial containing Na₂CO₃ (1.216 ml, 2.432 mmol), (6-fluoro-2-methoxypyridin-3-yl)boronic acid (0.166 g, 0.973 mmol) and 1-chloro-N-(pyrimidin-4-yl)isoquinoline-6-sulfonamide (0.26 g, 0.811 mmol) and Dioxane (4.05 ml) was added tetrakis(triphenylphosphine)palladium (0.094 g, 0.081 mmol) and purged with nitrogen and irradiated at 100° C. for 30 min. The reaction mixture was diluted with DMSO to dissolve the observed yellow ppt. Purification was done on reverse phase HPLC with 0.1% NH4OH in ACN and water as mobile phase to obtain 1-(6-fluoro-2-methoxypyridin-3-yl)-N-(pyrimidin-4-yl)isoquinoline-6-sulfonamide (133.2 mg, 0.324 mmol, 39.9% yield) as yellow solid; m/z (ESI) 412.0 (M+H)⁺.

STEP 2: 1-(6-ISOBUTOXY-2-METHOXYPYRIDIN-3-YL)-N-(PYRIMIDIN-4-YL)ISOQUINOLINE-6-SULFONAMIDE

To a ice cold solution of 2-methylpropan-1-ol (110 mg, 1.483 mmol) in DMF (1483 μl) was added sodium hydride (59.3 mg, 1.483 mmol) under nitrogen and stirred for 10 min to this was then added a solution of 1-(6-fluoro-2-methoxypyridin-3-yl)-N-(pyrimidin-4-yl)isoquinoline-6-sulfonamide (122 mg, 0.297 mmol) in DMF (1483 μl) and stirred for 16 h slowly raising the temperature to ambient temperature. The reaction mixture was quenched with MeOH, concentrated and purified via reverse phase HPLC (0.1% NH₄OH in ACN and water as mobile phase) to obtain 1-(6-isobutoxy-2-methoxypyridin-3-yl)-N-(pyrimidin-4-yl)isoquinoline-6-sulfonamide as light yellow solid (56 mg, 120 mmol, 41% yield). m/z (ESI) 466.2 (M+H)⁺.

EXAMPLE 419

N-(4-CHLOROTHIAZOL-2-YL)-1-(2-METHOXY-4-(TRIFLUOROMETHYL)PHENYL)ISOQUINOLINE-6-SULFONAMIDE

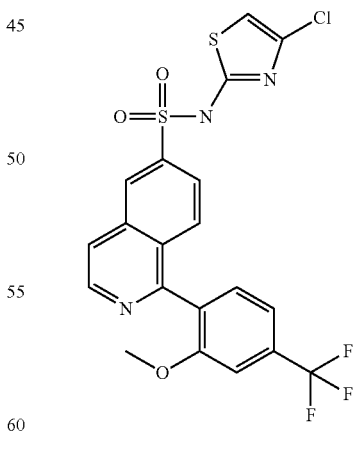

Intermediate LLL (100 mg, 0.182 mmol) and 4-chlorothiazol-2-ylamine (28.2 mg, 0.209 mmol) were combined in a microwave tube and sealed. The tube was evacuated and backfilled with N₂. THF (910 μl) was added and the tube was cooled to 0° C. Lithium bis(trimethylsilyl)amide (382 μl, 0.382 mmol) was added drop wise and the reaction mixture was allowed to warm to room temperature. The reaction mixture was purified by trifluoroacetic acid-modified preparative HPLC: The crude reaction mixture was taken up in minimal methanol and purified {15-85% (0.1% TFA in CH3CN) in H₂O over 20 min}. Clean fractions were combined and concentrated on the lyophilizer to afford pure N-(4-chlorothiazol-2-yl)-1-(2-methoxy-4-(trifluoromethyl)phenyl)isoquinoline-6-sulfonamide as a tan solid. m/z (ESI) 500.1 (M+H)+.

EXAMPLE 420

N-(5-CHLOROTHIAZOL-2-YL)-1-(2-METHOXY-4-(TRIFLUOROMETHYL)PHENYL)ISOQUINOLINE-6-SULFONAMIDE

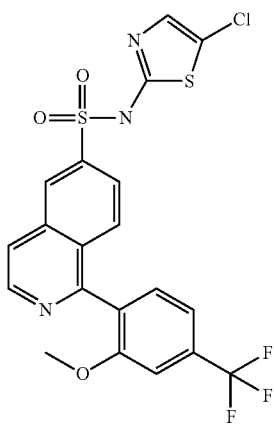 [SMILES: COc1cc(C(F)(F)F)ccc1-c1nccc2cc(S(=O)(=O)Nc3ncc(Cl)s3)ccc12]

N-(5-chlorothiazol-2-yl)-1-(2-methoxy-4-(trifluoromethyl)phenyl)isoquinoline-6-sulfonamide was prepared in analogous fashion to Example 419, utilizing 2-amino-5-chlorothiazole hydrochloride instead of 4-chloro-thiazol-2-ylamine m/z (ESI) 500.1 (M+H)+.

EXAMPLE 421

N-(4-CYANOTHIAZOL-2-YL)-1-(2-METHOXY-4-(TRIFLUOROMETHYL)PHENYL)ISOQUINOLINE-6-SULFONAMIDE

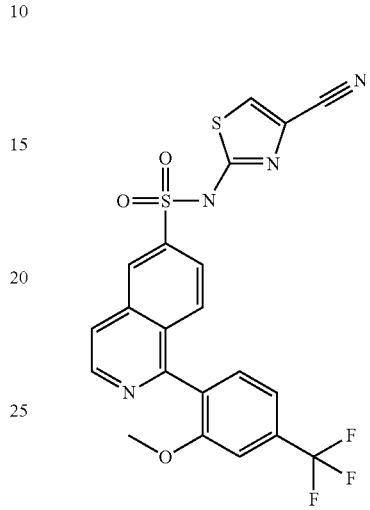

N-(4-cyanothiazol-2-yl)-1-(2-methoxy-4-(trifluoromethyl)phenyl)isoquinoline-6-sulfonamide was prepared in analogous fashion to Example 419, utilizing 2-amino-4-cyanothiazole instead of 4-chloro-thiazol-2-ylamine and utilizing ammonium hydroxide as a modifier for the HPLC purification instead of TFA. m/z (ESI) 491.0 (M+H)+.

EXAMPLE 422

N-(6-CHLOROPYRIMIDIN-4-YL)-1-(2-METHOXY-4-(TRIFLUOROMETHYL)PHENYL)ISOQUINOLINE-6-SULFONAMIDE

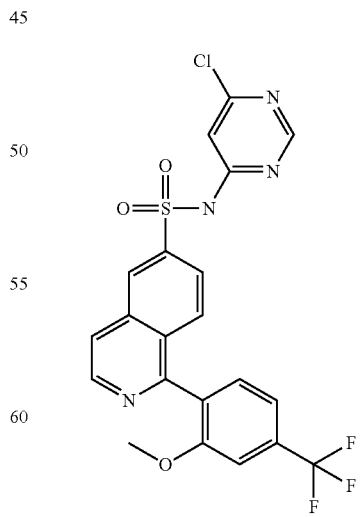

N-(6-chloropyrimidin-4-yl)-1-(2-methoxy-4-(trifluoromethyl)phenyl)isoquinoline-6-sulfonamide was prepared in analogous fashion to Example 419, utilizing 6-chloropyrimidin-4-amine instead of 4-chloro-thiazol-2-ylamine m/z (ESI) 495.0 (M+H)+.

EXAMPLE 423

N-(6-CHLOROPYRIMIDIN-4-YL)-1-(2-METHOXY-4-(TRIFLUOROMETHYL)PHENYL)ISOQUINOLINE-6-SULFONAMIDE

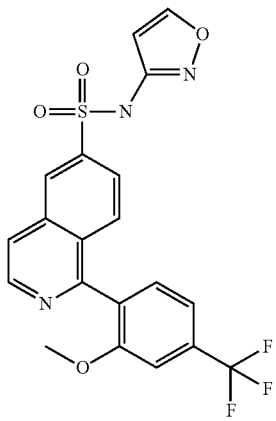 [SMILES: COc1cc(C(F)(F)F)ccc1-c1nccc2cc(S(=O)(=O)Nc3ccon3)ccc12]

N-(6-chloropyrimidin-4-yl)-1-(2-methoxy-4-(trifluoromethyl)phenyl)isoquinoline-6-sulfonamide was prepared in analogous fashion to Example 419, utilizing 3-aminoisoxazole instead of 4-chloro-thiazol-2-ylamine m/z (ESI) 450.0 (M+H)+.

EXAMPLE 424

1-(2-METHOXY-4-(TRIFLUOROMETHYL)PHENYL)-N-(4-METHYLTHIAZOL-2-YL)ISOQUINOLINE-6-SULFONAMIDE

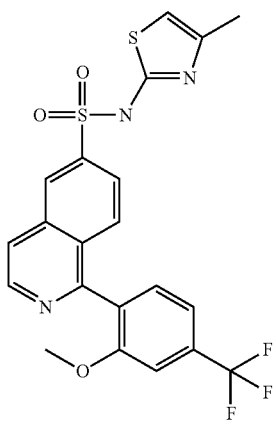 [SMILES: COc1cc(C(F)(F)F)ccc1-c1nccc2cc(S(=O)(=O)Nc3nc(C)cs3)ccc12]

1-(2-methoxy-4-(trifluoromethyl)phenyl)-N-(4-methylthiazol-2-yl)isoquinoline-6-sulfonamide was prepared in analogous fashion to Example 419, utilizing 2-amino-4-methylthiazole instead of 4-chloro-thiazol-2-ylamine m/z (ESI) 480.0 (M+H)+.

EXAMPLE 425

N-(5-CHLORO-1,3,4-THIADIAZOL-2-YL)-1-(2-METHOXY-4-(TRIFLUOROMETHYL)PHENYL) ISOQUINOLINE-6-SULFONAMIDE

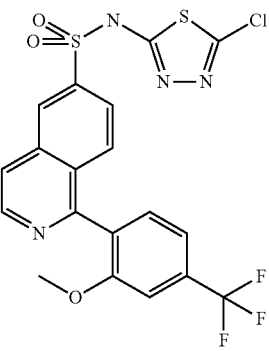 [SMILES: COc1cc(C(F)(F)F)ccc1-c1nccc2cc(S(=O)(=O)Nc3nnc(Cl)s3)ccc12]

Cesium carbonate (32.8 μl, 0.410 mmol), Intermediate LLL (75 mg, 0.137 mmol), and 5-chloro-1,3,4-thiadiazol-2-amine (37.0 mg, 0.273 mmol) were combined in a microwave tube. The tube was evacuated and backfilled with $N_2$, and then DMF (683 μl) was added. The reaction mixture was stirred at room temp for 2 hrs. LCMS analysis indicated the presence of N-(5-chloro-1,3,4-thiadiazol-2-yl)-1-(2-methoxy-4-(trifluoromethyl)phenyl)isoquinoline-6-sulfonamide. The residue was purified using reverse-phase HPLC with a Waters-Xbridge C18, 19×100 mm, 10 μm column with a gradient 5-95% acetonitrile and water with 0.1% ammonium hydroxide modifier to yield N-(5-chloro-1,3,4-thiadiazol-2-yl)-1-(2-methoxy-4-(trifluoromethyl)phenyl)isoquinoline-6-sulfonamide. m/z (ESI) 503.0 (M+H)+.

EXAMPLE 426

N-(5-CHLORO-1,3,4-THIADIAZOL-2-YL)-1-(2-METHOXY-4-(TRIFLUOROMETHYL)PHENYL) ISOQUINOLINE-6-SULFONAMIDE

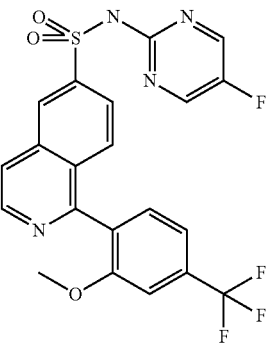 [SMILES: COc1cc(C(F)(F)F)ccc1-c1nccc2cc(S(=O)(=O)Nc3ncc(F)cn3)ccc12]

N-(5-chloro-1,3,4-thiadiazol-2-yl)-1-(2-methoxy-4-(trifluoromethyl)phenyl)isoquinoline-6-sulfonamide was prepared in analogous fashion to Example 419, utilizing 5-fluoropyrimidin-2-amine instead of 4-chloro-thiazol-2-ylamine m/z (ESI) 479.1 (M+H)+.

EXAMPLE 427

N-(5-FLUOROPYRIDIN-2-YL)-1-(2-METHOXY-4-(TRIFLUOROMETHYL)PHENYL)ISOQUINO-LINE-6-SULFONAMIDE

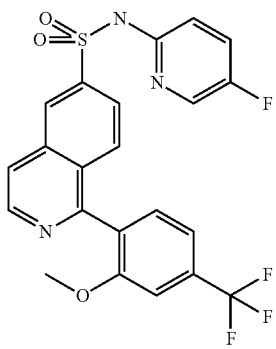 [SMILES: COc1cc(C(F)(F)F)ccc1-c1nccc2cc(S(=O)(=O)Nc3ccc(F)cn3)ccc12]

N-(5-fluoropyridin-2-yl)-1-(2-methoxy-4-(trifluoromethyl)phenyl)isoquinoline-6-sulfonamide was prepared in analogous fashion to Example 419, utilizing 2-amino-5-fluoropyridine instead of 4-chloro-thiazol-2-ylamine m/z (ESI) 477.9 (M+H)+.

EXAMPLE 428

1-(2-METHOXY-4-(TRIFLUOROMETHYL)PHE-NYL)-N-(4-(TRIFLUOROMETHYL)THIAZOL-2-YL)ISOQUINOLINE-6-SULFONAMIDE

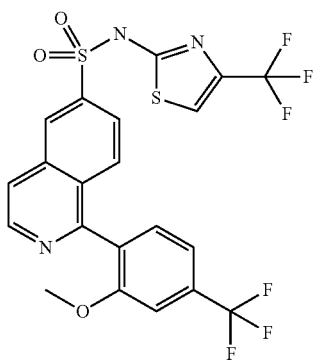 [SMILES: COc1cc(C(F)(F)F)ccc1-c1nccc2cc(S(=O)(=O)Nc3nc(C(F)(F)F)cs3)ccc12]

1-(2-methoxy-4-(trifluoromethyl)phenyl)-N-(4-(trifluoromethyl)thiazol-2-yl)isoquinoline-6-sulfonamide was prepared in an analogous fashion to Example 425 utilizing 4-(trifluoromethyl)thiazol-2-amine instead of 5-chloro-1,3,4-thiadiazol-2-amine m/z (ESI) 534.0 (M+H)+.

EXAMPLE 429

1-(1-(3-CHLOROPHENYL)-1H-PYRAZOL-4-YL)-N-(PYRIMIDIN-4-YL)ISOQUINOLINE-6-SUL-FONAMIDE

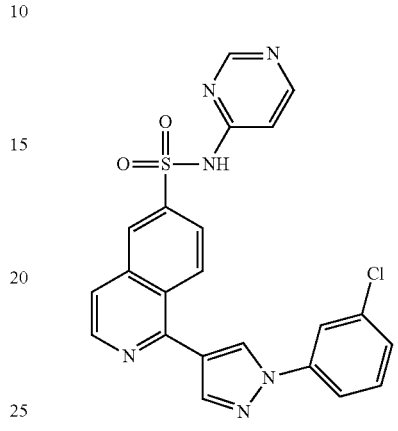

A vial was charged with 1-chloro-N-(pyrimidin-4-yl)isoquinoline-6-sulfonamide (Intermediate GG) (53 mg, 0.17 mmol), (1-(3-chlorophenyl)-1H-pyrazol-4-yl)boronic acid (44 mg, 0.200 mmol), Pd(AmPhos)$_2$Cl$_2$ (12 mg, 0.017 mmol), potassium phosphate (106 mg, 0.500 mmol), dioxane (1.042 µl), and water (0.347 µl). The vial was sealed and heated in an oil bath overnight at 100° C. The crude reaction mixture was purified using reverse-phase HPLC with a Waters-Xbridge C18, 19×100 mm, 10 µm column with a gradient 5-95% acetonitrile and water with 0.1% ammonium hydroxide modifier to yield 1-(1-(3-chlorophenyl)-1H-pyrazol-4-yl)-N-(pyrimidin-4-yl)isoquinoline-6-sulfonamide. m/z (ESI) 463.0 (M+H)$^+$.

EXAMPLE 430

1-(5-ISOPROPYL-1H-INDAZOL-4-YL)-N-(PYRI-MIDIN-4-YL)ISOQUINOLINE-6-SULFONAMIDE

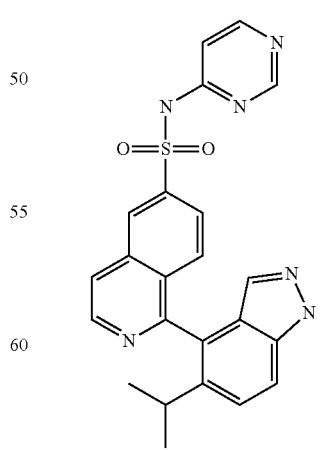

1-(5-isopropyl-1H-indazol-4-yl)-N-(pyrimidin-4-yl)isoquinoline-6-sulfonamide was prepared in an analogous fashion to Example 429, utilizing (5-isopropyl-1H-indazol-4-yl) boronic acid instead of (1-(3-chlorophenyl)-1H-pyrazol-4-yl)boronic acid. m/z (ESI) 445.0 (M+H)+.

EXAMPLE 431

1-(3-((4-METHYLPIPERAZIN-1-YL)METHYL) PHENYL)-N-(PYRIMIDIN-4-YL)ISOQUINO-LINE-6-SULFONAMIDE

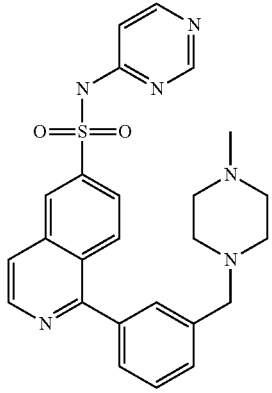 [SMILES: CN1CCN(Cc2cccc(-c3nccc4cc(S(=O)(=O)Nc5ccncn5)ccc34)c2)CC1]

1-(3-((4-methylpiperazin-1-yl)methyl)phenyl)-N-(pyrimidin-4-yl)isoquinoline-6-sulfonamide was prepared in an analogous fashion to Example 429, utilizing (3-((4-methylpiperazin-1-yl)methyl)phenyl)boronic acid instead of (1-(3-chlorophenyl)-1H-pyrazol-4-yl)boronic acid. m/z (ESI) 474.8 (M+H)+.

EXAMPLE 432

1-(2,3-DIFLUORO-4-(PIPERIDIN-1-YL)PHE-NYL)-N-(PYRIMIDIN-4-YL)ISOQUINOLINE-6-SULFONAMIDE

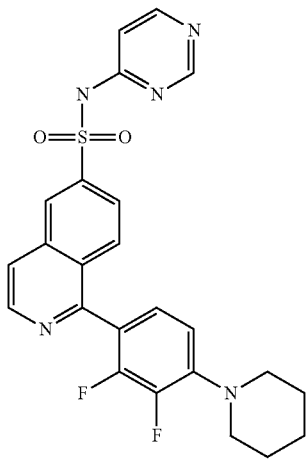 [SMILES: O=S(=O)(Nc1ccncn1)c1ccc2c(-c3ccc(N4CCCCC4)c(F)c3F)nccc2c1]

1-(2,3-difluoro-4-(piperidin-1-yl)phenyl)-N-(pyrimidin-4-yl)isoquinoline-6-sulfonamide was prepared in an analogous fashion to Example 429, utilizing (2,3-difluoro-4-(piperidin-1-yl)phenyl)boronic acid instead of (1-(3-chlorophenyl)-1H-pyrazol-4-yl)boronic acid. m/z (ESI) 482.0 (M+H)+.

EXAMPLE 433

1-(4-(N,N-DIMETHYLSULFAMOYL)-2-METH-YLPHENYL)-N-(PYRIMIDIN-4-YL)ISOQUINO-LINE-6-SULFONAMIDE

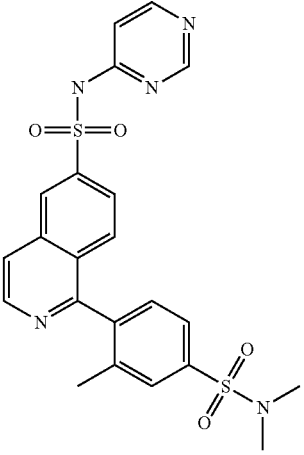 [SMILES: Cc1cc(S(=O)(=O)N(C)C)ccc1-c1nccc2cc(S(=O)(=O)Nc3ccncn3)ccc12]

1-(4-(N,N-dimethylsulfamoyl)-2-methylphenyl)-N-(pyrimidin-4-yl)isoquinoline-6-sulfonamide was prepared in an analogous fashion to Example 429, utilizing (4-(N,N-dimethylsulfamoyl)-2-methylphenyl)boronic acid instead of (1-(3-chlorophenyl)-1H-pyrazol-4-yl)boronic acid. m/z (ESI) 483.8 (M+H)+.

EXAMPLE 434

1-(1H-INDOL-7-YL)-N-(PYRIMIDIN-4-YL)ISO-QUINOLINE-6-SULFONAMIDE

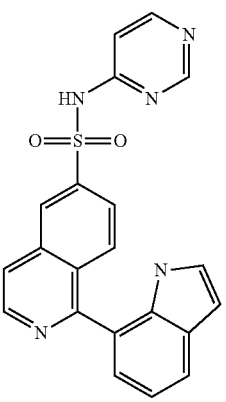 [SMILES: O=S(=O)(Nc1ccncn1)c1ccc2c(-c3cccc4cc[nH]c34)nccc2c1]

1-(1H-indol-7-yl)-N-(pyrimidin-4-yl)isoquinoline-6-sulfonamide was prepared in an analogous fashion to Example 429 utilizing (1H-indol-7-yl)boronic acid instead of (1-(3-chlorophenyl)-1H-pyrazol-4-yl)boronic acid. m/z (ESI) 402.0 (M+H)+.

EXAMPLE 440

1-(2-METHOXY-4-(TRIFLUOROMETHYL)PHENYL)-N-(OXAZOL-4-YL)ISOQUINOLINE-6-SULFONAMIDE

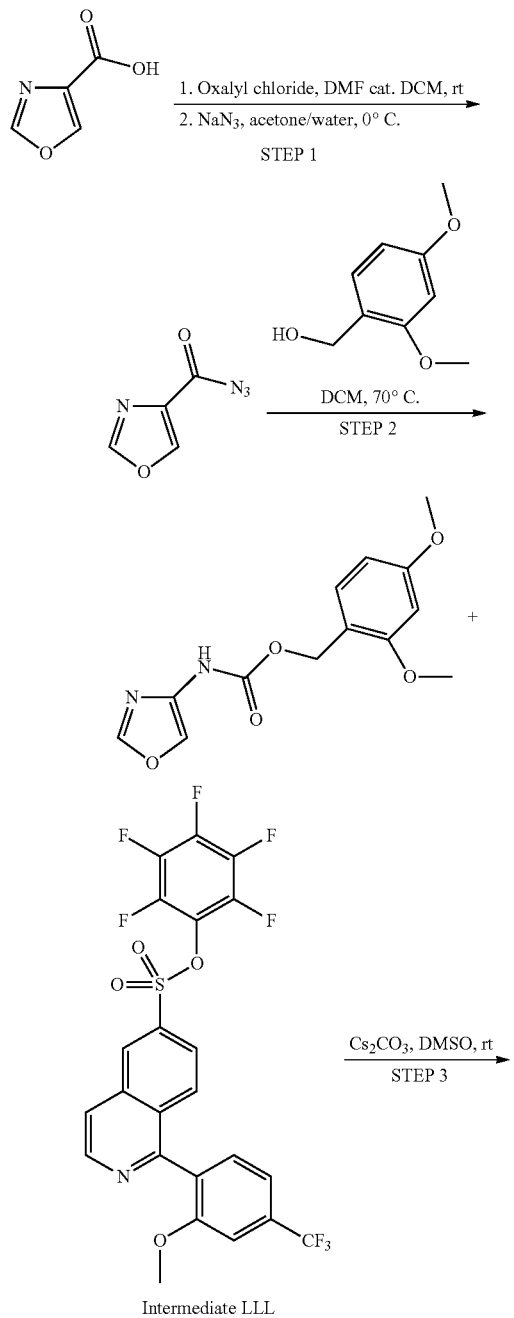

Intermediate LLL

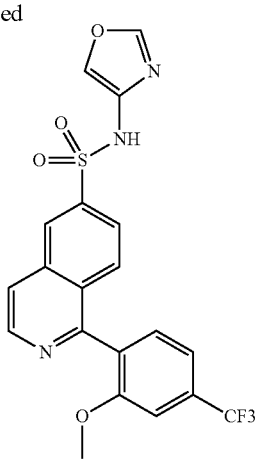

STEP 1: OXAZOLE-4-CARBONYL AZIDE

In a 10-mL round bottom flask under $N_2$ were dissolved 4-oxazolecarboxylic acid (500 mg, 4.42 mmol) and oxalyl chloride (1.94 mL, 22.1 mmol) with 2 drop of DMF in 10 mL of DCM. The reaction was stirred at rt for 2 h. The reaction mixture was concentrated under reduced pressure and the material was carried forward crude. Under $N_2$, oxazole-4-carbonyl chloride (crude) was dissolved in 10 mL of acetone and treated at 0° C. with a solution of sodium azide (575 mg, 8.84 mmol) in 1.0 mL of water. After 1 h, the reaction mixture was diluted with AcOEt then neutralized with $H_2O$. The aqueous phase was extracted 3× with AcOEt then the organic layers were dried over $Na_2SO_4$, filtered and concentrated under reduced pressure. The crude oxazole-4-carbonyl azide (590 mg, 4.27 mmol, 97% yield) was carried forward without further purification into the next step. MS (ESI, positive ion) [M+1]+: 139.0.

STEP 2: 2,4-DIMETHOXYBENZYL OXAZOL-4-YLCARBAMATE

In a 10-mL sealed tube under $N_2$ were dissolved (2,4-dimethoxyphenyl)methanol (1.12 g, 6.63 mmol) and crude oxazole-4-carbonyl azide (590 mg, 4.27 mmol) in 5 mL of DCM and then the reaction was heated at 70° C. for 10 h. The reaction mixture was concentrated under reduced pressure. The crude mixture was purified by silica gel chromatography (ISCO) with Hexanes:AcOEt 100:0 to 0:100 to afford 2,4-dimethoxybenzyl oxazol-4-ylcarbamate (0.850 g, 3.05 mmol, 69.1% yield) as a white solid. MS (ESI, positive ion) [M+1]+: 301.0.

STEP 3: 1-(2-METHOXY-4-(TRIFLUOROMETHYL)PHENYL)-N-(OXAZOL-4-YL)ISOQUINOLINE-6-SULFONAMIDE

In a 5-mL round bottom flask under $N_2$ were dissolved 2,4-dimethoxybenzyl oxazol-4-ylcarbamate (100 mg, 0.359 mmol), perfluorophenyl 1-(2-methoxy-4-(trifluoromethyl)phenyl)isoquinoline-6-sulfonate (182 mg, 0.395 mmol) (Intermediate LLL) and cesium carbonate (351 mg, 1.078 mmol) in 1 mL of DMSO, and then the mixture was stirred at rt for 10 h. The reaction mixture was diluted with AcOEt then neutralized with $NH_4Cl$/Ice. The aqueous phase was extracted 3× with AcOEt then the organic layers were dried over $Na_2SO_4$, filtered and concentrated under reduced pressure. The crude mixture was purified by MPLC (ISCO) with Hexanes:AcOEt 100:0 to 0:100 to afforded 1-(2-methoxy-4-(trifluoromethyl)phenyl)-N-(oxazol-4-yl)isoquinoline-6-sulfonamide (15 mg, 0.033 mmol, 9.29%) as a white solid. MS (ESI, positive ion) [M+1]+: 450.0.

EXAMPLE 441

1-(3-METHOXY-2'-METHYL-[1,1'-BIPHENYL]-4-YL)-N-(PYRIMIDIN-4-YL)ISOQUINOLINE-6-SULFONAMIDE

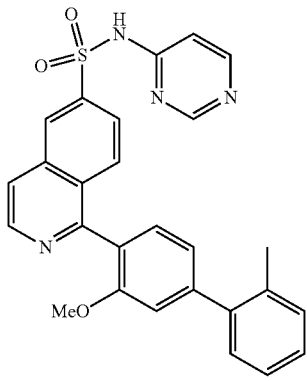 [SMILES: COc1cc(-c2ccccc2C)ccc1-c1nccc2cc(S(=O)(=O)Nc3ccncn3)ccc12]

A microwave vial charged with 2-methylphenylboronic acid (0.022 g, 0.158 mmol), 2-dicyclohexylphosphino-2',6'-dimethoxy-1'1'-biphenyl (4.33 mg, 10.54 μmol), chloro(2-dicyclohexylphosphino-2',6'-dimethoxy-1,1'-biphenyl)[2-(2-aminoethylphenyl)]palladium(ii) dichloromethane (7.99 mg, 10.54 μmol), 1-(4-chloro-2-methoxyphenyl)-N-(pyrimidin-4-yl)isoquinoline-6-sulfonamide (From Example 160; 45 mg, 0.105 mmol), potassium phosphate (90 mg, 0.422 mmol), 1 mL dioxane and 0.25 mL water was heated to 150° C. in the microwave for 30 minutes. LC/MS showed mostly product, so the aqueous layer was removed. The reaction mixture was acidified with 4N HCl in dioxane then was concentrated. The crude product was purified by reverse phase column chromatography [PREP LC/MS-2 System Column: XBridge 19×100 mm 12230326114 03 Mobile phase: 0.1% NH4OH in water/acetonitrile Flow rate: 40 ml/min Inj: 2200 uL. Gradient: 10 min 10-40%_LV_NH3] yielding 1-(3-methoxy-2'-methyl-[1,1'-biphenyl]-4-yl)-N-(pyrimidin-4-yl)isoquinoline-6-sulfonamide (0.017 g, 0.034 mmol, 32.6% yield). 1H NMR (500 MHz, DMSO-d6) δ ppm 2.36 (s, 3H) 3.68 (s, 3H) 6.95 (br. s., 1H) 7.08 (d, J=7.27 Hz, 1H) 7.14 (s, 1H) 7.27 (br. s., 1H) 7.29-7.44 (m, 5H) 7.78 (d, J=8.82 Hz, 1H) 7.97 (d, J=8.71 Hz, 1H) 8.08 (d, J=5.96 Hz, 1H) 8.18 (br. s., 1H) 8.52 (br. s., 1H) 8.62 (br. s., 1H) 8.68 (d, J=5.56 Hz, 1H); (M+H)+=483.0.

EXAMPLE 442

1-(3-METHOXY-3'-METHYL-[1,1'-BIPHENYL]-4-YL)-N-(PYRIMIDIN-4-YL)ISOQUINOLINE-6-SULFONAMIDE

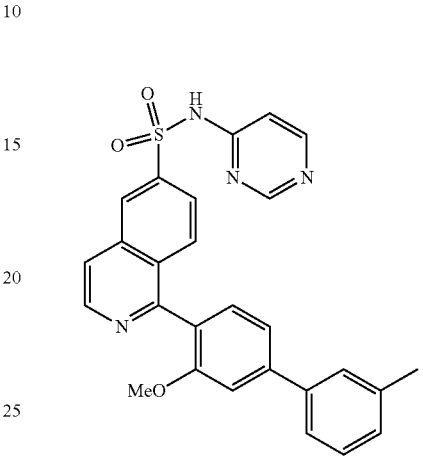

The title compound was prepared in a manner analogous to example 441 except 3-methylphenylboronic acid was used instead of 2-methylphenylboronic acid. 1H NMR (500 MHz, DMSO-d6) δ ppm 2.42 (s, 3H) 3.75 (s, 3H) 7.01 (br. s., 1H) 7.24 (d, J=6.36 Hz, 1H) 7.31-7.46 (m, 4H) 7.56-7.67 (m, 2H) 7.78 (d, J=8.65 Hz, 1H) 7.95 (d, J=8.71 Hz, 1H) 8.08 (d, J=5.84 Hz, 1H) 8.22 (br. s., 1H) 8.55 (s, 1H) 8.63 (br. s., 1H) 8.69 (d, J=5.15 Hz, 1H); (M+H)+=483.0.

EXAMPLE 443

1-(3-METHOXY-4'-METHYL-[1,1'-BIPHENYL]-4-YL)-N-(PYRIMIDIN-4-YL)ISOQUINOLINE-6-SULFONAMIDE

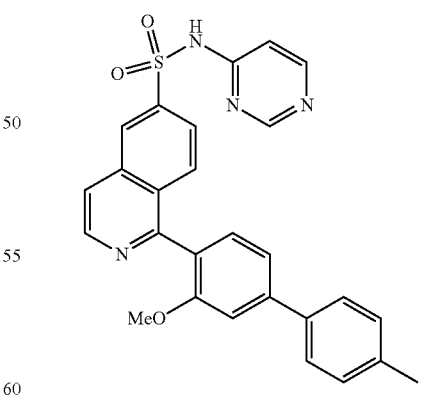

The title compound was prepared in a manner analogous to example 441 except 4-methylphenylboronic acid was used instead of 2-methylphenylboronic acid. 1H NMR (500 MHz, DMSO-d6) δ ppm 2.38 (s, 3H) 3.74 (s, 3H) 7.00 (br. s., 1H) 7.33 (d, J=7.45 Hz, 3H) 7.36-7.44 (m, 3H) 7.72 (d, J=7.67 Hz, 2H) 7.78 (d, J=8.53 Hz, 1H) 7.95 (d, J=8.36 Hz, 1H) 8.08 (d, J=5.50 Hz, 1H) 8.22 (br. s., 1H) 8.55 (s, 1H) 8.63 (br. s., 1H) 8.68 (d, J=5.56 Hz, 1H); (M+H)⁺=483.0.

EXAMPLE 444

1-(2',3'-difluoro-3-methoxy-[1,1'-biphenyl]-4-yl)-N-(pyrimidin-4-yl)isoquinoline-6-sulfonamide

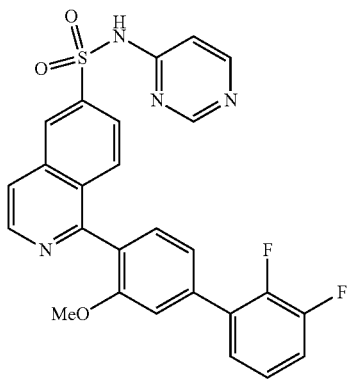 [SMILES: COc1cc(-c2cccc(F)c2F)ccc1-c1nccc2cc(S(=O)(=O)Nc3ccncn3)ccc12]

The title compound was prepared in a manner analogous to example 441 except 2,3-difluorophenylboronic acid was used instead of 2-methylphenylboronic acid. ¹H NMR (500 MHz, DMSO-d6) δ ppm 3.71 (s, 3H) 6.95 (br. s., 1H) 7.33 (d, J=7.50 Hz, 1H) 7.39 (br. s., 2H) 7.46 (d, J=7.27 Hz, 1H) 7.52 (d, J=5.33 Hz, 2H) 7.76 (d, J=8.42 Hz, 1H) 7.96 (d, J=7.96 Hz, 1H) 8.09 (d, J=5.27 Hz, 1H) 8.18 (br. s., 1H) 8.51 (s, 1H) 8.62 (br. s., 1H) 8.68 (d, J=5.38 Hz, 1H); (M+H)+=505.0.

EXAMPLE 445

1-(2',4'-DIFLUORO-3-METHOXY-[1,1'-BIPHE-NYL]-4-YL)-N-(PYRIMIDIN-4-YL)ISOQUINO-LINE-6-SULFONAMIDE

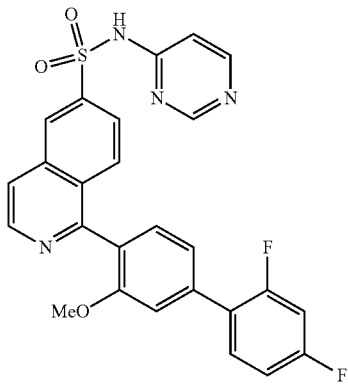 [SMILES: COc1cc(-c2ccc(F)cc2F)ccc1-c1nccc2cc(S(=O)(=O)Nc3ccncn3)ccc12]

The title compound was prepared in a manner analogous to example 441 except 2,4-difluorophenylboronic acid was used instead of 2-methylphenylboronic acid. ¹H NMR (500 MHz, DMSO-d6) δ ppm 3.71 (s, 3H) 7.01 (br. s., 1H) 7.24-7.31 (m, 2H) 7.34 (br. s., 1H) 7.44 (d, J=8.02 Hz, 2H) 7.78 (d, J=8.76 Hz, 2H) 7.97 (d, J=7.73 Hz, 1H) 8.10 (d, J=5.44 Hz, 1H) 8.23 (br. s., 1H) 8.56 (s, 1H) 8.65 (br. s., 1H) 8.69 (d, J=5.21 Hz, 1H); (M+H)⁺=505.0.

EXAMPLE 446

1-(2',5'-DIFLUORO-3-METHOXY-[1,1'-BIPHE-NYL]-4-YL)-N-(PYRIMIDIN-4-YL)ISOQUINO-LINE-6-SULFONAMIDE

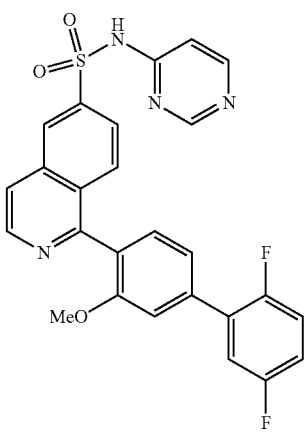 [SMILES: COc1cc(-c2cc(F)ccc2F)ccc1-c1nccc2cc(S(=O)(=O)Nc3ccncn3)ccc12]

The title compound was prepared in a manner analogous to example 441 except 2,5-difluorophenylboronic acid was used instead of 2-methylphenylboronic acid. ¹H NMR (500 MHz, DMSO-d6) δ ppm 3.72 (s, 3H) 6.99 (br. s., 1H) 7.34 (br. s., 3H) 7.39 (br. s., 1H) 7.41-7.47 (m, 2H) 7.61 (br. s., 1H) 7.76 (d, J=8.71 Hz, 1H) 7.96 (d, J=8.59 Hz, 1H) 8.10 (d, J=5.50 Hz, 1H) 8.21 (br. s., 1H) 8.54 (s, 1H) 8.64 (br. s., 1H) 8.69 (d, J=4.87 Hz, 1H); (M+H)+=505.0.

EXAMPLE 447

1-(2',6'-DIFLUORO-3-METHOXY-[1,1'-BIPHE-NYL]-4-YL)-N-(PYRIMIDIN-4-YL)ISOQUINO-LINE-6-SULFONAMIDE

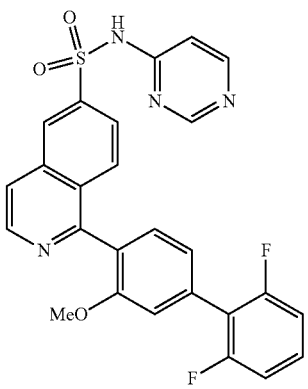 [SMILES: COc1cc(-c2c(F)cccc2F)ccc1-c1nccc2cc(S(=O)(=O)Nc3ccncn3)ccc12]

The title compound was prepared in a manner analogous to example 441 except 2,6-difluorophenylboronic acid was used instead of 2-methylphenylboronic acid. ¹H NMR (500 MHz, DMSO-d6) δ ppm 3.67 (s, 3H) 6.65 (br. s., 1H) 6.98 (br. s., 1H) 7.26 (br. s., 4H) 7.33 (d, J=6.82 Hz, 2H) 7.43 (br. s., 1H) 7.94 (br. s., 2H) 8.45-8.60 (m., 3H); (M+H)+=505.0.

EXAMPLE 448

1-(3',4'-DIFLUORO-3-METHOXY-[1,1'-BIPHENYL]-4-YL)-N-(PYRIMIDIN-4-YL)ISOQUINOLINE-6-SULFONAMIDE

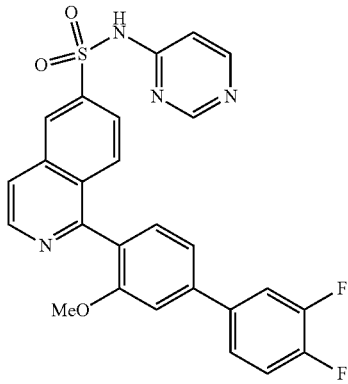 [SMILES: COc1cc(-c2ccc(F)c(F)c2)ccc1-c1nccc2cc(S(=O)(=O)Nc3ccncn3)ccc12]

The title compound was prepared in a manner analogous to example 441 except 3,4-difluorophenylboronic acid was used instead of 2-methylphenylboronic acid. ¹H NMR (500 MHz, DMSO-d6) δ ppm 3.76 (s, 3H) 7.00 (br. s., 1H) 7.43 (d, J=6.47 Hz, 2H) 7.48 (s, 1H) 7.57 (d, J=9.16 Hz, 1H) 7.70 (br. s., 1H) 7.76 (d, J=9.28 Hz, 1H) 7.95 (d, J=7.39 Hz, 2H) 8.09 (d, J=5.79 Hz, 1H) 8.21 (br. s., 1H) 8.55 (s, 1H) 8.64 (br. s., 1H) 8.69 (d, J=5.84 Hz, 2H); (M+H)+=505.0.

EXAMPLE 449

1-(3',5'-DIFLUORO-3-METHOXY-[1,1'-BIPHENYL]-4-YL)-N-(PYRIMIDIN-4-YL)ISOQUINOLINE-6-SULFONAMIDE

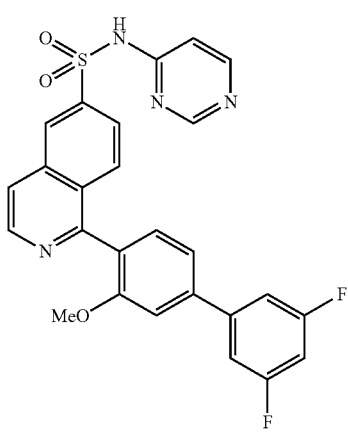 [SMILES: COc1cc(-c2cc(F)cc(F)c2)ccc1-c1nccc2cc(S(=O)(=O)Nc3ccncn3)ccc12]

The title compound was prepared in a manner analogous to example 441 except 3,5-difluorophenylboronic acid was used instead of 2-methylphenylboronic acid. ¹H NMR (500 MHz, DMSO-d6) δ ppm 3.76 (s, 3H) 7.00 (br. s., 1H) 7.29 (br. s., 2H) 7.43 (d, J=7.05 Hz, 1H) 7.47-7.57 (m, 2H) 7.63 (d, J=7.56 Hz, 2H) 7.75 (d, J=9.16 Hz, 1H) 7.95 (d, J=8.76 Hz, 1H) 8.10 (d, J=5.56 Hz, 1H) 8.22 (br. s., 1H) 8.55 (br. s., 1H) 8.64 (br. s., 1H) 8.69 (d, J=5.10 Hz, 1H); (M+H)+=505.0.

EXAMPLE 450

1-(2-METHOXY-4-(PYRIDIN-3-YL)PHENYL)-N-(PYRIMIDIN-4-YL)ISOQUINOLINE-6-SULFONAMIDE

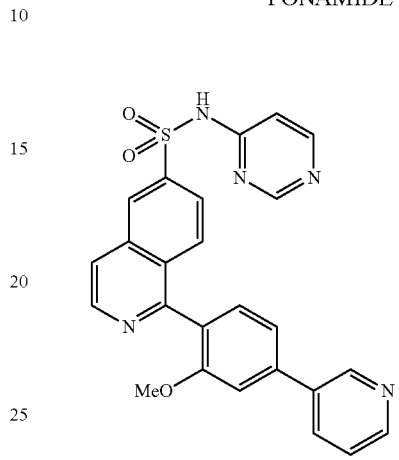

The title compound was prepared in a manner analogous to example 441 except pyridine-3-boronic acid was used instead of 2-methylphenylboronic acid. ¹H NMR (500 MHz, DMSO-d6) δ ppm 3.76 (s, 3H) 6.92 (d, J=5.61 Hz, 1H) 7.44-7.51 (m, 2H) 7.51-7.67 (m, 2H) 7.75 (d, J=8.88 Hz, 1H) 7.95 (d, J=8.13 Hz, 1H) 8.08 (d, J=5.50 Hz, 1H) 8.16 (d, J=5.96 Hz, 1H) 8.23 (d, J=8.02 Hz, 1H) 8.49 (s, 1H) 8.57-8.77 (m, 3H) 9.06 (br. s., 1H); (M+H)+=471.0.

EXAMPLE 451

1-(2-METHOXY-4-(PYRIDIN-4-YL)PHENYL)-N-(PYRIMIDIN-4-YL)ISOQUINOLINE-6-SULFONAMIDE

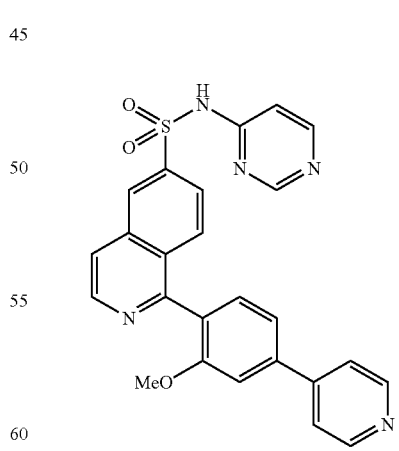

The title compound was prepared in a manner analogous to example 441 except pyridine-4-boronic acid was used instead of 2-methylphenylboronic acid. ¹H NMR (500 MHz, DMSO-d6) δ ppm 3.77 (s, 3H) 7.00 (br. s., 1H) 7.48 (d, J=7.68 Hz, 1H) 7.52-7.63 (m, 2H) 7.76 (d, J=8.48 Hz, 1H) 7.80-7.89 (m, 2H) 7.95 (d, J=9.85 Hz, 1H) 8.10 (d, J=5.67 Hz, 1H) 8.22 (br. s., 1H) 8.55 (s, 1H) 8.64 (br. s., 1H) 8.67-8.74 (m, 3H); (M+H)+=471.0.

INTERMEDIATE NNNNN: 2-(4-(DIFLUOROMETHYL)-2,5-DIMETHOXYPHENYL)-4,4,5,5-TETRAMETHYL-1,3,2-DIOXABOROLANE

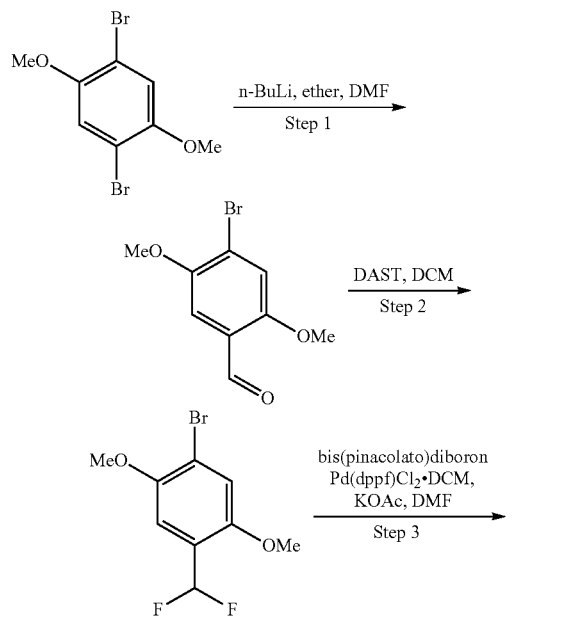

STEP 1: 4-BROMO-2,5-DIMETHOXYBENZALDEHYDE

A solution of 1,4-dibromo-2,5-dimethoxybenzene (7.00 g, 23.65 mmol) in 100 mL ether was cooled to −78° C. and was treated with n-butyllithium (10.41 ml, 26.0 mmol). After stirring for 10 minutes, the reaction mixture was quenched with DMF (3.66 ml, 47.3 mmol), and the cooling bath was removed. After stirring for an additional hour, LC/MS showed mostly product, so the reaction mixture was washed with 1N citric acid solution, the organics dried over MgSO4 and concentrated. The crude product was carried forward in step two without purification. (M+H)+=245.1.

STEP 2: 1-BROMO-4-(DIFLUOROMETHYL)-2,5-DIMETHOXYBENZENE

The crude residue from step one was dissolved in 40 mL DCM, placed under argon, and was cooled to 0° C. DAST (3.12 ml, 23.65 mmol) was added, and the reaction mixture was allowed to warm to room temperature overnight. LC/MS showed mostly product, so the reaction mixture was quenched with saturated NaHCO3 solution. The organics were separated, dried over MgSO4 and concentrated yielding 1-bromo-4-(difluoromethyl)-2,5-dimethoxybenzene (2.68 g, 10.03 mmol, 42.4% yield) with impurities. (M+H)+=267.0.

STEP 3: 2-(4-(DIFLUOROMETHYL)-2,5-DIMETHOXYPHENYL)-4,4,5,5-TETRAMETHYL-1,3,2-DIOXABOROLANE

A solution of PdCl2(dppf)-CH2Cl2 adduct (0.410 g, 0.502 mmol), bis(pinacolato)diboron (5.10 g, 20.07 mmol), 1-bromo-4-(difluoromethyl)-2,5-dimethoxybenzene (2.68 g, 10.03 mmol), and potassium acetate (2.370 g, 40.1 mmol) in 20 mL DMF was heated to 110° C. for 4 hours. LC/MS showed mostly product, so the reaction mixture was allowed to cool to room temperature then was diluted with ether. The reaction mixture was filtered through a plug of Celite then concentrated. Purification of the crude residue by silica gel column chromatography (0-20% EtOAc/heptane) gave 2-(4-(difluoromethyl)-2,5-dimethoxyphenyl)-4,4,5,5-tetramethyl-1,3,2-dioxaborolane (2.80 g, 8.91 mmol, 89% yield) with impurities. (M+H)+=315.3.

EXAMPLE 452

1-(4-(DIFLUOROMETHYL)-2,5-DIMETHOXYPHENYL)-N-(THIAZOL-2-YL)ISOQUINOLINE-6-SULFONAMIDE

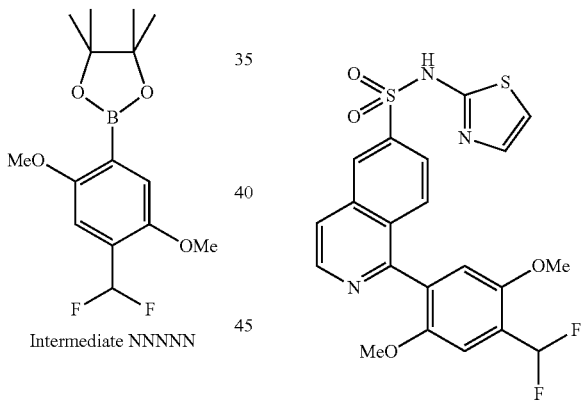

A solution of PdCl2(dppf)-CH2Cl2 adduct (7.78 mg, 9.53 μmol), 2-(4-(difluoromethyl)-2,5-dimethoxyphenyl)-4,4,5,5-tetramethyl-1,3,2-dioxaborolane (Intermediate NNNNN; 0.078 g, 0.248 mmol), 1-chloro-N-(4-methoxybenzyl)-N-(thiazol-2-yl)isoquinoline-6-sulfonamide (Intermediate JJJ; 0.085 g, 0.191 mmol), and potassium carbonate (0.079 g, 0.572 mmol) in 2 mL dioxane, 1 mL water was heated to 100° C. overnight. LC/MS showed mostly product, so the reaction mixture was allowed to cool to room temperature. The aqueous layer was then removed. The reaction mixture was treated with HCl (4N in dioxane) (0.953 ml, 3.81 mmol) and was heated to 100° C. for one hour. LC/MS showed mostly product, so the reaction mixture was concentrated. Purification of the crude residue by reverse phase column chromatography [Redisolv Flash C18 30μ, 10-100% (0.1% NH4OH in MeOH)/(0.1% NH4OH in water)] gave 1-(4-(difluoromethyl)-2,5-dimethoxyphenyl)-N-(thiazol-2-yl)isoquinoline-6-sulfonamide (0.016 g, 0.034 mmol, 17.58% yield). $^1$H NMR (MeCN-d3) δ: 8.68 (d, J=5.7 Hz, 1H), 8.51 (s, 1H), 7.93 (d, J=6.0 Hz, 1H), 7.87 (d, J=8.9 Hz, 1H), 7.73 (d, J=8.8 Hz, 1H), 7.32 (s, 1H), 7.10 (d, J=6.1 Hz, 1H), 6.99 (d, J=4.7 Hz, 1H), 6.61 (d, J=4.7 Hz, 1H), 3.81 (s, 3H), 3.65 (s, 3H); (M+H)+=478.0.

EXAMPLE 453

1-(4-(DIFLUOROMETHYL)-2,5-DIMETHOXYPHENYL)-N-(PYRIMIDIN-4-YL)ISOQUINOLINE-6-SULFONAMIDE

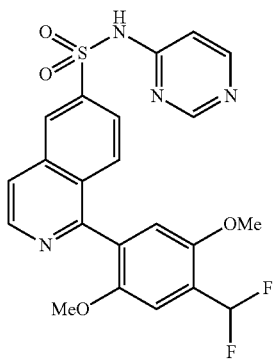 [SMILES: COc1cc(C(F)F)c(OC)cc1-c1nccc2cc(S(=O)(=O)Nc3ccncn3)ccc12]

This compound was prepared in a manner analogous to example 452 except using 1-chloro-N-(4-methoxybenzyl)-N-(pyrimidin-4-yl)isoquinoline-6-sulfonamide (Intermediate ZZZZ) instead of 1-chloro-N-(4-methoxybenzyl)-N-(thiazol-2-yl)isoquinoline-6-sulfonamide. $^1$H NMR (MeCN-d3) δ: 8.71 (d, J=5.8 Hz, 1H), 8.64 (d, J=1.8 Hz, 1H), 8.48 (br. s., 1H), 7.92-7.98 (m, 2H), 7.77 (d, J=8.8 Hz, 1H), 7.32 (s, 1H), 6.91-7.24 (m, 3H), 6.30 (d, J=6.7 Hz, 1H), 3.79-3.82 (m, 3H), 3.63 (s, 3H) (M+H)+=473.0.

EXAMPLE 454

1-(2-METHOXY-4-(1-METHYL-1H-PYRAZOL-4-YL)PHENYL)-N-(PYRIMIDIN-4-YL)ISOQUINOLINE-6-SULFONAMIDE

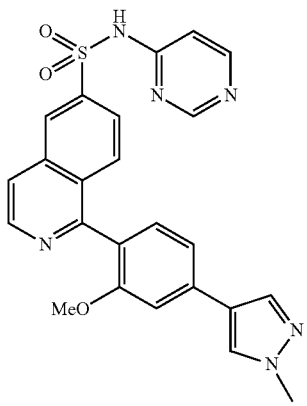 [SMILES: COc1cc(-c2cnn(C)c2)ccc1-c1nccc2cc(S(=O)(=O)Nc3ccncn3)ccc12]

Prepared in a manner analogous to example 441 except 1-methylpyrazole-4-boronic acid pinacol ester was used instead of 2-methylphenylboronic acid. $^1$H NMR (MeCN-d3) δ: 8.67 (d, J=5.7 Hz, 1H), 8.60 (s, 1H), 8.47 (s, 1H), 8.20 (d, J=6.3 Hz, 1H), 7.85-7.97 (m, 3H), 7.80 (d, J=9.0 Hz, 1H), 7.57 (s, 1H), 7.50 (s, 1H), 7.26-7.34 (m, 3H), 7.04 (d, J=6.4 Hz, 1H), 3.91 (s, 3H), 3.70 (s, 3H); (M+H)+=473.0.

EXAMPLE 455

1-(4'-CYANO-3-METHOXY-[1,1'-BIPHENYL]-4-YL)-N-(PYRIMIDIN-4-YL)ISOQUINOLINE-6-SULFONAMIDE

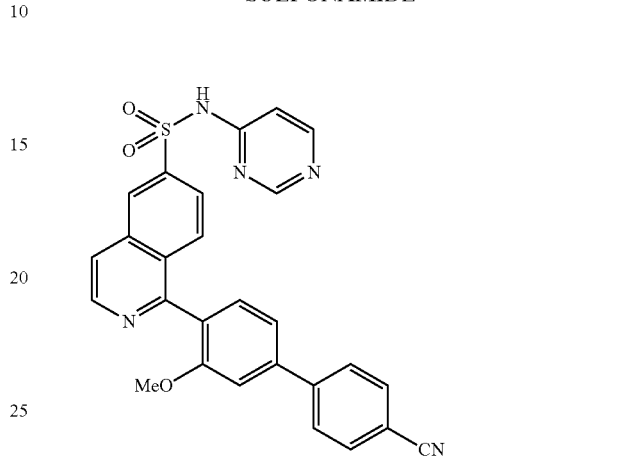

Prepared in a manner analogous to example 441 except 4-cyanophenylboronic acid was used instead of 2-methylphenylboronic acid. $^1$H NMR (ACETONITRILE-d$_3$) δ: 8.67 (d, J=5.8 Hz, 1H), 8.58 (s, 1H), 8.45 (s, 1H), 8.13 (d, J=6.2 Hz, 1H), 7.83-7.97 (m, 6H), 7.75 (d, J=8.9 Hz, 1H), 7.40-7.48 (m, 3H), 6.97 (d, J=6.2 Hz, 1H), 3.74 (s, 3H); (M+H)+=494.0.

INTERMEDIATE OOOOO: 2-(3-METHOXY-4-(4,4,5,5-TETRAMETHYL-1,3,2-DIOXABOROLAN-2-YL)PHENYL)THIAZOLE

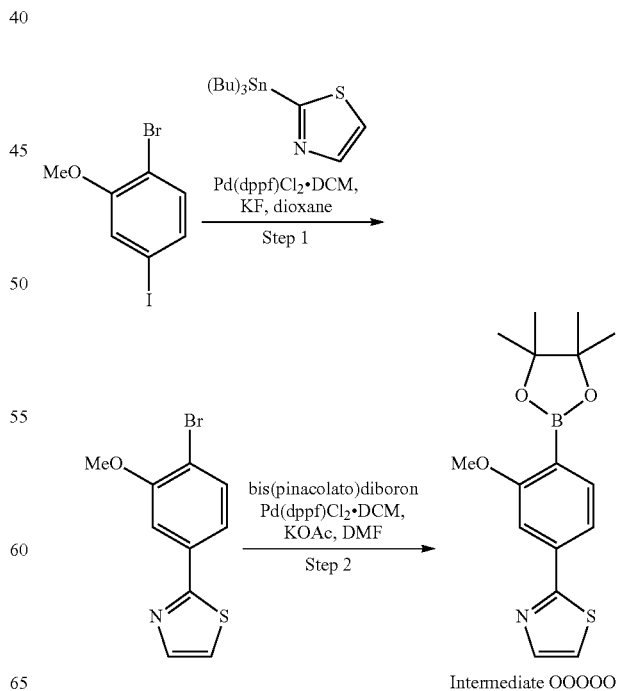

Intermediate OOOOO

STEP 1: 2-(4-BROMO-3-METHOXYPHENYL)THIAZOLE

A solution of PdCl$_2$(dppf)-CH$_2$Cl$_2$ adduct (0.391 g, 0.479 mmol), 2-tributylstannylthiazole (3.01 ml, 9.59 mmol), 1-bromo-4-iodo-2-methoxybenzene (3.00 g, 9.59 mmol), and potassium fluoride (1.499 g, 38.3 mmol) in 10 mL dioxane was heated to 100° C. overnight. LC/MS showed mostly product, so the reaction mixture was diluted with DCM and washed with water. The organics were dried over MgSO$_4$ and concentrated. Purification of the crude residue by silica gel column chromatography (0-100% EtOAc/heptane) gave 2-(4-bromo-3-methoxyphenyl)thiazole (1.858 g, 6.88 mmol, 71.7% yield). (M+H)+=271.2.

STEP 2: 2-(3-METHOXY-4-(4,4,5,5-TETRAMETHYL-1,3,2-DIOXABOROLAN-2-YL)PHENYL)THIAZOLE

A solution of PdCl$_2$(dppf)-CH$_2$Cl$_2$ adduct (0.559 g, 0.685 mmol), bis(pinacolato)diboron (2.61 g, 10.27 mmol), 2-(4-bromo-3-methoxyphenyl)thiazole (1.850 g, 6.85 mmol), and potassium acetate (1.617 g, 27.4 mmol) in 7 mL DMF was heated to 120° C. for 2 hours. LC/MS showed product, so the reaction mixture was diluted with DCM and filtered through a plug of celite. The filtrate was concentrated. Purification of the crude residue by silica gel column chromatography (0-100% EtOAc/heptane) gave 2-(3-methoxy-4-(4,4,5,5-tetramethyl-1,3,2-dioxaborolan-2-yl)phenyl)thiazole (1.64 g, 5.17 mmol, 75% yield). (M+H)+=318.3.

EXAMPLE 456

1-(2-METHOXY-4-(THIAZOL-2-YL)PHENYL)-N-(PYRIMIDIN-4-YL)ISOQUINOLINE-6-SULFONAMIDE

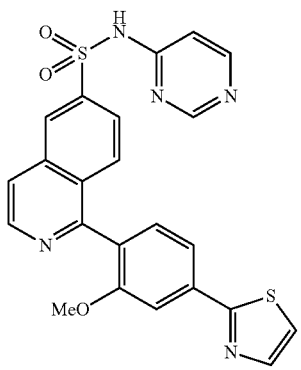 [SMILES: COc1cc(-c2nccs2)ccc1-c1nccc2cc(S(=O)(=O)Nc3ccncn3)ccc12]

A solution of PdCl$_2$(dppf)-CH$_2$Cl$_2$ adduct (0.127 g, 0.156 mmol), 2-(3-methoxy-4-(4,4,5,5-tetramethyl-1,3,2-dioxaborolan-2-yl)phenyl)thiazole (Intermediate OOOOO; 0.643 g, 2.026 mmol), 1-chloro-N-(pyrimidin-4-yl)isoquinoline-6-sulfonamide (Intermediate GG) (0.500 g, 1.559 mmol), and potassium carbonate (0.862 g, 6.24 mmol) in 6 mL dioxane/2 mL water was heated to 110° C. for 2 hours. LC/MS showed mostly product, so the reaction mixture was allowed to cool to room temperature. The aqueous layer was removed, and the reaction mixture was treated with HCl (4N in dioxane) (1.559 ml, 6.24 mmol). After stirring for an additional 10 minutes, the reaction mixture was concentrated. Purification of the crude residue by reverse phase column chromatography [Puriflash C18 30μ, 10-100% (0.1% NH4OH in MeOH)/(0.1% NH4OH in water)] gave 1-(2-methoxy-4-(thiazol-2-yl)phenyl)-N-(pyrimidin-4-yl)isoquinoline-6-sulfonamide (0.507 g, 1.066 mmol, 68.4% yield). $^1$H NMR (MeCN-d$_3$) δ: 8.71 (d, J=5.7 Hz, 1H), 8.63 (s, 1H), 8.48 (s, 1H), 8.21 (d, J=6.3 Hz, 1H), 7.91-7.97 (m, 3H), 7.75-7.84 (m, 2H), 7.72 (sd, J=7.8 Hz, 1H), 7.60 (d, J=3.2 Hz, 1H), 7.45 (d, J=7.8 Hz, 1H), 7.06 (s, J=6.3 Hz, 1H), 3.75 (s, 3H); (M+H)+=476.0.

EXAMPLE 457

1-(5-CHLORO-4-(DIFLUOROMETHYL)-2-METHOXYPHENYL)-N-(PYRIMIDIN-4-YL)ISOQUINOLINE-6-SULFONAMIDE

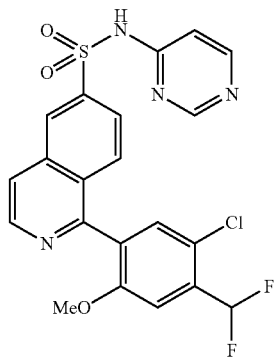 [SMILES: COc1cc(C(F)F)c(Cl)cc1-c1nccc2cc(S(=O)(=O)Nc3ccncn3)ccc12]

The title compound was prepared in a manner analogous to example 456 except using 2-(5-chloro-4-(difluoromethyl)-2-methoxyphenyl)-4,4,5,5-tetramethyl-1,3,2-dioxaborolane (Intermediate IIII) instead of 2-(3-methoxy-4-(4,4,5,5-tetramethyl-1,3,2-dioxaborolan-2-yl)phenyl)thiazole. $^1$H NMR (MeCN-d$_3$) δ: 8.70 (d, J=5.8 Hz, 1H), 8.64 (s, 1H), 8.47 (s, 1H), 8.21 (d, J=6.3 Hz, 1H), 7.90-8.00 (m, 2H), 7.75 (d, J=8.9 Hz, 1H), 7.50 (s, 1H), 7.43 (s, 1H), 6.97-7.28 (m, 2H), 3.71 (s, 3H); (M+H)+=477.0.

EXAMPLE 458

1-(4-(5-CHLOROTHIAZOL-2-YL)-2-METHOXYPHENYL)-N-(PYRIMIDIN-4-YL)ISOQUINOLINE-6-SULFONAMIDE

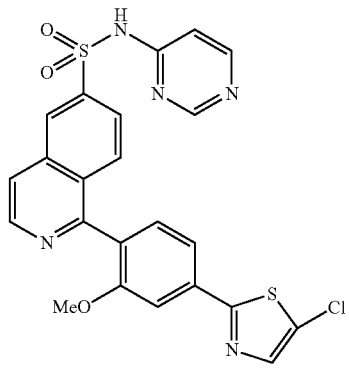 [SMILES: COc1cc(-c2ncc(Cl)s2)ccc1-c1nccc2cc(S(=O)(=O)Nc3ccncn3)ccc12]

A solution of 1-(2-methoxy-4-(thiazol-2-yl)phenyl)-N-(pyrimidin-4-yl)isoquinoline-6-sulfonamide (0.100 g, 0.210 mmol) in 2 mL MeOH was treated with 1,3-dichloro-5,5-dimethylhydantoin (0.028 ml, 0.210 mmol) and was allowed to stir overnight at room temperature then was heated to reflux for two hours. LC/MS showed product, so the reaction mixture was concentrated. Purification of the crude residue by reverse phase column chromatography [Puriflash C18 30μ, 10-100% (0.1% NH4OH in MeOH)/(0.1% NH4OH in water)] gave 1-(4-(5-chlorothiazol-2-yl)-2-methoxyphenyl)-N-(pyrimidin-4-yl)isoquinoline-6-sulfonamide (0.006 g, 0.012 mmol, 5.59% yield). $^1$H NMR (MeCN-d3) δ: 8.60-8.64 (m, 1H), 8.52-8.56 (m, 1H), 8.10-8.13 (m, 1H), 8.05-8.09 (m, 1H), 7.95-8.00 (m, 1H), 7.91-7.95 (m, 1H), 7.87-7.91 (m, 1H), 7.74-7.78 (m, 1H), 7.66-7.74 (m, 2H), 7.57-7.61 (m, 1H), 7.42-7.47 (m, 1H), 3.76 (s, 3H); (M+H)+=510.1.

EXAMPLE 459

1-(5-CYCLOPROPYL-4-(DIFLUOROMETHYL)-2-METHOXYPHENYL)-N-(PYRIMIDIN-4-YL)ISOQUINOLINE-6-SULFONAMIDE

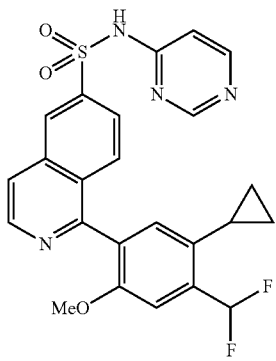 [SMILES: COc1cc(C(F)F)c(C2CC2)cc1-c1nccc2cc(S(=O)(=O)Nc3ccncn3)ccc12]

A solution of 2-dicyclohexylphosphino-2',6'-dimethoxy-1'1'-biphenyl (4.59 mg, 0.011 mmol), chloro(2-dicyclohexylphosphino-2',6'-dimethoxy-1,1'-biphenyl)[2-(2-aminoethylphenyl)]palladium(ii) methyl-t-butylether (8.48 mg, 0.011 mmol), potassium phosphate (0.190 g, 0.895 mmol), cyclopropylboronic acid (0.038 g, 0.448 mmol), and 1-(5-chloro-4-(difluoromethyl)-2-methoxyphenyl)-N-(pyrimidin-4-yl)isoquinoline-6-sulfonamide (From Example 457; 0.108 g, 0.224 mmol) in 1.5 mL dioxane/0.5 mL water was heated to 180° C. in the microwave for 45 minutes. LC/MS showed product, so the aqueous layer was removed. The reaction mixture was treated with HCl (4N in dioxane) (0.224 ml, 0.895 mmol) and was allowed to stir for 10 minutes. The reaction mixture was then concentrated. Purification of the crude residue by reverse phase column chromatography [Puriflash C18, 10-100% (0.1% NH₄OH in MeOH)/(0.1% NH4OH in water)] gave 1-(5-cyclopropyl-4-(difluoromethyl)-2-methoxyphenyl)-N-(pyrimidin-4-yl)isoquinoline-6-sulfonamide (0.040 g, 0.083 mmol, 37.0% yield). $^1$H NMR (MeCN-d₃) δ: 8.65 (d, J=5.7 Hz, 1H), 8.58 (s, 1H), 8.44 (s, 1H), 8.14 (d, J=6.3 Hz, 1H), 7.86-7.95 (m, 2H), 7.63-7.69 (m, 1H), 7.15-7.45 (m, 2H), 7.12 (s, 1H), 6.96 (s, J=6.3, 1H), 3.67 (s, 3H), 2.03-2.14 (m, 1H), 0.88-1.00 (m, 2H), 0.59-0.70 (m, 2H); (M+H)+=483.0.

EXAMPLE 460

1-(4'-CHLORO-2',3-DIMETHOXY-[1,1'-BIPHENYL]-4-YL)-N-(PYRIMIDIN-4-YL)ISOQUINOLINE-6-SULFONAMIDE

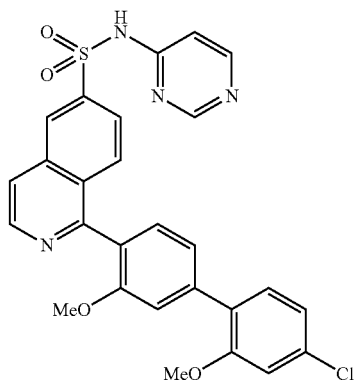 [SMILES: COc1cc(Cl)ccc1-c1ccc(-c2nccc3cc(S(=O)(=O)Nc4ccncn4)ccc23)c(OC)c1]

A solution of Pd(Amphos)₂Cl₂ (0.442 g, 0.624 mmol), (4-chloro-2-methoxyphenyl)boronic acid (1.278 g, 6.86 mmol), 1-chloro-N-(pyrimidin-4-yl)isoquinoline-6-sulfonamide (2.000 g, 6.24 mmol), and potassium phosphate (5.29 g, 24.94 mmol) in 30 mL dioxane/12 mL water was heated to 110° C. for 2 hours. LC/MS showed product, so the reaction mixture was allowed to cool to room temperature. The aqueous layer was removed, and the reaction mixture was treated with HCl (4N in dioxane) (6.24 ml, 24.94 mmol). After stirring for 10 minutes, the reaction mixture was concentrated. Purification of the crude residue by reverse phase column chromatography [RediSep Gold C18, 10-100% (0.1% NH4OH in MeOH)/(0.1% NH4OH in water)] gave 1-(4'-chloro-2',3-dimethoxy-[1,1'-biphenyl]-4-yl)-N-(pyrimidin-4-yl)isoquinoline-6-sulfonamide (0.073 g, 0.137 mmol, 2.197% yield). $^1$H NMR (MeCN-d3) δ: 8.69 (m, 1H), 8.62 (s, 1H), 8.44-8.52 (m, 1H), 8.21 (d, J=6.4 Hz, 1H), 7.89-7.99 (m, 2H), 7.81 (d, J=9.0 Hz, 1H), 7.42 (m, 1H), 7.32-7.39 (m, 1H), 7.29 (s, 1H), 7.24 (m, 1H), 7.16 (d, 1H), 7.03-7.12 (m, 2H), 3.84-3.88 (m, 3H), 3.64-3.67 (m, 3H); (M+H)+=533.0.

EXAMPLE 461

1-(2-METHOXY-4-(5-METHYLFURAN-2-YL) PHENYL)-N-(PYRIMIDIN-4-YL)ISOQUINO- LINE-6-SULFONAMIDE

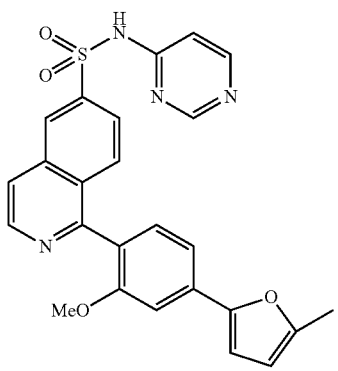 [SMILES: COc1cc(-c2ccc(C)o2)ccc1-c1nccc2cc(S(=O)(=O)Nc3ccncn3)ccc12]

A microwave vial charged with Pd(Amphos)₂Cl₂ (0.012 g, 0.018 mmol), 4,4,5,5-tetramethyl-2-(5-methylfuran-2-yl)-1, 3,2-dioxaborolane (0.073 g, 0.351 mmol), 1-(4-chloro-2-methoxyphenyl)-N-(pyrimidin-4-yl)isoquinoline-6-sulfonamide (From Example 160; 0.075 g, 0.176 mmol), potassium phosphate (0.149 g, 0.703 mmol), 1.5 mL dioxane and 0.25 mL water was heated to 150° C. in the microwave for 30 minutes. LC/MS showed mostly product. The aqueous layer was removed, and the reaction mixture was treated with HCl (4N in dioxane). Purification of the crude residue by reverse phase column chromatography [RediSep Gold C18, 10-100% (0.1% NH4OH in MeOH)/(0.1% NH4OH in water)] gave the titled compound.

EXAMPLE 462

1-(4-(4-FLUOROPHENOXY)-2-METHOXYPHE- NYL)-N-(PYRIMIDIN-4-YL)ISOQUINOLINE-6- SULFONAMIDE

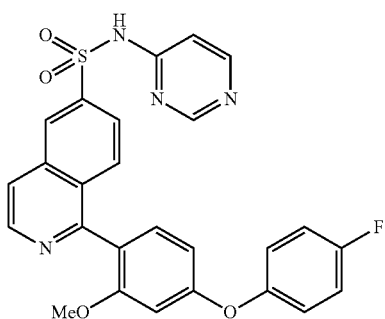 [SMILES: COc1cc(Oc2ccc(F)cc2)ccc1-c1nccc2cc(S(=O)(=O)Nc3ccncn3)ccc12]

A microwave vial charged with di-tert-butyl(2',4',6'-triiso- propyl-3,4,5,6-tetramethyl-[1,1'-biphenyl]-2-yl)phosphine (0.017 g, 0.035 mmol), 4-fluorophenol (0.039 g, 0.351 mmol), 1-(4-chloro-2-methoxyphenyl)-N-(pyrimidin-4-yl) isoquinoline-6-sulfonamide (0.075 g, 0.176 mmol), potassium phosphate (0.149 g, 0.703 mmol), 1.5 mL dioxane was heated to 135° C. in the microwave for 30 minutes. LC/MS showed mostly product, so the reaction mixture was filtered through a 0.45 µm syringe filter and was treated with HCl (4N in dioxane) (0.176 ml, 0.703 mmol). After stirring for 10 minutes, the reaction mixture was concentrated. Purification of the crude residue by reverse phase column chromatography [RediSep Gold C18, 10-100% (0.1% NH4OH in MeOH)/ (0.1% NH4OH in water)] gave 1-(4-(4-fluorophenoxy)-2-methoxyphenyl)-N-(pyrimidin-4-yl)isoquinoline-6-sulfonamide (0.020 g, 0.040 mmol, 22.65% yield). ¹H NMR (MeCN-d3) δ: 8.68 (d, J=5.7 Hz, 1H), 8.62 (s, 1H), 8.48 (s, 1H), 8.23 (d, J=8.5 Hz, 1H), 7.88-7.98 (m, 2H), 7.83 (d, J=9.0 Hz, 1H), 7.25-7.33 (m, 1H), 7.13-7.21 (m, 4H), 7.08 (d, J=5.4 Hz, 1H), 6.83 (s, 1H), 6.62-6.69 (m, 1H), 3.60 (s, 3H); (M+H)+=503.0.

EXAMPLE 463

1-(4-(5-HYDROXYPENTANOYL)-2-METHOX- YPHENYL)-N-(PYRIMIDIN-4-YL)ISOQUINO- LINE-6-SULFONAMIDE

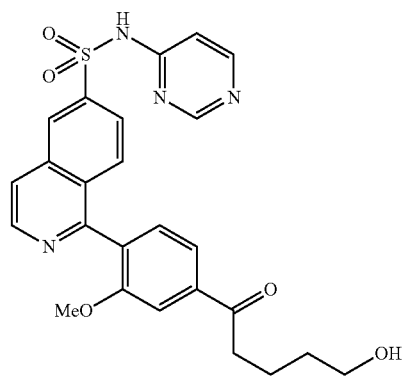 [SMILES: COc1cc(C(=O)CCCCO)ccc1-c1nccc2cc(S(=O)(=O)Nc3ccncn3)ccc12]

The title compound was prepared in a manner analogous to example 461 except using 2-(3,4-dihydro-2H-pyran-6-yl)-4, 4,5,5-tetramethyl-1,3,2-dioxaborolane instead of 4,4,5,5-tet- ramethyl-2-(5-methylfuran-2-yl)-1,3,2-dioxaborolane. ¹H NMR (MeCN-d3) δ: 8.67-8.72 (m, 1H), 8.63 (s, 1H), 8.47 (s, 1H), 8.20 (d, J=6.4 Hz, 1H), 7.90-7.98 (m, 2H), 7.66-7.77 (m, 3H), 7.47 (m, 1H), 7.01-7.07 (m, 1H), 3.68-3.76 (m, 3H), 3.52-3.59 (m, 2H), 3.07-3.16 (m, 2H), 1.70-1.84 (m, 2H), 1.51-1.65 (m, 2H); (M+H)+=493.0.

EXAMPLE 464

1-(4-(3-FLUOROPHENOXY)-2-METHOXYPHENYL)-N-(PYRIMIDIN-4-YL)ISOQUINOLINE-6-SULFONAMIDE

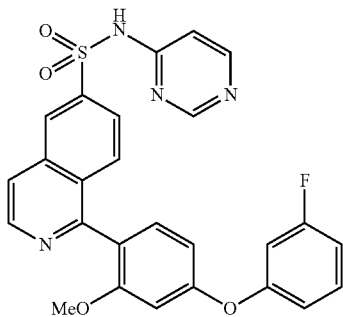 [SMILES: COc1cc(Oc2cccc(F)c2)ccc1-c1nccc2cc(S(=O)(=O)Nc3ccncn3)ccc12]

A microwave vial charged with di-tert-butyl(2',4',6'-triisopropyl-3,4,5,6-tetramethyl-[1,1'-biphenyl]-2-yl)phosphine (0.034 g, 0.070 mmol), 3-fluorophenol (0.079 g, 0.703 mmol), 1-(4-chloro-2-methoxyphenyl)-N-(pyrimidin-4-yl)isoquinoline-6-sulfonamide (0.150 g, 0.351 mmol), potassium phosphate (0.298 g, 1.406 mmol), and 1.5 mL dioxane was heated to 165° C. in the microwave for 30 minutes. LC/MS showed product, so the reaction mixture was filtered through a 0.45 μm syringe filter and was treated with HCl (4N in dioxane) (0.351 ml, 1.406 mmol). After stirring for 10 minutes, the reaction mixture was concentrated. Purification of the crude residue by reverse phase column chromatography [RediSep Gold C18, 10-100% (0.1% NH4OH in MeOH)/(0.1% NH4OH in water)] gave 1-(4-(3-fluorophenoxy)-2-methoxyphenyl)-N-(pyrimidin-4-yl)isoquinoline-6-sulfonamide (0.015 g, 0.030 mmol, 8.49% yield). $^1$H NMR (MeCN-d3) δ: 8.69 (d, J=5.7 Hz, 1H), 8.62 (s, 1H), 8.48 (s, 1H), 8.22 (d, J=6.3 Hz, 1H), 7.89-7.97 (m, 2H), 7.80-7.88 (m, 1H), 7.38-7.47 (m, 1H), 7.35 (d, J=8.2 Hz, 1H), 7.08 (d, J=5.9 Hz, 1H), 6.87-6.99 (m, 4H), 6.76 (d, J=8.3 Hz, 1H), 3.59-3.62 (m, 3H); (M+H)+=503.0.

EXAMPLE 465

1-(4-(2-FLUOROPHENOXY)-2-METHOXYPHENYL)-N-(PYRIMIDIN-4-YL)ISOQUINOLINE-6-SULFONAMIDE

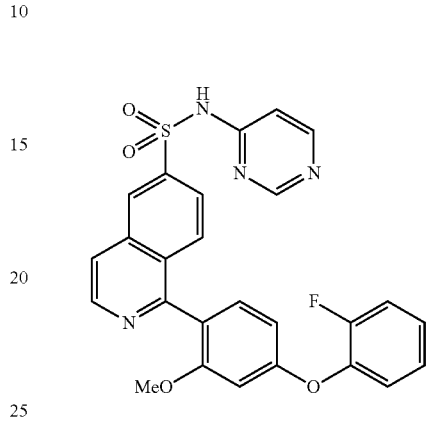

The title compound was prepared in a manner analogous to example 464 except using 2-fluorophenol instead of 3-fluorophenol. $^1$H NMR (MeCN-d3) δ: 8.68 (d, J=5.6 Hz, 1H), 8.62 (s, 1H), 8.48 (br. s., 1H), 8.17-8.27 (br. s., 1H), 7.89-7.97 (m, 2H), 7.82 (d, J=8.7 Hz, 1H), 7.21-7.35 (m, 5H), 7.09 (br. s., 1H), 6.85 (s, 1H), 6.63 (d, J=8.2 Hz, 1H), 3.61 (s, 3H); (M+H)+=503.0.

EXAMPLE 466

1-(2',3-DIMETHOXY-[1,1'-BIPHENYL]-4-YL)-N-(PYRIMIDIN-4-YL)ISOQUINOLINE-6-SULFONAMIDE

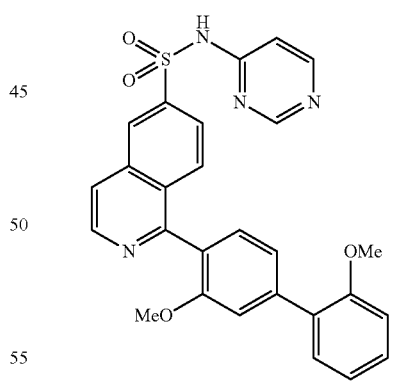

A microwave vial charged with Pd(Amphos)$_2$Cl$_2$ (0.008 g, 0.012 mmol), 2-methoxyphenylboronic acid (0.036 g, 0.234 mmol), 1-(4-chloro-2-methoxyphenyl)-N-(pyrimidin-4-yl)isoquinoline-6-sulfonamide (From example 160; 0.050 g, 0.117 mmol), potassium phosphate (0.099 g, 0.469 mmol), 1.5 mL dioxane, and 0.25 mL water was heated to 150° C. in the microwave for 30 minutes. LC/MS showed mostly product, so the aqueous layer was removed and the reaction mixture was treated with HCl (4N in dioxane) (117 μl, 0.469 mmol). After stirring for 10 minutes, the reaction mixture was concentrated. The crude residue was purified by [PREP LC/MS-2 System Column: XBridge 19×100 mm 12230326114 03 Mobile phase: 0.1% NH4OH in water/acetonitrile Flow rate: 40 ml/min Inj: 2200 uL. Gradient: 10 min10-40%_LV_NH3] yielding 1-(2',3-dimethoxy-[1,1'-biphenyl]-4-yl)-N-(pyrimidin-4-yl)isoquinoline-6-sulfonamide (0.014 g, 0.028 mmol, 24.0%). $^1$H NMR (500 MHz, DMSO-d6) δ ppm 3.67 (s, 3H) 3.79-3.88 (m, 3H) 6.99-7.13 (m, 2H) 7.17 (d, J=8.12 Hz, 1H) 7.22-7.32 (m, 2H) 7.32-7.48 (m, 3H) 7.81 (d, J=8.76 Hz, 1H) 7.98 (d, J=9.03 Hz, 1H) 8.09 (d, J=5.61 Hz, 1H) 8.26 (br. s., 1H) 8.58 (s, 1H) 8.61-8.72 (m, 2H); (M+H)+=499.3.

EXAMPLE 467

1-(3,3'-DIMETHOXY-[1,1'-BIPHENYL]-4-YL)-N-(PYRIMIDIN-4-YL)ISOQUINOLINE-6-SULFONAMIDE

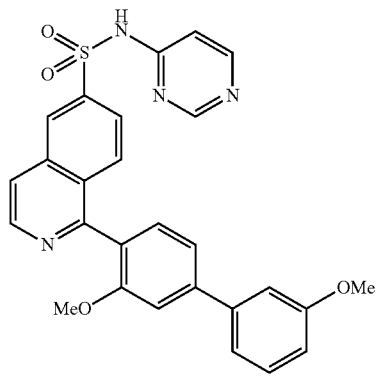 [SMILES: COc1cccc(-c2ccc(-c3nccc4cc(S(=O)(=O)Nc5ccncn5)ccc34)c(OC)c2)c1]

The title compound was prepared in a manner analogous to example 466 except using 3-methoxyphenylboronic acid instead of 2-methoxyphenylboronic acid. $^1$H NMR (500 MHz, DMSO-d6) δ ppm 3.75 (s, 3H) 3.86 (s, 3H) 7.00 (d, J=8.39 Hz, 2H) 7.32-7.51 (m, 6H) 7.79 (d, J=8.71 Hz, 1H) 7.96 (d, J=9.03 Hz, 1H) 8.10 (d, J=5.66 Hz, 1H) 8.26 (br. s., 1H) 8.58 (s, 1H) 8.61-8.76 (m, 2H); (M+H)+=499.3.

EXAMPLE 468

1-(3,4'-DIMETHOXY-[1,1'-BIPHENYL]-4-YL)-N-(PYRIMIDIN-4-YL)ISOQUINOLINE-6-SULFONAMIDE

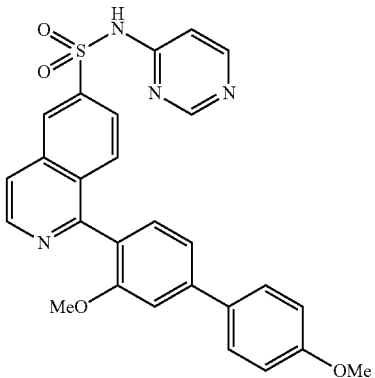 [SMILES: COc1ccc(-c2ccc(-c3nccc4cc(S(=O)(=O)Nc5ccncn5)ccc34)c(OC)c2)cc1]

The title compound was prepared in a manner analogous to example 466 except using 4-methoxyphenylboronic acid instead of 2-methoxyphenylboronic acid. $^1$H NMR (500 MHz, DMSO-d6) δ ppm 3.74 (s, 3H) 3.83 (s, 3H) 6.97-7.12 (m, 3H) 7.25-7.45 (m, 3H) 7.69-7.82 (m, 3H) 7.95 (d, J=7.75 Hz, 1H) 8.08 (d, J=5.82 Hz, 1H) 8.25 (br. s., 1H) 8.57 (s, 1H) 8.61-8.71 (m, 2H); (M+H)+=499.3.

EXAMPLE 469

1-(3-METHOXY-3',4'-DIMETHYL-[1,1'-BIPHENYL]-4-YL)-N-(PYRIMIDIN-4-YL)ISOQUINOLINE-6-SULFONAMIDE

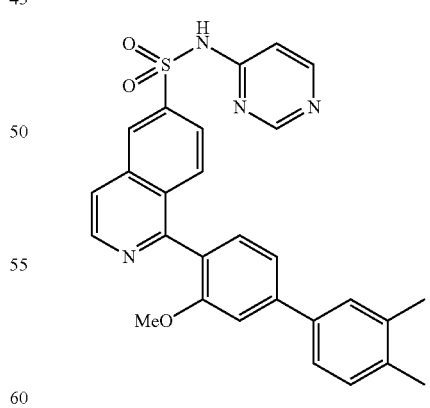

The title compound was prepared in a manner analogous to example 466 except using 3,4-dimethylphenylboronic acid instead of 2-methoxyphenylboronic acid. $^1$H NMR (500 MHz, DMSO-d6) δ ppm 2.29 (s, 3H) 2.34 (s, 3H) 3.74 (s, 3H) 7.05 (br. s., 1H) 7.27 (d, J=7.75 Hz, 1H) 7.34-7.46 (m, 3H) 7.53 (d, J=8.12 Hz, 1H) 7.60 (s, 1H) 7.72-7.85 (m, 1H) 7.95

(d, J=7.48 Hz, 1H) 8.09 (d, J=5.61 Hz, 1H) 8.25 (br. s., 1H) 8.57 (br. s., 1H) 8.61-8.71 (m, 2H); (M+H)+=497.5.

EXAMPLE 470

1-(3-METHOXY-3',5'-DIMETHYL-[1,1'-BIPHE-NYL]-4-YL)-N-(PYRIMIDIN-4-YL)ISOQUINO-LINE-6-SULFONAMIDE

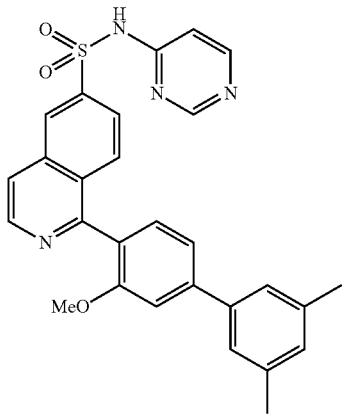 [SMILES: COc1cc(-c2cc(C)cc(C)c2)ccc1-c1nccc2cc(S(=O)(=O)Nc3ccncn3)ccc12]

The title compound was prepared in a manner analogous to example 466 except using 3,5-dimethylphenylboronic acid instead of 2-methoxyphenylboronic acid. $^1$H NMR (DMSO-$d_6$) δ: 8.69 (d, J=5.7 Hz, 1H), 8.65 (br. s., 1H), 8.58 (s, 1H), 8.25 (br. s., 1H), 8.09 (d, J=5.4 Hz, 1H), 7.96 (d, J=10.0 Hz, 1H), 7.79 (d, J=9.0 Hz, 1H), 7.34-7.46 (m, 5H), 7.05 (br. s., 2H), 3.74 (s, 3H), 2.38 (s, 6H); (M+H)+=497.5.

EXAMPLE 471

1-(3'-FLUORO-3-METHOXY-4'-METHYL-[1,1'-BIPHENYL]-4-YL)-N-(PYRIMIDIN-4-YL)ISO-QUINOLINE-6-SULFONAMIDE

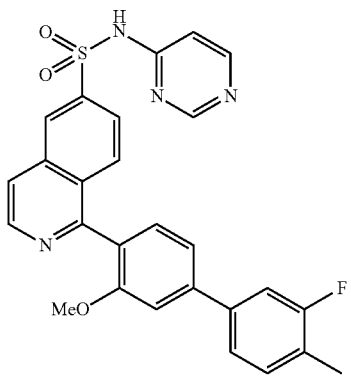 [SMILES: COc1cc(-c2ccc(C)c(F)c2)ccc1-c1nccc2cc(S(=O)(=O)Nc3ccncn3)ccc12]

The title compound was prepared in a manner analogous to example 466 except using 3-fluoro-4-methylphenylboronic acid instead of 2-methoxyphenylboronic acid. $^1$H NMR (500 MHz, DMSO-d6) δ ppm 2.27-2.33 (m, 3H) 3.75 (s, 3H) 7.34-7.52 (m, 6H) 7.59 (d, J=8.39 Hz, 1H) 7.65 (d, J=10.90 Hz, 1H) 7.78 (d, J=8.12 Hz, 1H) 7.95 (d, J=7.96 Hz, 1H) 8.10 (d, J=5.50 Hz, 1H) 8.57 (br. s., 1H) 8.62-8.71 (m, 2H); (M+H)+=501.1.

EXAMPLE 472

1-(3'-FLUORO-3-METHOXY-5'-METHYL-[1,1'-BIPHENYL]-4-YL)-N-(PYRIMIDIN-4-YL)ISO-QUINOLINE-6-SULFONAMIDE

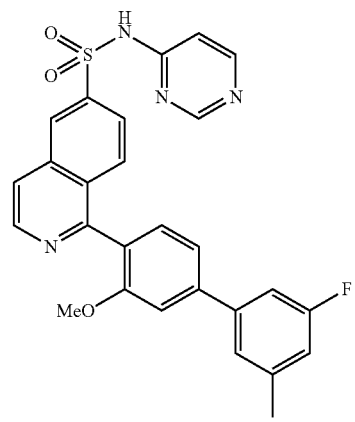 [SMILES: COc1cc(-c2cc(C)cc(F)c2)ccc1-c1nccc2cc(S(=O)(=O)Nc3ccncn3)ccc12]

The title compound was prepared in a manner analogous to example 466 except using 3-fluoro-5-methylphenylboronic acid instead of 2-methoxyphenylboronic acid. $^1$H NMR (500 MHz, DMSO-d6) δ ppm 2.42 (s, 3H) 3.76 (s, 3H) 6.99-7.12 (m, 2H) 7.38-7.56 (m, 7H) 7.77 (d, J=8.82 Hz, 1H) 7.96 (d, J=7.27 Hz, 1H) 8.10 (d, J=5.40 Hz, 1H) 8.25 (br. s., 1H) 8.57 (s, 1H) 8.62-8.72 (m, 2H) (M+H)+=501.1.

EXAMPLE 473

1-(4-(2-FLUOROPYRIDIN-3-YL)-2-METHOX-YPHENYL)-N-(PYRIMIDIN-4-YL)ISOQUINO-LINE-6-SULFONAMIDE

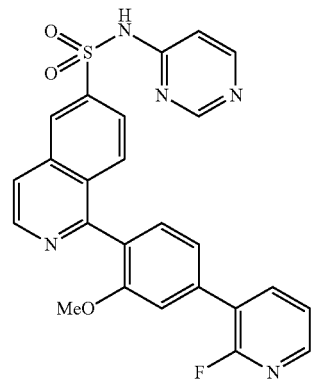 [SMILES: COc1cc(-c2cccnc2F)ccc1-c1nccc2cc(S(=O)(=O)Nc3ccncn3)ccc12]

The title compound was prepared in a manner analogous to example 466 except using 2-fluoro-3-pyridylboronic acid instead of 2-methoxyphenylboronic acid. $^1$H NMR (500 MHz, DMSO-d6) δ ppm 3.67 (s, 3H) 6.97 (d, J=6.78 Hz, 1H) 7.19 (d, J=8.01 Hz, 1H) 7.26-7.40 (m, 2H) 7.41-7.49 (m, 1H) 7.70 (d, J=8.76 Hz, 1H) 7.87-8.02 (m, 1H) 8.03-8.14 (m, 1H)

8.19 (d, J=6.09 Hz, 1H) 8.31 (br. s., 1H) 8.52 (br. s., 1H) 8.58-8.71 (m, 3H); (M+H)+=488.2.

EXAMPLE 474

1-(4-(2-FLUOROPYRIDIN-4-YL)-2-METHOXYPHENYL)-N-(PYRIMIDIN-4-YL)ISOQUINOLINE-6-SULFONAMIDE

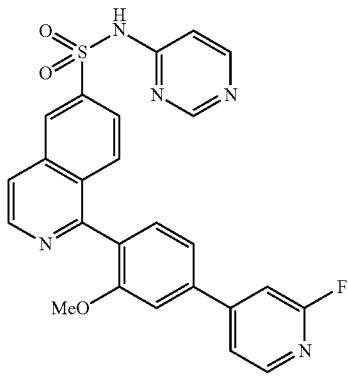 [SMILES: COc1cc(-c2ccnc(F)c2)ccc1-c1nccc2cc(S(=O)(=O)Nc3ccncn3)ccc12]

The title compound was prepared in a manner analogous to example 466 except using 2-fluoro-4-pyridylboronic acid instead of 2-methoxyphenylboronic acid. $^1$H NMR (500 MHz, DMSO-d6) δ ppm 3.78 (s, 3H) 7.03 (br. s., 1H) 7.49 (d, J=7.69 Hz, 1H) 7.61-7.68 (m, 2H) 7.68-7.80 (m, 2H) 7.87 (br. s., 1H) 7.96 (d, J=8.87 Hz, 1H) 8.11 (d, J=5.66 Hz, 1H) 8.24 (br. s., 1H) 8.37 (d, J=5.08 Hz, 1H) 8.56 (s, 1H) 8.65-8.85 (m, 3H); (M+H)+=488.2.

EXAMPLE 475

1-(4-(5-FLUOROPYRIDIN-3-YL)-2-METHOXYPHENYL)-N-(PYRIMIDIN-4-YL)ISOQUINOLINE-6-SULFONAMIDE

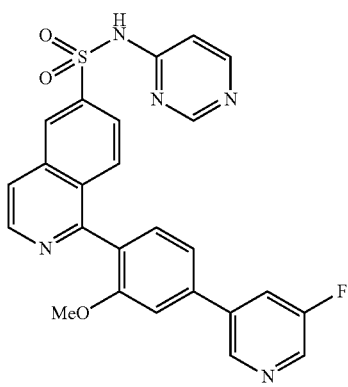 [SMILES: COc1cc(-c2cncc(F)c2)ccc1-c1nccc2cc(S(=O)(=O)Nc3ccncn3)ccc12]

The title compound was prepared in a manner analogous to example 466 except using 5-fluoro-3-pyridylboronic acid instead of 2-methoxyphenylboronic acid. $^1$H NMR (500 MHz, DMSO-d6) δ ppm 3.77 (s, 3H) 7.01 (d, J=6.04 Hz, 1H) 7.47 (d, J=7.75 Hz, 1H) 7.52-7.62 (m, 2H) 7.76 (d, J=8.76 Hz, 1H) 7.96 (d, J=7.43 Hz, 1H) 8.10 (d, J=5.72 Hz, 1H) 8.19-

8.27 (m, 2H) 8.55 (s, 1H) 8.60-8.67 (m, 2H) 8.70 (d, J=5.61 Hz, 1H) 8.97 (s, 1H); (M+H)+=488.2.

EXAMPLE 476

1-(2-METHOXY-4-(2-METHYLPYRIDIN-3-YL)PHENYL)-N-(PYRIMIDIN-4-YL)ISOQUINOLINE-6-SULFONAMIDE

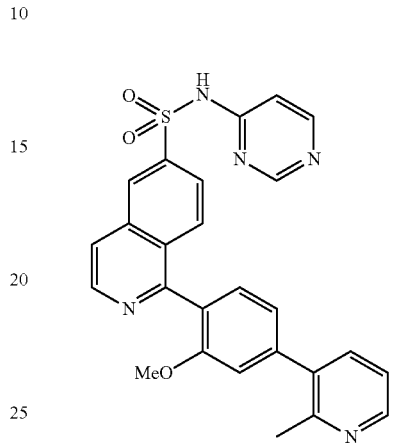

The title compound was prepared in a manner analogous to example 466 except using 2-methyl-3-pyridylboronic acid instead of 2-methoxyphenylboronic acid. $^1$H NMR (500 MHz, DMSO-d6) δ ppm 2.53-2.59 (m, 3H) 3.69 (s, 3H) 6.99 (d, J=6.57 Hz, 1H) 7.15 (d, J=7.48 Hz, 1H) 7.22 (s, 1H) 7.30-7.39 (m, 1H) 7.42 (d, J=7.59 Hz, 1H) 7.79 (d, J=8.82 Hz, 1H) 7.76 (d, J=7.69 Hz, 1H) 7.97 (d, J=8.92 Hz, 1H) 8.09 (d, J=5.45 Hz, 1H) 8.21 (d, J=6.20 Hz, 1H) 8.47-8.58 (m, 2H) 8.64 (s, 1H) 8.69 (d, J=5.61 Hz, 1H); (M+H)+=484.3.

EXAMPLE 477

1-(2-METHOXY-4-(6-METHYLPYRIDIN-3-YL)PHENYL)-N-(PYRIMIDIN-4-YL)ISOQUINOLINE-6-SULFONAMIDE

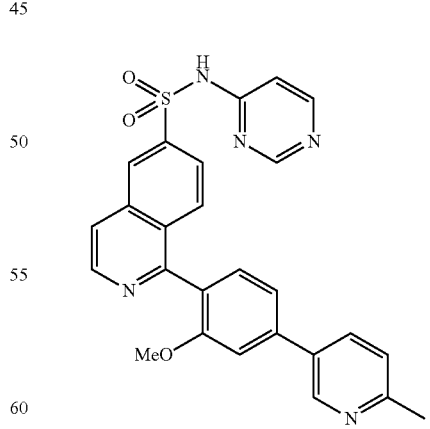

The title compound was prepared in a manner analogous to example 466 except using 6-methyl-3-pyridylboronic acid instead of 2-methoxyphenylboronic acid. $^1$H NMR (500 MHz, DMSO-d6) δ ppm 2.55 (s, 3H) 3.75 (s, 3H) 7.02 (d, J=5.77 Hz, 1H) 7.32-7.52 (m, 4H) 7.78 (d, J=8.92 Hz, 1H)

7.95 (d, J=10.42 Hz, 1H) 8.02-8.15 (m, 2H) 8.23 (d, J=5.45 Hz, 1H) 8.56 (s, 1H) 8.64 (s, 1H) 8.69 (d, J=5.56 Hz, 1H) 8.91 (s, 1H); (M+H)+=484.3.

EXAMPLE 478

1-(2-METHOXY-4-(5-METHYLPYRIDIN-3-YL)PHENYL)-N-(PYRIMIDIN-4-YL)ISOQUINOLINE-6-SULFONAMIDE

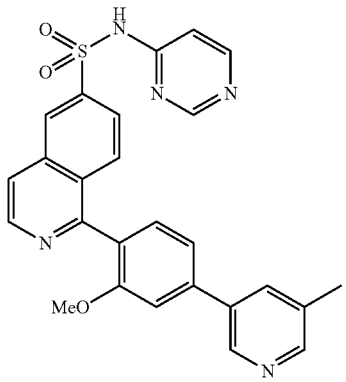 [SMILES: COc1cc(-c2cncc(C)c2)ccc1-c1nccc2cc(S(=O)(=O)Nc3ccncn3)ccc12]

The title compound was prepared in a manner analogous to example 466 except using 5-methyl-3-pyridylboronic acid instead of 2-methoxyphenylboronic acid. $^1$H NMR (500 MHz, DMSO-d6) δ ppm 2.42 (s, 3H) 3.76 (s, 3H) 6.99 (d, J=5.61 Hz, 1H) 7.33-7.50 (m, 2H) 7.52 (s, 1H) 7.77 (d, J=8.76 Hz, 1H) 7.95 (d, J=7.27 Hz, 1H) 8.01-8.13 (m, 2H) 8.21 (d, J=6.68 Hz, 1H) 8.47 (s, 1H) 8.54 (s, 1H) 8.64 (s, 1H) 8.69 (d, J=5.66 Hz, 1H) 8.85 (s, 1H); (M+H)+=484.3.

EXAMPLE 479

1-(2-METHOXY-4-(2-METHYLPYRIDIN-4-YL)PHENYL)-N-(PYRIMIDIN-4-YL)ISOQUINOLINE-6-SULFONAMIDE

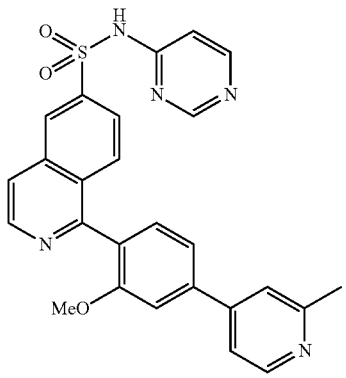 [SMILES: COc1cc(-c2ccnc(C)c2)ccc1-c1nccc2cc(S(=O)(=O)Nc3ccncn3)ccc12]

The title compound was prepared in a manner analogous to example 466 except using 2-methyl-4-pyridylboronic acid instead of 2-methoxyphenylboronic acid. $^1$H NMR (500 MHz, DMSO-d6) δ ppm 2.58 (s, 3H) 3.77 (s, 3H) 7.04 (br. s., 1H) 7.47 (d, J=7.69 Hz, 1H) 7.51-7.60 (m, 2H) 7.66 (d, J=3.53 Hz, 1H) 7.71-7.80 (m, 2H) 7.96 (d, J=7.43 Hz, 1H) 8.11 (d, J=5.50 Hz, 1H) 8.24 (br. s., 1H) 8.50-8.61 (m, 2H) 8.62-8.72 (m, 2H); (M+H)+=484.3.

EXAMPLE 480

1-(4-(2-FLUORO-4-METHYLPYRIDIN-3-YL)-2-METHOXYPHENYL)-N-(PYRIMIDIN-4-YL)ISOQUINOLINE-6-SULFONAMIDE

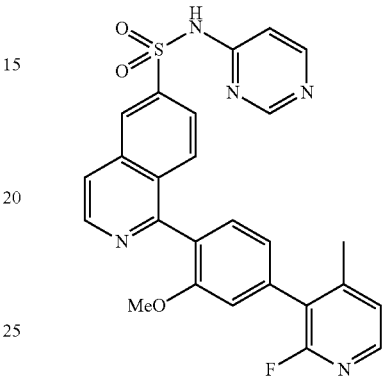

The title compound was prepared in a manner analogous to example 466 except using 2-fluoro-4-methyl-3-pyridylboronic acid instead of 2-methoxyphenylboronic acid. $^1$H NMR (500 MHz, DMSO-d6) δ ppm 2.33 (s, 3H) 3.53-3.74 (m, 3H) 7.10 (d, J=8.07 Hz, 1H) 7.16-7.26 (m, 1H) 7.28-7.42 (m, 1H) 7.45 (d, J=7.53 Hz, 1H) 7.80 (d, J=8.44 Hz, 1H) 7.92-8.05 (m, 1H) 8.08-8.21 (m, 2H) 8.27 (br. s., 1H) 8.58 (br. s., 1H) 8.63-8.85 (m, 3H); (M+H)+=502.3.

EXAMPLE 481

1-(4-(6-FLUORO-5-METHYLPYRIDIN-3-YL)-2-METHOXYPHENYL)-N-(PYRIMIDIN-4-YL)ISOQUINOLINE-6-SULFONAMIDE

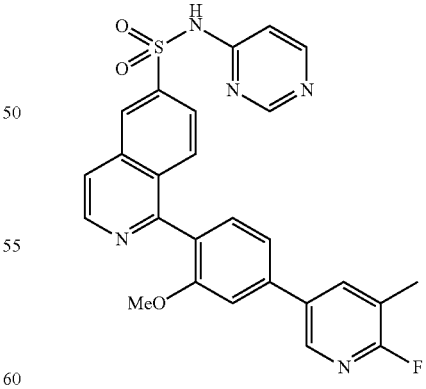

The title compound was prepared in a manner analogous to example 466 except using 2-fluoro-3-methyl-5-pyridylboronic acid instead of 2-methoxyphenylboronic acid. $^1$H NMR (500 MHz, DMSO-d6) δ ppm 2.36 (s, 3H) 3.76 (s, 3H) 7.03 (br. s., 1H) 7.43-7.49 (m, 2H) 7.52 (s, 1H) 7.76 (d, J=8.92 Hz, 1H) 7.96 (d, J=8.92 Hz, 1H) 8.10 (d, J=5.56 Hz, 1H) 8.24 (br.

s., 1H) 8.32 (d, J=9.72 Hz, 1H) 8.51 (br. s., 1H) 8.56 (s, 1H) 8.65 (s, 1H) 8.69 (d, J=5.77 Hz, 2H); (M+H)+=502.3.

EXAMPLE 482

1-(2-METHOXY-4-(2-METHOXYPYRIDIN-3-YL)PHENYL)-N-(PYRIMIDIN-4-YL)ISOQUINOLINE-6-SULFONAMIDE

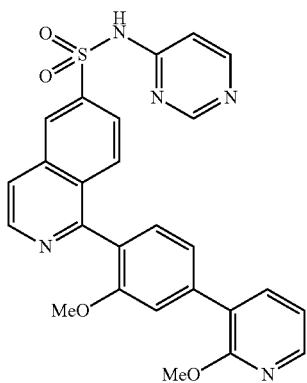 [SMILES: COc1cc(-c2cccnc2OC)ccc1-c1nccc2cc(S(=O)(=O)Nc3ccncn3)ccc12]

The title compound was prepared in a manner analogous to example 466 except using 2-methoxy-3-pyridylboronic acid instead of 2-methoxyphenylboronic acid. $^1$H NMR (500 MHz, DMSO-d6) δ ppm 3.69 (s, 3H) 3.95 (s, 3H) 7.03 (br. s., 1H) 7.16 (dd, J=7.13, 5.16 Hz, 1H) 7.23-7.36 (m, 1H) 7.36-7.41 (m, 2H) 7.79 (d, J=8.92 Hz, 1H) 7.87-8.02 (m, 2H) 8.09 (d, J=5.50 Hz, 1H) 8.23 (d, J=3.15 Hz, 2H) 8.56 (s, 1H) 8.65 (s, 1H) 8.69 (d, J=5.61 Hz, 1H); (M+H)+=500.2.

EXAMPLE 483

1-(2-METHOXY-4-(6-METHOXYPYRIDIN-3-YL)PHENYL)-N-(PYRIMIDIN-4-YL)ISOQUINOLINE-6-SULFONAMIDE

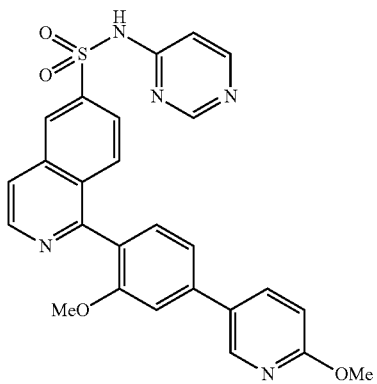 [SMILES: COc1ccc(-c2ccc(-c3nccc4cc(S(=O)(=O)Nc5ccncn5)ccc34)c(OC)c2)cn1]

The title compound was prepared in a manner analogous to example 466 except using 6-methoxy-3-pyridylboronic acid instead of 2-methoxyphenylboronic acid. $^1$H NMR (500 MHz, DMSO-d6) δ ppm 3.75 (s, 3H) 3.93 (s, 3H) 6.97 (d, J=8.66 Hz, 1H) 7.03 (br. s., 1H) 7.42 (s, 2H) 7.47 (s, 1H) 7.79 (d, J=8.71 Hz, 1H) 7.96 (d, J=9.03 Hz, 1H) 8.09 (d, J=5.56 Hz, 1H) 8.17 (dd, J=8.41, 2.54 Hz, 1H) 8.25 (br. s., 1H) 8.57 (s, 1H) 8.61-8.71 (m, 3H); (M+H)+=500.2.

EXAMPLE 484

1-(4'-FLUORO-3,3'-DIMETHOXY-[1,1'-BIPHENYL]-4-YL)-N-(PYRIMIDIN-4-YL)ISOQUINOLINE-6-SULFONAMIDE

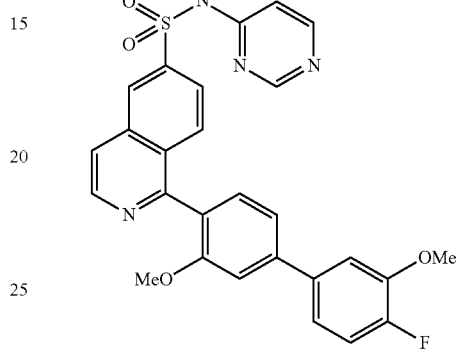

A microwave vial charged with PdCl$_2$(Amphos)$_2$ (0.025 g, 0.035 mmol), 4-fluoro-3-methoxyphenylboronic acid (0.119 g, 0.703 mmol), 1-(4-chloro-2-methoxyphenyl)-N-(pyrimidin-4-yl)isoquinoline-6-sulfonamide (0.150 g, 0.351 mmol), potassium phosphate (0.298 g, 1.406 mmol), 1.5 mL dioxane, and 0.5 mL water was heated to 150° C. in the microwave for 40 minutes. LC/MS showed product, so the aqueous layer was removed. The reaction mixture was treated with excess HCl (4N in dioxane) and was allowed to stir for 10 minutes. The reaction mixture was then concentrated. Purification of the crude residue by reverse phase column chromatography [Puriflash C18, 10-100% (0.1% NH4OH in MeOH)/(0.1% NH4OH in water)] gave 1-(4'-fluoro-3,3'-dimethoxy-[1,1'-biphenyl]-4-yl)-N-(pyrimidin-4-yl)isoquinoline-6-sulfonamide (0.030 g, 0.058 mmol, 16.5%). $^1$H NMR (MeCN-d3) δ: 8.69 (d, J=5.7 Hz, 1H), 8.62 (s, 1H), 8.48 (s, 1H), 8.20 (d, J=6.4 Hz, 1H), 7.89-7.98 (m, 2H), 7.80 (d, J=9.0 Hz, 1H), 7.34-7.47 (m, 4H), 7.19-7.33 (m, 2H), 7.06 (d, J=6.3 Hz, 1H), 3.98 (s, 3H), 3.71-3.75 (m, 3H) (M+H)+=517.1.

EXAMPLE 485

1-(3'-FLUORO-3,5'-DIMETHOXY-[1,1'-BIPHENYL]-4-YL)-N-(PYRIMIDIN-4-YL)ISOQUINOLINE-6-SULFONAMIDE

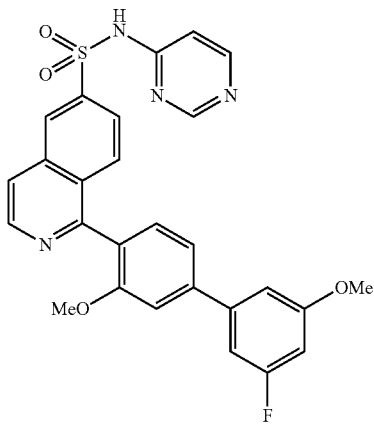 [SMILES: COc1cc(F)cc(-c2ccc(-c3nccc4cc(S(=O)(=O)Nc5ccncn5)ccc34)c(OC)c2)c1]

The title compound was prepared in a manner analogous to example 484 except using 3-fluoro-5-methoxyphenylboronic acid instead of 4-fluoro-3-methoxyphenylboronic acid. $^1$H NMR (MeCN-d3) δ: 8.69 (d, J=5.8 Hz, 1H), 8.62 (s, 1H), 8.48 (s, 1H), 8.21 (d, J=6.3 Hz, 1H), 7.89-7.99 (m, 2H), 7.79 (d, J=9.0 Hz, 1H), 7.34-7.45 (m, 3H), 7.09-7.18 (m, 2H), 7.06 (d, J=6.3, Hz, 1H), 6.77 (dt, J=10.9, 2.3 Hz, 1H), 3.89 (s, 3H), 3.72-3.75 (m, 3H); (M+H)+=517.1.

EXAMPLE 486

1-(3'-CYANO-4'-FLUORO-3-METHOXY-[1,1'-BIPHENYL]-4-YL)-N-(PYRIMIDIN-4-YL)ISOQUINOLINE-6-SULFONAMIDE

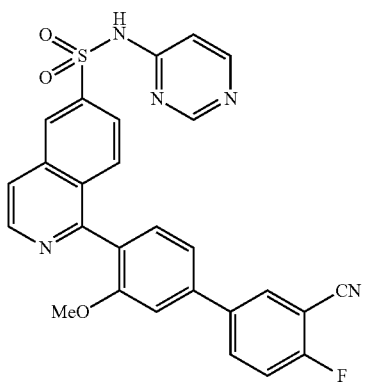 [SMILES: COc1cc(-c2ccc(F)c(C#N)c2)ccc1-c1nccc2cc(S(=O)(=O)Nc3ccncn3)ccc12]

The title compound was prepared in a manner analogous to example 484 except using 3-cyano-4-fluorophenylboronic acid instead of 4-fluoro-3-methoxyphenylboronic acid. $^1$H NMR (MeCN-d3) δ: 8.70 (d, J=5.8 Hz, 1H), 8.61-8.67 (m, 1H), 8.48 (s, 1H), 8.22 (d, J=6.5 Hz, 1H), 8.17 (d, J=6.0, 1H), 8.05-8.13 (m, 1H), 7.91-8.00 (m, 2H), 7.80 (d, J=9.0 Hz, 1H), 7.43-7.51 (m, 2H), 7.35-7.42 (m, 2H), 7.07 (d, J=6.3 Hz, 1H), 3.74 (s, 3H); (M+H)+=512.0.

EXAMPLE 487

1-(3'-CYANO-5'-FLUORO-3-METHOXY-[1,1'-BIPHENYL]-4-YL)-N-(PYRIMIDIN-4-YL)ISOQUINOLINE-6-SULFONAMIDE

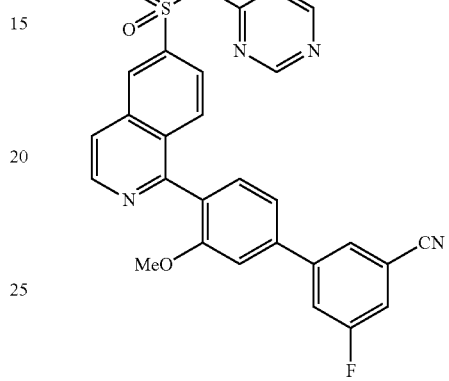

The title compound was prepared in a manner analogous to example 484 except using 3-cyano-5-fluorophenylboronic acid instead of 4-fluoro-3-methoxyphenylboronic acid. $^1$H NMR (MeCN-d3) δ: 8.69 (d, J=5.7 Hz, 1H), 8.63 (s, 1H), 8.48 (s, 1H), 8.21 (d, J=6.4 Hz, 1H), 7.91-8.03 (m, 3H), 7.85 (dt, J=10.1, 1.8 Hz, 1H), 7.78 (d, J=8.9 Hz, 1H), 7.56 (dd, J=8.3, 1.4 Hz, 1H), 7.38-7.48 (m, 3H), 7.02-7.08 (m, 1H), 3.74 (s, 3H); (M+H)+=512.0.

EXAMPLE 488

1-(4'-FLUORO-3-METHOXY-3'-METHYL-[1,1'-BIPHENYL]-4-YL)-N-(PYRIMIDIN-4-YL)ISOQUINOLINE-6-SULFONAMIDE

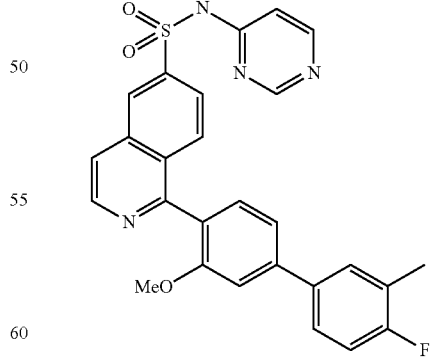

The title compound was prepared in a manner analogous to example 484 except using 4-fluoro-3-methylphenylboronic acid instead of 4-fluoro-3-methoxyphenylboronic acid. $^1$H NMR (MeCN-d3) δ: 8.68 (d, J=5.7 Hz, 1H), 8.60 (s, 1H), 8.47 (s, 1H), 8.18 (d, J=5.6 Hz, 1H), 7.88-7.99 (m, 2H), 7.79 (d, J=8.8 Hz, 1H), 7.66 (d, J=7.0 Hz, 1H), 7.59 (d, J=8.4 Hz, 1H), 7.38-7.44 (m, 1H), 7.31-7.38 (m, 2H), 7.17 (t, J=9.1 Hz, 1H), 7.02 (d, J=6.6 Hz, 1H), 3.72 (s, 3H), 2.37 (s, 3H); (M+H)+ =501.0.

EXAMPLE 489

1-(4-(1H-INDOL-5-YL)-2-METHOXYPHENYL)-N-(PYRIMIDIN-4-YL)ISOQUINOLINE-6-SULFONAMIDE

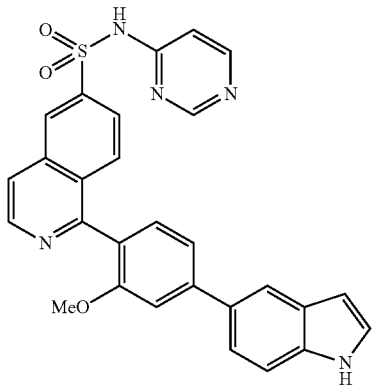 [SMILES: COc1cc(-c2ccc3[nH]ccc3c2)ccc1-c1nccc2cc(S(=O)(=O)Nc3ccncn3)ccc12]

The title compound was prepared in a manner analogous to example 484 except using indole-5-boronic acid instead of 4-fluoro-3-methoxyphenylboronic acid. $^1$H NMR (MeCN-d3) δ: 9.41 (br. s., 1H), 8.71 (d, J=5.7 Hz, 1H), 8.64 (s, 1H), 8.49 (s, 1H), 8.23 (d, J=6.2 Hz, 1H), 7.90-8.02 (m, 3H), 7.87 (d, J=8.9 Hz, 1H), 7.57 (s, 2H), 7.36-7.48 (m, 3H), 7.29-7.36 (m, 1H), 7.08 (d, J=6.3 Hz, 1H), 6.58 (d, J=2.2 Hz, 1H), 3.73-3.77 (m, 3H); (M+H)+=508.0.

EXAMPLE 490

1-(3'-CHLORO-4'-FLUORO-3-METHOXY-[1,1'-BIPHENYL]-4-YL)-N-(PYRIMIDIN-4-YL)ISOQUINOLINE-6-SULFONAMIDE

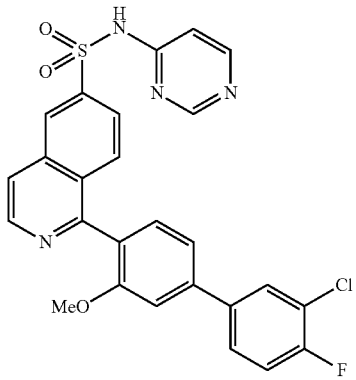 [SMILES: COc1cc(-c2ccc(F)c(Cl)c2)ccc1-c1nccc2cc(S(=O)(=O)Nc3ccncn3)ccc12]

The title compound was prepared in a manner analogous to example 484 except using 3-chloro-4-fluorophenylboronic acid instead of 4-fluoro-3-methoxyphenylboronic acid. $^1$H NMR (MeCN-d3) δ: 8.70 (d, J=5.7 Hz, 1H), 8.63 (s, 1H), 8.48 (s, 1H), 8.22 (d, J=6.4 Hz, 1H), 7.85-7.99 (m, 3H), 7.77-7.84 (m, 1H), 7.69-7.75 (m, 1H), 7.39-7.45 (m, 1H), 7.31-7.39 (m, 3H), 7.07 (d, J=6.4 Hz, 1H), 3.71-3.75 (m, 3H); (M+H)+ =521.0.

EXAMPLE 491

1-(3'-CHLORO-5'-FLUORO-3-METHOXY-[1,1'-BIPHENYL]-4-YL)-N-(PYRIMIDIN-4-YL)ISOQUINOLINE-6-SULFONAMIDE

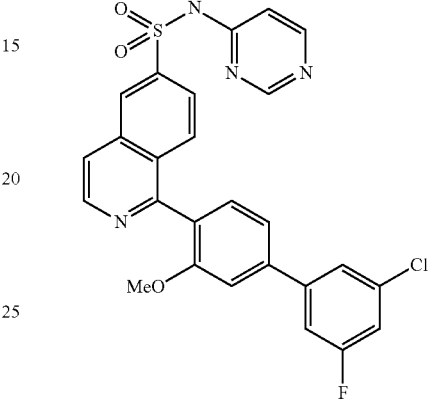

The title compound was prepared in a manner analogous to example 484 except using 3-chloro-5-fluorophenylboronic acid instead of 4-fluoro-3-methoxyphenylboronic acid. $^1$H NMR (MeCN-d3) δ: 8.71 (d, J=5.9 Hz, 1H), 8.64 (s, 1H), 8.48 (br. s., 1H), 7.91-7.99 (m, 3H), 7.80 (d, J=9.3 Hz, 1H), 7.67 (s, 1H), 7.52 (d, J=10.0 Hz, 1H), 7.37-7.47 (m, 3H), 7.27 (d, J=8.5 Hz, 1H), 7.04-7.12 (br. s., 1H), 3.74 (s, 3H); (M+H)+ =521.0.

EXAMPLE 492

1-(4'-CHLORO-3'-FLUORO-3-METHOXY-[1,1'-BIPHENYL]-4-YL)-N-(PYRIMIDIN-4-YL)ISOQUINOLINE-6-SULFONAMIDE

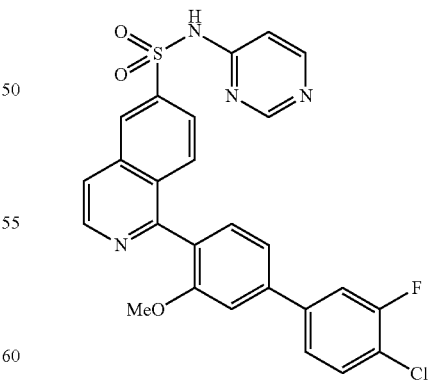

The title compound was prepared in a manner analogous to example 484 except using 4-chloro-3-fluorophenylboronic acid instead of 4-fluoro-3-methoxyphenylboronic acid. $^1$H NMR (MeCN-d3) δ: 8.70 (d, J=5.7 Hz, 1H), 8.64 (s, 1H), 8.48 (s, 1H), 8.22 (d, J=6.2 Hz, 1H), 7.90-7.98 (m, 2H), 7.81 (d, J=9.0 Hz, 1H), 7.65-7.73 (m, 1H), 7.57-7.64 (m, 2H), 7.36-7.47 (m, 3H), 7.08 (d, J=6.4 Hz, 1H), 3.72-3.76 (m, 3H); (M+H)+=521.0.

EXAMPLE 493

1-(4'-CHLORO-3-METHOXY-3'-METHYL-[1,1'-BIPHENYL]-4-YL)-N-(PYRIMIDIN-4-YL)ISO-QUINOLINE-6-SULFONAMIDE

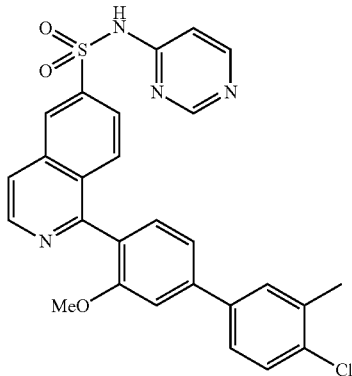 [SMILES: COc1cc(-c2ccc(Cl)c(C)c2)ccc1-c1nccc2cc(S(=O)(=O)Nc3ccncn3)ccc12]

The title compound was prepared in a manner analogous to example 484 except using 4-chloro-3-methylphenylboronic acid instead of 4-fluoro-3-methoxyphenylboronic acid. $^1$H NMR (MeCN-d3) δ: 8.66 (d, J=5.9 Hz, 1H), 8.57 (s, 1H), 8.44 (s, 1H), 8.12 (d, J=5.7 Hz, 1H), 7.94 (d, J=9.1 Hz, 1H), 7.89 (d, J=5.7 Hz, 1H), 7.70-7.78 (m, 2H), 7.54-7.61 (m, 1H), 7.46-7.52 (m, 1H), 7.33-7.44 (m, 3H), 6.93 (d, J=6.3 Hz, 1H), 3.73 (s, 3H), 2.47 (s, 3H); (M+H)+=517.0.

EXAMPLE 494

1-(3'-CHLORO-3-METHOXY-4'-METHYL-[1,1'-BIPHENYL]-4-YL)-N-(PYRIMIDIN-4-YL)ISO-QUINOLINE-6-SULFONAMIDE

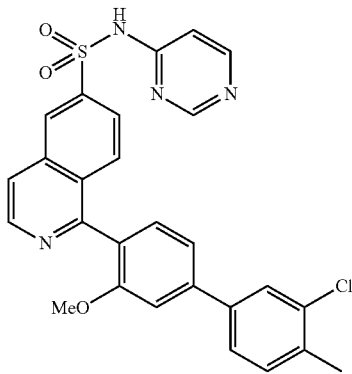 [SMILES: COc1cc(-c2ccc(C)c(Cl)c2)ccc1-c1nccc2cc(S(=O)(=O)Nc3ccncn3)ccc12]

The title compound was prepared in a manner analogous to example 484 except using 3-chloro-4-methylphenylboronic acid instead of 4-fluoro-3-methoxyphenylboronic acid. $^1$H NMR (MeCN-d3) δ: 8.70 (d, J=5.7 Hz, 1H), 8.63 (s, 1H), 8.48 (s, 1H), 8.22 (d, J=6.4 Hz, 1H), 7.90-7.98 (m, 2H), 7.77-7.84 (m, 2H), 7.62 (d, J=7.9 Hz, 1H), 7.35-7.45 (m, 4H), 7.08 (d, J=6.4 Hz, 1H), 3.73 (s, 3H), 2.44 (s, 3H); (M+H)+=517.0.

EXAMPLE 495

1-(3'-CHLORO-3-METHOXY-5'-METHYL-[1,1'-BIPHENYL]-4-YL)-N-(PYRIMIDIN-4-YL)ISO-QUINOLINE-6-SULFONAMIDE

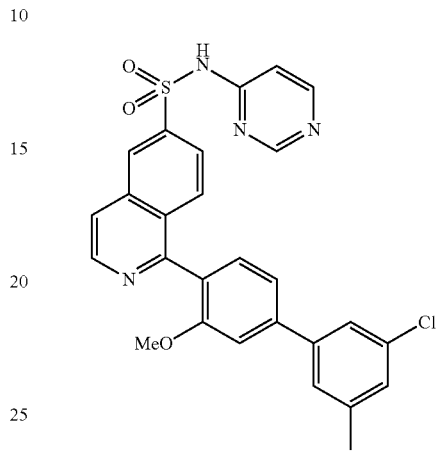

The title compound was prepared in a manner analogous to example 484 except using 3-chloro-5-methylphenylboronic acid instead of 4-fluoro-3-methoxyphenylboronic acid. $^1$H NMR (MeCN-d3) δ: 8.70 (d, J=5.7 Hz, 1H), 8.63 (s, 1H), 8.48 (s, 1H), 8.23 (d, J=6.1 Hz, 1H), 7.90-7.99 (m, 2H), 7.81 (d, J=8.9 Hz, 1H), 7.60 (s, 1H), 7.55 (s, 1H), 7.36-7.44 (m, 3H), 7.28 (s, 1H), 7.08 (d, J=5.8 Hz, 1H), 3.74 (s, 3H), 2.44 (s, 3H); (M+H)+=517.0.

EXAMPLE 496

1-(2-METHOXY-4-(TRIFLUOROMETHYL)PHE-NYL)-N-(6-(TRIFLUOROMETHYL)PYRIMIDIN-4-YL)ISOQUINOLINE-6-SULFONAMIDE

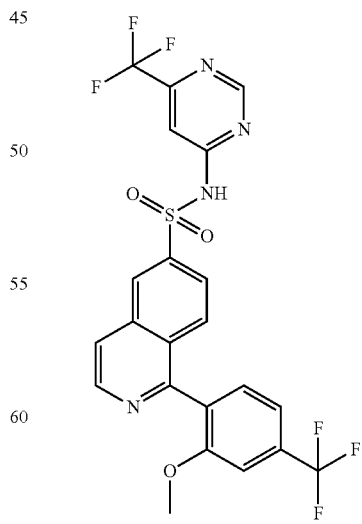

A round-bottom flask was charged with 6-(trifluoromethyl)pyrimidin-4-amine (0.030 g, 0.182 mmol)) and THF (0.910 ml), and the vessel was cooled to −78° C. for 15 minutes. Lithium bis(trimethylsilyl)amide (0.218 ml, 0.218 mmol),) was then added drop wise over 1 minute. The reaction was stirred for 10 minutes, and then a solution of perfluorophenyl 1-(2-methoxy-4-(trifluoromethyl)phenyl)isoquinoline-6-sulfonate (Intermediate LLL; 0.100 g, 0.182 mmol) in THF (1.6 mL) was added drop wise. The bath was removed, and the resulting mixture was stirred for 45 minutes. The reaction was diluted with saturated ammonium chloride (aq.) solution (30 mL), and was washed with ethyl acetate (20 mL×3). The organic layers were combined, dried over magnesium sulfate, filtered and concentrated. The resulting material was purified via silica gel chromatography (ISCO, 40 g), eluting with 0 to 100% ethyl acetate in heptanes. The fractions were concentrated under reduced pressure to yield 1-(2-methoxy-4-(trifluoromethyl)phenyl)-N-(6-(trifluoromethyl)pyrimidin-4-yl)isoquinoline-6-sulfonamide (0.015 g, 0.028 mmol, 15.60% yield). m/z (ESI) 528.9 (M+H)$^+$.

INTERMEDIATE PPPPP:
N-(4-METHOXYBENZYL)THIAZOL-4-AMINE

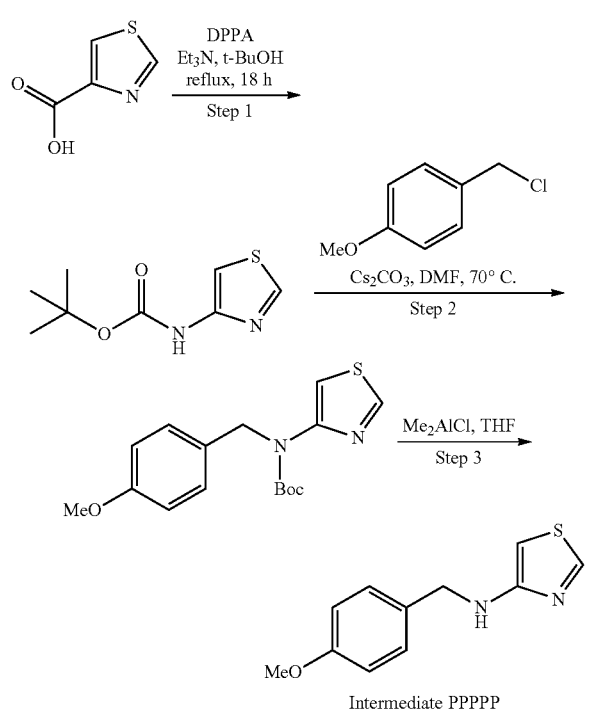

Intermediate PPPPP

STEP 1: TERT-BUTYL THIAZOL-4-YLCARBAMATE

To a suspension of thiazole-4-carboxylic acid (19.6 g, 151 mmol, GLR) in tert-butyl alcohol (400 mL) was added triethylamine (24.8 mL, 181 mmol, Finar) and diphenylphosphoryl azide (41.7 mL, 182 mmol, Aldrich) and the reaction mixture was heated at reflux for 18 h. The reaction mixture was cooled to room temperature and concentrated under reduced pressure. The residue was taken up in ethyl acetate (500 mL), washed with water (500 mL) and then with saturated aqueous NaHCO$_3$ solution (500 mL). The organic layer was dried over sodium sulfate, filtered and concentrated under reduced pressure to obtain the crude material which was further purified by column chromatography (silica gel 100-200 mesh and 0-20% ethyl acetate in hexanes) to obtain tert-butyl thiazol-4-ylcarbamate (20.0 g, 66.6%) as an off-white solid. MS (ESI, positive ion) m/z=201 (M+1)$^+$.

STEP 2: TERT-BUTYL 4-METHOXYBENZYL(THIAZOL-4-YL)CARBAMATE

To a solution of tert-butyl thiazol-4-ylcarbamate (13.0 g, 64.9 mmol) in DMF (150 mL) was added Cs$_2$CO$_3$ (42.3 g, 130 mmol) and 1-(chloromethyl)-4-methoxybenzene (12.1 g, 78.0 mmol, Spectrochem). The reaction mixture was stirred at 80° C. for 6 h. The reaction mixture was allowed to cool to room temperature and water (500 mL) was added. The aqueous layer was extracted with diethyl ether (2×500 mL). The combined organic layer was dried over sodium sulfate, filtered and concentrated under reduced pressure to obtain the crude material which was further purified by column chromatography (silica gel 100-200 mesh and 0-20% ethyl acetate in hexanes) to obtain tert-butyl 4-methoxybenzyl(thiazol-4-yl)carbamate (15.0 g, 80%) as an off-white solid. MS (ESI, positive ion) m/z=321 (M+1)$^+$.

STEP 3: N-(4-METHOXYBENZYL)THIAZOL-4-AMINE

To a solution of tert-butyl 4-methoxybenzyl(thiazol-4-yl)carbamate (20.0 g, 62.4 mmol) in THF (100 mL) was added Me$_2$AlCl (1M in THF, Aldrich) (93.6 mL, 93.6 mmol) at 0° C. The reaction was allowed to stir at room temperature for 5 h. The reaction mixture was poured into ice-cold water and extracted with ethyl acetate (2×500 mL). The combined organic layer was dried over sodium sulfate, filtered and concentrated under reduced pressure to obtain the crude material which was further purified by column chromatography (silica gel 100-200 mesh and 0-50% ethyl acetate in hexanes) to obtain N-(4-methoxybenzyl)thiazol-4-amine (9.8 g, 73%) as an off-white solid. MS (ESI, positive ion) m/z=220.9 (M+1)$^+$. $^1$H NMR (400 MHz, DMSO) δ 8.73 (d, J=2.2 Hz, 1H), 7.28 (d, J=8.5 Hz, 2H), 6.96-6.76 (m, 2H), 6.54 (t, J=6.3 Hz, 1H), 5.76 (d, J=2.2 Hz, 1H), 4.18 (d, J=6.2 Hz, 2H), 3.71 (s, 3H).

EXAMPLE 497

1-(2-METHOXY-4-(TRIFLUOROMETHYL)PHENYL)-N-(THIAZOL-4-YL)ISOQUINOLINE-6-SULFONAMIDE

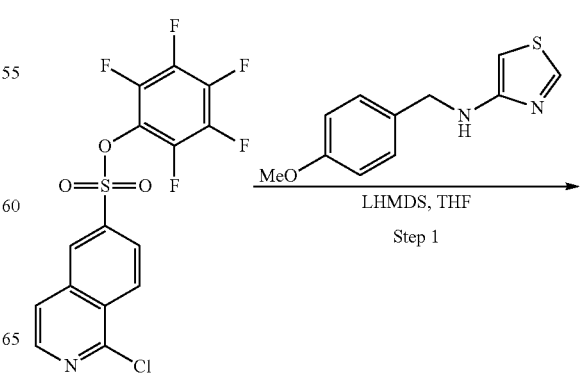

-continued

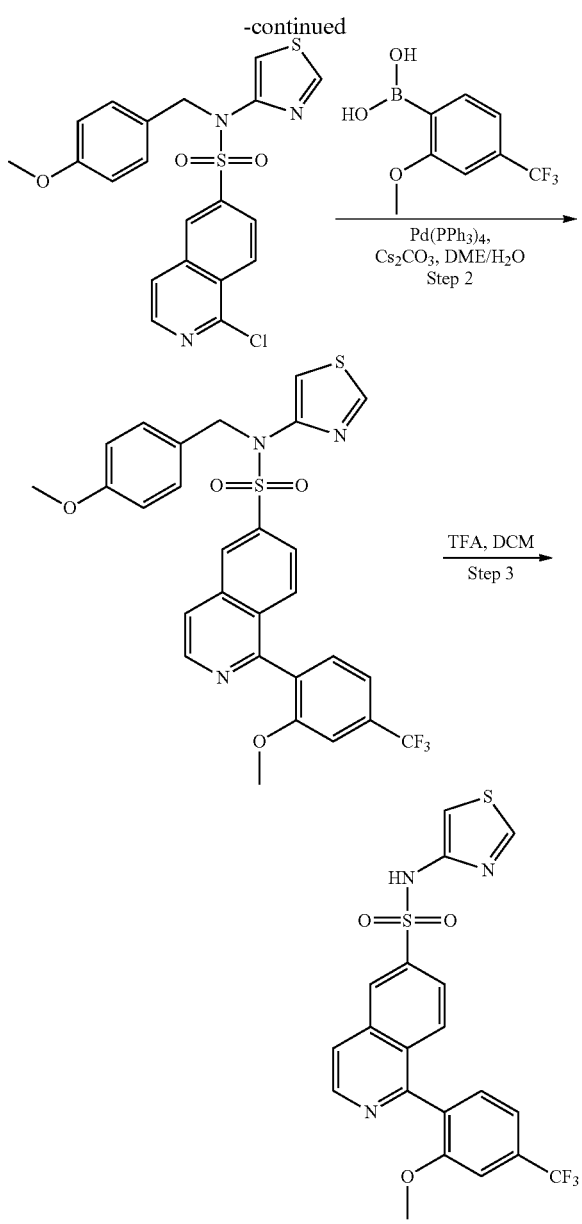

STEP 1: 1-CHLORO-N-(4-METHOXYBENZYL)-N-(THIAZOL-4-YL)ISOQUINOLINE-6-SULFONAMIDE

To a flask containing ice cold suspension of N-(4-methoxybenzyl)thiazol-4-amine (Intermediate PPPPP; 0.085 g, 0.384 mmol) in THF (1.408 ml) was added lithium bis(trimethylsilyl)amide (0.403 ml, 0.403 mmol) drop wise over 10 min. The mixture was stirred for 15 minutes prior to the addition of a solution of perfluorophenyl-1-chloroisoquinoline-6-sulfonate (From Step 1 in Example 73; 0.15 g, 0.366 mmol) in THF (1.0 ml). After 45 minutes of stirring (ice melt) LCMS indicated that the reaction was nearly complete. The mixture was allowed to stir and slowly warm to room temperature overnight. LCMS indicated that the reaction was complete. The reaction was quenched by the addition of acetic acid (~2 ml) and the resulting mixture was dried under reduced pressure and purified via silica gel chromatography (40 g silicycle HP column) ramping EtOAc in heptane (0-50%) providing product 1-chloro-N-(4-methoxybenzyl)-N-(thiazol-4-yl)isoquinoline-6-sulfonamide. m/z (ESI) 446.1 (M+H)$^+$.

STEP 2: 1-(2-METHOXY-4-(TRIFLUOROMETHYL)PHENYL)-N-(4-METHOXYBENZYL)-N-(THIAZOL-4-YL)ISOQUINOLINE-6-SULFONAMIDE

To a solution of 1-chloro-N-(4-methoxybenzyl)-N-(thiazol-4-yl)isoquinoline-6-sulfonamide (0.10 g, 0.224 mmol), (2-methoxy-4-(trifluoromethyl)phenyl)boronic acid (0.064 g, 0.292 mmol) and cesium carbonate (0.292 g, 0.897 mmol) in DME (2.437 ml) and Water (0.366 ml) was added Pd(PPh$_3$)$_4$ (0.026 g, 0.022 mmol) in one portion. The resulting mixture was heated to 125° C. in the microwave for 2 hours. The resulting mixture was transferred to a seperatory funnel and the aqueous layer was washed 3x with EtOAc. The organic layers were combined, dried with MgSO$_4$, filtered and concentrated to an oil. The crude mixture was purified by the silica gel chromatography (100% hexanes to 25% EtOAc in hexanes to 90% EtOAc in heptanes). m/z (ESI) 586.2 (M+H)$^+$.

STEP 3: 1-(2-METHOXY-4-(TRIFLUOROMETHYL)PHENYL)-N-(THIAZOL-4-YL)ISOQUINOLINE-6-SULFONAMIDE

To a solution of 1-(2-methoxy-4-(trifluoromethyl)phenyl)-N-(4-methoxybenzyl)-N-(thiazol-4-yl)isoquinoline-6-sulfonamide (0.070 g, 0.120 mmol) in DCM (1.195 ml) was added TFA (0.276 ml, 3.59 mmol) at room temperature. The resulting mixture stirred for a total of 3 weeks, monitoring every few days by LCMS. The crude mixture was concentrated by allowing the DCM to evaporate and taken up in DMSO. The DMSO solution was injected directly onto the Gilson HPLC for purification to provide 24 mgs (43% yield) of desired product. m/z (ESI) 465.9 (M+H)$^+$.

EXAMPLE 498

1-(5-CHLORO-6-(3-FLUOROPHENYL)-2-METHOXYPYRIDIN-3-YL)-N-(1,3,4-THIADIAZOL-2-YL)ISOQUINOLINE-6-SULFONAMIDE

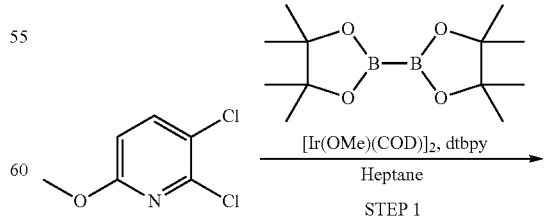

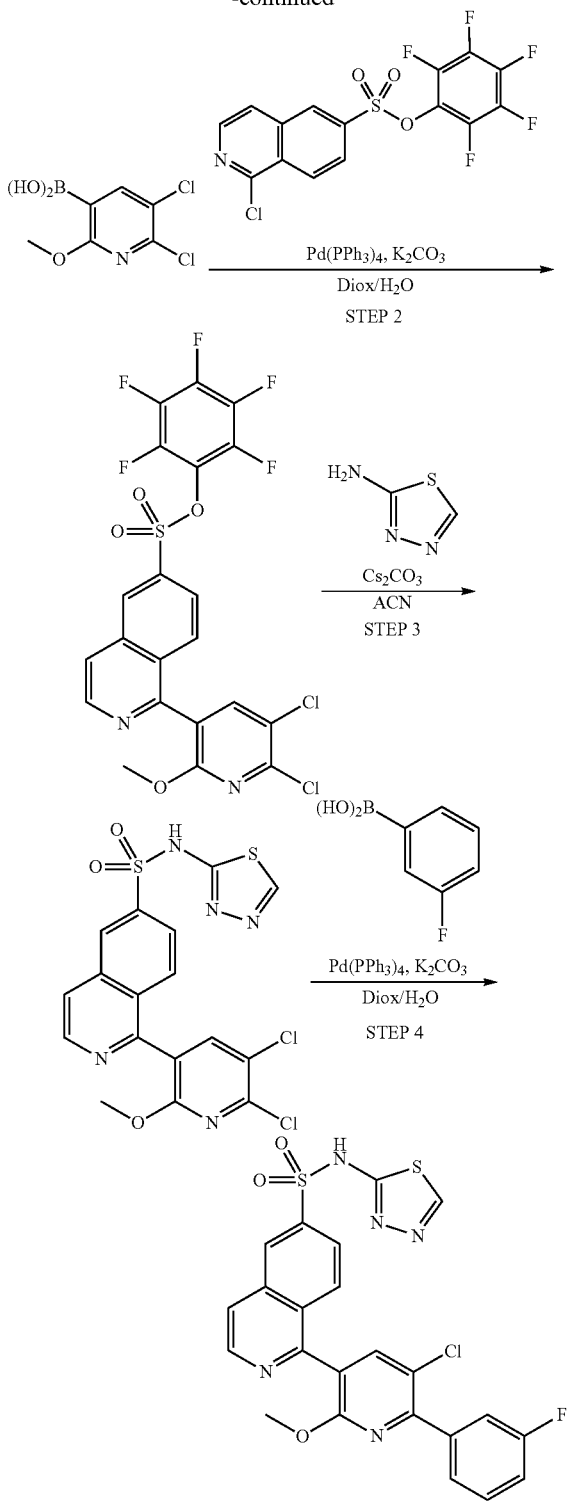

STEP 1: (5,6-DICHLORO-2-METHOXYPYRIDIN-3-YL)BORONIC ACID

To a round-bottomed flask was added (1,5-cyclooctadiene)(methoxy)-iridium(i) dimer (0.223 g, 0.337 mmol), 4,4-di-tert-butyl-2,2-dipyridyl (0.181 g, 0.674 mmol) and bis(pinacolato)diboron (2.85 g, 11.23 mmol) in heptane (112 ml). The reaction mixture was vacuumed and refilled with dry nitrogen (3×). After stirring for 10 minutes, 2,3-dichloro-6-methoxypyridine (2.0 g, 11.23 mmol) was added. The resulting reaction mixture was stirred at rt overnight. The reaction was diluted with ethyl acetate and washed twice with 1N HCl solution. The organic layer was extracted twice with 1N sodium hydroxide solution, and the combined aqueous layers were acidified with concentrated HCl solution and extracted twice with ethyl acetate. The combined organic layers were dried over sodium sulfate, filtered, and concentrated to afford (5,6-dichloro-2-methoxypyridin-3-yl)boronic acid as an oily light yellow solid. m/z (ESI) 222.1 (M+H)$^+$.

STEP 2: PERFLUOROPHENYL 1-(5,6-DICHLORO-2-METHOXYPYRIDIN-3-YL)ISOQUINOLINE-6-SULFONATE

A vial was charged with perfluorophenyl 1-chloroisoquinoline-6-sulfonate (From Step 1 in Example 73; 0.050 g, 0.122 mmol), (5,6-dichloro-2-methoxypyridin-3-yl)boronic acid (0.030 g, 0.134 mmol), potassium carbonate (0.051 g, 0.366 mmol), and Pd(Ph$_3$P)$_4$ (0.014 g, 0.012 mmol). The vial was flushed with Ar (g), then dioxane (0.915 ml) and water (0.305 ml) were added. The reaction was heated at 40° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-50% EtOAc:Heptane) to afford perfluorophenyl 1-(5,6-dichloro-2-methoxypyridin-3-yl)isoquinoline-6-sulfonate as a white solid. (ESI) 551.0 (M+H)$^+$.

STEP 3: 1-(5,6-DICHLORO-2-METHOXYPYRIDIN-3-YL)-N-(1,3,4-THIADIAZOL-2-YL)ISOQUINOLINE-6-SULFONAMIDE

A vial was charged with perfluorophenyl 1-(5,6-dichloro-2-methoxypyridin-3-yl)isoquinoline-6-sulfonate (0.042 g, 0.076 mmol), 1,3,4-thiadiazol-2-amine (8.48 mg, 0.084 mmol), and cesium carbonate (0.074 g, 0.229 mmol). The vial was flushed with Ar (g), then acetonitrile (0.381 ml) was added. The reaction was stirred for four hours at room temperature. The mixture was diluted with EtOAc and 1 N aq. HCl. The layers were separated, and the aq. layer was extracted with EtOAc (2×). The combined organic extracts were dried over sodium sulfate, filtered, and concentrated to afford crude 1-(5,6-dichloro-2-methoxypyridin-3-yl)-N-(1,3,4-thiadiazol-2-yl)isoquinoline-6-sulfonamide as a yellow solid. (ESI) 470.0 (M+H)$^+$.

STEP 4: 1-(5-CHLORO-6-(3-FLUOROPHENYL)-2-METHOXYPYRIDIN-3-YL)-N-(1,3,4-THIADIAZOL-2-YL)ISOQUINOLINE-6-SULFONAMIDE

A microwave vial was charged with 1-(5,6-dichloro-2-methoxypyridin-3-yl)-N-(1,3,4-thiadiazol-2-yl)isoquinoline-6-sulfonamide (0.032 g, 0.068 mmol), (3-fluorophenyl)boronic acid (0.014 g, 0.102 mmol), potassium carbonate (0.028 g, 0.205 mmol), and Pd(Ph$_3$P)$_4$ (7.90 mg, 6.83 μmol). The vial was flushed with Ar (g), then Dioxane (0.512 ml) and Water (0.171 ml) were added. The reaction was microwaved at 90° C. for one hour. The reaction was diluted with ethyl acetate and washed with water. The aqueous layer was extracted with ethyl acetate, and the combined organic layers were dried with sodium sulfate, filtered, and concentrated.

The material was purified via column chromatography (RediSep Gold 12 g, gradient elution 0-10% MeOH:DCM) to afford 1-(5-chloro-6-(3-fluorophenyl)-2-methoxypyridin-3-yl)-N-(1,3,4-thiadiazol-2-yl)isoquinoline-6-sulfonamide as a tan solid. $^1$H NMR (400 MHz, DMSO-$d_6$) δ=8.80 (s, 1H), 8.74 (d, J=5.7 Hz, 1H), 8.60 (s, 1H), 8.19 (d, J=5.9 Hz, 1H), 8.12 (s, 1H), 7.91 (s, 2H), 7.74 (d, J=8.0 Hz, 1H), 7.72-7.67 (m, J=2.2, 9.7 Hz, 1H), 7.61 (dt, J=6.1, 7.9 Hz, 1H), 7.37 (dt, J=2.2, 8.5 Hz, 1H), 3.82 (s, 3H). m/z (ESI) 528.2 (M+H)$^+$.

EXAMPLE 499

1-(6-(3,4-DIFLUOROPHENYL)-2-METHOXYPYRIDIN-3-YL)-N-(PYRIMIDIN-4-YL)ISOQUINOLINE-6-SULFONAMIDE

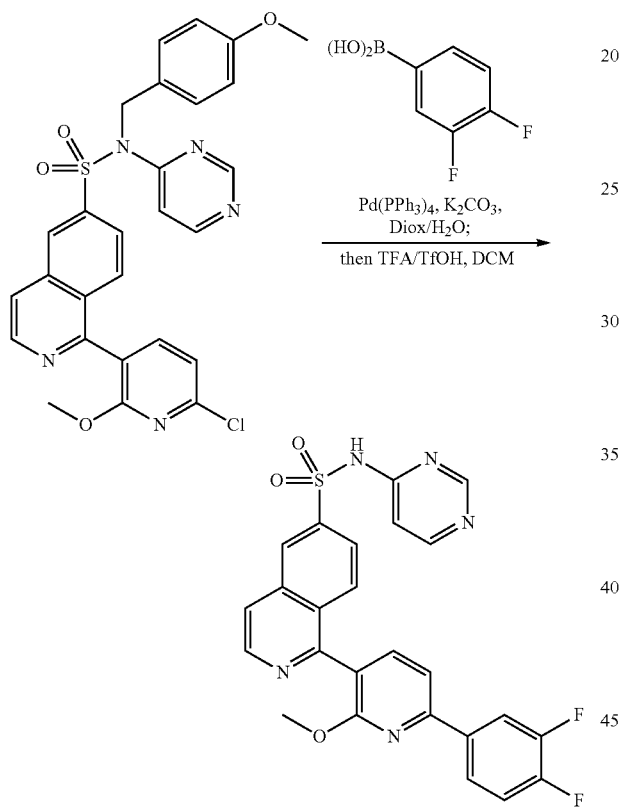

A microwave vial was charged with 1-(6-chloro-2-methoxypyridin-3-yl)-N-(4-methoxybenzyl)-N-(pyrimidin-4-yl)isoquinoline-6-sulfonamide (Intermediate EEEEE; 0.052 g, 0.095 mmol), (3,4-difluorophenyl)boronic acid (0.022 g, 0.142 mmol), potassium carbonate (0.039 g, 0.285 mmol), and Pd(Ph$_3$P)$_4$ (10.96 mg, 9.49 μmol). The vial was flushed with Ar (g), then Dioxane (0.712 mL) and Water (0.237 mL) were added. The reaction was microwaved at 90° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-50% EtOAc:Heptane) to afford 1-(6-(3,4-difluorophenyl)-2-methoxypyridin-3-yl)-N-(4-methoxybenzyl)-N-(pyrimidin-4-yl)isoquinoline-6-sulfonamide. The material was dissolved in DCM and TFA (0.1 mL, 1.298 mmol) was added. The reaction was stirred overnight at room temperature. Triflic acid (0.050 mL, 0.563 mmol) was added and the reaction was stirred for one hour. The reaction was concentrated and the material was purified via column chromatography (RediSep Gold 12 g, gradient elution 0-10% MeOH:DCM) to afford 1-(6-(3,4-difluorophenyl)-2-methoxypyridin-3-yl)-N-(pyrimidin-4-yl)isoquinoline-6-sulfonamide as a yellow solid. $^1$H NMR (400 MHz, DMSO-$d_6$) δ=8.78-8.71 (m, 2H), 8.59 (s, 1H), 8.33-8.28 (m, 1H), 8.28-8.23 (m, 2H), 8.13 (br. s., 1H), 8.02 (d, J=1.9 Hz, 1H), 7.98 (d, J=7.6 Hz, 2H), 7.88 (d, J=7.9 Hz, 2H), 7.62 (td, J=8.6, 10.4 Hz, 1H), 7.03 (d, J=6.0 Hz, 1H), 3.91 (s, 3H). m/z (ESI) 506.1 (M+H)$^+$.

EXAMPLE 501

1-(5-CHLORO-2-METHOXYPHENYL)-4-OXO-N-(THIAZOL-2-YL)-3,4-DIHYDROPHTHALAZINE-6-SULFONAMIDE

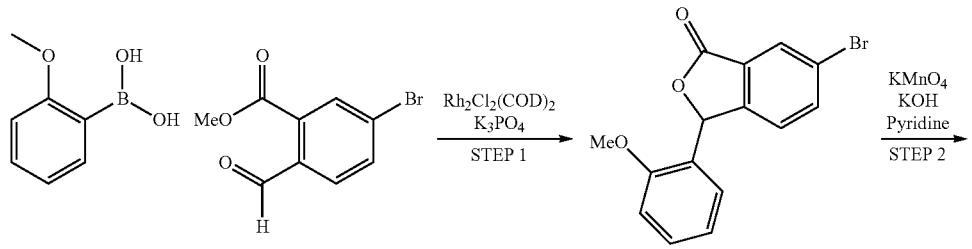

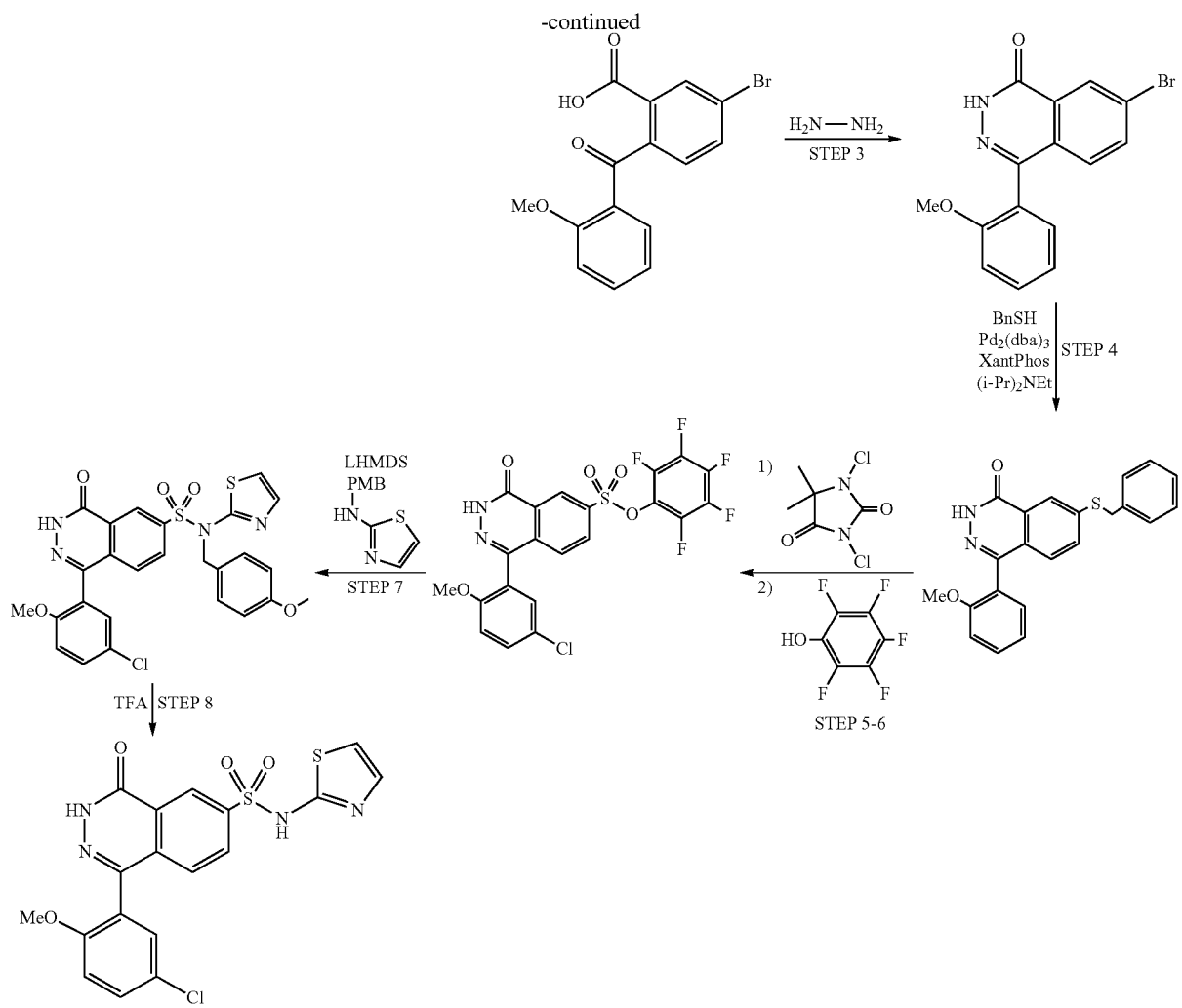

STEP 1:
6-BROMO-3-(2-METHOXYPHENYL)ISOBENZOFURAN-1(3H)-ONE (2-Methoxyphenyl)boronic acid (4.69 g, 30.9 mmol), methyl 5-bromo-2-formylbenzoate (5.00 g, 20.6 mmol; GLSyntech, LLC), tripotassium phosphate (17.5 g, 82.0 mmol) and THF (103 mL) were added to a pressure tube. The tube was purged with argon. Then chloro(1,5-cyclooctadiene)rhodium(I) dimer (0.507 g, 1.03 mmol) was added. The tube was sealed and stirred at rt. After 30 min, LCMS showed lactone product. TLC confirmed a complete conversion of methyl 5-bromo-2-formylbenzoate to a lower spot. The reaction was filtered with the aid of EtOAc. The filtrate was concentrated and the crude material was absorbed onto a plug of silica gel and purified by chromatography through a Redi-Sep pre-packed silica gel column (120 g), eluting with a gradient of 0% to 30% EtOAc in hexanes, to provide 6-bromo-3-(2-methoxyphenyl)isobenzofuran-1(3H)-one (5.15 g, 78% yield). m/z (ESI) 319.0 (M+H)+, 321.0 (M+3H)+.

STEP 2:
5-BROMO-2-(2-METHOXYBENZOYL)BENZOIC ACID

This compound was prepared according to Ukita et al *J. Med. Chem.* 2001, 44, 2204. To a stirred mixture of 6-bromo-3-(2-methoxyphenyl)isobenzofuran-1(3H)-one (5.15 g, 16.1 mmol), KOH (25% aqueous) (64.5 mL, 16.1 mmol) and pyridine (32.3 mL, 16.1 mmol) in a pressure tube was added powder potassium permanganate (3.83 g, 24.2 mmol). The reaction was heated at 100° C. After 4 h, LCMS showed ~95% conversion to product. The reaction was cooled to rt. The mixture was filtered, and the solid residue was washed with water. The filtrate was acidified with concentrated HCl until pH=2. A sticky white solid was filtered off with the aid of water and dried to afford 5-bromo-2-(2-methoxybenzoyl) benzoic acid (4.2 g, 78% yield). m/z (ESI) 335.0 (M+H)+, 337.0 (M+3H)+.

STEP 3:
7-BROMO-4-(2-METHOXYPHENYL)PHTHALAZIN-1(2H)-ONE

In a screw-capped vial, 5-bromo-2-(2-methoxybenzoyl) benzoic acid (4.20 g, 12.5 mmol), hydrazine (1.18 mL, 37.6 mmol), and ethanol (25.1 mL) were heated at 80° C. After 2 h, white solid precipitated out of the reaction. LCMS showed a complete conversion of SM to product. The reaction was cooled to rt. The solid was filtered with the aid of heptane and dried to give the first batch as white solid (3.22 g). The filtrate was concentrated and was absorbed onto a plug of silica gel and purified by chromatography through a Redi-Sep pre-packed silica gel column (40 g), eluting with a gradient of 0% to 100% EtOAc in hexanes, to provide a second batch as white solid (0.21 g). Overall, 7-bromo-4-(2-methoxyphenyl)phthalazin-1(2H)-one (3.43 g, 83% yield) was obtained in good yield over two steps. m/z (ESI) 331.0 (M+H)$^+$, 333.0 (M+3H)$^+$.

STEP 4: 7-(BENZYLTHIO)-4-(2-METHOXYPHENYL)PHTHALAZIN-1(2H)-ONE

To a pressure tube containing a solution of 7-bromo-4-(2-methoxyphenyl)phthalazin-1(2H)-one (3.43 g, 10.4 mmol) and N,N-diisopropylethylamine (3.60 mL, 20.1 mmol) in 1,4-Dioxane (72.4 mL) was added Xantphos (0.300 g, 0.518 mmol) and tris(dibenzylideneacetone) dipalladium (0) (0.237 g, 0.259 mmol) followed by (mercaptomethyl)benzene (1.28 mL, 10.9 mmol). The tube was purged with nitrogen. The tube was sealed and heated at 80° C. for 30 min. After 1.5 h, LCMS showed a complete conversion of SM to mainly product. The reaction was cooled to rt and was passed through a pad of Celite with the aid of EtOAc (250 mL) until the solvents came out colorless. The filtrate was concentrated to afford a yellow solid. The crude material was absorbed onto a plug of silica gel and purified by chromatography through a Redi-Sep pre-packed silica gel column (120 g), eluting with a gradient of 0% to 50% EtOAc in hexanes. However, the product did not elute. Thus, the column was flushed with 100% of 90:10:1 DCM:MeOH:NH$_4$OH. Fractions containing the product only were combined and concentrated to afford creamy crystals (2.81 g). Impure fractions were combined and concentrated. This material was absorbed onto a plug of silica gel and purified by chromatography through a Redi-Sep pre-packed silica gel column (80 g), eluting with a gradient of 50% to 100% 1M NH$_3$.MeOH in CH$_2$Cl$_2$, to provide a second batch (1.02 g) as yellow solid. Overall, 7-(benzylthio)-4-(2-methoxyphenyl)phthalazin-1(2H)-one (3.83 g, 99% yield) was obtained in good yield. m/z (ESI) 375.2 (M+H)$^+$.

STEP 5 AND 6: 1-(5-CHLORO-2-METHOXYPHENYL)-4-OXO-3,4-DIHYDROPHTHALAZINE-6-SULFONYL CHLORIDE AND PERFLUOROPHENYL 1-(5-CHLORO-2-METHOXYPHENYL)-4-OXO-3,4-DIHYDROPHTHALAZINE-6-SULFONATE

A round-bottom flask was charged with 7-(benzylthio)-4-(2-methoxyphenyl)phthalazin-1(2H)-one (150 mg, 0.401 mmol), acetonitrile (3770 µl), acetic Acid (141 µl), and water (94 µl) to give a yellow suspension. The mixture was sonicated to give a yellow suspension. The flask was cooled in an ice-bath for 30 min, then 1,3-dichloro-5,5-dimethylimidazolidine-2,4-dione (158 mg, 0.801 mmol) was added in one portion. After 20 min, LCMS showed SM (m/z=375), sulfoxide (m/z=391), sulfonyl chloride (m/z=352), Cl-sulfonyl chloride (m/z=385,387). DCM (0.5 mL) was added to give a yellow solution. After 1.5 h, an orange suspension was formed. LCMS showed mainly 1-(5-chloro-2-methoxyphenyl)-4-oxo-3,4-dihydrophthalazine-6-sulfonyl chloride. Then, 2,3,4,5,6-pentafluorophenol (147 mg, 0.801 mmol) was added at 0° C., followed by drop wise addition of triethylamine (223 µl, 1.602 mmol) via an addition funnel. After 15 min, LCMS showed mainly PFP sulfonate product. The mixture was diluted with EtOAc (20 mL) and washed with water (2×10 mL), washed with brine, and dried over sodium sulfate. The crude material was absorbed onto a plug of silica gel and purified by chromatography through a Redi-Sep pre-packed silica gel column (40 g), eluting with a gradient of 0% to 50% EtOAc in hexanes, to provide perfluorophenyl 1-(5-chloro-2-methoxyphenyl)-4-oxo-3,4-dihydrophthalazine-6-sulfonate (128 mg, 60.0% yield) as white solid. HMBC connectivities and ROESY cross-peaks confirmed the structure of perfluorophenyl 1-(5-chloro-2-methoxyphenyl)-4-oxo-3,4-dihydrophthalazine-6-sulfonate (128 mg, 60% yield). Specifically, the chlorine was para to the methoxy substitutent. m/z (ESI) 533.0 (M+H)$^+$.

STEP 7: 1-(5-CHLORO-2-METHOXYPHENYL)-N-(4-METHOXYBENZYL)-4-OXO-N-(THIAZOL-2-YL)-3,4-DIHYDROPHTHALAZINE-6-SULFONAMIDE

A round-bottom flask was charged with N-(4-methoxybenzyl)thiazol-2-amine (63.5 mg, 0.288 mmol) and THF (1.60 mL) to give a clear solution. The flask was cooled in a dry ice-acetone bath for 5 min to give a suspension. Lithium bis(trimethylsilyl)amide (1M in THF, 961 µl, 0.961 mmol) was added drop wise to give a light yellow solution. The mixture was stirred for 15 min. Then, a solution of perfluorophenyl 1-(5-chloro-2-methoxyphenyl)-4-oxo-3,4-dihydrophthalazine-6-sulfonate (128 mg, 0.240 mmol) in THF (1.60 mL)) was added drop wise. LCMS after 1 h showed a complete conversion of SM to mainly product. The reaction was quenched with saturated aqueous ammonium chloride (0.5 mL) at −78° C. and then warmed to rt. The product was extracted with EtOAc. The organic layers was dried over sodium sulfate, filtered, and concentrated. The residue was purified by chromatography on silica gel (40-g Redi-Sep Gold column, 20-50% EtOAc/heptanes) to give 1-(5-chloro-2-methoxyphenyl)-N-(4-methoxybenzyl)-4-oxo-N-(thiazol-2-yl)-3,4-dihydrophthalazine-6-sulfonamide (56 mg, 41.0% yield) as an off-white solid. m/z (ESI) 569.0 (M+H)$^+$.

STEP 8: 1-(5-CHLORO-2-METHOXYPHENYL)-4-OXO-N-(THIAZOL-2-YL)-3,4-DIHYDROPHTHALAZINE-6-SULFONAMIDE

In a vial, 1-(5-chloro-2-methoxyphenyl)-N-(4-methoxybenzyl)-4-oxo-N-(thiazol-2-yl)-3,4-dihydrophthalazine-6-sulfonamide (56 mg, 0.098 mmol) was dissolved in DCM (984 µl, 0.098 mmol) and then TFA (37.9 µl, 0.492 mmol) was added. After 30 min at rt, LCMS showed product. The reaction was quenched with saturated aqueous NaHCO$_3$ (1 mL). White solid precipitated out of the solution and was filtered off with the aid of water. The solid was washed with 3 mL of water and dried to afford 1-(5-chloro-2-methoxyphenyl)-4- oxo-N-(thiazol-2-yl)-3,4-dihydrophthalazine-6-sulfonamide (32 mg, 72.4% yield). m/z (ESI) 449.0 (M+H)+.

EXAMPLE 504

1-(5-CHLORO-2-METHOXYPHENYL)-4-OXO-N-(PYRIMIDIN-4-YL)-3,4-DIHYDROPHTHALAZINE-6-SULFONAMIDE

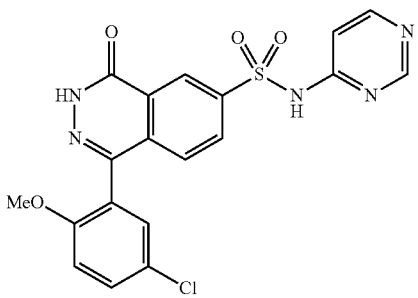 [SMILES: COc1ccc(Cl)cc1-c1n[nH]c(=O)c2cc(S(=O)(=O)Nc3ccncn3)ccc12]

A vial was charged with perfluorophenyl 1-(5-chloro-2-methoxyphenyl)-4-oxo-3,4-dihydrophthalazine-6-sulfonate (From Step 6, Example 501; 126 mg, 0.236 mmol), pyrimidin-4-amine (33.7 mg, 0.355 mmol), and THF (1.18 mL). The resulting solution was cooled in an ice-water bath for 10 min, then lithium bis(trimethylsilyl)amide (1M in THF) (591 µl, 0.591 mmol) was added drop wise. LCMS after 2 h showed complete conversion of SM to product. The reaction was quenched with 1 mL of MeOH. Purification was done via RPLC with 0.1% NH4OH in ACN and water as mobile phase to afford 1-(5-chloro-2-methoxyphenyl)-4-oxo-N-(pyrimidin-4-yl)-3,4-dihydrophthalazine-6-sulfonamide (27 mg, 25.7% yield). m/z (ESI) 444.0 (M+H)+.

EXAMPLE 505

1-(5-CHLORO-2-METHOXYPHENYL)-4-OXO-N-(1,2,4-THIADIAZOL-5-YL)-3,4-DIHYDROPHTHALAZINE-6-SULFONAMIDE

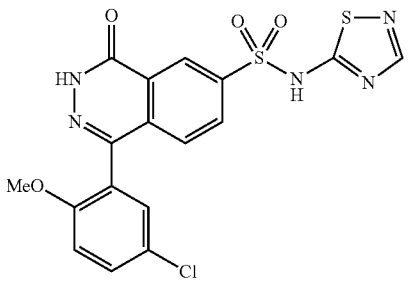 [SMILES: COc1ccc(Cl)cc1-c1n[nH]c(=O)c2cc(S(=O)(=O)Nc3ncns3)ccc12]

A vial was charged with N-(2,4-dimethoxybenzyl)-1,2,4-thiadiazol-5-amine (70.7 mg, 0.282 mmol) and THF (938 µl). The resulting solution was cooled to −78° C. for 10 min. Then lithium bis(trimethylsilyl)amide (1M in THF) (413 µl, 0.413 mmol) was added drop wise. The vial was removed from the cold bath temporarily to ensure complete deprotonation of PMB-aminothiadiazole. When the suspension became homogenous, the reaction was cooled back down to −78° C. Then perfluorophenyl 1-(5-chloro-2-methoxyphenyl)-4-oxo-3,4-dihydrophthalazine-6-sulfonate (100 mg, 0.188 mmol) in 0.5 mL of THF was added drop wise. LCMS after 15 min showed complete conversion of SM to product. The reaction was warmed to rt, quenched with 1 mL of MeOH and concentrated. The crude material was absorbed onto a plug of silica gel and purified by chromatography through a Redi-Sep pre-packed silica gel column (12 g), eluting with a gradient of 0% to 70% EtOAc in heptane, to provide 1-(5-chloro-2-methoxyphenyl)-N-(2,4-dimethoxybenzyl)-4-oxo-N-(1,2,4-thiadiazol-5-yl)-3,4-dihydrophthalazine-6-sulfonamide (38 mg, 33.7% yield) as white solid. m/z (ESI) 600.0 (M+H)+, 622.0 (M+Na)+. 1-(5-Chloro-2-methoxyphenyl)-N-(2,4-dimethoxybenzyl)-4-oxo-N-(1,2,4-thiadiazol-5-yl)-3,4-dihydrophthalazine-6-sulfonamide (38 mg, 0.063 mmol) was dissolved in DCM (633 µl, 0.063 mmol) and then TFA (24.4 µl, 0.317 mmol) was added. After 30 min at rt, LCMS showed a complete conversion of SM to product. Purification was done with 0.1% NH4OH in ACN and water as mobile phase to afford 1-(5-chloro-2-methoxyphenyl)-4-oxo-N-(1,2,4-thiadiazol-5-yl)-3,4-dihydrophthalazine-6-sulfonamide (17 mg, 59.7% yield) and NH4OH as a triplet at ~7.07 ppm. To remove NH4OH, the product was dissolved in MeOH (1 mL) and loaded onto a 2 g SCX column. The product was flushed out with MeOH. Concentration afforded 1-(5-chloro-2-methoxyphenyl)-4-oxo-N-(1,2,4-thiadiazol-5-yl)-3,4-dihydrophthalazine-6-sulfonamide as white solid. m/z (ESI) 450.0 (M+H)+.

EXAMPLE 506

1-(2-METHOXY-4-(TRIFLUOROMETHYL)PHENYL)-4-OXO-N-(PYRIMIDIN-4-YL)-3,4-DIHYDROPHTHALAZINE-6-SULFONAMIDE

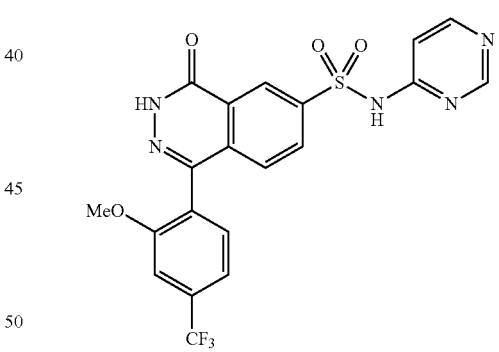

A vial was charged with perfluorophenyl 1-(2-methoxy-4-(trifluoromethyl)phenyl)-4-oxo-3,4-dihydrophthalazine-6-sulfonate (From Step 5, Example 293; 126 mg, 0.222 mmol), pyrimidin-4-amine (31.7 mg, 0.334 mmol), and THF (1.11 mL). The resulting solution was cooled in an ice-water bath for 10 min, then lithium bis(trimethylsilyl)amide (1M in THF) (489 µl, 0.489 mmol) was added drop wise. LCMS after 15 min showed complete conversion of SM to product. The reaction was quenched with 1 mL of MeOH and concentrated. Purification was done on OJ-H column, with 20% methanol and 0.2% diethylamine. Since the product contained some DEA, it was purified further by mass directed LC purification with TFA to afford 1-(2-methoxy-4-(trifluoromethyl)phenyl)-4-oxo-N-(pyrimidin-4-yl)-3,4-dihydrophthalazine-6-sulfonamide (23 mg, 21.7% yield). m/z (ESI) 478.0 (M+H)+.

EXAMPLE 507

1-(5-CHLORO-2-METHOXYPHENYL)-N-(5-FLUOROTHIAZOL-2-YL)-4-OXO-3,4-DIHYDROPHTHALAZINE-6-SULFONAMIDE

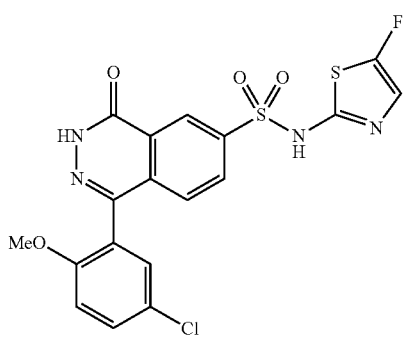 [SMILES: COc1ccc(Cl)cc1-c1n[nH]c(=O)c2cc(S(=O)(=O)Nc3ncc(F)s3)ccc12]

A vial was charged with 5-fluoro-N-(4-methoxybenzyl)thiazol-2-amine (67.1 mg, 0.282 mmol), perfluorophenyl 1-(5-chloro-2-methoxyphenyl)-4-oxo-3,4-dihydrophthalazine-6-sulfonate (100 mg, 0.188 mmol), and THF (938 µl). The resulting solution was cooled to 0° C. for 10 min. Then lithium bis(trimethylsilyl)amide (1M in THF) (413 µl, 0.413 mmol) was added drop wise. LCMS after 15 min showed incomplete conversion of SM. Additional LHMDS (400 µL, 1M in THF) was added. After 15 min, TLC showed complete conversion of PFP-sulfonate to a lower spot. The crude material was absorbed onto a plug of silica gel and purified by chromatography through a Redi-Sep pre-packed silica gel column (12 g), eluting with a gradient of 0% to 70% EtOAc in heptane, to provide 1-(5-chloro-2-methoxyphenyl)-N-(5-fluorothiazol-2-yl)-N-(4-methoxybenzyl)-4-oxo-3,4-dihydrophthalazine-6-sulfonamide (65 mg, 59.0% yield) as a brown solid. m/z (ESI) 587.0 (M+H)+, 609.0 (M+Na)+. 1-(5-Chloro-2-methoxyphenyl)-N-(2,4-dimethoxybenzyl)-N-(5-fluorothiazol-2-yl)-4-oxo-3,4-dihydrophthalazine-6-sulfonamide (65 mg, 0.105 mmol) was dissolved in DCM (1053 µl, 0.105 mmol) and then TFA (40.6 µl, 0.527 mmol) was added. After 30 min at rt, LCMS showed a complete conversion of SM to product. Purification was done with 0.1% NH4OH in ACN and water as mobile phase to afford impure product. The product was purified further by RPLC on the acidic Gilson. Fractions containing the product were combined and washed with sat. NaHCO3. The product was extracted with DCM. The organic phase was washed with brine, dried over MgSO4, filtered, and concentrated to afford 1-(5-chloro-2-methoxyphenyl)-N-(5-fluorothiazol-2-yl)-4-oxo-3,4-dihydrophthalazine-6-sulfonamide (1.3 mg, 2.64% yield) as off-white solid. m/z (ESI) 467.0 (M+H)+.

EXAMPLE 508

1-(2-METHOXYPHENYL)-4-OXO-N-(1,2,4-THIADIAZOL-5-YL)-3,4-DIHYDROPHTHALAZINE-6-SULFONAMIDE

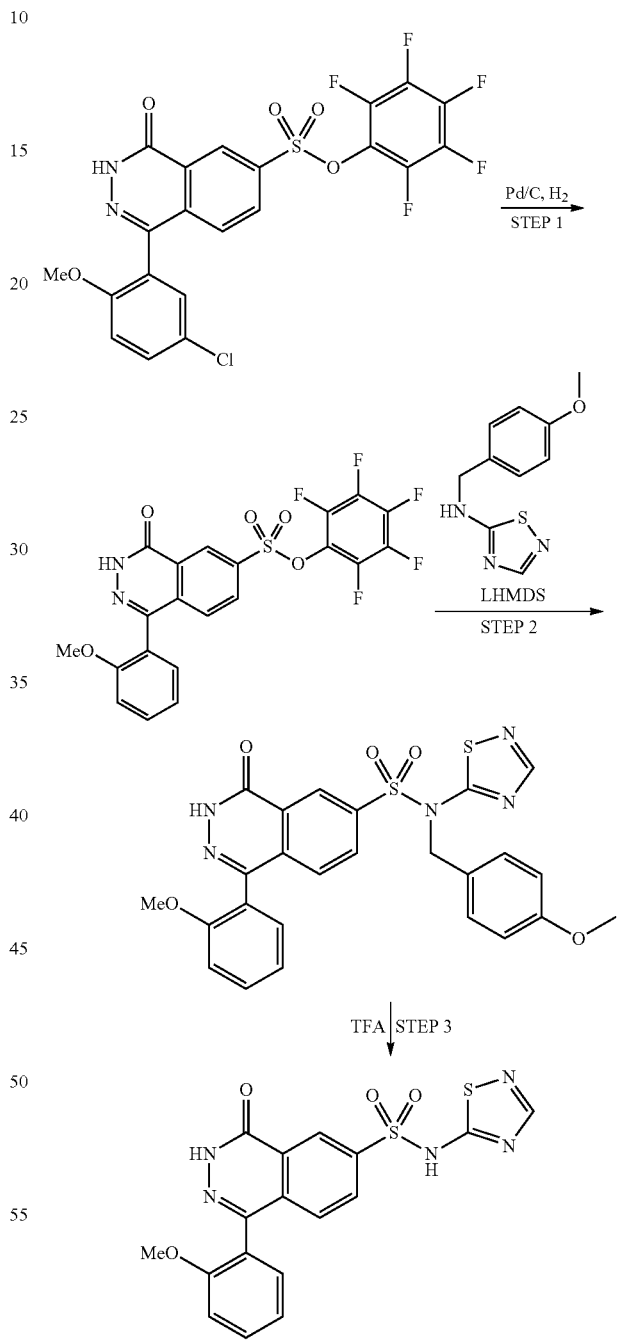

STEP 1. PERFLUOROPHENYL 1-(5-CHLORO-2-METHOXYPHENYL)-4-OXO-3,4-DIHYDROPHTHALAZINE-6-SULFONATE

A RBF was charged with perfluorophenyl 1-(5-chloro-2-methoxyphenyl)-4-oxo-3,4-dihydrophthalazine-6-sulfonate (1.25 g, 2.35 mmol). The reaction was purged with N2. Then ethyl acetate (23.5 mL) was added followed by palladium, 10 wt % on activated carbon (0.749 g, 0.704 mmol). The flask was evacuated and back filled with $N_2$ (3×). The flask was evacuated again and then pressurized with hydrogen to 42 PSI. The reaction was heated to 75° C. After 2 d, LCMS showed 92:8 ratio of product:SM. The reaction was cooled to rt and filtered through a pad of Celite with the aid of EtOAc. The filtrate was concentrated. The crude material was absorbed onto a plug of silica gel and purified by chromatography through a Redi-Sep pre-packed silica gel column (80 g), eluting with a gradient of 0% to 30% EtOAc in heptane, to provide perfluorophenyl 1-(2-methoxyphenyl)-4-oxo-3,4-dihydrophthalazine-6-sulfonate (613 mg, 52.4% yield) as off-white solid. m/z (ESI) 499.0 $(M+H)^+$.

STEP 2. N-(4-METHOXYBENZYL)-1-(2-METH-OXYPHENYL)-4-OXO-N-(1,2,4-THIADIAZOL-5-YL)-3,4-DIHYDROPHTHALAZINE-6-SULFONA-MIDE

A vial was charged with perfluorophenyl perfluorophenyl 1-(2-methoxyphenyl)-4-oxo-3,4-dihydrophthalazine-6-sulfonate (120 mg, 0.241 mmol), N-(4-methoxybenzyl)-1,2,4-thiadiazol-5-amine (133 mg, 0.602 mmol), and THF (1204 µl). The reaction was purged with argon. The resulting solution was cooled in an ice-water bath for 10 min, then lithium bis(trimethylsilyl)amide (1M in THF) (602 µl, 0.602 mmol) was added drop wise. A homogenous yellow solution was formed. After 1 h, LCMS of an aliquot in MeOH showed complete conversion of SM to mainly product. The reaction was warmed to rt and concentrated. The crude material was absorbed onto a plug of silica gel and purified by chromatography through a Redi-Sep pre-packed silica gel column (12 g), eluting with a gradient of 0% to 50% EtOAc in heptane, to provide N-(4-methoxybenzyl)-1-(2-methoxyphenyl)-4-oxo-N-(1,2,4-thiadiazol-5-yl)-3,4-dihydrophthalazine-6-sulfonamide (103 mg, 80% yield) as white solid. m/z (ESI) 536.0 $(M+H)^+$, 558.0 $((M+Na)^+$.

STEP 3. 1-(2-METHOXYPHENYL)-4-OXO-N-(1,2,4-THIADIAZOL-5-YL)-3,4-DIHYDROPHTHALA-ZINE-6-SULFONAMIDE

N-(4-methoxybenzyl)-1-(2-methoxyphenyl)-4-oxo-N-(1,2,4-thiadiazol-5-yl)-3,4-dihydrophthalazine-6-sulfonamide (65.0 mg, 0.121 mmol) was dissolved in DCM (1.21 mL) and then TFA (46.7 µl, 0.607 mmol) was added. After 1 d at rt, LCMS showed mainly product. The reaction was quenched with 1 mL of saturated aqueous $NaHCO_3$ and was concentrated. Chromatography was performed using reverse phase Isolera through a pre-packed C18 column (12 g), eluting with a gradient of 0% to 60% MeCN with 1% TFA in water with 1% TFA. Fractions containing the product were combined and concentrated. White solid precipitated out of the water. The solid was filtered off with an aid of water and dried to afford 1-(2-methoxyphenyl)-4-oxo-N-(1,2,4-thiadiazol-5-yl)-3,4-dihydrophthalazine-6-sulfonamide (11 mg, 21.8% yield). m/z (ESI) 416.0 $(M+H)^+$.

EXAMPLE 509

1-(3'-FLUORO-4-METHOXY-[1,1'-BIPHENYL]-3-YL)-4-OXO-N-(PYRIMIDIN-4-YL)-3,4-DIHY-DROPHTHALAZINE-6-SULFONAMIDE

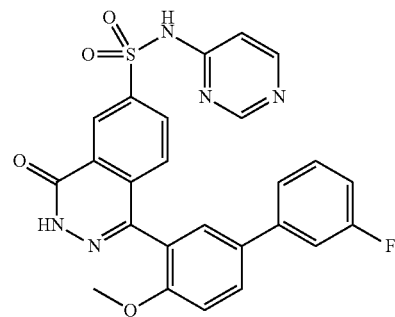 [SMILES: COc1ccc(-c2cccc(F)c2)cc1-c1n[nH]c(=O)c2cc(S(=O)(=O)Nc3ccncn3)ccc12]

A vial was charged with 1-(5-chloro-2-methoxyphenyl)-4-oxo-N-(pyrimidin-4-yl)-3,4-dihydrophthalazine-6-sulfonamide (Example 504; 76.3 mg, 0.172 mmol), (3-fluorophenyl)boronic acid (48.1 mg, 0.344 mmol), dicyclohexyl(2',6'-dimethoxy-[1,1'-biphenyl]-2-yl)phosphine (3.53 mg, 8.59 µmol), chloro(2-dicyclohexylphosphino-2',6'-dimethoxy-1,1'-biphenyl)[2-(2-aminoethylphenyl)]palladium(ii) dichloromethane (13.02 mg, 0.017 mmol) and potassium phosphate (146 mg, 0.688 mmol). The vial was flushed with Ar (g), then 1,4-dioxane (781 µl) and water (78 µl) were added in sequence. The vial was sealed and heated in a Biotage Initiator microwave reactor for 3 h at 100° C. The mixture was extracted with EtOAc (1×), then with 1,4-dioxane (2×), and the combined organic extracts were concentrated. The residue was purified by chromatography on silica gel (12-g Redi-Sep Gold column, 4% MeOH/DCM, then 10% MeOH/DCM) to give ca. 55 mg of a tan solid. The material was further purified by chromatography (25-g Interchim 15-micron column, 5% MeOH/DCM). Selected fractions containing product were combined and concentrated to give 1-(3'-fluoro-4-methoxy-[1,1'-biphenyl]-3-yl)-4-hydroxy-N-(pyrimidin-4-yl)phthalazine-6-sulfonamide as a white solid. $^1H$ NMR (400 MHz, DMSO-$d_6$) δ=13.08 (br. s., 1H), 8.77-8.67 (m, 2H), 8.58 (s, 1H), 8.24 (br. s., 1H), 8.15 (d, J=5.6 Hz, 1H), 7.98 (dd, J=1.8, 8.9 Hz, 1H), 7.80-7.72 (m, 2H), 7.71-7.61 (m, 3H), 7.55 (dt, J=6.2, 8.0 Hz, 1H), 7.39 (d, J=7.9 Hz, 1H), 7.28-7.19 (m, 1H), 7.03 (br. s., 1H), 2.06 (s, 3H). m/z (ESI) 504.2 (M+H)+.

INTERMEDIATE QQQQQ: 4-(2-METHOXY-4-(TRIFLUOROMETHYL)PHENYL)-2-METHYLQUINAZOLINE-7-SULFONYL CHLORIDE

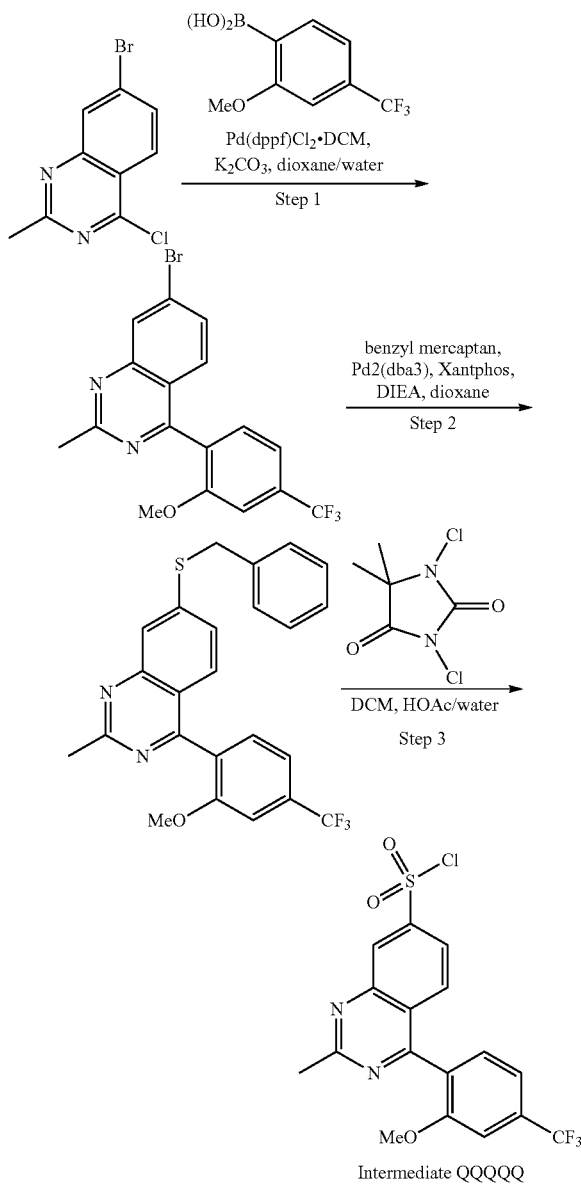

STEP 1: 7-BROMO-4-(2-METHOXY-4-(TRIFLUOROMETHYL)PHENYL)-2-METHYLQUINAZOLINE

A solution of PdCl$_2$(dppf)-CH$_2$Cl$_2$ adduct (0.159 g, 0.194 mmol), (2-methoxy-4-(trifluoromethyl)phenyl)boronic acid (0.940 g, 4.27 mmol), 7-bromo-4-chloro-2-methylquinazoline (ACES Pharma, 1.000 g, 3.88 mmol), and potassium carbonate (2.147 g, 15.53 mmol) in 12 mL dioxane was treated with 4 mL water and was allowed to stir overnight at room temperature. LC/MS showed mostly product, so the aqueous layer was removed, and the reaction mixture was concentrated. Purification of the crude residue by silica gel column chromatography (0-50% EtOAc/heptane) gave 7-bromo-4-(2-methoxy-4-(trifluoromethyl)phenyl)-2-methylquinazoline (0.797 g, 2.007 mmol, 51.7% yield). (M+H)+=396.9.

STEP 2: 7-(BENZYLTHIO)-4-(2-METHOXY-4-(TRIFLUOROMETHYL)PHENYL)-2-METHYLQUINAZOLINE

A solution of Pd$_2$(dba)$_3$ (0.046 g, 0.050 mmol), Xantphos (0.058 g, 0.100 mmol), 7-bromo-4-(2-methoxy-4-(trifluoromethyl)phenyl)-2-methylquinazoline (0.797 g, 2.007 mmol), and n,n-diisopropylethylamine (1.051 ml, 6.02 mmol) in 10 mL dioxane was heated to 60° C. and was treated with benzyl mercaptan (0.237 ml, 2.007 mmol). After stirring for one hour, LC/MS showed mostly product, so the reaction mixture was concentrated. This material was carried on to step 3 without purification. (M+H)+=441.0.

STEP 3: 4-(2-METHOXY-4-(TRIFLUOROMETHYL)PHENYL)-2-METHYLQUINAZOLINE-7-SULFONYL CHLORIDE

The crude residue from Step 2 was dissolved in 30 mL DCM and was treated with 0.3 mL (1.5:1 HOAc/water) and cooled to 0° C. 1,3-dichloro-5,5-dimethylimidazolidine-2,4-dione (0.791 g, 4.01 mmol) was added, and the reaction mixture was allowed to stir for 10 minutes. LC/MS showed mostly product, so the reaction mixture was dried over MgSO4 and concentrated. Purification of the crude residue by silica gel column chromatography (0-30% EtOAc/heptane) gave 4-(2-methoxy-4-(trifluoromethyl)phenyl)-2-methylquinazoline-7-sulfonyl chloride (0.420 g, 1.008 mmol, 50.2% yield). (M+H)+=417.0.

EXAMPLE 510

4-(2-METHOXY-4-(TRIFLUOROMETHYL)PHENYL)-2-METHYL-N-(THIAZOL-2-YL)QUINAZOLINE-7-SULFONAMIDE

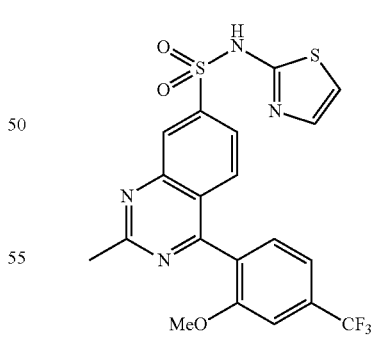

A solution of 4-(2-methoxy-4-(trifluoromethyl)phenyl)-2-methylquinazoline-7-sulfonyl chloride (Intermediate QQQQQ; 0.210 g, 0.504 mmol) and thiazol-2-amine (0.252 g, 2.52 mmol) in 5 mL MeCN was flooded with argon, and was treated with 1-methylimidazole (0.040 ml, 0.504 mmol). After stirring for 2 hours, LC/MS showed mostly product, so the reaction mixture was concentrated. Purification of the crude residue by reverse phase column chromatography [Puriflash C18, 30μ, 55 g, 10-100% (0.1% NH4OH in MeOH)/(0.1% NH4OH in water)] gave 4-(2-methoxy-4-(trifluoromethyl)phenyl)-2-methyl-N-(thiazol-2-yl)quinazoline-7-sulfonamide (0.160 g, 0.333 mmol, 66.1% yield) as an off-white solid. $^1$H NMR (MeCN-$d_3$) δ: 8.39 (d, J=1.7 Hz, 1H), 7.86 (dd, J=8.7, 1.8 Hz, 1H), 7.70 (d, J=8.7 Hz, 1H), 7.52-7.57 (m, 1H), 7.44-7.50 (m, 2H), 7.01 (d, J=4.7 Hz, 1H), 6.63 (d, J=4.7 Hz, 1H), 3.75 (s, 3H), 2.85 (s, 3H); (M+H)+=481.0.

INTERMEDIATE RRRRR: 2-METHOXY-4-(2-METHOXY-4-(TRIFLUOROMETHYL)PHENYL)QUINAZOLINE-7-SULFONYL CHLORIDE

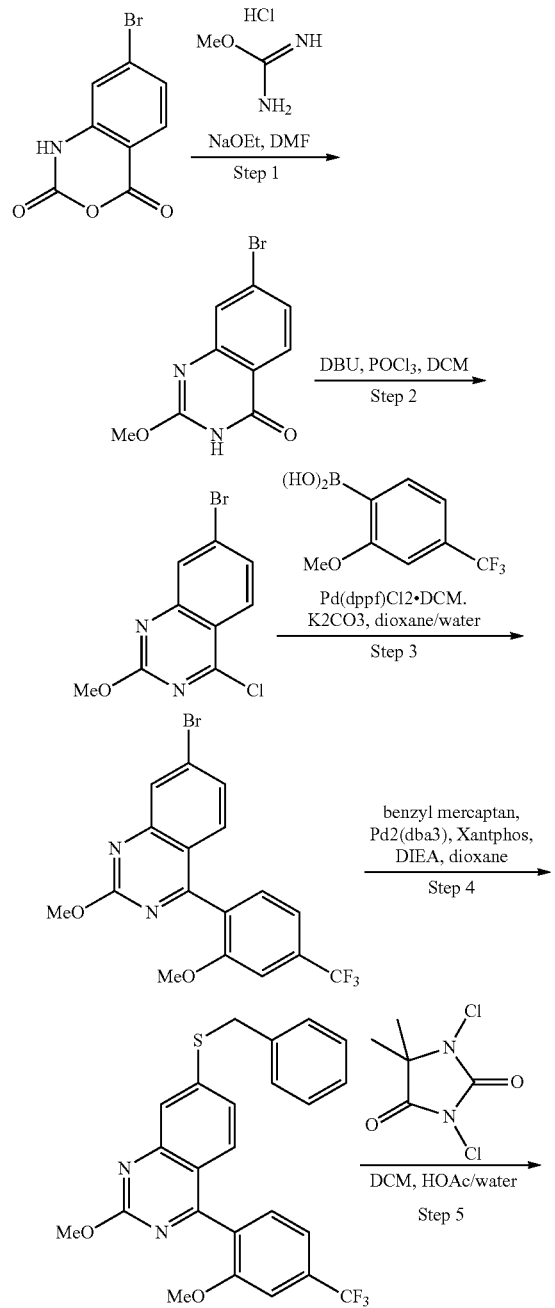

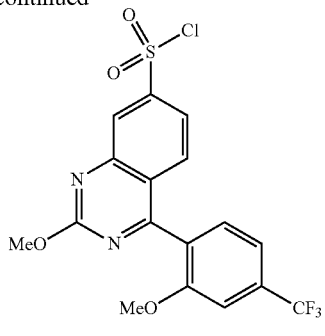

Intermediate RRRRR

STEP 1: 7-BROMO-2-METHOXYQUINAZOLIN-4(3H)-ONE

A solution of o-methylisourea hydrochloride (1.256 g, 11.36 mmol) and 4-bromoisatoic anhydride (2.500 g, 10.33 mmol) in 10 mL DMF was treated with sodium ethoxide (1.476 g, 21.69 mmol) and was allowed to stir at room temperature overnight. LC/MS showed mostly product, so the reaction mixture was poured into water and the resulting solid was filtered and dried yielding 7-bromo-2-methoxyquinazolin-4(3H)-one (2.57 g, 10.08 mmol, 98% yield) with impurities. (M+H)+=255.0.

STEP 2: 7-BROMO-4-CHLORO-2-METHOXYQUINAZOLINE

A solution of 7-bromo-2-methoxyquinazolin-4(3H)-one (1.900 g, 7.45 mmol) in 30 mL DCM was treated with DBU (1.123 ml, 7.45 mmol) and was allowed to stir for 20 minutes. The cloudy purple solution was then treated with POCl$_3$ (0.833 ml, 8.94 mmol) and was allowed to stir for one hour at room temperature. LC/MS showed mostly product, so the reaction mixture was concentrated. The crude residue was carried on to step 3 without purification. (M+H)+=271.2.

STEP 3: 7-BROMO-2-METHOXY-4-(2-METHOXY-4-(TRIFLUOROMETHYL)PHENYL)QUINAZOLINE

The crude residue from step 2 was dissolved in 22 mL dioxane and was treated with PdCl$_2$(dppf)-CH$_2$Cl$_2$ adduct (0.608 g, 0.745 mmol), (2-methoxy-4-(trifluoromethyl)phenyl)boronic acid (1.802 g, 8.19 mmol), potassium carbonate (4.12 g, 29.8 mmol), and 8 mL water was added. The reaction mixture was allowed to stir at room temperature overnight. LC/MS showed product, so the aqueous layer was removed, and the reaction mixture was concentrated. Purification of the crude residue by silica gel column chromatography (0-50% EtOAc/heptane) gave 7-bromo-2-methoxy-4-(2-methoxy-4-(trifluoromethyl)phenyl)quinazoline (0.166 g, 0.402 mmol, 5.39% yield). (M+H)+=413.0.

STEP 4: 7-(BENZYLTHIO)-2-METHOXY-4-(2-METHOXY-4-(TRIFLUOROMETHYL)PHENYL)QUINAZOLINE

A solution of Pd$_2$(dba)$_3$ (9.20 mg, 10.04 μmol), Xantphos (0.012 g, 0.020 mmol), 7-bromo-2-methoxy-4-(2-methoxy-4-(trifluoromethyl)phenyl)quinazoline (0.166 g, 0.402 mmol), and n,n-diisopropylethylamine (0.211 ml, 1.205 mmol) in 2 mL dioxane was heated to 60° C. and was treated with benzyl mercaptan (0.048 ml, 0.402 mmol). After stirring for one hour, LC/MS showed mostly product, so the reaction mixture was concentrated. This material was carried on to step 5 without purification. (M+H)+=457.2.

STEP 5: 2-METHOXY-4-(2-METHOXY-4-(TRIFLUOROMETHYL)PHENYL)QUINAZOLINE-7-SULFONYL CHLORIDE

The crude residue from step 4 was dissolved in 8 mL DCM was treated with 0.8 mL (1.5:1 HOAc/water) and cooled to 0° C. 1,3-dichloro-5,5-dimethylimidazolidine-2,4-dione (0.158 g, 0.804 mmol) was added, and the reaction mixture was allowed to stir for 10 minutes. LC/MS showed mostly product, so the reaction mixture was dried over MgSO4 and concentrated. Purification of the crude residue by silica gel column chromatography (0-30% EtOAc/heptane) gave 2-methoxy-4-(2-methoxy-4-(trifluoromethyl)phenyl) quinazoline-7-sulfonyl chloride (0.141 g, 0.326 mmol, 81% yield). (M+H)+=432.9.

EXAMPLE 511

2-methoxy-4-(2-methoxy-4-(trifluoromethyl)phenyl)-N-(thiazol-2-yl)quinazoline-7-sulfonamide

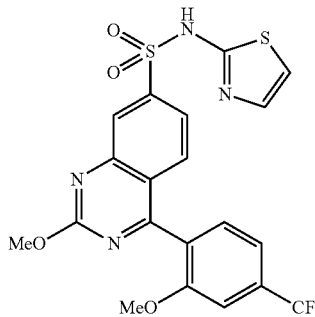

A solution of 2-methoxy-4-(2-methoxy-4-(trifluoromethyl)phenyl)quinazoline-7-sulfonyl chloride (0.141 g, 0.326 mmol) and thiazol-2-amine (0.163 g, 1.629 mmol) in 5 mL MeCN was flooded with argon, and was treated with 1-methylimidazole (0.026 ml, 0.326 mmol). After stirring for 2 hours, LC/MS showed mostly product, so the reaction mixture was concentrated. Purification of the crude residue by reverse phase column chromatography [Puriflash C18, 30µ, 55 g, 10-100% (0.1% NH4OH in MeOH)/(0.1% NH4OH in water)] gave 2-methoxy-4-(2-methoxy-4-(trifluoromethyl)phenyl)-N-(thiazol-2-yl)quinazoline-7-sulfonamide (0.100 g, 0.201 mmol, 61.8% yield) as an off-white solid. $^1$H NMR (MeCN-d$_3$) δ: 8.26 (d, J=1.7 Hz, 1H), 7.70-7.76 (m, 1H), 7.63-7.68 (m, 1H), 7.54-7.57 (m, 1H), 7.42-7.48 (m, 2H), 7.01 (d, J=4.7 Hz, 1H), 6.64 (d, J=4.7 Hz, 1H), 4.13 (s, 3H), 3.76 (s, 3H). m/z (M+H)+=497.0.

INTERMEDIATE SSSSS: 2-(4-(DIFLUOROMETHYL)-5-FLUORO-2-METHOXYPHENYL)-4,4,5,5-TETRAMETHYL-1,3,2-DIOXABOROLANE

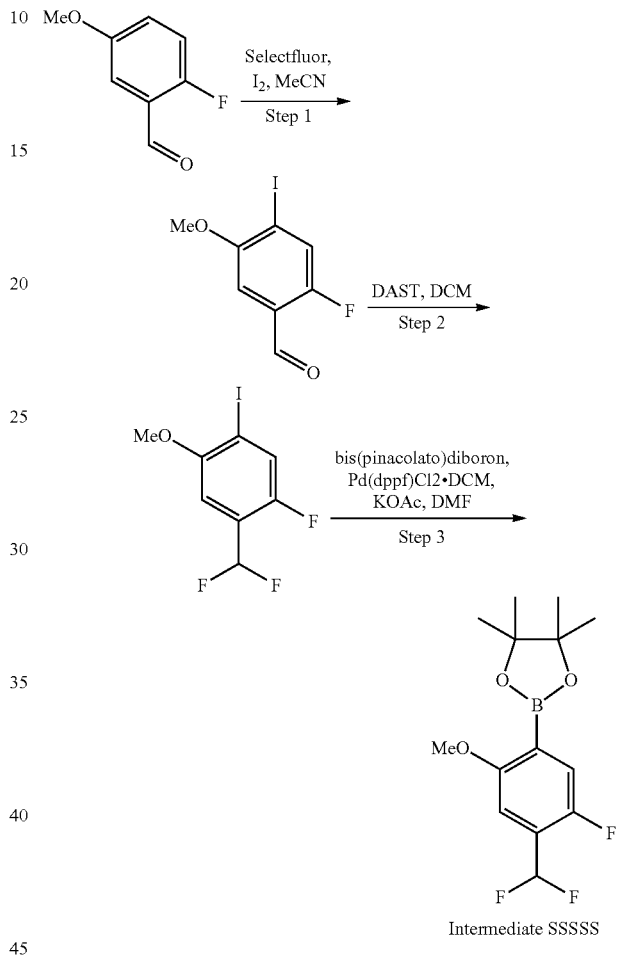

STEP 1: 2-FLUORO-4-IODO-5-METHOXYBENZALDEHYDE

A solution of 2-fluoro-5-methoxybenzaldehyde (Oakwood, 6.000 g, 38.9 mmol) and Selectfluor (13.79 g, 38.9 mmol) in 40 mL MeCN was treated with iodine (10.87 g, 42.8 mmol) and was heated to 80° C. for one hour. LC/MS showed mostly product, so the reaction mixture was poured into water and was extracted with DCM. The organic were dried over MgSO4 and concentrated. Purification of the crude residue by silica gel column chromatography (0-20% EtOAc/heptane) gave 2-fluoro-4-iodo-5-methoxybenzaldehyde (8.92 g, 31.9 mmol, 82% yield) as a 3:1 mixture with starting material. (M+H)+=281.0.

STEP 2: 1-(DIFLUOROMETHYL)-2-FLUORO-4-IODO-5-METHOXYBENZENE

A solution of 2-fluoro-4-iodo-5-methoxybenzaldehyde (8.92 g, 31.9 mmol) in 100 mL DCM was cooled to 0° C. and was treated with dast (5.05 ml, 38.2 mmol). After stirring for 30 minutes, the cooling bath was removed, and the reaction mixture was allowed to stir at room temperature for 9 days. LC/MS showed mostly product, so the reaction mixture was quenched with saturated NaHCO3 solution. The layers were separated, and the organics were dried over MgSO4 and concentrated. The crude residue was carried on to step 3 without purification. (M+H)+=does not ionize.

STEP 3: 2-(4-(DIFLUOROMETHYL)-5-FLUORO-2-METHOXYPHENYL)-4,4,5,5-TETRAMETHYL-1,3,2-DIOXABOROLANE

The crude residue from step 2 was dissolved in 30 mL DMF and was treated with bis(pinacolato)diboron (12.13 g, 47.8 mmol), PdCl$_2$(dppf)-CH$_2$Cl$_2$ adduct (2.60 g, 3.19 mmol), and potassium acetate (12.50 g, 127 mmol). The reaction mixture was heated to 100° C. overnight. LC/MS showed mostly product, so the reaction mixture was allowed to cool to room temperature and was diluted with ether. The reaction mixture was filtered through a plug of Celite and the filtrate was concentrated. Purification of the crude residue by reverse phase column chromatography [Redisep Gold C18, 10-100% (0.1% NH4OH in MeOH)/(0.1% NH4OH in water)] gave 2-(4-(difluoromethyl)-5-fluoro-2-methoxyphenyl)-4,4,5,5-tetramethyl-1,3,2-dioxaborolane (0.95 g, 4.32 mmol, 13.56% yield) as yellow oil. (M+H)+=303.3.

INTERMEDIATE TTTTT: 4-(4-(DIFLUOROMETHYL)-5-FLUORO-2-METHOXYPHENYL)QUINAZOLINE-7-SULFONYL CHLORIDE

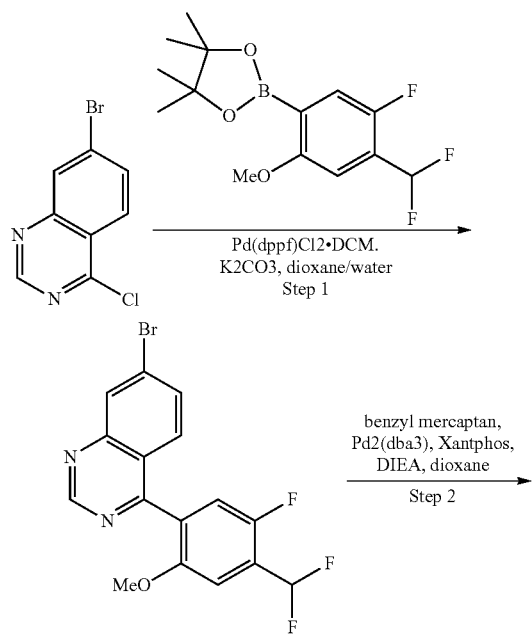

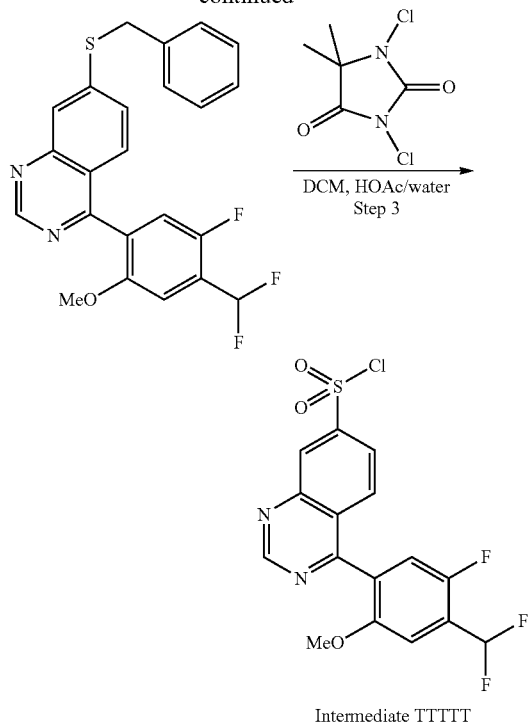

Intermediate TTTTT

STEP 1: 7-BROMO-4-(4-(DIFLUOROMETHYL)-5-FLUORO-2-METHOXYPHENYL)QUINAZOLINE

A solution of PdCl$_2$(dppf)-CH$_2$Cl$_2$ adduct (0.101 g, 0.123 mmol), 2-(4-(difluoromethyl)-5-fluoro-2-methoxyphenyl)-4,4,5,5-tetramethyl-1,3,2-dioxaborolane (Intermediate SSSSS; 1.365 g, 4.52 mmol), 7-bromo-4-chloroquinazoline (Synnovator, 1.000 g, 4.11 mmol), and potassium carbonate (2.270 g, 16.43 mmol) in 12 mL dioxane was treated with 4 mL water and was allowed to stir at room temperature overnight. LC/MS showed mostly product, so the reaction mixture was diluted with DCM and filtered through a plug of Celite. The aqueous layer was removed and the organics concentrated. The crude residue was carried on to step 2 without purification. (M+H)+=384.9.

STEP 2: 7-(BENZYLTHIO)-4-(4-(DIFLUOROMETHYL)-5-FLUORO-2-METHOXYPHENYL)QUINAZOLINE

The crude residue from step one was dissolved in 33 mL dioxane, was treated with Pd$_2$(dba)$_3$ (0.094 g, 0.103 mmol), Xantphos (0.119 g, 0.205 mmol), and n,n-diisopropylethylamine (2.152 ml, 12.32 mmol), and was heated to 60° C. benzyl mercaptan (0.486 ml, 4.11 mmol) was added, and the reaction mixture was allowed to stir for one hour at 60° C. LC/MS showed mostly product, so the reaction mixture was concentrated. Purification of the crude residue by silica gel column chromatography (0-75% EtOAc/heptane) gave 7-(benzylthio)-4-(4-(difluoromethyl)-5-fluoro-2-methoxyphenyl)quinazoline (0.966 g, 2.265 mmol, 55.2% yield) with minor impurities. (M+H)+=427.2.

STEP 3: 4-(4-(DIFLUOROMETHYL)-5-FLUORO-2-METHOXYPHENYL)QUINAZOLINE-7-SULFONYL CHLORIDE

A solution of 7-(benzylthio)-4-(4-(difluoromethyl)-5-fluoro-2-methoxyphenyl)quinazoline (0.966 g, 2.265 mmol) in 22 mL DCM and 0.44 mL (3:2 HOAc/water) solution was cooled to 0° C. and was treated with 1,3-dichloro-5,5-dimethylimidazolidine-2,4-dione (0.893 g, 4.53 mmol). After stirring for 15 minutes, LC/MS showed mostly product, so the reaction mixture was diluted with water. The layers were separated, and the organics were dried over MgSO$_4$ and concentrated. Purification of the crude residue by silica gel column chromatography gave 4-(4-(difluoromethyl)-5-fluoro-2-methoxyphenyl)quinazoline-7-sulfonyl chloride (0.634 g, 1.574 mmol, 69.5% yield) as a white solid. (M+H)+=402.9.

EXAMPLE 512

4-(4-(DIFLUOROMETHYL)-5-FLUORO-2-METHOXYPHENYL)-N-(THIAZOL-2-YL)QUINAZOLINE-7-SULFONAMIDE

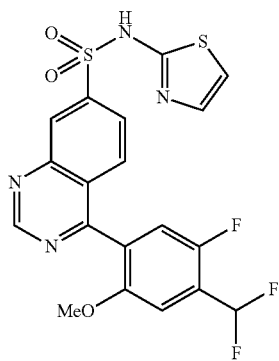 [SMILES: COc1cc(C(F)F)c(F)cc1-c1ncnc2cc(S(=O)(=O)Nc3nccs3)ccc12]

A solution of 4-(4-(difluoromethyl)-5-fluoro-2-methoxyphenyl)quinazoline-7-sulfonyl chloride (0.334 g, 0.829 mmol) and thiazol-2-amine (0.249 g, 2.488 mmol) in 4 mL MeCN was placed under argon and was treated with 1-methylimidazole (0.081 ml, 0.829 mmol). After stirring for 3 hours at room temperature, LC/MS showed mostly product, so the reaction mixture was concentrated. Purification of the crude residue by reverse phase column chromatography [Puriflash C18 30μ, 10-100% (0.1% NH4OH in MeOH)/(0.1% NH4OH in water)] gave 4-(4-(difluoromethyl)-5-fluoro-2-methoxyphenyl)-N-(thiazol-2-yl)quinazoline-7-sulfonamide (0.171 g, 0.367 mmol, 44.2% yield). $^1$H NMR (MeCN-d3) δ: 9.42 (s, 1H), 8.52 (s, 1H), 7.96 (d, J=8.7 Hz, 1H), 7.80 (d, J=8.8 Hz, 1H), 7.38 (d, J=5.4 Hz, 1H), 7.32 (d, J=9.9 Hz, 1H), 6.93-7.24 (m, 2H), 6.64 (d, J=4.7 Hz, 1H), 3.70-3.73 (s, 3H); (M+H)+=467.0.

EXAMPLE 513

4-(4-(difluoromethyl)-5-fluoro-2-methoxyphenyl)-N-(thiazol-4-yl)quinazoline-7-sulfonamide

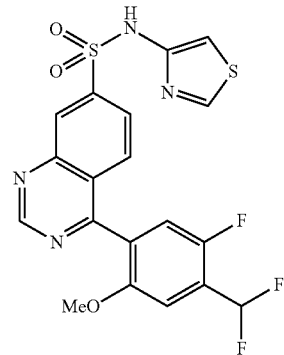 [SMILES: COc1cc(C(F)F)c(F)cc1-c1ncnc2cc(S(=O)(=O)Nc3cscn3)ccc12]

A solution of 4-(4-(difluoromethyl)-5-fluoro-2-methoxyphenyl)quinazoline-7-sulfonyl chloride (0.300 g, 0.745 mmol) and N-(4-methoxybenzyl)thiazol-4-amine (Intermediate PPPPP; 0.492 g, 2.234 mmol) in 6 mL MeCN was placed under argon and was treated with 1-methylimidazole (0.073 ml, 0.745 mmol). After stirring for 3 hours at room temperature, LC/MS showed mostly product, so the reaction mixture was concentrated. The crude residue was dissolved in TFA (2.295 ml, 29.8 mmol) and was heated to 100° C. for 2 hours. LC/MS showed mostly product, so the reaction mixture was concentrated. Purification of the crude residue by reverse phase column chromatography [Puriflash C18 30μ, 10-100% (0.1% NH4OH in MeOH)/(0.1% NH4OH in water)] gave 4-(4-(difluoromethyl)-5-fluoro-2-methoxyphenyl)-N-(thiazol-4-yl)quinazoline-7-sulfonamide (0.141 g, 0.302 mmol, 40.6% yield). $^1$H NMR (MeCN-d3) δ: 9.43 (s, 1H), 8.61 (s, 1H), 8.51 (s, 1H), 7.93 (d, J=8.8 Hz, 1H), 7.79-7.86 (m, 1H), 7.37 (d, J=5.4 Hz, 1H), 7.32 (d, J=9.9 Hz, 1H), 6.92-7.25 (m, 2H), 3.71 (s, 3H). (M+H)+=467.0.

INTERMEDIATE UUUUU: 4-(4-(DIFLUOROMETHYL)-5-FLUORO-2-METHOXYPHENYL)-2-METHYLQUINAZOLINE-7-SULFONYL CHLORIDE

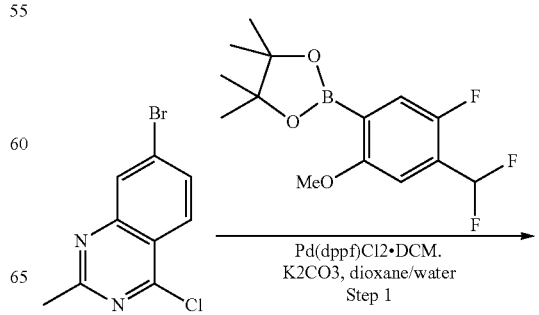

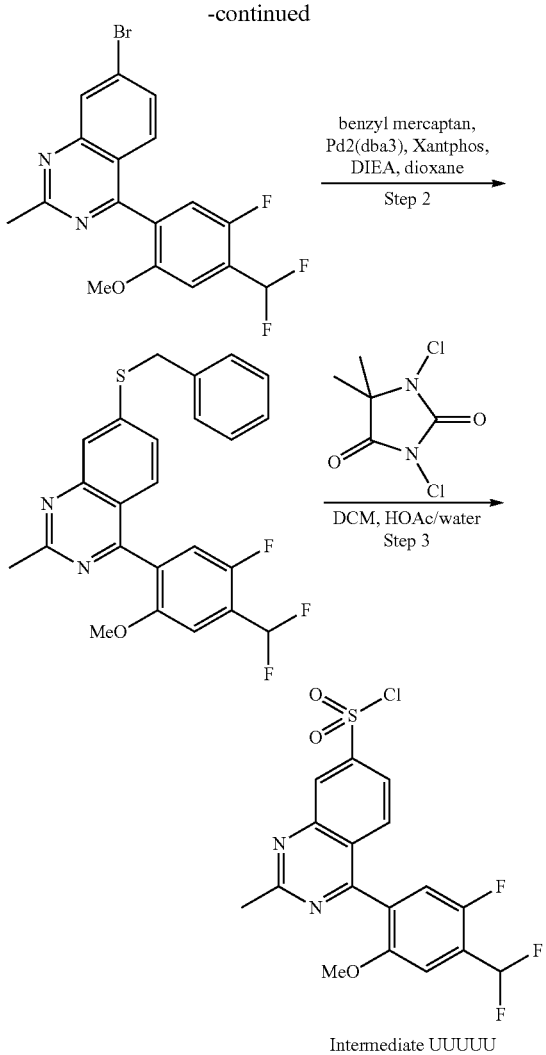

Intermediate UUUUU

STEP 1: 7-BROMO-4-(4-(DIFLUOROMETHYL)-5-FLUORO-2-METHOXYPHENYL)-2-METHYLQUINAZOLINE

A solution of PdCl$_2$(dppf)-CH$_2$Cl$_2$ adduct (0.095 g, 0.116 mmol), 2-(4-(difluoromethyl)-5-fluoro-2-methoxyphenyl)-4,4,5,5-tetramethyl-1,3,2-dioxaborolane (Intermediate SSSSS; 1.290 g, 4.27 mmol), 7-bromo-4-chloro-2-methylquinazoline (ACES Pharma, 1.000 g, 3.88 mmol), and potassium carbonate (2.147 g, 15.53 mmol) in 12 mL dioxane was treated with 4 mL water and was allowed to stir at room temperature overnight. LC/MS showed mostly product, so the reaction mixture was diluted with DCM and filtered through a plug of Celite. The aqueous layer was removed and the organics concentrated. The crude residue was carried on to step 2 without purification. (M+H)+=399.0.

STEP 2: 7-(BENZYLTHIO)-4-(4-(DIFLUOROMETHYL)-5-FLUORO-2-METHOXYPHENYL)-2-METHYLQUINAZOLINE

The crude residue from step one was dissolved in 33 mL dioxane, was treated with Pd$_2$(dba)$_3$ (0.089 g, 0.097 mmol), Xantphos (0.112 g, 0.194 mmol), and n,n-diisopropylethylamine (2.035 ml, 11.65 mmol), and was heated to 60° C. Benzyl mercaptan (0.459 ml, 3.88 mmol) was added, and the reaction mixture was allowed to stir for one hour at 60° C. LC/MS showed mostly product, so the reaction mixture was concentrated. Purification of the crude residue by silica gel column chromatography (0-75% EtOAc/heptane) gave 7-(benzylthio)-4-(4-(difluoromethyl)-5-fluoro-2-methoxyphenyl)-2-methylquinazoline (0.995 g, 2.259 mmol, 58.2% yield) 117740-47-2 with minor impurities. (M+H)+=441.0.

STEP 3: 4-(4-(DIFLUOROMETHYL)-5-FLUORO-2-METHOXYPHENYL)-2-METHYLQUINAZOLINE-7-SULFONYL CHLORIDE

A solution of 7-(benzylthio)-4-(4-(difluoromethyl)-5-fluoro-2-methoxyphenyl)-2-methylquinazoline (0.995 g, 2.259 mmol) in 22 mL DCM and 0.44 mL (3:2 HOAc/water) solution was cooled to 0° C. and was treated with 1,3-dichloro-5,5-dimethylimidazolidine-2,4-dione (0.890 g, 4.52 mmol). After stirring for 15 minutes, LC/MS showed mostly product, so the reaction mixture was diluted with water. The layers were separated, and the organics were dried over MgSO4 and concentrated. Purification of the crude residue by silica gel column chromatography (0-75% EtOAc/heptane) gave 4-(4-(difluoromethyl)-5-fluoro-2-methoxyphenyl)-2-methylquinazoline-7-sulfonyl chloride (0.550 g, 1.320 mmol, 58.4% yield) white solid. (M+H)+=417.0.

EXAMPLE 514

4-(4-(difluoromethyl)-5-fluoro-2-methoxyphenyl)-2-methyl-N-(thiazol-2-yl)quinazoline-7-sulfonamide

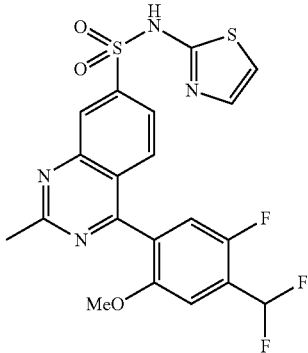 [SMILES: COc1cc(C(F)F)c(F)cc1-c1nc(C)nc2cc(S(=O)(=O)Nc3nccs3)ccc12]

The title compound was prepared in a manner analogous to example 512 except 4-(4-(difluoromethyl)-5-fluoro-2-methoxyphenyl)-2-methylquinazoline-7-sulfonyl chloride (Intermediate UUUUU) was used instead of 4-(4-(difluoromethyl)-5-fluoro-2-methoxyphenyl)quinazoline-7-sulfonyl chloride (Intermediate TTTTT). $^1$H NMR (MeCN-d3) δ: 8.39 (s, 1H), 7.87 (d, J=8.7 Hz, 1H), 7.73 (d, J=8.7 Hz, 1H), 7.36

(d, J=5.4 Hz, 1H), 7.28 (d, J=9.9 Hz, 2H), 6.92-7.24 (m, 2H), 6.63 (d, J=4.7 Hz, 1H), 3.69-3.74 (m, 3H), 2.85 (s, 3H); (M+H)+=481.0.

INTERMEDIATE VVVVV: 4-(4-(DIFLUOROMETHYL)-2-METHOXYPHENYL)-2-METHYLQUINAZOLINE-7-SULFONYL CHLORIDE

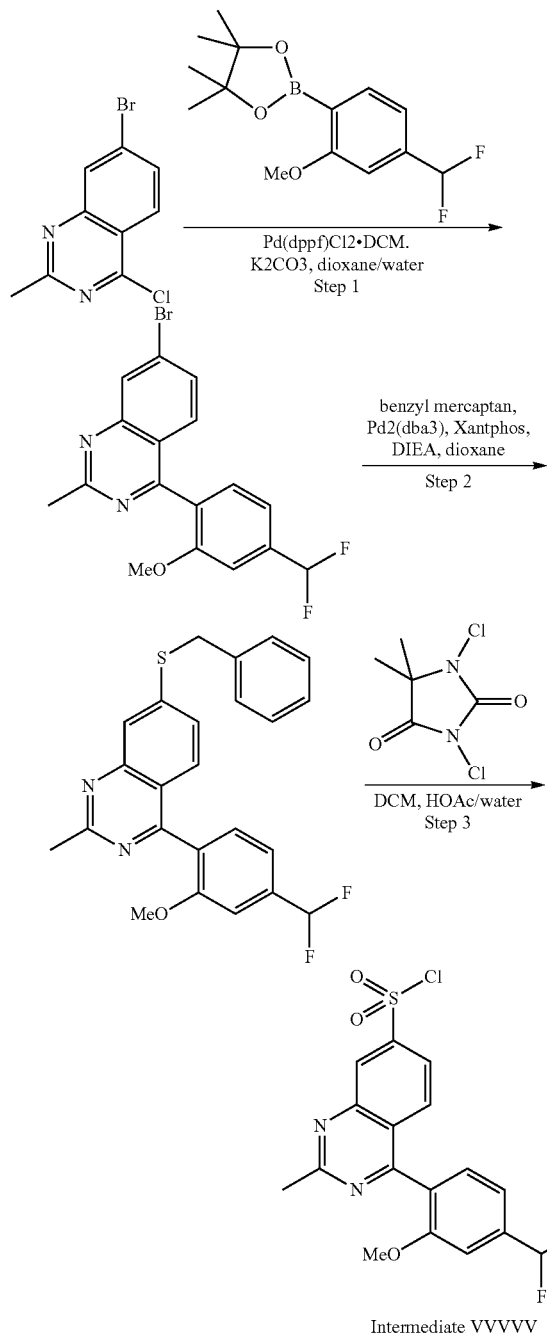

Intermediate VVVVV

STEP 1: 7-BROMO-4-(4-(DIFLUOROMETHYL)-2-METHOXYPHENYL)-2-METHYLQUINAZOLINE

A solution of PdCl$_2$(dppf)-CH$_2$Cl$_2$ adduct (0.095 g, 0.116 mmol), 2-(4-(difluoromethyl)-2-methoxyphenyl)-4,4,5,5-tetramethyl-1,3,2-dioxaborolane (Intermediate TTT) (0.863 g, 4.27 mmol), 7-bromo-4-chloro-2-methylquinazoline (ACES Pharma, 1.000 g, 3.88 mmol), and potassium carbonate (2.147 g, 15.53 mmol) in 12 mL dioxane was treated with 4 mL water and was allowed to stir at room temperature overnight. LC/MS showed mostly product, so the reaction mixture was diluted with DCM and filtered through a plug of Celite. The aqueous layer was removed and the organics concentrated. The crude residue was carried on to step 2 without purification. (M+H)+=381.0.

STEP 2: 7-(BENZYLTHIO)-4-(4-(DIFLUOROMETHYL)-2-METHOXYPHENYL)-2-METHYLQUINAZOLINE

The crude residue from step one was dissolved in 33 mL dioxane, was treated with Pd$_2$(dba)$_3$ (0.089 g, 0.097 mmol), Xantphos (0.112 g, 0.194 mmol), and n,n-diisopropylethylamine (2.035 ml, 11.65 mmol), and was heated to 60° C. Benzyl mercaptan (0.459 ml, 3.88 mmol) was added, and the reaction mixture was allowed to stir for one hour at 60° C. LC/MS showed mostly product, so the reaction mixture was concentrated. Purification of the crude residue by silica gel column chromatography (0-50% EtOAc/heptane) gave 7-(benzylthio)-4-(4-(difluoromethyl)-2-methoxyphenyl)-2-methylquinazoline (0.380 g, 0.899 mmol, 23.16% yield) with minor impurities. (M+H)+=423.0.

STEP 3: 4-(4-(DIFLUOROMETHYL)-2-METHOXYPHENYL)-2-METHYLQUINAZOLINE-7-SULFONYL CHLORIDE

A solution of 7-(benzylthio)-4-(4-(difluoromethyl)-2-methoxyphenyl)-2-methylquinazoline (0.380 g, 0.899 mmol) in 11 mL DCM and 0.22 mL (3:2 HOAc/water) solution was cooled to 0° C. and was treated with 1,3-dichloro-5,5-dimethylimidazolidine-2,4-dione (0.354 g, 1.799 mmol). After stirring for 15 minutes, LC/MS showed mostly product, so the reaction mixture was diluted with water. The layers were separated, and the organics were dried over MgSO$_4$ and concentrated. Purification of the crude residue by silica gel column chromatography gave 4-(4-(difluoromethyl)-2-methoxyphenyl)-2-methylquinazoline-7-sulfonyl chloride (0.180 g, 0.451 mmol, 50.2% yield) as a white solid. (M+H)+=399.0.

EXAMPLE 515

4-(4-(difluoromethyl)-2-methoxyphenyl)-2-methyl-N-(thiazol-2-yl)quinazoline-7-sulfonamide

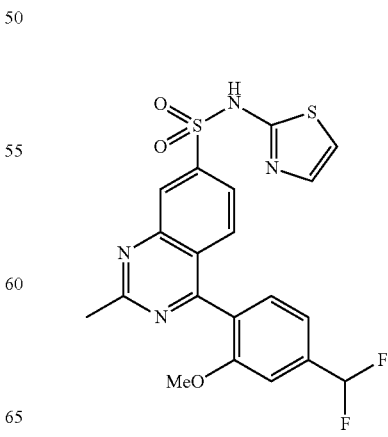

The title compound was prepared in a manner analogous to example 512 except 4-(4-(difluoromethyl)-2-methoxyphenyl)-2-methylquinazoline-7-sulfonyl chloride (Intermediate VVVVV) was used instead of 4-(4-(difluoromethyl)-5-fluoro-2-methoxyphenyl)quinazoline-7-sulfonyl chloride (Intermediate TTTTT). $^1$H NMR (MeCN-d3) δ: 8.38 (s, 1H), 7.85 (d, J=8.8 Hz, 1H), 7.70 (d, J=8.7 Hz, 1H), 7.49 (d, J=7.7 Hz, 1H), 7.30-7.38 (m, 2H), 6.73-7.05 (m, 2H), 6.63 (d, J=4.7 Hz, 1H), 3.73 (s, 3H), 2.84 (s, 3H); (M+H)+=462.9.

INTERMEDIATE WWWWW: 4-(4-(3-FLUOROOXETAN-3-YL)-2-METHOXYPHENYL)-2-METHYLQUINAZOLINE-7-SULFONYL CHLORIDE

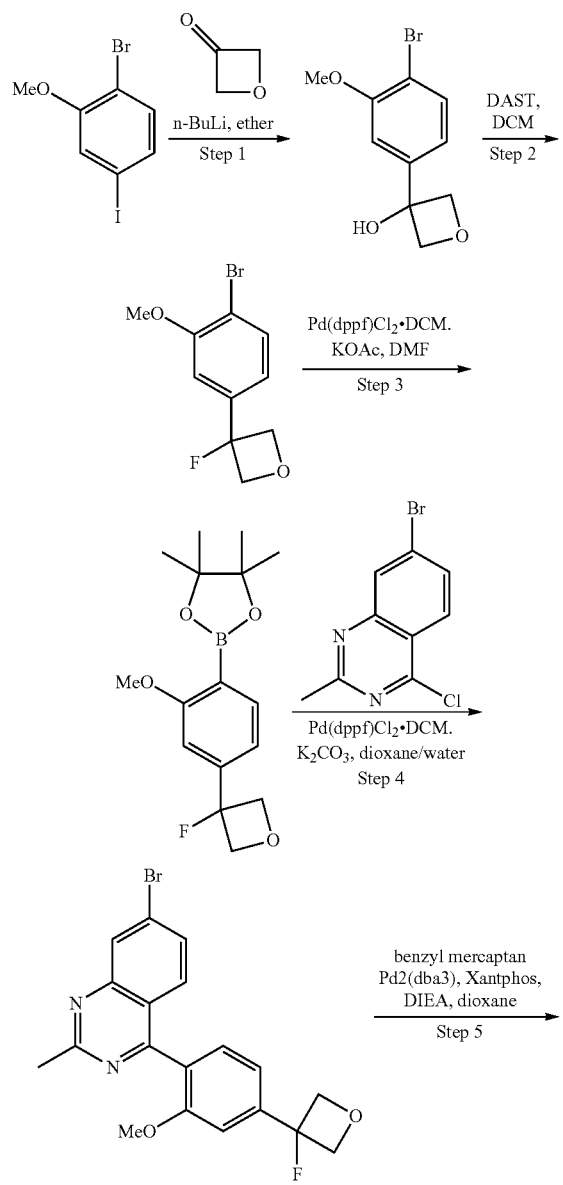

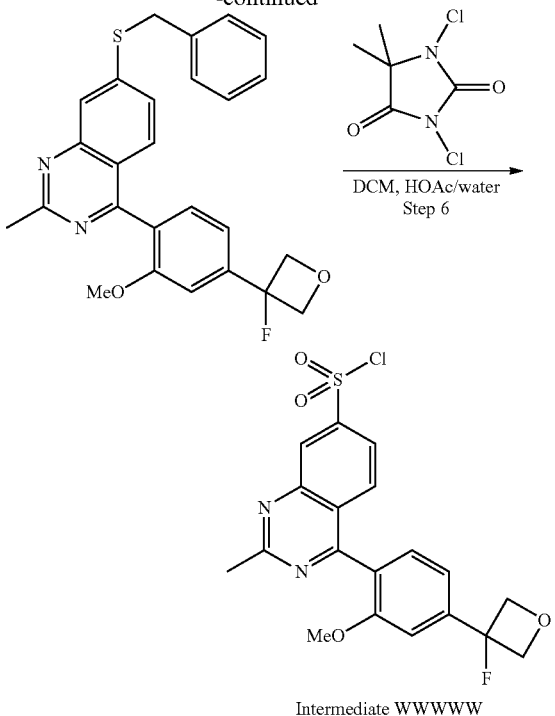

Intermediate WWWWW

STEP 1: 3-(4-BROMO-3-METHOXYPHENYL)OXETAN-3-OL

A solution of 1-bromo-4-iodo-2-methoxybenzene (Combi-Blocks, 3.00 g, 9.59 mmol) in 40 mL ether was cooled to −78° C. and was treated with n-butyllithium (4.22 ml, 10.55 mmol). After stirring for 10 minutes, the reaction mixture was quenched with 3-oxetanone (0.967 ml, 13.42 mmol), and the cooling bath was removed. After stirring for an additional hour, LC/MS showed mostly product, so the reaction mixture was washed with 1N citric acid solution, the organics dried over MgSO$_4$ and concentrated. This material was carried on to step two without purification. (M+H)+ =240.9.

STEP 2: 3-(4-BROMO-3-METHOXYPHENYL)-3-FLUOROOXETANE

The crude residue from step one was dissolved in 40 mL DCM, placed under argon, and was cooled to 0° C. DAST (1.393 ml, 10.55 mmol) was added, and the reaction mixture was allowed to warm to room temperature overnight. LC/MS showed mostly product, so the reaction mixture was quenched with saturated NaHCO$_3$ solution. The organics were separated, dried over MgSO$_4$ and concentrated. Purification of the crude residue by silica gel column chromatography (0-20% EtOAc/heptane) gave 3-(4-bromo-3-methoxyphenyl)-3-fluorooxetane (0.594 g, 2.275 mmol, 23.73% yield) as a white solid. (M+H)+=243.0.

STEP 3: 2-(4-(3-FLUOROOXETAN-3-YL)-2-METHOXYPHENYL)-4,4,5,5-TETRAMETHYL-1,3,2-DIOXABOROLANE

A solution of PdCl$_2$(dppf)-CH$_2$Cl$_2$ adduct (0.186 g, 0.228 mmol), bis(pinacolato)diboron (0.867 g, 3.41 mmol), 3-(4- bromo-3-methoxyphenyl)-3-fluorooxetane (0.594 g, 2.275 mmol), and potassium acetate (0.893 g, 9.10 mmol) in 4 mL DMF was heated to 100° C. overnight. LC/MS showed mostly product, so the reaction mixture was allowed to cool to room temperature and was diluted with ether. The reaction mixture was filtered through a plug of Celite and the filtrate was concentrated. Purification of the crude residue by silica gel column chromatography (0-20% EtOAc/heptane) gave 2-(4-(3-fluorooxetan-3-yl)-2-methoxyphenyl)-4,4,5,5-tetramethyl-1,3,2-dioxaborolane (0.343 g, 1.113 mmol, 48.9% yield) as a white solid. (M+H)+=309.3.

STEP 4: 7-BROMO-4-(4-(3-FLUOROOXETAN-3-YL)-2-METHOXYPHENYL)-2-METHYLQUINAZOLINE

A solution of PdCl$_2$(dppf)-CH$_2$Cl$_2$ adduct (0.041 g, 0.051 mmol), 24443-fluorooxetan-3-yl)-2-methoxyphenyl)-4,4,5,5-tetramethyl-1,3,2-dioxaborolane (0.343 g, 1.113 mmol), 7-bromo-4-chloro-2-methylquinazoline (ACES Pharma, 0.261 g, 1.012 mmol), and potassium carbonate (0.559 g, 4.05 mmol) in 3 mL dioxane was treated with 1 mL water and was allowed to stir at room temperature overnight. LC/MS showed mostly product, so the aqueous layer was removed. The crude reaction mixture was carried on to step 5 without purification. (M+H)+=405.0.

STEP 5: 7-(BENZYLTHIO)-4-(4-(3-FLUOROOXETAN-3-YL)-2-METHOXYPHENYL)-2-METHYLQUINAZOLINE

The reaction mixture from step 4 was treated with Pd$_2$(dba)$_3$ (0.023 g, 0.025 mmol), Xantphos (0.029 g, 0.051 mmol), and n,n-diisopropylethylamine (0.530 ml, 3.04 mmol), and was heated to 60° C. Benzyl mercaptan (0.120 ml, 1.012 mmol) was added, and the reaction mixture was allowed to stir for one hour at 60° C. LC/MS showed mostly product, so the reaction mixture was concentrated. Purification of the crude residue by silica gel column chromatography (0-75% EtOAc/heptane) gave 7-(benzylthio)-4-(4-(3-fluorooxetan-3-yl)-2-methoxyphenyl)-2-methylquinazoline (0.189 g, 0.423 mmol, 41.8% yield) with minor impurities. (M+H)+=447.0.

STEP 6: 4-(4-(3-FLUOROOXETAN-3-YL)-2-METHOXYPHENYL)-2-METHYLQUINAZOLINE-7-SULFONYL CHLORIDE

A solution of 7-(benzylthio)-4-(4-(3-fluorooxetan-3-yl)-2-methoxyphenyl)-2-methylquinazoline (0.189 g, 0.423 mmol) in 8 mL DCM and 0.2 mL (3:2 HOAc/water) solution was cooled to 0° C. and was treated with 1,3-dichloro-5,5-dimethylimidazolidine-2,4-dione (0.167 g, 0.847 mmol). After stirring for 15 minutes, LC/MS showed mostly product, so the reaction mixture was diluted with water. The layers were separated, and the organics were dried over MgSO$_4$ and concentrated. Purification of the crude residue by silica gel column chromatography (0-50% EtOAc/heptane) gave 4-(4-(3-fluorooxetan-3-yl)-2-methoxyphenyl)-2-methylquinazoline-7-sulfonyl chloride (0.112 g, 0.265 mmol, 62.6% yield) as a white solid. (M+H)+=423.0.

EXAMPLE 516

4-(4-(3-FLUOROOXETAN-3-YL)-2-METHOXYPHENYL)-2-METHYL-N-(THIAZOL-2-YL)QUINAZOLINE-7-SULFONAMIDE

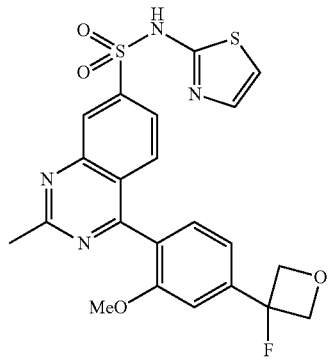 [SMILES: COc1cc(C2(F)COC2)ccc1-c1nc(C)nc2cc(S(=O)(=O)Nc3nccs3)ccc12]

The title compound was prepared in a manner analogous to example 512 except 4-(4-(3-fluorooxetan-3-yl)-2-methoxyphenyl)-2-methylquinazoline-7-sulfonyl chloride (Intermediate WWWWW) was used instead of 4-(4-(difluoromethyl)-5-fluoro-2-methoxyphenyl)quinazoline-7-sulfonyl chloride (Intermediate TTTTT). $^1$H NMR (MeCN-d3) δ: 8.37 (s, 1H), 7.86 (d, J=8.7, 1H), 7.73 (d, J=8.7 Hz, 1H), 7.42-7.49 (m, 1H), 7.29-7.38 (m, 2H), 7.01 (d, J=4.7 Hz, 1H), 6.63 (d, J=4.7 Hz, 1H), 4.92-5.14 (m, 4H), 3.74 (s, 3H), 2.82-2.89 (m, 3H); (M+H)+=487.0.

INTERMEDIATE XXXXX: 4-(4-CYANO-2-METHOXYPHENYL)-2-METHYLQUINAZOLINE-7-SULFONYL CHLORIDE

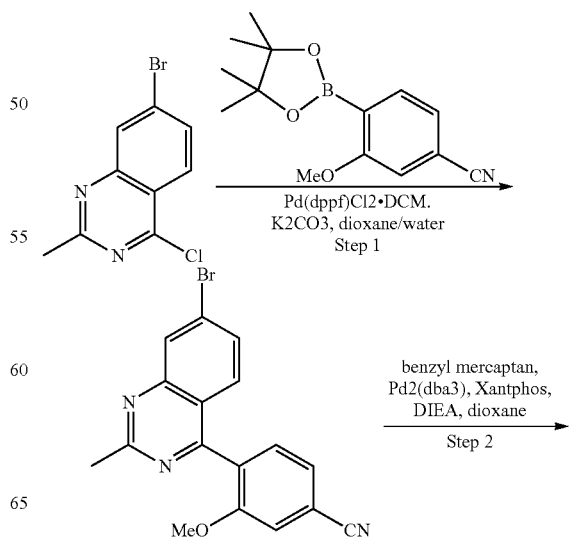

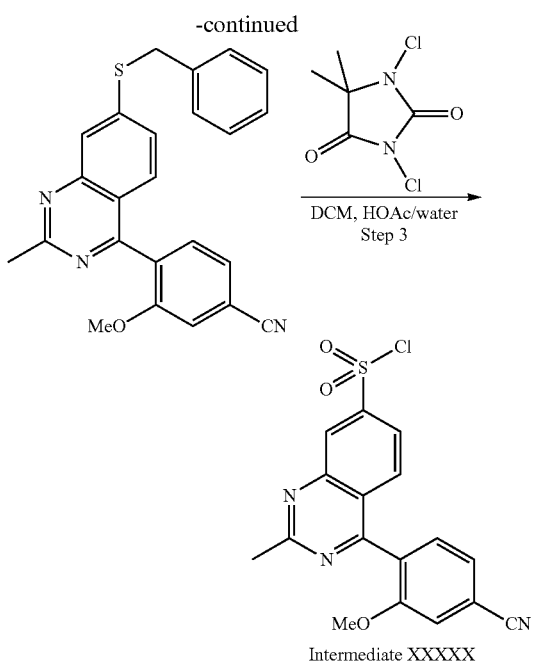

STEP 1: 4-(7-BROMO-2-METHYLQUINAZOLIN-4-YL)-3-METHOXYBENZONITRILE

A solution of $PdCl_2$(dppf)-$CH_2Cl_2$ adduct (0.072 g, 0.088 mmol), 3-methoxy-4-(4,4,5,5-tetramethyl-1,3,2-dioxaborolan-2-yl)benzonitrile (Intermediate GGGG) (0.500 g, 1.930 mmol), 7-bromo-4-chloro-2-methylquinazoline (0.452 g, 1.754 mmol), and potassium carbonate (0.970 g, 7.02 mmol) in 3 mL dioxane was treated with 1 mL water and was allowed to stir at room temperature 3 hours. LC/MS showed mostly product, so the reaction mixture was diluted with DCM and washed with water. The aqueous layer was removed and the reaction mixture was concentrated. The crude residue was carried forward to step 2 without purification. (M+H)+=354.0.

STEP 2: 4-(7-(BENZYLTHIO)-2-METHYLQUINAZOLIN-4-YL)-3-METHOXYBENZONITRILE

The crude residue from step one was taken up in 3 mL dioxane and was treated with $Pd_2$(dba)$_3$ (0.040 g, 0.044 mmol), Xantphos (0.051 g, 0.088 mmol), and n,n-diisopropylethylamine (0.919 ml, 5.26 mmol), and was heated to 60° C. Benzyl mercaptan (0.208 ml, 1.754 mmol) was added, and the reaction mixture was allowed to stir for one hour at 60° C. LC/MS showed mostly product, so the reaction mixture was concentrated. Purification of the crude residue by silica gel column chromatography (0-75% EtOAc/heptane) gave 4-(7-(benzylthio)-2-methylquinazolin-4-yl)-3-methoxybenzonitrile (0.371 g, 0.933 mmol, 53.2% yield) with minor impurities. (M+H)+=398.1.

STEP 3: 4-(4-CYANO-2-METHOXYPHENYL)-2-METHYLQUINAZOLINE-7-SULFONYL CHLORIDE

A solution of 4-(7-(benzylthio)-2-methylquinazolin-4-yl)-3-methoxybenzonitrile (0.371 g, 0.933 mmol) in 8 mL DCM and 0.2 mL (3:2 HOAc/water) solution was cooled to 0° C. and was treated with 1,3-dichloro-5,5-dimethylimidazolidine-2,4-dione (0.368 g, 1.867 mmol). After stirring for 15 minutes, LC/MS showed mostly product, so the reaction mixture was diluted with water. The layers were separated, and the organics were dried over $MgSO_4$ and concentrated. Purification of the crude residue by silica gel column chromatography (0-50% EtOAc/heptane) gave 4-(4-cyano-2-methoxyphenyl)-2-methylquinazoline-7-sulfonyl chloride (0.214 g, 0.572 mmol, 61.3% yield). (M+H)+=374.1.

EXAMPLE 517

4-(4-CYANO-2-METHOXYPHENYL)-2-METHYL-N-(THIAZOL-2-YL)QUINAZOLINE-7-SULFONAMIDE

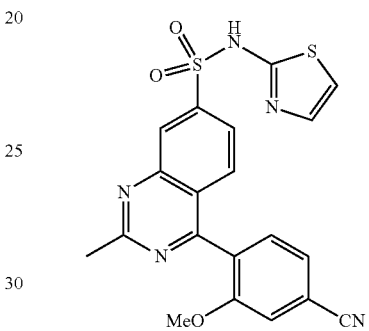

The title compound was prepared in a manner analogous to example 512 except 4-(4-cyano-2-methoxyphenyl)-2-methylquinazoline-7-sulfonyl chloride (Intermediate XXXXX) was used instead of 4-(4-(difluoromethyl)-5-fluoro-2-methoxyphenyl)quinazoline-7-sulfonyl chloride (Intermediate TTTTT). $^1$H NMR (MeCN-d3) δ: 8.39 (s, 1H), 7.86 (d, J=8.7 Hz, 1H), 7.68 (d, J=8.7 Hz, 1H), 7.50-7.56 (m, 3H), 7.01 (d, J=4.7 Hz, 1H), 6.63 (d, J=4.7 Hz, 1H), 3.73 (s, 3H), 2.84 (s, 3H) (M+H)+=438.0.

EXAMPLE 518

4-(2-METHOXY-4-(TRIFLUOROMETHYL)PHENYL)-2-METHYL-N-(PYRIMIDIN-4-YL)QUINAZOLINE-7-SULFONAMIDE

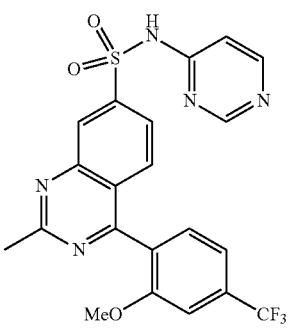 [SMILES: COc1cc(C(F)(F)F)ccc1-c1nc(C)nc2cc(S(=O)(=O)Nc3ccncn3)ccc12]

The title compound was prepared in a manner analogous to example 510 except 4-aminopyrimidine was used instead of 2-aminothiazole. $^1$H NMR (MeCN-d$_3$) δ: 8.42-8.50 (m, 2H), 8.15 (d, J=6.4 Hz, 1H), 7.93 (d, J=8.7 Hz, 1H), 7.70 (d, J=8.7 Hz, 1H), 7.51-7.56 (m, 1H), 7.38-7.49 (m, 2H), 7.03 (dd, J=6.4 Hz, 1H), 3.72-3.75 (m, 3H), 2.84 (s, 3H); (M+H)+ =476.0.

EXAMPLE 519

4-(4-(DIFLUOROMETHYL)-5-FLUORO-2-METHOXYPHENYL)-N-(4,5-DIHYDROTHIAZOL-2-YL)QUINAZOLINE-7-SULFONAMIDE

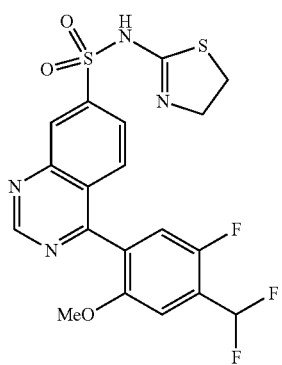 [SMILES: COc1cc(C(F)F)c(F)cc1-c1ncnc2cc(S(=O)(=O)NC3=NCCS3)ccc12]

The title compound was prepared in a manner analogous to example 512 except 4,5-dihydrothiazol-2-amine (Pfaltz & Bauer) was used instead of 2-aminothiazole. (M+H)+=469.0.

EXAMPLE 520

N-(4,5-DIHYDROTHIAZOL-2-YL)-4-(2-METHOXY-4-(TRIFLUOROMETHYL)PHENYL)QUINAZOLINE-7-SULFONAMIDE

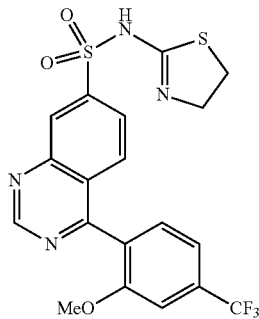 [SMILES: COc1cc(C(F)(F)F)ccc1-c1ncnc2cc(S(=O)(=O)NC3=NCCS3)ccc12]

The title compound was prepared in a manner analogous to example 512 except 4,5-dihydrothiazol-2-amine (Pfaltz & Bauer) was used instead of 2-aminothiazole and 4-(2-methoxy-4-(trifluoromethyl)phenyl)quinazoline-7-sulfonyl chloride was used instead of 4-(4-(difluoromethyl)-5-fluoro-2-methoxyphenyl)quinazoline-7-sulfonyl chloride. (M+H)+ =469.0.

INTERMEDIATE YYYYY: 7-(BENZYLTHIO)-4-CHLOROQUINAZOLINE

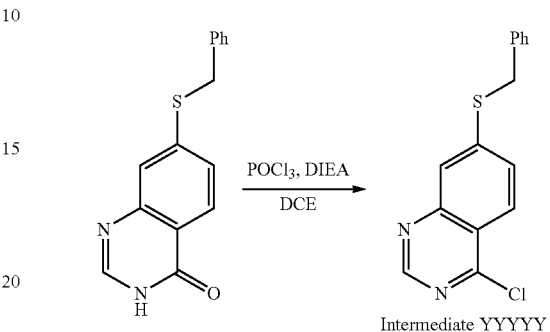

A flask was charged with 7-(benzylthio)quinazolin-4(3H)-one (5.0 g, 18.63 mmol) and DCE (93 ml). POCl₃ (5.21 ml, 55.9 mmol) was added, followed by Hunig's base (16.27 ml, 93 mmol). The flask was fitted with a reflux condensor, and the reaction was for two hours at 90° C. The reaction was washed with water and the layers were separated. The aqueous layer was extracted with ethyl acetate, and the combined organic layers were washed with brine, dried over sodium sulfate, filtered, and concentrated. The material was purified via column chromatography (RediSep Gold 80 g, gradient elution 0-75% EtOAc:Heptane) to afford 7-(benzylthio)-4-chloroquinazoline as a light yellow solid. (ESI) 287.0 (M+H)⁺.

INTERMEDIATE ZZZZZ: PERFLUOROPHENYL 4-(2-CHLORO-3'-FLUORO-5-METHOXY-[1,1'-BIPHENYL]-4-YL)QUINAZOLINE-7-SULFONATE

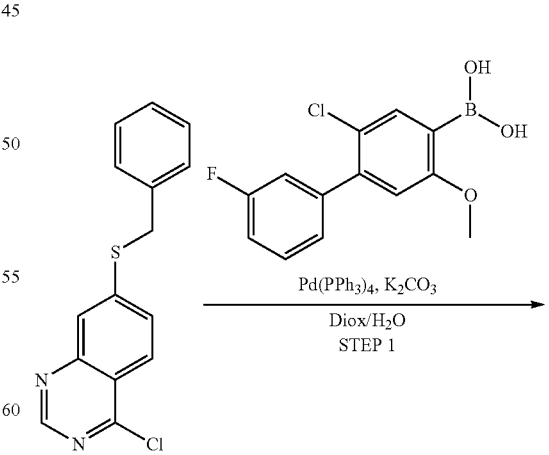

-continued

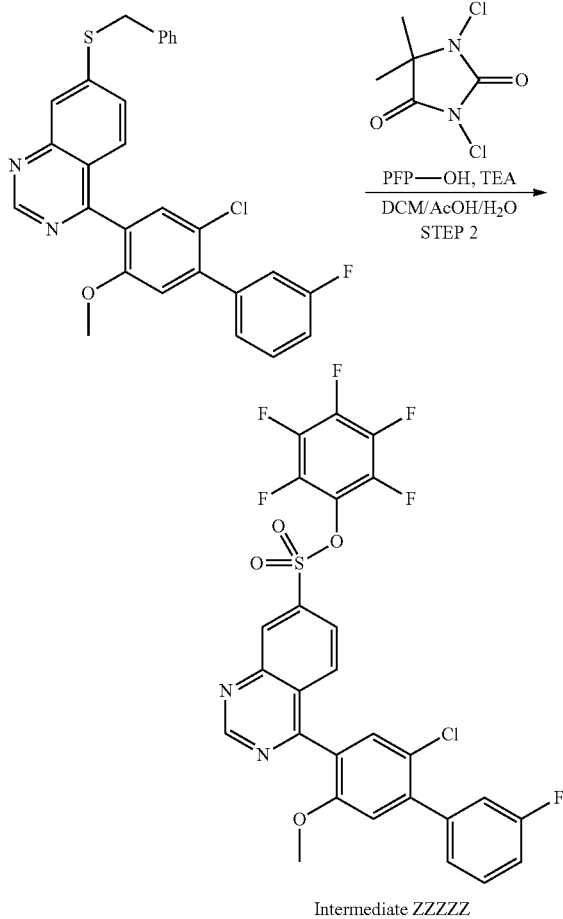

Intermediate ZZZZZ

STEP 1: 7-(BENZYLTHIO)-4-(2-CHLORO-3'-FLUORO-5-METHOXY-[1,1'-BIPHENYL]-4-YL)QUINAZOLINE

A microwave vial was charged with 7-(benzylthio)-4-chloroquinazoline (0.372 g, 1.298 mmol), (2-chloro-3'-fluoro-5-methoxy-[1,1'-biphenyl]-4-yl)boronic acid (0.364 g, 1.298 mmol), tetrakis(triphenylphosphine)palladium(0) (0.150 g, 0.130 mmol), and potassium carbonate (0.897 g, 6.49 mmol). Dioxane (3.24 ml) and Water (1.081 ml) were added; the vial was flushed with argon and sealed, and microwaved at 90° C. for 30 minutes. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-75% EtOAc:Heptane) to afford 7-(benzylthio)-4-(2-chloro-3'-fluoro-5-methoxy-[1,1'-biphenyl]-4-yl)quinazoline as a yellow solid. (ESI) 487.1 (M+H)⁺.

STEP 2: PERFLUOROPHENYL 4-(2-CHLORO-3'-FLUORO-5-METHOXY-[1,1'-BIPHENYL]-4-YL)QUINAZOLINE-7-SULFONATE

A round-bottom flask was charged with 7-(benzylthio)-4-(2-chloro-3'-fluoro-5-methoxy-[1,1'-biphenyl]-4-yl)quinazoline (0.490 g, 1.006 mmol), DCM (9.47 ml), DCM (9.47 ml), Acetic Acid (0.355 ml), and Water (0.237 ml) to give a thin suspension. The flask was cooled in an ice-bath for 10 min, then 1,3-dichloro-5,5-dimethylimidazolidine-2,4-dione (0.496 g, 2.52 mmol) was added in one portion, leading to a solution. The reaction was stirred for 15 minutes. 2,3,4,5,6-pentafluorophenol (0.211 ml, 2.012 mmol) was added followed by drop wise addition of triethylamine (0.351 ml, 2.52 mmol). The reaction was stirred for 30 minutes. The reaction was concentrated and purified via column chromatography (RediSep Gold 40 g, gradient elution 0-50% EtOAc:Heptane) to afford perfluorophenyl 4-(2-chloro-3'-fluoro-5-methoxy-[1,1'-biphenyl]-4-yl)quinazoline-7-sulfonate as a light yellow solid. (ESI) 611.2 (M+H)⁺.

EXAMPLE 521

4-(2-CHLORO-3'-FLUORO-5-METHOXY-[1,1'-BIPHENYL]-4-YL)-N-(1,2,4-THIADIAZOL-5-YL)QUINAZOLINE-7-SULFONAMIDE

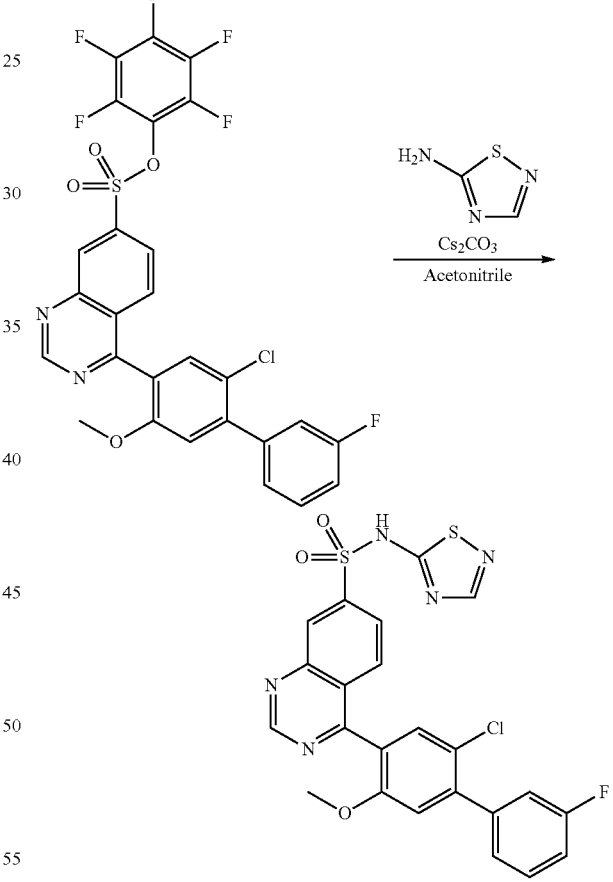

A vial was charged with perfluorophenyl 4-(2-chloro-3'-fluoro-5-methoxy-[1,1'-biphenyl]-4-yl)quinazoline-7-sulfonate (0.060 g, 0.098 mmol), 1,2,4-thiadiazol-5-amine (10.93 mg, 0.108 mmol), and cesium carbonate (0.096 g, 0.295 mmol). The vial was flushed with Ar (g), then acetonitrile (0.491 ml) was added. The reaction was stirred overnight at room temperature. The mixture was diluted with EtOAc and 1 N aq. HCl. The layers were separated, and the aq. layer was extracted with EtOAc (2×). The combined organic extracts were dried over sodium sulfate, filtered, and concentrated. The residue was purified by chromatography on silica gel (12-g Redi-Sep Gold column, 0-10% MeOH/DCM) to give 4-(2-chloro-3'-fluoro-5-methoxy-[1,1'-biphenyl]-4-yl)-N-(1,2,4-thiadiazol-5-yl)quinazoline-7-sulfonamide as an off-white solid. $^1$H NMR (400 MHz, DMSO-$d_6$) δ=9.55-9.42 (m, 1H), 8.44-8.35 (m, 2H), 8.01 (td, J=2.0, 8.8 Hz, 1H), 7.96-7.89 (m, 1H), 7.67 (dd, J=1.5, 2.3 Hz, 1H), 7.63-7.54 (m, 1H), 7.49-7.41 (m, 2H), 7.38-7.28 (m, 2H), 3.75 (d, J=2.2 Hz, 3H). m/z (ESI) 529.8 (M+H)$^+$.

EXAMPLE 522

4-(2-CHLORO-3'-FLUORO-5-METHOXY-[1,1'-BIPHENYL]-4-YL)-N-(1,3,4-THIADIAZOL-2-YL)QUINAZOLINE-7-SULFONAMIDE

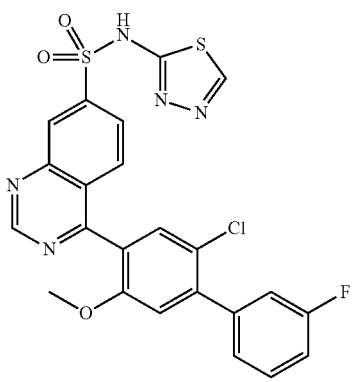 [SMILES: COc1cc(-c2cccc(F)c2)c(Cl)cc1-c1ncnc2cc(S(=O)(=O)Nc3nncs3)ccc12]

The title compound was prepared in an analogous manner to that of EXAMPLE 521, except that 1,3,4-thiadiazol-2-amine was used instead of 1,2,4-thiadiazol-5-amine to afford 4-(2-chloro-3'-fluoro-5-methoxy-[1,1'-biphenyl]-4-yl)-N-(1,3,4-thiadiazol-2-yl)quinazoline-7-sulfonamide as a light yellow solid. $^1$H NMR (400 MHz, DMSO-$d_6$) δ=9.55-9.47 (m, 1H), 8.85-8.79 (m, 1H), 8.41 (s, 1H), 8.04-7.99 (m, 1H), 7.97-7.92 (m, 1H), 7.69-7.65 (m, 1H), 7.63-7.55 (m, 1H), 7.44 (dd, J=2.2, 4.5 Hz, 2H), 7.39-7.29 (m, 2H), 3.75 (d, J=1.2 Hz, 3H). m/z (ESI) 527.8 (M+H)$^+$.

EXAMPLE 523

4-(2-CHLORO-3'-FLUORO-5-METHOXY-[1,1'-BIPHENYL]-4-YL)-N-(PYRIMIDIN-4-YL)QUINAZOLINE-7-SULFONAMIDE

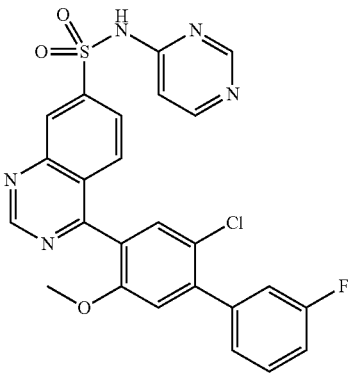 [SMILES: COc1cc(-c2cccc(F)c2)c(Cl)cc1-c1ncnc2cc(S(=O)(=O)Nc3ccncn3)ccc12]

A flask was charged with perfluorophenyl 4-(2-chloro-3'-fluoro-5-methoxy-[1,1'-biphenyl]-4-yl)quinazoline-7-sulfonate (Intermediate ZZZZZ; 0.060 g, 0.098 mmol), pyrimidin-4-amine (9.81 mg, 0.103 mmol), and THF (0.982 ml) and cooled to 0° C. LHMDS (1.0M in THF) (0.206 ml, 0.206 mmol) was added drop wise and the reaction was stirred for 30 minutes. The reaction was quenched with saturated ammonium chloride solution, diluted with ethyl acetate and washed with water. The aqueous layer was extracted with ethyl acetate, and the combined organic layers were dried with sodium sulfate, filtered, and concentrated. The material was purified via column chromatography (RediSep Gold 80 g, gradient elution 0-10% MeOH:DCM) to afford 4-(2-chloro-3'-fluoro-5-methoxy-[1,1'-biphenyl]-4-yl)-N-(pyrimidin-4-yl)quinazoline-7-sulfonamide (0.044 g, 0.084 mmol, 86% yield) as an -off-white solid. $^1$H NMR (400 MHz, DMSO-$d_6$) δ=9.49 (s, 1H), 8.57 (s, 1H), 8.51 (d, J=1.6 Hz, 1H), 8.22 (d, J=6.9 Hz, 1H), 8.08 (dd, J=1.8, 8.8 Hz, 1H), 7.91 (d, J=8.9 Hz, 1H), 7.67 (s, 1H), 7.59 (dt, J=6.3, 8.1 Hz, 1H), 7.48-7.41 (m, 2H), 7.37-7.29 (m, 2H), 7.00 (d, J=5.0 Hz, 1H), 3.74 (s, 3H). m/z (ESI) 522.0 (M+H)+.

INTERMEDIATE AAAAAA: PERFLUOROPHE-NYL 4-(4-CHLORO-2-METHOXYPHENYL)QUINAZOLINE-7-SULFONATE

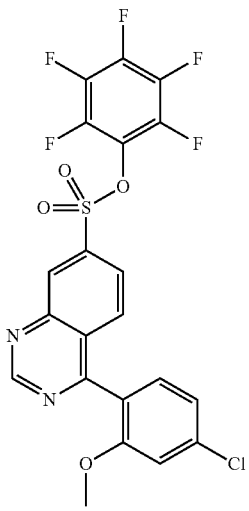 [SMILES: COc1cc(Cl)ccc1-c1ncnc2cc(S(=O)(=O)Oc3c(F)c(F)c(F)c(F)c3F)ccc12]

The title compound was prepared in an analogous manner to that of INTERMEDIATE ZZZZZ, except that (4-chloro-2-methoxyphenyl)boronic acid was used instead of (2-chloro-3'-fluoro-5-methoxy-[1,1'-biphenyl]-4-yl)boronic acid in STEP 1 to afford perfluorophenyl 4-(4-chloro-2-methoxyphenyl)quinazoline-7-sulfonate as a yellow solid. (ESI) 517.0 (M+H)+.

EXAMPLE 524

4-(4-CHLORO-2-METHOXYPHENYL)-N-(1,2,4-THIADIAZOL-5-YL)QUINAZOLINE-7-SULFONAMIDE

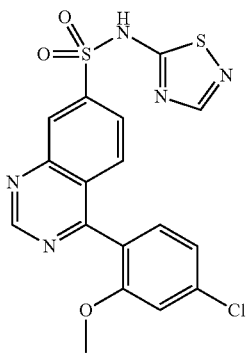 [SMILES: COc1cc(Cl)ccc1-c1ncnc2cc(S(=O)(=O)Nc3ncns3)ccc12]

A solution of N-(2,4-dimethoxybenzyl)-1,2,4-thiadiazol-5-amine (0.112 g, 0.445 mmol) in tetrahydrofuran (1.780 ml) was cooled in a dry ice-acetone bath for 5 min. Lithium bis(trimethylsilyl)amide (1M in THF) (0.490 ml, 0.490 mmol) was added dropwise, then the flask was removed from the cooling bath for 5 min. The flask was again cooled into a dry ice-acetone bath for 20 min, resulting in the formation of a thick slurry. A solution of perfluorophenyl 4-(4-chloro-2-methoxyphenyl)quinazoline-7-sulfonate (Intermediate AAAAAA; 0.230 g, 0.445 mmol) in THF (1.5 mL) was added drop wise, and the reaction was stirred for two hours. The reaction was warmed to room temperature and quenched with saturated ammonium chloride solution, diluted with ethyl acetate and washed with water. The aqueous layer was extracted with ethyl acetate, and the combined organic layers were dried with sodium sulfate, filtered, and concentrated. The filtrate was purified by chromatography on an 12-g Redi-Sep Gold column with 0-50% EtOAc/Heptane. The material was dissolved in DCM and TFA (0.1 ml, 1.298 mmol) was added. The reaction was stirred for 30 minutes at room temperature. The reaction was concentrated and purified via column chromatography (RediSep Gold 12 g, gradient elution 0-10% MeOH:DCM) to afford 4-(4-chloro-2-methoxyphenyl)-N-(1,2,4-thiadiazol-5-yl)quinazoline-7-sulfonamide as a white solid. $^1$H NMR (400 MHz, DMSO-d$_6$) δ=9.48 (s, 1H), 8.49 (s, 1H), 8.40 (d, J=1.6 Hz, 1H), 7.97 (dd, J=1.8, 8.7 Hz, 1H), 7.87 (d, J=8.8 Hz, 1H), 7.47 (d, J=8.1 Hz, 1H), 7.39 (d, J=1.7 Hz, 1H), 7.25 (dd, J=1.8, 8.1 Hz, 1H), 3.72 (s, 3H). m/z (ESI) 434.0 (M+H)+.

EXAMPLE 525

4-(3'-FLUORO-3-METHOXY-[1,1'-BIPHENYL]-4-YL)-N-(1,2,4-THIADIAZOL-5-YL)QUINAZOLINE-7-SULFONAMIDE

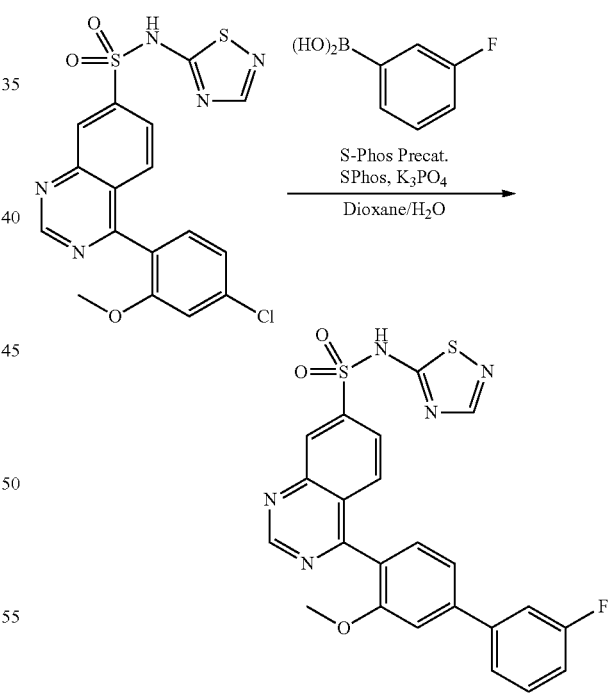

A vial was charged with 4-(4-chloro-2-methoxyphenyl)-N-(1,2,4-thiadiazol-5-yl)quinazoline-7-sulfonamide (Example 524; 0.050 g, 0.115 mmol), (3-fluorophenyl)boronic acid (0.032 g, 0.230 mmol), dicyclohexyl(2',6'-dimethoxy-[1,1'-biphenyl]-2-yl)phosphine (2.365 mg, 5.76 μmol), chloro(2-dicyclohexylphosphino-2',6'-dimethoxy-1,1'-biphenyl)[2-(2-aminoethylphenyl)]palladium(ii) dichloromethane (4.36 mg, 5.76 μmol), and potassium phosphate (0.073 g, 0.346 mmol). The vial was flushed with Ar (g), then 1,4-dioxane (0.524 ml) and Water (0.052 ml) were added in sequence. The vial was sealed and microwaved at 80° C. for three hours. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 12 g, gradient elution 0-10% MeOH:DCM) to afford 4-(3'-fluoro-3-methoxy-[1,1'-biphenyl]-4-yl)-N-(1,2,4-thiadiazol-5-yl)quinazoline-7-sulfonamide as an off-white solid. $^1$H NMR (400 MHz, DMSO-d$_6$) δ=9.47 (s, 1H), 8.39 (d, J=1.7 Hz, 1H), 8.34 (s, 1H), 8.00-7.97 (m, 1H), 7.91-7.87 (m, 1H), 7.75-7.72 (m, 1H), 7.72-7.68 (m, 2H), 7.61-7.49 (m, 4H), 7.31-7.23 (m, 1H), 3.81 (s, 3H). m/z (ESI) 494.2 (M+H)$^+$.

EXAMPLE 526

4-(4-CHLORO-2-METHOXYPHENYL)-N-(PYRIMIDIN-4-YL)QUINAZOLINE-7-SULFONAMIDE

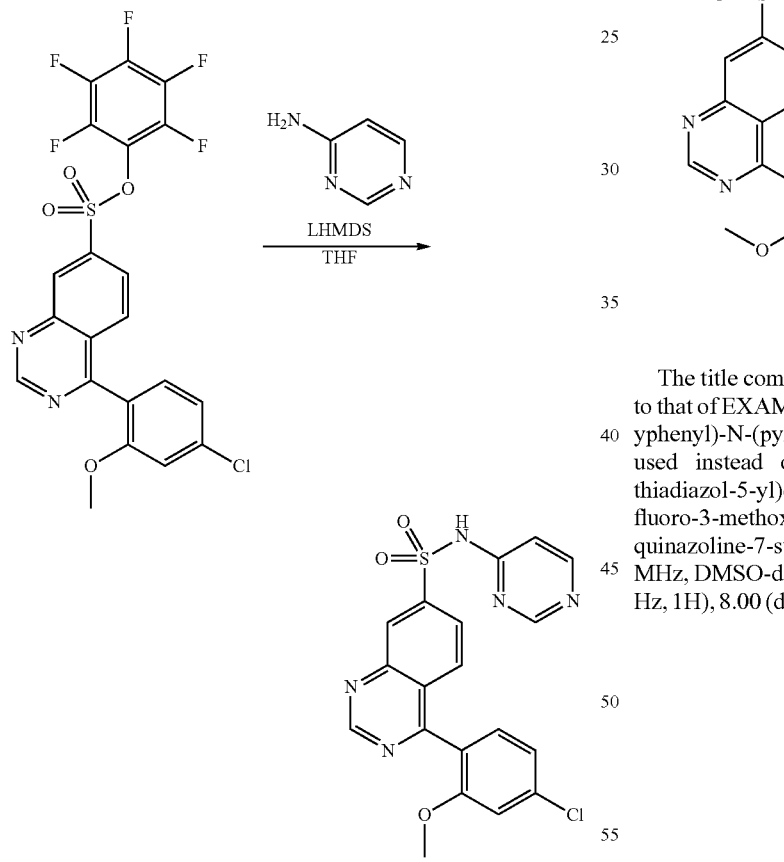

A flask was charged with perfluorophenyl 4-(4-chloro-2-methoxyphenyl)quinazoline-7-sulfonate (Intermediate AAAAAA; 1.0 g, 1.935 mmol), pyrimidin-4-amine (0.193 g, 2.032 mmol), and THF (19.35 ml) and cooled to 0° C. LHMDS (1.0M in THF) (4.06 ml, 4.06 mmol) was added drop wise and the reaction was stirred for 30 minutes. The reaction was quenched with saturated ammonium chloride solution, diluted with ethyl acetate and washed with water. The aqueous layer was extracted with ethyl acetate, and the combined organic layers were dried with sodium sulfate, filtered, and concentrated. The material was purified via column chromatography (RediSep Gold 80 g, gradient elution 0-10% MeOH:DCM) to afford 4-(4-chloro-2-methoxyphenyl)-N-(pyrimidin-4-yl)quinazoline-7-sulfonamide as a tan solid. $^1$H NMR (400 MHz, DMSO-d$_6$) δ=13.28 (br. s., 1H), 9.46 (s, 1H), 8.57 (t, J=1.0 Hz, 1H), 8.48 (d, J=1.7 Hz, 1H), 8.22 (d, J=6.5 Hz, 1H), 8.03 (dd, J=1.9, 8.8 Hz, 1H), 7.83 (d, J=8.7 Hz, 3H), 7.47 (d, J=8.1 Hz, 1H), 7.38 (d, J=1.9 Hz, 1H), 7.25 (dd, J=2.0, 8.1 Hz, 1H), 7.00 (d, J=6.7 Hz, 1H), 3.72 (s, 3H). m/z (ESI) 428.2 (M+H)$^+$.

EXAMPLE 527

4-(3'-FLUORO-3-METHOXY-[1,1'-BIPHENYL]-4-YL)-N-(PYRIMIDIN-4-YL)QUINAZOLINE-7-SULFONAMIDE

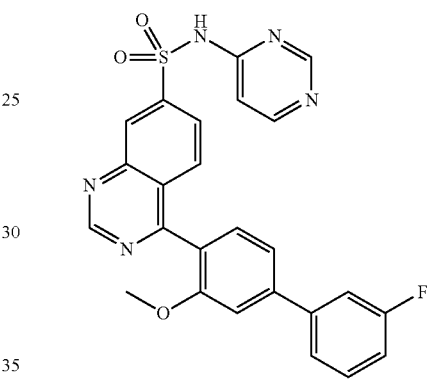

The title compound was prepared in an analogous manner to that of EXAMPLE 525, except that 4-(4-chloro-2-methoxyphenyl)-N-(pyrimidin-4-yl)quinazoline-7-sulfonamide was used instead of 4-(4-chloro-2-methoxyphenyl)-N-(1,2,4-thiadiazol-5-yl)quinazoline-7-sulfonamide to afford 4-(3'-fluoro-3-methoxy-[1,1'-biphenyl]-4-yl)-N-(pyrimidin-4-yl)quinazoline-7-sulfonamide as a white solid. $^1$H NMR (400 MHz, DMSO-d$_6$) δ=9.51 (s, 1H), 8.49 (s, 1H), 8.43 (d, J=1.7 Hz, 1H), 8.00 (dd, J=1.9, 8.7 Hz, 1H), 7.82 (dd, J=0.5, 8.8 Hz, 1H), 7.60-7.56 (m, 1H), 7.49-7.46 (m, 1H), 7.45-7.41 (m, 1H), 2.08 (s, 3H). m/z (ESI) 488.2 (M+H)+.

EXAMPLE 528

4-(3-METHOXY-3'-(TRIFLUOROMETHYL)-[1,1'-BIPHENYL]-4-YL)-N-(PYRIMIDIN-4-YL) QUINAZOLINE-7-SULFONAMIDE

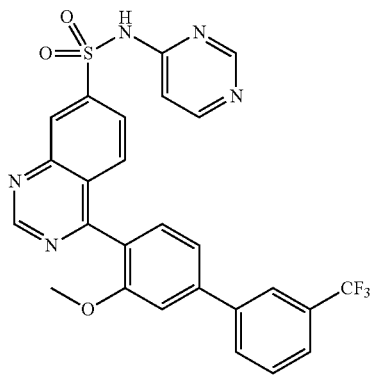 [SMILES: COc1cc(-c2cccc(C(F)(F)F)c2)ccc1-c1ncnc2cc(S(=O)(=O)Nc3ccncn3)ccc12]

The title compound was prepared in an analogous manner to that of EXAMPLE 525, except that 4-(4-chloro-2-methoxyphenyl)-N-(pyrimidin-4-yl)quinazoline-7-sulfonamide and (3-(trifluoromethyl)phenyl)boronic acid were used as the coupling partners to afford 4-(3-methoxy-3'-(trifluoromethyl)-[1,1'-biphenyl]-4-yl)-N-(pyrimidin-4-yl)quinazoline-7-sulfonamide as an off-white solid. ¹H NMR (400 MHz, DMSO-d₆) δ=9.48 (s, 1H), 8.58 (s, 1H), 8.50 (s, 1H), 8.23 (br. s., 1H), 8.19-8.11 (m, 2H), 8.10-8.01 (m, 1H), 7.89 (d, J=8.8 Hz, 1H), 7.85-7.72 (m, 2H), 7.62-7.53 (m, 3H), 7.01 (br. s., 1H), 3.82 (s, 6H). m/z (ESI) 538.2 (M+H)+.

EXAMPLE 529

4-(3'-FLUORO-3-METHOXY-[1,1'-BIPHENYL]-4-YL)-N-(1,3,4-THIADIAZOL-2-YL)QUINAZOLINE-7-SULFONAMIDE

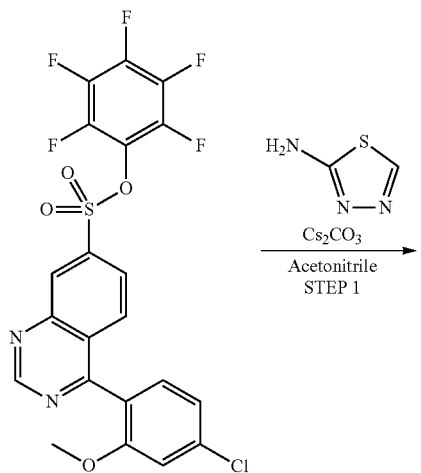

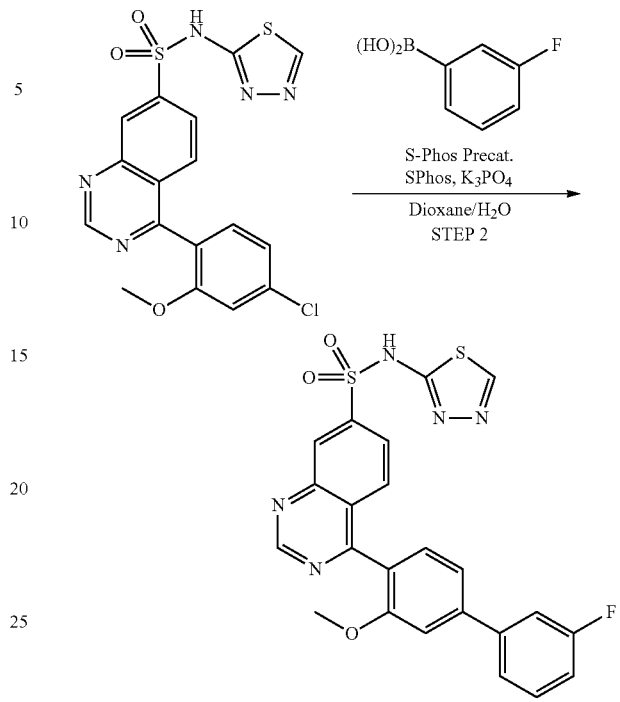

STEP 1: 4-(4-CHLORO-2-METHOXYPHENYL)-N-(1,3,4-THIADIAZOL-2-YL)QUINAZOLINE-7-SULFONAMIDE

The title compound was prepared in an analogous manner to that of EXAMPLE 521, except that perfluorophenyl 4-(4-chloro-2-methoxyphenyl)quinazoline-7-sulfonate and 1,3,4-thiadiazol-2-amine were used instead of perfluorophenyl 4-(2-chloro-3'-fluoro-5-methoxy-[1,1'-biphenyl]-4-yl) quinazoline-7-sulfonate and 1,2,4-thiadiazol-5-amine to afford 4-(4-chloro-2-methoxyphenyl)-N-(1,3,4-thiadiazol-2-yl)quinazoline-7-sulfonamide as a yellow solid. (ESI) 434.1 (M+H)+.

STEP 2: 4-(3'-FLUORO-3-METHOXY-[1,1'-BIPHENYL]-4-YL)-N-(1,3,4-THIADIAZOL-2-YL) QUINAZOLINE-7-SULFONAMIDE

The title compound was prepared in an analogous manner to that of EXAMPLE 525, except that 4-(4-chloro-2-methoxyphenyl)-N-(1,3,4-thiadiazol-2-yl)quinazoline-7-sulfonamide was used instead of 4-(4-chloro-2-methoxyphenyl)-N-(1,2,4-thiadiazol-5-yl)quinazoline-7-sulfonamide to afford 4-(3'-fluoro-3-methoxy-[1,1'-biphenyl]-4-yl)-N-(1,3,4-thiadiazol-2-yl)quinazoline-7-sulfonamide as an off-white solid. ¹H NMR (400 MHz, DMSO-d₆) δ=9.49 (s, 1H), 8.81 (s, 1H), 8.39 (d, J=1.7 Hz, 1H), 8.01-7.96 (m, 1H), 7.94-7.89 (m, 1H), 7.76-7.68 (m, 2H), 7.61-7.49 (m, 4H), 7.28 (dt, J=1.8, 8.6 Hz, 1H), 3.81 (s, 3H). m/z (ESI) 494.2 (M+H)$^+$.

EXAMPLE 530

4-(3',4'-DIFLUORO-3-METHOXY-[1,1'-BIPHENYL]-4-YL)-N-(1,3,4-THIADIAZOL-2-YL)QUINAZOLINE-7-SULFONAMIDE

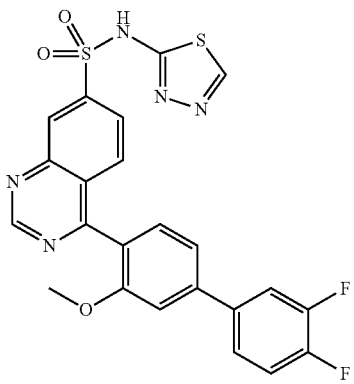 [SMILES: COc1cc(-c2ccc(F)c(F)c2)ccc1-c1ncnc2cc(S(=O)(=O)Nc3nncs3)ccc12]

The title compound was prepared in an analogous manner to that of EXAMPLE 529, except that (3,4-difluorophenyl)boronic acid was used instead of (3-fluorophenyl)boronic acid in STEP 2 to afford 4-(3',4'-difluoro-3-methoxy-[1,1'-biphenyl]-4-yl)-N-(1,3,4-thiadiazol-2-yl)quinazoline-7-sulfonamide as an off-white solid. $^1$H NMR (400 MHz, DMSO-d$_6$) δ=9.49 (s, 1H), 8.81 (s, 1H), 8.39 (s, 1H), 8.03-7.95 (m, 2H), 7.93-7.87 (m, 1H), 7.71 (br. s., 1H), 7.65-7.48 (m, 4H), 3.80 (s, 3H). m/z (ESI) 512.2 (M+H)$^+$.

EXAMPLE 531

4-(3',5'-DIFLUORO-3-METHOXY-[1,1'-BIPHENYL]-4-YL)-N-(1,3,4-THIADIAZOL-2-YL)QUINAZOLINE-7-SULFONAMIDE

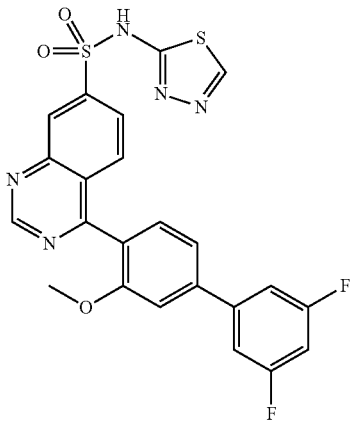 [SMILES: COc1cc(-c2cc(F)cc(F)c2)ccc1-c1ncnc2cc(S(=O)(=O)Nc3nncs3)ccc12]

=The title compound was prepared in an analogous manner to that of EXAMPLE 529, except that (3,5-difluorophenyl)boronic acid was used instead of (3-fluorophenyl)boronic acid in STEP 2 to afford 4-(3',5'-difluoro-3-methoxy-[1,1'-biphenyl]-4-yl)-N-(1,3,4-thiadiazol-2-yl)quinazoline-7-sulfonamide as an off-white solid. $^1$H NMR (400 MHz, DMSO-d$_6$) δ=9.48 (s, 1H), 8.79 (s, 1H), 8.38 (d, J=1.7 Hz, 1H), 8.00-7.95 (m, 1H), 7.91-7.86 (m, 1H), 7.64 (dd, J=2.2, 9.0 Hz, 2H), 7.58 (d, J=0.5 Hz, 1H), 7.55-7.53 (m, 2H), 7.31 (tt, J=2.3, 9.3 Hz, 1H), 3.80 (s, 3H). m/z (ESI) 512.2 (M+H)$^+$.

EXAMPLE 532

4-(4-CHLORO-2-METHYLPHENYL)-N-(1,2,4-THIADIAZOL-5-YL)QUINAZOLINE-7-SULFONAMIDE

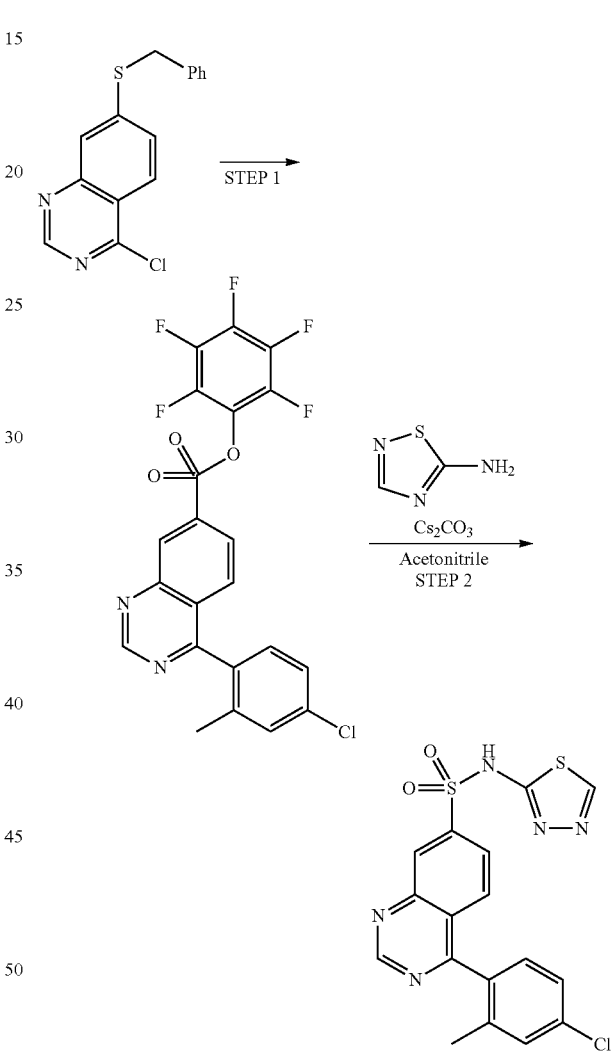

STEP 1: 4-(4-CHLORO-2-METHOXYPHENYL)-N-(1,3,4-THIADIAZOL-2-YL)QUINAZOLINE-7-SULFONAMIDE

The title compound was prepared in an analogous manner to that of INTERMEDIATE ZZZZZ, except that (4-chloro-2-methylphenyl)boronic acid was used instead of (2-chloro-3'-fluoro-5-methoxy-[1,1'-biphenyl]-4-yl)boronic acid in STEP 1 to afford perfluorophenyl 4-(4-chloro-2-methylphenyl)quinazoline-7-sulfonate as a yellow solid. (ESI) 501.0 (M+H)$^+$.

STEP 2: 4-(3'-FLUORO-3-METHOXY-[1,1'-BI-PHENYL]-4-YL)-N-(1,3,4-THIADIAZOL-2-YL)QUINAZOLINE-7-SULFONAMIDE

The title compound was prepared in an analogous manner to that of EXAMPLE 521, except that perfluorophenyl 4-(4-chloro-2-methylphenyl)quinazoline-7-sulfonate was used instead of perfluorophenyl 4-(2-chloro-3'-fluoro-5-methoxy-[1,1'-biphenyl]-4-yl)quinazoline-7-sulfonate to afford 4-(4-chloro-2-methylphenyl)-N-(1,2,4-thiadiazol-5-yl)quinazoline-7-sulfonamide as a white solid. $^1$H NMR (400 MHz, DMSO-$d_6$) δ=9.51 (s, 1H), 8.49 (s, 1H), 8.43 (d, J=1.7 Hz, 1H), 8.00 (dd, J=1.9, 8.7 Hz, 1H), 7.82 (dd, J=0.5, 8.8 Hz, 1H), 7.60-7.56 (m, 1H), 7.49-7.46 (m, 1H), 7.45-7.41 (m, 1H), 2.08 (s, 3H). m/z (ESI) 418.2 (M+H)$^+$.

EXAMPLE 533

4-(2-HYDROXY-4-(TRIFLUOROMETHYL)PHENYL)-N-(THIAZOL-2-YL)QUINAZOLINE-7-SULFONAMIDE

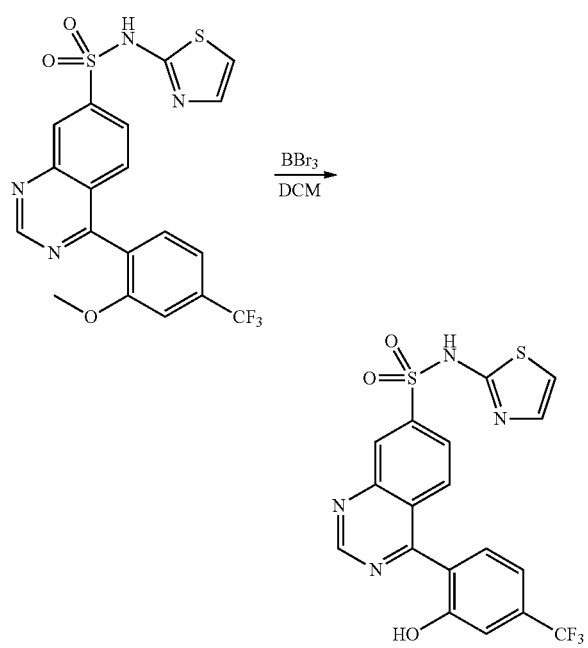

A vial was charged with 4-(2-methoxy-4-(trifluoromethyl)phenyl)-N-(thiazol-2-yl)quinazoline-7-sulfonamide (Example 261; 0.100 g, 0.214 mmol) and DCM (2.144 ml) to give a clear solution. Boron tribromide (0.101 ml, 1.072 mmol) was added in one portion at room temperature to give a dark red suspension. The mixture was stirred overnight. The reaction was diluted with ethyl acetate and washed with saturated sodium bicarbonate solution. The aqueous layer was extracted with ethyl acetate, and the combined organic layers were dried with sodium sulfate, filtered, and concentrated. The material was purified via column chromatography (RediSep Gold 40 g, gradient elution 0-10% MeOH:DCM) to afford 4-(2-hydroxy-4-(trifluoromethyl)phenyl)-N-(thiazol-2-yl)quinazoline-7-sulfonamide as a yellow solid. $^1$H NMR (400 MHz, DMSO-$d_6$) δ=13.02 (s, 1H), 10.65 (s, 1H), 9.49 (s, 1H), 8.41 (d, J=1.5 Hz, 1H), 8.02-7.96 (m, 1H), 7.94-7.88 (m, 1H), 7.63 (d, J=7.7 Hz, 1H), 7.38 (d, J=8.1 Hz, 1H), 7.34 (s, 1H), 7.31 (d, J=4.6 Hz, 1H), 6.90 (d, J=4.5 Hz, 1H). m/z (ESI) 453.2 (M+H)$^+$.

EXAMPLE 534

(R)-4-(2-(METHOXYMETHYL)PYRROLIDIN-1-YL)-N-(THIAZOL-2-YL)QUINAZOLINE-7-SULFONAMIDE

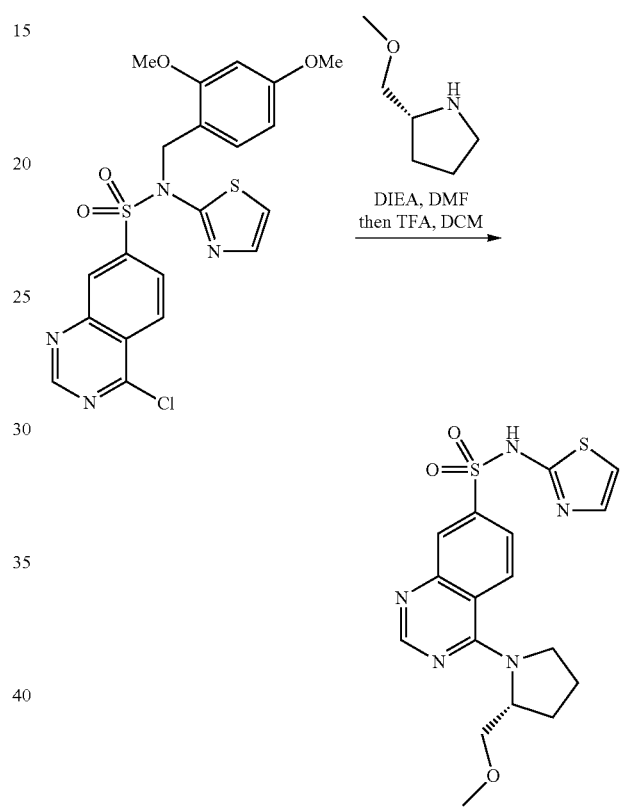

A vial was charged with 4-chloro-N-(2,4-dimethoxybenzyl)-N-(thiazol-2-yl)quinazoline-7-sulfonamide (Intermediate KKKK; 0.075 g, 0.157 mmol) and DMF (0.786 ml). (R)-2-(methoxymethyl)pyrrolidine (0.036 ml, 0.314 mmol) was added followed by Hunig's base (0.082 ml, 0.472 mmol). The reaction was stirred for 30 seconds at room temperature. TFA (0.2 ml, 2.60 mmol) was added and the reaction was stirred overnight at room temperature. The reaction was filtered through a frit, concentrated, and purified via Gilson HPLC (5-50% MeCN:H2O w/ 0.1% TFA modifier). The product fractions were passed through an Isolute SCX ion exchange column (pre-wetted with methanol). The column was flushed with methanol, then the product was liberated by flushing the column several times with 2.0 M ammonia in methanol. The product-containing filtrate was concentrated to afford (R)-4-(2-(methoxymethyl)pyrrolidin-1-yl)-N-(thiazol-2-yl)quinazoline-7-sulfonamide as an off-white solid. (ESI) 406.2 (M+H)⁺.

EXAMPLE 535

4-(2-ETHYLPIPERIDIN-1-YL)-N-(THIAZOL-2-YL)QUINAZOLINE-7-SULFONAMIDE

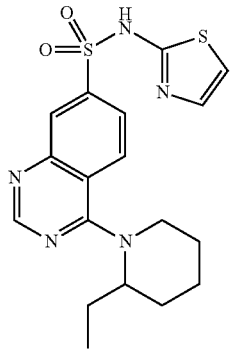 [SMILES: CCC1CCCCN1c1ncnc2cc(S(=O)(=O)Nc3nccs3)ccc12]

The title compound was prepared in an analogous manner to that of EXAMPLE 534, except that 2-ethylpiperidine was used instead of (R)-2-(methoxymethyl)pyrrolidine to afford 4-(2-ethylpiperidin-1-yl)-N-(thiazol-2-yl)quinazoline-7-sulfonamide as a light yellow solid. (ESI) 404.0 (M+H)⁺.

EXAMPLE 536

4-(2-(PYRIDIN-3-YL)PIPERIDIN-1-YL)-N-(THIAZOL-2-YL)QUINAZOLINE-7-SULFONAMIDE

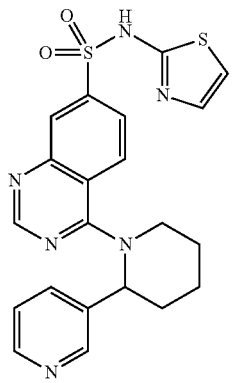 [SMILES: O=S(=O)(Nc1nccs1)c1ccc2c(N3CCCCC3c3cccnc3)ncnc2c1]

The title compound was prepared in an analogous manner to that of EXAMPLE 534, except that 3-(piperidin-2-yl)pyridine was used instead of (R)-2-(methoxymethyl)pyrrolidine to afford 4-(2-(pyridin-3-yl)piperidin-1-yl)-N-(thiazol-2-yl)quinazoline-7-sulfonamide as a light yellow solid. (ESI) 452.8 (M+H)⁺.

EXAMPLE 537

4-(2-PHENYLPYRROLIDIN-1-YL)-N-(THIAZOL-2-YL)QUINAZOLINE-7-SULFONAMIDE

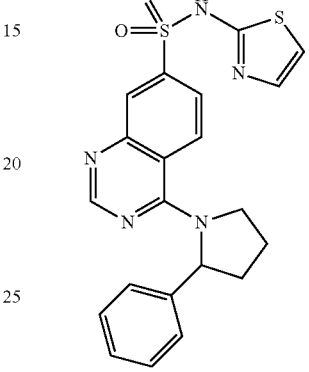

The title compound was prepared in an analogous manner to that of EXAMPLE 534, except that 2-phenylpyrrolidine was used instead of (R)-2-(methoxymethyl)pyrrolidine to afford 4-(2-phenylpyrrolidin-1-yl)-N-(thiazol-2-yl)quinazoline-7-sulfonamide as an off-white solid. (ESI) 438.2 (M+H)⁺.

EXAMPLE 538

4-(2-PHENYLPIPERIDIN-1-YL)-N-(THIAZOL-2-YL)QUINAZOLINE-7-SULFONAMIDE

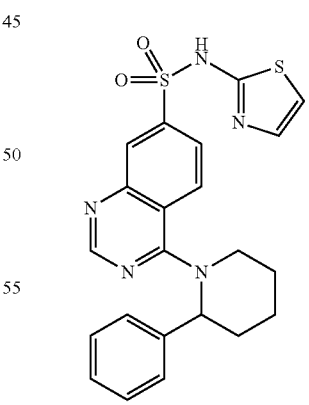

The title compound was prepared in an analogous manner to that of EXAMPLE 534, except that 2-phenylpiperidine hydrochloride was used instead of (R)-2-(methoxymethyl)

pyrrolidine to afford 4-(2-phenylpiperidin-1-yl)-N-(thiazol-2-yl)quinazoline-7-sulfonamide as a light yellow solid. (ESI) 452.2 (M+H)⁺.

EXAMPLE 539

4-(2-(PYRIDIN-4-YL)PYRROLIDIN-1-YL)-N-(1,2,4-THIADIAZOL-5-YL)QUINAZOLINE-7-SULFONAMIDE

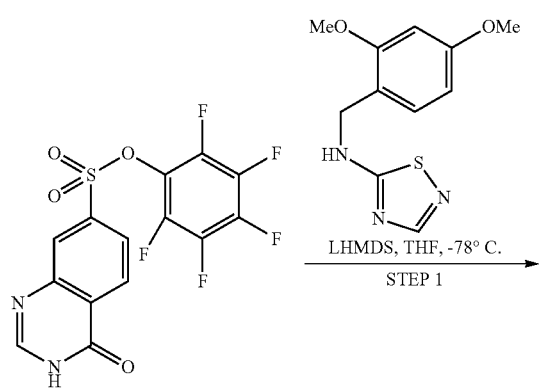

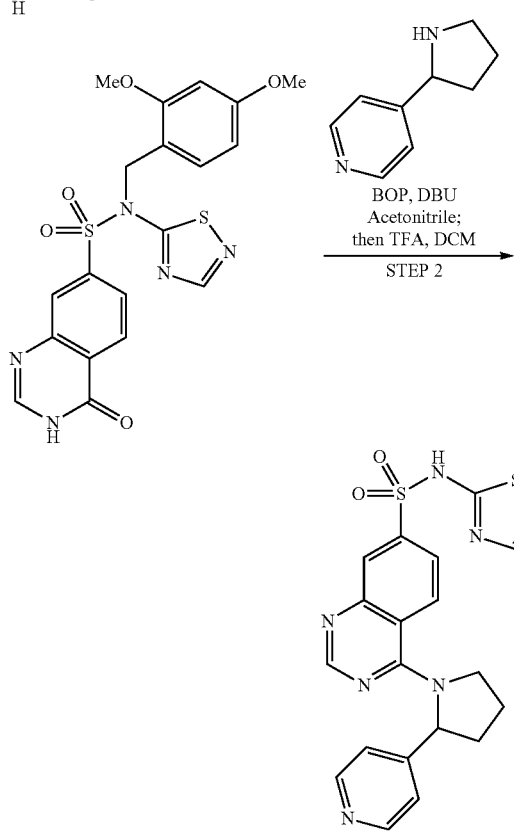

STEP 1: N-(2,4-DIMETHOXYBENZYL)-4-OXO-N-(1,2,4-THIADIAZOL-5-YL)-3,4-DIHYDROQUINAZOLINE-7-SULFONAMIDE

The title compound was prepared in an analogous manner to that of INTERMEDIATE KKKK, STEP 3, except that N-(2,4-dimethoxybenzyl)-1,2,4-thiadiazol-5-amine was used instead of N-(2,4-dimethoxybenzyl)thiazol-2-amine to afford 4 N-(2,4-dimethoxybenzyl)-4-oxo-N-(1,2,4-thiadiazol-5-yl)-3,4-dihydroquinazoline-7-sulfonamide as a white solid. (ESI) 482.1 (M+H)⁺.

STEP 2: 4-(2-(PYRIDIN-4-YL)PYRROLIDIN-1-YL)-N-(1,2,4-THIADIAZOL-5-YL)QUINAZOLINE-7-SULFONAMIDE

To a solution of N-(2,4-dimethoxybenzyl)-4-oxo-N-(1,2,4-thiadiazol-5-yl)-3,4-dihydroquinazoline-7-sulfonamide (0.611 g, 1.330 mmol) and BOP (0.765 g, 1.729 mmol) in acetonitrile (6.65 ml) was added DBU (0.301 ml, 1.995 mmol). The reaction was stirred for 10 minutes at 40° C. 4-(pyrrolidin-2-yl)pyridine (0.272 ml, 1.995 mmol) was added and the reaction was stirred for 8 hours at 40° C. 4-(pyrrolidin-2-yl)pyridine (0.272 ml, 1.995 mmol) was added and the reaction was stirred for four hours at 40° C. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 40 g, gradient elution 0-10% MeOH:DCM). The material was dissolved in DCM and TFA (0.2 ml, 2.60 mmol) was added. The reaction was stirred for one hour at room temperature. The reaction was concentrated and purified via column chromatography (RediSep Gold 12 g, gradient elution 0-10% MeOH:DCM) to afford 4-(2-(pyridin-4-yl)pyrrolidin-1-yl)-N-(1,2,4-thiadiazol-5-yl)quinazoline-7-sulfonamide as a light yellow solid. (ESI) 440.2 (M+H)⁺.

EXAMPLE 540

4-(2-CHLORO-4-(TRIFLUOROMETHYL)PHENYL)-N-(THIAZOL-2-YL)QUINAZOLINE-7-SULFONAMIDE

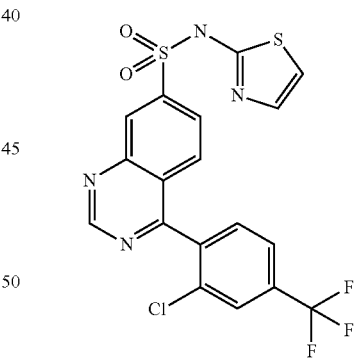

To a mixture of 4-chloro-N-(2,4-dimethoxybenzyl)-N-(thiazol-2-yl)quinazoline-7-sulfonamide (Intermediate KKKK; 0.07 g, 0.147 mmol), (2-chloro-4-(trifluoromethyl)phenyl)boronic acid (0.049 mg, 0.220 mmol) and potassium carbonate (0.101 g, 0.734 mmol) in Dioxane (Solvent Ratio: 3, Solvent Volume: 0.734 ml) and Water (Solvent Ratio: 1.000, Solvent Volume: 0.245 ml) was added Pd (PPh₃)₄ (17 mg, 0.015 mmol), degassed with nitrogen and irradiated in microwave at 100° C. for 1 h. The aqueous layer was discarded and the reaction mixture was filtered through SPE and concentrated. To this was then added DCM (1 ml) and TFA (1 ml) and the reaction was stirred for 2 h. The crude mixture was purified using reverse phase HPLC to obtain 4-(2-chloro-4-

(trifluoromethyl)phenyl)-N-(thiazol-2-yl)quinazoline-7-sulfonamide (16 mg, 23% yield) as white solid. m/z (ESI) 470.0 (M+H)$^+$.

EXAMPLE 541

4-(5-CHLORO-2-METHOXYPYRIDIN-3-YL)-N-(THIAZOL-2-YL)QUINAZOLINE-7-SULFONAMIDE

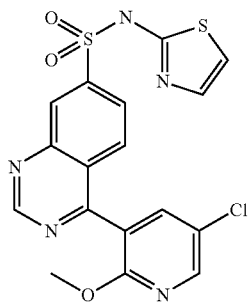 [SMILES: COc1ncc(Cl)cc1-c1ncnc2cc(S(=O)(=O)Nc3nccs3)ccc12]

The title compound was prepared in an analogous manner to that described for EXAMPLE 540, using (5-chloro-2-methoxypyridin-3-yl)boronic acid in place of (2-chloro-4-(trifluoromethyl)phenyl)boronic acid. m/z (ESI) 434.0 (M+H)$^+$.

EXAMPLE 542

4-(4-CYANO-2-METHYLPHENYL)-N-(THIAZOL-2-YL)QUINAZOLINE-7-SULFONAMIDE

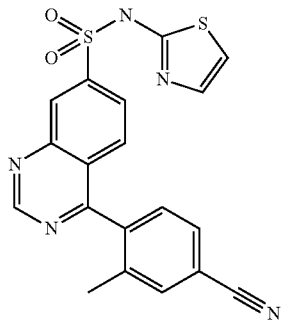 [SMILES: Cc1cc(C#N)ccc1-c1ncnc2cc(S(=O)(=O)Nc3nccs3)ccc12]

The title compound was prepared in an analogous manner to that described for Example EXAMPLE 540, using (4-cyano-2-methylphenyl)boronic acid in place of (2-chloro-4-(trifluoromethyl)phenyl)boronic acid. m/z (ESI) 408.0 (M+H)$^+$.

EXAMPLE 543

4-(2-METHOXY-4-(TRIFLUOROMETHYL)PHENYL)-2-OXO-N-(THIAZOL-2-YL)-1,2-DIHYDROQUINAZOLINE-7-SULFONAMIDE

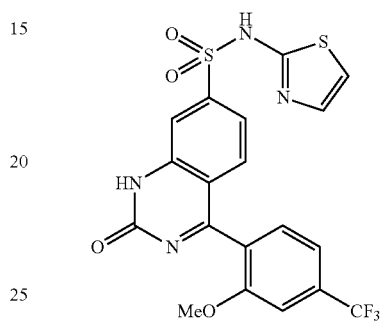

A solution of 2-methoxy-4-(2-methoxy-4-(trifluoromethyl)phenyl)-N-(thiazol-2-yl)quinazoline-7-sulfonamide (Example 511; 0.075 g, 0.151 mmol) in 5 mL MeOH was treated with acetyl chloride (0.215 ml, 3.02 mmol) and was allowed to stir overnight at room temperature. An additional portion of acetyl chloride (0.215 ml, 3.02 mmol) was added, and the reaction mixture was heated to 100° C. for one hour. LC/MS showed mostly product, so the reaction mixture was concentrated. Purification of the crude residue by reverse phase column chromatography [Puriflash C18, 30μ, 55 g, 10-100% (0.1% NH4OH in MeOH)/(0.1% NH4OH in water)] gave 4-(2-methoxy-4-(trifluoromethyl)phenyl)-2-oxo-N-(thiazol-2-yl)-1,2-dihydroquinazoline-7-sulfonamide (0.055 g, 0.114 mmol, 75% yield) as an off-white solid. $^1$H NMR (MeCN-d3) δ: 7.80 (s, 1H), 7.43-7.55 (m, 5H), 7.39 (d, J=8.4 Hz, 1H), 7.02 (d, J=4.7 Hz, 1H), 6.66 (d, J=4.7 Hz, 1H), 3.78 (s, 3H); (M+H)+=483.0.

EXAMPLE 544

4-(2-METHOXY-4-(TRIFLUOROMETHYL)PHENYL)-1-OXO-N-(THIAZOL-2-YL)-1,2-DIHYDROISOQUINOLINE-7-SULFONAMIDE

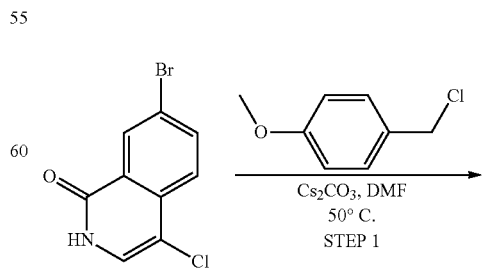

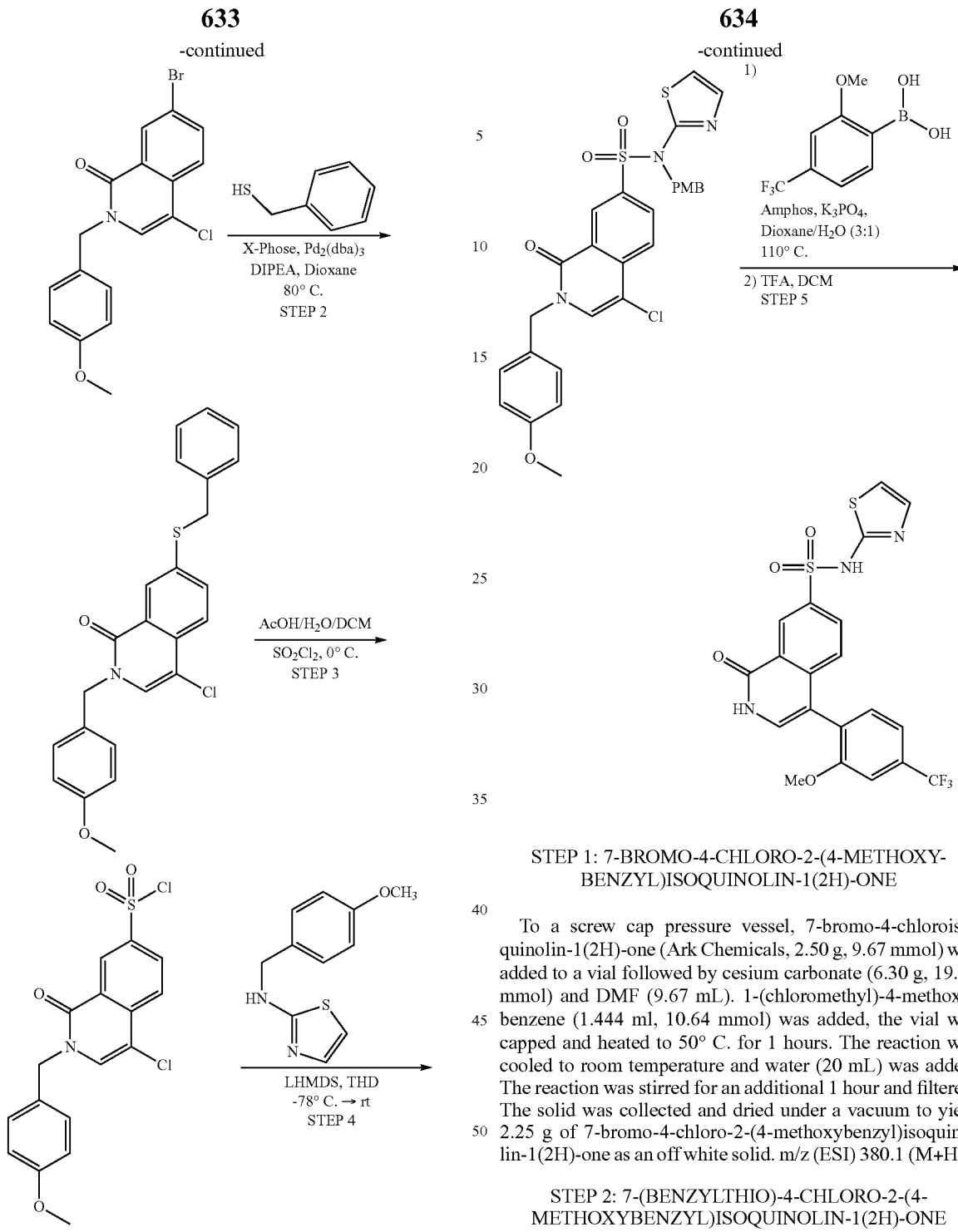

STEP 1: 7-BROMO-4-CHLORO-2-(4-METHOXY-BENZYL)ISOQUINOLIN-1(2H)-ONE

To a screw cap pressure vessel, 7-bromo-4-chloroisoquinolin-1(2H)-one (Ark Chemicals, 2.50 g, 9.67 mmol) was added to a vial followed by cesium carbonate (6.30 g, 19.34 mmol) and DMF (9.67 mL). 1-(chloromethyl)-4-methoxybenzene (1.444 ml, 10.64 mmol) was added, the vial was capped and heated to 50° C. for 1 hours. The reaction was cooled to room temperature and water (20 mL) was added. The reaction was stirred for an additional 1 hour and filtered. The solid was collected and dried under a vacuum to yield 2.25 g of 7-bromo-4-chloro-2-(4-methoxybenzyl)isoquinolin-1(2H)-one as an off white solid. m/z (ESI) 380.1 (M+H)+.

STEP 2: 7-(BENZYLTHIO)-4-CHLORO-2-(4-METHOXYBENZYL)ISOQUINOLIN-1(2H)-ONE

A screw cap vial was charged with 7-bromo-4-chloro-2-(4-methoxybenzyl)isoquinolin-1(2H)-one (3.6 g, 9.51 mmol), Xantphos (0.275 g, 0.475 mmol), tris(dibenzylideneacetone)dipalladium (0) (0.218 g, 0.238 mmol), 1,4-Dioxane (9.51 ml) and dipea (3.31 ml, 19.02 mmol). The vial was purged with Argon, sealed and heated to 80° C. for 10 minutes. The reaction was cooled to room temperature and benzyl mercaptan (1.18 ml, 9.98 mmol) was added and the reaction was continued heating at 80° C. for an additional 30 minutes. The reaction was cooled to room temperature, diluted with water and extracted with DCM (3×). The combined organics were washed with water and brine, dried over magnesium sulfate, filtered and concentrated. The resulting material was concentrated, dissolved in minimal DCM and purified via column chromatography (silica gel 40 g, gradient elution 0 to 50% EtOAc:Heptane) to afford 3.60 g of 7-(benzylthio)-4-chloro-2-(4-methoxybenzyl)isoquinolin-1(2H)-one. m/z (ESI) 442.1 (M+H)$^+$.

STEP 3: 4-CHLORO-2-(4-METHOXYBENZYL)-1-OXO-1,2-DIHYDROISOQUINOLINE-7-SULFONYL CHLORIDE

A round bottomed flask cooled to 0° C., was charged 7-(benzylthio)-4-chloro-2-(4-methoxybenzyl)isoquinolin-1 (2H)-one (0.400 g, 0.948 mmol), DCM (9.03 ml), Acetic Acid (0.226 ml), and Water (0.226 ml). After stirring for 5 minutes at 0° C., sulfuryl chloride (0.077 ml, 0.948 mmol) was added and stirring was continued for an additional 1 hour at 0° C. The reaction was concentrated, dissolved in minimal DCM and purified via column chromatography (silica gel 40 g, gradient elution 0 to 50% EtOAc:Heptane) to afford 0.342 g of 4-chloro-2-(4-methoxybenzyl)-1-oxo-1,2-dihydroisoquinoline-7-sulfonyl chloride. m/z (ESI) 399.2 (M+H)$^+$.

STEP 4: 4-CHLORO-N,2-BIS(4-METHOXYBENZYL)-1-OXO-N-(THIAZOL-2-YL)-1,2-DIHYDROISOQUINOLINE-7-SULFONAMIDE

A round-bottom flask was charged with N-(4-methoxybenzyl)thiazol-2-amine (0.213 g, 0.967 mmol) and THF (4.40 mL), and the vessel was cooled to −78° C. for 15 minutes. LHMDS (1.0 M in THF) (1.055 mL, 1.055 mmol) was then added drop wise over 1 minute. The reaction was stirred for 10 minutes, and then a solution of 4-chloro-2-(4-methoxybenzyl)-1-oxo-1,2-dihydroisoquinoline-7-sulfonyl chloride (0.350 g, 0.879 mmol) in THF (1.60 mL) was added drop wise. The bath was removed, and the resulting mixture was stirred for 45 minutes, until complete conversion to 4-chloro-N,2-bis(4-methoxybenzyl)-1-oxo-N-(thiazol-2-yl)-1,2-dihydroisoquinoline-7-sulfonamide. The reaction was diluted with saturated ammonium chloride (aq.) solution (30 mL), and was washed with ethyl acetate (20 mL×3). The organic layers were combined, dried over magnesium sulfate, filtered and concentrated. The resulting material was purified via silica gel chromatography (ISCO, 40 g), eluting with 0 to 100% ethyl acetate in heptanes to provide 0.250 g of 4-chloro-N,2-bis(4-methoxybenzyl)-1-oxo-N-(thiazol-2-yl)-1,2-dihydroisoquinoline-7-sulfonamide. m/z (ESI) 583.2 (M+H)$^+$.

STEP 5: 4-(2-METHOXY-4-(TRIFLUOROMETHYL)PHENYL)-1-OXO-N-(THIAZOL-2-YL)-1,2-DIHYDROISOQUINOLINE-7-SULFONAMIDE

A screw capped vial was charged with 2-methoxy-4-(trifluoromethyl)phenyl boronic acid (0.094 g, 0.429 mmol), 4-chloro-N,2-bis(4-methoxybenzyl)-1-oxo-N-(thiazol-2-yl)-1,2-dihydroisoquinoline-7-sulfonamide (0.250 g, 0.429 mmol), and potassium phosphate tribasic (0.273 ml, 1.288 mmol). Dioxane (1.72 ml) and Water (0.57 ml) were added and the vial was purged with Argon and Amphos (0.030 g, 0.043 mmol) was added. The vial was capped and heated to 110° C. After 4 hours, reaction was cooled to room temperature. The reaction was diluted with water (30 mL), and was washed with ethyl acetate (20 mL×3). The organic layers were combined, dried over magnesium sulfate, filtered and concentrated. The resulting material was purified via silica gel chromatography (ISCO, 40 g), eluting with 0 to 10% MeOH/DCM. The fractions were collected and the solvent was removed under reduced pressure. The resulting material was taken up in DCM (5 mL) and TFA (1 mL) was added. The reaction was stirred for 2 hours and then the solvent was removed under reduced pressure. The resulting material was taken up in DCM (30 mL) and washed with sodium bicarbonate (sat solution). The organic layer was dried over magnesium sulfate, filtered and concentrated. The resulting solid was triturated with diethyl ether (20 mL) and filtered. The solid was dried under reduced pressure to provide 0.052 g of 4-(2-methoxy-4-(trifluoromethyl)phenyl)-1-oxo-N-(thiazol-2-yl)-1,2-dihydroisoquinoline-7-sulfonamide as an off white solid. m/z (ESI) 482.1 (M+H)$^+$.

EXAMPLE 545

3-HYDROXY-4-(2-METHOXY-4-(TRIFLUOROMETHYL)PHENYL)-N-(THIAZOL-2-YL)ISOQUINOLINE-7-SULFONAMIDE

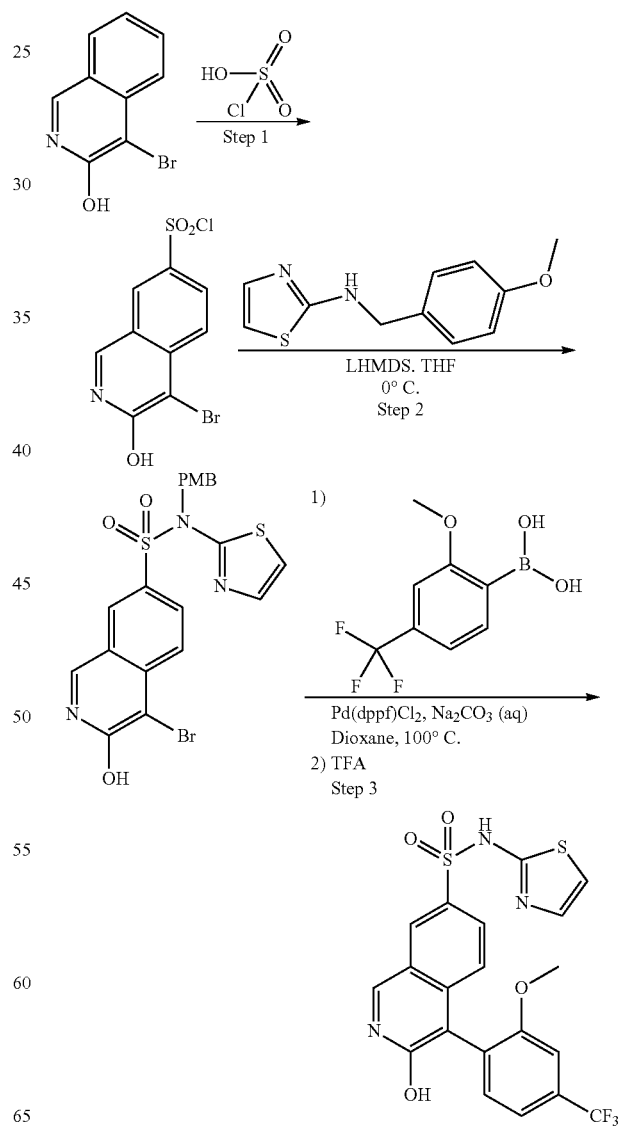

STEP 1: 4-BROMO-3-HYDROXYISOQUINOLINE-7-SULFONYL CHLORIDE

A vial charged with 4-bromoisoquinolin-3-ol (HDH Pharma, Inc; 1000 mg, 4.46 mmol) was added 10 mL of neat chlorosulfonic acid. The reaction mixture was heated to 100° C. overnight, at which time LCMS indicated clean conversion (with SM present) to a mixture of 4-bromo-3-hydroxyisoquinoline-7-sulfonyl chloride and 4-bromo-3-hydroxyisoquinoline-7-sulfonic acid. After cooling to rt, the reaction mixture was added to 20 ml of ice water, the suspension was filtered and the solid was washed with water providing 4-bromo-3-hydroxyisoquinoline-7-sulfonyl chloride as a solid which was air dried and was used without further purification. m/z (ESI) 323.8 (M+H)$^+$

STEP 2: 4-BROMO-3-HYDROXY-N-(4-METHOXYBENZYL)-N-(THIAZOL-2-YL)ISOQUINOLINE-7-SULFONAMIDE

To a vial charged with N-(4-methoxybenzyl)thiazol-2-amine (655 mg, 2.97 mmol) was added THF (6940 µl) and the mixture cooled in an ice water bath prior to the addition of lithium bis(trimethylsilyl)amide, 1.0M solution in tetrahydrofuran (3185 µl, 3.19 mmol), faster than drop wise. After 15 mins of stirring, a solution of 4-bromo-3-hydroxyisoquinoline-7-sulfonyl chloride (685 mg, 2.124 mmol) in THF (4 mL) was added drop wise (with 1 mL THF wash). The mixture was stirred for 1.5 hr (ice melt), LCMS indicated complete conversion to the desired product. The solution was added to ice, diluted with EtOAc and extracted with water and EtOAc. The combined organics were dried with $Na_2SO_4$, filtered, and dried under reduced pressure. The crude material was absorbed onto a plug of silica gel and purified by chromatography through a Redi-Sep pre-packed silica gel column (40 g), eluting with a gradient of 0% to 60% EtOAc in hexane, to provide 4-bromo-3-hydroxy-N-(4-methoxybenzyl)-N-(thiazol-2-yl)isoquinoline-7-sulfonamide. m/z (ESI) 506.0 (M+H)$^+$

Step 3: 3-HYDROXY-4-(2-METHOXY-4-(TRIFLUOROMETHYL)PHENYL)-N-(THIAZOL-2-YL)ISOQUINOLINE-7-SULFONAMIDE A solution of 1,1'-bis(diphenylphosphino)ferrocene-palladium(ii) dichloride dichloromethane adduct (28.2 mg, 0.035 mmol), 2-methoxy-4-(trifluoromethyl)phenylboronic acid (76 mg, 0.346 mmol), 4-bromo-3-hydroxy-N-(4-methoxybenzyl)-N-(thiazol-2-yl)isoquinoline-7-sulfonamide (175 mg, 0.346 mmol) and sodium carbonate (2M, 346 µl, 0.691 mmol) in Dioxane was heated to 100° C. in a microwave for 1 h. LC/MS showed mostly product, after cooling to rt, the crude material was purified by reverse-phase preparative HPLC using 0.1% TFA in $CH_3CN/H_2O$, gradient 10% to 90% over 20 min. The pure fractions were combined and concentrated in vacuo. The residue was dissolved in DCM (2 ml) and TFA (0.2 ml). The mixture was shaken at room temperature at 2 hr. LC-MS indicated product as the major species. The crude material was absorbed onto a plug of silica gel and purified by chromatography through a Redi-Sep pre-packed silica gel column (4 g), eluting with a gradient of 0% to 100% EtOAc in hexane and then washed with pure methanol, to provide 3-hydroxy-4-(2-methoxy-4-(trifluoromethyl)phenyl)-N-(thiazol-2-yl)isoquinoline-7-sulfonamide as yellow solid. m/z (ESI) 482.0 [M+1].

Nav 1.7 or Nav 1.5 IWQ In Vitro Assay

293 Cells stably transfected with either Nav 1.7 or Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the $26^{th}$ pulse to −20 mV was subtracted from the peak current evoked by the $26^{th}$ pulse to −20 mV to correct for leak current. Percent block was calculated for each concentration in duplicate, and $IC_{50}$ curves were fitted to percent block as a function of concentration.

Nav 1.7 In Vitro PX Assay 293 cells stably transfected with human Nav1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and $IC_{50}$ curves were fitted to percent inhibition as a function of concentration.

Nav 1.5 In Vitro PX Assay 293 cells stably transfected with Nav 1.5 were recorded in whole cell voltage clamp mode with the PatchXpress automated electrophysiology system according the manufacturer's specifications (Molecular Devices, LLC, Sunnyvale, Calif.). Cells were held at a holding potential of −50 mV to inactivate sodium channels. To elicit sodium currents the voltage was changed to −120 mV to recover a portion of the channels, followed by delivery of test pulses of 20 msec duration to 0 mV, at 0.1 Hz. A single concentration of test compound was applied to cells for a duration of 5 minutes. Peak sodium current was measured at the end of the compound addition period to determine percent inhibition. A minimum of two cells were tested per concentration. $IC_{50}$ curves were fitted to percent inhibition as a function of concentration.

Data for compounds of the present invention are shown in the table below.

| Exmple No. | Nav 1.7 IWQ $IC_{50}$ (µM) | Nav 1.5 PX $IC_{50}$ (µM) |
|---|---|---|
| 1 | .03 | >30.0 |
| 2 | .03 | >30.0 |
| 3 | .09 | 24.2 |
| 4 | .90 | 10.9 |
| 5 | .17 | 23.8 |
| 6 | .34 | |
| 7 | 7.76 | |
| 8 | .20 | 21.3 |
| 9 | .46 | 23.8 |
| 10 | .05 | 6.68 |

| Example No. | Nav 1.7 IWQ IC$_{50}$ (μM) | Nav 1.5 PX IC$_{50}$ (μM) |
|---|---|---|
| 11 | .08 | 5.07 |
| 12 | .01 | 11.6 |
| 13 | 3.56 | |
| 14 (isomer 2) | 1.8 | >30.0 |
| 14 (isomer 1) | .52 | |
| 14 (mixture of isomers) | .30 | |
| 15 | 1.29 | |
| 16 | 2.37 | |
| 17 | 4.56 | |
| 18 | .71 | |
| 19 | 1.18 | |
| 20 | 3.14 | |
| 21 | .02 | |
| 22 | .04 | >30.0 |
| 23 | .11 | 20.7 |
| 24 | .03 | |
| 25 | .05 | >30.0 |
| 26 | .02 | >30.0 |
| 27 | .02 | >30.0 |
| 28 | .05 | >30.0 |
| 29 | .05 | >30.0 |
| 30 | .004 | 19.9 |
| 31 | .11 | >30.0 |
| 32 | .17 | >30.0 |
| 33 | .19 | 9.58 |
| 34 | .19 | 5.96 |
| 35 | .21 | 9.99 |
| 36 | .21 | 15.1 |
| 37 | .43 | 14.4 |
| 38 | .49 | 23.1 |
| 39 | 1.54 | 7.77 |
| 40 | 1.97 | >30.0 |
| 41 | .29 | |
| 42 | .05 | |
| 43 | 4.89 | |
| 44 | 22.1 @ 4.9* | |
| 45 | .225 | |
| 46 | .036 | |
| 47 | .27 | 5.82 |
| 48 | .03 | |
| 49 | 4.87 | |
| 50 | .03 | >30.0 |
| 51 | .11 | >30.0 |
| 52 | 16% @ 4.9* | |
| 53 | .07 | >30.0 |
| 54 | .04 | >30.0 |
| 55 | .01 | >30.0 |
| 56 | .06 | |
| 57 | .22 | |
| 58 | .60 | |
| 59 | .06 | |
| 60 | 1.56 | |
| 61 | .07 | |
| 62 | .09 | |
| 63 | .33 | |
| 64 | .77 | |
| 65 | .32 | |
| 66 | .12 | |
| 67 | .08 | |
| 68 | 1.52 | |
| 69 | .06 | |
| 70 | .015 | |
| 71 | .02 | |
| 72 | .06 | |
| 73 | 44.8% @ 4.9* | |
| 74 | .08 | |
| 75 | .10 | |
| 76 | .07 | |
| 77 | .07 | |
| 78 | .09 | |
| 79 | .90 | |
| 80 | 1.20 | |
| 81 | .04 | |
| 82 | .07 | |
| 83 | .01 | |

| Example No. | Nav1.7 IWQ IC$_{50}$ IP (μM) | Nav1.7 Single Point Data IWQ (at 4.9 μM) (%) | Nav1.7 PX IC$_{50}$ IP (μM) | Nav1.5 PX IC$_{50}$ (μM) |
|---|---|---|---|---|
| 84 | 0.11 | | | 0.588 |
| 85 | 0.01 | | | 0.173 |
| 86 | 0.00 | | | 0.0627 |
| 87 | 0.46 | | | 1.32 |
| 88 | 0.02 | | | 0.238 |
| 89 | 0.29 | | | 2.33 |
| 90 | 0.00 | | | 0.0393 |
| 91 | 0.27 | | | 1.47 |
| 92 | 3.90 | | | 10.5 |
| 93 | 7.97 | | | |
| 94 | 0.01 | | | 0.0572 |
| 95 | 0.54 | | | 7.96 |
| 96 | 0.08 | | | 0.323 |
| 97 | 0.46 | | | 2.22 |
| 98 | 2.22 | | | 13 |
| 99 | 1.18 | | | 4.45 |
| 100 | 0.29 | | | 1.46 |
| 101 | 1.16 | | | 11.8 |
| 102 | 0.11 | | | 1.54 |
| 103 | 1.58 | | | 14.5 |
| 104 | 0.08 | | | 1.99 |
| 105 | 2.48 | | | 7.84 |
| 106 | 1.60 | | | 3.84 |
| 107 | 0.33 | | | 3.32 |
| 108 | 0.17 | | | 0.21 |
| 109 | 0.15 | | | 0.282 |
| 110 | 0.04 | | | 0.14 |
| 111 | 0.06 | | | 0.332 |
| 112 | 0.10 | | | 0.459 |
| 113 | 0.08 | | | 0.118 |
| 114 | 0.82 | | | 11.3 |
| 115 | 0.18 | | | 0.692 |
| 116 | 0.07 | | | 0.623 |
| 117 | 0.18 | | | 2.88 |
| 118 | 0.03 | | | 0.652 |
| 119 | 0.02 | | | 0.179 |
| 120 | 0.01 | | | 0.125 |
| 121 | 0.03 | | | 0.864 |
| 122 | 0.04 | | | 0.492 |
| 123 | 0.05 | | | 0.516 |
| 124 | 0.06 | | | 0.502 |
| 125 | 0.04 | | | 0.631 |
| 126 | 0.13 | | | 2.66 |
| 127 | | | | 2.22 |
| 128 | 3.96 | | | |
| 129 | | | | 8 |
| 130 | 0.50 | | | 4.51 |
| 131 | 0.81 | | | 4.19 |
| 132 | 0.87 | | | 7.9 |
| 133 | 1.83 | | | 34.1 |
| 132 | 3.07 | | | >30.0 |
| 135 | 3.30 | | | |
| 136 | 3.59 | | | >30.0 |
| 137 | 3.91 | | | >30.0 |
| 138 | 3.96 | | | |
| 139 | 0.01 | | | 0.415 |
| 140 | 0.09 | | | 10.7 |
| 141 | 2.30 | | | 29.6 |
| 142 | 0.06 | | | 1.79 |
| 143 | 0.46 | | | 18.3 |
| 144 | 6.73 | | | |
| 145 | 0.92 | | | 16.4 |
| 146 | 0.03 | | | 1.37 |
| 147 | 0.13 | | | 5.82 |
| 148 | 0.08 | | | 2.41 |
| 149 | 0.06 | | | 2.4 |
| 150 | 0.12 | | | 7.19 |

| Exmple No. | Nav 1.7 IWQ IC$_{50}$ (μM) | Nav 1.5 PX IC$_{50}$ (μM) | | Exmple No. | Nav 1.7 IWQ IC$_{50}$ (μM) | Nav 1.5 PX IC$_{50}$ (μM) |
|---|---|---|---|---|---|---|
| 151 | 0.03 | 1.02 | | 227 | 0.11 | 2.27 |
| 152 | 6.81 | | | 228 | 0.11 | 1.52 |
| 153 | 0.02 | 0.914 | | 229 | 0.01 | 0.42 |
| 154 | 0.04 | 2.18 | | 230 | 0.03 | 0.59 |
| 155 | 0.03 | 1.13 | | 231 | 0.04 | 0.27 |
| 156 | 0.22 | 2.85 | | 232 | | 0.38 20.4 |
| 157 | 6.39 | | | 233 | | 0.51 |
| 158 | 0.18 | 5.03 | | 234 | | 0.98 |
| 159 | 4.83 | | | 235 | 0.05 | 0.15 |
| 160 | 0.02 | | | 236 | 0.13 | 0.43 |
| 161 | 0.02 | 0.393 | | 237 | 0.74 | 1.23 |
| 162 | 4.12 | | | 238 | 0.14 | 0.77 |
| 163 | 0.57 | 10.8 | | 239 | 1.45 | 4.59 |
| 164 | 6.61 | | | 240 | 0.19 | 0.39 |
| 165 | 5.43 | >30.0 | | 241 | 0.24 | 0.48 |
| 166 | 1.39 | | | 242 | 2.50 | 3.89 |
| 167 | 0.05 | 4.26 | | 243 | 0.78 | 10.70 |
| 168 | 0.03 | 1.6 | | 244 | 1.17 | 11.30 |
| 169 | 5.17 | | | 245 | 2.22 | 30.80 |
| 170 | 2.65 | | | 246 | 2.15 | 27.40 |
| 171 | 0.73 | 23 | | 247 | >10.0 | 10.90 |
| 172 | 0.27 | 16.6 | | 248 | | 0.91 |
| 173 | 0.43 | 8.75 | | 249 | 0.03 | 0.29 |
| 174 | 0.64 | 29.8 | | 250 | 0.05 | 1.15 |
| 175 | | 0.393 >30.0 | | 251 | 0.08 | 1.99 |
| 176 | 0.03 | 0.507 | | 252 | 0.12 | 1.92 |
| 177 | | 0.5 >30.0 | | 253 | 0.02 | 0.34 |
| 178 | | 1.85 | | 254 | 0.26 | 5.26 |
| 179 | | 1.3 | | 255 | 0.02 | 0.15 |
| 180 | 0.04 | 0.439 | | 256 | 0.07 | 0.84 |
| 181 | 0.11 | 1.56 | | 257 | 0.26 | 1.23 |
| 182 | 4.26 | 11.7 | | 258 | 0.26 | 1.05 |
| 183 | 0.67 | 5.87 | | 259 | | 0.32 >30.0 |
| 184 | 0.32 | 0.912 | | 260 | | 1.27 |
| 185 | 0.27 | 2.7 | | 261 | 0.01 | 0.20 >30.0 |
| 186 | 2.34 | | | 262 | 0.04 | 0.96 |
| 186 | 0.37 | 3.97 | | 263 | 0.01 | 0.28 |
| 188 | 0.20 | 3.54 | | 264 | 0.17 | 1.87 |
| 189 | 0.46 | 5.96 | | 265 | 0.02 | 0.15 |
| 190 | | 13.5 | | 266 | 0.01 | 0.28 |
| 191 | | 13.9 | | 267 | 0.01 | 0.30 |
| 192 | | 0.33 >30.0 | | 268 | 1.10 | 2.52 |
| 193 | 4.98 | | | 269 | 0.02 | 0.47 |
| 194 | 0.01 | 0.255 | | 270 | | 0.15 7.44 |
| 195 | 0.01 | 0.134 >30.0 | | 271 | | 0.45 >30.0 |
| 196 | 0.01 | 0.298 | | 272 | | 0.46 >30.0 |
| 197 | 2.93 | 3.06 | | 273 | 0.02 | 0.50 |
| 198 | 0.04 | 0.422 | | 274 | 0.03 | 0.49 |
| 199 | 0.02 | 0.156 >30.0 | | 275 | 0.04 | 0.42 |
| 200 | 0.03 | 0.424 | | 276 | 0.05 | 0.35 12.3 |
| 201 | 0.02 | 0.315 | | 277 | 0.07 | 0.34 |
| 202 | 0.34 | 0.508 | | 278 | 0.22 | 2.02 |
| 203 | 0.31 | 3.29 | | 279 | | 0.58 |
| 204 | 0.03 | 0.614 | | 280 | | 4.45 |
| 205 | 0.02 | 0.47 | | 281 | | 1.93 |
| 206 | 0.11 | 4.42 | | 282 | | 3.29 |
| 207 | 2.10 | 7.29 | | 283 | 0.01 | 0.21 |
| 208 | 2.14 | 27.5 | | 284 | 0.06 | 0.32 |
| 209 | 0.06 | 0.385 | | 285 | 0.04 | 0.58 |
| 210 | 0.14 | 0.888 | | 286 | | 4.22 |
| 211 | 0.01 | 0.251 | | 287 | | 4.15 |
| 212 | 0.03 | 0.269 | | 288 | 0.04 | 0.60 |
| 213 | 0.01 | 0.36 | | 289 | | 0.34 >30.0 |
| 214 | 0.02 | 0.211 | | 290 | | 0.60 |
| 215 | 0.02 | 0.086 | | 291 | 0.16 | 2.53 |
| 216 | 0.04 | 0.559 | | 292 | 3.94 | |
| 217 | 0.04 | 0.692 | | 293 | | 0.15 >30.0 |
| 218 | 0.07 | 4.63 | | 294 | | 2.50 |
| 219 | 0.17 | 0.796 | | 295 | >10.0 | 36 |
| 220 | 0.06 | 0.45 | | 296 | >10.0 | 23 |
| 221 | 0.11 | 1.53 | | 297 | >10.0 | 38 |
| 222 | 0.02 | 0.905 | | 298 | >10.0 | 29 |
| 223 | 1.10 | 6.52 | | 299 | >10.0 | 49 |
| 224 | 0.02 | 0.313 | | 300 | >10.0 | 25 |
| 225 | 0.03 | 0.741 | | 301 | >10.0 | 40 |
| 226 | 0.09 | 0.60 | | 302 | >10.0 | 20 |

| Exmple No. | Nav 1.7 IWQ IC$_{50}$ (μM) | Nav 1.5 PX IC$_{50}$ (μM) |
|---|---|---|
| 303 | >10.0 | 40 |
| 304 | >10.0 | 32 |
| 305 | >10.0 | 24 |
| 306 | >10.0 | 35 |
| 307 | >10.0 | 40 |
| 308 | >10.0 | 45 |
| 309 | >10.0 | 27 |
| 310 | >10.0 | 46 |
| 311 | >10.0 | 29 |
| 312 | >10.0 | 47 |
| 313 | >10.0 | 39 |
| 314 | >10.0 | 39 |
| 315 | >10.0 | 37 |
| 316 | >10.0 | 26 |
| 317 | >10.0 | 30 |
| 318 | >10.0 | 32 | 37.40 |
| 319 | 0.407 | 2.79 |
| 320 | 0.155 | >30.0[2] |
| 321 | 0.251 | >30.0 |
| 322 | 0.333 | >30.0[2] |
| 323 | 2.3 | |
| 324 | 0.662 | >30.0 |
| 325 | 5.11 | |
| 326 | 0.66 | 2.5 |
| 327 | 2.34 | |
| 328 | 6.87 | |
| 329 | 0.581 | >30.0 |
| 330 | 0.118 | >30.0[2] |
| 331 | 0.023 | |
| 332 | 0.028 | 20.7 |
| 333 | 0.075 | 20.3 |
| 334 | 0.109 | |
| 335 | 0.052 | >30.0 |
| 336 | 0.156 | >30.0 |
| 337 | 0.388 | >30.0 |
| 338 | 0.029 | >30.0 |
| 339 | 0.031 | >30.0 |
| 340 | 0.056 | >30.0 |
| 341 | 0.069 | >30.0 |
| 342 | 0.122 | >30.0 |
| 343 | 0.145 | >30.0 |
| 344 | 0.034 | >30.0 |
| 345 | 0.075 | >30.0 |
| 346 | 0.132 | >30.0 |
| 347 | 0.040 | >30.0 |
| 348 | 0.102 | >30.0 |
| 349 | 0.038 | >30.0 |
| 350 | 0.161 | >30.0 |
| 351 | 0.076 | 26.6 |
| 352 | 1.87 | |
| 353 | 5.17 | |
| 354 | 0.11 | >30.0[2] |
| 355 | 0.048 | >30.0 |
| 356 | 27% | |
| 357 | 1.85 | |
| 358 | 0.394 | >30.0 |
| 359 | 2.38 | |
| 360 | 0.513 | >30.0 |
| 361 | 0.463 | >30.0 |
| 362 | 1.07 | |
| 363 | 0.54 | >30.0 |
| 364 | 0.036 | >30.0 |
| 365 | 0.041 | >30.0 |
| 366 | 0.048 | >30.0 |
| 367 | 1.42 | |
| 368 | 0.122 | >30.0 |
| 369 | 0.058 | >30.0 |
| 370 | 0.813 | >30.0 |
| 371 | 0.545 | >30.0 |
| 372 | 16.6 | |
| 373 | 0.153 | >30.0 |
| 374 | 0.309 | >30.0[2] |
| 375 | 0.544 | >30.0[2] |
| 376 | 2.94 | |
| 377 | 24.5 | |
| 378 | 2.42 | |
| 379 | | 5.16 |
| 380 | 40% | |
| 381 | 26.5% | |
| 382 | 27.8% | |
| 383 | 30.2% | |
| 384 | | 6.71 |
| 385 | 25.3% | |
| 386 | | 1.39 |
| 387 | 20.6% | |
| 388 | | 1.75 |
| 389 | | 2.79 |
| 390 | 19.8% | |
| 391 | 34.8% | |
| 392 | 0.111 | >30.0 |
| 393 | 0.304 | >30.0[2] |
| 394 | 0.338 | >30.0[2] |
| 395 | 0.761 | |
| 396 | 1.04 | |
| 397 | 3.52 | |
| 398 | 0.197 | >30.0 |
| 399 | 0.682 | |
| 400 | 1.33 | |
| 401 | 4.5 | |
| 402 | 36.4% | |
| 403 | 33.5% | |
| 404 | 0.428 | |
| 405 | 0.442 | >30.0 |
| 406 | 0.456 | >30.0[2] |
| 407 | 4.97 | |
| 408 | 0.986 | |
| 409 | 0.69 | |
| 410 | 1.67 | |
| 411 | 0.685 | |
| 412 | 1.03 | |
| 413 | 0.83 | |
| 414 | 7.11 | |
| 415 | 1.07 | |
| 416 | 1.22 | |
| 417 | 1.23 | |
| 418 | 2.13 | |
| 419 | 0.272 | >30.0 |
| 420 | 0.367 | |
| 421 | 0.786 | >30.0 |
| 422 | 0.835 | |
| 423 | 1.34 | |
| 424 | 1.66 | |
| 425 | 2.21 | |
| 426 | 2.49 | |
| 427 | 4.42 | |
| 428 | 4.57 | |
| 429 | 54.7 | >30.0 |
| 430 | 35.4% | |
| 431 | 20.2% | |
| 432 | 34.6% | |
| 433 | 21.2% | |
| 434 | 20.0% | |
| 439 | | 2.11 |
| 440 | | 4.1 |
| 441 | 0.077 | >30.0 |
| 442 | 0.087 | >30.0 |
| 443 | 0.28 | >30.0 |
| 444 | 0.185 | >30.0 |
| 445 | 0.218 | >30.0 |
| 446 | 0.152 | >30.0 |
| 447 | 0.237 | >30.0 |
| 448 | 0.038 | >30.0 |
| 449 | 0.034 | >30.0 |
| 450 | | 5.37 |
| 451 | 27.5% | |
| 452 | 0.284 | >30.0 |
| 453 | | 4.88 |
| 454 | <20% | |
| 455 | | 0.904 |
| 456 | | 4.7 |
| 457 | | 0.828 |
| 458 | 24.7% | |

-continued

| Exmple No. | Nav 1.7 IWQ IC$_{50}$ (μM) | Nav 1.5 PX IC$_{50}$ (μM) |
|---|---|---|
| 459 | | 0.532 >30.0 |
| 460 | | 0.106 >30.0 |
| 461 | | 1.78 |
| 462 | | 0.203 >30.0 |
| 463 | 41.1% | |
| 464 | | 0.38 >30.0 |
| 465 | | 0.567 |
| 466 | | 0.227 >30.0 |
| 467 | | 0.204 >30.0 |
| 468 | | 0.359 >30.0 |
| 469 | | 0.17 >30.0 |
| 470 | | 0.18 >30.0 |
| 471 | | 0.056 >30.0 |
| 472 | | 0.063 >30.0 |
| 473 | | 1.36 |
| 474 | | 2.61 |
| 475 | | 1.88 |
| 476 | | 2.89 |
| 477 | | 4.04 |
| 478 | | 3.64 |
| 479 | | |
| 480 | | 2.77 |
| 481 | | 0.788 |
| 482 | | 0.778 |
| 483 | | 1.4 |
| 484 | | 0.177 >30.0 |
| 485 | | 0.128 >30.0 |
| 486 | | 0.338 >30.0 |
| 487 | | 0.287 >30.0 |
| 488 | | 0.099 >30.0 |
| 489 | | 1.83 |
| 490 | | 0.062 >30.0 |
| 491 | | 0.101 >30.0 |
| 492 | | 0.069 >30.0 |
| 493 | | 0.086 >30.0 |
| 494 | | 0.078 >30.0 |
| 495 | | 0.095 19.1 |
| 496 | 24.7% | |
| 497 | | 0.786 >30.0 |
| 498 | | 0.76 >30.0 |
| 499 | | 0.83 |
| 501 | | 0.124 >30.0 |
| 504 | | 1.59 |
| 505 | | 0.258 >30.0 |
| 506 | | 3 |
| 507 | | 0.177 >30.0 |
| 508 | | 1.3 |
| 509 | | 0.218 >30.0 |
| 510 | | 0.464 >30.0 |
| 511 | | 0.257 >30.0 |
| 512 | | 0.234 >30.0[2] |
| 513 | | 0.783 >30.0 |
| 514 | | 0.383 >30.0[2] |
| 515 | | 0.478 >30.0[2] |
| 516 | | 1.05 |
| 517 | | 1.28 |
| 518 | | 2.6 |
| 519 | <20% | |
| 520 | <20% | |
| 521 | | 0.019 4.75 |
| 522 | | 0.034 >30.0 |
| 523 | | 0.065 6.59 |
| 524 | | 0.1 >30.0 |
| 525 | | 0.058 >30.0 |
| 526 | | 2.3 |
| 527 | | 0.252 >30.0 |
| 528 | | 0.058 >30.0 |
| 529 | | 0.258 >30.0 |
| 530 | | 0.233 >30.0 |
| 531 | | 0.231 >30.0 |
| 532 | | 0.996 >30.0 |
| 533 | | 4.09 |
| 534 | | 29.3 |
| 535 | 26% | |
| 536 | 28.3% | |
| 537 | 41.2% | |

-continued

| Exmple No. | Nav 1.7 IWQ IC$_{50}$ (μM) | Nav 1.5 PX IC$_{50}$ (μM) |
|---|---|---|
| 538 | 31.2% | |
| 539 | 20.3% | |
| 540 | | 0.971 |
| 541 | | 1.8 |
| 542 | | 5.02 |
| 543 | | 4.56 |
| 544 | | 0.709 |
| 545 | 23.7% | |

*percent inhibition at 4.9 μM;

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 μL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula: (−(Individual score−Vehicle average score)/Vehicle average score)) *100=% MPE Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then retuned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

What is claimed is:

1. A compound of Formula I, or a pharmaceutically acceptable salt thereof,

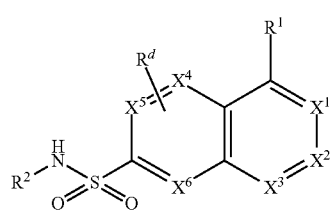

wherein:
$X^1$ is $CR^a$ or N;
$X^2$ is $CR^a$ or N;
$X^3$ is $CR^a$ or N;
$X^4$ is $CR^d$ or N;
$X^5$ is $CR^d$ or N;
$X^6$ is $CR^d$ or N;

each $R^a$ is independently hydrogen, halo, —OH, —NR$^b$R$^b$, —C$_{1-6}$alkyl, —OC$_{1-6}$alkyl, —C$_{1-6}$haloalkyl, —OC$_{1-6}$haloalkyl or —CN;

$R^1$ is —CN, —N(R$^e$)(CR$^e$R$^e$)$_m$A, -(C=O)N(R$^e$)(CR$^e$R$^e$)$_m$CF$_3$, —C(=O)A, —O(CR$^e$R$^e$)$_m$A, —O(CR$^e$R$^e$)$_m$OA, -(C=O)C$_{1-6}$alkyl or a 5 to 10 membered aryl or heteroaryl, or a 3 to 10 membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a C=O group, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, —OC$_{1-6}$alkylCF$_3$, —OC$_{1-6}$ alkylCN, A, —C$_{1-6}$ alkylOC$_{1-6}$ alkyl, -(SO$_2$)C$_{1-6}$ alkyl, -(SO$_2$)NR$^b$R$^b$, hydroxyC$_{1-6}$ alkyl, —CF$_3$, —CHF$_2$, —CH$_2$F, —OCF$_3$, —OCHF$_2$, —(CR$^e$R$^e$)$_m$CN, —C(=O)NR$^b$R$^b$, —C(=O)OR$^b$, —(CR$^e$R$^e$)$_m$A, —N(R$^e$)(CR$^e$R$^e$)$_m$A, —(C=N)OC$_{1-6}$alkyl, -(C=O)N(R$^e$)(CR$^e$R$^e$)$_m$A, (C=O)N(R$^e$)(CR$^e$R$^e$)$_m$CF$_3$, —O(CR$^e$R$^e$)$_m$A, —O(CR$^e$R$^e$)$_m$OA or —C(=O)A;

A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, —NR$^b$R$^b$, —C$_{1-6}$alkyl, —OC$_{1-6}$alkyl, -(CR$^e$R$^e$)$_m$OH, hydroxyC$_{1-6}$alkyl, —CF$_3$, —CHF$_2$, —CH$_2$F, —OCF$_3$, —CN, —C(=O)NR$^b$R$^b$, —O(CR$^e$R$^e$)$_m$B or -(CR$^e$R$^e$)$_m$B;

B is a 5 to 6 membered aryl, heteroaryl or heterocycloalkyl group, where the heteroaryl or heterocycloalkyl group can have from 1 to 3 heteroatoms independently selected from O, N or S, or a 3 to 5 membered cycloalkyl group, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —CF$_3$, —CHF$_2$, —CH$_2$F, —OCF$_3$, —CN or —C(=O)NR$^b$R$^b$;

$R^2$ is -(C=O)C$_{1-6}$alkyl, -(C=O)C$_{1-6}$haloalkyl or a 5 to 10 membered aryl or heteroaryl, or a 3 to 10 membered cycloalkyl or heterocycloalkyl group, where the heteroaryl or heterocycloalkyl group can have from 1 to 3 heteroatoms independently selected from O, N or S, or a carbon atom in the cycloalkyl or heterocycloalkyl group can be part of a C=O group, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^e$R$^c$)$_n$NR$^b$R$^b$, —CF$_3$, —CHF$_2$, —CH$_2$F, —OCF$_3$, —OCHF$_2$, —OCH$_2$F, —CN or —C(=O)NR$^b$R$^b$;

each n is independently 0, 1, 2, 3 or 4;
each m is independently 0, 1, 2, 3 or 4;
each R$^b$ is independently hydrogen or —C$_{1-6}$alkyl;
each R$^c$ is independently hydrogen or —C$_{1-6}$alkyl;
each R$^d$ is independently hydrogen, halo, —CN, —NR$^c$R$^c$, —OH, —C$_{1-6}$alkyl, —C$_{1-6}$haloalkyl, —OC$_{1-6}$haloalkyl or —OC$_{1-6}$alkyl; and
each R$^e$ is independently hydrogen, halo, —CN, —NR$^c$R$^c$, —OH, —C$_{1-6}$alkyl, —OC$_{1-6}$alkyl or a 5 to 6 membered heterocycloalkyl group having from 1 to 3 heteroatoms independently selected from O, N or S;

provided that the compound is not
1-(4-fluoro-2-(pyrimidin-5-yl)phenyl)-N-(thiazol-2-yl)isoquinoline-6-sulfonamide;
1-(4-fluoro-2-(pyrimidin-2-yloxy)phenyl)-N-(thiazol-2-yl)isoquinoline-6-sulfonamide;
5-methoxy-4-(2-methoxy-4-(trifluoromethyl)phenyl)-N-(thiazol-2-yl)quinoline-7-sulfonamide;
5-cyano-N-phenyl-2-naphthalenesufonamide;
N-(3,4-dimethyl-5-isoxazolyl)-5-(1-piperidinyl)-2-naphthalenesulfonamide; or
N-(3,4-dimethyl-5-isoxazolyl)-5-[(phenylmethyl)amino]-2-naphthalenesulfonamide.

2. A compound in accordance with claim 1, or a pharmaceutically acceptable salt thereof, wherein one of $X^1$, $X^2$ and $X^3$ is N and the other two of $X^1$, $X^2$ and $X^3$ is CR$^a$.

3. A compound in accordance with claim 1, or a pharmaceutically acceptable salt thereof, wherein two of $X^1$, $X^2$ and $X^3$ are N and the other one of $X^1$, $X^2$ and $X^3$ is CR$^a$.

4. A compound in accordance with claim 1, or a pharmaceutically acceptable salt thereof, wherein one of $X^1$, $X^2$ and $X^3$ is N and the other two of $X^1$, $X^2$ and $X^3$ is CH.

5. A compound in accordance with claim 1, or a pharmaceutically acceptable salt thereof, wherein two of $X^1$, $X^2$ and $X^3$ are N and the other one of $X^1$, $X^2$ and $X^3$ is CH.

6. A compound in accordance with claim 1, or a pharmaceutically acceptable salt thereof, wherein $X^1$, $X^2$ and $X^3$ are CH.

7. A compound in accordance with claim 1, or a pharmaceutically acceptable salt thereof, wherein $X^1$ is N, $X^2$ is CH and $X^3$ is CR$^a$.

8. A compound in accordance with claim 1, or a pharmaceutically acceptable salt thereof, wherein $X^1$ is N, $X^2$ is CH and $X^3$ is N.

9. A compound in accordance with claim 1, or a pharmaceutically acceptable salt thereof, wherein $X^1$ is CH, $X^2$ is CH and $X^3$ is N.

10. A compound in accordance with claim 1, or a pharmaceutically acceptable salt thereof, wherein $X^1$ is CH, $X^2$ is N and $X^3$ is CH.

11. A compound in accordance with any one of claim 1, or a pharmaceutically acceptable salt thereof, wherein $R^1$ is a 6 membered aryl, heteroaryl or heterocycloalkyl group, where the heteroaryl or heterocycloalkyl group can have from 1 to 3 heteroatoms independently selected from O, N or S, and the aryl, heteroaryl or heterocycloalkyl group can be unsubstituted or substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —CN, —C(=O)NR$^b$R$^b$—C(=O)OR$^b$ or A; and A is a 5 to 6 membered aryl or heteroaryl group, where the heteroaryl group can have from 1 to 3 heteroatoms independently selected from O, N or S, and the aryl, or heteroaryl group can be unsubstituted or substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —CN, or —C(=O)NR$^b$R$^b$.

12. A compound in accordance with any one of claim 1, or a pharmaceutically acceptable salt thereof, wherein $R^1$ is phenyl, substituted phenyl, morpholino, substituted morpholino, pyridyl or substituted pyridyl.

13. A compound in accordance with any one of claim 1, or a pharmaceutically acceptable salt thereof, wherein $R^1$ is phenyl, substituted phenyl, morpholino, substituted morpholino, pyridyl or substituted pyridyl, wherein any substituents are independently selected from —CF$_3$, halo, —OCH$_3$, 5 membered heteroaryl, substituted 5 membered heteroaryl, 6 membered heteroaryl, substituted 6 membered heteroaryl, 6 membered aryl, substituted 6 membered aryl, —$C_{1-6}$alkyl, —$OCF_3$, —$C(=O)N(CH_3)_2$, —$C(OH)(CH_3)_2$, —$C(=O)OCH_3$, —CN, $NH_2$, —$C(=O)NH_2$ or —$OCHF_2$.

14. A compound in accordance with any one of claim 1, or a pharmaceutically acceptable salt thereof, wherein $R^1$ is —$N(R^e)(CR^eR^e)_mA$.

15. A compound in accordance with any one of claim 1, or a pharmaceutically acceptable salt thereof, wherein $R^1$ is —$N(H)(CH_2)_mA$.

16. A compound in accordance with any one of claim 1, or a pharmaceutically acceptable salt thereof, wherein $R^1$ is —$N(R^e)(CR^eR^e)_mA$.

17. A compound in accordance with any one of claim 1, or a pharmaceutically acceptable salt thereof, wherein $R^1$ is —$N(H)(CH_2)_mA$.

18. A compound in accordance with any one of claim 1, or a pharmaceutically acceptable salt thereof, wherein $R^1$ is —$O(CR^eR^e)_mA$.

19. A compound in accordance with any one of claim 1, or a pharmaceutically acceptable salt thereof, wherein $R^1$ is —$O(CH_2)_mA$.

20. A compound in accordance with any one of claim 1, or a pharmaceutically acceptable salt thereof, wherein $R^2$ is thiadiazolyl, substituted thiadiazolyl, thiazolyl, substituted thiazolyl, oxazolyl, substituted oxazolyl, pyrimidinyl, substituted pyrimidinyl, isoxazolyl, substituted isoxazolyl, pyrazolyl, substituted pyrazolyl, pyridyl, substituted pyridyl, pyridazinyl, substituted pyridazinyl, pyrazinyl or substituted pyrazinyl.

21. A compound in accordance with any one of claim 1, or a pharmaceutically acceptable salt thereof, wherein $R^2$ is thiadiazolyl.

22. A compound in accordance with any one of claim 1, or a pharmaceutically acceptable salt thereof, wherein $R^2$ is pyrimidinyl.

23. A compound in accordance with any one of claim 1, or a pharmaceutically acceptable salt thereof, wherein $R^2$ is an optionally substituted thiazolyl.

24. A compound in accordance any one of claim 1, or a pharmaceutically acceptable salt thereof, wherein $R^d$ is hydrogen.

25. A compound in accordance with claim 1, or a pharmaceutically acceptable salt thereof, wherein $X^1$, $X^2$ and $X^3$ are CH and $R^2$ is thiadiazolyl.

26. A compound in accordance with claim 1, or a pharmaceutically acceptable salt thereof, wherein $R^2$ is thiadiazolyl and $X^1$ is N and $X^2$ and $X^3$ are CH.

27. A compound, or a pharmaceutically acceptable salt thereof, selected from:
5-(2-(1-methyl-1H-pyrazol-5-yl)-4-(trifluoromethyl)phenyl)-N-(1,2,4-thiadiazol-5-yl)naphthalene-2-sulfonamide;
5-(2-(pyridin-4-yl)-4-(trifluoromethyl)phenyl)-N-(1,2,4-thiadiazol-5-yl)naphthalene-2-sulfonamide;
5-(2-bromo-4-fluorophenyl)-N-(1,2,4-thiadiazol-5-yl)naphthalene-2-sulfonamide;
5-(2-chloro-4-(trifluoromethoxy)phenyl)-N-(1,2,4-thiadiazol-5-yl)naphthalene-2-sulfonamide;
5-(2-chloro-4-fluorophenyl)-N-(1,2,4-thiadiazol-5-yl)naphthalene-2-sulfonamide;
5-(2-chloro-4-methylphenyl)-N-(1,2,4-thiadiazol-5-yl)naphthalene-2-sulfonamide;
5-(pyridin-4-yl)-N-(1,2,4-thiadiazol-5-yl)naphthalene-2-sulfonamide;
5-(2-chlorophenyl)-N-(1,2,4-thiadiazol-5-yl)naphthalene-2-sulfonamide;
5-phenyl-N-(1,2,4-thiadiazol-5-yl)naphthalene-2-sulfonamide;
5-(2-ethoxy-4-(trifluoromethyl)phenyl)-N-(1,2,4-thiadiazol-5-yl)naphthalene-2-sulfonamide;
5-(2-methyl-4-(trifluoromethyl)phenyl)-N-(1,2,4-thiadiazol-5-yl)naphthalene-2-sulfonamide;
5-(2-methoxy-4-(trifluoromethyl)phenyl)-N-(1,2,4-thiadiazol-5-yl)naphthalene-2-sulfonamide;
5-morpholino-N-(1,2,4-thiadiazol-5-yl)naphthalene-2-sulfonamide;
5-(2-phenylmorpholino)-N-(1,2,4-thiadiazol-5-yl)naphthalene-2-sulfonamide;
5-(2-methyl-2-phenylmorpholino)-N-(1,2,4-thiadiazol-5-yl)naphthalene-2-sulfonamide;
5-(2-methylmorpholino)-N-(1,2,4-thiadiazol-5-yl)naphthalene-2-sulfonamide;
methyl 4-(6-(N-(1,2,4-thiadiazol-5-yl)sulfamoyl)naphthalen-1-yl)morpholine-2-carboxylate;
5-(2-ethylmorpholino)-N-(1,2,4-thiadiazol-5-yl)naphthalene-2-sulfonamide;
4-(6-(N-(1,2,4-thiadiazol-5-yl)sulfamoyl)naphthalen-1-yl)-n,n-dimethylmorpholine-2-carboxamide;
5-(2-(2-hydroxypropan-2-yl)morpholino)-N-(1,2,4-thiadiazol-5-yl)naphthalene-2-sulfonamide;
5-(2-(1H-pyrazol-4-yl)-4-(trifluoromethyl)phenyl)-N-(1,2,4-thiadiazol-5-yl)naphthalene-2-sulfonamide;
5-(2-cyano-4-(trifluoromethyl)phenyl)-N-(1,2,4-thiadiazol-5-yl)naphthalene-2-sulfonamide;
5-(2-bromo-4-(trifluoromethyl)phenyl)-N-(1,2,4-thiadiazol-5-yl)naphthalene-2-sulfonamide;
5-(4-chloro-2-(difluoromethoxy)phenyl)-N-(1,2,4-thiadiazol-5-yl)naphthalene-2-sulfonamide;
5-(4-chloro-2-(1-methyl-1h-pyrazol-5-yl)phenyl)-N-(1,2,4-thiadiazol-5-yl)naphthalene-2-sulfonamide;
5-(4-chloro-2-(1,2,3,6-tetrahydropyridin-4-yl)phenyl)-N-(1,2,4-thiadiazol-5-yl)naphthalene-2-sulfonamide;
5-(4-chloro-2-(1H-pyrazol-4-yl)phenyl)-N-(1,2,4-thiadiazol-5-yl)naphthalene-2 sulfonamide;
5-(4-chloro-2-(pyridin-4-yl)phenyl)-N-(1,2,4-thiadiazol-5-yl)naphthalene-2-sulfonamide;
5-(2-chloro-4-(trifluoromethyl)phenyl)-N-(1,2,4-thiadiazol-5-yl)naphthalene-2-sulfonamide;
5-(4-chloro-2-methoxyphenyl)-N-(1,2,4-thiadiazol-5-yl)naphthalene-2-sulfonamide;
5-(2-amino-4-chlorophenyl)-N-(1,2,4-thiadiazol-5-yl)naphthalene-2-sulfonamide;
2-(6-(N-(1,2,4-thiadiazol-5-yl)sulfamoyl)naphthalen-1-yl)-5-(trifluoromethyl)benzamide;
5-(4-chloro-2-methylphenyl)-N-(1,2,4-thiadiazol-5-yl)naphthalene-2-sulfonamide;
5-(4-chlorophenyl)-N-(1,2,4-thiadiazol-5-yl)naphthalene-2-sulfonamide;
5-(4-chloro-2-fluorophenyl)-N-(1,2,4-thiadiazol-5-yl)naphthalene-2-sulfonamide;
5-(2-fluoro-4-(trifluoromethyl)phenyl)-N-(1,2,4-thiadiazol-5-yl)naphthalene-2-sulfonamide;
N-(1,2,4-thiadiazol-5-yl)-5-(4-(trifluoromethyl)phenyl)naphthalene-2-sulfonamide;
5-(2-hydroxy-4-(trifluoromethyl)phenyl)-N-(1,2,4-thiadiazol-5-yl)naphthalene-2-sulfonamide;
5-(4-chloro-2-(trifluoromethyl)phenyl)-N-(1,2,4-thiadiazol-5-yl)naphthalene-2-sulfonamide;
5-(2,4-dichlorophenyl)-N-(1,2,4-thiadiazol-5-yl)naphthalene-2-sulfonamide;

5-(2-methoxy-4-(trifluoromethyl)phenyl)-N-(thiazol-2-yl)naphthalene-2-sulfonamide;

5-(2-methoxy-4-(trifluoromethyl)phenyl)-N-(pyrimidin-4-yl)naphthalene-2-sulfonamide;

5-(4-chloro-2-methoxyphenyl)-N-(1-(2-(dimethylamino)ethyl)-1h-pyrazol-3-yl)naphthalene-2-sulfonamide;

5-(4-chloro-2-methoxyphenyl)-N-(5-methylisoxazol-3-yl)naphthalene-2-sulfonamide;

5-(4-chloro-2-methoxyphenyl)-N-(oxazol-2-yl)naphthalene-2-sulfonamide;

5-(4-chloro-2-methoxyphenyl)-N-(thiazol-2-yl)naphthalene-2-sulfonamide;

5-(2-(1-methyl-1H-pyrazol-5-yl)-4-(trifluoromethyl)phenyl)-N-(thiazol-2-yl)naphthalene-2-sulfonamide;

N-(pyrimidin-4-yl)-5-(2-(1,2,3,6-tetrahydropyridin-4-yl)-4-(trifluoromethyl)phenyl)naphthalene-2-sulfonamide;

5-(2-chloro-4-(trifluoromethyl)phenyl)-N-(oxazol-2-yl)naphthalene-2-sulfonamide;

1-(2-bromo-4-(trifluoromethyl)phenyl)-N-(1,2,4-thiadiazol-5-yl)isoquinoline-6-sulfonamide;

1-(2-chloro-4-(trifluoromethyl)phenyl)-N-(thiazol-2-yl)isoquinoline-6-sulfonamide;

1-(2-chloro-4-(trifluoromethyl)phenyl)-N-(3-methoxypyridin-4-yl)isoquinoline-6-sulfonamide;

1-(2-(pyridin-4-yl)-4-(trifluoromethyl)phenyl)-N-(1,2,4-thiadiazol-5-yl)isoquinoline-6-sulfonamide;

1-(2-(1-methyl-1H-pyrazol-5-yl)-4-(trifluoromethyl)phenyl)-N-(1,2,4-thiadiazol-5-yl)isoquinoline-6-sulfonamide;

1-(2-(1H-pyrazol-4-yl)-4-(trifluoromethyl)phenyl)-N-(1,2,4-thiadiazol-5-yl)isoquinoline-6-sulfonamide;

1-(2-chloro-4-(trifluoromethyl)phenyl)-N-(1,2,4-thiadiazol-5-yl)isoquinoline-6-sulfonamide;

1-(3-chloro-4-(trifluoromethyl)phenyl)-N-(1,2,4-thiadiazol-5-yl)isoquinoline-6-sulfonamide;

1-(2-hydroxy-4-(trifluoromethyl)phenyl)-N-(1,2,4-thiadiazol-5-yl)isoquinoline-6-sulfonamide;

1-(2,4-dimethoxyphenyl)-N-(1,2,4-thiadiazol-5-yl)isoquinoline-6-sulfonamide;

N-(1,2,4-thiadiazol-5-yl)-1-(2,4,6-trimethoxyphenyl)isoquinoline-6-sulfonamide;

1-(2,4-dichlorophenyl)-N-(1,2,4-thiadiazol-5-yl)isoquinoline-6-sulfonamide;

1-(4-chloro-2-methylphenyl)-N-(1,2,4-thiadiazol-5-yl)isoquinoline-6-sulfonamide;

1-(4-chloro-2-(trifluoromethyl)phenyl)-N-(1,2,4-thiadiazol-5-yl)isoquinoline-6-sulfonamide;

1-(4-chlorophenyl)-N-(1,2,4-thiadiazol-5-yl)isoquinoline-6-sulfonamide;

1-(2-(pyridin-4-yl)-4-(trifluoromethyl)phenyl)-N-(pyrimidin-4-yl)isoquinoline-6-sulfonamide;

1-(2-bromo-4-(trifluoromethyl)phenyl)-N-(pyrimidin-4-yl)isoquinoline-6-sulfonamide;

1-(2-methoxy-4-(trifluoromethyl)phenyl)-N-(pyrimidin-4-yl)isoquinoline-6-sulfonamide;

1-(2-(1-methyl-1,2,3,6-tetrahydropyridin-4-yl)-4-(trifluoromethyl)phenyl)-N-(pyrimidin-4-yl)isoquinoline-6-sulfonamide;

N-(pyrimidin-4-yl)-1-(2-(1,2,3,6-tetrahydropyridin-4-yl)-4-(trifluoromethyl)phenyl)isoquinoline-6-sulfonamide 2,2,2-trifluoroacetate;

1-(2-(1,2,3,6-tetrahydropyridin-4-yl)-4-(trifluoromethyl)phenyl)-N-(thiazol-2-yl)isoquinoline-6-sulfonamide;

1-(2-(pyridin-4-yl)-4-(trifluoromethyl)phenyl)-N-(thiazol-2-yl)isoquinoline-6-sulfonamide;

1-(2-(1-methyl-1,2,3,6-tetrahydropyridin-4-yl)-4-(trifluoromethyl)phenyl)-N-(thiazol-2-yl)isoquinoline-6-sulfonamide;

1-morpholino-N-(thiazol-2-yl)isoquinoline-6-sulfonamide;

5-(2-(1-methyl-1H-pyrazol-5-yl)-4-(trifluoromethyl)phenyl)-N-(pyrimidin-4-yl)naphthalene-2-sulfonamide;

5-(2-(pyridin-4-yl)-4-(trifluoromethyl)phenyl)-N-(pyrimidin-4-yl)naphthalene-2-sulfonamide;

5-(2-(1-methyl-1,2,3,6-tetrahydropyridin-4-yl)-4-(trifluoromethyl)phenyl)-N-(pyrimidin-4-yl)naphthalene-2-sulfonamide;

5-(2-(1,2,3,6-tetrahydropyridin-4-yl)-4-(trifluoromethyl)phenyl)-N-(thiazol-2-yl)naphthalene-2-sulfonamide;

5-(2-(1-methyl-1,2,3,6-tetrahydropyridin-4-yl)-4-(trifluoromethyl)phenyl)-N-(thiazol-2-yl)naphthalene-2-sulfonamide;

5-(2-chloro-4-(trifluoromethyl)phenyl)-N-(thiazol-2-yl)naphthalene-2-sulfonamide;

5-(2-phenylpyrrolidin-1-yl)-N-(thiazol-2-yl)naphthalene-2-sulfonamide;

5-(2-(1-(azetidin-3-yl)-1H-pyrazol-5-yl)-4-(trifluoromethyl)phenyl)-N-(thiazol-2-yl)naphthalene-2-sulfonamide;

5-(2-(1-(1-methylazetidin-3-yl)-1H-pyrazol-5-yl)-4-(trifluoromethyl)phenyl)-N-(thiazol-2-yl)naphthalene-2-sulfonamide; or 5-(2-phenylpyrrolidin-1-yl)-N-(1,2,4-thiadiazol-5-yl)naphthalene-2-sulfonamide.

28. A compound, or a pharmaceutically acceptable salt thereof, selected from:

5-(2-(4-methylpiperazin-1-yl)-4-(trifluoromethyl)phenyl)-N-(thiazol-2-yl)naphthalene-2-sulfonamide;

5-(2-(pyridin-3-yl)pyrrolidin-1-yl)-N-(1,2,4-thiadiazol-5-yl)naphthalene-2-sulfonamide;

(S)-5-(2-(pyridin-3-yl)pyrrolidin-1-yl)-N-(1,2,4-thiadiazol-5-yl)naphthalene-2-sulfonamide;

(R)-5-(2-(pyridin-3-yl)pyrrolidin-1-yl)-N-(1,2,4-thiadiazol-5-yl)naphthalene-2-sulfonamide;

5-(2-(pyridin-4-yl)pyrrolidin-1-yl)-N-(1,2,4-thiadiazol-5-yl)naphthalene-2-sulfonamide;

((S)-5-(2-(pyridin-4-yl)pyrrolidin-1-yl)-N-(1,2,4-thiadiazol-5-yl)naphthalene-2-sulfonamide;

(R)-5-(2-(pyridin-4-yl)pyrrolidin-1-yl)-N-(1,2,4-thiadiazol-5-yl)naphthalene-2-sulfonamide;

5-(2-methylpyrrolidin-1-yl)-N-(1,2,4-thiadiazol-5-yl)naphthalene-2-sulfonamide;

5-(2-phenylazetidin-1-yl)-N-(1,2,4-thiadiazol-5-yl)naphthalene-2-sulfonamide;

5-(2-oxopyrrolidin-1-yl)-N-(1,2,4-thiadiazol-5-yl)naphthalene-2-sulfonamide;

5-(2-methoxyphenyl)-N-(1,2,4-thiadiazol-5-yl)naphthalene-2-sulfonamide;

5-(pyrrolidin-2-yl)-N-(1,2,4-thiadiazol-5-yl)naphthalene-2-sulfonamide;

5-(1-(pyridin-2-yl)pyrrolidin-2-yl)-N-(1,2,4-thiadiazol-5-yl)naphthalene-2-sulfonamide;

5-(1-benzylpyrrolidin-2-yl)-N-(1,2,4-thiadiazol-5-yl)naphthalene-2-sulfonamide;

5-(1-benzylpyrrolidin-2-yl)-N-(thiazol-2-yl)naphthalene-2-sulfonamide;

5-(benzylamino)-N-(1,2,4-thiadiazol-5-yl)naphthalene-2-sulfonamide;

5-(benzyl(methyl)amino)-N-(1,2,4-thiadiazol-5-yl)naphthalene-2-sulfonamide;

5-(1-benzoylpyrrolidin-2-yl)-N-(thiazol-2-yl)naphthalene-2-sulfonamide;

5-(1-(tetrahydro-2H-pyran-4-yl)pyrrolidin-2-yl)-N-(thiazol-2-yl)naphthalene-2-sulfonamide;
(S)-5-(1-(tetrahydro-2H-pyran-4-yl)pyrrolidin-2-yl)-N-(thiazol-2-yl)naphthalene-2-sulfonamide;
(R)-5-(1-(tetrahydro-2H-pyran-4-yl)pyrrolidin-2-yl)-N-(thiazol-2-yl)naphthalene-2-sulfonamide;
5-(1-(cyanomethyl)-5-fluoro-1H-indol-2-yl)-N-(pyrimidin-4-yl)naphthalene-2-sulfonamide;
5-(5-fluoro-1-methyl-1h-indol-2-yl)-N-(pyrimidin-4-yl)naphthalene-2-sulfonamide;
N-(5-fluorothiazol-2-yl)-5-(2-methoxy-4-(trifluoromethyl)phenyl)naphthalene-2-sulfonamide;
N-(5-fluorothiazol-2-yl)-5-(2-(1,2,3,6-tetrahydropyridin-4-yl)-4-(trifluoromethyl)phenyl)naphthalene-2-sulfonamide;
N-(5-fluorothiazol-2-yl)-5-(2-(1-methylpiperidin-4-yl)-4-(trifluoromethyl)phenyl)naphthalene-2-sulfonamide;
N-(5-fluorothiazol-2-yl)-5-(2-(1-methyl-1h-imidazol-5-yl)-4-(trifluoromethyl)phenyl)naphthalene-2-sulfonamide;
N-(5-fluorothiazol-2-yl)-5-(2-(1-methyl-1h-imidazol-2-yl)-4-(trifluoromethyl)phenyl)naphthalene-2-sulfonamide;
5-(2-(1H-imidazol-1-yl)-4-(trifluoromethyl)phenyl)-N-(5-fluorothiazol-2-yl)naphthalene-2-sulfonamide;
N-(5-fluorothiazol-2-yl)-5-(2-(piperidin-4-yl)-4-(trifluoromethyl)phenyl)naphthalene-2-sulfonamide;
5-(5-fluoro-1H-indol-2-yl)-N-(pyrimidin-4-yl)naphthalene-2-sulfonamide;
5-(3-methoxy-[1,1'-biphenyl]-4-yl)-N-(pyrimidin-4-yl)naphthalene-2-sulfonamide;
5-(2-(1-methylpiperidin-4-yl)-4-(trifluoromethyl)phenyl)-N-(pyrimidin-4-yl)naphthalene-2-sulfonamide;
5-(2-(methylsulfonyl)-4-(trifluoromethyl)phenyl)-N-(pyrimidin-4-yl)naphthalene-2-sulfonamide;
5-(2-(3-fluoroazetidin-3-yl)-4-(trifluoromethyl)phenyl)-N-(pyrimidin-4-yl)naphthalene-2-sulfonamide;
5-(2-(2,5-dihydro-1H-pyrrol-3-yl)-4-(trifluoromethyl)phenyl)-N-(pyrimidin-4-yl)naphthalene-2-sulfonamide;
5-(2-(piperidin-4-yl)-4-(trifluoromethyl)phenyl)-N-(pyrimidin-4-yl)naphthalene-2-sulfonamide;
5-(2-(1H-imidazol-1-yl)-4-(trifluoromethyl)phenyl)-N-(pyrimidin-4-yl)naphthalene-2-sulfonamide;
5-(2-(1-methyl-1,2,5,6-tetrahydropyridin-3-yl)-4-(trifluoromethyl)phenyl)-N-(pyrimidin-4-yl)naphthalene-2-sulfonamide;
5-(2-(1-methyl-1H-imidazol-5-yl)-4-(trifluoromethyl)phenyl)-N-(pyrimidin-4-yl)naphthalene-2-sulfonamide;
5-(2-(1-methyl-1H-imidazol-2-yl)-4-(trifluoromethyl)phenyl)-N-(pyrimidin-4-yl)naphthalene-2-sulfonamide;
5-(4-cyclopropyl-2-methoxyphenyl)-N-(pyrimidin-4-yl)naphthalene-2-sulfonamide;
1-(4-fluoro-2-(pyridin-4-yl)phenyl)-N-(thiazol-2-yl)isoquinoline-6-sulfonamide;
1-(2-(2,5-dihydrofuran-3-yl)-4-fluorophenyl)-N-(thiazol-2-yl)isoquinoline-6-sulfonamide;
1-(pyridin-3-ylmethoxy)-N-(pyrimidin-4-yl)isoquinoline-6-sulfonamide;
1-(4-fluoro-2-(1-methyl-1H-pyrazol-4-yl)phenyl)-N-(thiazol-2-yl)isoquinoline-6-sulfonamide;
1-((5-phenyloxazol-4-yl)methoxy)-N-(pyrimidin-4-yl)isoquinoline-6-sulfonamide;
(S)-1-((1-(4-chlorophenoxyl)propan-2-yl)oxy)-N-(pyrimidin-4-yl)isoquinoline-6-sulfonamide;
1-(3-(4-chlorophenyl)propoxy)-N-(pyrimidin-4-yl)isoquinoline-6-sulfonamide;
1-((1-(4-chlorobenzyl)-1H-imidazol-2-yl)methoxy)-N-(pyrimidin-4-yl)isoquinoline-6-sulfonamide;
(R)-1-((4-benzylmorpholin-2-yl)methoxy)-N-(pyrimidin-4-yl)isoquinoline-6-sulfonamide;
1-((1-cyanocyclopropyl)methoxy)-N-(pyrimidin-4-yl)isoquinoline-6-sulfonamide;
1-((1H-indazol-4-yl)methoxy)-N-(pyrimidin-4-yl)isoquinoline-6-sulfonamide;
1-((3-cyanobenzyl)oxy)-N-(pyrimidin-4-yl)isoquinoline-6-sulfonamide;
1-((5-methyl-2-phenyl-2H-1,2,3-triazol-4-yl)methoxy)-N-(pyrimidin-4-yl)isoquinoline-6-sulfonamide;
1-(2-methoxy-5-(trifluoromethyl)phenyl)-N-(pyrimidin-4-yl)isoquinoline-6-sulfonamide;
1-(2-methoxyphenyl)-N-(pyrimidin-4-yl)isoquinoline-6-sulfonamide;
N-(pyrimidin-4-yl)-1-(4-(trifluoromethyl)phenyl) isoquinoline-6-sulfonamide;
1-(4,5-difluoro-2-methoxyphenyl)-N-(pyrimidin-4-yl)isoquinoline-6-sulfonamide;
1-(6-chloro-4-methoxypyridin-3-yl)-N-(pyrimidin-4-yl)isoquinoline-6-sulfonamide;
1-(2-methoxypyridin-3-yl)-N-(pyrimidin-4-yl)isoquinoline-6-sulfonamide;
1-(2,6-dimethoxypyridin-3-yl)-N-(pyrimidin-4-yl)isoquinoline-6-sulfonamide;
1-(5-chloro-2-methoxyphenyl)-N-(pyrimidin-4-yl)isoquinoline-6-sulfonamide;
1-(2,5-dimethoxyphenyl)-N-(pyrimidin-4-yl)isoquinoline-6-sulfonamide;
1-(5-fluoro-2-methoxyphenyl)-N-(pyrimidin-4-yl)isoquinoline-6-sulfonamide;
1-(2-methoxy-5-methylphenyl)-N-(pyrimidin-4-yl)isoquinoline-6-sulfonamide;
1-(5-cyano-2-methoxyphenyl)-N-(pyrimidin-4-yl)isoquinoline-6-sulfonamide;
1-(2-methoxy-5-(trifluoromethoxy)phenyl)-N-(pyrimidin-4-yl)isoquinoline-6-sulfonamide;
1-(2-methoxy-3-(trifluoromethyl)phenyl)-N-(pyrimidin-4-yl)isoquinoline-6-sulfonamide;
1-(2-methoxy-4-(trifluoromethoxy)phenyl)-N-(pyrimidin-4-yl)isoquinoline-6-sulfonamide;
1-(4-fluoro-2-methoxy-5-methylphenyl)-N-(pyrimidin-4-yl)isoquinoline-6-sulfonamide;
1-(3-methoxynaphthalen-2-yl)-N-(pyrimidin-4-yl)isoquinoline-6-sulfonamide;
1-(2-chloro-4-(trifluoromethyl)phenyl)-N-(pyrimidin-4-yl)isoquinoline-6-sulfonamide;
1-(3-fluoro-2-methoxyphenyl)-N-(pyrimidin-4-yl)isoquinoline-6-sulfonamide;
1-(2-fluoro-6-methoxyphenyl)-N-(pyrimidin-4-yl)isoquinoline-6-sulfonamide;
1-(4-cyano-2-methylphenyl)-N-(pyrimidin-4-yl)isoquinoline-6-sulfonamide;
1-(4-chloro-2-methoxyphenyl)-N-(pyrimidin-4-yl)isoquinoline-6-sulfonamide;
1-(4,5-dichloro-2-methoxyphenyl)-N-(pyrimidin-4-yl)isoquinoline-6-sulfonamide;
1-(benzo[b]thiophen-7-yl)-N-(pyrimidin-4-yl)isoquinoline-6-sulfonamide;
1-(2-fluoro-5-(trifluoromethyl)phenyl)-N-(pyrimidin-4-yl)isoquinoline-6-sulfonamide;
1-(1-methyl-1H-indol-7-yl)-N-(pyrimidin-4-yl)isoquinoline-6-sulfonamide;

1-(1,5-dimethyl-1H-indazol-6-yl)-N-(pyrimidin-4-yl)isoquinoline-6-sulfonamide;
1-(5-fluoro-2-methoxypyridin-3-yl)-N-(pyrimidin-4-yl)isoquinoline-6-sulfonamide;
1-(4-fluoro-2-methoxyphenyl)-N-(pyrimidin-4-yl)isoquinoline-6-sulfonamide;
1-(5-chloro-2-methoxypyridin-3-yl)-N-(pyrimidin-4-yl)isoquinoline-6-sulfonamide;
1-(3-methoxypyridin-4-yl)-N-(pyrimidin-4-yl)isoquinoline-6-sulfonamide;
1-(4-methoxypyridin-3-yl)-N-(pyrimidin-4-yl)isoquinoline-6-sulfonamide;
1-(2,6-dimethoxyphenyl)-N-(pyrimidin-4-yl)isoquinoline-6-sulfonamide;
1-(2,4-dimethoxyphenyl)-N-(pyrimidin-4-yl)isoquinoline-6-sulfonamide;
1-(2-ethoxyphenyl)-N-(pyrimidin-4-yl)isoquinoline-6-sulfonamide;
N-(pyrimidin-4-yl)-1-(2-(2,2,2-trifluoroethoxy) phenyl)isoquinoline-6-sulfonamide;
1-(2-methoxy-4-methylphenyl)-N-(thiazol-2-yl)isoquinoline-6-sulfonamide;
1-(5-chloro-2-methoxypyridin-3-yl)-N-(thiazol-2-yl)isoquinoline-6-sulfonamide;
1-(4,5-dichloro-2-methoxyphenyl)-N-(thiazol-2-yl)isoquinoline-6-sulfonamide;
N-(thiazol-2-yl)-1-(o-tolyl)isoquinoline-6-sulfonamide;
1-(2-chlorophenyl)-N-(thiazol-2-yl)isoquinoline-6-sulfonamide;
1-(2-methoxy-5-(trifluoromethyl)phenyl)-N-(thiazol-2-yl)isoquinoline-6-sulfonamide;
1-(2-methoxy-4-(trifluoromethyl)phenyl)-N-(6-methoxypyrimidin-4-yl)isoquinoline-6-sulfonamide;
1-(2-methoxy-4-(trifluoromethyl)phenyl)-N-(2-methylpyrimidin-4-yl)isoquinoline-6-sulfonamide;
N-(5-fluoropyrimidin-4-yl)-1-(2-methoxy-4-(trifluoromethyl)phenyl)isoquinoline-6-sulfonamide;
1-(2-methoxy-4-(trifluoromethyl)phenyl)-N-(1,3,4-thiadiazol-2-yl)isoquinoline-6-sulfonamide;
1-(2-methoxy-4-(trifluoromethyl)phenyl)-N-(pyridazin-3-yl)isoquinoline-6-sulfonamide;
1-(2-methoxy-4-(trifluoromethyl)phenyl)-N-(pyrazin-2-yl)isoquinoline-6-sulfonamide;
1-(2-methoxy-4-(trifluoromethyl)phenyl)-N-(6-methylpyrimidin-4-yl)isoquinoline-6-sulfonamide;
1-(2-methoxy-4-(trifluoromethyl)phenyl)-N-(pyrimidin-2-yl)isoquinoline-6-sulfonamide;
1-(4-fluoro-2-hydroxyphenyl)-N-(thiazol-2-yl)isoquinoline-6-sulfonamide;
1-(4-fluoro-2-(pyridazin-3-yloxy)phenyl)-N-(thiazol-2-yl)isoquinoline-6-sulfonamide;
1-(4-fluoro-2-(pyridin-2-yloxy)phenyl)-N-(thiazol-2-yl)isoquinoline-6-sulfonamide;
1-(2-(cyanomethoxy)-4-fluorophenyl)-N-(thiazol-2-yl)isoquinoline-6-sulfonamide;
1-(3,4-dichlorophenoxy)-N-(pyrimidin-4-yl)isoquinoline-6-sulfonamide;
1-(2-methoxyphenyl)-N-(1,2,4-thiadiazol-5-yl)isoquinoline-6-sulfonamide;
1-(2-methoxy-4-(trifluoromethyl)phenyl)-N-(1,2,4-thiadiazol-5-yl)isoquinoline-6-sulfonamide;
1-(2-methoxy-4-(trifluoromethyl)phenyl)-N-(thiazol-2-yl)isoquinoline-6-sulfonamide;
N-(5-cyanothiazol-2-yl)-1-(2-methoxy-4-(trifluoromethyl)phenyl)isoquinoline-6-sulfonamide;
N-(5-fluorothiazol-2-yl)-1-(2-methoxy-4-(trifluoromethyl)phenyl)isoquinoline-6-sulfonamide;
1-(3'-fluoro-3-methoxy-[1,1'-biphenyl]-4-yl)-N-(pyrimidin-4-yl)isoquinoline-6-sulfonamide;
1-(3'-cyano-3-methoxy-[1,1'-biphenyl]-4-yl)-N-(pyrimidin-4-yl)isoquinoline-6-sulfonamide;
1-(4-chloro-2-methoxyphenyl)-N-(thiazol-2-yl)isoquinoline-6-sulfonamide;
1-(3'-fluoro-3-methoxy-[1,1'-biphenyl]-4-yl)-N-(thiazol-2-yl)isoquinoline-6-sulfonamide;
1-(2-methoxy-4-(1-methyl-1h-pyrazol-4-yl)phenyl)-N-(thiazol-2-yl)isoquinoline-6-sulfonamide;
1-(2-methoxy-4-(pyridin-3-yl)phenyl)-N-(thiazol-2-yl)isoquinoline-6-sulfonamide;
1-(4-cyano-2-methoxyphenyl)-N-(thiazol-2-yl)isoquinoline-6-sulfonamide;
1-(4-cyano-2-methoxyphenyl)-N-(pyrimidin-4-yl)isoquinoline-6-sulfonamide;
1-(1-phenyl-1H-pyrrol-3-yl)-N-(thiazol-2-yl)isoquinoline-6-sulfonamide;
1-(5-methyl-1-phenyl-1H-pyrazol-4-yl)-N-(thiazol-2-yl)isoquinoline-6-sulfonamide;
1-(4-chloro-2-methylphenyl)-N-(thiazol-2-yl)isoquinoline-6-sulfonamide;
1-(4-cyano-2-methylphenyl)-N-(thiazol-2-yl)isoquinoline-6-sulfonamide;
4-fluoro-1-(2-methoxyphenyl)-N-(thiazol-2-yl)isoquinoline-6-sulfonamide;
4-fluoro-1-(2-methoxy-4-(trifluoromethyl)phenyl)-N-(thiazol-2-yl)isoquinoline-6-sulfonamide;
4-fluoro-1-(4-fluoro-2-methoxyphenyl)-N-(thiazol-2-yl)isoquinoline-6-sulfonamide;
1-(4-cyano-2-methoxyphenyl)-4-fluoro-N-(thiazol-2-yl)isoquinoline-6-sulfonamide;
1-(4-chloro-2-methoxyphenyl)-4-fluoro-N-(thiazol-2-yl)isoquinoline-6-sulfonamide;
4-fluoro-1-(2-methoxy-4-(trifluoromethyl)phenyl)-N-(pyrimidin-4-yl)isoquinoline-6-sulfonamide;
1-(4-chloro-2-methoxyphenyl)-4-fluoro-N-(pyrimidin-4-yl)isoquinoline-6-sulfonamide;
1-(4-cyano-2-methoxyphenyl)-4-fluoro-N-(pyrimidin-4-yl)isoquinoline-6-sulfonamide;
3-chloro-1-(2-methoxy-4-(trifluoromethyl)phenyl)-N-(thiazol-2-yl)isoquinoline-6-sulfonamide;
3-cyano-1-(2-methoxy-4-(trifluoromethyl)phenyl)-N-(thiazol-2-yl)isoquinoline-6-sulfonamide;
3-methoxy-1-(2-methoxy-4-(trifluoromethyl)phenyl)-N-(thiazol-2-yl)isoquinoline-6-sulfonamide;
1-(2-methoxy-4-(trifluoromethyl)phenyl)-3-(methylamino)-N-(thiazol-2-yl)isoquinoline-6-sulfonamide;
3-(dimethylamino)-1-(2-methoxy-4-(trifluoromethyl)phenyl)-N-(thiazol-2-yl)isoquinoline-6-sulfonamide;
1-(4-(difluoromethyl)-2-methoxyphenyl)-N-(thiazol-2-yl)isoquinoline-6-sulfonamide;
1-(2-(methoxymethyl)-4-(trifluoromethyl)phenyl)-N-(thiazol-2-yl)isoquinoline-6-sulfonamide;
methyl 2-(6-(N-(thiazol-2-yl)sulfamoyl)isoquinolin-1-yl)-5-(trifluoromethyl)benzimidate;
2-(6-(N-(thiazol-2-yl)sulfamoyl)isoquinolin-1-yl)-5-(trifluoromethyl)benzamide;
1-(2-fluoro-4-(trifluoromethyl)phenyl)-N-(thiazol-2-yl)isoquinoline-6-sulfonamide;
1-(2-(1h-imidazol-1-yl)-4-(trifluoromethyl)phenyl)-N-(thiazol-2-yl)isoquinoline-6-sulfonamide;
1-(2-(2,3-dihydroxypropyl)-4-(trifluoromethyl)phenyl)-N-(thiazol-2-yl)isoquinoline-6-sulfonamide;
4-methoxy-1-(2-methoxy-4-(trifluoromethyl)phenyl)-N-(thiazol-2-yl)isoquinoline-6-sulfonamide;

4-hydroxy-1-(2-methoxy-4-(trifluoromethyl)phenyl)-N-(thiazol-2-yl)isoquinoline-6-sulfonamide;
1-(4-fluoro-2-methoxyphenyl)-4-hydroxy-N-(thiazol-2-yl)isoquinoline-6-sulfonamide;
4-hydroxy-1-(2-methoxyphenyl)-N-(thiazol-2-yl)isoquinoline-6-sulfonamide;
1-(2-bromo-4-(trifluoromethyl)phenyl)-N-(thiazol-2-yl)isoquinoline-6-sulfonamide;
1-(2-phenylpyrrolidin-1-yl)-N-(1,2,4-thiadiazol-5-yl)isoquinoline-6-sulfonamide;
1-(2-phenylpyrrolidin-1-yl)-N-(thiazol-2-yl)isoquinoline-6-sulfonamide;
(R)-1-(2-phenylpyrrolidin-1-yl)-N-(thiazol-2-yl)isoquinoline-6-sulfonamide;
(S)-1-(2-phenylpyrrolidin-1-yl)-N-(thiazol-2-yl)isoquinoline-6-sulfonamide;
4-cyano-1-(2-methoxy-4-(trifluoromethyl)phenyl)-N-(thiazol-2-yl)isoquinoline-6-sulfonamide;
1-(4-chloro-2-methoxyphenyl)-4-cyano-N-(2,4-dimethoxybenzyl)-N-(thiazol-2-yl)isoquinoline-6-sulfonamide;
4-cyano-1-(2-methoxy-4-(trifluoromethyl)phenyl)-N-(pyrimidin-4-yl)isoquinoline-6-sulfonamide;
1-(3-phenylpyrrolidin-1-yl)-N-(thiazol-2-yl)isoquinoline-6-sulfonamide;
1-(1-methyl-1h-pyrrol-2-yl)-N-(thiazol-2-yl)isoquinoline-6-sulfonamide;
1-(1-(tetrahydro-2h-pyran-4-yl)pyrrolidin-2-yl)-N-(thiazol-2-yl)isoquinoline-6-sulfonamide;
1-(1-(2-methoxyethyl)pyrrolidin-2-yl)-N-(thiazol-2-yl)isoquinoline-6-sulfonamide;
1-(4-(3,4-dichlorophenyl)piperazin-1-yl)-N-(thiazol-2-yl)isoquinoline-6-sulfonamide;
1-(2-methoxy-4-(trifluoromethyl)phenyl)-N-(4-oxothiazolidin-2-ylidene)isoquinoline-6-sulfonamide;
1-(4-chloro-2-methoxyphenyl)-N-(thiazol-2-yl)phthalazine-6-sulfonamide;
1-(4-fluoro-2-methoxyphenyl)-N-(thiazol-2-yl)phthalazine-6-sulfonamide;
1-(4-cyano-2-methoxyphenyl)-N-(thiazol-2-yl)phthalazine-6-sulfonamide;
1-(2-methoxyphenyl)-N-(thiazol-2-yl)phthalazine-6-sulfonamide;
1-(2-methoxy-4-(trifluoromethyl)phenyl)-N-(thiazol-2-yl)phthalazine-6-sulfonamide;
1-(2-methoxy-4-(trifluoromethyl)phenyl)-N-(pyrimidin-4-yl)phthalazine-6-sulfonamide;
N-(5-fluorothiazol-2-yl)-1-(2-methoxy-4-(trifluoromethyl)phenyl)phthalazine-6-sulfonamide;
1-(4-fluoro-2-methoxyphenyl)-N-(5-fluorothiazol-2-yl)phthalazine-6-sulfonamide;
1-(4-cyano-2-methoxyphenyl)-N-(thiazol-2-yl)phthalazine-6-sulfonamide;
1-(2-methoxyphenyl)-N-(thiazol-2-yl)phthalazine-6-sulfonamide;
4-(2-methoxy-4-(trifluoromethyl)phenyl)-N-(thiazol-2-yl)cinnoline-7-sulfonamide;
4-(2-methoxy-4-(trifluoromethyl)phenyl)-N-(pyrimidin-4-yl)cinnoline-7-sulfonamide;
4-(2-methoxy-4-(trifluoromethyl)phenyl)-N-(thiazol-2-yl)quinazoline-7-sulfonamide;
4-(2-methoxy-4-(trifluoromethyl)phenyl)-N-(pyrimidin-4-yl)quinazoline-7-sulfonamide;
N-(5-fluorothiazol-2-yl)-4-(2-methoxy-4-(trifluoromethyl)phenyl)quinazoline-7-sulfonamide;
4-(2-methoxy-4-(trifluoromethyl)phenyl)-N-(oxazol-2-yl)quinazoline-7-sulfonamide;
4-(2-methoxy-4-(trifluoromethyl)phenyl)-N-(1,2,4-thiadiazol-5-yl)quinazoline-7-sulfonamide;
4-(4-(difluoromethyl)-2-methoxyphenyl)-N-(thiazol-2-yl)quinazoline-7-sulfonamide;
4-(4-chloro-2-methoxyphenyl)-N-(thiazol-2-yl)quinazoline-7-sulfonamide;
4-(2-methoxy-4-(trifluoromethyl)phenyl)-N-(1,3,4-thiadiazol-2-yl)quinazoline-7-sulfonamide;
4-(4-cyano-2-methoxyphenyl)-N-(thiazol-2-yl)quinazoline-7-sulfonamide;
4-(5-chloro-4-(difluoromethyl)-2-methoxyphenyl)-N-(thiazol-2-yl)quinazoline-7-sulfonamide;
4-(4-fluoro-2-methoxyphenyl)-N-(thiazol-2-yl)quinazoline-7-sulfonamide;
4-(2-methoxyphenyl)-N-(thiazol-2-yl)quinazoline-7-sulfonamide;
4-(4-cyano-2-methoxyphenyl)-N-(thiazol-2-yl)quinoline-7-sulfonamide;
4-(4-fluoro-2-methoxyphenyl)-N-(thiazol-2-yl)quinoline-7-sulfonamide;
4-(4-chloro-2-methoxyphenyl)-N-(thiazol-2-yl)quinoline-7-sulfonamide;
4-(2-methoxy-4-(trifluoromethyl)phenyl)-N-(thiazol-2-yl)quinoline-7-sulfonamide;
4-(2-methoxyphenyl)-N-(thiazol-2-yl)quinoline-7-sulfonamide;
4-(2-chloro-4-(trifluoromethyl)phenyl)-N-(thiazol-2-yl)quinoline-7-sulfonamide;
4-(2-methoxy-4-(trifluoromethyl)phenyl)-N-(pyrimidin-4-yl)quinoline-7-sulfonamide;
4-(4-cyano-2-methoxyphenyl)-N-(pyrimidin-4-yl)quinoline-7-sulfonamide;
4-(2-methoxyphenyl)-N-(pyrimidin-4-yl)quinoline-7-sulfonamide;
4-(2-methoxy-4-(trifluoromethyl)phenyl)-5-methyl-N-(thiazol-2-yl)quinoline-7-sulfonamide;
3-amino-4-(2-methoxy-4-(trifluoromethyl)phenyl)-N-(thiazol-2-yl)quinoline-7-sulfonamide;
3-cyano-4-(2-methoxy-4-(trifluoromethyl)phenyl)-N-(thiazol-2-yl)quinoline-7-sulfonamide;
4-(2-methoxy-4-(trifluoromethyl)phenyl)-N-(pyrimidin-4-yl)isoquinoline-7-sulfonamide;
4-(4-cyano-2-methoxyphenyl)-N-(pyrimidin-4-yl)isoquinoline-7-sulfonamide;
4-(2-methoxyphenyl)-N-(pyrimidin-4-yl)isoquinoline-7-sulfonamide;
4-(2-methoxy-4-(trifluoromethyl)phenyl)-N-(thiazol-2-yl)isoquinoline-7-sulfonamide;
4-(2-methoxyphenyl)-N-(thiazol-2-yl)isoquinoline-7-sulfonamide;
4-(4-fluoro-2-methoxyphenyl)-N-(thiazol-2-yl)isoquinoline-7-sulfonamide;
8-(2-methoxy-4-(trifluoromethyl)phenyl)-N-(thiazol-2-yl)-1,7-naphthyridine-3-sulfonamide;
8-(2-methoxy-4-(trifluoromethyl)phenyl)-N-(pyrimidin-4-yl)-1,7-naphthyridine-3-sulfonamide;
1-(2-methoxy-4-(trifluoromethyl)phenyl)-4-oxo-N-(thiazol-2-yl)-3,4-dihydrophthalazine-6-sulfonamide;
4-(2-methoxy-4-(trifluoromethyl)phenyl)-N-(thiazol-2-yl)-1,6-naphthyridine-7-sulfonamide;
1-((1-methyl-1H-1,2,4-triazol-5-yl)methoxy)-N-(pyrimidin-4-yl)isoquinoline-6-sulfonamide;
1-(2-(1H-1,2,3-triazol-1-yl)ethoxy)-N-(pyrimidin-4-yl)isoquinoline-6-sulfonamide;
1-((6,7-dihydro-5H-pyrazolo[5,1-b][1,3]oxazin-2-yl)methoxy)-N-(pyrimidin-4-yl)isoquinoline-6-sulfonamide;

1-((2-morpholinopyridin-3-yl)methoxy)-N-(pyrimidin-4-yl)isoquinoline-6-sulfonamide;
1-(2,2-difluoro-2-(tetrahydro-2H-pyran-4-yl)ethoxy)-N-(pyrimidin-4-yl)isoquinoline-6-sulfonamide;
1-(3-(6-methylpyridin-2-yl)propoxy)-N-(pyrimidin-4-yl)isoquinoline-6-sulfonamide;
1-((4-(1H-imidazol-1-yl)benzyl)oxy)-N-(pyrimidin-4-yl)isoquinoline-6-sulfonamide;
N-(pyrimidin-4-yl)-1-(3-(5-(trifluoromethyl)-1H-pyrazol-4-yl)propoxy)isoquinoline-6-sulfonamide;
1-(2-(1H-pyrrol-1-yl)ethoxy)-N-(pyrimidin-4-yl)isoquinoline-6-sulfonamide;
1-((4-morpholinobenzyl)oxy)-N-(pyrimidin-4-yl)isoquinoline-6-sulfonamide;
1-(2-(1-methyl-1H-pyrazol-4-yl)ethoxy)-N-(pyrimidin-4-yl)isoquinoline-6-sulfonamide;
1-(1-methyl-1H-indazol-7-yl)-N-(pyrimidin-4-yl)isoquinoline-6-sulfonamide;
1-(1,4-dimethyl-1H-indazol-5-yl)-N-(pyrimidin-4-yl)isoquinoline-6-sulfonamide;
1-(1,6-dimethyl-1H-indazol-5-yl)-N-(pyrimidin-4-yl)isoquinoline-6-sulfonamide;
1-(1,5-dimethyl-1H-indazol-4-yl)-N-(pyrimidin-4-yl)isoquinoline-6-sulfonamide;
N-(pyrimidin-4-yl)-1-(quinolin-8-yl)isoquinoline-6-sulfonamide;
1-(3,5-dimethylisoxazol-4-yl)-N-(pyrimidin-4-yl)isoquinoline-6-sulfonamide;
1-(1-methyl-3-(trifluoromethyl)-1H-pyrazol-5-yl)-N-(pyrimidin-4-yl)isoquinoline-6-sulfonamide;
1-(2-methoxy-4-(trifluoromethyl)phenyl)-N-(2-methoxypyrimidin-4-yl)isoquinoline-6-sulfonamide;
N-((1-(2-methoxy-4-(trifluoromethyl)phenyl)isoquinolin-6-yl)sulfonyl)acetamide;
1-(1-methyl-1H-imidazol-2-yl)-N-(thiazol-2-yl)isoquinoline-6-sulfonamide;
N-(pyrimidin-4-yl)-1-(1-(tetrahydro-2H-pyran-4-yl)pyrrolidin-2-yl)isoquinoline-6-sulfonamide;
5-cyano-N-(1,2,4-thiadiazol-5-yl)naphthalene-2-sulfonamide; or
methyl 6-(N-(1,2,4-thiadiazol-5-yl)sulfamoyl)-1-naphthoate.

29. A compound, or a pharmaceutically acceptable salt thereof, selected from:
6-fluoro-4-(2-methoxy-4-(trifluoromethyl)phenyl)-N-(thiazol-2-yl)quinoline-7-sulfonamide 2,2,2-trifluoroacetate;
4-(2-methoxyphenyl)-n-(1,2,4-thiadiazol-5-yl)quinoline-7-sulfonamide 2,2,2-trifluoroacetate;
4-(3'-fluoro-4-methoxy-[1,1'-biphenyl]-3-yl)-N-(pyrimidin-4-yl)quinoline-7-sulfonamide;
4-(4-chloro-2-methylphenyl)-N-(1,2,4-thiadiazol-5-yl)quinoline-7-sulfonamide;
3-cyano-4-(2-methoxyphenyl)-N-(thiazol-2-yl)quinoline-7-sulfonamide;
4-(2-methoxy-4-(trifluoromethyl)phenyl)-6-methyl-N-(thiazol-2-yl)quinoline-7-sulfonamide;
1-(3'-fluoro-3-methoxy-[1,1'-biphenyl]-4-yl)-N-(pyrimidin-4-yl)phthalazine-6-sulfonamide;
5-(4-cyano-2-methoxyphenyl)-N-(1,2,4-thiadiazol-5-yl)naphthalene-2-sulfonamide;
1-(2-chloro-3'-fluoro-5-methoxy-[1,1'-biphenyl]-4-yl)-N-(1,2,4-thiadiazol-5-yl)isoquinoline-6-sulfonamide;
1-(2-chloro-3'-fluoro-5-methoxy-[1,1'-biphenyl]-4-yl)-N-(1,3,4-thiadiazol-2-yl)isoquinoline-6-sulfonamide;
1-(2-chloro-3'-fluoro-5-methoxy-[1,1'-biphenyl]-4-yl)-N-(pyrimidin-4-yl)isoquinoline-6-sulfonamide;
1-(2-chloro-3'-fluoro-5-methoxy-[1,1'-biphenyl]-4-yl)-N-(1,2,5-thiadiazol-3-yl)isoquinoline-6-sulfonamide;
1-(2-chloro-3'-fluoro-5-methoxy-[1,1'-biphenyl]-4-yl)-N-(isoxazol-3-yl)isoquinoline-6-sulfonamide;
1-(4-chloro-5-cyano-2-methoxyphenyl)-N-(1,2,4-thiadiazol-5-yl)isoquinoline-6-sulfonamide;
1-(4-chloro-5-cyano-2-methoxyphenyl)-N-(1,3,4-thiadiazol-2-yl)isoquinoline-6-sulfonamide;
1-(2-cyano-3',5'-difluoro-5-methoxy-[1,1'-biphenyl]-4-yl)-N-(1,3,4-thiadiazol-2-yl)isoquinoline-6-sulfonamide;
1-(2-cyano-5-methoxy-3'-(trifluoromethyl)-[1,1'-biphenyl]-4-yl)-N-(1,3,4-thiadiazol-2-yl)isoquinoline-6-sulfonamide;
1-(2-cyano-3'-fluoro-5-methoxy-[1,1'-biphenyl]-4-yl)-N-(1,2,4-thiadiazol-5-yl)isoquinoline-6-sulfonamide;
1-(2-cyano-3'-fluoro-5-methoxy-[1,1'-biphenyl]-4-yl)-N-(1,3,4-thiadiazol-2-yl)isoquinoline-6-sulfonamide;
1-(2-cyano-3'-fluoro-5-methoxy-[1,1'-biphenyl]-4-yl)-N-(isoxazol-3-yl)isoquinoline-6-sulfonamide;
1-(2-cyano-3',5'-difluoro-5-methoxy-[1,1'-biphenyl]-4-yl)-N-(isoxazol-3-yl)isoquinoline-6-sulfonamide;
1-(4-methoxy-3'-(trifluoromethyl)-[1,1'-biphenyl]-3-yl)-N-(1,3,4-thiadiazol-2-yl)isoquinoline-6-sulfonamide;
1-(3'-fluoro-4-methoxy-[1,1'-biphenyl]-3-yl)-N-(1,3,4-thiadiazol-2-yl)isoquinoline-6-sulfonamide;
1-(5-chloro-2-methoxyphenyl)-N-(1,2,4-thiadiazol-5-yl)isoquinoline-6-sulfonamide;
1-(3'-fluoro-4-methoxy-[1,1'-biphenyl]-3-yl)-N-(1,2,4-thiadiazol-5-yl)isoquinoline-6-sulfonamide;
1-(3'-fluoro-4-methoxy-[1,1'-biphenyl]-3-yl)-N-(pyrimidin-4-yl)isoquinoline-6-sulfonamide;
1-(4-methoxy-3'-(trifluoromethyl)-[1,1'-biphenyl]-3-yl)-N-(pyrimidin-4-yl)isoquinoline-6-sulfonamide;
1-(4'-fluoro-3-methoxy-[1,1'-biphenyl]-4-yl)-N-(pyrimidin-4-yl)isoquinoline-6-sulfonamide;
1-(3-methoxy-3'-(trifluoromethyl)-[1,1'-biphenyl]-4-yl)-N-(pyrimidin-4-yl)isoquinoline-6-sulfonamide;
1-(3',5'-difluoro-3-methoxy-[1,1'-biphenyl]-4-yl)-N-(1,3,4-thiadiazol-2-yl)isoquinoline-6-sulfonamide 2,2,2-trifluoroacetate;
1-(3'-fluoro-3-methyl-[1,1'-biphenyl]-4-yl)-N-(pyrimidin-4-yl)isoquinoline-6-sulfonamide;
1-(4-isobutoxy-2-methoxyphenyl)-N-(pyrimidin-4-yl)isoquinoline-6-sulfonamide;
N-(1,3,4-thiadiazol-2-yl)-1-(2,3',5'-trifluoro-5-methoxy-[1,1'-biphenyl]-4-yl)isoquinoline-6-sulfonamide;
N-(1,3,4-thiadiazol-2-yl)-1-(2,3',4'-trifluoro-5-methoxy-[1,1'-biphenyl]-4-yl)isoquinoline-6-sulfonamide;
1-(2,3'-difluoro-5-methoxy-[1,1'-biphenyl]-4-yl)-N-(1,3,4-thiadiazol-2-yl)isoquinoline-6-sulfonamide;
1-(4-chloro-2-methoxyphenyl)-N-(1,2,4-thiadiazol-5-yl)isoquinoline-6-sulfonamide;
1-(3'-fluoro-3-methoxy-[1,1'-biphenyl]-4-yl)-N-(1,2,4-thiadiazol-5-yl)isoquinoline-6-sulfonamide;
1-(3',5'-difluoro-3-methoxy-[1,1'-biphenyl]-4-yl)-N-(2-methylpyrimidin-4-yl)isoquinoline-6-sulfonamide;
1-(3',5'-difluoro-3-methoxy-[1,1'-biphenyl]-4-yl)-N-(6-methylpyrimidin-4-yl)isoquinoline-6-sulfonamide;
1-(4-chloro-2-(cyanomethoxy)phenyl)-N-(thiazol-2-yl)isoquinoline-6-sulfonamide 2,2,2-Trifluoroacetate;
1-(2-(cyanomethoxy)-4-(trifluoromethyl)phenyl)-N-(thiazol-2-yl)isoquinoline-6-sulfonamide;
1-(2-(cyanomethoxy)phenyl)-N-(thiazol-2-yl)isoquinoline-6-sulfonamide 2,2,2-Trifluoroacetate;
4-fluoro-1-(2-methoxy-4-(trifluoromethyl)phenyl)-N-(1,2,4-thiadiazol-5-yl)isoquinoline-6-sulfonamide;

4-fluoro-1-(2-methoxyphenyl)-N-(1,2,4-thiadiazol-5-yl)isoquinoline-6-sulfonamide;
4-fluoro-1-(4-fluoro-2-methoxyphenyl)-N-(1,2,4-thiadiazol-5-yl)isoquinoline-6-sulfonamide;
1-(4-cyano-2-methoxyphenyl)-4-fluoro-N-(1,2,4-thiadiazol-5-yl)isoquinoline-6-sulfonamide;
4-cyano-1-(4-fluoro-2-methoxyphenyl)-N-(thiazol-2-yl)isoquinoline-6-sulfonamide;
1-(4-chloro-2-(cyanomethoxy)phenyl)-N-(1,2,4-thiadiazol-5-yl)isoquinoline-6-sulfonamide 2,2,2-Trifluoroacetate;
1-(4-fluoro-2-methoxyphenyl)-N-(thiazol-2-yl)isoquinoline-6-sulfonamide;
1-(2-methoxyphenyl)-N-(thiazol-2-yl)isoquinoline-6-sulfonamide;
1-(2-methoxy-5-(trifluoromethyl)pyridin-3-yl)-N-(thiazol-2-yl)isoquinoline-6-sulfonamide;
1-(2-methoxy-5-methylpyridin-3-yl)-N-(thiazol-2-yl)isoquinoline-6-sulfonamide;
1-(2-(difluoromethoxy)-5-fluorophenyl)-N-(thiazol-2-yl)isoquinoline-6-sulfonamide;
N-(4-chlorothiazol-2-yl)-1-(2-methoxy-4-(trifluoromethyl)phenyl)isoquinoline-6-sulfonamide;
N-(5-chlorothiazol-2-yl)-1-(2-methoxy-4-(trifluoromethyl)phenyl)isoquinoline-6-sulfonamide;
N-(4-cyanothiazol-2-yl)-1-(2-methoxy-4-(trifluoromethyl)phenyl)isoquinoline-6-sulfonamide;
N-(6-chloropyrimidin-4-yl)-1-(2-methoxy-4-(trifluoromethyl)phenyl)isoquinoline-6-sulfonamide;
1-(3-methoxy-2'-methyl-[1,1'-biphenyl]-4-yl)-N-(pyrimidin-4-yl)isoquinoline-6-sulfonamide;
1-(3-methoxy-3'-methyl-[1,1'-biphenyl]-4-yl)-N-(pyrimidin-4-yl)isoquinoline-6-sulfonamide;
1-(3-methoxy-4'-methyl-[1,1'-biphenyl]-4-yl)-N-(pyrimidin-4-yl)isoquinoline-6-sulfonamide;
1-(2',3'-difluoro-3-methoxy-[1,1'-biphenyl]-4-yl)-N-(pyrimidin-4-yl)isoquinoline-6-sulfonamide;
1-(2',4'-difluoro-3-methoxy-[1,1'-biphenyl]-4-yl)-N-(pyrimidin-4-yl)isoquinoline-6-sulfonamide;
1-(2',5'-difluoro-3-methoxy-[1,1'-biphenyl]-4-yl)-N-(pyrimidin-4-yl)isoquinoline-6-sulfonamide;
1-(2',6'-difluoro-3-methoxy-[1,1'-biphenyl]-4-yl)-N-(pyrimidin-4-yl)isoquinoline-6-sulfonamide;
1-(3',4'-difluoro-3-methoxy-[1,1'-biphenyl]-4-yl)-N-(pyrimidin-4-yl)isoquinoline-6-sulfonamide;
1-(3',5'-difluoro-3-methoxy-[1,1'-biphenyl]-4-yl)-N-(pyrimidin-4-yl)isoquinoline-6-sulfonamide;
1-(4-(difluoromethyl)-2,5-dimethoxyphenyl)-N-(thiazol-2-yl)isoquinoline-6-sulfonamide;
1-(5-chloro-4-(difluoromethyl)-2-methoxyphenyl)-N-(pyrimidin-4-yl)isoquinoline-6-sulfonamide;
1-(5-cyclopropyl-4-(difluoromethyl)-2-methoxyphenyl)-N-(pyrimidin-4-yl)isoquinoline-6-sulfonamide;
1-(4'-chloro-2',3-dimethoxy-[1,1'-biphenyl]-4-yl)-N-(pyrimidin-4-yl)isoquinoline-6-sulfonamide;
1-(4-(4-fluorophenoxy)-2-methoxyphenyl)-N-(pyrimidin-4-yl)isoquinoline-6-sulfonamide;
1-(4-(3-fluorophenoxy)-2-methoxyphenyl)-N-(pyrimidin-4-yl)isoquinoline-6-sulfonamide;
1-(4-(2-fluorophenoxy)-2-methoxyphenyl)-N-(pyrimidin-4-yl)isoquinoline-6-sulfonamide;
1-(2',3-dimethoxy-[1,1'-biphenyl]-4-yl)-N-(pyrimidin-4-yl)isoquinoline-6-sulfonamide;
1-(3,3'-dimethoxy-[1,1'-biphenyl]-4-yl)-N-(pyrimidin-4-yl)isoquinoline-6-sulfonamide;
1-(3,4'-dimethoxy-[1,1'-biphenyl]-4-yl)-N-(pyrimidin-4-yl)isoquinoline-6-sulfonamide;
1-(3-methoxy-3',4'-dimethyl-[1,1'-biphenyl]-4-yl)-N-(pyrimidin-4-yl)isoquinoline-6-sulfonamide;
1-(3-methoxy-3',5'-dimethyl-[1,1'-biphenyl]-4-yl)-N-(pyrimidin-4-yl)isoquinoline-6-sulfonamide;
1-(3'-fluoro-3-methoxy-4'-methyl-[1,1'-biphenyl]-4-yl)-N-(pyrimidin-4-yl)isoquinoline-6-sulfonamide;
1-(3'-fluoro-3-methoxy-5'-methyl-[1,1'-biphenyl]-4-yl)-N-(pyrimidin-4-yl)isoquinoline-6-sulfonamide;
1-(4-(6-fluoro-5-methylpyridin-3-yl)-2-methoxyphenyl)-N-(pyrimidin-4-yl)isoquinoline-6-sulfonamide;
1-(2-methoxy-4-(2-methoxypyridin-3-yl)phenyl)-N-(pyrimidin-4-yl)isoquinoline-6-sulfonamide;
1-(4'-fluoro-3,3'-dimethoxy-[1,1'-biphenyl]-4-yl)-N-(pyrimidin-4-yl)isoquinoline-6-sulfonamide;
1-(3'-fluoro-3,5'-dimethoxy-[1,1'-biphenyl]-4-yl)-N-(pyrimidin-4-yl)isoquinoline-6-sulfonamide;
1-(3'-cyano-4'-fluoro-3-methoxy-[1,1'-biphenyl]-4-yl)-N-(pyrimidin-4-yl)isoquinoline-6-sulfonamide;
1-(3'-cyano-5'-fluoro-3-methoxy-[1,1'-biphenyl]-4-yl)-N-(pyrimidin-4-yl)isoquinoline-6-sulfonamide;
1-(4'-fluoro-3-methoxy-3'-methyl-[1,1'-biphenyl]-4-yl)-N-(pyrimidin-4-yl)isoquinoline-6-sulfonamide;
1-(4-(1h-indol-5-yl)-2-methoxyphenyl)-N-(pyrimidin-4-yl)isoquinoline-6-sulfonamide;
1-(3'-chloro-4'-fluoro-3-methoxy-[1,1'-biphenyl]-4-yl)-N-(pyrimidin-4-yl)isoquinoline-6-sulfonamide;
1-(3'-chloro-5'-fluoro-3-methoxy-[1,1'-biphenyl]-4-yl)-N-(pyrimidin-4-yl)isoquinoline-6-sulfonamide;
1-(4'-chloro-3'-fluoro-3-methoxy-[1,1'-biphenyl]-4-yl)-N-(pyrimidin-4-yl)isoquinoline-6-sulfonamide;
1-(4'-chloro-3-methoxy-3'-methyl-[1,1'-biphenyl]-4-yl)-N-(pyrimidin-4-yl)isoquinoline-6-sulfonamide;
1-(3'-chloro-3-methoxy-4'-methyl-[1,1'-biphenyl]-4-yl)-N-(pyrimidin-4-yl)isoquinoline-6-sulfonamide;
1-(3'-chloro-3-methoxy-5'-methyl-[1,1'-biphenyl]-4-yl)-N-(pyrimidin-4-yl)isoquinoline-6-sulfonamide;
1-(2-methoxy-4-(trifluoromethyl)phenyl)-N-(thiazol-4-yl)isoquinoline-6-sulfonamide;
1-(5-chloro-6-(3-fluorophenyl)-2-methoxypyridin-3-yl)-N-(1,3,4-thiadiazol-2-yl)isoquinoline-6-sulfonamide;
1-(5-chloro-2-methoxyphenyl)-4-oxo-N-(thiazol-2-yl)-3,4-dihydrophthalazine-6-sulfonamide;
1-(5-chloro-2-methoxyphenyl)-4-oxo-N-(1,2,4-thiadiazol-5-yl)-3,4-dihydrophthalazine-6-sulfonamide;
1-(5-chloro-2-methoxyphenyl)-N-(5-fluorothiazol-2-yl)-4-oxo-3,4-dihydrophthalazine-6-sulfonamide;
1-(3'-fluoro-4-methoxy-[1,1'-biphenyl]-3-yl)-4-hydroxy-N-(pyrimidin-4-yl)phthalazine-6-sulfonamide;
4-(2-methoxy-4-(trifluoromethyl)phenyl)-2-methyl-N-(thiazol-2-yl)quinazoline-7-sulfonamide;
2-methoxy-4-(2-methoxy-4-(trifluoromethyl)phenyl)-N-(thiazol-2-yl)quinazoline-7-sulfonamide;
4-(4-(difluoromethyl)-5-fluoro-2-methoxyphenyl)-N-(thiazol-2-yl)quinazoline-7-sulfonamide;
4-(4-(difluoromethyl)-5-fluoro-2-methoxyphenyl)-N-(thiazol-4-yl)quinazoline-7-sulfonamide;
4-(4-(difluoromethyl)-5-fluoro-2-methoxyphenyl)-2-methyl-N-(thiazol-2-yl)quinazoline-7-sulfonamide;
4-(4-(difluoromethyl)-2-methoxyphenyl)-2-methyl-N-(thiazol-2-yl)quinazoline-7-sulfonamide;
4-(2-chloro-3'-fluoro-5-methoxy-[1,1'-biphenyl]-4-yl)-N-(1,2,4-thiadiazol-5-yl)quinazoline-7-sulfonamide;
4-(2-chloro-3'-fluoro-5-methoxy-[1,1'-biphenyl]-4-yl)-N-(1,3,4-thiadiazol-2-yl)quinazoline-7-sulfonamide;
4-(2-chloro-3'-fluoro-5-methoxy-[1,1'-biphenyl]-4-yl)-N-(pyrimidin-4-yl)quinazoline-7-sulfonamide;

4-(4-chloro-2-methoxyphenyl)-N-(1,2,4-thiadiazol-5-yl)quinazoline-7-sulfonamide;

4-(3'-fluoro-3-methoxy-[1,1'-biphenyl]-4-yl)-N-(1,2,4-thiadiazol-5-yl)quinazoline-7-sulfonamide;

4-(3'-fluoro-3-methoxy-[1,1'-biphenyl]-4-yl)-N-(pyrimidin-4-yl)quinazoline-7-sulfonamide;

4-(3-methoxy-3'-(trifluoromethyl)-[1,1'-biphenyl]-4-yl)-N-(pyrimidin-4-yl)quinazoline-7-sulfonamide;

4-(3'-fluoro-3-methoxy-[1,1'-biphenyl]-4-yl)-N-(1,3,4-thiadiazol-2-yl)quinazoline-7-sulfonamide;

4-(3',4'-difluoro-3-methoxy-[1,1'-biphenyl]-4-yl)-N-(1,3,4-thiadiazol-2-yl)quinazoline-7-sulfonamide;

4-(3',5'-difluoro-3-methoxy-[1,1'-biphenyl]-4-yl)-N-(1,3,4-thiadiazol-2-yl)quinazoline-7-sulfonamide;

4-(4-chloro-2-methylphenyl)-N-(1,2,4-thiadiazol-5-yl)quinazoline-7-sulfonamide; or 4-(2-methoxy-4-(trifluoromethyl)phenyl)-1-oxo-N-(thiazol-2-yl)-1,2-dihydroisoquinoline-7-sulfonamide.

30. A method of treating pain, the method comprising administering to a patient in need thereof a therapeutically effective amount of a compound in accordance with any one of claim 1, or a pharmaceutically acceptable salt thereof.

31. The method of claim 30 wherein the treatment is for chronic pain, acute pain, neuropathic pain, pain associated with rheumatoid arthritis, pain associated with osteoarthritis or pain associated with cancer.

32. A pharmaceutical composition comprising a compound in accordance with any one of claim 1, or a pharmaceutically acceptable salt thereof, and a pharmaceutically acceptable excipient.

* * * * *